US010508109B2

(12) United States Patent
Matsuo et al.

(10) Patent No.: US 10,508,109 B2
(45) Date of Patent: Dec. 17, 2019

(54) BICYCLIC COMPOUND AND USE THEREOF FOR INHIBITING SUV39H2

(71) Applicant: ONCOTHERAPY SCIENCE, INC., Kanagawa (JP)

(72) Inventors: Yo Matsuo, Kanagawa (JP); Shoji Hisada, Kawasaki (JP); Yusuke Nakamura, Kawasaki (JP); Anjan Chakrabarti, Singapore (SG); Manish Rawat, New Delhi (IN); Sanjay Rai, Hyderabad (IN); Arvapalli Venkata Satyanarayana, Singapore (SG); Zhiyong Duan, Singapore (SG); Arindam Talukdar, West Bengal (IN); Srinivas Ravula, Secunderabad (IN); Helene Decornez, Clifton Park, NY (US)

(73) Assignee: ONCOTHERAPY SCIENCE, INC., Kanagawa (JP)

( * ) Notice: Subject to any disclaimer, the term of this patent is extended or adjusted under 35 U.S.C. 154(b) by 0 days.

(21) Appl. No.: 15/763,389

(22) PCT Filed: Sep. 12, 2016

(86) PCT No.: PCT/US2016/051350
§ 371 (c)(1),
(2) Date: Mar. 26, 2018

(87) PCT Pub. No.: WO2017/058503
PCT Pub. Date: Apr. 6, 2017

(65) Prior Publication Data
US 2018/0273529 A1 Sep. 27, 2018

Related U.S. Application Data

(60) Provisional application No. 62/234,183, filed on Sep. 29, 2015.

(51) Int. Cl.
*C07D 471/04* (2006.01)
*C07D 451/00* (2006.01)
*C07D 487/04* (2006.01)
*C07D 519/00* (2006.01)
*C07F 9/6561* (2006.01)
*A61P 35/00* (2006.01)

(52) U.S. Cl.
CPC ............ *C07D 471/04* (2013.01); *A61P 35/00* (2018.01); *C07D 451/00* (2013.01); *C07D 487/04* (2013.01); *C07D 519/00* (2013.01); *C07F 9/6561* (2013.01)

(58) Field of Classification Search
CPC ................................................ C07D 451/00; C07D 471/045; C07D 487/04; C07D 519/00; C07F 9/6561
See application file for complete search history.

(56) References Cited

U.S. PATENT DOCUMENTS

| 6,596,731 | B2 | 7/2003 | Mutel et al. |
| 2006/0194199 | A1 | 8/2006 | Nakamura et al. |
| 2009/0208514 | A1 | 8/2009 | Nakamura et al. |
| 2011/0009441 | A1 | 1/2011 | Trabanco-Suarez et al. |
| 2012/0021946 | A1 | 1/2012 | Nakamura et al. |

FOREIGN PATENT DOCUMENTS

| EP | 0166609 | A2 | 1/1986 | |
| WO | 2004/031410 | A2 | 4/2004 | |
| WO | 2005/071102 | A2 | 8/2005 | |
| WO | 2007/013671 | A2 | 2/2007 | |
| WO | WO 2009054497 | * | 4/2009 | ........... C07D 471/04 |
| WO | 2012/074126 | A1 | 6/2012 | |
| WO | 2014/177458 | A1 | 11/2012 | |
| WO | 2013/003298 | A2 | 1/2013 | |
| WO | 2014/187762 | A1 | 11/2014 | |
| WO | 2014/187922 | A1 | 11/2014 | |
| WO | WO 2015/000715 | * | 1/2015 | ........... C07D 471/04 |

OTHER PUBLICATIONS

Allis, et al. "New nomenclature for chromatin-modifying enzymes." Cell 131, No. 4 (2007): 633-636.
Cho, et al. "Demethylation of RB regulator MYPT1 by histone demethylase LSD1 promotes cell cycle progression in cancer cells." Cancer research (2010): canres-2446.
Hamamoto, et al. "Enhanced SMYD3 expression is essential for the growth of breast cancer cells." Cancer science 97, No. 2 (2006): 113-118.
Hamamoto, et al. "SMYD3 encodes a histone methyltransferase involved in the proliferation of cancer cells." Nature cell biology 6, No. 8 (2004): 731.
Hayami, et al. "Overexpression of LSD1 contributes to human carcinogenesis through chromatin regulation in various cancers." International journal of cancer 128, No. 3 (2011): 574-586.
Huertas, et al.. "Chromatin dynamics coupled to DNA repair." Epigenetics 4, No. 1 (2009): 31-42.
International Search Report in PCT/US2016/51350, dated Oct. 26, 2016.
Kouzarides "Histone methylation in transcriptional control." Current opinion in genetics & development 12, No. 2 (2002): 198-209.
Kouzarides "Chromatin modifications and their function." Cell 128, No. 4 (2007): 693-705.
Kunizaki, et al. "The lysine 831 of vascular endothelial growth factor receptor 1 is a novel target of methylation by SMYD3." Cancer research 67, No. 22 (2007): 10759-10765.
Luco, et al. "Regulation of alternative splicing by histone modifications." Science 327, No. 5968 (2010): 996-1000.
Martin, et al. "The diverse functions of histone lysine methylation." Nature reviews Molecular cell biology 6, No. 11 (2005): 838.

(Continued)

*Primary Examiner* — Erich A Leeser
(74) *Attorney, Agent, or Firm* — Kilpatrick Townsend & Stockton LLP

(57) ABSTRACT

The present invention directs to a compound represented by formula (I).

17 Claims, No Drawings

(56) References Cited

OTHER PUBLICATIONS

O'Carroll, et al. "Isolation and Characterization ofSuv39h2, a Second Histone H3 Methyltransferase Gene That Displays Testis-Specific Expression." Molecular and cellular biology 20, No. 24 (2000): 9423-9433.

Peterson, et al. "Histones and histone modifications." Current Biology 14, No. 14 (2004): R546-R551.

Schneider, et al. "Unsafe SETs: histone lysine methyltransferases and cancer." Trends in biochemical sciences 27, No. 8 (2002): 396-402.

Silva et al., "Enhanced methyltransferase activity of SMYD3 by the cleavage of its N-terminal region in human cancer cells." Oncogene 27, No. 19 (2008): 2686.

Strahl, et al. "The language of covalent histone modifications." Nature 403, No. 6765 (2000): 41.

Tsuge, et al. "A variable No. Of tandem repeats polymorphism in an E2F-1 binding element in the 5' flanking region of SMYD3 is a risk factor for human cancers." Nature genetics 37, No. 10 (2005): 1104.

Yoshimatsu, et al. "Dysregulation of PRMT1 and PRMT6, Type I arginine methyltransferases, is involved in various types of human cancers." International journal of cancer 128, No. 3 (2011): 562-573.

Kasiviswanadharaju Pericherla et al: "Copper catalyzed tandem oxidative C-H amination/cyclizations: Direct access to imidazo[I,2-a]pyridines", *RSC Advances*; vol. 3; No. 41; Jan. 1, 2013; p. 18923.

Espérance Moine et al: "A small-molecule cell-based screen led to the identification of biphenylimidazoazines with highly potent and broad-spectrum anti-apicomplexan activity", *European Journal of Medicinal Chemistry*; vol. 89; Jan. 1, 2015; pp. 386-400.

Ma A et al: "Discovery of a selective, substrate-competitive inhibitor of the lysine methyltransferase SETD8" *Journal of Medicinal Chemistry*; vol. 57; No. 15; Aug. 1, 2014; pp. 6822-6833.

Supplementary European Search Report in EP 16852299.3; dated May 16, 2019.

\* cited by examiner

BICYCLIC COMPOUND AND USE THEREOF FOR INHIBITING SUV39H2

CROSS-REFERENCE TO RELATED PATENT APPLICATION

The present patent application claims benefit of priority to US Provisional Application No. 62/234,183, filed Sep. 29, 2015, the disclosure of which is incorporated herein in its entirety.

TECHNICAL FIELD

The present invention relates to a compound having an inhibitory activity against SUV39H2, a method for the preparation thereof, and a pharmaceutical composition containing the compound as an active ingredient. The present invention relates to a method for treatment or prevention of a disease that involves overexpression of SUV39H2.

BACKGROUND ART

The nucleosome, the basic unit of DNA packaging in eukaryotes that consists of a 147-bp DNA wound in sequence around a histone protein core, is a fundamental unit of chromatin structures [Non-Patent Document 1]. All four core histones (H3, H4, H2A and H2B) possess unstructured N-terminal tails and these N-termini of histones are particularly subjected to a diverse array of post-translational modifications: acetylation, methylation, phosphorylation, ubiquitination, SUMOylation and ADP-ribosylation [Non-Patent Document 2]. These histone modifications cause dynamic changes to the chromatin structure and thereby impinge on transcriptional regulation, DNA replication, DNA repair, and alternative splicing [Non-Patent Documents 3 and 4]. Among these epigenetic marks on histones, the methylation process is particularly crucial for transcriptional regulation [Non-Patent Document 5]. Five lysine residues (H3K4, H3K9, H3K27, H3K36 and H4K20) are located in the N-terminal tails and are representative lysines that can become mono-, di-, or trimethylated. Whereas H3K9, H3K27 and H4K20 methylation mainly represses transcription, methylation marks on H3K4 and H3K36 are associated with the induction of active transcription [Non-Patent Document 6]. For instance, methylation of histone H3 at lysine 9 (H3K9) is one of the most abundant and stable histone modifications, and is involved in both gene repression and heterochromatin formation. H3K9 can be mono-, di- or trimethylated on H3K9, whereas silent euchromatin regions are enriched for mono- and dimethylated H3K9 [Non-Patent Document 17]. In mammals, heterochromatic regions are highly trimethylated on H3K9, whereas silent euchromatic regions are enriched for mono- and dimethylated H3K9 [Non-Patent Document 17]. H3K9 methylation has been linked to de novo gene silencing and DNA methylation, and it is inherited after mitosis in a manner coupled to DNA methylation.

It has previously been reported that some histone methyltransferases and demethylases are deeply involved in human carcinogenesis [Non-Patent Document 7, 8, 9, 10 and 11]. For instance, SMYD3, PRMT1, PRMT6, SUV420H1 and SUV420H1-2 have been shown to stimulate the proliferation of cells through its enzymatic activity [Patent Document 1, 8, 9, 12, 13, 14, and 18].

SUV39H2, also known as KMT1B [Non-Patent Document 15], is a SET-domain containing histone methyltransferase and is known to methylate the H3K9 lysine residue. Suv39h2, the murine homologue of human SUV39H2, has been isolated and characterized as the second murine Suv39h gene, and demonstrated to share 59% identity with Suv39h1 [Non-Patent Document 16]. The expression of Suv39h2 is restricted to adult testis, and immunolocalization of endogenous Suv39h2 protein reveals enriched distributions at heterochromatin during the first meiotic prophase and in the early stages of sperminogenesis. During mid-pachytene, Suv39h2 specifically accumulates within the chromatin of the silenced sex chromosomes present in the XY body. In addition, the histone methyltransferase activity of Suv39h2 appears to play an important role in regulating higher-order chromatin dynamics during male meiosis [Non-Patent Document 16].

CITATION LIST

Patent Document

1. WO2005/071102.

Non-Patent Document

1. Strahl B D et al. Nature 2000; 403: 41-45;
2. Kouzarides T et al. Cell 2007; 128: 693-705
3. Huertas D et al. Epigenetics 2009; 4: 31-42;
4. Luco R F et al. Science 2010; 327: 996-1000;
5. Kouzarides T et al. Curr Opin Genet Dev 2002; 12: 198-209;
6. Peterson C L et al. Curr Biol 2004; 14: R546-551;
7. Cho H S et al. Cancer Res 2010;
8. Hamamoto R et al. Nat Cell Biol 2004; 6:731-40;
9. Hamamoto R et al. Cancer Sci 2006; 97: 113-8;
10. Yoshimatsu M et al. Int J Cancer 2011; 128: 562-573;
11. Hayami S et al. Int J Cancer 2011; 128: 574-586;
12. Kunizaki M et al. Cancer Res 2007; 67:10759-65;
13. Silva F P et al. Oncogene 2008; 27:2686-92;
14. Tsuge M et al. Nat Genet 2005; 37:1104-7;
15. Allis C D et al. Cell 2007; 131: 633-636;
16. O'Carroll D et al. Mol Cell Biol 2000; 20: 9423-9433;
17. Martin C et al. Nat Rev Mol Cell Biol 2005; 6:838-49; and
18. Schneider R et al. Trends Biochem Sci 2002; 27:396-402.

SUMMARY OF INVENTION

The present inventors have endeavored to develop an effective inhibitor of SUV39H2 and have found that a compound can selectively inhibit the activity of SUV39H2. The present invention relates to the following (1) to (17).

(1) A compound represented by formula (I) or a pharmaceutically acceptable salt thereof:

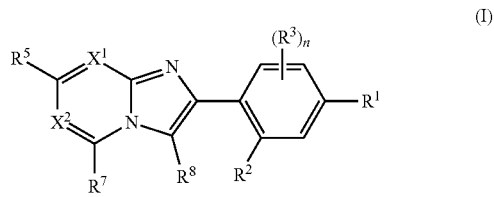

(I)

wherein
$R^1$ is selected from the group consisting of a halogen atom, hydroxy, $C_1$-$C_6$ alkyl, and $C_1$-$C_6$ alkoxy, wherein the alkyl and the alkoxy may be substituted with one or more substituents selected from $A^1$;

$R^2$ is selected from the group consisting of a hydrogen atom, a halogen atom, hydroxy, $C_1$-$C_6$ alkyl, $C_1$-$C_6$ alkoxy, and $C_3$-$C_{10}$ cycloalkoxy, wherein the alkyl and the alkoxy may be substituted with one or more substituents selected from $A^2$;

$R^3$ is independently selected from the group consisting of a halogen atom, cyano, nitro, hydroxy, carboxy, $C_1$-$C_6$ alkyl, $C_1$-$C_6$ alkoxy, ($C_1$-$C_6$ alkoxy)carbonyl, $C_1$-$C_6$ alkylthio, $C_1$-$C_6$ alkylsulfinyl, and $C_1$-$C_6$ alkylsulfonyl;

n is an integer selected from 0 to 3;

$X^1$ is N, or $CR^4$;

$X^2$ is N, or $CR^6$;

$R^4$ is selected from the group consisting of a hydrogen atom, a halogen atom, $C_1$-$C_6$ alkyl, and $C_1$-$C_6$ alkoxy;

$R^5$ and $R^6$ are independently selected from the group consisting of a hydrogen atom, a halogen atom, and Y, wherein at least one of $R^5$ and $R^6$ is Y;

Y is independently selected from the group consisting of hydroxy, $C_1$-$C_6$ alkyl optionally substituted with one or more substituents selected from $A^3$, $C_1$-$C_6$ alkoxy optionally substituted with one or more substituents selected from $A^3$, —$NR^{11}R^{12}$, —$CONR^{13}R^{14}$, $C_3$-$C_{10}$ cycloalkyl optionally substituted with one or more substituents selected from Rc, $C_6$-$C_{10}$ aryl optionally substituted with one or more substituents selected from Rd, 3- to 12-membered non-aromatic heterocyclyl optionally substituted with one or more substituents selected from Re, 5- to 10-membered heteroaryl optionally substituted with one or more substituents selected from Rf, and —$OR^{15}$;

$R_{11}$ is selected from the group consisting of a hydrogen atom, $C_1$-$C_6$ alkyl optionally substituted with one or more substituents selected from Ra, $C_3$-$C_{10}$ cycloalkyl optionally substituted with one or more substituents selected from Rb, $C_6$-$C_{10}$ aryl optionally substituted with one or more substituents selected from Rb, 5- to 10-membered heteroaryl optionally substituted with one or more substituents selected from Rb, 3- to 12-membered non-aromatic heterocyclyl optionally substituted with one or more substituents selected from Rb, ($C_1$-$C_6$ alkoxy)carbonyl optionally substituted with one or more substituents selected from Ra, ($C_1$-$C_6$ alkyl)carbonyl optionally substituted with one or more substituents selected from Ra, ($C_3$-$C_{10}$ cycloalkyl)carbonyl optionally substituted with one or more substituents selected from Rg, ($C_6$-$C_{10}$ aryl)carbonyl optionally substituted with one or more substituents selected from Rh, (3- to 12-membered non-aromatic heterocyclyl)carbonyl optionally substituted with one or more substituents selected from Rg, (5- to 10-membered heteroaryl)carbonyl optionally substituted with one or more substituents selected from Rg, aminocarbonyl, ($C_1$-$C_6$ alkyl)aminocarbonyl, and di($C_1$-$C_6$ alkyl)aminocarbonyl;

$R^{12}$ is selected from the group consisting of a hydrogen atom, and $C_1$-$C_6$ alkyl optionally substituted with one or more substituents selected from Ra;

$R^{13}$ is selected from the group consisting of a hydrogen atom, $C_1$-$C_6$ alkyl optionally substituted with one or more substituents selected from Ra, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

$R^{14}$ is selected from the group consisting of a hydrogen atom, and $C_1$-$C_6$ alkyl optionally substituted with one or more substituents selected from Ra;

$R^{15}$ is selected from the group consisting of $C_1$-$C_{10}$ cycloalkyl optionally substituted with one or more substituents selected from Rc, $C_6$-$C_{10}$ aryl optionally substituted with one or more substituents selected from Rd, 4- to 12-membered heterocyclyl optionally substituted with one or more substituents selected from Re, and 5- to 10-membered heteroaryl optionally substituted with one or more substituents selected from Rf, $A^1$ is independently selected from the group consisting of a halogen atom and cyano;

$A^2$ is independently selected from the group consisting of a halogen atom, cyano, amino, $C_1$-$C_6$ alkylamino, di($C_1$-$C_6$ alkyl)amino, $C_1$-$C_6$ alkylthio, $C_1$-$C_6$ alkylsulfinyl, $C_1$-$C_6$ alkylsulfonyl $C_3$-$C_{10}$ cycloalkyl, and $C_1$-$C_6$ alkoxy;

$A^3$ independently is selected from the group consisting of a halogen atom, cyano, amino, $C_1$-$C_6$ alkylamino, di($C_1$-$C_6$ alkyl)amino, $C_1$-$C_6$ alkylthio, $C_1$-$C_6$ alkylsulfinyl, $C_1$-$C_6$ alkylsulfonyl, $C_3$-$C_{10}$ cycloalkylsulfonyl, $C_3$-$C_{10}$ cycloalkyl, and $C_1$-$C_6$ alkoxy;

Ra is independently selected from the group consisting of a halogen atom, hydroxy, $C_1$-$C_6$ alkoxy, cyano, ($C_1$-$C_6$ alkoxy)carbonyl, carboxy, ($C_1$-$C_6$ alkoxy)carbonylamino, ($C_1$-$C_6$ alkyl)carbonylamino, amino, $C_1$-$C_6$ alkylamino, di($C_1$-$C_6$ alkyl)amino, aminocarbonyl, ($C_1$-$C_6$ alkyl)aminocarbonyl, di($C_1$-$C_6$ alkyl)aminocarbonyl, $C_1$-$C_6$ alkylsulfonylamino, $C_3$-$C_{10}$ cycloalkylsulfonylamino, di($C_1$-$C_6$ alkyl)phosphono, $C_7$-$C_{14}$ aralkyl, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 4- to 12-membered non-aromatic heterocyclyl optionally substituted with one or more substituents selected from Rg;

Rb is independently selected from the group consisting of a halogen atom, hydroxy, $C_1$-$C_6$ alkyl optionally substituted with one or more substituents selected from Ra, $C_1$-$C_6$ alkoxy optionally substituted with one or more substitutents selected from Ra, cyano, ($C_1$-$C_6$ alkoxy)carbonyl, carboxy, —$NR^{21}R^{22}$, —$CONR^{13}R^{24}$, di($C_1$-$C_6$ alkyl)phosphono, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

Rc, Re and Rf are independently selected from the group consisting of a halogen atom, hydroxy, cyano, carboxy, —$NR^{21}R^{22}$, —$CONR^{23}R^{24}$, —N=CH—$R^{25}$, $C_1$-$C_6$ alkyl optionally substituted with one or more substituents selected from Ra, ($C_1$-$C_6$ alkoxy)$C_1$-$C_6$ alkyl optionally substituted with one or more substituents selected from Ra, ($C_1$-$C_6$ alkyl)carbonyl optionally substituted with one or more substituents selected from Ra, ($C_1$-$C_6$ alkoxy)carbonyl, ($C_6$-$C_{10}$ aryl)carbonyl optionally substituted with one or more substituents selected from Rh, ($C_3$-$C_{10}$ cycloalkyl)carbonyl optionally substituted with one or more substituents selected from Rg, (3- to 12-membered non-aromatic heterocyclyl)carbonyl optionally substituted with one or more substituents selected from Rg, $C_3$-$C_{10}$ cycloalkyl optionally substituted with one or more substituents selected from Rg, 3- to 12-membered non-aromatic heterocyclyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl)aminocarbonyl optionally substituted with one or more substituents selected from Ra, [($C_1$-$C_6$ alkyl)aminocarbonyl]$C_1$-$C_6$ alkyl optionally substituted with one or more substituents selected from Ra, [di($C_1$-$C_6$ alkyl)aminocarbonyl]$C_1$-$C_6$ alkyl optionally substituted with one or more substituents selected from Ra, 5- to 10-membered heteroaryl optionally substituted with one or more substituents selected from Rg, $C_1$-$C_6$ alkylsulfonyl optionally substituted with one or more halogen atoms, $C_3$-$C_{10}$ cycloalkylsulfonyl optionally substituted with one or more substituents selected from Rg, ($C_6$-$C_{10}$ aryl)sulfonyl optionally substituted with one or more substituents selected from Rh, $C_7$-$C_{14}$ aralkylsulfonyl, (3- to 12-membered non-aromatic heterocyclyl)sulfonyl optionally substituted with one or more substituents selected from Rg, 5- to 10-membered heteroarylcarbonyl optionally substituted with one or more substituents selected from Rg, 5- to 10-membered heteroarylsulfonyl optionally substituted with one or more substituents selected from Rg, aminosulfonyl, $C_1$-$C_6$ alkylaminosulfonyl, di($C_1$-$C_6$ alkyl)aminosulfonyl, di($C_1$-$C_6$ alkyl)phosphono, and oxo;

Rd is independently selected from the group consisting of a halogen atom, hydroxy, cyano, carboxy, —NR$^{21}$R$^{22}$, —CONR$^{23}$R$^{24}$, $C_1$-$C_6$ alkyl optionally substituted with one or more substituents selected from Ra, ($C_1$-$C_6$ alkoxy)$C_1$-$C_6$ alkyl optionally substituted with one or more substituents selected from Ra, ($C_1$-$C_6$ alkyl)carbonyl optionally substituted with one or more substituents selected from Ra, ($C_1$-$C_6$ alkoxy)carbonyl, ($C_6$-$C_{10}$ aryl)carbonyl optionally substituted with one or more substituents selected from Rh, ($C_3$-$C_{10}$ cycloalkyl)carbonyl optionally substituted with one or more substituents selected from Rg, (3- to 12-membered non-aromatic heterocyclyl)carbonyl optionally substituted with one or more substituents selected from Rg, $C_3$-$C_{10}$ cycloalkyl optionally substituted with one or more substituents selected from Rg, 3- to 12-membered non-aromatic heterocyclyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl)aminocarbonyl optionally substituted with one or more substituents selected from Ra, [($C_1$-$C_6$ alkyl)aminocarbonyl]$C_1$-$C_6$ alkyl optionally substituted with one or more substituents selected from Ra, [di($C_1$-$C_6$ alkyl)aminocarbonyl]$C_1$-$C_6$ alkyl optionally substituted with one or more substituents selected from Ra, 5- to 10-membered heteroaryl optionally substituted with one or more substituents selected from Rg, $C_1$-$C_6$ alkylsulfonyl optionally substituted with one or more halogen atoms, $C_3$-$C_{10}$ cycloalkylsulfonyl optionally substituted with one or more substituents selected from Rg, ($C_6$-$C_{10}$ aryl)sulfonyl optionally substituted with one or more substituents selected from Rh, $C_7$-$C_{14}$ aralkylsulfonyl, (3- to 12-membered non-aromatic heterocyclyl)sulfonyl optionally substituted with one or more substituents selected from Rg, 5- to 10-membered heteroarylsulfonyl optionally substituted with one or more substituents selected from Rg, aminosulfonyl, $C_1$-$C_6$ alkylaminosulfonyl, di($C_1$-$C_6$ alkyl)aminosulfonyl, and di($C_1$-$C_6$ alkyl)phosphono;

Rg is independently selected from the group consisting of nitro, hydroxy, $C_1$-$C_6$ alkyl optionally substituted with one or more halogen atoms, $C_1$-$C_6$ alkoxy optionally substituted with one or more halogen atoms, a halogen atom, amino, cyano, $C_1$-$C_6$ alkylamino optionally substituted with one or more hydroxy groups, di($C_1$-$C_6$ alkyl)amino optionally substituted with one or more hydroxy groups, $C_3$-$C_{10}$ cycloalkylamino, ($C_1$-$C_6$ alkyl)carbonyl, ($C_1$-$C_6$ alkoxy)carbonyl, $C_1$-$C_6$ alkylsulfonyl, $C_3$-$C_{10}$ cycloalkylsulfonyl, $C_7$-$C_{14}$ aralkyl optionally substituted with one or more substituents selected from Ri, $C_6$-$C_{10}$ aryl optionally substituted with one or more substituents selected from Ri, $C_3$-$C_{10}$ cycloalkyl optionally substituted with one or more substituents selected from Ri, 3- to 12-membered non-aromatic heterocyclyl optionally substituted with one or more substituents selected from Ri, 5- to 10-membered heteroaryl optionally substituted with one or more substituents selected from Ri, and oxo;

Rh is independently selected from the group consisting of nitro, hydroxy, $C_1$-$C_6$ alkyl optionally substituted with one or more halogen atoms, $C_1$-$C_6$ alkoxy optionally substituted with one or more halogen atoms, a halogen atom, amino, cyano, $C_1$-$C_6$ alkylamino, di($C_1$-$C_6$ alkyl)amino, $C_1$-$C_6$ alkylcarbonyl, ($C_1$-$C_6$ alkoxy)carbonyl, ($C_1$-$C_6$ alkoxy)carbonylamino, N—($C_1$-$C_6$ alkoxy)carbonyl-N—($C_1$-$C_6$ alkyl)amino, $C_1$-$C_6$ alkylsulfonyl, $C_3$-$C_8$ cycloalkylsulfonyl, $C_7$-$C_{14}$ aralkyl optionally substituted with one or more substituents selected from Ri, $C_6$-$C_{10}$ aryl optionally substituted with one or more substituents selected from Ri, $C_3$-$C_8$ cycloalkyl optionally substituted with one or more substituents selected from Ri, 3- to 12-membered non-aromatic heterocyclyl optionally substituted with one or more substituents selected from Ri, and 5- to 10-membered heteroaryl optionally substituted with one or more substituents selected from Ri;

Ri is independently selected from the group consisting of nitro, hydroxy, $C_1$-$C_6$ alkyl optionally substituted with one or more substituents selected from a halogen atom and hydroxy, a halogen atom, amino, cyano, $C_1$-$C_6$ alkylamino, di($C_1$-$C_6$ alkyl)amino, $C_1$-$C_6$ alkylcarbonyl optionally substituted with one or more substituents selected from phenyl and hydroxy, ($C_1$-$C_6$ alkoxy)carbonyl optionally substituted with one or more substituents selected from phenyl and hydroxy, $C_1$-$C_6$ alkylsulfonyl, $C_3$-$C_8$ cycloalkylsulfonyl, $C_1$-$C_6$ alkylsulfonylamino, $C_3$-$C_8$ cycloalkylsulfonylamino, and oxo;

R$^{21}$ is selected from the group consisting of a hydrogen atom, $C_1$-$C_6$ alkyl optionally substituted with one or more substituents selected from Ra, $C_6$-$C_{10}$ aryl optionally substituted with one or more substituents selected from Rh, 4- to 12-membered heterocyclyl optionally substituted with one or more substituents selected from Rg, 5- to 10-membered heteroaryl optionally substituted with one or more substituents selected from Rg, ($C_1$-$C_6$ alkoxy)carbonyl optionally substituted with one or more substituents selected from Ra, ($C_1$-$C_6$ alkyl)carbonyl optionally substituted with one or more substituents selected from Ra, ($C_3$-$C_{10}$ cycloalkyl)carbonyl, ($C_6$-$C_{10}$ aryl)carbonyl optionally substituted with one or more substituents selected from Rh, (3- to 12-membered non-aromatic heterocyclyl)carbonyl optionally substituted with one or more substituents selected from Rg, (5- to 10-membered heteroaryl) carbonyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl) aminocarbonyl optionally substituted with one or more substituents selected from Ra, $C_1$-$C_6$ alkylsulfonyl optionally substituted with one or more halogen atoms, $C_7$-$C_{14}$ aralkylsulfonyl, $C_3$-$C_{10}$ cycloalkylsulfonyl, aminosulfonyl, $C_1$-$C_6$ alkylaminosulfonyl, di($C_1$-$C_6$ alkyl)aminosulfonyl, and di($C_1$-$C_6$ alkyl)phosphono;

$R^{22}$ is selected from the group consisting of a hydrogen atom, and $C_1$-$C_6$ alkyl optionally substituted with one or more substituents selected from Ra;

$R^{23}$ is selected from the group consisting of a hydrogen atom, $C_1$-$C_6$ alkyl optionally substituted with one or more substituents selected from Ra, [($C_1$-$C_6$ alkyl)amino]$C_1$-$C_6$ alkyl optionally substituted with one or more substituents selected from Ra, [di($C_1$-$C_6$ alkyl)amino]$C_1$-$C_6$ alkyl optionally substituted with one or more substituents selected from Ra, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

$R^{24}$ is selected from the group consisting of a hydrogen atom, and $C_1$-$C_6$ alkyl optionally substituted with one or more substituents selected from Ra;

$R^{25}$ is selected from the group consisting of $C_1$-$C_6$ alkyl optionally substituted with one or more substituents selected from Ra, $C_3$-$C_{10}$ cycloalkyl optionally substituted with one or more substituents selected from Re, $C_6$-$C_{10}$ aryl optionally substituted with one or more substituents selected from Rd, 4- to 12-membered heterocyclyl optionally substituted with one or more substituents selected from Re, and 5- to 10-membered heteroaryl optionally substituted with one or more substituents selected from Rf;

$R^7$ is selected from the group consisting of a hydrogen atom, a halogen atom, $C_1$-$C_6$ alkyl, and $C_1$-$C_6$ alkoxy;

$R^8$ is selected from the group consisting of a hydrogen atom, a halogen atom, $C_1$-$C_6$ alkyl, and $C_1$-$C_6$ alkoxy; and wherein a sulfer atom included in heterocyclyl or heteroaryl may be oxidized to be SO or $SO_2$.

(2) A compound or a pharmaceutically acceptable salt thereof according to (1): wherein $R^1$ is selected from the group consisting of a halogen atom, hydroxy, $C_1$-$C_6$ alkyl, and $C_1$-$C_6$ alkoxy, wherein the alkyl and the alkoxy may be substituted with one or more substituents selected from $A^1$;

$R^2$ is selected from the group consisting of a hydrogen atom, a halogen atom, hydroxy, $C_1$-$C_6$ alkyl, $C_1$-$C_6$ alkoxy, and $C_3$-$C_{10}$ cycloalkoxy, wherein the alkyl and the alkoxy may be substituted with one or more substituents selected from $A^2$;

$R^3$ is independently selected from the group consisting of a halogen atom, cyano, nitro, hydroxy, carboxy, $C_1$-$C_6$ alkyl, $C_1$-$C_6$ alkoxy, ($C_1$-$C_6$ alkoxy)carbonyl, $C_1$-$C_6$ alkylthio, $C_1$-$C_6$ alkylsulfinyl, and $C_1$-$C_6$ alkylsulfonyl;

n is an integer selected from 0 to 3;

$X^1$ is N, or $CR^4$;

$X^2$ is N, or $CR^6$;

$R^4$ is selected from the group consisting of a hydrogen atom, a halogen atom, $C_1$-$C_6$ alkyl, and $C_1$-$C_6$ alkoxy;

$R^1$ and $R^6$ are independently selected from the group consisting of a hydrogen atom, a halogen atom, and Y, wherein at least one of $R^1$ and $R^6$ is Y;

Y is independently selected from the group consisting of hydroxy, $C_1$-$C_6$ alkyl optionally substituted with one or more substituents selected from $A^3$, $C_1$-$C_6$ alkoxy optionally substituted with one or more substituents selected from $A^3$, —$N^{11}R^{12}$, —$CONR^{13}R^{14}$, $C_3$-$C_{10}$ cycloalkyl optionally substituted with one or more substituents selected from Rc, $C_6$-$C_{10}$ aryl optionally substituted with one or more substituents selected from Rd, 3- to 12-membered non-aromatic heterocyclyl optionally substituted with one or more substituents selected from Re, 5- to 10-membered heteroaryl optionally substituted with one or more substituents selected from Rf, and —$OR^{15}$;

$R^{11}$ is selected from the group consisting of a hydrogen atom, $C_1$-$C_6$ alkyl optionally substituted with one or more substituents selected from Ra, $C_3$-$C_{10}$ cycloalkyl optionally substituted with one or more substituents selected from Rb, $C_6$-$C_{10}$ aryl optionally substituted with one or more substituents selected from Rb, 5- to 10-membered heteroaryl optionally substituted with one or more substituents selected from Rb, 3- to 12-membered non-aromatic heterocyclyl optionally substituted with one or more substituents selected from Rb, ($C_1$-$C_6$ alkoxy)carbonyl optionally substituted with one or more substituents selected from Ra, ($C_1$-$C_6$ alkyl)carbonyl optionally substituted with one or more substituents selected from Ra, ($C_3$-$C_{10}$ cycloalkyl)carbonyl optionally substituted with one or more substituents selected from Rg, ($C_6$-$C_{10}$ aryl)carbonyl optionally substituted with one or more substituents selected from Rh, (3- to 12-membered non-aromatic heterocyclyl)carbonyl optionally substituted with one or more substituents selected from Rg, (5- to 10-membered heteroaryl)carbonyl optionally substituted with one or more substituents selected from Rg, aminocarbonyl, ($C_1$-$C_6$ alkyl)aminocarbonyl, and di($C_1$-$C_6$ alkyl)aminocarbonyl;

$R^{12}$ is selected from the group consisting of a hydrogen atom, and $C_1$-$C_6$ alkyl optionally substituted with one or more substituents selected from Ra;

$R^{13}$ is selected from the group consisting of a hydrogen atom, $C_1$-$C_6$ alkyl optionally substituted with one or more substituents selected from Ra, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

$R^{14}$ is selected from the group consisting of a hydrogen atom, and $C_1$-$C_6$ alkyl optionally substituted with one or more substituents selected from Ra;

$R^{15}$ is selected from the group consisting of $C_3$-$C_{10}$ cycloalkyl optionally substituted with one or more substituents selected from Rc, $C_6$-$C_{10}$ aryl optionally substituted with one or more substituents selected from Rd, 3- to 12-membered non-aromatic heterocyclyl optionally substituted with one or more substituents selected from Re, and 5- to 10-membered heteroaryl optionally substituted with one or more substituents selected from Rf;

$A^1$ is independently selected from the group consisting of a halogen atom and cyano;

$A^2$ is independently selected from the group consisting of a halogen atom, cyano, amino, $C_1$-$C_6$ alkylamino, di($C_1$-$C_6$ alkyl)amino, $C_1$-$C_6$ alkylthio, $C_1$-$C_6$ alkylsulfinyl, $C_1$-$C_6$ alkylsulfonyl $C_3$-$C_{10}$ cycloalkyl, and $C_1$-$C_6$ alkoxy;

$A^3$ independently is selected from the group consisting of a halogen atom, cyano, amino, $C_1$-$C_6$ alkylamino, di($C_1$-$C_6$ alkyl)amino, $C_1$-$C_6$ alkylthio, $C_1$-$C_6$ alkylsulfinyl, $C_1$-$C_6$ alkylsulfonyl, $C_3$-$C_{10}$ cycloalkylsulfonyl, $C_3$-$C_{10}$ cycloalkyl, and $C_1$-$C_6$ alkoxy;

Ra is independently selected from the group consisting of a halogen atom, hydroxy, $C_1$-$C_6$ alkoxy, cyano, ($C_1$-$C_6$ alkoxy)carbonyl, carboxy, ($C_1$-$C_6$ alkoxy)carbonylamino, ($C_1$-$C_6$ alkyl)carbonylamino, amino, $C_1$-$C_6$ alkylamino, di($C_1$-$C_6$ alkyl)amino, aminocarbonyl, ($C_1$-$C_6$ alkyl)aminocarbonyl, di($C_1$-$C_6$ alkyl)aminocarbonyl, $C_1$-$C_6$ alkylsulfonylamino, $C_3$-$C_{10}$ cycloalkylsulfonylamino, di($C_1$-$C_6$ alkyl)phosphono, $C_7$-$C_{14}$ aralkyl, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

Rb is independently selected from the group consisting of a halogen atom, hydroxy, $C_1$-$C_6$ alkyl optionally substituted with one or more substitutents selected from Ra, $C_1$-$C_6$ alkoxy optionally substituted with one or more substitutents selected from Ra, cyano, ($C_1$-$C_6$ alkoxy)carbonyl, carboxy, —$NR^{21}R^{22}$, —$CONR^{23}R^{24}$, di($C_1$-$C_6$ alkyl)phosphono, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

Rc, Re and Rf are independently selected from the group consisting of a halogen atom, hydroxy, cyano, carboxy, —$NR^{21}R^{22}$, —$CONR^{23}R^{24}$, $C_1$-$C_6$ alkyl optionally substituted with one or more substituents selected from Ra, ($C_1$-$C_6$ alkoxy)$C_1$-$C_6$ alkyl optionally substituted with one or more substituents selected from Ra, ($C_1$-$C_6$ alkyl)carbonyl optionally substituted with one or more substituents selected from Ra, ($C_1$-$C_6$ alkoxy)carbonyl, ($C_6$-$C_{10}$ aryl)carbonyl optionally substituted with one or more substituents selected from Rh, ($C_3$-$C_{10}$ cycloalkyl)carbonyl optionally substituted with one or more substituents selected from Rg, (3- to 12-membered non-aromatic heterocyclyl)carbonyl optionally substituted with one or more substituents selected from Rg, $C_3$-$C_{10}$ cycloalkyl optionally substituted with one or more substituents selected from Rg, 3- to 12-membered non-aromatic heterocyclyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl)aminocarbonyl optionally substituted with one or more substituents selected from Ra, [($C_1$-$C_6$ alkyl)aminocarbonyl]$C_1$-$C_6$ alkyl optionally substituted with one or more substituents selected from Ra, [di($C_1$-$C_6$ alkyl)aminocarbonyl]$C_1$-$C_6$ alkyl optionally substituted with one or more substituents selected from Ra, 5- to 10-membered heteroaryl optionally substituted with one or more substituents selected from Rg, $C_1$-$C_6$ alkylsulfonyl optionally substituted with one or more halogen atoms, $C_3$-$C_{10}$ cycloalkylsulfonyl optionally substituted with one or more substituents selected from Rg, ($C_6$-$C_{10}$ aryl)sulfonyl optionally substituted with one or more substituents selected from Rh, $C_7$-$C_{14}$ aralkylsulfonyl, (3- to 12-membered non-aromatic heterocyclyl)sulfonyl optionally substituted with one or more substituents selected from Rg, 5- to 10-membered heteroarylsulfonyl optionally substituted with one or more substituents selected from Rg, aminosulfonyl, $C_1$-$C_6$ alkylaminosulfonyl, di($C_1$-$C_6$ alkyl)aminosulfonyl, di($C_1$-$C_6$ alkyl)phosphono, and oxo;

Rd is independently selected from the group consisting of a halogen atom, hydroxy, cyano, carboxy, —$NR^{21}R^{22}$, —$CONR^{23}R^{24}$, $C_1$-$C_6$ alkyl optionally substituted with one or more substituents selected from Ra, ($C_1$-$C_6$ alkoxy)$C_1$-$C_6$ alkyl optionally substituted with one or more substituents selected from Ra, ($C_1$-$C_6$ alkyl)carbonyl optionally substituted with one or more substituents selected from Ra, ($C_1$-$C_6$ alkoxy)carbonyl, ($C_6$-$C_{10}$ aryl)carbonyl optionally substituted with one or more substituents selected from Rh, ($C_3$-$C_{10}$ cycloalkyl)carbonyl optionally substituted with one or more substituents selected from Rg, (3- to 12-membered non-aromatic heterocyclyl)carbonyl optionally substituted with one or more substituents selected from Rg, $C_3$-$C_{10}$ cycloalkyl optionally substituted with one or more substituents selected from Rg, 3- to 12-membered non-aromatic heterocyclyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl)aminocarbonyl optionally substituted with one or more substituents selected from Ra, [($C_1$-$C_6$ alkyl)aminocarbonyl]$C_1$-$C_6$ alkyl optionally substituted with one or more substituents selected from Ra, [di($C_1$-$C_6$ alkyl)aminocarbonyl]$C_1$-$C_6$ alkyl optionally substituted with one or more substituents selected from Ra, 5- to 10-membered heteroaryl optionally substituted with one or more substituents selected from Rg, $C_1$-$C_6$ alkylsulfonyl optionally substituted with one or more halogen atoms, $C_3$-$C_{10}$ cycloalkylsulfonyl optionally substituted with one or more substituents selected from Rg, ($C_6$-$C_{10}$ aryl)sulfonyl optionally substituted with one or more substituents selected from Rh, $C_7$-$C_{14}$ aralkylsulfonyl, (3- to 12-membered non-aromatic heterocyclyl)sulfonyl optionally substituted with one or more substituents selected from Rg, 5- to 10-membered heteroarylsulfonyl optionally substituted with one or more substituents selected from Rg, aminosulfonyl, $C_1$-$C_6$ alkylaminosulfonyl, di($C_1$-$C_6$ alkyl)aminosulfonyl, and di($C_1$-$C_6$ alkyl)phosphono;

Rg is independently selected from the group consisting of nitro, hydroxy, $C_1$-$C_6$ alkyl optionally substituted with one or more halogen atoms, a halogen atom, amino, cyano, $C_1$-$C_6$ alkylamino, di($C_1$-$C_6$ alkyl)amino, ($C_1$-$C_6$ alkyl)carbonyl, ($C_1$-$C_6$ alkoxy)carbonyl, $C_1$-$C_6$ alkylsulfonyl, $C_3$-$C_{10}$ cycloalkylsulfonyl, $C_7$-$C_{14}$ aralkyl optionally substituted with one or more substituents selected from Ri, $C_6$-$C_{10}$ aryl optionally substituted with one or more substituents selected from Ri, $C_3$-$C_{10}$ cycloalkyl optionally substituted with one or more substituents selected from Ri, 3- to 12-membered non-aromatic heterocyclyl optionally substituted with one or more substituents selected from Ri, 5- to 10-membered heteroaryl optionally substituted with one or more substituents selected from Ri, and oxo;

Rh is independently selected from the group consisting of nitro, hydroxy, $C_1$-$C_6$ alkyl optionally substituted with one or more halogen atoms, a halogen atom, amino, cyano, $C_1$-$C_6$ alkylamino, di($C_1$-$C_6$ alkyl)amino, $C_1$-$C_6$ alkylcarbonyl, ($C_1$-$C_6$ alkoxy)carbonyl, $C_1$-$C_6$ alkylsulfonyl, $C_3$-$C_8$ cycloalkylsulfonyl, $C_7$-$C_{14}$ aralkyl optionally substituted with one or more substituents selected from Ri, $C_6$-$C_{10}$ aryl optionally substituted with one or more substituents selected from Ri, $C_3$-$C_8$ cycloalkyl optionally substituted with one or more substituents selected from Ri, 3- to 12-membered non-aromatic heterocyclyl optionally substituted with one or more substituents selected from Ri, and 5- to 10-membered heteroaryl optionally substituted with one or more substituents selected from Ri;

Ri is independently selected from the group consisting of nitro, hydroxy, $C_1$-$C_6$ alkyl optionally substituted with one or more halogen atoms, a halogen atom, amino, cyano, $C_1$-$C_6$ alkylamino, di($C_1$-$C_6$ alkyl)amino, $C_1$-$C_6$ alkylcarbonyl, ($C_1$-$C_6$ alkoxy)carbonyl, $C_1$-$C_6$ alkylsulfonyl, and $C_3$-$C_8$ cycloalkylsulfonyl;

$R^{21}$ is selected from the group consisting of a hydrogen atom, $C_1$-$C_6$ alkyl optionally substituted with one or more substituents selected from Ra, $C_6$-$C_{10}$ aryl optionally substituted with one or more substituents selected from Rh, 3- to 12-membered non-aromatic heterocyclyl optionally substituted with one or more substituents selected from Rg, 5- to 10-membered heteroaryl optionally substituted with one or more substituents selected from Rg, ($C_1$-$C_6$ alkoxy)carbonyl optionally substituted with one or more substituents selected from Ra, ($C_1$-$C_6$ alkyl)carbonyl optionally substituted with one or more substituents selected from Ra, ($C_3$-$C_{10}$ cycloalkyl)carbonyl, ($C_6$-$C_{10}$ aryl)carbonyl optionally substituted with one or more substituents selected from Rh, (3- to 12-membered non-aromatic heterocyclyl)carbonyl optionally substituted with one or more substituents selected from Rg, (5- to 10-membered heteroaryl)carbonyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl)aminocarbonyl optionally substituted with one or more substituents selected from Ra, $C_1$-$C_6$ alkylsulfonyl optionally substituted with one or more halogen atoms, $C_7$-$C_{14}$ aralkylsulfonyl, $C_3$-$C_{10}$ cycloalkylsulfonyl, aminosulfonyl, $C_1$-$C_6$ alkylaminosulfonyl, di($C_1$-$C_6$ alkyl)aminosulfonyl, and di($C_1$-$C_6$ alkyl) phosphono;

$R^{22}$ is selected from the group consisting of a hydrogen atom, and $C_1$-$C_6$ alkyl optionally substituted with one or more substituents selected from Ra;

$R^{23}$ is selected from the group consisting of a hydrogen atom, $C_1$-$C_6$ alkyl optionally substituted with one or more substituents selected from Ra, [($C_1$-$C_6$ alkyl)amino]$C_1$-$C_6$ alkyl optionally substituted with one or more substituents selected from Ra, [di($C_1$-$C_6$ alkyl)amino]$C_1$-$C_6$ alkyl optionally substituted with one or more substituents selected from Ra, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

$R^{24}$ is selected from the group consisting of a hydrogen atom, and $C_1$-$C_6$ alkyl optionally substituted with one or more substituents selected from Ra;

$R^7$ is selected from the group consisting of a hydrogen atom, a halogen atom, $C_1$-$C_6$ alkyl, and $C_1$-$C_6$ alkoxy;

$R^8$ is selected from the group consisting of a hydrogen atom, a halogen atom, $C_1$-$C_6$ alkyl, and $C_1$-$C_6$ alkoxy; and wherein a sulfer atom included in heterocyclyl or heteroaryl may be oxidized to be SO or $SO_2$.

(3) The compound or a pharmaceutically acceptable salt thereof according to (1) or (2), wherein the compound is represented by Formula (Ia):

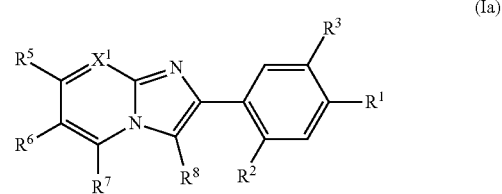

(Ia)

wherein $R^1$, $R^2$, $R^3$, $R^5$, $R^6$, $R^7$, $R^8$ and $X^1$ are as defined in (1) or (2).

(4) The compound or a pharmaceutically acceptable salt thereof according to (1) or (2), wherein the compound is represented by Formula (Ia):

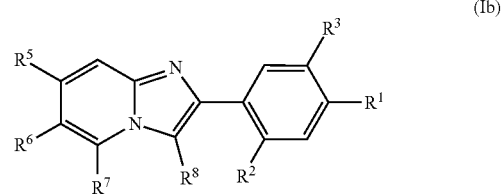

(Ib)

wherein $R^1$, $R^2$, $R^3$, $R^5$, $R^6$, $R^7$, and $R^8$ are as defined in (1) or (2).

(5) The compound or a pharmaceutically acceptable salt thereof according to any one of (1) to (4), wherein $R^1$ is methoxy.

(6) The compound or a pharmaceutically acceptable salt thereof according to any one of (1) to (5), wherein $R^7$ and $R^8$ are hydrogen atoms.

(7) The compound or a pharmaceutically acceptable salt thereof according to any one of (1) to (6), wherein $R^3$ is a halogen atom.

(8) The compound or a pharmaceutically acceptable salt thereof according to any one of (1) to (7), wherein $R^2$ is methoxy.

(9) The compound or a pharmaceutically acceptable salt thereof according to any one of (1) to (8), wherein $R^5$ is Y and $R^6$ is a hydrogen atom.

(10) The compound or a pharmaceutically acceptable salt thereof according to any one of (1) to (9), wherein Y is independently selected from the group consisting of —NR¹¹R¹², C₃-C₁₀ cycloalkyl optionally substituted with one or more substituents selected from Rc, C₆-C₁₀ aryl optionally substituted with one or more substituents selected from Rd, 3- to 12-membered non-aromatic heterocyclyl optionally substituted with one or more substituents selected from Re, and 5- to 10-membered heteroaryl optionally substituted with one or more substituents selected from Rf

(11) The compound or a pharmaceutically acceptable salt thereof according to any one of (1) to (10), wherein Y is selected from the group consisting of:
  piperazin-1-yl substituted with one or more substituents selected from Re;
  pyrrolidin-1-yl substituted with one or more substituents selected from Re;
  1,4-diazepan-1-yl substituted with one or more substituents selected from Re;
  8-azabicyclo[3.2.1]octan-3-ylamino wherein the 8-azabicyclo[3.2.1]octan-3-yl moiety is substituted with one or more substituents selected from Rb;
  piperidine-4-ylamino wherein the piperidine-4-yl moiety is substituted with one or more substituents selected from Rb; and
  cyclohexylamino wherein the cyclohexyl moiety is substituted with one or more substituents selected from Rb.

(12) The compound or a pharmaceutically acceptable salt thereof according to any one of (1) to (11), wherein Y is selected from the group consisting of:
  piperazin-1-yl substituted at 4-position with 5- to 10-membered heteroaryl optionally substituted with one or more substituents selected from Rg;
  1,4-diazepan-1-yl substituted at 4-position with methyl substituted with a substituent selected from Ra;
  pyrrolidin-1-yl substituted at 3-position with a group —NHR²¹, wherein R²¹ is methyl substituted with a substituent selected from Ra;
  8-azabicyclo[3.2.1]octan-3-ylamino wherein the 8-azabicyclo[3.2.1]octan-3-yl moiety is substituted at 8-position with methyl substituted with a substituent selected from Ra,
  piperidine-4-ylamino wherein the piperidine-4-yl moiety is substituted at 1-position with methyl substituted with a substituent selected from Ra, and
  cyclohexylamino wherein the cyclohexyl moiety is substituted at 4-position with a group —NHR²¹, wherein R²¹ is methyl substituted with a substituent selected from Ra.

(13) The compound or a pharmaceutically acceptable salt thereof according to any one of (1) to (12), wherein Y is selected from the group consisting of:
  piperazin-1-yl substituted with one or more substituents selected from Re,
  pyrrolidin-1-yl substituted with one or more substituents selected from Re, and
  cyclohexylamino wherein the cyclohexyl moiety is substituted with one or more substituents selected from Rb.

(14) The compound or a pharmaceutically acceptable salt thereof according to any one of (1) to (13), wherein Y is selected from the group consisting of:
  piperazin-1-yl substituted at 4-position with 5- to 10-membered heteroaryl optionally substituted with one or more substituents selected from Rg;
  pyrrolidin-1-yl substituted at 3-position with a group —NHR²¹, wherein R²¹ is methyl substituted with a substituent selected from Ra; and
  cyclohexylamino wherein the cyclohexyl moiety is substituted at 4-position with 5- to 10-membered heteroarylamino wherein the heteroaryl moiety may be substituted with one or more substituents selected from Rg.

(15) The compound or a pharmaceutically acceptable salt thereof according to (1), which is selected from the group consisting of:
2-(5-bromo-2,4-dimethoxyphenyl)-N-methylimidazo[1,2-a]pyridin-7-amine;
2-(5-chloro-2,4-dimethoxyphenyl)-7-(4-(cyclopropylsulfonyl)piperazin-1-yl)imidazo-[1,2-a]pyridine;
N-(1-(2-(5-chloro-2,4-dimethoxyphenyl)imidazo[1,2-a]pyridine-7-yl)piperidin-4-yl)-methanesulfonamide;
2-(5-chloro-2,4-dimethoxyphenyl)-7-(4-(cyclopropylsulfonyl)piperazin-1-yl)imidazo-[1,2-a]pyrimidine;
tert-butyl (1-(2-(5-chloro-2-(3-(dimethylamino)propoxy)-4-methoxyphenyl)imidazo-[1,2-a]pyridine-7-yl)piperidin-4-yl)carbamate;
1-(2-(5-chloro-2-(3-(dimethylamino)propoxy)-4-methoxyphenyl)imidazo[1,2-a]-pyridine-7-yl)piperidin-4-amine;
4-(2-(5-chloro-2,4-dimethoxyphenyl)imidazo[1,2-a]pyridine-7-yl)-N,N-dimethyl-piperazine-1-sulfonamide;
N-(1-(2-(5-chloro-2,4-dimethoxyphenyl)imidazo[1,2-a]pyridine-7-yl)piperidin-4-yl)ethanesulfonamide;
N-(1-(2-(5-chloro-2,4-dimethoxyphenyl)imidazo[1,2-a]pyridine-7-yl)piperidin-4-yl)-1,1,1-trifluoromethanesulfonamide;
2-(5-chloro-2,4-dimethoxyphenyl)-7-(4-(isopropylsulfonyl)piperazin-1-yl)imidazo-[1,2-a]pyridine;
7-(4-(N,N-dimethylaminosulfonylamino)piperidin-1-yl)-2-(5-chloro-2,4-dimethoxyphenyl)imidazo[1,2-a]pyridine;
dimethyl (4-(2-(5-chloro-2,4-dimethoxyphenyl)imidazo[1,2-a]pyridine-7-yl)-5,6-dihydropyridin-1(2H)-yl)phosphonate;
2-(5-chloro-2,4-dimethoxyphenyl)-7-(4-(cyclopentylsulfonyl)piperazin-1-yl)imidazo[1,2-a]pyrimidine;
2-(5-chloro-2,4-dimethoxyphenyl)-7-(4-(isopropylsulfonyl)piperazin-1-yl)imidazo[1,2-a]pyrimidine;
tert-butyl 4-(2-(5-chloro-2-(3-(dimethylamino)propoxy)-4-methoxyphenyl)-imidazo[1,2-a]pyridine-7-yl)-1,4-diazepane-1-carboxylate;
2-(5-chloro-2-methoxy-4-methylphenyl)-7-(4-(cyclopropylsulfonyl)piperazin-1-yl)-imidazo[1,2-a]pyridine;
tert-butyl 4-(2-(5-chloro-2,4-dimethoxyphenyl)imidazo[1,2-a]pyridine-7-yl)piperazine-1-carboxylate;
2-(5-chloro-2-ethyl-4-methoxyphenyl)-7-(4-(cyclopropylsulfonyl)piperazin-1-yl)-imidazo[1,2-a]pyridine
(S)—N-(2-(5-chloro-2,4-dimethoxyphenyl)imidazo[1,2-a]pyridine-7-yl)-1-methylpyrrolidine-2-carboxamide
tert-butyl (2-((2-(4-(2-(5-chloro-2,4-dimethoxyphenyl)imidazo[1,2-a]pyridin-7-yl)benzamido)ethyl)amino)ethyl)carbamate;
N-((1H-imidazol-2-yl)methyl)-4-(2-(5-chloro-2,4-dimethoxyphenyl)imidazo-[1,2-a]pyridin-7-yl)aniline;
(S)—N-(2-(5-chloro-2,4-dimethoxyphenyl)imidazo[1,2-a]pyridin-7-yl)-2-(dimethylamino)-3-methylbutanamide;
N-(4-(2-(5-chloro-2,4-dimethoxyphenyl)imidazo[1,2-a]pyridin-7-yl)phenyl)-2-(methylamino)acetamide;
(S)-2-amino-1-(4-(2-(5-chloro-2,4-dimethoxyphenyl)imidazo[1,2-a]pyridin-7-yl)phenyl)propan-1-one;
tert-butyl 4-(2-(5-chloro-2,4-dimethoxyphenyl)imidazo[1,2-a]pyridin-7-yl)-2-methylpiperazine-1-carboxylate;
2-(5-chloro-2,4-dimethoxyphenyl)-7-(4-(pyridin-2-yl)piperazin-1-yl)imidazo-[1,2-a]pyridine;
methyl (4-((2-(5-chloro-2,4-dimethoxyphenyl)imidazo[1,2-a]pyridin-7-yl)-trans-amino)cyclohexyl)carbamate;

trans-N-(4-((4-benzylpiperazin-1-yl)methyl)cyclohexyl)-2-(5-chloro-2,4-dimethoxy-phenyl)imidazo[1,2-a]pyridin-7-amine trifluoroacetate,
4-(4-(2-(5-chloro-2,4-dimethoxyphenyl)imidazo[1,2-a]pyridin-7-yl)piperazin-1-yl)pyrimidin-2-amine;
2-(5-chloro-2,4-dimethoxyphenyl)-7-((1-(thiophen-2-ylsulfonyl)piperidin-4-yl)oxy)imidazo[1,2-a]pyridine;
2-(5-chloro-2,4-dimethoxyphenyl)-7-(4-(6-fluoropyridin-2-yl)piperazin-1-yl)imidazo[1,2-a]pyridine,
2-(5-chloro-2,4-dimethoxyphenyl)-7-(4-phenylpiperazin-1-yl)imidazo-[1,2-a]pyridine;
2-(4-(2-(5-chloro-2,4-dimethoxyphenyl)imidazo[1,2-a]pyridin-7-yl)piperazin-1-yl)nicotinonitrile;
4-(4-((2-(5-chloro-2,4-dimethoxyphenyl)imidazo[1,2-a]pyridin-7-yl)oxy)piperidin-1-yl)pyrimidin-2-amine;
2-(5-chloro-2,4-dimethoxyphenyl)-7-(4-(pyrazin-2-yl)piperazin-1-yl)imidazo-[1,2-a]pyridine;
2-(4-(2-(5-chloro-2,4-dimethoxyphenyl)imidazo[1,2-a]pyridin-7-yl)piperazin-1-yl)pyrimidin-4-amine;
$N^1$-(2-(5-chloro-2,4-dimethoxyphenyl)imidazo[1,2-a]pyridin-7-yl)-$N^4$-(pyridin-2-yl)-trans-cyclohexane-1,4-diazine;
2-(5-chloro-2,4-dimethoxyphenyl)-7-((1-((1-methyl-1H-imidazol-2-yl)sulfonyl)-piperidin-4-yl)oxy)imidazo[1,2-a]pyridine;
2-(5-chloro-2,4-dimethoxyphenyl)-trans-N-(4-((4-(methylsulfonyl)piperazin-1-yl)methyl)cyclohexyl)imidazo[1,2-a]pyridin-7-amine;
tert-butyl 4-(2-(5-chloro-2,4-dimethoxyphenyl)-3-iodoimidazo[1,2-a]pyridin-7-yl)piperazine-1-carboxylate;
$N^1$-benzyl-$N^4$-(2-(5-chloro-2,4-dimethoxyphenyl)imidazo[1,2-a]pyridin-7-yl)-trans-cyclohexane-1,4-diamine;
2-(5-chloro-2,4-dimethoxyphenyl)-7-(4-(pyridin-4-ylmethyl)piperazin-1-yl)imidazo[1,2-a]pyridine;
6-(4-(2-(5-chloro-2,4-dimethoxyphenyl)imidazo[1,2-a]pyridin-7-yl)piperazin-1-yl)nicotinonitrile;
4-(4-(4-(2-(5-chloro-2,4-dimethoxyphenyl)imidazo[1,2-a]pyridin-7-yl)piperazin-1-yl)pyrimidin-2-yl)morpholine;
2-(5-chloro-2,4-dimethoxyphenyl)-7-(4-(2-(piperidin-1-yl)pyrimidin-4-yl)piperazin-1-yl)imidazo[1,2-a]pyridine;
2-(5-chloro-2,4-dimethoxyphenyl)-7-(4-(pyridin-3-yl)piperazin-1-yl)imidazo-[1,2-a]pyridine;
4-(4-(2-(5-chloro-2,4-dimethoxyphenyl)imidazo[1,2-a]pyridin-7-yl)piperazin-1-yl)-N,N-dimethylpyrimidin-2-amine;
(S)-1-(2-(5-chloro-2,4-dimethoxyphenyl)imidazo[1,2-a]pyridin-7-yl)-N-(pyridin-4-ylmethyl)pyrrolidin-3-amine;
(S)-1-(2-(5-chloro-2,4-dimethoxyphenyl)imidazo[1,2-a]pyridin-7-yl)-N-(pyridin-2-ylmethyl)pyrrolidin-3-amine;
(S)-1-(2-(5-chloro-2,4-dimethoxyphenyl)imidazo[1,2-a]pyridin-7-yl)-N-(pyridin-3-ylmethyl)pyrrolidin-3-amine;
(S)—N-benzyl-1-(2-(5-chloro-2,4-dimethoxy phenyl)imidazo[1,2-a]pyridin-7-yl)pyrrolidin-3-amine;
(S)-1-(2-(5-chloro-2,4-dimethoxyphenyl)imidazo[1,2-a]pyridin-7-yl)-N-(4-fluorobenzyl)pyrrolidin-3-amine;
(S)-1-(2-(5-chloro-2,4-dimethoxyphenyl)imidazo[1,2-a]pyridin-7-yl)-N-(4-(trifluoromethyl)benz)yl)pyrrolidin-3-amine;
(S)-1-(2-(5-chloro-2,4-dimethoxyphenyl)imidazo[1,2-a]pyridin-7-yl)-N-(4-nitrobenzyl)pyrrolidin-3-amine;
(S)-1-(2-(5-chloro-2,4-dimethoxyphenyl)imidazo[1,2-a]pyridin-7-yl)-N-(4-methylbenzyl)pyrrolidin-3-amine; and
a pharmaceutically acceptable salt thereof.

(16) The compound or a pharmaceutically acceptable salt thereof according to (1), which is selected from the group consisting of:

2-(4-(2-(5-chloro-2,4-dimethoxyphenyl)imidazo[1,2-a]pyridin-7-yl)piperazin-1-yl)nicotinonitrile;
(S)-1-(2-(5-chloro-2,4-dimethoxyphenyl)imidazo[1,2-a]pyridin-7-yl)-N-(pyridin-4-ylmethyl)pyrrolidin-3-amine;
2-(5-chloro-2,4-dimethoxyphenyl)-7-(4-(pyridine-4-ylmethyl)-1,4-diazepan-1-yl)imidazo[1,2-a]pyridine;
2-(5-chloro-2,4-dimethoxyphenyl)-7-(4-(4-(piperazin-1-yl)pyrimidin-2-yl)piperazin-1-yl)imidazo[1,2-a]pyridine;
1-(2-(4-(2-(5-chloro-2,4-dimethoxyphenyl)imidazo[1,2-a]pyridine-7-yl)piperazin-1-yl)pyrimidin-5-yl)piperidin-4-amine;
1-(5-(4-(2-(5-chloro-2,4-dimethoxyphenyl)imidazo[1,2-a]pyridine-7-yl)piperazin-1-yl)pyrimidin-2-yl)-N-methylpyrrolidin-3-amine;
4-(4-(2-(5-chloro-2,4-dimethoxyphenyl)imidazo[1,2-a]pyridine-7-yl)piperazin-1-yl)-6-morpholino-1,3,5-triazin-2-amine;
2-(5-chloro-2,4-dimethoxyphenyl)-N-(1-((5-nitrothiophen-3-yl)methyl)piperidin-4-yl)imidazo[1,2-a]pyridin-7-amine;
2-(5-chloro-2,4-dimethoxyphenyl)-N-((1R,3r,5S)-8-(pyridine-4-ylmethyl)-8-azabicyclo[3.2.1]octan-3-yl)imidazo[1,2-a]pyridine-7-amine;
tert-butyl 4-((((1s,4s)-4-((2-(5-chloro-2,4-dimethoxyphenyl)imidazo[1,2-a]pyridine-7-yl)amino)cyclohexyl)amino)methyl)piperidine-1-carboxylate; and a pharmaceutically acceptable salt thereof.

(17) A pharmaceutical composition comprising as an active ingredient a compound or a pharmaceutically acceptable salt thereof according to any one of (1) to (16).

(18) A pharmaceutical composition according to (17) for use in treating or preventing cancer.

(19) A pharmaceutical composition according to (18), wherein the cancer is selected from the group consisting of lung cancer, cervical cancer, bladder cancer, esophageal cancer, osteosarcoma, prostate cancer and soft tissue tumor.

(20) A method for treating or preventing a disease that involves overexpression of SUV39H2, which comprises administering an effective amount of a compound or a pharmaceutically acceptable salt thereof according to any one of (1) to (16) to a subject in need thereof.

(21) A method according to (20), wherein the disease is cancer.

(22) Use of a compound or a pharmaceutically acceptable salt thereof according to any one of (1) to (16) in the manufacture of a medicament for use in treatment or prevention of a disease that involves overexpression of SUV39H2.

DESCRIPTION OF EMBODIMENTS

An object of the present invention is to provide a compound having inhibitory activity against MELK, which is useful for treating proliferative diseases such as cancer, and a pharmaceutical composition comprising the compound. Another object of the present invention is to provide a method for treating and/or preventing a proliferative disease. A further object is to provide a process for preparing the compound.

Hereinafter, a compound represented by formula (I) will be referred to as compound (I). The same applies to the compounds represented by the other formula numbers. It must be noted that as used herein and in the appended claims, the singular forms "a", "an", and "the" include plural reference unless the context clearly dictates otherwise. Thus, for example, reference to a "group" is a reference to one or more groups, unless otherwise noted.

In the definitions of each of the groups of formulas indicated above, the "$C_1$-$C_6$ alkyl", and the $C_1$-$C_6$ alkyl portion of "$C_1$-$C_6$ alkoxy", "$C_1$-$C_6$ alkylamino", "di($C_1$-$C_6$ alkyl)amino", "($C_1$-$C_6$ alkyl)carbonyl", "$C_1$-$C_6$ alkylthio", "$C_1$-$C_6$ alkylsulfinyl", "$C_1$-$C_6$ alkylsulfonyl" and the like mean a straight-chain or branched-chain alkyl group having one to six carbon atoms. Specifically, examples of the "$C_1$-$C_6$ alkyl" and the "$C_1$-$C_6$ alkyl portion" include methyl, ethyl, propyl, isopropyl, butyl, isobutyl, sec-butyl, tert-butyl, pentyl, 1-methylbutyl, 1-ethylpropyl, 2-methylbutyl, isopentyl, tert-pentyl, 1,2-dimethylpropyl neopentyl, hexyl, 1-methylpentyl, 1-ethylbutyl, 2-methylpentyl, 3-methylpentyl, 4-methylpentyl, isohexyl, 1,1-dimethylbutyl, 1,2-dimethylbutyl, 1,3-dimethylbutyl, 1-isopropylpropyl, 1-ethyl-1-methylpropyl, 2,3-dimethylbutyl, 3,3-dimethylbutyl, 2,2-dimethylbutyl, 2-ethylbutyl, and 3-ethylbutyl, but are not limited thereto.

In this specification, the $C_1$-$C_6$ alkyl portion in each group has the same definition as the aforementioned "$C_1$-$C_6$ alkyl portion" unless otherwise noted. In a case that a group contains plural $C_1$-$C_6$ alkyl portions, the $C_1$-$C_6$ alkyl portions may be same or different.

Specific examples of "$C_1$-$C_6$ alkoxy" include methoxy, ethoxy, propoxy, isopropoxy, isobutyloxy, tert-butyloxy, butoxy, pentyloxy, and hexyloxy, but are not limited thereto.

The "$C_1$-$C_6$ alkoxycarbonyl" refers to a monovalent group represented by —C(=O)O—($C_1$-$C_6$ alkyl). Specific examples of "($C_1$-$C_6$ alkoxy)carbonyl" include methoxycarbonyl, ethoxycarbonyl, propoxycarbonyl, isopropoxycarbonyl, isobutyloxycarbonyl, tert-butoxycarbonyl, butoxycarbonyl, pentyloxycarbonyl, and hexyloxycarbonyl, but are not limited thereto.

The "($C_1$-$C_6$ alkyl)carbonyl" refers to a monovalent group represented by —C(=O)—($C_1$-$C_6$ alkyl). Specific examples of "($C_1$-$C_6$ alkyl)carbonyl" include methylcarbonyl (i.e. acetyl), ethylcarbonyl, propylcarbonyl, isopropylcarbonyl, isobutylcarbonyl, tert-butylcarbonyl, butylcarbonyl, pentylcarbonyl, and hexylcarbonyl, but are not limited thereto.

Specific examples of "$C_1$-$C_6$ alkylamino" include methylamino, ethylamino, propylamino, isopropylamino, butylamino, isobutylamino, sec-butylamino, and tert-butylamino, pentylamino, but are not limited thereto.

The alkyl portions of "di($C_1$-$C_6$ alkyl)amino" may be same or different. Specific examples of "di($C_1$-$C_6$ alkyl)amino" include dimethylamino, diethylamino, dipropylamino, diisopropylamino, dibutylamino, diisobutylamino, di(sec-butyl)amino, di(tert-butyl)amino, dipentylamino, ethyl(methyl)amino, propyl(methyl)amino, isopropyl(methyl)amino, butyl(methyl)amino, isobutyl(methyl)amino, sec-butyl(methyl)amino, tert-butyl(methyl)amino, and pentyl(methyl)amino, but are not limited thereto.

Specific examples of "a halogen atom" include a fluorine, a chlorine, a bromine, and an iodine atoms.

The term "$C_3$-$C_{10}$ cycloalkyl" refers to a saturated monocyclic hydrocarbon group having three to ten carbon atoms, and a bridged cyclic hydrocarbon group having four to ten carbon atoms which is formed when two or more saturated monocyclic hydrocarbons share two or more carbon atoms. The term "$C_3$-$C_{10}$ cycloalkyl" also encompasses a cycloalkyl group condensed with an aromatic or non-aromatic carbocyclic ring to form a bicyclic group. Specifically, examples of "$C_3$-$C_{10}$ cycloalkyl" include saturated monocyclic hydrocarbon groups such as cyclopropyl, cyclobutyl, cyclopentyl, cyclohexyl, cycloheptyl, and cyclooctyl, and bridged cyclic hydrocarbon groups such as adamantyl, but are not limited thereto.

In the definitions of each of the groups of formulas indicated above, the $C_3$-$C_{10}$ cycloalkyl portion of "$C_3$-$C_{10}$ cycloalkoxy", "($C_3$-$C_{10}$ cycloalkyl)carbonyl", "($C_3$-$C_{10}$ cycloalkyl)sulfonyl", "($C_3$-$C_{10}$ cycloalkyl)sulfonylamino" and the like mean the same as described above. Specifically, examples of "$C_3$-$C_{10}$ cycloalkoxy" include cyclopropoxy, cyclobutoxy, cyclopentoxy, cyclohexyloxy, cycloheptyloxy, and cyclooctyloxy, and bridged cyclic hydrocarbon groups such as adamantyloxy, but are not limited thereto.

The term "$C_6$-$C_{10}$ aryl" refers to an aromatic carbocyclic group having six to ten carbon atoms, and encompasses an aromatic carbocyclic group condensed with an aromatic or non-aromatic carbocyclic ring to form a bicyclic group. Specific examples include phenyl, 1-naphthyl, 2-naphthyl, and 2,3-dihydro-1H-indenyl, but are not limited thereto.

The term "$C_7$-$C_{14}$ aralkyl" refers to an alkyl group substituted with an aryl group that has 7 to 14 carbon atoms. Specific examples include benzyl, 2-phenylethyl, 1-phenylethyl, naphtha-1-ylmethyl, naphtha-2-ylmethyl, and 2,3-dihydro-1H-inden-4-ylmethyl, but are not limited thereto.

In the definitions of each of the groups of formulas indicated above, the $C_7$-$C_{14}$ aralkyl portion of "$C_7$-$C_{14}$ aralkylsulfonyl" and the like mean the same as described above. Specifically, examples of "$C_7$-$C_4$ aralkylsulfonyl" include benzylsulfonyl, but are not limited thereto.

The term "5- to 10-membered heteroaryl" refers to an aromatic heterocyclic group having one or more heteroatoms, preferably one to three heteroatoms, selected from the group consisting of a nitrogen atom, an oxygen atom, and a sulfur atom. The term "5- to 10-membered heteroaryl" encompasses an aromatic heterocyclic group condensed with an aromatic or non-aromatic carbocyclic ring or an aromatic or non-aromatic heterocyclic ring to form a bicyclic group, and also encompasses an aromatic carbocyclic group condensed with an aromatic or non-aromatic heterocyclic ring to form a bicyclic group. Specific examples include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, 1H-indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, pyridopyrimidinyl, [1,2,4] triazolo[1,5-a]pyridyl, and pyrrolo[2,3-b]pyridyl, but are not limited thereto. Particularly, thienyl, pyrrolyl, imidazolyl, isoxazolyl, pyridyl, pyrimidinyl, pyrazolyl, 1H-indazolyl, benzimidazolyl, [1,2,4]triazolo[1,5-a]pyridyl, or pyrrolo[2,3-b]pyridyl is preferred. The term "5- to 10-membered heteroarylcarbonyl" refers to a group containing a 5- to 10-membered heteroaryl group that are as defined in the foregoing.

The term "3- to 12-membered non-aromatic heterocyclyl" refers to a non-aromatic heterocyclic group having one or more heteroatoms, preferably one to three heteroatoms, selected from the group consisting of a nitrogen atom, an oxygen atom, and a sulfur atom.

The term "3- to 12-membered non-aromatic heterocyclyl" encompasses a non-aromatic heterocyclic group condensed with an aromatic or non-aromatic carbocyclic ring or an aromatic or non-aromatic heterocyclic ring to form a bicyclic group, and also encompasses a non-aromatic carbocyclic group condensed with an aromatic or non-aromatic heterocyclic ring to form a bicyclic group. Specific examples include aziridinyl, azetidinyl, pyrrolidinyl, piperidyl (including piperidino), azepanyl, 1,2,5,6-tetrahydropyridyl, 1,2,3,6-tetrahydropyridyl, imidazolidinyl, pyrazolidinyl, piperazinyl, homopiperazinyl, 1,4-diazepanyl, pyrazolinyl, oxiranyl, tetrahydrofuranyl, tetrahydro-2H-pyranyl, 5,6-dihydro-2H-pyranyl, oxazolidinyl, morpholinyl (including morpholino), tetrahydrothiophenyl, tetrahydro-2H-thiopyranyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, 2,3-dihydrobenzimidazolyl, 2,3-dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, oxetanyl, 1,2-dihydropyridyl, 1-azabicyclo[2.2.2]octan-3-yl, 2,5-azabicyclo[2.2.1]heptyl, 8-azabicyclo[3.2.1]octyl, piperidin-4-spiro-3'-pyrrolidin-1-yl, and isoindolyl, but are not limited thereto. In particular, azetidinyl, pyrrolidinyl, piperidino, piperidyl, piperazinyl, morpholino, morpholinyl, 1,2-dihydropyridyl, 1,2,5,6-tetrahydropyridyl, 1-azabicyclo[2.2.2]octan-3-yl, 2,5-azabicyclo[2.2.1]heptyl, 8-azabicyclo[3.2.1]octyl, 2,3-dihydrobenzimidazolyl, or piperidin-4-spiro-3'-pyrrolidin-1-yl is preferred.

The term "3- to 12-membered nitrogen-containing heterocyclyl" refers to an aromatic or non-aromatic heterocyclic group having one nitrogen atom and one or more additional heteroatoms, preferably one to three heteroatoms, selected from the group consisting of a nitrogen atom, an oxygen atom, and a sulfur atom. The term "3- to 12-membered nitrogen-containing heterocyclyl" encompasses a heterocyclic group condensed with an aromatic or non-aromatic carbocyclic ring or an aromatic or non-aromatic heterocyclic ring to form a bicyclic group. Specific examples include aziridinyl, azetidinyl, pyrrolyl, pyrrolidinyl, piperidyl (including piperidino), azepanyl, imidazolyl, pyrazolyl, triazolyl, tetrazolyl, piperazinyl, and morpholinyl.

Pharmaceutically acceptable salts of compound (I) mean, for example, pharmaceutically acceptable acid-added salts, amino acid-added salts, or such. Specific examples of the pharmaceutically acceptable acid-added salts of compound (I) include inorganic acid salts such as hydrochloride, sulfate, and phosphate, organic acid salts such as acetate, maleate, fumarate, citrate, and such, and examples of pharmaceutically acceptable amino acid-added salts include addition salts such as of lysine, glycine, phenylalanine, asparagine acid, or glutamic acid. Particularly, Pharmaceutically acceptable salts of compound (I) include hydrochloride salt, dihydrochloride salt, and trihydrochloride salt.

Examples of diseases involving overexpression of SUV39H2, which may be treated and/or prevented by pharmaceutical compositions comprising as an active ingredient a compound or a pharmaceutically acceptable salt thereof of the present invention, include cancer, breast cancer, bladder cancer, cervical cancer, cholangiocellular carcinoma, chronic myeloid leukemia (CML), colorectal cancer, endometriosis, esophagus cancer, gastric cancer, liver cancer, non-small cell lung cancer (NSCLC), lymphoma, osteosarcoma, ovarian cancer, pancreatic cancer, prostate cancer, renal carcinoma and small cell lung cancer (SCC), but are not limited thereto. Examples of the cancer which may be treated and/or prevented include breast cancer, bladder cancer, cervical cancer, cholangiocellular carcinoma, CML, colorectal cancer, endometriosis, esophagus cancer, gastric cancer, liver cancer, NSCLC, lymphoma, osteosarcoma, ovarian cancer, pancreatic cancer, prostate cancer, renal carcinoma and SCC, but are not limited thereto. In one embodiment, the examples of cancer includes lung cancer, cervical cancer, bladder cancer, esophageal cancer, osteosarcoma, prostate cancer and soft tissue tumor.

Compound (1) includes compounds which may have stereoisomers such as regioisomers, geometrical isomers, optical isomers, and tautomers, and all possible isomers including them and mixtures thereof are included in the present invention.

Compound (1) also includes compounds having one or more minor stable isotopes or radio isotopes such as $^2$H, $^3$H, $^3$C, $^4$C, $^{15}$N, $^{18}$O and the like, which can be prepared in line with conventional procedures for preparing a compound with one or more isotopes indicated above.

Furthermore, compound (1) and pharmaceutically acceptable salts thereof may exist in a form of solvate with water (hydrate) or various other solvents, and these solvates are also included in the present invention.

Specific examples of Compound (1) of the present invention are shown in Tables 1 and 2 (Examples 1 to 460). However, compounds of the present invention are not limited thereto.

TABLE 1

Compounds Table:

| Ex. No. | Structure | Name | MS Ionization | MS |
|---|---|---|---|---|
| 1 | 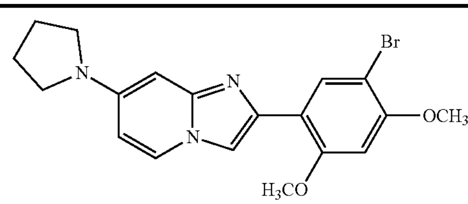 | 2-(5-bromo-2,4-dimethoxyphenyl)-7-(pyrrolidin-1-yl)imidazo[1,2-a]pyridine | APCI | 404 |
| 2 | 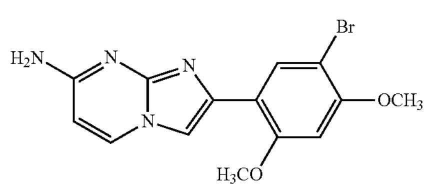 | 2-(5-bromo-2,4-dimethoxyphenyl)imidazo[1,2-a]pyrimidin-7-amine | APCI | 351 |

TABLE 1-continued

Compounds Table:

| Ex. No. | Structure | Name | MS Ionization | MS |
|---|---|---|---|---|
| 3 | 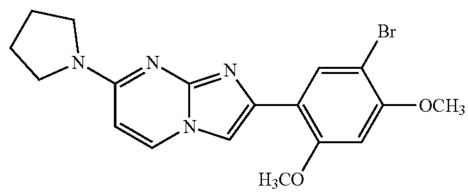 | 2-(5-bromo-2,4-dimethoxyphenyl)-7-(pyrrolidin-1-yl)imidazo[1,2-a]pyrimidine | APCI | 405 |
| 4 | 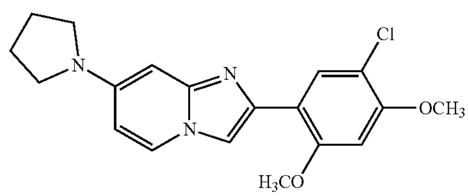 [SMILES: COc1cc(OC)c(-c2cn3ccc(N4CCCC4)cc3n2)cc1Cl] | 2-(5-chloro-2,4-dimethoxyphenyl)-7-(pyrrolidin-1-yl)imidazo[1,2-a]pyridine | APCI | 358 |
| 5 | 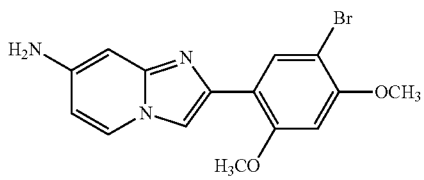 | 2-(5-bromo-2,4-dimethoxyphenyl)imidazo[1,2-a]pyridin-7-amine | ESI | 350 |
| 6 | 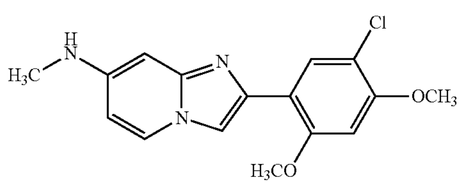 [SMILES: CNc1ccn2cc(-c3cc(Cl)c(OC)cc3OC)nc2c1] | 2-(5-chloro-2,4-dimethoxyphenyl)-N-methylimidazo[1,2-a]pyridin-7-amine | APCI | 318 |
| 7 | 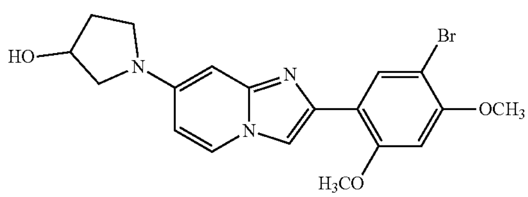 [SMILES: COc1cc(OC)c(-c2cn3ccc(N4CCC(O)C4)cc3n2)cc1Br] | 1-(2-(5-bromo-2,4-dimethoxyphenyl)imidazo[1,2-a]pyridin-7-yl)pyrrolidin-3-ol | ESI | 420 |
| 8 | 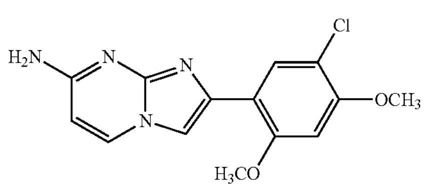 [SMILES: COc1cc(OC)c(-c2cn3ccc(N)nc3n2)cc1Cl] | 2-(5-chloro-2,4-dimethoxyphenyl)imidazo[1,2-a]pyrimidin-7-amine | ESI | 305 |
| 9 | 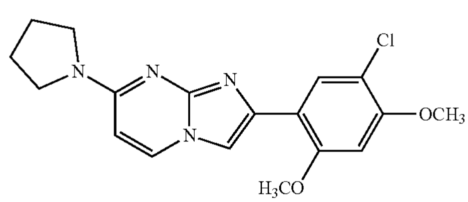 | 2-(5-chloro-2,4-dimethoxyphenyl)-7-(pyrrolidin-1-yl)imidazo[1,2-a]pyrimidine | ESI | 359 |

TABLE 1-continued

Compounds Table:

| Ex. No. | Structure | Name | MS Ionization | MS |
|---|---|---|---|---|
| 10 | 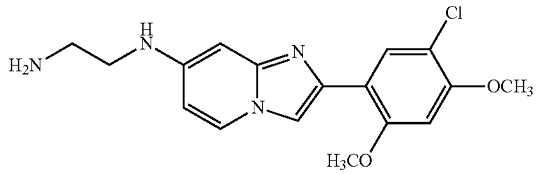 [SMILES: COc1cc(OC)c(-c2cn3ccc(NCCN)cc3n2)cc1Cl] | N$^1$-(2-(5-chloro-2,4-dimethoxyphenyl)imidazo[1,2-a]pyridin-7-yl)ethane-1,2-diamine | APCI | 347 |
| 11 | 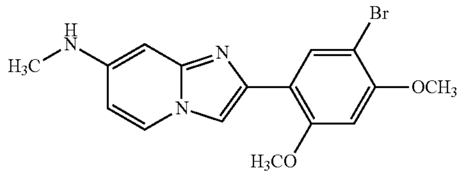 [SMILES: CNc1ccn2cc(-c3cc(Br)c(OC)cc3OC)nc2c1] | 2-(5-bromo-2,4-dimethoxyphenyl)-N-methylimidazo[1,2-a]pyridin-7-amine | ESI | 362 |
| 12 | 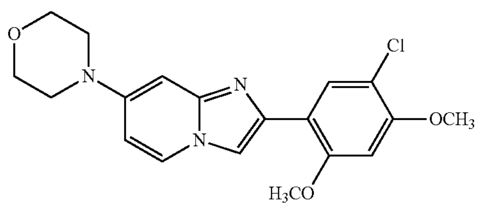 [SMILES: COc1cc(OC)c(-c2cn3ccc(N4CCOCC4)cc3n2)cc1Cl] | 4-(2-(5-chloro-2,4-dimethoxyphenyl)imidazo[1,2-a]pyridin-7-yl)morpholine | APCI | 374 |
| 13 | 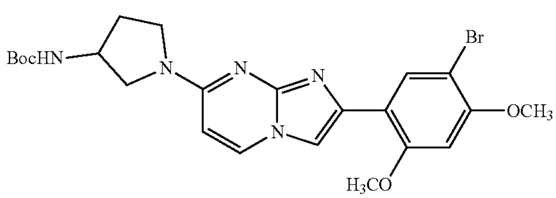 [SMILES: COc1cc(OC)c(-c2cn3ccc(N4CCC(NC(=O)OC(C)(C)C)C4)nc3n2)cc1Br] | tert-butyl (1-(2-(5-bromo-2,4-dimethoxyphenyl)imidazo[1,2-a]pyrimidin-7-yl)pyrrolidin-3-yl)carbamate | APCI | 520 |
| 14 | 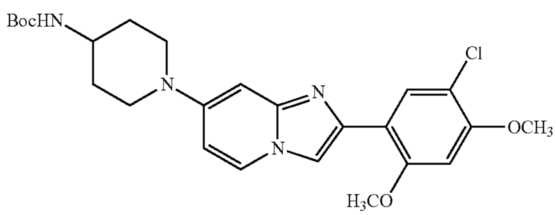 [SMILES: COc1cc(OC)c(-c2cn3ccc(N4CCC(NC(=O)OC(C)(C)C)CC4)cc3n2)cc1Cl] | tert-butyl (1-(2-(5-chloro-2,4-dimethoxyphenyl)imidazo[1,2-a]pyridin-7-yl)piperidin-4-yl)carbamate | APCI | 487 |
| 15 | 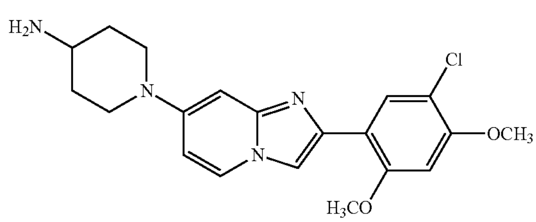 [SMILES: COc1cc(OC)c(-c2cn3ccc(N4CCC(N)CC4)cc3n2)cc1Cl] | 1-(2-(5-chloro-2,4-dimethoxyphenyl)imidazo[1,2-a]pyridin-7-yl)piperidin-4-amine | APCI | 387 |
| 16 | 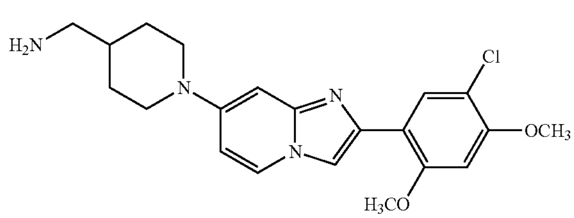 [SMILES: COc1cc(OC)c(-c2cn3ccc(N4CCC(CN)CC4)cc3n2)cc1Cl] | (1-(2-(5-chloro-2,4-dimethoxyphenyl)imidazo[1,2-a]pyridin-7-yl)piperidin-4-yl)methanamine | APCI | 401 |

TABLE 1-continued

Compounds Table:

| Ex. No. | Structure | Name | MS Ionization | MS |
|---|---|---|---|---|
| 17 | 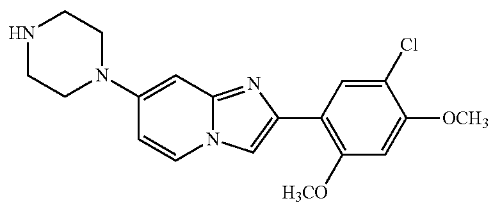 [SMILES: COc1cc(OC)c(-c2cn3ccc(N4CCNCC4)cc3n2)cc1Cl] | 2-(5-chloro-2,4-dimethoxyphenyl)-7-(piperazin-1-yl)imidazo[1,2-a]pyridine | APCI | 373 |
| 18 | 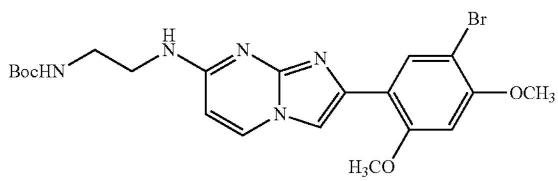 [SMILES: COc1cc(OC)c(-c2cn3ccc(NCCNC(=O)OC(C)(C)C)nc3n2)cc1Br] | tert-butyl (2-((2-(5-bromo-2,4-dimethoxyphenyl)imidazo[1,2-a]pyrimidin-7-yl)amino)ethyl)carbamate | APCI | 494 |
| 19 | 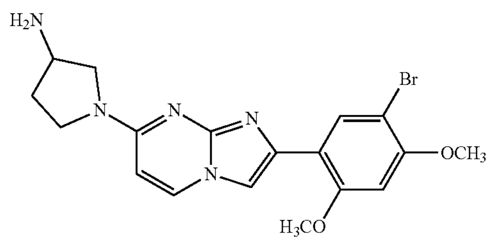 [SMILES: COc1cc(OC)c(-c2cn3ccc(N4CCC(N)C4)nc3n2)cc1Br] | 1-(2-(5-bromo-2,4-dimethoxyphenyl)imidazo[1,2-a]pyrimidin-7-yl)pyrrolidin-3-amine | APCI | 420 |
| 20 | 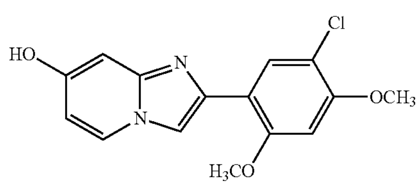 [SMILES: COc1cc(OC)c(-c2cn3ccc(O)cc3n2)cc1Cl] | 2-(5-chloro-2,4-dimethoxyphenyl)imidazo[1,2-a]pyridin-7-ol | ESI | 305 |
| 21 | 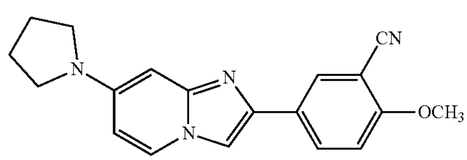 [SMILES: COc1ccc(-c2cn3ccc(N4CCCC4)cc3n2)cc1C#N] | 2-methoxy-5-(7-(pyrrolidin-1-yl)imidazo[1,2-a]pyridin-2-yl)benzonitrile | ESI | 319 |
| 22 | 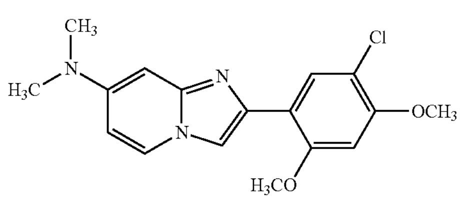 [SMILES: COc1cc(OC)c(-c2cn3ccc(N(C)C)cc3n2)cc1Cl] | 2-(5-chloro-2,4-dimethoxyphenyl)-N,N-dimethylimidazo[1,2-a]pyridin-7-amine | ESI | 332 |
| 23 | 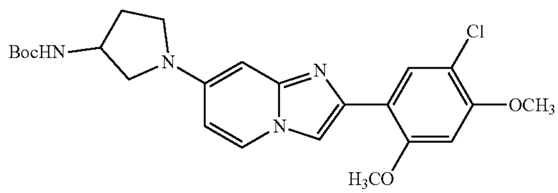 | tert-butyl (1-(2-(5-chloro-2,4-dimethoxyphenyl)imidazo[1,2-a]pyridin-7-yl)pyrrolidin-3-yl)carbamate | ESI | 473 |

TABLE 1-continued

Compounds Table:

| Ex. No. | Structure | Name | MS Ionization | MS |
|---|---|---|---|---|
| 24 | 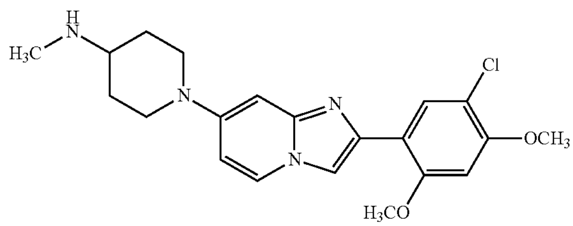 [SMILES: CNC1CCN(c2ccn3cc(-c4cc(Cl)c(OC)cc4OC)nc3c2)CC1] | 1-(2-(5-chloro-2,4-dimethoxyphenyl)imidazo[1,2-a]pyridin-7-yl)-N-methylpiperidin-4-amine | APCI | 401 |
| 25 | 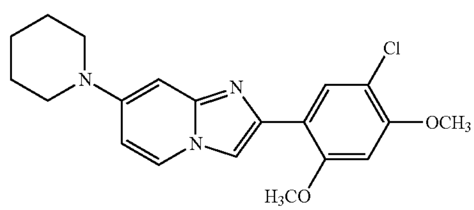 [SMILES: COc1cc(OC)c(-c2cn3ccc(N4CCCCC4)cc3n2)cc1Cl] | 2-(5-chloro-2,4-dimethoxyphenyl)-7-(piperidin-1-yl)imidazo[1,2-a]pyridine | APCI | 372 |
| 26 | 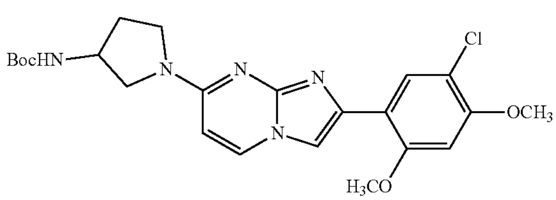 | tert-butyl (1-(2-(5-chloro-2,4-dimethoxyphenyl)imidazo[3,2-a]pyrimidin-7-yl)pyrrolidin-3-yl)carbamate | ESI | 474 |
| 27 | 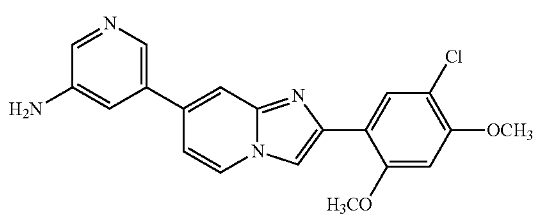 [SMILES: COc1cc(OC)c(-c2cn3ccc(-c4cncc(N)c4)cc3n2)cc1Cl] | 5-(2-(5-chloro-2,4-dimethoxyphenyl)imidazo[1,2-a]pyridin-7-yl)pyridin-3-amine | ESI | 381 |
| 28 | 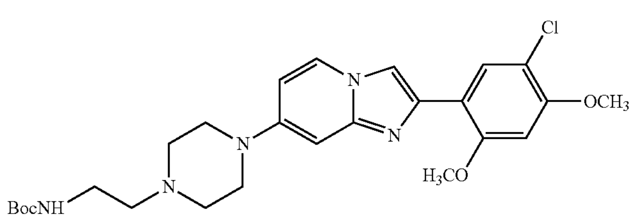 [SMILES: COc1cc(OC)c(-c2cn3ccc(N4CCN(CCNC(=O)OC(C)(C)C)CC4)cc3n2)cc1Cl] | tert-butyl (2-(4-(2-(5-chloro-2,4-dimethoxyphenyl)imidazo[1,2-a]pyridin-7-yl)piperazin-1-yl)ethyl)carbamate | APCI | 516 |
| 29 | 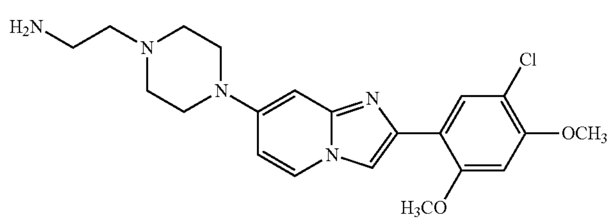 | 2-(4-(2-(5-chloro-2,4-dimethoxyphenyl)imidazo[1,2-a]pyridin-7-yl)piperazin-1-yl)ethanamine | ESI | 416 |

TABLE 1-continued

Compounds Table:

| Ex. No. | Structure | Name | MS Ionization | MS |
|---|---|---|---|---|
| 30 | 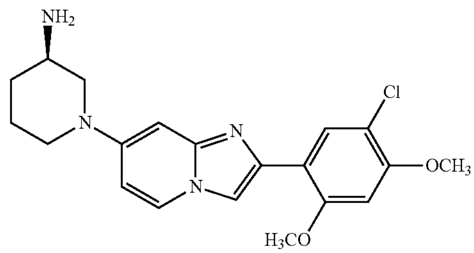 [SMILES: COc1cc(OC)c(-c2cn3ccc(N4CCC[C@@H](N)C4)cc3n2)cc1Cl] | (R)-1-(2-(5-chloro-2,4-dimethoxyphenyl)imidazo[1,2-a]pyridine-7-yl)piperidin-3-amine | ESI | 387 |
| 31 | 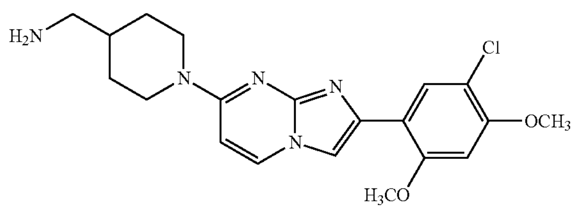 [SMILES: COc1cc(OC)c(-c2cn3ccc(N4CCC(CN)CC4)nc3n2)cc1Cl] | (1-(2-(5-chloro-2,4-dimethoxyphenyl)imidazo[1,2-a]pyrimidin-7-yl)piperidin-4-yl)methanamine | ESI | 402 |
| 32 | 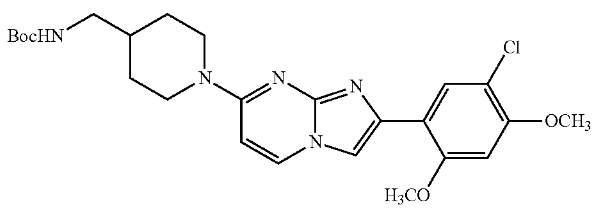 [SMILES: COc1cc(OC)c(-c2cn3ccc(N4CCC(CNC(=O)OC(C)(C)C)CC4)nc3n2)cc1Cl] | tert-butyl ((1-(2-(5-chloro-2,4-dimethoxyphenyl)imidazo[1,2-a]pyrimidin-7-yl)piperidin-4-yl)methyl)carbamate | ESI | 502 |
| 33 | 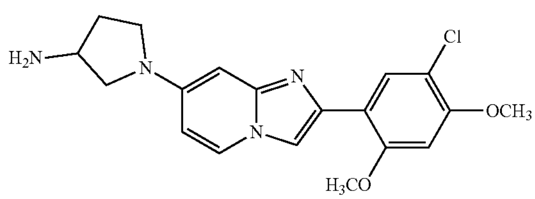 [SMILES: COc1cc(OC)c(-c2cn3ccc(N4CCC(N)C4)cc3n2)cc1Cl] | 1-(2-(5-chloro-2,4-dimethoxyphenyl)imidazo[1,2-a]pyridine-7-yl)pyrrolidin-3-amine | ESI | 373 |
| 34 | 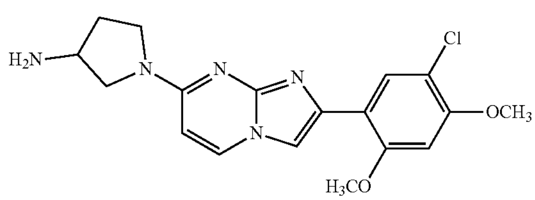 [SMILES: COc1cc(OC)c(-c2cn3ccc(N4CCC(N)C4)nc3n2)cc1Cl] | 1-(2-(5-chloro-2,4-dimethoxyphenyl)imidazo[1,2-a]pyrimidin-7-yl)pyrrolidin-3-amine | ESI | 374 |
| 35 | 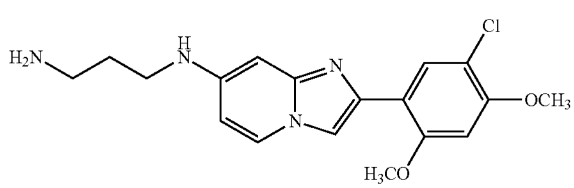 [SMILES: COc1cc(OC)c(-c2cn3ccc(NCCCN)cc3n2)cc1Cl] | $N^1$-(2-(5-chloro-2,4-dimethoxyphenyl)imidazo[2-a]pyridine-7-yl)propane-1,3-diamine | ESI | 361 |
| 36 | 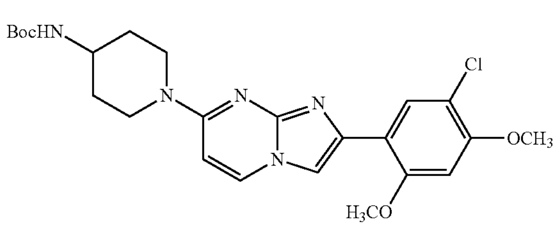 | tert-butyl (1-(2-(5-chloro-2,4-dimethoxyphenyl)imidazo[1,2-a]pyrimidin-7-yl)piperidin-4-yl)carbamate | APCI | 488 |

TABLE 1-continued

Compounds Table:

| Ex. No. | Structure | Name | MS Ionization | MS |
|---|---|---|---|---|
| 37 | 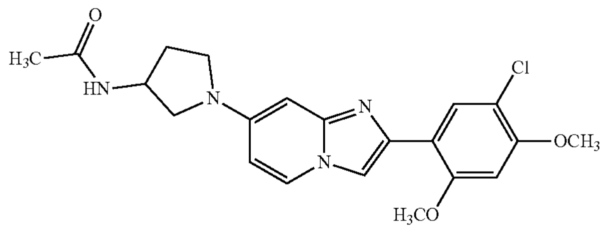 | N-(1-(2-(5-chloro-2,4-dimethoxyphenyl)imidazo[1,2-a]pyridin-7-yl)pyrrolidin-3-yl)acetamide | ESI | 415 |
| 38 | 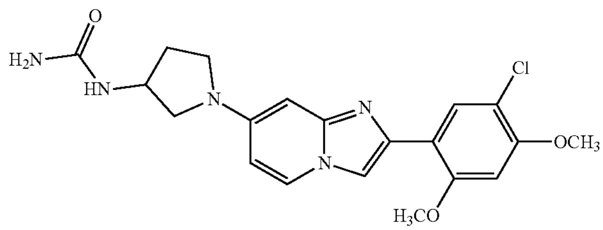 [SMILES: COc1cc(OC)c(-c2cn3ccc(N4CCC(NC(C)=O)C4)cc3n2)cc1Cl] | 1-(1-(2-(5-chloro-2,4-dimethoxyphenyl)imidazo[1,2-a]pyridine-7-yl)pyrrolidin-3-yl)urea | ESI | 416 |
| 39 | 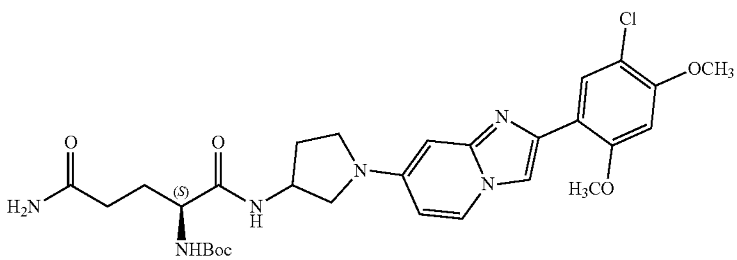 | tert-butyl ((2S)-5-amino-1-((1-(2-(5-chloro-2,4-dimethoxyphenyl)imidazo[1,2-a]pyridin-7-yl)pyrrolidin-3-yl)amino)-1,5-dioxopentan-2-yl)carbamate | ESI | 601 |
| 40 | 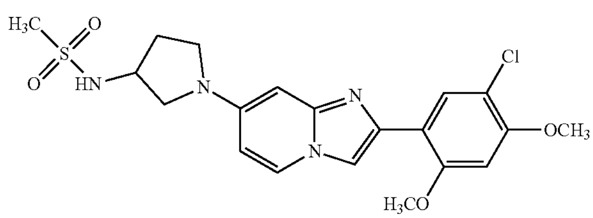 [SMILES: COc1cc(OC)c(-c2cn3ccc(N4CCC(NS(C)(=O)=O)C4)cc3n2)cc1Cl] | N-(1-(2-(5-chloro-2,4-dimethoxyphenyl)imidazo[1,2-a]pyridine-7-yl)pyrrolidin-3-yl)methanesulfonamide | ESI | 451 |
| 41 | 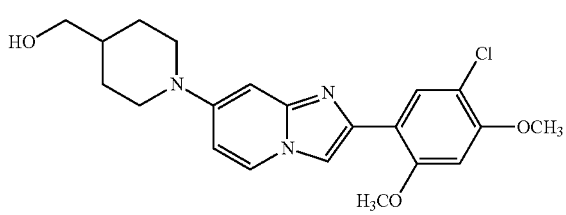 [SMILES: COc1cc(OC)c(-c2cn3ccc(N4CCC(CO)CC4)cc3n2)cc1Cl] | (1-(2-(5-chloro-2,4-dimethoxyphenyl)imidazo[1,2-a]pyridine-7-yl)piperidin-4-yl)methanol | ESI | 402 |
| 42 | 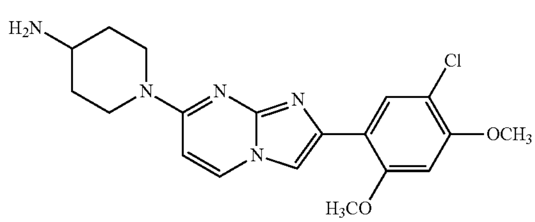 | 1-(2-(5-chloro-2,4-dimethoxyphenyl)imidazo[1,2-a]pyrimidin-7-yl)piperidin-4-amine | ESI | 388 |

TABLE 1-continued

Compounds Table:

| Ex. No. | Structure | Name | MS Ionization | MS |
|---|---|---|---|---|
| 43 | 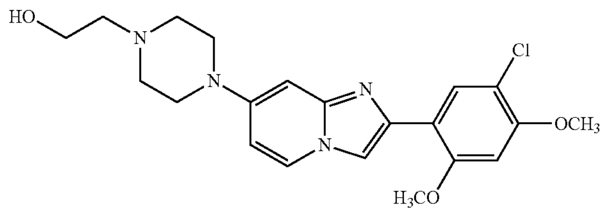 [SMILES: COc1cc(OC)c(-c2cn3ccc(N4CCN(CCO)CC4)cc3n2)cc1Cl] | 2-(4-(2-(5-chloro-2,4-dimethoxyphenyl)imidazo[1,2-a]pyridine-7-yl)piperazin-1-yl)ethanol | ESI | 417 |
| 44 | 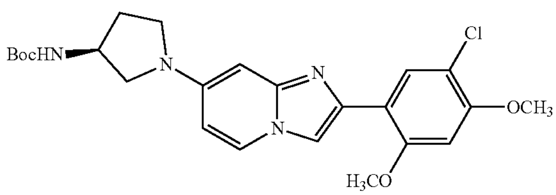 | (S)-tert-butyl (1-(2-(5-chloro-2,4-dimethoxyphenyl)imidazo[1,2-a]pyridine-7-yl)pyrrolidin-3-yl)carbamate | ESI | 473 |
| 45 | 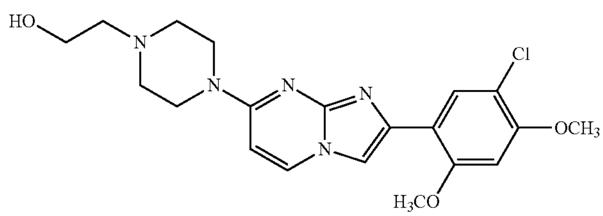 [SMILES: COc1cc(OC)c(-c2cn3ccc(N4CCN(CCO)CC4)nc3n2)cc1Cl] | 2-(4-(2-(5-chloro-2,4-dimethoxyphenyl)imidazo[1,2-a]pyrimidin-7-yl)piperazin-1-yl)ethanol | ESI | 418 |
| 46 | 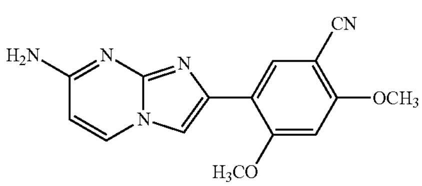 | 5-(7-aminoimidazo[1,2-a]pyrimidin-2-yl)-2,4-dimethoxybenzonitrile | ESI | 296 |
| 47 | 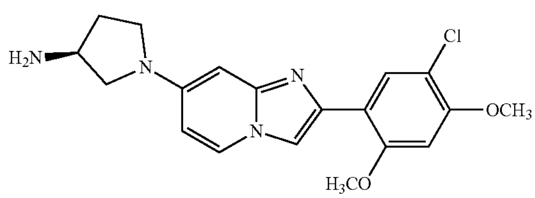 | (S)-1-(2-(5-chloro-2,4-dimethoxyphenl)imidazo[1,2-a]pyridine-7-yl)pyrrolidin-3-amine | ESI | 373 |
| 48 | 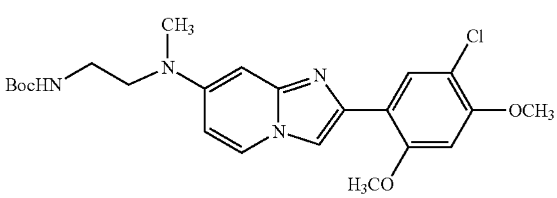 [SMILES: COc1cc(OC)c(-c2cn3ccc(N(C)CCNC(=O)OC(C)(C)C)cc3n2)cc1Cl] | tert-butyl (2-((2-(5-chloro-2,4-dimethoxyphenyl)imidazo[1,2-a]pyridine-7-yl)(methyl)-amino)ethyl)carbamate | ESI | 461 |
| 49 | 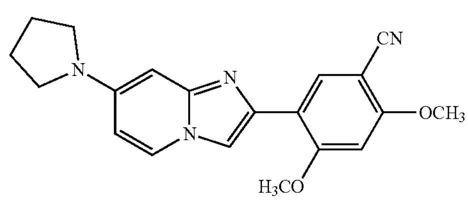 [SMILES: COc1cc(OC)c(-c2cn3ccc(N4CCCC4)cc3n2)cc1C#N] | 2,4-dimethoxy-5-(7-(pyrrolidin-1-yl)imidazo[1,2-a]pyridine-2-yl)benzonitrile | ESI | 349 |

TABLE 1-continued

Compounds Table:

| Ex. No. | Structure | Name | MS Ionization | MS |
|---|---|---|---|---|
| 50 | 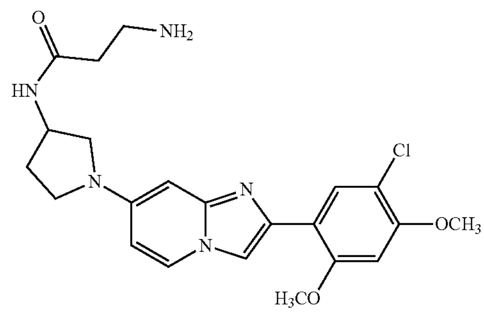 [SMILES: COc1cc(OC)c(-c2cn3ccc(N4CCC(NC(=O)CCN)C4)cc3n2)cc1Cl] | 3-amino-N-(1-(2-(5-chloro-2,4-dimethoxyphenyl)imidazo[1,2-a]pyridine-7-yl)pyrrolidin-3-yl)propanamide | ESI | 444 |
| 51 | 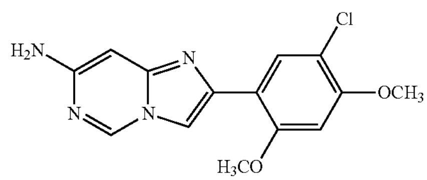 [SMILES: COc1cc(OC)c(-c2cn3cnc(N)cc3n2)cc1Cl] | 2-(5-chloro-2,4-dimethoxyphenyl)imidazo[1,2-c]pyrimidin-7-amine | ESI | 305 |
| 52 | 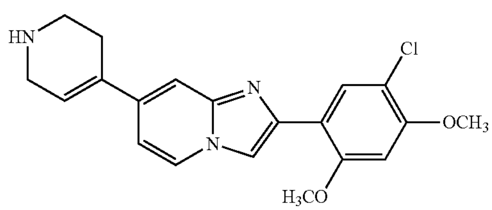 [SMILES: COc1cc(OC)c(-c2cn3ccc(C4=CCNCC4)cc3n2)cc1Cl] | 2-(5-chloro-2,4-dimethoxyphenyl)-7-(1,2,3,6-tetrahydropyridin-4-yl)imidazo[1,2-a]pyridine | ESI | 370 |
| 53 | 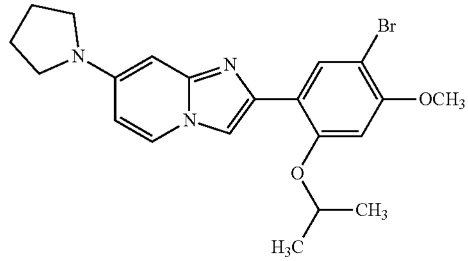 [SMILES: COc1cc(OC(C)C)c(-c2cn3ccc(N4CCCC4)cc3n2)cc1Br] | 2-(5-bromo-2-isopropoxy-4-methoxyphenyl)-7-(pyrrolidin-1-yl)imidazo[1,2-a]pyridine | ESI | 430 |
| 54 | 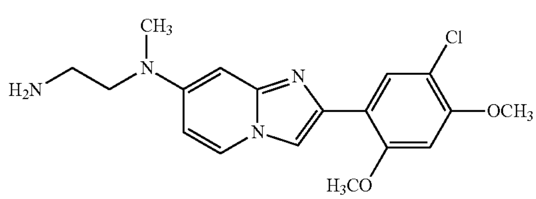 [SMILES: COc1cc(OC)c(-c2cn3ccc(N(C)CCN)cc3n2)cc1Cl] | $N^1$-(2-(5-chloro-2,4-dimethoxyphenyl)imidazo[1,2-a)pyridine-7-yl)-N1-methylethane-1,2-diamine | ESI | 361 |
| 55 | 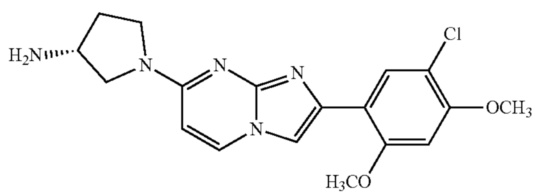 | (R)-1-(2-(5-chloro-2,4-dimethoxyphenyl)imidazo[1,2-a]pyrimidin-7-yl)pyrrolidin-3-amine | ESI | 374 |

TABLE 1-continued

Compounds Table:

| Ex. No. | Structure | Name | MS Ionization | MS |
|---|---|---|---|---|
| 56 | 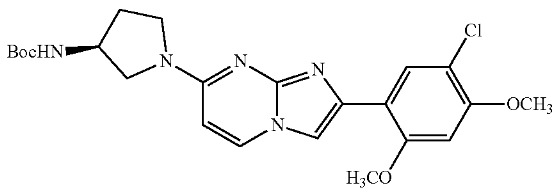 [SMILES: COc1cc(OC)c(-c2cn3ccc(N4CC[C@H](NC(=O)OC(C)(C)C)C4)nc3n2)cc1Cl] | (S)-tert-butyl (1-(2-(5-chloro-2,4-dimethoxyphenyl)imidazo[1,2-a]pyrimidin-7-yl)pyrrolidin-3-yl)carbamate | ESI | 474 |
| 57 | 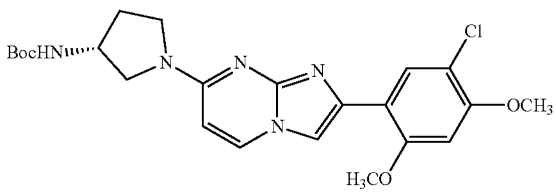 | (R)--tert-butyl (1-(2-(5-chloro-2,4-dimethoxyphenyl)imidazo[1,2-a]pyrimidin-7-yl)pyrrolidin-3-yl)carbamate | ESI | 474 |
| 58 | 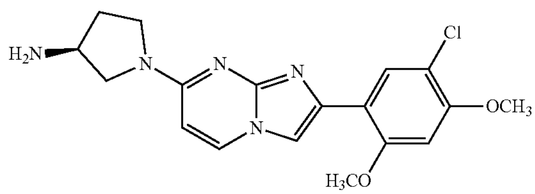 [SMILES: COc1cc(OC)c(-c2cn3ccc(N4CC[C@H](N)C4)nc3n2)cc1Cl] | (S)-1-(2-(5-chloro-2,4-dimethoxyphenyl)imidazo[1,2-a]pyrimidin-7-yl)pyrrolidin-3-amine | ESI | 374 |
| 59 | 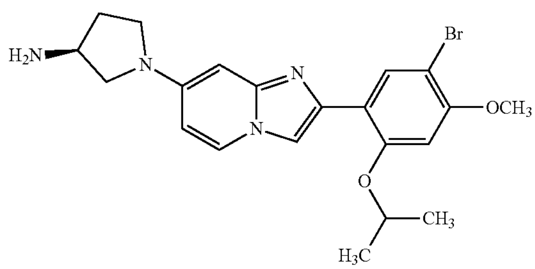 [SMILES: COc1cc(OC(C)C)c(-c2cn3ccc(N4CC[C@H](N)C4)cc3n2)cc1Br] | (S)-1-(2-(5-bromo-2-isopropoxy-4-methoxyphenyl)imidazo[1,2-a]pyridine-7-yl)pyrrolidin-3-amine | ESI | 445 |
| 60 | 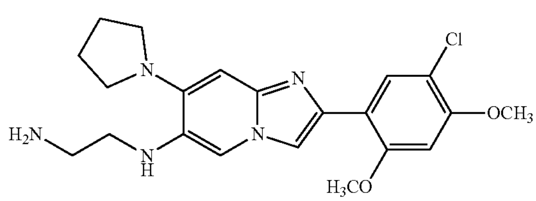 [SMILES: COc1cc(OC)c(-c2cn3cc(NCCN)c(N4CCCC4)cc3n2)cc1Cl] | $N^1$-(2-(5-chloro-2,4-dimethoxyphenyl)-7-(pyrrolidin-1-yl)imidazo[1,2-a]pyridine-6-yl)ethane-1,2-diamine | ESI | 416 |
| 61 | 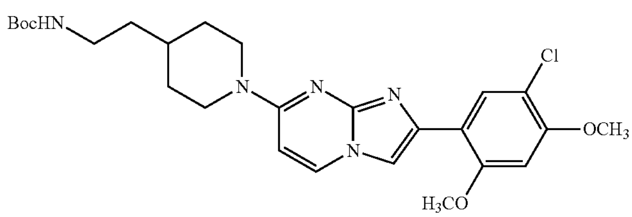 [SMILES: COc1cc(OC)c(-c2cn3ccc(N4CCC(CCNC(=O)OC(C)(C)C)CC4)nc3n2)cc1Cl] | tert-butyl (2-(1-(2-(5-chloro-2,4-dimethoxyphenyl)imidazo[1,2-a]pyrimidin-7-yl)piperidin-4-yl)ethyl)carbamate | ESI | 516 |

TABLE 1-continued

Compounds Table:

| Ex. No. | Structure | Name | MS Ionization | MS |
|---|---|---|---|---|
| 62 | 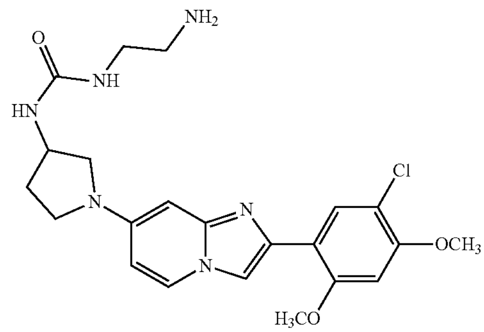 [SMILES: COc1cc(OC)c(-c2cn3ccc(N4CCC(NC(=O)NCCN)C4)cc3n2)cc1Cl] | 1-(2-aminoethyl)-3-(1-(2-(5-chloro-2,4-dimethoxyphenyl)-imidazo[1,2-a]pyridine-7-yl)pyrrolidin-3-yl)urea | ESI | 459 |
| 63 | 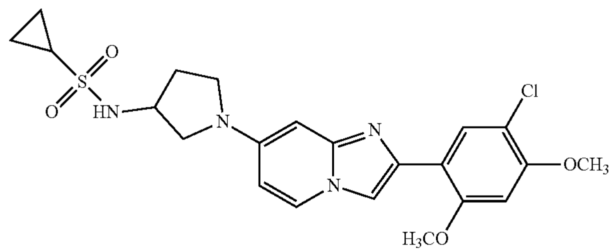 [SMILES: COc1cc(OC)c(-c2cn3ccc(N4CCC(NS(=O)(=O)C5CC5)C4)cc3n2)cc1Cl] | N-(1-(2-(5-chloro-2,4-dimethoxyphenyl)imidazo[1,2-a]pyridine-7-yl)pyrrolidin-3-yl)cyclopropanesulfonamide | ESI | 477 |
| 64 | 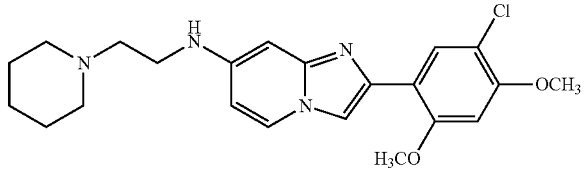 [SMILES: COc1cc(OC)c(-c2cn3ccc(NCCN4CCCCC4)cc3n2)cc1Cl] | 2-(5-chloro-2,4-dimethoxyphenyl)-N-(2-(piperidin-1-yl)ethyl)-imidazo[1,2-a]pyridine-7-amine | ESI | 417 |
| 65 | 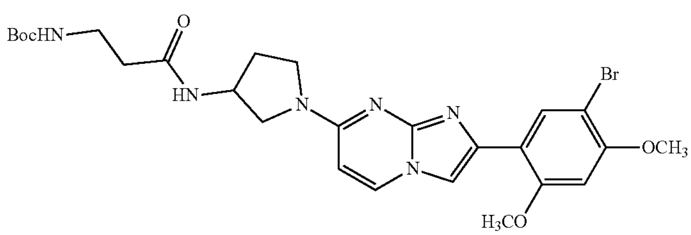 [SMILES: COc1cc(OC)c(-c2cn3ccc(N4CCC(NC(=O)CCNC(=O)OC(C)(C)C)C4)nc3n2)cc1Br] | tert-butyl (3-((1-(2-(5-bromo-2,4-dimethoxyphenyl)-imidazo[1,2-a]pyrimidin-7-yl)pyrrolidin-3-yl)amino)-3-oxopropyl)carbamate | ESI | 589 |
| 66 | 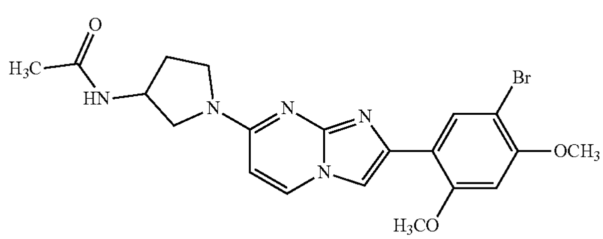 | N-(1-(2-(5-bromo-2,4-dimethoxyphenyl)imidazo[1,2-a]pyrimidin-7-yl)pyrrolidin-3-yl)acetamide | ESI | 460 |
| 67 | 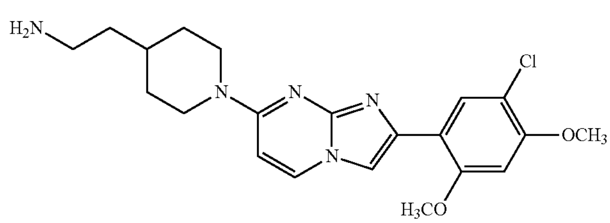 [SMILES: COc1cc(OC)c(-c2cn3ccc(N4CCC(CCN)CC4)nc3n2)cc1Cl] | 2-(1-(2-(5-chloro-2,4-dimethoxyphenyl)imidazo[1,2-a]pyrimidin-7-yl)piperidin-4-yl)ethanamine | ESI | 416 |

TABLE 1-continued

Compounds Table:

| Ex. No. | Structure | Name | MS Ionization | MS |
|---|---|---|---|---|
| 68 | 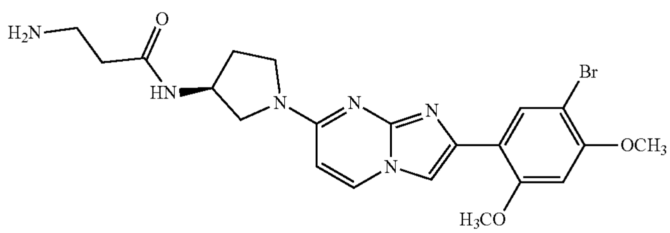 [SMILES: COc1cc(OC)c(-c2cn3ccc(N4CC[C@H](NC(=O)CCN)C4)nc3n2)cc1Br] | 3-amino-N-(1-(2-(5-bromo-2,4-dimethoxyphenyl)imidazo[1,2-a]pyrimidin-7-yl)pyrrolidin-3-yl)propanamide | APCI | 489 |
| 69 | 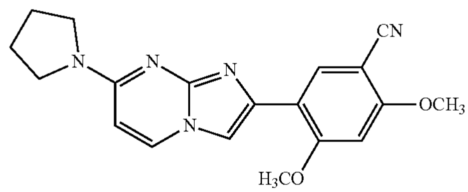 [SMILES: COc1cc(OC)c(-c2cn3ccc(N4CCCC4)nc3n2)cc1C#N] | 2,4-dimethoxy-5-(7-(pyrrolidin-1-yl)imidazo[1,2-a]pyrimidin-2-yl)benzonitrile | ESI | 350 |
| 70 | 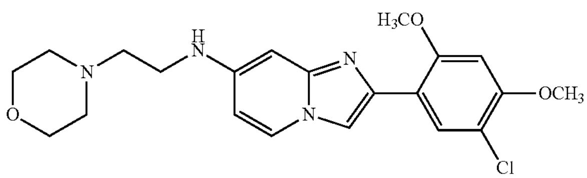 [SMILES: COc1cc(OC)c(-c2cn3ccc(NCCN4CCOCC4)cc3n2)cc1Cl] | 2-(5-chloro-2,4-dimethoxyphenyl)-N-(2-morpholinoethyl)imidazo[1,2-a]pyridine-7-amine | APCI | 417 |
| 71 | 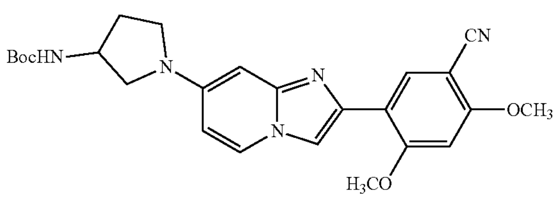 [SMILES: COc1cc(OC)c(-c2cn3ccc(N4CCC(NC(=O)OC(C)(C)C)C4)cc3n2)cc1C#N] | tert-butyl (1-(2-(5-cyano-2,4-dimethoxyphenyl)imidazo[1,2-a]pyridine-7-yl)pyrrolidin-3-yl)carbamate | ESI | 464 |
| 72 | 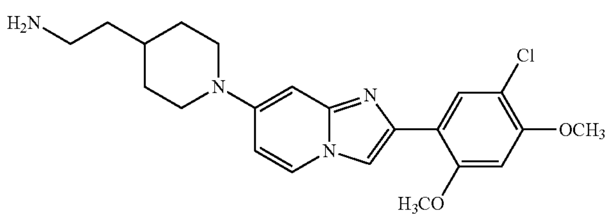 | 2-(1-(2-(5-chloro-2,4-dimethoxyphenyl)imidazo[1,2-a]pyridine-7-yl)piperidin-4-yl)ethanamine | APCI | 415 |
| 73 | 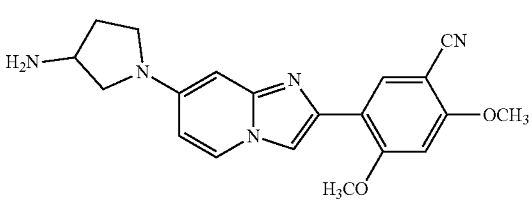 [SMILES: COc1cc(OC)c(-c2cn3ccc(N4CCC(N)C4)cc3n2)cc1C#N] | 5-(7-(3-aminopyrrolidin-1-yl)imidazo[1,2-a]pyridine-2-yl)-2,4-dimethoxybenzonitrile | APCI | 364 |
| 74 | 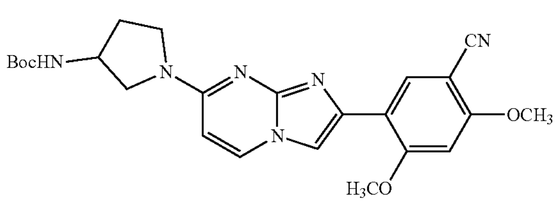 | tert-butyl (1-(2-(5-cyano-2,4-dimethoxyphenyl)imidazo[3,2-a]pyrimidin-7-yl)pyrrolidin-3-yl)carbamate | ESI | 465 |

TABLE 1-continued

Compounds Table:

| Ex. No. | Structure | Name | MS Ionization | MS |
|---|---|---|---|---|
| 75 | 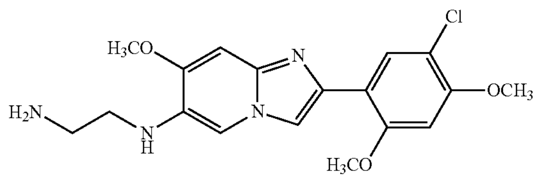 [SMILES: COc1cc(OC)c(-c2cn3cc(NCCN)c(OC)cc3n2)cc1Cl] | $N^1$-(2-(5-chloro-2,4-dimethoxyphenyl)-7-methoxyimidazo[1,2-a]pyridine-6-yl)ethane-1,2-diamine | ESI | 377 |
| 76 | 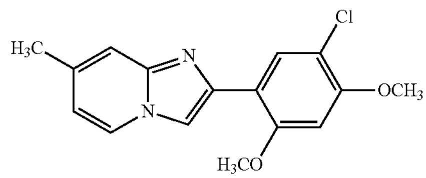 | 2-(5-chloro-2,4-dimethoxyphenyl)-7-methylimidazo[1,2-a]pyridine | ESI | 303 |
| 77 | 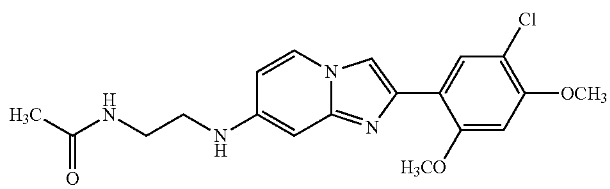 [SMILES: COc1cc(OC)c(-c2cn3ccc(NCCNC(C)=O)cc3n2)cc1Cl] | N-(2-((2-(5-chloro-2,4-dimethoxyphenyl)imidazo[1,2-a]pyridine-7-yl)amino)ethyl)acetamide | ESI | 389 |
| 78 | 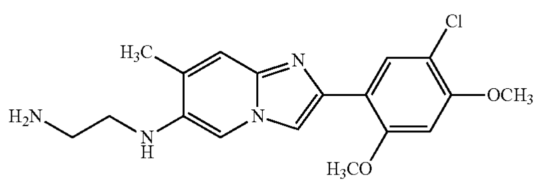 [SMILES: COc1cc(OC)c(-c2cn3cc(NCCN)c(C)cc3n2)cc1Cl] | $N^1$-(2-(5-chloro-2,4-dimethoxyphenyl)-7-methylimidazo[1,2-a]pyridine-6-yl)ethane-1,2-diamine | APCI | 361 |
| 79 | 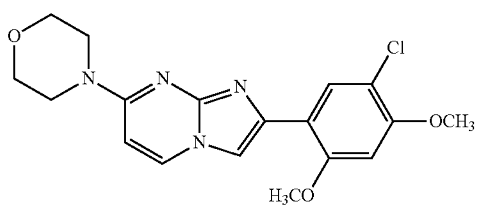 | 4-(2-(5-chloro-2,4-dimethoxyphenyl)imidazo[1,2-a]pyrimidin-7-yl)morpholine | APCI | 375 |
| 80 | 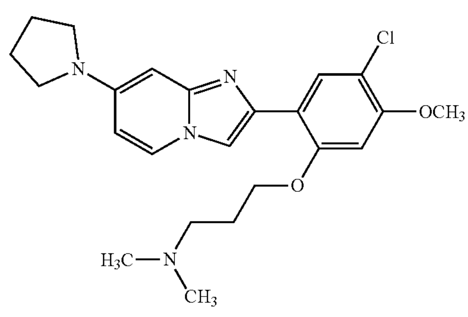 [SMILES: COc1cc(OCCCN(C)C)c(-c2cn3ccc(N4CCCC4)cc3n2)cc1Cl] | 3-(4-chloro-5-methoxy-2-(7-(pyrrolidin-1-yl)imidazo[1,2-a]pyridine-2-yl)phenoxy)-N,N-dimethylpropan-1-amine | APCI | 429 |
| 81 | 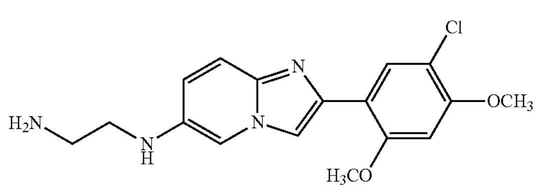 [SMILES: COc1cc(OC)c(-c2cn3cc(NCCN)ccc3n2)cc1Cl] | $N^1$-(2-(5-chloro-2,4-dimethoxyphenyl)imidazo[1,2-a]pyridine-6-yl)ethane-1,2-diamine | ESI | 347 |

TABLE 1-continued

Compounds Table:

| Ex. No. | Structure | Name | MS Ionization | MS |
|---|---|---|---|---|
| 82 | 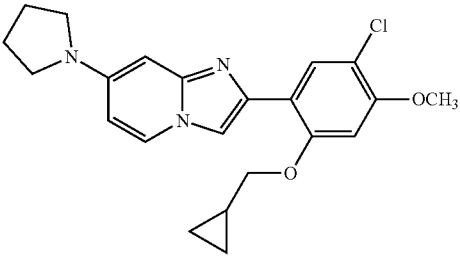 [SMILES: COc1cc(OCC2CC2)c(-c2cn3ccc(N4CCCC4)cc3n2)cc1Cl] | 2-(5-chloro-2-(cyclopropylmethoxy)-4-methoxyphenyl)-7-(pyrrolidin-1-yl)imidazo[1,2-a]pyridine | ESI | 398 |
| 83 | 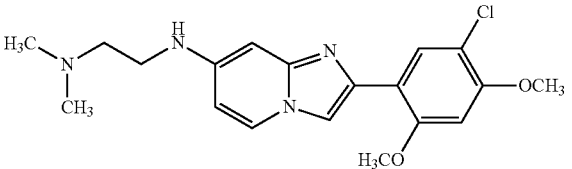 | N$^1$-(2-(5-chloro-2,4-dimethoxyphenyl)imidazo[1,2-a]pyridine-7-yl)-N$^2$,N$^2$-dimethylethane-1,2-diamine | APCI | 375 |
| 84 | 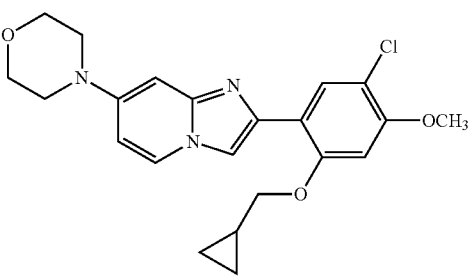 [SMILES: COc1cc(OCC2CC2)c(-c2cn3ccc(N4CCOCC4)cc3n2)cc1Cl] | 4-(2-(5-chloro-2-(cyclopropylmethoxy)-4-methoxyphenyl)imidazo[1,2-a]pyridine-7-yl)morpholine | APCI | 414 |
| 85 | 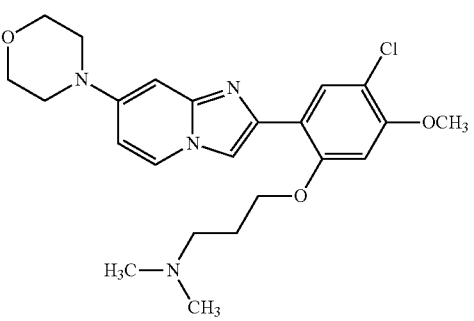 [SMILES: COc1cc(OCCCN(C)C)c(-c2cn3ccc(N4CCOCC4)cc3n2)cc1Cl] | 3-(4-chloro-5-methoxy-2-(7-morpholinoimidazo[1,2-a]pyridine-2-yl)phenoxy)-N,N-dimethylpropan-1-amine | APCI | 445 |
| 86 | 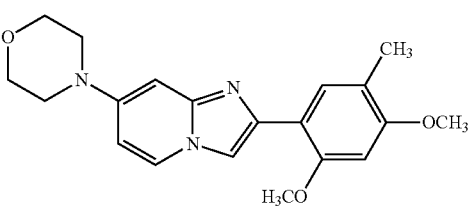 | 4-(2-(2,4-dimethoxy-5-methylphenyl)imidazo[1,2-a]pyridine-7-yl)morpholine | APCI | 354 |
| 87 | 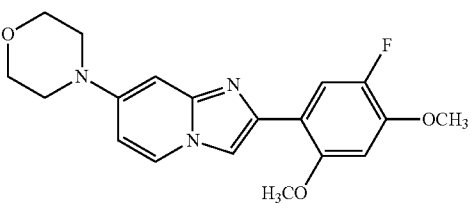 [SMILES: COc1cc(OC)c(-c2cn3ccc(N4CCOCC4)cc3n2)cc1F] | 4-(2-(5-fluoro-2,4-dimethoxyphenyl)imidazo[1,2-a]pyridine-7-yl)morpholine | APCI | 358 |

TABLE 1-continued

Compounds Table:

| Ex. No. | Structure | Name | MS Ionization | MS |
|---|---|---|---|---|
| 88 | 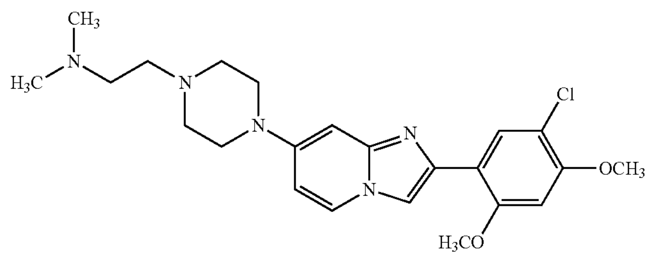 | 2-(4-(2-(5-chloro-2,4-dimethoxyphenyl)imidazo[1,2-a]pyridine-7-yl)piperazin-1-yl)-N,N-dimethylethanamine | APCI | 444 |
| 89 | 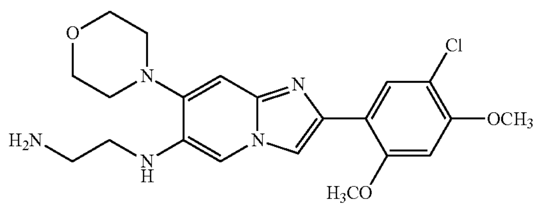 [SMILES: COc1cc(OC)c(-c2cn3cc(NCCN)c(N4CCOCC4)cc3n2)cc1Cl] | N¹-(2-(5-chloro-2,4-dimethoxyphenyl)-7-morpholinoimidazo[1,2-a]pyridine-6-yl)ethane-1,2-diamine | ESI | 432 |
| 90 | 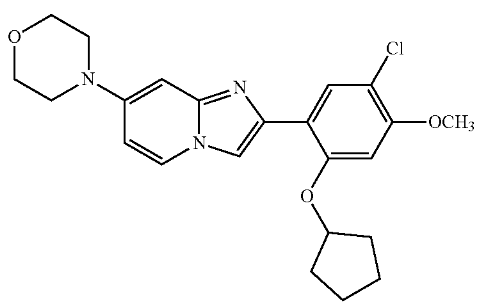 [SMILES: COc1cc(OC2CCCC2)c(-c2cn3ccc(N4CCOCC4)cc3n2)cc1Cl] | 4-(2-(5-chloro-2-(cyclopentyloxy)-4-methoxyphenyl)imidazo[1,2-a]pyridine-7-yl)morpholine | APCI | 428 |
| 91 | 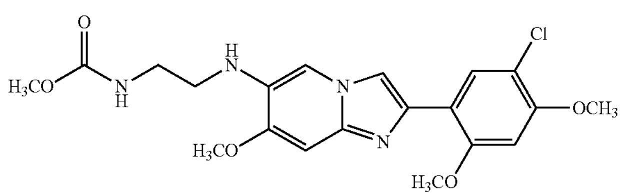 [SMILES: COC(=O)NCCNc1cn2cc(-c3cc(Cl)c(OC)cc3OC)nc2cc1OC] | methyl (2-((2-(5-chloro-2,4-dimethoxyphenyl)-7-methoxyimidazo[1,2-a]pyridine-6-yl)amino)ethyl)carbamate | ESI | 435 |
| 92 | 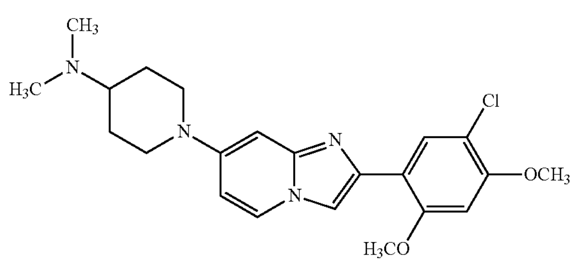 | 1-(2-(5-chloro-2,4-dimethoxyphenyl)imidazo[1,2-a]pyridine-7-yl)-N,N-dimethylpiperidin-4-amine | APCI | 415 |
| 93 | 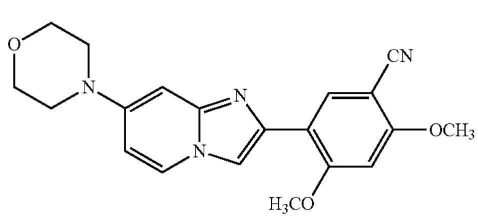 | 2,4-dimethoxy-5-(7-morpholinoimidazo[1,2-a]pyridine-2-yl)benzonitrile | ESI | 365 |

TABLE 1-continued

Compounds Table:

| Ex. No. | Structure | Name | MS Ionization | MS |
|---|---|---|---|---|
| 94 | 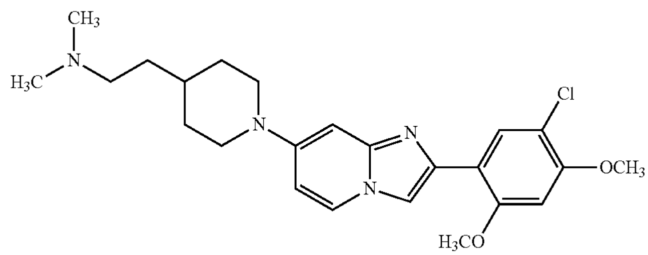 [SMILES: COc1cc(OC)c(-c2cn3ccc(N4CCC(CCN(C)C)CC4)cc3n2)cc1Cl] | 2-(1-(2-(5-chloro-2,4-dimethoxyphenyl)imidazo[1,2-a]pyridine-7-yl)piperidin-4-yl)-N,N-dimethylethanamine | ESI | 443 |
| 95 | 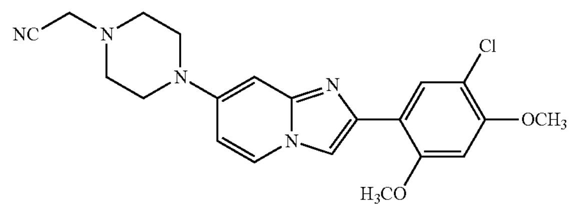 [SMILES: COc1cc(OC)c(-c2cn3ccc(N4CCN(CC#N)CC4)cc3n2)cc1Cl] | 2-(4-(2-(5-chloro-2,4-dimethoxyphenyl)imidazo[1,2-a]pyridine-7-yl)piperazin-1-yl)acetonitrile | ESI | 412 |
| 96 | 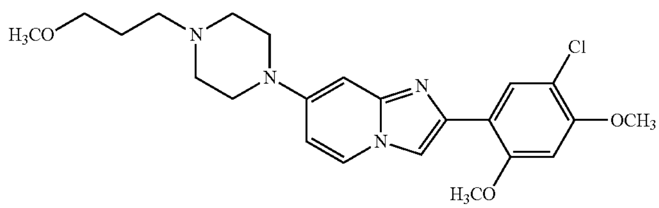 [SMILES: COCCCN1CCN(c2ccn3cc(-c4cc(Cl)c(OC)cc4OC)nc3c2)CC1] | 2-(5-chloro-2,4-dimethoxyphenyl)-7-(4-(3-methoxypropyl)piperazin-1-yl)imidazo[1,2-a]pyridine | APCI | 445 |
| 97 | 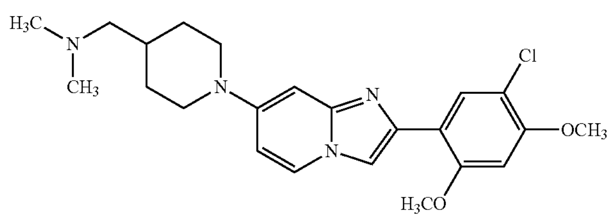 [SMILES: COc1cc(OC)c(-c2cn3ccc(N4CCC(CN(C)C)CC4)cc3n2)cc1Cl] | 1-(1-(2-(5-chloro-2,4-dimethoxyphenyl)imidazo[1,2-a]pyridine-7-yl)piperidin-4-yl)-N,N-dimethylmethanamine | ESI | 429 |
| 98 | 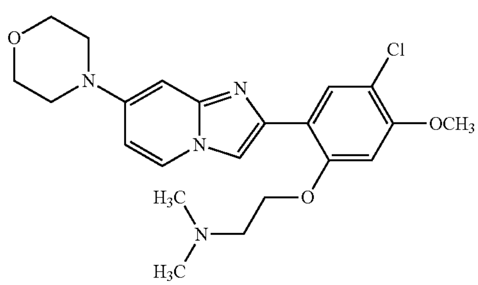 [SMILES: COc1cc(OCCN(C)C)c(-c2cn3ccc(N4CCOCC4)cc3n2)cc1Cl] | 2-(4-chloro-5-methoxy-2-(7-morpholinoimidazo[1,2-a]pyridine-2-yl)phenoxy)-N,N-dimethylethanamine | ESI | 431 |
| 99 | 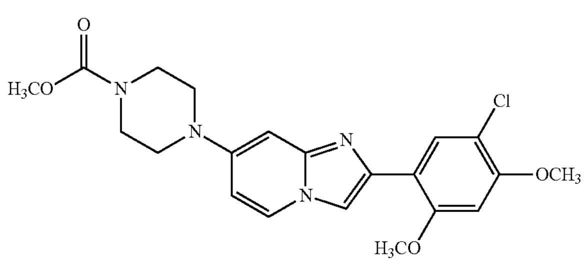 [SMILES: COC(=O)N1CCN(c2ccn3cc(-c4cc(Cl)c(OC)cc4OC)nc3c2)CC1] | methyl 4-(2-(5-chloro-2,4-dimethoxyphenyl)imidazo[1,2-a]pyridine-7-yl)piperazine-1-carboxylate | ESI | 431 |

TABLE 1-continued

Compounds Table:

| Ex. No. | Structure | Name | MS Ionization | MS |
|---|---|---|---|---|
| 100 | 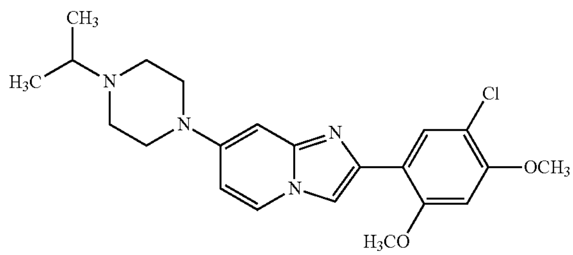 [SMILES: COc1cc(OC)c(-c2cn3ccc(N4CCN(C(C)C)CC4)cc3n2)cc1Cl] | 2-(5-chloro-2,4-dimethoxyphenyl)-7-(4-isopropylpiperazin-1-yl)imidazo[1,2-a]pyridine | APCI | 415 |
| 101 | 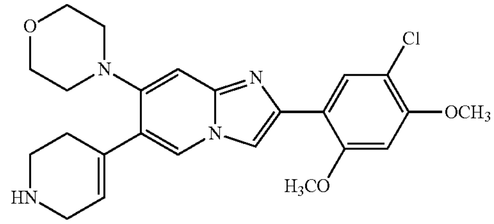 [SMILES: COc1cc(OC)c(-c2cn3cc(C4=CCNCC4)c(N4CCOCC4)cc3n2)cc1Cl] | 4-(2-(5-chloro-2,4-dimethoxyphenyl)-6-(1,2,3,6-tetrahydropyridin-4-yl)imidazo[1,2-a]pyridine-7-yl)morpholine | ESI | 455 |
| 102 | 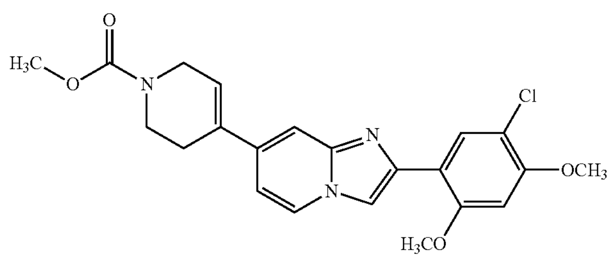 [SMILES: COC(=O)N1CC=C(c2ccn3cc(-c4cc(Cl)c(OC)cc4OC)nc3c2)CC1] | methyl 4-(2-(5-chloro-2,4-dimethoxyphenyl)imidazo[1,2-a]pyridine-7-yl)-5,6-dihydropyridine-1(2H)-carboxylate | ESI | 428 |
| 103 | 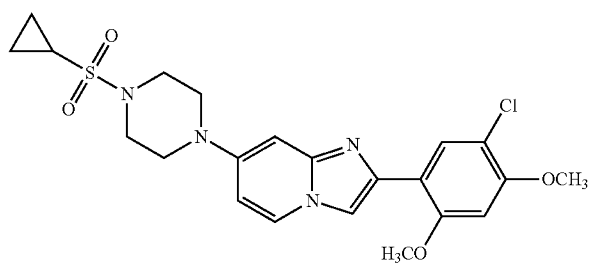 [SMILES: COc1cc(OC)c(-c2cn3ccc(N4CCN(S(=O)(=O)C5CC5)CC4)cc3n2)cc1Cl] | 2-(5-chloro-2,4-dimethoxyphenyl)-7-(4-(cyclopropylsulfonyl)piperazin-1-yl)imidazo[1,2-a]pyridine | ESI | 477 |
| 104 | 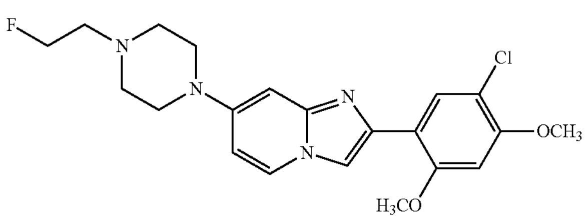 [SMILES: COc1cc(OC)c(-c2cn3ccc(N4CCN(CCF)CC4)cc3n2)cc1Cl] | 2-(5-chloro-2,4-dimethoxyphenyl)-7-(4-(2-fluoroethyl)piperazin-1-yl)imidazo[1,2-a]pyridine | ESI | 419 |
| 105 | 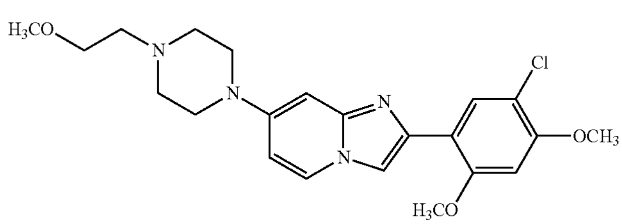 [SMILES: COCCN1CCN(c2ccn3cc(-c4cc(Cl)c(OC)cc4OC)nc3c2)CC1] | 2-(5-chloro-2,4-dimethoxyphenyl)-7-(4-(2-methoxyethyl)piperazin-1-yl)imidazo[1,2-a]pyridine | APCI | 431 |

TABLE 1-continued

Compounds Table:

| Ex. No. | Structure | Name | MS Ionization | MS |
|---|---|---|---|---|
| 106 | 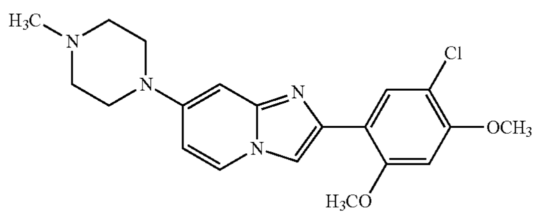 | 2-(5-chloro-2,4-dimethoxyphenyl)-7-(4-methylpiperazin-1-yl)imidazo[1,2-a]pyridine | ESI | 387 |
| 107 | 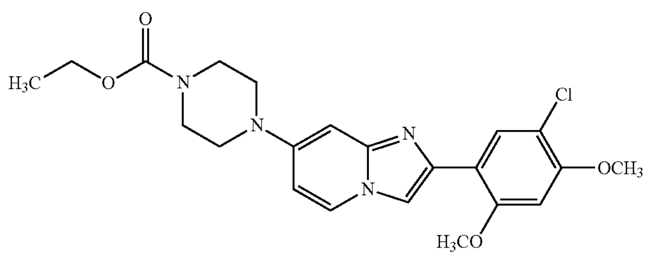 [SMILES: CCOC(=O)N1CCN(c2ccn3cc(-c4cc(Cl)c(OC)cc4OC)nc3c2)CC1] | ethyl 4-(2-(5-chloro-2,4-dimethoxyphenyl)imidazo[1,2-a]pyridine-7-yl)piperazine-1-carboxylate | ESI | 445 |
| 108 | 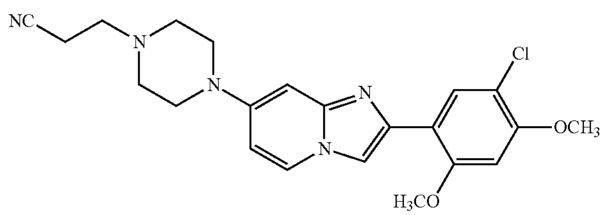 | 3-(4-(2-(5-chloro-2,4-dimethoxyphenyl)imidazo[1,2-a]pyridine-7-yl)piperazin-1-yl)propanenitrile | APCI | 426 |
| 109 | 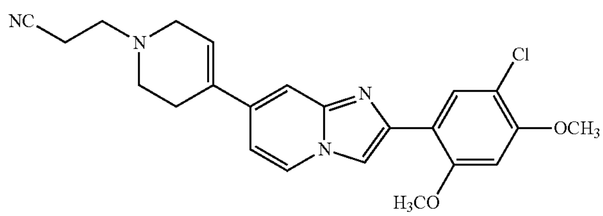 | 3-(4-(2-(5-chloro-2,4-dimethoxyphenyl)imidazo[1,2-a]pyridine-7-yl)-5,6-dihydropyridin-1(2H)-yl)propanenitrile | ESI | 423 |
| 110 | 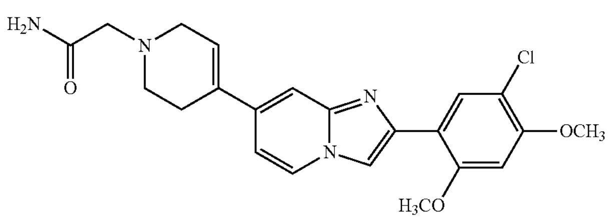 [SMILES: COc1cc(OC)c(-c2cn3ccc(C4=CCN(CC(N)=O)CC4)cc3n2)cc1Cl] | 2-(4-(2-(5-chloro-2,4-dimethoxyphenyl)imidazo[1,2-a]pyridine-7-yl)-5,6-dihydropyridin-1(2H)-yl)acetamide | ESI | 427 |
| 111 | 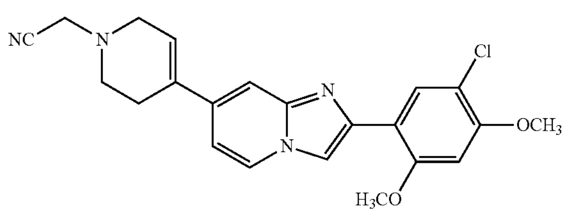 | 2-(4-(2-(5-chloro-2,4-dimethoxyphenyl)imidazo[1,2-a]pyridine-7-yl)-5,6-dihydropyridin-1(2H)-yl)acetonitrile | ESI | 409 |

TABLE 1-continued

Compounds Table:

| Ex. No. | Structure | Name | MS Ionization | MS |
|---|---|---|---|---|
| 112 | 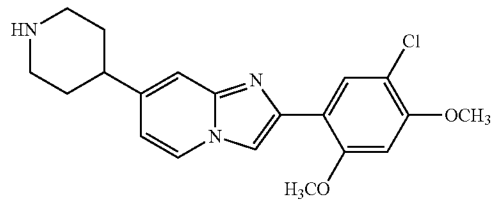 [SMILES: COc1cc(OC)c(-c2cn3ccc(C4CCNCC4)cc3n2)cc1Cl] | 2-(5-chloro-2,4-dimethoxyphenyl)-7-(piperidin-4-yl)imidazo[1,2-a]pyridine | ESI | 372 |
| 113 | 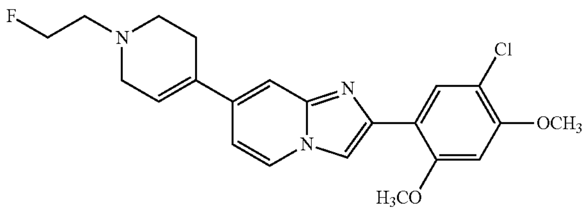 [SMILES: COc1cc(OC)c(-c2cn3ccc(C4=CCN(CCF)CC4)cc3n2)cc1Cl] | 2-(5-chloro-2,4-dimethoxyphenyl)-7-(1-(2-fluoroethyl)-1,2,3,6-tetrahydropyridin-4-yl)imidazo[1,2-a]pyridine | ESI | 416 |
| 114 | 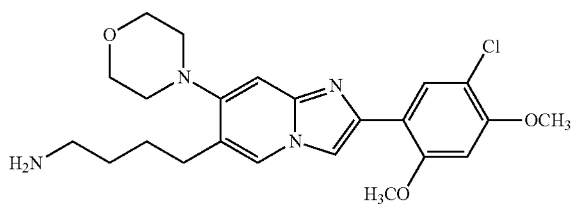 [SMILES: COc1cc(OC)c(-c2cn3cc(CCCCN)c(N4CCOCC4)cc3n2)cc1Cl] | 4-(2-(5-chloro-2,4-dimethoxyphenyl)-7-morpholinoimidazo[1,2-a]pyridine-6-yl)butan-1-amine | APCI | 445 |
| 115 | 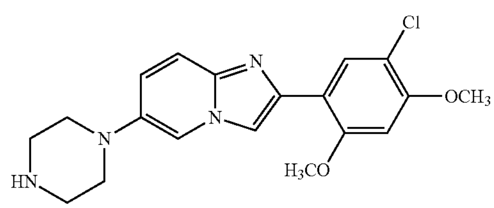 [SMILES: COc1cc(OC)c(-c2cn3cc(N4CCNCC4)ccc3n2)cc1Cl] | 2-(5-chloro-2,4-dimethoxyphenyl)-6-(piperazin-1-yl)imidazo[1,2-a]pyridine | APCI | 373 |
| 116 | 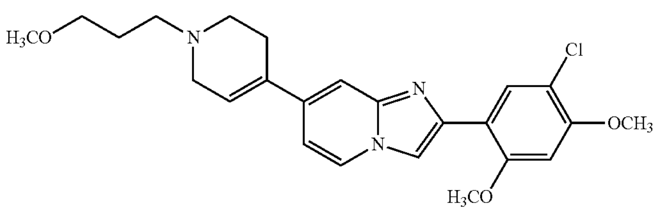 [SMILES: COCCCN1CC=C(c2ccn3cc(-c4cc(Cl)c(OC)cc4OC)nc3c2)CC1] | 2-(5-chloro-2,4-dimethoxyphenyl)-7-(1-(3-methoxypropyl)-1,2,3,6-tetrahydropyridin-4-yl)imidazo[1,2-a]pyridine | ESI | 442 |
| 117 | 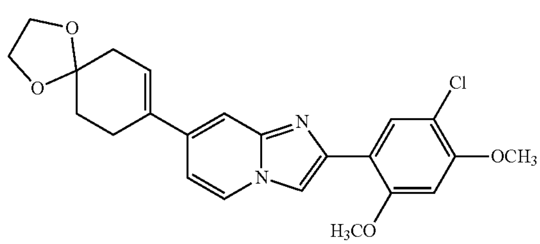 [SMILES: COc1cc(OC)c(-c2cn3ccc(C4=CCC5(CC4)OCCO5)cc3n2)cc1Cl] | 2-(5-chloro-2,4-dimethoxyphenyl)-7-(1,4-dioxaspiro[4.5]dec-7-en-8-yl)imidazo[1,2-a]pyridine | ESI | 427 |
| 118 | 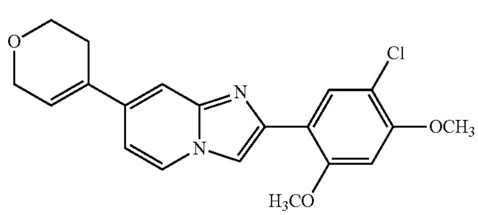 [SMILES: COc1cc(OC)c(-c2cn3ccc(C4=CCOCC4)cc3n2)cc1Cl] | 2-(5-chloro-2,4-dimethoxyphenyl)-7-(3,6-dihydro-2H-pyran-4-yl)imidazo[1,2-a]pyridine | ESI | 371 |

TABLE 1-continued

Compounds Table:

| Ex. No. | Structure | Name | MS Ionization | MS |
|---|---|---|---|---|
| 119 | 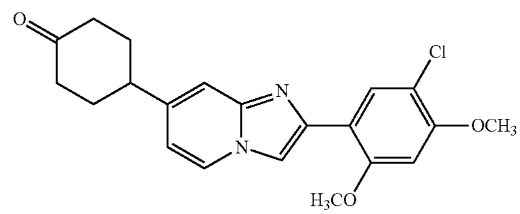 [SMILES: COc1cc(OC)c(-c2cn3ccc(C4CCC(=O)CC4)cc3n2)cc1Cl] | 4-(2-(5-chloro-2,4-dimethoxyphenyl)imidazo[1,2-a]pyridine-7-yl)cyclohexanone | ESI | 385 |
| 120 | 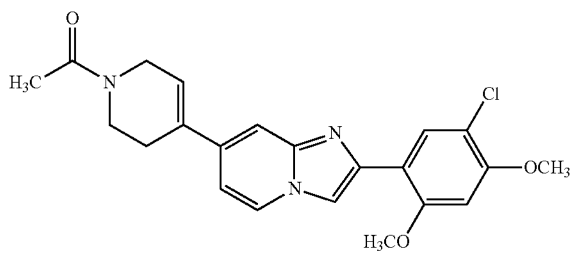 [SMILES: COc1cc(OC)c(-c2cn3ccc(C4=CCN(C(C)=O)CC4)cc3n2)cc1Cl] | 1-(4-(2-(5-chloro-2,4-dimethoxyphenyl)imidazo[1,2-a]pyridine-7-yl)-5,6-dihydropyridin-1(2H)-yl)ethanone | ESI | 412 |
| 121 | 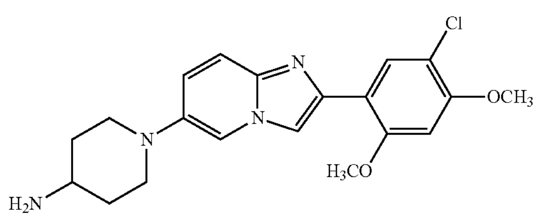 [SMILES: COc1cc(OC)c(-c2cn3cc(N4CCC(N)CC4)ccc3n2)cc1Cl] | 1-(2-(5-chloro-2,4-dimethoxyphenyl)imidazo[1,2-a]pyridine-6-yl)piperidin-4-amine | ESI | 387 |
| 122 | 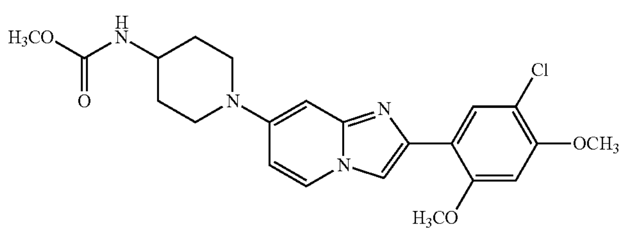 [SMILES: COC(=O)NC1CCN(c2ccn3cc(-c4cc(Cl)c(OC)cc4OC)nc3c2)CC1] | methyl (1-(2-(5-chloro-2,4-dimethoxyphenyl)imidazo[1,2-a]pyridine-7-yl)piperidin-4-yl)carbamate | ESI | 445 |
| 123 | 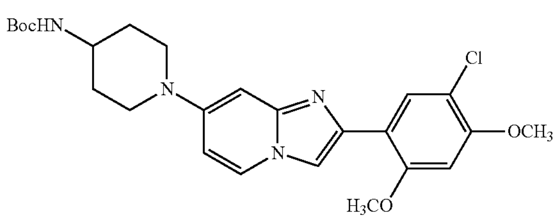 [SMILES: COc1cc(OC)c(-c2cn3ccc(N4CCC(NC(=O)OC(C)(C)C)CC4)cc3n2)cc1Cl] | N-(1-(2-(5-chloro-2,4-dimethoxyphenyl)imidazo[1,2-a]pyridine-7-yl)piperidin-4-yl)pivalamide | ESI APCI | 471 |
| 124 | 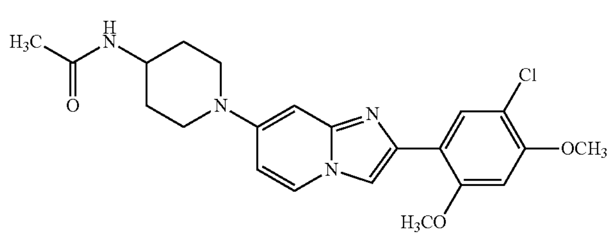 [SMILES: COc1cc(OC)c(-c2cn3ccc(N4CCC(NC(C)=O)CC4)cc3n2)cc1Cl] | N-(1-(2-(5-chloro-2,4-dimethoxyphenyl)imidazo[1,2-a]pyridine-7-yl)piperidin-4-yl)acetamide | ESI | 429 |

TABLE 1-continued

Compounds Table:

| Ex. No. | Structure | Name | MS Ionization | MS |
|---|---|---|---|---|
| 125 | 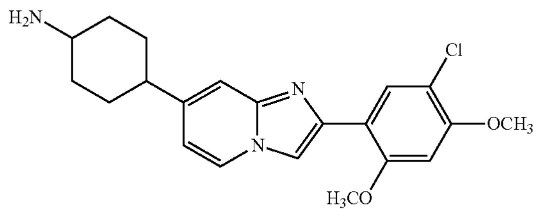 | 4-(2-(5-chlolo-2,4-dimethoxyphenyl)imidazo[1,2-a]pyridine-7-yl)cyclohexanamine | APCI | 386 |
| 126 | 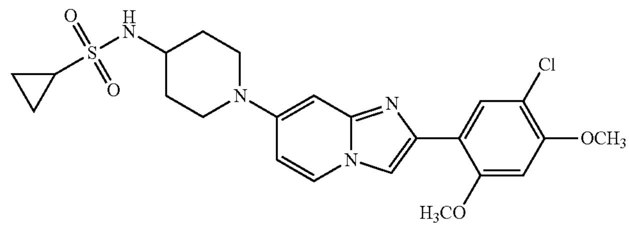 [SMILES: COc1cc(OC)c(-c2cn3ccc(N4CCC(NS(=O)(=O)C5CC5)CC4)cc3n2)cc1Cl] | N-(1-(2-(5-chloro-2,4-dimethoxyphenyl)imidazo[1,2-a]pyridine-7-yl)piperidin-4-yl)cyclopropanesulfonamide | APCI | 491 |
| 127 | 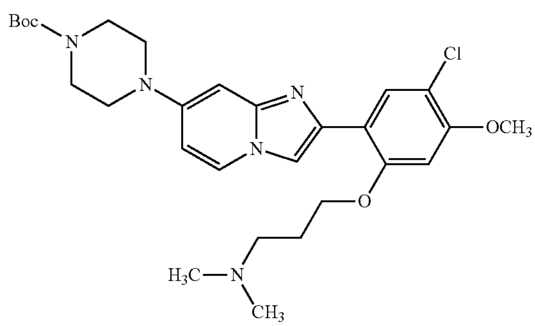 [SMILES: COc1cc(OCCCN(C)C)c(-c2cn3ccc(N4CCN(C(=O)OC(C)(C)C)CC4)cc3n2)cc1Cl] | tert-butyl 4-(2-(5-chloro-2-(3-(dimethylamino)propoxy)-4-methoxyphenyl)imidazo[1,2-a]pyridine-7-yl)piperazine-1-carboxylate | ESI | 544 |
| 128 | 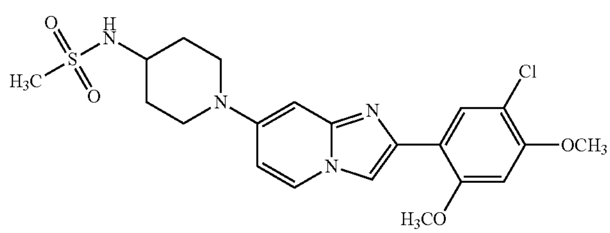 [SMILES: COc1cc(OC)c(-c2cn3ccc(N4CCC(NS(C)(=O)=O)CC4)cc3n2)cc1Cl] | N-(1-(2-(5-chloro-2,4-dimethoxyphenyl)imidazo[1,2-a]pyridine-7-yl)piperidin-4-yl)methanesulfonamide | APCI | 465 |
| 129 | 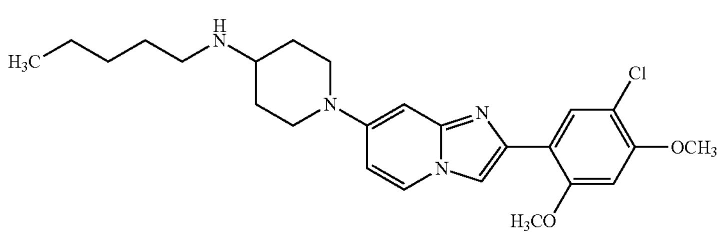 [SMILES: CCCCCNC1CCN(c2ccn3cc(-c4cc(Cl)c(OC)cc4OC)nc3c2)CC1] | 1-(2-(5-chloro-2,4-dimethoxyphenyl)imidazo[1,2-a]pyridine-7-yl)-N-pentylpiperidin-4-amine | APCI | 457 |
| 130 | 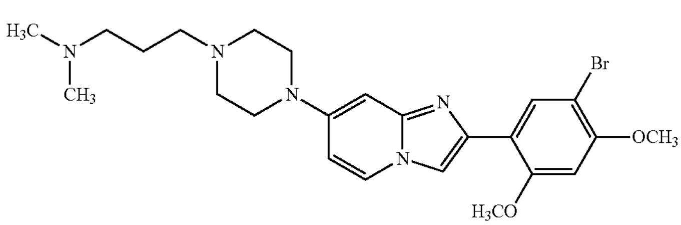 [SMILES: COc1cc(OC)c(-c2cn3ccc(N4CCN(CCCN(C)C)CC4)cc3n2)cc1Br] | 3-(4-(2-(5-bromo-2,4-dimethoxyphenyl)imidazo[1,2-a]pyridine-7-yl)piperazin-1-yl)-N,N-methylpropan-1-amine | APCI | 502 |

TABLE 1-continued

Compounds Table:

| Ex. No. | Structure | Name | MS Ionization | MS |
|---|---|---|---|---|
| 131 | 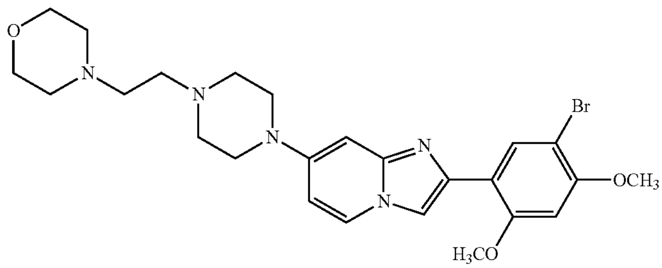 [SMILES: COc1cc(OC)c(-c2cn3ccc(N4CCN(CCN5CCOCC5)CC4)cc3n2)cc1Br] | 4-(2-(4-(2-(5-bromo-2,4-dimethoxyphenyl)imidazo[1,2-a]pyridine-7-yl)piperazin-1-yl)ethyl)morpholine | APCI | 530 |
| 132 | 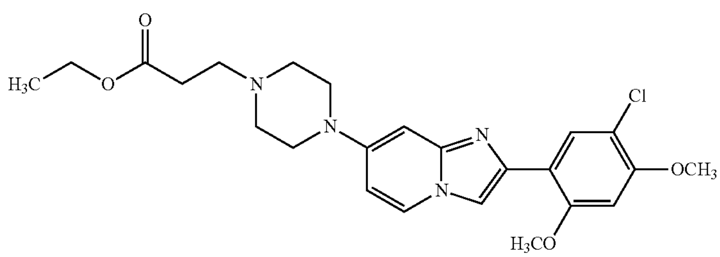 [SMILES: CCOC(=O)CCN1CCN(c2ccn3cc(-c4cc(Cl)c(OC)cc4OC)nc3c2)CC1] | ethyl 3-(4-(2-(5-chloro-2,4-dimethoxyphenyl)imidazo[1,2-a]pyridine-7-yl)piperazin-1-yl)propanoate | ESI | 473 |
| 133 | 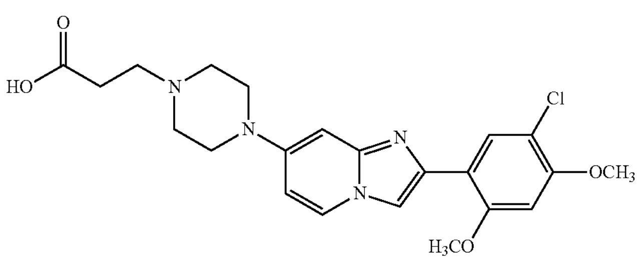 | 3-(4-(2-(5-chloro-2,4-dimethoxyphenyl)imidazo[1,2-a]pyridine-7-yl)piperazin-1-yl)propanoic acid | ESI | 445 |
| 134 | 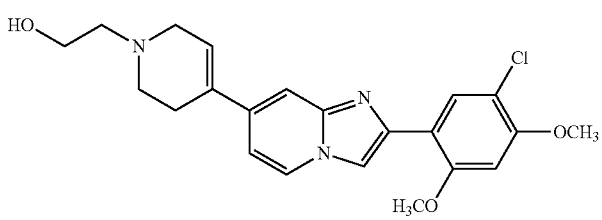 [SMILES: COc1cc(OC)c(-c2cn3ccc(C4=CCN(CCO)CC4)cc3n2)cc1Cl] | 2-(4-(2-(5-chloro-2,4-dimethoxyphenyl)imidazo[1,2-a]pyridine-7-yl)-5,6-dihydropyridin-3(2H)-yl)ethanol | ESI | 414 |
| 135 | 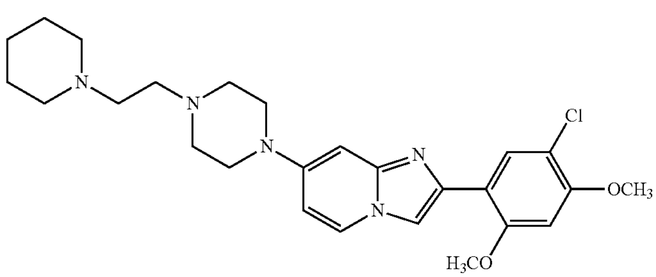 [SMILES: COc1cc(OC)c(-c2cn3ccc(N4CCN(CCN5CCCCC5)CC4)cc3n2)cc1Cl] | 2-(5-chloro-2,4-dimethoxyphenyl)-7-(4-(2-(piperidin-1-yl)ethyl)piperazin-1-yl)imidazo[1,2-a]pyridine | ESI | 484 |

TABLE 1-continued

Compounds Table:

| Ex. No. | Structure | Name | MS Ionization | MS |
|---|---|---|---|---|
| 136 | 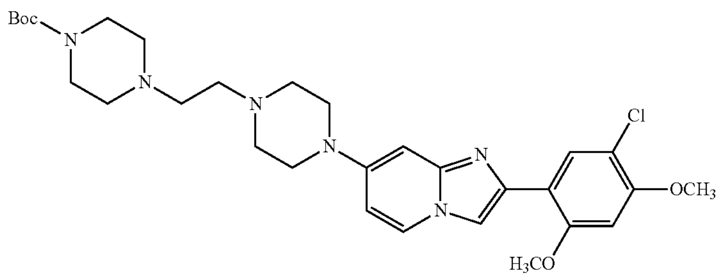 [SMILES: COc1cc(OC)c(-c2cn3ccc(N4CCN(CCN5CCN(C(=O)OC(C)(C)C)CC5)CC4)cc3n2)cc1Cl] | tert-butyl 4-(2-(4-(2-(5-chloro-2,4-dimethoxyphenyl)imidazo[1,2-a]pyridine-7-yl)piperazin-1-yl)ethyl)piperazine-3-carboxylate | ESI | 585 |
| 137 | 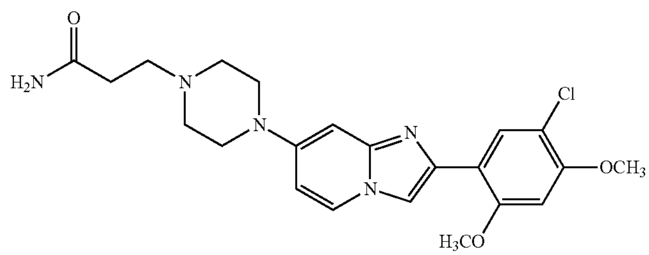 [SMILES: COc1cc(OC)c(-c2cn3ccc(N4CCN(CCC(N)=O)CC4)cc3n2)cc1Cl] | 3-(4-(2-(5-chloro-2,4-dimethoxyphenyl)imidazo[1,2-a]pyridine-7-yl]piperazin-1-yl)propanamide | ESI | 444 |
| 138 | 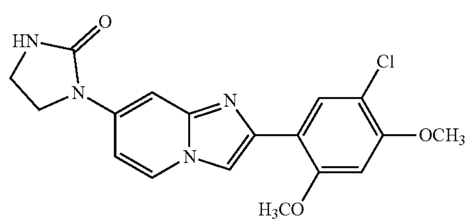 [SMILES: COc1cc(OC)c(-c2cn3ccc(N4CCNC4=O)cc3n2)cc1Cl] | 1-(2-(5-chloro-2,4-dimethoxyphenyl)imidazo[1,2-a]pyridine-7-yl)imidazolidin-2-one | ESI | 373 |
| 139 | 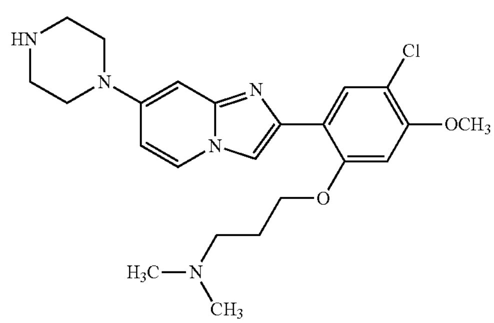 | 3-(4-chloro-5-methoxy-2-(7-(piperazin-1-yl)imidazo[1,2-a]pyridine-2-yl)phenoxy)-N,N-dimethylpropan-1-amine | ESI | 444 |
| 140 | 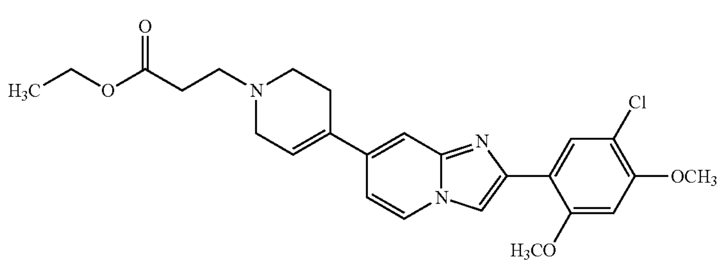 [SMILES: CCOC(=O)CCN1CC=C(c2ccn3cc(-c4cc(Cl)c(OC)cc4OC)nc3c2)CC1] | ethyl 3-(4-(2-(5-chloro-2,4-dimethoxyphenyl)imidazo[1,2-a]pyridine-7-yl)-5,6-dihydropyridin-1(2H)-yl)propanoate | ESI | 470 |

TABLE 1-continued

Compounds Table:

| Ex. No. | Structure | Name | MS Ionization | MS |
|---|---|---|---|---|
| 141 | 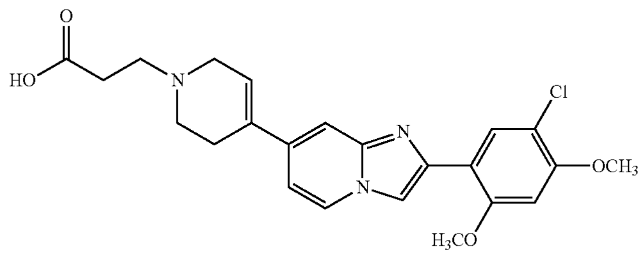 [SMILES: COc1cc(OC)c(-c2cn3ccc(C4=CCN(CCC(=O)O)CC4)cc3n2)cc1Cl] | 3-(4-(2-(5-chloro-2,4-dimethoxyphenyl)imidazo[1,2-a]pyridine-7-yl)-5,6-dihydropyridin-1(2H)-yl)propanoic acid | ESI | 442 |
| 142 | 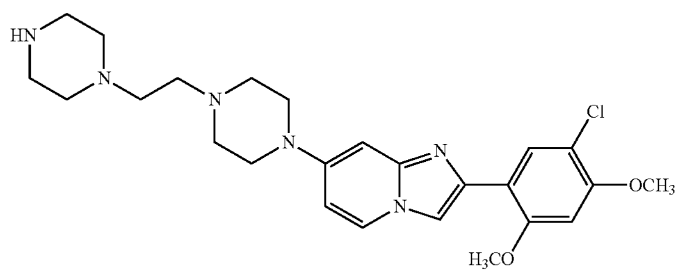 [SMILES: COc1cc(OC)c(-c2cn3ccc(N4CCN(CCN5CCNCC5)CC4)cc3n2)cc1Cl] | 2-(5-chloro-2,4-dimethoxyphenyl)-7-(4-(2-(piperazin-1-yl)ethyl)piperazin-1-yl)imidazo[1,2-a]pyridine | ESI | 485 |
| 143 | 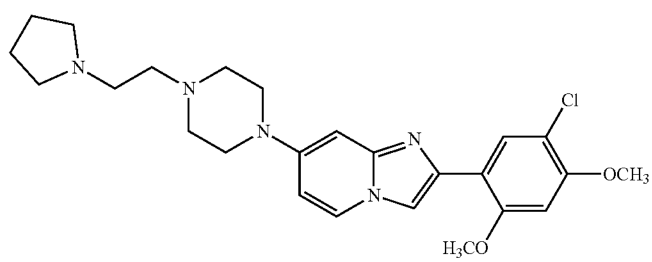 [SMILES: COc1cc(OC)c(-c2cn3ccc(N4CCN(CCN5CCCC5)CC4)cc3n2)cc1Cl] | 2-(5-chloro-2,4-dimethoxyphenyl)-7-(4-(2-(pyrrolidin-1-yl)ethyl)piperazin-1-yl)imidazo[1,2-a]pyridine | ESI | 470 |
| 144 | 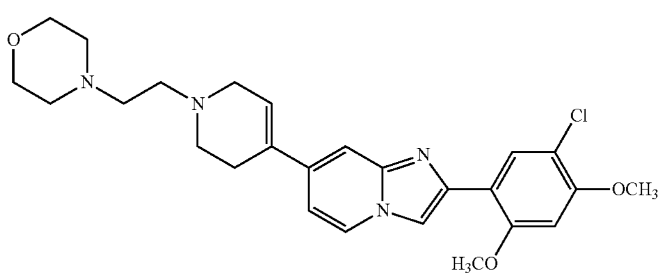 [SMILES: COc1cc(OC)c(-c2cn3ccc(C4=CCN(CCN5CCOCC5)CC4)cc3n2)cc1Cl] | 4-(2-(4-(2-(5-chloro-2,4-dimethoxyphenyl)imidazo[1,2-a]pyridine-7-yl)-5,6-dihydropyridin-1(2H)-yl)ethyl)morpholine | ESI | |
| 145 | 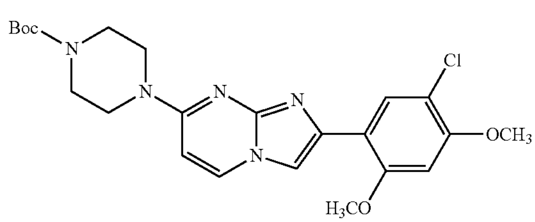 [SMILES: COc1cc(OC)c(-c2cn3ccc(N4CCN(C(=O)OC(C)(C)C)CC4)nc3n2)cc1Cl] | tert-butyl 4-(2-(5-chloro-2,4-dimethoxyphenyl)imidazo[1,2-a]pyrimidin-7-yl)piperazine-1-carboxylate | ESI | 474 |

TABLE 1-continued

Compounds Table:

| Ex. No. | Structure | Name | MS Ionization | MS |
|---|---|---|---|---|
| 146 | 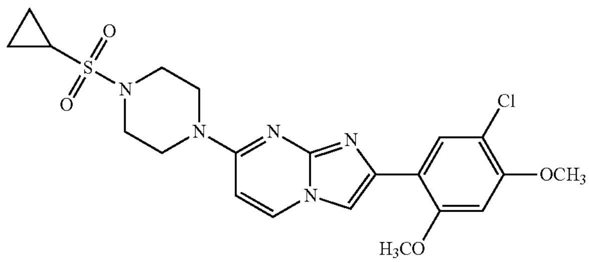 | 2-(5-chloro-2,4-dimethoxyphenyl)-7-(4-(cyclopropylsulfonyl)piperazin-1-yl)imidazo[1,2-a]pyrimidine | ESI | 478 |
| 147 | 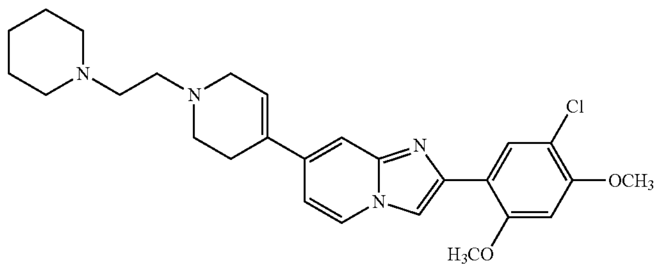 | 2-(5-chloro-2,4-dimethoxyphenyl)-7-(1-(2-(piperidin-1-yl)ethyl)-1,2,3,6-tetrahydropyridin-4-yl)imidazo[1,2-a]pyridine | ESI | 482 |
| 148 | 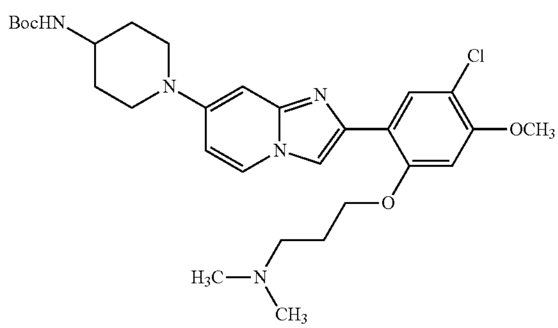 [SMILES: COc1cc(OCCCN(C)C)c(-c2cn3ccc(N4CCC(NC(=O)OC(C)(C)C)CC4)cc3n2)cc1Cl] | tert-butyl (1-(2-(5-chloro-2-(3-(dimethylamino)propoxy)-4-methoxyphenyl)imidazo[1,2-a]pyridine-7-yl)piperidin-4-yl)carbamate | APCI | 558 |
| 149 | 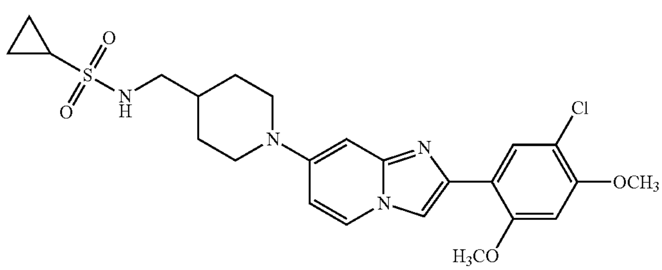 [SMILES: COc1cc(OC)c(-c2cn3ccc(N4CCC(CNS(=O)(=O)C5CC5)CC4)cc3n2)cc1Cl] | N-((1-(2-(5-chloro-2,4-dimethoxyphenyl)imidazo[1,2-a]pyridine-7-yl)piperidin-4-yl)methyl)cyclopropane-sulfonamide | APCI | 505 |
| 150 | 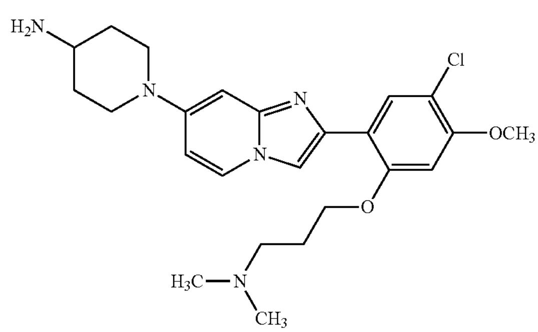 | 1-(2-(5-chloro-2-(3-(dimethylamino)propoxy)-4-methoxyphenyl)imidazo[1,2-a]pyridine-7-yl)piperidin-4-amine | APCI | 458 |

TABLE 1-continued

Compounds Table:

| Ex. No. | Structure | Name | MS Ionization | MS |
|---|---|---|---|---|
| 151 | 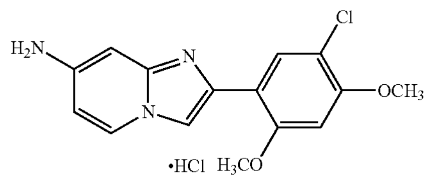 [SMILES: COc1cc(OC)c(-c2cn3ccc(N)cc3n2)cc1Cl ; Cl] | 2-(5-chloro-2,4-dimethoxyphenyl)imidazo[1,2-a]pyridine-7-amine hydrochloride | ESI | 304 |
| 152 | 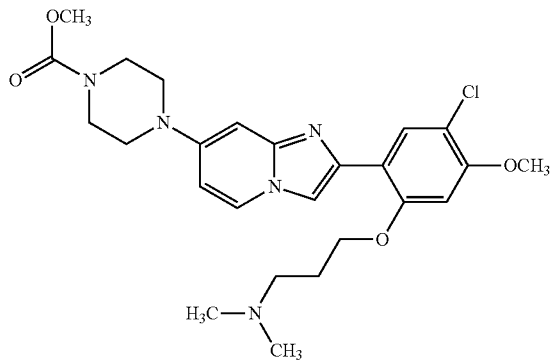 [SMILES: COC(=O)N1CCN(c2ccn3cc(-c4cc(Cl)c(OC)cc4OCCCN(C)C)nc3c2)CC1] | methyl 4-(2-(5-chloro-2-(3-(dimethylamino)propoxy)-4-methoxyphenyl)imidazo[1,2-a]pyridine-7-yl)piperazine-1-carboxylate | ESI | 502 |
| 153 | 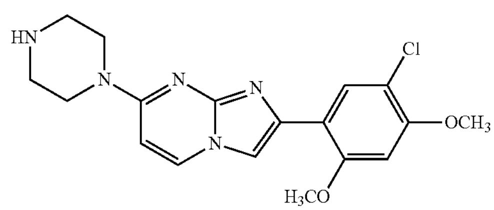 [SMILES: COc1cc(OC)c(-c2cn3ccc(N4CCNCC4)nc3n2)cc1Cl] | 2-(5-chloro-2,4-dimethoxyphenyl)-7-(piperazin-1-yl)imidazo[1,2-a]pyrimidine | ESI | 374 |
| 154 | 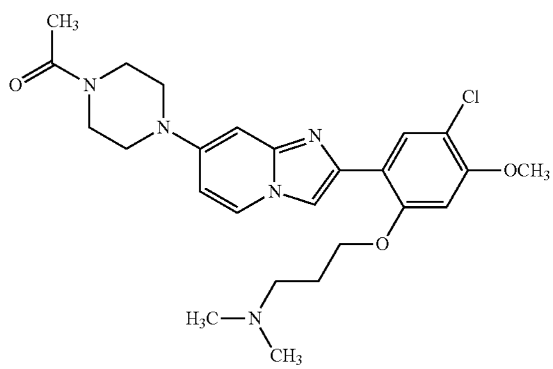 [SMILES: COc1cc(OCCCN(C)C)c(-c2cn3ccc(N4CCN(C(C)=O)CC4)cc3n2)cc1Cl] | 1-(4-(2-(5-chloro-2-(3-(dimethylamino)propoxy)-4-methoxyphenyl)imidazo[1,2-a]pyridine-7-yl)piperazin-1-yl)ethanone | ESI | 486 |
| 155 | 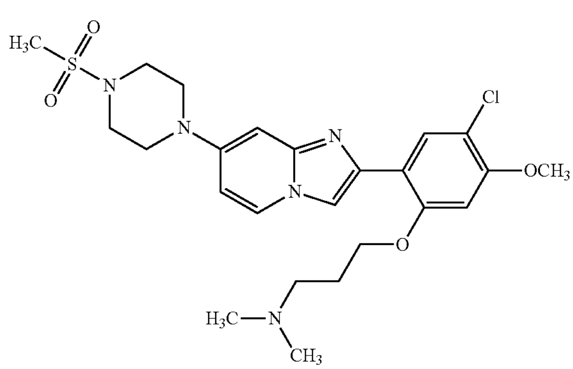 [SMILES: COc1cc(OCCCN(C)C)c(-c2cn3ccc(N4CCN(S(C)(=O)=O)CC4)cc3n2)cc1Cl] | 3-(4-chloro-5-methoxy-2-(7-(4-(methylsulfonyl)piperazin-1-yl)imidazo[1,2-a]pyridine-2-yl)phenoxy)-N,N-dimethylpropan-1-amine | APCI | 522 |

TABLE 1-continued

Compounds Table:

| Ex. No. | Structure | Name | MS Ionization | MS |
|---|---|---|---|---|
| 156 | 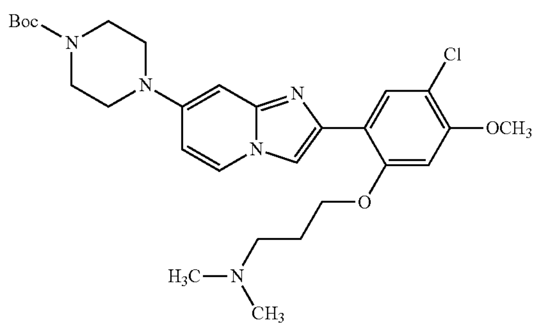 | 1-(4-(2-(5-chloro-2-(3-(dimethylamino)propoxy)-4-methoxyphenyl)imidazo[1,2-a]pyridine-7-yl)piperazin-1-yl)-2,2-dimethylpropan-1-one | ESI | 528 |
| 157 | 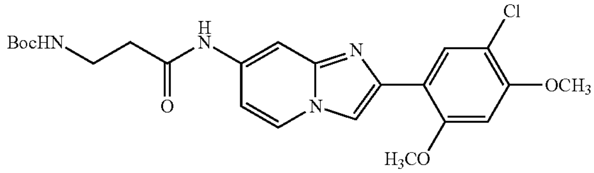 [SMILES: COc1cc(OC)c(-c2cn3ccc(NC(=O)CCNC(=O)OC(C)(C)C)cc3n2)cc1Cl] | tert-butyl (3-((2-(5-chloro-2,4-dimethoxyphenyl)imidazo[1,2-a]pyridine-7-yl)amino)-3-oxopropyl)carbamate | ESI | 475 |
| 158 | 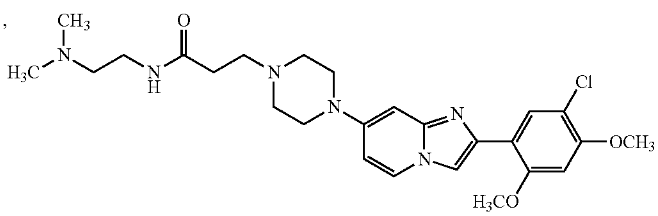 [SMILES: COc1cc(OC)c(-c2cn3ccc(N4CCN(CCC(=O)NCCN(C)C)CC4)cc3n2)cc1Cl] | 3-(4-(2-(5-chloro-2,4-dimethoxyphenyl)imidazo[1,2-a]pyridine-7-yl)piperazin-1-yl)-N-(2-(dimethylamino)ethyl)-propanamide | ESI | 515 |
| 159 | 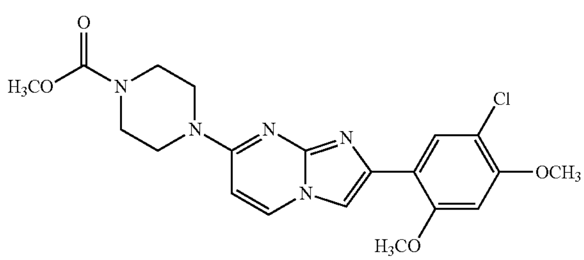 | methyl 4-(2-(5-chloro-2,4-dimethoxyphenyl)imidazo[1,2-a]pyrimidin-7-yl)piperazine-1-carboxylate | ESI | 432 |
| 160 | 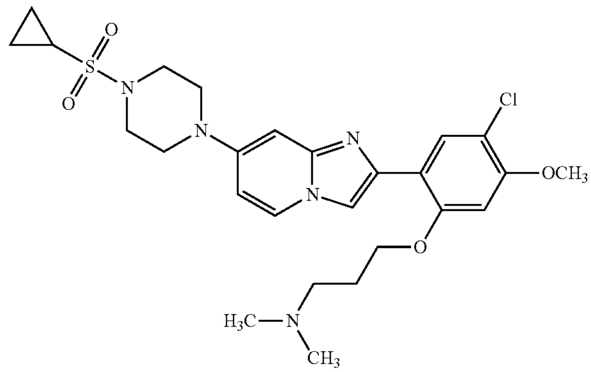 [SMILES: COc1cc(OCCCN(C)C)c(-c2cn3ccc(N4CCN(S(=O)(=O)C5CC5)CC4)cc3n2)cc1Cl] | 3-(4-chloro-2-(7-(4-(cyclopropylsulfonyl)piperazin-1-yl)imidazo[1,2-a]pyridine-2-yl)-5-methoxyphenoxy)-N,N-dimethylpropan-1-amine | ESI | 548 |

TABLE 1-continued

Compounds Table:

| Ex. No. | Structure | Name | MS Ionization | MS |
|---|---|---|---|---|
| 161 | 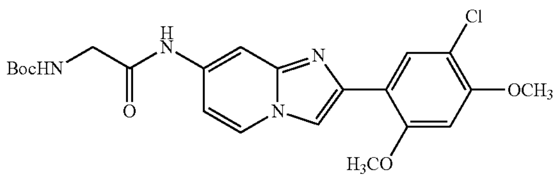 [SMILES: COc1cc(OC)c(-c2cn3ccc(NC(=O)CNC(=O)OC(C)(C)C)cc3n2)cc1Cl] | tert-butyl (2-((2-(5-chloro-2,4-dimethoxyphenyl)imidazo[1,2-a]pyridine-7-yl)amino)-2-oxoethyl)carbamate | ESI | 461 |
| 162 | 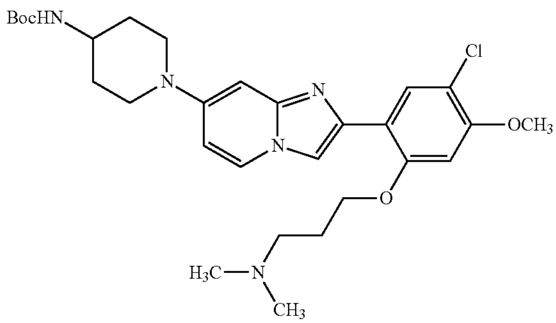 [SMILES: COc1cc(OCCCN(C)C)c(-c2cn3ccc(N4CCC(NC(=O)OC(C)(C)C)CC4)cc3n2)cc1Cl] | N-(1-(2-(5-chloro-2-(3-(dimethylamino)propoxy)-4-methoxyphenyl)imidazo[1,2-a]pyridine-7-yl)piperidin-4-yl)pivalamide | APCI | 542 |
| 163 | 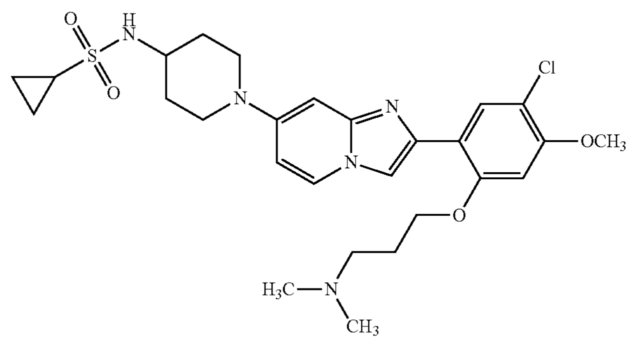 [SMILES: COc1cc(OCCCN(C)C)c(-c2cn3ccc(N4CCC(NS(=O)(=O)C5CC5)CC4)cc3n2)cc1Cl] | N-(1-(2-(5-chloro-2-(3-(dimethylamino)propoxy)-4-methoxyphenyl)imidazo[1,2-a]pyridine-7-yl)piperidin-4-yl)cyclopropanesulfonamide | ESI | 562 |
| 164 | 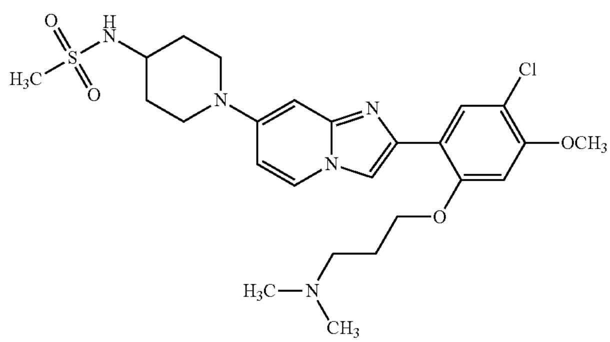 [SMILES: COc1cc(OCCCN(C)C)c(-c2cn3ccc(N4CCC(NS(C)(=O)=O)CC4)cc3n2)cc1Cl] | N-(1-(2-(5-chloro-2-(3-(dimethylamino)propoxy)-4-methoxyphenyl)imidazo[1,2-a]pyridine-7-yl)piperidin-4-yl)methanesulfonamide | APCI | 536 |
| 165 | 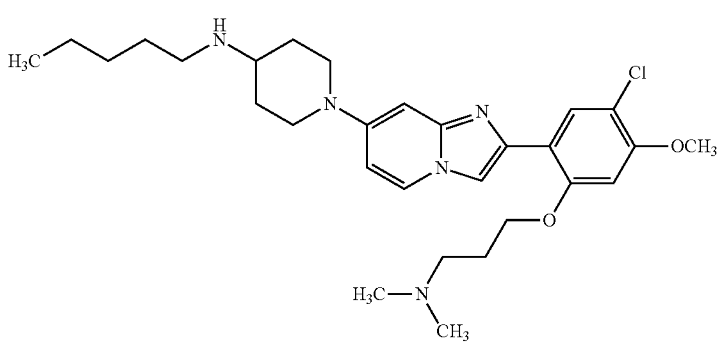 [SMILES: CCCCCNC1CCN(c2ccn3cc(-c4cc(Cl)c(OC)cc4OCCCN(C)C)nc3c2)CC1] | 1-(2-(5-chloro-2-(3-(dimethylamino)propoxy)-4-methoxyphenyl)imidazo[1,2-a]pyridine-7-yl)-N-pentylpiperidin-4-amine | APCI | 528 |

TABLE 1-continued

Compounds Table:

| Ex. No. | Structure | Name | MS Ionization | MS |
|---|---|---|---|---|
| 166 | 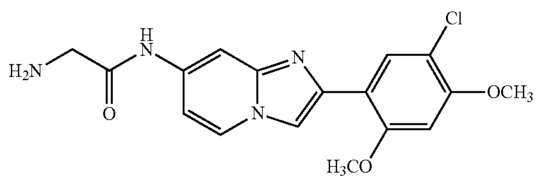 [SMILES: COc1cc(OC)c(-c2cn3ccc(NC(=O)CN)cc3n2)cc1Cl] | 2-amino-N-(2-(5-chloro-2,4-dimethoxyphenyl)imidazo[1,2-a]pyridine-7-yl)acetamide | ESI | 361 |
| 167 | 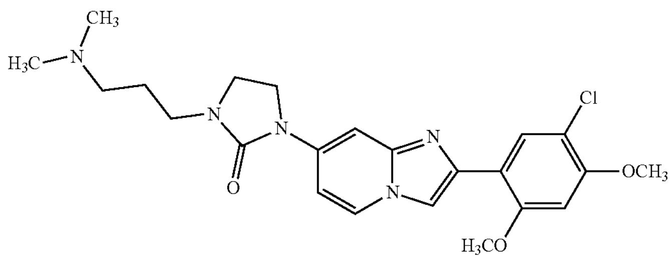 [SMILES: COc1cc(OC)c(-c2cn3ccc(N4CCN(CCCN(C)C)C4=O)cc3n2)cc1Cl] | 1-(2-(5-chloro-2,4-dimethoxyphenyl)imidazo[1,2-a]pyridine-7-yl)-3-(3-(dimethylamino)propyl)imidazolidin-2-one | ESI | 458 |
| 168 | 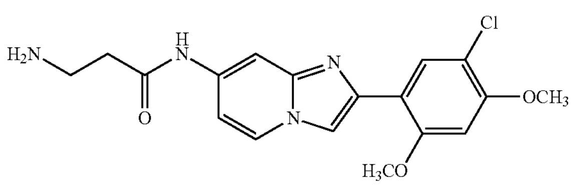 [SMILES: COc1cc(OC)c(-c2cn3ccc(NC(=O)CCN)cc3n2)cc1Cl] | 3-amino-N-(2-(5-chloro-2,4-dimethoxyphenyl)imidazo[1,2-a]pyridine-7-yl)propanamide | ESI | 375 |
| 169 | 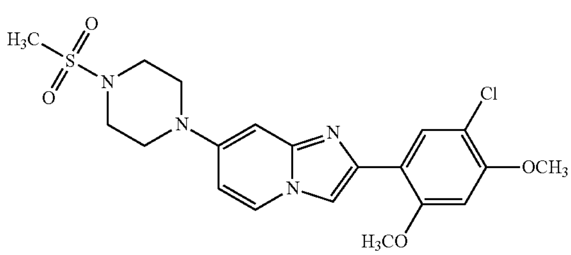 [SMILES: COc1cc(OC)c(-c2cn3ccc(N4CCN(S(C)(=O)=O)CC4)cc3n2)cc1Cl] | 2-(5-chloro-2,4-dimethoxyphenyl)-7-(4-(methylsulfonyl)piperazin-1-yl)imidazo[1,2-a]pyridine | ESI | 451 |
| 170 | 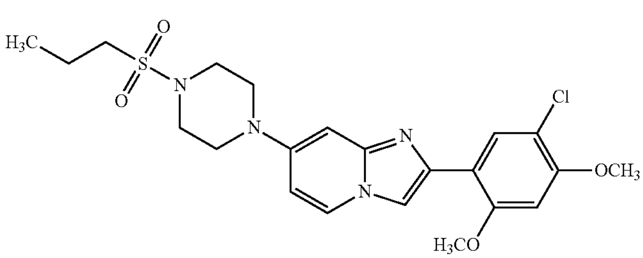 [SMILES: CCCS(=O)(=O)N1CCN(c2ccn3cc(-c4cc(Cl)c(OC)cc4OC)nc3c2)CC1] | 2-(5-chloro-2,4-dimethoxyphenyl)-7-(4-(propylsulfonyl)piperazin-1-yl)imidazo[1,2-a]pyridine | ESI | 479 |
| 171 | 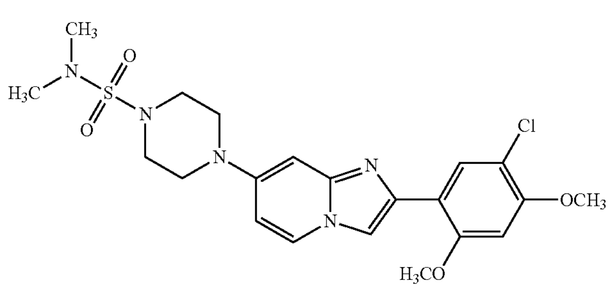 [SMILES: COc1cc(OC)c(-c2cn3ccc(N4CCN(S(=O)(=O)N(C)C)CC4)cc3n2)cc1Cl] | 4-(2-(5-chloro-2,4-dimethoxyphenyl)imidazo[1,2-a]pyridine-7-yl)-N,N-dimethylpiperazine-1-sulfonamide | ESI | 480 |

TABLE 1-continued

Compounds Table:

| Ex. No. | Structure | Name | MS Ionization | MS |
|---|---|---|---|---|
| 172 | 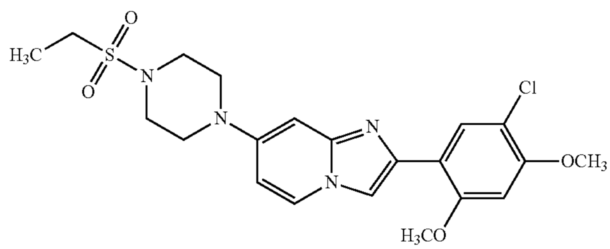 [SMILES: CCS(=O)(=O)N1CCN(c2ccn3cc(-c4cc(Cl)c(OC)cc4OC)nc3c2)CC1] | 2-(5-chloro-2,4-dimethoxyphenyl)-7-(4-(ethylsulfonyl)piperazin-1-yl)imidazo[1,2-a]pyridine | ESI | 465 |
| 173 | 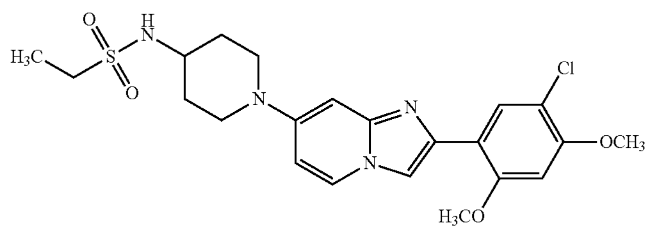 [SMILES: CCS(=O)(=O)NC1CCN(c2ccn3cc(-c4cc(Cl)c(OC)cc4OC)nc3c2)CC1] | N-(1-(2-(5-chloro-2,4-dimethoxyphenyl)imidazo[1,2-a]pyridine-7-yl)piperidin-4-yl)ethanesulfonamide | ESI | 479 |
| 174 | 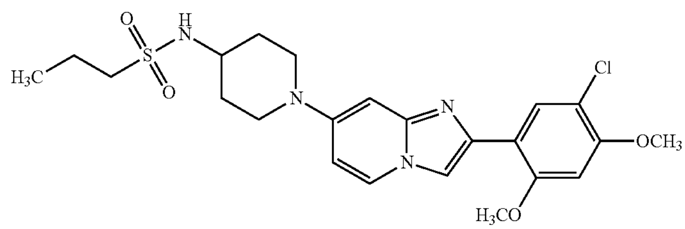 [SMILES: CCCS(=O)(=O)NC1CCN(c2ccn3cc(-c4cc(Cl)c(OC)cc4OC)nc3c2)CC1] | N-(1-(2-(5-chloro-2,4-dimethoxyphenyl)imidazo[1,2-a]pyridine-7-yl)piperidin-4-yl)propane-1-sulfonamide | ESI | 493 |
| 175 | 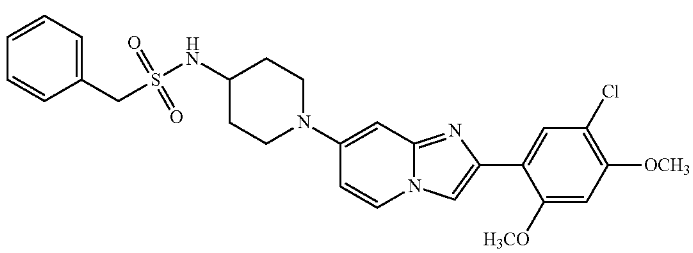 [SMILES: COc1cc(OC)c(-c2cn3ccc(N4CCC(NS(=O)(=O)Cc5ccccc5)CC4)cc3n2)cc1Cl] | N-(1-(2-(5-chloro-2,4-dimethoxyphenyl)imidazo[1,2-a]pyridine-7-yl)piperidin-4-yl)-1-phenylmethanesulfonamide | ESI | 541 |
| 176 | 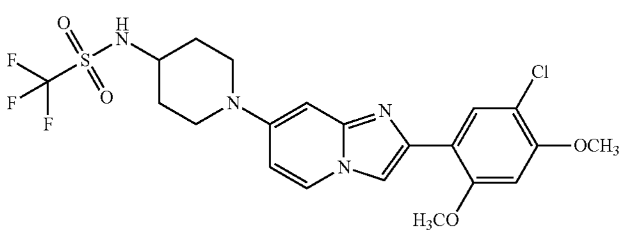 [SMILES: COc1cc(OC)c(-c2cn3ccc(N4CCC(NS(=O)(=O)C(F)(F)F)CC4)cc3n2)cc1Cl] | N-(1-(2-(5-chloro-2,4-dimethoxyphenyl)imidazo[1,2-a]pyridine-7-yl)piperidin-4-yl)-1,1,1-trifluoromethanesulfonamide | ESI | 519 |
| 177 | 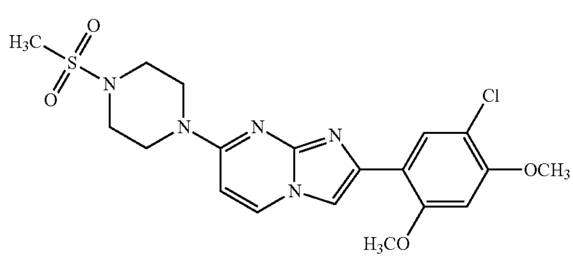 [SMILES: COc1cc(OC)c(-c2cn3ccc(N4CCN(S(C)(=O)=O)CC4)nc3n2)cc1Cl] | 2-(5-chloro-2,4-dimethoxyphenyl)-7-(4-(methylsulfonyl)piperazin-1-yl)imidazo[1,2-a]pyrimidine | ESI | 452 |

TABLE 1-continued

Compounds Table:

| Ex. No. | Structure | Name | MS Ionization | MS |
|---|---|---|---|---|
| 178 | 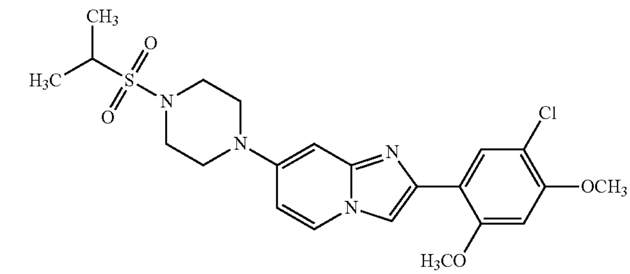 | 2-(5-chloro-2,4-dimethoxyphenyl)-7-(4-(isopropylsulfonyl)piperazin-1-yl)imidazo[1,2-a]pyridine | ESI | 479 |
| 179 | 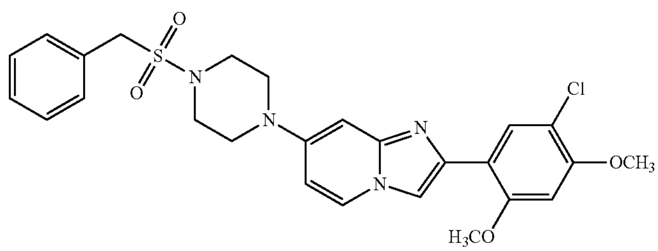 [SMILES: COc1cc(OC)c(-c2cn3ccc(N4CCN(S(=O)(=O)Cc5ccccc5)CC4)cc3n2)cc1Cl] | 7-(4-(benzylsulfonyl)piperazin-1-yl)-2-(5-chloro-2,4-dimethoxyphenyl)imidazo[1,2-pyridine | ESI | 527 |
| 180 | 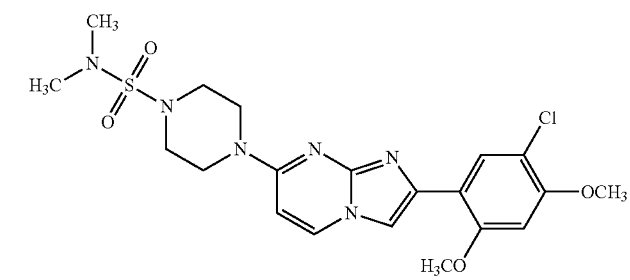 [SMILES: COc1cc(OC)c(-c2cn3ccc(N4CCN(S(=O)(=O)N(C)C)CC4)nc3n2)cc1Cl] | 4-(2-(5-chloro-2,4-dimethoxyphenyl)imidazo[1,2-a]pyrimidin-7-yl)-N,N-dimethylpiperazine-1-sulfonamide | ESI | 481 |
| 181 | 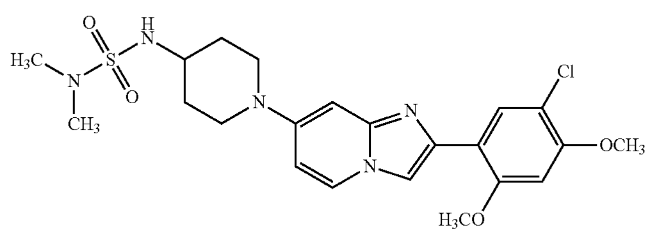 [SMILES: COc1cc(OC)c(-c2cn3ccc(N4CCC(NS(=O)(=O)N(C)C)CC4)cc3n2)cc1Cl] | 7-(4-(N,N-dimethylaminosulfonylamino)piperidin-1-yl)-2-(5-chloro-2,4-dimethoxyphenyl)imidazo[1,2-a]pyridine | ESI | 494 |
| 182 | 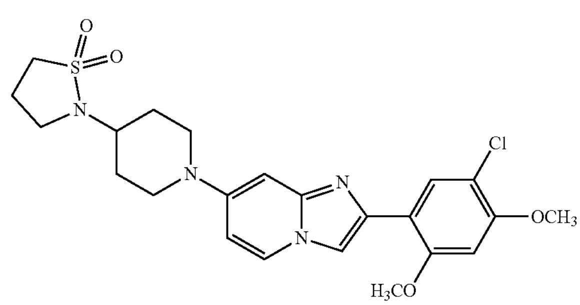 [SMILES: COc1cc(OC)c(-c2cn3ccc(N4CCC(N5CCCS5(=O)=O)CC4)cc3n2)cc1Cl] | 2-(1-(2-(5-chloro-2,4-dimethoxyphenyl)imidazo[1,2-a]pyridine-7-yl)piperidin-4-yl)isothiazolidine 1,1-dioxide | ESI | 491 |
| 183 | 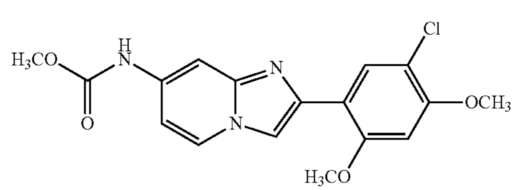 [SMILES: COC(=O)Nc1ccn2cc(-c3cc(Cl)c(OC)cc3OC)nc2c1] | methyl (2-(5-chloro-2,4-dimethoxyphenyl)imidazo[1,2-a]pyridine-7-yl)carbamate | ESI | 362 |

TABLE 1-continued

Compounds Table:

| Ex. No. | Structure | Name | MS Ionization | MS |
|---|---|---|---|---|
| 184 | 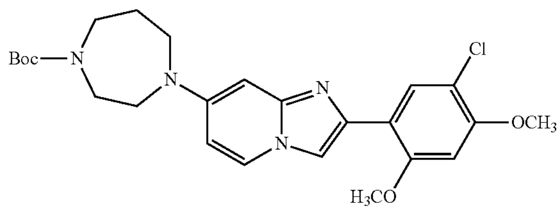 [SMILES: COc1cc(OC)c(-c2cn3ccc(N4CCCN(C(=O)OC(C)(C)C)CC4)cc3n2)cc1Cl] | tert-butyl 4-(2-(5-chloro-2,4-dimethoxyphenyl)imidazo[1,2-a]pyridine-7-yl)-1,4-diazepane-1-carboxylate | ESI | 487 |
| 185 | 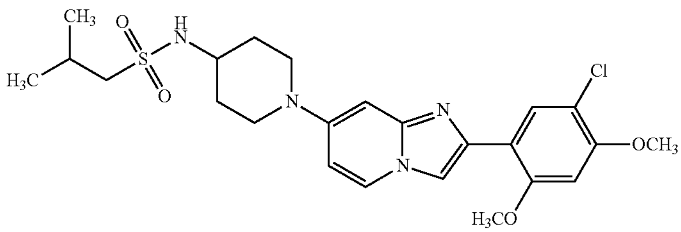 [SMILES: COc1cc(OC)c(-c2cn3ccc(N4CCC(NS(=O)(=O)CC(C)C)CC4)cc3n2)cc1Cl] | N-(1-(2-(5-chloro-2,4-dimethoxyphenyl)imidazo[1,2-a]pyridine-7-yl)piperidin-4-yl)-2-methylpropane-1-sulfonamide | ESI | 507 |
| 186 | 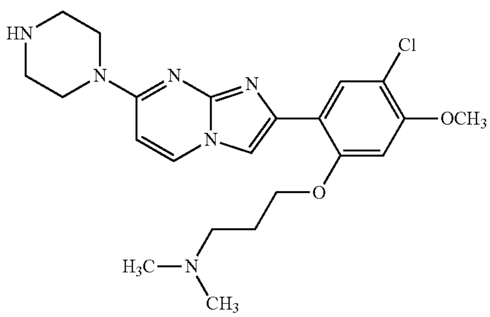 [SMILES: COc1cc(OCCCN(C)C)c(-c2cn3ccc(N4CCNCC4)nc3n2)cc1Cl] | 3-(4-chloro-5-methoxy-2-(7-(piperazin-1-yl)imidazo[1,2-a]pyrimidin-2-yl)phenoxy)-N,N-dimethylpropan-1-amine | ESI | 445 |
| 187 | 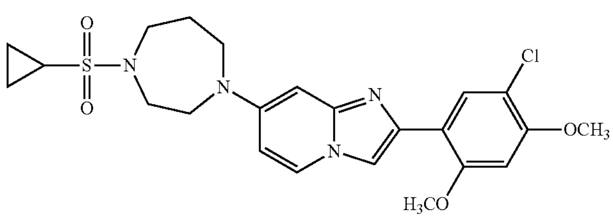 [SMILES: COc1cc(OC)c(-c2cn3ccc(N4CCCN(S(=O)(=O)C5CC5)CC4)cc3n2)cc1Cl] | 2-(5-chloro-2,4-dimethoxyphenyl)-7-(4-(cyclopropylsulfonyl)-1,4-diazepan-1-yl)imidazo[1,2-a]pyridine | ESI | 491 |
| 188 | 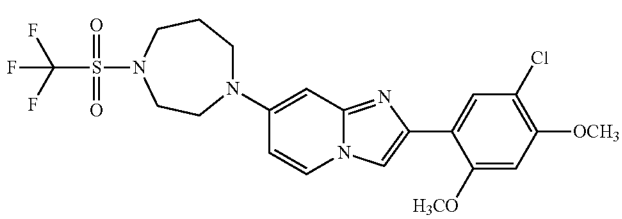 [SMILES: COc1cc(OC)c(-c2cn3ccc(N4CCCN(S(=O)(=O)C(F)(F)F)CC4)cc3n2)cc1Cl] | 2-(5-chloro-2,4-dimethoxyphenyl)-7-(4-((trifluoromethyl)sulfonyl)-1,4-diazepan-1-yl)imidazo[1,2-a]pyridine | ESI | 519 |
| 189 | 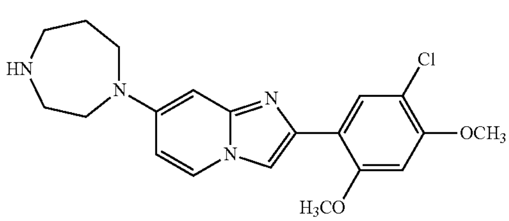 [SMILES: COc1cc(OC)c(-c2cn3ccc(N4CCCNCC4)cc3n2)cc1Cl] | 2-(5-chloro-2,4-dimethoxyphenyl)-7-(1,4-diazepan-1-yl)imidazo[1,2-a]pyridine | ESI | 387 |

TABLE 1-continued

Compounds Table:

| Ex. No. | Structure | Name | MS Ionization | MS |
|---|---|---|---|---|
| 190 | 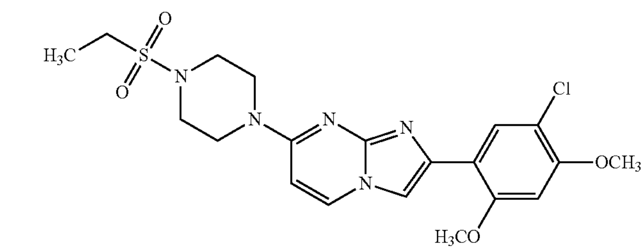 | 2-(5-chloro-2,4-dimethoxyphenyl)-7-(4-(ethylsulfonyl)piperazin-1-yl)imidazo[1,2-a]pyrimidine | APCI | 466 |
| 191 | 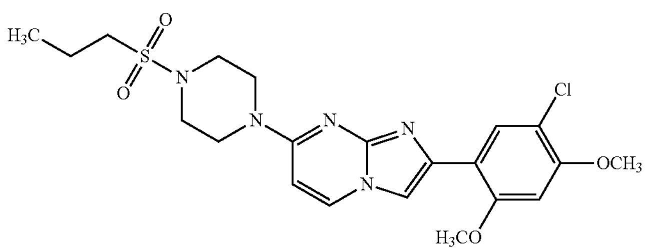 | 2-(5-chloro-2,4-dimethoxyphenyl)-7-(4-(propylsulfonyl)piperazin-1-yl)imidazo[1,2-a]pyrimidine | APCI | 480 |
| 192 | 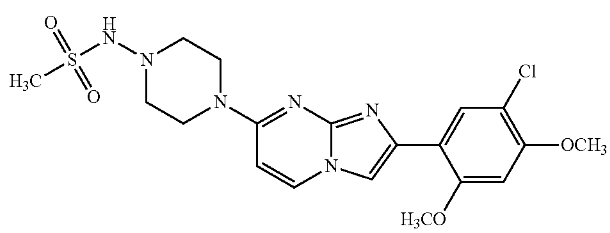 [SMILES: COc1cc(OC)c(-c2cn3ccc(N4CCN(NS(C)(=O)=O)CC4)nc3n2)cc1Cl] | N-(1-(2-(5-chloro-2,4-dimethoxyphenyl)imidazo[1,2-a]pyrimidin-7-yl)piperidin-4-yl)methanesulfonamide | ESI | 466 |
| 193 | 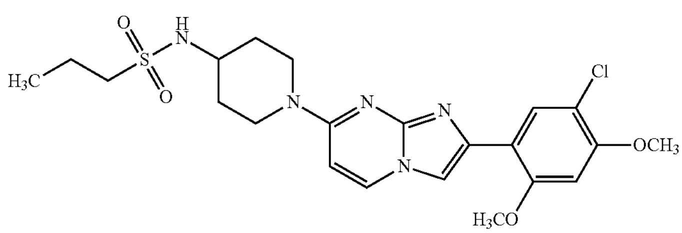 | N-(1-(2-(5-chloro-2,4-dimethoxyphenyl)imidazo[1,2-a]pyrimidin-7-yl)piperidin-4-yl)propane-1-sulfonamide | ESI | 474 |
| 194 | 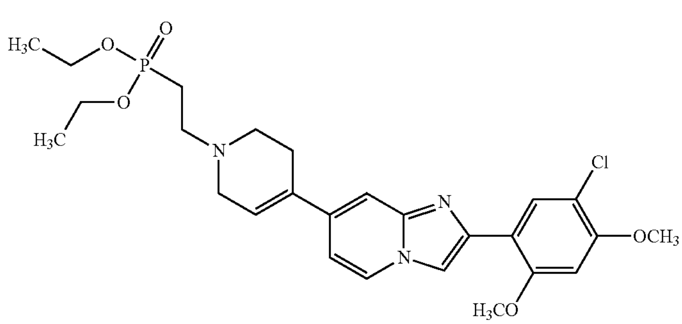 [SMILES: CCOP(=O)(CCN1CC=C(c2ccn3cc(-c4cc(Cl)c(OC)cc4OC)nc3c2)CC1)OCC] | diethyl (2-(4-(2-(5-chloro-2,4-dimethoxyphenyl)imidazo[1,2-a]pyridine-7-yl)-5,6-dihydropyridin-1(2H)-yl)ethyl)phosphonate | ESI | 534 |

TABLE 1-continued

Compounds Table:

| Ex. No. | Structure | Name | MS Ionization | MS |
|---|---|---|---|---|
| 195 | 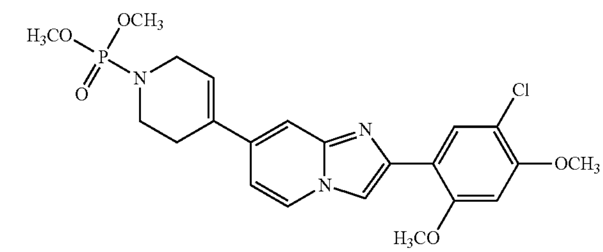 | dimethyl (4-(2-(5-chloro-2,4-dimethoxyphenyl)imidazo[1,2-a]pyridine-7-yl)-5,6-dihydropyridin-1(2H)-yl)phosphonate | APCI | 478 |
| 196 | 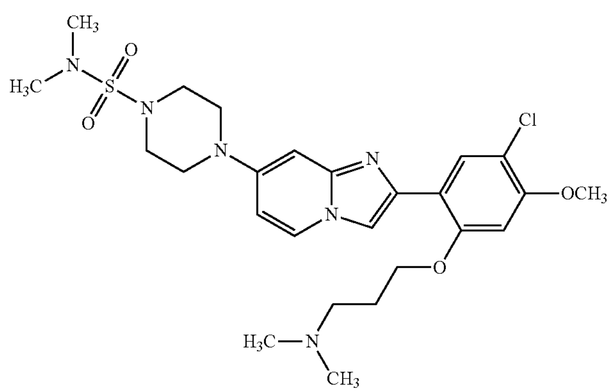 [SMILES: COc1cc(OCCCN(C)C)c(-c2cn3ccc(N4CCN(S(=O)(=O)N(C)C)CC4)cc3n2)cc1Cl] | 4-(2-(5-chloro-2-(3-(dimethylamino)propoxy)-4-methoxyphenyl)imidazo[1,2-a]pyridine-7-yl)-N,N-dimethylpiperazine-1-sulfonamide | ESI | 551 |
| 197 | 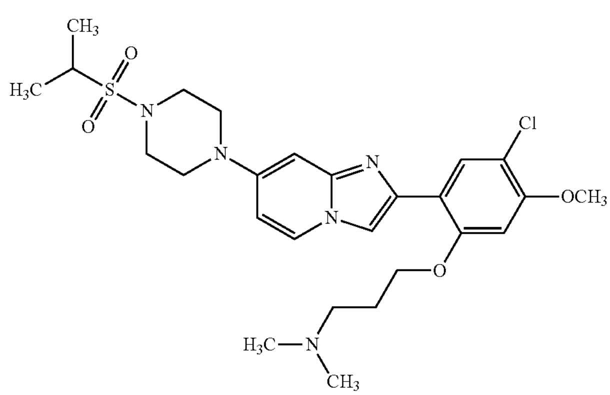 [SMILES: COc1cc(OCCCN(C)C)c(-c2cn3ccc(N4CCN(S(=O)(=O)C(C)C)CC4)cc3n2)cc1Cl] | 3-(4-chloro-2-(7-(4-(isopropylsulfonyl)piperazin-1-yl)imidazo[1,2-a]pyridine-2-yl)-5-methoxyphenoxy)-N,N-dimethylpropan-1-amine | ESI | 550 |
| 198 | 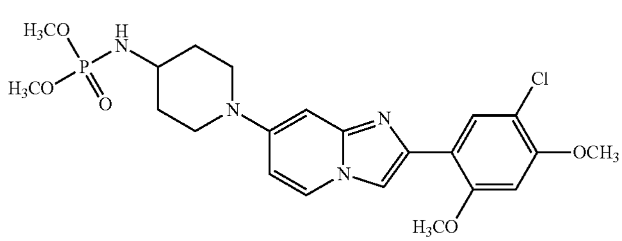 [SMILES: COc1cc(OC)c(-c2cn3ccc(N4CCC(NP(=O)(OC)OC)CC4)cc3n2)cc1Cl] | dimethyl (1-(2-(5-chloro-2,4-dimethoxyphenyl)imidazo[1,2-a]pyridine-7-yl)piperidin-4-yl)phosphoramidate | ESI | 495 |

TABLE 1-continued

Compounds Table:

| Ex. No. | Structure | Name | MS Ionization | MS |
|---|---|---|---|---|
| 199 | 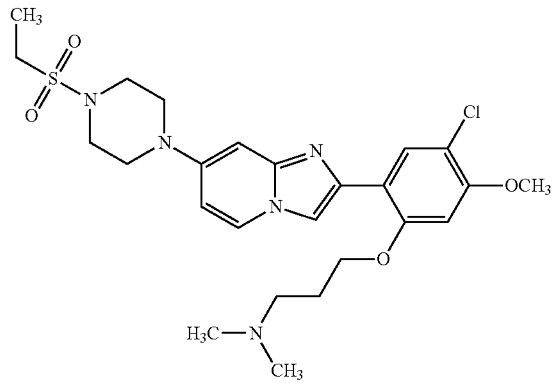 [SMILES: CCS(=O)(=O)N1CCN(c2ccn3cc(-c4cc(Cl)c(OC)cc4OCCCN(C)C)nc3c2)CC1] | 3-(4-chloro-2-(7-(4-(ethylsulfonyl)piperazin-1-yl)imidazo[1,2-a]pyridine-2-yl)-5-methoxyphenoxy)-N,N-dimethylpropan-1-amine | APCI | 536 |
| 200 | 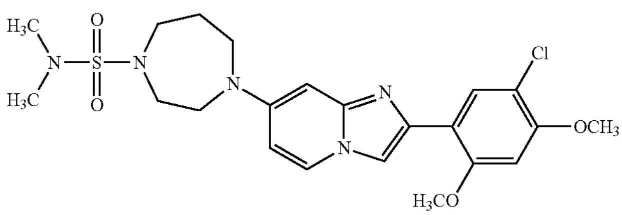 [SMILES: COc1cc(OC)c(-c2cn3ccc(N4CCCN(S(=O)(=O)N(C)C)CC4)cc3n2)cc1Cl] | 4-(2-(5-chloro-2,4-dimethoxyphenyl)imidazo[1,2-a]pyridine-7-yl)-N,N-dimethyl-1,4-diazepane-1-sulfonamide | ESI | 494 |
| 201 | 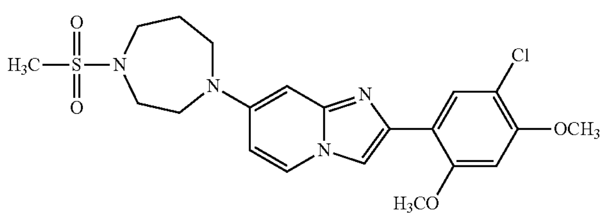 [SMILES: COc1cc(OC)c(-c2cn3ccc(N4CCCN(S(C)(=O)=O)CC4)cc3n2)cc1Cl] | 2-(5-chloro-2,4-dimethoxyphenyl)-7-(4-(methylsulfonyl)-1,4-diazepan-1-yl)imidazo[1,2-a]pyridine | ESI | 465 |
| 202 | 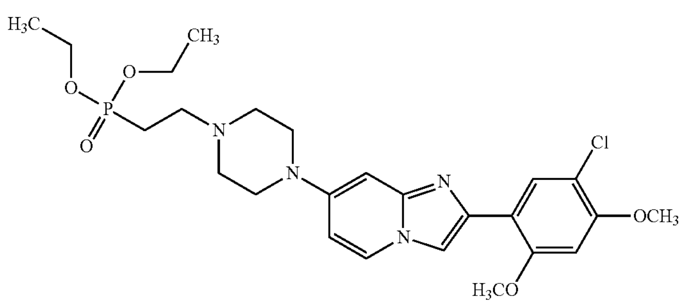 [SMILES: CCOP(=O)(CCN1CCN(c2ccn3cc(-c4cc(Cl)c(OC)cc4OC)nc3c2)CC1)OCC] | diethyl (2-(4-(2-(5-chloro-2,4-dimethoxyphenyl)imidazo[1,2-a]pyridine-7-yl)piperazin-1-yl)ethyl)phosphonate | APCI | 537 |
| 203 | 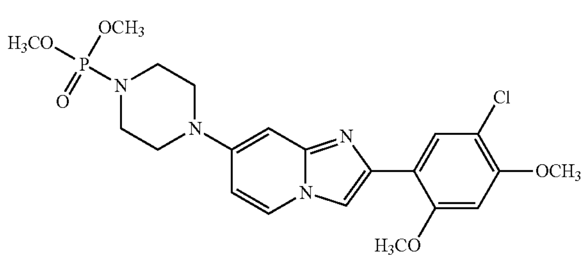 [SMILES: COc1cc(OC)c(-c2cn3ccc(N4CCN(P(=O)(OC)OC)CC4)cc3n2)cc1Cl] | dimethyl (4-(2-(5-chloro-2,4-dimethoxyphenyl)imidazo[1,2-a]pyridine-7-yl)piperazin-1-yl)phosphonate | ESI | 481 |

TABLE 1-continued

Compounds Table:

| Ex. No. | Structure | Name | MS Ionization | MS |
|---|---|---|---|---|
| 204 | 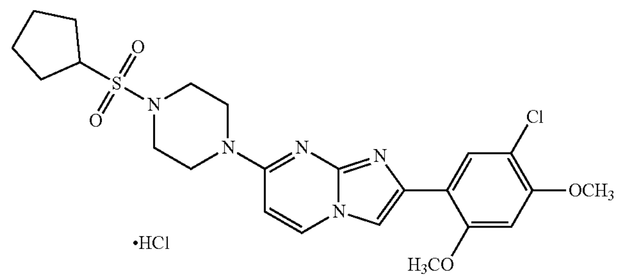 [SMILES: COc1cc(OC)c(-c2cn3ccc(N4CCN(S(=O)(=O)C5CCCC5)CC4)nc3n2)cc1Cl ; Cl] | 2-(5-chloro-2,4-dimethoxyphenyl)-7-(4-(cyclopentylsulfonyl)piperazin-1-yl)imidazo[1,2-a]pyrimidine hydrochloride | ESI | 506 |
| 205 | 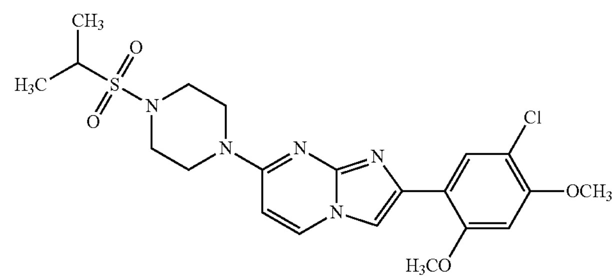 [SMILES: COc1cc(OC)c(-c2cn3ccc(N4CCN(S(=O)(=O)C(C)C)CC4)nc3n2)cc1Cl] | 2-(5-chloro-2,4-dimethoxyphenyl)-7-(4-(isopropylsulfonyl)piperazin-1-yl)imidazo[1,2-a]pyrimidine | ESI | 480 |
| 206 | 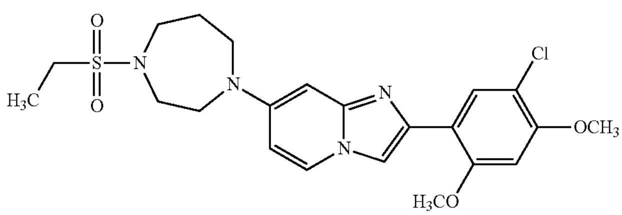 [SMILES: CCS(=O)(=O)N1CCCN(c2ccn3cc(-c4cc(Cl)c(OC)cc4OC)nc3c2)CC1] | 2-(5-chloro-2,4-dimethoxyphenyl)-7-(4-(ethylsulfonyl)-1,4-diazepan-1-yl)imidazo[1,2-a]pyridine | ESI | 479 |
| 207 | 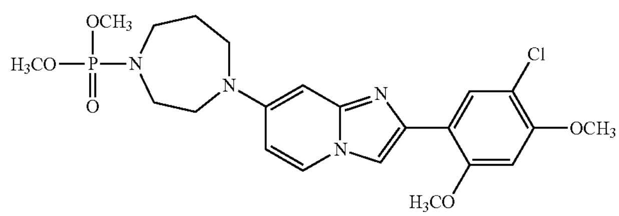 [SMILES: COc1cc(OC)c(-c2cn3ccc(N4CCCN(P(=O)(OC)OC)CC4)cc3n2)cc1Cl] | dimethyl (4-(2-(5-chloro-2,4-dimethoxyphenyl)imidazo[1,2-a]pyridine-7-yl)-1,4-diazepan-1-yl)phosphonate | ESI | 495 |
| 208 | 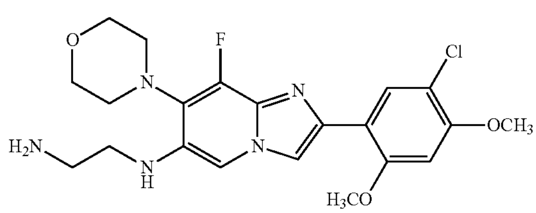 | $N^1$-(2-(5-chloro-2,4-dimethoxyphenyl)-8-fluoro-7-morpholinoimidazo[1,2-a]pyridine-6-yl)ethane-1,2-diamine | ESI | 450 |
| 209 | 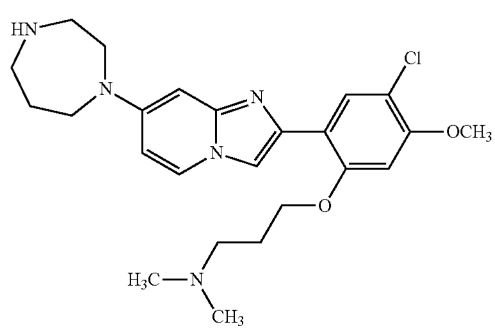 [SMILES: COc1cc(OCCCN(C)C)c(-c2cn3ccc(N4CCCNCC4)cc3n2)cc1Cl] | 3-(2-(7-(1,4-diazepan-1-yl)imidazo[1,2-a]pyridine-2-yl)-4-chloro-5-methoxyphenoxy)-N,N-dimethylpropan-1-amine | APCI | 458 |

TABLE 1-continued

Compounds Table:

| Ex. No. | Structure | Name | MS Ionization | MS |
|---|---|---|---|---|
| 210 | 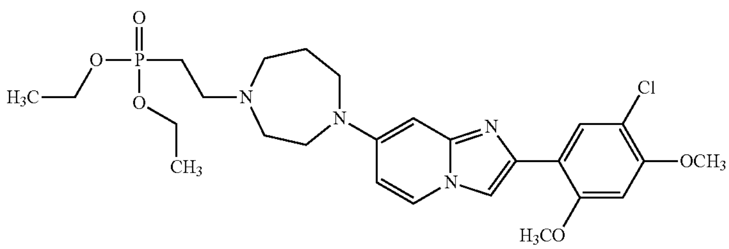 [SMILES: CCOP(=O)(CCN1CCCN(c2ccn3cc(-c4cc(Cl)c(OC)cc4OC)nc3c2)CC1)OCC] | diethyl (2-(4-(2-(5-chloro-2,4-dimethoxyphenyl)imidazo[1,2-a]pyridine-7-yl)-1,4-diazepan-1-yl)ethyl)phosphonate | ESI | 551 |
| 211 | 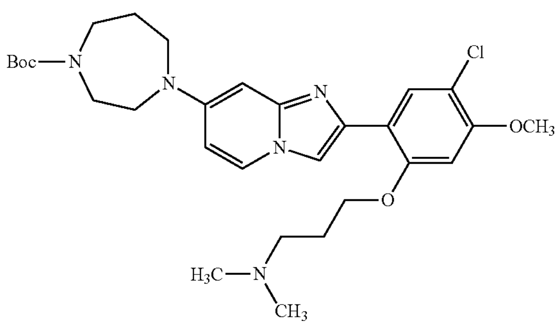 [SMILES: COc1cc(OCCCN(C)C)c(-c2cn3ccc(N4CCCN(C(=O)OC(C)(C)C)CC4)cc3n2)cc1Cl] | tert-butyl 4-(2-(5-chloro-2-(3-(dimethylamino)propoxy)-4-methoxyphenyl)imidazo[1,2-a]pyridine-7-yl)-1,4-diazepane-1-carboxylate | ESI | 558 |
| 212 | 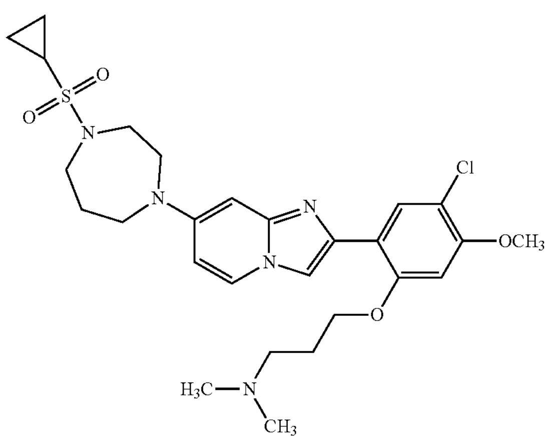 [SMILES: COc1cc(OCCCN(C)C)c(-c2cn3ccc(N4CCCN(S(=O)(=O)C5CC5)CC4)cc3n2)cc1Cl] | 3-(4-chloro-2-(7-(4-(cyclopropylsulfonyl)-1,4-diazepan-1-yl)imidazo[1,2-a]pyridine-2-yl)-5-methoxyphenoxy)-N,N-dimethylpropan-1-amine | ESI | 562 |
| 213 | 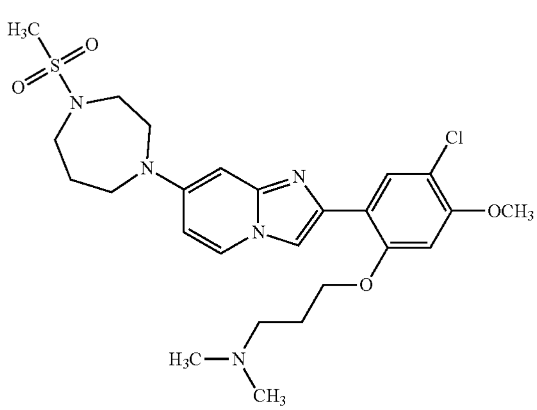 [SMILES: COc1cc(OCCCN(C)C)c(-c2cn3ccc(N4CCCN(S(C)(=O)=O)CC4)cc3n2)cc1Cl] | 3-(4-chloro-5-methoxy-2-(7-(4-(methylsulfonyl)-1,4-diazepan-1-yl)imidazo[1,2-a]pyridine-2-yl)phenoxy)-N,N-dimethylpropan-1-amine | ESI | 536 |

TABLE 1-continued

Compounds Table:

| Ex. No. | Structure | Name | MS Ionization | MS |
|---|---|---|---|---|
| 214 | 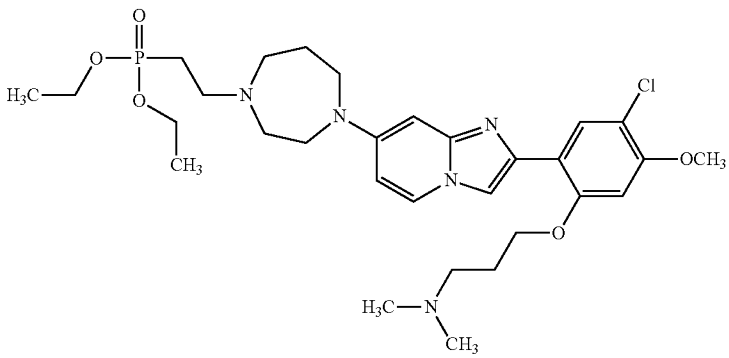 [SMILES: CCOP(=O)(CCN1CCCN(c2ccn3cc(-c4cc(Cl)c(OC)cc4OCCCN(C)C)nc3c2)CC1)OCC] | diethyl (2-(4-(2-(5-chloro-2-(3-(dimethylamino)propoxy)-4-methoxyphenyl)imidazo[1,2-a]pyridine-7-yl)-1,4-diazepan-1-yl)ethyl)phosphonate | ESI | 622 |
| 215 | 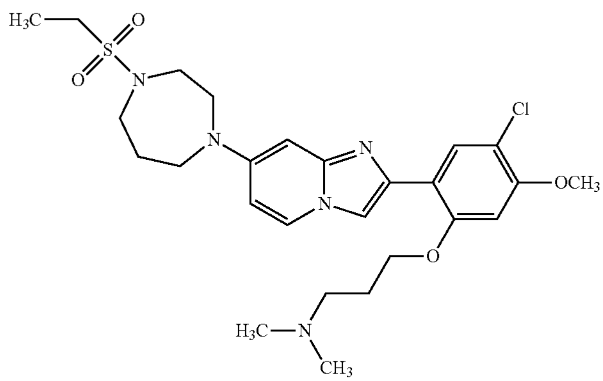 [SMILES: CCS(=O)(=O)N1CCCN(c2ccn3cc(-c4cc(Cl)c(OC)cc4OCCCN(C)C)nc3c2)CC1] | 3-(4-chloro-2-(7-(4-(ethylsulfonyl)-1,4-diazepan-1-yl)imidazo[1,2-a]pyridine-2-yl)-5-methoxyphenoxy)-N,N-dimethylpropan-1-amine | ESI | 550 |
| 216 | 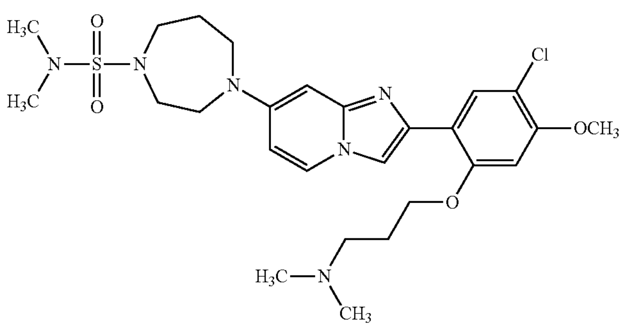 [SMILES: COc1cc(OCCCN(C)C)c(-c2cn3ccc(N4CCCN(S(=O)(=O)N(C)C)CC4)cc3n2)cc1Cl] | 4-(2-(5-chloro-2-(3-(dimethylamino)propoxy)-4-methoxyphenyl)imidazo[1,2-a]pyridine-7-yl)-N,N-dimethyl-1,4-diazepane-1-sulfonamide | ESI | 565 |
| 217 | 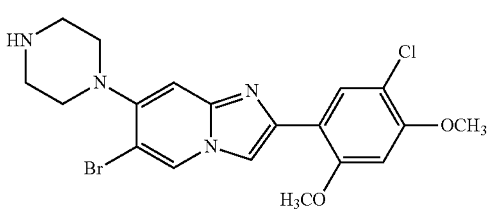 | 6-bromo-2-(5-chloro-2,4-dimethoxyphenyl)-7-(piperazin-1-yl)imidazo[1,2-a]pyridine | APCI | 453 |
| 218 | 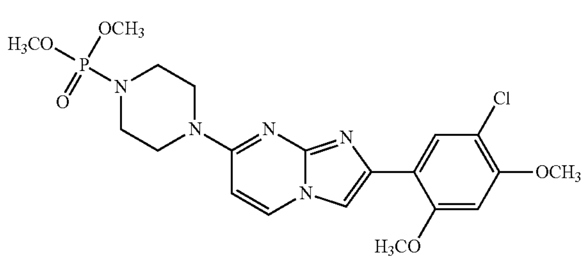 | dimethyl (4-(2-(5-chloro-2,4-dimethoxyphenyl)imidazo[1,2-a]pyrimidin-7-yl)piperazin-1-yl)phosphonate | ESI | 482 |

TABLE 1-continued

Compounds Table:

| Ex. No. | Structure | Name | MS Ionization | MS |
|---|---|---|---|---|
| 219 | 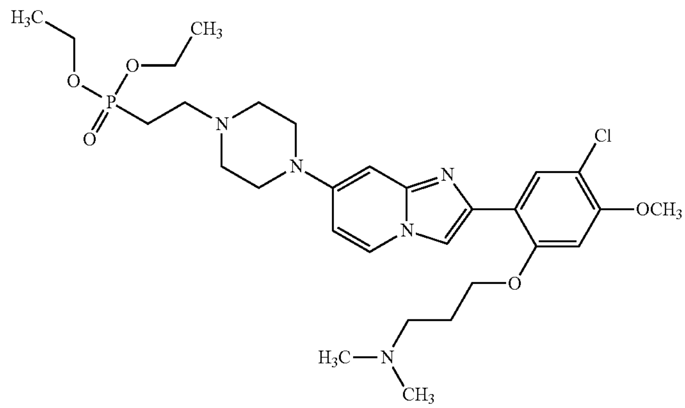 [SMILES: CCOP(=O)(CCN1CCN(c2ccn3cc(-c4cc(Cl)c(OC)cc4OCCCN(C)C)nc3c2)CC1)OCC] | diethyl (2-(4-(2-(5-chloro-2-(3-(dimethylamino)propoxy)-4-methoxyphenyl)imidazo[1,2-a]pyridine-7-yl)piperazin-1-yl)ethyl)phosphonate | ESI | 608 |
| 220 | 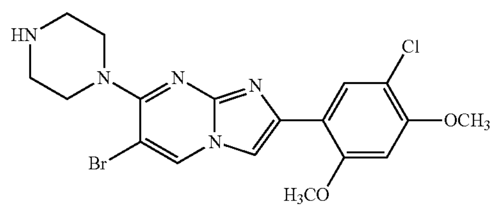 [SMILES: COc1cc(OC)c(-c2cn3cc(Br)c(N4CCNCC4)nc3n2)cc1Cl] | 6-bromo-2-(5-chloro-2,4-dimethoxyphenyl)-7-(piperazin-1-yl)imidazo[1,2-a]pyrimidine | ESI | 454 |
| 221 | 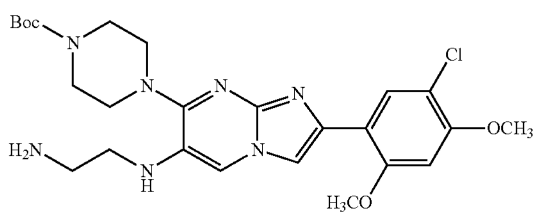 [SMILES: COc1cc(OC)c(-c2cn3cc(NCCN)c(N4CCN(C(=O)OC(C)(C)C)CC4)nc3n2)cc1Cl] | tert-butyl 4-(6-((2-aminoethyl)amino)-2-(5-chloro-2,4-dimethoxyphenyl)imidazo[1,2-a]pyrimidin-7-yl)piperazine-1-carboxylate | ESI | 532 |
| 222 | 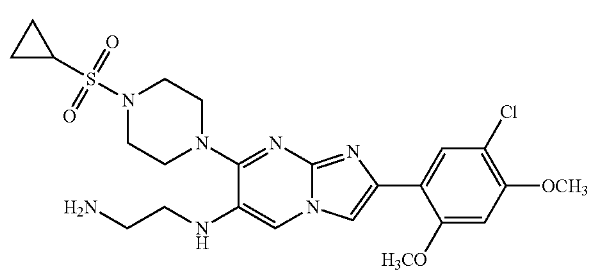 [SMILES: COc1cc(OC)c(-c2cn3cc(NCCN)c(N4CCN(S(=O)(=O)C5CC5)CC4)nc3n2)cc1Cl] | $N^1$-(2-(5-chloro-2,4-dimethoxyphenyl)-7-(4-(cyclopropylsulfonyl)piperazin-1-yl)imidazo[1,2-a]pyrimidin-6-yl)ethane-1,2-diamine | ESI | 536 |
| 223 | 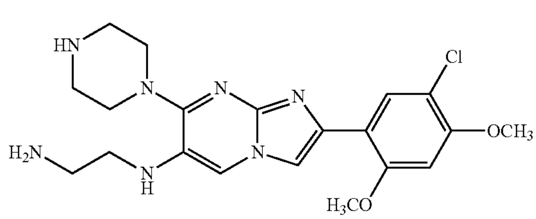 [SMILES: COc1cc(OC)c(-c2cn3cc(NCCN)c(N4CCNCC4)nc3n2)cc1Cl] | $N^1$-(2-(5-chloro-2,4-dimethoxyphenyl)-7-(piperazin-1-yl)imidazo[1,2-a]pyrimidin-6-yl)ethane-1,2-diamine | ESI | 432 |

TABLE 1-continued

Compounds Table:

| Ex. No. | Structure | Name | MS Ionization | MS |
|---|---|---|---|---|
| 224 | 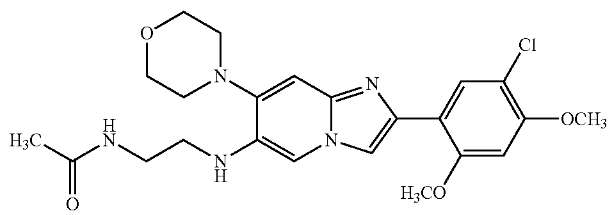 [SMILES: COc1cc(OC)c(-c2cn3cc(NCCNC(C)=O)c(N4CCOCC4)cc3n2)cc1Cl] | N-(2-((2-(5-chloro-2,4-dimethoxyphenyl)-7-morpholinoimidazo[1,2-a]pyridine-6-yl)amino)ethyl)acetamide | ESI | 474 |
| 225 | 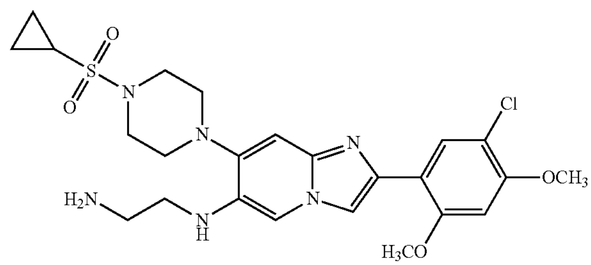 | N¹-(2-(5-chloro-2,4-dimethoxyphenyl)-7-(4-(cyclopropylsulfonyl)piperazin-1-yl)imidazo[1,2-a]pyridine-6-yl)ethane-1,2-diamine | ESI | 535 |
| 226 | 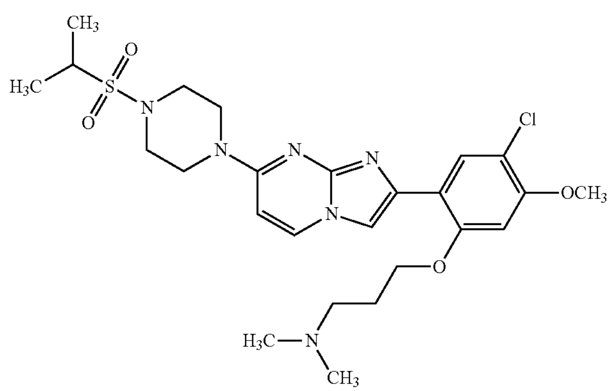 [SMILES: COc1cc(OCCCN(C)C)c(-c2cn3ccc(N4CCN(S(=O)(=O)C(C)C)CC4)nc3n2)cc1Cl] | 3-(4-chloro-2-(7-(4-(isopropylsulfonyl)piperazin-1-yl)imidazo[1,2-a]pyrimidin-2-yl)-5-methoxyphenoxy)-N,N-dimethylpropan-1-amine | ESI | 551 |
| 227 | 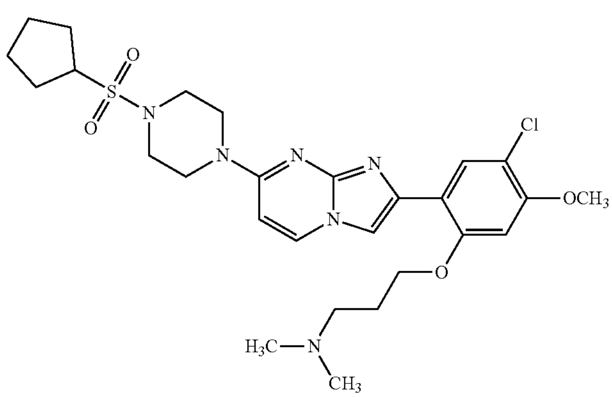 [SMILES: COc1cc(OCCCN(C)C)c(-c2cn3ccc(N4CCN(S(=O)(=O)C5CCCC5)CC4)nc3n2)cc1Cl] | 3-(4-chloro-2-(7-(4-(cyclopentylsulfonyl)piperazin-1-yl)imidazo[1,2-a]pyrimidin-2-yl)-5-methoxyphenoxy)-N,N-dimethylpropan-1-amine | ESI | 577 |
| 228 | 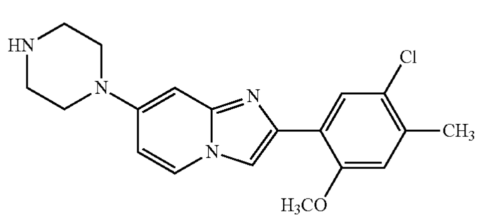 [SMILES: COc1cc(C)c(Cl)cc1-c1cn2ccc(N3CCNCC3)cc2n1] | 2-(5-chloro-2-methoxy-4-methylphenyl)-7-(piperazin-1-yl)imidazo[1,2-a]pyridine | ESI | 357 |

TABLE 1-continued

Compounds Table:

| Ex. No. | Structure | Name | MS Ionization | MS |
|---|---|---|---|---|
| 229 | 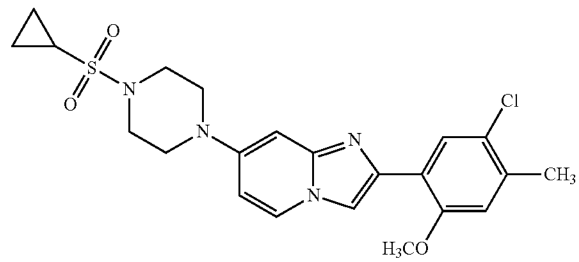 [SMILES: COc1cc(C)c(Cl)cc1-c1cn2ccc(N3CCN(S(=O)(=O)C4CC4)CC3)cc2n1] | 2-(5-chloro-2-methoxy-4-methylphenyl)-7-(4-(cyclopropylsulfonyl)piperazin-1-yl)imidazo[1,2-a]pyridine | ESI | 461 |
| 230 | 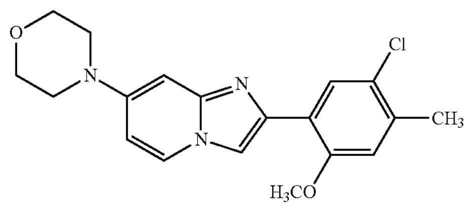 [SMILES: COc1cc(C)c(Cl)cc1-c1cn2ccc(N3CCOCC3)cc2n1] | 4-(2-(5-chloro-2-methoxy-4-methylphenyl)imidazo[1,2-a]pyridine-7-yl)morpholine | ESI | 358 |
| 231 | 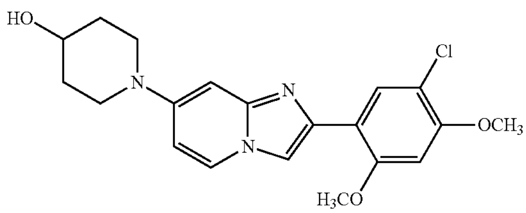 [SMILES: COc1cc(OC)c(-c2cn3ccc(N4CCC(O)CC4)cc3n2)cc1Cl] | 1-(2-(5-chloro-2,4-dimethoxyphenyl)imidazo[1,2-a]pyridine-7-yl)piperidin-4-ol | ESI | 388 |
| 232 | 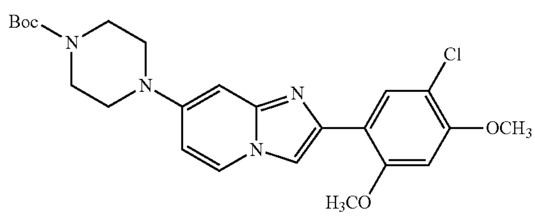 | tert-butyl 4-(2-(5-chloro-2,4-dimethoxyphenyl)imidazo[1,2-a]pyridine-7-yl)piperazine-1-carboxylate | ESI | 473 |
| 233 | 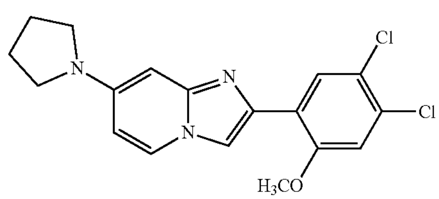 [SMILES: COc1cc(Cl)c(Cl)cc1-c1cn2ccc(N3CCCC3)cc2n1] | 2-(4,5-dichloro-2-methoxyphenyl)-7-(pyrrolidin-1-yl)imidazo[1,2-a]pyridine | APCI | 362 |
| 234 | 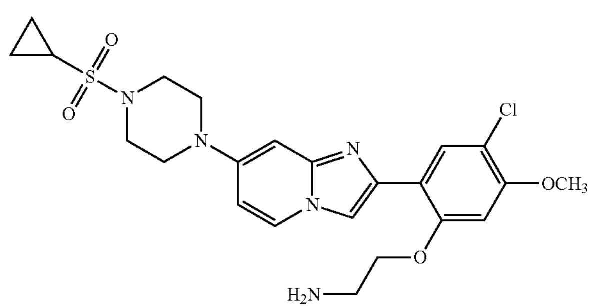 | 2-(4-chloro-2-(7-(4-(cyclopropylsulfonyl)piperazin-1-yl)imidazo[1,2-a]pyridine-2-yl)-5-methoxyphenoxy)ethanamine | ESI | 506 |

TABLE 1-continued

Compounds Table:

| Ex. No. | Structure | Name | MS Ionization | MS |
|---|---|---|---|---|
| 235 | 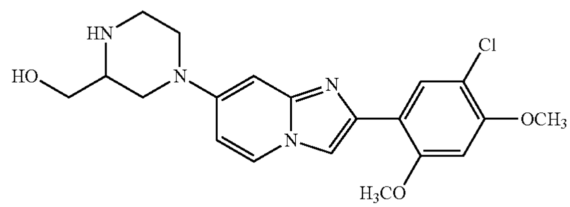 [SMILES: COc1cc(OC)c(-c2cn3ccc(N4CCNC(CO)C4)cc3n2)cc1Cl] | (4-(2-(5-chloro-2,4-dimethoxyphenyl)imidazo[1,2-a]pyridine-7-yl)piperazin-2-yl)methanol | APCI | 403 |
| 236 | 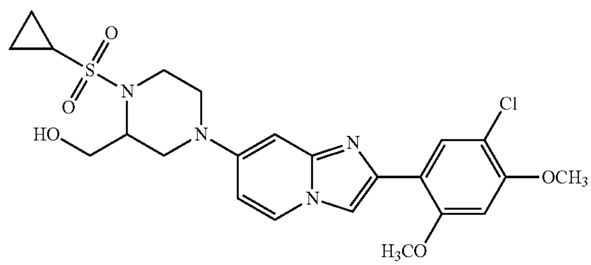 [SMILES: COc1cc(OC)c(-c2cn3ccc(N4CCN(S(=O)(=O)C5CC5)C(CO)C4)cc3n2)cc1Cl] | (4-(2-(5-chloro-2,4-dimethoxyphenyl)imidazo[1,2-a]pyridine-7-yl)-1-(cyclopropylsulfonyl)piperazin-2-yl)methanol | APCI | 507 |
| 237 | 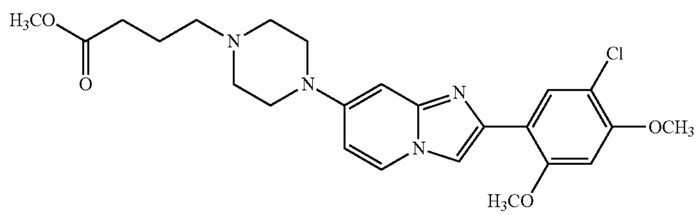 [SMILES: COC(=O)CCCN1CCN(c2ccn3cc(-c4cc(Cl)c(OC)cc4OC)nc3c2)CC1] | methyl 4-(4-(2-(5-chloro-2,4-dimethoxyphenyl)imidazo[1,2-a]pyridine-7-yl)piperazin-1-yl)butanoate | ESI | 473 |
| 238 | 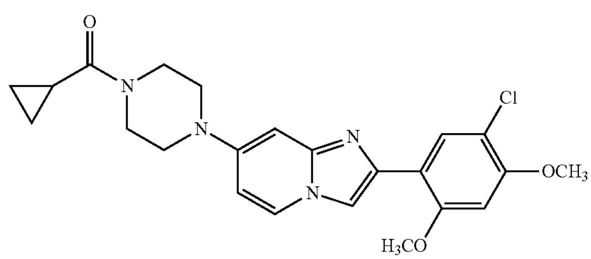 [SMILES: COc1cc(OC)c(-c2cn3ccc(N4CCN(C(=O)C5CC5)CC4)cc3n2)cc1Cl] | (4-(2-(5-chloro-2,4-dimethoxyphenyl)imidazo[1,2-a]pyridine-7-yl)piperazin-1-yl)(cyclopropyl)methanone | ESI | 441 |
| 239 | 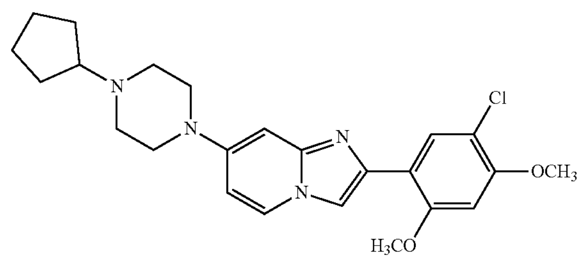 [SMILES: COc1cc(OC)c(-c2cn3ccc(N4CCN(C5CCCC5)CC4)cc3n2)cc1Cl] | 2-(5-chloro-2,4-dimethoxyphenyl)-7-(4-cyclopentylpiperazin-1-yl)imidazo[1,2-a]pyridine | ESI | 441 |
| 240 | 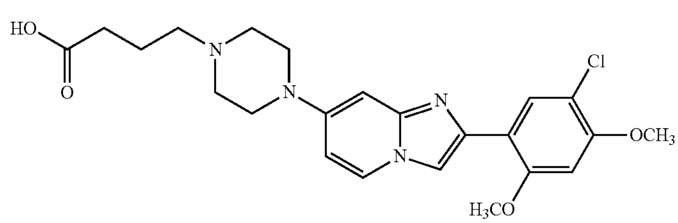 [SMILES: COc1cc(OC)c(-c2cn3ccc(N4CCN(CCCC(=O)O)CC4)cc3n2)cc1Cl] | 4-(4-(2-(5-chloro-2,4-dimethoxyphenyl)imidazo[1,2-a]pyridine-7-yl)piperazin-1-yl)butanoic acid | ESI | 459 |

TABLE 1-continued

Compounds Table:

| Ex. No. | Structure | Name | MS Ionization | MS |
|---|---|---|---|---|
| 241 | 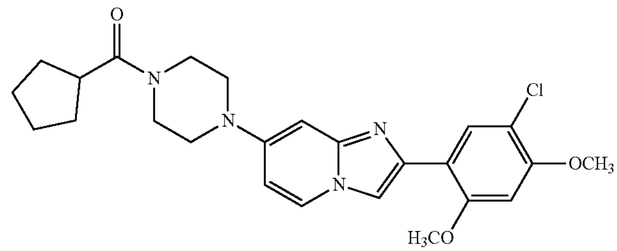 | (4-(2-(5-chloro-2,4-dimethoxyphenyl)imidazo[1,2-a]pyridine-7-yl)piperazin-1-yl)(cyclopentyl)methanone | ESI | 469 |
| 242 | 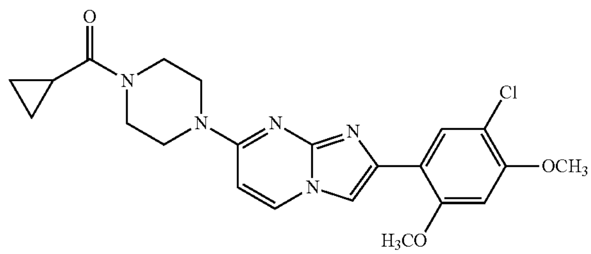 [SMILES: COc1cc(OC)c(-c2cn3ccc(N4CCN(C(=O)C5CC5)CC4)nc3n2)cc1Cl] | (4-(2-(5-chloro-2,4-dimethoxyphenyl)imidazo[1,2-a]pyrimidin-7-yl)piperazin-1-yl)(cyclopropyl)methanone | ESI | 442 |
| 243 | 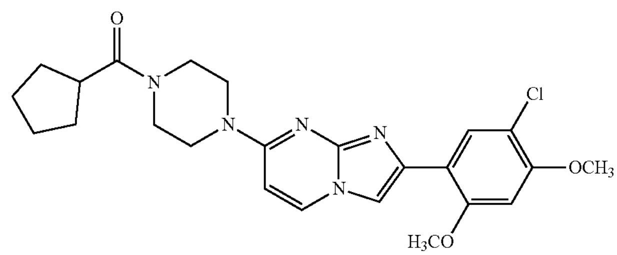 [SMILES: COc1cc(OC)c(-c2cn3ccc(N4CCN(C(=O)C5CCCC5)CC4)nc3n2)cc1Cl] | (4-(2-(5-chloro-2,4-dimethoxyphenyl)imidazo[1,2-a]pyrimidin-7-yl)piperazin-1-yl)(cyclopentyl)methanone | ESI | 470 |
| 244 | 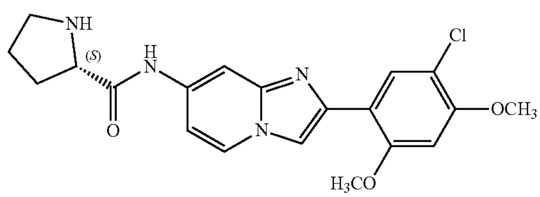 | (S)-N-(2-(5-chloro-2,4-dimethoxyphenyl)imidazo[1,2-a]pyridine-7-yl)pyrrolidine-2-carboxamide | ESI | 401 |
| 245 | 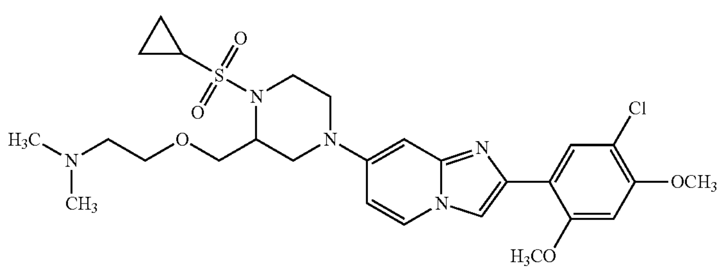 [SMILES: COc1cc(OC)c(-c2cn3ccc(N4CCN(S(=O)(=O)C5CC5)C(COCCN(C)C)C4)cc3n2)cc1Cl] | 2-((4-(2-(5-chloro-2,4-dimethoxyphenyl)imidazo[1,2-a]pyridine-7-yl)-1-(cyclopropylsulfonyl)piperazin-2-yl)methoxy)-N,N-dimethylethanamine | APCI | 578 |
| 246 | 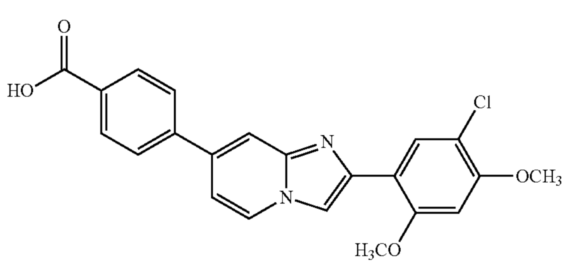 [SMILES: COc1cc(OC)c(-c2cn3ccc(-c4ccc(C(=O)O)cc4)cc3n2)cc1Cl] | 4-(2-(5-chloro-2,4-dimethoxyphenyl)imidazo[1,2-a]pyridine-7-yl)benzoic acid | ESI | 409 |

TABLE 1-continued

Compounds Table:

| Ex. No. | Structure | Name | MS Ionization | MS |
|---|---|---|---|---|
| 247 | 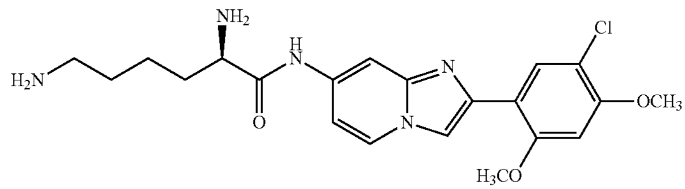 [SMILES: COc1cc(OC)c(-c2cn3ccc(NC(=O)[C@H](N)CCCCN)cc3n2)cc1Cl] | (S)-2,6-diamino-N-(2-(5-chloro-2,4-dimethoxyphenyl)imidazo[1,2-a]pyridine-7-yl)hexanamide | APCI | 432 |
| 248 | 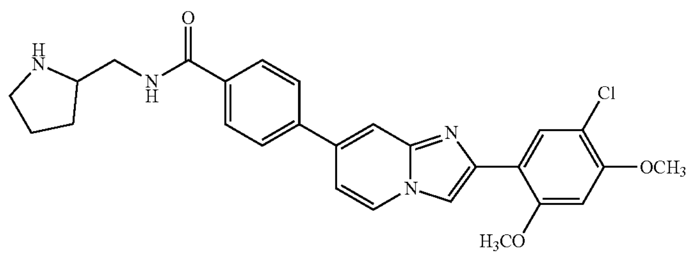 [SMILES: COc1cc(OC)c(-c2cn3ccc(-c4ccc(C(=O)NCC5CCCN5)cc4)cc3n2)cc1Cl] | 4-(2-(5-chloro-2,4-dimethoxyphenyl)imidazo[1,2-a]pyridine-7-yl)-N-(pyrrolidin-2-ylmethyl)benzamide | APCI | 491 |
| 249 | 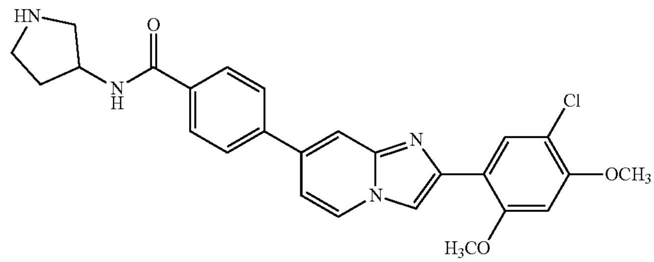 [SMILES: COc1cc(OC)c(-c2cn3ccc(-c4ccc(C(=O)NC5CCNC5)cc4)cc3n2)cc1Cl] | 4-(2-(5-chloro-2,4-dimethoxyphenyl)imidazo[1,2-a]pyridine-7-yl)-N-(pyrrolidin-3-yl)benzamide | APCI | 477 |
| 250 | 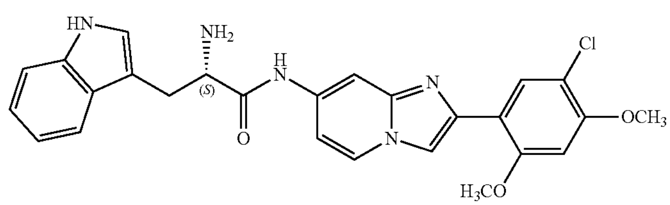 | (S)-2-amino-N-(2-(5-chloro-2,4-dimethoxyphenyl)imidazo[1,2-a]pyridine-7-yl)-3-(1H-indol-3-yl)propanamide | APCI | 490 |
| 251 | 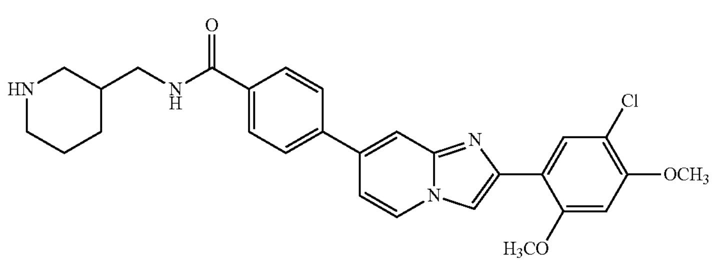 [SMILES: COc1cc(OC)c(-c2cn3ccc(-c4ccc(C(=O)NCC5CCCNC5)cc4)cc3n2)cc1Cl] | 4-(2-(5-chloro-2,4-dimethoxyphenyl)imidazo[1,2-a]pyridine-7-yl)-N-(piperidin-3-ylmethyl)benzamide | APCI | 505 |
| 252 | 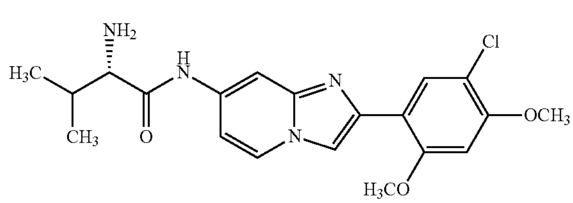 [SMILES: COc1cc(OC)c(-c2cn3ccc(NC(=O)[C@@H](N)C(C)C)cc3n2)cc1Cl] | (S)-2-amino-N-(2-(5-chloro-2,4-dimethoxyphenyl)imidazo[1,2-a]pyridine-7-yl)-3-methylbutanamide | ESI | 403 |

TABLE 1-continued

Compounds Table:

| Ex. No. | Structure | Name | MS Ionization | MS |
|---|---|---|---|---|
| 253 | 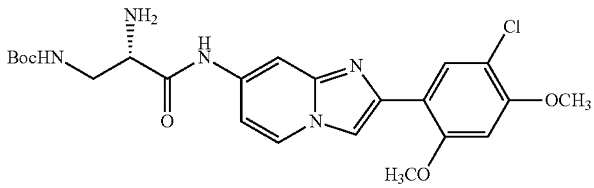 [SMILES: COc1cc(OC)c(-c2cn3ccc(NC(=O)[C@@H](N)CNC(=O)OC(C)(C)C)cc3n2)cc1Cl] | (S)-tert-butyl (1-((2-(5-chloro-2,4-dimethoxyphenyl)imidazo[1,2-a]pyridine-7-yl)amino)-1-oxopropan-2-yl)carbamate | ESI | 475 |
| 254 | 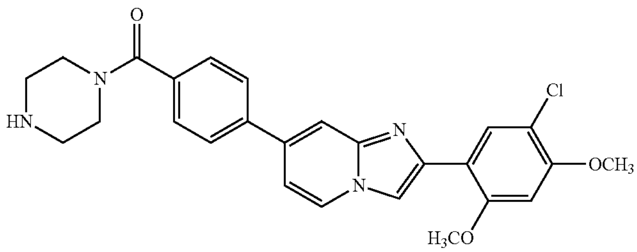 [SMILES: COc1cc(OC)c(-c2cn3ccc(-c4ccc(C(=O)N5CCNCC5)cc4)cc3n2)cc1Cl] | (4-(2-(5-chloro-2,4-dimethoxyphenyl)imidazo[1,2-a]pyridine-7-yl)phenyl)(piperazin-1-yl)methanone | APCI | 477 |
| 255 | 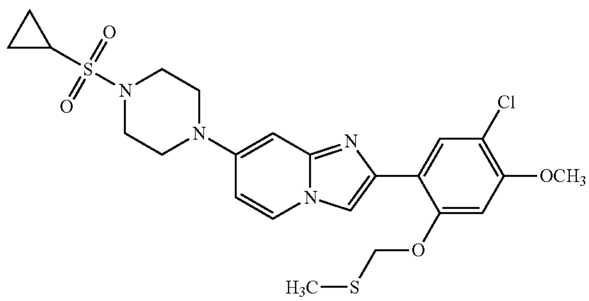 [SMILES: COc1cc(OCSC)c(-c2cn3ccc(N4CCN(S(=O)(=O)C5CC5)CC4)cc3n2)cc1Cl] | 2-(5-chloro-4-methoxy-2-((methylthio)methoxy)phenyl)-7-(4-(cyclopropylsulfonyl)-piperazin-1-yl)imidazo[1,2-a]pyridine | ESI | 523 |
| 256 | 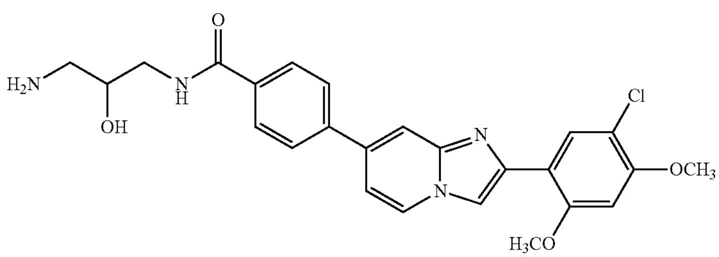 [SMILES: COc1cc(OC)c(-c2cn3ccc(-c4ccc(C(=O)NCC(O)CN)cc4)cc3n2)cc1Cl] | N-(3-amino-2-hydroxypropyl)-4-(2-(5-chloro-2,4-dimethoxyphenyl)imidazo[1,2-a]pyridine-7-yl)benzamide | APCI | 481 |
| 257 | 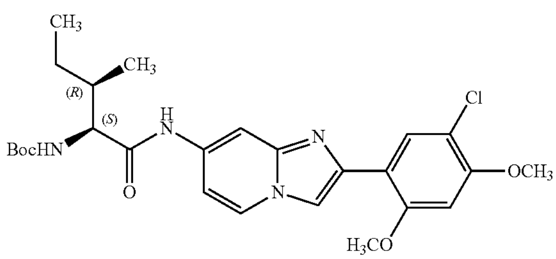 | tert-butyl ((2S,3R)-1-((2-(5-chloro-2,4-dimethoxyphenyl)-imidazo[1,2-a]pyridine-7-yl)amino)-3-methyl-1-oxopentan-2-yl)carbamate | ESI | 517 |
| 258 | 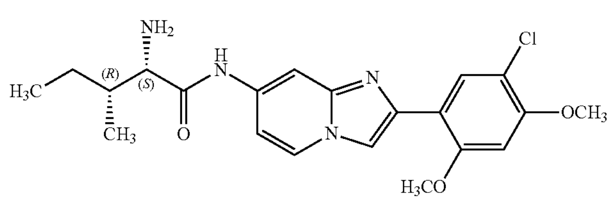 | (2S,3R)-2-amino-N-(2-(5-chloro-2,4-dimethoxyphenyl)imidazo[1,2-a]pyridine-7-yl)-3-methylpentanamide | ESI | 417 |

TABLE 1-continued

Compounds Table:

| Ex. No. | Structure | Name | MS Ionization | MS |
|---|---|---|---|---|
| 259 | 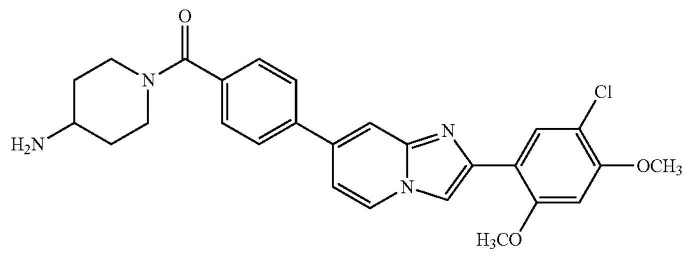 [SMILES: COc1cc(OC)c(-c2cn3ccc(-c4ccc(C(=O)N5CCC(N)CC5)cc4)cc3n2)cc1Cl] | (4-aminopiperidin-1-yl)(4-(2-(5-chloro-2,4-dimethoxyphenyl)imidazo[1,2-a]pyridine-7-yl)phenyl)methanone | APCI | 491 |
| 260 | 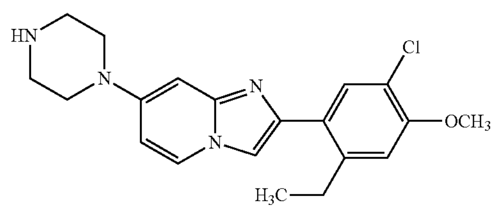 [SMILES: CCc1cc(OC)c(Cl)cc1-c1cn2ccc(N3CCNCC3)cc2n1] | 2-(5-chloro-2-ethyl-4-methoxyphenyl)-7-(piperazin-1-yl)imidazo[1,2-a]pyridine | ESI | 371 |
| 261 | 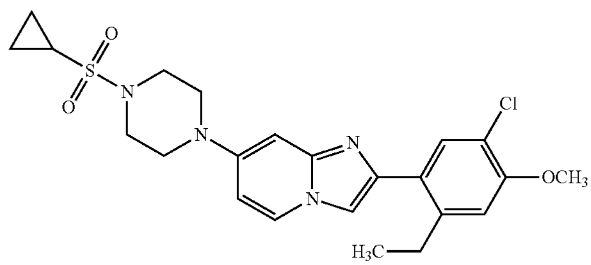 | 2-(5-chloro-2-ethyl-4-methoxyphenyl)-7-(4-(cyclopropylsulfonyl)piperazin-1-yl)imidazo[1,2-a]pyridine | ESI | 475 |
| 262 | 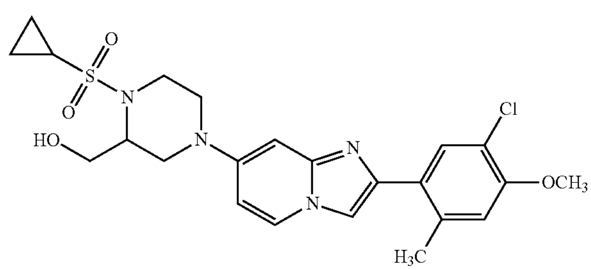 [SMILES: COc1cc(C)c(-c2cn3ccc(N4CCN(S(=O)(=O)C5CC5)C(CO)C4)cc3n2)cc1Cl] | (4-(2-(5-chloro-4-methoxy-2-methylphenyl)imidazo[1,2-a]pyridine-7-yl)-1-(cyclopropylsulfonyl)piperazin-2-yl)methanol | ESI | 491 |
| 263 | 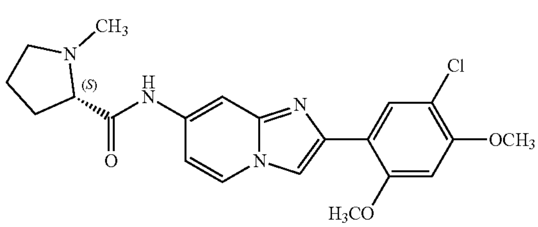 | (S)-N-(2-(5-chloro-2,4-dimethoxyphenyl)imidazo[1,2-a]pyridine-7-yl)-1-methylpyrrolidine-2-carboxamide | ESI | 415 |
| 264 | 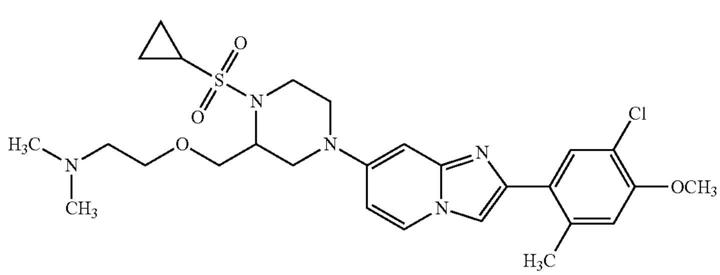 [SMILES: COc1cc(C)c(-c2cn3ccc(N4CCN(S(=O)(=O)C5CC5)C(COCCN(C)C)C4)cc3n2)cc1Cl] | 2-((4-(2-(5-chloro-4-methoxy-2-methylphenyl)imidazo[1,2-a]pyridine-7-yl)-1-(cyclopropylsulfonyl)piperazin-2-yl)methoxy)-N,N-dimethylethanamine | APCI | 562 |

TABLE 1-continued

Compounds Table:

| Ex. No. | Structure | Name | MS Ionization | MS |
|---|---|---|---|---|
| 265 | 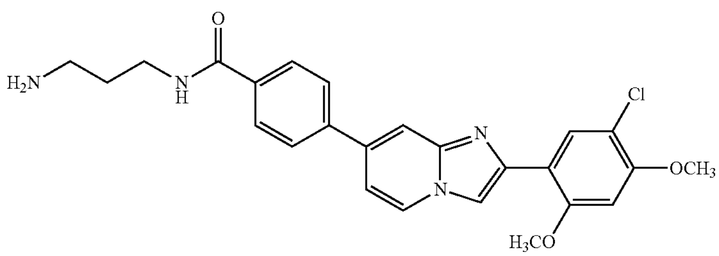 [SMILES: COc1cc(OC)c(-c2cn3ccc(-c4ccc(C(=O)NCCCN)cc4)cc3n2)cc1Cl] | N-(3-aminopropyl)-4-(2-(5-chloro-2,4-dimethoxyphenyl)-imidazo[1,2-a]pyridine-7-yl)benzamide | ESI | 465 |
| 266 | 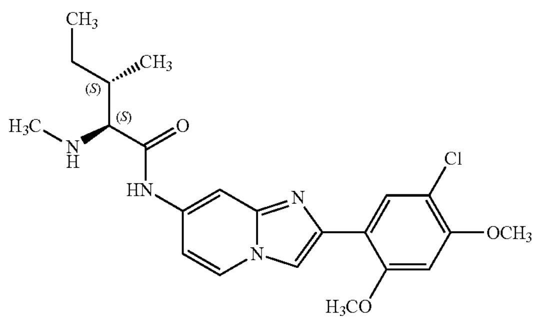 | (2S,3S)-N-(2-(5-chloro-2,4-dimethoxyphenyl)imidazo[1,2-a]pyridine-7-yl)-3-methyl-2-(methylamino)pentanamide | ESI | 431 |
| 267 | 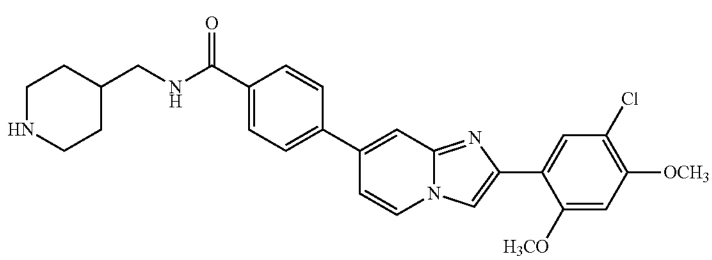 [SMILES: COc1cc(OC)c(-c2cn3ccc(-c4ccc(C(=O)NCC5CCNCC5)cc4)cc3n2)cc1Cl] | 4-(2-(5-chloro-2,4-dimethoxyphenyl)imidazo[1,2-a]pyridin-7-yl)-N-(piperidin-4-ylmethyl)benzamide | ESI | 505 |
| 268 | 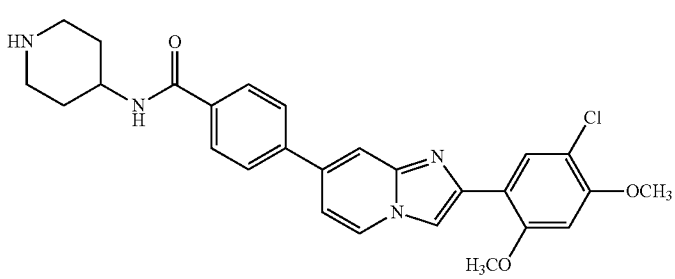 [SMILES: COc1cc(OC)c(-c2cn3ccc(-c4ccc(C(=O)NC5CCNCC5)cc4)cc3n2)cc1Cl] | 4-(2-(5-chloro-2,4-dimethoxyphenyl)imidazo[1,2-a]pyridin-7-yl)-N-(piperidin-4-yl)benzamide | ESI | 491 |
| 269 | 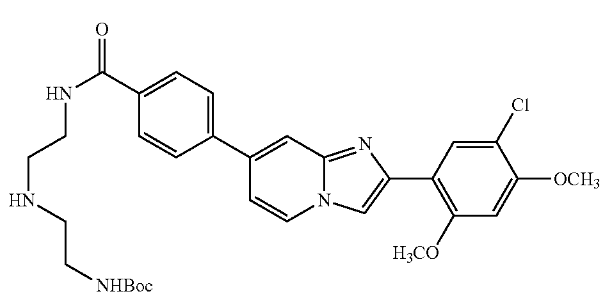 [SMILES: COc1cc(OC)c(-c2cn3ccc(-c4ccc(C(=O)NCCNCCNC(=O)OC(C)(C)C)cc4)cc3n2)cc1Cl] | tert-butyl (2-((2-(4-(2-(5-chloro-2,4-dimethoxyphenyl)imidazo-[1,2-a]pyridin-7-yl)benzamido)-ethyl)amino)ethyl)carbamate | ESI | 594 |

TABLE 1-continued

Compounds Table:

| Ex. No. | Structure | Name | MS Ionization | MS |
|---|---|---|---|---|
| 270 | 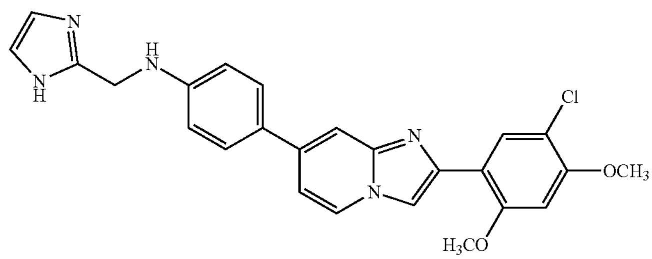 [SMILES: COc1cc(OC)c(-c2cn3ccc(-c4ccc(NCc5ncc[nH]5)cc4)cc3n2)cc1Cl] | N-((1H-imidazol-2-yl)methyl)-4-(2-(5-chloro-2,4-dimethoxyphenyl)imidazo[1,2-a]pyridin-7-yl)aniline | ESI | 460 |
| 271 | 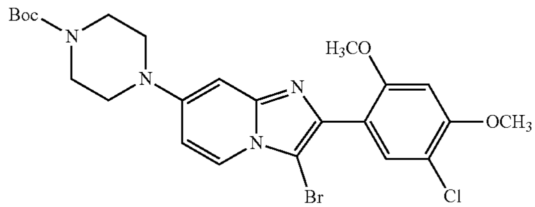 [SMILES: COc1cc(OC)c(-c2nc3cc(N4CCN(C(=O)OC(C)(C)C)CC4)ccn3c2Br)cc1Cl] | tert-butyl 4-(3-bromo-2-(5-chloro-2,4-dimethoxyphenyl)-imidazo[1,2-a]pyridin-7-yl)piperazine-1-carboxylate | ESI | 553 |
| 272 | 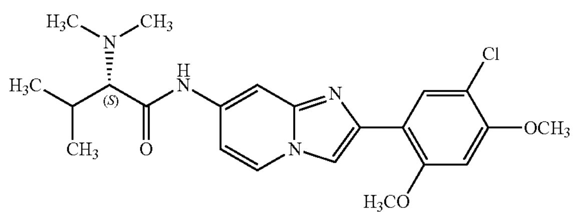 | (S)-N-(2-(5-chloro-2,4-dimethoxyphenyl)imidazo[1,2-a]pyridin-7-yl)-2-(dimethylamino)-3-methylbutanamide | ESI | 431 |
| 273 | 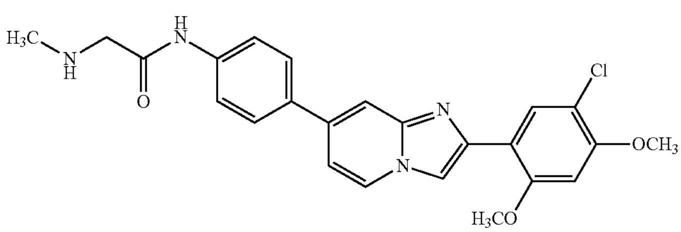 [SMILES: CNCC(=O)Nc1ccc(-c2ccn3cc(-c4cc(Cl)c(OC)cc4OC)nc3c2)cc1] | N-(4-(2-(5-chloro-2,4-dimethoxyphenyl)imidazo[1,2-a]pyridin-7-yl)phenyl)-2-(methylamino)acetamide | ESI + APCI | 450 |
| 274 | 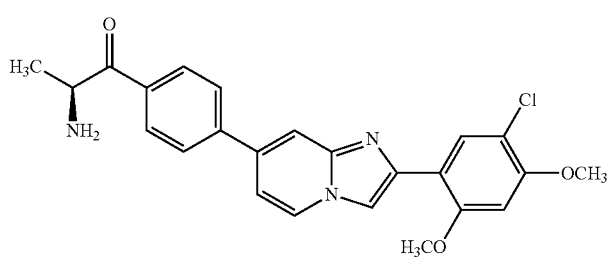 [SMILES: COc1cc(OC)c(-c2cn3ccc(-c4ccc(C(=O)[C@H](C)N)cc4)cc3n2)cc1Cl] | (S)-2-amino-1-(4-(2-(5-chloro-2,4-dimethoxyphenyl)imidazo[1,2-a]pyridin-7-yl)phenyl)propan-1-one | ESI + APCI | 435 |
| 275 | 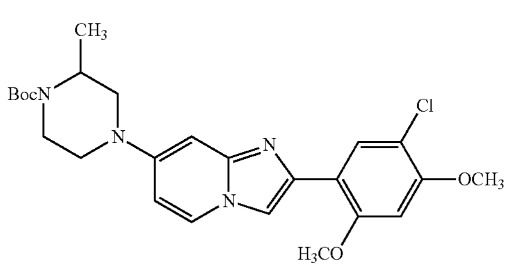 [SMILES: COc1cc(OC)c(-c2cn3ccc(N4CCN(C(=O)OC(C)(C)C)C(C)C4)cc3n2)cc1Cl] | tert-butyl 4-(2-(5-chloro-2,4-dimethoxyphenyl)imidazo[1,2-a]pyridin-7-yl)-2-methylpiperazine-1-carboxylate | ESI + APCI | 487 |

TABLE 1-continued

Compounds Table:

| Ex. No. | Structure | Name | MS Ionization | MS |
|---|---|---|---|---|
| 276 | 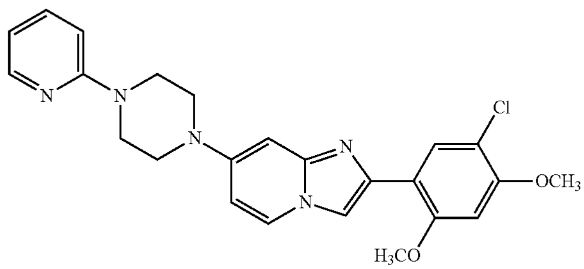 [SMILES: COc1cc(OC)c(-c2cn3ccc(N4CCN(c5ccccn5)CC4)cc3n2)cc1Cl] | 2-(5-chloro-2,4-dimethoxyphenyl)-7-(4-(pyridin-2-yl)piperazin-1-yl)imidazo[1,2-a]pyridine | ESI + APCI | 450 |
| 277 | 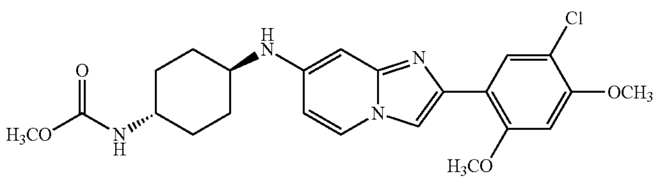 [SMILES: COC(=O)N[C@H]1CC[C@H](Nc2ccn3cc(-c4cc(Cl)c(OC)cc4OC)nc3c2)CC1] | (methyl(4-((2-(5-chloro-2,4-dimethoxyphenyl)imidazo[1,2-a]pyridin-7-yl)-trans-amino)cyclohexyl)carbamate | ESI + APCI | 459 |
| 278 | 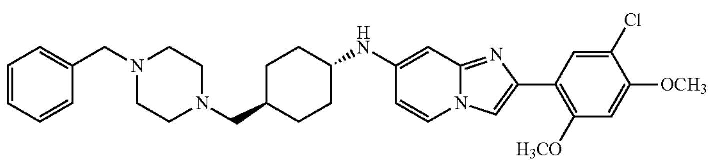 [SMILES: COc1cc(OC)c(-c2cn3ccc(N[C@H]4CC[C@H](CN5CCN(Cc6ccccc6)CC5)CC4)cc3n2)cc1Cl] | trans-N-(4-((4-benzylpiperazin-1-yl)methyl)cyclohexyl)-2-(5-chloro-2,4-dimethoxyphenyl)-imidazo[1,2-a]pyridin-7-amine | ESI + APCI | 574 |
| 279 | 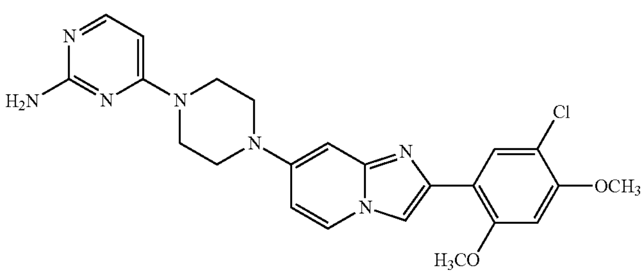 | 4-(4-(2-(5-chloro-2,4-dimethoxyphenyl)imidazo[1,2-a]pyridin-7-yl)piperazin-1-yl)pyrimidin-2-amine | ESI + APCI | 466 |
| 280 | 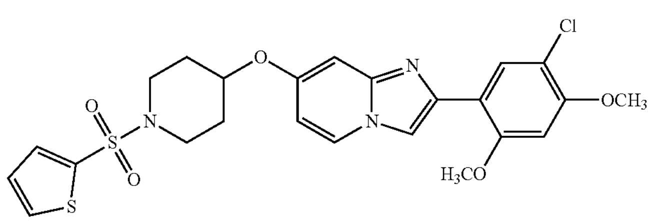 [SMILES: COc1cc(OC)c(-c2cn3ccc(OC4CCN(S(=O)(=O)c5cccs5)CC4)cc3n2)cc1Cl] | 2-(5-chloro-2,4-dimethoxyphenyl)-7-((3-(thiophen-2-ylsulfonyl)-piperidin-4-yl)oxy)imidazo[1,2-a]pyridine | ESI + APCI | 534 |
| 281 | 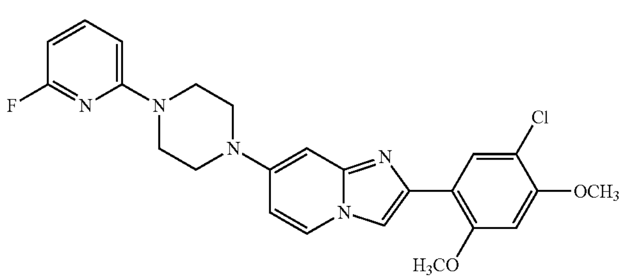 [SMILES: COc1cc(OC)c(-c2cn3ccc(N4CCN(c5cccc(F)n5)CC4)cc3n2)cc1Cl] | 2-(5-chloro-2,4-dimethoxyphenyl)-7-(4-(6-fluoropyridin-2-yl)piperazin-1-yl)imidazo[1,2-a]pyridine | ESI + APCI | 468 |

TABLE 1-continued

Compounds Table:

| Ex. No. | Structure | Name | MS Ionization | MS |
|---|---|---|---|---|
| 282 | 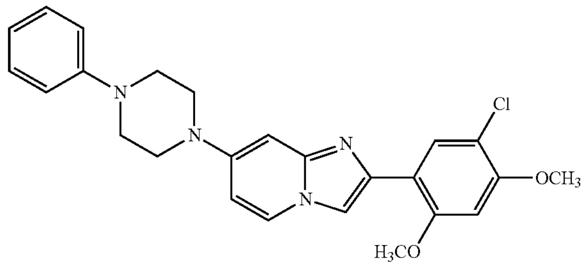 | 2-(5-chloro-2,4-dimethoxyphenyl)-7-(4-phenylpiperazin-1-yl)imidazo[1,2-a]pyridine | ESI + APCI | 449 |
| 283 | 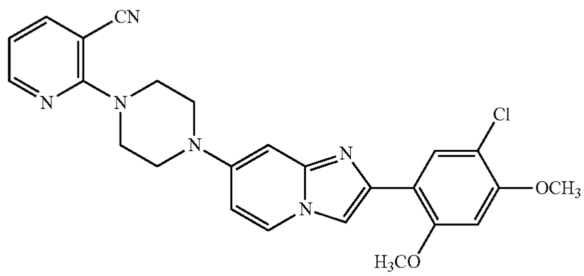 [SMILES: COc1cc(OC)c(-c2cn3ccc(N4CCN(c5ncccc5C#N)CC4)cc3n2)cc1Cl] | 2-(4-(2-(5-chloro-2,4-dimethoxyphenyl)imidazo[1,2-a]pyridin-7-yl)piperazin-1-yl)nicotinonitrile | ESI + APCI | 475 |
| 284 | 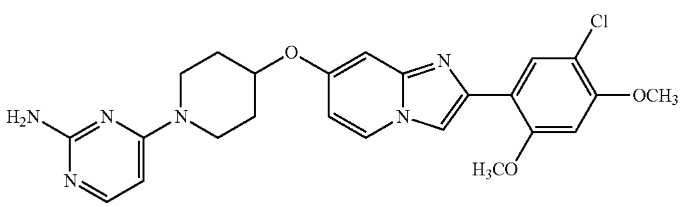 [SMILES: COc1cc(OC)c(-c2cn3ccc(OC4CCN(c5ccnc(N)n5)CC4)cc3n2)cc1Cl] | 4-(4-((2-(5-chloro-2,4-dimethoxyphenyl)imidazo[1,2-a]pyridin-7-yl)oxy)piperidin-1-yl)pyrimidin-2-amine | ESI + APCI | 481 |
| 285 | 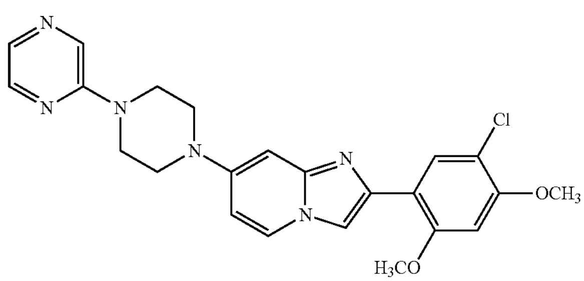 [SMILES: COc1cc(OC)c(-c2cn3ccc(N4CCN(c5cnccn5)CC4)cc3n2)cc1Cl] | 2-(5-chloro-2,4-dimethoxyphenyl)-7-(4-(pyrazin-2-yl)piperazin-1-yl)imidazo[1,2-a]pyridine | ESI + APCI | 451 |
| 286 | 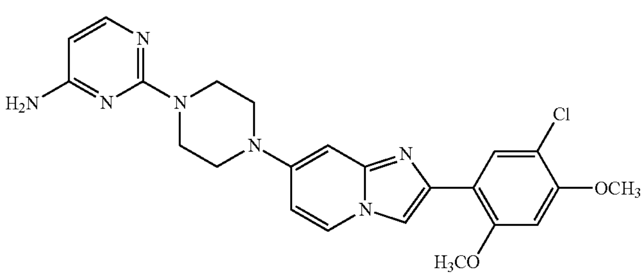 [SMILES: COc1cc(OC)c(-c2cn3ccc(N4CCN(c5nccc(N)n5)CC4)cc3n2)cc1Cl] | 2-(4-(2-(5-chloro-2,4-dimethoxyphenyl)imidazo[1,2-a]pyridin-7-yl)piperazin-1-yl)pyrimidin-4-amine | ESI + APCI | 466 |
| 287 | 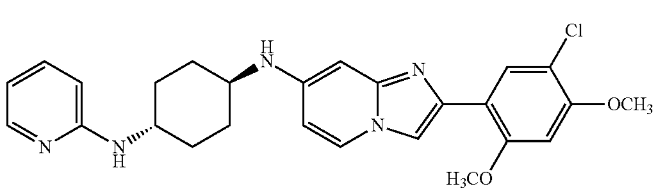 [SMILES: COc1cc(OC)c(-c2cn3ccc(N[C@H]4CC[C@H](Nc5ccccn5)CC4)cc3n2)cc1Cl] | $N^1$-(2-(5-chloro-2,4-dimethoxyphenyl)imidazo[1,2-a]pyridin-7-yl)-$N^4$-(pyridin-2-yl)-trans-cyclohexane-1,4-diamine | ESI + APCI | 478 |

TABLE 1-continued

Compounds Table:

| Ex. No. | Structure | Name | MS Ionization | MS |
|---|---|---|---|---|
| 288 | 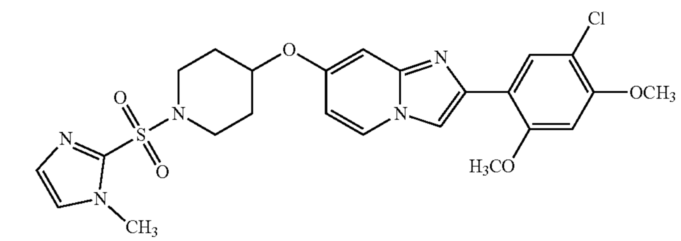 [SMILES: COc1cc(OC)c(-c2cn3ccc(OC4CCN(S(=O)(=O)c5nccn5C)CC4)cc3n2)cc1Cl] | 2-(5-chloro-2,4-dimethoxyphenyl)-7-((1-((1-methyl-1H-imidazol-2-yl)sulfonyl)piperidin-4-yl)oxy)imidazo[1,2-a]pyridine | ESI + APCI | 532 |
| 289 | 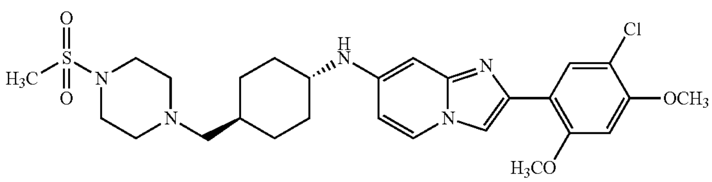 [SMILES: COc1cc(OC)c(-c2cn3ccc(N[C@H]4CC[C@H](CN5CCN(S(C)(=O)=O)CC5)CC4)cc3n2)cc1Cl] | 2-(5-chloro-2,4-dimethoxyphenyl)-trans-N-(4-((4-(methylsulfonyl)piperazin-1-yl)methyl)cyclohexyl)imidazo[1,2-a]pyridin-7-amine | ESI + APCI | 562 |
| 290 | 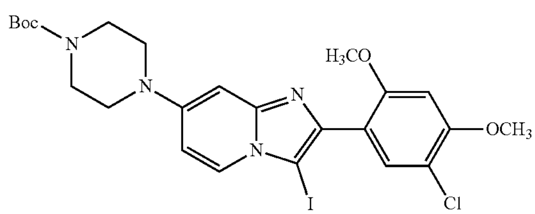 [SMILES: COc1cc(OC)c(-c2nc3cc(N4CCN(C(=O)OC(C)(C)C)CC4)ccn3c2I)cc1Cl] | tert-butyl 4-(2-(5-chloro-2,4-dimethoxyphenyl)-3-iodoimidazo[1,2-a]pyridin-7-yl)piperazine-1-carboxylate | ESI | 599 |
| 291 | 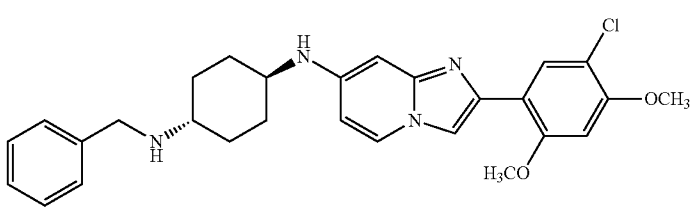 [SMILES: COc1cc(OC)c(-c2cn3ccc(N[C@H]4CC[C@H](NCc5ccccc5)CC4)cc3n2)cc1Cl] | N1-benzyl-N4-(2-(5-chloro-2,4-dimethoxyphenyl)imidazo[1,2-a]pyridin-7-yl)-trans-cyclohexane-1,4-diamine | ESI + APCI | 491 |
| 292 | 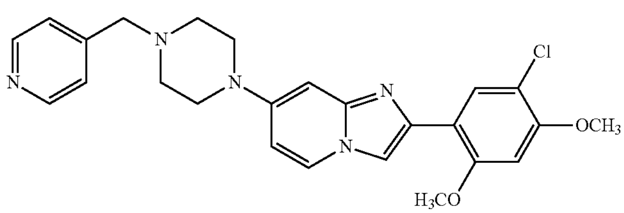 [SMILES: COc1cc(OC)c(-c2cn3ccc(N4CCN(Cc5ccncc5)CC4)cc3n2)cc1Cl] | 2-(5-chloro-2,4-dimethoxyphenyl)-7-(4-(pyridin-4-ylmethyl)piperazin-1-yl)imidazo[1,2-a]pyridine | ESI + APCI | 464 |
| 293 | 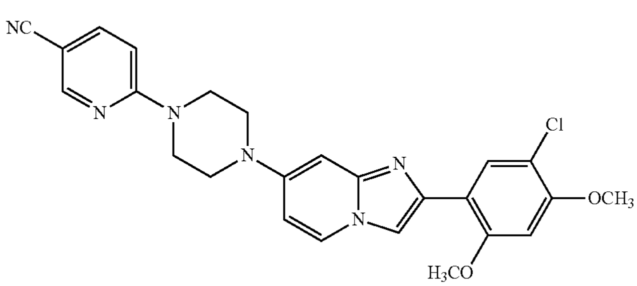 [SMILES: COc1cc(OC)c(-c2cn3ccc(N4CCN(c5ccc(C#N)cn5)CC4)cc3n2)cc1Cl] | 6-(4-(2-(5-chloro-2,4-dimethoxyphenyl)imidazo[1,2-a]pyridin-7-yl)piperazin-1-yl)nicotinonitrile | ESI + APCI | 475 |

TABLE 1-continued

Compounds Table:

| Ex. No. | Structure | Name | MS Ionization | MS |
|---|---|---|---|---|
| 294 | 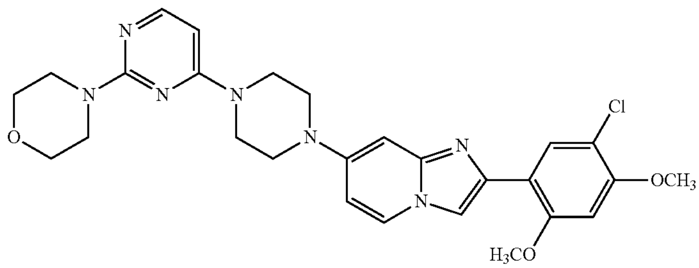 [SMILES: COc1cc(OC)c(-c2cn3ccc(N4CCN(c5ccnc(N6CCOCC6)n5)CC4)cc3n2)cc1Cl] | 4-(4-(4-(2-(5-chloro-2,4-dimethoxyphenyl)imidazo[1,2-a]pyridin-7-yl)piperazin-1-yl)pyrimidin-2-yl)morpholine | ESI + APCI | 536 |
| 295 | 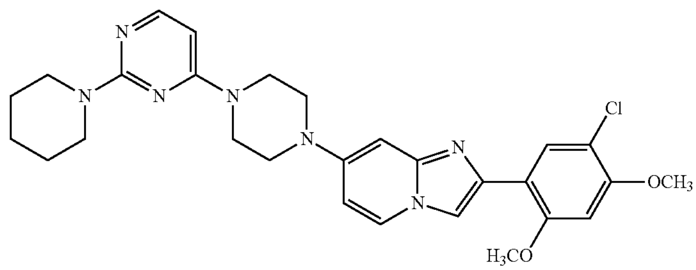 [SMILES: COc1cc(OC)c(-c2cn3ccc(N4CCN(c5ccnc(N6CCCCC6)n5)CC4)cc3n2)cc1Cl] | 2-(5-chloro-2,4-dimethoxyphenyl)-7-(4-(2-(piperidin-1-yl)pyrimidin-4-yl)piperazin-1-yl)imidazo[1,2-a]pyridine | ESI + APCI | 534 |
| 296 | 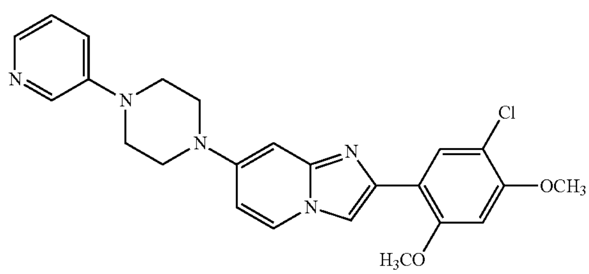 [SMILES: COc1cc(OC)c(-c2cn3ccc(N4CCN(c5cccnc5)CC4)cc3n2)cc1Cl] | 2-(5-chloro-2,4-dimethoxyphenyl)-7-(4-(pyridin-3-yl)piperazin-1-yl)imidazo[1,2-a]pyridine | ESI + APCI | 450 |
| 297 | 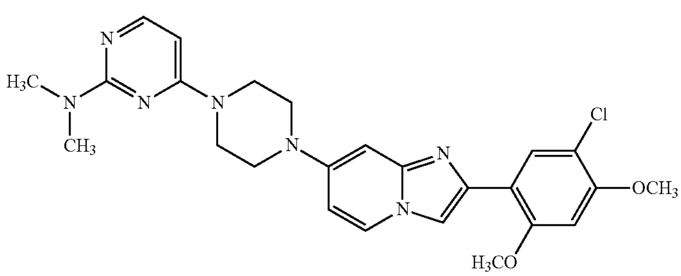 [SMILES: COc1cc(OC)c(-c2cn3ccc(N4CCN(c5ccnc(N(C)C)n5)CC4)cc3n2)cc1Cl] | 4-(4-(2-(5-chloro-2,4-dimethoxyphenyl)imidazo[1,2-a]pyridin-7-yl)piperazin-1-yl)-N,N-dimethylpyrimidin-2-amine | ESI + APCI | 494 |
| 298 | 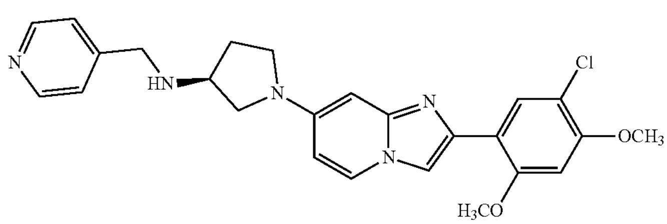 [SMILES: COc1cc(OC)c(-c2cn3ccc(N4CC[C@H](NCc5ccncc5)C4)cc3n2)cc1Cl] | (S)-1-(2-(5-chloro-2,4-dimethoxyphenyl)imidazo[1,2-a]pyridin-7-yl)-N-(pyridin-4-ylmethyl)pyrrolidin-3-amine | ESI | 464 |

TABLE 1-continued

Compounds Table:

| Ex. No. | Structure | Name | MS Ionization | MS |
|---|---|---|---|---|
| 299 | 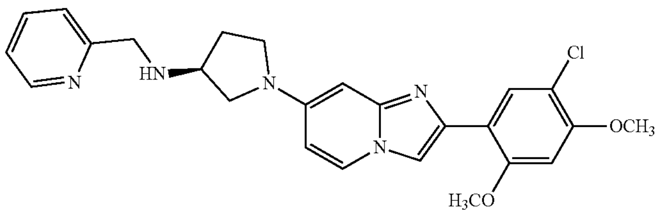 [SMILES: COc1cc(OC)c(-c2cn3ccc(N4CC[C@H](NCc5ccccn5)C4)cc3n2)cc1Cl] | (S)-1-(2-(5-chloro-2,4-dimethoxyphenyl)imidazo[1,2-a]pyridin-7-yl)-N-(pyridin-2-ylmethyl)pyrrolidin-3-amine | ESI | 464 |
| 300 | 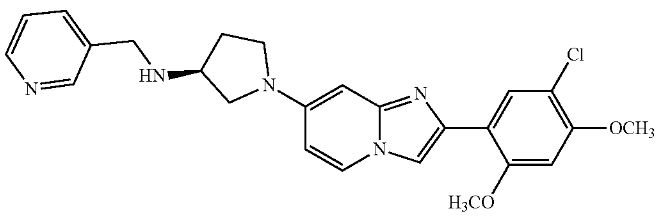 [SMILES: COc1cc(OC)c(-c2cn3ccc(N4CC[C@H](NCc5cccnc5)C4)cc3n2)cc1Cl] | (S)-1-(2-(5-chloro-2,4-dimethoxyphenyl)imidazo[1,2-a]pyridin-7-yl)-N-(pyridin-3-ylmethyl)pyrrolidin-3-amine | ESI | 464 |
| 301 | 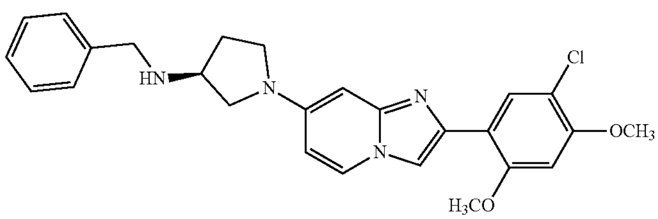 [SMILES: COc1cc(OC)c(-c2cn3ccc(N4CC[C@H](NCc5ccccc5)C4)cc3n2)cc1Cl] | (S)-N-benzyl-1-(2-(5-chloro-2,4-dimethoxyphenyl)imidazo[1,2-a]pyridin-7-yl)pyrrolidin-3-amine | ESI | 463 |
| 302 | 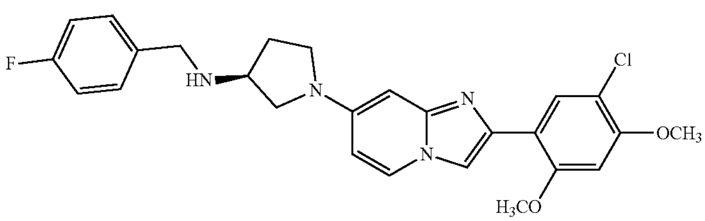 [SMILES: COc1cc(OC)c(-c2cn3ccc(N4CC[C@H](NCc5ccc(F)cc5)C4)cc3n2)cc1Cl] | (S)-1-(2-(5-chloro-2,4-dimethoxyphenyl)imidazo[1,2-a]pyridin-7-yl)-N-(4-fluorobenzyl)pyrrolidin-3-amine | ESI | 481 |
| 303 | 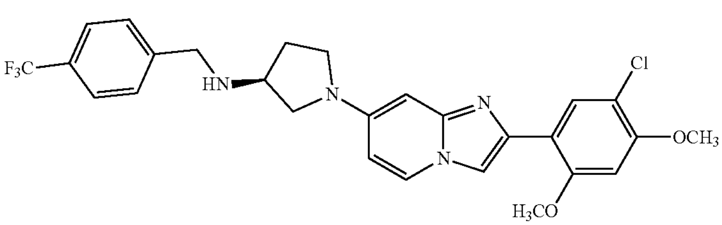 [SMILES: COc1cc(OC)c(-c2cn3ccc(N4CC[C@H](NCc5ccc(C(F)(F)F)cc5)C4)cc3n2)cc1Cl] | (S)-1-(2-(5-chloro-2,4-dimethoxyphenyl)imidazo[1,2-a]pyridin-7-yl)-N-(4-(trifluoromethyl)benzyl)pyrrolidin-3-amine | ESI | 531 |
| 304 | 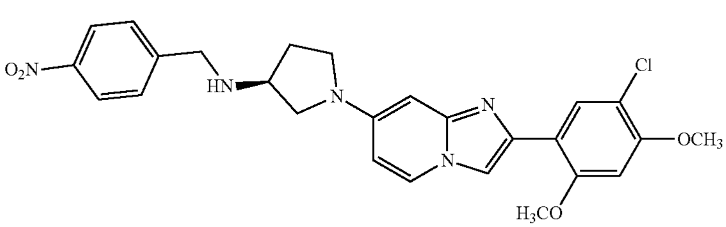 [SMILES: COc1cc(OC)c(-c2cn3ccc(N4CC[C@H](NCc5ccc([N+](=O)[O-])cc5)C4)cc3n2)cc1Cl] | (S)-1-(2-(5-chloro-2,4-dimethoxyphenyl)imidazo[1,2-a]pyridin-7-yl)-N-(4-nitrobenzyl)pyrrolidin-3-amine | ESI | 508 |

TABLE 1-continued

Compounds Table:

| Ex. No. | Structure | Name | MS Ionization | MS |
|---|---|---|---|---|
| 305 | 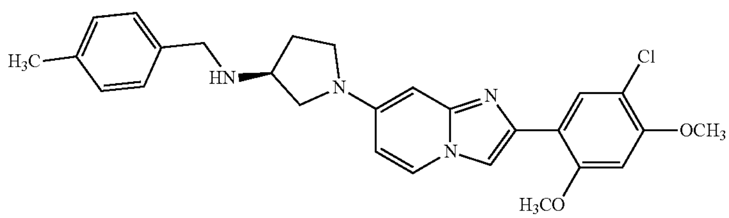 [SMILES: COc1cc(OC)c(-c2cn3ccc(N4CC[C@H](NCc5ccc(C)cc5)C4)cc3n2)cc1Cl] | (S)-1-(2-(5-chloro-2,4-dimethoxyphenyl)imidazo[1,2-a]pyridin-7-yl)-N-(4-methylbenzyl)pyrrolidin-3-amine | ESI | 477 |
| 306 | 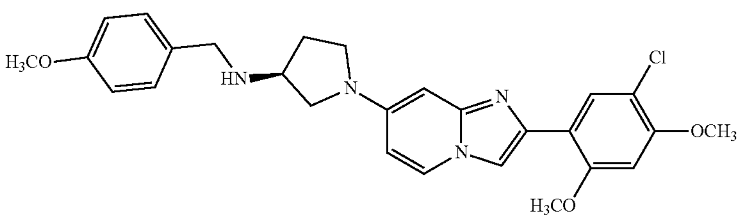 [SMILES: COc1ccc(CN[C@H]2CCN(c3ccn4cc(-c5cc(Cl)c(OC)cc5OC)nc4c3)C2)cc1] | (S)-1-(2-(5-chloro-2,4-dimethoxyphenyl)imidazo[1,2-a]pyridin-7-yl)-N-(4-methoxybenzyl)pyrrolidin-3-amine | ESI | 493 |

TABLE 2

Compounds Table:

| Ex. | Structure | Name | MS | MS |
|---|---|---|---|---|
| 307 | 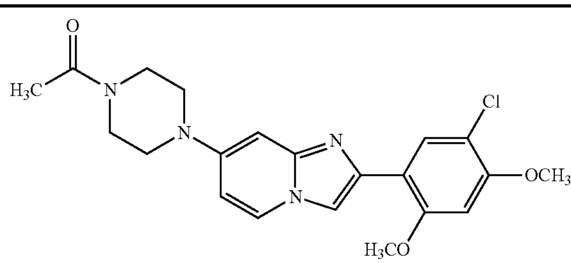 | 1-(4-(2-(5-chloro-2,4-dimethoxyphenyl)imidazo[1,2-a]pyridin-7-yl)piperazin-1-yl)ethanone | ESI + APCI | 414 |
| 308 | 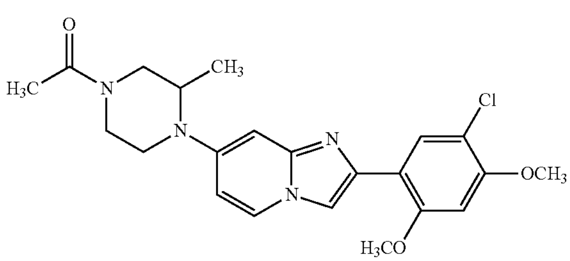 | 1-(4-(2-(5-chloro-2,4-dimethoxyphenyl)imidazo[1,2-a]pyridin-7-yl)-3-methylpiperazin-1-yl)ethanone | ESI + APCI | 429 |
| 309 | 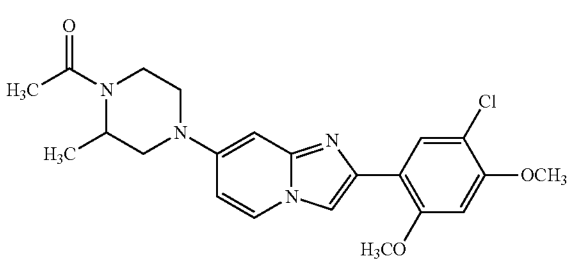 [SMILES: COc1cc(OC)c(-c2cn3ccc(N4CCN(C(C)=O)C(C)C4)cc3n2)cc1Cl] | 1-(4-(2-(5-chloro-2,4-dimethoxyphenyl)imidazo[1,2-a]pyridin-7-yl)-2-methylpiperazin-1-yl)ethanone | ESI + APCI | 429 |

TABLE 2-continued

Compounds Table:

| Ex. | Structure | Name | MS | MS |
|---|---|---|---|---|
| 310 | 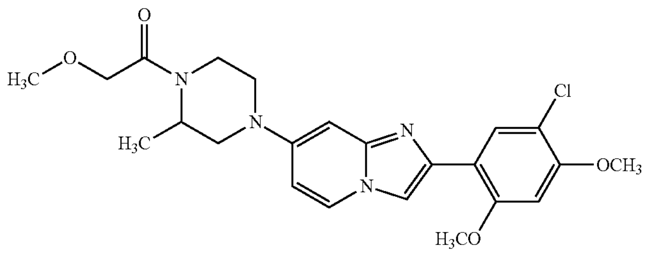 [SMILES: COCC(=O)N1CCN(c2ccn3cc(-c4cc(Cl)c(OC)cc4OC)nc3c2)CC1C] | 1-(4-(2-(5-chloro-2,4-dimethoxyphenyl)imidazo[1,2-a]pyridin-7-yl)-2-methylpiperazin-1-yl)-2-methoxyethanone | ESI + APCI | 459 |
| 311 | 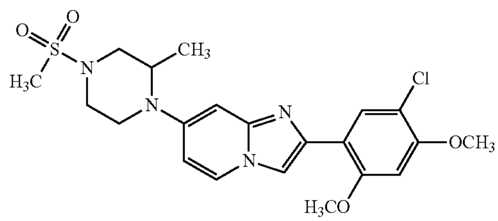 [SMILES: COc1cc(OC)c(-c2cn3ccc(N4CCN(S(C)(=O)=O)CC4C)cc3n2)cc1Cl] | 2-(5-chloro-2,4-dimethoxyphenyl)-7-(2-methyl-4-(methylsulfonyl)piperazin-1-yl)imidazo[1,2-a]pyridine | ESI + APCI | 465 |
| 312 | 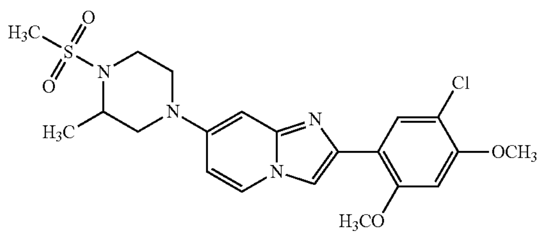 [SMILES: COc1cc(OC)c(-c2cn3ccc(N4CCN(S(C)(=O)=O)C(C)C4)cc3n2)cc1Cl] | 2-(5-chloro-2,4-dimethoxyphenyl)-7-(3-methyl-4-(methylsulfonyl)piperazin-1-yl)imidazo[1,2-a]pyridine | ESI + APCI | 465 |
| 313 | 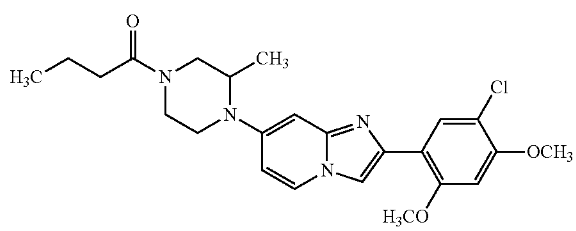 [SMILES: CCCC(=O)N1CCN(c2ccn3cc(-c4cc(Cl)c(OC)cc4OC)nc3c2)C(C)C1] | 1-(4-(2-(5-chloro-2,4-dimethoxyphenyl)imidazo[1,2-a]pyridin-7-yl)-3-methylpiperazin-1-yl)-2-methoxyethanone | ESI + APCI | 459 |
| 314 | 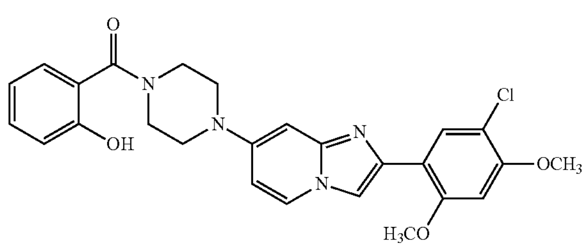 [SMILES: COc1cc(OC)c(-c2cn3ccc(N4CCN(C(=O)c5ccccc5O)CC4)cc3n2)cc1Cl] | (4-(2-(5-chloro-2,4-dimethoxyphenyl)imidazo[1,2-a]pyridin-7-yl)piperazin-1-yl)(2-hydroxyphenyl)methanone | ESI + APCI | 493 |
| 315 | 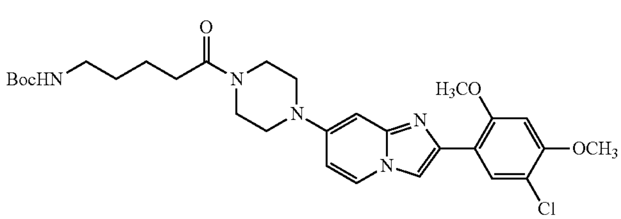 [SMILES: COc1cc(OC)c(-c2cn3ccc(N4CCN(C(=O)CCCCNC(=O)OC(C)(C)C)CC4)cc3n2)cc1Cl] | tert-butyl (5-(4-(2-(5-chloro-2,4-dimethoxyphenyl)imidazo[1,2-a]pyridin-7-yl)piperazin-1-yl)-5-oxopentyl)carbamate | ESI + APCI | 572 |

TABLE 2-continued

Compounds Table:

| Ex. | Structure | Name | MS | MS |
|---|---|---|---|---|
| 316 | 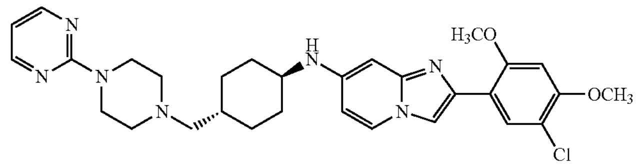 [SMILES: COc1cc(OC)c(-c2cn3ccc(N[C@H]4CC[C@H](CN5CCN(c6ncccn6)CC5)CC4)cc3n2)cc1Cl] | 2-(5-chloro-2,4-dimethoxyphenyl)-N-(1r,4r)-4-((4-(pyrimidin-2-yl)piperazin-1-yl)methyl)cyclohexyl)imidazo[1,2-a]pyridin-7-amine | ESI + APCI | 562 |
| 317 | 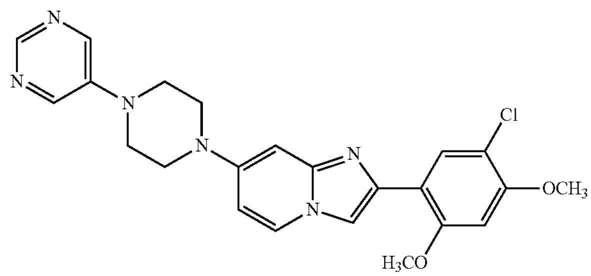 [SMILES: COc1cc(OC)c(-c2cn3ccc(N4CCN(c5cncnc5)CC4)cc3n2)cc1Cl] | 2-(5-chloro-2,4-dimethoxyphenyl)-7-(4-(pyrimidin-5-yl)piperazin-1-yl)imidazo[1,2-a]pyridine | ESI + APCI | 451 |
| 318 | 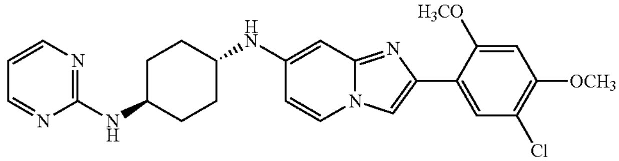 [SMILES: COc1cc(OC)c(-c2cn3ccc(N[C@H]4CC[C@H](Nc5ncccn5)CC4)cc3n2)cc1Cl] | (1r,4r)-$N^1$-(2-(5-chloro-2,4-dimethoxyphenyl)imidazo[1,2-a]pyridin-7-yl)-$N^4$-(pyrimidin-2-yl)cyclohexane-1,4-diamine | ESI | 479 |
| 319 | 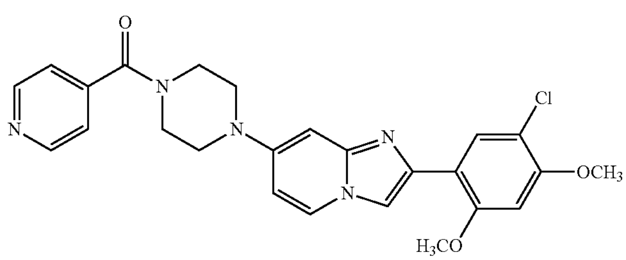 [SMILES: COc1cc(OC)c(-c2cn3ccc(N4CCN(C(=O)c5ccncc5)CC4)cc3n2)cc1Cl] | (4-(2-(5-chloro-2,4-dimethoxyphenyl)imidazo[1,2-a]pyridin-7-yl)piperazin-1-yl)(pyridin-4-yl)methanone | ESI + APCI | 478 |
| 320 | 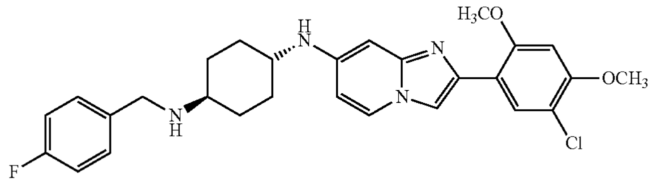 | (1r,4r)-$N^1$-(2-(5-chloro-2,4-dimethoxyphenyl)imidazo[1,2-a]pyridin-7-yl)-$N^4$-(4-fluorobenzyl)cyclohexane-1,4-diamine | ESI + APCI | 509 |
| 321 | 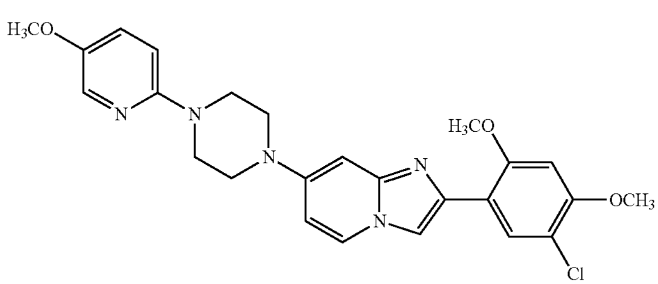 [SMILES: COc1ccc(N2CCN(c3ccn4cc(-c5cc(Cl)c(OC)cc5OC)nc4c3)CC2)nc1] | 2-(5-chloro-2,4-dimethoxyphenyl)-7-(4-(5-methoxypyridin-2-yl)piperazin-1-yl)imidazo[1,2-a]pyridine | ESI + APCI | 480 |

TABLE 2-continued

Compounds Table:

| Ex. | Structure | Name | MS | MS |
|---|---|---|---|---|
| 322 | 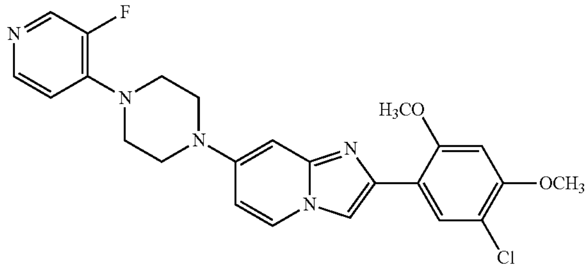 [SMILES: COc1cc(OC)c(-c2cn3ccc(N4CCN(c5ccncc5F)CC4)cc3n2)cc1Cl] | 2-(5-chloro-2,4-dimethoxyphenyl)-7-(4-(3-fluoropyridin-4-yl)piperazin-1-yl)imidazo[1,2-a]pyridine | ESI + APCI | 468 |
| 323 | 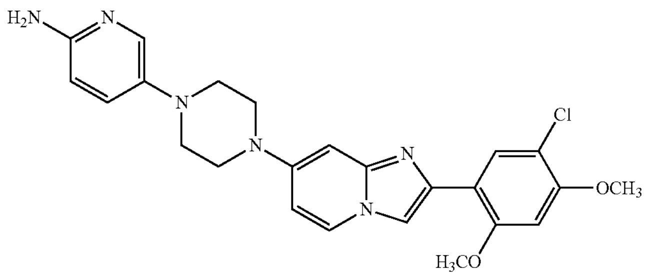 [SMILES: COc1cc(OC)c(-c2cn3ccc(N4CCN(c5ccc(N)nc5)CC4)cc3n2)cc1Cl] | 5-(4-(2-(5-chloro-2,4-dimethoxyphenyl)imidazo[1,2-a]pyridin-7-yl)piperazin-1-yl)pyridin-2-amine | ESI + APCI | 465 |
| 324 | 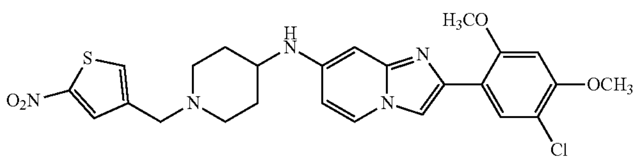 [SMILES: COc1cc(OC)c(-c2cn3ccc(NC4CCN(Cc5csc([N+](=O)[O-])c5)CC4)cc3n2)cc1Cl] | 2-(5-chloro-2,4-dimethoxyphenyl)-N-(1-((5-nitrothiophen-3-yl)methyhl)piperidin-4-yl)imidazo[1,2-a]pyridin-7-amine | ESI + APCI | 528 |
| 325 | 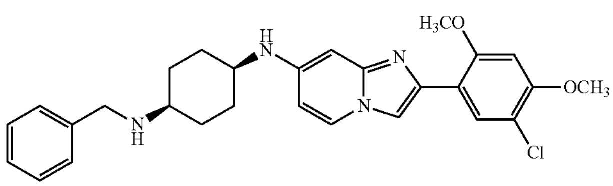 [SMILES: COc1cc(OC)c(-c2cn3ccc(N[C@H]4CC[C@@H](NCc5ccccc5)CC4)cc3n2)cc1Cl] | (1s,4S)-$N^1$-benzyl-$N^4$-(2-(5-chloro-2,4-dimethoxyphenyl)imidazo[1,2-a]pyridin-7-yl)cyclohexane-1,4-diamine | ESI + APCI | 491 |
| 326 | 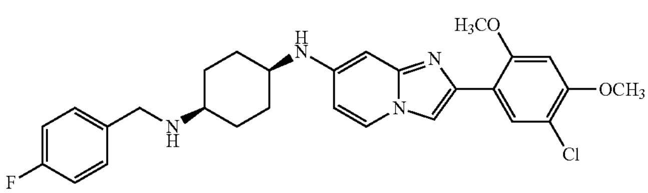 [SMILES: COc1cc(OC)c(-c2cn3ccc(N[C@H]4CC[C@@H](NCc5ccc(F)cc5)CC4)cc3n2)cc1Cl] | (1s,4s)-$N^1$-(2-(5-chloro-2,4-dimethoxyphenyl)imidazo[1,2-a]pyridin-7-yl)-$N^4$-(4-fluorobenzyl)cyclohexane-1,4-diamine | ESI + APCI | 509 |
| 327 | 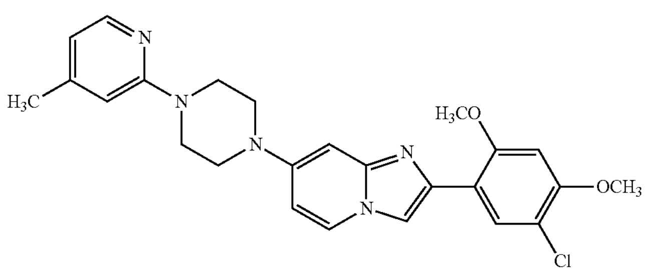 [SMILES: COc1cc(OC)c(-c2cn3ccc(N4CCN(c5cc(C)ccn5)CC4)cc3n2)cc1Cl] | 2-(5-chloro-2,4-dimethoxyphenyl)-7-(4-(4-methylpyridin-2-yl)piperazin-1-yl)imidazo[1,2-a]pyridine | ESI + APCI | 464 |
| 328 | 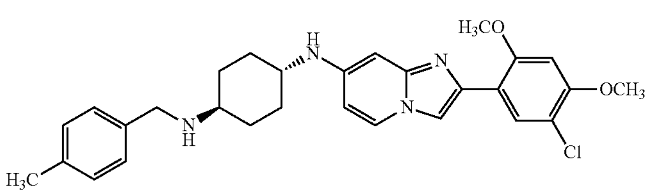 [SMILES: COc1cc(OC)c(-c2cn3ccc(N[C@H]4CC[C@H](NCc5ccc(C)cc5)CC4)cc3n2)cc1Cl] | (1r,4r)-$N^1$-(2-(5-chloro-2,4-dimethoxyphenyl)imidazo[1,2-a]pyridin-7-yl)-$N^4$-(4-methylbenzyl)cyclohexane-1,4-diamine | ESI + APCI | 505 |

TABLE 2-continued

Compounds Table:

| Ex. | Structure | Name | MS | MS |
|---|---|---|---|---|
| 329 | 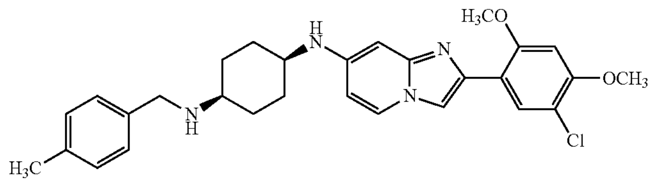 [SMILES: COc1cc(OC)c(-c2cn3ccc(N[C@H]4CC[C@@H](NCc5ccc(C)cc5)CC4)cc3n2)cc1Cl] | (1s,4s)-N¹-(2-(5-chloro-2,4-dimethoxyphenyl)imidazo[1,2-a]pyridin-7-yl)-N⁴-(4-methylbenzyl)cyclohexane-1,4-diamine | ESI + APCI | 505 |
| 330 | 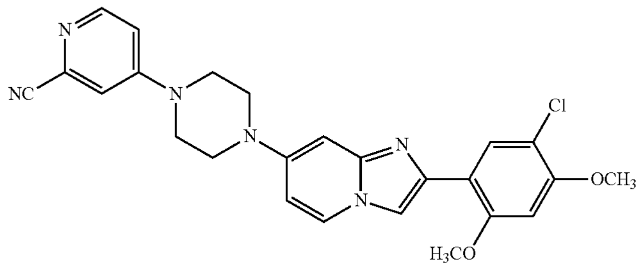 [SMILES: COc1cc(OC)c(-c2cn3ccc(N4CCN(c5ccnc(C#N)c5)CC4)cc3n2)cc1Cl] | 4-(4-(2-(5-chloro-2,4-dimethoxyphenyl)imidazo[1,2-a]pyridin-7-yl)piperazin-1-yl)picolinonitrile | ESI + APCI | 475 |
| 331 | 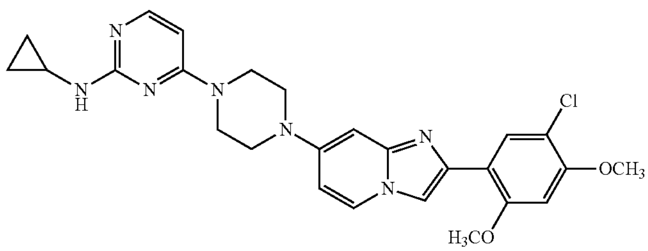 [SMILES: COc1cc(OC)c(-c2cn3ccc(N4CCN(c5ccnc(NC6CC6)n5)CC4)cc3n2)cc1Cl] | 4-(4-(2-(5-chloro-2,4-dimethoxyphenyl)imidazo[1,2-a]pyridin-7-yl)piperazin-1-yl)-N-cyclopropylpyrimidin-2-amine | ESI + APCI | 506 |
| 332 | 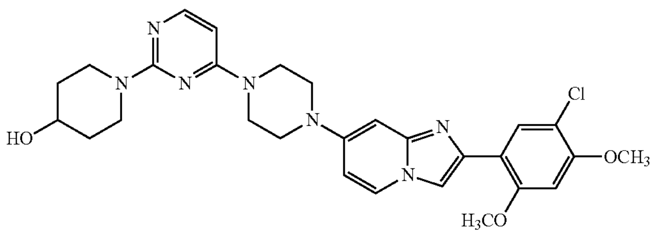 [SMILES: COc1cc(OC)c(-c2cn3ccc(N4CCN(c5ccnc(N6CCC(O)CC6)n5)CC4)cc3n2)cc1Cl] | 1-(4-(4-(2-(5-chloro-2,4-dimethoxyphenyl)imidazo[1,2-a]pyridin-7-yl)piperazin-1-yl)pyrimidin-2-yl)piperidin-4-ol | ESI + APCI | 506 |
| 333 | 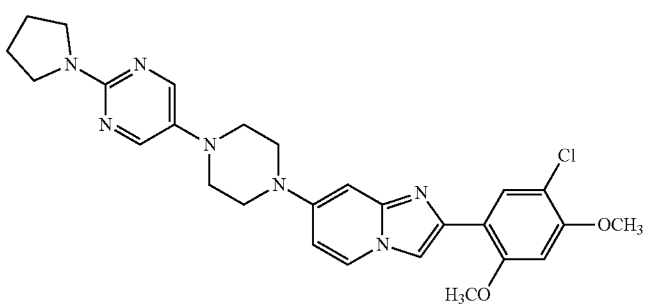 [SMILES: COc1cc(OC)c(-c2cn3ccc(N4CCN(c5cnc(N6CCCC6)nc5)CC4)cc3n2)cc1Cl] | 2-(5-chloro-2,4-dimethoxyphenyl)-7-(4-(2-(pyrrolidin-1-yl)pyrimidin-5-yl)piperazin-1-yl)imidazo[1,2-a]pyridine | ESI + APCI | 520 |
| 334 | 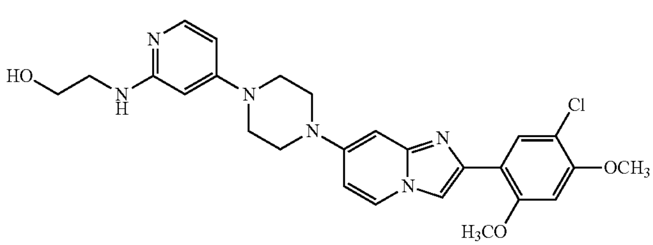 [SMILES: COc1cc(OC)c(-c2cn3ccc(N4CCN(c5ccnc(NCCO)c5)CC4)cc3n2)cc1Cl] | 2-((4-(4-(2-(5-chloro-2,4-dimethoxyphenyl)imidazo[1,2-a]pyridin-7-yl)piperazin-1-yl)pyrimidin-2-yl)amino)ethanol | ESI + APCI | 510 |

TABLE 2-continued

Compounds Table:

| Ex. | Structure | Name | MS | MS |
|---|---|---|---|---|
| 335 | 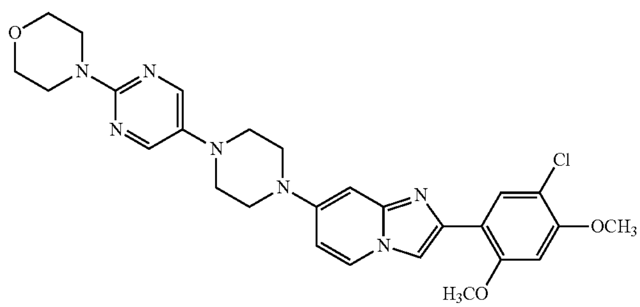 [SMILES: COc1cc(OC)c(-c2cn3ccc(N4CCN(c5cnc(N6CCOCC6)nc5)CC4)cc3n2)cc1Cl] | 4-(5-(4-(2-(5-chloro-2,4-dimethoxyphenyl)imidazo[1,2-a]pyridin-7-yl)piperazin-1-yl)pyrimidin-2-yl)morpholine | ESI + APCI | 536 |
| 336 | 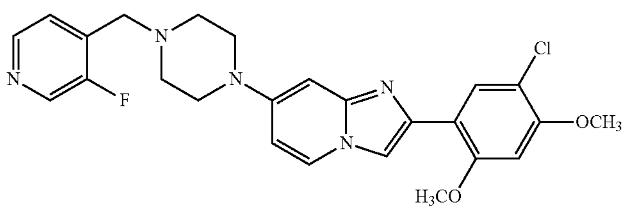 [SMILES: COc1cc(OC)c(-c2cn3ccc(N4CCN(Cc5ccncc5F)CC4)cc3n2)cc1Cl] | 2-(5-chloro-2,4-dimethoxyphenyl)-7-(4-((3-fluoropyridin-4-yl)methyl)piperazin-1-yl)imidazo[1,2-a]pyridine | ESI + APCI | 482 |
| 337 | 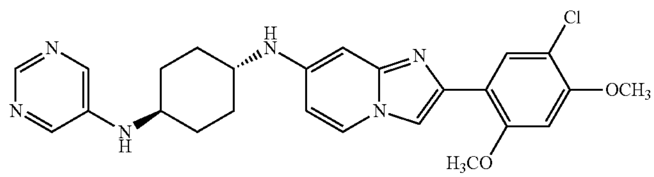 [SMILES: COc1cc(OC)c(-c2cn3ccc(N[C@H]4CC[C@H](Nc5cncnc5)CC4)cc3n2)cc1Cl] | (1r,4r)-N$^1$-(2-(5-chloro-2,4-dimethoxyphenyl)imidazo[1,2-a]pyridin-7-yl)-N$^4$-(pyrimidin-5-yl)cyclohexane-1,4-diamine | ESI + APCI | 479 |
| 338 | 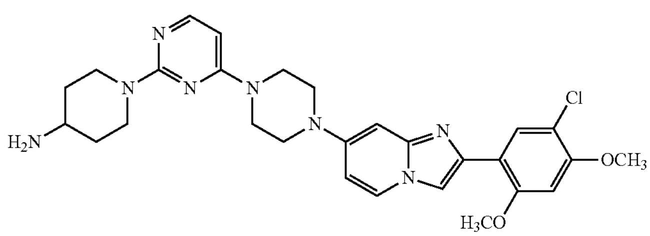 | 1-(4-(4-(2-(5-chloro-2,4-dimethoxyphenyl)imidazo[1,2-a]pyridin-7-yl)piperazin-1-yl)pyrimidin-2-yl)piperidin-4-amine | ESI + APCI | 549 |
| 339 | 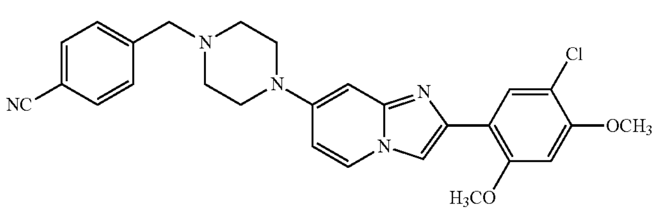 [SMILES: COc1cc(OC)c(-c2cn3ccc(N4CCN(Cc5ccc(C#N)cc5)CC4)cc3n2)cc1Cl] | 5-((4-(2-(5-chloro-2,4-dimethoxyphenyl)imidazo[1,2-a]pyridin-7-yl)piperazin-1-yl)methyl)picolinonitrile | ESI + APCI | 489 |
| 340 | 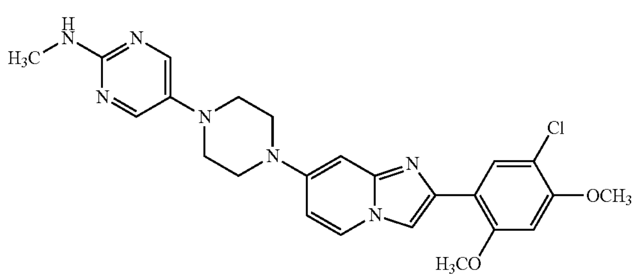 [SMILES: CNc1ncc(N2CCN(c3ccn4cc(-c5cc(Cl)c(OC)cc5OC)nc4c3)CC2)cn1] | 5-(4-(2-(5-chloro-2,4-dimethoxyphenyl)imidazo[1,2-a]pyridin-7-yl)piperazin-1-yl)-N-methylpyrimidin-2-amine | ESI + APCI | 480 |

TABLE 2-continued

Compounds Table:

| Ex. | Structure | Name | MS | MS |
|---|---|---|---|---|
| 341 | 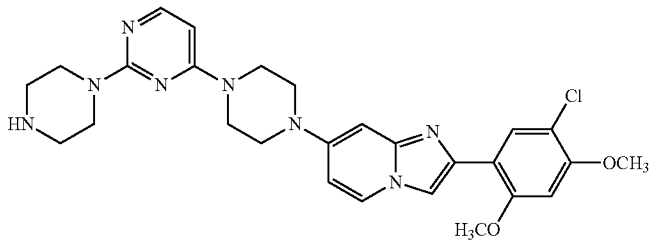 [SMILES: COc1cc(OC)c(-c2cn3ccc(N4CCN(c5ccnc(N6CCNCC6)n5)CC4)cc3n2)cc1Cl] | 2-(5-chloro-2,4-dimethoxyphenyl)-7-(4-(2-(pipenizin-1-yl)pyrimidin-4-yl)piperazin-1-yl)imidazo[1,2-a]pyridine | ESI + APCI | 535 |
| 342 | 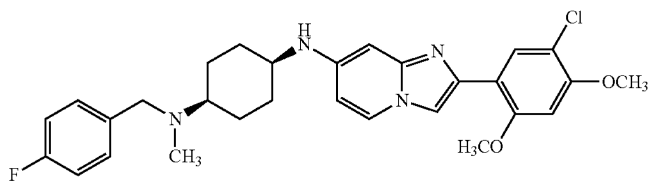 [SMILES: COc1cc(OC)c(-c2cn3ccc(N[C@H]4CC[C@@H](N(C)Cc5ccc(F)cc5)CC4)cc3n2)cc1Cl] | (1s,4s)-N$^1$-(2-(5-chloro-2,4-dimethoxyphenyl)imidazo[1,2-a]pyridin-7-yl)-N$^4$-(4-fluorobenzyl)-N$^4$-methylcyclohexane-1,4-diamine | ESI + APCI | 523 |
| 343 | 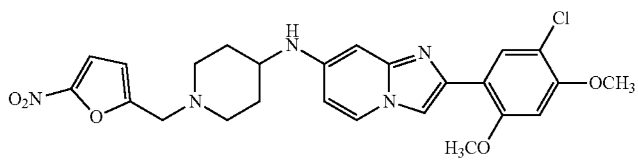 [SMILES: COc1cc(OC)c(-c2cn3ccc(NC4CCN(Cc5ccc([N+](=O)[O-])o5)CC4)cc3n2)cc1Cl] | 2-(5-chloro-2,4-dimethoxyphenyl)-N-(1-((5-nitrofuran-2-yl)methyl)piperidin-4-yl)imidazo[1,2-a]pyridin-7-amine | ESI + APCI | 512 |
| 344 | 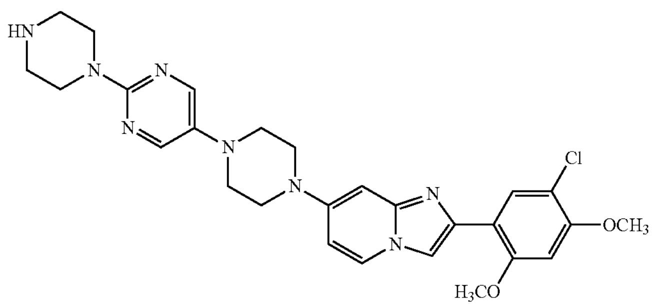 [SMILES: COc1cc(OC)c(-c2cn3ccc(N4CCN(c5cnc(N6CCNCC6)nc5)CC4)cc3n2)cc1Cl] | 2-(5-chloro-2,4-dimethoxyphenyl)-7-(4-(2-(piperazin-1-yl)pyrimidin-5-yl)piperazin-1-yl)imidazo[1,2-a]pyridine | ESI + APCI | 534 |
| 345 | 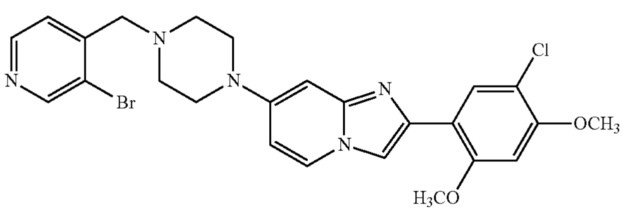 [SMILES: COc1cc(OC)c(-c2cn3ccc(N4CCN(Cc5ccncc5Br)CC4)cc3n2)cc1Cl] | 7-4-((3-bromopyridin-4-yl)-methyl)piperdzin-1-yl)-2-(5-chloro-2,4-dimethoxyphenyl)imidazo[1,2-a]pyridine | ESI + APCI | 542 |
| 346 | 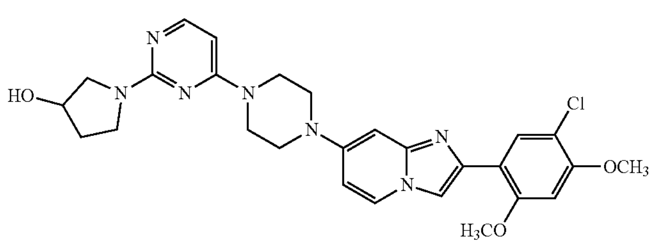 [SMILES: COc1cc(OC)c(-c2cn3ccc(N4CCN(c5ccnc(N6CCC(O)C6)n5)CC4)cc3n2)cc1Cl] | 1-(4-(4-(2-(5-chloro-2,4-dimethoxyphenyl)imidazol[1,2-a]pyridin-7-yl)piperazin-1-yl)pyrimidin-2-yl)pyrrolidin-3-ol | ESI + APCI | 536 |
| 347 | 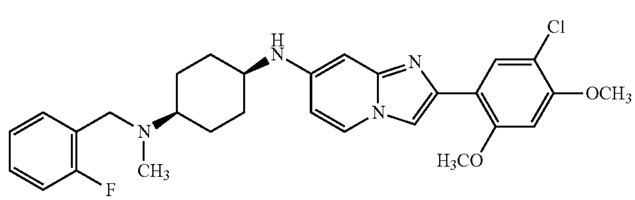 [SMILES: COc1cc(OC)c(-c2cn3ccc(N[C@H]4CC[C@@H](N(C)Cc5ccccc5F)CC4)cc3n2)cc1Cl] | (1s,4s)-N$^1$-(2-(5-chloro-2,4-dimethoxyphenyl)imidazo[1,2-a]pyridin-7-yl)-N$^4$-(2-fluorobenzyl)-N$^4$-methylcyclohexane-1,4-diamine | ESI + APCI | 523 |

TABLE 2-continued

Compounds Table:

| Ex. | Structure | Name | MS | MS |
|---|---|---|---|---|
| 348 | 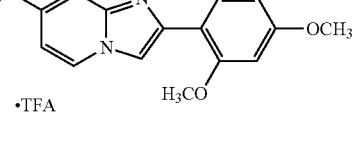 | (1s,4s)-N$^1$-(2-(5-chloro-2,4-dimethoxyphenyl)imidazo[1,2-a]pyridin-7-yl)-N$^4$-methyl-N$^4$-(2-methylbenzyl)cyclohexane-1,4-diamine | ESI + APCI | 519 |
| 349 | 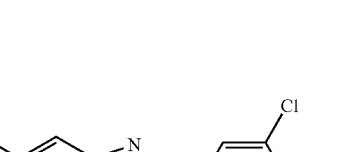 | 2-(4-(2-(5-chloro-2,4-dimethoxyphenyl)imidazo[1,2-a]pyridin-7-yl)piperazin-1-yl)-5-nitronicotinonitrile | ESI + APCI | 520 |
| 350 | 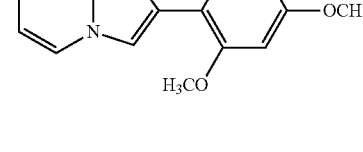 | 1-(5-(4-(2-(5-chloro-2,4-dimethoxyphenyl)imidazo[1,2-a]pyridin-7-yl)piperazin-1-yl)pyrimidin-2-yl)piperidin-4-amine | ESI + APCI | 549 |
| 351 | 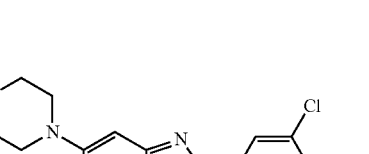 | 2-(5-chloro-2,4-dimethoxyphenyl)-7-(4-(2-(4-methylpiperazin-1-yl)pyrimidin-4-yl)piperazin-1-yl)imidazo[1,2-a]pyridine | ESI + APCI | 549 |
| 352 | 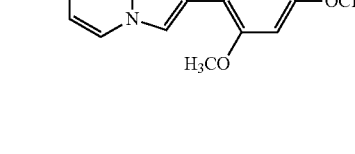 | 2-(5-chloro-2,4-dimethoxyphenyl)-7-(4-(pyrimidin-2-ylmethyl)piperazin-1-yl)imidazo[1,2-a]pyridine | ESI + APCI | 465 |
| 353 | 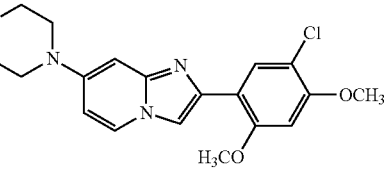 | 2-(5-chloro-2,4-dimethoxyphenyl)-7-(4-(6-(piperidin-1-yl)pyrimidin-4-yl)piperazin-1-yl)imidazo[1,2-a]pyridine | ESI + APCI | 534 |

TABLE 2-continued

Compounds Table:

| Ex. | Structure | Name | MS | MS |
|---|---|---|---|---|
| 354 | 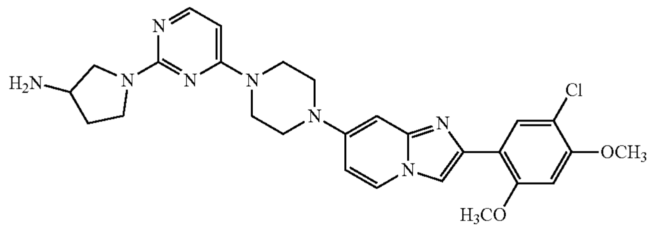 [SMILES: COc1cc(OC)c(-c2cn3ccc(N4CCN(c5ccnc(N6CCC(N)C6)n5)CC4)cc3n2)cc1Cl] | 1-(4-(4-(2-(5-chloro-2,4-dimethoxyphenyl)imidazo[1,2-a]pyridin-7-yl)piperazin-1-yl)pyrimidin-2-yl)pyrrolidin-3-amine | ESI + APCI | 535 |
| 355 | 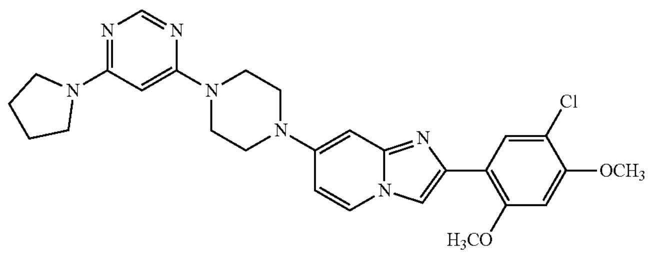 [SMILES: COc1cc(OC)c(-c2cn3ccc(N4CCN(c5cc(N6CCCC6)ncn5)CC4)cc3n2)cc1Cl] | 2-(5-chloro-2,4-dimethoxyphenyl)-7-(4-(6-(pyrrolidin-1-yl)pyrimidin-4-yl)piperazin-1-yl)imidazo[1,2-a]pyridine | ESI + APCI | 520 |
| 356 | 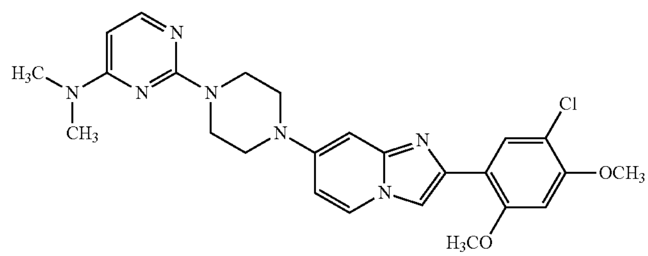 [SMILES: COc1cc(OC)c(-c2cn3ccc(N4CCN(c5nccc(N(C)C)n5)CC4)cc3n2)cc1Cl] | 2-(4-(2-(5-chloro-2,4-dimethoxyphenyl)imidazo[1,2-a]pyridin-7-yl)piperazin-1-yl)-N,N-dimethylpyrimidin-4-amine | ESI + APCI | 494 |
| 357 | 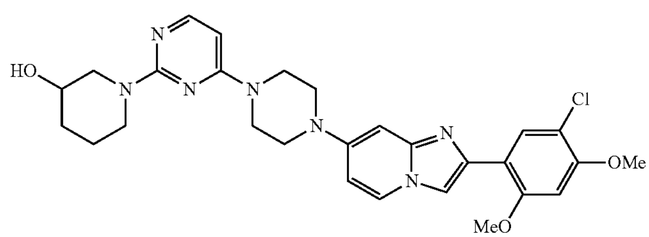 [SMILES: COc1cc(OC)c(-c2cn3ccc(N4CCN(c5ccnc(N6CCCC(O)C6)n5)CC4)cc3n2)cc1Cl] | 1-(4-(4-(2-(5-chloro-2,4-dimethoxyphenyl)imidazo[1,2-a]pyridin-7-yl)piperazin-1-yl)pyrimidin-2-yl)piperidin-3-ol | ESI + APCI | 550 |
| 358 | 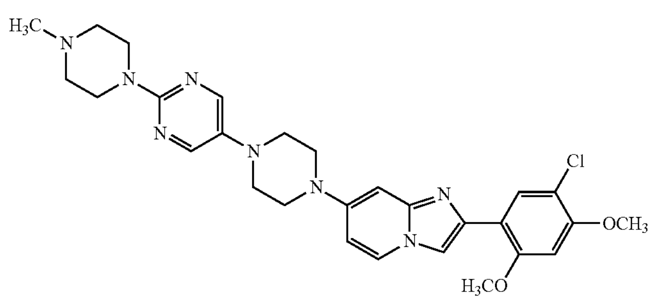 [SMILES: COc1cc(OC)c(-c2cn3ccc(N4CCN(c5cnc(N6CCN(C)CC6)nc5)CC4)cc3n2)cc1Cl] | 2-(5-chloro-2,4-dimethoxyphenyl)-7-(4-(2-(4-methylpiperazin-1-yl)pyrimidin-5-yl)piperazin-1-yl)imidazo[1,2-a]pyridine | ESI | 549 |
| 359 | 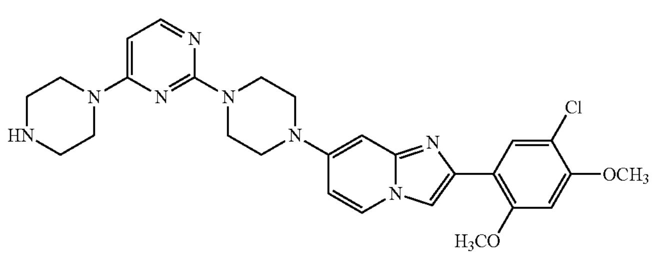 [SMILES: COc1cc(OC)c(-c2cn3ccc(N4CCN(c5nccc(N6CCNCC6)n5)CC4)cc3n2)cc1Cl] | 2-(5-chloro-2,4-dimethoxyphenyl)-7-(4-(4-(piperazin-1-yl)pyrimidin-2-yl)piperazin-1-yl)imidazo[1,2-a]pyridine | ESI + APCI | 535 |

TABLE 2-continued

Compounds Table:

| Ex. | Structure | Name | MS | MS |
|---|---|---|---|---|
| 360 | 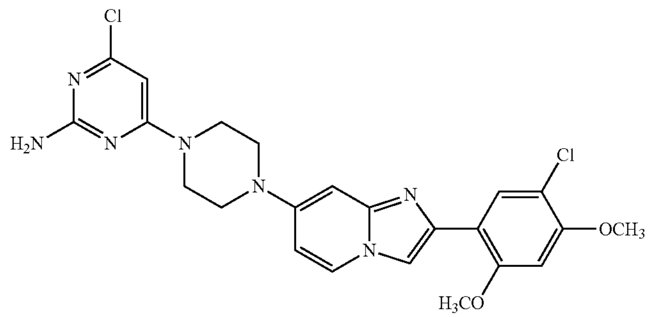 [SMILES: COc1cc(OC)c(-c2cn3ccc(N4CCN(c5cc(Cl)nc(N)n5)CC4)cc3n2)cc1Cl] | 4-chloro-6-(4-(2-(5-chloro-2,4-dimethoxyphenyl)imidazo[1,2-a]pyridin-7-yl)piperazin-1-yl)pyrimidin-2-amine | ESI + APCI | 500 |
| 361 | 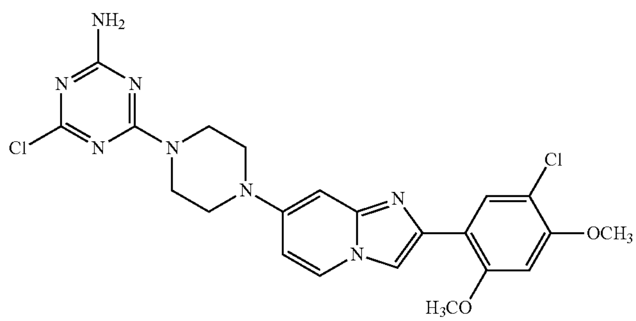 [SMILES: COc1cc(OC)c(-c2cn3ccc(N4CCN(c5nc(N)nc(Cl)n5)CC4)cc3n2)cc1Cl] | 4-chloro-6-(4-(2-(5-chloro-2,4-dimethoxyphenyl)imidazo[1,2-a]pyridine-7-yl)piperazin-1-yl)-1,3,5-triazin-2-amine | ESI + APCI | 501 |
| 362 | 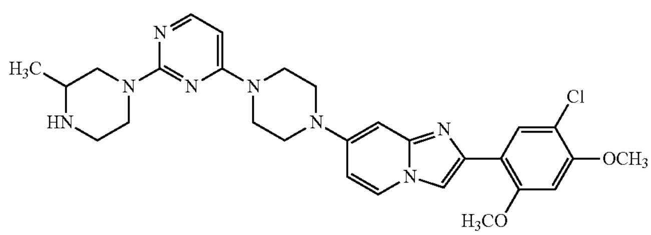 [SMILES: COc1cc(OC)c(-c2cn3ccc(N4CCN(c5ccnc(N6CCNC(C)C6)n5)CC4)cc3n2)cc1Cl] | 2-(5-chloro-2,4-dimethoxyphenyl)-7-(4-(2-(3-methylpiperazin-1-yl)pyrimidin-4-yl)piperazin-1-yl)imidazo[1,2-a]pyridine | ESI + APCI | 549 |
| 363 | 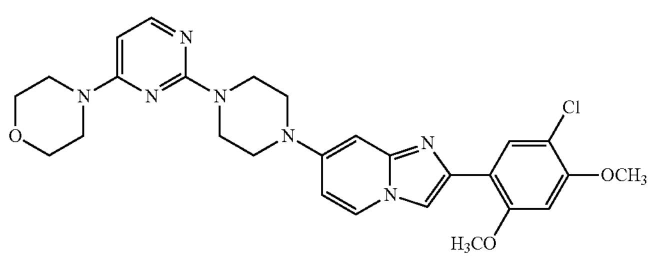 [SMILES: COc1cc(OC)c(-c2cn3ccc(N4CCN(c5nccc(N6CCOCC6)n5)CC4)cc3n2)cc1Cl] | 4-(2-(4-2-(5-chloro-2,4-dimethoxyphenyl)imidazo[1,2-a]pyridine-7-yl)piperazin-1-yl)pyrmidin-4-yl)morpholine | ESI + APCI | 536 |
| 364 | 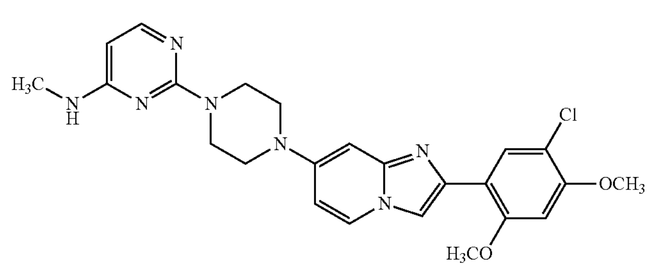 [SMILES: CNc1ccnc(N2CCN(c3ccn4cc(-c5cc(Cl)c(OC)cc5OC)nc4c3)CC2)n1] | 2-(4-(2-(5-chloro-2,4-dimethoxyphenyl)imidazo[1,2-a]pyridine-7-yl)piperazin-1-yl)-N-methylpyrimidin-4-amine | ESI + APCI | 480 |

TABLE 2-continued

Compounds Table:

| Ex. | Structure | Name | MS | MS |
|---|---|---|---|---|
| 365 | 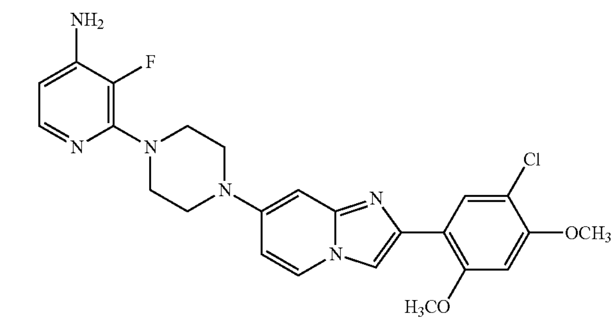 [SMILES: COc1cc(OC)c(-c2cn3ccc(N4CCN(c5nccc(N)c5F)CC4)cc3n2)cc1Cl] | 2-(4-(2-(5-chloro-2,4-dimethoxyphenyl)imidazo[1,2-a]pyridine-7-yl)piperazin-1-yl)-3-fluoropyridin-4-amine | ESI + APCI | 483 |
| 366 | 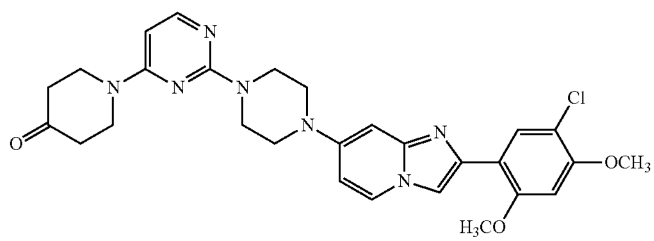 [SMILES: COc1cc(OC)c(-c2cn3ccc(N4CCN(c5nccc(N6CCC(=O)CC6)n5)CC4)cc3n2)cc1Cl] | 1-(2-(4-(2-(5-chloro-2,4-dimethoxyphenyl)imidazo[1,2-a]pyridine-7-yl)piperazin-1-yl)pyrimidin-4-yl)piperidin-4-one | ESI + APCI | 548 |
| 367 | 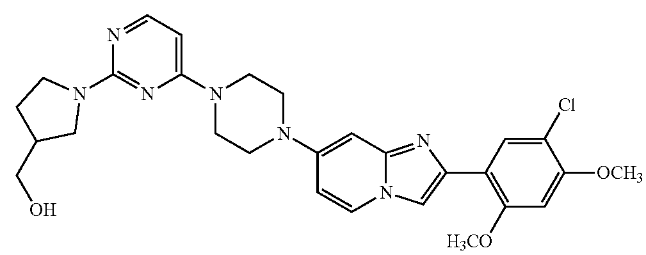 [SMILES: COc1cc(OC)c(-c2cn3ccc(N4CCN(c5ccnc(N6CCC(CO)C6)n5)CC4)cc3n2)cc1Cl] | (1-(4-(4-(2-(5-chloro-2,4-dimethoxyphenyl)imidazo[1,2-a]pyridine-7-yl)piperazin-1-yl)pyrimidin-2-yl)pyrrolidin-3-yl)methanol | ESI + APCI | 550 |
| 368 | 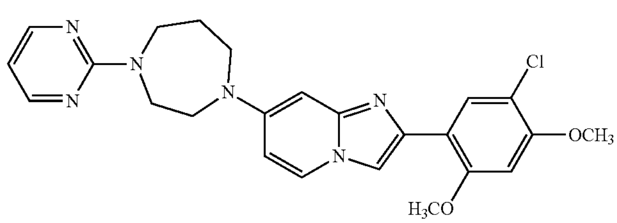 [SMILES: COc1cc(OC)c(-c2cn3ccc(N4CCCN(c5ncccn5)CC4)cc3n2)cc1Cl] | 2-(5-chloro-2,4-dimethoxyphenyl)-7-(4-(pyrimidin-2-yl)-1,4-diazepan-1-yl)imidazo[1,2-a]pyridine | ESI + APCI | 465 |
| 369 | 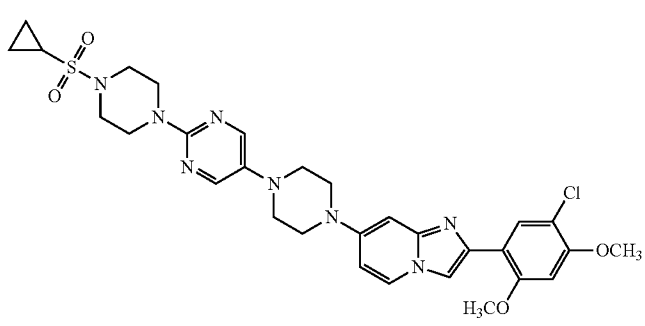 [SMILES: COc1cc(OC)c(-c2cn3ccc(N4CCN(c5cnc(N6CCN(S(=O)(=O)C7CC7)CC6)nc5)CC4)cc3n2)cc1Cl] | 2-(5-chloro-2,4-dimethoxyphenyl)-7-(4-(2-(4-(cyclopropylsulfonyl)piperazin-1-yl)pyrimidin-5-yl)piperazin-1-yl)imidazo[1,2-a]pyridine | ESI + APCI | 639 |

TABLE 2-continued

Compounds Table:

| Ex. | Structure | Name | MS | MS |
|---|---|---|---|---|
| 370 | 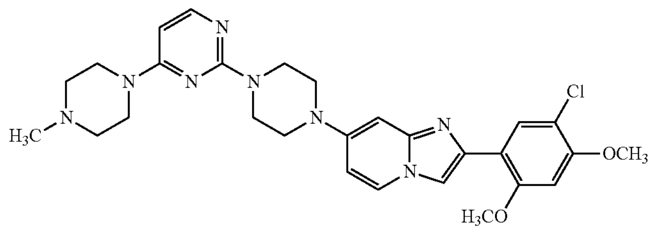 | 2-(5-chloro-2,4-dimethoxyphenyl)-7-(4-(4-(4-methylpiperazin-1-yl)pyrimidin-2-yl)piperazin-1-yl)imidazo[1,2-a-]pyridine | ESI + APCI | 549 |
| 371 | 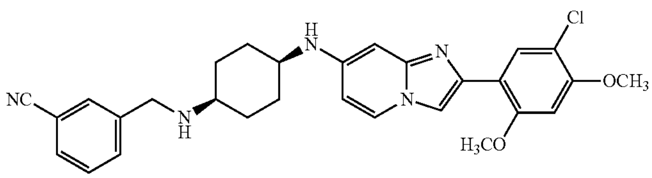 [SMILES: COc1cc(OC)c(-c2cn3ccc(N[C@H]4CC[C@@H](NCc5cccc(C#N)c5)CC4)cc3n2)cc1Cl] | 3-((((1s,4s)-4-((2-(5-chloro-2,4-dimethoxyphenyl)imidazo[1,2-a]pyridine-7-yl)amino)cyclohexyl)-amino)methyl)benzonitrile | ESI + APCI | 516 |
| 372 | 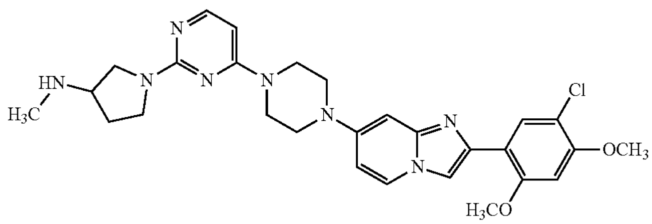 [SMILES: CNC1CCN(c2nccc(N3CCN(c4ccn5cc(-c6cc(Cl)c(OC)cc6OC)nc5c4)CC3)n2)C1] | 1-(4-(4-(2-(5-chloro-2,4-dimethoxyphenyl)imidazo[1,2-a]pyridine-7-yl)piperazin-1-yl)pyrimidin-2yl)-N-methylpyrrolidin-3-amine | ESI + APCI | 549 |
| 373 | 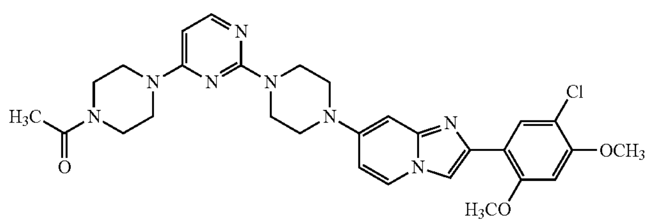 [SMILES: COc1cc(OC)c(-c2cn3ccc(N4CCN(c5nccc(N6CCN(C(C)=O)CC6)n5)CC4)cc3n2)cc1Cl] | 1-(4-(2-(4-(2-(5-chloro-2,4-dimethoxyphenyl)imidazo[1,2-a]pyridine-7-yl)piperazin-1-yl)pyrimidin-4-yl)piperazin-1-yl)ethanone | ESI + APCI | 577 |
| 374 | 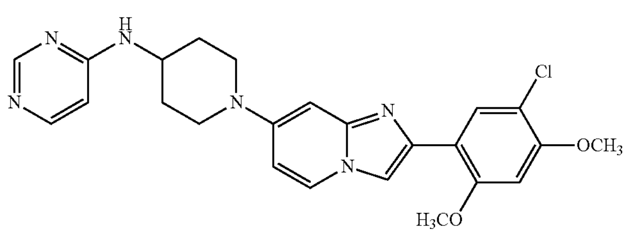 [SMILES: COc1cc(OC)c(-c2cn3ccc(N4CCC(Nc5ccncn5)CC4)cc3n2)cc1Cl] | N-(1-(2-(5-chloro-2,4-dimethoxyphenyl)imidazo[1,2-a]pyridine-7-yl)piperidin-4-yl)pyrimidin-4-amine | ESI + APCI | 465 |
| 375 | 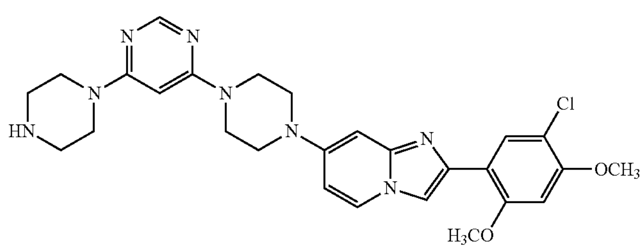 | 2-(5-chloro-2,4-dimethoxyphenyl)-7-(4-(6-(piperazin-1-yl)pyrimidin-4-yl)piperazin-1-yl)imidazo[1,2-a]pyridine | ESI + APCI | 535 |

TABLE 2-continued

Compounds Table:

| Ex. | Structure | Name | MS | MS |
|---|---|---|---|---|
| 376 | 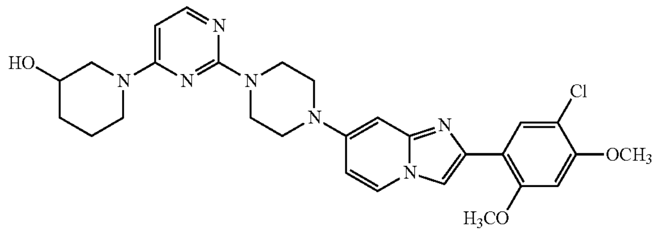 [SMILES: COc1cc(OC)c(-c2cn3ccc(N4CCN(c5nccc(N6CCCC(O)C6)n5)CC4)cc3n2)cc1Cl] | 1-2-(4-(2-5-chloro-2,4-dimethoxyphenyl)imidazo[1,2-a]pyridine-7-yl)piperazin-1-yl)pyrimidin-4-yl)piperidin-3-ol | ESI + APCI | 550 |
| 377 | 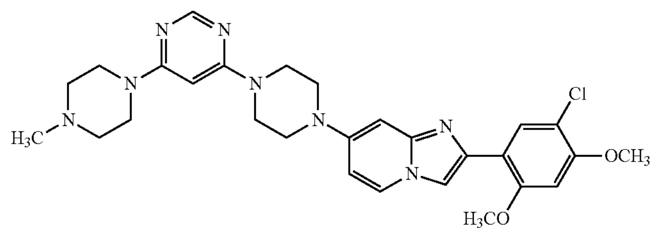 [SMILES: COc1cc(OC)c(-c2cn3ccc(N4CCN(c5cc(N6CCN(C)CC6)ncn5)CC4)cc3n2)cc1Cl] | 2-(5-chloro-2,4-dimethoxyphenyl)-7-(4-(6-(4-methylpiperazin-1-yl)pyrimidin-4-yl)piperazin-1-yl)imidazo[1,2-a]pyridine | ESI + APCI | 549 |
| 378 | 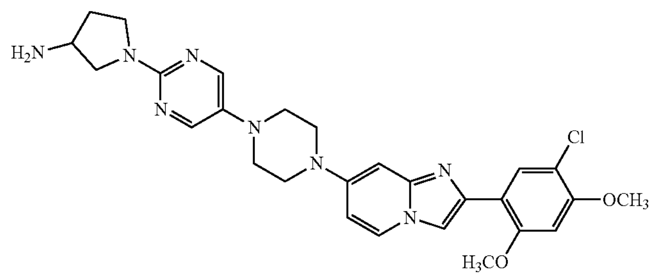 [SMILES: COc1cc(OC)c(-c2cn3ccc(N4CCN(c5cnc(N6CCC(N)C6)nc5)CC4)cc3n2)cc1Cl] | 1-(5-(4-(2-(5-chloro-2,4-dimethoxyphenyl)imidazo[1,2-a]pyridine-7-yl)piperazin-1-yl)pyrimidin-2-yl)pyrrolidin-3-amine | ESI + APCI | 535 |
| 379 | 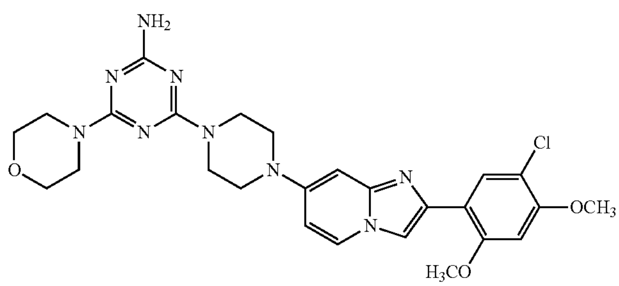 [SMILES: COc1cc(OC)c(-c2cn3ccc(N4CCN(c5nc(N)nc(N6CCOCC6)n5)CC4)cc3n2)cc1Cl] | 4-(4-(2-(5-chloro-2,4-dimethoxyphenyl)imidazo[1,2-a]pyridine-7-yl)piperazin-1-yl)-6-morpholino-1,3,5-triazin-2-amine | ESI + APCI | 552 |
| 380 | 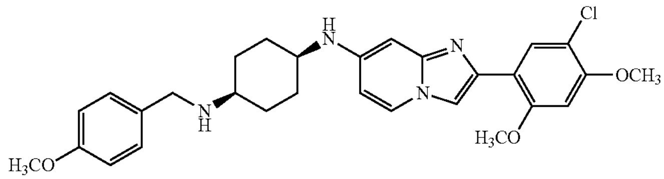 [SMILES: COc1ccc(CN[C@H]2CC[C@@H](Nc3ccn4cc(-c5cc(Cl)c(OC)cc5OC)nc4c3)CC2)cc1] | (1s,4s)-$N^1$-(2-(5-chloro-2,4-dimethoxyphenyl)imidazo[1,2-a]pyridine-7-yl)-$N^4$-(4-methoxybenzyl)cyclohexane-1,4-diamine | ESI + APCI | 521 |
| 381 | 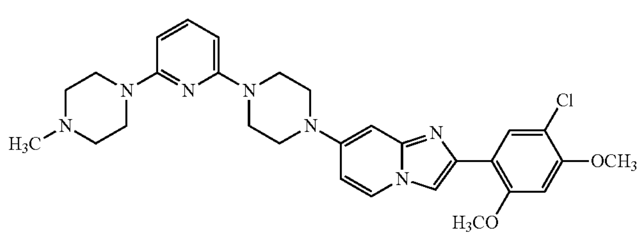 | 2-(5-chloro-2,4-dimethoxyphenyl)-7-(4-(6-(4-methylpiperazin-1-yl)pyridine-2-yl)piperazin-1-yl)imidazo[1,2-a]pyridine | ESI + APCI | 548 |

TABLE 2-continued

Compounds Table:

| Ex. | Structure | Name | MS | MS |
|---|---|---|---|---|
| 382 | 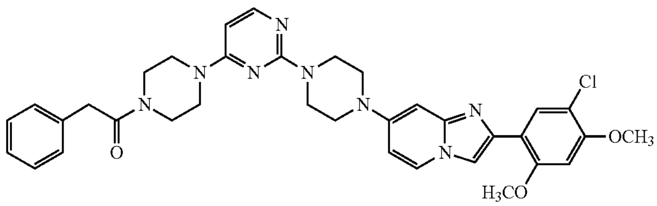 [SMILES: COc1cc(OC)c(-c2cn3ccc(N4CCN(c5nccc(N6CCN(C(=O)Cc7ccccc7)CC6)n5)CC4)cc3n2)cc1Cl] | 1-(4-(2-(4-(2-(5-chloro-2,4-dimethoxyphenyl)imidazo[1,2-a]pyridine-7-yl)piperazin-1-yl)pyrimidin-4-yl)piperazin-1-yl)-2-phenylethanone | ESI + APCI | 653 |
| 383 | 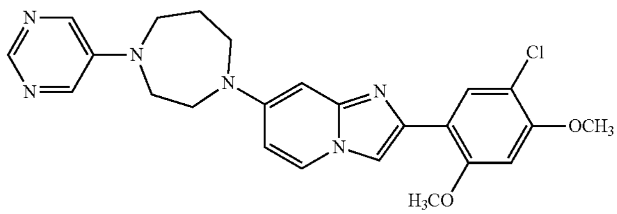 | 2-(5-chloro-2,4-dimethoxyphenyl)-7-(4-(pyrimidin-5-yl)-1,4-diazepan-1-yl)imidazo[1,2-a]pyridine | ESI + APCI | 465 |
| 384 | 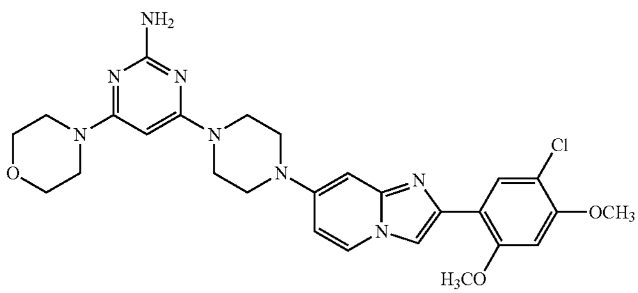 [SMILES: COc1cc(OC)c(-c2cn3ccc(N4CCN(c5cc(N6CCOCC6)nc(N)n5)CC4)cc3n2)cc1Cl] | 4-(4-(2-(5-chloro-2,4-dimethoxyphenyl)imidazo[1,2-a]pyridine-7-yl)piperazin-1-yl)-6-morpholinopyrimidin-2-amine | ESI + APCI | 551 |
| 385 | 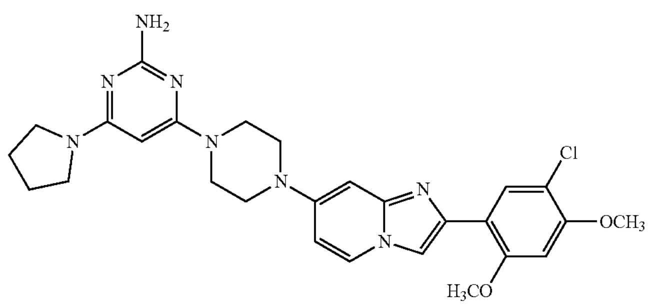 [SMILES: COc1cc(OC)c(-c2cn3ccc(N4CCN(c5cc(N6CCCC6)nc(N)n5)CC4)cc3n2)cc1Cl] | 4-(4-(2-(5-chloro-2,4-dimethoxyphenyl)imidazo[1,2-a]pyridine-7-yl)piperazin-1-yl)-6-(pyrrolidin-1-yl)pyrimidin-2-amine | ESI + APCI | 535 |
| 386 | 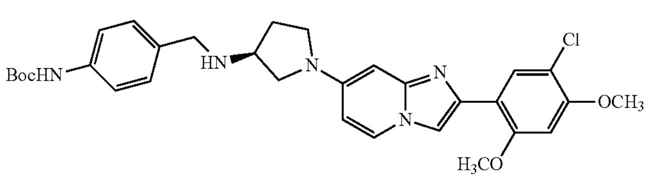 [SMILES: COc1cc(OC)c(-c2cn3ccc(N4CC[C@H](NCc5ccc(NC(=O)OC(C)(C)C)cc5)C4)cc3n2)cc1Cl] | (S)-tert-butyl (4-(((1-(2-(5-chloro-2,4-dimethoxyphenyl)imidazo[1,2-a]pyridine-7-yl)pyrrolidin-3-yl)amino)methyl)phenyl)carbamate | ESI + APCI | 578 |
| 387 | 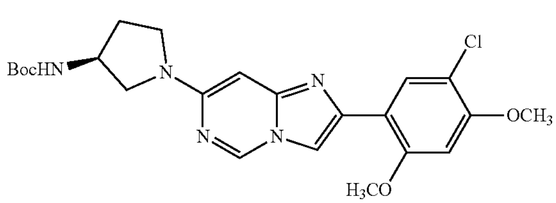 [SMILES: COc1cc(OC)c(-c2cn3cnc(N4CC[C@H](NC(=O)OC(C)(C)C)C4)cc3n2)cc1Cl] | (S)-tert-butyl (1-(2-(5-chloro-2,4-dimethoxyphenyl)imidazo[1,2-c]pyrimidin-7-yl)pyrrolidin-3-yl)carbamate | ESI | 474 |

TABLE 2-continued

Compounds Table:

| Ex. | Structure | Name | MS | MS |
|---|---|---|---|---|
| 388 | 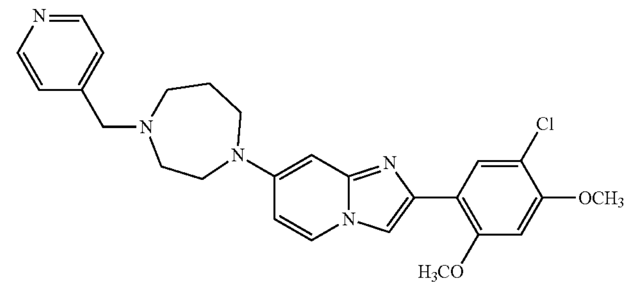 [SMILES: COc1cc(OC)c(-c2cn3ccc(N4CCCN(Cc5ccncc5)CC4)cc3n2)cc1Cl] | 2-(5-chloro-2,4-dimethoxyphenyl)-7-(4-(pyridine-4-ylmethyl)-1,4-diazepan-1-yl)imidazo[1,2-a]pyridine | ESI + APCI | 478 |
| 389 | 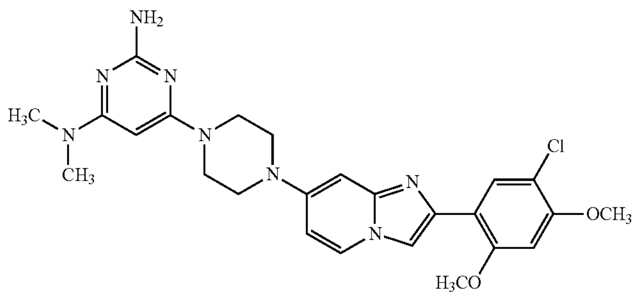 [SMILES: COc1cc(OC)c(-c2cn3ccc(N4CCN(c5cc(N(C)C)nc(N)n5)CC4)cc3n2)cc1Cl] | 6-(4-(2-(5-chloro-2,4-dimethoxyphenyl)imidazo[1,2-a]pyridine-7-yl]piperazin-1-yl)-$N^4,N^4$-dimethylpyrimidine-2,4-diamine dihydrochloride | ESI + APCI | 509 |
| 390 | 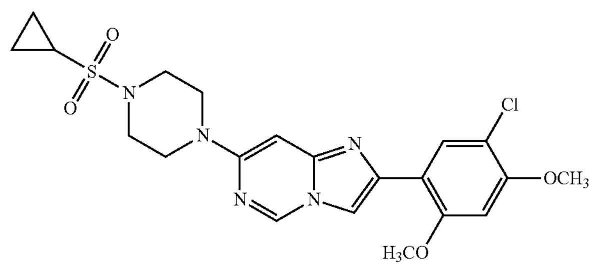 [SMILES: COc1cc(OC)c(-c2cn3cnc(N4CCN(S(=O)(=O)C5CC5)CC4)cc3n2)cc1Cl] | 2-(5-chloro-2,4-dimethoxyphenyl)-7-(4-(cyclopropylsulfonyl)piperazin-1-yl)imidazo[1,2-c]pyrimidine | ESI | 478 |
| 391 | 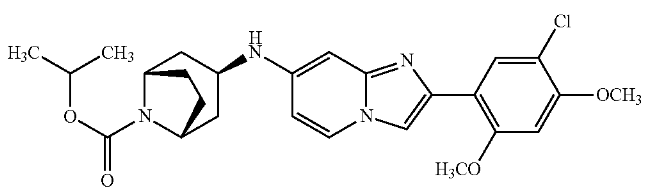 [SMILES: COc1cc(OC)c(-c2cn3ccc(N[C@H]4C[C@H]5CC[C@@H](C4)N5C(=O)OC(C)C)cc3n2)cc1Cl] | (1R,3r,5S)-isopropyl 3-((2-(5-chloro-2,4-dimethoxyphenyl)imidazo[1,2-a]pyridine-7-yl)amino)-8-azabicyclo[3.2.1]octane-8-carboxylate | ESI + APCI | 499 |
| 392 | 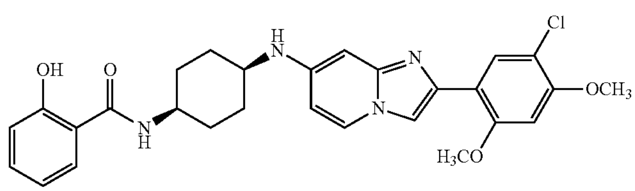 [SMILES: COc1cc(OC)c(-c2cn3ccc(N[C@H]4CC[C@@H](NC(=O)c5ccccc5O)CC4)cc3n2)cc1Cl] | N-((1s,4s)-4-((2-(5-chloro-2,4-dimethoxyphenyl)imidazo[1,2-a]pyridine-7-yl)amino)cyclohexyl)-2-hydroxybenzamide | ESI + APCI | 521 |
| 393 | 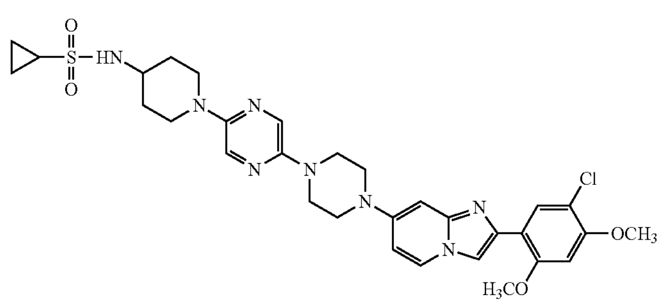 [SMILES: COc1cc(OC)c(-c2cn3ccc(N4CCN(c5cnc(N6CCC(NS(=O)(=O)C7CC7)CC6)cn5)CC4)cc3n2)cc1Cl] | N-1-(5-(4-(2-(5-chloro-2,4-dimethoxyphenyl)imidazo[1,2-a]pyridine-7-yl)piperazin-1-yl)pyrimidin-2-yl)piperidin-4-yl)cyclopropanesulfonamide | ESI + APCI | 653 |

TABLE 2-continued

Compounds Table:

| Ex. | Structure | Name | MS | MS |
|---|---|---|---|---|
| 394 | 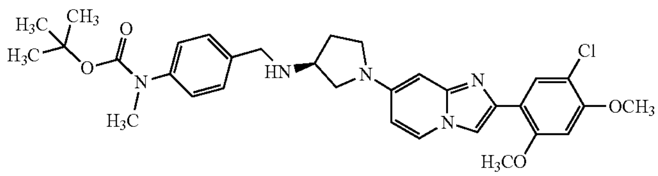 [SMILES: COc1cc(OC)c(-c2cn3ccc(N4CC[C@H](NCc5ccc(N(C)C(=O)OC(C)(C)C)cc5)C4)cc3n2)cc1Cl] | (S)-tert-butyl (4-(((1-(2-(5-chloro-2,4-dimethoxyphenyl)imidazo[1,2-a]pyridine-7-yl)pyrrolidin-3-yl)amino)methyl)phenyl(methyl) carbamate | ESI | 592 |
| 395 | 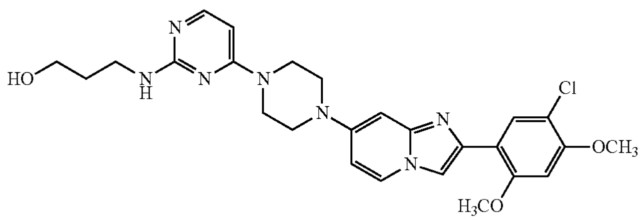 [SMILES: COc1cc(OC)c(-c2cn3ccc(N4CCN(c5ccnc(NCCCO)n5)CC4)cc3n2)cc1Cl] | 3-((4-(4-(2-(5-chloro-2,4-dimethoxyphenyl)imidazo[1,2-a]pyridine-7-yl)piperazin-1-yl)pyrimidin-2-yl)amino)propan-1-ol | ESI + APCI | 524 |
| 396 | 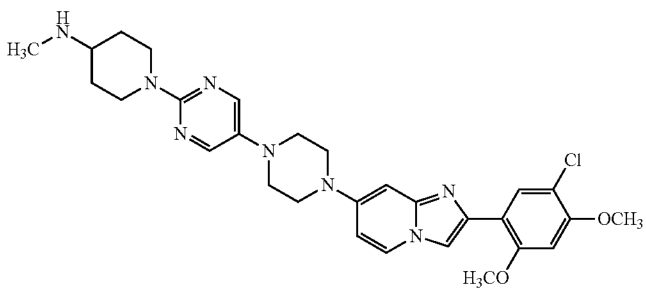 [SMILES: CNC1CCN(c2ncc(N3CCN(c4ccn5cc(-c6cc(Cl)c(OC)cc6OC)nc5c4)CC3)cn2)CC1] | 1-(5-(4-(2-(5-chloro-2,4-dimethoxyphenyl)imidazo[1,2-a]pyridine-7-yl)piperazin-1-yl)pyrimidin-2-yl)-N-methylpiperidin-4-amine | ESI + APCI | 563 |
| 397 | 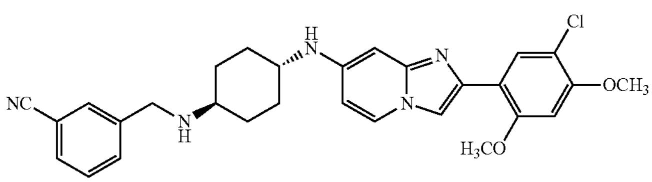 [SMILES: COc1cc(OC)c(-c2cn3ccc(N[C@H]4CC[C@H](NCc5cccc(C#N)c5)CC4)cc3n2)cc1Cl] | 3-((((1r,4r)-4-((2-(5-chloro-2,4-dimethoxyphenyl)imidazo[1,2-a]pyridine-7-yl)amino)cyclohexyl)-amino)methyl)-benzonitrile | ESI + APCI | 516 |
| 398 | 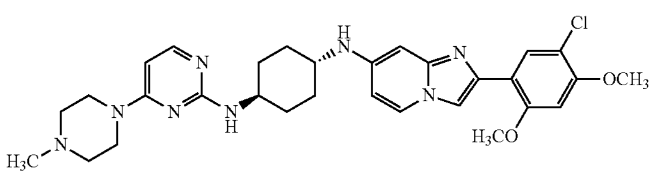 [SMILES: COc1cc(OC)c(-c2cn3ccc(N[C@H]4CC[C@H](Nc5nccc(N6CCN(C)CC6)n5)CC4)cc3n2)cc1Cl] | (1r,4r)-$N^1$-(2-(5-chloro-2,4-dimethoxyphenyl)imidazo[1,2-a]pyridine-7-yl)-$N^4$-(4-(4-methylpiperazin-1-yl)pyrimidin-2-yl)cyclohexane-1,4-diamine | ESI + APCI | 577 |
| 399 | 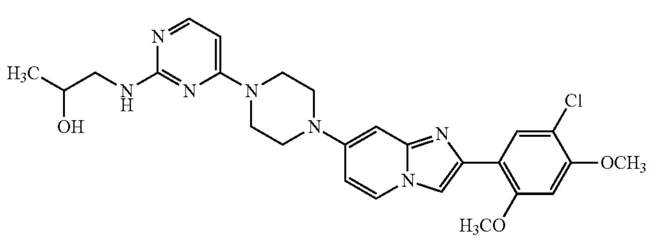 [SMILES: COc1cc(OC)c(-c2cn3ccc(N4CCN(c5ccnc(NCC(C)O)n5)CC4)cc3n2)cc1Cl] | 1-((4-(4-(2-(5-chloro-2,4-dimethoxyphenyl)imidazo[1,2-a]pyridine-7-yl)piperazin-1-yl)pyrimidin-2-yl)amino)propan-2-ol | ESI + APCI | 524 |
| 400 | 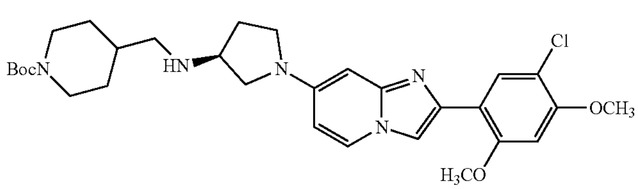 [SMILES: COc1cc(OC)c(-c2cn3ccc(N4CC[C@H](NCC5CCN(C(=O)OC(C)(C)C)CC5)C4)cc3n2)cc1Cl] | (S)-tert-butyl 4-(((1-(2-(5-chloro-2,4-dimethoxyphenyl)imidazo[1,2-a]pyridine-7-yl)pyrrolidin-3-yl)amino)methyl)piperidine-1-carboxylate | ESI | 570 |

TABLE 2-continued

Compounds Table:

| Ex. | Structure | Name | MS | MS |
|---|---|---|---|---|
| 401 | 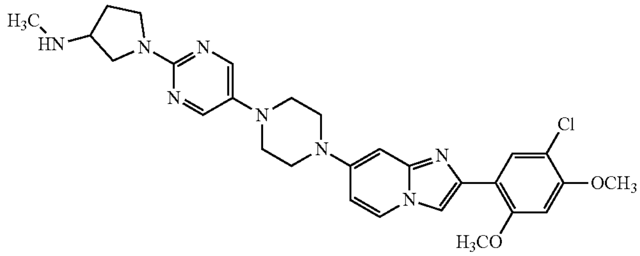 [SMILES: CNC1CCN(c2ncc(N3CCN(c4ccn5cc(-c6cc(Cl)c(OC)cc6OC)nc5c4)CC3)cn2)C1] | 1-(5-(4-(2-(5-chloro-2,4-dimethoxyphenyl)imidazo[1,2-a]pyridine-7-yl)piperazin-1-yl)pyrimidin-2-yl)-N-methylpyrrolidin-3-amine | ESI + APCI | 549 |
| 402 | 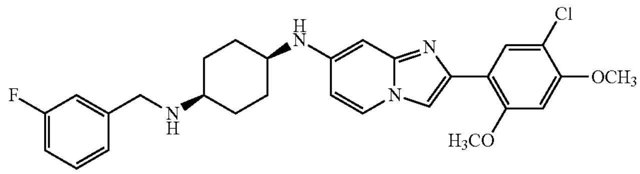 [SMILES: COc1cc(OC)c(-c2cn3ccc(N[C@H]4CC[C@@H](NCc5cccc(F)c5)CC4)cc3n2)cc1Cl] | (1s,4s)-N$^1$-(2-(5-chloro-2,4-dimethoxyphenyl)imidazo[1,2-a]pyridine-7-yl)-N$^4$-(3-flurobenzyl)cyclohexane-1,4-diamine | ESI + APCI | 509 |
| 403 | 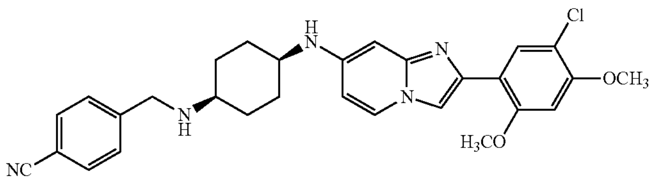 [SMILES: COc1cc(OC)c(-c2cn3ccc(N[C@H]4CC[C@@H](NCc5ccc(C#N)cc5)CC4)cc3n2)cc1Cl] | 4-((((1s,4s)-4-((2-(5-chloro-2,4-dimethoxyphenyl)imidazo[1,2-a]pyridine-7-yl)amino)cyclohexyl)amino)methyl)benzonitrile | ESI + APCI | 516 |
| 404 | 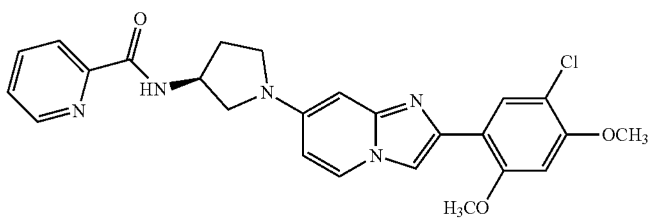 [SMILES: COc1cc(OC)c(-c2cn3ccc(N4CC[C@H](NC(=O)c5ccccn5)C4)cc3n2)cc1Cl] | (S)-N-(1-(2-(5-chloro-2,4-dimethoxyphenyl)imidazo[1-2-a]pyridin-7-yl)pyrrolidin-3-yl)picolinamide | ESI | 478 |
| 405 | 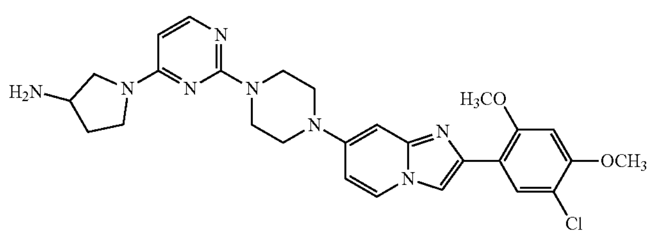 [SMILES: COc1cc(OC)c(-c2cn3ccc(N4CCN(c5nccc(N6CCC(N)C6)n5)CC4)cc3n2)cc1Cl] | 1-(2-(4-(2-(5-chloro-2,4-dimethoxy-phenyl)imidazo[1,2-a]pyridine-7-yl)piperazin-1-yl)pyrimidin-4-yl)pyrrolidin-3-amine | ESI + APCI | 535 |
| 406 | 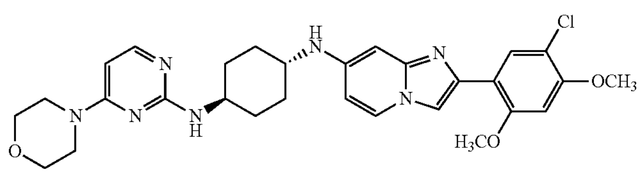 [SMILES: COc1cc(OC)c(-c2cn3ccc(N[C@H]4CC[C@H](Nc5nccc(N6CCOCC6)n5)CC4)cc3n2)cc1Cl] | (1r,4r)-N$^1$-(2-(5-chloro-2,4-dimethoxyphenyl)imidazo[1,2-a]pyridine-7-yl)-N$^4$-(4-morpholinopyrimidin-2-yl)cyclohexane-1,4-diamine | ESI + APCI | 564 |
| 407 | 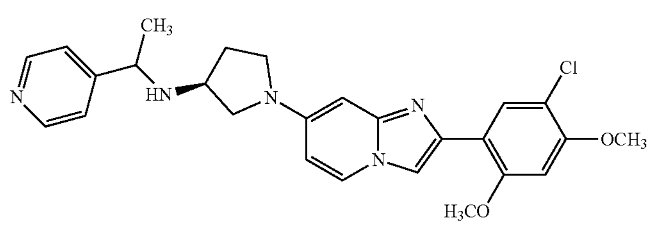 [SMILES: COc1cc(OC)c(-c2cn3ccc(N4CC[C@H](NC(C)c5ccncc5)C4)cc3n2)cc1Cl] | (3S)-1-(2-(5-chloro-2,4-dimethoxyphenyl)imidazo[1,2-a]pyrine-7-yl)-N-(1-(pyridine-4-yl)ethyl)pyrrolidin-3-amine | ESI | 478 |

TABLE 2-continued

Compounds Table:

| Ex. | Structure | Name | MS | MS |
|---|---|---|---|---|
| 408 | 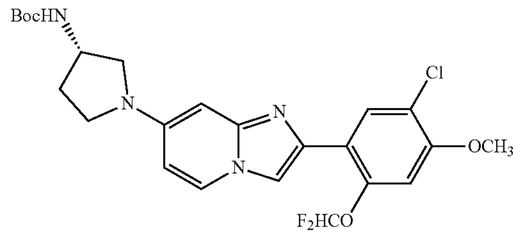 [SMILES: COc1cc(OC(F)F)c(-c2cn3ccc(N4CC[C@H](NC(=O)OC(C)(C)C)C4)cc3n2)cc1Cl] | (S)-tert-butyl (1-(2-(5-chloro-2-(difluoromethoxy)-4-methoxyphenyl)imidazo[1,2-a]pyridine-7-yl)pyrrolidin-3-yl)carbamate | ESI | 509 |
| 409 | 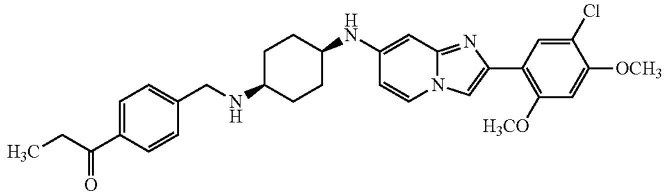 [SMILES: CCC(=O)c1ccc(CN[C@H]2CC[C@@H](Nc3ccn4cc(-c5cc(Cl)c(OC)cc5OC)nc4c3)CC2)cc1] | methyl 4-(((((1s,4s)-4-((2-(5-chloro-2,4-dimethoxy-phenyl)imidazo[1,2-a]pyridine-7-yl)amino)cyclohexyl)-amino)methyl)benzoate | ESI + APCI | 549 |
| 410 | 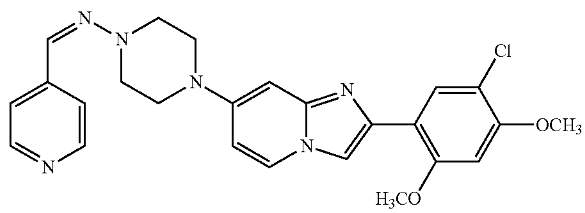 [SMILES: COc1cc(OC)c(-c2cn3ccc(N4CCN(/N=C\c5ccncc5)CC4)cc3n2)cc1Cl] | (Z)-4-(2-(5-chloro-2,4-dimethoxyphenyl)imidazo[1,2-a]pyridine-7-yl)-N-(pyridine-4-ylmethylene)piperazin-1-amine | ESI + APCI | 477 |
| 411 | 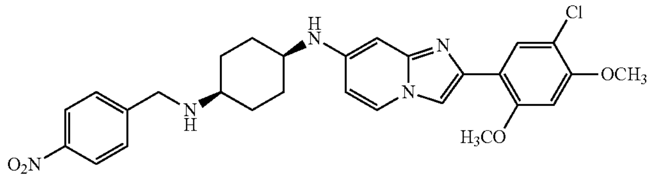 [SMILES: COc1cc(OC)c(-c2cn3ccc(N[C@H]4CC[C@@H](NCc5ccc([N+](=O)[O-])cc5)CC4)cc3n2)cc1Cl] | (1s,4s)-$N^1$-(2-(5-chloro-2,4-dimethoxyphentyl)imidazo[1,2-a]pyridine-7-yl)-$N^4$-(4-nitrobenzyl)cyclohexane-1,4-diamine | ESI + APCI | 536 |
| 412 | 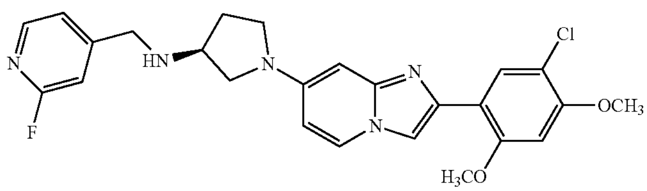 | (S)-1-(2-(5-chloro-2,4-dimethoxyphenyl)imidazo[1,2-a]pyridine-7-yl-N-((2-fluoropyridin-4-yl)methyl)pyrrolidin-3-amine | ESI | 482 |
| 413 | 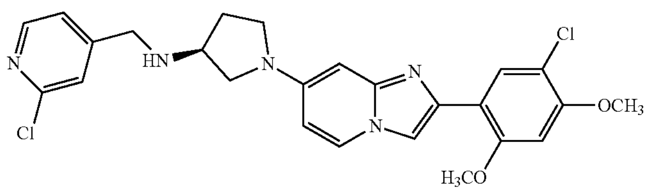 [SMILES: COc1cc(OC)c(-c2cn3ccc(N4CC[C@H](NCc5ccnc(Cl)c5)C4)cc3n2)cc1Cl] | (S)-1-(2-(5-chloro-2,4-dimethoxyphenyl)imidazo[1,2-a]pyridine-7-yl)-N-((2-chloropyridin-4-yl)methyl)pyrrolidin-3-amine | ESI | 498 |
| 414 | 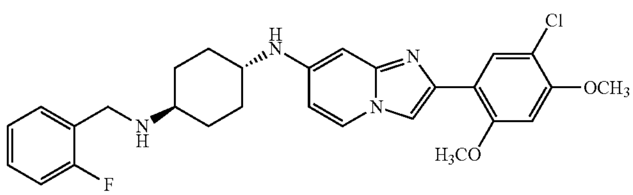 [SMILES: COc1cc(OC)c(-c2cn3ccc(N[C@H]4CC[C@H](NCc5ccccc5F)CC4)cc3n2)cc1Cl] | (1r,4r)-$N^1$-(2-(5-chloro-2,4-dimethoxyphenyl)imidazo[1,2-a]pyridine-7-yl)-$N^4$-(2-fluorobenzyl)cyclohexane-1,4-diamine | ESI + APCI | 509 |

TABLE 2-continued

Compounds Table:

| Ex. | Structure | Name | MS | MS |
|---|---|---|---|---|
| 415 | 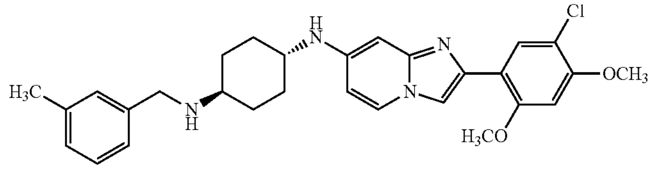 [SMILES: COc1cc(OC)c(-c2cn3ccc(N[C@H]4CC[C@H](NCc5cccc(C)c5)CC4)cc3n2)cc1Cl] | (1r-,4r)-N¹-(2-(5-chloro-2,4-dimethoxyphenyl)imidazo[1,2-a]pyridine-7-yl)-N⁴-(3-methylbenzyl)cyclohexane-1,4-diamine | ESI + APCI | 505 |
| 416 | 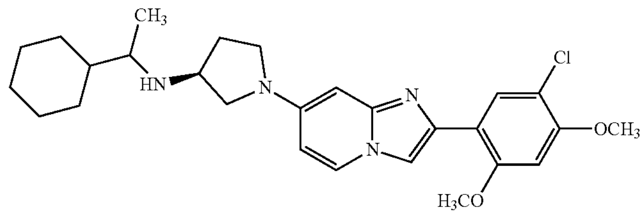 [SMILES: COc1cc(OC)c(-c2cn3ccc(N4CC[C@H](NC(C)C5CCCCC5)C4)cc3n2)cc1Cl] | (3S)-1-(2-(5-chloro)-2,4-dimethoxyphenyl)imidazo[1,2-a]pyridine-7-yl)-N-(1-cyclohexylethyl)pyrrolidin-3-amine | ESI | 483 |
| 417 | 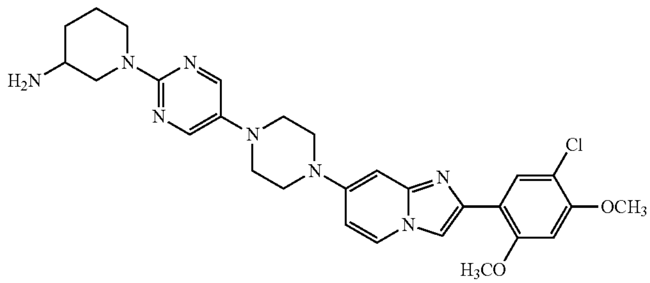 [SMILES: COc1cc(OC)c(-c2cn3ccc(N4CCN(c5cnc(N6CCCC(N)C6)nc5)CC4)cc3n2)cc1Cl] | 1-(5-(4-(2-(5-chloro-2,4-dimethoxyphenyl)imidazo[1,2-a]pyridine-7-yl)piperazin-1-yl)pyrimidin-2-yl)piperidin-3-amine | ESI + APCI | 549 |
| 418 | 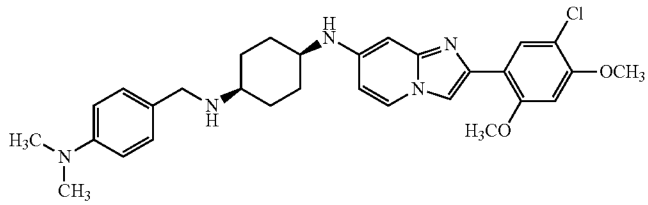 [SMILES: COc1cc(OC)c(-c2cn3ccc(N[C@H]4CC[C@@H](NCc5ccc(N(C)C)cc5)CC4)cc3n2)cc1Cl] | (1s,4s)-N¹-(2-(5-chloro-2,4-dimethoxyphenyl)imidazo[1,2-a]pyridine-7-yl)-N⁴-(4-(dimethylamino)benzyl)cyclohexane-1,4-diamine | ESI + APCI | 534 |
| 419 | 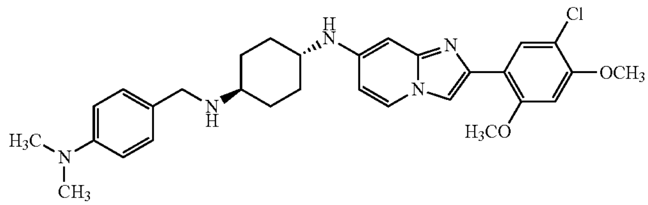 [SMILES: COc1cc(OC)c(-c2cn3ccc(N[C@H]4CC[C@H](NCc5ccc(N(C)C)cc5)CC4)cc3n2)cc1Cl] | (1r,4r)-N¹-(2-(5-chloro-2,4-dimethoxyphenyl)imidazo[1,2-a]pyridine-7-yl)-N⁴-(4-(dimethylamino)benzyl)cyclohexane-1,4-diamine | ESI + APCI | 534 |
| 420 | 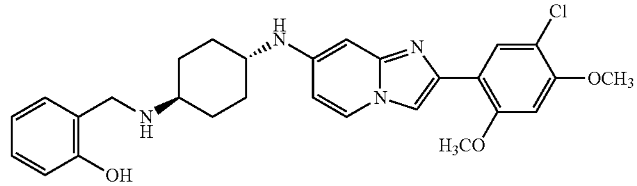 [SMILES: COc1cc(OC)c(-c2cn3ccc(N[C@H]4CC[C@H](NCc5ccccc5O)CC4)cc3n2)cc1Cl] | 2-((((1r,4r)-4-((2-(5-chloro-2,4-dimethoxyphenyl)imidazo[1,2-a]pyridine-7-yl)amino)cyclohexyl-amino)methyl)phenol | ESI + APCI | 507 |
| 421 | 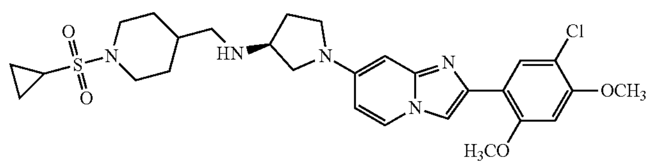 [SMILES: COc1cc(OC)c(-c2cn3ccc(N4CC[C@H](NCC5CCN(S(=O)(=O)C6CC6)CC5)C4)cc3n2)cc1Cl] | (S)-1-(2-(5-chloro-2,4-dimethoxyphenyl)imidazo[1,2-a]pyridine-7-yl)-N-((1-(cyclopropylsulfonyl)piperidin-4-yl)methyl)pyrrolidin-3-amine | ESI | 574 |

TABLE 2-continued

Compounds Table:

| Ex. | Structure | Name | MS | MS |
|---|---|---|---|---|
| 422 | 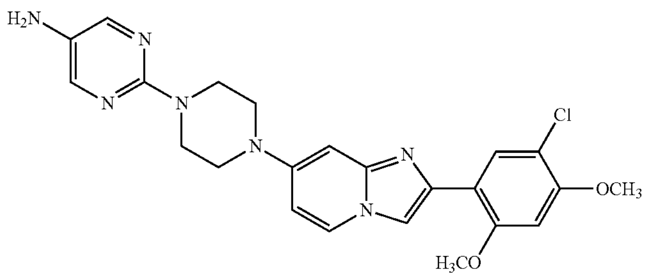 [SMILES: COc1cc(OC)c(-c2cn3ccc(N4CCN(c5ncc(N)cn5)CC4)cc3n2)cc1Cl] | 2-(4-(2-(5-chloro-2,4-dimethoxyphenyl)imidazo[1,2-a]pyridine-7-yl)piperazin-1-yl(pyrimidin-5-amine | ESI + APCI | 466 |
| 423 | 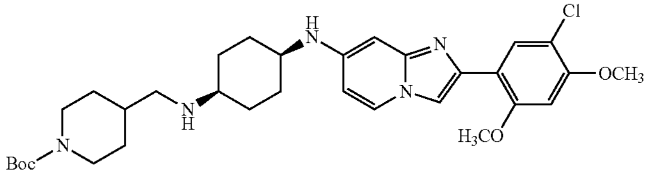 [SMILES: COc1cc(OC)c(-c2cn3ccc(N[C@H]4CC[C@@H](NCC5CCN(C(=O)OC(C)(C)C)CC5)CC4)cc3n2)cc1Cl] | tert-butyl 4-((((1s,4s)-4-((2-(5-choro-2,4-dimethoxyphenyl)imidazo[1,2 a]pyridine-7-yl)amino)cyclohexyl)-amino)methyl)piperidine-1-carboxylate | ESI + APCI | 598 |
| 424 | 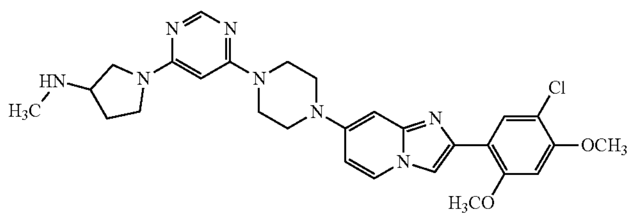 | 1-(6-(4-(2-(5-chloro-2,4-dimethoxyphenyl)imidazo[1,2-a]pyridine-7-yl)piperazin-1-yl)pyrimidin-4-yl)-N-methylpyrrolidin-3-amine | ESI + APCI | 549 |
| 425 | 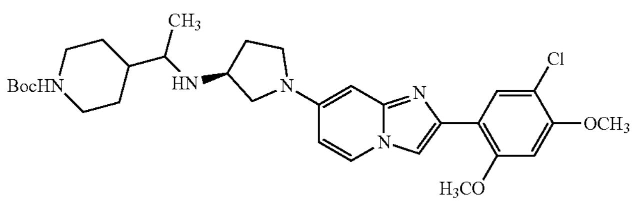 | tert-butyl 4-(1-(((S)-1-(2-(5-chloro-2,4-dimethoxyphenyl)imidazo[1,2-a]pyridine-7-yl)pyrrolidin-3-yl)amino)ethyl)piperidine-1-carboxylate | ESI | 584 |
| 426 | 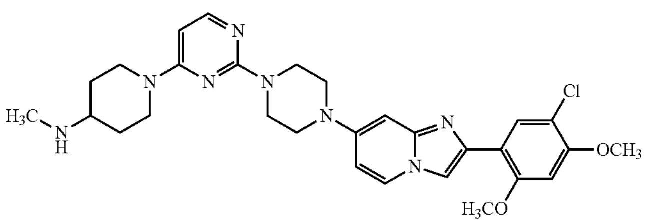 | 1-(2-(4-(2-(5-chloro-2,4-dimethoxyphenyl)imidazo[1,2-a]pyridine-7-yl)piperazin-1-yl)pyrimidin-4-yl)-N-methylpiperidin-4-amine | ESI + APCI | 563 |
| 427 | 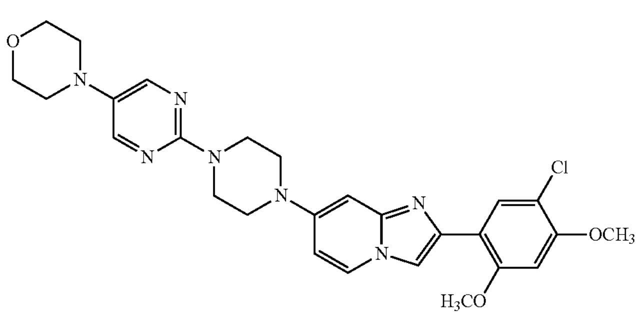 | 4-(2-(4-(2-(5-chloro-2,4-dimethoxyphenyl)imidazo[1,2-a]pyridine-7-yl)piperazin-1-yl)pyrimidin-5-yl)morpholine | ESI + APCI | 536 |

TABLE 2-continued

Compounds Table:

| Ex. | Structure | Name | MS | MS |
|---|---|---|---|---|
| 428 | 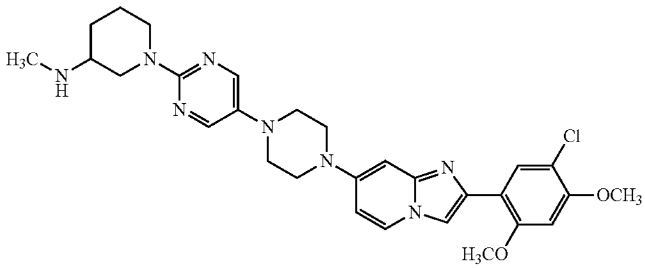 [SMILES: CNC1CCCN(c2ncc(N3CCN(c4ccn5cc(-c6cc(Cl)c(OC)cc6OC)nc5c4)CC3)cn2)C1] | 1-(5-(4-(2-(5-chloro-2,4-dimethoxyphenyl)imidazo[1,2-a]pyridine-7-yl)piperazin-1-yl)pyrimidin-2-yl)-N-methylpiperidin-3-amine | ESI + APCI | 563 |
| 429 | 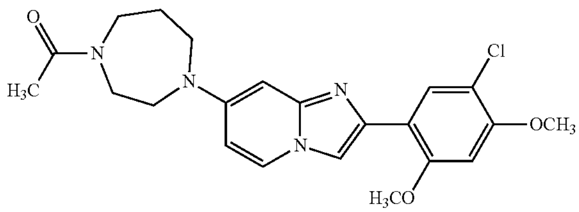 [SMILES: COc1cc(OC)c(-c2cn3ccc(N4CCCN(C(C)=O)CC4)cc3n2)cc1Cl] | 1-(4-(2-(5-chloro-2,4-dimethoxyphenyl)imidazo[1,2-a]pyridin-7-yl)-1,4-diazepan-1-yl)ethanone | ESI + APCI | 429 |
| 430 | 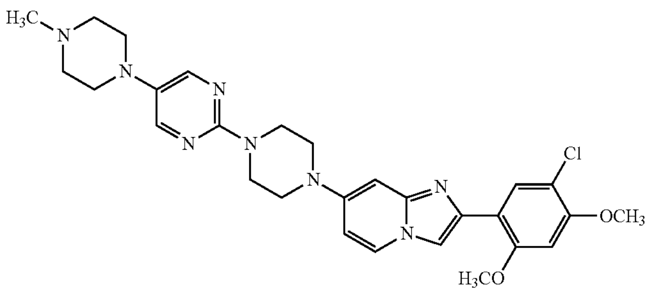 | 2-(5-chloro-2,4-dimethoxyphenyl)-7-(4-(5-(4-methylpiperazin-1-yl)pyrimidin-2-yl)piperazin-1-yl)imidazo[1,2-a]pyridine | ESI + APCI | 549 |
| 431 | 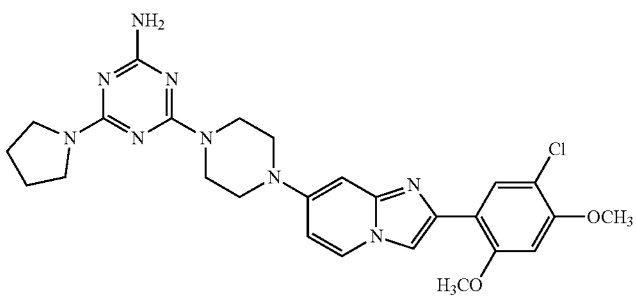 [SMILES: COc1cc(OC)c(-c2cn3ccc(N4CCN(c5nc(N)nc(N6CCCC6)n5)CC4)cc3n2)cc1Cl] | 4-(4-(2-(5-chloro-2,4-dimethoxyphenyl)imidazo[1,2-a]pyridin-7-yl)piperazin-1-yl)-6-(pyrrolidin-1-yl)-1,3,5-triazin-2-amine | ESI + APCI | 536 |
| 432 | 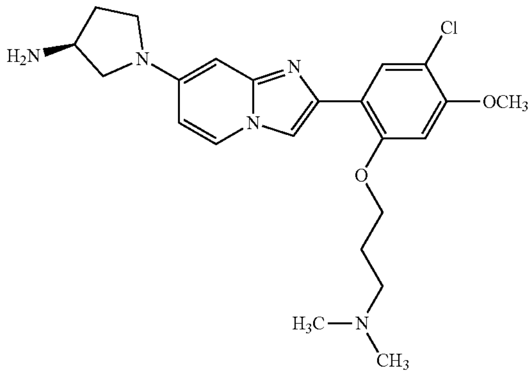 [SMILES: COc1cc(OCCCN(C)C)c(-c2cn3ccc(N4CC[C@H](N)C4)cc3n2)cc1Cl] | (S)-1-(2-(5-chloro-2-(3-(dimethylamino)propoxy)-4-methoxyphenyl)imidazol[1,2-a]pyridine-7-yl)pyrrolidin-3-amine | ESI | 444 |

TABLE 2-continued

Compounds Table:

| Ex. | Structure | Name | MS | MS |
|---|---|---|---|---|
| 433 | 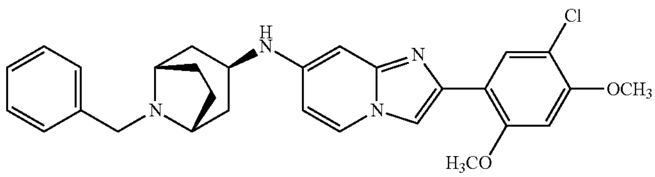 [SMILES: COc1cc(OC)c(-c2cn3ccc(N[C@H]4C[C@H]5CC[C@@H](C4)N5Cc4ccccc4)cc3n2)cc1Cl] | N-((1R,3r,5S)-8-benzyl-8-azabicyclo[3.2.1]octan-3-yl)-2-(5-chloro-2,4-dimethoxyphenyl)imidazo[1,2-a]pyridine-7-amine | ESI + APCI | 503 |
| 434 | 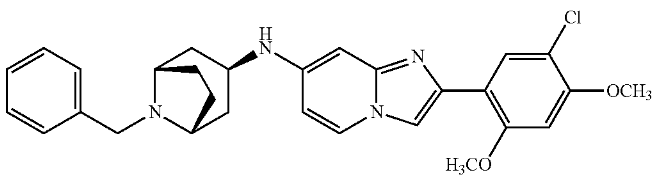 [SMILES: COc1cc(OC)c(-c2cn3ccc(N[C@H]4C[C@H]5CC[C@@H](C4)N5Cc4ccccc4)cc3n2)cc1Cl] | 2-(5-chloro-2,4-dimethoxyphenyl)-N-(1R,3r,5S)-8-(cyclohexylmethyl)-8-azabicyclo[3.2.1]octan-3-yl)imidazo[1,2-a]pyridine-7-amine | ESI + APCI | 509 |
| 435 | 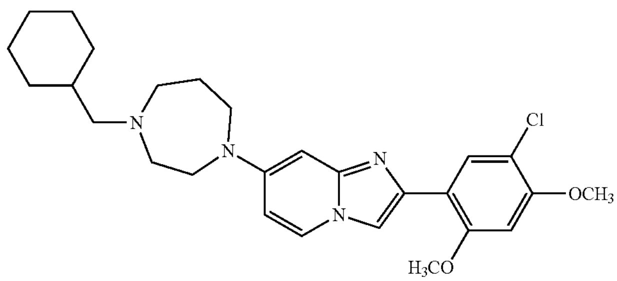 [SMILES: COc1cc(OC)c(-c2cn3ccc(N4CCCN(CC5CCCCC5)CC4)cc3n2)cc1Cl] | 2-(5-chloro-2,4-dimethoxyphenyl-7-(4-(cyclohexylmethyl)-1,4-diazepan-1-yl)imidazo[1,2-a]pyridine | ESI + APCI | 483 |
| 436 | 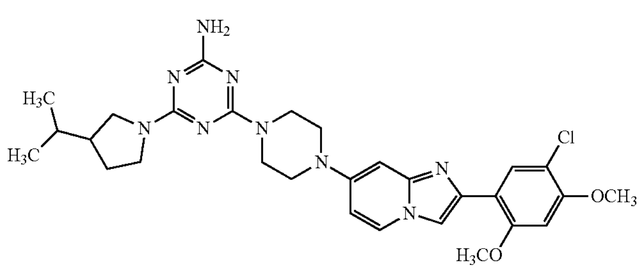 [SMILES: COc1cc(OC)c(-c2cn3ccc(N4CCN(c5nc(N)nc(N6CCC(C(C)C)C6)n5)CC4)cc3n2)cc1Cl] | 4-(4-(2-(5-chloro-2,4-dimethoxyphenyl)imidazo[1,2-a]pyridine-7-yl)piperazin-1-yl)-6-(3-(dimethylamino)pyrrolidin-1-yl)-1,3,5-triazin-2-amine | ESI + APCI | 579 |
| 437 | 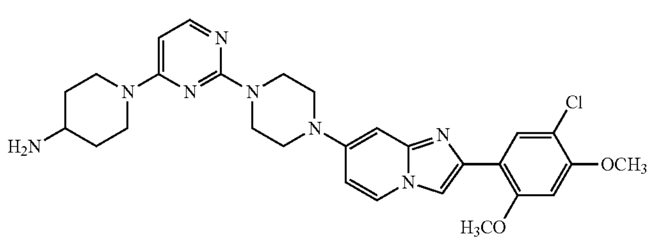 | 1-(2-(4-(2-(5-chloro-2,4-dimethoxyphenyl)imidazo[1,2-a]pyridine-7-yl)piperazin-1-yl)pyrimidin-4-yl)piperidin-4-amine | ESI + APCI | 549 |
| 438 | 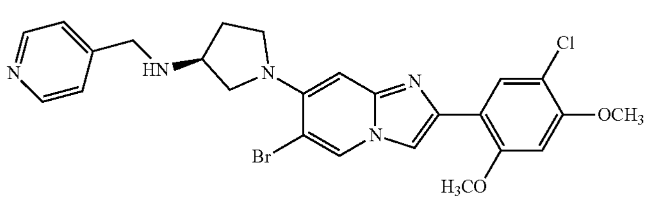 [SMILES: COc1cc(OC)c(-c2cn3cc(Br)c(N4CC[C@H](NCc5ccncc5)C4)cc3n2)cc1Cl] | (S)-1-(6-bromo-2-(5-chloro-2,4-dimethoxyphenyl)imidazo[1,2-a]pyridin-7-yl)-N-(pyridin-4-ylmethyl)pyrrolidin-3-amine | ESI | 544 |

TABLE 2-continued

Compounds Table:

| Ex. | Structure | Name | MS | MS |
|---|---|---|---|---|
| 439 | 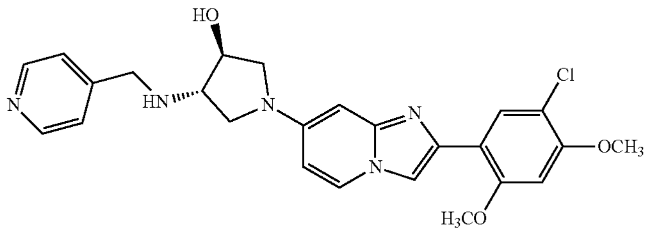 [SMILES: COc1cc(OC)c(-c2cn3ccc(N4C[C@H](NCc5ccncc5)[C@@H](O)C4)cc3n2)cc1Cl] | (3S,4S)-1-(2-(5-chloro-2,4-dimethoxyphenyl)imidazo[1,2-a]pyridin-7-yl)-4-((pyridin-4-ylmethyl)amino)pyrrolidin-3-ol | ESI | 480 |
| 440 | 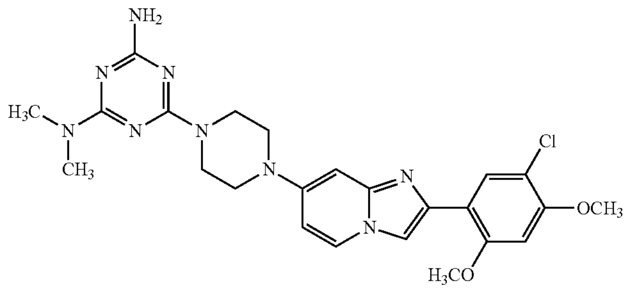 [SMILES: COc1cc(OC)c(-c2cn3ccc(N4CCN(c5nc(N)nc(N(C)C)n5)CC4)cc3n2)cc1Cl] | 6-(4-(2-(5-chloro-2,4-dimethoxyphenyl)imidazo[1,2-a]pyridine-7-yl)piperazin-1-yl-$N^2,N^2$-dimethyl-1,3,5-triazine-2,4-diamine | ESI + APCI | 510 |
| 441 | 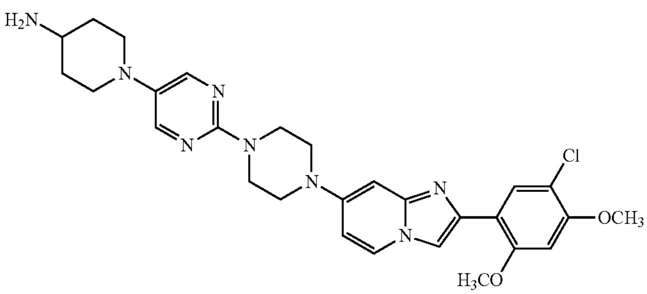 | 1-(2-(4-2-(5-chloro-2,4-dimethoxyphenyl)imidazo[1,2-a]pyridine-7-yl)piperazin-1-yl)pyrimidin-5-yl)piperidin-4-amine | ESI + APCI | 549 |
| 442 | 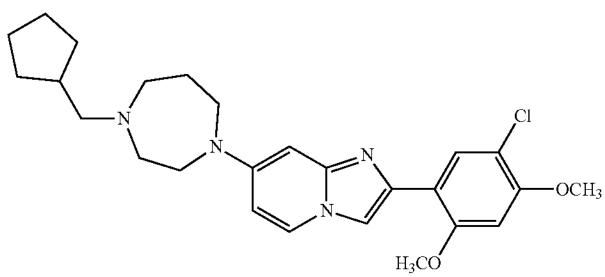 [SMILES: COc1cc(OC)c(-c2cn3ccc(N4CCCN(CC5CCCC5)CC4)cc3n2)cc1Cl] | 2-(5-chloro-2,4-dimethoxyphenyl)-7-(4-(cyclopentylmethyl)-1,4-diazepan-1-yl)imidazo[1,2-a]pyridine | ESI + APCI | 469 |
| 443 | 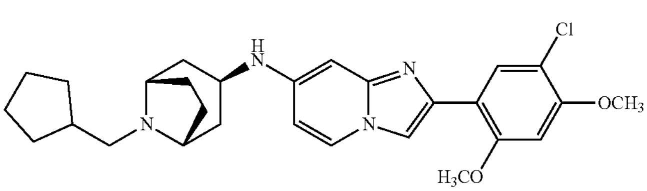 [SMILES: COc1cc(OC)c(-c2cn3ccc(N[C@H]4C[C@H]5CC[C@@H](C4)N5CC4CCCC4)cc3n2)cc1Cl] | 2-(5-chloro-2,4-dimethoxyphenyl)-N-((1R,3r,5S)-8-(cyclopentylmethyl)-8-azabicyclo[3.2.1]octan-3-yl)imidazo[1,2-a]pyridine-7-amine | ESI + APCI | 495 |
| 444 | 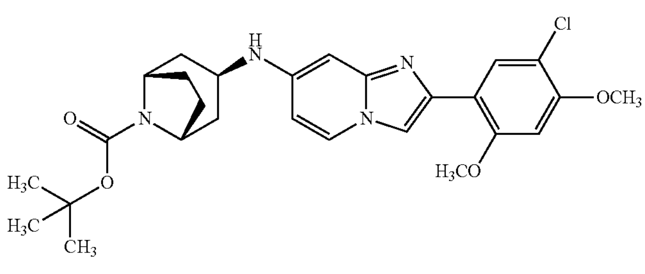 [SMILES: COc1cc(OC)c(-c2cn3ccc(N[C@H]4C[C@H]5CC[C@@H](C4)N5C(=O)OC(C)(C)C)cc3n2)cc1Cl] | (1R,3r,5S)-tert-butyl 3-((2-(5-chloro-2,4-(dimethoxyphenyl)imidazo[1,2-a]pyridine-7-yl)amino)-8-azabicyclo[3.2.1]octane-8-carboxylate | ESI + APCI | 513 |

TABLE 2-continued

Compounds Table:

| Ex. | Structure | Name | MS | MS |
|---|---|---|---|---|
| 445 | 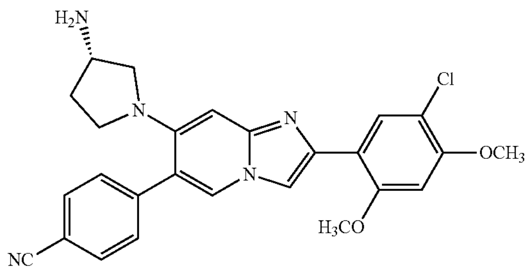 [SMILES: COc1cc(OC)c(-c2cn3cc(-c4ccc(C#N)cc4)c(N4CC[C@H](N)C4)cc3n2)cc1Cl] | (S)-4-(7-(3-aminopyrrolidin-1-yl)-2-(5-chloro-2,4-dimethoxyphenyl)imidazo[1,2-a]pyridine-6-yl)benzonitrile | APCI | 474 |
| 446 | 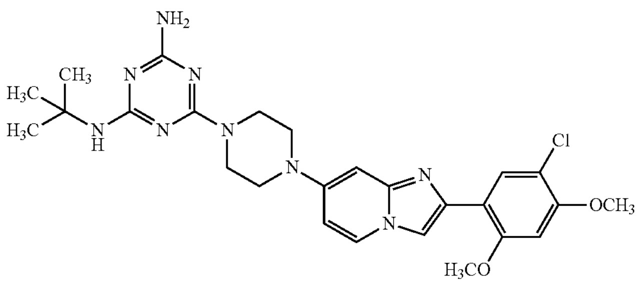 [SMILES: COc1cc(OC)c(-c2cn3ccc(N4CCN(c5nc(N)nc(NC(C)(C)C)n5)CC4)cc3n2)cc1Cl] | N²-(tert-butyl)-6-4-(2-(5-chloro-2,4-dimethoxyphenyl)imidazo[1,2-a]pyridine-7-yl)piperrazin-1-yl)-1,3,5-triazine-2,4-diamine | ESI + APCI | 538 |
| 447 | 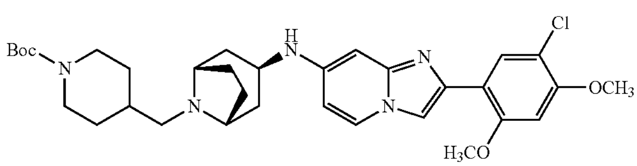 [SMILES: COc1cc(OC)c(-c2cn3ccc(N[C@H]4C[C@H]5CC[C@@H](C4)N5CC4CCN(C(=O)OC(C)(C)C)CC4)cc3n2)cc1Cl] | tert-butyl 4-(((1R3r,5S)-3-((2-(5-chloro-2,4-dimethoxyphenyl)-imidazo[1,2-a]pyridine-7-yl)amino)-8-azabicyclo[3.2.1]octan-8-yl)methyl)piperidine-1-carboxylate | ESI + APCI | 610 |
| 448 | 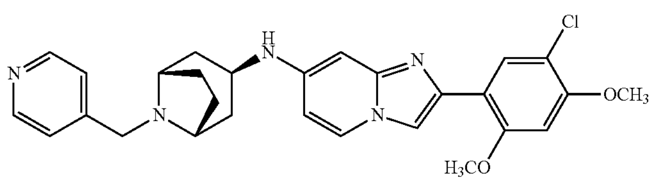 [SMILES: COc1cc(OC)c(-c2cn3ccc(N[C@H]4C[C@H]5CC[C@@H](C4)N5Cc4ccncc4)cc3n2)cc1Cl] | 2-(5-chloro-2,4-dimethoxyphenyl)-N-((1R,3r,5S)-8-(pyridine-4-ylmethyl)-8-azabicyclo[3.2.1]octan-3-yl)imidazo[1,2-a]pyridine-7-amine | ESI + APCI | 504 |
| 449 | 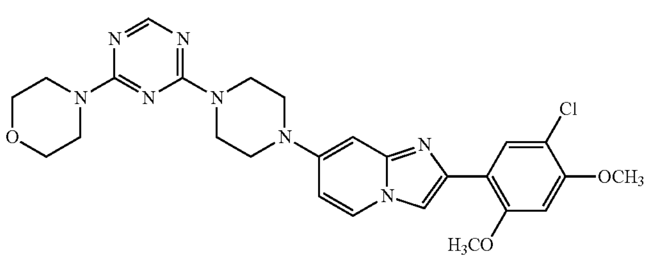 [SMILES: COc1cc(OC)c(-c2cn3ccc(N4CCN(c5ncnc(N6CCOCC6)n5)CC4)cc3n2)cc1Cl] | 4-(4-(4-(2-(5-chloro-2,4-dimethoxyphenyl)imidazo[1,2-a]pyridine-7-yl)piperazin-1-yl)-1,3,5-triazin-2-yl)morpholino | ESI + APCI | 537 |
| 450 | 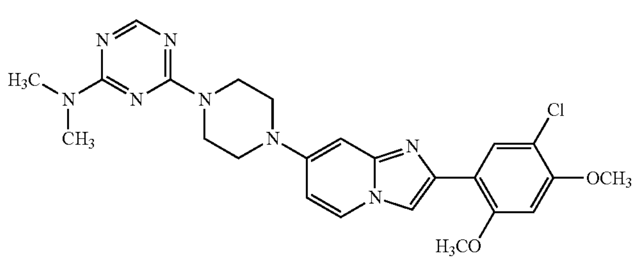 | 4-(4-(2-(5-chloro-2,4-dimethoxyphenyl)imidazo[1,2-a]pyridine-7-yl)piperazin-1-yl)-N,N-dimethyl-1,3,5-triazin-2-amine | ESI + APCI | 495 |

TABLE 2-continued

Compounds Table:

| Ex. | Structure | Name | MS | MS |
|---|---|---|---|---|
| 451 | 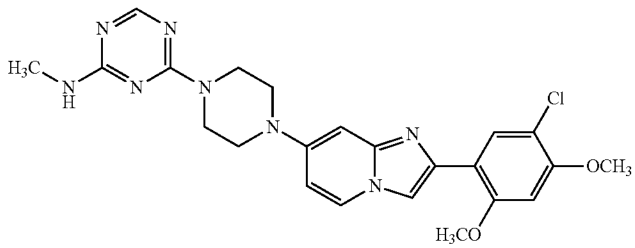 [SMILES: CNc1ncnc(N2CCN(c3ccn4cc(-c5cc(Cl)c(OC)cc5OC)nc4c3)CC2)n1] | 4-(4-(2-(5-chloro-2,4-dimethoxyphenyl)imidazo[1,2-a]pyridine-7-yl)piperazin-1-yl)-N-methyl-1,3,5-triazin-2-amine | ESI + APCI | 481 |
| 452 | 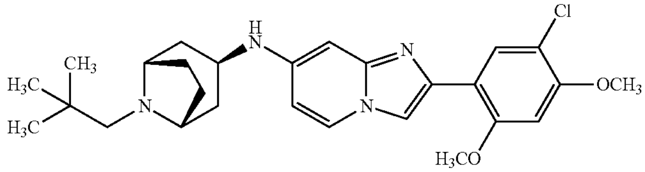 [SMILES: COc1cc(OC)c(-c2cn3ccc(N[C@H]4C[C@H]5CC[C@@H](C4)N5CC(C)(C)C)cc3n2)cc1Cl] | 2-(5-chloro-2,4-dimethoxyphenyl)-N-((1R,3r,5S)-8-neopentyl-8-azabicyclo[3.2.1]octan-3-yl)imidazo[1,2-a]pyridine-7-amine | ESI + APCI | 483 |
| 453 | 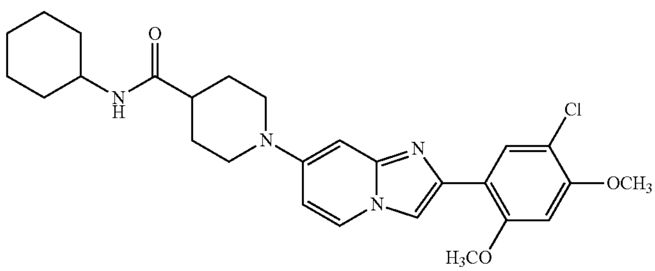 [SMILES: COc1cc(OC)c(-c2cn3ccc(N4CCC(C(=O)NC5CCCCC5)CC4)cc3n2)cc1Cl] | 1-(2-(5-chloro-2,4-dimethoxyphenyl)imidazo[1,2-a]pyridine-7-yl)-N-cyclohexylpiperidine-4-carboxamide | ESI + APCI | 497 |
| 454 | 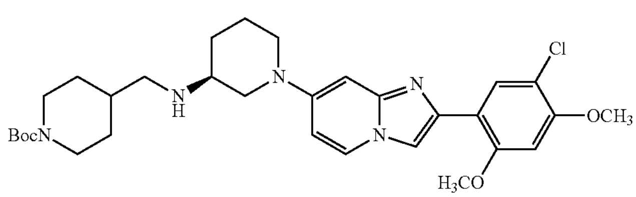 [SMILES: COc1cc(OC)c(-c2cn3ccc(N4CCC[C@H](NCC5CCN(C(=O)OC(C)(C)C)CC5)C4)cc3n2)cc1Cl] | (S)-tert-butyl 4-(((1-(2-(5-chloro-2,4-dimethoxyphenyl)imidazo[1,2-a]pyridine-7-yl)piperidin-3-yl)amino)methyl)piperidine-1-carboxylate | ESI + APCI | 584 |
| 455 | 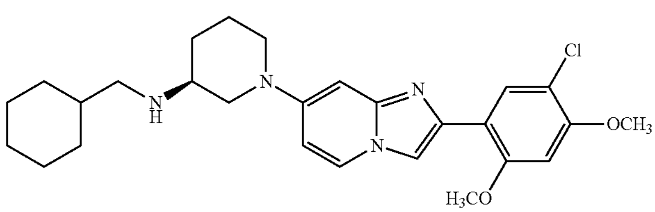 [SMILES: COc1cc(OC)c(-c2cn3ccc(N4CCC[C@H](NCC5CCCCC5)C4)cc3n2)cc1Cl] | (S)-1-(2-(5-chloro-2,4-dimethoxyphenyl)imidazo[1,2-a]pyridine-7-yl)-N-(cyclohexylmethyl)piperidin-3-amine | ESI + APCI | 483 |
| 456 | 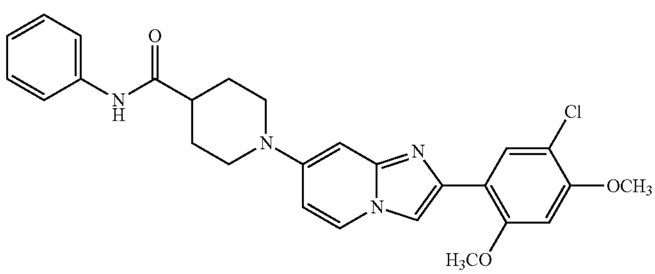 [SMILES: COc1cc(OC)c(-c2cn3ccc(N4CCC(C(=O)Nc5ccccc5)CC4)cc3n2)cc1Cl] | 1-(2-(5-chloro-2,4-dimethoxyphenyl)imidazo[1,2-a]pyridine-7-yl)-N-phenylpiperidine-4-carboxamide | ESI + APCI | 491 |

TABLE 2-continued

Compounds Table:

| Ex. | Structure | Name | MS | MS |
|---|---|---|---|---|
| 457 | 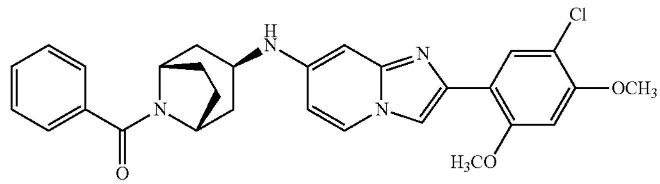 [SMILES: COc1cc(OC)c(-c2cn3ccc(N[C@H]4C[C@H]5CC[C@@H](C4)N5C(=O)c4ccccc4)cc3n2)cc1Cl] | ((1R,3r,5S)-3-((2-(5-chloro-2,4-dimethoxyphenyl)imidazo[1,2-a]pyridine-7-yl)amino)-8-azabicyclo[3.2.1]octan-8-yl)(phenyl)methanone | ESI + APCI | 517 |
| 458 | 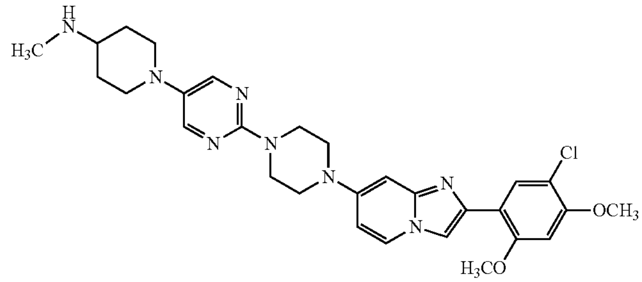 [SMILES: CNC1CCN(c2cnc(N3CCN(c4ccn5cc(-c6cc(Cl)c(OC)cc6OC)nc5c4)CC3)nc2)CC1] | 1-(2-(4-(2-(5-chloro-2,4-dimethoxyphenyl)imidazo[1,2-a]pyridine-7-yl)piperizin-1-yl)pyrimidin-5-yl)-N-methylpiperidin-4-amine | ESI + APCI | 563 |
| 459 | 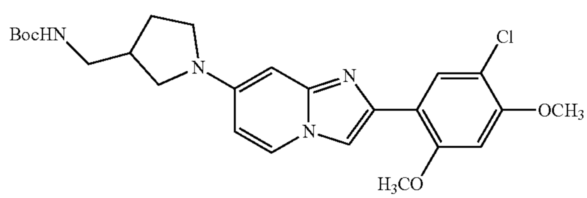 [SMILES: COc1cc(OC)c(-c2cn3ccc(N4CCC(CNC(=O)OC(C)(C)C)C4)cc3n2)cc1Cl] | tert-butyl ((1-(2-(5-chloro-2,4-dimethoxyphenyl)imidazo[1,2-a]pyridine-7-yl)pyrrolidin-3-yl)methyl)carbamate | ESI + APCI | 487 |
| 460 | 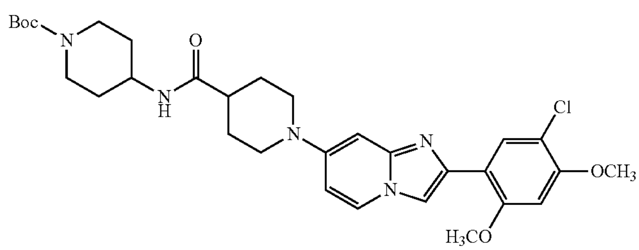 [SMILES: COc1cc(OC)c(-c2cn3ccc(N4CCC(C(=O)NC5CCN(C(=O)OC(C)(C)C)CC5)CC4)cc3n2)cc1Cl] | tert-butyl 4-(1-(2-(5-chloro-2,4-dimethoxyphenyl)imidazo[1,2-a]pyridine-7-yl)piperidine-4-carboxamido)piperidine-1-carboxylate | ESI + APCI | 598 |

Compound (I) and pharmaceutically acceptable salts thereof may be administered singly as they are; however, ordinarily, they are desirably provided as various types of pharmaceutical formulations. Such pharmaceutical formulations are used for animals or humans.

Pharmaceutical formulations of the present invention may comprise as an active ingredient compound (I) or a pharmaceutically acceptable salt thereof alone, or a mixture with any other active ingredients for treatment. Furthermore, these pharmaceutical formulations are produced by any methods well known in the technical field of drug formulation by mixing the active ingredient together with one or more types of pharmaceutically acceptable carriers (for example, diluents, solvents, and excipients).

Desirably, the most effective route of administration is used for the treatment, and examples include oral route, or parenteral route such as intravenous route.

The form of administration is, for example, tablets and injections.

Tablets are appropriate for oral administration and can be produced using excipients such as lactose, disintegrants such as starch, lubricants such as magnesium stearate, and binders such as hydroxypropylcellulose.

Injections are appropriate for parenteral administration, and can be produced using, for example, solvents or diluents such as salt solutions, glucose solutions, or a mixture of salt water and glucose solution.

The dose of compound (I) or a pharmaceutically acceptable salt thereof, and the number of doses differs depending on the form of administration, the age and body weight of the patient, the nature of the symptom to be treated or severity, and such, but ordinarily for oral administration, it is 0.01 mg to 1000 mg, preferably in the range of 0.05 mg to 100 mg for an adult, and it is administered once to several times a day. In the case of parenteral administration such as intravenous administration, 0.001 mg to 1000 mg, or preferably 0.01 mg to 100 mg is administered to an adult once to several times a day. However, these doses and the number of doses vary depending on the various conditions mentioned above.

The intermediates and compounds of interest in the following Examples can be isolated and purified by subjecting them to separation and purification methods commonly used in synthetic organic chemistry unless otherwise specified, and examples include filtration, extraction, washing, drying, concentration, recrystallization, and various types of chromatographies. Alternatively, intermediates can be subjected to the next reaction without purification.

Hereinbelow, the present invention will be specifically described with reference to the Examples, but the scope of the present invention is not to be construed as being limited thereto.

Furthermore, in the Examples shown below, unless otherwise specified, if a defined group becomes altered under the conditions of the production method or is unsuitable for carrying out the method, the compound of interest can be produced by using the methods for introducing and removing protecting groups commonly used in synthetic organic chemistry (for example, "Protective Groups in Organic Synthesis", T. W. Greene, John Wiley & Sons Inc., 1999). Furthermore, the order of the reaction processes such as substituent introduction can be changed as necessary.

EXAMPLES

Abbreviations

| | | | |
|---|---|---|---|
| Ac$_2$O | Acetic anhydride | MW | Microwave |
| AcOH | Acetic acid | Na(CN)BH$_3$ | Sodium cyanoborohydride |
| CDI | Carbonyl diimidazole | Na$_2$SO$_4$ | Sodium sulfate |
| CH$_2$Cl$_2$ | Methylene chloride | NaH | Sodiun hydride |
| CH$_3$CN | Acetonitrile | NaHCO$_3$ | Sodium bicarbonate |
| CH$_3$MgCl | Methyl magnesiumchloride | NaN$_3$ | Sodium azide |
| DIAD | Diisopropylazodicarboxylate | NH$_4$Cl | Ammonium chloride |
| DIPEA | Diisopropylethylamine | NMP | N-Methylpyrrolidinone |
| DMAP | Dimethylaminopyridine | P(CH$_3$)$_3$ | Trimethylphosphine |
| DMF | Dimehtylformamide | MeOH | Methanol |
| MsCl | Methanesulfonyl chloride | Pd/C | Palladium on carbon |
| Et$_3$N | Triethylamine | PPh$_3$ | Triphenylphosphine |
| EtOAc | Ethyl acetate | I$_2$ | Iodine |
| EtOH | Ethanol | TBDMSCl | tert-Butyldimethylsilyl chloride |
| H$_2$ | Hydrogen gas | t-BuONa | Sodium tert-butoxide |
| H$_2$O | Water | TFA | Trifluoroacetic acid |
| HCl | Hydrochloric acid | THF | Tetrahydrofuran |
| EDCI | 1-Ethyl-3-(3-dimethylaminopropyl)carbodiimide | HATU | O-(7-Azabenzotriazol-1-yl)-N,N,N',N'-tetramethyluronium hexafluorophosphate |
| HOBt | 1-Hydroxybenzotriazole | T$_3$P | n-propylphosphonic cyclic anhydride |
| K$_2$CO$_3$ | Potassium carbonate | Pd(PPh$_3$)$_4$ | Tetrakis(triphenylphosphine)-palladium(0) |
| LiCl | Lithium chloride | LiOH | Lithium hydroxide |

Experimentals

Unless otherwise noted, reagents and solvents were used as received from commercial suppliers. Proton nuclear magnetic resonance spectra were obtained on a Bruker AVANCE 300 spectrometer at 300 MHz, and Bruker AVANCE 400 spectrometer at 400 MHz. Tetramethylsilane was used as an internal standard for proton spectra. Thin-layer chromatography was performed using Merck TLC silica-gel 60F$_{254}$ plates. Visualization of TLC plates was performed using UV light (254 nm). The mass spectra were obtained on a Shimadzu LCMS-2010EV spectrometer using electrospray ionization and atmospheric-pressure chemical ionization. HPLC analyses were performed using Method 1 to Method 9.

HPLC Method 1
  Column: SunFire C18 (4.6×150 mm, 5.0 μm)
  Column Temperature: Ambient
  Detection: UV@254 nm
  Sample Diluent: Acetonitrile
  Mobile Phase A: Water (with 0.05% TFA)
  Mobile Phase B: Acetonitrile (with 0.05% TFA)

TABLE A

| Method 1 Gradient | | | |
|---|---|---|---|
| Time (Minutes) | Flow (mL/min) | % Mobile Phase A | % Mobile Phase B |
| 0:01 | 1.2 | 90 | 10 |
| 2:00 | 1.2 | 90 | 10 |
| 12:00 | 1.2 | 10 | 90 |
| 16:00 | 1.2 | 10 | 90 |
| 19:00 | 1.2 | 90 | 10 |
| 26:00 | 1.2 | 90 | 10 |

HPLC Method 2
  Column: XTerra MS (4.6×150 mm, 5.0 μm)
  Column Temperature: Ambient
  Detection: UV@254 nm
  Sample Diluent: Acetonitrile
  Mobile Phase A: Water (with 0.05% TFA)
  Mobile Phase B: Acetonitrile (with 0.05% TFA)

TABLE B

| Method 2 Gradient | | | |
|---|---|---|---|
| Time (Minutes) | Flow (mL/min) | % Mobile Phase A | % Mobile Phase B |
| 0:01 | 1.0 | 90 | 10 |
| 5:00 | 1.0 | 90 | 10 |
| 17:00 | 1.0 | 10 | 90 |
| 28:00 | 1.0 | 10 | 90 |
| 33:00 | 1.0 | 90 | 10 |
| 40:00 | 1.0 | 90 | 10 |

HPLC Method 3
  Column: Luna C18(2) (4.6×250 mm, 5.0 μm)
  Column Temperature: Ambient
  Detection: UV@254 nm
  Sample Diluent: Acetonitrile
  Mobile Phase A: Water (with 0.05% TFA)

Mobile Phase B: Acetonitrile (with 0.05% TFA)

TABLE C

| Method 3 Gradient | | | |
|---|---|---|---|
| Time (Minutes) | Flow (mL/min) | % Mobile Phase A | % Mobile Phase B |
| 0:01 | 1.0 | 90 | 10 |
| 5:00 | 1.0 | 90 | 10 |
| 17:00 | 1.0 | 10 | 90 |
| 28:00 | 1.0 | 10 | 90 |
| 33:00 | 1.0 | 90 | 10 |
| 40:00 | 1.0 | 90 | 10 |

HPLC Method 4
  Column: Alltima C18 (4.6×250 mm, 5.0 μm)
  Column Temperature: Ambient
  Detection: UV@254 nm
  Sample Diluent: Acetonitrile
  Mobile Phase A: Water (with 0.05% TFA)
  Mobile Phase B: Acetonitrile (with 0.05% TFA)

TABLE D

| Method 4 Gradient | | | |
|---|---|---|---|
| Time (Minutes) | Flow (mL/min) | % Mobile Phase A | % Mobile Phase B |
| 0:01 | 1.0 | 90 | 10 |
| 5:00 | 1.0 | 90 | 10 |
| 17:00 | 1.0 | 10 | 90 |
| 28:00 | 1.0 | 10 | 90 |
| 33:00 | 1.0 | 90 | 10 |
| 40:00 | 1.0 | 90 | 10 |

HPLC Method 5
  Column: XTerra RP (4.6×150 mm, 5.0 μm)
  Column Temperature: Ambient
  Detection: UV@254 nm
  Sample Diluent: Acetonitrile
  Mobile Phase A: Water (with 0.05% TFA)
  Mobile Phase B: Acetonitrile (with 0.05% TFA)

TABLE E

| Method 5 Gradient | | | |
|---|---|---|---|
| Time (Minutes) | Flow (mL/min) | % Mobile Phase A | % Mobile Phase B |
| 0:01 | 1.0 | 90 | 10 |
| 5:00 | 1.0 | 90 | 10 |
| 17:00 | 1.0 | 10 | 90 |
| 28:00 | 1.0 | 10 | 90 |
| 33:00 | 1.0 | 90 | 10 |
| 40:00 | 1.0 | 90 | 10 |

HPLC Method 6
  Column: Eclipse XDB C18 (4.6×150 mm, 5.0 μm)
  Column Temperature: Ambient
  Detection: UV@220 nm
  Sample Diluent: Acetonitrile: H$_2$O (50:50)
  Mobile Phase A: Water (with 0.05% TFA)
  Mobile Phase B: Acetonitrile (with 0.05% TFA)

TABLE F

| Method 6 Gradient | | | |
|---|---|---|---|
| Time (Minutes) | Flow (mL/min) | % Mobile Phase A | % Mobile Phase B |
| 0:00 | 1.0 | 95 | 5 |
| 5:00 | 1.0 | 95 | 5 |
| 15:00 | 1.0 | 10 | 90 |
| 20:00 | 1.0 | 10 | 90 |
| 20:10 | 1.0 | 95 | 5 |
| 25:00 | 1.0 | 95 | 5 |

HPLC Method 7
  Column: Eclipse XDB C18 (4.6×150 mm, 5.0 μm)
  Column Temperature: Ambient
  Detection: UV a 230 nm
  Sample Diluent: Acetonitrile: H$_2$O (50:50)
  Mobile Phase A: Water (with 0.05% TFA)
  Mobile Phase B: Acetonitrile (with 0.05% TFA)

TABLE G

| Method 7 Gradient | | | |
|---|---|---|---|
| Time (Minutes) | Flow (mL/min) | % Mobile Phase A | % Mobile Phase B |
| 0:00 | 1.0 | 95 | 5 |
| 5:00 | 1.0 | 95 | 5 |
| 15:00 | 1.0 | 10 | 90 |
| 20:00 | 1.0 | 10 | 90 |
| 20:10 | 1.0 | 95 | 5 |
| 25:00 | 1.0 | 95 | 5 |

HPLC Method 8
  Column: Symmetry C18(2) (4.6×250 mm, 5.0 μm)
  Column Temperature: Ambient
  Detection: UV@254 nm
  Sample Diluent: Acetonitrile
  Mobile Phase A: Water (with 0.05% TFA)
  Mobile Phase B: Acetonitrile (with 0.05% TFA)

TABLE H

| Method 8 Gradient | | | |
|---|---|---|---|
| Time (Minutes) | Flow (mL/min) | % Mobile Phase A | % Mobile Phase B |
| 0:00 | 1.0 | 95 | 5 |
| 5:00 | 1.0 | 95 | 5 |
| 15:00 | 1.0 | 10 | 90 |
| 20:00 | 1.0 | 10 | 90 |
| 20:10 | 1.0 | 95 | 5 |
| 25:00 | 1.0 | 95 | 5 |

HPLC Method 9
  Column: Eclipse XDB C18 (4.6×150 mm, 5.0 μm)
  Column Temperature: Ambient
  Detection: UV@254 nm
  Sample Diluent: Acetonitrile: H$_2$O (50:50)
  Mobile Phase A: Water (with 0.05% TFA)
  Mobile Phase B: Acetonitrile (with 0.05% TFA)

TABLE I

| | Method 9 Gradient | | |
|---|---|---|---|
| Time (Minutes) | Flow (mL/min) | % Mobile Phase A | % Mobile Phase B |
| 0:00 | 1.0 | 95 | 5 |
| 5:00 | 1.0 | 95 | 5 |
| 15:00 | 1.0 | 10 | 90 |
| 20:00 | 1.0 | 10 | 90 |
| 20:10 | 1.0 | 95 | 5 |
| 25:00 | 1.0 | 95 | 5 |

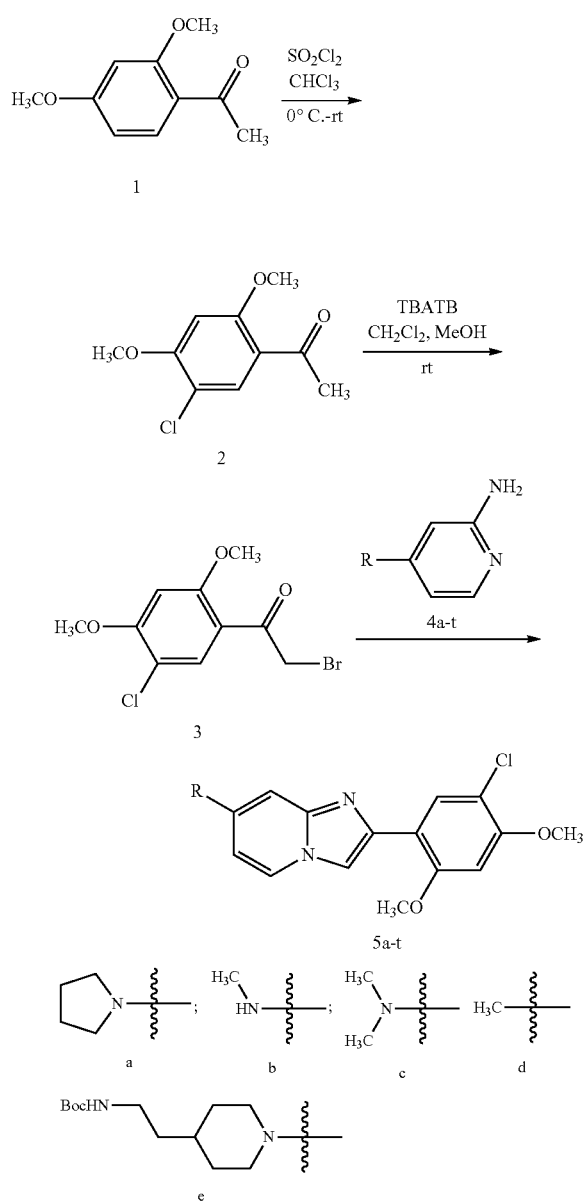

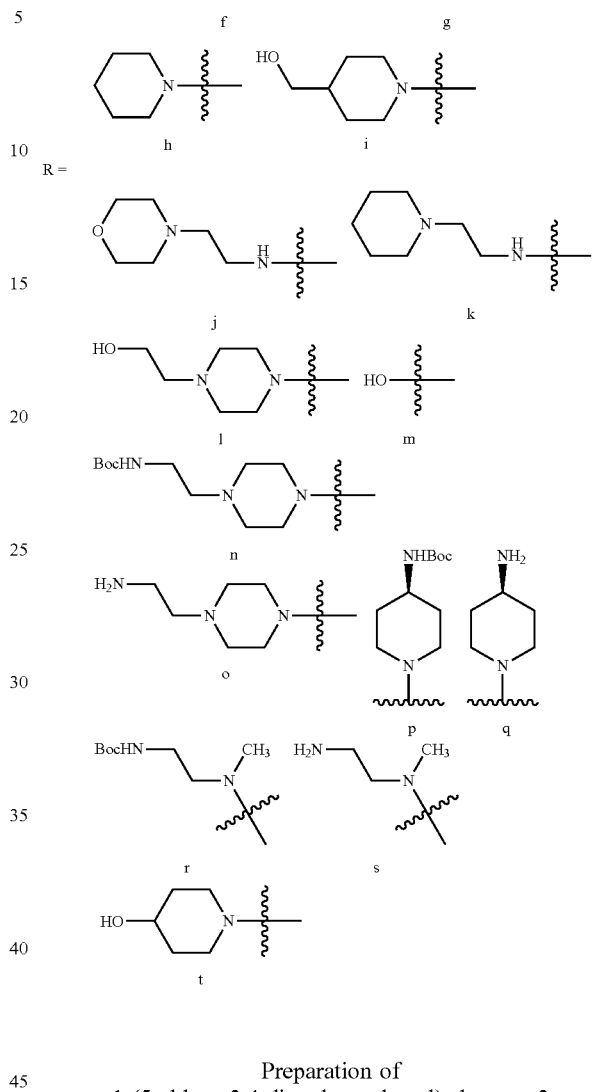

Preparation of 1-(5-chloro-2,4-dimethoxyphenyl)ethanone 2

A solution of 1-(2,4-dimethoxyphenyl)ethanone 1 (2.00 g, 0.11 mmol) in chloroform (30 mL) was cooled to 0° C., and $SO_2Cl_2$ (1.50 g, 0.11 mmol) was added. The reaction mixture was stirred at 0° C. for 30 min and at room temperature for 1 h. The reaction mixture was diluted with chloroform (100 mL) and washed with sodium bicarbonate solution (2×30 mL). The organic layer was dried over sodium sulfate and concentrated under reduced pressure, and the product was purified by column chromatography (silica gel, 10% EtOAc/hexanes) to provide 1-(5-chloro-2,4-dimethoxyphenyl)ethanone 2 (1.33 g, 56%) as a white solid.

$^1$H NMR (300 MHz, DMSO-$d_6$): δ 7.65 (s, 1H), 6.85 (s, 1H), 3.97 (s, 3H), 3.96 (s, 3H), 2.49 (s, 3H).

Preparation of 2-bromo-1-(5-chloro-2,4-dimethoxyphenyl)ethanone 3

To a solution of 1-(5-chloro-2,4-dimethoxyphenyl)ethanone 2 (1.33 g, 6.2 mmol) in $CH_2Cl_2$/MeOH (20 mL/15 mL)

was added tetrabutylammonium tribromide (TBATB, 3.0 g, 6.2 mmol). The reaction mixture was diluted with methanol, cooled to 0° C., and stirred at 0° C. for 30 min. The precipitate was collected by filtration and washed with cold methanol to give (836 mg, 46%) of desired 2-bromo-1-(5-chloro-2,4-dimethoxyphenyl)ethanone 3 as a white solid.

$^1$H NMR (400 MHz, CDCl$_3$): δ 7.94 (s, 1H), 6.84 (s, 1H), 4.52 (s, 2H), 3.98 (s, 3H), 3.98 (s, 3H).

Preparation of 2-(5-chloro-2,4-dimethoxyphenyl)-7-(pyrrolidin-1-yl)imidazo[1,2-a]pyridine hydrobromide 5a (Example 4)

A solution of 2-bromo-1-(5-chloro-2,4-dimethoxyphenyl) ethanone 3 (70 mg, 0.24 mmol) and 4-(pyrrolidin-1-yl)pyridin-2-amine 4a (39 mg, 0.24 mmol) in acetone (3 mL) was heated at 75° C. for 16 h. The reaction mixture was cooled to room temperature; the white precipitate was collected by filtration, washed with acetone, and dried under reduced pressure to afford 2-(5-chloro-2,4-dimethoxyphenyl)-7-(pyrrolidin-1-yl)imidazo[1,2-a]pyridine hydrobromide 5a (45 mg, 43%) as a pink solid.

$^1$H NMR (300 MHz, DMSO-d$_6$): δ 13.03 (s, 1H), 8.50 (d, J=7.6 Hz, 1H), 8.20 (s, 1H), 7.89 (s, 1H), 6.97 (s, 1H), 6.95 (dd, J=2.2, 7.6 Hz, 1H), 6.30 (d, J=2.0 Hz, 1H), 4.05 (s, 3H), 3.99 (s, 3H), 3.48-3.38 (m, 4H), 2.08-1.98 (m, 4H); HPLC (Method 4) 98.7% (AUC), $t_R$=19.02 min. APCI MS m/z 358 [M+H]$^+$.

Preparation of 2-(5-chloro-2,4-dimethoxyphenyl)-N-methylimidazo[1,2-a]pyridin-7-amine hydrobromide 5b (Example 6)

Compound 2-(5-chloro-2,4-dimethoxyphenyl)-N-methylimidazo[1,2-a]pyridin-7-amine hydrobromide 5b was prepared in the same manner as 2-(5-chloro-2,4-dimethoxyphenyl)-7-(pyrrolidin-1-yl)imidazo[1,2-a]pyridine hydrobromide 5a and was obtained as an off-white solid (40 mg, 41%).

$^1$H NMR (400 MHz, DMSO-d$_6$): δ 13.40 (br s, 1H), 8.37 (d, J=7.4 Hz, 1H), 8.20 (s, 1H), 7.98 (s, 1H), 7.79-7.68 (m, 1H), 6.96 (s, 1H), 6.80 (dd, J=2.2, 7.4 Hz, 1H), 6.35 (s, 1H), 4.04 (s, 3H), 3.98 (s, 3H), 2.83 (d, J=4.8 Hz, 3H); HPLC (Method 2) >99% (AUC), $t_R$=17.57 min.; ESI MS m/z 318 [M+H]$^+$.

Preparation of 2-(5-chloro-2,4-dimethoxyphenyl)-N,N-dimethylimidazo[1,2-a]pyridin-7-amine hydrobromide 5c (Example 22)

Compound 2-(5-chloro-2,4-dimethoxyphenyl)-N,N-dimethylimidazo[1,2-a]pyridin-7-amine hydrobromide 5c was prepared in the same manner as 2-(5-chloro-2,4-dimethoxyphenyl)-7-(pyrrolidin-1-yl)imidazo[1,2-a]pyridine hydrobromide 5a and was obtained as a white solid (64% yield).

$^1$H NMR (400 MHz, DMSO-d$_6$): δ 13.07 (br s, 1H), 8.50 (d, J=7.8 Hz, 1H), 8.22 (s, 1H), 7.90 (s, 1H), 7.09 (br s, 1H), 6.97 (s, 1H), 6.43 (s, 1H), 4.05 (s, 3H), 3.98 (s, 3H), 3.14 (s, 6H); HPLC (Method 4) >99% (AUC), $t_R$=18.29 min.; ESI MS m/z 332 [M+H]$^+$.

Preparation of 2-(5-chloro-2,4-dimethoxyphenyl)-7-methylimidazo[1,2-a]pyridine hydrobromide 5d (Example 76)

Compound 2-(5-chloro-2,4-dimethoxyphenyl)-7-methylimidazo[1,2-a]pyridine hydrobromide 5d was prepared in the same manner as 2-(5-chloro-2,4-dimethoxyphenyl)-7-(pyrrolidin-1-yl)imidazo[1,2-a]pyridine hydrobromide 5a and was obtained as a white solid (10% yield).

$^1$H NMR (400 MHz, DMSO-d$_6$): δ 14.19 (s, 1H), 8.76 (d, 1H, J=6.9 Hz), 8.61 (s, 1H), 8.02 (s, 1H), 7.69 (s, 1H), 7.35 (dd, J=1.3, 6.8 Hz, 1H), 7.00 (s, 1H), 4.08 (s, 3H), 4.00 (s, 3H), 2.55 (s, 3H); ESI MS m/z 303 [M+H]$^+$.

Preparation of tert-butyl (2-(1-(2-(5-chloro-2,4-dimethoxyphenyl)imidazo[1,2-a]pyridin-7-yl)piperidin-4-yl)ethyl)carbamate 5e A solution of 2-bromo-1-(5-chloro-2,4-dimethoxyphenyl) ethanone 3 (221 mg, 0.754 mmol), sodium bicarbonate (90.4 mg, 1.07 mmol), tert-butyl (2-(1-(2-aminopyridin-4-yl)piperidin-4-yl)ethyl)carbamate 4e (230 mg, 0.718 mmol) in DMF (5 mL) was heated at 90° C. for 3 h. The reaction mixture was cooled to room temperature; the white precipitate was collected by filtration, washed with water, and dried under reduced pressure. The residue was purified by combiflash chromatography (silica gel, 95:5 CHCl$_3$/methanol) to yield tert-butyl(2-(1-(2-(5-chloro-2,4-dimethoxyphenyl) imidazo-[1,2-a]pyridin-7-yl)piperidin-4-yl)ethyl)carbamate 5e (100 mg, 33%) as a green solid.

$^1$H NMR (400 MHz, CDCl$_3$): δ 8.37 (s, 1H), 7.86 (d, J=7.5 Hz, 1H), 7.84 (s, 1H), 6.82 (s, 1H), 6.58-6.53 (m, 2H), 4.48 (br s, 1H), 3.99 (s, 3H), 3.95 (s, 3H), 3.71 (d, J=12.6 Hz, 2H), 3.23-3.15 (m, 2H), 2.81-2.72 (m, 2H), 1.86-1.79 (m, 2H), 1.50-1.46 (m, 2H), 1.45 (s, 9H), 1.42-1.30 (m, 3H).

Preparation of 2-(1-(2-(5-chloro-2,4-dimethoxyphenyl)imidazo[1,2-a]pyridin-7-yl)piperidin-4-yl)ethanamine hydrochloride 5f (Example 72)

A solution of tert-butyl (2-(1-(2-(5-chloro-2,4-dimethoxyphenyl)imidazo[1,2-a]pyridin-7-yl)piperidin-4-yl)ethyl)carbamate 5e (70 mg) in 4M HCl in dioxane (3 mL) was stirred at room temperature for 2 h. Solvent was removed; the yellow residue collected by filtration; The solid was washed with ether, and dried under reduced pressure to yield 2-(1-(2-(5-chloro-2,4-dimethoxyphenyl)imidazo[1,2-a]pyridin-7-yl)piperidin-4-yl)ethanamine hydrochloride 5f (50 mg, 61%) as a yellow solid.

$^1$H NMR (400 MHz, DMSO-d$_6$): δ 13.81 (s, 1H), 8.51 (d, J=7.7 Hz, 1H), 8.24 (s, 1H), 8.07 (s, 1H), 7.97 (br s, 3H), 7.29 (dd, J=2.3, 7.8 Hz, 1H), 6.97 (s, 1H), 6.70 (s, 1H), 4.09-3.96 (m, 8H), 3.08-2.98 (m, 2H), 2.88-2.79 (m, 2H), 1.85-1.76 (m, 2H), 1.75-1.65 (m, 1H), 1.58-1.49 (m, 2H), 1.26-1.14 (m, 2H); HPLC (Method 2) 94.9% (AUC), $t_R$=16.01 min.; APCI MS m/z 415 [M+H]$^+$.

Preparation of 4-(2-(5-chloro-2,4-dimethoxyphenyl) imidazo[1,2-a]pyridin-7-yl)morpholine hydrobromide 5g (Example 12)

Compound 4-(2-(5-chloro-2,4-dimethoxyphenyl)imidazo [1,2-a]pyridin-7-yl)morpholine hydrobromide 5g was prepared in the same manner as 2-(5-chloro-2,4-dimethoxyphenyl)-7-(pyrrolidin-1-yl)imidazo[1,2-a]pyridine 5a, and was obtained as a white solid (58 mg, 44% yield).

$^1$H NMR (300 MHz, DMSO-d$_6$): δ 8.58 (d, J=7.6 Hz, 1H), 8.29 (s, 1H), 7.93 (s, 1H), 7.33 (d, J=7.6 Hz, 1H), 6.98 (s, 1H), 6.72 (s, 1H), 4.05 (s, 3H), 3.99 (s, 3H), 3.79-3.76 (m, 4H), 3.49-3.47 (m, 4H); HPLC (Method 4) 99.6% (AUC), $t_R$=17.83 min.; APCI MS m/z 374 [M+H]$^+$.

Preparation of 2-(5-chloro-2,4-dimethoxyphenyl)-7-(piperidin-1-yl)imidazo[1,2-a]pyridine hydrobromide 5h (Example 25)

Compound 2-(5-chloro-2,4-dimethoxyphenyl)-7-(piperidin-1-yl)imidazo[1,2-a]pyridine hydrobromide 5h was prepared in the same manner as 2-(5-chloro-2,4-dimethoxyphenyl)-7-(pyrrolidin-1-yl)imidazo[1,2-a]pyridine 5a, and was obtained as a white solid (35 mg, 41% yield).

$^1$H NMR (400 MHz, DMSO-d$_6$): δ 13.1 (br s, 1H), 8.49 (d, J=7.76 Hz, 1H), 8.23 (s, 1H), 7.91 (s, 1H), 7.29 (d, J=7.7 Hz, 1H), 6.97 (s, 1H), 6.66 (s, 1H), 4.05 (s, 3H), 3.98 (s, 3H), 3.56-3.50 (m, 4H), 1.72-1.56 (m, 6H); HPLC (Method 5) 98.9% (AUC), $t_R$=17.75 min; APCI MS m/z 372 [M+H]$^+$.

Preparation of (1-(2-(5-chloro-2,4-dimethoxyphenyl)imidazo[1,2-a]pyridin-7-yl)piperidin-4-yl)methanol 5i (Example 41)

Compound (1-(2-(5-chloro-2,4-dimethoxyphenyl)imidazo[1,2-a]pyridin-7-yl)piperidin-4-yl)methanol 5i was prepared in the same manner as 2-(5-chloro-2,4-dimethoxyphenyl)-7-(pyrrolidin-1-yl)imidazo[1,2-a]pyridine 5a. The obtained salt was basified with aqueous ammonia, washed with water, filtered and dried. The product was obtained as a white solid (58 mg, 8% yield).

$^1$H NMR (400 MHz, CDCl$_3$): δ δ 8.36 (s, 1H), 7.87 (d, J=7.50 Hz, 1H), 7.84 (s, 1H), 6.81 (s, 1H), 6.57 (s, 1H), 6.56 (s, 1H), 3.99 (s, 3H), 3.95 (s, 3H), 3.80-3.72 (m, 2H), 3.55 (d. J=6.4 Hz, 2H), 2.84-2.75 (m, 2H), 1.91-1.83 (m, 2H), 1.78-1.67 (m, 2H), 1.47-1.34 (m, 2H). HPLC (Method 5) >99% (AUC), $t_R$=15.65 min; ESI MS m/z 402 [M+H]$^+$.

Preparation of 2-(5-chloro-2,4-dimethoxyphenyl)-N-(2-morpholinoethyl)imidazo[1,2-a]-pyridin-7-amine 5j (Example 70)

Compound 2-(5-chloro-2,4-dimethoxyphenyl)-N-(2-morpholinoethyl)-imidazo[1,2-a]pyridin-7-amine 5j was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e, and was obtained as a white solid (9 mg, 7% yield).

$^1$H NMR (400 MHz, CDCl$_3$): δ 8.36 (s, 1H), 7.81 (d, J=7.5 Hz, 1H), 7.84 (s, 1H), 6.57 (s, 1H), 6.49 (s, 1H), 6.4 (s, 1H), 4.55 (s, 1H), 3.95 (s, 3H), 3.95 (s, 3H), 3.74-3.72 (m, 4H), 3.22-3.19 (m, 2H), 2.62 (d, J=6.4 Hz, 2H), 2.50-2.48 (m, 2H. HPLC (Method 2) 97.9% (AUC), $t_R$=15.23 min; APCI MS m/z 417 [M+H]$^+$.

Preparation of 2-(5-chloro-2,4-dimethoxyphenyl)-N-(2-(piperidin-1-yl)ethyl)-imidazo[1,2-a]pyridin-7-amine 5k (Example 64)

Compound 2-(5-chloro-2,4-dimethoxyphenyl)-N-(2-(piperidin-1-yl)ethyl)-imidazo[1,2-a]pyridin-7-amine 5k was prepared in the same manner as 2-(5-chloro-2,4-dimethoxyphenyl)-7-(pyrrolidin-1-yl)imidazo[1,2-a]pyridine 5a. Obtained salt was basified with aqueous ammonia, washed with water, filtered and dried. The product was obtained as a white solid (60 mg, 42% yield).

$^1$H NMR (400 MHz, CDCl$_3$): δ δ 8.36 (s, 1H), 7.80 (s, 1H), 7.70 (d, J=7.0 Hz, 1H), 6.57 (s, 1H), 6.47 (d, J=2.0 Hz, 1H), 6.22 (dd, J=2.2, 7.2 Hz, 1H), 4.66-4.60 (m, 1H), 3.98 (s, 3H), 3.94 (s, 3H), 3.16 (dd, J=5.2, 11.6 Hz, 2H), 2.61 (t, J=6.1 Hz, 2H), 2.40 (brs s, 4H), 1.58-1.54 (m, 2H), 1.49-1.42 (m, 2H); HPLC (Method 3) 94.7% (AUC), $t_R$=15.62 min.; ESI MS 417 [(M+2)+H]$^+$

Preparation of 2-(4-(2-(5-chloro-2,4-dimethoxyphenyl)imidazo[1,2-a]pyridin-7-yl)piperazin-1-yl)ethanol hydrochloride 5l (Example 43)

A solution of 2-bromo-1-(5-chloro-2,4-dimethoxyphenyl)ethanone 3 (138 mg, 0.45 mmol) and 4-(pyrrolidin-1-yl)pyridin-2-amine 41 (100 mg, 0.45 mmol) in acetone (5 mL) was heated at 75° C. for 16 h. The reaction mixture was cooled to room temperature, the white precipitate was collected by filtration, treated with HCl in dioxane, and dried under reduced pressure to yield 2-(4-(2-(5-chloro-2,4-dimethoxyphenyl)imidazo[1,2-a]pyridin-7-yl)piperazin-1-yl)ethanol hydrochloride 5l (55 mg, 48% yield) as a yellow solid.

$^1$H NMR (400 MHz, DMSO-d$_6$): δ 13.99 (br s, 1H), 10.80 (s, 1H), 8.64 (d, J 7.71 Hz, 1H), 8.33 (s, 1H), 8.08 (s, 1H), 7.35 (dd, J=7.76 Hz, 1H), 6.98 (s, 1H), 6.89 (s, 1H), 5.38 (br s, 1H), 4.06 (s, 3H), 3.99 (s, 3H), 3.88-3.79 (m, 2H), 3.74-3.43 (m, 4H), 3.29-3.15 (m, 4H); HPLC (Method 2) 98.3% (AUC), $t_R$=14.95 min; ESI MS m/z 417 [M+H]$^+$.

Preparation of 2-(5-chloro-2,4-dimethoxyphenyl)imidazo[1,2-a]pyridin-7-ol 5m (Example 20)

Compound 2-(5-chloro-2,4-dimethoxyphenyl)imidazo[1,2-a]pyridin-7-ol 5m was prepared in the same manner as 2-(5-chloro-2,4-dimethoxyphenyl)-N-(2-(piperidin-1-yl)ethyl)imidazo[1,2-a]pyridin-7-amine 5k; and was obtained as a yellow solid (11% yield).

$^1$H NMR (400 MHz, CD$_3$OD): δ 8.11 (d, J=7.5 Hz, 1H), 7.92 (s, 1H), 7.86 (s, 1H), 6.82 (s, 1H), 6.56-6.48 (m, 2H), 4.03 (s, 3H), 3.96 (s, 3H); HPLC (Method 4) 96.77% (AUC), $t_R$=17.12 min.; ESI MS m 305 [M+H]$^+$.

Preparation of tert-butyl (2-(4-(2-(5-chloro-2,4-dimethoxyphenyl)imidazo[1,2-a]pyridin-7-yl)piperazin-1-yl)ethyl)carbamate 5n (Example 28)

Compound tert-butyl (2-(4-(2-(5-chloro-2,4-dimethoxyphenyl)imidazo[1,2-a]pyridin-7-yl)piperazin-1-yl)ethyl)carbamate 5n was prepared in the same manner as 2-(5-chloro-2,4-dimethoxyphenyl)-7-(pyrrolidin-1-yl)imidazo[1,2-a]pyridine 5a, and was obtained as a white solid (80 mg, 49% yield).

A solution of 5n (100 mg) in MeOH was added HCl in MeOH (1.2 N, 2.0 mL). The reaction mixture was stirred at room temperature for 3 hours. The precipitation formed was collected by filtration and the solid obtained was washed with cold MeOH, dried in vacuum oven at 50° C. for 24 hours to give the tert-butyl (2-(4-(2-(5-chloro-2,4-dimethoxyphenyl)imidazo[1,2-a]pyridin-7-yl)piperazin-1-yl)ethyl)carbamate dihydrochloride (Example 28) as an amorphous white solid (80 mg, 71%).

$^1$H NMR (400 MHz, DMSO-d$_6$): δ 14.15 (s, 1H), 11.36 (s, 1H), 8.63 (d, J=7.7 Hz, 1H), 8.32 (s, 1H), 8.12 (s, 1H), 7.36 (dd, J=2.3, 7.7 Hz, 1H), 7.16 (bs, 1H), 6.98 (s, 1H), 6.90 (s, 1H), 4.26-4.12 (m, 2H), 4.06 (s, 3H), 3.99 (s, 3H), 3.73-3.60 (m, 2H), 3.59-3.47 (m, 2H), 3.45-3.37 (m, 2H), 3.26 (bs, 4H), 1.40 (s, 9H); HPLC (Method 5) >99% (AUC), $t_R$=15.30 min.; APCI MS m/z 516 [M+H]$^+$.

Preparation of 2-(4-(2-(5-chloro-2,4-dimethoxyphenyl)imidazo[1,2-a]pyridin-7-yl)piperazin-1-yl)ethanamine hydrochloride 5o (Example 29)

Compound 2-(4-(2-(5-chloro-2,4-dimethoxyphenyl)imidazo[1,2-a]pyridin-7-yl)piperazin-1-yl)ethanamine hydrochloride 5o was prepared in the same manner as 2-(1-(2-(5-chloro-2,4-dimethoxyphenyl)imidazo[1,2-a]pyridin-7-yl)piperidin-4-yl)ethanamine hydrochloride 5f and was obtained as a white solid (22 mg, 50% yield).
$^1$H NMR (400 MHz, CD$_3$OD): δ 8.48 (d, J=7.7 Hz, 1H), 8.18 (s, 1H), 7.29 (dd, J=7.7 Hz, 1H), 6.98 (s, 1H), 6.90 (s, 1H), 4.08 (s, 3H), 4.00 (s, 3H), 3.97-3.75 (m, 2H), 3.56-3.37 (m, 8H); HPLC (Method 4) >99% (AUC), $t_R$=15.36 min; ESI MS m/z 416 [M+H]$^+$.

Preparation of tert-butyl (1-(2-(5-chloro-2,4-dimethoxyphenyl)imidazo[1,2-a]pyridin-7-yl)piperidin-4-yl)carbamate 5p Compound tert-butyl (1-(2-(5-chloro-2,4-dimethoxyphenyl)imidazo[1,2-a]pyridin-7-yl)piperidin-4-yl)carbamate 5p was prepared in the same manner as 2-(5-chloro-2,4-dimethoxyphenyl)-7-(pyrrolidin-1-yl)imidazo[1,2-a]pyridine 5a, and was obtained as a white solid (35 mg, 14% yield).

Preparation of 1-(2-(5-chloro-2,4-dimethoxyphenyl)imidazo[1,2-a]pyridin-7-yl)piperidin-4-amine hydrochloride 5q (Example 30)

Compound 1-(2-(5-chloro-2,4-dimethoxyphenyl)imidazo[1,2-a]pyridin-7-yl)piperidin-4-amine hydrochloride 5q was prepared in the same manner as 2-(1-(2-(5-chloro-2,4-dimethoxyphenyl)imidazo[1,2-a]pyridin-7-yl)piperidin-4-yl)ethanamine hydrochloride 5f and was obtained as a white solid (10 mg, 52% yield).
$^1$H NMR (400 MHz, CD$_3$OD): δ 8.49 (d, J=7.8 Hz, 1H), 8.14 (s, 1H), 7.79 (s, 1H), 7.19 (s, 1H), 6.93 (s, 1H), 6.90 (s, 1H), 4.08 (s, 3H), 4.06-4.01 (br s, 1H), 4.00 (s, 3H), 3.84-3.75 (m, 1H), 3.53-3.43 (m, 1H), 3.41-3.22 (m, 2H), 2.24-2.13 (m, 1H), 2.05-1.93 (m, 1H), 1.85-1.72 (m, 1H); HPLC (Method 4) 96.3% (AUC), $t_R$=15.84 min; ESI MS m/z 387 [M+H]$^+$.

Preparation of tert-butyl (2-((2-(5-chloro-2,4-dimethoxyphenyl)imidazo[1,2-a]pyridin-7-yl)(methyl)amino)ethyl) carbamate 5r (Example 48)

Compound tert-butyl (2-((2-(5-chloro-2,4-dimethoxyphenyl)imidazo[1,2-a]pyridin-7-yl)(methyl)amino)ethyl)carbamate 5r was prepared in the same manner as 2-(5-chloro-2,4-dimethoxyphenyl)-7-(pyrrolidin-1-yl)imidazo[1,2-a]pyridine 5a, and was obtained as a white solid (35 mg, 14% yield).
$^1$H NMR (400 MHz, CDCl$_3$): δ δ 8.37 (s, 1H), 7.86 (d, J=7.3 Hz, 1H), 7.82 (s, 1H), 6.59-6.58 (m, 2H), 6.52-6.51 (m, 1H), 4.13 (s, 3H), 3.96 (s, 3H), 3.52-3.50 (m, 2H), 3.34-3.32 (m, 2H), 3.01 (s, 3H), 1.47 (s, 9H); HPLC (Method 3) 98.8% (AUC), $t_R$=18.28 min; ESI MS m/z 461 [M+H]$^+$.

Preparation of N1-(2-(5-chloro-2,4-dimethoxyphenyl)imidazo[1,2-a]pyridin-7-yl)-N1-methylethane-1,2-diamine hydrochloride 5s (Example 54)

Compound N$^1$-(2-(5-chloro-2,4-dimethoxyphenyl)imidazo[1,2-a]pyridin-7-yl)-N$^1$-methylethane-1,2-diamine hydrochloride 5s was prepared in the same manner as 2-(1-(2-(5-chloro-2,4-dimethoxyphenyl)imidazo[1,2-a]pyridin-7-yl)piperidin-4-yl)ethanamine hydrochloride 5f and was obtained as a white solid (20 mg, 51% yield).
$^1$H NMR (400 MHz, CD$_3$OD): δ 8.44 (d, J=7.8 Hz, 1H), 8.11 (s, 1H), 7.76 (s, 1H), 7.12 (d, J=7.8 Hz 1H), 6.89 (s, 1H), 6.80 (s, 1H), 4.08 (s, 3H), 4.00 (s, 3H), 4.00 (s, 3H), 3.91-3.87 (m, 2H), 3.27-3.24 (m, 5H); HPLC (Method 3) 97.5% (AUC), $t_R$=14.62 min; ESI MS m/z 361 [M+H]$^+$.

Preparation of 1-(2-(5-chloro-2,4-dimethoxyphenyl)imidazo[1,2-a]pyridin-7-yl)piperidin-4-ol 5t (Example 231)

Compound 1-(2-(5-chloro-2,4-dimethoxyphenyl)imidazo[1,2-a]pyridin-7-yl)piperidin-4-ol 5t was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e, and was obtained as a white solid (206 mg, 71% yield).
$^1$H NMR (400 MHz, DMSO-d$_6$): δ 8.27 (d, J=7.4 Hz, 1H), 8.27 (s, 1H), 8.17 (s, 1H), 7.99 (s, 1H), 6.86 (d, J=7.4 Hz, 1H), 6.64 (s, 1H), 4.70 (br s, 1H), 4.00 (s, 3H), 3.93 (s, 3H), 3.78-3.76 (m, 1H), 3.65-3.64 (m, 2H), 2.94-2.92 (m, 2H), 1.88-1.86 (m, 2H), 1.59-1.57 (m, 2H); HPLC (Method 1) 96.9% (AUC), $t_R$=10.14 min: ESI MS m/z 388 [M+H]$^+$.

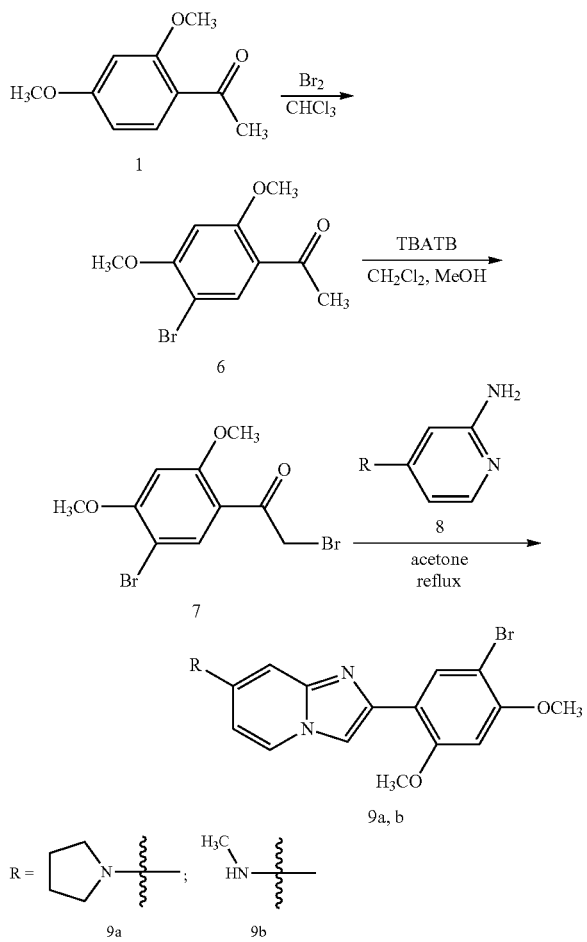

Scheme 2

Preparation of 1-(5-bromo-2,4-dimethoxyphenyl)ethanone 6

A solution of 1-(2,4-dimethoxyphenyl)ethanone 1 (2.00 g, 11.0 mmol) and bromine (543 µL, 10.5 mmol) in chloroform (30 mL) was stirred at room temperature for 16 h. The reaction mixture was diluted with water and extracted with DCM. The organic phase was dried and concentrated under reduced pressure. The crude product was purified by column chromatography (silica gel, MeOH/DCM) to provide the desired compound 1-(5-bromo-2,4-dimethoxyphenyl)ethanone 6 (2.07 g, 72%) as an off-white solid.

Preparation of 2-(5-bromo-2,4-dimethoxyphenyl)-7-(pyrrolidin-1-yl)imidazo[1,2-a]pyridine 9a (Example 1)

A solution of 2-bromo-1-(5-bromo-2,4-dimethoxyphenyl)ethanone 7 (124 mg, 0.367 mmol) and 4-(pyrrolidin-1-yl)pyridin-2-amine 8 (60 mg, 0.367 mmol) in acetone (4 mL) was heated at 75° C. for 16 h. The reaction mixture was cooled to room temperature, the white precipitate was collected by filtration and solid was washed with acetone. The solid was suspended in aqueous ammonia solution (10 mL) and stirred for 2 h. The free base was collected by filtration and solid was washed with water, dried under reduced pressure to yield 2-(5-bromo-2,4-dimethoxyphenyl)-7-(pyrrolidin-1-yl)imidazo[1,2-a]pyridine 9a (51 mg, 35%) as an off-white solid.
$^1$H NMR (300 MHz, CDCl$_3$): δ 8.55 (s, 1H), 7.83 (d, J=7.4 Hz, 1H), 7.80 (s, 1H), 6.55 (s, 1H), 6.43 (d, J=2.2 Hz, 1H), 6.33 (dd, J=2.2, 7.4 Hz, 1H), 3.99 (s, 3H), 3.94 (s, 3H), 3.40-3.30 (m, 4H), 2.10-2.00 (m, 4H); HPLC (Method 2) >99% (AUC), t$_R$=19.12 min; APCI MS m/z 404 [M+H]$^+$.

Preparation of 2-(5-bromo-2,4-dimethoxyphenyl)-N-methylimidazo[1,2-a]pyridin-7-amine hydrobromide 9b (Example 11)

Compound 2-(5-bromo-2,4-dimethoxyphenyl)-N-methylimidazo[1,2-a]pyridin-7-amine hydrobromide 9b was prepared in the same manner as 2-(5-bromo-2,4-dimethoxyphenyl)-7-(pyrrolidin-1-yl)imidazo[1,2-a]pyridine 9a and was obtained as an off-white solid (44% yield).
$^1$H NMR (300 MHz, DMSO-d$_6$): δ 13.02 (br s, 1H), 8.36 (d, J=7.4 Hz, 1H), 8.20 (s, 1H), 8.00 (s, 1H), 7.68-7.62 (m, 1H), 6.94 (s, 1H), 6.82 (dd, J=2.1, 7.4 Hz, 1H), 6.30 (br s, 1H), 4.04 (s, 3H), 3.97 (s, 3H), 2.84 (d, J=4.8 Hz, 3H); HPLC (Method 4) >99% (AUC), t$_R$=17.98 min; ESI MS m/z 362 [M+H]$^+$.

Preparation of 1-(2-(5-bromo-2,4-dimethoxyphenyl)imidazo[1,2-a]pyridin-7-yl)pyrrolidin-3-ol 9c (Example 7)

Compound 1-(2-(5-bromo-2,4-dimethoxyphenyl)imidazo[1,2-a]pyridin-7-yl)pyrrolidin-3-ol 9c was prepared in the same manner as 2-(5-bromo-2,4-dimethoxyphenyl)-7-(pyrrolidin-1-yl)imidazo[1,2-a]pyridine 9a and was obtained as an amorphous off-white solid (89/o yield).
$^1$H NMR (300 MHz, DMSO-d$_6$): δ 8.32 (s, 1H), 8.25 (d, J=7.4 Hz, 1H), 7.93 (s, 1H), 6.82 (s, 1H), 6.44 (dd, J=2.0, 7.4 Hz, 1H), 6.19 (s, 1H), 4.99 (d, J=3.7 Hz, 1H), 4.41 (bs, 1H), 3.99 (s, 3H), 3.92 (s, 3H), 3.51-3.31 (m, 3H), 3.15 (d, J=10.6 Hz, 1H), 2.12-1.99 (m, 1H), 1.96-1.86 (m, 1H); HPLC (Method 2) >99% (AUC), t$_R$=17.29 min.; ESI MS m/z 420 [(M+2)+H]$^+$.

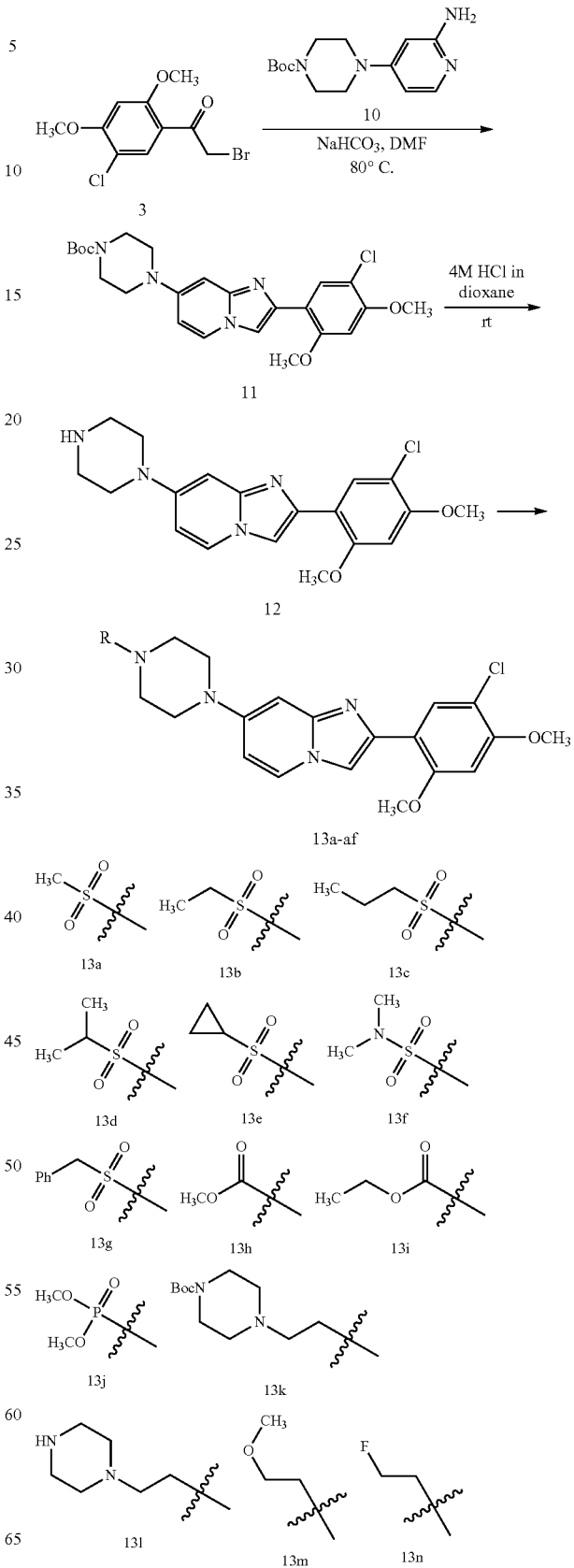

Scheme 3

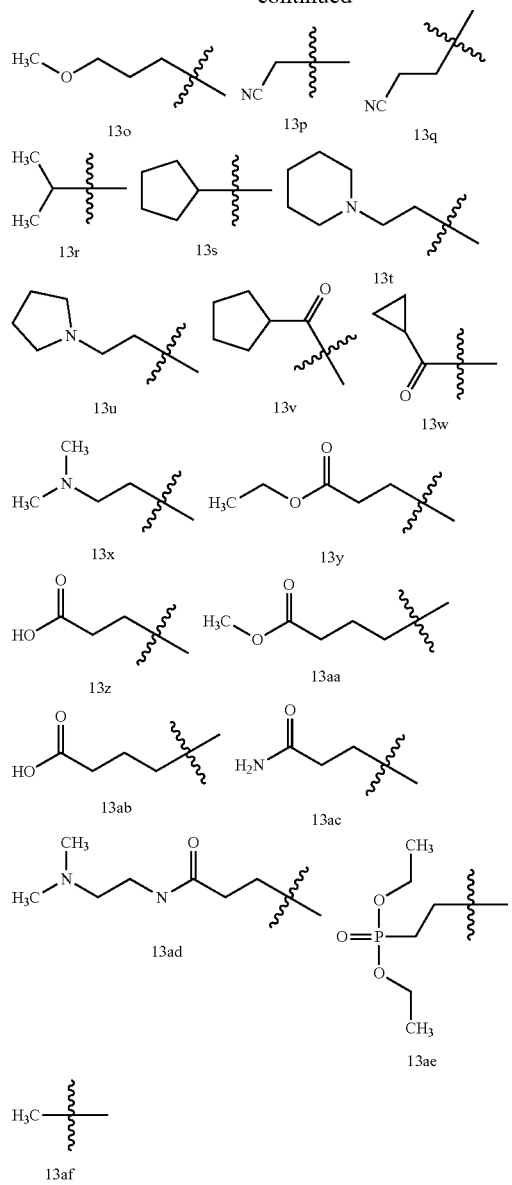

3.60 (t, J=4.9 Hz, 4H), 3.18 (t, J=5.2 Hz, 4H), 1.49 (s, 9H); HPLC (Method 1) 96.6% (AUC), $t_R$=11.55 min.; ESI MS m/z 473 [M+H]$^+$.

Preparation of 2-(5-chloro-2,4-dimethoxyphenyl)-7-(piperazin-1-yl)imidazo[1,2-a]pyridine 12 (Example 17)

A solution of tert-butyl 4-[2-(5-chloro-2,4-dimethoxyphenyl)imidazo[1,2-a]pyridin-7-yl]piperazine-1-carboxylate 11 (50 mg, 0.12 mmol) in 4.0 M HCl in dioxane (3 mL) was stirred at room temperature for 3 h. The reaction mixture was filtered and solid was washed with dioxane, and dried under reduced pressure to give the HCl salt of the compound 2-(5-chloro-2,4-dimethoxyphenyl)-7-(piperazin-1-yl)imidazo[1,2-a]pyridine 12 (38 mg, 48%) as a brown solid. The salt was neutralized for the synthesis of 13. The compound was suspended in 10 mL of aqueous ammonia, diluted with water and extracted by using chloroform (2×20 mL). The organic layer was dried and concentrated to give 2-(5-chloro-2,4-dimethoxyphenyl)-7-(piperazin-1-yl)imidazo[1,2-a]pyridine 12 (38 mg, 48%) as an off-white solid.

$^1$H NMR (400 MHz, DMSO-$d_6$): δ 14.00 (br s, 1H), 9.48 (s, 1H), 8.62 (d, J=7.7 Hz, 1H), 8.31 (s, 1H), 8.09 (s, 1H), 7.33 (dd, J=2.4, 7.7 Hz, 1H), 6.98 (s, 1H), 6.87 (d, J=2.2 Hz, 1H), 4.06 (s, 3H), 3.99 (s, 3H), 3.78-3.72 (m, 4H), 3.26 (br s, 4H); HPLC (Method 2) 95.3% (AUC), $t_R$=14.95 min.; ESI MS m/z 373 [M+H]$^+$.

Preparation of sulfonamide 2-(5-chloro-2,4-dimethoxyphenyl)-7-[4-(methylsulfonyl)-piperazin-1-yl]imidazo[1,2-a]pyridine 13a (Example 169)

To a solution of 2-(5-chloro-2,4-dimethoxyphenyl)-7-(piperazin-1-yl)imidazo[1,2-a]pyridine 12 (60 mg, 0.16 mmol) and DIPEA (42 μL, 0.32 mmol) in dichloromethane (1 mL) was added methanesulfonyl chloride (28 μL, 0.242 mmol). The reaction mixture was stirred at room temperature for 3 h. The reaction mixture was concentrated, suspended in aqueous ammonia solution, and stirred for 2 h. The precipitate was collected by filtration. The solid was washed with water, dried under reduced pressure, and purified by column chromatography (silica gel, 9:1 MeOH/DCM) to provide the desired sulfonamide 2-(5-chloro-2,4-dimethoxyphenyl)-7-[4-(methylsulfonyl)piperazin-1-yl]imidazo[1,2-a]pyridine 13a (43%) as an off-white solid.

$^1$H NMR (400 MHz, CDCl$_3$): δ 8.36 (s, 1H), 7.93 (d, J=7.4 Hz, 1H), 7.90 (s, 1H), 6.85 (d, J=2.4 Hz, 1H), 6.58 (s, 1H), 6.53 (dd, J=2.4, 7.4 Hz, 1H), 3.99 (s, 3H), 3.95 (s, 3H), 3.50-3.25 (m, 8H), 2.83 (s, 3H). HPLC (Method 1) 97.7% (AUC), $t_R$=10.45 min. ESI MS m/z 451 [M+H]$^+$.

Preparation of 2-(5-chloro-2,4-dimethoxyphenyl)-7-[4-(ethylsulfonyl)piperazin-1-yl]imidazo[1,2-a]pyridine 13b (Example 172)

Preparation of tert-butyl 4-[2-(5-chloro-2,4-dimethoxyphenyl)imidazo[1,2-a]pyridin-7-yl]piperazine-1-carboxylate 11 (Example 232)

A mixture of 2-bromo-1-(5-chloro-2,4-dimethoxyphenyl)ethanone 3 (2.50 g, 8.49 mmol), tert-butyl 4-(2-aminopyridin-4-yl)piperazine-1-carboxylate 10 (2.26 g, 8.09 mmol), and NaHCO$_3$ (1.36 g, 16.18 mmol) in DMF (5 mL) was heated at 90° C. for 2 h. The reaction mixture was cooled to room temperature and poured into water. The precipitate obtained was collected by filtration and washed with water, and dried under reduced pressure. The crude material was purified by column chromatography (silica gel, 4% MeOH/DCM) to provide tert-butyl 4-[2-(5-chloro-2,4-dimethoxyphenyl)imidazo[1,2-a]pyridin-7-yl]piperazine-1-carboxylate 11 (2.3 g, 60%) as a light yellow solid.

$^1$H NMR (300 MHz, CDCl$_3$): δ 8.36 (s, 1H), 7.90 (d, J=7.5 Hz, 1H), 7.88 (s, 1H), 6.81 (d, J=1.8 Hz, 1H), 6.58 (s, 1H), 6.54 (dd, J=2.3, 7.5 Hz, 1H), 3.99 (s, 3H), 3.95 (s, 3H),

Compound 2-(5-chloro-2,4-dimethoxyphenyl)-7-[4-(ethylsulfonyl)piperazin-1-yl]imidazo[1,2-a]pyridine 13b was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (37% yield).

$^1$H NMR (400 MHz, CDCl$_3$): δ δ 8.37 (s, 1H), 7.93 (d, J=7.4 Hz, 1H), 7.90 (s, 1H), 6.84 (d, J=2.2 Hz, 1H), 6.58 (s, 1H), 6.53 (dd, J=2.2, 7.4 Hz, 1H), 3.99 (s, 3H), 3.95 (s, 3H), 3.53-3.43 (m, 4H), 3.35-3.27 (m, 4H), 3.01 (q, J=7.4 Hz,

2H), 1.41 (d, J=7.4 Hz, 3H); HPLC (Method 1) 98.7% (AUC), t$_R$=10.68 min.; ESI MS m/z 465 [M+H]$^+$.

Preparation of 2-(5-chloro-2,4-dimethoxyphenyl)-7-[4-(propylsulfonyl)piperazin-1-yl]imidazo-[1,2-a]pyridine 13c (Example 170)

Compound 2-(5-chloro-2,4-dimethoxyphenyl)-7-[4-(propylsulfonyl)piperazin-1-yl]imidazo[1,2-a]pyridine 13c was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (28% yield).

$^1$H NMR (400 MHz, CDCl$_3$): δ 8.37 (s, 1H), 7.93 (d, J=7.4 Hz, 1H), 7.90 (s, 1H), 6.84 (d, J=2.2 Hz, 1H), 6.59 (s, 1H), 6.53 (dd, J=2.2, 7.4 Hz, 1H), 4.00 (s, 3H), 3.96 (s, 3H), 3.49-3.43 (m, 4H), 3.35-3.29 (m, 4H), 2.97-2.89 (m, 2H), 1.95-1.83 (m, 2H), 1.08 (t, J=7.8 Hz, 3H); HPLC (Method 1) 98.1% (AUC), t$_R$=11.02 min.; ESI MS m/z 479 [M+H]$^+$.

Preparation of 2-(5-chloro-2,4-dimethoxyphenyl)-7-[4-(isopropylsulfonyl)piperazin-1-yl]imidazo[1,2-a]pyridine 13d (Example 178)

Compound 2-(5-chloro-2,4-dimethoxyphenyl)-7-[4-(isopropylsulfonyl)piperazin-1-yl]-imidazo[1,2-a]pyridine 13d was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (39% yield).

$^1$H NMR (400 MHz, CDCl$_3$): δ δ 8.36 (s, 1H), 7.92 (d, J=7.4 Hz, 1H), 7.89 (s, 1H), 6.83 (d, J=2.2 Hz, 1H), 6.58 (s, 1H), 6.53 (dd, J=2.2, 7.4 Hz, 1H), 3.99 (s, 3H), 3.95 (s, 3H), 3.58-3.48 (m, 4H), 3.32-3.26 (m, 4H), 3.25-3.18 (m, 1H), 1.38 (d, J=6.8 Hz, 6H); HPLC (Method 1) >99% (AUC), t$_R$=10.93 min; ESI MS m/z 479 [M+H]$^+$.

Preparation of 2-(5-chloro-2,4-dimethoxyphenyl)-7-[4-(cyclopropylsulfonyl)piperazin-1-yl]imidazo[1,2-a]pyridine 13e (Example 103)

To a solution of 2-(5-chloro-2,4-dimethoxyphenyl)-7-(piperazin-1-yl)imidazo[1,2-a]-pyridine 12 (75 mg, 0.20 mmol) in pyridine (1.5 mL) was added with cyclopropane sulfonyl chloride (61 μL, 0.60 mmol). The reaction mixture was stirred at room temperature for 3 h, concentrated under reduced pressure, and purified by column chromatography (silica gel, MeOH/DCM) to provide the desired sulfonamide 2-(5-chloro-2,4-dimethoxyphenyl)-7-[4-(cyclopropylsulfonyl)piperazin-1-yl]imidazo[1,2-a]pyridine 13e (60 mg, 63% yield) as an off-white solid.

$^1$H NMR (400 MHz, DMSO-d$_6$): δ 8.42 (d, J=7.6 Hz, 1H), 8.11 (s, 1H), 8.10 (s, 1H), 6.98 (d, J=6.2 Hz, 1H), 6.90 (s, 1H), 6.76-6.73 (m, 1H), 4.02 (s, 3H), 3.95 (s, 3H), 3.46-3.39 (m, 4H), 3.38-3.33 (m, 4H), 2.69-2.63 (m, 1H), 1.05-0.92 (m, 4H); HPLC (Method 2) 97.6% (AUC), t$_R$=18.47 min; ESI MS m/z 477 [M+H]$^+$.

Preparation of 4-[2-(5-chloro-2,4-dimethoxyphenyl)imidazo[1,2-a]pyridin-7-yl]-N,N-dimethylpiperazine-1-sulfonamide 13f (Example 171)

Compound 4-[2-(5-chloro-2,4-dimethoxyphenyl)imidazo[1,2-a]pyridin-7-yl]-N,N-dimethylpiperazine-1-sulfonamide 13f was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (30% yield).

$^1$H NMR (400 MHz, CDCl$_3$): δ 8.37 (s, 1H), 7.93 (d, J=7.4 Hz, 1H), 7.89 (s, 1H), 6.83 (d, J=2.2 Hz, 1H), 6.58 (s, 1H), 6.53 (dd, J=2.2, 7.4 Hz, 1H), 4.00 (s, 3H), 3.96 (s, 3H), 3.45-3.47 (m, 4H), 3.33-3.25 (m, 4H), 2.88 (s, 6H); HPLC (Method 1) >99% (AUC), t$_R$=10.90 min; ESI MS m/z 480 [M+H]$^+$.

Preparation of Compound 7-[4-(benzylsulfonyl)piperazin-1-yl]-2-(5-chloro-2,4-dimethoxyphenyl)imidazo[1,2-a]pyridine 13e (Example 179)

Compound 7-[4-(benzylsulfonyl)piperazin-1-yl]-2-(5-chloro-2,4-dimethoxyphenyl)-imidazo[1,2-a]pyridine 13g was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (44% yield).

$^1$H NMR (300 MHz, CDCl$_3$): δ 8.36 (s, 1H), 7.90 (d, J=7.4 Hz, 1H), 7.89 (s, 1H), 7.47-7.35 (m, 5H), 6.77 (d, J=2.2 Hz, 1H), 6.58 (s, 1H), 6.47 (dd, J=2.2, 7.4 Hz, 1H), 4.28 (s, 2H), 3.99 (s, 3H), 3.96 (s, 3H), 3.31-3.23 (m, 4H), 3.19-3.11 (m, 4H); HPLC (Method 1) 95.8% (AUC), t$_R$=11.54 min.; ESI MS m/z 527 [M+H]$^+$.

Preparation of methyl 4-[2-(5-chloro-2,4-dimethoxyphenyl)imidazo[1,2-a]pyridine-7-yl]piperazine-1-carboxylate 13h (Example 99)

Compound methyl 4-[2-(5-chloro-2,4-dimethoxyphenyl)imidazo[1,2-a]pyridine-7-yl]piperazine-1-carboxylate 13h was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (70 mg, 81% yield).

$^1$H NMR (400 MHz, CDCl$_3$): δ 8.36 (s, 1H), 7.91 (d, J=7.4 Hz, 1H), 7.88 (s, 1H), 6.83 (br s, 1H), 6.58 (s, 1H), 6.54 (dd, J=2.4, 7.5 Hz, 1H), 3.99 (s, 3H), 3.95 (s, 3H), 3.74 (s, 3H), 3.65 (t, J=4.8 Hz, 4H), 3.23-3.18 (m, 4H), HPLC (Method 3) 97.5% (AUC), t$_R$=17.22 min.; ESI MS m/z 431 [M+H]$^+$.

Preparation of ethyl 4-[2-(5-chloro-2,4-dimethoxyphenyl)imidazo[1,2-a]pyridin-7-yl]-piperazine-1-carboxylate 13i (Example 107)

Compound ethyl 4-[2-(5-chloro-2,4-dimethoxyphenyl)imidazo[1,2-a]pyridin-7-yl]-piperazine-1-carboxylate 13i was prepared in the same manner as 2-(5-chloro-2,4-dimethoxyphenyl)-7-[4-(methylsulfonyl)piperazin-1-yl]imidazo[1,2-a]pyridine 13a and was obtained as a green yellow solid (73% yield).

$^1$H NMR (400 MHz, CDCl$_3$): δ 8.36 (s, 1H), 7.91 (d, J=7.5 Hz, 1H), 7.87 (s, 1H), 6.86 (s, 1H), 6.59-6.53 (m, 2H), 4.18 (dd, J=7.0, 14.0 Hz, 2H), 3.99 (s, 3H), 3.95 (s, 3H), 3.65 (t, J=5.0 Hz, 4H), 3.26-3.17 (m, 4H), 1.29 (t, J=7.0 Hz, 3H); HPLC (Method 2) 97.2% (AUC), t$_R$=18.63 min.; ESI MS m/z 445 [M+H]$^+$.

Preparation of dimethyl {4-[2-(5-chloro-2,4-dimethoxyphenyl)imidazo[1,2-a]pyridin-7-yl]piperazin-1-yl}phosphonate 13i (Example 203)

A mixture of 2-(5-chloro-2,4-dimethoxyphenyl)-7-(piperazin-1-yl)imidazo-[1,2-a]pyridine 12 (100 mg, 0.30 mmol), triethylamine (130 μL, 0.90 mmol), and dimethyl chlorophosphate (42 μL, 0.33 mmol) in DCM (2 mL) was stirred at room temperature for 2 h. The reaction mixture was diluted with DCM (50 mL), washed with NH$_4$OH solution (10 mL) and brine (10 mL), dried over sodium sulfate, filtered, and concentrated under reduced pressure. The residue was purified by combi-flash chromatography (silica gel, 9:1 DCM/methanol) to afford dimethyl {4-[2-(5-chloro-2,4-dimethoxyphenyl)imidazo[1,2-a]pyridin-7-yl]piperazin-1-yl}phosphonate 13j (40 mg, 31%) as an off-white solid.

$^1$H NMR (300 MHz, CDCl$_3$): δ 8.35 (s, 1H), 7.91 (d, J=7.8 Hz, 1H), 7.86 (s, 1H), 6.86 (s, 1H), 6.58 (s, 1H), 6.55 (dd, J=2.4 Hz, 7.6 Hz, 1H), 3.99 (s, 3H), 3.95 (s, 3H), 3.75 (s, 3H), 3.71 (s, 3H), 3.37-3.28 (m, 4H), 3.24-3.17 (m, 4H). HPLC (Method 1) 98.0% (AUC), t$_R$=10.35 min.; ESI MS m/z 481 [M+H]$^+$.

Preparation of tert-butyl 4-(2-(4-(2-(5-chloro-2,4-dimethoxyphenyl)imidazo[1,2-a]pyridin-7-yl)piperazin-1-yl)ethyl)piperazine-1-carboxylate 13k (Example 136)

A mixture of 2-(5-chloro-2,4-dimethoxyphenyl)-7-(piperazin-1-yl)imidazo[1,2-a]-pyridine 12 (200 mg, 0.50 mmol), tert-butyl 4-(2-bromoethyl)piperazine-1-carboxylate (160 mg, 0.53 mmol), and potassium carbonate (140 mg, 1.00 mmol) in acetonitrile (4 mL) was heated to reflux for 3 h. The reaction mixture was filtered and the filtrate was distilled under reduced pressure. The residue was purified by combi-flash chromatography (silica gel, 9:1 DCM/MeOH) to afford tert-butyl 4-(2-(4-(2-(5-chloro-2,4-dimethoxyphenyl)imidazo[1,2-a]-pyridin-7-yl)piperazin-1-yl)ethyl)piperazine-1-carboxylate 13k (130 mg, 42%) as a pale yellow solid.

$^1$H NMR (400 MHz, CDCl$_3$): δ 8.38 (s, 1H), 7.88 (d, J=7.6 Hz, 1H), 7.86 (s, 1H), 6.80 (d, J=7.5 Hz, 1H), 6.57 (s, 1H), 6.55 (dd, J=2.3, 7.6 Hz, 1H), 3.99 (s, 3H), 3.95 (s, 3H), 3.44 (t, J=5.1 Hz, 4H), 3.24 (t, J=5.1 Hz, 4H), 2.66 (t, J=5.0 Hz, 4H), 2.61-2.54 (m, 4H), 2.44 (t, J=5.0 Hz, 4H), 1.46 (s, 9H); HPLC (Method 1) 99.0% (AUC), t$_R$=9.55 min.; ESI MS m/z 585 [M+H]$^+$.

Preparation of 2-(5-chloro-2,4-dimethoxyphenyl)-7-(4-(2-(piperazin-1-yl)ethyl)piperazin-1-yl)imidazo-[1,2-a]pyridine 13l (Example 142)

A solution of tert-butyl 4-(2-(4-(2-(5-chloro-2,4-dimethoxyphenyl)imidazo[1,2-a]-pyridin-7-yl)piperazin-1-yl)ethyl)piperazine-1-carboxylate 13k (120 mg) in 4M HCl in dioxane (5 mL) was stirred at room temperature for 4 h. The Solvent was removed and the yellow residue was neutralized with aqueous ammonia solution. The precipitate was collected by filtration and solid was washed with water and dried under reduced pressure to afford 2-(5-chloro-2,4-dimethoxyphenyl)-7-(4-(2-(piperazin-1-yl)ethyl)piperazin-1-yl)-imidazo[1,2-a]pyridine 13l (90 mg, 91%) as an off-white solid.

$^1$H NMR (400 MHz, CD$_3$OD): δ 8.14 (d, J=7.58 Hz, 1H), 8.06 (s, 1H), 7.96 (s, 1H), 6.78 (s, 1H), 6.76 (d, J=7.6 Hz, 1H), 6.66 (s, 1H), 4.01 (s, 3H), 3.94 (s, 3H), 3.30-3.27 (m, 4H), 3.01-2.92 (m, 4H), 2.72-2.65 (m, 4H), 2.64-2.55 (m, 8H); HPLC (Method 3) 98.0% (AUC), t$_R$=14.88 min; ESI MS m/z 485 [M+H]$^+$.

Preparation of 2-(5-chloro-2,4-dimethoxyphenyl)-7-(4-(2-methoxyethyl)piperazin-1-yl)imidazo[1,2-a]pyridine 13m (Example 105)

A mixture of 2-(5-chloro-2,4-dimethoxyphenyl)-7-(piperazin-1-yl)imidazo[1,2-a]-pyridine 12 (75 mg, 0.20 mmol), 1-bromo-2-methoxyethane (21 μL, 0.53 mmol), and sodium tert butoxide (48 mg, 0.50 mmol) in I-butanol (3 mL) was heated to reflux for 4 h. The reaction mixture was quenched with water and extracted with chloroform. The organic phase was dried over sodium sulphate and concentrated. The residue was purified by combi-flash chromatography (silica gel, 9:1 DCM/MeOH) to afford 2-(5-chloro-2,4-dimethoxyphenyl)-7-(4-(2-methoxyethyl)piperazin-1-yl)imidazo[1,2-a]pyridine 13m (46 mg, 51%) as off-white solid.

$^1$H NMR (400 MHz, CDCl$_3$): δ 8.38 (s, 1H), 7.88 (d, J=7.6 Hz, 1H), 7.85 (s, 1H), 6.82 (s, 1H), 6.58-6.50 (m, 1H), 3.99 (s, 3H), 3.94 (s, 3H), 3.56 (t, J=5.5 Hz, 2H), 3.38 (s, 3H), 3.30-3.25 (m, 4H), 2.70-2.62 (m, 6H); HPLC (Method 3) 96.7% (AUC), t$_R$=15.36 min.; APCI MS m/z 431 [M+H]$^+$.

Preparation of 2-(5-chloro-2,4-dimethoxyphenyl)-7-(4-(2-fluoroethyl)piperazin-1-yl)-imidazo[1,2-a]pyridine 13n (Example 104)

Compound 2-(5-chloro-2,4-dimethoxyphenyl)-7-(4-(2-fluoroethyl)piperazin-1-yl)-imidazo[1,2-a]pyridine 13n was prepared in the same manner as 2-(5-chloro-2,4-dimethoxyphenyl)-7-(4-(2-methoxyethyl)piperazin-1-yl)imidazo[1,2-a]pyridine 13m and was obtained as off-white solid (47 mg, 56% yield).

$^1$H NMR (400 MHz, CDCl$_3$): δ δ 8.37 (s, 1H), 7.89 (d, J=7.5 Hz, 1H), 7.86 (s, 1H), 6.84-6.81 (m, 1H), 6.57 (s, 1H), 6.55 (dd, J=2.4, 7.6 Hz, 1H), 4.67 (t, J=4.8 Hz, 1H), 4.55 (t, J=4.8 Hz, 1H), 3.99 (s, 3H), 3.94 (s, 3H), 3.30-3.25 (m, 4H), 2.80 (t, J=4.8 Hz, 1H), 2.75-2.69 (m, 5H); HPLC (Method 3) 97.37% (AUC), t$_R$=15.36 min; APCI MS m/z 419 [M+H]$^+$.

Preparation of 2-(5-chloro-2,4-dimethoxyphenyl)-7-(4-(3-methoxypropyl)piperazin-1-yl)imidazo[1,2-a]pyridine 13o (Example 96)

Compound 2-(5-chloro-2,4-dimethoxyphenyl)-7-(4-(3-methoxypropyl)piperazin-1-yl)imidazo[1,2-a]pyridine 13n was prepared in the same manner as 2-(5-chloro-2,4-dimethoxyphenyl)-7-(4-(2-methoxyethyl)piperazin-1-yl)imidazo[1,2-a]pyridine 13m and was obtained as light yellow solid (60 mg, 66% yield).

$^1$H NMR (400 MHz, CDCl$_3$): δ 8.37 (s, 1H), 7.88 (d, J=7.4 Hz, 1H), 7.82 (s, 1H), 6.83 (s, 1H), 6.59-6.54 (m, 2H), 3.99 (s, 3H), 3.95 (s, 3H), 3.45 (t, J=6.4 Hz, 2H), 3.34 (s, 3H), 3.26 (t, J=4.9 Hz, 4H), 2.62 (t, J=5.0 Hz, 4H), 2.49 (t, J=7.3 Hz, 2H), 1.85-1.76 (m, 2H), HPLC (Method 3) 96.6% (AUC), t$_R$=15.47 min.; APCI MS m/z 445 [M+H]$^+$.

Preparation of 2-(4-(2-(5-chloro-2,4-dimethoxyphenyl)imidazo[1,2-a]pyridin-7-yl)-piperazin-1-yl)acetonitrile 13D (Example 95)

Compound 2-(4-(2-(5-chloro-2,4-dimethoxyphenyl)imidazo[1,2-a]pyridin-7-yl)piperazin-1-yl)acetonitrile 13p was prepared in the same manner as 2-(5-chloro-2,4-dimethoxyphenyl)-7-(4-(2-methoxyethyl)piperazin-1-yl)imidazo[1,2-a]pyridine 13m and was obtained as light yellow solid (30 mg, 37% yield).

$^1$H NMR (400 MHz, CDCl$_3$): δ δ 8.36 (s, 1H), 7.91 (d, J=7.7 Hz, 1H), 7.88 (s, 1H), 6.83 (d, J=1.9 Hz, 1H), 6.58 (s, 1H), 6.55 (dd, J=2.4, 7.5 Hz, 1H), 3.99 (s, 3H), 3.95 (s, 3H), 3.59 (s, 2H), 3.29 (t, J=5.0 Hz, 4H), 2.78 (t, J=5.2 Hz, 4H); ESI MS m/z 412 [M+H]$^+$.

Preparation of 3-(4-(2-(5-chloro-2,4-dimethoxyphenyl)imidazo[1,2-a]pyridin-7-yl)piperazin-1-yl)propanenitrile 13a (Example 108)

A mixture of 2-(5-chloro-2,4-dimethoxyphenyl)-7-(piperazin-1-yl)imidazo[1,2-a]-pyridine 12 (75 mg, 0.50 mmol) and acrylonitrile (21 µL, 0.40 mmol), in methanol (5 mL) was stirred at room temperature for 8 h. The solvent was removed under reduced pressure. The residue was washed with dilute aqueous ammonia solution to afford 3-(4-(2-(5-chloro-2,4-dimethoxyphenyl)imidazo[1,2-a]pyridin-7-yl)piperazin-1-yl)propanenitrile 13q (65 mg, 76%) as off-white solid.

$^1$H NMR (400 MHz, CDCl$_3$): δ 8.37 (s, 1H), 7.89 (d, J=7.6 Hz, 1H), 7.87 (s, 1H), 6.81 (s, 1H), 6.59-6.51 (m, 1H), 3.99 (s, 3H), 3.95 (s, 3H), 3.30-3.23 (m, 4H), 2.76 (t, J=6.9 Hz, 2H), 2.71-2.65 (m, 4H), 2.55 (t, J=6.8 Hz, 2H); HPLC (Method 3) 97.6% (AUC), t$_R$=15.44 min.; APCI MS m/z 426 [M+H]$^+$.

Preparation of 2-(5-chloro-2,4-dimethoxyphenyl)-7-(4-isopropylpiperazin-1-yl)imidazo-[1,2-a]pyridine 13r (Example 100)

Compound 2-(5-chloro-2,4-dimethoxyphenyl)-7-(4-isopropylpiperazin-1-yl)imidazo-[1,2-a]pyridine 13r was prepared in the same manner as 2-(5-chloro-2,4-dimethoxyphenyl)-7-(4-(2-methoxyethyl)piperazin-1-yl)imidazo[1,2-a]pyridine 13m and was obtained as an off-white solid (45 mg, 52% yield).

$^1$H NMR (400 MHz, CDCl$_3$): δ 8.37 (s, 1H), 7.88 (d, J=7.5 Hz, 1H), 7.86 (s, 1H), 6.82 (d, J=2.2 Hz, 1H), 6.58-6.54 (m, 21-H), 3.99 (s, 3H), 3.95 (s, 3H), 3.26 (t, J=5.0 Hz, 4H), 2.78-2.67 (m, 5H), 1.10 (s, 3H), 1.09 (s, 3H); HPLC (Method 2) 99.10% (AUC), t$_R$=15.30 min; APCI MS m/z 415 [M+H]$^+$.

Preparation of 2-(5-chloro-2,4-dimethoxyphenyl)-7-(4-cyclopentylpiperazin-1-yl)imidazo-[1,2-a]pyridine 13s (Example 239)

A mixture of 2-(5-chloro-2,4-dimethoxyphenyl)-7-(piperazin-1-yl)imidazo-[1,2-a]pyridine 12 (100 mg, 0.30 mmol), tert-butyl 4-(2-bromoethyl)piperazine-1-carboxylate (59 mg, 0.40 mmol), and cesium carbonate (200 mg, 0.60 mmol) in acetonitrile (2 mL) was heated to reflux for 16 h. The reaction was quenched with water and extracted with dichloromethane. The organic phase was dried and concentrated. The residue was purified by combi-flash chromatography (silica gel, 9:1 DCM/MeOH) to afford 2-(5-chloro-2,4-dimethoxyphenyl)-7-(4-cyclopentylpiperazin-1-yl)imidazo[1,2-a]pyridine 13s (50 mg, 42%) as off-white solid.

$^1$H NMR (300 MHz, CDCl$_3$): δ 8.37 (s, 1H), 7.88 (d, J=7.50 Hz, 1H), 7.86 (s, 1H), 6.81 (br s, 1H), 6.57 (s, 1H), 6.56 (d, J=7.5 Hz, 1H), 3.99 (s, 3H), 3.95 (s, 3H), 3.30-3.23 (m, 4H), 2.71-2.63 (m, 4H), 2.60-2.49 (m, 1H), 1.96-1.83 (m, 2H), 1.79-1.66 (m, 2H), 1.52-1.38 (m, 2H); HPLC (Method 1) 97.7% (AUC), t$_R$=9.32 min; ESI MS m/z 441 [M+H]$^+$.

Preparation of 2-(5-chloro-2,4-dimethoxyphenyl)-7-(4-(2-(piperidin-1-yl)ethyl)piperazin-1-yl)imidazo[1,2-a]pyridine 13t (Example 135)

A mixture of 2-(5-chloro-2,4-dimethoxyphenyl)-7-(piperazin-1-yl)imidazo[1,2-a]-pyridine 12 (100 mg, 0.30 mmol), 1-(2-chloroethyl)piperidine hydrochloride (92 mg, 0.50 mmol), and potassium carbonate (120 mg, 0.9 mmol) in acetonitrile (4 mL) was heated to reflux for 3 h. The reaction mixture was filtered and the filtrate was concentrated under reduced pressure. The residue was purified by combi-flash chromatography (silica gel, 9:1 DCM/MeOH) to afford 2-(5-chloro-2,4-dimethoxyphenyl)-7-(4-(2-(piperidin-1-yl)ethyl)piperazin-1-yl)imidazo[1,2-a]pyridine 13t (80 mg, 62%) as off white solid.

$^1$H NMR (400 MHz, CDCl$_3$): δ 8.37 (s, 1H), 7.88 (d, J=7.5 Hz, 1H), 7.86 (s, 1H), 6.79 (s, 1H), 6.57 (s, 1H), 6.55 (d, J=7.5 Hz, 1H), 3.99 (s, 3H), 3.94 (s, 3H), 3.27-3.22 (m, 4H), 2.68-2.64 (m, 4H), 2.63-2.59 (m, 2H), 2.58-2.52 (m, 2H), 2.51-2.43 (m, 4H), 1.66-1.57 (m, 4H), 1.49-1.41 (m, 2H); HPLC (Method 3) 99.0% (AUC), t$_R$=15.13 min; ESI MS m/z 484 [M+H]$^+$.

Preparation of 2-(5-chloro-2,4-dimethoxyphenyl)-7-(4-(2-(pyrrolidin-1-yl)ethyl)piperazin-1-yl)imidazo[1,2-a]pyridine 13u (Example 143)

Compound 2-(5-chloro-2,4-dimethoxyphenyl)-7-(4-(2-(pyrrolidin-1-yl)ethyl)piperazin-1-yl)imidazo[1,2-a]pyridine 13u was prepared in the same manner as 2-(5-chloro-2,4-dimethoxyphenyl)-7-(4-(2-(piperidin-1-yl)ethyl)piperazin-1-yl)imidazo[1,2-a]pyridine 13t and was obtained as off-white solid (80 mg, 63% yield).

$^1$H NMR (300 MHz, CDCl$_3$): δ 8.36 (s, 1H), 7.92 (d, J=7.4 Hz, 1H), 7.89 (s, 1H), 6.81 (s, 1H), 6.58 (s, 1H), 6.54 (d, J=7.4 Hz, 1H), 4.30-4.27 (m, 2H), 4.00 (s, 3H), 3.95 (s, 3H), 3.69-3.63 (m, 4H), 3.24-3.16 (m, 4H), 2.80-2.78 (m, 2H), 2.64-2.55 (m, 2H), 1.83-1.77 (m, 4H); HPLC (Method 1) 96.7% (AUC), t$_R$=9.41 min; ESI MS m/z 470 [M+H]$^+$.

Preparation of (4-(2-(5-chloro-2,4-dimethoxyphenyl)imidazo[1,2-a]pyridin-7-yl)-piperazin-1-yl)(cyclopentyl)methanone 13v (Example 241)

A mixture of 2-(5-chloro-2,4-dimethoxyphenyl)-7-(piperazin-1-yl)imidazo[1,2-a]-pyridine 12 (75 mg, 0.20 mmol), cyclopentanecarbonyl chloride (32 mg, 0.24 mmol), and triethyl amine (60 mg, 0.6 mmol) in DCM (1.5 mL) was stirred at 0° C. for 1 h followed by 2 h at room temperature. The reaction mixture was quenched with sodium bicarbonate aqueous solution extracted with dichloromethane. The organic phase was concentrated. The residue was purified by combi-flash chromatography (silica gel, 9:1 DCM/MeOH) to afford (4-(2-(5-chloro-2,4-dimethoxyphenyl)imidazo[1,2-a]pyridin-7-yl)piperazin-1-yl)(cyclopentyl)methanone 13v (50 mg, 53%) as a yellow solid.

$^1$H NMR (300 MHz, CDCl$_3$): δ 8.35 (s, 1H), 7.92 (d, J=7.4 Hz, 1H), 7.88 (s, 1H), 6.83 (s, 1H), 6.58 (s, 1H), 6.55 (d, J=7.4 Hz, 1H), 3.99 (s, 3H), 3.95 (s, 3H), 3.85-3.67 (m, 4H), 3.28-3.18 (m, 4H), 3.01-2.88 (m, 1H), 1.79-1.51 (m, 5H); HPLC (Method 1) 98.0% (AUC), t$_R$=11.06 min: ESI MS m/z 469 [M+H]$^+$.

Preparation of (4-(2-(5-chloro-2,4-dimethoxyphenyl)imidazo[1,2-a]pyridin-7-yl)piperazin-1-yl)(cyclopropyl)methanone 13w (Example 238)

Compound (4-(2-(5-chloro-2,4-dimethoxyphenyl)imidazo[1,2-a]pyridin-7-yl)piperazin-1-yl)(cyclopropyl)methanone 13w was prepared in the same manner as (4-(2-(5-chloro-2,4-dimethoxyphenyl)imidazo[1,2-a]pyridin-7-yl)piperazin-1-yl)(cyclopentyl)methanone 13v and was obtained as an off-white solid (46 mg, 39% yield).

¹H NMR (300 MHz, DMSO-d₆): δ 8.34 (d, J=7.5 Hz, 1H), 8.17 (s, 1H), 8.03 (s, 1H), 6.86 (s, 1H), 6.82 (d, J=7.5 Hz, 1H), 6.70 (s, 1H), 4.01 (s, 3H), 3.93 (s, 3H), 3.83 (m, 2H), 3.63 (m, 4H), 3.31 (m, 2H), 3.21 (m, 2H), 2.01-1.98 (m, 1H), 0.75-0.72 (m, 4H); HPLC (Method 1) 97.9% (AUC), $t_R$=10.49 min; ESI MS m/z 441 [M+H]⁺.

Preparation of 2-(4-(2-(5-chloro-2,4-dimethoxyphenyl)imidazo[1,2-a]pyridin-7-yl)-piperazin-1-yl)-N,N-dimethylethanamine 13x (Example 88)

A mixture of 2-(4-(2-(5-chloro-2,4-dimethoxyphenyl)imidazo[1,2-a]pyridin-7-yl)-piperazin-1-yl)ethanamine hydrochloride 5o (100 mg, 0.24 mmol), sodium cyanoborohydride (121 mg, 1.92 mmol), formaldehyde (37%) (0.1 mL) and acetic acid (110 μL, 1.92 mmol) in methanol (1.5 mL) was stirred at room temperature for 16 h. The reaction mixture was filtered and solid was obtained. The solid was washed with chloroform and suspended in aqueous ammonia solution. The precipitate was collected by filtration and washed with water to afford 2-(4-(2-(5-chloro-2,4-dimethoxyphenyl)imidazo[1,2-a]pyridin-7-yl)piperazin-1-yl)-N,N-dimethylethanamine 13x (51 mg, 53%) as an off-white solid.

¹H NMR (400 MHz, CDCl₃) δ 8.33 (s, 1H), 7.88 (d, J=7.5 Hz, 1H), 7.85 (s, 1H), 6.81 (d, J=2.3 Hz, 1H), 6.60-6.54 (m, 2H), 3.99 (s, 3H), 3.95 (s, 3H), 3.31-3.24 (m, 4H), 2.69-2.63 (m, 4H), 2.58-2.48 (m, 4H), 2.30 (s, 6H); HPLC (Method 2) 94.0% (AUC), $t_R$=14.89 min; APCI MS m/z 444 [M+H]⁺.

Preparation of ethyl 3-(4-(2-(5-chloro-2,4-dimethoxyphenyl)imidazo[1,2-a]pyridin-7-yl)piperazin-1-yl)propanoate 13v (Example 132)

Compound ethyl 3-(4-(2-(5-chloro-2,4-dimethoxyphenyl)imidazo[1,2-a]pyridin-7-yl)piperazin-1-yl)propanoate 13y was prepared in the same manner as 2-(5-chloro-2,4-dimethoxyphenyl)-7-(4-(2-(piperidin-1-yl)ethyl)piperazin-1-yl)imidazo[1,2-a]pyridine 13t and was obtained as off white solid (150 mg, 40% yield).

¹H NMR (300 MHz, CDCl₃); δ 8.37 (s, 1H), 7.89 (s, 1H), 7.86 (s, 1H), 6.80 (s, 1H), 6.57 (s, 1H), 6.56-6.52 (m, 1H), 4.19-4.12 (m, 2H), 3.99 (s, 3H), 3.95 (s, 3H), 3.26-3.23 (m, 4H), 2.78-2.76 (m, 2H), 2.67-2.60 (m, 4H), 2.5-2.50 (m, 2H), 1.30-1.27 (m, 3H); HPLC (Method 1) 97.6% (AUC), $t_R$=9.27 min; ESI MS m/z 473 [M+H]⁺.

Preparation of 3-(4-(2-(5-chloro-2,4-dimethoxyphenyl)imidazo[1,2-a]pyridin-7-yl)-piperazin-1-yl)propanoic acid 13z (Example 133)

A mixture of ethyl 3-(4-(2-(5-chloro-2,4-dimethoxyphenyl)imidazo[1,2-a]pyridin-7-yl)-piperazin-1-yl)propanoate 13y (80 mg, 0.17 mmol), lithium hydroxide (14 mg, 0.34 mmol) and water (1.6 mL) in THF (1.6 mL) was stirred at room temperature for 3 h. Solvent was removed and residue was neutralized with dilute HCl to (pH 6.0). Precipitate obtained was filtered and the solid was washed with water. The solid was dried to afford 3-(4-(2-(5-chloro-2,4-dimethoxyphenyl)imidazo[1,2-a]pyridin-7-yl)piperazin-1-yl)propanoic acid 13z (60 mg, 80%) as off white solid.

¹H NMR (300 MHz, DMSO-d₆): δ 8.45 (d, J=7.5 Hz, 1H), 8.16 (s, 1H), 8.09 (s, 1H), 7.09 (d, J=7.5 Hz, 1H), 6.93 (s, 1H), 6.76 (s, 1H), 4.03 (s, 3H), 3.96 (s, 3H), 3.56-3.41 (m, 4H), 2.93-2.77 (m, 6H), 2.64-2.54 (m, 2H); HPLC (Method 1) 98.8% (AUC), $t_R$=9.03 min; ESI MS m/z 445 [M+H]⁺.

Preparation of methyl 4-(4-(2-(5-chloro-2,4-dimethoxyphenyl)imidazo[1,2-a]pyridin-7-yl)-piperazin-1-yl)butanoate 13aa (Example 237)

A mixture of 2-(5-chloro-2,4-dimethoxyphenyl)-7-(piperazin-1-yl)imidazo[1,2-a]-pyridine 12 (50 mg, 0.13 mmol), methyl 4-bromobutanoate (29 mg, 0.16 mmol), and cesium carbonate (87 mg, 0.26 mmol) in DMF (3 mL) was heated to 80° C. for 3 h. The reaction mixture was quenched with ammonia solution then extracted with ethyl acetate. Organic phase was concentrated. The residue was purified by combiflash chromatography (silica gel, 9:1 DCM/MeOH) to afford methyl 4-(4-(2-(5-chloro-2,4-dimethoxyphenyl)imidazo[1,2-a]pyridin-7-yl)piperazin-1-yl)butanoate 13aa (14 mg, 40%) as a pale yellow solid.

¹H NMR (400 MHz, DMSO-d₆): δ 8.30 (d, J=7.5 Hz, 1H), 8.15 (s, 1H), 8.03 (s, 1H), 6.87 (s, 1H), 6.79 (d, J=7.5 Hz, 1H), 6.69 (s, 1H), 4.00 (s, 3H), 3.98 (s, 3H), 3.59 (s, 3H), 3.28-3.26 (m, 3H), 3.24-3.22 (m, 3H), 2.48-2.46 (m, 2H), 2.36-2.34 (m, 4H); HPLC (Method 1) 96.5% (AUC), $t_R$=9.30 min; ESI MS m/z 473 [M+H]⁺.

Preparation of 4-(4-(2-(5-chloro-2,4-dimethoxyphenyl)imidazo[1,2-a]pyridin-7-yl)-piperazin-1-yl)butanoic acid 13ab (Example 240)

Compound ethyl 4-(4-(2-(5-chloro-2,4-dimethoxyphenyl)imidazo[1,2-a]pyridin-7-yl)-piperazin-1-yl)butanoic acid 13ab was prepared in the same manner as 3-(4-(2-(5-chloro-2,4-dimethoxyphenyl)imidazo[1,2-a]pyridin-7-yl)piperazin-1-yl)propanoic acid 13z and was obtained as an off-white solid (29 mg, 55% yield).

¹H NMR (300 MHz, DMSO-d₆ with D₂O): δ 8.56 (d, J=7.5 Hz, 1H), 8.28 (s, 1H), 7.92 (s, 1H), 7.26 (d, J=7.5 Hz, 1H), 6.92 (s, 1H), 4.00 (s, 3H), 3.97 (s, 3H), 3.92-3.91 (m, 2H), 3.67 (m, 2H), 3.52-3.48 (m, 4H), 3.21-3.18 (m, 2H), 2.42-2.38 (m, 2H), 2.00-1.97 (m, 2H). HPLC (Method 1) 99.4% (AUC), $t_R$=9.11 min: ESI MS m/z 459 [M+H]⁺.

Preparation of 3-(4-(2-(5-chloro-2,4-dimethoxyphenyl)imidazo[1,2-a]pyridin-7-yl)-piperazin-1-yl)propanamide 13ac (Example 137)

To a solution of 2-(5-chloro-2,4-dimethoxyphenyl)-7-(piperazin-1-yl)imidazo[1,2-a]-pyridine 12 (100 mg, 0.30 mmol) in acetonitrile (2 mL), K₂CO₃ (80 mg, 0.60 mmol) and 3-bromo propionamide (60 mg, 0.40 mmol) was added. The reaction mixture was heated to reflux for 3 h. The solvent was removed under reduced pressure and the residue was extracted with CH₂Cl₂ (2×25 ml) and washed with water. The combined organics was washed with brine (50 ml), dried over Na₂SO₄ and concentrated under reduced pressure to give 3-(4-(2-(5-chloro-2,4-dimethoxyphenyl)imidazo[1,2-a]pyridin-7-yl)piperazin-1-yl)propanamide 13ac (50 mg, 42% yield) as an off-white solid.

¹H NMR (400 MHz, CD₃OD): δ 8.15 (d, J=7.6 Hz, 1H), 8.06 (s, 1H), 7.97 (s, 1H), 6.79 (s, 1H), 6.77 (d, J=7.6 Hz, 1H), 6.68 (s, 1H), 4.01 (s, 3H), 3.95 (s, 3H), 2.77-2.71 (m, 2H), 2.70-2.65 (m, 4H), 2.49-2.43 (m, 2H); HPLC (Method 1) >99% (AUC), $t_R$=8.95 min, ESI MS m/z 444 [M+H]⁺.

Preparation of methyl 3-(4-(2-(5-chloro-2,4-dimethoxyphenyl)imidazo[1,2-a]pyridin-7-yl)piperazin-1-yl)-N-(2-(dimethylamino)ethyl)propanamide 13ad (Example 158)

A mixture of 3-(4-(2-(5-chloro-2,4-dimethoxyphenyl)imidazo[1,2-a]pyridin-7-yl)piperazin-1-yl)propanoic acid 13z (60 mg, 0.13 mmol), $N^1,N^1$-dimethylethane-1,2-diamine (12 mg, 0.14 mmol), TBTU (50 mg, 0.16 mmol), and N,N-Diisopropylethylamine (50 µL, 0.40 mmol) in DMF (1 mL) was stirred at room temperature for 16 h. The reaction mixture was quenched with water and extracted with ethyl acetate. The organic phase was dried over $Na_2SO_4$ and concentrated. The residue was purified by combi-flash chromatography (silica gel, 9:1 DCM/MeOH) to afford to afford 3-(4-(2-(5-chloro-2,4-dimethoxyphenyl)imidazo[1,2-a]pyridin-7-yl)piperazin-1-yl)-N-(2-(dimethylamino)ethyl)propanamide 13ad (15 mg, 22%) as a pale yellow solid.

$^1$H NMR (400 MHz, $CD_3OD$): δ 8.15 (d, J=7.6 Hz, 1H), 8.06 (s, 1H), 7.97 (s, 1H), 6.78 (s, 1H), 6.77 (d, J=7.6 Hz, 1H), 6.67 (s, 1H), 4.01 (s, 3H), 3.94 (s, 3H), 3.35-3.30 (m, 6H), 2.73 (t, J=7.2 Hz, 2H), 2.70-2.65 (m, 4H), 2.49-2.41 (m, 4H), 2.26 (m, 6H); HPLC (Method 1) 96.7% (AUC), $t_R$=8.69 min; ESI MS m/z 515 $[M+H]^+$.

Preparation of diethyl (2-(4-(2-(5-chloro-2,4-dimethoxyphenyl)imidazo[1,2-a]pyridin-7-yl)piperazin-1-yl)ethyl)phosphonate 13ae (Example 202)

A mixture of 2-(5-chloro-2,4-dimethoxyphenyl)-7-(piperazin-1-yl)imidazo-[1,2-a]pyridine 12 (100 mg, 0.30 mmol), cesium carbonate (300 mg, 0.90 mmol), and diethyl (2-chloroethyl)phosphonate (88 µL, 0.33 mmol) in DCM (2 mL) was stirred at room temperature for 2 h. The reaction mixture was diluted with DCM (50 mL), washed with $NH_4OH$ solution (10 mL) and brine (10 mL), dried over sodium sulphate, filtered, and concentrated under reduced pressure. The residue was purified by combi-flash chromatography (silica gel, 9:1 DCM/methanol) to afford diethyl (2-(4-(2-(5-chloro-2,4-dimethoxyphenyl)imidazo[1,2-a]-pyridin-7-yl)piperazin-1-yl)ethyl)phosphonate 13ae (30 mg, 21%) as an off-white solid.

$^1$H NMR (400 MHz, $CDCl_3$): δ 8.35 (s, 1H), 7.89 (d, J=7.5 Hz, 1H), 7.83 (s, 1-), 6.92 (br s, 1H), 6.59 (br s, 1H), 6.58 (s, 1H), 4.18-4.07 (m, 4H), 4.00 (s, 3H), 3.95 (s, 3H), 3.32-3.25 (m, 4H), 2.77-2.69 (m, 2H), 2.65-2.63 (m, 4H), 2.06-1.96 (m, 2H), 1.37-1.34 (m, 6H); HPLC (Method 1) >99% (AUC), $t_R$=9.34 min; ESI MS m/z 537 $[M+H]^+$.

Preparation of 2-(5-chloro-2,4-dimethoxyphenyl)-7-(4-methylpiperazin-1-yl)imidazo[1,2-a]-pyridine 13af (Example 106)

A mixture of 2-(5-chloro-2,4-dimethoxyphenyl)-7-(piperazin-1-yl)imidazo[1,2-a]-pyridine 12 (75 mg, 0.20 mmol), sodium cyanoborohydride (12.5 mg, 0.20 mmol) and paraformaldehyde (9 mg) in methanol (3 mL) was stirred at room temperature for 1 h. Reaction mixture was concentrated. The residue was purified by combi-flash chromatography (silica gel, 9:1 DCM/methanol) to afford 2-(5-chloro-2,4-dimethoxyphenyl)-7-(4-methylpiperazin-1-yl)imidazo[1,2-a]pyridine 13af (22 mg, 28%) as an off-white solid.

$^1$H NMR (400 MHz, $CDCl_3$); δ 8.36 (s, 1H), 7.89 (d, J=7.6 Hz, 1H), 7.84 (s, 1H), 6.87 (s, 1H), 6.60-6.55 (m, 1H), 3.99 (s, 3H), 3.95 (s, 3H), 3.31-3.25 (m, 4H), 2.62-2.55 (m, 4H), 2.36 (s, 3H); ESI MS m/z 387 $[M+H]^+$.

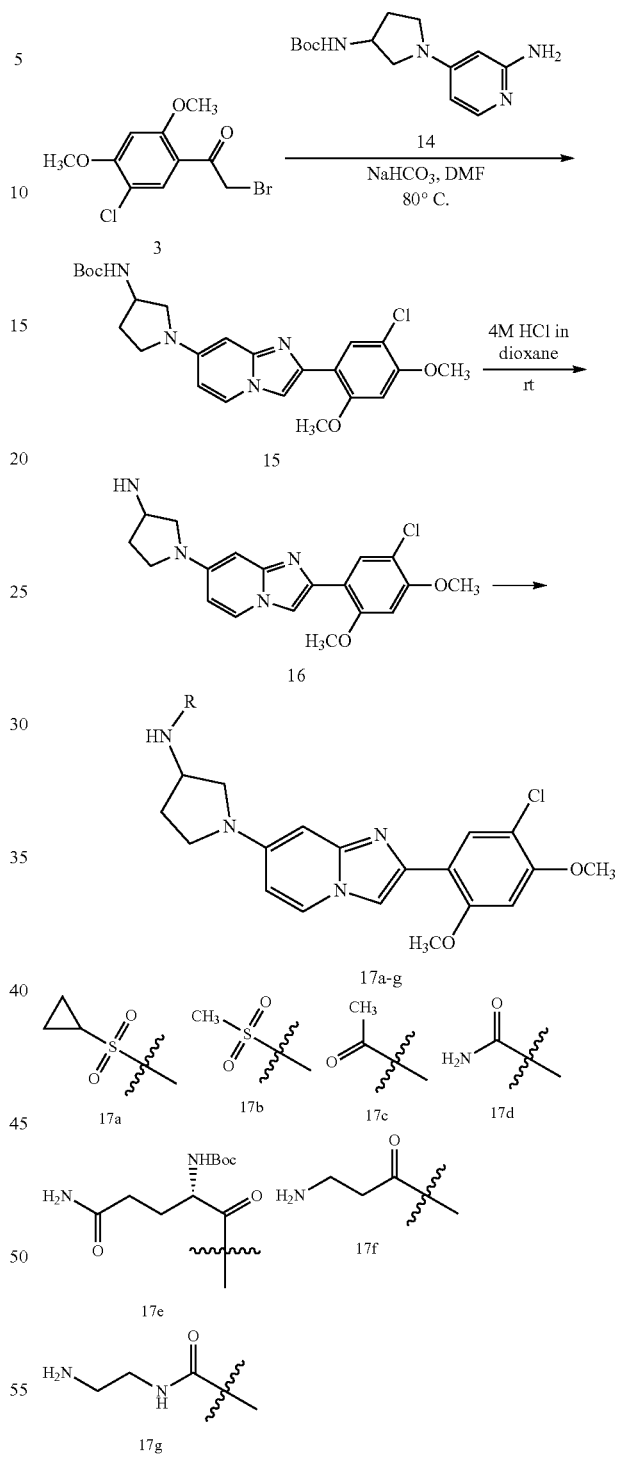

Preparation of tert-butyl{1-[2-(5-chloro-2,4-dimethoxyphenyl)imidazo[1,2-a]pyridin-7-yl]pyrrolidin-3-yl}carbamate 15 (Example 23)

Compound tert-butyl {1-[2-(5-chloro-2,4-dimethoxyphenyl)imidazo[1,2-a]pyridin-7-yl]pyrrolidin-3-yl)carbamate} 15 was prepared in the same manner as tert-butyl-4-[2-(5- chloro-2,4-dimethoxyphenyl)imidazo[1,2-a]pyridin-7-yl]piperazine-1-carboxylate 11 and was obtained as a white solid (27% yield).

$^1$H NMR (400 MHz, CDCl$_3$): δ 8.17 (s, 1H), 7.96 (d, J=7.4 Hz, 1H), 7.72 (s, 1H), 6.93 (br s, 1H), 6.55 (s, 1H), 6.46-6.42 (m, 1H), 4.78 (br s, 1H), 4.37 (br s, 1H), 4.05 (s, 3H), 3.95 (s, 3H), 3.71-3.67 (m, 1H), 3.57-3.50 (m, 1H), 3.49-3.42 (m, 1H), 3.31-3.24 (m, 1H), 2.23-2.22 (m, 1H), 2.03-1.99 (m, 1H), 1.46 (s, 9H); HPLC (Method 2) 98.9% (AUC), t$_R$=17.04 min; ESI MS m/z 473 [M+H]$^+$.

Preparation of 1-[2-(5-chloro-2,4-dimethoxyphenyl)imidazo[1,2-a]pyridin-7-yl]pyrrolidin-3-amine 16 (Example 33)

Compound 1-[2-(5-chloro-2,4-dimethoxyphenyl)imidazo[1,2-a]pyridin-7-yl]pyrrolidin-3-amine 16 was prepared in the same manner as 2-(5-chloro-2,4-dimethoxyphenyl)-7-(piperazin-1-yl)imidazo[1,2-a]pyridine 12 and was obtained as a green solid (85% yield).

$^1$H NMR (400 MHz, CD$_3$OD): δ 8.11 (d, J=7.4 Hz, 1H), 8.02 (s, 1H), 7.90 (s, 1H), 6.78 (s, 1H), 6.53 (dd, J=2.3, 7.5 Hz, 1H), 6.29 (s, 1H), 4.01 (s, 3H), 3.94 (s, 3H), 3.75-3.69 (m, 1H), 3.62-3.55 (m, 2H), 3.45-3.39 (m, 1H), 3.18-3.15 (m, 1H), 2.33-2.24 (m, 1H), 1.96-1.88 (m, 1H); HPLC (Method 4) 96.4% (AUC), t$_R$=15.74 min; ESI MS m/z 373 [M+H]$^+$.

Preparation of N-{1-[2-(5-chloro-2,4-dimethoxyphenyl)imidazo[1,2-a]pyridin-7-yl]pyrrolidin-3-yl}cyclopropanesulfonamide 17a (Example 63)

Compound N-{1-[2-(5-chloro-2,4-dimethoxyphenyl)imidazo[1,2-a]pyridin-7-yl]pyrrolidin-3-yl}cyclopropanesulfonamide 17 was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (18% yield).

$^1$H NMR (400 MHz, DMSO-d$_6$): δ 8.28 (d, J=7.4 Hz, 1H), 8.16 (s, H), 7.95 (s, H), 7.49 (d, J=7.6 Hz, 1H), 6.85 (s, 1H), 6.49 (dd, J=2.3, 7.4 Hz, 1H), 6.24 (d, J=2.0 Hz, 1H), 4.12-4.05 (m, 1H), 4.00 (s, 3H), 3.92 (s, 3H), 3.67-3.61 (m, 1H), 3.49-3.43 (m, 1H), 3.37-3.32 (m, 1H), 3.25-3.21 (m, 1H), 2.67-2.61 (m, 1H), 2.33-2.24 (m, 1H), 2.01-1.93 (m, 2H), 1.02-0.93 (m, 4H); HPLC (Method 2) 96.7% (AUC), t$_R$=18.28 min.; ESI MS m/z 477 [M+H]$^+$.

Preparation of N-(1-(2-(5-chloro-2,4-dimethoxyphenyl)imidazo[1,2-a]pyridin-7-yl)pyrrolidin-3-yl)methanesulfonamide 17b (Example 40)

Compound N-(1-(2-(5-chloro-2,4-dimethoxyphenyl)imidazo[1,2-a]pyridin-7-yl)pyrrolidin-3-yl)methanesulfonamide 17b was prepared in the same manner as 2-(5-chloro-2,4-dimethoxyphenyl)-7-[4-(methylsulfonyl)piperazin-1-yl]imidazo[1,2-a]pyridine 13a and was obtained as a light green solid (20% yield).

$^1$H NMR (400 MHz, DMSO-d$_6$): δ 8.32 (d, J=7.4 Hz, 1H), 8.11 (s, 1H), 8.01 (s, 1H), 7.45 (d, J=6.8 Hz, 1H), 6.88 (s, 1H), 6.62-6.56 (m, 1H), 6.26 (s, 1H), 4.15-4.05 (m, 1H), 4.01 (s, 3H), 3.94 (s, 3H), 3.86-3.79 (m, 1H), 3.71-3.61 (m, 1H), 3.53-3.42 (m, 2H), 3.00 (s, 3H), 2.36-2.20 (m, 1H), 2.05-1.94 (m, 1H); ESI MS m/z 451 [M+H]$^+$.

Preparation of N-(1-(2-(5-chloro-2,4-dimethoxyphenyl)imidazo[1,2-a]pyridin-7-yl)pyrrolidin-3-yl)acetamide 17c (Example 37)

A mixture of 1-[2-(5-chloro-2,4-dimethoxyphenyl)imidazo[1,2-a]pyridin-7-yl]pyrrolidin-3-amine 16 (50 mg, 0.13 mmol), acetyl chloride (8.6 µL, 0.12 mmol), and triethyl amine (37 µL, 0.6 mmol) in DCM (1.5 mL) was stirred at 0° C. for 1 h then at room temperature by 2 h at room temperature. The reaction mixture was quenched with sodium bicarbonate solution extracted with dichloromethane. The organic phase was dried over sodium sulphate, filtered, and concentrated under reduced pressure. The residue was purified by combi-flash chromatography (silica gel, 9:1 DCM/MeOH) to afford N-(1-(2-(5-chloro-2,4-dimethoxy-phenyl)imidazo[1,2-a]pyridin-7-yl)pyrrolidin-3-yl) acetamide 17c (28 mg, 59%) as green solid.

$^1$H NMR (400 MHz, CDCl$_3$): δ 8.12 (d, J=7.4 Hz, 1H), 8.03 (s, 1H), 7.91 (s, 1H), 6.78 (s, 1H), 6.56-6.50 (m, 1H), 6.30 (s, 1H), 4.55-4.46 (m, 1H), 4.01 (s, 3H), 3.94 (s, 3H), 3.71-3.62 (m, 1H), 3.59-3.49 (m, 1H), 3.49-3.41 (m, 1H), 3.27-3.24 (m, 1H), 2.37-2.26 (m, 1H), 2.09-2.00 (m, 1H), 1.95 (s, 3H); HPLC (Method 2) 94.9% (AUC), t$_R$=16.98 min.; ESI MS m/z 415 [M+H]$^+$.

Preparation of 1-(1-(2-(5-chloro-2,4-dimethoxyphenyl)imidazo[1,2-a]pyridin-7-yl)-pyrrolidin-3-yl)urea 17d (Example 38)

A mixture of phenyl (1-(2-(5-chloro-2,4-dimethoxyphenyl)imidazo[1,2-a]pyridin-7-yl)pyrrolidin-3-yl)carbamate (65 mg, 0.17 mmol), and ammonia in ethanol (10 mL, 2.0 M) in ethanol (1.5 mL) was heated at 80° C. for 16 h. The reaction mixture was cooled to room temperature and concentrated. The residue was purified by preparative TLC (9:1 DCM/MeOH) to afford 1-(1-(2-(5-chloro-2,4-dimethoxyphenyl)imidazo[1,2-a]pyridin-7-yl)pyrrolidin-3-yl)urea 17d (20 mg, 40%) as an off-white solid.

$^1$H NMR (400 MHz, CDCl$_3$): δ 8.28 (d, J=7.4 Hz, 1H), 8.15 (s, 1H), 7.96 (s, 1H), 6.86 (s, 1H), 6.52-6.48 (m, 1H), 6.32 (d, J=7.1 Hz, 1H), 6.23 (s, 1H), 5.43 (s, 2H), 4.28-4.18 (m, 1H), 4.00 (s, 3H), 3.93 (s, 3H), 3.57-3.49 (m, 1H), 3.45-3.32 (m, 2H), 3.19-3.08 (m, 2H), 2.21-2.11 (m, 1H), 1.90-1.81 (m, 1H); HPLC (Method 2) 94.0% (AUC), t$_R$=16.67 min.; ESI MS m/z 416 [M+H]$^+$.

Preparation of tert-butyl ((2S)-5-amino-1-((1-(2-(5-chloro-2,4-dimethoxyphenyl)imidazo-[1,2-a]-pyridin-7-yl)pyrrolidin-3-yl)amino)-1,5-dioxopentan-2-yl)carbamate 17e (Example 39)

A mixture of 1-[2-(5-chloro-2,4-dimethoxyphenyl)imidazo[1,2-a]pyridin-7-yl]-pyrrolidin-3-amine 16 (100 mg, 0.27 mmol), (S)-5-amino-2-((tert-butoxycarbonyl)amino)-5-oxopentanoic acid (132 mg, 0.54 mmol), HATU (305 mg, 0.80 mmol), and DIPEA (280 µL, 1.60 mmol) in DCM (10 mL) was stirred at room temperature for 16 h. The reaction mixture was quenched with water and extracted with dichloromethane. The organic phase was dried over sodium sulphate, filtered, and concentrated under reduced pressure. The residue was purified by combi-flash chromatography (silica gel, 9:1 DCM/MeOH) to afford tert-butyl ((2S)-5-amino-1-((1-(2-(5-chloro-2,4-dimethoxyphenyl)imidazo[1,2-a]pyridin-7-yl)pyrrolidin-3-yl)amino)-1,5-dioxopentan-2-yl)carbamate 17e (80 mg, 50%) as a light green solid.

$^1$H NMR (400 MHz, CD$_3$OD): δ 8.17 (d, J=7.5 Hz, 1H), 7.95-7.91 (m, 2H), 6.80 (s, 1H), 6.65-6.60 (m, 1H), 6.33 (s, 1H), 4.56-4.49 (m, 1H), 4.05-3.98 (m, 4H), 3.95 (s, 3H), 3.73-3.66 (m, 1H), 3.62-3.54 (m, 1H), 3.52-3.45 (m, 1H), 3.37-3.31 (m, 1H), 2.38-2.25 (m, 3H), 2.15-2.06 (m, 1H), 2.04-1.93 (m, 1H), 1.90-1.80 (m, 1H), 1.42 (s, 9H); HPLC (Method 2) 96.0% (AUC), t$_R$=17.69 min.; ESI MS m/z 601 [M+H]$^+$.

Preparation of 3-amino-N-(1-(2-(5-chloro-2,4-dimethoxyphenyl)imidazo[1,2-a]pyridin-7-yl)pyrrolidin-3-yl)propanamide 17f (Example 50)

A solution of tert-butyl (3-((1-(2-(5-chloro-2,4-dimethoxyphenyl)imidazo[1,2-a]-pyridin-7-yl)pyrrolidin-3-yl)amino)-3-oxopropyl)carbamate (75 mg, 0.16 mmol) in 4.0 M HCl in dioxane (3 mL) was stirred at room temperature for 3 h. The reaction mixture was filtered, washed with dioxane, and dried under reduced pressure to give 3-amino-N-(1-(2-(5-chloro-2,4-dimethoxyphenyl)imidazo[1,2-a]pyridin-7-yl)pyrrolidin-3-yl)propanamide. The hydrochloride salt was suspended in 10 mL of aqueous ammonia, stirred for 1 h at room temperature, and extracted with chloroform (2×20 mL). The organic layer was dried over sodium sulphate and concentrated to give 3-amino-N-(1-(2-(5-chloro-2,4-dimethoxyphenyl)imidazo[1,2-a]pyridin-7-yl)pyrrolidin-3-yl)propanamide 17f (50 mg, 82%) as an off-white solid.

$^1$H NMR (400 MHz, CDCl$_3$): δ 8.36 (d, J=7.5 Hz, 1H), 8.06 (s, 1H), 7.75 (s, 1H), 6.92-6.88 (m, 2H), 6.48 (s, 1H), 4.62-4.55 (m, 1H), 4.07 (s, 3H), 3.99 (s, 3H), 3.83-3.76 (m, 1H), 3.71-3.55 (m, 2H), 3.45-3.38 (m, 2H), 3.32 (t, J=6.4 Hz, 2H), 2.64 (t, J=6.8 Hz, 2H), 2.44-2.33 (m, 1H), 2.19-2.10 (m, 1H); ESI MS m/z 444 [M+H]$^+$.

Preparation of 1-(2-aminoethyl)-3-(1-(2-(5-chloro-2,4-dimethoxyphenyl)imidazo[1,2-a]-pyridin-7-yl)pyrrolidin-3-yl)urea 172 (Example 62)

Compound 1-(2-aminoethyl)-3-(1-(2-(5-chloro-2,4-dimethoxyphenyl)imidazo-[1,2-a]pyridin-7-yl)pyrrolidin-3-yl)urea 17g was prepared in the same manner as 3-amino-N-(1-(2-(5-chloro-2,4-dimethoxyphenyl)imidazo[1,2-a]pyridin-7-yl)pyrrolidin-3-yl)propanamide 17f and was obtained as a brown solid (10 mg, 24% yield);

$^1$H NMR (400 MHz, DMSO-d$_6$): δ 8.26 (d, J=6.8, 1H), 8.16 (s, 1H), 7.94 (s, 1H), 6.85 (s, 1H), 6.48 (d, J=6.8, 1H), 6.35-6.18 (m, 2H), 5.84 (br s, 1H), 4.26 (br s, 1H), 3.99 (s, 3H), 3.92 (s, 3H), 3.56-3.50 (m, 2H), 3.12-2.94 (m, 4H), 2.22-2.11 (m, 1H), 1.90-1.79 (m, 1H); ESI MS m/z 459 [M+H]$^+$.

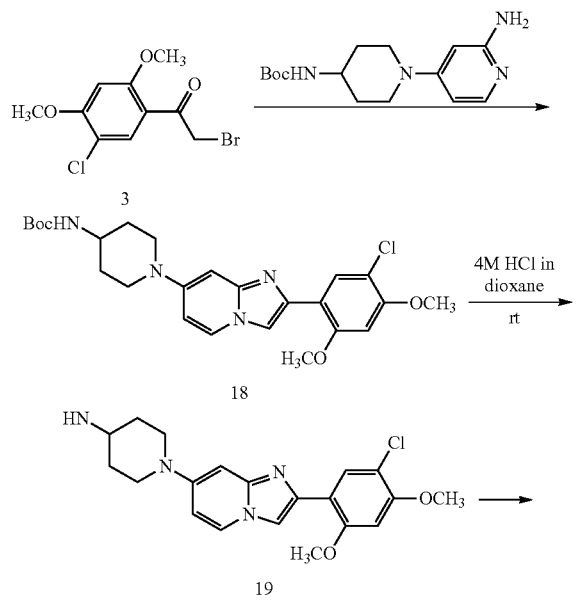

Scheme 5

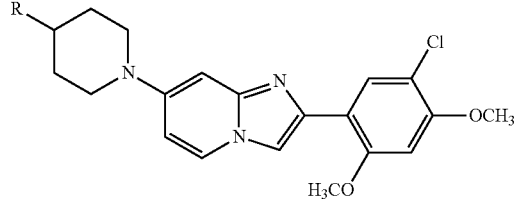

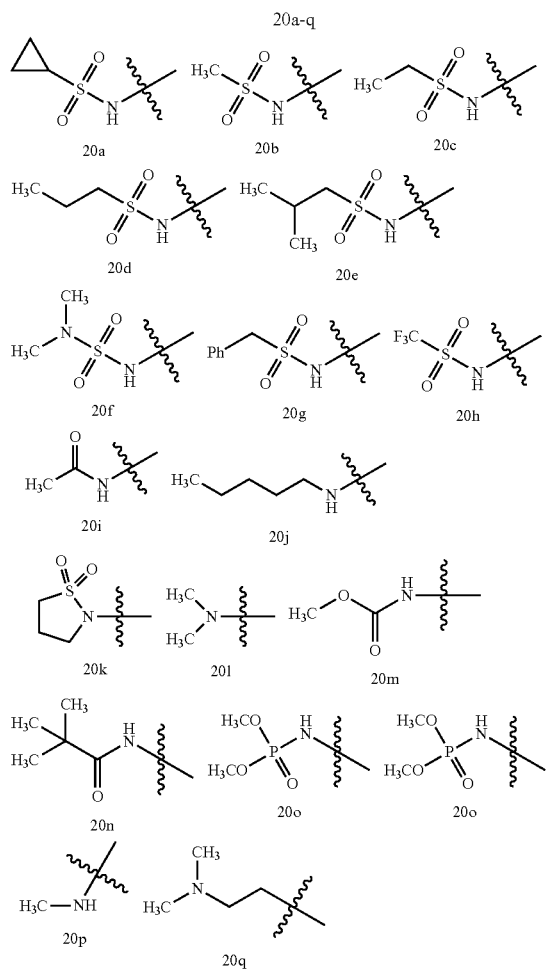

Preparation of tert-butyl{1-[2-(5-chloro-2,4-dimethoxyphenyl)imidazo[1,2-a]pyridin-7-yl]-piperidin-4-yl}carbamate 18 (Example 14)

A solution of 2-bromo-1-(5-chloro-2,4-dimethoxyphenyl)ethanone 3 (200 mg, 0.681 mmol) and tert-butyl (1-(2-aminopyridin-4-yl)piperidin-4-yl)carbamate (198 mg, 0.681 mmol) in acetone (5 mL) was heated at 75° C. for 16 h. The reaction mixture was cooled to room temperature; the white precipitate was collected by filtration and washed with acetone. The precipitate was suspended in aqueous ammonia (10 mL) and stirred for 2 h. The solid was filtered, resuspended in minimum amount of methanol, concentrated, and dried under reduced pressure to give tert-butyl {1-[2-(5-chloro-2,4-dimethoxyphenyl)imidazo[1,2-a]pyridin-7-yl]piperidin-4-yl}carbamate 18 (155 mg, 47%) as a green-blue solid.

$^1$H NMR (300 MHz, CDCl$_3$): δ 8.37 (s, 1H), 7.89-7.85 (m, 2H), 6.82-6.79 (m, 1H), 6.58 (s, 1H), 6.53 (dd, J=2.4, 7.7

Hz, 1H), 4.56-4.35 (m, 1H), 3.99 (s, 3H), 3.95 (s, 3H), 3.70-3.60 (m, 3H), 2.98-2.86 (m, 2H), 2.11-2.01 (m, 2H), 1.63-1.49 (m, 2H), 1.45 (s, 9H); HPLC (Method 4) 98.3% (AUC), $t_R$=19.17 min.; APCI MS m/z 487 [M+H]$^+$.

Preparation of 1-[2-(5-chloro-2,4-dimethoxyphenyl)imidazo[1,2-a]pyridin-7-yl]piperidin-4-amine 19 (Example 15)

A solution of tert-butyl {1-[2-(5-chloro-2,4-dimethoxyphenyl)imidazo[1,2-a]pyridin-7-yl]piperidin-4-yl}carbamate 18 (50 mg, 0.103 mmol) in 1 M HCl in methanol (3 mL) was heated at 55° C. for 1 h. The reaction mixture was cooled to room temperature and the solvent was removed under reduced pressure. The residue was triturated with ethyl acetate (2×2 mL) and dried under reduced pressure to give 1-[2-(5-chloro-2,4-dimethoxyphenyl)imidazo[1,2-a]-pyridin-7-yl]piperidin-4-amine hydrochloride 19 (35 mg, 74%) as an off-white solid. The salt was suspended in 10 mL of aqueous ammonia, stirred for 1 h at room temperature, and reaction mixture was extracted with chloroform (2×20 mL). The organic layer was dried and concentrated to give 1-[2-(5-chloro-2,4-dimethoxyphenyl)imidazo[1,2-a]pyridin-7-yl]piperidin-4-amine 19 in 65% overall yield.

$^1$H NMR (300 MHz, CD$_3$OD): δ 8.40 (d, J=7.7 Hz, 1H), 8.12 (s, 1H), 7.76 (s, 1H), 7.24 (dd, J=2.5, 7.7 Hz, 1H), 6.90-6.86 (m, 2H), 4.26-4.16 (m, 2H), 4.08 (s, 3H), 4.00 (s, 3H), 3.58-3.42 (m, 1H), 3.26-3.14 (m, 2H), 2.24-2.13 (m, 2H), 1.79-1.64 (m, 2H); APCI MS m/z 387 [M+H]$^+$.

Preparation of N-{1-[2-(5-chloro-2,4-dimethoxyphenyl)imidazo[1,2-a]pyridin-7-yl]piperidin-4-yl}cyclopropanesulfonamide 20a (Example 126)

A solution of 1-[2-(5-chloro-2,4-dimethoxyphenyl)imidazo[1,2-a]pyridin-7-yl]piperidin-4-amine 19 (50 mg, 0.13 mmol) and triethylamine (72 μL, 0.52 mmol) in dichloromethane (3 mL) was charged with cyclopropyl sulfonyl chloride (36 mg, 0.26 mmol). The reaction mixture was stirred at room temperature for 16 h. After 16 h, the reaction mixture was concentrated, suspended in aqueous ammonia solution, and stirred for 2 h. The precipitate was collected by filtration, washed with water, dried under reduced pressure and purified by column chromatography (silica gel, MeOH/DCM) to provide N-{1-[2-(5-chloro-2,4-dimethoxyphenyl)imidazo[1,2-a]pyridin-7-yl]piperidin-4-yl}cyclopropanesulfonamide 20a (20 mg, 31% yield) as a green solid.

$^1$H NMR (400 MHz, CDCl$_3$): δ 8.35 (s, 1H), 7.89 (d, J=7.5 Hz, 1H), 7.85 (s, 1H), 6.87 (s, 1H), 6.57 (s, 1H), 6.55 (dd, J=2.4, 7.5 Hz, 1H), 4.29 (d, J=4.8 Hz, 1H), 4.00 (s, 3H), 3.95 (s, 3H), 3.72-3.65 (m, 2H), 3.59-3.50 (m, 1H), 2.99-2.90 (m, 2H), 2.50-2.42 (m, 1H), 2.19-2.11 (m, 2H), 1.75-1.63 (m, 2H), 1.23-1.18 (m, 2H), 1.06-1.00 (m, 2H). HPLC (Method 1) 94.0% (AUC), $t_R$=10.75 min. APCI MS m/z 491 [M+H]$^+$.

Preparation of N-{1-[2-(5-chloro-2,4-dimethoxyphenyl)imidazo[1,2-a]pyridin-7-yl]piperidin-4-yl}methanesulfonamide 20b (Example 128)

N-{(1-[2-(5-Chloro-2,4-dimethoxyphenyl)imidazo[1,2-a]pyridin-7-yl]piperidin-4-yl}methanesulfonamide 20b was prepared in the same manner as N-{1-[2-(5-chloro-2,4-dimethoxyphenyl)imidazo[1,2-a]pyridin-7-yl]piperidin-4-yl}cyclopropanesulfonamide 20a and was obtained as an off-white solid (58% yield).

$^1$H NMR (400 MHz, CDCl$_3$): δ δ 8.36 (s, 1H), 7.89 (d, J=7.5 Hz, 1H), 7.87 (s, 1H), 6.81 (d, J=1.9 Hz, 1H), 6.58 (s, 1H), 6.52 (dd, J=2.3, 7.5 Hz, 1H), 4.32 (d, J=7.2 Hz, 1H), 3.99 (s, 3H), 3.95 (s, 3H), 3.67 (d, J=13.1 Hz, 2H), 3.59-3.48 (m, 1H), 3.02 (s, 3H), 2.97-2.88 (m, 2H), 2.13 (d, J=11.1 Hz, 2H), 1.74-1.62 (m, 2H); HPLC (Method 2) 98.1% (AUC), $t_R$=17.73 min; APCI MS m/z 465 [M+H]$^+$.

Preparation of N-{1-[2-(5-chloro-2,4-dimethoxyphenyl)imidazo[1,2-a]pyridin-7-yl]piperidin-4-yl}ethanesulfonamide 20c (Example 173)

N-{1-[2-(5-Chloro-2,4-dimethoxyphenyl)imidazo[1,2-a]pyridin-7-yl]piperidin-4-yl}ethanesulfonamide 20c was prepared in the same manner as N-{1-[2-(5-chloro-2,4-dimethoxyphenyl)imidazo[1,2-a]pyridin-7-yl]piperidin-4-yl}cyclopropanesulfonamide 20a and was obtained as a green solid (45% yield).

$^1$H NMR (400 MHz, CDCl$_3$): δ 8.36 (s, 1H), 7.89 (d, J=7.6 Hz, 1H), 7.86 (s, 1H), 6.85 (s, 1H), 6.58 (s, 1H), 6.54 (dd, J=2.3, 7.5 Hz, 1H), 4.09 (d, J=7.7 Hz, 1H), 4.00 (s, 3H), 3.95 (s, 3H), 3.68 (d, J=12.7 Hz, 2H), 3.55-3.47 (m, 1H), 3.08 (dd, J=7.3, 14.7 Hz, 2H), 2.96-2.89 (m, 2H), 2.16-2.11 (m, 2H), 1.72-1.62 (m, 2H), 1.40 (t, J=7.3 Hz, 3H); HPLC (Method 1) 95.2% (AUC), $t_R$=10.61 min; ESI MS m/z 479 [M+H]$^+$.

Preparation of N-{1-[2-(5-chloro-2,4-dimethoxyphenyl)imidazo[1,2-a]pyridin-7-yl]piperidin-4-yl}propane-1-sulfonamide 20d (Example 174)

N-{1-[2-(5-Chloro-2,4-dimethoxyphenyl)imidazo[1,2-a]pyridin-7-yl]piperidin-4-yl}propane-1-sulfonamide 20d was prepared in the same manner as N-{(1-[2-(5-chloro-2,4-dimethoxyphenyl)imidazo[1,2-a]pyridin-7-yl]piperidin-4-yl}cyclopropanesulfonamide 20a and was obtained as a green solid (22% yield).

$^1$H NMR (400 MHz, CDCl$_3$): δ 8.33 (s, 1H), 7.89 (d, J=7.4 Hz, 1H), 7.84 (s, 1H), 6.86-6.83 (m, 1H), 6.57 (s, 1H), 6.53 (dd, J=2.2, 7.5 Hz, 1H), 4.44 (br s, 1H), 3.99 (s, 3H), 3.94 (s, 3H), 3.68 (d, J=12.9 Hz, 2H), 3.55-3.44 (m, 1H), 3.07-2.99 (m, 2H), 2.98-2.88 (m, 2H), 2.15-2.07 (m, 2H), 1.91-1.82 (m, 2H), 1.71-1.61 (m, 2H), 1.07 (t, J=7.4 Hz, 3H); ESI MS m/z 493 [M+H]$^+$.

Preparation of N-[1-[2-(5-chloro-2,4-dimethoxyphenyl)imidazo[1,2-a]pyridin-7-yl]piperidin-4-yl}-2-methylpropane-1-sulfonamide 20e (Example 185)

N-{1-[2-(5-Chloro-2,4-dimethoxyphenyl)imidazo[1,2-a]pyridin-7-yl]piperidin-4-yl}-2-methylpropane-1-sulfonamide 20e was prepared in the same manner as N-{1-[2-(5-chloro-2,4-dimethoxyphenyl)imidazo[1,2-a]pyridin-7-yl]piperidin-4-yl}cyclopropanesulfonamide 20a and was obtained as a yellow-green solid (61% yield).

$^1$H NMR (400 MHz, CDCl$_3$): δ 8.35 (s, 1H), 7.89 (d, J=7.5 Hz, 1H), 7.85 (s, 1H), 6.84 (br s, 1H), 6.57 (s, 1H), 6.53 (dd, J=2.4, 7.5 Hz, 1H), 4.22 (d, J=7.1 Hz, 1H), 3.99 (s, 3H), 3.95 (s, 3H), 3.68 (d, J=13 Hz, 2H), 3.52-3.49 (m, 1H), 2.96-2.89 (m, 4H), 2.33-2.23 (m, 1H), 2.13-2.06 (m, 2H), 1.71-1.61 (m, 2H), 1.12 (d, 6H, J=6.7 Hz); HPLC (Method 1) 98.6% (AUC), $t_R$=11.09 min.; ESI MS m/z 507 [M+H]$^+$.

Preparation of N-{1-[2-(5-chloro-2,4-dimethoxyphenyl)imidazo[1,2-a]pyridine-7-yl]piperidin-4-yl}N,N-dimethylsulfonamide 20f (Example 181)

N-{1-[2-(5-Chloro-2,4-dimethoxyphenyl)imidazo[1,2-a]pyridin-7-yl]piperidin-4-yl}N,N-dimethylsulfonamide 20f was prepared in the same manner as N-{l-[2-(5-chloro-2,4-dimethoxyphenyl)imidazo[1,2-a]pyridin-7-yl]piperidin-4-yl}cyclopropanesulfonamide 20a and was obtained as a green solid (44% yield).
$^1$H NMR (400 MHz, CDCl$_3$): δ 8.36 (s, 1H), 7.88 (d, J=7.5 Hz, 1H), 7.86 (s, 1H), 6.83-6.81 (m, 1H), 6.58 (s, 1H), 6.53 (dd, J=2.4, 7.5 Hz, 1H), 4.05 (d, J=7.6 Hz, 1H), 3.99 (s, 3H), 3.95 (s, 3H), 3.66 (d, J=13.2 Hz, 2H), 3.46-3.37 (m, 1H), 2.95-2.88 (m, 2H), 2.82 (s, 6H), 2.18-2.11 (m, 2H), 1.69-1.59 (m, 2H); HPLC (Method 1) 97.4% (AUC), t$_R$=10.83 min; ESI MS m/z 494 [M+H]$^+$.

Preparation of N-{1-[2-(5-chloro-2,4-dimethoxyphenyl)imidazo[1,2-a]pyridin-7-yl]piperidin-4-yl}-1-phenylmethanesulfonamide 20g (Example 175)

N-{1-[2-(5-Chloro-2,4-dimethoxyphenyl)imidazo[1,2-a]pyridin-7-yl]piperidin-4-yl}-1-phenylmethanesulfonamide 20g was prepared in the same manner as N-{1-[2-(5-chloro-2,4-dimethoxyphenyl)imidazo[1,2-a]pyridin-7-yl]piperidin-4-yl}cyclopropanesulfonamide 20a and was obtained as a green solid (11% yield).
$^1$H NMR (400 MHz, CDCl$_3$): δ 8.34 (s, 1H), 7.88 (d, J=7.5 Hz, 1H), 7.83 (s, 1H), 7.45-7.38 (m, 5H), 6.85 (s, 1H), 6.57 (s, 1H), 6.52 (dd, J=2.2, 7.5 Hz, 1H), 4.29 (s, 2H), 4.20-4.12 (m, 1H), 3.99 (s, 3H), 3.95 (s, 3H), 3.61 (d, J=13.0 Hz, 2H), 3.27-3.19 (m, 1H), 2.86-2.76 (m, 2H), 2.02-1.94 (m, 2H), 1.59-1.49 (m, 2H); ESI MS m/z 541 [M+H]$^+$.

Preparation of N-{1-[2-(5-chloro-2,4-dimethoxyphenyl)imidazo[1,2-a]pyridin-7-yl]piperidin-4-yl}-1,1,1-trifluoromethanesulfonamide 20h (Example 176)

N-{1-[2-(5-Chloro-2,4-dimethoxyphenyl)imidazo[1,2-a]pyridin-7-yl]piperidin-4-yl}-1,1,1-trifluoromethanesulfonamide 20h was prepared in the same manner as N-{1-[2-(5-chloro-2,4-dimethoxyphenyl)imidazo[1,2-a]pyridin-7-yl]piperidin-4-yl}cyclopropanesulfonamide 20a and was obtained as a green solid (25% yield).
$^1$H NMR (400 MHz, CDCl$_3$): δ 8.34 (s, 1H), 7.89 (d, J=7.5 Hz, 1H), 7.86 (s, 1H), 6.84-6.82 (m, 1H), 6.58 (s, 1H), 6.52 (dd, J=2.4, 7.5 Hz, 1H), 3.99 (s, 3H), 3.95 (s, 3H), 3.73-3.66 (m, 3H), 2.98-2.89 (m, 2H), 2.19-2.12 (m, 2H), 1.80-1.68 (m, 2H); HPLC (Method 1) 96.9% (AUC), t$_R$=11.66 min.; ESI MS m/z 519 [M+H]$^+$.

Preparation of N-{1-[2-(5-chloro-2,4-dimethoxyphenyl)imidazo[1,2-a]pyridin-7-yl]piperidin-4-yl}acetamide 20i (Example 124)

N-{1-[2-(5-Chloro-2,4-dimethoxyphenyl)imidazo[1,2-a]pyridin-7-yl]piperidin-4-yl}acetamide 20i was prepared in the same manner as N-{1-[2-(5-chloro-2,4-dimethoxyphenyl)imidazo[1,2-a]pyridin-7-yl]piperidin-4-yl}cyclopropanesulfonamide 20a and was obtained as an off-white solid (72% yield).
$^1$H NMR (400 MHz, CDCl$_3$): δ 8.36 (s, 1H), 7.88 (d, J=7.5 Hz, 1H), 7.86 (s, 1H), 6.81 (d, J=2.2 Hz, 1H), 6.58 (s, 1H), 6.53 (dd, J=2.4, 7.5 Hz, 1H), 5.37 (d, J=7.7 Hz, 1H), 4.04-3.97 (m, 1H), 3.99 (s, 3H), 3.95 (s, 3H), 3.68 (d, J=13.1 Hz, 2H), 3.00-2.90 (m, 2H), 2.10-2.02 (m, 2H), 1.99 (s, 3H), 1.57-1.49 (m, 2H); HPLC (Method 1) 97.2% (AUC), t$_R$=10.09 min.; ESI MS m/z 429 [M+H]$^+$.

Preparation of 1-[2-(5-chloro-2,4-dimethoxyphenyl)imidazo[1,2-a]pyridin-7-yl]-N-pentylpiperidin-4-amine 20j (Example 129)

A solution of 1-[2-(5-chloro-2,4-dimethoxyphenyl)imidazo[1,2-a]pyridin-7-yl]piperidin-4-amine 19 (50 mg, 0.129 mmol) and valeraldehyde (11 mg, 0.129 mmol) in methanol (3 mL) was charged with sodium cyanoborohydride (16 mg, 0.258 mmol). The reaction mixture was stirred at room temperature for 3 h. The solvent was removed under reduced pressure and the residue was diluted with ammonium hydroxide (10 mL) and extracted with chloroform (2×10 mL). The organic layer was dried over sodium sulphate, filtered and concentrated under reduced pressure. The residue was purified by column chromatography (silica gel, MeOH/DCM) to provide 1-[2-(5-chloro-2,4-dimethoxyphenyl)imidazo[1,2-a]pyridin-7-yl]-N-pentylpiperidin-4-amine 20j (23 mg, 39% yield) as a yellow-brown solid.
$^1$H NMR (400 MHz, CDCl$_3$): δ 8.36 (s, 1H), 7.86 (d, J=7.5 Hz, 1H), 7.84 (s, 1H), 6.80 (d, J=2.2 Hz, 1H), 6.57 (s, 1H), 6.55 (dd, J=2.4, 7.6 Hz, 1H), 3.99 (s, 3H), 3.95 (s, 3H), 3.75-3.67 (m, 2H), 2.88-2.78 (m, 2H), 2.77-2.65 (m, 3H), 2.04 (d, J=10.9 Hz, 2H), 1.64-1.50 (m, 4H), 1.39-1.27 (m, 4H), 0.90 (t, J=6.8 Hz, 3H); HPLC (Method 1) 97.4% (AUC), t$_R$=9.74 min, APCI MS m/z 457 [M+H]$^+$.

Preparation of 2-{1-[2-(5-chloro-2,4-dimethoxyphenyl)imidazo[1,2-a]pyridin-7-yl]piperidin-4-yl}isothiazolidine 1,1-dioxide 20k (Example 182)

To a solution of 1-[2-(5-chloro-2,4-dimethoxyphenyl)imidazo[1,2-a]pyridin-7-yl]-piperidin-4-amine 19 (50 mg, 0.13 mmol) and triethylamine (54 μL, 0.39 mmol) in dichloromethane (3 mL) was added with 3-chloropropane-1-sulfonyl chloride (23 mg, 0.13 mmol). The reaction mixture was stirred at room temperature for 16 h then concentrated. The residue was suspended in aqueous ammonia, and stirred for 2 h. The precipitate was collected by filtration, washed with water, and dried under reduced pressure to give 55 mg of crude residue. A solution of the crude residue in DMF (3 mL) was charged with NaH (7.5 mg, 0.31 mmol) under nitrogen atmosphere. The reaction mixture was stirred at room temperature for 1 h. The reaction was quenched with cold water (10 mL) and extracted with chloroform (2×25 mL). The organic layers were combined, dried over sodium sulphate, filtered and concentrated under reduced pressure, and the residue was purified by column chromatography (silica gel. MeOH/DCM) to provide the desired 2-{1-[2-(5-chloro-2,4-dimethoxyphenyl)imidazo[1,2-a]-pyridin-7-yl]piperidin-4-yl}isothiazolidine 1,1-dioxide 20k (28 mg, 55% yield) as a yellow solid.
$^1$H NMR (300 MHz, CDCl$_3$): δ 8.37 (s, 1H), 7.89 (d, J=7.5 Hz, 1H), 7.87 (s, 1H), 6.85-6.82 (m, 1H), 6.57 (s, 1H), 6.54 (dd, J=2.3, 7.5 Hz, 1H), 4.00 (s, 3H), 3.95 (s, 3H), 3.78 (d, J=13.0 Hz, 2H), 3.67-3.60 (m, 1H), 3.29 (t, J=7.2 Hz, 2H), 3.17 (t, J=7.6 Hz, 2H), 2.95-2.88 (m, 2H), 2.40-2.31 (m, 2H), 2.07-1.98 (m, 2H), 1.95-1.82 (m, 2H); HPLC (Method 1) 97.1% (AUC), t$_R$=10.69 min.; ESI MS m/z 491 [M+H]$^+$.

Preparation of 1-(2-(5-chloro-2,4-dimethoxyphenyl)imidazo[1,2-a]pyridin-7-yl)-N,N-dimethylpiperidin-4-amine 20l (Example 92)

Compound 1-(2-(5-chloro-2,4-dimethoxyphenyl)imidazo[1,2-a]pyridin-7-yl)-N,N-dimethylpiperidin-4-amine 20l was prepared in the same manner as 2-(5-chloro-2,4-dimethoxyphenyl)-7-(4-methylpiperazin-1-yl)imidazo[1,2-a]pyridine 13af and was obtained as a white solid (12% yield).
¹H NMR (400 MHz, CDCl₃): δ 8.37 (s, 1H), 7.89-7.84 (m, 2H), 6.81 (d, J=2.3 Hz, 1H), 6.58-6.54 (m, 1H), 3.99 (s, 3H), 3.95 (s, 3H), 3.76 (d, J=12.7 Hz, 2H), 2.83-2.74 (m, 2H), 2.36-2.26 (m, 7H), 1.95 (d, J=12.8 Hz, 2H), 1.71-1.59 (m, 2H); HPLC (Method 2) 96.5% (AUC), t$_R$=15.45 min; APCI MS m/z 415 [M+H]⁺.

Preparation of methyl (1-(2-(5-chloro-2,4-dimethoxyphenyl)imidazo[1,2-a]pyridin-7-yl)piperidin-4-yl)carbamate 20m (Example 122)

Compound methyl (1-(2-(5-chloro-2,4-dimethoxyphenyl)imidazo[1,2-a]pyridin-7-yl)piperidin-4-yl)carbamate 20m was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (59% yield).
¹H NMR (400 MHz, CDCl₃): δ 8.36 (br s, 11), 7.88 (d, J=7.6 Hz, 1H), 7.86 (s, 1H), 6.81 (s, 1H), 6.57 (s, 1H), 6.54 (d, J=7.6 Hz, 1H), 4.60 (br s, 1H), 3.99 (s, 3H), 3.95 (s, 3H), 3.71-3.62 (m, 6H), 2.13-2.01 (m, 2H), 1.57-1.48 (m, 2H); HPLC (Method 1) 97.5% (AUC), t$_R$=10.61 min; ESI MS m/z 445 [M+H]⁺.

Preparation of N-(1-(2-(5-chloro-2,4-dimethoxyphenyl)imidazo[1,2-a]pyridin-7-yl)piperidin-4-yl)pivalamide 20n (Example 123)

Compound N-(1-(2-(5-chloro-2,4-dimethoxyphenyl)imidazo[1,2-a]pyridin-7-yl)piperidin-4-yl)pivalamide 20n was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (45% yield).
¹H NMR (400 MHz, CDCl₃): δ 8.37 (s, 1H), 7.88 (d, J=7.6 Hz, 1H), 7.86 (s, 1H), 6.81 (s, 1H), 6.58 (s, 1H), 6.54 (d, J=7.6 Hz, 1H), 5.47 (br s, 1H), 3.99 (s, 3H), 3.95 (s, 3H), 3.72-3.64 (m, 2H), 3.02-2.93 (m, 2H), 2.08-2.00 (m, 2H), 1.58-1.48 (m, 2H), 1.19 (s, 9H); HPLC (Method 1) 97.9% (AUC), t$_R$=10.98 min: ESI MS m/z 471 [M+H]⁺.

Preparation of dimethyl(1-(2-(5-chloro-2,4-dimethoxyphenyl)imidazo[1,2-a]pyridin-7-yl)piperidin-4-yl)phosphoramidate 20o (Example 198)

Dimethyl (1-(2-(5-chloro-2,4-dimethoxyphenyl)imidazo[1,2-a]pyridin-7-yl)piperidin-4-yl)phosphoramidate 20o was prepared in the same manner diethyl (2-(4-(2-(5-chloro-2,4-dimethoxyphenyl)imidazo[1,2-a]pyridin-7-yl)piperazin-1-yl)ethyl)phosphonate 13ae and was obtained as a brown hygroscopic solid (23% yield).
¹H NMR (400 MHz, CDCl₃): δ 8.13 (d, J=7.5 Hz, 1H), 8.05 (s, 1H), 7.95 (s, 1H), 6.78 (s, 1H), 6.77 (d, J=7.5 Hz, 1H), 6.67 (s, 1H), 4.01 (s, 3H), 3.95 (s, 3H), 3.94-3.92 (m, 2H), 3.82 (s, 3H), 3.79 (s, 3H), 3.29-3.27 (m, 1H), 2.94-2.91 (m, 2H), 2.02-2.00 (m, 2H), 1.63-1.61 (m, 2H); HPLC (Method 1) 97.1% (AUC), t$_R$=10.37 min; APCI MS m/z 495 [M+H]⁺.

Preparation of 1-(2-(5-chloro-2,4-dimethoxyphenyl)imidazo[1,2-a]pyridin-7-yl)-N-methylpiperidin-4-amine hydrochloride 20o (Example 24)

Compound tert-butyl (1-(2-(5-chloro-2,4-dimethoxyphenyl)imidazo[1,2-a]pyridin-7-yl)piperidin-4-yl)carbamate (145 mg, 2.31 mmol), was dissolved in 1 ml of 1.2 M HCl in methanol and stirred for 3 h. Solvent was removed to afford of 1-(2-(5-chloro-2,4-dimethoxyphenyl)imidazo[1,2-a]pyridin-7-yl)-N-methylpiperidin-4-amine hydrochloride 20p as a white solid (76% yield).
¹H NMR (300 MHz, CD₃OD): δ 8.41 (d, J=7.7 Hz, 1H), 8.11 (s, 1H), 7.77 (s, 1H), 6.89 (d, J=7.7 Hz, 1H), 6.82 (m, 2H), 4.26-4.20 (m, 2H), 4.08 (s, 3H), 4.00 (s, 3H), 3.42-3.41 (m, 1H), 3.29-3.21 (m, 2H), 2.80 (s, 3H), 2.36-2.30 (m, 2H), 1.73-1.69 (m, 2H); HPLC (Method 4)=99.4% (AUC), t$_R$=14.37 min; APCI MS m/z 401 [M+H]⁺.

Preparation of 2-(1-(2-(5-chloro-2,4-dimethoxyphenyl)imidazo[1,2-a]pyridin-7-yl)piperidin-4-yl)-N,N-dimethylethanamine 20a (Example 94)

A mixture of 2-(1-(2-(5-chloro-2,4-dimethoxyphenyl)imidazo[1,2-a]pyridin-7-yl)piperidin-4-yl)ethanamine (120 mg, 0.28 mmol), sodium cyanoborohydride (145.2 mg, 2.31 mmol), formaldehyde (37%) (117 μL) and acetic acid (132 μL, 0.23 mmol) in methanol (1.5 mL) was stirred at room temperature for 16 h. Reaction mixture was filtered and residue was partitioned between water and chloroform. The organic layers were combined, dried over sodium sulphate, filtered and concentrated under reduced pressure, and the residue was purified by column chromatography (silica gel, MeOH/DCM) to afford 2-(1-(2-(5-chloro-2,4-dimethoxyphenyl)imidazo[1,2-a]pyridin-7-yl)piperidin-4-yl)-N,N-dimethylethanamine 20q (15 mg, 9%) as brown solid.
¹H NMR (400 MHz, CDCl₃): δ 8.37 (s, 1H), 7.86 (d, J=7.5 Hz, 1H), 7.84 (s, 1H), 6.82-6.79 (m, 1H), 6.57 (s, 1H), 6.55 (dd, J=2.4, 7.6 Hz, 1H), 3.99 (s, 3H), 3.95 (s, 3H), 3.71 (d, J=12.6 Hz, 2H), 2.82-2.73 (m, 2H), 2.48-2.41 (m, 2H), 2.33 (s, 6H), 1.85-1.77 (m, 2H), 1.57-1.48 (m, 3H), 1.45-1.32 (m, 3H); HPLC (Method 2) 95.9% (AUC), t$_R$=16.21 min.; ESI MS m/z 443 [M+H]⁺.

Scheme 6

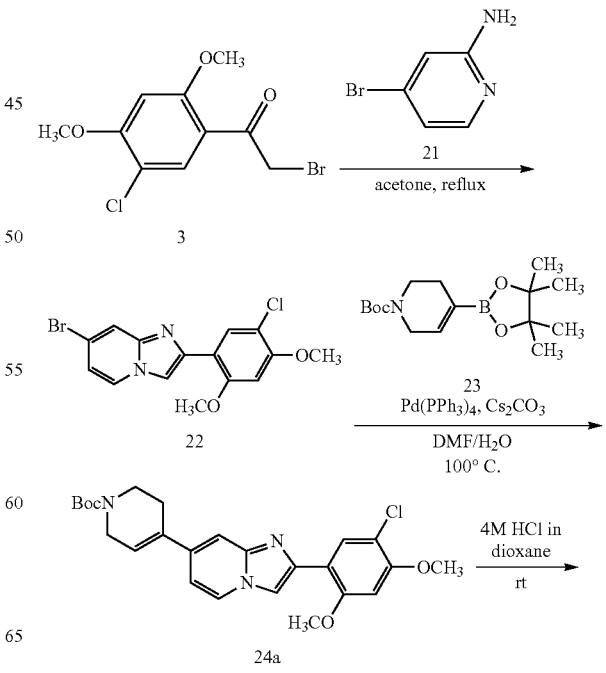

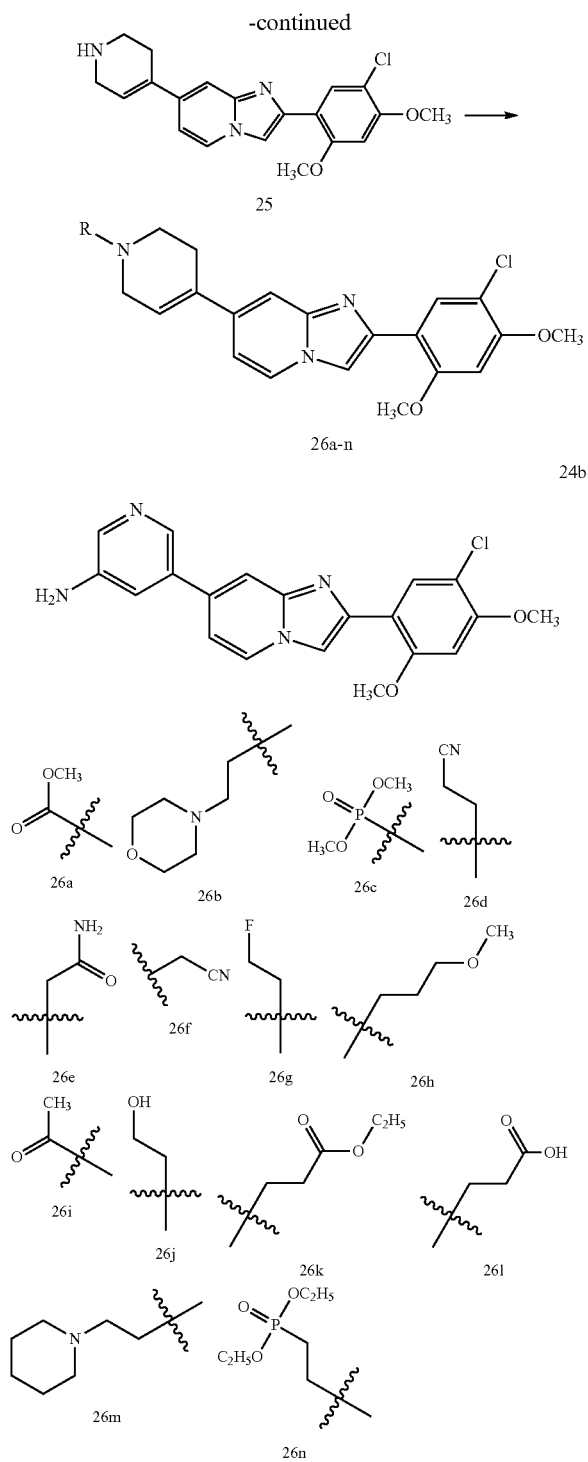

Preparation of 7-bromo-2-(5-chloro-2,4-dimethoxyphenyl)imidazo[1,2-a]pyridine 22

A solution of 2-bromo-1-(5-chloro-2,4-dimethoxyphenyl)ethanone 3 (678 mg, 2.31 mmol) and 4-bromopyridin-2-amine 21 (400 mg, 2.31 mmol) in acetone (10 mL) was heated at 75° C. for 16 h. The reaction mixture was cooled to room temperature; the white precipitate was filtered, washed with acetone, and dried under reduced pressure. Compound 7-bromo-2-(5-chloro-2,4-dimethoxyphenyl)imidazo[1,2-a]pyridine hydrobromide 22 (500 mg, 48%) was obtained as an off-white solid. The HBr salt (450 mg, 1.0 mmol) was suspended in aqueous ammonia (10 mL) and stirred for 2 h. The solid was collected by filtration and dried under reduced pressure to give 7-bromo-2-(5-chloro-2,4-dimethoxyphenyl)imidazo[1,2-a]pyridine 22 (310 mg, 86% yield) as an off-white solid.

$^1$H NMR (400 MHz, DMSO-$d_6$): δ 8.77 (dd, J=0.6, 7.2 Hz, 1H), 8.65 (d, J=0.6 Hz, 1H), 8.17-8.11 (m, 1H), 8.06 (s, 1H), 7.6 (dd, J=2.0, 7.2 Hz, 1H), 4.08 (s, 3H), 4.00 (s, 3H); HPLC (Method 2) >99% (AUC), $t_R$=17.43 min.; APCI MS m/z 369 [M+H]$^+$.

Preparation of tert-butyl 4-[2-(5-chloro-2,4-dimethoxyphenyl)imidazo[1,2-a]pyridin-7-yl]-5,6-dihydropyridine-1(2H1-carboxylate 24a A mixture of 7-bromo-2-(5-chloro-2,4-dimethoxyphenyl)imidazo[1,2-a]pyridine 22 (100 mg, 0.272 mmol), tert-butyl 4-(4,4,5,5-tetramethyl-1,3,2-dioxaborolan-2-yl)-5,6-dihydropyridine-1(2H)-carboxylate 23 (101 mg, 0.326 mmol), and Cs$_2$CO$_3$ (221 mg, 0.680 mmol) in DMF/H$_2$O (2 mL/0.4 mL) was degassed with nitrogen then Pd(PPh$_3$)$_4$ (16 mg, 0.136 mmol) was added. The reaction mixture was heated at 90° C. in microwave for 30 min and poured in water (20 mL). The precipitate so obtained was collected by filtration, washed with water, and dried under reduced pressure. The solid was purified by column chromatography (silica gel, 2:10 EtOAc/Hexanes) to provide tert-butyl 4-[2-(5-chloro-2,4-dimethoxyphenyl)-imidazo[1,2-a]pyridin-7-yl]-5,6-dihydropyridine-1(2H)-carboxylate 24a (80 mg, 62%) as an off-white solid.

$^1$H NMR (400 MHz, CDCl$_3$): δ 8.39 (s, 1H), 8.03 (s, 1H), 8.02-7.98 (m, 1H), 7.51 (s, 1H), 6.88 (dd, J=1.6, 7.1 Hz, 1H), 6.58 (s, 1H), 6.21 (br s, 1H), 4.16-4.09 (m, 2H), 4.00 (s, 3H), 3.95 (s, 3H), 3.66 (t, J=5.6 Hz, 2H), 2.56 (br s, 2H), 1.50 (s, 9H); HPLC (Method 2) 97.6% (AUC), $t_R$=22.16 min.; ESI MS m/z 470 [M+H]$^+$.

Preparation of 5-[2-(5-chloro-2,4-dimethoxyphenyl)imidazo[1,2-a]pyridin-7-yl]pyridin-3-amine 24b (Example 27)

5-[2-(5-Chloro-2,4-dimethoxyphenyl)imidazo[1,2-a]pyridin-7-yl]pyridin-3-amine 24b was prepared in the same manner as tert-butyl 4-[2-(5-chloro-2,4-dimethoxyphenyl)-imidazo[1,2-a]pyridin-7-yl]-5,6-dihydropyridine-1(2H)-carboxylate 24a, by using (5-aminopyridin-3-yl) boronic acid instead of tert-butyl 4-(4,4,5,5-tetramethyl-1,3,2-dioxaborolan-2-yl)-5,6-dihydropyridine-1(2H)-carboxylate 23 and was obtained as an off-white solid (24% yield).

$^1$H NMR (300 MHz, DMSO-$d_6$): δ 8.62 (d, J=7.1 Hz, 1H), 8.34 (s, H), 8.25 (s, H), 8.17 (d, J=1.7 Hz, 1H), 7.97 (d, J=2.3 Hz, 1H), 7.76 (s, 1H), 7.25 (t, J=2.2 Hz, 1H), 7.16 (dd, J=1.5, 7.1 Hz, 1H), 6.91 (s, 1H), 5.48 (s, 2H), 4.04 (s, 3H), 3.95 (s, 3H); HPLC (Method 4) 96.3% (AUC), t=15.74 min.; ESI MS m/z 381 [M+H]$^+$.

Preparation of 2-(5-chloro-2,4-dimethoxyphenyl)-7-(3,6-dihydro-2H-pyran-4-yl)-imidazo[1,2-a]pyridine 24c (Example 118)

Compound 2-(5-chloro-2,4-dimethoxyphenyl)-7-(3,6-dihydro-2H-pyran-4-yl)-imidazo[1,2-a]pyridine 24c was prepared in the same manner as 24a, by using 2-(3,6-dihydro-2H-pyran-4-yl)-4,4,5,5-tetramethyl-1,3,2-dioxaborolane in place of tert-butyl 4-(4,4,5,5-tetramethyl-1,3,2-dioxaborolan-2-yl)-5,6-dihydropyridine-1(2H)-carboxylate 23, and was obtained as an off-white solid (33% yield).

$^1$H NMR (400 MHz, CDCl$_3$): δ 8.45 (s, 1H), 8.04 (s, 1H), 8.02 (dd, J=0.7, 7.2 Hz, 1H), 7.52 (s, 1H), 6.91 (dd, J=1.8, 7.2 Hz, 1H), 6.59 (s, 1H), 6.31-6.27 (m, 1H), 4.39-4.35 (m, 2H), 4.01 (s, 3H), 3.99-3.94 (m, 5H), 2.59-2.53 (m, 2H); HPLC (Method 1) >99% (AUC), t$_R$=10.43 min.; ESI MS m/z 371 [M+H]$^+$.

Preparation of 2-(5-chloro-2,4-dimethoxyphenyl)-7-(piperidin-4-yl)imidazo[1,2-a]pyridine 24d (Example 112)

To a solution of 2-(5-chloro-2,4-dimethoxyphenyl)-7-(1,2,3,6-tetrahydropyridin-4-yl)-imidazo[1,2-a]pyridine 25 (100 mg) in THF (8.0 mL, with a few drops of MeOH), was added Pd/C (10%, 10 mg). The resulted suspension was degassed with hydrogen for 15 minutes and left stirred overnight. The reaction mixture was filtered through a pad of celite; and the celite was washed with MeOH. The combined filtrate was then concentrated to give a crude material, which was further triturated with 20% CHCl$_3$/Hexanes to give the desired product 2-(5-chloro-2,4-dimethoxyphenyl)-7-(piperidin-4-yl)imidazo[1,2-a]pyridine 24d as a white solid (80 mg, 80%).

$^1$H NMR (400 MHz, CDCl$_3$): δ 8.39 (s, 1H), 8.03-7.99 (m, 2H), 7.39 (s, 1H), 6.65 (d, J=7.4 Hz, 1H), 6.59 (s, 1H), 4.00 (s, 3H), 3.96 (s, 3H), 3.24 (d, J=12.3 Hz, 2H), 2.83-2.74 (m, 2H), 2.70-2.60 (m, 2H), 1.91 (d, J=13.1 Hz, 2H), 1.72-1.65 (m, 2H); HPLC (Method 2) 98.5% (AUC), t$_R$=14.96 min.; ESI MS m/z 372 [M+H]$^+$.

Preparation of 2-(5-chloro-2,4-dimethoxyphenyl)-7-(1,2,3,6-tetrahydropyridin-4-yl)-imidazo[1,2-a]pyridine 25 (Example 52)

A solution of tert-butyl 4-[2-(5-chloro-2,4-dimethoxyphenyl)imidazo[1,2-a]pyridin-7-yl]-5,6-dihydropyridine-1(2H)-carboxylate 24a (55 mg, 0.117 mmol) in 4.0 M HCl in dioxane (2 mL) was stirred at room temperature for 3 h. The reaction mixture was filtered, and solid was washed with dioxane, and dried under reduced pressure to give 2-(5-chloro-2,4-dimethoxyphenyl)-7-(1,2,3,6-tetrahydropyridin-4-yl)imidazo-[1,2-a]pyridine hydrochloride 25 (25 mg, 48%) as an off-white solid. The salt was suspended in 10 mL of aqueous ammonia, stirred for 1 h at room temperature, and extracted with chloroform (2×20 mL). The organic layer was dried and concentrated to give the free base of 2-(5-chloro-2,4-dimethoxyphenyl)-7-(1,2,3,6-tetrahydropyridin-4-yl)imidazo[1,2-a]pyridine 25 as an off-white solid.

$^1$H NMR (400 MHz, CDCl$_3$): δ 8.40 (s, 1H), 8.04 (d, J=0.6 Hz, 1H), 8.02 (dd, J=0.6, 7.2 Hz, 1H), 7.52 (s, 1H), 6.80 (dd, J=1.4, 7.2 Hz, 1H), 6.59 (s, 1H), 6.22 (s, 1H), 4.18 (s, 2H), 3.96 (s, 3H), 3.76 (s, 3H), 3.75-3.65 (m, 2H), 2.58 (s, 2H); HPLC (Method 3) 98.9% (AUC), t$_R$=17.32 min.; ESI MS m/z 428 [M+H]$^+$.

Preparation of methyl 4-[2-(5-chloro-2,4-dimethoxyphenyl)imidazo[1,2-a]pyridin-7-yl]-5,6-dihydropyridine-1(2H)-carboxylate 26a (Example 102)

Methyl 4-[2-(5-chloro-2,4-dimethoxyphenyl)imidazo[1,2-a]pyridin-7-yl]-5,6-dihydro-pyridine-1(2H)-carboxylate 26a was prepared in the same manner as methyl 4-[2-(5-chloro-2,4-dimethoxyphenyl)imidazo[1,2-a]pyridin-7-yl]piperazine-1-carboxylate 13h and was obtained as a yellow-green solid (52% yield).

$^1$H NMR (400 MHz, CDCl$_3$): δ 8.40 (s, 1H), 8.04 (d, J=0.6 Hz, 1H), 8.02 (dd, J=0.6, 7.2 Hz, 1H), 7.52 (s, 1H), 6.80 (dd, J=1.4, 7.2 Hz, 1H), 6.59 (s, 1H), 6.22 (s, 1H), 4.18 (s, 2H), 4.01 (s, 3H), 3.96 (s, 3H), 3.76 (s, 3H), 3.75-3.65 (m, 2H), 2.58 (s, 2H); HPLC (Method 3) 98.9% (AUC), t$_R$=17.32 min.; ESI MS m/z 428 [M+H]$^+$.

Preparation of 4-(2-{4-[2-(5-chloro-2,4-dimethoxyphenyl)imidazo[1,2-a]pyridin-7-yl]-5,6-dihydropyridin-1(2H)-yl}ethyl)morpholine 26b (Example 144)

A mixture of 2-(5-chloro-2,4-dimethoxyphenyl)-7-(1,2,3,6-tetrahydropyridin-4-yl)imidazo[1,2-a]pyridine 25 (100 mg, 0.27 mmol), potassium carbonate (74 mg, 0.54 mmol), and 4-(2-chloroethyl) morpholine (45 μL, 0.29 mmol) in acetonitrile (5 mL) was refluxed for 3 h. The reaction mixture was filtered through the filter pad and rinsed with DCM (10 mL). The combined filtrates were concentrated under reduced pressure. The residue was purified by combiflash chromatography (silica gel, 9:1 DCM/methanol) to afford 4-(2-{4-[2-(5-chloro-2,4-dimethoxyphenyl)imidazo[1,2-a]pyridin-7-yl]-5,6-dihydropyridin-1(2H)-yl}ethyl) morpholine 26b (62 mg, 47%) as an off-white solid.

$^1$H NMR (300 MHz, CH$_3$OD): δ 8.22 (d, J=7.6 Hz, 1H), 8.08 (s, 1H), 7.97 (s, 1H), 7.31 (s, 1H), 7.04 (d, J=7.6 Hz, 1H), 6.71 (s, 1H), 6.34 (br s, 1H), 4.32 (t, J=5.2 Hz, 2H), 4.17-4.14 (m, 2H), 4.00 (s, 3H), 3.92 (s, 3H), 3.74-3.71 (m, 6H), 2.83 (t, J=5.2 Hz, 2H), 2.72-2.69 (m, 4H), 2.56-2.52 (m, 2H); HPLC (Method 2) 98.54% (AUC), t$_R$=15.69 min.; LCMS-ESI m/z 481 [M–H]$^-$.

Preparation of dimethyl{4-[2-(5-chloro-2,4-dimethoxyphenyl)imidazo[1,2-a]pyridin-7-yl]-5,6-dihydropyridin-1(2H)-yl}phosphonate 26c (Example 195)

Dimethyl {4-[2-(5-chloro-2,4-dimethoxyphenyl)imidazo[1,2-a]pyridin-7-yl]-5,6-dihydro pyridin-1(2H)-yl}phosphonate 26c was prepared in the same manner as tert-butyl 4-[2-(5-chloro-2,4-dimethoxyphenyl)imidazo[1,2-a]pyridin-7-yl]-5,6-dihydropyridine-1(2H)-carboxylate 24a and was obtained as an off-white solid (31% yield).

$^1$H NMR (400 MHz, CDCl$_3$): δ 8.39 (s, 1H), 8.05 (s, 1H), 8.03 (dd, J=0.6, 7.1 Hz, 1H), 7.53 (br s, 1I), 6.90 (dd, J=1.8 Hz, 7.3 Hz, 1H), 6.59 (s, 1H), 6.27 (t, J=1.5 Hz, 1H), 4.01 (s, 3H), 3.96 (s, 3H), 3.89 (dd, J=3.0 Hz, 5.6 Hz, 2H), 3.73 (s, 3H), 3.70 (s, 3H), 3.46-3.39 (m, 2H), 2.58-2.51 (m, 2H), HPLC (Method 1) >99% (AUC), t$_R$=10.30 min. ESI MS m/z 478 [M+H]$^+$.

Preparation of 3-(4-(2-(5-chloro-2,4-dimethoxyphenyl)imidazo[1,2-a]pyridin-7-yl)-5,6-dihydropyridin-1(2H)-yl)propanenitrile 26d (Example 109)

3-(4-(2-(5-Chloro-2,4-dimethoxyphenyl)imidazo[1,2-a]pyridin-7-yl)-5,6-dihydropyridin-1(2H)-yl)propanenitrile 26d was prepared in the same manner as 3-(4-(2-(5-chloro-2,4-dimethoxyphenyl)imidazo[1,2-a]pyridin-7-yl)piperazin-1-yl)propanenitrile 13q and was obtained as an off-white solid (65% yield).

$^1$H NMR (400 MHz, CDCl$_3$): δ 8.39 (s, 1H), 8.03 (s, 1H), 8.00 (dd, J=0.7, 7.2 Hz, 1H), 7.52 (s, 1H), 6.90 (dd, J=1.8, 7.2 Hz, 1H), 6.59 (s, 1H), 6.22 (br s, 1H), 4.00 (s, 3H), 3.96 (s, 3H), 3.32-3.27 (m, 2H), 2.89-2.78 (m, 4H), 2.66-2.56 (m, 4H); HPLC (Method 3) >99% (AUC), t$_R$=15.31 min; ESI MS m/z 423 [M+H]$^+$.

Preparation of 2-(4-(2-(5-chloro-2,4-dimethoxyphenyl)imidazo[1,2-a]pyridin-7-yl)-5,6-dihydropyridin-1(2H)-yl)acetamide 26e (Example 110)

2-(4-(2-(5-Chloro-2,4-dimethoxyphenyl)imidazo[1,2-a]pyridin-7-yl)-5,6-dihydropyridin-1(2H)-yl)acetamide 26e was prepared in the same manner as 2-(5-chloro-2,4-dimethoxyphenyl)-7-(4-(2-methoxyethyl)piperazin-1-yl)imidazo[1,2-a]pyridine 13m and was obtained as an off-white solid (42% yield).

$^1$H NMR (400 MHz, CDCl$_3$): δ 8.39 (s, 1H), 8.05 (s, 1H), 8.02 (dd, J=0.8, 7.2 Hz, 1H), 7.52 (br s, 1H), 6.91 (dd, J=2.1, 7.2 Hz, 1H), 6.59 (s, 1H), 6.25 (br s, 1H), 5.42 (br s, 1H), 4.01 (s, 3H), 3.96 (s, 3H), 3.34-3.30 (m, 2H), 3.17 (s, 2H), 2.86 (t, J=5.6 Hz, 2H), 2.66-2.60 (m, 2H); HPLC (Method 3) 99.1% (AUC), t$_R$=15.10 min; ESI MS m/z 427 [M+H]$^+$.

Preparation of 2-(4-(2-(5-chloro-2,4-dimethoxyphenyl)imidazo[1,2-a]pyridin-7-yl)-5,6-dihydropyridin-1(2H)-yl)acetonitrile 26f (Example 1H)

2-(4-(2-(5-Chloro-2,4-dimethoxyphenyl)imidazo[1,2-a]pyridin-7-yl)-5,6-dihydropyridin-1(2H)-yl)acetonitrile 26f was prepared in the same manner as 2-(5-chloro-2,4-dimethoxyphenyl)-7-(4-(2-methoxyethyl)piperazin-1-yl)imidazo[1,2-a]pyridine 13m and was obtained as an off-white solid (43% yield).

$^1$H NMR (400 MHz, CDCl$_3$): δ 8.39 (s, 1H), 8.04 (s, 1H), 8.02 (dd, J=0.7, 7.2 Hz, 1H), 7.52 (br s, 1H), 6.90 (dd, J=2.0, 7.2 Hz, 1H), 6.59 (s, 1H), 6.25 (br s, 1H), 4.01 (s, 3H), 3.96 (s, 3H), 3.69 (s, 2H), 3.40-3.35 (m, 2H), 2.89 (t, J=5.6 Hz, 2H), 2.72-2.65 (m, 2H); HPLC (Method 3) >99% (AUC), t$_R$=16.79 min; ESI MS m/z 409 [M+H]$^+$.

Preparation of 2-(5-chloro-2,4-dimethoxyphenyl)-7-(1-(2-fluoroethyl)-1,2,3,6-tetrahydropyridin-4-yl)imidazo[1,2-a]pyridine 26e (Example 113)

2-(5-Chloro-2,4-dimethoxyphenyl)-7-(1-(2-fluoroethyl)-1,2,3,6-tetrahydropyridin-4-yl)imidazo[1,2-a]pyridine 26g was prepared in the same manner as 2-(5-chloro-2,4-dimethoxyphenyl)-7-(4-(3-methoxypropyl)piperazin-1-yl)imidazo[1,2-a]pyridine 13n and was obtained as an off-white solid (38% yield).

$^1$H NMR (400 MHz, CDCl$_3$): δ 8.40 (s, 1H), 8.03 (s, 1H), 7.99 (dd, J=7.2 Hz, 1H), 7.52 (br s, 1H), 6.91 (dd, J=7.2 Hz, 1H), 6.59 (s, 1H), 6.25 (br s, 1H), 4.71 (t, J=4.9 Hz, 1H), 4.59 (t, J=4.9 Hz, 1H), 4.00 (s, 3H), 3.96 (s, 3H), 3.34-3.30 (m, 2H), 2.91-2.80 (m, 4H), 2.67-2.61 (m, 4H); HPLC (Method 3) >99% (AUC), t$_R$=15.32 min; ESI MS m/z 416 [M+H]$^+$.

Preparation of 2-(5-chloro-2,4-dimethoxyphenyl-7-(1-(3-methoxypropyl)-1,2,3,6-tetrahydropyridin-4-yl)imidazo[1,2-a]pyridine 26h (Example 116)

2-(5-Chloro-2,4-dimethoxyphenyl)-7-(1-(3-methoxypropyl)-1,2,3,6-tetrahydropyridin-4-yl)imidazo[1,2-a]pyridine 26h was prepared in the same manner as 2-(5-chloro-2,4-dimethoxyphenyl)-7-(4-(2-methoxyethyl)piperazin-1-yl)imidazo[1,2-a]pyridine 13m and was obtained as an off-white solid (35% yield).

$^1$H NMR (400 MHz, CDCl$_3$): δ 8.40 (s, 1H), 8.02 (s, 1H), 7.99 (dd, J=0.8, 7.2 Hz, 1H), 7.52 (br s, 1H), 6.91 (dd, J=2.1, 7.2 Hz, 1H), 6.59 (s, 1H), 6.26 (br s, 1H), 4.00 (s, 3H), 3.96 (s, 3H), 3.47 (t, J=6.4 Hz, 2H), 3.35 (s, 3H), 3.23-3.20 (m, 2H), 2.76-2.72 (m, 2H), 2.65-2.54 (m, 4H), 1.91-1.81 (m, 2H); HPLC (Method 3) 97.4% (AUC), t$_R$=15.43 min: ESI MS m/z 442 [M+H]$^+$.

Preparation of 1-(4-(2-(5-chloro-2,4-dimethoxyphenyl)imidazo[1,2-a]pyridin-7-yl)-5,6-dihydropyridin-1(2H)-yl)ethanone 26i (Example 120)

A mixture of 2-(5-chloro-2,4-dimethoxyphenyl)-7-(1,2,3,6-tetrahydropyridin-4-yl)-imidazo[1,2-a]pyridine 25 (70 mg, 0.18 mmol), acetic anhydride (73 μL, 0.36 mmol), and DIPEA (73 μL, 0.56 mmol) in DCM (1 mL) was stirred at rt for 3 h. The reaction mixture was diluted with water and extracted with DCM (10 mL). The organic phase was concentrated under reduced pressure. The residue was purified by combi-flash chromatography (silica gel, 9:1 DCM/methanol) to afford 1-(4-(2-(5-chloro-2,4-dimethoxyphenyl)imidazo[1,2-a]-pyridin-7-yl)-5,6-dihydropyridin-1(2H)-yl)ethanone 26i (53 mg, 65%) as an off-white solid.

$^1$H NMR (400 MHz, CDCl$_3$): δ 8.39 (s, 1H), 8.05 (s, 1H), 8.03 (dd, J=0.9, 7.3 Hz, 1H), 7.54 (br s, 1H), 7.49 (s, 1H), 6.92-6.85 (m, 1H), 6.59 (s, 1H), 6.29-6.16 (m, 1H), 4.32-4.28 (m, 1H), 4.20-4.17 (m, 1H), 4.01 (s, 3H), 3.96 (s, 3H), 3.88-3.82 (m, 1H), 3.73-3.68 (m, 1H), 2.66-2.55 (m, 2H), 2.17 (s, 3H); HPLC (Method 1) >99% (AUC), t$_R$=10.06 min: ESI MS m/z 412 [M+H]$^+$

Preparation of 2-(4-(2-(5-chloro-2,4-dimethoxyphenyl)imidazo[1,2-a]pyridin-7-yl)-5,6-dihydropyridin-1(2H)-yl)ethanol 26j (Example 134)

Compound 2-(4-(2-(5-chloro-2,4-dimethoxyphenyl)imidazo[1,2-a]pyridin-7-yl)-5,6-dihydropyridin-1(2H)-yl)ethanol 26j was prepared in the same manner as 4-<2-{4-[2-(5-chloro-2,4-dimethoxyphenyl)imidazo[1,2-a]pyridin-7-yl]-5,6-dihydropyridin-1(2H)-yl}ethyl>morpholine 26b and was obtained as an off-white solid (61% yield).

$^1$H NMR (300 MHz, DMSO-d$_6$): δ 8.45 (d, J=7.2 Hz, 1H), 8.24 (m, 2H), 7.42 (s, 1H), 7.10-7.08 (m, 1H), 6.89 (m, 1H), 6.40 (m, 1H), 4.41 (m, 1H), 4.02 (s, 3H), 3.94 (s, 3H), 3.57-3.55 (m, 2H), 3.17 (m, 2H), 2.69-2.67 (m, 2H), 2.53-2.51 (m, 4H); HPLC (Method 2) >99% (AUC), t$_R$=14.78 min.; ESI MS m/z 414 [M+H]$^+$.

Preparation of ethyl 3-(4-(2-(5-chloro-2,4-dimethoxyphenyl)imidazo[1,2-a]pyridin-7-yl)-5,6-dihydropyridin-1(2H)-yl)propanoate 26k (Example 140)

Compound ethyl 3-(4-(2-(5-chloro-2,4-dimethoxyphenyl)imidazo[1,2-a]pyridin-7-yl)-5,6-dihydropyridin-1(2H)-yl)propanoate 26k was prepared in the same manner as 4-(2-{4-[2-(5-chloro-2,4-dimethoxyphenyl)imidazo[1,2-a]pyridin-7-yl]-5,6-dihydro-pyridin-1(2H)-yl}ethyl)morpholine 26b and was obtained as an off-white solid (56% yield).

$^1$H NMR (300 MHz, DMSO-d$_6$): δ 8.46-8.48 (d, J=7.2 Hz, 1H), 8.26-8.21 (m, 2H), 7.48 (m, 1H), 7.12-7.10 (m, 1H), 6.89 (m, 1H), 6.41 (m, 1H), 4.13-4.11 (m, 2H), 4.08-4.06 (m, 3H), 4.03-3.95 (m, 3H), 3.44-3.31 (m, 3H), 2.97 (s, 3H), 2.69-2.65 (m, 4H), 1.23-1.18 (m, 3H); HPLC (Method 1) 95.6% (AUC), t$_R$=9.28 min. ESI MS m 470 [M+H]$^+$.

Preparation of 3-(4-(2-(5-chloro-2,4-dimethoxyphenyl)imidazo[1,2-a]pyridin-7-yl)-5,6-dihydropyridin-1(2H)-yl)propanoic acid 26l (Example 141)

A mixture of ethyl 3-(4-(2-(5-chloro-2,4-dimethoxyphenyl)imidazo[1,2-a]pyridin-7-yl)-5,6-dihydropyridin-1(2H)- yl)propanoate 26k (70 mg, 0.14 mmol), lithium hydroxide (7 mg, 0.28 mmol), and water (0.5 mL) in methanol (5 mL) was stirred at it for 8 h. The reaction mixture was concentrated under reduced pressure. The residue was acidify with dilute HCl and precipitate was collected by filtration; washed with water and dried to afford 3-(4-(2-(5-chloro-2,4-dimethoxyphenyl)imidazo[1,2-a]pyridin-7-yl)-5,6-dihydropyridin-1(2H)-yl)propanoic acid 261 (29 mg, 45%) as an off-white solid.

$^1$H NMR (300 MHz, DMSO-d$_6$): δ 11.80 (br s, 1H), 8.52-8.49 (d, J=7.2 Hz, 1H), 8.29 (s, 1H), 8.21 (s, 1H), 7.75 (m, 1H), 7.15-7.13 (m, 1H), 6.90 (s, 1H), 6.43 (m, 1H), 4.03 (s, 3H), 3.95 (s, 3H), 3.74 (m, 2H), 3.22 (m, 4H), 2.78 (m, 4H); HPLC (Method 1) >99% (AUC), t$_R$=14.96 min.; ESI MS m/z 442 [M+H]$^+$.

Preparation of 2-(5-chloro-2,4-dimethoxyphenyl)-7-(1-(2-(piperidin-1-yl)ethyl)-1,2,3,6-tetrahydropyridin-4-yl)imidazo[1,2-a]pyridine 26m (Example 147)

A mixture of 2-(5-chloro-2,4-dimethoxyphenyl)-7-(1,2,3,6-tetrahydropyridin-4-yl)imidazo[1,2-a]pyridine 25 (100 mg, 0.27 mmol), cesium carbonate (74 mg, 0.54 mmol), and 4-(2-chloroethyl) piperidine hydrochloride (50 mg, 0.29 mmol) in DMF (5 mL) was refluxed for 16 h. The reaction was quenched with water and basified with ammonia solution (2 mL). The reaction mixture was extracted with ethyl acetate and washed with water. The organic phase was concentrated under reduced pressure. The residue was purified by combi-flash chromatography (silica gel, 9:1 DCM/methanol) to afford 2-(5-chloro-2,4-dimethoxyphenyl)-7-(1-(2-(piperidin-1-yl)ethyl)-1,2,3,6-tetrahydropyridin-4-yl)imidazo[1,2-a]pyridine 26m (66 mg, 51%) as an off-white solid.

$^1$H NMR (300 MHz, DMSO-d$_6$): 8.56 (d, J=7.2 Hz, 1H), 8.45 (s, 1H), 8.26 (s, 1H), 7.45 (m, 1H), 7.13-6.93 (m, 1H), 6.89 (s, 1H), 6.42 (m, 1H), 4.03 (s, 3H), 3.95 (s, 3H), 3.21 (m, 2H), 2.80-2.78 (m, 3H), 2.72-2.68 (m, 5H), 2.66-2.64 (m, 2H), 1.62-1.60 (m, 5H), 1.48-1.44 (m, 3H); HPLC (Method 1) >99% (AUC), t$_R$=8.83 min, ESI MS m/z 481 [M+H]$^+$.

Preparation of diethyl (2-(4-(2-(5-chloro-2,4-dimethoxyphenyl)imidazo[1,2-a]pyridin-7-yl)-5,6-dihydropyridin-1(2H)-yl)ethyl)phosphonate 26n (Example 194)

Diethyl (2-(4-(2-(5-chloro-2,4-dimethoxyphenyl)imidazo[1,2-a]pyridin-7-yl)-5,6-dihydropyridin-1(2H)-yl)ethyl) phosphonate 26n was prepared in the same manner diethyl (2-(4-(2-(5-chloro-2,4-dimethoxyphenyl)imidazo[1,2-a]pyridin-7-yl)piperazin-1-yl)ethyl)phosphonate 13ae and was obtained as a yellow-brown hygroscopic solid (35% yield).

$^1$H NMR (300 MHz, CDCl$_3$): δ 8.39 (s, 1H), 8.03 (s, 1H), 7.99 (d, J=7.3 Hz, 1H), 6.59 (s, 1H), 6.25 (br s, 1H), 4.19-4.06 (m, 4H), 4.00 (s, 3H), 3.95 (s, 3H), 3.26-3.20 (m, 2H), 2.86-2.72 (m, 4H), 2.62 (br s, 2H), 2.13-1.99 (m, 2H), 1.37-1.34 (m, 6H); HPLC (Method 1) 98.5% (AUC), t$_R$=9.27 min; ESI MS m/z 534 [M+H]$^+$.

Scheme 7

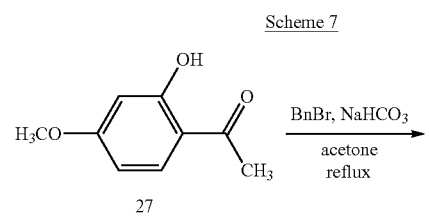

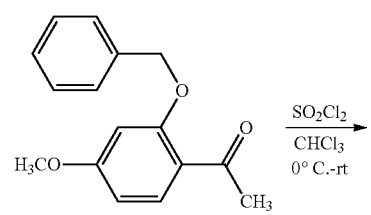

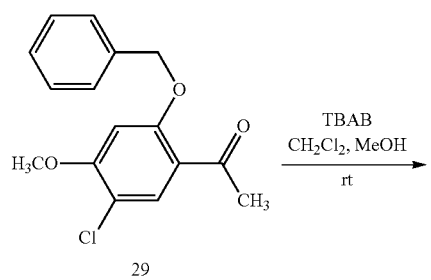

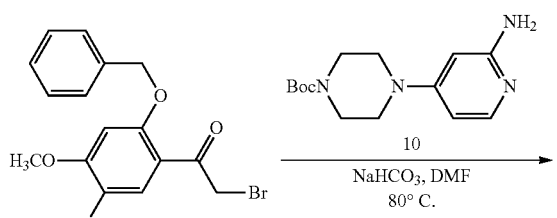

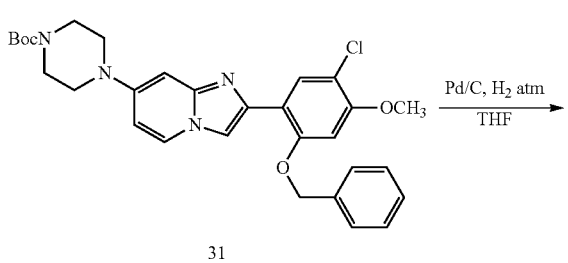

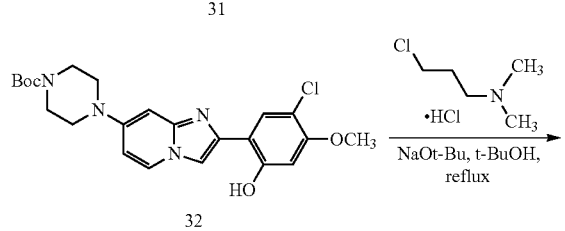

-continued

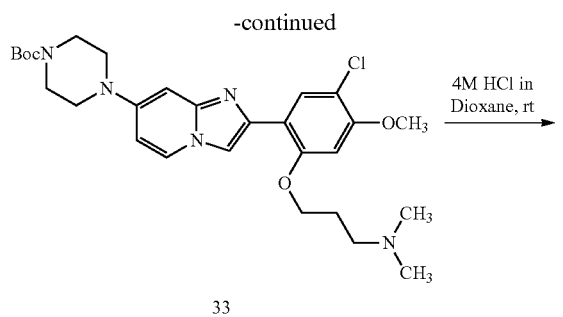

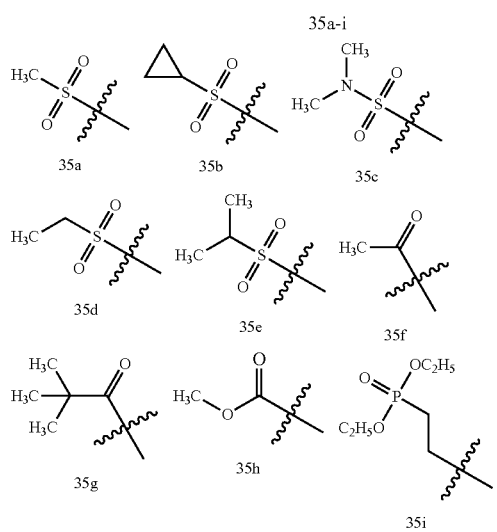

Preparation of tert-butyl 4-{2-[2-(benzyloxyl)-5-chloro-4-methoxyphenyl]imidazo[1,2-a]-pyridin-7-yl}piperazine-1-carboxylate 31

A solution of 1-[2-(benzyloxy)-5-chloro-4-methoxyphenyl]-2-bromoethanone 30 (132 mg, 0.359 mmol) and tert-butyl 4-(2-aminopyridin-4-yl)piperazine-1-carboxylate 10 (100 mg, 0.359 mmol) in acetone (2 mL) was heated at 75° C. for 16 h. The reaction mixture was cooled to room temperature; the white precipitate was collected by filtration and washed with acetone. The solid was suspended in aqueous ammonia (10 mL) and stirred for 2 h. The reaction mixture was filtered and dried under reduced pressure to give the desired compound tert-butyl 4-{2-[2-(benzyloxy)-5-chloro-4-methoxyphenyl]imidazo[1,2-a]pyridin-7-yl}piperazine-1-carboxylate 31 (140 mg, 71%) as a white solid.

$^1$H NMR (300 MHz, CD$_3$OD): δ 8.30 (d, J=7.7 Hz, 1H), 7.99 (s, 1H), 7.77 (s, 1H), 7.52-7.46 (m, 2H), 7.45-7.31 (m, 3H), 7.15 (m, 1H), 6.69 (s, 1H), 6.79-6.74 (m, 1H), 5.40 (s, 2H), 3.90 (s, 3H), 3.67-3.51 (m, 8H), 1.49 (s, 9H); HPLC (Method 3) >99% (AUC), t$_R$=19.63 min.; ESI MS m/z 549 [M+H]$^+$.

Preparation of tert-butyl 4-[2-(5-chloro-2-hydroxy-4-methoxyphenyl)imidazo[1,2-a]-pyridin-7-yl]piperazine-1-carboxylate 32

To a solution of 31 (400 mg, 0.73 mmol) in THF was charged with Pd/C (100 mg). The reaction mixture was stirred at room temperature under H$_2$ atmosphere (1 atm) for 6 h. The reaction mixture was filtered through a small pad of Celite and pad was washed with chloroform. The combined organic filtrate was concentrated under reduced pressure and the residue was purified by column chromatography (silica gel, 10:1 DCM/MeOH) to provide tert-butyl 4-[2-(5-chloro-2-hydroxy-4-methoxyphenyl) imidazo[1,2-a]pyridin-7-yl] piperazine-1-carboxylate 32 (200 mg, 60%) as a green-blue solid.

$^1$H NMR (400 MHz, CDCl$_3$): δ 7.79 (d, J=7.5 Hz, 1H), 7.52 (s, 1H), 7.49 (s, 1H), 6.74 (d, J=2.2 Hz, 1H), 6.63 (dd, J=2.4, 7.5 Hz, 1H), 6.60 (s, 1H), 3.90 (s, 3H), 3.61 (t, J=5.0 Hz, 4H), 3.23 (t, J=5.1 Hz, 4H), 1.49 (s, 9H); HPLC (Method 1) >99% (AUC), t$_R$=11.20 min.; ESI MS m/z 459 [M+H]$^+$.

Preparation of tert-butyl 4-(2-{5-chloro-2-[3-(dimethylamino)propoxy]-4-methoxyphenyl}imidazo[1,2-a]pyridin-7-yl)piperazine-1-carboxylate 33 (Example 127)

To a mixture of tert-butyl 4-[2-(5-chloro-2-hydroxy-4-methoxyphenyl)imidazo-[1,2-a]pyridin-7-yl]piperazine-1-carboxylate 32 (200 mg, 0.44 mmol) and dimethylaminepropylchloride (93 mg, 0.52 mmol) in tBuOH was added with NaOtBu (126 mg, 1.39 mmol). After stirring at 90° C. for 4 h, the reaction mixture was diluted with CH$_2$Cl$_2$/MeOH (20 mL/2 mL). The organic layer was washed with brine (10 mL), dried over sodium sulfate, and concentrated under reduced pressure. The residue was purified by column chromatography (silica gel, 1:10:0.1 methanol/DCM/ammonia hydroxide/) to afford tert-butyl 4-<2-{5-chloro-2-[3-(dimethylamino)propoxy]-4-methoxyphenyl}imidazo[1,2-a]pyridin-7-yl>piperazine-1-carboxylate 33 (130 mg, 55%) as a green-blue solid.

$^1$H NMR (400 MHz, CDCl$_3$): δ 8.38 (s, 1H), 7.92 (d, J=7.4 Hz, 1H), 7.91 (s, 1H), 6.81 (d, J=2.4 Hz, 1H), 6.59 (s, 1H), 6.55 (dd, J=2.4, 7.4 Hz, 1H), 4.19 (t, J=6.6 Hz, 2H), 3.93 (s, 3H), 3.64-3.56 (m, 4H), 3.23-3.15 (m, 4H), 2.54 (t, J=6.6 Hz, 2H), 2.29 (s, 6H), 2.20-2.08 (m, 2H), 1.49 (s, 9H); HPLC (Method 3) 97.6% (AUC), t$_R$=10.00 min.; ESI MS m/z 544 [M+H]$^+$

Preparation of 3-{4-chloro-5-methoxy-2-[7-(piperazin-1-yl)imidazo[1,2-a]pyridin-2-yl]phenoxy}-N,N-dimethylpropan-1-amine 34 (Example 139)

A solution of tert-butyl 4-(2-{5-chloro-2-[3-(dimethylamino)propoxy]-4-methoxyphenyl}imidazo[1,2-a]pyridin- 7-yl)piperazine-1-carboxylate 33 (35 mg, 0.064 mmol) in 4.0 M HCl in dioxane (1 mL) was heated at 50° C. for 1 h. The reaction mixture was cooled to room temperature and concentrated under reduced pressure, and the residue was suspended in aqueous ammonia (10 mL). The suspension was stirred at room temperature for 2 h and extracted with chloroform (2×10 mL). The combined organic layer was dried over sodium sulphate, filtered and concentrated under reduced pressure, and the residue was purified by column chromatography (silica gel, 1:10:0.1 methanol/DCM/ammonium hydroxide) to afford 3-{4-chloro-5-methoxy-2-[7-(piperazin-1-yl)imidazo[1,2-a]pyridin-2-yl]phenoxy)}-N,N-dimethylpropan-1-amine 34 (20 mg, 71%) as a blue-green solid.

$^1$H NMR (400 MHz, CDCl$_3$): δ 8.39 (s, 1H), 7.90 (d, J=7.4 Hz, 1H), 7.89 (s, 1H), 6.80 (d, J=2.4 Hz, 1H), 6.58 (s, 1H), 6.55 (dd, J=2.4, 7.4 Hz, 1H), 4.18 (t, J=6.6 Hz, 2H), 3.90 (s, 3H), 3.22-3.17 (m, 4H), 3.07-3.02 (m, 4H), 2.54 (t, J=6.6 Hz, 2H), 2.29 (s, 6H), 2.19-2.08 (m, 2H); HPLC (Method 3) 96.4% (AUC), t$_R$=14.35 min: ESI MS m/z 444 [M+H]$^+$.

Preparation of 3-(4-chloro-5-methoxy-2-{7-[4-(methylsulfonyl)piperazin-1-yl]-imidazo[1,2-a]pyridin-2-yl}phenoxy)-N,N-dimethylpropan-1-amine 35a (Example 155)

3-(4-Chloro-5-methoxy-2-{7-[4-(methylsulfonyl)piperazin-1-yl]imidazo-[1,2-a]pyridin-2-yl}phenoxy)-N,N-dimethylpropan-1-amine 35a was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (47% yield).

$^1$H NMR (400 MHz, CDCl$_3$): δ 8.38 (s, 1H), 8.00 (d, J=7.4 Hz, 1H), 7.95 (s, 1H), 6.85 (d, J=2.4 Hz, 1H), 6.58 (s, 1H), 6.53 (dd, J=2.4, 7.4 Hz, 1H), 4.19 (t, J=6.6 Hz, 2H), 3.94 (s, 3H), 3.45-3.30 (m, 8H), 2.84 (s, 3H), 2.58 (t, J=6.6 Hz, 2H), 2.32 (s, 6H), 2.22-2.10 (m, 2H); HPLC (Method 1) >99% (AUC), t$_R$=9.21 min.; APCI MS m/z 522 [M+H]$^+$.

Preparation of 3-(4-chloro-{7-[4-(cyclopropylsulfonyl)piperazin-1-yl]imidazo[1,2-a]-pyridin-2-yl}-5-methoxyphenoxy)N,N-dimethylpropan-1-amine 35b (Example 160)

3-(4-Chloro-2-{7-[4-(cyclopropylsulfonyl)piperazin-1-yl]imidazo[1,2-a]pyridin-2-yl}-5-methoxyphenoxy)-N,N-dimethylpropan-1-amine 35b was prepared in the same manner as 2-(5-chloro-2,4-dimethoxyphenyl)-7-[4-(methylsulfonyl)piperazin-1-yl]imidazo[1,2-a]-pyridine 13a and was obtained as an off-white solid (57% yield).

$^1$H NMR (400 MHz, CDCl$_3$): δ 8.38 (s, 1H), 7.94 (d, J=7.4 Hz, 1H), 7.93 (s, 1H), 6.84 (d, J=2.4 Hz, 1H), 6.59 (s, 1H), 6.53 (dd, J=2.4, 7.4 Hz, 1H), 4.19 (t, J=6.6 Hz, 2H), 3.94 (s, 3H), 3.52-3.46 (m, 4H), 3.38-3.30 (m, 4H), 2.53 (t, J=6.6 Hz, 2H), 2.34-3.29 (m, 1H), 2.29 (s, 6H), 2.18-2.08 (m, 2H), 1.26-1.18 (m, 2H), 1.06-0.98 (m, 2H); HPLC (Method 1) >99% (AUC), t$_R$=9.46 min; ESI MS m/z 548 [M+H]$^+$.

Preparation of 4(2-{5-chloro-2-[3-(dimethylamino)propoxy]-4-methoxyphenyl}imidazo[1,2-a]pyridin-7-yl)N,N-dimethylpiperazine-1-sulfonamide 35c (Example 196)

4-(2-{5-Chloro-2-[3-(dimethylamino)propoxy]-4-methoxyphenyl}imidazo[1,2-a]pyridin-7-yl)-N,N-dimethylpiperazine-1-sulfonamide 35c was prepared in the same manner as 2-(5-chloro-2,4-dimethoxyphenyl)-7-[4-(methylsulfonyl)piperazin-1-yl]imidazo[1,2-a]pyridine 13a and was obtained as a yellow solid (37% yield).

$^1$H NMR (400 MHz, CDCl$_3$): δ 8.37 (s, 1H), 7.96 (d, J=7.4 Hz, 1H), 7.93 (s, 1H), 6.82 (d, J=2.2 Hz, 1H), 6.58 (s, 1H), 6.53 (dd, J=2.3, 7.5 Hz, 1H), 4.19 (t, J=6.3 Hz, 2H), 3.93 (s, 3H), 3.43-3.40 (m, 4H), 3.29-3.27 (m, 4H), 2.87 (s, 6H), 2.56 (t, J=7.0 Hz, 2H), 2.30 (s, 6H), 2.18-2.13 (m, 2H); HPLC (Method 1) 98.4% (AUC), t$_R$=9.55 min.; ESI MS m/z 551 [M+H]$^+$.

Preparation of 3-(4-chloro-2-(7-(4-(ethylsulfonyl)piperazin-1-yl)imidazo[1,2-a]pyridin-2-yl)-5-methoxyphenoxy)-N,N-dimethylpropan-1-amine 35d (Example 199)

3-(4-Chloro-2-(7-(4-(ethylsulfonyl)piperazin-1-yl)imidazo[1,2-a]pyridin-2-yl)-5-methoxyphenoxy)-N,N-dimethylpropan-1-amine 35d was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (58% yield).

$^1$H NMR (400 MHz, CDCl$_3$): δ 8.37 (s, 1H), 7.95 (d, J=7.6, 1H), 7.93 (s, 1H), 6.83 (d, J=2.4, 1H), 6.58 (s, 1H), 6.52 (dd, J=2.4, 7.6, 1H), 4.19 (t, J=6.4, 2H), 3.93 (s, 3H), 3.50-3.45 (m, 4H), 3.34-3.29 (m, 4H), 3.01 (dd, J=7.6, 15.2, 2H), 2.35 (t, J=6.9, 2H), 2.30 (s, 6H), 2.18-2.11 (m, 2H), 1.40 (t, J=7.6, 3H); HPLC (Method 1) 94.42% (AUC), t$_R$=9.38 min.; APCI MS m/z 536 [M+H]$^+$.

Preparation of 3-(4-chloro-2-(7-(4-(isopropylsulfonyl)piperazin-1-yl)imidazo[1,2-a]-pyridin-2-yl)-5-methoxyphenoxy)-N,N-dimethylpropan-1-amine 35e (Example 197); 3-(4-Chloro-2-(7-(4-(isopropylsulfonyl)piperazin-1-yl)imidazo[1,2-a]pyridin-2-yl)-5-methoxyphenoxy)-N,N-dimethylpropan-1-amine 35e was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (22% yield).

$^1$H NMR (400 MHz, CDCl$_3$): δ 8.37 (s, 1H), 8.00 (d, J=7.3, 1H), 7.95 (s, 1H), 6.82 (d, J=2.2, 1H), 6.57 (s, 1H), 6.53 (dd, J=2.2, 7.3, 1H), 4.19 (t, J=6.4, 2H), 3.93 (s, 3H), 3.55-3.50 (m, 4H), 3.31-3.20 (m, 5H), 2.60 (t, J=7.0, 2H), 2.33 (s, 6H), 2.22-2.13 (m, 2H), 1.39 (s, 3H), 1.37 (s, 3H); HPLC (Method 1) 96.93% (AUC), t$_R$=9.57 min.; ESI MS m/z 550 [M+H]$^+$.

Preparation of 1-(4-(2-(5-chloro-2-(3-(dimethylamino)propoxy)-4-methoxyphenyl)-imidazo[1,2-a]pyridin-7-yl)piperazin-1-yl)ethanone 35f (Example 154)

Compound 1-(4-(2-(5-chloro-2-(3-(dimethylamino)propoxy)-4-methoxyphenyl)-imidazo[1,2-a]pyridin-7-yl)piperazin-1-yl)ethanone 35f was prepared in the same manner as 1-(4-(2-(5-chloro-2,4-dimethoxyphenyl)imidazo[1,2-a]pyridin-7-yl)-5,6-dihydropyridin-1(2H)-yl)ethanone 26i and was obtained as an off-white solid (66% yield).

$^1$H NMR (400 MHz, CDCl$_3$): δ 8.36 (s, 1H), 7.94 (dd, J=0.9, 7.5 Hz, 1H), 7.92 (s, 1H), 6.81 (s, 1H), 6.59 (s, 1H), 6.55 (m, 1H), 4.19 (t, J=6.5 Hz, 2H), 3.93 (s, 3H), 3.81-3.77 (m, 2H), 3.68-3.63 (m, 2H), 3.26-3.19 (m, 4H), 2.53 (t, J=7.0 Hz, 2H), 2.28 (s, 6H), 2.16 (s, 3H), 2.15-2.09 (m, 2H). HPLC (Method 1) >99% (AUC), t$_R$=8.93 min; ESI MS m/z 486 [M+H]$^+$.

Preparation of 1-(4-(2-(5-chloro-2-(3-(dimethylamino)propoxy)-4-methoxyphenyl)-imidazo[1,2-a]pyridin-7-yl)piperazin-1-yl)-2,2-dimethylpropan-1-one 35e (Example 154)

Compound 1-(4-(2-(5-chloro-2-(3-(dimethylamino)propoxy)-4-methoxyphenyl)-imidazo[1,2-a]pyridin-7-yl)piperazin-1-yl)-2,2-dimethylpropan-1-one 35g was prepared in the same manner as 1-(4-(2-(5-chloro-2,4-dimethoxyphenyl)imidazo[1,2-a]pyridin-7-yl)-5,6-dihydropyridin-1(2H)-yl)ethanone 26i and was obtained as an off-white solid (52% yield).

$^1$H NMR (400 MHz, CDCl$_3$): δ 8.37 (s, 1H), 7.99 (dd, J=7.4 Hz, 1H), 7.94 (s, 1H), 6.80 (br s, 1H), 6.58 (s, 1H), 6.55 (m, 1H), 4.19 (t, J=6.3 Hz, 2H), 3.93 (s, 3H), 3.84-3.80 (m, 4H), 3.24-3.19 (m, 4H), 2.59 (t, =7.1 Hz, 2H), 2.32 (s, 6H), 2.21-2.13 (m, 2H), 1.32 (s, 9H); HPLC (Method 1) 99.0% (AUC), t$_R$=9.58 min; ESI MS m/z 528 [M+H]$^+$.

Preparation of methyl 4-(2-(5-chloro-2-(3-(dimethylamino)propoxy-4-methoxyphenyl)-imidazo[1,2-a]pyridin-7-yl)piperazine-1-carboxylate 35h (Example 152)

Compound methyl 4-(2-(5-chloro-2-(3-(dimethylamino)propoxy)-4-methoxyphenyl)-imidazo[1,2-a]pyridin-7-yl)piperazine-1-carboxylate 35h was prepared in the same manner as 1-(4-(2-(5-chloro-2,4-dimethoxyphenyl)imidazo[1,2-a]pyridin-7-yl)-5,6-dihydropyridin-1(2H)-yl)ethanone 26i and was obtained as an off-white solid (72% yield).

$^1$H NMR (400 MHz, CDCl$_3$): δ 8.37 (s, 1H), 7.99 (dd, J=0.9, 7.5 Hz, 1H), 7.94 (s, 1H), 6.81 (s, 1H), 6.57 (s, 1H), 6.55 (dd, J=2.1, 7.52 Hz, 1H), 4.19 (t, J=6.3 Hz, 2H), 3.93 (s, 3H), 3.74 (s, 3H), 3.68-3.63 (m, 4H), 3.23-3.17 (m, 4H), 2.60 (t, J=7.2 Hz, 2H), 2.33 (s, 6H), 2.21-2.13 (m, 2H); HPLC (Method 1) >99% (AUC), t$_R$=9.29 min; ESI MS m/z 502 [M+H]$^+$.

Preparation of diethyl (2-(4-(2-(5-chloro-2-(3-(dimethylamino)propoxy)-4-methoxyphenyl)-imidazo[1,2-a]pyridin-7-yl)piperazin-1-yl)ethyl)phosphonate 35i (Example 219)

Diethyl (2-(4-(2-(5-chloro-2-(3-(dimethylamino)propoxy)-4-methoxyphenyl)imidazo[1,2-a]pyridin-7-yl)piperazin-1-yl)ethyl)phosphonate 35i was prepared in the same manner as diethyl (2-(4-(2-(5-chloro-2,4-dimethoxyphenyl)imidazo[1,2-a]pyridin-7-yl)piperazin-1-yl)ethyl)phosphonate 13ae and was obtained as a brown hygroscopic solid (12 mg, 8% yield).

$^1$H NMR (400 MHz, CDCl$_3$): δ 8.38 (s, 1H), 7.93 (d, J=7.6, 1H), 7.91 (s, 1H), 6.80 (d, J=2.2, 1H), 6.58 (s, 1H), 6.55 (dd, J=2.4, 7.6 Hz, 1H), 4.22-4.06 (m, 6H), 3.93 (s, 3H), 3.25 (t, J=4.9, 4H), 2.77-2.69 (m, 2H), 2.64 (t, J=4.9, 4H), 2.57 (t, J=7.0, 2H), 2.31 (s, 6H), 2.19-2.11 (m, 2H), 2.06-1.95 (m, 2H), 1.34 (t, J=7.0, 6H); ESI MS m/z 608 [M+H]$^+$.

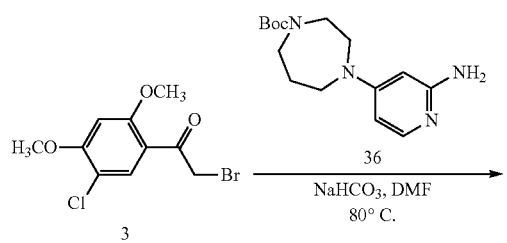

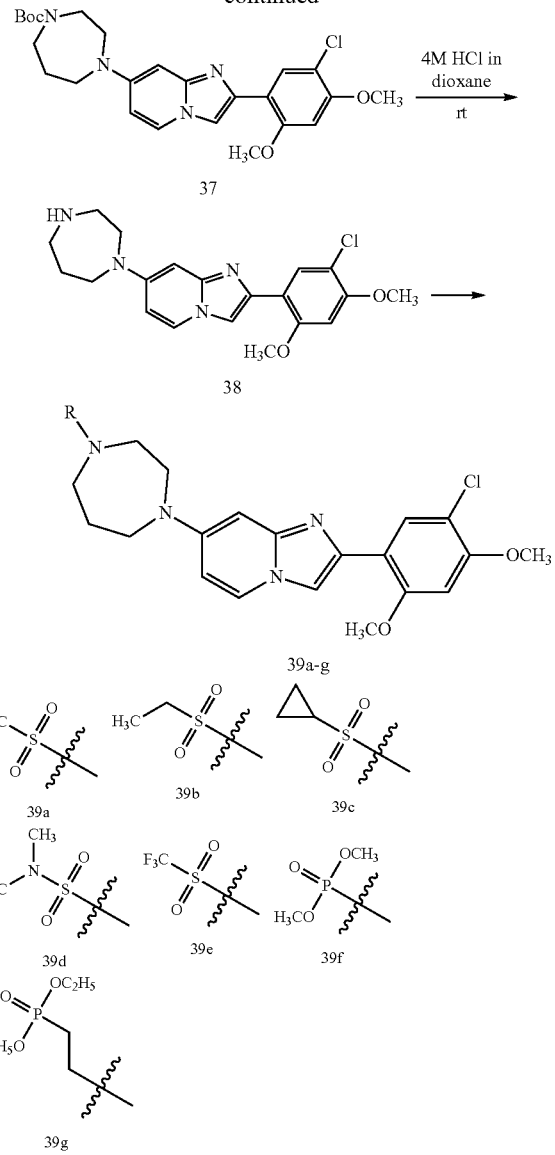

Preparation of tert-butyl 4-[2-(5-chloro-2,4-dimethoxyphenyl)imidazo[1,2-a]-pyridin-7-yl]-1,4-diazepane-1-carboxylate 37 (Example 184)

A solution of 2-bromo-1-(5-chloro-2,4-dimethoxyphenyl)ethanone 3 (200 mg, 0.681 mmol) and tert-butyl 4-(2-aminopyridin-4-yl)-1,4-diazepane-1-carboxylate 36 (198 mg, 0.681 mmol) in acetone (5 mL) was heated at 75° C. for 16 h. The reaction mixture was cooled to room temperature; the white precipitate was collected by filtration and washed with acetone. The precipitate was suspended in aqueous ammonia (10 mL) and stirred for 2 h. The solid was filtered. The solid obtained was azeotropically distilled with methanol and dried under reduced pressure to give tert-butyl 4-[2-(5-chloro-2,4-dimethoxyphenyl)imidazo[1,2-a]pyridin-7-yl]-1,4-diazepane-1-carboxylate 37 (155 mg, 47%) as a green-blue solid.

$^1$H NMR (300 MHz, CDCl$_3$): δ 8.37 (s, 1H), 7.89-7.85 (m, 2H), 6.82-6.79 (m, 1H), 6.58 (s, 1H), 6.53 (dd, J=2.4, 7.7 Hz, 1H), 4.56-4.35 (m, 1H), 3.99 (s, 3H), 3.95 (s, 3H), 3.70-3.60 (m, 3H), 2.98-2.86 (m, 2H), 2.11-2.01 (m, 2H), 1.63-1.49 (m, 2H), 1.45 (s, 9H); ESI MS m/z 487 [M+H]$^+$.

Preparation of 2-(5-chloro-2,4-dimethoxyphenyl)-7-(1,4-diazepan-1-yl)imidazo[1,2-a]-pyridine 38 (Example 189)

2-(5-Chloro-2,4-dimethoxyphenyl)-7-(1,4-diazepan-1-yl)imidazo[1,2-a]pyridine 38 was prepared in the same manner as 2-(5-chloro-2,4-dimethoxyphenyl)-7-(1,2,3,6-tetrahydropyridin-4-yl)imidazo[1,2-a]pyridine 25 and was obtained as an off-white solid (82% yield).
$^1$H NMR (300 MHz, CD$_3$OD): δ 8.37 (s, 1H), 7.85 (d, J=7.7 Hz, 1H), 7.81 (s, 1H), 6.61 (d, J=2.1 Hz, 1H), 6.58 (s, 1H), 6.44 (dd, J=2.1, 7.7 Hz, 1H), 3.99 (s, 3H), 3.95 (s, 3H), 3.63 (t, J=6.4 Hz, 2H), 3.59 (t, J=6.4 Hz, 2H), 3.06 (t, J=6.4 Hz, 2H), 2.84 (t, J=6.4 Hz, 2H), 2.00-1.90 (2H, m); ESI MS m/z 387 [M+H]$^+$.

Preparation of 2-(5-chloro-2,4-dimethoxyphenyl)-7-[4-(methylsulfonyl)-1,4-diazepan-1-yl]imidazo[1,2-a]pyridine 39a (Example 201)

Compound 2-(5-chloro-2,4-dimethoxyphenyl)-7-[4-(methylsulfonyl)-1,4-diazepan-1-yl]imidazo[1,2-a]pyridine 39a was prepared in the same manner as 2-(5-chloro-2,4-dimethoxyphenyl)-7-[4-(methylsulfonyl)piperazin-1-yl]imidazo[1,2-a]pyridine 13a and was obtained as a yellow-green solid (46% yield).
$^1$H NMR (400 MHz, CDCl$_3$): δ 8.37 (s, 1H), 7.89 (d, J=7.4 Hz, 1H), 7.82 (s, 1H), 6.67 (br s, 1H), 6.58 (s, 1H), 6.44 (dd, J=2.5, 7.5 Hz, 1H), 4.00 (s, 3H), 3.95 (s, 3H), 3.76-3.71 (m, 4H), 3.54 (t, J=5.4 Hz, 2H), 3.26 (t, J=6.0 Hz, 2H), 2.79 (s, 3H), 2.13-2.08 (m, 2H); HPLC (Method 1) 95.4% (AUC), t$_R$=10.52 min. ESI MS m/z 465 [M+H]$^+$.

Preparation of 2-(5-chloro-2,4-dimethoxyphenyl)-7-[4-(ethylsulfonyl)-1,4-diazepan-1-yl]imidazo[1,2-a]pyridine 39b (Example 206)

2-(5-Chloro-2,4-dimethoxyphenyl)-7-[4-(ethylsulfonyl)-1,4-diazepan-1-yl]imidazo[1,2-a]pyridine 39b was prepared in the same manner as sulfonamide 2-(5-chloro-2,4-dimethoxyphenyl)-7-[4-(methylsulfonyl)piperazin-1-yl]imidazo[1,2-a]pyridine 13a and was obtained as a yellow-green solid (29% yield).
$^1$H NMR (400 MHz, CDCl$_3$): δ 8.33 (s, 1H), 7.89 (d, J=7.5 Hz, 1H), 7.81 (s, 1H), 6.72 (br s, 1H), 6.57 (s, 1H), 6.46 (dd, J=2.3, 7.5 Hz, 1H), 4.00 (s, 3H), 3.95 (s, 3H), 3.77-3.71 (m, 4H), 3.56 (t, J=5.2 Hz, 2H), 3.27 (t, J=5.9 Hz, 2H), 2.98 (dd, J=7.4, 14.8 Hz, 2H), 2.14-2.08 (m, 2H), 1.30 (t, J=7.3 Hz, 3H); HPLC (Method 1) 96.5% (AUC), t$_R$=10.73 min. ESI MS m/z 479 [M+H]$^+$.

Preparation of 2-(5-chloro-2,4-dimethoxyphenyl)-7-[4-(cyclopropylsulfonyl)-1,4-diazepan-1-yl]imidazo[1,2-a]pyridine 39c (Example 187)

2-(5-Chloro-2,4-dimethoxyphenyl)-7-[4-(cyclopropylsulfonyl)-1,4-diazepan-1-yl]imidazo[1,2-a]pyridine 39c was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (33% yield).
$^1$H NMR (300 MHz, CDCl$_3$): δ 8.30 (s, 1H), 7.91 (d, J=7.4 Hz, 1H), 7.78 (s, 1H), 6.85 (s, 1H), 6.56 (s, 1H), 6.51 (dd, J=2.4, 7.4 Hz, 1H), 4.40 (s, 3H), 3.95 (s, 3H), 3.79-3.67 (m, 4H), 3.65-3.55 (m, 2H), 3.33 (t, J=5.9 Hz, 2H), 2.38-2.00 (m, 3H), 1.21-1.05 (m, 2H), 0.99-0.83 (m, 2H); HPLC (Method 1) 98.0% (AUC), t$_R$=10.88 min: ESI MS m/z 491 [M+H]$^+$.

Preparation of 4-[2-(5-chloro-2,4-dimethoxyphenyl)imidazo[1,2-a]pyridin-7-yl]-N,N-dimethyl-1,4-diazepane-1-sulfonamide 39d (Example 200)

4-[2-(5-Chloro-2,4-dimethoxyphenyl)imidazo[1,2-a]pyridin-7-yl]-N,N-dimethyl-1,4-diazepane-1-sulfonamide 39d was prepared in the same manner as 2-(5-chloro-2,4-dimethoxyphenyl)-7-[4-(methylsulfonyl)piperazin-1-yl]imidazo[1,2-a]pyridine 13a and was obtained as a yellow-green solid (51% yield).
$^1$H NMR (400 MHz, CDCl$_3$): δ 8.35 (s, 1H), 7.88 (d, J=7.5 Hz, 1H), 7.82 (s, 1H), 6.64 (br s, 1H), 6.57 (s, 1H), 6.44 (dd, J=2.4, 7.6 Hz, 1H), 3.99 (s, 3H), 3.95 (s, 3H), 3.75-3.69 (m, 4H), 3.54 (t, J=5.4 Hz, 2H), 3.29 (t, J=6.0 Hz, 2H), 2.73 (s, 6H), 2.13-2.07 (m, 2H). HPLC (Method 2) 97.7% (AUC), t$_R$=18.52 min. ESI MS m/z 494 [M+H]$^+$.

Preparation of 2-(5-chloro-2,4-dimethoxyphenyl)-7-{4-[(trifluoromethyl)sulfonyl]-1,4-diazepan-1-yl}imidazo[1,2-a]pyridine 39e (Example 188)

2-(5-Chloro-2,4-dimethoxyphenyl)-7-{4-[(trifluoromethyl)sulfonyl]-1,4-diazepan-1-yl}imidazo[1,2-a]pyridine 39e was prepared in the same manner as 2-(5-chloro-2,4-dimethoxyphenyl)-7-[4-(methylsulfonyl)piperazin-1-yl]imidazo[1,2-a]pyridine 13a and was obtained as a yellow-green solid (61% yield).
$^1$H NMR (300 MHz, DMSO-d$_6$): δ 8.48 (d, J=7.8 Hz, 1H), 8.17 (s, 1H), 8.03 (s, 1H), 7.08 (d, J=7.8 Hz, 1H), 6.95 (s, 1H), 6.62 (d, J=2.2 Hz, 1), 4.04 (s, 3H), 3.97 (s, 3H), 3.54-3.92 (m, 8H), 1.82-2.04 (m, 2H); HPLC (Method 1) 99.0% (AUC), t$_R$=11.69 min: ESI MS m/z 519 [M+H]$^+$.

Preparation of dimethyl (4-(2-(5-chloro-2,4-dimethoxyphenyl)imidazo[1,2-a]pyridin-7-yl)-1,4-diazepan-1-yl)phosphonate 39f (Example 207)

Dimethyl (4-(2-(5-chloro-2,4-dimethoxyphenyl)imidazo[1,2-a]pyridin-7-yl)-1,4-diazepan-1-yl)phosphonate 39f was prepared in the same manner diethyl (2-(4-(2-(5-chloro-2,4-dimethoxyphenyl)imidazo[1,2-a]pyridin-7-yl)piperazin-1-yl)ethyl)phosphonate 13ae and was obtained as a brown hygroscopic solid (32% yield).
$^1$H NMR (400 MHz, CDCl$_3$): δ 8.33 (s, 1H), 7.89 (d, J=7.8 Hz, 1H), 7.77 (s, 1H), 6.83 (br s, 1H), 6.57 (s, 1H), 6.50 (dd, J=2.3, 7.6 Hz, 1H), 4.01 (s, 3H), 3.95 (s, 3H), 3.72-3.60 (m, 10H), 3.43-3.36 (m, 2H), 3.18-3.10 (m, 2H), 2.04-1.97 (m, 2H); HPLC (Method 1) 94.08% (AUC), t$_R$=10.37 min.; ESI MS m/z 495 [M+H]$^+$.

Preparation of diethyl (2-(4-(2-(5-chloro-2,4-dimethoxyphenyl)imidazo[1,2-a]pyridin-7-yl)-1,4-diazepan-1-yl)ethyl)phosphonate 392 (Example 210)

Diethyl (2-(4-(2-(5-chloro-2,4-dimethoxyphenyl)imidazo[1,2-a]pyridin-7-yl)-1,4-diazepan-1-yl)ethyl)phosphonate 39g was prepared in the same manner diethyl (2-(4-(2-(5-chloro-2,4-dimethoxyphenyl)imidazo[1,2-a]pyridin-7-yl)piperazin-1-yl)ethyl)phosphonate 13ae and was obtained as a brown hygroscopic solid (18% yield).
$^1$H NMR (400 MHz, CDCl$_3$): δ 8.34 (s, 1H), 7.86 (d, J=7.5 Hz, 1H), 7.75 (s, 1H), 6.79 (br s, 1H), 6.57 (s, 1H), 6.49 (d, J=6.4 Hz, 1H), 4.13-4.03 (m, 4H), 4.01 (s, 3H), 3.95 (s, 3H), 3.63-3.53 (m, 4H), 2.88-2.78 (m, 4H), 2.62 (t, J=5.4 Hz, 2H), 2.03-1.89 (m, 4H), 1.30 (t, J=7.1 Hz, 6H); HPLC (Method 1) 96.35% (AUC), $t_R$=9.47 min.; ESI MS m/z 551 [M+H]$^+$.

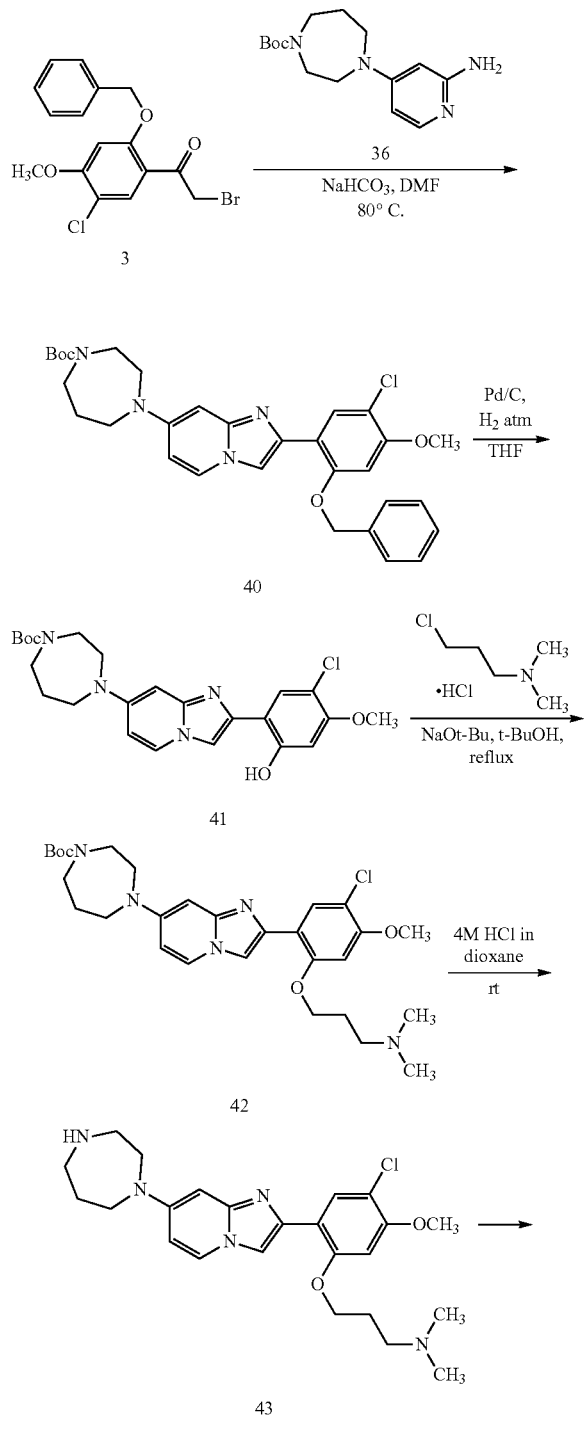

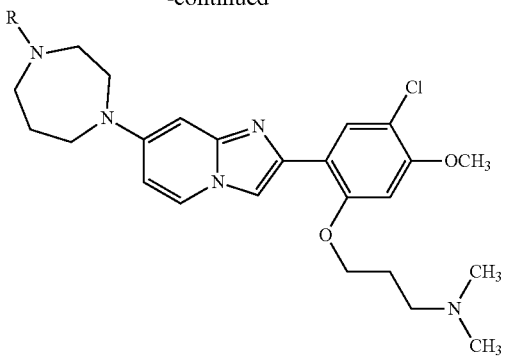

Preparation of tert-butyl 4-{2-[2-(benzyloxy)-5-chloro-4-methoxyphenyl]imidazo[1,2-a]-pyridin-7-yl}-1,4-diazepane-1-carboxylate 40 tert-Butyl 4-{2-[2-(benzyloxy)-5-chloro-4-methoxyphenyl]imidazo[1,2-a]pyridin-7-yl}-1,4-diazepane-1-carboxylate 40 was prepared in the same manner as 4-[2-(5-chloro-2,4-dimethoxyphenyl)imidazo[1,2-a]pyridin-7-yl]piperazine-1-carboxylate 11 and was obtained as a brown solid (99% yield).

$^1$H NMR (400 MHz, CDCl$_3$): δ 8.41 (s, 1H), 7.76-7.71 (m, 2H), 7.51-7.46 (m, 2H), 7.45-7.34 (m, 3H), 6.68 (br s, 1H), 6.61 (s, 1H), 6.41 (dd, J=2.2, 5.8 Hz, 1H), 5.23 (s, 2H), 3.87 (s, 3H), 3.64-3.54 (m, 6H), 3.36-3.21 (m, 2H), 2.05-1.96 (m, 2H), 1.42 (s, 9H). ESI MS m/z 563 [M+H]$^+$.

Preparation of tert-butyl 4-[2-(5-chlor-2-hydroxy-4-methoxyphenyl)imidazo[1,2-a]-pyridin-7-yl]-1,4-diazepane-1-carboxylate 41 tert-Butyl 4-[2-(5-chloro-2-hydroxy-4-methoxyphenyl)imidazo[1,2-a]pyridin-7-yl]-1,4-diazepane-1-carboxylate 41 was prepared in the same manner as 4-[2-(5-chloro-2-hydroxy-4-methoxyphenyl)imidazo[1,2-a]pyridin-7-yl]piperazine-1-carboxylate 32 and was obtained as a brown solid (81% yield).

$^1$H NMR (400 MHz, CDCl$_3$): δ 7.88 (d, J=7.4 Hz, 1H), 7.47 (s, 1H), 7.44 (s, 1H), 6.60 (s, 1H), 6.56-6.46 (m, 2H), 3.89 (s, 3H), 3.67-3.56 (m, 6H), 3.39-3.24 (m, 2H), 2.05-1.96 (m, 2H), 1.42 (s, 9H). ESI MS m/z 473 [M+H]$^+$.

Preparation of tert-butyl 4-(2-{5-chloro-2-[3-(dimethylamino)propoxy]-4-methoxyphenyl}imidazo[1,2-a]pyridin-7-yl)-1,4-diazepane-1-carboxylate 42 (Example 211)

tert-Butyl 4-(2-{5-chloro-2-[3-(dimethylamino)propoxy]-4-methoxyphenyl}imidazo-[1,2-a]pyridin-7-yl)-

1,4-diazepane-1-carboxylate 42 was prepared in the same manner as tert-butyl 4-(2-{5-chloro-2-[3-(dimethylamino)propoxy]-4-methoxyphenyl}imidazo-[1,2-a]pyridin-7-yl)piperazine-1-carboxylate 33 and was obtained as a light yellow solid (70% yield).

$^1$H NMR (400 MHz, CDCl$_3$): δ 8.38 (s, 1H), 7.89 (d, J=7.4 Hz, 1H), 7.85 (s, 1H), 6.61 (br s, 1H), 6.58 (s, 1H), 6.43 (dd, J=2.4, 7.6 Hz, 1H), 4.18 (t, J=6.6 Hz, 2H), 3.93 (s, 3H), 3.65-3.56 (m, 6H), 3.33-3.23 (m, 2H), 2.56 (t, J=6.6 Hz, 2H), 2.30 (s, 6H), 2.14 (q, J=6.4 Hz, 2H), 2.01 (t, J=5.9 Hz, 2H), 1.44-1.37 (m, 9H); HPLC (Method 1) >99% (AUC), t$_R$=9.93 min.; ESI MS m/z 558 [M+H]$^+$.

Preparation of 3-{2-[7-(1,4-diazepan-1-yl)imidazo[1,2-a]pyridin-2-yl]-4-chloro-5-methoxyphenoxy}-N,N-dimethylpropan-1-amine 43 (Example 209)

3-{2-[7-(1,4-Diazepan-1-yl)imidazo[1,2-a]pyridin-2-yl]-4-chloro-5-methoxyphenoxy}-N,N-dimethylpropan-1-amine 43 was prepared in the same manner as 2-(5-chloro-2,4-dimethoxyphenyl)-7-(piperazin-1-yl)imidazo[1,2-a]pyridine 12 and was obtained as a light yellow solid (71% yield).

$^1$H NMR (400 MHz, CDCl$_3$): δ 8.38 (s, 1H), 7.86 (d, J=7.5 Hz, 1H), 7.84 (s, 1H), 6.62-6.55 (m, 2H), 6.47-6.41 (m, 1H), 4.18 (t, J=6.4 Hz, 2H), 3.92 (s, 3H), 3.66-3.55 (m, 4H), 3.05 (t, J=5.3 Hz, 2H), 2.84 (t, J=5.6 Hz, 2H), 2.55 (t, J=7.0 Hz, 2H), 2.30 (s, 6H), 2.18-2.09 (m, 2H), 1.97-1.89 (m, 2H); HPLC (Method 1) >99% (AUC), t$_R$=9.93 min.; ESI MS m/z 558 [M+H]$^+$.

Preparation of 4-(2-{5-chloro-2-[3-(dimethylamino)propoxy]-4-methoxyphenyl}-imidazo[1,2-a]pyridin-7-yl)-N,N-dimethyl-1,4-diazepane-1-sulfonamide 44a (Example 216)

4-(2-{5-Chloro-2-[3-(dimethylamino)propoxy]-4-methoxyphenyl}imidazo[1,2-a]-pyridin-7-yl)-N,N-dimethyl-1,4-diazepane-1-sulfonamide 44 was prepared in the same manner as 2-(5-chloro-2,4-dimethoxyphenyl)-7-[4-(methylsulfonyl)piperazin-1-yl]imidazo[1,2-a]pyridine 13a and was obtained as a green yellow solid (35% yield).

$^1$H NMR (400 MHz, CDCl$_3$): δ 8.35 (s, 1H), 8.08 (d, J=7.4 Hz, 1H), 7.92 (s, 1H), 6.65 (d, J=2.1 Hz, 1H), 6.56 (s, 1H), 6.45 (dd, J=2.1, 7.4 Hz, 1H), 4.19 (t, J=6.1 Hz, 2H), 3.92 (s, 3H), 3.75-3.70 (m, 4H), 3.54 (t, J=5.6 Hz, 2H), 3.29 (t, J=5.7 Hz, 2H), 2.70 (s, 8H), 2.41 (s, 6H), 2.28-2.20 (m, 2H), 2.13-2.05 (m, 2H); HPLC (Method 1) 96.6% (AUC), t$_R$=9.52 min; ESI MS m/z 565 [M+H]$^+$.

Preparation of 3-(4-chloro-2-(7-(4-(methylsulfonyl)-1,4-diazepan-1-yl)imidazo-[1,2-a]pyridin-2-yl)-5-methoxyphenoxy)-N,N-dimethylpropan-1-amine 44b (Example 213)

Compound 3-(4-chloro-2-(7-(4-(methylsulfonyl)-1,4-diazepan-1-yl)imidazo[1,2-a]-pyridin-2-yl)-5-methoxyphenoxy)-N,N-dimethylpropan-1-amine 44b was prepared in the same manner as 2-(5-chloro-2,4-dimethoxyphenyl)-7-[4-(methylsulfonyl)piperazin-1-yl]imidazo-[1,2-a]pyridine 13a and was obtained as a green yellow solid (70% yield).

$^1$H NMR (400 MHz, CDCl$_3$): δ 8.37 (s, 1H), 7.91 (d, J=7.8, 1H), 7.87 (s, 1H), 6.61 (d, J=2.3, 1H), 6.58 (s, 1H), 6.43 (dd, J=2.6, 7.5, 1H), 4.19 (t, J=6.3 Hz, 2H), 3.93 (s, 3H), 3.76-3.70 (m, 4H), 3.56-3.52 (m, 2H), 3.27 (t, J=6.0, 2H), 2.79 (s, 3H), 2.55 (t, J=7.2, 2H), 2.30 (s, 6H), 2.16-2.09 (m, 4H); HPLC (Method 1) 93.74% (AUC), t$_R$=9.23 min.; ESI MS m/z 536 [M+H]$^+$.

Preparation of 3-(4-chloro-2-(7-(4-(cyclopropylsulfonyl)-1,4-diazepan-1-yl)imidazo[1,2-a]-pyridin-2-yl)-5-methoxyphenoxy)-N,N-dimethylpropan-1-amine 44c (Example 212)

Compound 3-(4-chloro-2-(7-(4-(cyclopropylsulfonyl)-1,4-diazepan-1-yl)imidazo-[1,2-a]pyridin-2-yl)-5-methoxyphenoxy)-N,N-dimethylpropan-1-amine 44c was prepared in the same manner as 2-(5-chloro-2,4-dimethoxyphenyl)-7-[4-(methylsulfonyl)piperazin-1-yl]imidazo[1,2-a]pyridine 13a and was obtained as a green yellow solid (32% yield).

$^1$H NMR (400 MHz, CDCl$_3$): δ 8.37 (s, 1H), 7.94 (d, J=7.4, 1H), 7.88 (s, 1H), 6.62 (d, J=2.4, 1H), 6.57 (s, 1H), 6.43 (dd, J=2.7, 7.8, 1H), 4.19 (t, J=6.7, 2H), 3.93 (s, 3H), 3.75-3.68 (m, 4H), 3.62-3.57 (m, 2H), 3.32 (t, J=5.9, 2H), 2.58 (t, J=7.0, 2H), 2.32 (s, 6H), 2.27-2.19 (m, 1H), 2.19-2.07 (m, 4H), 1.17-1.12 (m, 2H), 094-0.88 (m, 2H); HPLC (Method 1) 93.82% (AUC), t$_R$=9.49 min.; ESI MS m/% 562 [M+H]$^+$.

Preparation of 3-(4-chloro-2-(7-(4-(ethylsulfonyl)-1,4-diazepan-1-yl)imidazo[1,2-a]pyridin-2-yl)-5-methoxyphenoxy)-N,N-dimethylpropan-1-amine 44d (Example 215)

Compound 3-(4-chloro-2-(7-(4-(ethylsulfonyl)-1,4-diazepan-1-yl)imidazo-[1,2-a]pyridin-2-yl)-5-methoxyphenoxy)-N,N-dimethylpropan-1-amine 44d was prepared in the same manner as 2-(5-chloro-2,4-dimethoxyphenyl)-7-[4-(methylsulfonyl)piperazin-1-yl]imidazo[1,2-a]pyridine 13a and was obtained as a green yellow solid (30% yield).

$^1$H NMR (400 MHz, CDCl$_3$): δ 8.37 (s, 1H), 8.03 (d, J=7.5 Hz, 1H), 7.91 (s, 1H), 6.63 (d, J=2.3 Hz, 1H), 6.57 (s, 1H), 6.44 (dd, J=2.5, 7.6 Hz, 1H), 4.19 (t, J=6.3 Hz, 1H), 3.93 (s, 3H), 3.77-3.68 (m, 4H), 3.55 (t, J=5.4 Hz, 2H), 3.26 (t, J=6.0 Hz, 2H), 2.98 (q, 2H, J=7.5, 14.9 Hz), 2.67 (t, 2H, J=7.3 Hz), 2.38 (s, 6H), 2.25-2.17 (m, 2H), 2.15-2.08 (m, 2H), 1.30 (t, 3H. J=7.5 Hz); ESI MS m/z 550 [M+H]$^+$.

Preparation of diethyl (2-(4-(2-(5-chloro-2-(3-(dimethylamino)propoxy)-4-methoxyphenyl)-imidazo[1,2-a]pyridin-7-yl)-1,4-diazepan-1-yl)ethyl)phosphonate 44e (Example 214)

Compound diethyl(2-(4-(2-(5-chloro-2-(3-(dimethylamino)propoxy)-4-methoxyphenyl)imidazo[1,2-a]pyridin-7-yl)-1,4-diazepan-1-yl)ethyl)phosphonate was prepared in the same manner diethyl (2-(4-(2-(5-chloro-2,4-dimethoxyphenyl)imidazo[1,2-a]pyridin-7-yl)piperazin-1-yl)ethyl)phosphonate 13ae and was obtained as a brown hygroscopic solid (15% yield).

$^1$H NMR (400 MHz, CDCl$_3$); δ 8.38 (s, 1H), 7.92 (d, J=7.4 Hz, 1H), 7.85 (s, 1H), 6.60 (d, J=2.2 Hz, 1H), 6.57 (s, 1H), 6.43 (dd, J=2.5, 7.6 Hz, 1H), 4.19 (t, J=6.3 Hz, 2H), 4.13-4.02 (m, 4H), 3.93 (s, 3H), 3.62-3.52 (m, 4H), 2.88-2.77 (m, 4H), 2.64-2.57 (m, 4H), 2.34 (s, 6H), 2.22-2.13 (m, 2H), 2.02-1.88 (m, 4H), 1.30 (t, J=7.1 Hz, 6H). HPLC (Method 1) 95.23% (AUC), t$_R$=8.76 min.; ESI MS m/z 622 [M+H]$^+$.

Scheme 10
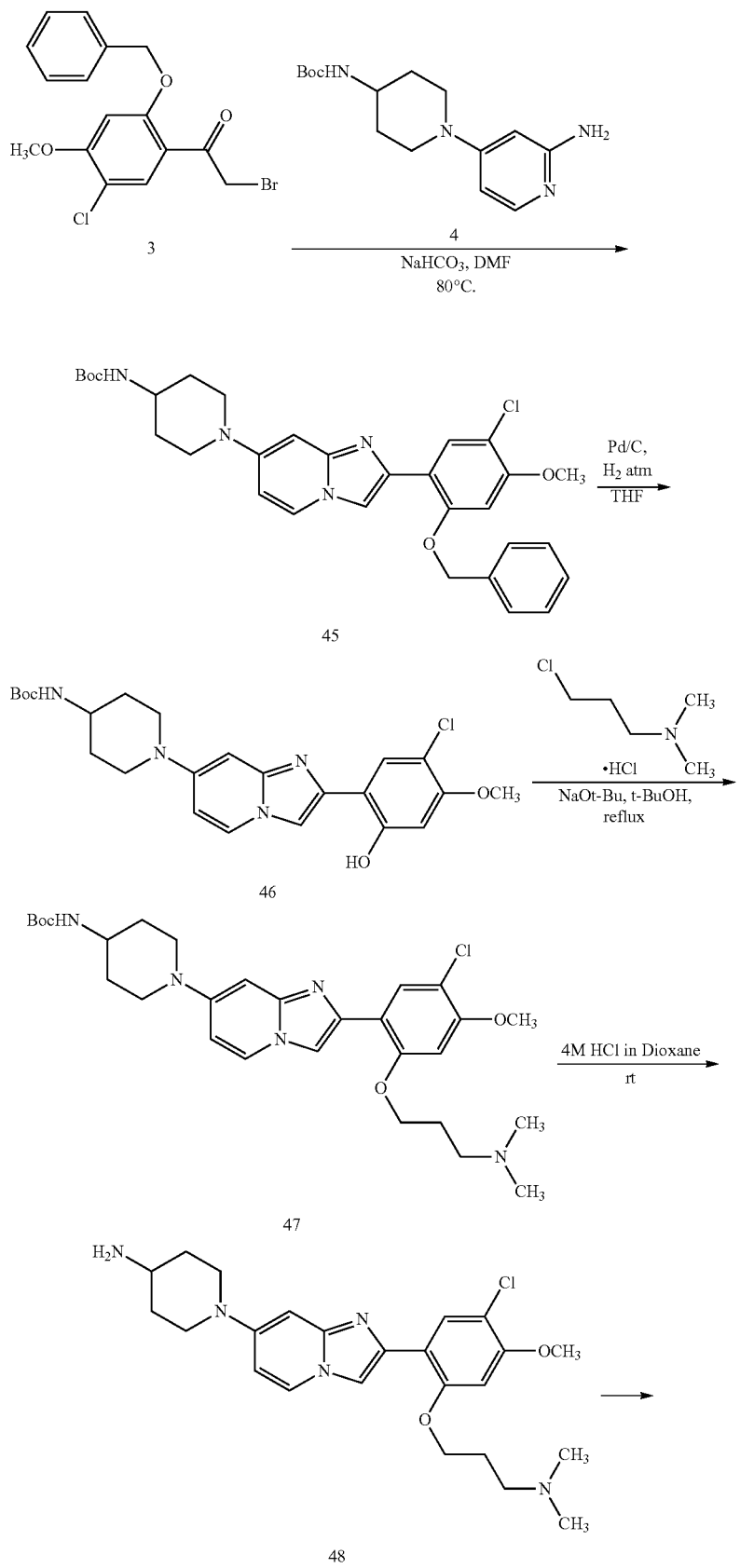

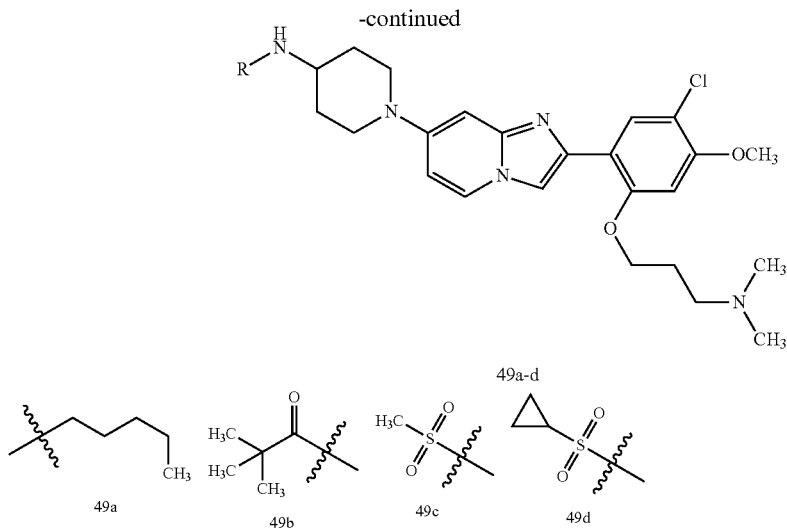

Preparation of tert-butyl (1-{2-[2-(benzyloxy)-5-chloro-4-methoxyphenyl]imidazo[1,2-a]-pyridin-7-yl}piperidin-4-yl)carbamate 45 tert-Butyl (1-{2-[2-(benzyloxy)-5-chloro-4-methoxyphenyl]imidazo[1,2-a]-pyridin-7-yl}piperidin-4-yl)carbamate 45 was prepared in the same manner as 4-[2-(5-chloro-2,4-dimethoxyphenyl)imidazo[1,2-a]pyridin-7-yl]piperazine-1-carboxylate 11 and was obtained as a yellow solid (73% yield).

$^1$H NMR (400 MHz, CDCl$_3$): δ 8.41 (s, 1H), 7.78 (s, 1H), 7.74 (d, J=7.5 Hz, 1H), 7.51-7.46 (m, 2H), 7.45-7.35 (m, 3H), 6.80 (d, J=2.2 Hz, 1H), 6.61 (s, 1H), 6.49 (dd, J=2.4, 7.5 Hz, 1H), 5.22 (s, 2H), 4.47 (br s, 1H), 3.87 (s, 3H), 3.67-3.60 (m, 3H), 2.96 (m, 2H), 2.05 (d, J=9.7 Hz, 2H), 1.57-1.47 (s, 2H), 1.45 (s, 9H). ESI MS m/z 563 [M+H]$^+$.

Preparation of tert-butyl {1-[2-(5-chloro-2-hydroxy-4-methoxyphenyl)imidazo[1,2-a]-pyridin-7-yl]piperidin-4-yl}carbamate 46 tert-Butyl {1-[2-(5-chloro-2-hydroxy-4-methoxyphenyl)imidazo[1,2-a]-pyridin-7-yl]piperidin-4-yl}carbamate 46 was prepared in the same manner as 4-[2-(5-chloro-2-hydroxy-4-methoxyphenyl)imidazo[1,2-a]pyridin-7-yl]piperazine-1-carboxylate 32 and was obtained as a yellow-brown solid (77% yield).

$^1$H NMR (400 MHz, CDCl$_3$): δ 7.90 (d, J=7.5 Hz, 1H), 7.49 (s, 1H), 7.48 (s, 1H), 6.74 (d, J=1.8 Hz, 1H), 6.65-6.59 (m, 2H), 4.48 (br s, 1H), 3.89 (s, 3H), 3.75-3.63 (m, 3H), 3.01-2.91 (m, 2H), 2.13-2.04 (m, 2H), 1.59-1.51 (m, 2H), 1.46 (s, 9H).

Preparation of tert-butyl (1-(2-{5-chloro-2-[3-(dimethylamino)propoxy]-4-methoxyphenyl}imidazo[1,2-a]pyridin-7-yl)piperidin-4-yl)carbamate 47 (Example 148)

tert-Butyl (1-(2-{5-chloro-2-[3-(dimethylamino)propoxy]-4-methoxyphenyl}-imidazo[1,2-a]pyridin-7-yl)piperidin-4-yl)carbamate 47 was prepared in the same manner as tert-butyl 4-(2-{5-chloro-2-[3-(dimethylamino)propoxy]-4-methoxyphenyl}imidazo[1,2-a]-pyridine-7-yl)piperazine-1-carboxylate 33 and was obtained as a yellow solid (68% yield).

$^1$H NMR (300 MHz, CDCl$_3$): δ 8.38 (s, 1H), 7.91 (d, J=7.6 Hz, 1H), 7.89 (s, 1H), 6.80 (d, J=2.2 Hz, 1H), 6.57 (s, 1H), 6.53 (dd, J=2.3, 7.5 Hz, 1H), 4.46 (br s, 1H), 4.18 (t, J=6.4 Hz, 2H), 3.93 (s, 3H), 3.70-3.60 (m, 3H), 2.95-2.87 (m, 2H), 2.56 (t, J=14.4 Hz, 2H), 2.30 (s, 6H), 2.19-2.05 (m, 4H), 1.60-1.48 (m, 2H), 1.46 (s, 9H). HPLC (Method 1) >99% (AUC), t$_R$=10.03 min. APCI MS m/z 558 [M+H]$^+$.

Preparation of 1-(2-{5-chloro-2-[3-(dimethylamino)propoxy]-4-methoxyphenyl}-imidazo[1,2-a]pyridin-7-yl)piperidin-4-amine 48 (Example 150)

1-(2-{5-Chloro-2-[3-(dimethylamino)propoxy]-4-methoxyphenyl}imidazo-[1,2-a]pyridin-7-yl)piperidin-4-amine 48 was prepared in the same manner as 2-(5-chloro-2,4-dimethoxyphenyl)-7-(piperazin-1-yl)imidazo[1,2-a]pyridine 12 and was obtained as a yellow solid (66% yield).

$^1$H NMR (300 MHz, CDCl$_3$): δ 8.38 (s, 1H), 7.88 (t, J=3.9 Hz, 2H), 6.80 (d, J=2.2 Hz, 1H), 6.58 (s, 1H), 6.55 (d, J=2.4 Hz, 1H), 4.18 (t, J=12.8 Hz, 2H), 3.93 (s, 3H), 3.74-3.65 (m, 2H), 2.92-2.79 (m, 3H), 2.54 (t, J=14.4 Hz, 2H), 2.29 (s, 6H), 2.18-2.09 (m, 2H), 1.99-1.89 (m, 2H), 1.56-1.41 (m, 2H). APCI MS m/z 458 [M+H]$^+$.

Preparation of 1-(2-{5-chloro-2-[3-(dimethylamino)propoxy]-4-methoxyphenyl}imidazo-[1,2-a]pyridin-7-yl)-N-pentylpiperidin-4-amine 49a (Example 165)

1-(2-{5-Chloro-2-[3-(dimethylamino)propoxy]-4-methoxyphenyl}imidazo-[1,2-a]pyridin-7-yl)-N-pentylpiperidin-4-amine 49 was prepared in the same manner as tert-butyl 4-(2-{5-chloro-2-[3-(dimethylamino)propoxy]-4-methoxyphenyl}imidazo-[1,2-a]pyridine-7-yl)piperazine-1-carboxylate 33 and was obtained as a thick yellow syrup (20% yield).

$^1$H NMR (400 MHz, CDCl$_3$): δ 8.38 (s, 1H), 7.89-7.87 (m, 2H), 6.80 (d, J=2.3 Hz, 1H), 6.58 (s, 1H), 6.56 (dd, J=2.4, 7.6 Hz, 1H), 4.18 (t, J=6.4 Hz, 2H), 3.93 (s, 3H), 3.70 (d, J=12.9 Hz, 2H), 2.87-2.81 (m, 2H), 2.66 (t, J=7.3 Hz, 3H), 2.55 (t, J=7.0 Hz, 2H), 2.30 (s, 6H), 2.19-2.11 (m, 2H), 2.04-1.98 (m, 2H), 1.53-1.48 (m, 3H), 1.36-1.28 (m, 4H), 0.92-0.88 (m, 4H); HPLC (Method 1) 97.1% (AUC), t$_R$=8.99 min.; APCI MS m/z 528 [M+H]$^+$.

Preparation of N-(1-(2-(5-chloro-2-(3-(dimethyl-amino)propoxy)-4-methoxyphenyl)-imidazo[1,2-a]pyridin-7-yl)piperidin-4-yl)pivalamide 49b (Example 162)

N-(1-(2-(5-Chloro-2-(3-(dimethylamino)propoxy)-4-methoxyphenyl)imidazo-[1,2-a]pyridin-7-yl)piperidin-4-yl)pivalamide 49b was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (33% yield).

$^1$H NMR (400 MHz, CDCl$_3$): δ 8.38 (s, 1H), 7.91-7.87 (m, 2H), 6.81 (d, J=2.1, 1H), 6.58 (s, 1H), 6.54 (dd, J=2.4, 7.6 Hz, 1H), 5.47 (d, J=7.6 Hz, 1H), 4.18 (t, J=6.4 Hz, 2H), 4.02-3.95 (m, 1H), 3.93 (s, 3H), 3.68 (d, J=12.7 Hz, 2H), 3.01-2.92 (m, 2H), 2.54 (t, J=7.0, 2 Hz, 2H), 2.29 (s, 6H), 2.17-2.10 (m, 2H), 2.08-2.00 (m, 2H), 1.59-1.48 (m, 2H), 1.19 (s, 9H); APCI MS m/z 542 [M+H]$^+$.

Preparation of N-(1-(2-(5-chloro-2-(3-(dimethyl-amino)propoxy)-4-methoxyphenyl)-imidazo[1,2-a]pyridin-7-yl)piperidin-4-yl)methanesulfonamide 49c (Example 164)

N-(1-(2-(5-Chloro-2-(3-(dimethylamino)propoxy)-4-methoxyphenyl)imidazo-[1,2-a]pyridin-7-yl)piperidin-4-yl)methanesulfonamide 49c was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (61% yield).

$^1$H NMR (400 MHz, CDCl$_3$); δ 8.37 (s, 1H), 7.92-7.89 (m, 2H), 6.81 (d, J=2.3 Hz, 1H), 6.51 (s, 1H), 6.52 (dd, J=2.4, 7.5 Hz, 1H), 4.40 (d, J=6.3 Hz, 1H), 4.18 (t, J=6.4 Hz, 2H), 3.93 (s, 3H), 3.70-3.63 (m, 2H), 3.58-3.48 (m, 1H), 3.02 (s, 3H), 2.97-2.88 (m, 2H), 2.54 (t, J=7.0 Hz, 1H), 2.29 (s, 6H), 2.17-2.09 (m, 4H), 1.74-1.69 (m, 2H); APCI MS m/z 536 [M+H]$^+$.

Preparation of N-(1-(2-(5-chloro-2-(3-(dimethyl-amino)propoxy)-4-methoxyphenyl)imidazo-[1,2-a]pyridin-7-yl)piperidin-4-yl)cyclopropanesulfonamide 49d (Example 163)

N-(1-(2-(5-Chloro-2-(3-(dimethylamino)propoxy)-4-methoxyphenyl)imidazo-[1,2-a]pyridin-7-yl)piperidin-4-yl)cyclopropanesulfonamide 49d was prepared in the same manner as 2-(5-chloro-2,4-dimethoxyphenyl)-7-[4-(methylsulfonyl)piperazin-1-yl]imidazo[1,2-a]pyridine 13a and was obtained as an yellow solid (51% yield).

$^1$H NMR (400 MHz, CDCl$_3$): δ 8.37 (s, 1H), 7.93 (d, J=7.5 Hz, 1H), 7.91 (s, 1H), 6.81 (d, J=2.2 Hz, 1H), 6.58 (s, 1H), 6.53 (dd, J=2.4, 7.6 Hz, 1H), 4.24 (d, J=7.7 Hz, 1H), 4.19 (t, J=6.4 Hz, 2H), 3.93 (s, 3H), 3.70-3.63 (m, 2H), 3.59-3.50 (m, 1H), 2.97-2.88 (m, 2H), 2.57 (t, J=7.0 Hz, 2H), 2.49-2.42 (m, 1H), 2.31 (s, 6H), 2.19-2.11 (m, 4H), 1.75-1.66 (m, 2H), 1.23-1.18 (m, 2H), 1.06-1.00 (m, 2H); HPLC (Method 1) 97.23% (AUC), t$_R$=9.42 min.; ESI MS m/z 562 [M+H]$^+$.

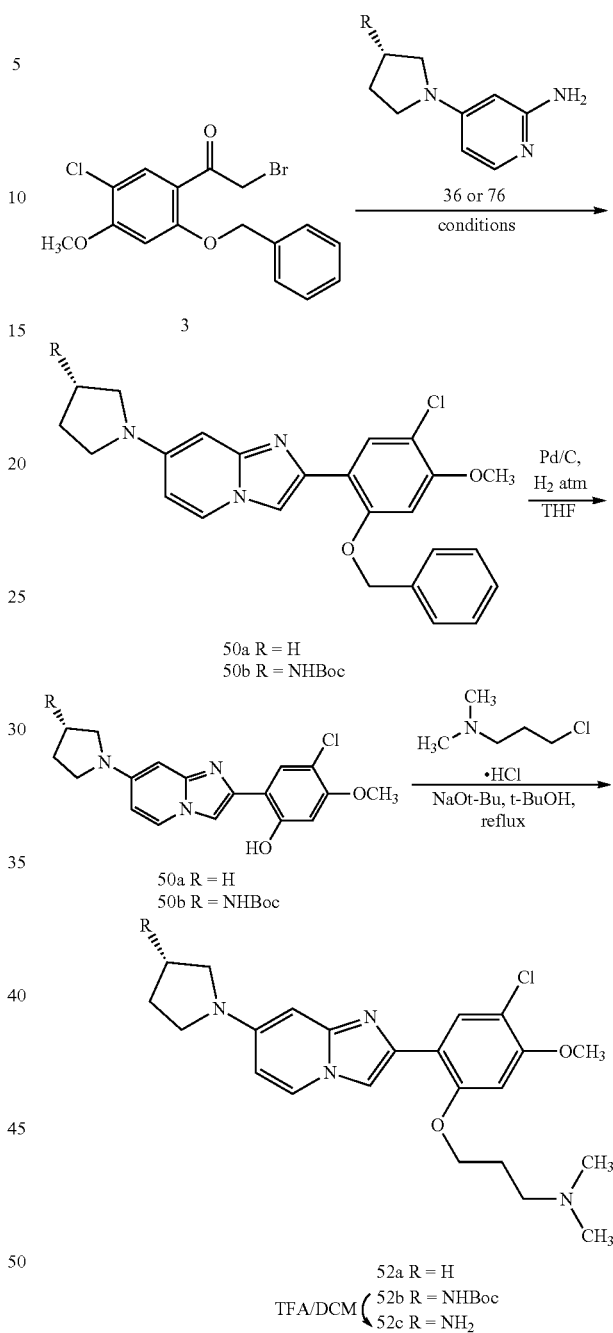

Scheme 11

50a R = H
50b R = NHBoc

50a R = H
50b R = NHBoc

52a R = H
52b R = NHBoc
52c R = NH$_2$

TFA/DCM

Preparation of 2-[2-(benzyloxy)-5-chloro-4-methoxyphenyl]-7-(pyrrolidin-1-yl)imidazo-[1,2-a]pyridine 50a Compound 2-[2-(benzyloxy)-5-chloro-4-methoxyphenyl]-7-(pyrrolidin-1-yl)imidazo-[1,2-a]pyridine 50a was prepared in the same manner as tert-butyl 4-{2-[2-(benzyloxy)-5-chloro-4-methoxyphenyl]imidazo[1,2-a]pyridin-7-yl}piperazine-1-carboxylate 31 and was obtained as an off-white solid (80% yield).

$^1$H NMR (400 MHz, CDCl$_3$): δ 8.43 (s, 1H), 7.78 (s, 1H), 7.71 (d, J=7.4 Hz, 1H), 7.52-7.48 (m, 2H), 7.45-7.34 (m,

3H), 6.60 (s, 1H), 6.42 (d, J=2.0 Hz, 1H), 6.29 (dd, J=2.3, 7.4 Hz, 1H), 5.23 (s, 2H), 3.87 (s, 3H), 3.37-3.31 (m, 4H), 2.06-2.01 (m, 4H); ESI MS m/z 434 [M+H]⁺.

Preparation of (S)-tert-butyl (1-(2-(2-(benzyloxy)-5-chloro-4-methoxyphenyl)imidazo[1,2-a]pyridin-7-yl)pyrrolidin-3-yl)carbamate 50b Compound (S)-tert-butyl (1-(2-(2-(benzyloxy)-5-chloro-4-methoxyphenyl)imidazo[1,2-a]pyridin-7-yl)pyrrolidin-3-yl)carbamate 50b was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e and was obtained as an off-white solid (74% yield).
¹H NMR (400 MHz, CDCl₃): δ δ8.42 (s, 1H), 7.76 (s, 1H), 7.73 (d, J=7.5 Hz, 1H), 7.53-7.47 (m, 2H), 7.46-7.37 (m, 3H), 6.61 (s, 1H), 6.43 (s, 1H), 6.26 (dd, J=2.2, 7.4 Hz, 1H), 5.23 (s, 2H), 4.70 (bs, 1H), 4.36 (bs, 1H), 3.87 (s, 3H), 3.68-3.58 (m, 1H), 3.52-3.33 (m, 3H), 3.26-3.16 (m, 1H), 2.38-2.24 (m, 1H), 2.04-1.92 (m, 1H), 1.46 (s, 9H); HPLC (Method 1) 95.2% (AUC), t$_R$=12.46 min.; ESI MS m/z 549 [M+H]⁺.

Preparation of 4-chloro-5-methoxy-2-[7-(pyrrolidin-1-yl)imidazo[1,2-a]pyridin-2-yl]phenol 51a 4-Chloro-5-methoxy-2-[7-(pyrrolidin-1-yl)imidazo[1,2-a]pyridin-2-yl]phenol 51a was prepared in the same manner as 4-[2-(5-chloro-2-hydroxy-4-methoxyphenyl)imidazo-[1,2-a]pyridin-7-yl]piperazine-1-carboxylate 32 and was obtained as a brown solid (76% yield).
¹H NMR (400 MHz, CDCl₃): δ 7.85 (d, J=7.4 Hz, 1H), 7.47 (s, 1H), 7.42 (s, 1H), 6.61 (s, 1H), 6.39 (dd, J=2.4, 7.4 Hz, 1H), 6.34 (s, 1H), 3.89 (s, 3H), 3.39-3.33 (m, 4H), 2.09-2.03 (m, 4H); HPLC (Method 3) 97.56% (AUC), t$_R$=17.45 min.; ESI MS m/z 344 [M+H]⁺.

Preparation of (S)-tert-butyl (1-(2-(5-chloro-2-hydroxy-4-methoxyphenyl)imidazo[1,2-a]pyridin-7-yl)pyrrolidin-3-yl)carbamate 51b Compound (S)-tert-butyl (1-(2-(5-chloro-2-hydroxy-4-methoxyphenyl)imidazo[1,2-a]pyridin-7-yl)pyrrolidin-3-yl)carbamate 51b was prepared in the same manner as tert-butyl 4-[2-(5-chloro-2-hydroxy-4-methoxyphenyl)imidazo[1,2-a]pyridin-7-yl]piperazine-1-carboxylate 32 and was obtained as a brown solid (93% yield).
¹H NMR (400 MHz, CDCl₃): δ 7.87 (d, J=6.5 Hz, 1H), 7.47 (s, 1H), 7.44 (s, 1H), 6.60 (s, 1H), 6.39-6.33 (m, 2H), 4.72 (bs, 1H), 4.38 (bs, 1H), 3.89 (s, 3H), 3.69-3.62 (m, 1H), 3.53-3.38 (m, 2H), 3.26-3.20 (m, 1H), 2.38-2.28 (m, 1H), 2.05-1.95 (m, 1H), 1.46 (s, 9H); HPLC (Same as Method 1, UV was 220 nM) 97.7% (AUC), t$_R$=11.37 min.; ESI MS m/z 459 [M+H]⁺.

Preparation of 3-{4-chloro-5-methoxy-2-[7-(pyrrolidin-1-yl)imidazo[1,2-a]pyridin-2-yl]-phenoxy}-N,N-dimethylpropan-1-amine 52a (Example 80)

3-{4-Chloro-5-methoxy-2-[7-(pyrrolidin-1-yl)imidazo[1,2-a]pyridin-2-yl]-phenoxy}-N,N-dimethylpropan-1-amine 52 was prepared in the same manner as tert-butyl 4-<2-{5-chloro-2-[3-(dimethylamino)propoxy]-4-methoxyphenyl}imidazo[1,2-a]pyridine-7-yl>piperazine-1-carboxylate 33 and was obtained as a brown solid (56% yield).
¹H NMR (400 MHz, CDCl₃): δ 8.41 (s, 1H), 7.86 (d, J=7.4 Hz, 1H), 7.83 (s, 1H), 6.57 (s, 1H), 6.44 (s, 1H), 6.33 (dd, J=2.2, 7.4 Hz, 1H), 4.18 (t, J=6.4 Hz, 2H), 3.92 (s, 3H), 3.38-3.32 (m, 4H), 2.56 (t, J=7.0 Hz, 2H), 2.30 (s, 6H), 2.19-2.10 (m, 2H), 2.06-2.02 (m, 4H); HPLC (Method 3) 95.6% (AUC), t$_R$=15.89 min; APCI MS m/z 429 [M+H]⁺.

Preparation of (S)-tert-butyl (1-(2-(5-chloro-2-(3-(dimethylamino)propoxy)-4-methoxyphenyl)imidazo[1,2-a]pyridin-7-yl)pyrrolidin-3-yl)carbamate 52b Compound (S)-tert-butyl (1-(2-(5-chloro-2-(3-(dimethylamino)propoxy)-4-methoxyphenyl)imidazo[1,2-a]pyridin-7-yl)pyrrolidin-3-yl)carbamate 52b was prepared in the same manner as tert-butyl 4-(2-{5-chloro-2-[3-(dimethylamino)propoxy]-4-methoxyphenyl}imidazo[1,2-a]pyridine-7-yl)piperazine-1-carboxylate 33 and was obtained as a light purple solid (520% yield).
¹H NMR (400 MHz, CDCl₃): δ 8.39 (s, 1H), 7.89-7.84 (m, 2H), 6.57 (s, 1H), 6.43 (d, J=2.1 Hz, 1H), 6.31 (dd, J=2.5, 7.6 Hz, 1H), 4.72 (bs, 1H), 4.38 (bs, 1H), 4.18 (t, J=6.5, 13 Hz, 2H), 3.93 (s, 3H), 3.68-3.61 (m, 1H), 3.52-3.44 (m, 1H), 3.44-3.36 (m, 1H), 3.26-3.19 (m, 1H), 2.54 (t, J=7.2, 14.4 Hz, 2H), 2.38-2.26 (m, 7H), 2.18-2.09 (m, 2H), 2.03-1.94 (m, 1H), 1.46 (s, 9H); HPLC (Method 1) 98.2% (AUC), t$_R$=10.04 min; ESI MS m/z 544 [M+H]⁺.

Preparation of (S)-1-(2-(5-chloro-2-(3-(dimethylamino)propoxy)-4-methoxyphenyl)imidazo[1,2-a]pyridin-7-yl)pyrrolidin-3-amine 52c (Example 432)

Compound (S)-tert-butyl (1-(2-(5-chloro-2-(3-(dimethylamino)propoxy)-4-methoxyphenyl)imidazo[1,2-a]pyridin-7-yl)pyrrolidin-3-yl)carbamate 52b was treated with TFA/CH₂Cl₂ for 2 h at room temperature, concentrated and basified with ammonium hydroxide to give (S)-1-(2-(5-chloro-2-(3-(dimethylamino)propoxy)-4-methoxyphenyl)imidazo[1,2-a]pyridin-7-yl)pyrrolidin-3-amine 52c as amorphous purple solid (95% yield).
¹H NMR (400 MHz, CDCl₃): δ 8.40 (s, 1H), 7.88-7.82 (m, 2H), 6.57 (s, 1H), 6.42 (d, J=2.3 Hz, 1H), 6.31 (dd, J=2.3, 7.4 Hz, 1H), 4.18 (t, J=6.5, 13.0 Hz, 2H), 3.92 (s, 3H), 3.80-3.73 (m, 1H), 3.61-3.50 (m, 2H), 3.42-3.36 (m, 1H), 3.11-3.05 (m, 1H), 2.54 (t, J=6.8, 14.3 Hz, 2H), 2.29 (s, 6H), 2.28-2.21 (m, 1H), 2.18-2.09 (m, 2H), 1.89-1.79 (m, 1H); HPLC (Method 1) >99% (AUC), t$_R$=15.23 min; ESI MS m/z 444 [M+H]⁺.

Scheme 12

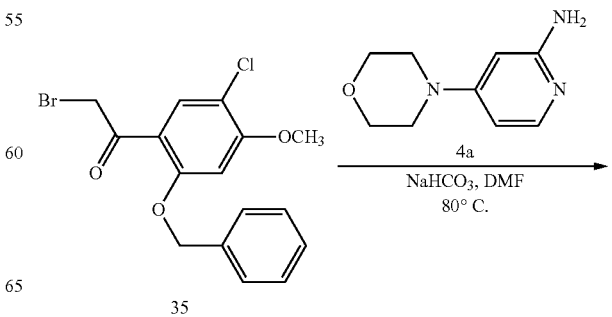

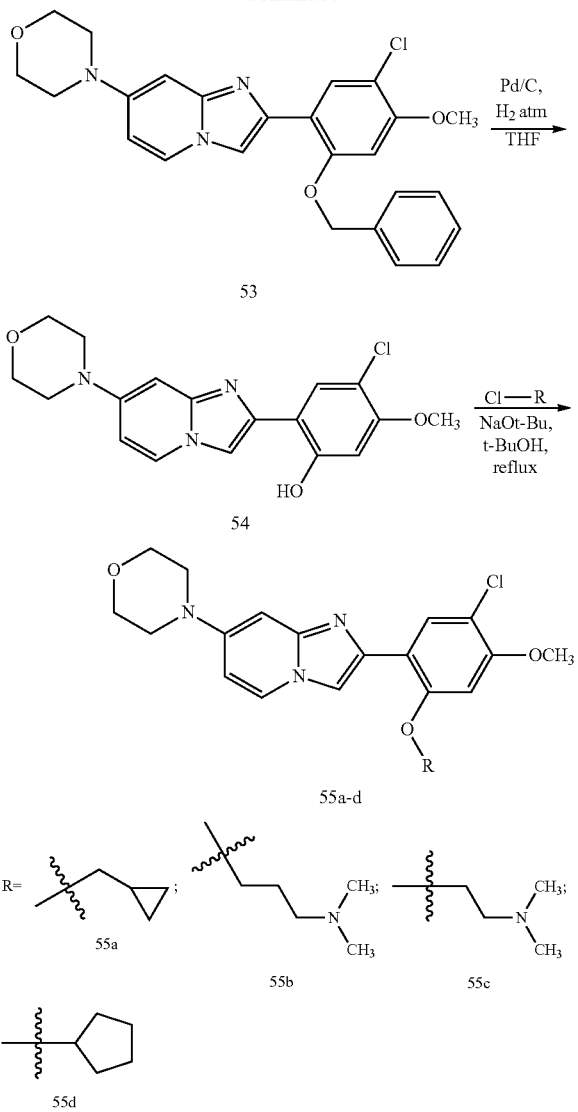

Preparation of 4-(2-(2-(benzyloxy)-5-chloro-4-methoxyphenyl)imidazo[1,2-a]pyridin-7-yl)-morpholine 53

Compound 2-[2-(benzyloxy)-5-chloro-4-methoxyphenyl]-7-(pyrrolidin-1-yl)imidazo-[1,2-a]pyridine 50 was prepared in the same manner as tert-butyl 4-{2-[2-(benzyloxy)-5-chloro-4-methoxyphenyl]imidazo[1,2-a]pyridin-7-yl}piperazine-1-carboxylate 31 and was obtained as an off-white solid (94% yield).

Preparation of 4-chloro-5-methoxy-2-(7-morpholinoimidazo[1,2-a]pyridin-2-yl)phenol 54

Compound 4-chloro-5-methoxy-2-(7-morpholinoimidazo[1,2-a]pyridin-2-yl)phenol 54 was prepared in the same manner as 4-[2-(5-chloro-2-hydroxy-4-methoxyphenyl)imidazo[1,2-a]-pyridin-7-yl]piperazine-1-carboxylate 32 and was obtained as off white solid (62% yield).

Preparation of 4-(2-(5-chloro-2-(cyclopropylmethoxy)-4-methoxyphenyl)imidazo-[1,2-a]pyridin-7-yl)morpholine 55a (Example 84)

Compound 4-(2-(5-chloro-2-(cyclopropylmethoxy)-4-methoxyphenyl)imidazo-[1,2-a]pyridin-7-yl)morpholine 55a was prepared in the same manner as tert-butyl 4-(2-{5-chloro-2-[3-(dimethylamino)propoxy]-4-methoxyphenyl}imidazo[1,2-a]pyridine-7-yl)piperazine-1-carboxylate 33 and was obtained as a brown solid (56% yield).

$^1$H NMR (400 MHz, CDCl$_3$): δ 8.40 (s, 1H), 8.03 (s, 1H), 7.92 (d, J=7.5 Hz, 1H), 6.83 (s, 1H), 6.54 (dd, J=2.4, 7.5 Hz, 1H), 6.52 (s, 1H), 3.96 (d, J=7.0 Hz, 1H), 3.92 (s, 3H), 3.90-3.85 (m, 4H), 3.23-3.18 (m, 4H), 0.76-0.70 (m, 2H), 0.47-0.42 (m, 2H); HPLC (Method 3) 98.50% (AUC), $t_R$=18.03 min; APCI MS m z 414 [M+H]$^+$.

Preparation of 3-(4-chloro-5-methoxy-2-(7-morpholinoimidazo[1,2-a]pyridin-2-yl)-phenoxy)-N,N-dimethylpropan-1-amine 55b (Example 85)

Compound 3-(4-chloro-5-methoxy-2-(7-morpholinoimidazo[1,2-a]pyridin-2-yl)-phenoxy)-N,N-dimethylpropan-1-amine 55b was prepared in the same manner as tert-butyl 4-(2-{5-chloro-2-[3-(dimethylamino)propoxy]-4-methoxyphenyl}imidazo[1,2-a]pyridine-7-yl)piperazine-1-carboxylate 33 and was obtained as a brown solid (52% yield).

$^1$H NMR (400 MHz, CDCl$_3$): δ 8.38 (s, 1H), 7.96 (d, J=7.5 Hz, 1H), 7.92 (s, 1H), 6.81 (d, J=2.3 Hz, 1H), 6.57 (s, 1H), 6.54 (dd, J=2.4, 7.5 Hz, 1H), 4.19 (t, J=6.4 Hz, 2H), 3.93 (s, 3H), 3.90-3.85 (m, 4H), 3.23-3.27 (m, 4H), 2.57 (t, J=7.0 Hz, 2H), 2.32 (s, 6H), 2.20-2.11 (m, 2H); HPLC (Method 3) 98.13% (AUC), $t_R$=15.36 min; APCI MS m/z 445 [M+H]$^+$.

Preparation of 2-(4-chloro-5-methoxy-2-(7-morpholinoimidazo[1,2-a]pyridin-2-yl)-phenoxy)-N,N-dimethylethanamine 55c (Example 98)

Compound 2-(4-chloro-5-methoxy-2-(7-morpholinoimidazo[1,2-a]pyridin-2-yl)-phenoxy)-N,N-dimethylethanamine 55c was prepared in the same manner as tert-butyl 4-(2-{5-chloro-2-[3-(dimethylamino)propoxy]-4-methoxyphenyl}imidazo[1,2-a]pyridine-7-yl)piperazine-1-carboxylate 33 and was obtained as a brown solid (63% yield).

$^1$H NMR (400 MHz, CDCl$_3$): δ 8.37 (s, 1H), 8.09 (s, 1H), 7.91 (d, J=7.30 Hz, 1H), 6.81 (br s, 1H), 6.59 (s, 1H), 6.52 (d, J=7.30 Hz, 1H), 4.23-4.21 (m, 2H), 3.93 (s, 3H), 3.89-3.87 (m, 4H), 3.22-3.20 (m, 4H), 2.88-2.86 (m, 2H), 2.39 (s, 6H); HPLC (Method 3) 99.0% (AUC), $t_R$=15.19 min; ESI MS m/z 431 [M+H]$^+$.

Preparation of 4-(2-(5-chloro-2-(cyclopentyloxy)-4-methoxyphenyl)imidazo[1,2-a]-pyridin-7-yl)morpholine 55d (Example 90)

Compound 4-(2-(5-chloro-2-(cyclopentyloxy)-4-methoxyphenyl)imidazo[1,2-a]-pyridin-7-yl)morpholine 55d was prepared in the same manner as tert-butyl 4-(2-{5-chloro-2-[3-(dimethylamino)propoxy]-4-methoxyphenyl}imidazo[1,2-a]pyridine-7-yl)piperazine-1-carboxylate 33 and was obtained as a brown solid (30% yield).

¹H NMR (400 MHz, CDCl₃): δ 8.39 (s, 1H), 7.92 (d, J=7.5 Hz, 1H), 7.85 (s, 1H), 6.86 (s, 1H), 6.59-6.51 (m, 2H), 4.97-4.91 (m, 1H), 3.93 (s, 3H), 3.90-3.83 (m, 4H), 3.25-3.17 (m, 4H), 2.07-1.96 (m, 4H), 1.92-1.81 (m, 2H), 1.77-1.68 (m, 2H); HPLC (Method 2) 97.69% (AUC), $t_R$=19.79 min; APCI MS m/z 428 [M+H]⁺.

Scheme 13

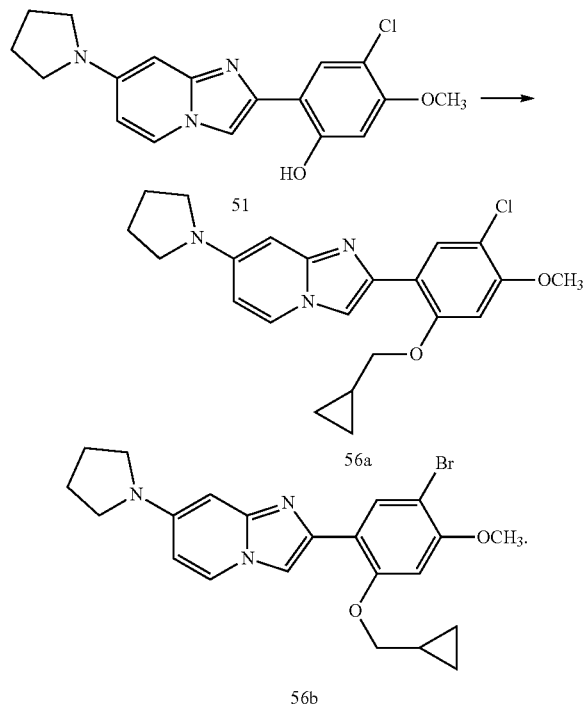

56b was prepared in the same manner as 56a from the corresponding C-5' bromo analogue Preparation of 2-(5-chloro-2-(cyclopropylmethoxy)-4-methoxyphenyl)-7-(pyrrolidin-1-yl)imidazo[1,2-a]pyridine 56a (Example 82)

2-(5-Chloro-2-(cyclopropylmethoxy)-4-methoxyphenyl)-7-(pyrrolidin-1-yl)-imidazo[1,2-a]pyridine 56c was prepared in the same manner as tert-butyl 4-(2-{5-chloro-2-[3-(dimethylamino)propoxy]-4-methoxyphenyl}imidazo[1,2-a]pyridine-7-yl)piperazine-1-carboxylate 33 and was obtained as a brown solid (31% yield).

¹H NMR (400 MHz, CDCl₃): δ 8.43 (s, 1H), 7.94 (s, 1H), 7.85 (d, J=7.4 Hz, 1H), 6.51 (s, 2H), 6.37-6.33 (m, 1H), 3.96 (d, J=7.0 Hz, 2H), 3.91 (s, 3H), 3.40-3.33 (m, 4H), 2.09-2.01 (m, 4H), 0.76-0.70 (m, 2H), 0.47-0.42 (m, 2H); ESI MS ml: 398 [M+H]⁺.

Preparation of 2-(5-bromo-2-(cyclopropylmethoxy)-4-methoxyphenyl)-7-(pyrrolidin-1-yl)-imidazo[1,2-a]pyridine hydrobromide 56b (Example 53)

2-(5-Bromo-2-(cyclopropylmethoxy)-4-methoxyphenyl)-7-(pyrrolidin-1-yl)-imidazo[1,2-a]pyridine hydrobromide 56b was prepared in the same manner as 2-(5-chloro-2-(cyclopropylmethoxy)-4-methoxyphenyl)-7-(pyrrolidin-1-yl)imidazo[1,2-a]pyridine 56a by using 2-bromo-1-(5-bromo-2,4-dimethoxyphenyl)ethanone 7 and was obtained as a white solid (39% yield).

¹H NMR (400 MHz, DMSO-d₆): δ 13.04 (s, 1H), 8.61 (d, J=7.5 Hz, 1H), 8.11 (s, 1H), 8.02 (s, 1H), 6.95 (s, 1H), 6.93 (s, 1H), 6.27 (s, 1H), 5.06-4.97 (m, 1H), 3.94 (s, 3H), 3.48-3.40 (m, 4H), 2.06-1.99 (m, 4H), 1.44 (s, 3H), 1.42 (s, 3H). HPLC (Method 3) >99% (AUC), $t_R$=18.93 min; ESI MS m/z 430 [M+H]⁺.

Scheme 14

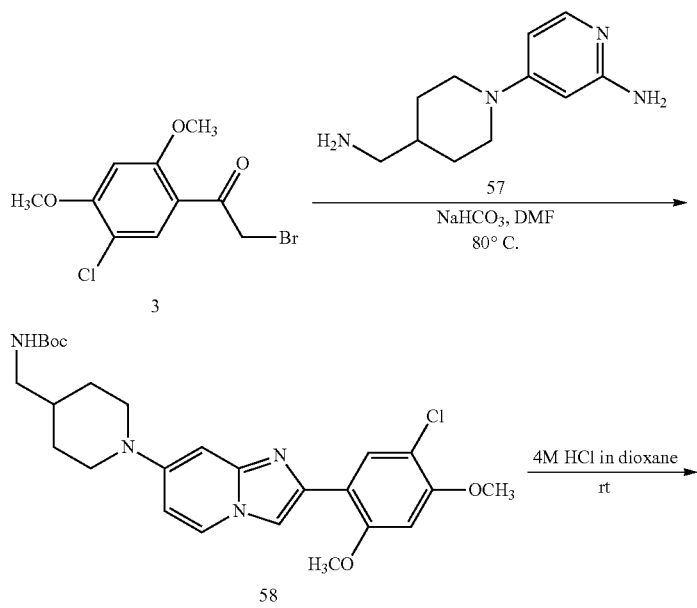

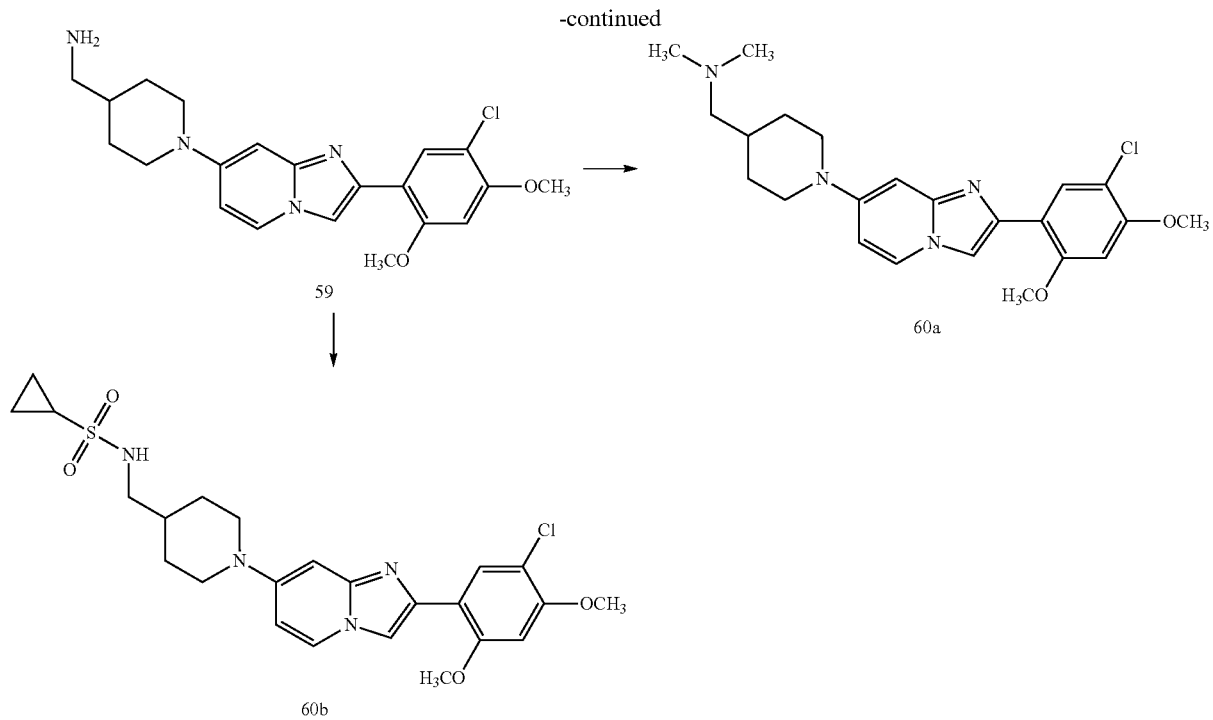

tert-Butyl ((1-(2-(5-chloro-2,4-dimethoxyphenyl) imidazo[1,2-a]pyridin-7-yl)piperidin-4-yl)methyl) carbamate 58 tert-Butyl ((1-(2-(5-chloro-2,4-dimethoxyphenyl)imidazo [1,2-a]pyridin-7-yl)-piperidin-4-yl)methyl)carbamate 58 was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e and was obtained as an off-white solid (74% yield).

(1-(2-(5-Chloro-2,4-dimethoxyphenyl)imidazo[1,2-a]pyridin-7-yl)piperidin-4-yl)-methanamine hydrochloride 59 (Example 16)

(1-(2-(5-Chloro-2,4-dimethoxyphenyl)imidazo[1,2-a] pyridin-7-yl)piperidin-4-yl)methanamine hydrochloride 59 was prepared in the same manner as 2-(1-(2-(5-chloro-2,4-dimethoxyphenyl)imidazo[1,2-a]pyridin-7-yl)piperidin-4-yl)ethanamine 5f and was obtained as a white solid (68% yield).
$^1$H NMR (400 MHz, DMSO-$d_6$): δ 13.69 (br s, 1H), 8.52 (d, J=7.8 Hz, 1H), 8.25 (s, 1H), 8.04 (s, 1H), 8.01 (br s, 3H), 7.33 (dd, J=7.8 Hz, 1H), 6.98 (s, 1H), 6.76 (s, 1H), 4.08 (br s, 2H), 4.05 (s, 3H), 3.98 (s, 3H), 3.11-3.02 (m, 2H), 2.78-2.70 (m, 2H), 2.00-1.84 (m, 3H), 1.33-1.21 (m, 2H); HPLC (Method 4) 96.3% (AUC), $t_R$=15.72 min: ESI MS m/z 401 [M+H]$^+$.

1-(1-(2-(5-Chloro-2,4-dimethoxyphenyl)imidazo[1,2-a]pyridin-7-yl)piperidin-4-yl)-N,N-dimethylmethanamine 60a (Example 97)

1-(1-(2-(5-Chloro-2,4-dimethoxyphenyl)imidazo[1,2-a] pyridin-7-yl)piperidin-4-yl)-N,N-dimethylmethanamine 60 was prepared in the same manner as 2-(4-(2-(5-chloro-2,4-dimethoxy phenyl)imidazo[1,2-a]pyridin-7-yl)piperazin-1-yl)-N,N-dimethylethanamine 13x and was obtained as a brown solid (7 mg, 6% yield).
$^1$H NMR (400 MHz, CDCl$_3$): δ 8.37 (s, 1H), 7.86 (d, J=7.6 Hz, 1H), 7.84 (s, 1H), 6.83 (s, 1H), 6.61-6.55 (m, 2H), 3.99 (s, 3H), 3.95 (s, 3H), 3.74 (d, J=12.4 Hz, 2H), 2.79 (t, J=10.7 Hz, 2H), 2.32-2.17 (m, 8H), 1.90 (d, J=12.0 Hz, 2H), 1.41-1.23 (m, 4H); ESI MS m/z 429 [M+H]$^+$.

N-((1-(2-(5-Chloro-2,4-dimethoxyphenyl)imidazo[1,2-a]pyridin-7-yl)piperidin-4-yl)methyl)cyclopropanesulfonamide 60b (Example 149)

Compound N-((1-(2-(5-chloro-2,4-dimethoxyphenyl)imidazo[1,2-a]pyridin-7-yl)piperidin-4-yl)methyl) cyclopropanesulfonamide 60b was prepared in the same manner as 2-(5-chloro-2,4-dimethoxyphenyl)-7-[4-(methylsulfonyl) piperazin-1-yl]imidazo[1,2-a]pyridine 13a and was obtained as an off-white solid (15 mg, 27% yield).
$^1$H NMR (400 MHz, CDCl$_3$): δ 8.36 (s, 1H), 7.87 (d, J=7.7 Hz, 1H), 7.85 (s, 1H), 6.81 (d, J=2.2 Hz, 1H), 6.58 (s, 1H), 6.55 (dd, J=2.4, 7.5 Hz, 1H), 4.33 (br s, 1H), 3.99 (s, 3H), 3.95 (s, 3H), 3.75 (d, J=12.5 Hz, 2H), 3.10 (t, J=5.9 Hz, 2H), 2.83-2.74 (m, 2H), 2.46-2.39 (m, 1H), 1.89 (d, J=12.5 Hz, 2H), 1.77-1.68 (m, 1H), 1.45-1.34 (m, 2H), 1.21-1.15 (m, 2H), 1.04-0.97 (m, 2H); HPLC (Method 1) 94.0% (AUC), $t_R$=11.01 min APCI MS m/z 505 [M+H]$^+$ Scheme 15

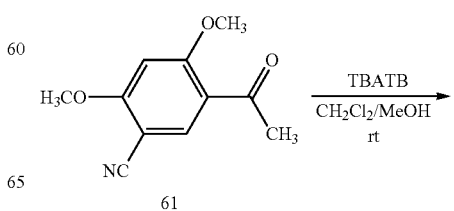

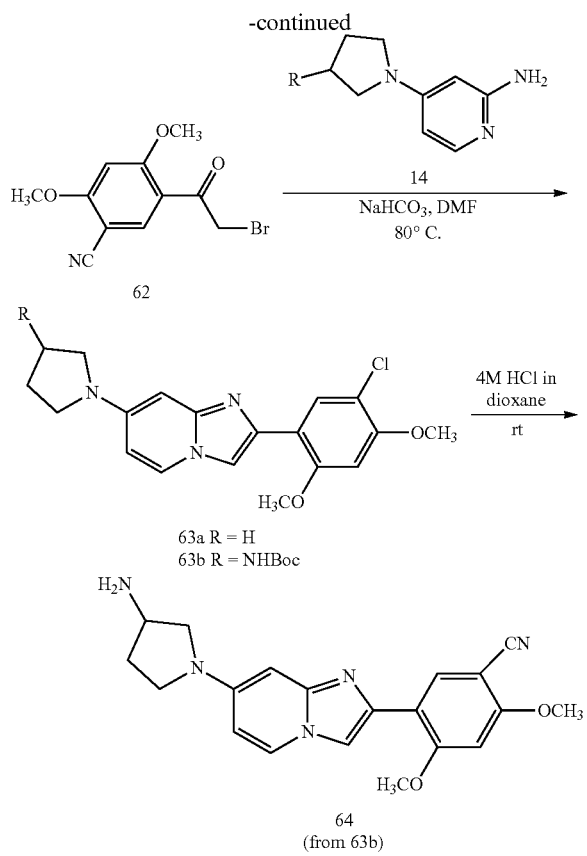

Preparation of 2,4-dimethoxy-5-[7-(pyrrolidin-1-yl)imidazo[1,2-a]pyridin-2-yl]benzonitrile 63a hydrobromide (Example 49)

2,4-Dimethoxy-5-[7-(pyrrolidin-1-yl)imidazo[1,2-a]pyridin-2-yl]benzonitrile 63a was prepared in the same manner as 2-(5-bromo-2,4-dimethoxyphenyl)-7-(pyrrolidin-1-yl)imidazo[1,2-a]pyridine 9a and was obtained as an off-white solid (62% yield). The resulting compound was treated with HBr to obtain the desired hydrobromide salt.

$^1$H NMR (400 MHz, DMSO-$d_6$): δ 8.49 (d, J=7.4 Hz, 1H), 8.23 (s, 1H), 8.14 (s, 1H), 7.00 (s, 1H), 6.97-6.91 (m, 1H), 6.31 (s, 1H), 4.12 (s, 3H), 4.04 (s, 3H), 3.44 (s, 4H), 2.03 (s, 4H). HPLC (Method 2) 97.12% (AUC), $t_R$=18.09 min. ESI MS m/z 349 [M+H]$^+$.

Preparation of tert-butyl {1-[2-(5-cyano-2,4-dimethoxyphenyl)imidazo[1,2-a]pyridin-7-yl]pyrrolidin-3-yl}carbamate 63b (Example 71)

tert-Butyl {1-[2-(5-cyano-2,4-dimethoxyphenyl)imidazo[1,2-a]pyridin-7-yl]-pyrrolidin-3-yl}carbamate 63b was prepared in the same manner as tert-butyl 4-[2-(5-chloro-2,4-dimethoxyphenyl)imidazo[1,2-a]pyridin-7-yl]piperazine-1-carboxylate 11 and was obtained as a green solid (32% yield).

$^1$H NMR (400 MHz, CDCl$_3$): δ 8.57 (s, 1H), 7.86 (d, J=7.3 Hz, 1H), 7.78 (s, 1H), 6.52 (s, 1H), 6.44 (s, 1H), 6.33 (dd, J=2.3, 7.4 Hz, 1H), 4.72 (br s, 1H), 4.38 (br s, 1H), 4.05 (s, 3H), 3.97 (s, 3H), 3.69-3.63 (m, 1H), 3.52-3.38 (m, 2H), 3.23 (dd, J=4.1, 9.9 Hz, 1H), 2.37-2.28 (m, 1H), 2.05-1.95 (m, 1H), 1.46 (s, 9H); ESI MS m/z 464 [M+H]$^+$.

Preparation of 2-methoxy-5(7-(pyrrolidin-1-yl)imidazo[1,2-a]pyridin-2-yl)benzonitrile hydrobromide 63c (Example 21)

Compound 2-methoxy-5-(7-(pyrrolidin-1-yl)imidazo[1,2-a]pyridin-2-yl)benzonitrile hydrobromide 63c was prepared in the same manner as 63a, from 5-acetyl-2-methoxybenzonitrile in place of 5-acetyl-2,4-dimethoxybenzonitrile 61 via bromination and cyclization. The desired product was obtained as an amorphous off-white solid.

$^1$H NMR (400 MHz, DMSO-$d_6$): δ 8.50 (d, J=7.5 Hz, 1H), 8.29 (s, 1H), 8.24 (s, 1H), 8.11 (d, J=7.8 Hz, 1H), 7.47 (d, J=8.7 Hz, 1H), 6.94 (d, J=6.1 Hz, 1H), 6.32 (s, 1H), 4.00 (s, 3H), 3.45 (bs, 4H), 2.03 (bs, 4H); HPLC (Method 4) >99% (AUC), $t_R$=17.73 min.; ESI MS m/z 319 [M+H]$^+$.

Preparation of 5-[7-(3-aminopyrrolidin-1-yl)imidazo[1,2-a]pyridin-2-yl]-2,4-dimethoxybenzonitrile 64 (Example 73)

5-[7-(3-Aminopyrrolidin-1-yl)imidazo[1,2-a]pyridin-2-yl]-2,4-dimethoxybenzonitrile 64 was prepared in the same manner as 2-(5-chloro-2,4-dimethoxyphenyl)-7-(piperazin-1-yl)imidazo[1,2-a]pyridine 12 and was obtained as an off-white solid (49% yield).

$^1$H NMR (400 MHz, DMSO-$d_6$): δ 8.54 (d, J=7.5 Hz, 1H), 8.35 (br s, 3H), 8.25 (s, 2H), 7.01 (s, 1H), 6.98 (d, J=6.7 Hz, 1H), 6.42 (s, 1H), 4.13 (s, 3H), 4.04 (s, 3H), 4.03-4.00 (m, 1H), 3.79-3.73 (m, 1H), 3.72-3.64 (m, 1H), 3.59-3.50 (m, 2H), 2.41-2.34 (m, 1H), 2.21-2.18 (m, 1H); HPLC (Method 2) 95.4% (AUC), $t_R$=14.48 min: APCI MS m/z 364 [M+H]$^+$.

Scheme 16

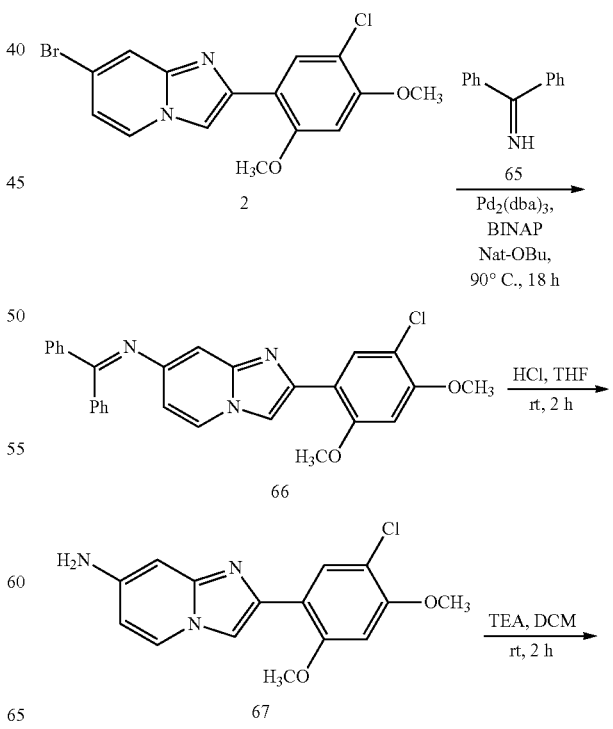

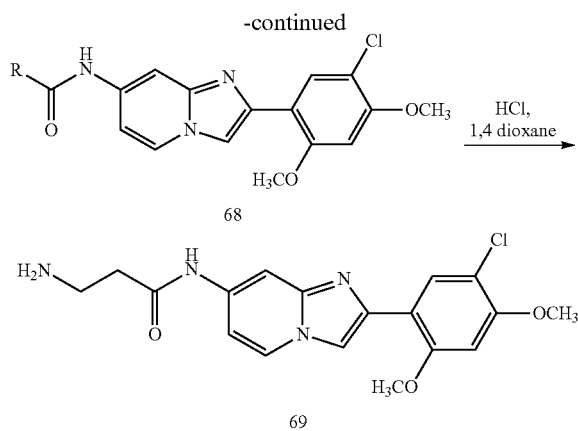

Preparation of 2-(5-chloro-2,4-dimethoxyphenyl)-N-(diphenylmethylene)imidazo[1,2-a]-pyridin-7-amine 66

A mixture of 7-bromo-2-(5-chloro-2,4-dimethoxyphenyl)imidazo[1,2-a]pyridine 22 (2.5 g, 6.80 mmol), benzophenone imine (1.8 g, 10.20 mmol), dibenzylidene acetone dipalladium (270 mg, 0.30 mmol), BINAP (500 mg, 0.80 mmol), and sodium tert-butoxide (1.6 g, 17.0 mmol) were taken in toluene (37.5 mL) and degassed with argon. The reaction mixture was heated to 90° C. for 18 h. The reaction mass was cooled to room temperature, diluted with ethyl acetate (100 mL), and filtered through a celite bed. The filtrate was distilled under reduced pressure and the residue was purified by combi-flash chromatography (silica gel, 7:3 hexane/EtOAc) to afford 2-(5-chloro-2,4-dimethoxyphenyl)-N-(diphenylmethylene)imidazo-[1,2-a]pyridin-7-amine 66 (2 g, 79%) as a brown solid.

Preparation of 2-(5-chloro-2,4-dimethoxyphenyl)imidazo[1,2-a]pyridin-7-amine 67 (Example 151)

A solution of 2-(5-chloro-2,4-dimethoxyphenyl)-N-(diphenylmethylene)imidazo[1,2-a]-pyridin-7-amine 66 (1.5 g, 3.20 mmol) in THF (20 mL) was charged with concentrated HCl (6 mL) and the reaction mixture was stirred at room temperature for 2 h. The solvent was distilled under reduced pressure. The residue was triturated with MTBE, filtered, and dried under reduced pressure to afford 2-(5-chloro-2,4-dimethoxyphenyl)imidazo[1,2-a]pyridin-7-amine 67 as HCl salt (960 mg, 98%) as a brown solid.
$^1$H NMR (300 MHz, DMSO-$d_6$): δ 8.37 (d, J=7.3 Hz, 1H), 8.18 (s, 1H), 7.93 (s, 1H), 7.08 (br s, 2H), 6.96 (s, 1H), 6.78 (dd, J=2.2 Hz, 7.3 Hz, 1H), 6.61 (d, J=2.1 Hz, 1H), 4.04 (s, 3H), 3.98 (s, 3H); HPLC (Method 1) 95.8% (AUC), t=10.08 min: ESI MS m/z 304 [M+H]$^+$.

Preparation of methyl [2-(5-chloro-2,4-dimethoxyphenyl)imidazo[1,2-a]pyridin-7-yl]-carbamate 68a (Example 183)

A mixture of 2-(5-chloro-2,4-dimethoxyphenyl)imidazo[1,2-a]pyridin-7-amine 67 (100 mg, 0.30 mmol), triethylamine (130 μL, 0.90 mmol), and methylchloroformate (25 μL, 0.33 mmol) in DCM (2 mL) was stirred at room temperature for 2 h. The reaction mixture was dried under reduced pressure and the residue was purified by combi-flash chromatography (silica gel, 9:1 DCM/methanol) to afford methyl [2-(5-chloro-2,4-dimethoxyphenyl)imidazo[1,2-a]-pyridin-7-yl]carbamate 68a (40 mg, 33.3%) as an off-white solid.
$^1$H NMR (300 MHz, CDCl$_3$): δ 8.37 (s, 1H), 8.02 (s, 1H), 8.00 (s, 1H), 7.47 (d, J=2.1 Hz, 1H), 7.07 (br s, 1H), 6.78 (br s, 1H), 6.58 (s, 1H), 4.00 (s, 3H), 3.96 (s, 3H), 3.81 (s, 3H), HPLC (Method 3) 97.4% (AUC), t$_R$=16.98 min.; ESI MS m/z 362 [M+H]$^+$.

Preparation of tert-butyl (3-{[2-(5-chloro-2,4-dimethoxyphenyl)imidazo[1,2-a]pyridin-7-yl]amino}-3-oxopropyl)carbamate 68b (Example 157)

A mixture of 2-(5-chloro-2,4-dimethoxyphenyl)imidazo[1,2-a]pyridin-7-amine 63 (120 mg, 0.40 mmol) and N-Boc-beta-alanine (83 mg, 0.44 mmol) in N,N-dimethylformamide (1.2 mL) was charged with N,N-diisopropylethylamine (230 μL, 1.20 mmol) followed by dropwise addition of 1-propane phosphonic acid anhydride (50% in DMF) (190 μL, 0.60 mmol). The reaction mixture was stirred at room temperature for 16 h. The reaction mixture was quenched with water (10 mL), the precipitate was collected by filtration and dried under reduced pressure. The solid was purified by combi-flash chromatography (silica gel, 9:1 DCM/methanol) to afford tert-butyl (3-{[2-(5-chloro-2,4-dimethoxyphenyl)imidazo[1,2-a]pyridin-7-yl]amino}-3-oxopropyl)carbamate 68b (90 mg, 48%) as an off-white solid.
$^1$H NMR (400 MHz, DMSO-$d_6$): δ 10.81 (s, 1H), 8.69 (d, J=7.4 Hz, 1H), 8.51 (s, 1H), 8.37 (s, 1H), 7.95 (s, 1H), 7.32 (d, J=6.6 Hz, 1H), 6.99 (s, 1H), 6.94 (t, J=5.3 Hz, 1H), 4.06 (s, 3H), 3.99 (s, 3H), 3.29-3.23 (m, 2H), 2.60 (t, J=6.9 Hz, 2H), 1.37 (s, 9H); HPLC (Method 1) 95.4% (AUC), t$_R$=10.96 min.; ESI MS m/z 475 [M+H]$^+$.

Preparation of 3-amino-N-[2-(5-chloro-2,4-dimethoxyphenyl)imidazo[1,2-a]pyridin-7-yl]-propanamide 69 (Example 168)

A mixture of tert-butyl (3-{[2-(5-chloro-2,4-dimethoxyphenyl)imidazo[1,2-a]pyridin-7-yl]amino}-3-oxopropyl)carbamate 68b (50 mg, 0.10 mmol) and 4 M HCl in 1,4-dioxane (2 mL) were stirred at room temperature for 3 h. The solvent was distilled under reduced pressure and the residue was basified with aqueous ammonia solution (30%) to afford 3-amino-N-[2-(5-chloro-2,4-dimethoxyphenyl)imidazo[1,2-a]pyridin-7-yl]propanamide 69 (25 mg, 64%) as an off-white solid.
$^1$H NMR (300 MHz, CH$_3$OD): δ 8.30 (d, J=7.5 Hz, 1H), 8.14 (s, 1H), 8.10 (s, 1H), 8.01 (br s, 1H), 7.01-6.99 (m, 1H), 6.79 (s, 3H), 4.03 (s, 3H), 3.95 (s, 3H), 3.11 (t, J=6.3 Hz, 2H), 2.69 (t, J=6.3 Hz, 2H); HPLC (Method 1) 96.2% (AUC), t$_R$=8.95 min. ESI MS m/z 375 [M+H]$^+$.

Scheme 17

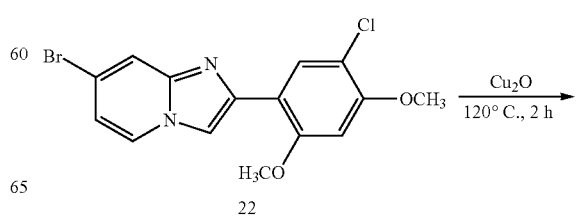

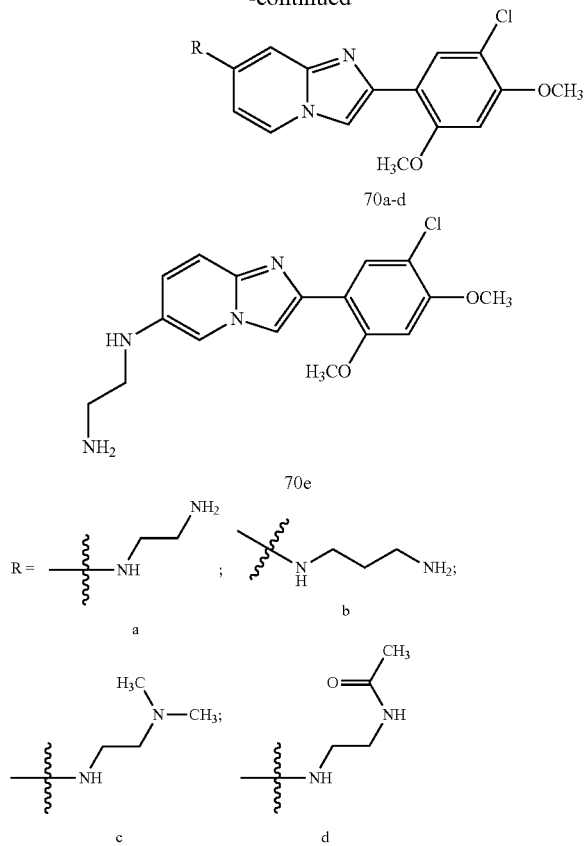

70e was synthesized in a similar way to that of 70a-d, from 6-bromo ananlogue of 22

Preparation of $N^1$-(2-(5-chloro-2,4-dimethoxyphenyl)imidazo[1,2-a]pyridin-7-yl)ethane-1,2-diamine dihydrochloride 70a (Example 10)

A mixture of 7-bromo-2-(5-chloro-2,4-dimethoxyphenyl)imidazo[1,2-a]pyridine 22 (200 mg, 0.54 mmol) and Cu$_2$O (25 mg) in ethylenediamine (3.0 mL) was heated at 120° C. for two hours. Solvent was removed. The solid was purified by combi-flash chromatography (silica gel, 9:0.8:0.2 DCM/methanol/ammonia) to afford the free base, which was converted to the dihydrochloride salt $N^1$-(2-(5-chloro-2,4-dimethoxyphenyl)imidazo[1,2-a]pyridin-7-yl)ethane-1,2-diamine dihydrochloride 70a as an off-white solid.

$^1$H NMR (400 MHz, DMSO-d$_6$): δ 13.8 (s, 1H), 8.44 (d, J=7.4 Hz, 1H), 8.32 (bs, 3H), 8.12-8.04 (m, 1H), 8.09 (s, 1H), 6.96 (s, 1H), 6.91 (dd, J=1.8, 7.3 Hz, 1H), 6.54 (s, 1H), 4.04 (s, 3H), 3.98 (s, 3H), 3.52-3.46 (m, 2H), 3.08 (bs, 2H); HPLC (Method 4) 97.6% (AUC), t$_R$=15.65 min.; ESI MS m/z 347 [M+H]$^+$.

Preparation of $N^1$-(2-(5-chloro-2,4-dimethoxyphenyl)imidazo[1,2-a]pyridin-7-yl)propane-1,3-diamine 70b (Example 35)

Compound $N^1$-(2-(5-chloro-2,4-dimethoxyphenyl)imidazo[1,2-a]pyridin-7-yl)propane-1,3-diamine 70b was prepared in the same manner as $N^1$-(2-(5-chloro-2,4-dimethoxyphenyl)-imidazo[1,2-a]pyridin-7-yl)ethane-1,2-diamine 70a; and was obtained as a white solid (16%).

$^1$H NMR (400 MHz, CD$_3$OD): δ 8.95 (s, 1H), 8.92 (d, J=7.4 Hz, 1H), 8.68 (s, 1H), 7.66 (s, 1H), 7.17 (d, J=7.4 Hz, 1H), 6.99 (s, 1H), 6.97 (s, 1H), 4.80 (s, 3H), 4.74 (s, 3H), 3.93-3.87 (m, 2H), 3.47 (t, J=6.7 Hz, 2H), 2.50-2.43 (m, 2H); HPLC (Method 4) >99% (AUC), t$_R$=15.79 min; ESI MS m/z 361 [M+H]$^+$.

Preparation $N^1$-(2-(5-chloro-2,4-dimethoxyphenyl)imidazo[1,2-a]pyridin-7-yl)-$N^2$,$N^2$-dimethylethane-1,2-diamine 70c (Example 83)

Compound $N^1$-(2-(5-chloro-2,4-dimethoxyphenyl)imidazo[1,2-a]pyridin-7-yl)-$N^2$,$N^2$-dimethylethane-1,2-diamine 70c was prepared in the same manner as 2-(4-(2-(5-chloro-2,4-dimethoxyphenyl)imidazo[1,2-a]pyridin-7-yl)piperazin-1-yl)-N,N-dimethylethanamine 13x and was obtained as a white solid (51%).

$^1$H NMR (400 MHz, CDCl$_3$): δ 8.36 (s, 1H), 7.80 (s, 1H), 7.77 (d, J=7.3 Hz, 1H), 6.57 (s, 1H), 6.47 (s, 1H), 6.24-6.20 (m, 1H), 4.56 (s, 3H), 3.98 (s, 3H), 3.94 (s, 3H), 3.19-3.14 (m, 2H), 2.61-2.57 (m, 2H), 2.26 (s, 6H); HPLC (Method 3) 97.3% (AUC), t$_R$=15.37 min: ESI MS m/z 375 [M+H]$^+$.

Preparation of N-(2-((2-(5-chloro-2,4-dimethoxyphenyl)imidazo[1,2-a]pyridin-7-yl)amino)ethyl)acetamide 70d (Example 77)

A mixture of $N^1$-(2-(5-chloro-2,4-dimethoxyphenyl)imidazo[1,2-a]pyridin-7-yl)ethane-1,2-diamine 70a (100 mg, 0.28 mmol) and Ac$_2$O (28 μL) in pyridine (2.0 mL) was stirred at room temperature for four hours. Solvent was removed. The solid was purified by combi-flash chromatography (silica gel, 9:0.8:0.2 DCM/methanol/ammonia) to afford N-(2-((2-(5-chloro-2,4-dimethoxyphenyl)imidazo[1,2-a]pyridin-7-yl)amino)ethyl)acetamide 70d as an off-white solid.

$^1$H NMR (400 MHz, CD$_3$OD): δ 8.14 (d, J=7.3 Hz, 1H), 7.96 (s, 1H), 7.85 (s, 1H), 6.87 (s, 1H), 6.63 (dd, J=2.2, 7.4 Hz, 1H), 6.50 (s, 1H), 4.40 (s, 3H), 3.97 (s, 3H), 3.49-3.41 (m, 21-H), 3.37-3.32 (m, 2H), 1.96 (s, 3H); HPLC (Method 3) 94.7% (AUC), t$_R$=16.42 min.; ESI MS m/z 389 [M+H]$^+$.

Preparation of $N^4$-(2-(5-chloro-2,4-dimethoxyphenyl)imidazo[1,2-a]pyridin-6-yl)ethane-1,2-diamine 70e (Example 81)

Compound $N^1$-(2-(5-chloro-2,4-dimethoxyphenyl)imidazo[1,2-a]pyridin-6-yl)ethane-1,2-diamine 70e was prepared in the same manner as $N^1$-(2-(5-chloro-2,4-dimethoxyphenyl)-imidazo[1,2-a]pyridin-7-yl)ethane-1,2-diamine 70a by using 6-bromo-2-(5-chloro-2,4-methoxyphenyl)imidazo[1,2-a]pyridine and was obtained as white solid.

$^1$H NMR (400 MHz, CDCl$_3$): δ 8.35 (s, 1H), 7.76 (s, 1H), 7.51 (d, J=7.3 Hz, 1H), 7.43 (s, 1H), 6.76 (s, 1H), 6.22 (d, J=7.3 Hz, 1H), 6.58 (s, 1H), 4.02 (s, 3H), 3.90 (s, 3H), 3.11-3.08 (m, 4H); HPLC (Method 3) 98.2% (AUC), t$_R$=15.17 min: ESI MS m/z 347 [M+H]$^+$.

Scheme 18

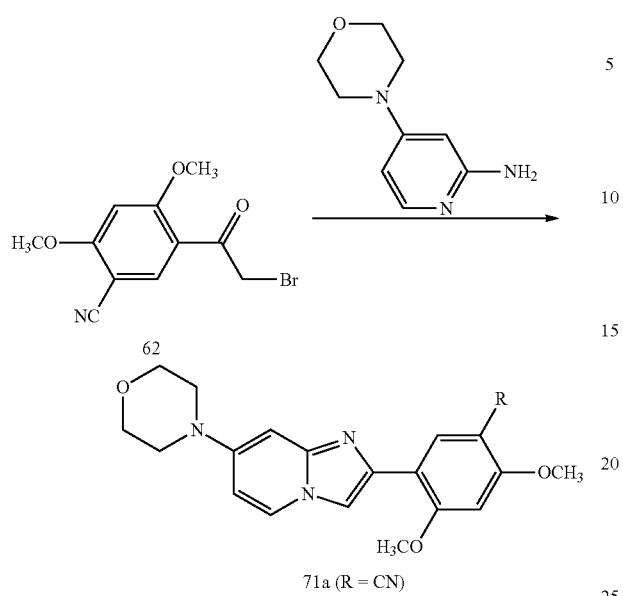

71a (R = CN)
71b (R = CH₃) and 71c (R = F) were synthesized in a similar way to 71a Preparation of 2,4-dimethoxy-5-(7-morpholinoimidazo[1,2-a]pyridin-2-yl)benzonitrile 71a (Example 93)

2,4-Dimethoxy-5-(7-morpholinoimidazo[1,2-a]pyridin-2-yl)benzonitrile 71a was prepared in the same manner as 2-(5-bromo-2,4-dimethoxyphenyl)-7-(pyrrolidin-1-yl)imidazo[1,2-a]pyridine 9a and was obtained as an off-white solid (50% yield).
$^1$H NMR (300 MHz, DMSO-d₆): δ 8.35 (s, 1H), 8.34 (d, J=7.5 Hz, 1H), 8.06 (s, 1H), 6.91 (s, 1H), 6.85 (d, 7.6 Hz, 1H), 6.67 (s, 1H), 4.09 (s, 3H), 4.00 (s, 3H), 3.78-3.72 (m, 4H), 3.24-3.18 (m, 4H); HPLC (Method 3) 98.5% (AUC), $t_R$=16.48 min: ESI MS m/z 365 [M+H]⁺.

Preparation of 4-(2-(2,4-dimethoxy-5-methylphenyl)imidazo[1,2-a]pyridin-7-yl)morpholine 71b (Example 86)

4-(2-(2,4-Dimethoxy-5-methylphenyl)imidazo[1,2-a]pyridin-7-yl)morpholine 71b was prepared in the same manner as 2-(5-bromo-2,4-dimethoxyphenyl)-7-(pyrrolidin-1-yl)imidazo[1,2-a]pyridine 9a and was obtained as an off-white solid (38% yield).
$^1$H NMR (300 MHz, DMSO-d₆): δ 8.32 (d, J=7.5 Hz, 1H), 7.98 (s, 1H), 7.97 (s, 1H), 6.81-6.76 (m, 1H), 6.68 (s, 11H), 6.67 (s, 1H), 3.95 (s, 3H), 3.85 (s, 3H), 3.79-3.71 (m, 4H), 3.23-3.14 (m, 4H), 2.14 (s, 3H); HPLC (Method 5) 97.5% (AUC), $t_R$=17.7 min; ESI MS m/z 465 [M+H]⁺.

Preparation of 4-(2-(5-fluoro-2,4-dimethoxyphenyl)imidazo[1,2-a]pyridin-7-yl)morpholine hydrobromide 71c; (Example 87)

4-(2-(5-Fluoro-2,4-dimethoxyphenyl)imidazo[1,2-a]pyridin-7-yl)morpholine 71c was prepared in the same manner as 2-(5-bromo-2,4-dimethoxyphenyl)-7-(pyrrolidin-1-yl)-imidazo[1,2-a]pyridine 9a and was obtained as an off-white solid (70% yield).

$^1$H NMR (400 MHz, DMSO-d₆): δ 13.25 (br s, 1H), 8.57 (d, J=7.7 Hz, 1H), 8.28 (s, 1H), 7.75 (d, J=7.7 Hz, 1H), 7.33-7.30 (m, 1H), 7.02 (s, 1H), 7.01 (s, 1H), 6.74 (s, 1H), 4.02 (s, 3H), 3.97 (s, 3H), 3.80-3.75 (m, 4H), 3.50-3.45 (m, 4H); HPLC (Method 5) >99% (AUC), $t_R$=18.15 min; APCI MS m/z 358 [M+H]⁺.

Scheme 19

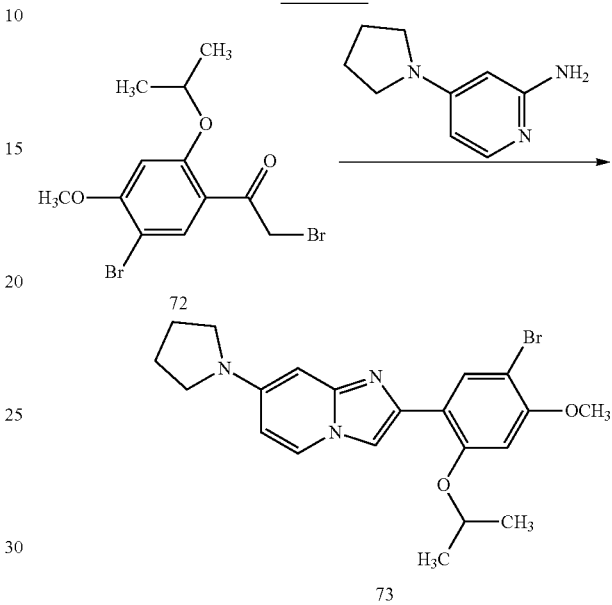

Preparation of 2-(5-bromo-2-isopropoxy-4-methoxyphenyl)-7-(pyrrolidin-1-yl)-imidazo[1,2-a]pyridine hydrobromide 73

2-(5-Bromo-2-isopropoxy-4-methoxyphenyl)-7-(pyrrolidin-1-yl)imidazo[1,2-a]-pyridine hydrobromide 73 was prepared in the same manner as 2-(5-bromo-2,4-dimethoxyphenyl)-7-(pyrrolidin-1-yl)imidazo[1,2-a]pyridine 9a and was obtained as an off-white solid (26% yield).
$^1$H NMR (400 MHz, DMSO-d₆): δ 13.04 (s, 1H), 8.61 (d, J=7.6 Hz, 1H), 8.11 (s, 1H), 8.02 (s, 11H), 6.95 (s, 11H), 6.93 (s, 1H), 6.27 (s, 1H), 5.06-4.97 (m, 1H), 3.94 (s, 3H), 3.48-3.40 (m, 4H), 2.06-1.99 (m, 4H), 1.44 (s, 3H), 1.42 (s, 3H); HPLC (Method 3) >99% (AUC), $t_R$=18.93 min; ESI MS m/z 430 [M+H]⁺

Scheme 20

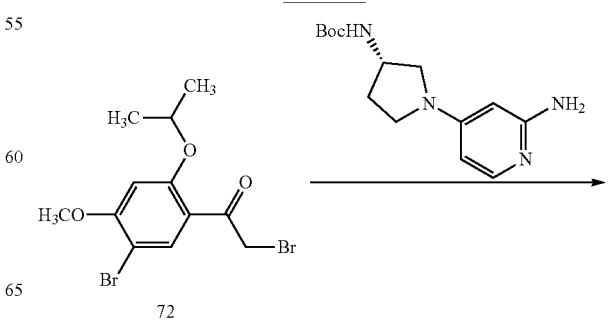

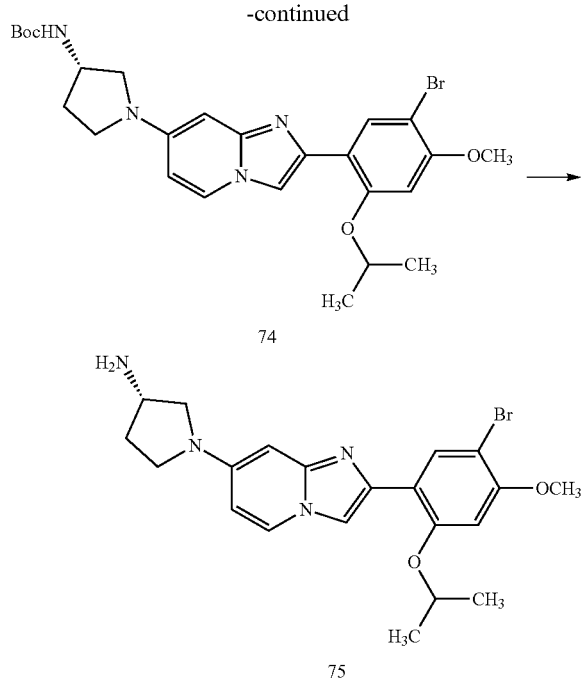
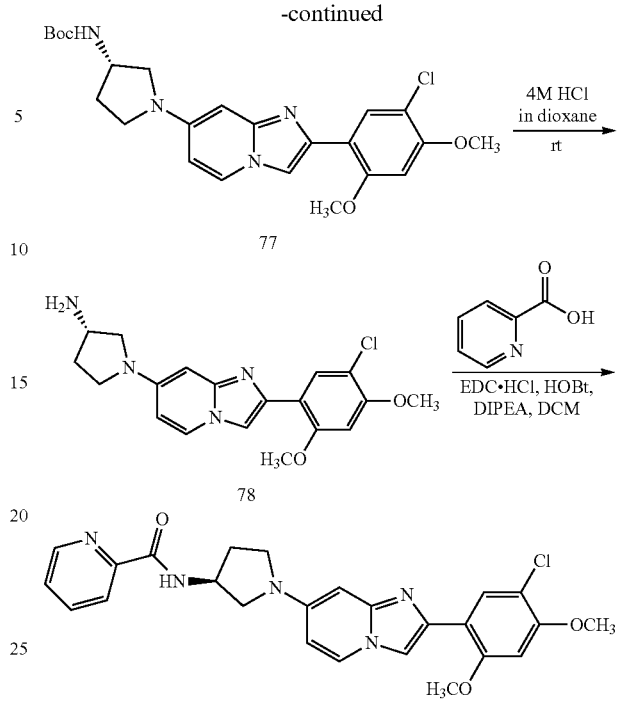

Preparation of (S)-tert-butyl(1-(2-(5-bromo-2-isopropoxy-4-methoxyphenyl)imidazo[1,2-a]pyridin-7-yl)pyrrolidin-3-yl)carbamate 74

Compound (S)-tert-butyl (1-(2-(5-bromo-2-isopropoxy-4-methoxyphenyl)imidazo-[1,2-a]pyridin-7-yl)pyrrolidin-3-yl)carbamate 74 was prepared in the same manner as 2-(5-bromo-2,4-dimethoxyphenyl)-7-(pyrrolidin-1-yl)imidazo[1,2-a]pyridine 9a and was obtained as an off-white solid.

Preparation of (S)-1-(2-(5-bromo-2-isopropoxy-4-methoxyphenyl)imidazo[1,2-a]pyridin-7-yl)pyrrolidin-3-amine hydrochloride 75 (Example 59)

(S)-1-(2-(5-Bromo-2-isopropoxy-4-methoxyphenyl)imidazo[1,2-a]pyridin-7-yl)-pyrrolidin-3-amine hydrochloride 75 was prepared in the same manner as 2-(1-(2-(5-chloro-2,4-dimethoxyphenyl)imidazo[1,2-a]pyridin-7-yl)piperidin-4-yl)ethanamine 5f and was obtained as an off-white solid (62% yield).

$^1$H NMR (400 MHz, CD$_3$OD): δ 8.52 (d, J=7.2 Hz, 1H), 8.07 (s, 1H), 7.90 (s, 1H), 6.97 (d, J=7.2 Hz, 1H), 6.95 (s, 1H), 6.56-6.54 (m, 1H), 4.95-4.54 (m, 1H), 4.16-4.14 (m, 1H), 4.02 (s, 3H), 3.95-3.93 (m, 1H), 3.79-3.78 (m, 1H), 3.57-3.56 (m, 2H), 2.62-2.60 (m, 2H), 2.30-2.28 (m, 2H), 1.49 (s, 6H); HPLC (Method 3) 98.1% (AUC), t$_R$=16.02 min: ESI MS m/z 445 [M+H]$^+$.

Scheme 21

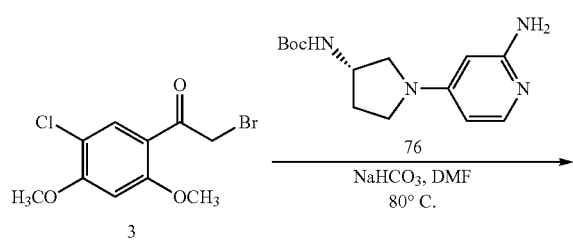

(S)-tert-butyl (1-(2-(5-chloro-2,4-dimethoxyphenyl)imidazo[1,2-a]pyridin-7-yl)-pyrrolidin-3-yl)carbamate 77 (Example 44)

(S)-tert-Butyl (1-(2-(5-chloro-2,4-dimethoxyphenyl)imidazo[1,2-a]pyridin-7-yl)pyrrolidin-3-yl)carbamate 77 was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e, and was obtained as a white solid (75 mg, 44% yield).

$^1$H NMR (400 MHz, CD$_3$OD): δ 8.35 (s, 1H), 7.87 (d, J=7.2 Hz, 1H), 7.81 (s, 1H), 6.57 (s, 1H), 6.50-6.48 (m, 1H), 6.33 (d, J=7.2 Hz, 1H), 4.79 (br s, 1H), 4.45 (br s, 1H), 3.99 (s, 3H), 3.98 (s, 3H), 3.71-3.69 (m, 1H), 3.53-3.48 (m, 2H), 3.29-3.27 (m, 1H), 2.33-2.31 (m, 1H), 2.08-1.99 (m, 1H), 1.46 (s, 9H); HPLC (Method 2) 94.1% (AUC), t$_R$=19.68 min; ESI MS m/z 473 [M+H]$^+$.

(S)-1-(2-(5-Chloro-2,4-dimethoxyphenyl)imidazo[1,2-a]pyridin-7-yl)pyrrolidin-3-amine hydrochloride 78 (Example 47)

(S)-1-(2-(5-Chloro-2,4-dimethoxyphenyl)imidazo[1,2-a]pyridin-7-yl)pyrrolidin-3-amine hydrochloride 78 was prepared in the same manner as 2-(1-(2-(5-chloro-2,4-dimethoxyphenyl)imidazo[1,2-a]pyridin-7-yl)piperidin-4-yl)ethanamine 5f, and was obtained as a white solid (35 mg, 72% yield).

$^1$H NMR (400 MHz, DMSO-d$_6$): δ 13.70 (s, 1H), 8.58-8.44 (m, 4H), 8.27 (s, 1H), 8.05 (s, 1H), 7.03-6.94 (m, 2H), 6.44 (s, 1H), 4.09-3.95 (m, 7H), 3.80-3.64 (m, 2H), 3.61-3.50 (m, 2H), 2.42-2.33 (m, 1H), 2.26-2.17 (m, 1H); ESI MS m/z 373 [M+H]$^+$.

Preparation of (S)—N-(1-(2-(5-chloro-2,4-dimethoxyphenyl)imidazo[1,2-a]pyridin-7-yl)pyrrolidin-3-yl)picolinamide (Example 404)

Compound (S)—N-(1-(2-(5-chloro-2,4-dimethoxyphenyl)imidazo[1,2-a]pyridin-7-yl)pyrrolidin-3-yl)picolinamide was prepared in the same manner as tert-butyl (2-((2-(4-(2-(5-chloro-2,4-dimethoxyphenyl)imidazo[1,2-a]pyridin-7-yl)benzamido)ethyl)amino)-ethyl)carbamate 236 (Example 248) and was obtained as a light brown solid (62%).

$^1$H NMR (400 MHz, DMSO-$d_6$): 8.93 (d, J=7.7 Hz, 1H), 8.66-8.63 (m, 1H), 8.28 (d, J=7.5 Hz, 1H), 8.16 (s, 1H), 8.08-7.93 (m, 2H), 7.95 (s, 1H), 7.63-7.58 (m, 1H), 6.85 (s, 1H), 6.51 (dd, J=2.3, 7.5 Hz, 1H), 6.25 (s, 1H), 4.73-4.64 (m, 1H), 4.00 (s, 3H), 3.93 (s, 3H), 3.69-3.62 (m, 1H), 3.56-3.49 (m, 1H), 3.43-3.34 (m, 2H), 2.34-2.25 (m, 1H), 2.24-2.14 (m, 1H). HPLC (same as Method 1, except detection @ 220 nm) 95.5% (AUC), $t_R$=10.99 min; ESI MS m/z 478 [M+H]$^+$.

Preparation of 2-(5-chloro-2,4-dimethoxyphenyl)-7-(1,4-dioxaspiro[4.5]decan-8-yl)imidazo-[1,2-a]pyridine 81

A solution of 2-(5-chloro-2,4-dimethoxyphenyl)-7-(1,4-dioxaspiro[4.5]dec-7-en-8-yl)-imidazo[1,2-a]pyridine 80 (50 mg, 0.117 mmol) and Pd/C (50 mg) in THF (10 mL) was stirred at room temperature for 16h. The reaction mixture was filtered, washed with THF, and dried under reduced pressure to give the desired compound 2-(5-chloro-2,4-dimethoxyphenyl)-7-(1,4-dioxaspiro[4.5]decan-8-yl)imidazo[1,2-a]pyridine (25 mg) as an off-white solid.

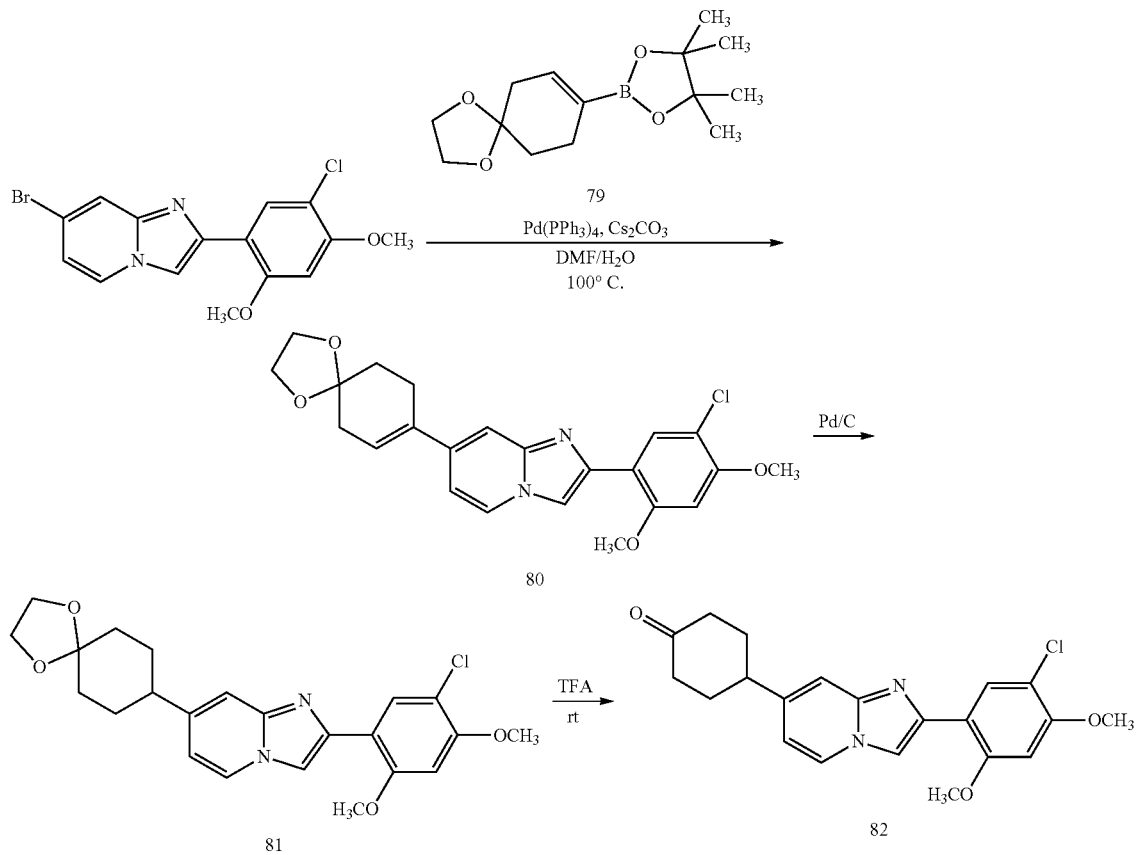

Scheme 22

Preparation of 2-(5-chloro-2,4-dimethoxyphenyl)-7-(1,4-dioxaspiro[4.5]dec-7-en-8-yl)-imidazo[1,2-a]pyridine 80 (Example 117)

2-(5-Chloro-2,4-dimethoxyphenyl)-7-(1,4-dioxaspiro[4.5]dec-7-en-8-yl)imidazo[1,2-a]pyridine 80 was prepared in the same manner as tert-butyl 4-[2-(5-chloro-2,4-dimethoxyphenyl)-imidazo[1,2-a]pyridin-7-yl]-5,6-dihydropyridine-1(2H)-carboxylate 24a, and was obtained as an off-white solid (120 mg, 40% yield).

$^1$H NMR (400 MHz, CDCl$_3$): δ 8.40 (s, 1H), 8.02 (s, 1H), 7.99 (d, J=7.30 Hz, 1H), 7.54 (s, 1H), 6.92 (d, J=7.30 Hz, 1H), 6.58 (s, 1H), 6.21-6.19 (m, 1H), 4.00-3.96 (m, 10H), 2.72-2.70 (m, 2H), 2.52-2.50 (m, 2H), 1.96-1.94 (m, 2H); HPLC (Method 1) 98.6% (AUC), $t_R$=10.78 min; ESI MS m/z 427 [M+H]$^+$.

Preparation of 4-(2-(5-chloro-2,4-dimethoxyphenyl)imidazo[1,2-a]pyridin-7-yl)-cyclohexanone 82 (Example 119)

A solution of 2-(5-chloro-2,4-dimethoxyphenyl)-7-(1,4-dioxaspiro[4.5]decan-8-yl)-imidazo[1,2-a]pyridine 80 (10 mg, 0.02 mmol) and TFA (2 mL) in water (0.5 mL) was stirred at room temperature for 72 h. Solvent was removed under reduced pressure to give the desired compound 4-(2-(5-chloro-2,4-dimethoxyphenyl)imidazo[1,2-a]pyridin-7-yl)cyclohexanone 82 (9 mg, 88%) as an off-white solid.

$^1$H NMR (400 MHz, CDCl$_3$): δ 8.39 (s, 1H), 8.06-8.03 (m, 2H), 7.44 (s, 1H), 6.65 (dd, J=1.7, 7.0 Hz, 1H), 6.59 (s, 1H), 4.00 (s, 3H), 3.95 (s, 3H), 3.10-3.01 (m, 1H), 2.57-2.51 (m, 4H), 2.33-2.35 (m, 2H), 2.02-1.90 (m, 2H); HPLC (Method 2) 94.06% (AUC), $t_R$=17.36 min; ESI MS m/z 385 [M+H]$^+$.

Scheme 23

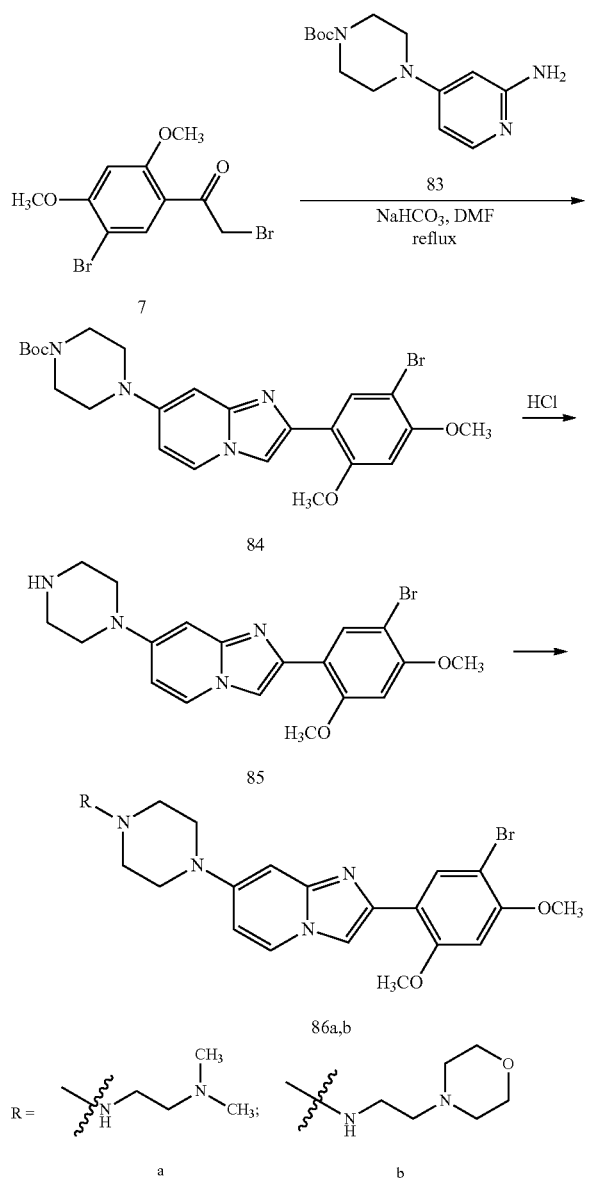

Preparation of tert-butyl 4-(2-(5-bromo-2,4-dimethoxyphenyl)imidazo[1,2-a]pyridin-7-yl)piperazine-1-carboxylate 84 tert-Butyl 4-(2-(5-bromo-2,4-dimethoxyphenyl)imidazo[1,2-a]pyridin-7-yl)piperazine-1-carboxylate 77 was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e, and was obtained as a white solid.

Preparation of 2-(5-bromo-2,4-dimethoxyphenyl)-7-(piperazin-1-yl)imidazo[1,2-a]pyridine 85

2-(5-Bromo-2,4-dimethoxyphenyl)-7-(piperazin-1-yl)imidazo[1,2-a]pyridine 85 was prepared in the same manner as 2-(1-(2-(5-chloro-2,4-dimethoxyphenyl)imidazo[1,2-a]pyridin-7-yl)piperidin-4-yl)ethanamine 5f, and was obtained as a yellow solid.

Preparation of 3-(4-(2-(5-bromo-2,4-dimethoxyphenyl)imidazo[1,2-a]pyridin-7-yl)-piperazin-1-yl)-N,N-dimethylpropan-1-amine 86a (Example 130)

A mixture of 2-(5-bromo-2,4-dimethoxyphenyl)-7-(piperazin-1-yl)imidazo[1,2-a]-pyridine 12 (100 mg, 0.30 mmol), N,N-dimethylpropan-1-amine hydrochloride (63 mg, 0.40 mmol), and cesium carbonate (290 mg, 0.9 mmol) in DMF (2 mL) was heated to reflux for 3 h. The reaction mixture was quenched with water and extracted with ethyl acetate. Solvent was removed under reduced pressure. The residue was purified by combi-flash chromatography (silica gel, 9:1 DCM/MeOH) to afford 3-(4-(2-(5-bromo-2,4-dimethoxyphenyl)imidazo[1,2-a]-pyridin-7-yl)piperazin-1-yl)-N,N-dimethylpropan-1-amine 86a (48 mg, 38%) as off white solid.

$^1$H NMR (300 MHz, CDCl$_3$): δ 8.36 (s, 1H), 8.92-7.90 (m, 2H), 6.82 (s, 1H), 6.55 (s, 1H), 6.53 (m, 1H), 4.19 (m, 2H), 4.15 (s, 3H), 3.99 (s, 3H), 3.76-3.72 (m, 4H), 3.23-3.20 (m, 4H), 2.37-2.34 (m, 2H), 2.22 (s, 6H), 1.80-1.82 (m, 2H); HPLC (Method 1) 97.63% (AUC), t$_R$=9.42 min.; ESI MS m/z 502 [M+H]$^+$.

Preparation of 4-(2-(4-(2-(5-bromo-2,4-dimethoxyphenyl)imidazo[1,2-a]pyridin-7-yl)-piperazin-1-yl)ethyl)morpholine 86b (Example 131)

4-(2-(4-(2-(5-Bromo-2,4-dimethoxyphenyl)imidazo[1,2-a]pyridin-7-yl)piperazin-1-yl)ethyl)morpholine 86b was prepared in the same manner as 3-(4-(2-(5-bromo-2,4-dimethoxy-phenyl)imidazo[1,2-a]pyridin-7-yl)piperazin-1-yl)-N,N-dimethylpropan-1-amine 86a and was obtained as a white solid (40 mg, 33%).

$^1$H NMR (300 MHz, CDCl$_3$): δ 8.36 (s, 1H), 7.93 (d, J=7.2 Hz, 1H), 7.88 (s, 1H), 6.82 (m, 1H), 6.58 (s, 1H), 6.54 (d, J=7.2 Hz, 1H), 4.28 (m, 2H), 4.00 (s, 3H), 3.95 (s, 3H), 3.73-3.71 (m, 4H), 3.69-3.67 (m, 4H), 3.22-3.19 (m, 4H), 2.68-2.66 (m, 2H), 2.54-2.52 (m, 4H); HPLC (Method 1)=98.0% (AUC), t$_R$=9.40 min; ESI MS m/z 530 [M+H]$^+$.

Scheme 24

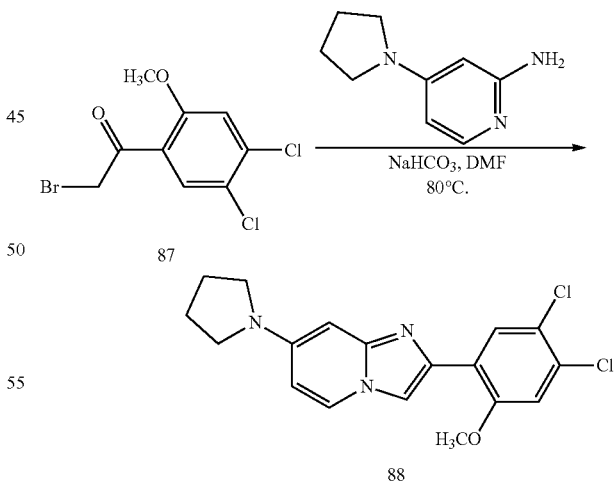

Preparation of 2-(4,5-dichloro-2-methoxyphenyl-7-(pyrrolidin-1-yl)imidazo[1,2-a]pyridine 88 (Example 233)

Compound 2-(4,5-dichloro-2-methoxyphenyl)-7-(pyrrolidin-1-yl)imidazo[1,2-a]-pyridine 88 was prepared in the same manner as 2-(5-chloro-2,4-dimethoxyphenyl)-7-(pyrrolidin-1-yl)imidazo[1,2-a]pyridine 5a. The resulting hydrobromic acid salt was neutralized with dilute aqueous ammonia to obtain free base and as an off-white solid (48 mg, 72%).

$^1$H NMR (400 MHz, CDCl$_3$): δ 8.48 (s, 1H), 7.87 (s, 1H), 7.85 (d, J=7.6 Hz, 1H), 7.02 (s, 1H), 6.42 (br s, 1H), 6.36 (dd, 1H, J=2.4 Hz, 7.5), 3.97 (s, 3H), 3.38-3.33 (m, 4H), 2.07-2.03 (m, 4H); HPLC (Method 1) 99.73% (AUC), t$_R$=11.76 min.; APCI MS m/z 362 [M+H]$^+$.

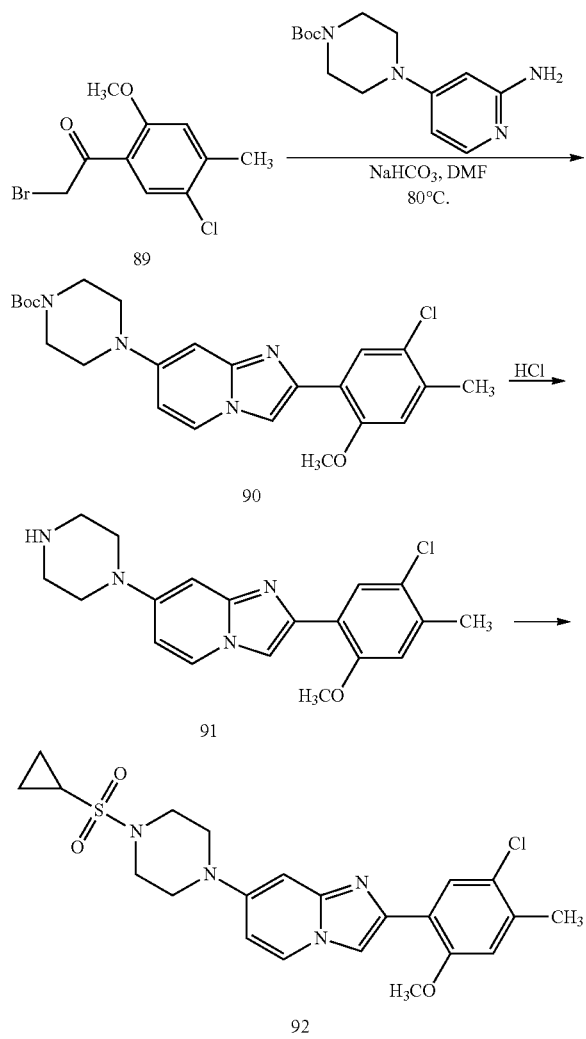

2-(5-chloro-2-methoxy-4-methylphenyl)-7-(piperazin-1-yl)imidazo[1,2-a]pyridine hydrochloride 91 (Example 228)

A solution of tert-butyl 4-(2-(5-chloro-2-methoxy-4-methylphenyl)imidazo[1,2-a]pyridin-7-yl)-piperazine-1-carboxylate 90 (40 mg, 0.08 mmol) in 4M HCl in dioxane (1.5 mL) was stirred at 55° C. for 1.5 h. Solvent was removed; the yellow precipitate was washed with ether, and dried under reduced pressure to yield 2-(5-chloro-2-methoxy-4-methylphenyl)-7-(piperazin-1-yl)-imidazo[1,2-a]pyridine hydrochloride 91 (30 mg, 96% yield) as a yellow solid.

$^1$H NMR (400 MHz, CD$_3$OD): δ 8.50 (d, J=7.64 Hz, 1H), 8.27 (s, 1H), 7.78 (s, 1H), 7.30 (dd, J=7.64 Hz, 1H), 7.19 (s, 1H), 6.99 (s, 1H), 4.03 (s, 3H), 3.86-3.82 (m, 4H), 3.46-3.41 (m, 4H), 2.45 (s, 3H). HPLC (Method 1) 98.4% (AUC), t$_R$=15.65 min: ESI MS m/z 357 [M+H]$^+$.

Preparation of 2-(5-chloro-2-methoxy-4-methylphenyl)-7-(4-(cyclopropylsulfonyl)-piperazin-1-yl)imidazo[1,2-a]pyridine 92 (Example 229)

Compound 2-(5-chloro-2-methoxy-4-methylphenyl)-7-(4-(cyclopropylsulfonyl)-piperazin-1-yl)imidazo[1,2-a]pyridine 92 was prepared in the same manner as 2-(5-chloro-2,4-dimethoxyphenyl)-7-[4-(cyclopropylsulfonyl)piperazin-1-yl]imidazo[1,2-a]pyridine 13e, and was obtained as a white solid (19 mg, 37% yield).

$^1$H NMR (400 MHz, CDCl$_3$): δ 8.33 (s, 1H), 7.95 (s, 1H), 7.94 (d, J=7.59 Hz, 1H), 6.86 (s, 1H), 6.82 (s, 1H), 6.54 (dd, J=7.59 Hz, 1H), 3.96 (s, 3H), 3.50-3.46 (m, 4H), 3.36-3.32 (m, 4H), 2.40 (s, 3H), 2.3-2.26 (m, 1H), 1.31-1.20 (m, 2H), 1.15-1.01 (m, 2H). HPLC (Method 1) 98.9% (AUC), t$_R$=11.16 min; ESI MS m/z 461 [M+H]$^-$

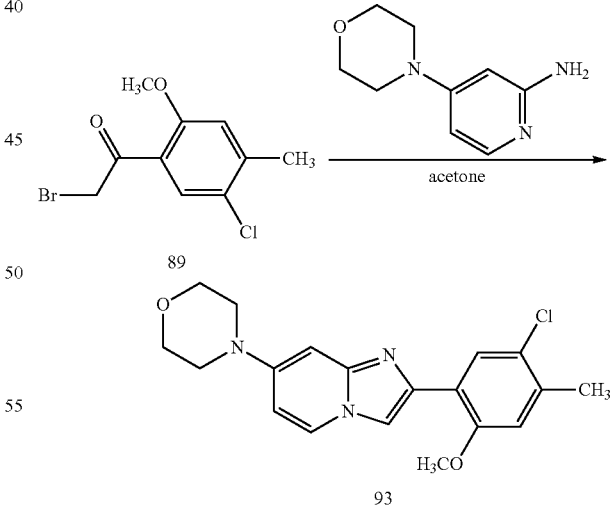

4-(2-(5-chloro-2-methoxy-4-methylphenyl)imidazo[1,2-a]pyridin-7-yl)morpholine 93 (Example 230)

Compound 4-(2-(5-chloro-2-methoxy-4-methylphenyl)imidazo[1,2-a]pyridin-7-yl)morpholine 93 was prepared in the same manner as 2-(5-chloro-2,4-dimethoxyphenyl)-7-

Preparation of tert-butyl 4-(2-(5-chloro-2-methoxy-4-methylphenyl)imidazo[1,2-a]pyridin-7-yl)piperazine-1-carboxylate 90

Compound tert-butyl 4-(2-(5-chloro-2-methoxy-4-methylphenyl)imidazo[1,2-a]pyridin-7-yl)piperazine-1-carboxylate 90 was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e, and was obtained as a white solid (150 mg, 45% yield).

(pyrrolidin-1-yl)imidazo[1,2-a]pyridine 5a and was obtained as a white solid (89 mg, 59% yield).

$^1$H NMR (400 MHz, CDCl$_3$): δ 8.33 (s, 1H), 7.94 (s, 1H), 7.92 (d, J=7.55 Hz, 1H), 6.82 (s, 1H), 6.81 (s, 1H), 6.55 (m, 1H), 3.96 (s, 3H), 3.89-3.85 (m, 4H), 3.23-3.18 (m, 4H), 2.40 (s, 3H); HPLC (Method 2) >99% (AUC), t$_R$=18.15 min; ESI MS m/z 358 [M+H]$^+$.

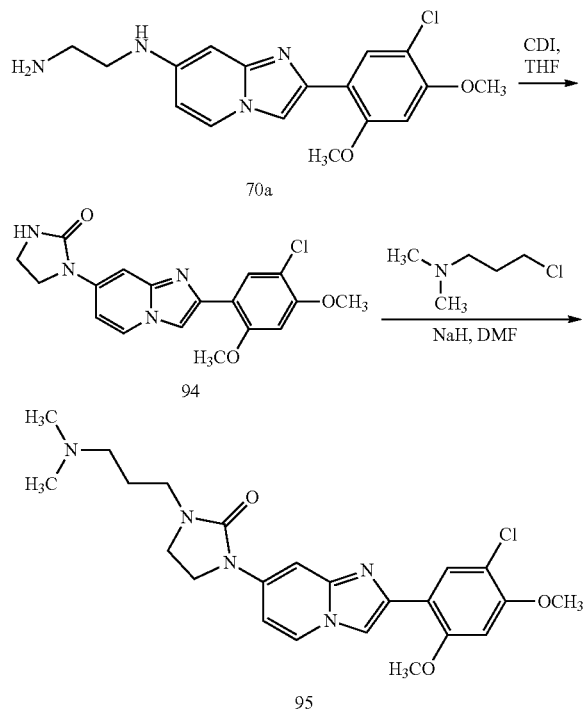

Preparation of 1-(2-(5-chloro-2,4-dimethoxyphenyl) imidazo[1,2-a]pyridin-7-yl)-imidazolidin-2-one 94 (Example 138)

To a solution of N$^1$-(2-(5-chloro-2,4-dimethoxyphenyl) imidazo[1,2-a]pyridin-7-yl)-ethane-1,2-diamine 70a (75 mg, 0.20 mmol) in tetrahydrofuran (3 mL) was added 1,1-carbonyldiimidazole (48 mg, 0.3 mmol) and stirred at room temperature for 2 h. The reaction mixture was concentrated and the residue was triturated with acetonitrile to provide the desired compound 1-(2-(5-chloro-2,4-dimethoxyphenyl)imidazo[1,2-a]pyridin-7-yl)imidazolidin-2-one 94 (50 mg, 62%) as an off-white solid.

$^1$H NMR (300 MHz, DMSO-d$_6$): δ 8.41 (d, J=7.5 Hz, 1H), 8.18 (s, 1H), 8.14 (s, 1H), 7.73 (d, J=7.5 Hz, 1H), 7.19 (s, 1H), 7.15 (s, 1H), 6.88 (s, 1H), 4.02 (s, 3H), 3.94 (s, 3H), 3.93-3.85 (m, 2H), 3.50-3.40 (m, 2H), HPLC (Method 1) >99% (AUC), t$_R$=9.96 min; ESI MS m/z 373 [M+H]$^+$.

Preparation of 1-(2-(5-chloro-2,4-dimethoxyphenyl) imidazo[1,2-a]pyridin-7-yl-3-(3-(dimethylamino) propyl)imidazolidin-2-one 95 (Example 167)

To a solution of 1-(2-(5-chloro-2,4-dimethoxyphenyl)imidazo[1,2-a]pyridin-7-yl)-imidazolidin-2-one 94 (100 mg, 0.30 mmol) in N,N-dimethylformamide (3 mL) was added 60% NaH (40 mg, 1.50 mmol) followed by N,N-dimethyl-aminopropyl chloride (60 mg, 0.4 mmol). The reaction mixture was stirred at room temperature for 4 h. The reaction mixture was quenched with 10% ammonium chloride solution (20 mL) and extracted with chloroform (100 mL). The organic layer was concentrated under reduced pressure and the residue was purified by combiflash chromatography (silica gel, DCM/methanol) to afford 1-(2-(5-chloro-2,4-dimethoxyphenyl)imidazo[1,2-a]pyridin-7-yl)-3-(3-(dimethylamino)propyl)imidazolidin-2-one 6 (25 mg, 20%) as an off-white solid.

$^1$H NMR (300 MHz, CD$_3$OD): δ 8.26 (d, J=7.6 Hz, 1H), 8.09 (s, 2H), 7.77 (d, J=7.6 Hz, 1H), 7.12 (s, 1H), 6.79 (s, 1H), 4.02 (s, 3H), 3.95 (s, 3H), 3.94-3.89 (m, 2H), 3.64-3.56 (m, 2H), 2.48-2.39 (m, 2H), 2.31 (m, 6H), 1.87-1.74 (m, 2H). HPLC (Method 1) 98.4% (AUC), t$_R$=9.16 min; ESI MS m/z 458 [M+H]$^+$.

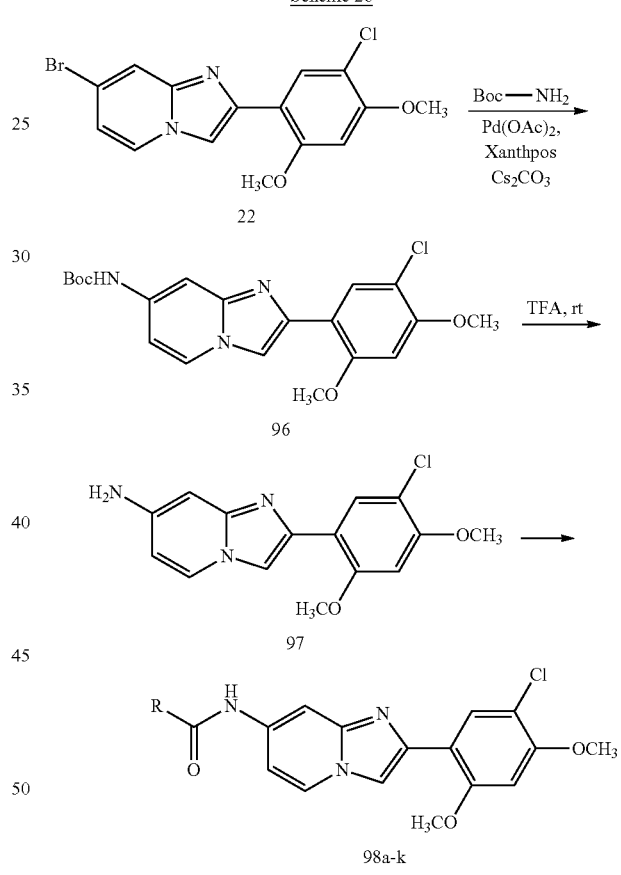

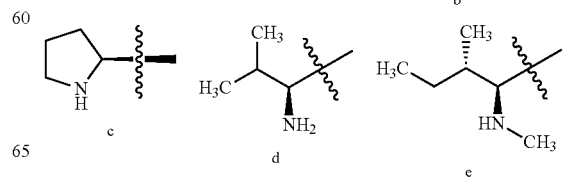

-continued

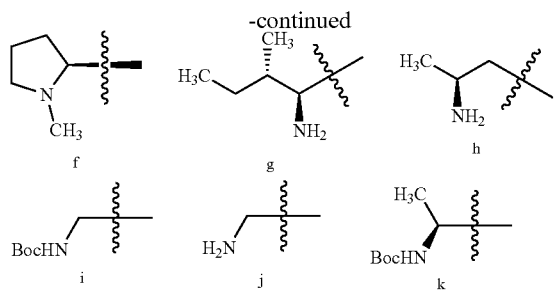

Preparation of tert-butyl (2-(5-chloro-2,4-dimethoxyphenyl)imidazo[1,2-a]pyridin-7-yl)-carbamate 96

A mixture of 7-bromo-2-(5-chloro-2,4-dimethoxyphenyl)imidazo[1,2-a]pyridine 22 (1.00 g, 2.70 mmol), tert-butyl carbamate (470 mg, 4.00 mmol), palladium acetate (220 mg, 0.10 mmol), Xanthpos (170 mg, 0.30 mmol) and cesium carbonate (2.2 g, 6.8 mmol) were taken in 1,4-dioxane (20 mL) and degassed with argon. The reaction mixture was heated to 100° C. for 3 h. The reaction mass was cooled to room temperature, diluted with ethyl acetate (100 mL) and filtered through celite bed. The filtrate was distilled under reduced pressure and the residue was purified by combi-flash chromatography (silica gel, 7:3 Hexane/EtOAc) to afford tert-butyl (2-(5-chloro-2,4-dimethoxyphenyl)imidazo[1,2-a]pyridin-7-yl)carbamate (800 mg, 87%) as a yellow solid.

Preparation of 2-(5-chloro-2,4-dimethoxyphenyl)imidazo[1,2-a]pyridin-7-amine 97

A mixture of tert-butyl (2-(5-chloro-2,4-dimethoxyphenyl)imidazo[1,2-a]pyridin-7-yl)-carbamate 96 (4.0 g, 9.90 mmol) and trifluoroacetic acid (20 mL) in dichloromethane (40 mL) were stirred at room temperature for 4 h. The solvent was distilled under reduced pressure and the residue was basified with aqueous ammonia solution (30%) to afford 2-(5-chloro-2,4-dimethoxyphenyl)imidazo[1,2-a]pyridin-7-amine 4 (2.95 g, 89%) as pale yellow solid. Compound 4 was then treated with 4M HCl in 1,4-dioxane (10 mL) and concentrated under reduced pressure to afford the title compound 2-(5-chloro-2,4-dimethoxyphenyl)imidazo[1,2-a]pyridin-7-amine as HCl salt.

Preparation of (S)-2,6-diamino-N-(2-(5-chloro-2,4-dimethoxyphenyl)imidazo[1,2-a]-pyridin-7-yl)hexanamide 98a (Example 247)

To a mixture of HCl salt of 2-(5-chloro-2,4-dimethoxyphenyl)imidazo[1,2-a]pyridin-7-amine 4 (120 mg, 0.40 mmol) and Acid (140 mg, 0.40 mmol) in DMF (2 mL) was added HATU (150 mg, 0.40 mmol) followed by diisopropylethylamine (160 mg, 1.2 mmol). The reaction mixture was stirred at room temperature for 16 h. The reaction mixture was poured into water and the precipitate was collected by filtration. The crude was purified by combi-flash chromatography (silica gel, MeOH/DCM) to afford bis-boc protected form of (S)-2,6-diamino-N-(2-(5-chloro-2,4-dimethoxyphenyl)imidazo[1,2-a]pyridin-7-yl)hexanamide as an off-white solid. The compound was treated with 4M HCl in 1,4-dioxane (2 mL) and concentrated under reduced pressure to afford (S)-2,6-diamino-N-(2-(5-chloro-2,4-dimethoxyphenyl)imidazo-[1,2-a]pyridin-7-yl)hexanamide 98a (30 mg, 16%) as an off-white solid.

$^1$H NMR (400 MHz, CD$_3$OD): δ 8.32 (d, J=7.4 Hz, 1H), 8.15 (s, 1H), 8.11 (s, 1H), 8.05 (s, 1H), 7.08 (d, J=7.4 Hz, 1H), 6.80 (s, 1H), 4.03 (s, 3H), 3.95 (s, 3H), 3.57 (t, J=6.4 Hz, 1H), 2.94 (t, J=7.4 Hz, 2H), 1.91-1.81 (m, 1H), 1.71-1.66 (m, 3H), 1.58-1.47 (m, 2H); HPLC (Method 1) 98.9% (AUC), t$_R$=8.52 min; ESI MS m/z 432 [M+H]$^+$.

Preparation of (S)-2-amino-N-(2-(5-chloro-2,4-dimethoxyphenyl)imidazo[1,2-a]pyridin-7-yl)-3-(1H-indol-3-yl)propanamide 98b (Example 250)

Compound (S)-2-amino-N-(2-(5-chloro-2,4-dimethoxyphenyl)imidazo[1,2-a]pyridin-7-yl)-3-(1H-indol-3-yl)propanamide 98b was prepared in the same manner as (S)-2,6-diamino-N-(2-(5-chloro-2,4-dimethoxyphenyl)imidazo[1,2-a]pyridin-7-yl)hexanamide 98a and was obtained as an off-white solid (30 mg, 20% yield).

$^1$H NMR (300 MHz, DMSO-d$_6$): δ 10.82 (s, 1H), 8.42 (d, J=7.3 Hz, 1H), 8.20 (s, 1H), 8.17 (s, 1H), 7.97 (s, 1H1), 7.59 (d, J=7.3 Hz, 1H), 7.32 (d, J=8.1 Hz, 1H), 7.17 (s, 1H), 7.08-7.00 (m, 2H), 6.95 (t, J=7.1 Hz, 1H), 6.88 (s, 1H), 4.02 (s, 3H), 3.94 (s, 3H), 3.69-3.62 (m, 1H), 3.20-3.12 (m, 1H), 2.97-2.88 (m, 1H), HPLC (Method 1) 94.1% (AUC), t$_R$=9.81 min: ESI MS m/z 490 [M+H]$^+$.

Preparation of (S)—N-(2-(5-chloro-2,4-dimethoxyphenyl)imidazo[1,2-a]pyridin-7-yl)-pyrrolidine-2-carboxamide 98c (Example 244)

Compound (S)—N-(2-(5-chloro-2,4-dimethoxyphenyl)imidazo[1,2-a]pyridin-7-yl)-pyrrolidine-2-carboxamide 98c was prepared in the same manner as (S)-2,6-diamino-N-(2-(5-chloro-2,4-dimethoxyphenyl)imidazo[1,2-a]pyridin-7-yl)hexanamide 98a and was obtained as an off-white solid (60 mg, 39% yield).

$^1$H NMR (400 MHz, DMSO-d$_6$): δ 10.23 (br s, 1H), 8.44 (d, J=7.3 Hz, 1H), 8.19 (s, 1H), 8.17 (s, 1H), 7.98 (s, 1H), 7.09 (d, J=7.3 Hz, 1H), 6.87 (s, 1H), 4.01 (s, 3H), 3.93 (s, 3H), 3.84-3.79 (m, 1H), 2.96 (t, J=6.9 Hz, 2H), 2.16-2.05 (m, 1H), 1.89-1.78 (m, 1H), 1.76-1.65 (m, 2H); HPLC (Method 1) 96.1% (AUC), t$_R$=8.50 min; ESI MS m % z 401 [M+H]$^+$.

Preparation of (S)-2-amino-N-(2-(5-chloro-2,4-dimethoxyphenyl)imidazo[1,2-a]pyridin-7-yl)-3-methylbutanamide 98d (Example 252)

Compound (S)-2-amino-N-(2-(5-chloro-2,4-dimethoxyphenyl)imidazo[1,2-a]pyridin-7-yl)-3-methylbutanamide 98d was prepared in the same manner as (S)-2,6-diamino-N-(2-(5-chloro-2,4-dimethoxyphenyl)imidazo[1,2-a]pyridin-7-yl)hexanamide 98a and was obtained as yellow solid (25 mg, 22% yield).

$^1$H NMR (300 MHz, DMSO-d$_6$): δ 8.43 (d, J=7.43 Hz, 1H), 8.19 (s, 1H), 8.17 (s, 1H), 7.97 (s, 1H), 7.04 (m, 1H), 6.88 (s, 1H), 4.01 (s, 3H), 3.94 (s, 3H), 3.16-3.11 (m, 1H), 2.00-1.91 (m, 1H), 0.94 (d, J=6.80 Hz, 3H), 0.87 (d, J=6.80 Hz, 3H); HPLC (Method 1) 98.1% (AUC), t$_R$=9.31 min: ESI MS m/z 403 [M+H]$^+$.

Preparation of (2S,3S)—N-(2-(5-chloro-2,4-dimethoxyphenyl)imidazo[1,2-a]pyridin-7-yl)-3-methyl-2-(methylamino)pentanamide 98e (Example 266)

Compound (2S,3S)—N-(2-(5-chloro-2,4-dimethoxyphenyl)imidazo[1,2-a]pyridin-7-yl)-3-methyl-2-(methylamino)

pentanamide 98e was prepared in the same manner as (S)-2,6-diamino-N-(2-(5-chloro-2,4-dimethoxyphenyl)imidazo[1,2-a]pyridin-7-yl)hexanamide 98a and was obtained as a yellow-brown solid (40 mg, 21% yield).

$^1$H NMR (400 MHz, CD$_3$OD): δ 8.31 (d, J=7.2 Hz, 1H), 8.14 (s, 1H), 8.11 (s, 1H), 8.01 (s, 1H), 7.11 (d, J=7.2 Hz, 1H), 6.79 (s, 1H), 4.02 (s, 3H), 3.95 (s, 3H), 3.01 (br s, 1H), 2.38 (s, 3H), 1.82-1.58 (m, 2H), 1.44-1.17 (m, 1H), 1.08-0.82 (m, 6H); HPLC (Method 1) 96.7% (AUC), $t_R$=9.54 min; ESI MS m/z 431 [M+H]$^+$.

Preparation of (S)—N-(2-(5-chloro-2,4-dimethoxyphenyl)imidazo[1,2-a]pyridin-7-yl)-1-methylpyrrolidine-2-carboxamide 98f (Example 263)

To a mixture of HCl salt of 2-(5-chloro-2,4-dimethoxyphenyl)imidazo[1,2-a]pyridin-7-amine 97 (120 mg, 0.40 mmol) and Acid (65 mg, 0.50 mmol) in DMF (2 mL) was added HATU (190 mg, 0.50 mmol) followed by DIPEA (150 mg, 1.2 mmol). The reaction mixture was stirred at room temperature for 16 h. The reaction mixture was poured into water and the precipitate was collected by filtration. The crude was purified by combi-flash chromatography (silica gel, MeOH/DCM) to afford and was obtained as a yellow solid (50 mg, 34% yield).

$^1$H NMR (300 MHz, CDCl$_3$): δ 9.49 (s, 1H), 8.34 (s, 1H), 8.02 (d, J=7.3 Hz, 1H), 7.99 (s, 1H), 7.70 (br s, 1H), 7.32 (d, J=7.3 Hz, 1H), 6.58 (s, 1H), 4.00 (s, 3H), 3.95 (s, 3H), 3.27-3.20 (m, 1H), 3.08-3.02 (m, 1H), 2.48 (s, 3H), 2.46-2.41 (m, 1H), 2.36-2.24 (m, 1H), 2.04-1.93 (m, 1H), 1.89-1.79 (m, 2H); HPLC (Method 1) >99% (AUC), $t_R$=9.08 min; ESI MS m/z 415 [M+H]$^+$.

Preparation of tert-butyl ((2S,3R)-1-((2-(5-chloro-2,4-dimethoxyphenyl)imidazo[1,2-a]-pyridin-7-yl)amino)-3-methyl-1-oxopentan-2-yl)carbamate 98h (Example 257)

tert-Butyl ((2S,3R)-1-((2-(5-chloro-2,4-dimethoxyphenyl)imidazo[1,2-a]pyridin-7-yl)amino)-3-methyl-1-oxopentan-2-yl)carbamate 98h was prepared in the same manner as bis-boc protected form of (S)-2,6-diamino-N-(2-(5-chloro-2,4-dimethoxyphenyl)imidazo-[1,2-a]pyridin-7-yl)hexanamide during synthesis of (S)-2,6-diamino-N-(2-(5-chloro-2,4-dimethoxyphenyl)imidazo[1,2-a]pyridin-7-yl) hexanamide 98a and was obtained as an off-white solid (50 mg, 33% yield).

$^1$H NMR (300 MHz, CDCl$_3$): δ 8.84 (br s, 1H), 8.13 (s, 1H), 8.95 (d, J=7.3 Hz, 1H), 7.88 (s, 1H), 7.78 (s, 1H), 6.86 (br s, 1H), 6.42 (s, 1H), 5.24 (br s, 1H), 4.11 (t, J=7.8 Hz, 1H), 3.92 (s, 3H), 3.91 (s, 3H), 1.96 (br s, 1H), 1.48 (s, 9H), 1.31-1.20 (m, 2H), 1.02 (d, J=6.8 Hz, 3H), 0.93 (t, J=7.3 Hz, 3H); HPLC (Method 1) 98.8% (AUC), $t_R$=11.85 min; ESI MS m/z 517 [M+H]$^+$.

Preparation of (2S,3R)-2-amino-N-(2-(5-chloro-2,4-dimethoxyphenyl)imidazo[1,2-a]-pyridin-7-yl)-3-methylpentanamide 98h (Example 258)

Compound (2S,3R)-2-amino-N-(2-(5-chloro-2,4-dimethoxyphenyl)imidazo[1,2-a]-pyridin-7-yl)-3-methylpentanamide 98h was prepared in the same manner as (S)-2,6-diamino-N-(2-(5-chloro-2,4-dimethoxyphenyl)imidazo[1,2-a]pyridin-7-yl)hexanamide 98a and was obtained as an off-white solid (25 mg, 20% yield).

$^1$H NMR (400 MHz, DMSO-d$_6$): δ 8.43 (s, 1H), 8.18 (s, 1H), 7.98 (s, 1H), 7.05 (s, 1H), 6.88 (s, 1H), 4.02 (s, 3H), 3.94 (s, 3H), 3.17 (s, 1H), 1.69 (s, 1H), 1.52 (s, 1H), 1.28-1.09 (m, 1H), 0.90 (s, 3H), 0.93 (s, 3H); HPLC (Method 1) 98.8% (AUC), $t_R$=9.5 min; ESI MS m/z 417 [M+H]$^+$.

Preparation of tert-butyl (2-((2-(5-chloro-2,4-dimethoxyphenyl)imidazo[1,2-a]pyridin-7-yl)-amino)-2-oxoethyl)carbamate 98i (Example 161)

Compound tert-butyl (2-((2-(5-chloro-2,4-dimethoxyphenyl)imidazo[1,2-a]pyridin-7-yl)amino)-2-oxoethyl)carbamate 98i was prepared in the same manner as bis-boc protected form of (S)-2,6-diamino-N-(2-(5-chloro-2,4-dimethoxyphenyl)imidazo[1,2-a]pyridin-7-yl)hexanamide and was obtained as an yellow solid (60 mg, 43% yield).

$^1$H NMR (300 MHz, CDCl$_3$): δ 8.50 (br s, 1H), 8.35 (s, 1H), 8.00 (s, 1H), 7.98 (s, 1H), 7.68 (s, 1H), 7.11 (d, J=6.2 Hz, 1H), 6.56 (s, 1H), 5.28 (br s, 1H), 3.98 (s, 3H), 3.95 (s, 3H), 3.93-3.90 (m, 2H), 1.49 (s, 9H); HPLC (Method 3) 96.9% (AUC), $t_R$=17.5 min; ESI MS m/z 461 [M+H]$^+$.

Preparation of 2-amino-N-(2-(5-chloro-2,4-dimethoxyphenyl)imidazo[1,2-a]pyridin-7-yl)-acetamide 98j (Example 166)

Compound (2-amino-N-(2-(5-chloro-2,4-dimethoxyphenyl)imidazo[1,2-a]pyridin-7-yl)-acetamide 98j was prepared in the same manner as (S)-2,6-diamino-N-(2-(5-chloro-2,4-dimethoxyphenyl)imidazo[1,2-a]pyridin-7-yl) hexanamide 98a and was obtained as an off-white solid (30 mg, 77% yield).

$^1$H NMR (300 MHz, DMSO-d$_6$): δ 8.44 (d, J=7.3 Hz, 1H), 8.19 (s, 1H), 8.17 (s, 1H), 7.97 (s, 1H), 7.04 (d, J=7.3 Hz, 1H), 6.88 (s, 1H), 4.01 (s, 3H), 3.94 (s, 3H), 3.34 (m, 2H); HPLC (Method 1) 97.6% (AUC), $t_R$=8.8 min; ESI MS m/z 361 [M+H]$^+$.

Preparation of (S)-tert-butyl (1-((2-(5-chloro-2,4-dimethoxyphenyl)imidazo[1,2-a]-pyridin-7-yl)amino)-1-oxopropan-2-yl)carbamate 98k (Example 253)

Compound (S)-tert-butyl (1-((2-(5-chloro-2,4-dimethoxyphenyl)imidazo[1,2-a]pyridin-7-yl)amino)-1-oxopropan-2-yl)carbamate 98k was prepared in the same manner as bis-boc protected form of (S)-2,6-diamino-N-(2-(5-chloro-2,4-dimethoxyphenyl)imidazo[1,2-a]pyridin-7-yl)hexanamide during synthesis of (S)-2,6-diamino-N-(2-(5-chloro-2,4-dimethoxyphenyl)-imidazo[1,2-a]pyridin-7-yl) hexanamide 98a and was obtained as an off-white solid (70 mg, 50% yield).

$^1$H NMR (400 MHz, CDCl$_3$): δ 8.87 (br s, 1H), 8.37 (s, 1H), 7.96 (d, J=7.2 Hz, 1H), 7.94 (s, 1H), 7.71 (s, 1H), 7.00 (s, 1H), 6.52 (s, 1H), 5.00 (br s, 1H), 4.34 (br s, 1H), 3.96 (s, 3H), 3.94 (s, 3H), 1.48 (s, 9H), 1.45 (d, J=7.0 Hz, 3H); HPLC (Method 1) >99% (AUC), $t_R$=11.05 min: ESI MS m/z 475 [M+H]$^+$.

Scheme 29

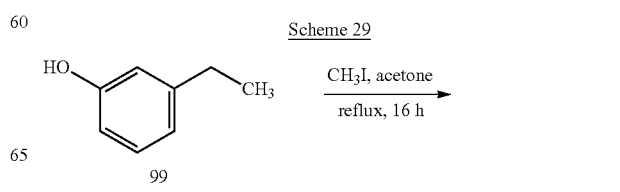

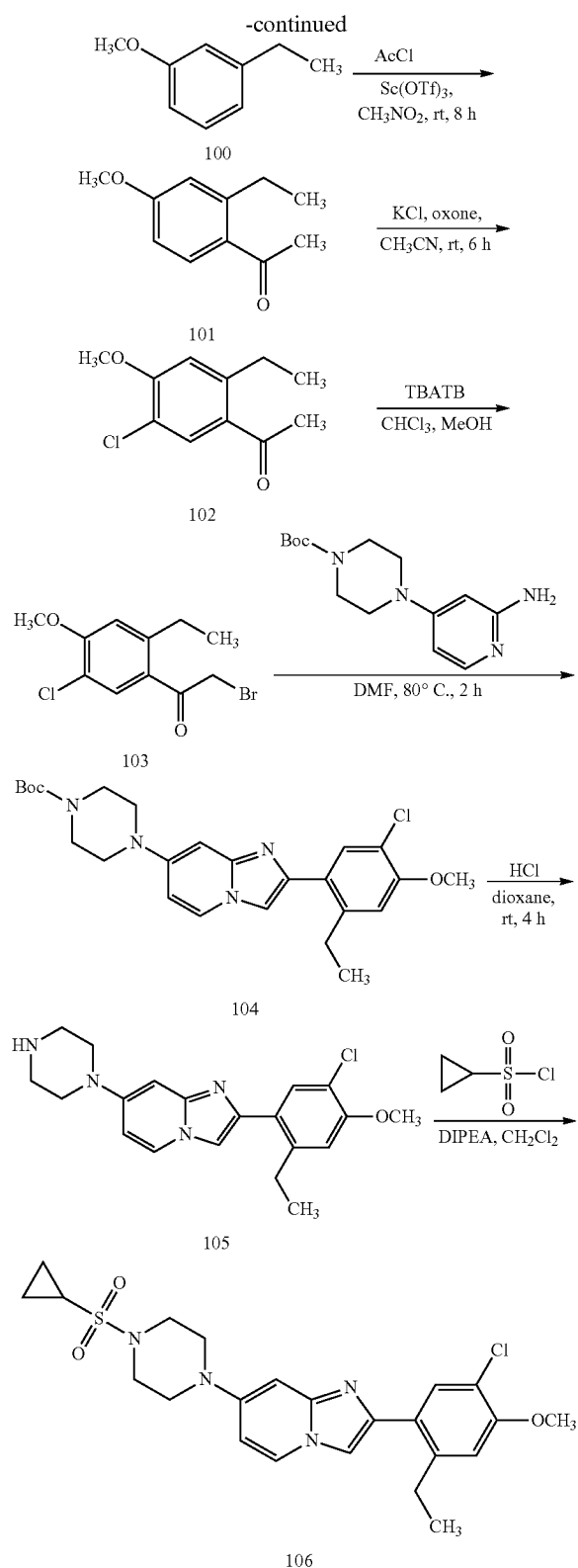

Preparation of 1-ethyl-3-methoxybenzene 100

To a solution of 3-ethylphenol 99 (5.00 g, 40.9 mmol) in acetone (50 mL) was added potassium carbonate (11.30 g, 81.80 mmol) followed by iodo methane (7.53 g, 53.10 mmol). The reaction mixture was heated to reflux for 16 h. The reaction mixture was filtered and the filtrate was concentrated under reduced pressure. The residue was taken in ethyl acetate (200 mL) and washed with 10% sodium hydroxide solution (100 mL). The organic layer was concentrated under reduced pressure to provide the desired compound 1-ethyl-3-methoxybenzene 100 (5.00 g, 90%) as a pale-yellow liquid.

Preparation of 1-(2-ethyl-4-methoxyphenyl)ethanone 101

To a solution of 1-ethyl-3-methoxybenzene 100 (3.25 g, 23.7 mmol) in nitromethane (30 mL) was added acetyl chloride (2.78 g, 35.5 mmol) followed by Scandium triflate (1.2 g, 2.4 mmol). The reaction mixture was stirred at room temperature for 8 h. The reaction mixture was concentrated under reduced pressure. The residue was purified by column chromatography (silica gel, EtOAc/Hexane) to afford 1-(2-ethyl-4-methoxyphenyl)ethanone 101 (550 mg, 23%) as a pale-yellow liquid.

Preparation of 1-(5-chloro-2-ethyl-4-methoxyphenyl)ethanone 102

To a solution of 1-(2-ethyl-4-methoxyphenyl)ethanone 101 (550 mg, 3.10 mmol) in 1:1 water/acetonitrile mixture (11 mL) was added potassium chloride (250 mg, 3.40 mmol) followed by oxone (2.1 g, 3.40 mmol). The reaction mixture was stirred at room temperature for 3 h. The reaction mixture was extracted with ethyl acetate (100 mL) and the organic layer was concentrated under reduced pressure. The residue was purified by column chromatography (silica gel, EtOAc/Hexane) to afford 1-(5-chloro-2-ethyl-4-methoxyphenyl)ethanone 102 (250 mg, 38%/o) as a colourless liquid.

Preparation of 2-bromo-1-(5-chloro-2-ethyl-4-methoxyphenyl)ethanone 103

A mixture of 1-(5-chloro-2-ethyl-4-methoxyphenyl)ethanone 102 (250 mg, 1.20 mmol) and tetrabutyl ammoniumtribromide (580 mg, 1.20 mmol) in 3:1 DCM/MeOH (8 mL) was stirred at room temperature for 16 h. The reaction mixture was concentrated under reduced pressure and purified by column chromatography (silica gel, DCM/Hexane) to afford 2-bromo-1-(5-chloro-2-ethyl-4-methoxyphenyl)ethanone 103 (270 mg, 79%) as an orange semisolid.

Preparation of tert-butyl 4-(2-(5-chloro-2-ethyl-4-methoxyphenyl)imidazo[1,2-a]pyridin-7-yl)piperazine-1-carboxylate 104

A mixture of 2-bromo-1-(5-chloro-2-ethyl-4-methoxyphenyl)ethanone 103 (260 mg, 0.90 mmol), tert-butyl 4-(2-aminopyridin-4-yl)piperazine-1-carboxylate (250 g, 0.90 mmol), and NaHCO₃ (230 mg, 2.70 mmol) in DMF (5 mL) was heated at 90° C. for 2 h. The reaction mixture was cooled to room temperature and poured into water. The precipitate so obtained was filtered, washed with water, and dried under reduced pressure. The precipitate was purified by column chromatography (silica gel, MeOH/DCM) to provide tert-butyl 4-(2-(5-chloro-2-ethyl-4-methoxyphenyl) imidazo[1,2-a]pyridin-7-yl)piperazine-1-carboxylate 104 (300 mg, 71.4%) as a pale yellow solid.

Preparation of 2-(5-chloro-2-ethyl-4-methoxyphenyl)-7-(piperazin-1-yl)imidazo-[1,2-a]pyridine 105 (Example 260)

A solution of tert-butyl 4-(2-(5-chloro-2-ethyl-4-methoxyphenyl)imidazo[1,2-a]-pyridin-7-yl)piperazine-1-carboxylate 104 (200 mg, 0.40 mmol) in 4.0 M HCl in dioxane (5 mL) was stirred at room temperature for 4 h. The reaction mixture was filtered, washed with dioxane, and dried under reduced pressure to give the HCl salt of the desired compound 2-(5-chloro-2,4-dimethoxyphenyl)-7-(piperazin-1-yl)imidazo[1,2-a]pyridine 105 (120 mg, 71%) as a yellow solid. The compound was suspended in 10 mL of aqueous ammonia, stirred for 1 h at room temperature, and the solid precipitated was filtered to give the free base of 2-(5-chloro-2-ethyl-4-methoxyphenyl)-7-(piperazin-1-yl)imidazo[1,2-a]pyridine 105 as an off-white solid.

$^1$H NMR (300 MHz, CDCl$_3$): δ 7.91 (d, J=7.3 Hz, 1H), 7.79 (s, 1H), 7.39 (s, 1H), 6.84 (s, 1H), 6.81 (s, 1H), 6.59 (d, J=7.3 Hz, 1H), 3.94 (s, 3H), 3.23-3.17 (m, 4H), 3.07-3.02 (m, 4H), 2.94-2.86 (m, 2H), 1.23 (t, J=7.6 Hz, 3H); HPLC (Method 1) 97.3% (AUC), t$_R$=9.24 min; ESI MS m/z 371 [M+H]$^+$.

Preparation of 2-(5-chloro-2-ethyl-4-methoxyphenyl)-7-(4-(cyclopropylsulfonyl)piperazin-1-yl)imidazo[1,2-a]pyridine 106 (Example 261)

A solution of 2-(5-chloro-2-ethyl-4-methoxyphenyl)-7-(piperazin-1-yl)imidazo-[1,2-a]pyridine 105(120 mg, 0.30 mmol) and DIPEA (120 mg, 0.90 mmol) in dichloromethane (2 mL) was charged with cyclopropylsulfonyl chloride (60 mg, 0.40 mmol). The reaction mixture was stirred at room temperature for 3 h. After 3 h, the reaction mixture was concentrated, suspended in aqueous ammonia, and stirred for 2 h. The precipitate was filtered, washed with water, dried under reduced pressure, and purified by column chromatography (silica gel, MeOH/DCM) to provide the desired sulfonamide 2-(5-chloro-2-ethyl-4-methoxyphenyl)-7-(4-(cyclopropylsulfonyl)piperazin-1-yl)imidazo[1,2-a]pyridine 106(70 mg, 46%) as an off-white solid.

$^1$H NMR (400 MHz, CDCl$_3$): δ 7.96 (d, J=7.38 Hz, 1H), 7.76 (s, 1H), 7.41 (s, 1H), 6.92 (br s, 1H), 6.85 (s, 1H), 6.60 (d, J=7.4 Hz, 1H), 3.94 (s, 3H), 3.51-3.46 (m, 41H), 3.39-3.34 (m, 4H), 2.94-2.86 (m, 2H), 2.34-2.26 (m, 1H), 1.26-1.19 (m, 5H), 1.06-1.00 (m, 2H); HPLC (Method 1) 97.9% (AUC), t$_R$=11.06 min; ESI MS m/z 475 [M+H]$^+$.

Scheme 30

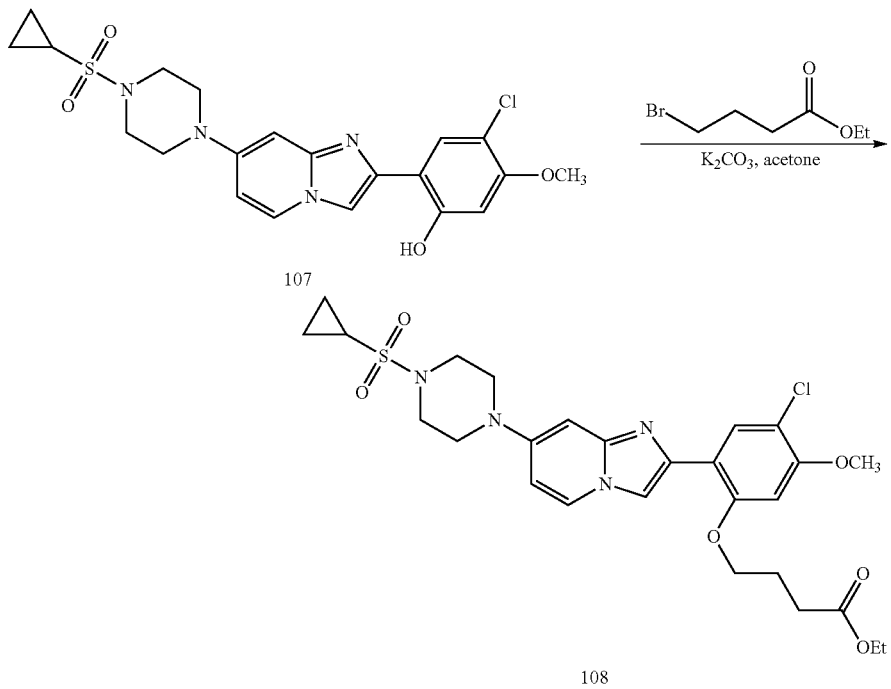

Preparation of ethyl 4-(4-chloro-2-(7-(4-(cyclopropylsulfonyl)piperazin-1-yl)-imidazo[1,2-a]pyridin-2-yl)-5-methoxyphenoxy)butanoate 108

To a solution of 4-chloro-2-(7-(4-(cyclopropylsulfonyl)piperazin-1-yl)imidazo-[1,2-a]pyridin-2-yl)-5-methoxyphenol 107 (1.0 g, 2.16 mmol) in acetone (15 mL), K$_2$CO$_3$ (0.9 g, 4.66 mmol) and ethyl 4-bromobutanoate (0.4 mL, 2.59 mmol) was added. The reaction mixture was heated to reflux for 24 h. The solvent was removed under reduced pressure and the residue was extracted with CH$_2$Cl$_2$ (2×25 ml) and washed with water. The combined organics was washed with brine (50 ml), dried over Na$_2$SO$_4$ and concentrated under reduced pressure to give ethyl 4-(4-chloro-2-(7-(4-(cyclopropylsulfonyl)piperazin-1-yl)imidazo[1,2-a]pyridin-2-yl)-5-methoxyphenoxy)butanoate 108 (80%) as a brown solid.

$^1$H NMR (400 MHz, CDCl$_3$): δ 8.37 (s, 1H), 7.96 (d, J=8.0 Hz, 1H), 7.88 (s, 1H), 6.85 (d, J=1.9 Hz, 1H), 6.59 (s, 1H), 6.56 (dd, J=2.2, 7.8 Hz, 1H), 4.20-4.12 (m, 4H), 3.93 (s, 3H), 3.49-4.47 (m, 4H), 3.35-3.32 (m, 4H), 2.58 (t, J=6.7

Hz, 2H), 2.30-2.26 (m, 3H), 1.25 (t, J=6.9 Hz, 3H), 1.16-1.12 (m, 2H), 1.03-0.96 (m, 2H); HPLC (Method 1) 95.3%; APCI MS m/z 577 [M+H]+.

Preparation of 2-(4-chloro-2-(7-(4-(cyclopropylsulfonyl)piperazin-1-yl)imidazo[1,2-a]-pyridin-2-yl)-5-methoxyphenoxy)ethanamine 108b (Example 234)

Compound tert-butyl (2-(4-chloro-2-(7-(4-(cyclopropylsulfonyl)piperazin-1-yl)imidazo-[1,2-a]pyridin-2-yl)-5-methoxyphenoxy)ethyl)carbamate 108a was prepared in a similar manner to that of ethyl 4-(4-chloro-2-(7-(4-(cyclopropylsulfonyl)piperazin-1-yl)imidazo[1,2-a]pyridin-2-yl)-5-methoxyphenoxy)butanoate 108, by using tert-butyl(2-bromoethyl)carbamate as the alkylating reagent, in 80% yield, tert-Butyl (2-(4-chloro-2-(7-(4-(cyclopropylsulfonyl)-piperazin-1-yl)imidazo[1,2-a]pyridin-2-yl)-5-methoxyphenoxy)ethyl)carbamate 108a was treated with TFA/CH$_2$Cl$_2$ to afford the free base of 2-(4-chloro-2-(7-(4-(cyclopropylsulfonyl)-piperazin-1-yl)imidazo[1,2-a]pyridin-2-yl)-5-methoxyphenoxy)ethanamine 108b, after neutralization with NaOH, as off-white solid (60% yield).

$^1$H NMR (400 MHz, CDCl$_3$): δ 8.22 (s, 1H), 7.99 (d, J=7.4 Hz, 1H), 7.83 (s, 1H), 6.90 (d, J=2.2 Hz, 1H), 6.58 (s, 1H), 6.56 (dd, J=2.2, 7.6 Hz, 1H), 4.22 (t, J=5.1 Hz, 2H), 3.93 (s, 3H), 3.49-4.47 (m, 4H), 3.39-3.35 (m, 4H), 3.27 (t, J=5.3 Hz, 2H), 2.32-2.30 (m, 1H), 1.24-1.18 (m, 2H), 1.05-0.96 (m, 2H); HPLC (Method 2) 95.4% (AUC), t$_R$=15.93 min; ESI MS m/z 506 [M+H]+ 1

Scheme 31

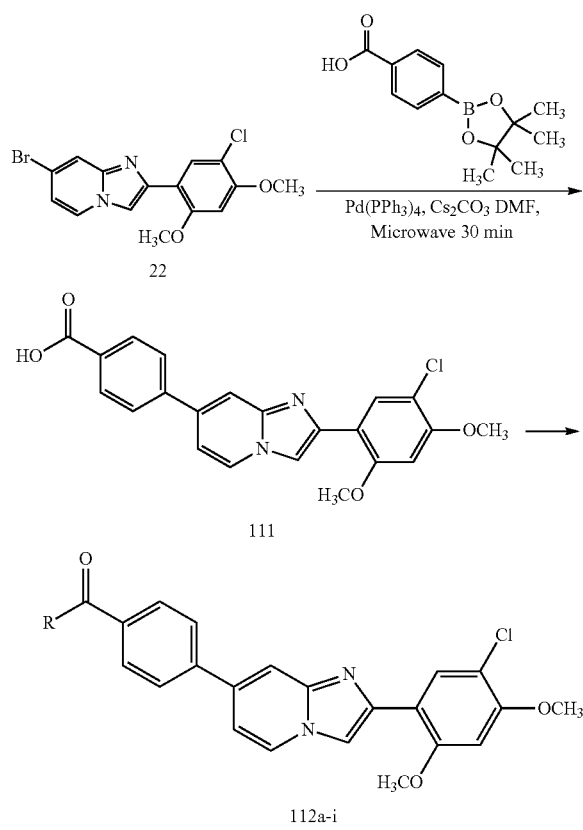

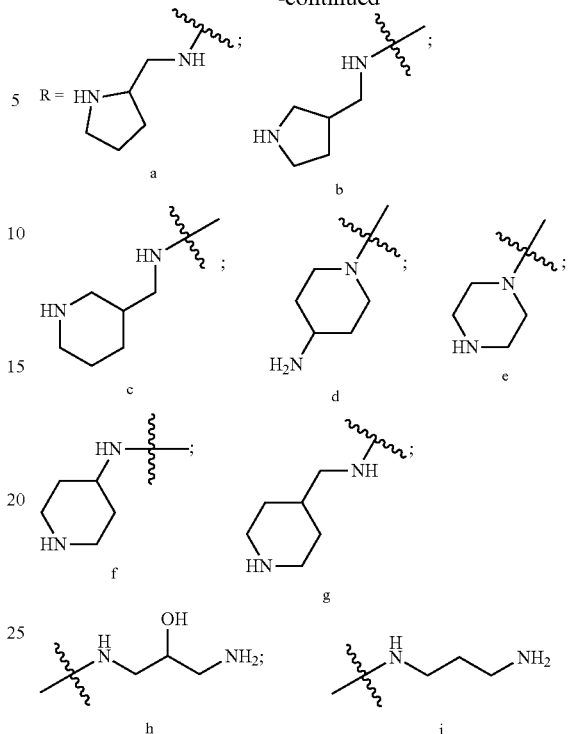

Preparation of 4-(2-(5-chloro-2,4-dimethoxyphenyl)imidazo[1,2-a]pyridin-7-yl)benzoic acid 111 (Example 246)

To a solution of 22 (300 mg, 0.81 mmol) in 1,4-dioxane (30 mL) were added boronic ester (403 mg, 1.62 mmol), Cs$_2$O$_3$ (660 mg, 4.0 mmol) and Pd catalyst (40 mg, 0.057 mmol). The reaction mixture was heated in microwave for 30 min at 90° C. The reaction mixture was diluted with water and extracted with 10% MeOH/CH$_2$Cl$_2$ (2×25 ml) and water. The combined organics washed with brine (50 ml), dried over Na$_2$SO$_4$ and concentrated under reduced pressure to give 4-(2-(5-chloro-2,4-dimethoxyphenyl)imidazo[1,2-a]pyridin-7-yl)-benzoic acid 111 (70% yield) as a yellow solid.

$^1$H NMR (400 MHz, CD$_3$OD): δ 8.47 (d, J=7.2 Hz, 1H), 8.28 (s, 1H), 8.17 (s, 1H), 8.07 (d, J=8.4 Hz, 2H), 7.76-7.79 (m, 3H), 7.26 (dd, J=1.9, 7.3 Hz, 1H), 6.82 (s, 1H), 4.06 (s, 3H), 3.98 (s, 3H); HPLC (Method 1) 98.8%; ESI MS m/z 409 [M+H]+.

Preparation of 4-(2-(5-chloro-2,4-dimethoxyphenyl)imidazo[1,2-a]pyridin-7-yl)-N-(pyrrolidin-2-ylmethyl)benzamide 112a (Example 248)

To a solution of 4-(2-(5-chloro-2,4-dimethoxyphenyl)imidazo[1,2-a]pyridin-7-yl)-benzoic acid 111 (40 mg, 0.1 mmol) in DCM (5 mL) at room temperature was added EDC (28 mg, 0.15 mmol), HOBt (26 mg, 0.2 mmol), DIPEA (0.05 mL, 0.3 mmol) and tert-butyl 2-(aminomethyl)pyrrolidine-1-carboxylate (24 mg, 0.12 mmol). The reaction mixture was stirred at room temperature overnight. The solvent was removed under reduced pressure and the residue was extracted with 10% MeOH/CH$_2$C$_2$ (2×25 ml) and washed with water. The combined organics was washed with brine (50 ml), dried over Na$_2$SO$_4$ and concentrated under reduced pressure to give boc protected 4-(2-(5-chloro-2,4-dimethoxyphenyl)imidazo[1,2-a]-pyridin-7-yl)-N-(pyrrolidin-2-ylmethyl)benzamide as yellow solid.

Further, the solid compound: boc-protected 4-(2-(5-chloro-2,4-dimethoxyphenyl)imidazo [1,2-a]pyridin-7-yl)-N-(pyrrolidin-2-ylmethyl)benzamide (50 mg, 0.08 mmol) was added in 4.0 M HCl in dioxane (1 mL) and MeOH (1 mL). Reaction was stirred at 50° C. for 1 h. The reaction mixture was cooled to room temperature and concentrated under reduced pressure, and the residue was suspended in aqueous ammonia (10 mL). The suspension was stirred at room temperature for 2 h and extracted with chloroform (2×10 mL). The combined organic layer was dried over sodium sulfate and concentrated under reduced pressure, and the residue was purified by column chromatography (silica gel, 1:0.1:10 methanol/ammonium hydroxide/DCM) to give 4-(2-(5-chloro-2,4-dimethoxyphenyl)imidazo[1,2-a]pyridin-7-yl)-N-(pyrrolidin-2-ylmethyl)benzamide 112a as a yellow solid (60% yield).

$^1$H NMR (400 MHz, CDCl$_3$): δ 8.45 (d, J=6.9 Hz, 1H), 8.25 (s, 1H), 8.14 (s, 1H), 7.97 (d, J=8.0 Hz, 2H), 7.83 (d, J=8.0 Hz, 2H), 7.78 (s, 1H), 7.24 (d, J=6.9 Hz, 1H), 6.79 (s, 1H), 4.04 (s, 3H), 3.96 (s, 3H), 3.58-3.41 (m, 2H), 3.40-3.32 (m, 1H), 3.09-2.97 (m, 1H), 2.92-2.84 (m, 1H), 2.02-1.92 (m, 1H), 1.91-1.73 (m, 2H), 1.62-1.50 (m, 1H); APCI m/z 491 [M+H]; HPLC (Method 1) >99%.

Preparation of 4-(2-(5-chloro-2,4-dimethoxyphenyl)imidazo[1,2-a]pyridin-7-yl)-N-(pyrrolidin-2-ylmethyl)benzamide 112b (Example 249)

4-(2-(5-Chloro-2,4-dimethoxyphenyl)imidazo[1,2-a]pyridin-7-yl)-N-(pyrrolidin-2-ylmethyl)benzamide 112b was prepared in the same manner as 4-(2-(5-chloro-2,4-dimethoxyphenyl)imidazo[1,2-a]pyridin-7-yl)-N-(pyrrolidin-2-ylmethyl)benzamide 112a and was obtained as a brown solid (36% yield).

$^1$H NMR (400 MHz, CD$_3$OD): δ 8.42 (d, J=7.1 Hz, 1H), 8.22 (s, 1H), 8.13 (s, 1H), 7.93 (d, J=8.0 Hz, 2H), 7.81 (d, J=8.0 Hz, 2H), 7.75 (s, 1H), 7.21 (d, J=6.8 Hz, 1H), 6.77 (s, 1H), 4.84-4.81 (m, 1H), 4.03 (s, 3H), 3.95 (s, 3H), 3.28-319 (m, 1H), 3.18-3.07 (m, 1H), 3.02-2.92 (m, 1H), 2.91-2.85 (m, 1H), 2.30-2.18 (m, 1H), 1.95-1.80 (m, 1H); HPLC (Method 1) 98.4%. APCI MS m/z 477 [M+H]$^+$.

Preparation of 4-(2-(5-chloro-2,4-dimethoxyphenyl)imidazo[1,2-a]pyridin-7-yl)-N-(piperidin-3-ylmethyl)benzamide 112c (Example 251)

Compound 4-(2-(5-chloro-2,4-dimethoxyphenyl)imidazo[1,2-a]pyridin-7-yl)-N-(piperidin-3-ylmethyl)benzamide 112c was prepared in the same manner as 4-(2-(5-chloro-2,4-dimethoxyphenyl)imidazo[1,2-a]pyridin-7-yl)-N-(pyrrolidin-2-ylmethyl)benzamide 112a and was obtained as a brown solid (32% yield).

$^1$H NMR (400 MHz, CD$_3$OD): δ 8.47 (d, J=7.4 Hz, 1H), 8.28 (s, 1H), 8.16 (s, 1H), 7.94 (d, J=8.3 Hz, 2H), 7.85 (d, J=8.3 Hz, 2H), 7.80 (s, 1H), 7.27 (d, J=6.8 Hz, 1H), 6.82 (s, 1H), 4.03 (s, 3H), 3.97 (s, 3H), 3.18-3.09 (m, 1H), 3.08-2.95 (m, 1H), 2.67-2.53 (m, 1H), 2.47-2.36 (m, 1H), 1.99-1.83 (m, 2H), 1.82-1.69 (m, 1H), 1.63-1.47 (m, 1H), 1.22-1.18 (m, 1H); HPLC (Method 1) 98.1%; APCI MS m/z 505 [M+H]$^+$.

Preparation of (4-aminopiperidin-1-yl)(4-(2-(5-chloro-2,4-dimethoxyphenyl)imidazo[1,2-a]pyridin-7-yl)phenyl)methanone 112d (Example 259)

Compound (4-aminopiperidin-1-yl)(4-(2-(5-chloro-2,4-dimethoxyphenyl)imidazo-[1,2-a]pyridin-7-yl)phenyl)methanone 112d was prepared in the same manner as 4-(2-(5-chloro-2,4-dimethoxyphenyl)imidazo[1,2-a]pyridin-7-yl)-N-(pyrrolidin-2-ylmethyl)benzamide 112a and was obtained as an brown solid (32% overall yield).

$^1$H NMR (400 MHz, CD$_3$OD): δ 8.48 (d, J=7.4 Hz, 1H), 8.28 (s, 1H), 8.16 (s, 1H), 7.95 (d, J=8.0 Hz, 2H), 7.85 (d, J=8.1 Hz, 2H), 7.79 (s, 1H), 7.27-7.24 (m, 1H), 6.82 (s, 1H), 4.06 (s, 3H), 3.97 (s, 3H), 3.26-3.17 (m, 2H), 2.88-2.78 (m, 2H), 2.29-2.00 (m, 2H), 1.72-1.60 (m, 2H); HPLC (Method 1) 94.1%; APCI MS m/z 491 [M+H]$^+$.

Preparation of (4-(2-(5-chloro-2,4-dimethoxyphenyl)imidazo[1,2-a]pyridin-7-yl)-phenyl)(piperazin-1-yl)methanone 112e (Example 254)

Compound (4-(2-(5-chloro-2,4-dimethoxyphenyl)imidazo[1,2-a]pyridin-7-yl)-phenyl)(piperazin-1-yl)methanone 112e was prepared in the same manner as 4-(2-(5-chloro-2,4-dimethoxyphenyl)imidazo[1,2-a]pyridin-7-yl)-N-(pyrrolidin-2-ylmethyl)benzamide 112a and was obtained as a brown solid (28% overall yield).

$^1$H NMR (400 MHz, CDCl$_3$): δ 8.43 (s, 1H), 8.17 (d, J=7.0 Hz, 1H), 8.12 (s, 1H), 7.83 (s, 1H), 7.69 (d, J=8.1 Hz, 2H), 7.53 (d, J=7.6 Hz, 2H), 7.03 (d, J=7.6 Hz, 1H), 6.61 (s, 1H), 4.03 (s, 3H), 3.97 (m, 3H), 3.79-3.49 (m, 4H), 3.00-2.79 (m, 1H); HPLC (Method 1) 94.22%, t$_R$=9.31 min.; APCI-MS m/z 477 [M+H]$^+$.

Preparation of 4-(2-(5-chloro-2,4-dimethoxyphenyl)imidazo[1,2-a]pyridin-7-yl)-N-(piperidin-4-yl)benzamide 112f (Example 268)

Compound 4-(2-(5-chloro-2,4-dimethoxyphenyl)imidazo[1,2-a]pyridin-7-yl)-N-(piperidin-4-yl)benzamide 112f was prepared in the same manner as 4-(2-(5-chloro-2,4-dimethoxyphenyl)imidazo[1,2-a]pyridin-7-yl)-N-(pyrrolidin-2-ylmethyl)benzamide 112a and was obtained as an brown solid (31% yield).

$^1$H NMR (400 MHz, CDCl$_3$): δ 8.43 (s, 1H), 8.17 (d, J=7.0 Hz, 1H), 8.12 (s, 1H), 7.88-7.85 (m, 3H), 7.72 (d, J=8.0 Hz, 2H), 7.06 (d, J=7.1 Hz, 1H), 6.61 (s, 1H), 6.02 (d, J=7.6 Hz, 1H), 4.12-4.10 (m, 1H), 4.03 (s, 3H), 3.97 (m, 3H), 3.14-3.11 (m, 2H), 2.81-2.74 (m, 2H), 2.15-2.05 (m, 2H), 1.49-1.46 (m, 2H); HPLC (Method 1) 97.68%, t$_R$=9.47 min.; APCI-MS m/z 491 [M+H]$^+$.

Preparation of 4-(2-(5-chloro-2,4-dimethoxyphenyl)imidazo[1,2-a]pyridin-7-yl)-N-(piperidin-4-ylmethyl)benzamide 112e (Example 267)

Compound 4-(2-(5-chloro-2,4-dimethoxyphenyl)imidazo[1,2-a]pyridin-7-yl)-N-(piperidin-4-ylmethyl)benzamide 112g was prepared in the same manner as 4-(2-(5-chloro-2,4-dimethoxyphenyl)imidazo[1,2-a]pyridin-7-yl)-N-(pyrrolidin-2-ylmethyl)benzamide 112a and was obtained as a brown solid (17 mg, 32% overall yield).

$^1$H NMR (400 MHz, CDCl$_3$): δ 8.43 (s, 1H), 8.17 (d, J=7.0 Hz, 1H), 8.12 (s, 1H), 7.88-7.85 (m, 3H), 7.72 (d, J=8.0 Hz, 2H), 7.06 (d, J=7.1 Hz, 1H), 6.61 (s, 1H), 6.25 (m, 1H), 4.12-4.10 (m, 1H), 4.03 (s, 3H), 3.97 (s, 3H), 3.40-3.37 (m, 2H), 3.12-3.09 (m, 2H), 2.65-2.59 (m, 2H), 1.78-1.75 (m, 3H), 1.27-1.19 (m, 3H); HPLC (Method 1) 97.36%, t$_R$=9.5 min.; ESI-MS m/z 505 [M+H]$^+$.

Preparation of N-(3-amino-2-hydroxypropyl)-4-(2-(5-chloro-2,4-dimethoxyphenyl)-imidazo[1,2-a]pyridin-7-yl)benzamide 112h (Example 256)

Compound N-(3-amino-2-hydroxypropyl)-4-(2-(5-chloro-2,4-dimethoxyphenyl)-imidazo[1,2-a]pyridin-7-yl)

benzamide 112h was prepared in the same manner as 4-(2-(5-chloro-2,4-dimethoxyphenyl)imidazo[1,2-a]pyridin-7-yl)-N-(pyrrolidin-2-ylmethyl)benzamide 112a and was obtained as a brown solid (28% overall yield).

$^1$H NMR (400 MHz, CD$_3$OD): δ 8.51 (s, 1H), 8.31 (s, 1H), 8.16 (s, 1H), 8.0 (d, J=8.2 Hz, 2H), 7.89 (d, J=8.2 Hz, 2H), 7.82 (s, 1H), 7.28 (d, J=6 Hz, 1H), 6.84 (s, 1H), 4.06 (s, 4H), 4.04 (s, 3H), 3.55-3.47 (m, 2H), 3.13-3.09 (m, 1H), 2.92-2.87 (m, 1H); HPLC (Method 1) 99.03%, $t_R$=9.34 min.; APCI-MS m/z 481 [M+H]$^+$.

Preparation of N-(3-aminopropyl)-4-(2-(5-chloro-2,4-dimethoxyphenyl)imidazo-[1,2-a]pyridin-7-yl)benzamide 112i (Example 265)

Compound N-(3-aminopropyl)-4-(2-(5-chloro-2,4-dimethoxyphenyl)imidazo[1,2-a]-pyridin-7-yl)benzamide 112i was prepared in the same manner as 4-(2-(5-chloro-2,4-dimethoxyphenyl)imidazo[1,2-a]pyridin-7-yl)-N-(pyrrolidin-2-ylmethyl)benzamide 112a and was obtained as a brown solid (30 mg, 46% yield).

$^1$H NMR (400 MHz, CD$_3$OD): δ 8.46 (d, J=7.0 Hz, 1H), 8.26 (s, 1H), 8.15 (s, 1H), 7.95-7.93 (m, 2H), 7.86-7.84 (m, 2H), 7.78 (s, 1H), 7.24 (d, J=7.1 Hz, 1H), 6.80 (s, 1H), 4.05 (s, 3H), 3.96 (s, 3H), 3.50 (t, J=12.4 Hz, 2H), 2.80 (t, J=6.9 Hz, 2H), 1.88-1.84 (m, 2H); HPLC (Method 1) 95.26%, $t_R$=9.39 min.; ESI-MS m/z 465 [M+H]$^+$.

Scheme 32

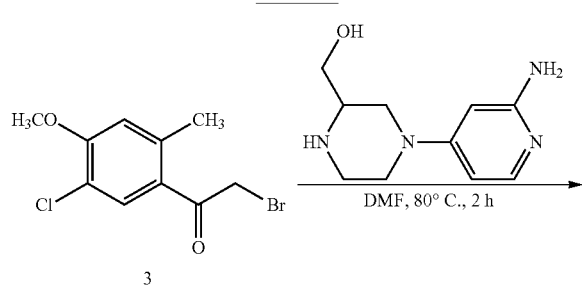

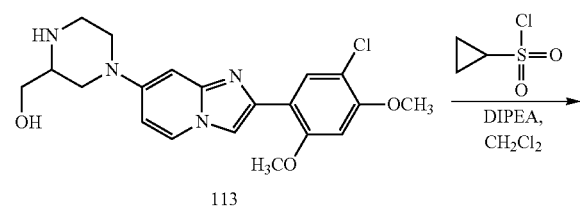

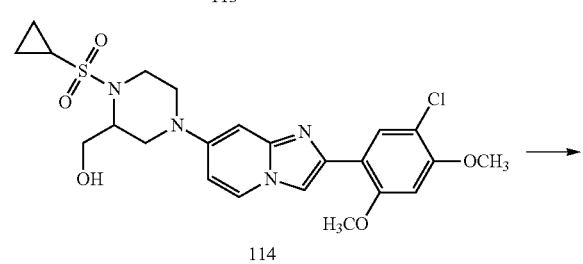

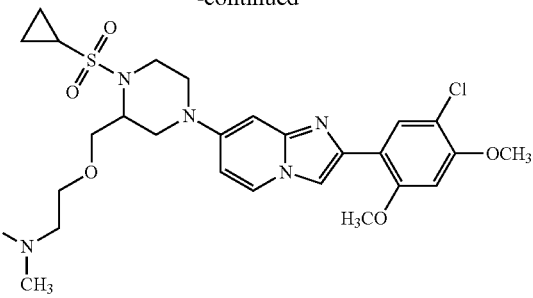

115a

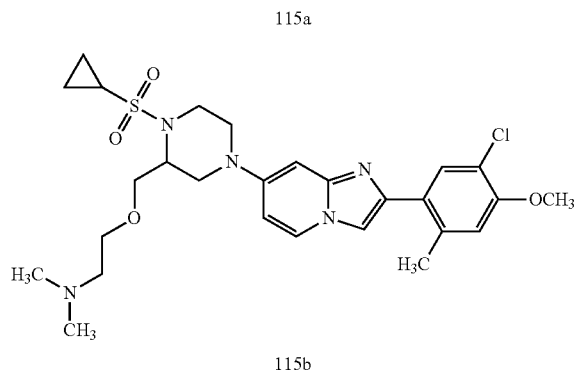

115b

Preparation of (4-(2-(5-chloro-2,4-dimethoxyphenyl)imidazo[1,2-a]pyridin-7-yl)-piperazin-2-yl)methanol 113 (Example 235)

A mixture of 2-bromo-1-(5-chloro-2,4-dimethoxyphenyl)ethanone 3 (197 mg, 0.67 mmol), (4-(2-aminopyridin-4-yl)piperazin-2-yl)methanol (200 mg, 0.96 mmol), and NaHCO$_3$ (161 g, 1.92 mmol) in ethanol (15 mL) was heated at 80° C. for 4 h. The reaction mixture was cooled to room temperature and solvent was removed. The residue was purified by column chromatography (silica gel, 15% MeOH/CHCl$_3$) to provide (4-(2-(5-chloro-2,4-dimethoxyphenyl)imidazo[1,2-a]pyridin-7-yl)piperazin-2-yl)methanol (90 mg, 23%) as a white solid.

$^1$H NMR (400 MHz, DMSO-d$_6$): δ 8.28 (d, J=7.4, 1H), 8.16 (s, 1H), 8.00 (s, 1H), 6.86 (s, 1H), 6.76 (dd, 1H, J=2.3, 7.6), 6.60 (d, J=2.1, 1H), 4.66 (t, 1H, J=5.3), 4.00 (s, 3H), 3.95 (s, 3H), 3.69-3.63 (m, 1H), 3.62-3.56 (m, 1H), 3.42-3.35 (m, 2H), 3.02-2.96 (m, 1H), 2.81-2.72 (m, 2H), 2.70-2.62 (m, 1H), 2.40-2.32 (m, 2H); HPLC (Method 2) 98.25% (AUC), $t_R$=11.35 min.; APCI MS m/z 403 [M+H]$^+$.

Preparation of (4-(2-(5-chloro-2,4-dimethoxyphenyl)imidazo[1,2-a]pyridin-7-yl)-1-(cyclopropylsulfonyl) piperazin-2-yl)methanol 114 (Example 236)

Compound (4-(2-(5-chloro-2,4-dimethoxyphenyl)imidazo[1,2-a]pyridin-7-yl)-1-(cyclopropylsulfonyl)piperazin-2-yl)methanol 114 was prepared in the same manner as 2-(5-chloro-2,4-dimethoxyphenyl)-7-[4-(methylsulfonyl)piperazin-1-yl]imidazo[1,2-a]pyridine 13a and was obtained as an off-white solid (8 mg, 10% yield).

$^1$H NMR (400 MHz, DMSO-d$_6$) δ 8.33 (s, 1H), 7.93 (s, 1H), 7.91 (s, 1H), 6.90 (s, 1H), 6.50 (s, 1H), 6.49 (s, 1H), 4.10 (br s, 1H), 4.05-3.85 (m, 9H), 3.85-3.80 (m, 2H), 3.65-3.55 (m, 1H), 3.55-3.45 (m, 1H), 3.25-3.10 (m, 1H), 3.05-2.95 (m, 1H), 2.55-2.45 (m, 1H), 1.28-1.25 (m, 2H), 1.15-1.03 (m, 2H); HPLC (Method 2) 96.04% (AUC), $t_R$=14.06 min.; APCI MS m/z 507 [M+H]$^+$.

Preparation of (4-(2-(5-chlor-4-methoxy-2-methyl-phenyl)imidazo[1,2-a]pyridin-7-yl)-1-(cyclopropyl-sulfonyl)piperazin-2-yl)methanol 114b (Example 262)

Compound (4-(2-(5-chloro-4-methoxy-2-methylphenyl)imidazo[1,2-a]pyridin-7-yl)-1-(cyclopropylsulfonyl)piperazin-2-yl)methanol 114b was prepared in the same manner as (4-(2-(5-chloro-2,4-dimethoxyphenyl)imidazo[1,2-a]pyridin-7-yl)-1 (cyclopropylsulfonyl) piperazin-2-yl)methanol 114 by using 2-bromo-1-(5-chloro-4-methoxy-2-methylphenyl) ethanone in place of 2-bromo-1-(5-chloro-2,4-dimethoxyphenyl)ethanone 3. The product was obtained as an amorphous off-white solid (30% yield).

$^1$H NMR (400 MHz, CDCl$_3$): δ 7.95 (d, J=6.7 Hz, 1H), 7.94 (s, 1H), 7.45 (s, 1H), 6.84 (d, J=2.2 Hz, 1H), 6.81 (s, 1H), 6.55 (dd, J=2.4, 7.5 Hz, 1H), 4.13-4.06 (m, 1H), 4.04-3.98 (m 1H), 3.95-3.89 (m, 4H), 3.93-3.77 (m, 2H), 3.59-3.45 (m, 2H), 3.08 (dd, J=3.8, 12.7 Hz, 1H), 3.04 (td, J=4.1, 11.8 Hz, 1H), 2.52 (s, 3H), 2.51-2.45 (m, 1H), 1.24-1.20 (m, 2H), 1.06-1.01 (m, 2H); HPLC (Method 1) 96.5% (AUC), $t_R$=10.36 min.; ESI MS m/z 491 [M+H]$^+$.

Preparation of 2-((4-(2-(5-chloro-2,4-dimethoxyphe-nyl)imidazo[1,2-a]pyridin-7-yl)-1-(cyclopropylsulfo-nyl)piperazin-2-yl)methoxy)-N,N-dimethylethan-amine 115a (Example 245)

A mixture of (4-(2-(5-chloro-2,4-dimethoxyphenyl)imidazo[1,2-a]pyridin-7-yl)-1-(cyclopropylsulfonyl)piperazin-2-yl)methanol 114 (80 mg, 0.15 mmol), N,N-dimethyl-ethanamine (72 mg, 0.47 mmol) and NaH (5.7 g, 0.23 mmol) in THF (5 mL) was stirred at room temperature for 48 h. Reaction was quenched with water and extracted with ethyl acetate. Solvent was removed and the residue was purified by column chromatography (silica gel, 15% MeOH/CHCl$_3$) to provide 2-((4-(2-(5-chloro-2,4-dimethoxyphenyl)imidazo[1,2-a]pyridin-7-yl)-1-(cyclopropylsulfonyl)piperazin-2-yl)methoxy)-N,N-dimethylethanamine (11 mg, 12%) as a white solid.

$^1$H NMR (400 MHz, CDCl$_3$): δ 8.36 (s, 1H), 7.91 (d, J=7.1 Hz, 1H), 7.88 (s, 1H), 6.82 (d, J=2.4 Hz, 1H), 6.58 (s, 1H), 6.55 (dd, J=2.4, 7.5 Hz, 1H), 4.20 (s, 1H), 4.01 (s, 3H) 3.96 (s, 3H), 3.90-3.84 (m, 1H), 3.81-3.75 (m, 3H), 3.65 (t, J=5.7 Hz, 2H), 3.56 (d, J=12.3 Hz, 1H), 3.45-3.35 (m, 1H), 3.04-2.92 (m, 2H), 2.67-2.56 (m, 2H), 2.55-2.48 (m, 1H), 2.34 (s, 6H), 1.22-1.17 (m, 2H), 1.03-0.98 (m, 2H); HPLC (Method 1) 93.78% (AUC), $t_R$=9.55 min.; APCI MS m/z 578 [M+H]$^+$.

Preparation of 2-((4-(2-(5-chloro-4-methoxy-2-methylphenyl)imidazo[1,2-a]pyridin-7-yl)-1-(cyclo-propylsulfonyl)piperazin-2-yl)methoxy)-N,N-dim-ethylethanamine 115b (Example 264)

Compound 2-((4-(2-(5-chloro-4-methoxy-2-methylphe-nyl)imidazo[1,2-a]pyridin-7-yl)-1-(cyclopropylsulfonyl)piperazin-2-yl)methoxy)-N,N-dimethylethanamine 115b was prepared in the same manner as 2-((4-(2-(5-chloro-2,4-dimethoxyphenyl)imidazo[1,2-a]pyridin-7-yl)-1-(cyclopro-pylsulfonyl)piperazin-2-yl)methoxy)-N,N-dimethylethan-amine 115a by using 2-bromo-1-(5-chloro-4-methoxy-2-methylphenyl)ethanone in place of 2-bromo-1-(5-chloro-2,4-dimethoxyphenyl)ethanone 3. The product was obtained as a yellow green solid (25 mg, 33% yield).

$^1$H NMR (400 MHz, CDCl$_3$): δ 7.94 (d, J=6.8 Hz, 2H), 7.46 (s, 1H), 6.82 (s, 1H), 6.81 (s, 1H), 6.59 (d, J=6.9 Hz, 1H), 4.23 (m, 1H), 3.93 (s, 3H), 3.86-3.82 (m, 1H), 3.80-3.78 (m, 3H), 3.64 (t, J=11.16 Hz, 2H), 3.55-3.53 (m, 1H), 3.41-3.38 (m, 1H), 3.04-2.96 (m, 2H), 2.61-2.51 (m, 2H), 2.50 (s, 4H), 2.33 (s, 6H), 1.25-1.19 (m, 2H), 1.02-1.00 (m, 2H); HPLC (Method 1) 96.48%, $t_R$=9.55 min.; APCI-MS m/z 562 [M+H]$^+$.

Scheme 33

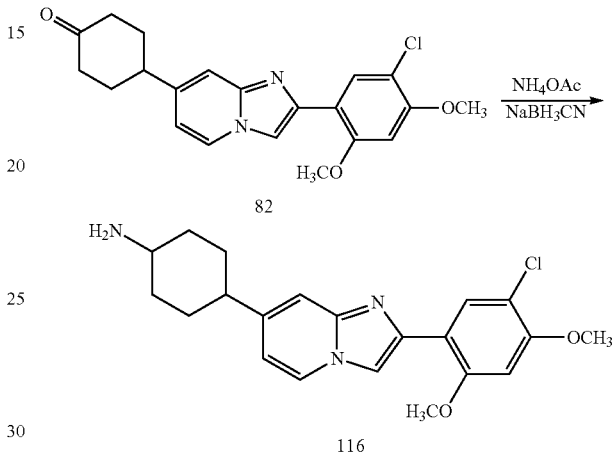

Preparation of 4-(2-(5-chloro-2,4-dimethoxyphenyl)imidazo[1,2-a]pyridin-7-yl)-cyclohexanamine 116 (Example 125)

A mixture of 4-(2-(5-chloro-2,4-dimethoxyphenyl)imidazo[1,2-a]pyridin-7-yl)-cyclohexanone 82 (200 mg, 0.53 mmol), ammonium acetate (123 mg, 1.60 mmol) and sodium cyano borohydride (99 mg, 1.60 mmol) in methanol (10 ml) were stirred at room temperature for 16 h. The reaction mixture was concentrated and washed with dilute ammonia solution. The residue was purified by column chromatography (silica gel, 10:1 DCM/MeOH) to provide 4-(2-(5-chloro-2,4-dimethoxyphenyl)imidazo[1,2-a]pyri-din-7-yl)cyclohexanamine 116(200 mg, 86%) as a light yellow solid.

$^1$H NMR (400 MHz, CDCl$_3$): δ 8.38 (s, 1H), 8.02-7.96 (m, 2H), 7.38 (s, 1H), 6.62 (dd, J=1.6, 7.0 Hz, 1H), 6.58 (s, 1H), 4.00 (s, 3H), 3.95 (s, 3H), 2.80 (br s, 1H), 2.55-2.46 (m, 1H), 2.08-1.95 (m, 4H), 1.59-1.46 (m, 2H), 1.38-1.26 (m, 2H); APCI MS m/z 386 [M+H]$^+$.

Scheme 34

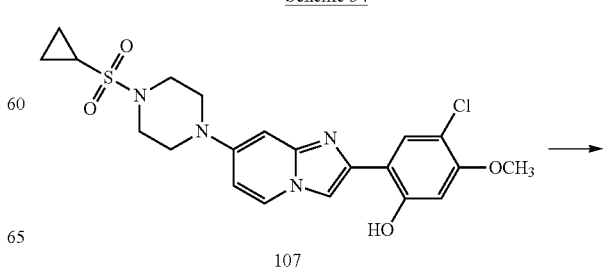

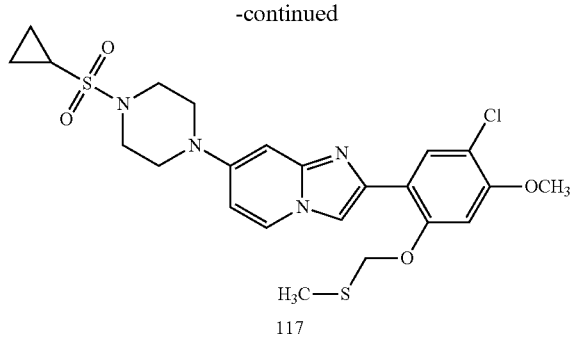

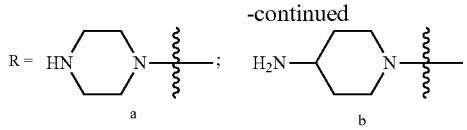

Preparation of 2-(5-chloro-4-methoxy-2-((methylthio)methoxy)phenyl)-7-(4-(cyclopropylsulfonyl)piperazin-1-yl)imidazo[1,2-a]pyridine 117 (Example 255)

Compound 2-(5-chloro-4-methoxy-2-((methylthio)methoxy)phenyl)-7-(4-(cyclo-propylsulfonyl)piperazin-1-yl)imidazo[1,2-a]pyridine 117 was prepared in the same manner as ethyl 4-(4-chloro-2-(7-(4-(cyclopropylsulfonyl)piperazin-1-yl)imidazo[1,2-a]-pyridin-2-yl)-5-methoxyphenoxy)butanoate 108 and was obtained as an off-white solid (59% yield).

$^1$H NMR (400 MHz, DMSO-$d_6$): δ 8.40-8.38 (m, 1H), 8.20 (s, 1H), 8.06 (s, 1H), 6.97 (s, 1H), 6.84-6.82 (m, 1H), 6.75 (s, 1H), 5.54 (s, 2H), 3.92-3.90 (m, 3H), 3.36-3.32 (m, 8H), 2.69-2.66 (m, 1H), 2.22 (s, 3H), 1.00-0.96 (m, 4H); ESI MS m/z 523 [M+H]$^+$.

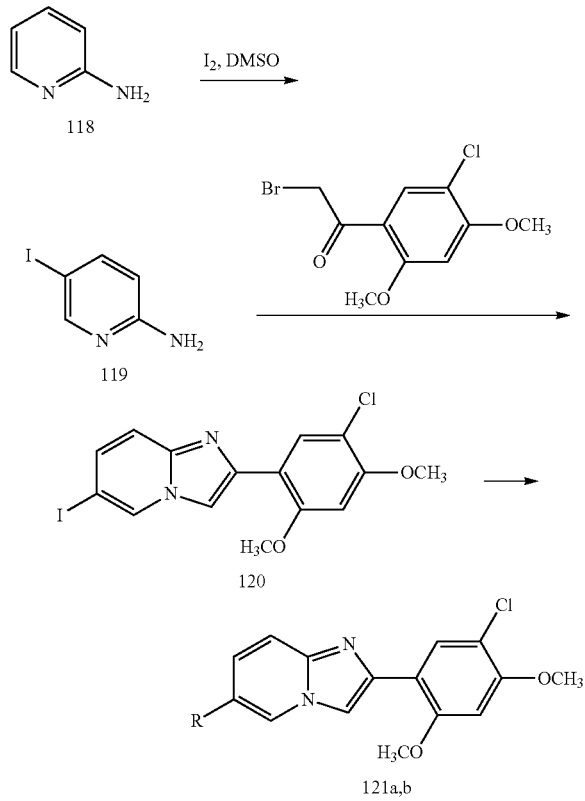

Preparation of 5-iodopyridin-2-amine 119

To a solution of 2-aminopyridine 118 (5.00 g, 53.0 mmol) in dimethylsulfoxide (100 mL) was added iodine granules (8.09 g, 31.8 mmol). The reaction mixture was heated at 100° C. for 30 min. The reaction mixture was cooled to room temperature and quenched with 10% sodium thiosulfate solution (100 mL) and extracted with ethyl acetate (250 mL). The organic layer was concentrated under reduced pressure, and purified by column chromatography (silica gel, MeOH/DCM) to afford 5-iodopyridin-2-amine 119 (2.8 g, 24%) as a dark-yellow solid.

Preparation of 2-(5-chloro-2,4-dimethoxyphenyl)-6-iodoimidazo[1,2-a]pyridine 120

A solution of 2-bromo-1-(5-bromo-2,4-dimethoxyphenyl)ethanone (3.50 g, 12.0 mmol) and 5-iodopyridin-2-amine 119 (2.50 g, 11.4 mmol) in acetone (25 mL) was heated at 75° C. for 16 h. The reaction mixture was cooled to room temperature; the white precipitate was filtered and washed with acetone. The precipitate was suspended in aqueous ammonia (10 mL) and stirred for 2 h. The precipitate was filtered, washed with water and dried under reduced pressure to yield 2-(5-chloro-2,4-dimethoxyphenyl)-6-iodoimidazo[1,2-a]pyridine 120 (4.00 g, 85%) as an off-white solid.

Preparation of 2-(5-chloro-2,4-dimethoxyphenyl)-6-(piperazin-1-yl)imidazo[1,2-a]-pyridine hydrochloride 121a (Example 115)

A mixture of 2-(5-chloro-2,4-dimethoxyphenyl)-6-iodoimidazo[1,2-a]pyridine 120 (200 mg, 0.50 mmol), N-Boc piperazine (110 mg, 0.60 mmol), copper(I)iodide (14 mg, 0.075 mmol), Ethylene glycol (60 mg, 1.00 mmol) and potassium phosphate (320 mg, 1.50 mmol) were taken in 2-propanol (2 mL) and degassed with argon. The reaction mixture was heated to 85° C. for 30 h. The reaction mixture was cooled to room temperature, diluted with DCM (20 mL) and filtered through celite bed. The filtrate was distilled under reduced pressure and the residue was purified by combi-flash chromatography (silica gel, MeOH/DCM) and the compound was treated with 4M HCl in 1,4-dioxane. The reaction mixture was concentrated under reduced pressure to afford 2-(5-chloro-2,4-dimethoxyphenyl)-6-(piperazin-1-yl)imidazo[1,2-a]pyridine hydrochloride salt 121a (30 mg, 17%) as a yellow solid.

$^1$H NMR (300 MHz, DMSO-$d_6$): δ 9.34 (s, 1H), 8.48 (s 1H), 8.46 (s, 1H), 8.14 (s, 1H), 7.83 (br s, 2H), 6.99 (s, 1H), 4.07 (s, 3H), 4.00 (s, 3H), 3.48-3.32 (m, 8H); HPLC (Method 1) >99% (AUC), $t_R$=8.89 min; APCI MS m/z 373 [M+H]$^+$.

Preparation of 1-(2-(5-chloro-2,4-dimethoxyphenyl)imidazo[1,2-a]pyridin-6-yl)piperidin-4-amine 121b (Example 121)

1-(2-(5-Chloro-2,4-dimethoxyphenyl)imidazo[1,2-a]pyridin-6-yl)piperidin-4-amine 121b was prepared in the same manner as 2-(5-chloro-2,4-dimethoxyphenyl)-6-(piperazin-1-yl)imidazo[1,2-a]pyridine.HCl salt 121a. The HCl salt of 1-(2-(5-chloro-2,4-dimethoxyphenyl)imidazo[1,2-a]pyridin-6-yl)piperidin-4-amine 121 b obtained was suspended in aqueous ammonia (2 mL) and stirred for 2 h. The precipitate was filtered, washed with water, dried under reduced pressure to yield 1-(2-(5-chloro-2,4-dimethoxyphenyl)imidazo[1,2-a]-pyridin-6-yl)piperidin-4-amine 121b (30 mg, 16%) as an off-white solid.

$^1$H NMR (400 MHz, CD$_3$OD): δ 8.13 (s, 1H), 8.08 (s, 1H), 7.90 (s, 1H), 7.39 (d, J=7.2, 1H), 7.22 (d, J=7.4, 1H), 6.79 (s, 1H), 4.02 (s, 3H), 3.95 (s, 3H), 3.60-3.50 (m, 2H), 2.91-2.80 (m, 1H), 2.77-2.65 (m, 2H), 2.04-1.94 (m, 2H), 1.67-1.53 (m, 2H); HPLC (Method 1) >99% (AUC), t$_R$=8.96 min; ESI MS m/z 387 [M+H]$^+$.

Scheme 36

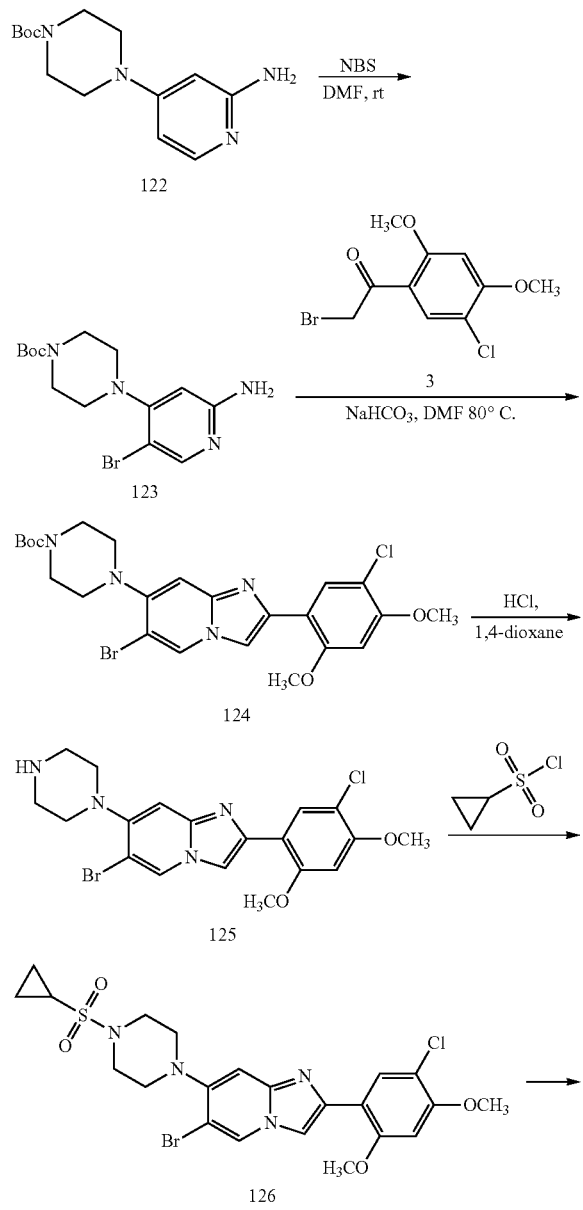

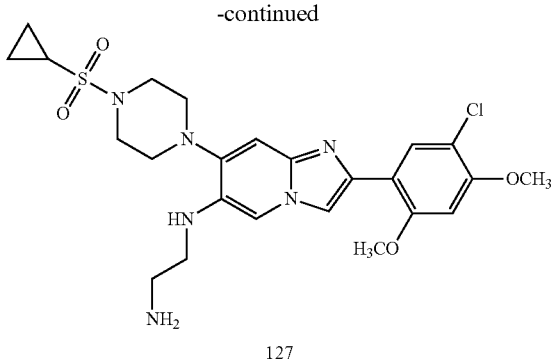

127

Preparation of tert-butyl 4-(2-amino-5-bromopyridin-4-yl)piperazine-1-carboxylate 123

To a solution of tert-butyl 4-(2-aminopyridin-4-yl)piperazine-1-carboxylate 122(250 mg, 0.90 mmol) in DMF (5 mL) was added N-bromosuccinimide (160 mg, 0.90 mmol). The reaction mixture was stirred at room temperature for 30 min. The reaction mixture was quenched with 10% sodium thiosulfate solution (100 mL) and extracted with chloroform (100 mL). The organic layer was concentrated under reduced pressure, and purified by column chromatography (silica gel, MeOH/DCM) to provide the desired compound tert-butyl 4-(2-amino-5-bromopyridin-4-yl)piperazine-1-carboxylate 123 (150 mg, 47%) as a pale-yellow solid.

Preparation of tert-butyl 4-(6-bromo-2-(5-chloro-2,4-dimethoxyphenyl)imidazo[1,2-a]-pyridin-7-yl)piperazine-1-carboxylate 124

To a solution of tert-butyl 4-(2-amino-5-bromopyridin-4-yl)piperazine-1-carboxylate 123 (750 mg, 2.10 mmol) in N,N-dimethylformamide (15 mL) was added 2-bromo-1-(5-chloro-2,4-dimethoxyphenyl)ethanone (620 mg, 2.10 mmol) followed by sodium bicarbonate (520 mg, 6.20 mmol). The reaction mixture was heated to 80° C. for 4 h. The reaction mixture was cooled to room temperature and quenched with water (25 mL) and the precipitate was filtered, dried under reduced pressure. The solid was purified by combi-flash chromatography (silica gel, 9:1 DCM/methanol) to afford tert-butyl 4-(6-bromo-2-(5-chloro-2,4-dimethoxyphenyl)imidazo-[1,2-a]pyridin-7-yl)piperazine-1-carboxylate 124 (800 mg, 69%) as an off white solid.

Preparation of 6-bromo-2-(5-chloro-2,4-dimethoxyphenyl)-7-(piperazin-1-yl)-imidazo[1,2-a]pyridine 125 (Example 217)

A solution of tert-butyl 4-(6-bromo-2-(5-chloro-2,4-dimethoxyphenyl)imidazo[1,2-a]-pyridin-7-yl)piperazine-1-carboxylate 124 (800 mg, 1.50 mmol) in 4.0 M HCl in dioxane (5 mL) was stirred at room temperature for 3 h. The reaction mixture was filtered, washed with dioxane, and dried under reduced pressure to give 6-bromo-2-(5-chloro-2,4-dimethoxyphenyl)-7-(piperazin-1-yl)imidazo[1,2-a]pyridine hydrochloride (600 mg, 92%) as a yellow solid. The solid was suspended in 10 mL of aqueous ammonia, stirred for 1 h at room temperature, and extracted using chloroform (2×20 mL). The organic layer was dried and concentrated to give 6-bromo-2-(5-chloro-2,4-dimethoxyphenyl)-7-(piperazin-1-yl)imidazo[1,2-a]pyridine 125 as an off-white solid.

¹H NMR (300 MHz, DMSO-d₆): δ 8.86 (s, 1H), 8.18 (s, 1H), 8.13 (s, 1H), 7.06 (s, 1H), 6.88 (s, 1H), 4.01 (s, 3H), 3.94 (s, 3H), 3.00-2.86 (m, 8H). HPLC (Method 1) 96.7% (AUC), $t_R$=9.17 min; ESI MS m/z 453 [M+H]⁺.

Preparation of 6-bromo-2-(5-chloro-2,4-dimethoxyphenyl)-7-(4-(cyclopropyl-sulfonyl)piperazin-1-yl)imidazo[1,2-a]pyridine 126

Compound 6-bromo-2-(5-chloro-2,4-dimethoxyphenyl)-7-(4-(cyclopropyl-sulfonyl)piperazin-1-yl)imidazo[1,2-a]pyridine 126 was prepared in the same manner as 2-(5-chloro-2,4-dimethoxyphenyl)-7-[4-(methylsulfonyl)piperazin-1-yl]imidazo[1,2-a]pyridine 13a and was obtained as a yellow solid (600 mg, 75% yield).

Preparation of N¹-(2-(5-chloro-2,4-dimethoxyphenyl)-7-(4-(cyclopropylsulfonyl-piperazin-1-yl)imidazo[1,2-a]pyridin-6-yl)ethane-1,2-diamine 127 (Example 225)

Compound N¹-(2-(5-chloro-2,4-dimethoxyphenyl)-7-(4-(cyclopropylsulfonyl)-piperazin-1-yl)imidazo[1,2-a]pyridin-6-yl)ethane-1,2-diamine 127 was prepared in the same manner as N¹-(2-(5-chloro-2,4-dimethoxyphenyl)imidazo[1,2-a]pyridin-7-yl)ethane-1,2-diamine 70a; and was obtained as a yellow solid (30 mg, 9% yield).

¹H NMR (300 MHz, CDCl₃): δ 8.33 (s, 1H), 7.90 (s, 1H), 7.30 (s, 1H), 7.10 (s, 1H), 6.57 (s, 1H), 4.56 (br s, 1H), 3.98 (s, 3H), 3.94 (s, 3H), 3.52-3.46 (m, 4H), 3.10-3.06 (m, 8H), 2.36-2.32 (m, 1H), 1.23-1.21 (m, 2H), 1.19-1.07 (m, 2H); HPLC (Method 1) 92.02% (AUC), $t_R$=9.60 min.; ESI MS m/z 535 [M+H]⁺.

Scheme 37

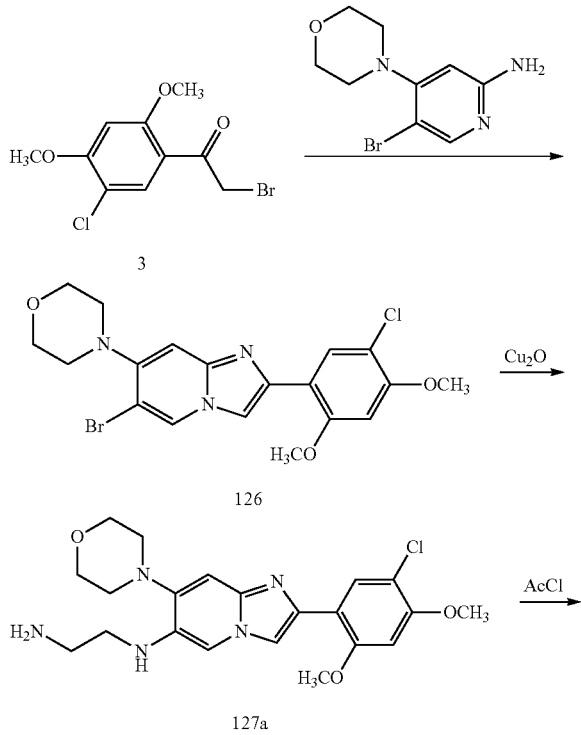

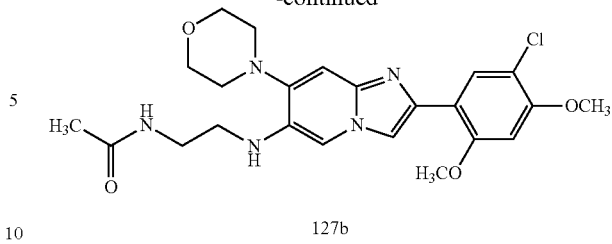

127b

Preparation of 4-(6-bromo-2-(5-chloro-2,4-dimethoxyphenyl)imidazo[1,2-a]pyridin-7-yl)morpholine 126

Compound 4-(6-bromo-2-(5-chloro-2,4-dimethoxyphenyl)imidazo[1,2-a]pyridin-7-yl)morpholine 126 was prepared in the same manner as 2-(5-chloro-2,4-dimethoxyphenyl)-7-(pyrrolidin-1-yl)imidazo[1,2-a]pyridine 5a and was obtained as a white solid (430 mg, 61%).

Preparation of N¹-(2-(5-chloro-2,4-dimethoxyphenyl-7-morpholinoimidazo[1,2-a]-pyridin-6-yl)ethane-1,2-diamine 127a (Example 89)

Compound N¹-(2-(5-chloro-2,4-dimethoxyphenyl)-7-morpholinoimidazo[1,2-a]-pyridin-6-yl)ethane-1,2-diamine 127a was prepared in the same manner as N¹-(2-(5-chloro-2,4-dimethoxyphenyl)imidazo[1,2-a]pyridin-7-yl)ethane-1,2-diamine 70a and was obtained as orange solid (170 mg, 32%).

¹H NMR (400 MHz, CDCl₃): δ 8.34 (s, 1H), 7.90 (d, 1H, J=7.6 Hz), 7.26 (s, 1H), 7.10 (s, 1H), 6.58 (s, 1H), 4.85 (br s, 1H), 3.99 (s, 3H), 3.95 (s, 3H), 3.88-3.81 (m, 4H), 3.07-3.03 (m, 4H), 3.01-2.98 (m, 4H); HPLC (Method 2) 92.6% (AUC), $t_R$=21.68 min.; ESI MS m/z 342 [M+H]⁺.

Preparation of N-(2-((2-(5-chloro-2,4-dimethoxyphenyl)-7-morpholinoimidazo[1,2-a]-pyridin-6-yl)amino)ethyl)acetamide 127b (Example 224)

Compound N-(2-((2-(5-chloro-2,4-dimethoxyphenyl)-7-morpholinoimidazo[1,2-a]-pyridin-6-yl)amino)ethyl)acetamide 127b was prepared in the same manner as afford N-(2-((2-(5-chloro-2,4-dimethoxyphenyl)imidazo[1,2-a]pyridin-7-yl)amino)ethyl)acetamide 70d. The product was obtained as white solid (28 mg, 51% yield).

¹H NMR (400 MHz, CDCl₃): δ 8.34 (s, 1H), 7.90 (d, J=7.6 Hz, 1H), 7.31 (s, 1H), 7.11 (s, 1H), 6.57 (s, 1H), 5.73 (br s, 1H), 3.99 (s, 3H), 3.95 (s, 3H), 3.91-3.88 (m, 4H), 3.64-3.62 (m, 2H), 3.18-3.16 (m, 2H), 2.98-2.97 (m, 4H), 2.03 (S, 3H); HPLC (Method 1) 97.46% (AUC), $t_R$=11.44 min.; ESI MS m/z 474 [M+H]⁺.

Preparation of N¹-(2-(5-chloro-2,4-dimethoxyphenyl)-8-fluoro-7-morpholinoimidazo-[1,2-a]pyridine-6-yl)ethane-1,2-diamine 127c (Example 208)

Compound N¹-(2-(5-chloro-2,4-dimethoxyphenyl)-8-fluoro-7-morpholinoimidazo-[1,2-a]pyridine-6-yl)ethane-1,2-diamine 127c was prepared in the same manner as 127a, following the sequence from 2-bromo-1-(5-chloro-2,4-dimethoxyphenyl)ethanone 3 using 5-bromo-3-fluoro-4-morpholinopyridin-2-amine. The desired product was obtained as an off-white solid (17% for 2 steps).

¹H NMR (300 MHz, CD₃OD): δ 8.15 (d, J=3.0 Hz, 1H), 8.06 (s, 1H), 7.7 (s, 1H), 6.82 (s, 1H), 4.03 (s, 3H), 3.96 (s, 3H), 3.87 (t, J=5.4 Hz, 4H), 3.48 (t, J=6.2 Hz, 2H), 3.28-3.17 (m, 6H); HPLC (Method 1) 98.7% (AUC), $t_R$=9.18 min.; ESI MS m/z 450 [M+H]⁺.

Scheme 38

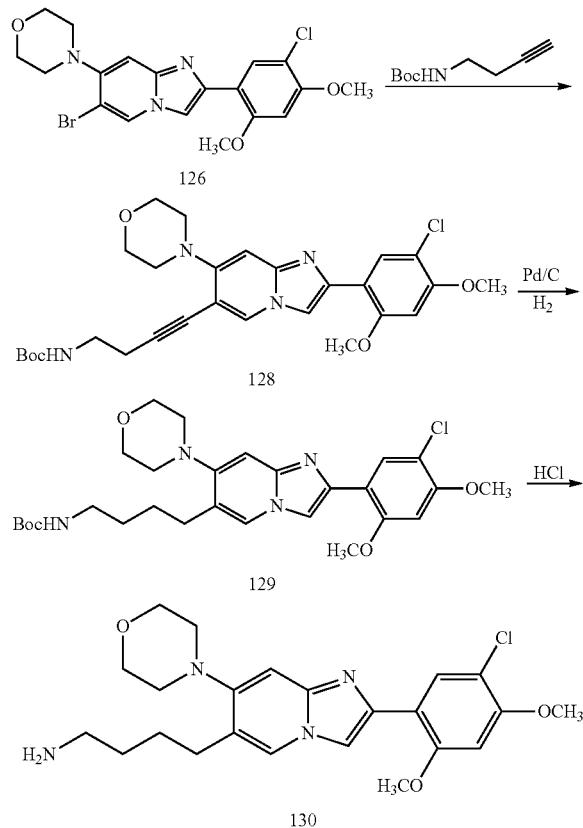

Preparation of tert-butyl (4-(2-(5-chloro-2,4-dimethoxyphenyl-7-morpholinoimidazo-[1,2-a]pyridin-6-yl)but-3-yn-1-yl)carbamate 128

A mixture of 4-(6-bromo-2-(5-chloro-2,4-dimethoxyphenyl)imidazo[1,2-a]pyridin-7-yl)morpholine 126 (275 mg, 0.60 mmol), tert-butyl but-3-yn-1-ylcarbamate (154 mg, 0.91 mmol), copper(I)iodide (5.7 mg, 0.03 mmol), tri-tert-butylphosphine (24.5 mg, 0.12 mmol) and triethylamine (323 μL, 2.42 mmol) were taken in acetonitrile (10 mL) and degassed with argon. Pd(PPh₃)₄(70 mg, 0.06 mmol) was added. The reaction mixture was heated to refluxed for 16 h. The reaction mass was cooled to room temperature, diluted with DCM (20 mL) and filtered through celite bed. The filtrate was distilled under reduced pressure and the residue was purified by combi-flash chromatography (silica gel, MeOH/DCM) to afford tert-butyl (4-(2-(5-chloro-2,4-dimethoxyphenyl)-7-morpholinoimidazo[1,2-a]pyridin-6-yl)but-3-yn-1-yl)carbamate 126 (150 mg, 45%) as an off-white solid.

Preparation of tert-butyl (4-(2-(5-chloro-2,4-dimethoxyphenyl)-7-morpholinoimidazo-[1,2-a]pyridin-6-yl)butyl)carbamate 129

A solution of tert-butyl (4-(2-(5-chloro-2,4-dimethoxyphenyl)-7-morpholinoimidazo-[1,2-a]pyridin-6-yl)but-3-yn-1-yl)carbamate 128 (140 mg, 0.25 mmol) in THF (10 ml) and methanol (1 ml) was charged with Pd/C (10 mg). The reaction mixture was stirred at room temperature under H₂ atmosphere (1 atm) for 16 h. The reaction mixture was filtered through a small pad of celite and washed with chloroform. The combined organic filtrate was concentrated under reduced pressure and the residue was purified by column chromatography (silica gel, 10:1 DCM/MeOH) to provide tert-butyl (4-(2-(5-chloro-2,4-dimethoxyphenyl)-7-morpholinoimidazo[1,2-a]pyridin-6-yl)butyl)carbamate 128 (88 mg, 78%) as a light yellow solid.

4-(2-(5-chloro-2,4-dimethoxyphenyl)-7-morpholinoimidazo[1,2-a]pyridin-6-yl)butan-1-amine 130
(Example 114)

Compound 4-(2-(5-chloro-2,4-dimethoxyphenyl)-7-morpholino-[1,2-a]pyridin-6-yl)butan-1-amine 130 was prepared in the same manner as 2-(5-chloro-2,4-dimethoxyphenyl)-7-(pyrrolidin-1-yl)imidazo[1,2-a]pyridine 5a. The salt obtained was basified with aqueous ammonia, washed with water, filtered and dried. The product was obtained as a white solid (62 mg, 87% yield).

¹H NMR (400 MHz, CDCl₃): δ 8.37 (s, 1H), 7.92 (s, 1H), 7.86 (s, 1H), 7.14 (s, 1H), 6.58 (s, 1H), 3.99 (s, 3H), 3.95 (s, 3H), 3.88-3.83 (m, 4H), 2.97-2.92 (m, 4H), 2.76 (t, J=6.8 Hz, 2H), 2.63 (t, J=7.6 Hz, 2H), 1.77-1.67 (m, 2H), 1.58-1.51 (m, 2H); HPLC (Method 1) 95.10% (AUC), $t_R$=9.25 min.; APCI MS m/z 445 [M+H]⁺.

Scheme 39

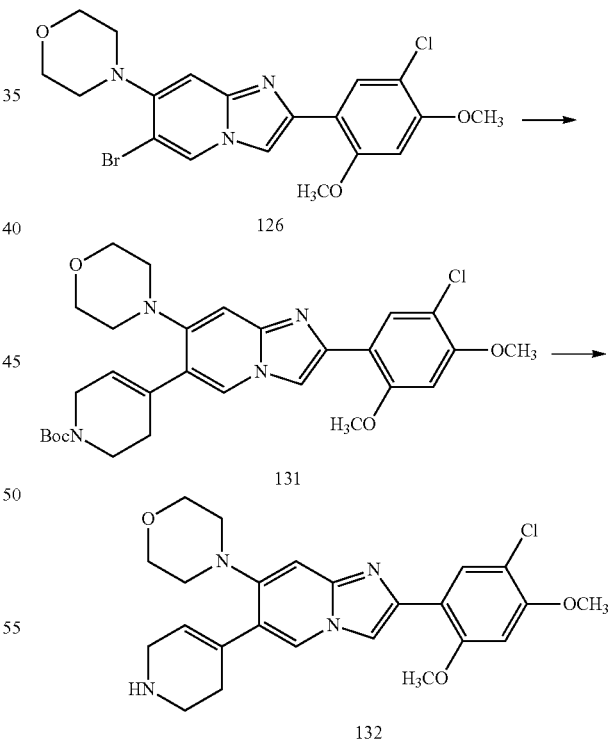

Preparation of tert-butyl 4-(2-(5-chloro-2,4-dimethoxyphenyl)-7-morpholinoimidazo[1,2-a]pyridin-6-yl)-5,6-dihydropyridine-1(2H)-carboxylate 131

Compound tert-butyl 4-(2-(5-chloro-2,4-dimethoxyphenyl)-7-morpholinoimidazo[1,2-a]pyridin-6-yl)-5,6-dihydropyridine-1(2H)-carboxylate 131 was prepared in the same manner as tert-butyl 4-[2-(5-chloro-2,4-dimethoxyphenyl)imidazo[1,2-a]pyridin-7-yl]-5,6-dihydropyridine-1(2H)-carboxylate 24a. The product was obtained as a white solid (100 mg, 54% yield).

Preparation of 4-(2-(5-chloro-2,4-dimethoxyphenyl)-6-(1,2,3,6-tetrahydropyridin-4-yl)imidazo[1,2-a]pyridin-7-yl)morpholine 132 (Example 101)

Compound 4-(2-(5-chloro-2,4-dimethoxyphenyl)-6-(1,2,3,6-tetrahydropyridin-4-yl)imidazo[1,2-a]pyridin-7-yl)morpholine 132 was prepared in the same manner as 2-(5-chloro-2,4-dimethoxyphenyl)-7-(pyrrolidin-1-yl)imidazo[1,2-a]pyridine 5a. The product was obtained as an off-white solid (25 mg, 64% yield).

$^1$H NMR (400 MHz, DMSO-$d_6$): δ 14.9 (brs, 1H), 9.50 (br s, 2H), 8.52 (s, 1H), 8.45 (s, 1H), 8.08 (s, 1H), 7.03 (s, 1H), 6.99 (s, 1H), 6.09 (s, 1H), 4.06 (s, 3H), 3.99 (s, 3H), 3.80-3.73 (m, 6H), 3.32-3.26 (m, 2H), 3.20-3.15 (m, 4H), 2.73-2.67 (m, 2H); ESI MS m/z 455 [M+H]$^+$.

rolidin-1-yl)imidazo[1,2-a]pyridine 5a. The product was obtained as white solid (310 mg, 52% yield).

Preparation of N$^1$-(2-(5-chloro-2,4-dimethoxyphenyl)-7-methoxyimidazo[1,2-a]-pyridin-6-yl)ethane-1,2-diamine 134 (Example 75)

Compound N1-(2-(5-chloro-2,4-dimethoxyphenyl)-7-methoxyimidazo[1,2-a]pyridin-6-yl)ethane-1,2-diamine 134 was prepared in the same manner as afford N$^1$-(2-(5-chloro-2,4-dimethoxyphenyl)imidazo[1,2-a]pyridin-7-yl)ethane-1,2-diamine 70a. The product was obtained as white solid (39 mg, 27% yield).

$^1$H NMR (400 MHz, CDCl$_3$): δ 8.33 (s, 1H), 7.84 (s, 1H), 7.23 (s, 1H), 6.84 (m, 1H), 6.57 (m, 1H), 3.98 (s, 3H), 3.94 (m, 6H), 3.11-3.06 (m, 4H); HPLC (Method 2) 98.70%, $t_R$=15.37 min.; ESI-MS m/z 377 [M+H]$^+$.

Preparation of methyl (2-((2-(5-chloro-2,4-dimethoxyphenyl)-7-methoxyimidazo[1,2-a]-pyridin-6-yl)amino)ethyl)carbamate 135 (Example 91)

Compound methyl (2-((2-(5-chloro-2,4-dimethoxyphenyl)-7-methoxyimidazo-[1,2-a]pyridin-6-yl)amino)ethyl)carbamate 135 was prepared in the same manner as afford N$^1$-(2-(5-chloro-2,4-dimethoxyphenyl)imidazo[1,2-a]pyridin-7-yl)ethane-1,2-diamine 70a. The product was obtained as an orange solid (25 mg, 28% yield).

$^1$H NMR (300 MHz, CDCl$_3$): δ 8.33 (s, 1H), 7.85 (s, 1H), 6.84 (s, 1H), 6.57 (m, 3H), 4.99 (br s, 1H), 4.14-4.10 (m, 1H), 3.99 (s, 3H), 3.94 (m, 3H), 3.92 (m, 3H), 3.71 (m, 3H), 3.46-3.44 (m, 2H), 3.23-3.21 (m, 2H); HPLC (Method 3) 98.91%, $t_R$=17.16 min.; ESI-MS m/z 435 [M+H]$^+$.

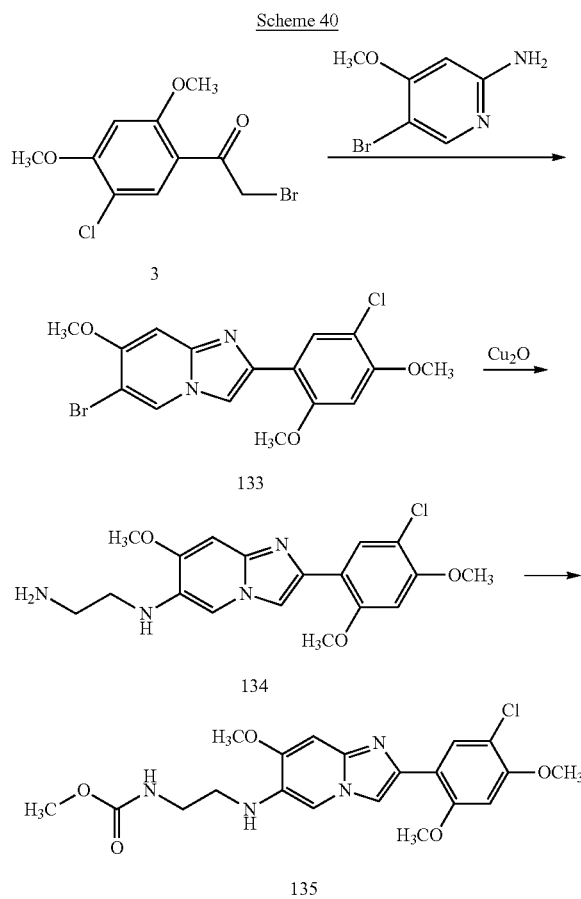

Scheme 40

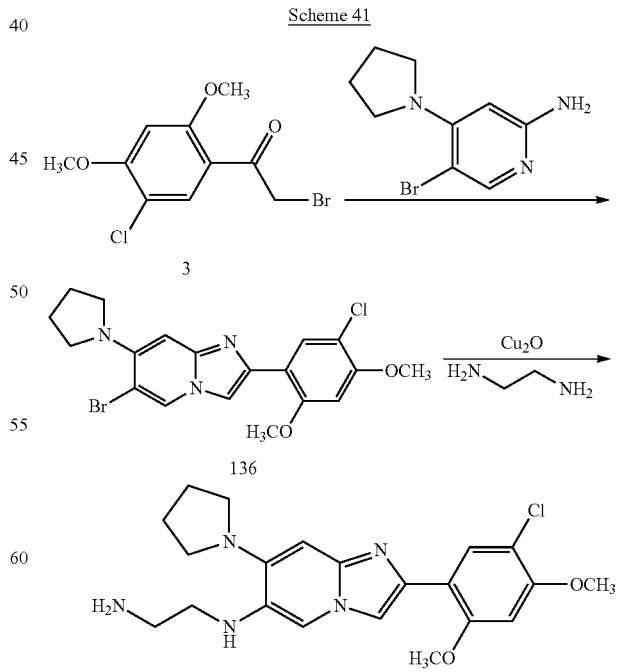

Scheme 41

Preparation of 6-bromo-2-(5-chloro-2,4-dimethoxyphenyl)-7-methoxyimidazo-[1,2-a]pyridine 133

Compound 6-bromo-2-(5-chloro-2,4-dimethoxyphenyl)-7-methoxyimidazo-[1,2-a]pyridine 133 was prepared in the same manner as 2-(5-chloro-2,4-dimethoxyphenyl)-7-(pyr-

Preparation of 6-bromo-2-(5-chloro-2,4-dimethoxyphenyl)-7-(pyrrolidin-1-yl)imidazo-[1,2-a]pyridine 136

Compound 6-bromo-2-(5-chloro-2,4-dimethoxyphenyl)-7-(pyrrolidin-1-yl)imidazo-[1,2-a]pyridine 136 was prepared in the same manner as 2-(5-chloro-2,4-dimethoxyphenyl)-7-(pyrrolidin-1-yl)imidazo[1,2-a]pyridine 5a and was obtained as white solid (490 mg, 57%).

Preparation of N¹-(2-(5-chloro-2,4-dimethoxyphenyl)-7-(pyrrolidin-1-yl)imidazo[1,2-a]-pyridin-6-yl)ethane-1,2-diamine 137 (Example 60)

Compound N¹-(2-(5-chloro-2,4-dimethoxyphenyl)-7-(pyrrolidin-1-yl)imidazo-[1,2-a]pyridin-6-yl)ethane-1,2-diamine 137 was prepared in the same manner as N¹-(2-(5-chloro-2,4-dimethoxyphenyl)imidazo[1,2-a]pyridin-7-yl)ethane-1,2-diamine 70a and was obtained as orange solid (45 mg, 15%).

$^1$H NMR (400 MHz, CD$_3$OD): δ 8.04 (s, 1H), 7.94 (s, 1H), 7.58 (s, 1H), 6.85 (s, 1H), 6.78 (s, 1H), 3.96 (s, 3H), 3.94 (s, 3H), 3.29-3.23 (m, 6H), 3.21-3.19 (m, 2H), 2.01-1.98 (m, 4H). HPLC (Method 3) 96.12% (AUC), $t_R$=15.79 min; ESI MS m/z 416 [M+H]$^+$.

Scheme 42

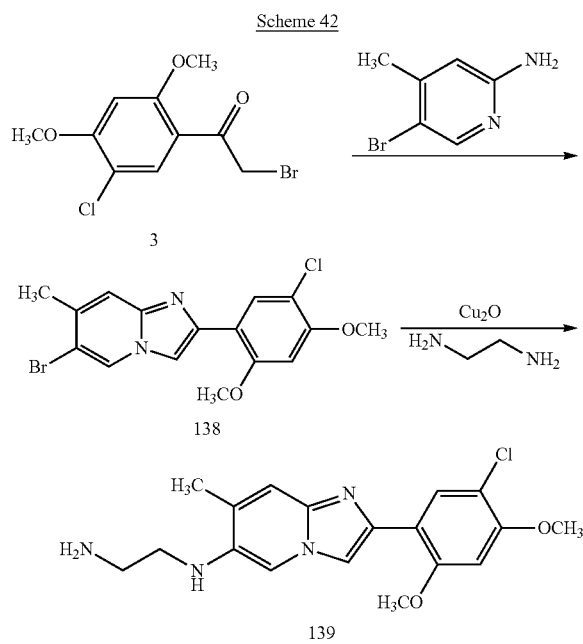

Preparation of 6-bromo-2-(5-chloro-2,4-dimethoxyphenyl)-7-methylimidazo[1,2-a]pyridine 138

Compound 6-bromo-2-(5-chloro-2,4-dimethoxyphenyl)-7-methylimidazo[1,2-a]-pyridine 138 was prepared in the same manner as 2-(5-chloro-2,4-dimethoxyphenyl)-7-(pyrrolidin-1-yl)imidazo[1,2-a]pyridine 5a and was obtained as white solid (198 mg, 49%).

Preparation of NM-(2-(5-chloro-2,4-dimethoxyphenyl)-7-methylimidazo[1,2-a]pyridin-6-yl)ethane-1,2-diamine 139 (Example 78)

Compound N¹-(2-(5-chloro-2,4-dimethoxyphenyl)-7-methylimidazo[1,2-a]pyridin-6-yl)ethane-1,2-diamine 139 was prepared in the same manner as N¹-(2-(5-chloro-2,4-dimethoxyphenyl)imidazo[1,2-a]pyridin-7-yl)ethane-1,2-diamine 70a and was obtained as orange solid (58 mg, 30%).

$^1$H NMR (400 MHz, CDCl$_3$): δ 8.35 (s, 1H), 7.93 (s, 1H), 7.26-7.24 (s, 2H), 6.57 (m, 1H), 3.98 (s, 3H), 3.94 (m, 6H), 3.81-3.80 (br s, 1H), 3.08-3.06 (m, 4H), 2.27 (S, 3H); HPLC (Method 3) 97.21%, $t_R$=15.28 min.; APCI-MS m/z 361 [M+H]$^+$.

Scheme 43

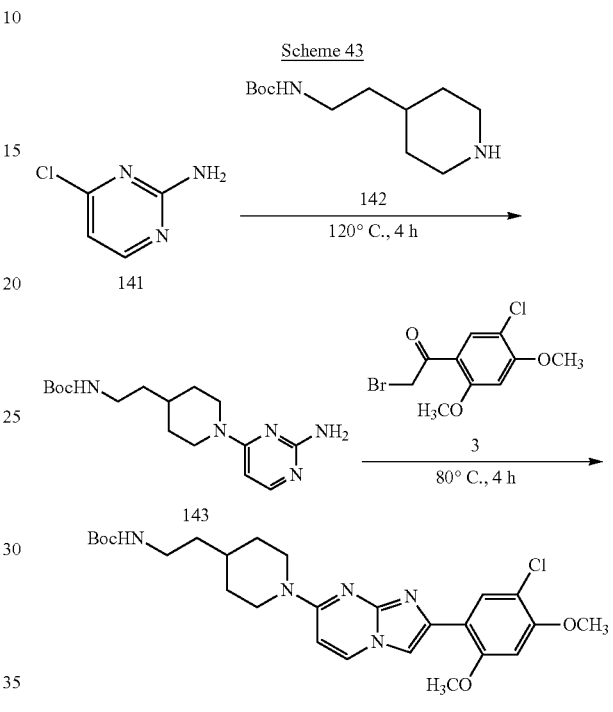

Preparation of tert-butyl {2-[1-(2-aminopyrimidin-4-yl)piperidin-4-yl]ethyl}carbamate 143

A sealed tube is charged with 2-amino-4-chloropyrimidine (200 mg, 1.60 mmol) and tert-butyl [2-(piperidin-4-yl)ethyl] carbamate 141 (430 mg, 1.90 mmol) in 1-butanol (2 mL). The reaction mixture was heated to 120° C. for 4 h. The reaction mixture was cooled to room temperature and the solvent was removed under reduced pressure. The residue was suspended in aqueous ammonia (10 mL) and stirred for 2 h. The precipitate was collected by filtration and dried under reduced pressure to afford tert-butyl {2-[1-(2-aminopyrimidin-4-yl)piperidin-4-yl]-ethyl}carbamate 143 (230 mg, 46%) as a pale yellow solid.

Preparation of tert-butyl (2-{1-[2-(5-chloro-2,4-dimethoxyphenyl)imidazo[1,2-a]pyrimidin-7-yl]piperidin-4-yl}-ethyl)carbamate 144 (Example 61)

A solution of tert-butyl {2-[1-(2-aminopyrimidin-4-yl)piperidin-4-yl]ethyl}carbamate 143 (200 mg, 0.60 mmol) in N,N-dimethylformamide (2 mL) was charged with 2-bromo-1-(5-chloro-2,4-dimethoxyphenyl)ethanone (200 mg, 0.70 mmol) followed by sodium bicarbonate (150 mg, 1.80 mmol). The reaction mixture was heated to 80° C. for 4 h. The reaction mixture was cooled to room temperature and quenched with water (25 mL) and the precipitate was collected by filtration and dried under reduced pressure. The solid was purified by combi-flash chromatography (silica gel, 9:1 DCM/methanol) to afford tert-butyl (2-{1-[2-(5-chloro-2,4-dimethoxyphenyl)imidazo[1,2-a]pyrimidin-7-yl]piperidin-4-yl}ethyl)carbamate 144 (220 mg, 69%) as an off-white solid.

$^1$H NMR (400 MHz, DMSO-d$_6$): δ 8.49 (d, J=7.7 Hz, 1H), 8.10 (s, 1H), 7.83 (s, 1H), 6.87 (s, 1H), 6.82 (d, J=7.7 Hz, 1H), 6.77 (t, J=5.3 Hz, 1H), 4.42 (d, J=12.9 Hz, 2H), 4.00 (s, 3H), 3.93 (s, 3H), 3.02-2.88 (m, 4H), 1.81-1.72 (m, 2H), 1.66-1.54 (m, 1H), 1.37 (s, 9H), 1.35-1.30 (m, 2H), 1.15-1.02 (m, 2H). HPLC (Method 3) 94.8% (AUC), t$_R$=18.72 min; ESI MS m/z 516 [M+H]$^+$.

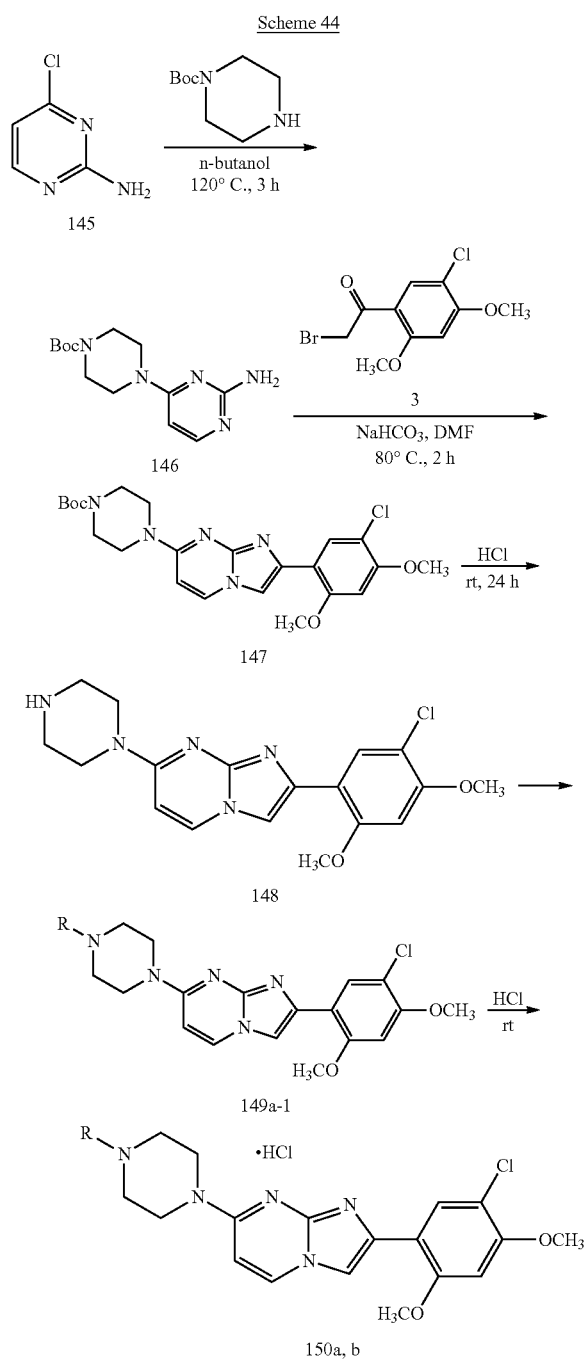

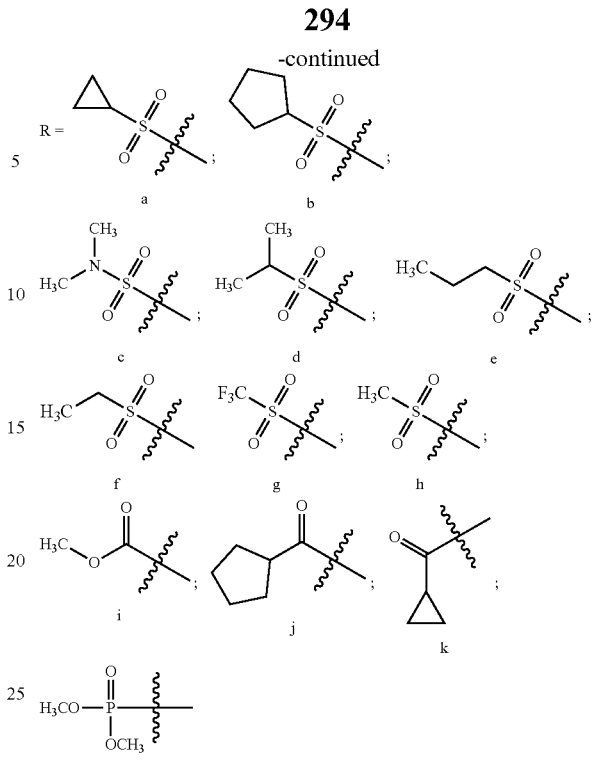

Preparation of tert-butyl 4-(2-aminopyrimidin-4-yl)piperazine-1-carboxylate 146

A mixture of 4-chloropyrimidin-2-amine 145 (3.0 g, 23.0 mmol), and t-butyl piperazine-1-carboxylate (5.2 g, 27.8 mmol) in n-butanol (30 mL) was heated at 120° C. for 3 h. The reaction mixture was concentrated under reduced pressure. The solid was washed with NH$_4$OH solution and filtered to afford 146 (5.00 g, 78.1%/6) as a yellow solid.

$^1$H NMR (300 MHz, DMSO-d$_6$): δ 7.78 (d, J=7.6 Hz, 1H), 6.00-5.98 (m, 3H), 3.51-3.47 (m, 4H), 3.36-3.33 (m, 4H), 1.41 (s, 9H).

Preparation of tert-butyl 4-[2-(5-chloro-2,4-dimethoxyphenyl)imidazo[1,2-a]pyrimidin-7-yl]piperazine-1-carboxylate 147 (Example 145)

A mixture of tert-butyl 4-(2-aminopyrimidin-4-yl)piperazine-1-carboxylate 146 (500 mg, 1.79 mmol), sodium bicarbonate (300 mg, 3.58 mmol), and 2-bromo-1-(5-chloro-2,4-dimethoxyphenyl)ethanone (525 mg, 1.96 mmol) in DMF (10 mL) was heated at 80° C. for 2 h. The reaction mixture was poured into ice water and filtered with the filter pad. The residue was purified by combi-flash chromatography (silica gel, 7:3 ethyl acetate/hexane) to afford 147(517 mg, 61%) as a white solid:

$^1$H NMR (300 MHz, DMSO-d$_6$): δ 8.55 (d, J=7.6 Hz, 1H), 8.13 (s, 1H), 7.84 (s, 1H), 6.86 (s, 1H), 6.77 (d, J=7.6 Hz, 1H), 4.00 (s, 3H), 3.93 (s, 3H), 3.69-3.63 (m, 4H), 3.46-3.41 (m, 4H), 1.43 (s, 9H). HPLC 94.04% (AUC), t$_R$=11.32 min. ESI MS m/z 474 [M+H]$^+$.

Preparation of 2-(5-chloro-2,4-dimethoxyphenyl)-7-(piperazin-1-yl)imidazo[1,2-a]-pyrimidine 148 (Example 153)

A mixture of tert-butyl 4-[2-(5-chloro-2,4-dimethoxyphenyl)imidazo[1,2-]-pyrimidin-7-yl]piperazine-1-carboxylate 147 (510 mg, 1.36 mmol), and hydrochloric acid in methanol (5.00 mL, 1.25 molar solution) in methanol (10 mL) was stirred at room temperature for 18 h. The reaction was concentrated under reduced pressure. The solid was washed with NH₄OH solution and filtered, and the residue was purified by combi-flash chromatography (silica gel, 9:1 DCM/methanol) to afford 2-(5-chloro-2,4-dimethoxyphenyl)-7-(piperazin-1-yl)imidazo[1,2-a]pyrimidine 148 (365 mg, 91%) as a yellow solid.

$^1$H NMR (300 MHz, DMSO-$d_6$): δ 8.16 (d, J=7.6 Hz, 1H), 7.46 (s, 1H), 7.09 (s, 1H), 6.85 (d, J=7.6 Hz, 1H), 6.34 (s, 1H), 4.00 (s, 3H), 3.97 (s, 3H), 3.82-3.69 (m, 4H), 3.37-3.29 (m, 4H), m/z 374 [M+H]$^+$.

Preparation of 2-(5-chloro-2,4-dimethoxyphenyl)-7-[4-(cyclopropylsulfonyl)piperazin-1-yl]imidazo[1,2-a]pyrimidine 149a (Example 146)

A mixture of 2-(5-chloro-2,4-dimethoxyphenyl)-7-(piperazin-1-yl)imidazo[1,2-a]-pyrimidine 148 (100 mg, 0.26 mmol), pyridine (65 μL, 0.78 mmol), and cyclopropanesulfonyl chloride (41 μL, 0.29 mmol) in DCM (8 mL) was stirred at room temperature for 18 h. The reaction was concentrated under reduced pressure. The residue was purified by combi-flash chromatography (silica gel, 9:1 DCM/methanol) to afford 2-(5-chloro-2,4-dimethoxyphenyl)-7-[4-(cyclopropylsulfonyl)piperazin-1-yl]imidazo[1,2-a]pyrimidine 149a (29 mg, 22%) as an off-white solid.

$^1$H NMR (300 MHz. CH₃OD): δ 8.69 (d, J=7.6 Hz, 1H), 8.05 (s, 1H), 8.03 (s, 1H), 7.13 (d, J=7.6 Hz, 1H), 6.93 (s, 1H), 4.03 (s, 3H), 3.96 (s, 3H), 3.93-3.87 (m, 4H), 3.37-3.33 (m, 4H), 2.68-2.65 (m, 1H), 1.04-0.93 (m, 4H); HPLC (Method 1) 98.51% (AUC), $t_R$=10.59 min.; ESI MS m/z 478 [M+H]$^+$.

Preparation of 2-(5-chloro-2,4-dimethoxyphenyl)-7-[4-(cyclopentylsulfonyl)piperazin-1-yl]imidazo[1,2-a]pyrimidine 149b A mixture of 2-(5-chloro-2,4-dimethoxyphenyl)-7-(piperazin-1-yl)imidazo[1,2-a]-pyrimidine 148 (100 mg, 0.26 mmol), triethylamine (100 μL, 0.80 mmol), and cyclopentanesulfonyl chloride (50 juL, 0.29 mmol) in DCM (10 mL) was stirred at room temperature for 2 h. The reaction was diluted with methylene chloride (50 mL), washed with NH₄OH solution (10 mL) and brine (10 mL), dried over sodium sulfate, filtered, and concentrated under reduced pressure. The residue was purified by combi-flash chromatography (silica gel, 9:1 DCM/methanol) to afford 2-(5-chloro-2,4-dimethoxyphenyl)-7-[4-(cyclopentyl-sulfonyl)piperazin-1-yl]imidazo[1,2-a]pyrimidine 149b (88 mg, 71%) as an off-white solid.

$^1$H NMR (400 MHz, DMSO-$d_6$): δ 8.58 (d, J=7.6 Hz, 1H), 8.11 (s, 1H), 7.88 (s, 1H), 6.87 (s, 1H), 6.86-6.81 (d, J=7.6 Hz, 1H), 4.00 (s, 3H), 3.93 (s, 3H), 3.82-3.74 (m, 4H), 3.70-3.64 (m, 1H), 3.35-3.64 (m, 3H), 3.22-3.18 (m, 1H), 2.01-1.91 (m, 2H), 1.86-1.76 (m, 2H), 1.69-1.61 (m, 2H), 1.59-1.50 (m, 2H). HPLC (Method 1) 92.04% (AUC), $t_R$=11.09 min; ESI MS m/z 506 [M+H]$^+$.

Preparation of 4-[2-(5-chloro-2,4-dimethoxyphenyl)imidazo[1,2-a]pyrimidin-7-yl]-N,N-dimethylpiperazine-1-sulfonamide 149(c) (Example 180)

Compound 4-[2-(5-chloro-2,4-dimethoxyphenyl)imidazo[1,2-a]pyrimidin-7-yl]-N,N-dimethylpiperazine-1-sulfonamide 149c was prepared in the same manner as 2-(5-chloro-2,4-dimethoxyphenyl)-7-[4-(cyclopentylsulfonyl)piperazin-1-yl]imidazo[1,2-a]pyrimidine 149b and was obtained as an off-white solid (39 mg, 31%).

$^1$H NMR (400 MHz, CDCl₃): δ 8.52 (s, 1), 8.07 (d, J=7.6 Hz, 1H), 7.72 (s, 1H), 6.56 (s, 1H), 6.37 (d, J=7.6 Hz, 1H), 3.99 (s, 3H), 3.94 (s, 3H), 3.82 (t, J=4.9 Hz, 4H), 3.34 (t, J=4.9 Hz, 4H), 2.86 (s, 6H). HPLC (Method 3) 98.13% (AUC), $t_R$=17.39 min; ESI MS m/z 481 [M+H]$^+$.

Preparation of 2-(5-chloro-2,4-dimethoxyphenyl)-7-[4-(isopropylsulfonyl)piperazin-1-yl]imidazo[1,2-a]pyrimidine 149(d) (Example 205)

Compound 2-(5-chloro-2,4-dimethoxyphenyl)-7-[4-(isopropylsulfonyl)piperazin-1-yl]imidazo[1,2-a]pyrimidine 149d was prepared in the same manner as 2-(5-chloro-2,4-dimethoxyphenyl)-7-[4-(cyclopentylsulfonyl)piperazin-1-yl]imidazo[1,2-a]pyrimidine 149b and was obtained as an off-white solid (52 mg, 41%).

$^1$H NMR (400 MHz, CH₃OD): δ 8.37 (d, J=7.6 Hz, 1H), 8.06 (s, 1H), 7.82 (s, 1H), 6.77 (s, 1H), 6.70 (d, J=7.6 Hz, 1H), 4.01 (s, 3H), 3.94 (s, 3H), 3.85-3.81 (m, 4H), 3.47-3.43 (m, 4H), 3.38-3.34 (m, 1H), 1.34 (s, 3H), 1.32 (s, 3H). ESI MS m/z 480 [M+H]$^+$.

Preparation of 2-(5-chloro-2,4-dimethoxyphenyl)-7-[4-(propylsulfonyl)piperazin-1-yl]-imidazo[1,2-a]pyrimidine 149e (Example 191)

Compound 2-(5-chloro-2,4-dimethoxyphenyl)-7-[4-(propylsulfonyl)piperazin-1-yl]-imidazo[1,2-a]pyrimidine 149e was prepared in the same manner as 2-(5-chloro-2,4-dimethoxyphenyl)-7-[4-(cyclopentylsulfonyl)piperazin-1-yl]imidazo[1,2-a]pyrimidine 149b and was obtained as an off-white solid (48 mg, 38%).

$^1$H NMR (300 MHz, DMSO-$d_6$): δ 8.57 (d, J=7.6 Hz, 1H), 8.13 (s, 1H), 7.85 (s, 1H), 6.86 (s, 1H), 7.79 (d, J=7.6 Hz, 1H), 4.00 (s, 3H), 3.93 (s, 3H), 3.79-3.75 (m, 4H), 3.30-3.26 (m, 4H), 3.09-3.02 (m, 2H), 1.73-1.68 (m, 2H), 1.80-1.60 (m, 3H). HPLC (Method 1) 99.08% (AUC), $t_R$=10.82 min. ESI MS m/z 480 [M+H]$^+$.

Preparation of 2-(5-chloro-2,4-dimethoxyphenyl)-7-[4-(ethylsulfonyl)piperazin-1-yl]imidazo[1,2-a]pyrimidine 149f (Example 190)

Compound 2-(5-chloro-2,4-dimethoxyphenyl)-7-[4-(ethylsulfonyl)piperazin-1-yl]-imidazo[1,2-a]pyrimidine 149f was prepared in the same manner as 2-(5-chloro-2,4-dimethoxyphenyl)-7-[4-(cyclopentylsulfonyl)piperazin-1-yl]imidazo[1,2-a]pyrimidine 149b and was obtained as an off-white solid (42 mg, 34%).

$^1$H NMR (300 MHz, DMSO-$d_6$): δ 8.57 (d, J=7.6 Hz, 1H), 8.13 (s, 1H), 7.85 (s, 1H), 6.86 (s, 1H), 6.80 (d, J=7.6 Hz, 1H), 4.00 (s, 3H), 3.93 (s, 3H), 3.79-3.75 (m, 4H), 3.32-3.26 (m, 4H), 3.12-3.08 (m, 2H), 1.23-1.19 (m, 3H). HPLC (Method 1) 98.69% (AUC), $t_R$=10.48 min. ESI MS m/z 466 [M+H]$^+$.

Preparation of 2-(5-chloro-2,4-dimethoxyphenyl-7-{4-[(trifluoromethyl)sulfonyl]-piperazin-1-yl}imidazo[1,2-a]pyrimidine 149g A mixture of 2-(5-chloro-2,4-dimethoxyphenyl)-7-(piperazin-1-yl)imidazo[1,2-a]-pyrimidine 148 (55 mg, 0.14 mmol), triethylamine (63 μL, 0.44 mmol), and trifluoromethanesulfonic anhydride (66 μL, 0.22 mmol) in DCM (3 mL) was stirred at room temperature for 0.5 h. The reaction was concentrated under reduced pressure. The crude compound was diluted with methylene chloride (8 mL), washed with NaHCO$_3$ solution (3 mL) and brine (10 mL), dried over sodium sulfate, filtered, and concentrated under reduced pressure. The residue was purified by combi-flash chromatography (silica gel, 9:1 DCM/methanol) to afford 2-(5-chloro-2,4-dimethoxyphenyl)-7-(4[(trifluoromethyl)sulfonyl]piperazin-1-yl)imidazo[1,2-a]pyrimidine 149g (20 mg, 31%) as a white solid.

$^1$H NMR (300 MHz, CDCl$_3$): δ 8.49 (s, 1H), 8.08 (d, J=7.6 Hz, 1H), 7.73 (s, 1H), 6.54 (s, 1H), 6.36 (d, J=7.6 Hz, 1H), 3.98 (s, 3H), 3.93 (s, 3H), 3.87-3.83 (m, 4H), 3.59-3.84 (m, 4H). HPLC (Method 1) 97.23% (AUC), $t_R$=11.43 min. ESI MS m 506 [M+H]$^+$.

Preparation of 2-(5-chloro-2,4-dimethoxyphenyl)-7-(4-(methylsulfonyl)piperazin-1-yl)-imidazo[1,2-a]pyrimidine 149h (Example 177)

Compound dimethyl (2-(5-chloro-2,4-dimethoxyphenyl)-7-(4-(methylsulfonyl)-piperazin-1-yl)imidazo[1,2-a]pyrimidine 149h was prepared in the same manner as 2-(5-chloro-2,4-dimethoxyphenyl)-7-[4-(cyclopentylsulfonyl)piperazin-1-yl]imidazo[1,2-a]pyrimidine 149b and was obtained as an off-white solid (42 mg, 31%).

$^1$H NMR (400 MHz, CDCl$_3$): δ 8.49 (S, 1H), 8.09 (d, J=7.6 Hz, 1H), 7.72 (s, 1H), 6.55 (s, 1H), 6.39 (d, J=7.7, 1H), 3.98 (s, 3H), 3.94 (s, 3H), 3.88-3.85 (m, 4H), 3.32-3.30 (m, 4H), 2.79 (s, 3H); HPLC (Method 1) 96.8%, $t_R$=10.23 min.; ESI-MS m/z 452 [M+H]$^+$.

Preparation of methyl 4-(2-(5-chloro-2,4-dimethoxyphenyl)imidazo[1,2-a]pyrimidin-7-yl)piperazine-1-carboxylate 149i (Example 159)

A mixture of 2-(5-chloro-2,4-dimethoxyphenyl)-7-(piperazin-1-yl)imidazo[1,2-a]-pyrimidine 148 (100 mg, 0.26 mmol), methyl carbonochloridate (25 μL, 0.26 mmol), and cesium carbonate (173 mg, 0.52 mmol) in DMF (5 mL) was heated to reflux for 16 h. The reaction mixture was quenched with ammonia solution and extracted with ethyl acetate. Organic phase was reduced to dryness. The residue was purified by combi-flash chromatography (silica gel, 9:1 DCM/MeOH) to afford methyl 4-(2-(5-chloro-2,4-dimethoxyphenyl)imidazo-[1,2-a]pyrimidin-7-yl)piperazine-1-carboxylate 149i (72 mg, 68%) as a pale yellow solid.

$^1$H NMR (400 MHz, DMSO-d$_6$): δ 8.56-8.54 (d, J=7.6 Hz, 1H), 8.13 (s, 1H), 7.84 (s, 1H), 6.86 (s, 1H), 6.77-6.75 (m, 1H), 3.99 (s, 3H), 3.93 (s, 3H), 3.70-3.67 (m, 4H), 3.64 (s, 3H), 3.50-3.48 (m, 4H). HPLC (Method 1) 97.38% (AUC), $t_R$=10.33 min. ESI MS m/z 432 [M+H]$^+$.

Preparation of (4-(2-(5-chloro-2,4-dimethoxyphenyl)imidazo[1,2-a]pyrimidin-7-yl)-piperazin-1-yl)(cyclopentyl)methanone 149i (Example 243)

A mixture of 2-(5-chloro-2,4-dimethoxyphenyl)-7-(piperazin-1-yl)imidazo[1,2-a]-pyrimidine 148 (100 mg, 0.26 mmol). DIPEA (93 μL, 0.53 mmol), and cyclopentanecarbonyl chloride (49 μL, 0.29 mmol) in DCM (5 mL) was stirred at room temperature for 1.5 h. The reaction quenched with water. Solid was obtained. The white solid was purified by combi-flash chromatography (silica gel, 9:1 DCM/methanol) to afford (4-(2-(5-chloro-2,4-dimethoxyphenyl)imidazo[1,2-a]pyrimidin-7-yl)piperazin-1-yl)(cyclopentyl)methanone (58 mg, 51%) as an off-white solid.

$^1$H NMR (400 MHz, DMSO): δ 13.78 (br s, 1H), 8.71 (d, J=8.0 Hz, 1H), 8.10 (s, 1H), 8.00 (s, 1H), 7.24 (d, J=8.0 Hz, 1H), 6.97 (s, 1H), 4.04 (s, 3H), 3.98 (s, 3H), 3.89-3.85 (m, 4H), 3.71-3.64 (m, 4H), 3.05-2.98 (m, 1H), 1.81-1.72 (m, 2H), 1.70-1.54 (m, 6H); HPLC (Method 1) 94.73%, $t_R$=10.82 min.; ESI-MS m/z 470 [M+H]$^+$.

Preparation of (4-(2-(5-chloro-2,4-dimethoxyphenyl)imidazo[1,2-a]pyrimidin-7-yl)-piperazin-1-yl) cyclopropyl)methanone 149k (Example 242)

(4-(2-(5-Chloro-2,4-dimethoxyphenyl)imidazo[1,2-a]pyrimidin-7-yl)-piperazin-1-yl)(cyclopropyl)methanone 149k was prepared in the same manner as (4-(2-(5-chloro-2,4-dimethoxyphenyl)imidazo[1,2-a]pyrimidin-7-yl)piperazin-1-yl)(cyclopentyl)methanone 149i and was obtained as an off-white solid (28 mg, 25%).

Preparation of dimethyl (4-(2-(5-chloro-2,4-dimethoxyphenyl)imidazo[1,2-a]pyrimidin-7-yl)piperazin-1-yl)phosphonate 149l (Example 218)

Compound dimethyl (4-(2-(5-chloro-2,4-dimethoxyphenyl)imidazo[1,2-a]pyrimidin-7-yl)piperazin-1-yl)phosphonate 149l was prepared in the same manner as 2-(5-chloro-2,4-dimethoxyphenyl)-7-[4-(cyclopentylsulfonyl)piperazin-1-yl]imidazo[1,2-a]pyrimidine 149b and was obtained as an off-white solid (42 mg, 31%).

$^1$H NMR (400 MHz, DMSO): δ 8.60 (d, J=8.0 Hz, 1H), 8.12 (s, 1H), 7.85 (s, 1H), 6.95 (s, 1H), 6.79 (d, J=8.0 Hz, 1H), 4.00 (s, 3H), 3.93 (s, 3H), 3.63-3.61 (m, 4H), 3.60 (s, 3H), 3.30 (s, 3H), 2.50-2.49 (m, 4H); HPLC (Method 1) 94.8%, $t_R$=10.12 min.; ESI-MS m/z 482 [M+H]$^+$.

Preparation of HCl salt of 2-(5-chloro-2,4-dimethoxyphenyl)-7-[4-(cyclopropylsulfonyl)-piperazin-1-yl]imidazo[1,2-a]pyrimidine 150a A mixture of 149a (120 mg, 0.25 mmol) and hydrochloric acid in methanol (2 mL) in methanol (5 mL) was stirred at room temperature for 15 minutes. The reaction was concentrated under reduced pressure to afford the HCl salt of 2-(5-chloro-2,4-dimethoxyphenyl)-7-[4-(cyclopropylsulfonyl)piperazin-1-yl]imidazo[1,2-a]pyrimidine 150(a) (111 mg, 86%) as a white solid:

$^1$H NMR (300 MHz, DMSO-d$_6$): δ 13.99 (br s, 1H), 8.83-8.75 (m, 1H), 8.15 (s, 1H), 8.11-8.04 (m, 1H), 7.32-7.30 (d, J=7.6 Hz, 1H), 6.95 (s, 1H), 4.04 (s, 3H), 3.98 (s, 3H), 3.96-3.91 (m, 4H), 3.40-3.35 (m, 4H), 2.72-2.64 (m, 1H), 1.03-0.95 (m, 4H); HPLC (Method 1) 95.8% (AUC), $t_R$=10.64 min. ESI MS m/z 478 [M+H]$^+$.

Preparation of HCl salt of 2-(5-chloro-2,4-dimethoxyphenyl)-7-[4-(cyclopentylsulfonyl)-piperazin-1-yl]imidazo[1,2-a]pyrimidine 150(b) (Example 204)

A mixture of 149a (70 mg, 0.25 mmol) and hydrochloric acid in methanol (1 mL) in methanol (4 mL) was stirred at room temperature for 15 minutes. The reaction was concentrated under reduced pressure to afford the HCl salt of 2-(5-chloro-2,4-dimethoxyphenyl)-7-[4-(cyclopentylsulfonyl)piperazin-1-yl]imidazo[1,2-a]pyrimidine 150(b) (69 mg, 93%) as a white solid.

$^1$H NMR (400 MHz, DMSO-d$_6$): δ 13.85 (br s, 1H), 8.74 (d, J=7.6 Hz, 1H), 8.12 (s, 1H), 8.02 (s, 1H), 7.28 (d, J=7.6 Hz, 1H), 6.97 (s, 1H), 4.04 (s, 3H), 3.98 (s, 3H), 3.96-3.87

(m, 41H), 3.73-3.67 (m, 1H), 3.42-3.35 (m, 41H), 2.02-1.92 (m, 2H), 1.86-1.76 (m, 2H), 1.71-1.62 (m, 2H), 1.61-1.51 (m, 2H). HPLC (Method 1) 96.0%0 (AUC), $t_R$10.61 min. ESI MS m/z 506 [M+H]$^+$.

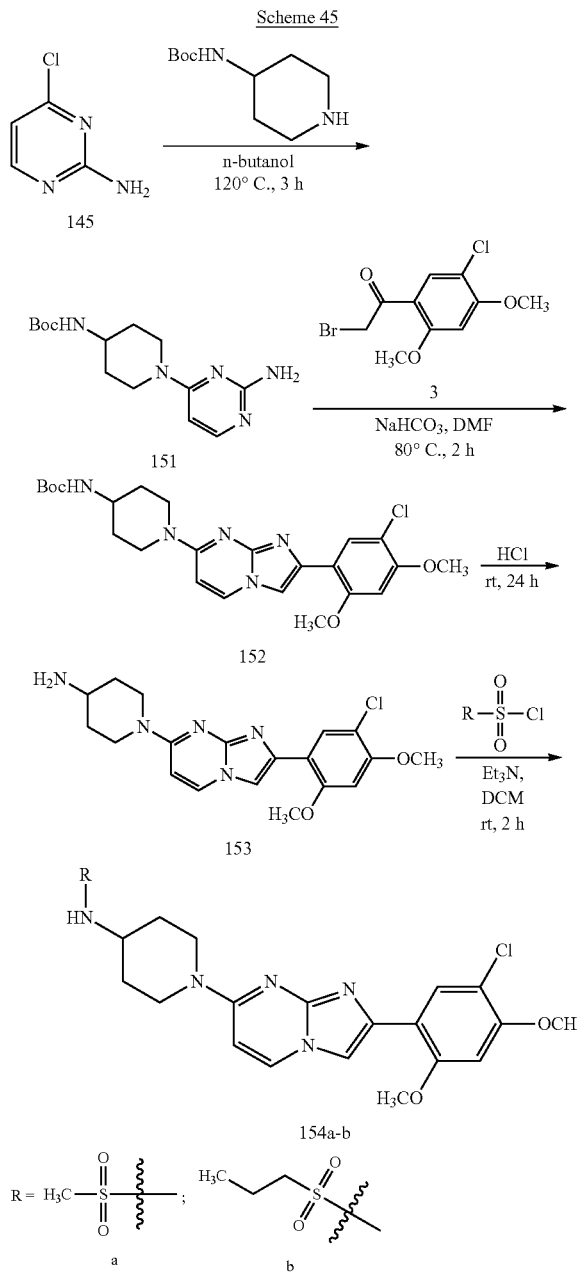

Preparation of tert-butyl (1-(2-(5-chloro-2,4-dimethoxyphenyl)imidazo[1,2-a]pyrimidin-7-yl)piperidin-4-yl)carbamate 152 (Example 36)

A mixture of tert-butyl (1-(2-aminopyrimidin-4-yl)piperidin-4-yl)carbamate 151 (1.00 g, 3.40 mmol), sodium bicarbonate (859 mg, 10.2 mmol), and 2-bromo-1-(5-chloro-2,4-dimethoxy-phenyl)ethanone 3 (1.00 g, 3.40 mmol) in DMF (10 mL) was heated at 80° C. for 3 h. The reaction was poured into ice water and solid was collected by filtration. The residue was purified by combi-flash chromatography (silica gel, 8:2 ethyl acetate/hexane) to afford 152 (769 mg, 48%) as a white solid:

$^1$H NMR (300 MHz, DMSO-d$_6$): δ 8.51 (d, J=7.6 Hz, 1H), 8.13 (s, 1H), 7.81 (s, 1H), 6.91 (d, J=7.6 Hz, 1H), 6.86 (s, 1H), 6.77 (d, J=7.6 Hz, 1H), 4.35-4.31 (m, 2H), 3.99 (s, 3H), 3.93 (s, 3H), 3.60-3.55 (m, 1H), 3.09-3.01 (m, 2H), 1.82-1.78 (m, 2H), 1.39 (s, 9H), 1.38-1.20 (m, 2H); HPLC 95.62% (AUC), $t_R$=11.31 min. ESI MS m/z 488 [M+H]$^+$.

Preparation of 1-(2-(5-chloro-2,4-dimethoxyphenyl) imidazo[1,2-a]pyrimidin-7-yl)-piperidin-4-amine hydrochloride 153 (Example 42)

A mixture of tert-butyl (1-(2-(5-chloro-2,4-dimethoxyphenyl)imidazo[1,2-a]pyrimidin-7-yl)piperidin-4-yl)carbamate 152 (50 mg, 0.10 mmol), and hydrochloric acid in methanol (5.00 mL, 1.25 molar solution) in methanol (5 mL) was stirred at room temperature for 18 h. The reaction was concentrated under reduced pressure. The solid was washed with water and filtered, and the residue was purified by combi-flash chromatography (silica gel, 8:2 DCM/methanol) to afford 1-(2-(5-chloro-2,4-dimethoxyphenyl)imidazo [1,2-a]pyrimidin-7-yl)piperidin-4-amine hydrochloride 153 (35 mg, 89%) as a yellow solid.

$^1$H NMR (400 MHz, CD$_3$OD): δ 8.70 (d, J=7.8 Hz, 1H), 8.39 (br s, 3H), 8.09 (s, 1H), 8.02 (s, 1H), 7.27 (d, J=7.8 Hz, 1H), 6.97 (s, 1H), 4.03 (s, 3H), 3.98 (s, 3H), 3.50-3.27 (m, 5H), 2.12-2.10 (m, 2H), 1.64-1.57 (m, 2H), m/z 388 [M+H]$^+$.

Preparation of N-(1-(2-(5-chloro-2,4-dimethoxyphenyl)imidazo[1,2-a]pyrimidin-7-yl)-piperidin-4-yl) methanesulfonamide 154(a) (Example 192)

A mixture of 1-(2-(5-chloro-2,4-dimethoxyphenyl)imidazo[1,2-a]pyrimidin-7-yl)piperidin-4-amine hydrochloride 153 (100 mg, 0.21 mmol), triethyl amine (121 µL, 0.84 mmol), and methylsulfonyl chloride (36 µL, 0.32 mmol) in DCM (6 mL) was stirred at room temperature for 2 h. The reaction mixture was concentrated under reduced pressure. The residue was purified by combi-flash chromatography (silica gel, 9:1 DCM/methanol) to afford N-(1-(2-(5-chloro-2,4-dimethoxyphenyl)-imidazo-[1,2-a]pyrimidin-7-yl)piperidin-4-yl)-methanesulfonamide 154(a) (42 mg, 41%) as an off-white solid.

$^1$H NMR (400 MHz, DMSO-d$_6$): δ 8.51 (d, J=7.6 Hz, 1H), 8.13 (s, 1H), 7.81 (s, 1H), 7.14 (d, J=7.6 Hz, 1H), 6.85 (s, 1H), 6.77 (d, J=7.6 Hz, 1H), 4.30 (d, J=9.0 Hz, 2H), 4.00 (s, 3H), 3.93 (s, 3H), 3.52-3.45 (m, 1H), 3.15-3.12 (m, 2H), 2.95 (s, 3H), 1.94-1.90 (m, 2H), 1.50-1.36 (m, 2H); HPLC (Method 1) 95.02% (AUC), $t_R$=10.24 min.; ESI MS m/z 466 [M+H]$^+$.

Preparation of N-(1-(2-(5-chloro-2,4-dimethoxyphenyl)imidazo[1,2-a]pyrimidin-7-yl)-piperidin-4-yl) propane-1-sulfonamide 154(b) (Example 193)

Compound N-(1-(2-(5-chloro-2,4-dimethoxyphenyl)imidazo[1,2-a]pyrimidin-7-yl)piperidin-4-yl)propane-1-sulfonamide 154(b) was prepared in the same manner as N-(1-(2-(5-chloro-2,4-dimethoxyphenyl)imidazo[1,2-a] pyrimidin-7-yl)piperidin-4-yl)methanesulfonamide 154a and was obtained as an off-white solid (41 mg, 38%).

$^1$H NMR (400 MHz, DMSO-d$_6$): δ 8.53 (d, J=7.6 Hz, 1H), 8.11 (s, 1H), 7.84 (s, 1H), 7.16 (d, J=7.6 Hz, 1H), 6.87 (s, 1H), 6.82 (m, 1H), 3.99 (s, 3H), 3.94 (s, 3H), 3.82 (t, J=4.9

Hz, 4H), 3.34 (t, J=4.9 Hz, 4H), 2.86 (s, 6H), 1.95-1.85 (m, 2H), 0.99 (t, J=7.4 Hz, 3H); HPLC (Method 3) 94.08% (AUC), $t_R$=10.70 min; ESI MS m/z 494 [M+H]$^+$.

Scheme 46

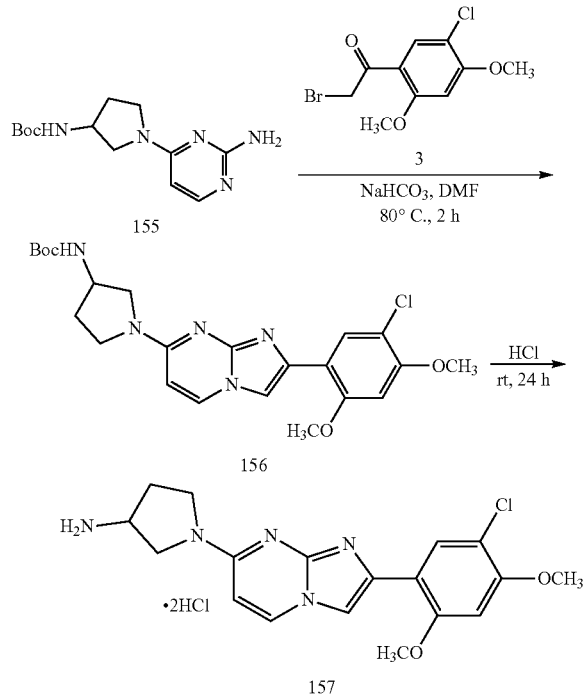

Preparation of tert-butyl (1-(2-(5-chloro-2,4-dimethoxyphenyl)imidazo[1,2-a]pyrimidin-7-yl)pyrrolidin-3-yl)carbamate 156 (Example 26)

A mixture of tert-butyl (1-(2-aminopyrimidin-4-yl)pyrrolidin-3-yl)carbamate 155 (600 mg, 2.14 mmol), sodium bicarbonate (216 mg, 2.57 mmol), and 2-bromo-1-(5-chloro-2,4-dimethoxyphenyl)ethanone 3 (751 mg, 2.57 mmol) in DMF (8 mL) was heated at 80° C. for 16 h. The reaction mixture was poured into ice water and filtered. The residue was purified by combi-flash chromatography (silica gel, 8:2 ethyl acetate/hexane) to afford 156 (570 mg, 57%) as a white solid:

$^1$H NMR (300 MHz, DMSO-d$_6$): δ 8.48 (d, J=7.6 Hz, 1H), 8.13 (s, 1H), 7.80 (s, 1H), 7.24-7.22 (m, 1H), 6.85 (s, 1H), 6.40 (d, J=7.6 Hz, 1H), 4.14 (br s, 1H), 3.99 (s, 3H), 3.71 (s, 3H), 3.69-3.34 (m, 4H), 2.19-2.09 (m, 1H), 1.96-1.86 (m, 1H), 1.40 (s, 9H).

HPLC (Method 3) 97.0% (AUC), $t_R$=18.66 min. ESI MS m 474 [M+H]$^+$.

Preparation of 1-(2-(5-chloro-2,4-dimethoxyphenyl)imidazo[1,2-a]pyrimidin-7-yl)pyrrolidin-3-amine hydrochloride 157 (Example 34)

A mixture of tert-butyl (1-(2-(5-chloro-2,4-dimethoxyphenyl)imidazo[1,2-a]-pyrimidin-7-yl)pyrrolidin-3-yl)carbamate 156 (550 mg, 1.16 mmol), and HCl in methanol (5.00 mL, 1.25 molar solution) in methanol (15 mL) was stirred at room temperature for 16 h. The reaction was concentrated under reduced pressure. The solid was washed with water and filtered, and the residue was purified by combi-flash chromatography (silica gel, 8:2 DCM/methanol) to afford 2-(5-chloro-2,4-dimethoxyphenyl)-7-(piperazin-1-yl)imidazo[1,2-a]-pyrimidine 157(380 mg, 60%) as a yellow solid.

$^1$H NMR (300 MHz, DMSO-d$_6$): δ 13.80-13.71 (br s, 1H), 8.74-8.71 (m, 4H), 8.14 (s, 1H), 8.02 (s, 1H), 6.96-6.94 (m, 2H), 4.04 (s, 3H), 3.98 (s, 3H), 3.91-3.64 (m, 5H), 2.49-2.20 (m, 2H). HPLC (Method 3) 95.0% (AUC), $t_R$=15.83 min. ESI MS m/z 374 [M+H]$^+$.

Scheme 47

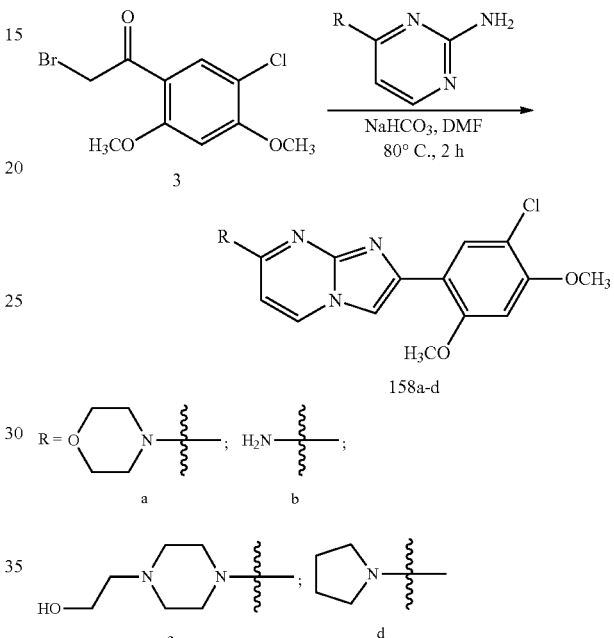

Preparation of 4-(2-(5-chloro-2,4-dimethoxyphenyl)imidazo[1,2-a]pyrimidin-7-yl)-morpholine hydrobromide 158a (Example 79)

A solution of 2-bromo-1-(5-chloro-2,4-dimethoxyphenyl)ethanone 3 (96 mg, 0.33 mmol) and 4-morpholinopyrimidin-2-amine (50 mg, 0.3 mmol) in acetone (5 mL) was heated to reflux for 4 h. The reaction mixture was cooled to room temperature, the white precipitate was filtered, washed with acetone, treated with water, filtered and dried under reduced pressure to yield 4-(2-(5-chloro-2,4-dimethoxyphenyl)imidazo[1,2-a]pyrimidin-7-yl)morpholine hydrobromide 158a (30 mg, 27%) as a white solid.

$^1$H NMR (400 MHz, DMSO-d$_6$) 13.64 (br s, 1H), 8.69 (d, J=7.76 Hz, 1H), 8.08 (s, 1H), 7.97 (s, 1H), 7.22 (d, J=7.76 Hz, 1H), 6.97 (s, 1H), 4.04 (s, 3H), 3.98 (s, 3H), 3.87-3.78 (m, 4H), 3.77-3.71 (m, 4H). HPLC (Method 3) >99% (AUC), $t_R$=16.76 min; ESI MS m/z 375 [M+H]$^+$.

Preparation of 2-(5-chloro-2,4-dimethoxyphenyl)imidazo[1,2-a]pyrimidin-7-amine 158b (Example 8)

A solution of 2-bromo-1-(5-chloro-2,4-dimethoxyphenyl)ethanone 3 (140 mg, 0.47 mmol) and pyrimidine-2,4-diamine (50 mg, 0.45 mmol) in acetone (5 mL) was heated to reflux for 16 h. The reaction mixture was cooled to room temperature. The precipitate was filtered and treated with dilute ammonia. Precipitate was filtered, washed with water, and dried under reduced pressure to yield 2-(5-chloro-2,4-dimethoxyphenyl)imidazo[1,2-a]pyrimidin-7-amine 158b (95 mg, 36%) as a white solid.

$^1$H NMR (300 MHz, DMSO-d$_6$) δ 8.36 (d, 1H, J=7.2 Hz), 8.09 (s, 1H), 7.76 (s, 1H), 6.84 (s, 1H), 6.76 (s, 2H), 6.22 (d, 1H, J=7.2 Hz), 3.98 (s, 3H), 3.92 (s, 3H); ESI MS m/z 305 [M+H]$^+$.

Preparation of 2-(4-(2-(5-chloro-2,4-dimethoxyphenyl)imidazo[1,2-a]pyrimidin-7-yl)-piperazin-1-yl)ethanol 158c (Example 45)

A solution of 2-bromo-1-(5-chloro-2,4-dimethoxyphenyl)ethanone 3 (146 mg, 0.49 mmol) and 2-(4-(2-aminopyrimidin-4-yl)piperazin-1-yl)ethanol (100 mg, 0.48 mmol) in acetone (5 mL) was heated to reflux for 6 h. The reaction mixture was cooled to room temperature. The precipitate was filtered and treated with dilute HCl, washed with water, and dried under reduced pressure to yield 2-(4-(2-(5-chloro-2,4-dimethoxyphenyl)imidazo[1,2-a]-pyrimidin-7-yl)piperazin-1-yl)ethanol 158c (92 mg, 42%) as a white solid.

$^1$H NMR (300 MHz, DMSO-d$_6$): δ 14.00 (br s, 1H), 11.50 (br s, 1H), 8.82-8.80 (m, 1H), 8.16 (s, 1H), 8.05 (m, 1H), 7.32-7.30 (m, 1H), 6.97 (s, 1H), 4.60-4.56 (br s, 1H), 4.04 (s, 3H), 3.98 (s, 3H), 3.84-3.70 (m, 3H), 3.39-3.20 (m, 8H); ESI MS m/z 418 [M+H]$^+$.

Preparation of 2-(5-chloro-2,4-dimethoxyphenyl)-7-(pyrrolidin-1-yl)imidazo-[1,2-a]pyrimidine hydrobromide 158d (Example 9)

A solution of 2-bromo-1-(5-chloro-2,4-dimethoxyphenyl)ethanone 3 (47 mg, 0.16 mmol) and 4-pyrrolidinopyrimidin-2-amine hydrobromide (25 mg, 0.15 mmol) in acetone (5 mL) was heated at reflux for 16 h. The reaction mixture was cooled to room temperature; the white precipitate was filtered, washed with acetone, filtered and dried under reduced pressure to yield 2-(5-chloro-2,4-dimethoxyphenyl)-7-(pyrrolidin-1-yl)imidazo[1,2-a]pyrimidine hydrobromide 158d (55 mg, 71%) as a white solid.

$^1$H NMR (300 MHz, DMSO-d$_6$): δ 13.63 (s, 1H), 8.63 (d, 1H, J=7.6 Hz), 8.07 (s, 1H), 7.98 (s, 1H), 6.96 (s, 1H), 6.89 (d, 1H, J=7.6 Hz), 4.03 (s, 3H), 3.97 (s, 3H), 3.65-3.54 (m, 4H), 2.08-1.93 (m, 4H); ESI MS m/z 359 [M+H]$^+$.

Scheme 48

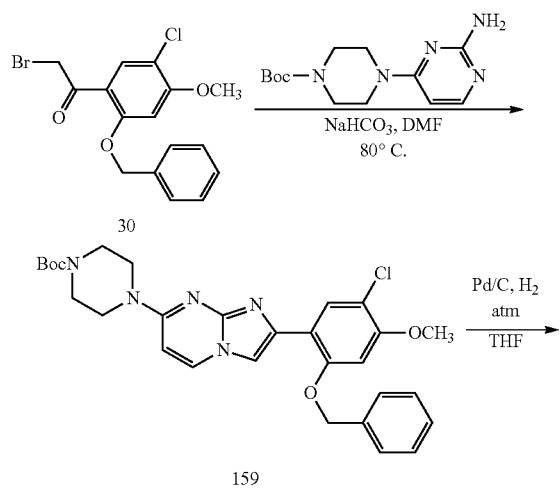

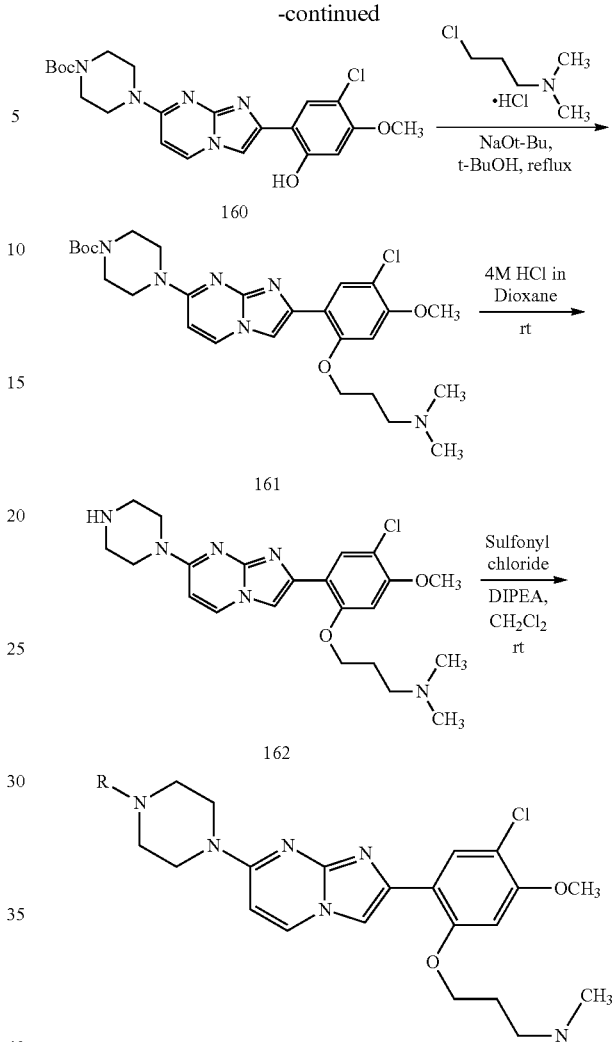

Preparation of tert-butyl 4-(2-(2-(benzyloxy)-5-chloro-4-methoxyphenyl)imidazo[1,2-a]-pyrimidin-7-yl)piperazine-1-carboxylate 159

A solution of 1-[2-(benzyloxy)-5-chloro-4-methoxyphenyl]-2-bromoethanone 30 (728 mg, 1.96 mmol), NaHCO$_3$ (300 mg, 3.58 mmol), and tert-butyl 4-(2-aminopyrimidin-4-yl)-piperazine-1-carboxylate (500 mg, 1.79 mmol) in DMF (10 mL) was heated at 80° C. for 2 h. The reaction mixture was quenched with water; the yellow precipitate was filtered and washed with water. The solid was filtered and dried under reduced pressure to give the desired compound tert-butyl 4-(2-(2-(benzyloxy)-5-chloro-4-methoxyphenyl)imidazo[1,2-a]pyrimidin-7-yl)piperazine-1-carboxylate 159 (738 mg, 75%) as a yellow solid.

¹H NMR (300 MHz, DMSO): δ 8.50 (d, J=7.5 Hz, 1H), 8.15 (s, 1H), 7.78 (s, 1H), 7.55 (m, 2H), 7.40 (m, 3H), 6.96 (s, 1H), 6.72 (d, J=7.5 Hz, 1H), 5.39 (s, 2H), 3.87 (s, 3H), 3.66 (m, 4H), 3.44 (m, 4H), 1.43 (s, 9H); HPLC (Method 1) 99.35%, $t_R$=12.08 min.; ESI-MS m/z 550 [M+H]⁺.

Preparation of tert-butyl 4-(2-(5-chloro-2-hydroxy-4-methoxyphenyl)imidazo[1,2-a]-pyrimidin-7-yl)piperazine-1-carboxylate 160

A solution of 159 (1.00 g, 1.80 mmol) in THF was charged with Pd/C (300 mg). The reaction mixture was stirred at room temperature under H₂ atmosphere (1 atm) for 3 h. The reaction mixture was filtered through a small pad of celite and washed with chloroform. The combined organic filtrate was concentrated under reduced pressure and the residue was purified by column chromatography (silica gel, 10:1 DCM/MeOH) to provide tert-butyl 4-(2-(5-chloro-2-hydroxy-4-methoxyphenyl)imidazo[1,2-a]pyrimidin-7-yl)piperazine-1-carboxylate 160 (600 mg, 71%) as a brown solid.
¹H NMR (400 MHz, CDCl₃): δ 8.06 (d, J=7.4 Hz, 1H), 7.45 (s, 1H), 7.32 (s, 1H), 6.60 (s, 1H), 6.45 (d, J=7.4 Hz, 1H), 3.89 (s, 3H), 3.74-3.72 (m, 4H), 3.58-3.56 (m, 4H), 1.49 (s, 9H); HPLC (Method 1)=99.2% (AUC), $t_R$=10.95 min: ESI MS m/z 460 [M+H]⁺.

Preparation of tert-butyl 4-(2-(5-chloro-2-(3-(dimethylamino)propoxy)-4-methoxyphenyl)-imidazo[1,2-a]pyrimidin-7-yl)piperazine-1-carboxylate 161

A mixture of tert-butyl 4-(2-(5-chloro-2-hydroxy-4-methoxyphenyl)imidazo[1,2-a]-pyrimidin-7-yl)piperazine-1-carboxylate 160 (100 mg, 0.20 mmol) and dimethylaminepropylchloride (63 mg, 0.40 mmol) in tBuOH was charged with NaOtBu (76 mg, 0.80 mmol). After stirring at 80° C. for 24 h, the reaction mixture was diluted with CH₂Cl₂/MeOH (20 mL/2 mL). The organic layer was washed with brine (10 mL), dried over sodium sulfate, and concentrated under reduced pressure. The residue was purified by column chromatography (silica gel, 1:0.1:10 methanol/ammonium hydroxide/DCM) to afford tert-butyl 4-(2-(5-chloro-2-hydroxy-4-methoxyphenyl)imidazo[1,2-a]pyrimidin-7-yl)piperazine-1-carboxylate 161 (30 mg, 25%) as a yellow solid.
¹H NMR (400 MHz, CDCl₃): δ 8.82 (d, J=7.4 Hz, 1H), 8.39 (s, 1H), 8.01 (s, 1H), 6.47 (s, 1H), 6.37 (d, J=7.4 Hz, 1H), 4.18 (t, J=5.3 Hz, 2H), 3.91 (s, 3H), 3.75-3.69 (m, 4H), 3.56-3.51 (m, 4H), 3.31-3.25 (m, 2H), 2.83 (s, 6H), 2.56-2.47 (m, 2H), 1.49 (s, 9H); HPLC (Method 1) 98.9% (AUC), $t_R$=9.81 min; ESI MS m/z 545 [M+H]⁺.

Preparation of 3-(4-chloro-5-methoxy-2-(7-(piperazin-1-yl)imidazo[1,2-a]pyrimidin-2-yl)phenoxy)-N,N-dimethylpropan-1-amine 162 (Example 186)

A solution tert-butyl 4-(2-(5-chloro-2-(3-(dimethylamino)propoxy)-4-methoxyphenyl)-imidazo[1,2-a]pyrimidin-7-yl)piperazine-1-carboxylate 161 (250 mg, 0.50 mmol) in 4.0 M HCl in dioxane (1 mL) was stirred at room temperature for 4 h. The reaction mixture was concentrated under reduced pressure, and the residue was suspended in aqueous ammonia (10 mL). The suspension was stirred at room temperature for 2 h and extracted with chloroform (2×10 mL). The combined organic layer was dried over sodium sulfate and concentrated under reduced pressure, and the residue was purified by column chromatography (silica gel, 1:0.1:10 methanol/ammonium hydroxide/DCM) to afford 3-(4-chloro-5-methoxy-2-(7-(piperazin-1-yl)-imidazo[1,2-a]pyrimidin-2-yl)phenoxy)-N,N-dimethylpropan-1-amine 162 (130 mg, 65%) as off white solid.
¹H NMR (400 MHz, DMSO-d₆): δ 8.55 (d, J=7.2 Hz, 1H), 8.12 (s, 1H), 7.80 (s, 1H), 6.83 (s, 1H), 6.74 (d, J=7.2 Hz, 1H), 4.28-4.16 (m, 2H), 3.91 (s, 3H), 3.67-3.55 (m, 4H), 2.90-2.71 (m, 4H), 2.21 (s, 6H), 2.10-1.99 (m, 2H); HPLC (Method 1) >99% (AUC), $t_R$=8.20 min: ESI MS m/z 445 [M+H]⁺.

Preparation of 3-(4-chloro-2-(7-(4-(cyclopentylsulfonyl)piperazin-1-yl)imidazo[1,2-a]-pyrimidin-2-yl)-5-methoxyphenoxy)-N,N-dimethylpropan-1-amine 163a (Example 227)

3-(4-Chloro-2-(7-(4-(cyclopentylsulfonyl)piperazin-1-yl)imidazo[1,2-a]-pyrimidin-2-yl)-5-methoxyphenoxy)-N,N-dimethylpropan-1-amine 163a was prepared in the same manner as 2-(5-chloro-2,4-dimethoxyphenyl)-7-[4-(methylsulfonyl)piperazin-1-yl]imidazo[1,2-a]pyridine 13a and was obtained as an white solid (38% yield).
¹H NMR (400 MHz, CDCl₃): δ 8.52 (s, 1H), 8.17 (d, J=7.4 Hz, 1H), 7.78 (s, 1H), 6.55 (s, 1H), 6.37 (d, J=7.4 Hz, 1H), 4.18 (t, J=6.3 Hz, 2H), 3.92 (s, 3H), 3.87-3.82 (m, 4H), 3.52-3.48 (m, 5H), 2.61 (t, J=7.1 Hz, 2H), 2.34 (s, 6H), 2.21-2.13 (m, 2H), 2.05-1.96 (m, 4H), 1.85-1.75 (m, 2H), 1.64-1.55 (m, 2H); HPLC (Method 1) 97.9% (AUC), $t_R$=9.79 min; ESI MS m/z 577 [M+H]⁺.

Preparation of 3-(4-chloro-2-(7-(4-(isopropylsulfonyl)piperazin-1-yl)imidazo[1,2-a]-pyrimidin-2-yl)-5-methoxyphenoxy)-N,N-dimethylpropan-1-amine 163b (Example 226)

3-(4-Chloro-2-(7-(4-(isopropylsulfonyl)piperazin-1-yl)imidazo[1,2-a]pyrimidin-2-yl)-5-methoxyphenoxy)-N,N-dimethylpropan-1-amine 163b was prepared in the same manner as 2-(5-chloro-2,4-dimethoxyphenyl)-7-[4-(methylsulfonyl)piperazin-1-yl]imidazo[1,2-a]-pyridine 13a and was obtained as an white solid (2.20 g, 44% yield).
¹H NMR (300 MHz, CD₃OD): δ 8.43 (d, J=7.6 Hz, 1H), 7.85 (s, 1H), 7.75 (s, 1H), 6.78-6.75 (m, 2H), 4.27 (t, J=5.8 Hz, 2H), 3.94 (s, 3H), 3.87-3.76 (m, 4H), 3.53-3.42 (m, 4H), 3.12-3.02 (m, 2H), 2.78 (s, 6H), 2.31-2.19 (m, 2H), 1.35 (s, 3H), 1.33 (s, 3H). HPLC (Method 1) 95.1% (AUC), $t_R$=9.45 min; ESI MS m/z 551 [M+H]⁺.

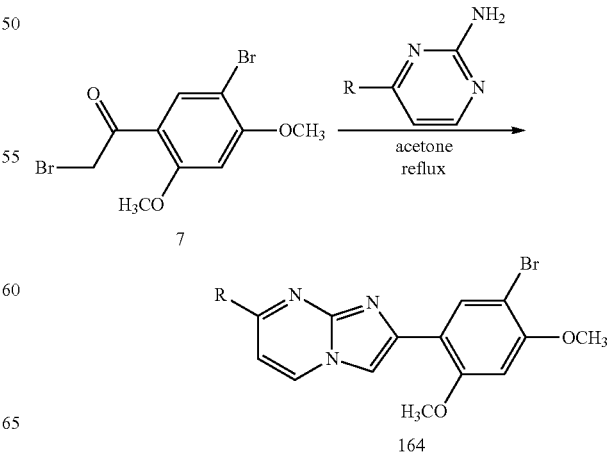

Scheme 49

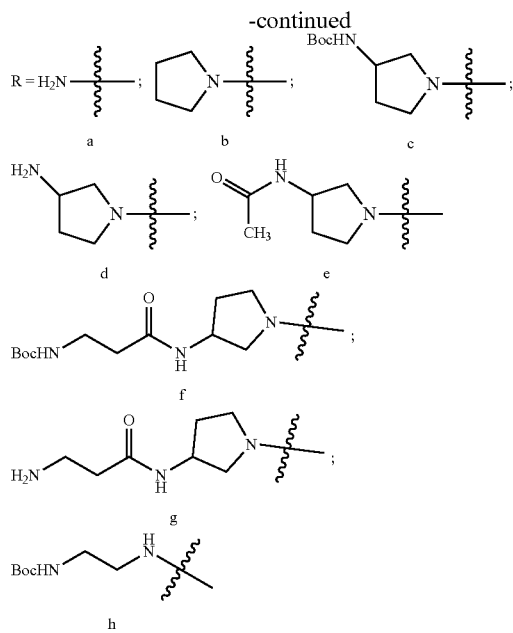

Preparation of 2-(5-bromo-2,4-dimethoxyphenyl) imidazo[1,2-a]pyrimidin-7-amine hydrochloride 164a (Example 2)

A solution of 2-bromo-1-(5-bromo-2,4-dimethoxyphenyl) ethanone 7 (62 mg, 0.0.21 mmol) and pyrimidine-2,4-diamine 164a (20 mg, 0.18 mmol) in acetone (5 mL) was heated to reflux for 3 h. The reaction mixture was cooled to room temperature, the white precipitate was filtered and washed with acetone. The precipitate was suspended in aqueous ammonia (10 mL) and stirred for 30 mins. The precipitate was filtered, washed with water. The solid was converted to HCl salt by treating it to dilute HCl. The precipitate obtained dried under reduced pressure to yield 2-(5-bromo-2,4-dimethoxyphenyl)imidazo[1,2-a]pyrimidin-7-amine hydrochloride 164a (18 mg, 44%) as an off-white solid.
$^1$H NMR (300 MHz, DMSO-$d_6$): δ 8.54-8.52 (d, J=7.6 Hz, 1H), 8.22 (br s, 2H), 8.11 (s, 1H), 8.07 (s, 1H), 6.92 (s, 3H), 6.71-6.68 (d, J=7.6 Hz, 1H), 4.03 (s, 3H), 3.97 (s, 3H). HPLC (Method 3) 97.8% (AUC), $t_R$=16.84 min; APCI MS m/z 351 [M+2+H]$^+$.

Preparation of 2-(5-bromo-2,4-dimethoxyphenyl)-7-(pyrrolidin-1-yl)imidazo[1,2-a]pyrimidine 164b (Example 3)

Compound 2-(5-bromo-2,4-dimethoxyphenyl)-7-(pyrrolidin-1-yl)imidazo[1,2-a]-pyrimidine 164b was prepared in the same manner as 2-(5-bromo-2,4-dimethoxyphenyl)-imidazo[1,2-a]pyrimidin-7-amine 164a and was obtained as free base (51% yield).
$^1$H NMR (400 MHz, DMSO-$d_6$): δ 8.48 (d, J=7.4 Hz, 1H), 8.37 (s, 1H), 7.79 (s, 1H), 6.83 (s, 1H), 6.41 (d, J=7.4 Hz, 1H), 3.99 (s, 3H), 3.92 (s, 3H), 3.48-3.46 (m, 4H), 1.88-1.84 (m, 4H). HPLC (Method 4)=96.3% (AUC), $t_R$=18.48 min. ESI MS m/z 405 [M+2+H]$^+$.

Preparation of tert-butyl (3-(2-(5-bromo-2,4-dimethoxyphenyl)imidazo[1,2-a]pyrimidin-7-yl)cyclopentyl)carbamate 164c (Example 13)

Compound tert-butyl (3-(2-(5-bromo-2,4-dimethoxyphenyl)imidazo[1,2-a]pyrimidin-7-yl)cyclopentyl)carbamate 164c was prepared in the same manner as 2-(5-bromo-2,4-dimethoxy-phenyl)imidazo[1,2-a]pyrimidin-7-amine 164a and was obtained as free base (200 mg, 77% yield).
$^1$H NMR (300 MHz, DMSO-$d_6$): δ 8.48 (d, J=7.4 Hz, 1H), 8.28 (s, 1H), 7.79 (s, 1H), 7.23 (s, 1H), 6.82 (s, 1H), 6.41 (d, J=7.4 Hz, 1H), 4.13 (br s, 1H), 3.99 (s, 3H), 3.92 (s, 3H), 3.73-3.64 (m, 1H), 3.61-3.53 (m, 1H), 3.52-3.45 (m, 1H), 3.39-3.32 (m, 1H), 2.22-2.08 (m, 1H), 1.96-1.83 (m, 1H), HPLC (Method 4) 97.8% (AUC), $t_R$=18.76 min; APCI MS m/z 520 [M+H]$^+$.

Preparation of 3-(2-(5-bromo-2,4-dimethoxyphenyl) imidazo[1,2-a]pyrimidin-7-yl)-cyclopentanamine hydrochloride 164d (Example 19)

Compound 3-(2-(5-bromo-2,4-dimethoxyphenyl)imidazo [1,2-a]pyrimidin-7-yl)cyclopentanamine hydrochloride 164d was prepared in the same manner 3-amino-N-(1-(2-(5-chloro-2,4-dimethoxyphenyl)imidazo[1,2-a]pyridin-7-yl)pyrrolidin-3-yl)propanamide 17f and was obtained as hydrochloride salt (70 mg, 76% yield).
$^1$H NMR (300 MHz, DMSO-$d_6$): δ 13.86 (br s, 1H), 8.72 (d, J=7.3 Hz, 4H), 8.13 (s, 2H), 6.96 (s, 1H), 6.93 (s, 1H), 4.04 (s, 3H), 3.97 (s, 3H), 3.93-3.81 (m, 3H), 3.80-3.64 (m, 2H), 2.45-2.17 (m, 2H). HPLC (Method 5) 98.3% (AUC), $t_R$=14.38 min: APCI MS m/z 420 [M+H]$^+$.

Preparation of N-(3-(2-(5-bromo-2,4-dimethoxyphenyl)imidazo[1,2-a]pyrimidin-7-yl)-cyclopentyl)acetamide 164e (Example 66)

Compound N-(3-(2-(5-bromo-2,4-dimethoxyphenyl)imidazo[1,2-a]pyrimidin-7-yl)-cyclopentyl)acetamide 164d was prepared in the same manner (4-(2-(5-chloro-2,4-dimethoxyphenyl)imidazo[1,2-a]pyridin-7-yl)piperazin-1-yl) (cyclopentyl)methanone 13t and was obtained as free base as a yellow solid (50 mg, 61% yield).
$^1$H NMR (400 MHz, DMSO-$d_6$): δ 8.49 (d, J=7.5 Hz, 1H), 8.28 (s, 1H), 8.16 (d, J=6.4 Hz, 1H), 7.80 (s, 1H), 6.83 (s, 1H), 6.43 (d, J=7.5 Hz, 1H), 4.36 (br s, 1H), 3.99 (s, 3H), 3.92 (s, 3H), 3.71-3.67 (m, 1H), 3.59-3.57 (m, 2H), 3.45 (br s, 1H), 2.20-2.12 (m, 1H), 1.95-1.85 (m, 1H), 1.82 (s, 3H). HPLC (Method 3) 98.1% (AUC), $t_R$=16.34 min; ESI MS m/z 460 [M+H]$^+$.

Preparation of tert-butyl (3-((3-(2-(5-bromo-2,4-dimethoxyphenyl)imidazo[1,2-a]pyrimidin-7-yl) cyclopentyl)amino)-3-oxopropyl)carbamate 164f (Example 65)

Compound tert-butyl (3-((3-(2-(5-bromo-2,4-dimethoxyphenyl)imidazo[1,2-a]-pyrimidin-7-yl)cyclopentyl)amino)-3-oxopropyl)carbamate 164f was prepared in the same manner tert-butyl (2-(1-(2-(5-chloro-2,4-dimethoxyphenyl)imidazo[1,2-a]pyridin-7-yl)piperidin-4-yl)ethyl)carbamate 5e and was obtained as a brown solid (70 mg, 50% yield).
$^1$H NMR (400 MHz, DMSO-$d_6$): δ 8.51 (d, J=7.3 Hz, 1H), 8.26 (s, 1H), 8.19 (d, J=6.4 Hz, 1H), 7.83 (s, 1H), 6.84 (s, 1H), 6.74 (br s, 1H), 6.48 (d, J=7.3 Hz, 1H), 4.37 (br s, 1H), 4.00 (s, 3H), 3.93 (s, 3H), 3.76-3.66 (m, 1H), 3.65-3.52 (m, 2H), 3.44-3.33 (m, 1H), 3.13-3.10 (m, 2H), 2.26-2.24 (m, 3H), 1.96-1.86 (m, 1H), 1.36 (s, 9H); HPLC (Method 3) 95.7% (AUC), $t_R$=17.34 min; ESI MS m/z 589 [M+H]$^+$.

Preparation of 3-amino-N-(3-(2-(5-bromo-2,4-dimethoxyphenyl)imidazo[1,2-a]pyrimidin-7-yl)cyclopentyl)propanamide hydrochloride 164e (Example 68)

Compound 3-amino-N-(3-(2-(5-bromo-2,4-dimethoxyphenyl)imidazo[1,2-a]-pyrimidin-7-yl)cyclopentyl)propanamide hydrochloride 164g was prepared in the same manner 3-amino-N-(1-(2-(5-chloro-2,4-dimethoxyphenyl)imidazo[1,2-a]pyridin-7-yl)pyrrolidin-3-yl)propanamide 17f and was obtained as hydrochloride salt as a pale yellow solid (30 mg, 64% yield).

$^1$H NMR (400 MHz, DMSO-d$_6$): δ 13.74 (s, 1H), 8.70-8.59 (m, 2H), 8.17 (s, 1H), 8.08 (s, 1H), 8.00-7.85 (m, 3H), 6.93 (s, 1H), 6.92-6.83 (br s, 1H), 4.52-4.37 (m, 1H), 4.04 (s, 3H), 3.97 (s, 3H), 3.86-3.78 (m, 2H), 3.77-3.66 (m, 2H), 3.62-3.42 (m, 2H), 3.05-2.94 (m, 2H), 2.35-2.14 (m, H), 2.14-1.95 (m, 1H). HPLC (Method 5) 96.1% (AUC), $t_R$=15.42 min; ESI MS m/z 489 [M+H]$^+$.

Preparation of tert-butyl (2-((2-(5-bromo-2,4-dimethoxyphenyl)imidazo[1,2-a]pyrimidin-7-yl)amino)ethyl)carbamate 164h (Example 18)

Compound tert-butyl (2-((2-(5-bromo-2,4-dimethoxyphenyl)imidazo[1,2-a]-pyrimidin-7-yl)amino)ethyl)carbamate 164h was prepared in the same manner tert-butyl (2-(1-(2-(5-chloro-2,4-dimethoxyphenyl)imidazo[1,2-a]pyridin-7-yl)piperidin-4-yl)ethyl)-carbamate 5e and was obtained as brown solid (100 mg, 25% yield).

$^1$H NMR (300 MHz, DMSO-d$_6$): δ 8.35 (d, J=7.3 Hz, 1H), 8.24 (s, 1H), 7.80 (s, 1H), 7.66 (br s, 1H), 6.91 (br s, 1H), 6.83 (s, 1H), 6.32 (d, J=7.3 Hz, 1H), 3.99 (s, 3H), 3.92 (s, 3H), 3.42-3.33 (m, 2H), 3.21-3.11 (m, 2H), 1.38 (s, 9H); HPLC (Method 4) %96.4% (AUC), $t_R$=18.45 min.; APCI MS m/z 494 [M+H]$^+$.

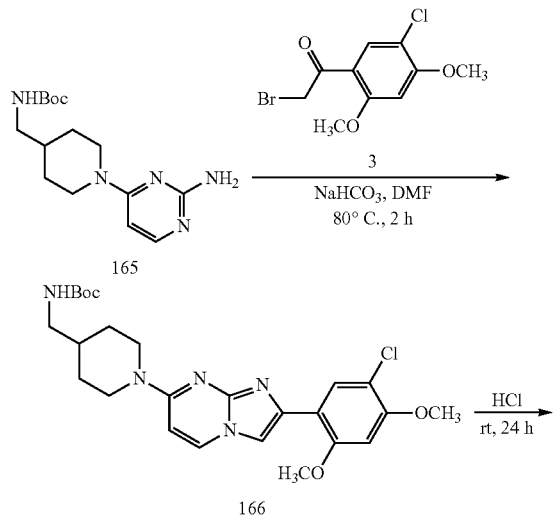

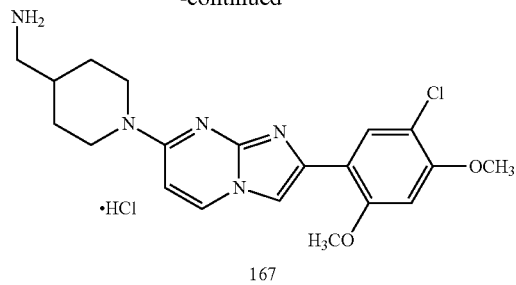

Preparation of tert-butyl ((1-(2-(5-chloro-2,4-dimethoxyphenyl)imidazo[1,2-a]pyrimidin-7-yl)piperidin-4-yl)methyl)carbamate 166 (Example 32)

A solution of tert-butyl ((1-(2-aminopyrimidin-4-yl)piperidin-4-yl)methyl)carbamate 165 (120 mg, 0.39 mmol) in DMF (5 mL) was charged with 2-bromo-1-(5-chloro-2,4-dimethoxy-phenyl)ethanone (107 mg, 0.42 mmol) followed by sodium bicarbonate (39 mg, 0.46 mmol). The reaction mixture was heated to 90° C. for 3 h. The reaction mixture was cooled to room temperature, quenched with water (25 mL), the precipitate was collected by filtration and dried under reduced pressure. The solid was purified by combiflash chromatography (silica gel, 9:1 DCM/methanol) to afford tert-butyl ((1-(2-(5-chloro-2,4-dimethoxyphenyl)imidazo[1,2-a]-pyrimidin-7-yl)piperidin-4-yl)methyl)carbamate 166 (135 mg, 69%) as an off-white solid.

$^1$H NMR (300 MHz, DMSO-d$_6$): δ 8.48 (d, J=7.6 Hz, 1H), 8.12 (s, 1H), 7.79 (s, 1H), 6.88-6.85 (m, 2H), 6.75 (d, J=7.6 Hz, 1H), 4.43-4.39 (m, 2H), 3.95 (s, 3H), 3.93 (s, 3H), 2.95-2.86 (m, 4H), 1.71-1.68 (m, 3H), 1.38 (s, 9H), 1.10-1.06 (m, 2H); HPLC (Method 3) 99.12% (AUC), $t_R$=19.01 min.; ESI MS m/z 502 [M+H]$^+$.

Preparation of (1-(2-(5-chloro-2,4-dimethoxyphenyl)imidazo[1,2-a]pyrimidin-7-yl)piperidin-4-yl)methanamine hydrochloride 167 (Example 31)

A mixture of tert-butyl ((1-(2-(5-chloro-2,4-dimethoxyphenyl)imidazo[1,2-a]pyrimidin-7-yl)piperidin-4-yl)methyl)carbamate 166 (90 mg, 1.79 mmol), and hydrochloric acid in methanol (2.00 mL, 1.25 molar solution) in methanol (5 mL) was stirred at room temperature for 16 h. The reaction was concentrated under reduced pressure to afford 1-(2-(5-chloro-2,4-dimethoxyphenyl)imidazo[1,2-a]pyrimidin-7-yl)piperidin-4-yl)methanamine hydrochloride 167 (78 mg, 92%) as a yellow solid.

$^1$H NMR (300 MHz, DMSO-d$_6$): δ 8.89-8.67 (d, J=7.6 Hz, 1H), 8.27 (br s, 3H), 8.08 (s, 1H), 8.03 (s, 1H), 7.29-7.27 (d, J=7.6 Hz, 1H), 6.96 (s, 1H), 4.04 (s, 3H), 3.98 (s, 3H), 3.39 (m, 3H), 3.17-3.15 (m, 2H), 2.75-2.71 (m, 2H), 2.06 (m, 1H), 1.96-1.91 (m, 2H), 1.30-1.19 (m, 2H). HPLC (Method 3) 97.5% (AUC), $t_R$=15.83 min. ESI MS m/z 402 [M+H]$^+$.

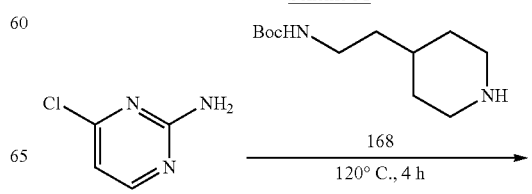

<sup>1</sup>H NMR (400 MHz, DMSO-d<sub>6</sub>): δ 8.49 (d, J=7.7 Hz, 1H), 8.10 (s, 1H), 7.83 (s, 1H), 6.87 (s, 1H), 6.82 (d, J=7.7 Hz, 1H), 6.77 (t, J=5.3 Hz, 1H), 4.42 (d, J=12.9 Hz, 2H), 4.00 (s, 3H), 3.93 (s, 3H), 3.02-2.88 (m, 4H), 1.81-1.72 (m, 2H), 1.66-1.54 (m, 1H), 1.37 (s, 9H), 1.35-1.30 (m, 2H), 1.15-1.02 (m, 2H). HPLC (Method 3) 94.8% (AUC), $t_R$=18.72 min; ESI MS m/z 516 [M+H]$^+$.

Preparation of 2-(1-(2-(5-chloro-2,4-dimethoxyphenyl)imidazo[1,2-a]pyrimidin-7-piperidin-4-yl)ethanamine 171 (Example 67)

A mixture of tert-butyl (2-(1-[2-(5-chloro-2,4-dimethoxyphenyl)imidazo[1,2-a]-pyrimidin-7-yl]piperidin-4-yl)ethyl) carbamate (70 mg, 0.13 mmol), and hydrochloric acid in dioxane (5.00 mL, 4.00 molar solution) was stirred at room temperature for 4 h. The reaction was concentrated under reduced pressure to afford 1-(2-(5-chloro-2,4-dimethoxyphenyl)imidazo-[1,2-a]pyrimidin-7-yl)piperidin-4-yl)methanamine hydrochloride 171 (30 mg, 53%) as a yellow solid.

<sup>1</sup>H NMR (400 MHz, DMSO-d<sub>6</sub>): δ 13.68 (br s, 1H), 8.66 (d, J=7.61 Hz, 1H), 8.14-8.05 (m, 4H), 8.03 (s, 1H), 7.26 (d, J=7.6 Hz, 1H), 6.96 (s, 1H), 4.85 (br s, 1H), 4.38 (br s, 1H), 4.04 (s, 3H), 3.98 (s, 3H), 3.16-3.13 (m, 2H), 2.82 (br s, 2H), 1.9-1.70 (m, 3H), 1.60-1.50 (m, 2H), 1.20-1.07 (m, 2H). ESI MS m/z 416 [M+H]$^+$.

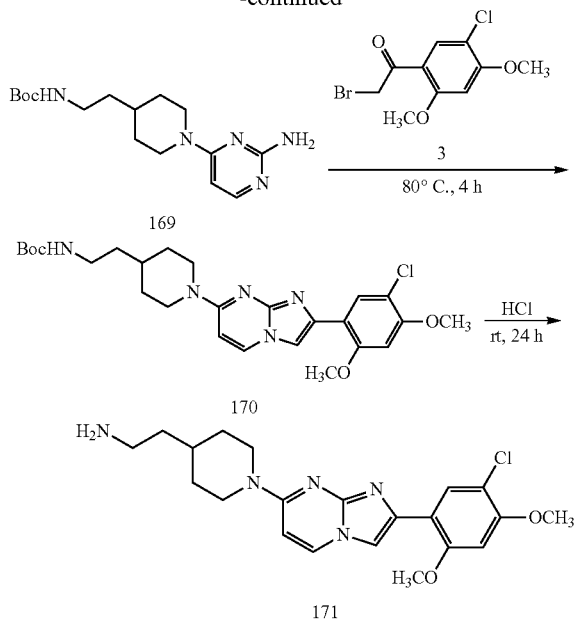

Preparation of tert-butyl {2-[1-(2-aminopyrimidin-4-yl)piperidin-4-yl]ethyl}carbamate 169

A solution of 2-amino-4-chloropyrimidine (200 mg, 1.60 mmol) in 1-butanol (2 mL) was charged with tert-butyl [2-(piperidin-4-yl)ethyl] carbamate 168 (430 mg, 1.90 mmol) and the reaction vessel was sealed well. The reaction mixture was heated to 120° C. for 4 h. The reaction mixture was cooled to room temperature and the solvent was removed under reduced pressure. The residue was suspended in aqueous ammonia (10 mL) and stirred for 2 h. The precipitate was filtered and dried under reduced pressure to afford tert-butyl {2-[1-(2-aminopyrimidin-4-yl)piperidin-4-yl]ethyl}carbamate 169 (230 mg, 46%) as a pale yellow solid.

<sup>1</sup>H NMR (300 MHz, DMSO-d<sub>6</sub>): δ 7.71 (d, J=6.1 Hz, 1H), 6.75 (br s, 1H), 5.99 (d, J=6.0 Hz, 1H), 5.88 (s, 2H), 4.27 (d, J=13.1 Hz, 2H), 2.95 (dd, J=6.7 Hz, 13.3 Hz, 2H), 2.71 (t, J=11.3 Hz, 2H), 1.67 (d, J=12.8 Hz, 2H), 1.60-1.43 (m, 1H), 1.37 (s, 9H), 1.34-1.25 (m, 2H), 1.07-0.90 (m, 2H). ESI MS m z 321 [M+H]$^+$.

Preparation of tert-butyl (2-{1-[2-(5-chloro-2,4-dimethoxyphenyl)imidazo[1,2-a]pyrimidin-7-yl] piperidin-4-yl}ethyl)carbamate 170 (Example 61)

A solution of tert-butyl {2-[1-(2-aminopyrimidin-4-yl) piperidin-4-yl]ethyl}carbamate 169 (200 mg, 0.60 mmol) in N,N-dimethylformamide (2 mL) was charged with 2-bromo-1-(5-chloro-2,4-dimethoxyphenyl)ethanone (200 mg, 0.70 mmol) followed by sodium bicarbonate (150 mg, 1.80 mmol). The reaction mixture was heated to 80° C. for 4 h. The reaction mixture was cooled to room temperature and quenched with water (25 mL) and the precipitate was filtered and dried under reduced pressure. The solid was purified by combi-flash chromatography (silica gel, 9:1 DCM/methanol) to afford tert-butyl (2-{1-[2-(5-chloro-2,4-dimethoxyphenyl)imidazo[1,2-a]pyrimidin-7-yl]piperidin-4-yl}ethyl) carbamate 170 (220 mg, 69%) as an off-white solid.

Scheme 52

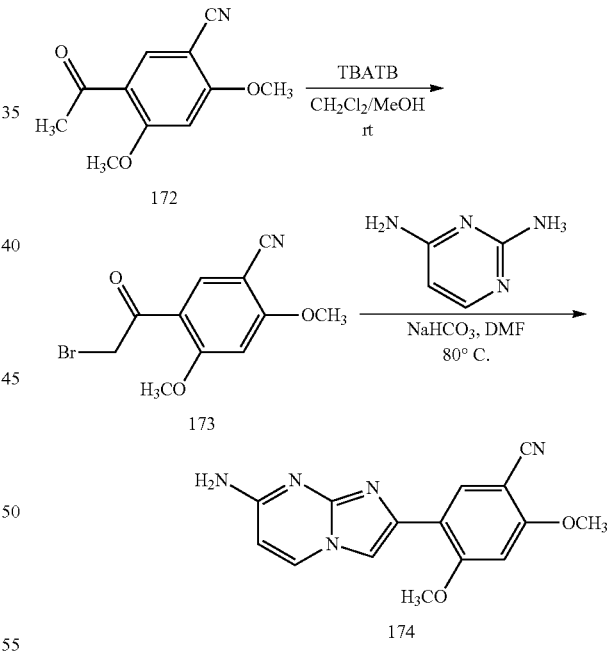

Preparation of 5-(7-aminoimidazo[1,2-a]pyrimidin-2-yl)-2,4-dimethoxybenzonitrile 174 (Example 46)

5-(7-Aminoimidazo[1,2-a]pyrimidin-2-yl)-2,4-dimethoxybenzonitrile 174 was prepared in the same manner as 2-(5-bromo-2,4-dimethoxyphenyl)-7-(pyrrolidin-1-yl)imidazo-[1,2-a]pyridine 9a and was obtained as an off-white solid (58% yield).

<sup>1</sup>H NMR (300 MHz, DMSO-d<sub>6</sub>): δ 8.37 (d, J=7.2 Hz, 1H), 7.79 (s, 1H), 6.91-6.81 (m, 3H), 6.26 (d, J=7.2 Hz, 1H), 4.07

Preparation of 5-(7-aminoimidazo[1,2-a]pyrimidin-2-yl)-2,4-dimethoxybenzonitrile hydrochloride (Example 46)

5-(7-Aminoimidazo[1,2-a]pyrimidin-2-yl)-2,4-dimethoxybenzonitrile hydrochloride was prepared in the same manner as 2-(5-chloro-2,4-dimethoxyphenyl)-7-(piperazin-1-yl)imidazo[1,2-a]pyridine 12 and was obtained as an off-white solid (92% yield).

$^1$H NMR (400 MHz, DMSO-$d_6$): δ 13.57 (br s, 1H), 8.53 (d, J=7.4 Hz, 1H), 8.37-8.24 (m, 2H), 8.22 (s, 3H), 6.99 (s, 1H), 6.70 (d, J=7.4 Hz, 1H), 4.10 (s, 3H), 4.04 (s, 3H). HPLC (Method 3) 97.3% (AUC), $t_R$=15.59 min: ESI MS m/z 296 [M+H]$^+$.

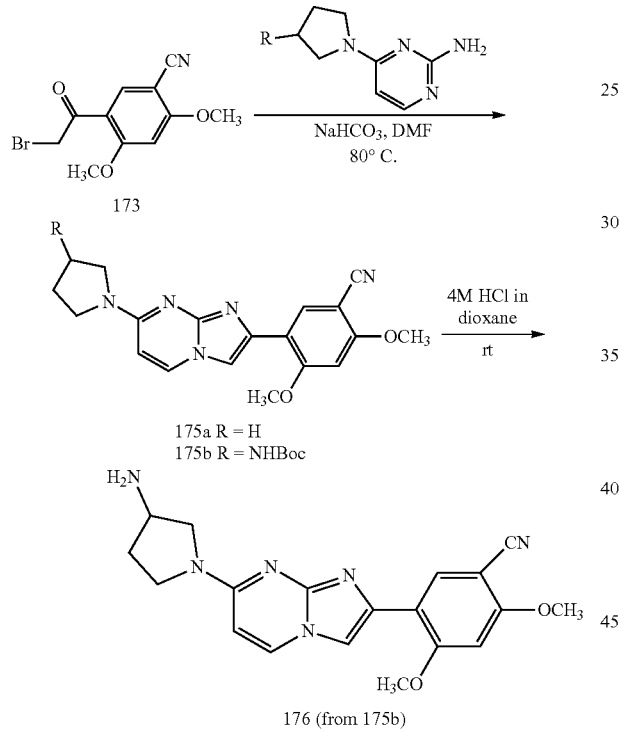

Scheme 53

175a R = H
175b R = NHBoc 176 (from 175b)

Preparation of tert-butyl (1-(2-(5-cyano-2,4-dimethoxyphenyl)imidazo[1,2-a]pyrimidin-7-yl)pyrrolidin-3-yl) carbamate 175b (Example 74)

Compound tert-butyl (1-(2-(5-cyano-2,4-dimethoxyphenyl)imidazo[1,2-a]pyrimidin-7-yl)pyrrolidin-3-yl)carbamate 175b was prepared in the same manner as tert-butyl 4-[2-(5-chloro-2,4-dimethoxyphenyl)imidazo[1,2-a]pyridin-7-yl]piperazine-1-carboxylate 11 and was obtained as a yellow solid (15 mg, 66% yield).

$^1$H NMR (400 MHz, DMSO-$d_6$): δ 8.48 (d, J=7.53 Hz, 1H), 8.32 (s, 1H), 7.82 (s, 1H), 7.23 (br s, 1H), 6.89 (s, 1H), 6.42 (d, J=7.53 Hz, 1H), 4.13 (br s, 1H), 4.07 (s, 3H), 3.99 (s, 3H), 3.72-3.66 (m, 1H), 3.6-3.57 (m, 1H), 3.55-3.47 (m, 1H), 3.41-3.32 (m, 1H), 2.20-2.10 (m, 1H), 1.97-1.85 (m, 1H), 1.40 (s, 9H). HPLC (Method 5) 97.5% (AUC), $t_R$=17.7 min, ESI MS m/z 465 [M+H]$^+$.

Preparation of 2,4-dimethoxy-5-(7-(pyrrolidin-1-yl)imidazo[1,2-a]pyrimidin-2-yl)-benzonitrile hydrochloride 175a (Example 69)

Compound 2,4-dimethoxy-5-(7-(pyrrolidin-1-yl)imidazo[1,2-a]pyrimidin-2-yl)-benzonitrile 175a was prepared in the same manner as tert-butyl 4-[2-(5-chloro-2,4-dimethoxyphenyl)imidazo[1,2-a]pyridin-7-yl]piperazine-1-carboxylate 11 and was obtained as an off-white solid (20 mg, 29% yield).

$^1$H NMR (400 MHz, DMSO-$d_6$): δ 13.66 (br s, 1H), 8.63 (d, J=7.6 Hz, 1H), 8.18 (s, 1H), 8.09 (s, 1H), 6.99 (s, 1H), 6.90 (d, J=7.6 Hz, 1H), 4.11 (s, 3H), 4.04 (s, 3H), 3.65-3.56 (m, 4H), 2.08-1.96 (m, 4H). HPLC (Method 5) >99% (AUC), $t_R$=17.1 min: ESI MS m/z 350 [M+H]$^+$.

Preparation of 5-(7-(3-aminopyrrolidin-1-yl)imidazo[1,2-a]pyrimidin-2-yl)-2,4-dimethoxy-benzonitrile 176

5-(7-(3-Aminopyrrolidin-1-yl)imidazo[1,2-a]pyrimidin-2-yl)-2,4-dimethoxybenzonitrile 176 was prepared in the same manner as 2-(5-chloro-2,4-dimethoxyphenyl)-7-(piperazin-1-yl)imidazo[1,2-a]pyridine 12 and was obtained as an off-white solid (76% yield).

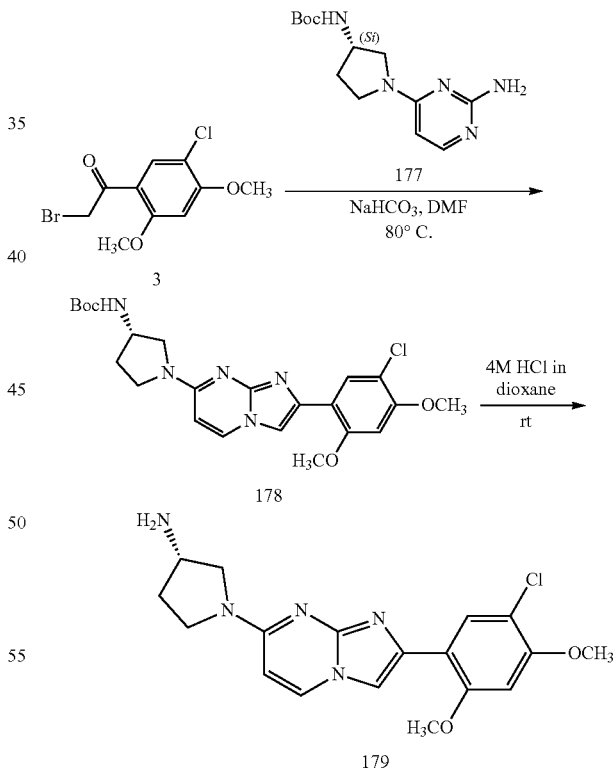

Scheme 54

Preparation of (S)-tert-butyl (1-(2-(5-chloro-2,4-dimethoxyphenyl)imidazo[1,2-a]-pyrimidin-7-yl)pyrrolidin-3-yl)carbamate 178 (Example 56)

(S)-tert-Butyl (1-(2-(5-chloro-2,4-dimethoxyphenyl)imidazo[1,2-a]pyrimidin-7-yl)pyrrolidin-3-yl)carbamate 178 was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e, and was obtained as a yellow solid (30 mg, 72% yield).

$^1$H NMR (400 MHz, DMSO-d$_6$): δ 8.48 (d, J=7.6 Hz, 1H), 8.12 (s, 1H), 7.80 (s, 1H), 7.23 (br s, 1H), 6.85 (s, 1H), 6.40 (d, J=7.6 Hz, 1H), 4.13 (br s, 1H), 3.99 (s, 3H), 3.93 (s, 3H), 3.73-3.64 (m, 1H), 3.63-3.56 (m, 1H), 3.55-3.45 (m, 1H), 3.40-3.32 (m, 1H), 2.22-2.08 (m, 1H), 1.95-1.84 (m, 1H), 1.40 (s, 9H). HPLC (Method 3) 94.5% (AUC), t$_R$=17.99 min; ESI MS m/z 474 [M+H]$^+$.

Preparation of (S)-1-(2-(5-chloro-2,4-dimethoxyphenyl)imidazo[1,2-a]pyrimidin-7-yl)-pyrrolidin-3-amine hydrochloride 179 (Example 58)

(S)-1-(2-(5-Chloro-2,4-dimethoxyphenyl)imidazo[1,2-a]pyrimidin-7-yl)pyrrolidin-3-amine hydrochloride 179 was prepared in the same manner as 2-(1-(2-(5-chloro-2,4-dimethoxyphenyl)imidazo[1,2-a]pyridin-7-yl)piperidin-4-yl)ethanamine 5f, and was obtained as an off-white solid (50 mg, 54% yield).

$^1$H NMR (400 MHz, DMSO-d$_6$): δ 13.83 (br s, 1H), 8.71 (d, J=7.56 Hz, 1H), 8.69-8.55 (m, 3H), 8.13 (s, 1H), 8.01 (s, 1H), 6.98-6.92 (m, 2H), 4.04 (s, 3H), 4.01 (s, 3H). 3.92-3.81 (m, 3H), 3.79-3.66 (m, 2H), 2.46-2.31 (m, 1H), 2.29-2.16 (m, 1H) HPLC (Method 3) 96.2% (AUC), t$_R$=15.13 min; ESI MS m/z 374 [M+H]$^+$.

Scheme 55

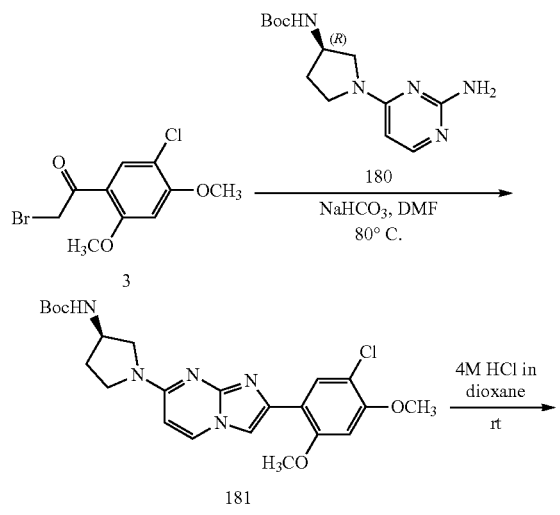

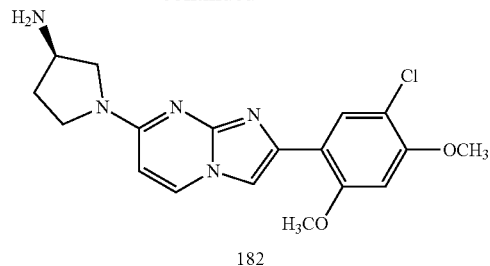

182

Preparation of ((R)-tert-butyl (1-(2-(5-chloro-2,4-dimethoxyphenyl)imidazo[1,2-a]-pyrimidin-7-yl)pyrrolidin-3-yl)carbamate 181 (Example 57)

(R)-tert-Butyl (1-(2-(5-chloro-2,4-dimethoxyphenyl)imidazo[1,2-a]pyrimidin-7-yl)-pyrrolidin-3-yl)carbamate 181 was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e, and was obtained as a yellow solid (20 mg, 80% yield).

$^1$H NMR (400 MHz, DMSO-d$_6$): δ 8.48 (d, J=7.4 Hz, 1H), 8.12 (s, 1H), 7.80 (s, 1H), 7.23 (br s, 1H), 6.85 (s, 1H), 6.40 (d, J=7.4 Hz, 1H), 4.13 (br s, 1H), 3.99 (s, 3H), 3.93 (s, 3H), 3.73-3.56 (m, 2H), 3.55-3.32 (m, 2H), 2.22-2.08 (m, 1H), 1.95-1.84 (m, 1H), 1.40 (s, 9H); ESI MS m/z 474 [M+H]$^+$.

(R)-1-(2-(5-Chloro-2,4-dimethoxyphenyl)imidazo[1,2-a]pyrimidin-7-yl)pyrrolidin-3-amine hydrochloride 182 (Example 55)

(R)-1-(2-(5-Chloro-2,4-dimethoxyphenyl)imidazo[1,2-a]pyrimidin-7-yl)pyrrolidin-3-amine hydrochloride 182 was prepared in the same manner as 2-(1-(2-(5-chloro-2,4-dimethoxyphenyl)imidazo[1,2-a]pyridin-7-yl)piperidin-4-yl)ethanamine 5f, and was obtained as a yellow solid (50 mg, 90%/o yield).

$^1$H NMR (400 MHz, DMSO-d$_6$): δ 13.85 (br s, 1H), 8.83-8.64 (m, 4H), 8.13 (s, 1H), 8.01 (s, 1H), 6.96 (s, 1H), 6.94 (s, 1H), 4.04 (s, 3H), 3.98 (s, 3H), 3.80-3.66 (m, 2-H), 2.46-2.18 (m, 2H); HPLC (Method 3) 98.8% (AUC), t$_R$=15.13 min; ESI MS m/z 374 [M+H]$^+$.

Scheme 56

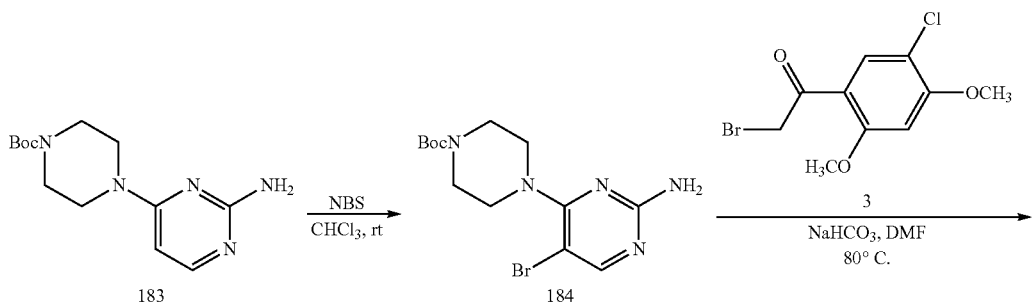

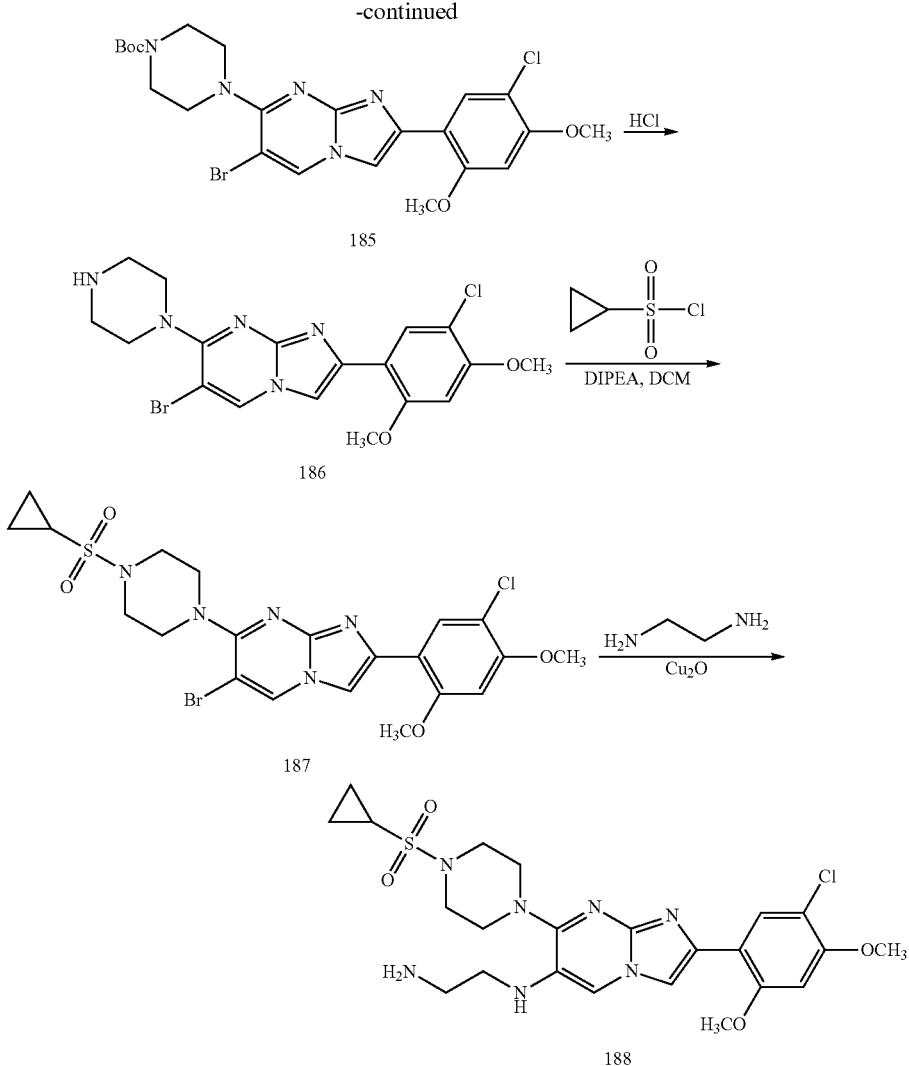

Preparation of tert-butyl 4-(2-amino-5-bromopyrimidin-4-yl)piperazine-1-carboxylate 184

To a solution of tert-butyl 4-(2-aminopyrimidin-4-yl)piperazine-1-carboxylate 3 (2.00 g, 7.20 mmol) in chloroform (60 mL) was added N-bromosuccinimide (1.28 g, 7.20 mmol). The reaction mixture was stirred at room temperature for 4 h. The reaction mixture was quenched with 10% sodium thiosulfate solution (100 mL) and extracted with chloroform (100 mL). The organic layer was concentrated under reduced pressure, and purified by column chromatography (silica gel, MeOH/DCM) to provide the desired compound tert-butyl 4-(2-amino-5-bromo-pyrimidin-4-yl)piperazine-1-carboxylate 184 (1.60 g, 62%) as a pale-yellow solid.

Preparation of tert-butyl 4-(6-bromo-2-(5-chloro-2,4-dimethoxyphenyl)imidazo[1,2-a]-pyrimidin-7-yl)piperazine-1-carboxylate 185

To a solution of tert-butyl 4-(2-amino-5-bromopyrimidin-4-yl)piperazine-1-carboxylate 184 (1.50 g, 4.20 mmol) in DMF (30 mL) was added 2-bromo-1-(5-chloro-2,4-dimethoxy-phenyl)ethanone 3 (1.23 g, 4.20 mmol) followed by sodium bicarbonate (1.06 g, 12.60 mmol). The reaction mixture was heated to 80° C. for 4 h. The reaction mixture was cooled to room temperature, quenched with water (25 mL) and the precipitate was collected by filtration, dried under reduced pressure. The solid was purified by combi-flash chromatography (silica gel, 9:1 DCM/methanol) to afford tert-butyl 4-(6-bromo-2-(5-chloro-2,4-dimethoxyphenyl)imidazo-[1,2-a]pyrimidin-7-yl)piperazine-1-carboxylate 185 (1.60 g, 69%) as an off white solid.

$^1$H NMR (400 MHz, CDCl$_3$): δ 8.51 (s, 1H), 8.37 (s, 1H), 7.79 (s, 1H), 6.56 (s, 1H), 3.99 (s, 3H), 3.95 (s, 3H), 3.63-3.57 (m, 4H), 3.55-3.49 (m, 4H), 1.49 (s, 9H). HPLC (Method 1) 98.1% (AUC), t$_R$=11.75 min; ESI MS m/z 537 [M+H]$^+$.

Preparation of 6-bromo-2-(5-chloro-2,4-dimethoxyphenyl)-7-(piperazin-1-yl)imidazo[1,2-a]pyrimidine 186 (Example 220)

A solution of tert-butyl 4-(6-bromo-2-(5-chloro-2,4-dimethoxyphenyl)imidazo[1,2-a]-pyrimidin-7-yl)piperazine-1-carboxylate 185 (100 mg, 0.18 mmol) in 4.0 M HCl in dioxane (2 mL) was stirred at room temperature for 3 h. The reaction mixture was filtered, washed with dioxane, and dried under reduced pressure to give the HCl salt of tert-butyl 4-(6-bromo-2-(5-chloro-2,4-dimethoxyphenyl)imidazo[1,2-a]pyrimidin-7-yl)piperazine-1-carboxylate 7 (60 mg, 73%) as a yellow solid. The compound was suspended in 10 mL of aqueous ammonia, stirred for 1 h at room temperature, and extracted using chloroform (2×20 mL). The organic layer was dried and concentrated to give 6-bromo-2-(5-chloro-2,4-dimethoxyphenyl)-7-(piperazin-1-yl)imidazo[1,2-a]pyrimidine 186 as an off-white solid.

$^1$H NMR (400 MHz, DMSO-$d_6$): δ 9.08 (s, 1H), 8.20 (s, 1H), 7.95 (s, 1H), 6.88 (s, 1H), 4.01 (s, 3H), 3.94 (s, 3H), 3.37-3.33 (m, 4H), 2.91-2.86 (m, 4H). HPLC (Method 1) 98.9% (AUC), $t_R$=9.01 min; ESI MS m/z 454 [M+H]$^+$.

Preparation of 6-bromo-2-(5-chloro-2,4-dimethoxyphenyl)-7-(4-(cyclopropyl-sulfonyl)piperazin-1-yl)imidazo[1,2-a]pyrimidine 187

A solution of 6-bromo-2-(5-chloro-2,4-dimethoxyphenyl)-7-(piperazin-1-yl)-imidazo[1,2-a]pyrimidine 7 (700 mg, 1.50 mmol) and diisopropylethylamine (450 mg, 4.50 mmol) in dichloromethane (15 mL) was charged with cyclopropanesulfonyl chloride (240 mg, 1.70 mmol). The reaction mixture was stirred at room temperature for 3 h. The reaction mixture was concentrated, suspended in aqueous ammonia, and stirred for 2 h. The precipitate was collected by filtration, washed with water, dried and purified by column chromatography (silica gel, MeOH/DCM) to afford 6-bromo-2-(5-chloro-2,4-dimethoxyphenyl)-7-(4-(cyclopropylsulfonyl)piperazin-1-yl)imidazo[1,2-a]pyrimidine 187 (500 mg, 58%) as a pale yellow solid.

$^1$H NMR (400 MHz, CDCl$_3$): δ 8.50 (s, 1H), 8.40 (s, 1H), 7.81 (s, 1H), 6.56 (s, 1H), 3.99 (s, 3H), 3.95 (s, 3H), 3.72-3.66 (m, 4H), 3.52-3.46 (m, 4H), 2.33-2.25 (m, 1H), 1.24-1.15 (m, 2H), 1.05-0.98 (m, 2H). HPLC (Method 1) 98.1% (AUC), $t_R$=10.98 min; ESI MS m/z 556 [M+H]$^+$.

Preparation of N$^1$-(2-(5-chloro-2,4-dimethoxyphenyl)-7-(4-(cyclopropylsulfonyl)-piperazin-1-yl)imidazo[1,2-a]pyrimidin-6-yl)ethane-1,2-diamine 188 (Example 222)

To a solution of 6-bromo-2-(5-chloro-2,4-dimethoxyphenyl)-7-(4-(cyclopropyl-sulfonyl)piperazin-1-yl)imidazo[1,2-a]pyrimidine 187 (100 mg, 0.20 mmol) in ethylene diamine (1 mL), Copper(I) oxide (10 mg) added and heated at 100° C. for 2 h. After 2 h, the reaction mixture was concentrated and purified by combi-flash chromatography (silica gel, 9:1 DCM/methanol) to afford N$^1$-(2-(5-chloro-2,4-dimethoxyphenyl)-7-(4-(cyclopropylsulfonyl)-piperazin-1-yl)imidazo[1,2-a]pyrimidin-6-yl)ethane-1,2-diamine 188 (10 mg, 10%) as a brown solid.

$^1$H NMR (400 MHz, CDCl$_3$): δ 8.54 (s, 1H), 7.60 (s, 1H), 6.58 (s, 1H), 5.51 (br s, 1H), 5.33 (s, 1H), 3.99 (s, 3H), 3.94 (s, 3H), 3.86-3.80 (m, 4H), 3.40-3.30 (m, 6H), 3.17-3.14 (m, 2H), 2.28-2.19 (m, 1H), 1.21-1.14 (m, 2H), 1.01-0.94 (m, 2H). HPLC (Method 1) 97.4% (AUC), $t_R$=9.66 min; ESI MS m/z 536 [M+H]$^+$.

Scheme 57

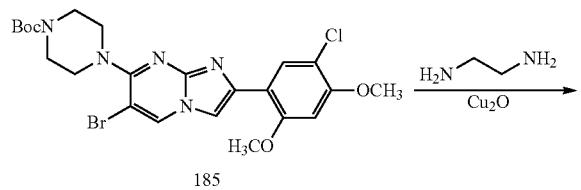

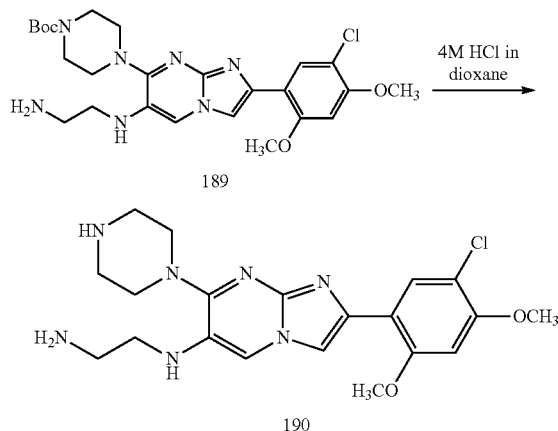

Preparation of tert-butyl 4-(6-((2-aminoethyl)amino)-2-(5-chloro-2,4-dimethoxyphenyl)imidazo[1,2-a]pyrimidin-7-yl)piperazine-1-carboxylate 189 (Example 221)

To a solution of tert-butyl 4-(6-bromo-2-(5-chloro-2,4-dimethoxyphenyl)imidazo-[1,2-a]pyrimidin-7-yl)piperazine-1-carboxylate 6 (400 mg, 0.70 mmol) in Ethylene diamine (4 mL), Copper oxide (40 mg) was added and heated at 100° C. for 2 h. After 2 h. the reaction mixture was concentrated and purified by combi-flash chromatography (silica gel, 9:1 DCM/methanol) to afford tert-butyl 4-(6-((2-aminoethyl)amino)-2-(5-chloro-2,4-dimethoxy-phenyl)imidazo[1,2-a]pyrimidin-7-yl)piperazine-1-carboxylate 189 (40 mg, 10%) as a brown solid.

$^1$H NMR (400 MHz, CDCl$_3$): δ 8.53 (s, 1H), 7.61 (s, 1H), 6.55 (s, 1H), 5.31 (s, 1H), 4.00 (s, 3H), 3.94 (s, 3H), 3.78-3.61 (m, 4H), 3.56-3.47 (m, 4H), 3.37-3.29 (m, 2H), 3.17-3.11 (m, 2H), 1.49 (s, 9H); HPLC (Method 1) 95.2% (AUC), $t_R$=10.11 min; ESI MS m/z 532 [M+H]$^+$.

Preparation of N$^1$-(2-(5-chloro-2,4-dimethoxyphenyl)-7-(piperazin-1-yl)imidazo[1,2-a]-pyrimidin-6-yl)ethane-1,2-diamine 190 (Example 223)

A mixture of tert-butyl 4-(6-((2-aminoethyl)amino)-2-(5-chloro-2,4-dimethoxyphenyl)imidazo[1,2-a]pyrimidin-7-yl)piperazine-1-carboxylate 189 (20 mg, 0.03 mmol) and 4.0 M HCl in dioxane (2 mL) was stirred at room temperature for 3 h. The reaction mixture was filtered, washed with dioxane, and dried under reduced pressure to give the HCl salt of the desired compound 190 (15 mg, 93%) as a yellow solid. The solid was suspended in 10 mL of aqueous ammonia, stirred for 1 h at room temperature, and extracted using chloroform (2×20 mL). The organic layer was dried and concentrated to give N$^1$-(2-(5-chloro-2,4-dimethoxy-phenyl)-7-(piperazin-1-yl)imidazo[1,2-a]pyrimidin-6-yl)ethane-1,2-diamine 190 as an off-white solid.

$^1$H NMR (400 MHz, DMSO-$d_6$): δ 8.16 (s, 1H), 7.99 (s, 1H), 6.84 (s, 1H), 5.54 (s, 1H), 4.01 (s, 3H), 3.92 (s, 3H), 3.53-3.50 (m, 4H), 2.83-2.72 (m, 6H); HPLC (Method 1) 95.0% (AUC), $t_R$=8.47 min; ESI MS m/z 432 [M+H]$^+$.

Scheme 58

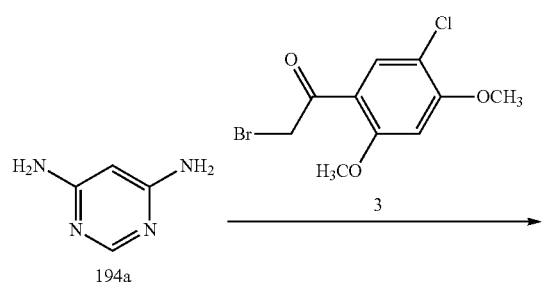

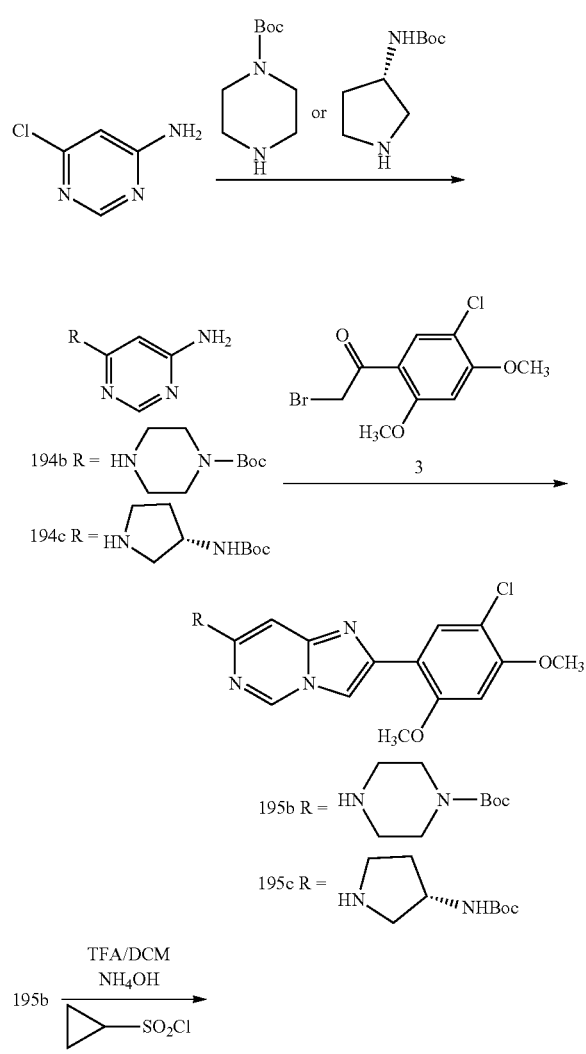

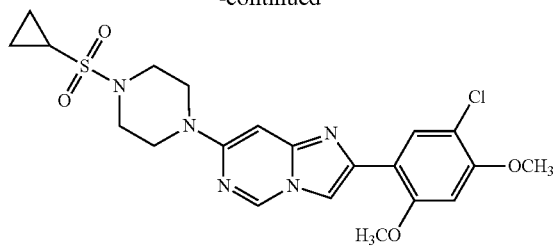

Preparation of 2-(5-chloro-2,4-dimethoxyphenyl)imidazo[1,2-c]pyrimidin-7-amine 195a (Example 51)

Compound 2-(5-chloro-2,4-dimethoxyphenyl)imidazo[1,2-c]pyrimidin-7-amine 195 was prepared in the same manner as 2-(5-chloro-2,4-dimethoxyphenyl)-7-(pyrrolidin-1-yl)-imidazo[1,2-a]pyridine 5a. Solid was basified with aqueous ammonia, washed with water, collected by filtration and dried. The product was obtained as a white solid (52 mg, 18% yield).

$^1$H NMR (300 MHz, DMSO-d$_6$): δ 8.96 (s, 1H), 8.14 (s, 1H), 7.99 (s, 1H), 6.87 (s, 1H), 6.15 (m, 2H), 4.01 (s, 3H), 3.94 (s, 3H); HPLC (Method 3) 95.12% (AUC), t$_R$=16.24 min; ESI MS m/z 305 [M+H]$^+$.

Preparation of tert-butyl 4-(6-aminopyrimidin-4-yl)piperazine-1-carboxylate 194b A mixture of 6-chloropyrimidin-4-amine (680 mg, 5.25 mmol), tert-butyl piperazine-1-carboxylate (1.17 g, 6.30 mmol) and DIPEA (2.6 mL, 16 mmol) in n-butanol (5 mL) was heated at 140° C. for 16 h. The reaction mixture was concentrated under reduced pressure and purified by column chromatography (silica gel, 10:1:0.1 DCM/methanol/ammonium hydroxide) to afford tert-butyl 4-(6-aminopyrimidin-4-yl) piperazine-1-carboxylate 194b (0.81 g, 55%) as an off-white solid.

$^1$H NMR (400 MHz, CD$_3$OD): δ 8.00 (s, 1H), 5.73 (s, 1H), 3.60-3.53 (m, 4H), 3.53-3.46 (m, 4H), 1.47 (s, 9H); ESI MS m/z 280 [M+H]$^+$.

Preparation of (S)-tert-butyl (1-(6-aminopyrimidin-4-yl)pyrrolidin-3-yl)carbamate 194c Compound (S)-tert-butyl (1-(6-aminopyrimidin-4-yl)pyrrolidin-3-yl) carbamate 194c was prepared in the same manner as tert-butyl 4-(6-aminopyrimidin-4-yl) piperazine-1-carboxylate 194b and was obtained as a light brown solid (78% yield).

$^1$H NMR (400 MHz, CD$_3$OD): δ 7.92 (s, 1H), 5.45 (s, 1H), 4.23-4.13 (m, 1H), 3.71-3.59 (m, 1H), 3.57-3.39 (m, 2H), 3.28-3.19 (m, 1H), 2.27-2.16 (m, 1H), 1.99-1.88 (m, 1H), 1.44 (s, 9H); ESI MS m/z 280 [M+H]$^+$.

Preparation of tert-butyl 4-(2-(5-chloro-2,4-dimethoxyphenyl)imidazo[1,2-c]pyrimidin-7-yl)piperazine-1-carboxylate 195b Compound tert-butyl 4-(2-(5-chloro-2,4-dimethoxyphenyl)imidazo[1,2-c]pyrimidin-7-yl)piperazine-1-carboxylate 195b was prepared in the same manner as tert-butyl (2-(1-

(2-(5-chloro-2,4-dimethoxyphenyl)imidazo[1,2-a]pyridin-7-yl)piperidin-4-yl)ethyl)carbamate 5e and was obtained as an off-white solid (51%).

$^1$H NMR (400 MHz, CDCl$_3$): δδ8.68 (s, 1H), 8.36 (s, 1H), 7.90 (s, 1H), 6.58 (s, 1H), 6.49 (s, 1H), 4.01 (s, 3H), 3.96 (s, 3H), 3.60-3.55 (m, 4H), 3.52-3.45 (m, 4H), 1.49 (s, 9H); HPLC (Method 1) 96.80% (AUC), t$_R$=11.66 min; ESI MS m/z 474 [M+H]$^+$.

Preparation of (S)-tert-butyl (1-(2-(5-chloro-2,4-dimethoxyphenyl)imidazo[1,2-c]pyrimidin-7-yl)pyrrolidin-3-yl)carbamate 195c (Example 387)

Compound (S)-tert-butyl (1-(2-(5-chloro-2,4-dimethoxyphenyl)imidazo[1,2-c]pyrimidin-7-yl)pyrrolidin-3-yl)carbamate 195c was prepared in the same manner as tert-butyl (2-(1-(2-(5-chloro-2,4-dimethoxyphenyl)imidazo[1,2-a]pyridin-7-yl)piperidin-4-yl)ethyl)carbamate 5e and was obtained as a yellow green solid (72%).

$^1$H NMR (400 MHz, CDCl$_3$): δ 8.64 (s, 1H), 8.37 (s, 1H), 7.86 (s, 1H), 6.57 (s, 1H), 6.21 (s, 1H), 4.71 (bs, 1H), 4.37 (bs, 1H), 4.01 (s, 3H), 3.95 (s, 3H), 3.78-3.72 (m, 1H), 3.60-3.47 (m, 2H), 3.40-3.33 (m, 2H), 2.36-2.26 (m, 1H), 2.03-1.94 (m, 1H), 1.46 (s, 9H). HPLC (Method 1) 94.3% (AUC), t$_R$=11.43 min; ESI MS m/z 474 [M+H]$^+$.

Preparation of 2-(5-chloro-2,4-dimethoxyphenyl)-7-(4-(cyclopropylsulfonyl)piperazin-1-yl)imidazo[1,2-c]pyrimidine: (Example 390)

Compound 2-(5-chloro-2,4-dimethoxyphenyl)-7-(4-(cyclopropylsulfonyl)piperazin-1-yl)imidazo[1,2-c]pyrimidine was prepared in the same manner as (S)-1-(2-(5-chloro-2,4-dimethoxyphenyl)imidazo[1,2-a]pyridin-7-yl)-N-((1-(cyclopropylsulfonyl)piperidin-4-yl)methyl)pyrrolidin-3-amine 240r from tert-butyl 4-(2-(5-chloro-2,4-dimethoxyphenyl)imidazo[1,2-c]pyrimidin-7-yl)piperazine-1-carboxylate 195b, and was obtained as a yellow green solid (70% yield for 2 steps).

$^1$H NMR (400 MHz, CDCl$_3$): δ 8.69 (s, 1H), 8.36 (s, 1H), 7.93 (s, 1H), 6.58 (s, 1H), 6.52 (s, 1H), 4.01 (s, 3H), 3.96 (s, 3H), 3.63 (t, J=4.8, 10.2 Hz, 4H), 3.45 (t, J=5.2, 10 Hz, 4H), 2.32-2.24 (m, 1H), 1.24-1.18 (m, 2H), 1.04-0.97 (m, 2H). HPLC (Method 1) 98.9% (AUC), t$_R$=10.99 min: ESI MS m/z 478 [M+H]$^+$.

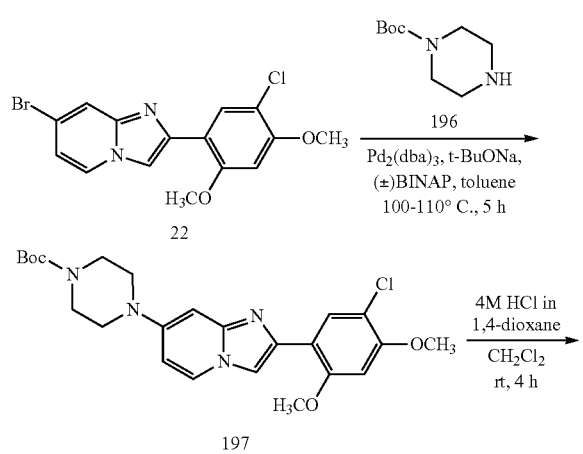

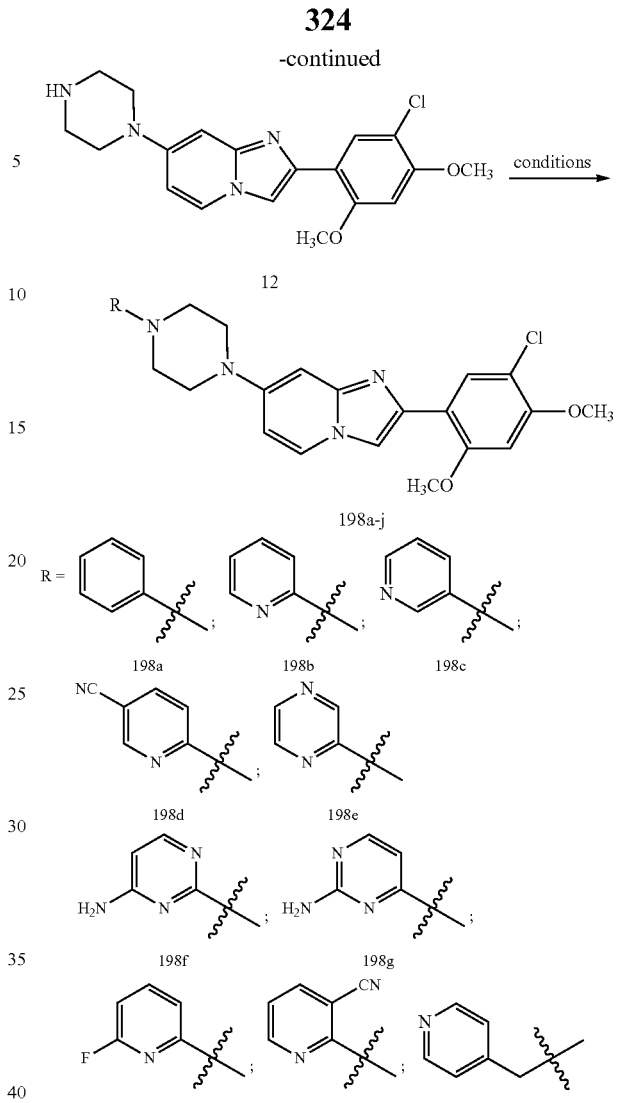

Preparation of tert-butyl 4-(2-(5-chloro-2,4-dimethoxyphenyl)imidazo[1,2-a]pyridin-7-yl)piperazine-1-carboxylate 197

A suspension of 7-bromo-2-(5-chloro-2,4-dimethoxyphenyl)imidazo[1,2-a]pyridine 22 (5.00 g, 13.6 mmol), tert-butyl piperazine-1-carboxylate 196 (3.80 g, 20.4 mmol), (±) BINAP (850 mg, 1.37 mmol) and t-BuONa (4.00 g, 41.6 mmol) in toluene (100 mL) was degassed with argon for 15 min. Then this mixture was charged with Pd$_2$(dba)$_3$ (650 mg, 0.71 mmol) and again degassed with argon for another 5 min. The resulting reaction mixture was stirred at 100-110° C. for 5 h in a sealed tube. The reaction mixture was cooled, filtered through a pad of celite and evaporated to dryness. The residue obtained was purified by combi-flash companion (silica gel, CH$_3$OH/CH$_2$Cl$_2$) to provide tert-butyl 4-(2-(5-chloro-2,4-dimethoxyphenyl)imidazo-[1,2-a]pyridin-7-yl)piperazine-1-carboxylate 197 (5.40 g, 84%) as a brown solid.

$^1$H NMR (400 MHz, CDCl$_3$): δ 8.37 (s, 1H), 7.91 (d, J=7.5 Hz, 1H), 7.87 (s, 1H), 6.85 (s, 1H), 6.58 (s, 1H), 6.56 (dd, J=2.2, 7.5 Hz, 1H), 4.00 (s, 3H), 3.95 (s, 3H), 3.61-3.58 (m, 4H), 3.22-3.20 (m, 4H), 1.49 (s, 9H); ESI+APCI MS m/z 473 [M+H]$^+$.

Preparation of 2-(5-chloro-2,4-dimethoxyphenyl)-7-(piperazin-1-yl)imidazo[1,2-a]pyridine 12

A solution of tert-butyl 4-(2-(5-chloro-2,4-dimethoxyphenyl)imidazo[1,2-a]pyridin-7-yl)piperazine-1-carboxylate 7 (5.40 g, 11.4 mmol) in $CH_2Cl_2$ (125 mL) was charged with 4.0 M HCl in 1,4-dioxane (25 mL) and stirred at room temperature for 4 h. The reaction mixture was filtered and the solid obtained was washed with $CH_2Cl_2$. The solid was then suspended in water (55 mL), basified with saturated sodium bicarbonate solution (55 mL), stirred for 1 h at room temperature and filtered to provide 2-(5-chloro-2,4-dimethoxyphenyl)-7-(piperazin-1-yl)-imidazo[1,2-a]pyridine 12 (4.0 g, 93%) as an brown solid.

$^1$H NMR (400 MHz, DMSO-$d_6$): δ 8.28 (d, J=7.2 Hz, 1H), 8.17 (s, 1H), 8.00 (s, 1H), 6.86 (s, 1H), 6.78 (d, J=7.0 Hz, 1H), 6.62 (s, 1H), 4.01 (s, 3H), 3.93 (s, 3H), 3.12 (br s, 4H), 2.83 (br s, 4H); ESI+APCI MS m/z 373 [M+H]$^+$.

Preparation of 2-(5-chloro-2,4-dimethoxyphenyl-7-(4-phenylpiperazin-1-yl)-imidazo[1,2-a]pyridine 198a (Example 282)

A solution of 2-(5-chloro-2,4-dimethoxyphenyl)-7-(piperazin-1-yl)imidazo-[1,2-a]pyridine 12 (200 mg, 0.54 mmol), phenylboronic acid (132 mg, 1.08 mmol) and pyridine (0.10 mL, 1.2 mmol) in $CH_2Cl_2$ (10 mL) was degassed with oxygen for 15 min. Then this mixture was charged with $Cu(OAc)_2$ (98 mg, 0.54 mmol) and again degassed with oxygen for another 5 min. The resulting reaction mixture was stirred at room temperature for 24 h and evaporated to dryness. The residue obtained was purified by combi-flash companion (silica gel, $CH_3OH/CH_2Cl_2$) to provide 2-(5-chloro-2,4-dimethoxyphenyl)-7-(4-phenylpiperazin-1-yl)-imidazo[1,2-a]pyridine 198a (25 mg, 10%) as an off-white solid.

$^1$H NMR (400 MHz, CDCl$_3$): δ 8.29 (s, 1H), 7.95 (d, J=7.3 Hz, 1H), 7.82 (s, 1H), 7.31 (t, J=7.5 Hz, 2H), 7.04 (s, 1H), 6.98 (d, J=8.0 Hz, 2H), 6.92 (t, J=7.2 Hz, 1H), 6.67 (d, J=6.6 Hz, 1H), 6.56 (s, 1H), 4.01 (s, 3H), 3.95 (s, 3H), 3.45-3.41 (m, 4H), 3.36-3.33 (m, 4H); HPLC (Method 6) 92.0% (AUC), $t_R$=13.88 min.; ESI+APCI MS m/z 449 [M+H].

Preparation of 2-(5-chloro-2,4-dimethoxyphenyl)-7-(4-(pyridin-2-yl)piperazin-1-yl)-imidazo[1,2-a]pyridine 198b (Example 276)

A suspension of 2-(5-chloro-2,4-dimethoxyphenyl)-7-(piperazin-1-yl)imidazo[1,2-a]-pyridine 12 (200 mg, 0.54 mmol) and cesium carbonate (350 mg, 1.07 mmol) in DMF (5 mL) was charged with 2-fluoropyridine (80 mg, 0.82 mmol) and the resulting reaction mixture was stirred at 150-160° C. for 24 h in a sealed tube. The reaction mixture was then cooled and evaporated to dryness. The residue was partitioned between ethyl acetate and water and the layers were separated. The organic layer was washed with water and brine; dried over sodium sulphate, filtered and concentrated. The crude obtained was purified by combi-flash companion (silica gel, $CH_3OH/CH_2Cl_2$) to provide 2-(5-chloro-2,4-dimethoxyphenyl)-7-(4-(pyridin-2-yl)piperazin-1-yl)imidazo[1,2-a]pyridine 198b (12 mg, 5%) as an off-white solid.

$^1$H NMR (400 MHz, DMSO-$d_6$): δ 8.34 (d, J=7.5 Hz, 1H), 8.18 (s, 1H), 8.15 (dd, J=1.4, 4.8 Hz, 1H), 8.03 (s, 1H), 7.59-7.54 (m, 1H), 6.91 (d, J=8.6 Hz, 1H), 6.88-6.85 (m, 2H), 6.72 (d, J=2.0 Hz, 1H), 6.69-6.65 (m, 1H), 4.01 (s, 3H), 3.94 (s, 3H), 3.67-3.63 (m, 4H), 3.36-3.32 (m, 4H); ESI+APCI MS m/z 450 [M+H]$^+$.

Preparation of 2-(5-chloro-2,4-dimethoxyphenyl)-7-(4-(pyridin-3-yl)piperazin-1-yl)imidazo[1,2-a]pyridine 198c (Example 296)

A suspension of 2-(5-chloro-2,4-dimethoxyphenyl)-7-(piperazin-1-yl)imidazo[1,2-a]-pyridine 12 (100 mg, 0.27 mmol), 3-bromopyridine (64 mg, 0.41 mmol), (±)BINAP (17 mg, 0.027 mmol) and t-BuONa (78 mg, 0.81 mmol) in DME (2 mL) was degassed with argon for 15 min. Subsequently the mixture was charged with Pd$_2$(dba)$_3$ (13 mg, 0.014 mmol) and again degassed with argon for another 5 min. The resulting reaction mixture was stirred at 100-110° C. for 5 h in a sealed tube. The reaction mixture was cooled, filtered through a pad of celite and evaporated to dryness. The residue obtained was purified by combi-flash companion (silica gel, $CH_3OH/CH_2Cl_2$) to provide 2-(5-chloro-2,4-dimethoxyphenyl)-7-(4-(pyridin-3-yl)-piperazin-1-yl)imidazo[1,2-a]pyridine 198c (60 mg, 50%) as an off-white solid.

$^1$H NMR (400 MHz, DMSO-$d_6$): δ 8.38 (d, J=2.8 Hz, 1H), 8.35 (d, J=7.5 Hz, 1H), 8.18 (s, 1H), 8.04-8.03 (m, 2H), 7.41 (dd, J=1.7, 8.4 Hz, 1H), 7.26-7.23 (m, 1H), 6.89 (d, J=2.2 Hz, 1H), 6.87 (s, 1H), 6.74 (d, J=1.8 Hz, 1H), 4.01 (s, 3H), 3.94 (s, 3H), 3.40-3.36 (m, 8H); HPLC (Method 6) 95.2% (AUC), $t_R$=11.65 min.; ESI+APCI MS m/z 450 [M+H]$^+$.

Preparation of 6-(4-(2-(5-chloro-2,4-dimethoxyphenyl)imidazo[1,2-a]pyridin-7-yl)-piperazin-1-yl)nicotinonitrile 198d (Example 293)

A solution of 2-(5-chloro-2,4-dimethoxyphenyl)-7-(piperazin-1-yl)imidazo[1,2-a]pyridine 12 (150 mg, 0.40 mmol) and N,N-diisopropylethylamine (0.2 mL, 1.2 mmol) in DMF (3 mL) was charged with 6-chloronicotinonitrile (111 mg, 0.80 mmol). The reaction mixture was stirred at 110-120° C. for 16 h in a sealed tube. The reaction mixture was cooled to room temperature, suspended in water and stirred for 1 h. The precipitate was collected by filtration, the solid obtained was washed with water, dried under reduced pressure, and purified by combi-flash companion (silica gel, $CH_3OH/CH_2Cl_2$) to provide 6-(4-(2-(5-chloro-2,4-dimethoxyphenyl)imidazo[1,2-a]pyridin-7-yl)piperazin-1-yl)nicotinonitrile 198d (35 mg, 18%) as an off-white solid.

$^1$H NMR (400 MHz, DMSO-$d_6$): δ 8.52 (d, J=2.0 Hz, 1H), 8.34 (d, J=7.6 Hz, 1H), 8.17 (s, 1H), 8.03 (s, 1H), 7.88 (dd, J=2.4, 9.2 Hz, 1H), 7.01 (d, J=9.2 Hz, 1H), 6.87 (s, 1H), 6.85 (d, J=2.4 Hz, 1H), 6.71 (d, J=1.6 Hz, 1H), 4.01 (s, 3H), 3.93 (s, 3H), 3.84 (t, J=5.0 Hz, 4H), 3.35 (t, J=5.2 Hz, 4H); HPLC (Method 6) 96.3% (AUC), $t_R$=13.70 min.; ESI+APCI MS m/z 475 [M+H]$^+$.

Preparation of 2-(5-chloro-2,4-dimethoxyphenyl)-7-(4-(pyrazin-2-yl)piperazin-1-yl)imidazo[1,2-a]pyridine 198e (Example 285)

Compound 2-(5-chloro-2,4-dimethoxyphenyl)-7-(4-(pyrazin-2-yl)piperazin-1-yl)imidazo[1,2-a]pyridine 198e was prepared in the same manner as 6-(4-(2-(5-chloro-2,4-dimethoxyphenyl)imidazo[1,2-a]pyridin-7-yl)piperazin-1-yl)nicotinonitrile 198d and was obtained as an off-white solid (21% yield) using 2-(5-chloro-2,4-dimethoxyphenyl)-7-(piperazin-1-yl) imidazo[1,2-a]pyridine 12 (100 mg, 0.27 mmol), 2-chloropyrazine (62 mg, 0.54 mmol) and N,N-diisopropylethylamine (0.2 mL, 1.2 mmol) in DMF (2 mL).

$^1$H NMR (400 MHz, DMSO-d$_6$): δ 8.40 (d, J=1.2 Hz, 1H), 8.34 (d, J=7.5 Hz, 1H), 8.18 (s, 1H), 8.13-8.11 (m, 1H), 8.04 (s, 1H), 7.87 (d, J=2.6 Hz, 1H), 6.89-6.86 (m, 2H), 6.73 (d, J=1.9 Hz, 1H), 4.01 (s, 3H), 3.94 (s, 3H), 3.76-3.73 (m, 4H), 3.39-3.35 (m, 4H); HPLC (Method 6) 95.9% (AUC), t$_R$=13.00 min.; ESI+APCI MS m/z 451 [M+H]$^+$.

Preparation of 2-(4-(2-(5-chloro-2,4-dimethoxyphenyl)imidazo[1,2-a]pyridin-7-yl)piperazin-1-yl)-pyrimidin-4-amine 198f (Example 286)

Compound 2-(4-(2-(5-chloro-2,4-dimethoxyphenyl)imidazo[1,2-a]pyridin-7-yl)-piperazin-1-yl)pyrimidin-4-amine 198f was prepared in the same manner as 6-(4-(2-(5-chloro-2,4-dimethoxyphenyl)imidazo[1,2-a]pyridin-7-yl)piperazin-1-yl)nicotinonitrile 198d and was obtained as an off-white solid (24% yield) using 2-(5-chloro-2,4-dimethoxyphenyl)-7-(piperazin-1-yl)imidazo[1,2-a]pyridine 12 (100 mg, 0.27 mmol), 2-chloropyrimidin-4-amine (70 mg, 0.54 mmol) and N,N-diisopropylethylamine (0.2 mL, 1.2 mmol) in DMF (2 mL).

$^1$H NMR (400 MHz, DMSO-d$_6$): δ 8.39 (d, J=7.6 Hz, 1H), 8.11 (s, 1H), 8.09 (s, 1H), 7.78 (d, J=5.6 Hz, 1H), 6.98 (d, J=7.3 Hz, 1H), 6.90 (s, 1H), 6.71 (s, 1H), 6.55 (br s, 2H), 5.79 (d, J=5.7 Hz, 1H), 4.02 (s, 3H), 3.95 (s, 3H), 3.82-3.79 (m, 4H), 3.36-3.32 (m, 4H); HPLC (Method 6) 96.5% (AUC), t$_R$=11.82 min.; ESI+APCI MS m z 466 [M+H]$^+$.

Preparation of 4-(4-(2-(5-chloro-2,4-dimethoxyphenyl)imidazo[1,2-a]pyridin-7-yl)-piperazin-1-yl)pyrimidin-2-amine 1982 (Example 279)

Compound 4-(4-(2-(5-chloro-2,4-dimethoxyphenyl)imidazo[1,2-a]pyridin-7-yl)-piperazin-1-yl)pyrimidin-2-amine 198g was prepared in the same manner as 6-(4-(2-(5-chloro-2,4-dimethoxyphenyl)imidazo[1,2-a]pyridin-7-yl)piperazin-1-yl)nicotinonitrile 198d and was obtained as an off-white solid (20% yield) using 2-(5-chloro-2,4-dimethoxyphenyl)-7-(piperazin-1-yl) imidazo[1,2-a]pyridine 12 (100 mg, 0.27 mmol), 4-chloropyrimidin-2-amine (70 mg, 0.54 mmol) and N,N-diisopropylethylamine (0.2 mL, 1.2 mmol) in DMF (2 mL).

$^1$H NMR (300 MHz, DMSO-d$_6$): δ 8.34 (d, J=10.0 Hz, 1H), 8.17 (s, 1H), 8.03 (s, 1H), 7.80 (d, J=8.0 Hz, 1H), 6.87-6.83 (m, 2H), 6.72 (s, 1H), 6.12-6.07 (m, 3H), 4.01 (s, 3H), 3.94 (s, 3H), 3.70 (br s, 4H), 3.31 (br s, 4H); HPLC (Method 6) 96.9% (AUC), t$_R$=11.75 min.; ESI+APCI MS m/z 466 [M+H]$^+$.

Preparation of 2-(5-chloro-2,4-dimethoxyphenyl)-7-(4-(6-fluoropyridin-2-yl)piperazin-1-yl)imidazo[1,2-a]pyridine 198h (Example 281)

Compound 2-(5-chloro-2,4-dimethoxyphenyl)-7-(4-(6-fluoropyridin-2-yl)piperazin-1-yl)imidazo[1,2-a]pyridine 198h was prepared in the same manner as 6-(4-(2-(5-chloro-2,4-dimethoxyphenyl)imidazo[1,2-a]pyridin-7-yl)piperazin-1-yl)nicotinonitrile 198d and was obtained as an off-white solid (51% yield) using 2-(5-chloro-2,4-dimethoxyphenyl)-7-(piperazin-1-yl)imidazo[1,2-a]pyridine 12 (100 mg, 0.27 mmol), 2,6-difluoropyridine (62 mg, 0.54 mmol) and N,N-diisopropylethylamine (0.2 mL, 1.2 mmol) in DMF (2 mL).

$^1$H NMR (400 MHz, DMSO-d$_6$): δ 8.34 (d, J=7.5 Hz, 1H), 8.18 (s, 1H), 8.04 (s, 1H), 7.70 (q, J=8.2 Hz, 1H), 6.87 (s, 1H), 6.85 (d, J=2.3 Hz, 1H), 6.77 (dd, J=2.5, 8.2 Hz, 1H), 6.72 (d, 1.8 Hz, 1H), 6.31 (dd, J=2.7, 7.7 Hz, 1H), 4.01 (s, 3H), 3.94 (s, 3H), 3.68-3.64 (m, 4H), 3.36-3.33 (m, 4H); HPLC (Method 1) 95.7% (AUC), t$_R$=14.19 min.; ESI+APCI MS m/z 468 [M+H]$^+$.

Preparation of 2-(4-(2-(5-chloro-2,4-dimethoxyphenyl)imidazo[1,2-a]pyridin-7-yl)-piperazin-1-yl)nicotinonitrile 198i (Example 283)

A solution of 2-(5-chloro-2,4-dimethoxyphenyl)-7-(piperazin-1-yl) imidazo[1,2-a]pyridine 12 (100 mg, 0.27 mmol) and N-methylmorpholine (0.2 mL, 1.8 mmol) in DMSO (2 mL) was charged with 2-chloronicotinonitrile (75 mg, 0.54 mmol). The reaction mixture was stirred at 110-120° C. for 16 h in a sealed tube. The reaction mixture was cooled and suspended in water and stirred for 1 h. The precipitate was collected by filtration, the solid obtained was washed with water, dried under reduced pressure, and purified by combi-flash companion (silica gel, CH$_3$OH/CH$_2$Cl$_2$) to provide 2-(4-(2-(5-chloro-2,4-dimethoxyphenyl)-imidazo[1,2-a]pyridin-7-yl)piperazin-1-yl)nicotinonitrile 9i (45 mg, 35%) as a brown solid.

$^1$H NMR (400 MHz, DMSO-d$_6$): δ 8.45 (dd, J=1.8, 4.7 Hz, 1H), 8.34 (d, J=7.5 Hz, 1H), 8.18 (s, 1H), 8.11 (dd, J=5.7, 7.6 Hz, 1H), 8.03 (s, 1H), 6.99-6.94 (m, 1H), 6.87 (s, 1H), 6.85 (d, J=2.3 Hz, 1H), 6.72 (s, 1H), 4.01 (s, 3H), 3.94 (s, 3H), 3.82-3.78 (m, 4H), 3.43-3.39 (m, 4H); HPLC (Method 6) 94.0% (AUC), t$_R$=13.78 min.; ESI+APCI MS m/z 475 [M+H]$^+$.

Preparation of 2-(5-chloro-2,4-dimethoxyphenyl)-7-(4-(pyridin-4-ylmethyl)piperazin-1-yl)imidazo[1,2-a]pyridine 198i (Example 292)

To a solution of compound 2-(5-chloro-2,4-dimethoxyphenyl)-7-(piperazin-1-yl)-imidazo[1,2-a]pyridine 12 (100 mg, 0.27 mmol) and 4-pyridinecarboxaldehyde (86 mg, 0.80 mmol) in CH$_2$Cl$_2$ was added acetic acid (0.1 mL) and the resulting mixture was stirred for 1 h. Sodium cyanoborohydride (84 mg, 1.3 mmol) was added and the reaction mixture was stirred at room temperature overnight. The solvent was removed under reduced pressure, the residue was basified with aqueous sodium bicarbonate solution and the crude material was purified by combi-flash companion (silica gel, CH$_3$OH/CH$_2$Cl$_2$) to afford 2-(5-chloro-2,4-dimethoxy-phenyl)-7-(4-(pyridin-4-ylmethyl)piperazin-1-yl)imidazo[1,2-a]pyridine 198j (25 mg, 20%) as an off-white solid.

$^1$H NMR (400 MHz, DMSO-d$_6$): δ 8.53 (d, I=1.2 Hz, 2H), 8.31 (d, J=7.2 Hz, 1H), 8.16 (s, 1H), 8.01 (s, 1H), 7.34 (dd, J=6.0, 19.6 Hz, 2H), 6.86 (s, 1H), 6.80 (dd, J=2.4, 7.6 Hz, 1H), 6.65 (d, J=2.0 Hz, 1H), 4.00 (s, 3H), 3.93 (s, 3H), 3.58 (s, 2H), 3.25 (t, J=4.8 Hz, 4H), 2.54 (t, J=4.4 Hz, 4H); HPLC (Method 6) 96.2% (AUC), t$_R$=11.05 min.; ESI+APCI MS m/z 464 [M+H]$^+$.

Scheme 60

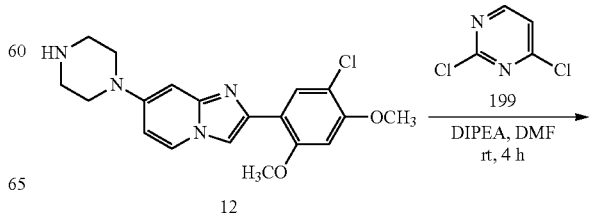

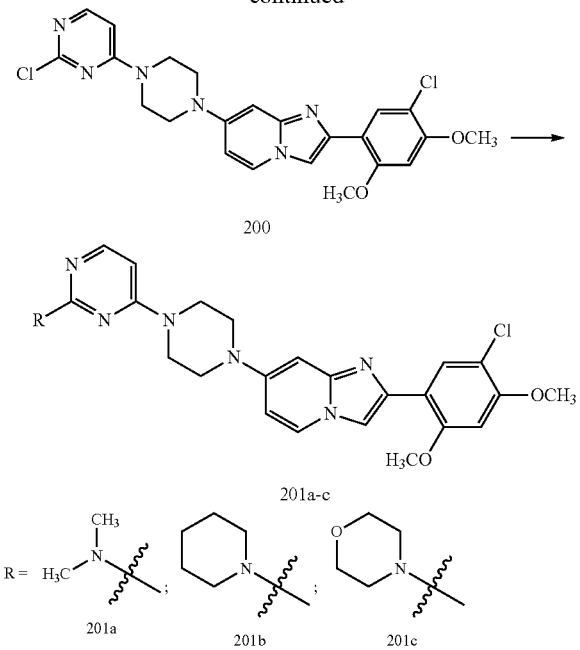

Preparation of 2-(5-chloro-2,4-dimethoxyphenyl)-7-(4-(2-chloropyrimidin-4-yl)piperazin-1-yl)imidazo[1,2-a]pyridine 200

A solution of 2-(5-chloro-2,4-dimethoxyphenyl)-7-(piperazin-1-yl)imidazo-[1,2-a]pyridine 12 (1.00 g, 2.68 mmol) and N,N-diisopropylethylamine (0.7 mL, 4.02 mmol) in DMF (10 mL) was charged with 2,4-dichloropyrimidine 199 (400 mg, 2.69 mmol) and the reaction mixture was stirred at room temperature for 4 h under nitrogen atmosphere. The reaction mixture was diluted with MTBE and stirred for 1 h. The precipitate was filtered, dried under reduced pressure and purified by combi-flash companion (silica gel, $CH_3OH/CH_2Cl_2$) to provide 2-(5-chloro-2,4-dimethoxyphenyl)-7-(4-(2-chloropyrimidin-4-yl)piperazin-1-yl)imidazo[1,2-a]pyridine 200 (600 mg, 46%) as a brown solid.

$^1$H NMR (400 MHz, DMSO-$d_6$): δ 8.34 (d, J=7.5 Hz, 1H), 8.20 (s, 1H), 8.10 (d, J=6.1 Hz, 1H), 8.04 (s, 1H), 6.89 (d, J=6.2 Hz, 1H), 6.87 (s, 1H), 6.83 (dd, J=2.2, 7.6 Hz, 1H), 6.72 (d, J=1.6 Hz, 1H), 4.02 (s, 3H), 3.94 (s, 3H), 3.79 (br s, 4H), 3.36-3.33 (m, 4H); ESI+APCI MS m/z 485 [M+H]$^+$.

Preparation of 4-(4-(2-(5-chloro-2,4-dimethoxyphenyl)imidazo[1,2-a]pyridin-7-yl)-piperazin-1-yl)-N,N-dimethylpyrimidin-2-amine 201a (Example 297)

A solution of 2-(5-chloro-2,4-dimethoxyphenyl)-7-(4-(2-chloropyrimidin-4-yl)-piperazin-1-yl)imidazo[1,2-a]pyridine 200 (50 mg, 0.10 mmol) in 2.0 M N,N-dimethylamine in THF (2.0 mL) was stirred at 60-70° C. in a sealed tube for 18 h. The reaction mixture was cooled to room temperature and diluted with water. The mixture was stirred at room temperature for 30 min and the precipitate was collected by filtration. The solid was further purified by crashing from DMF with water to provide 4-(4-(2-(5-chloro-2,4-dimethoxyphenyl)-imidazo[1,2-a]pyridin-7-yl)piperazin-1-yl)-N,N-dimethylpyrimidin-2-amine 201a (13 mg, 25%) as an off-white solid.

$^1$H NMR (300 MHz, DMSO-$d_6$): δ 8.34 (d, J=10.0 Hz, 1H), 8.18 (s, 1H), 8.03 (s, 1H), 7.90 (d, J=7.7 Hz, 1H), 6.88-6.84 (m, 2H), 6.71 (s, 1H), 6.12 (d, J=7.8 Hz, 1H), 4.01 (s, 3H), 3.94 (s, 3H), 3.72 (br s, 4H), 3.31 (br s, 4H), 3.06 (s, 6H); HPLC (Method 6) >99% (AUC), $t_R$=12.05 min.; ESI+APCI MS m/z 494 [M+H]$^+$.

Preparation of 2-(5-chloro-2,4-dimethoxyphenyl-7-(4-(2-(piperidin-1-yl)pyrimidin-4-yl)piperazin-1-yl) imidazo[1,2-a]pyridine 201b (Example 295)

A suspension of 2-(5-chloro-2,4-dimethoxyphenyl)-7-(4-(2-chloropyrimidin-4-yl)-piperazin-1-yl)imidazo[1,2-a]pyridine 200 (50 mg, 0.10 mmol) in piperidine (0.5 mL) was subjected to microwave irradiation at 100° C. for 30 min. The reaction mixture was cooled to room temperature, diluted with water and stirred for 30 min. The precipitate was collected by filtration to provide 2-(5-chloro-2,4-dimethoxyphenyl)-7-(4-(2-(piperidin-1-yl)pyrimidin-4-yl)piperazin-1-yl)imidazo[1,2-a]pyridine 201b (30 mg, 54%) as an off-white solid after drying under reduced pressure.

$^1$H NMR (400 MHz, DMSO-$d_6$): δ 8.34 (d, J=7.5 Hz, 1H), 8.17 (s, 1H), 8.03 (s, 1H), 7.90 (d, J=5.9 Hz, 1H), 6.87 (s, 1H), 6.85 (dd, J=2.2, 7.6 Hz, 1H), 6.71 (s, 1H), 6.10 (d, J=5.9 Hz, 1H), 4.01 (s, 3H), 3.93 (s, 3H), 3.70-3.66 (m, 8H), 3.31 (br s, 4H), 1.61-1.55 (m, 2H), 1.49-1.46 (m, 4H); HPLC (Method 7) 91.4% (AUC), $t_R$=12.54 min.; ESI+APCI MS m/z 534 [M+H]$^+$.

Preparation of 4-(4-(4-(2-(5-chloro-2,4-dimethoxyphenyl)imidazo[1,2-a]pyridin-7-yl)-piperazin-1-yl) pyrimidin-2-yl)morpholine 201c (Example 294)

A suspension of 2-(5-chloro-2,4-dimethoxyphenyl)-7-(4-(2-chloropyrimidin-4-yl)-piperazin-1-yl)imidazo[1,2-a] pyridine 200 (50 mg, 0.10 mmol) in morpholine (0.5 mL) was subjected to microwave irradiation at 100° C. for 30 min. The reaction mixture was cooled to room temperature, diluted with water and stirred for 30 min. The precipitate was collected by filtration, washed with water and dried under reduced pressure to afford 4-(4-(4-(2-(5-chloro-2,4-dimethoxyphenyl)imidazo[1,2-a]pyridin-7-yl)piperazin-1-yl)pyrimidin-2-yl)morpholine 201c (45 mg, 81%) as a yellow solid.

$^1$H NMR (400 MHz, DMSO-$d_6$): δ 8.34 (d, J=7.6 Hz, 1H), 8.18 (s, 1H), 8.03 (s, 1H), 7.93 (d, J=5.9 Hz, 1H), 6.87 (s, 1H), 6.84 (dd, J=2.2, 7.6 Hz, 1H), 6.71 (d, J=1.8 Hz, 1H), 6.20 (d, J=6.0 Hz, 1H), 4.01 (s, 3H), 3.93 (s, 3H), 3.72 (br s, 4H), 3.63 (s, 8H), 3.31 (br s, 4H); HPLC (Method 7) 93.5% (AUC), $t_R$=11.93 min.; ESI+APCI MS m/z 536 [M+H]$^+$.

Scheme 61

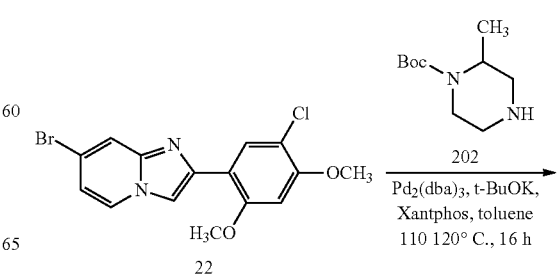

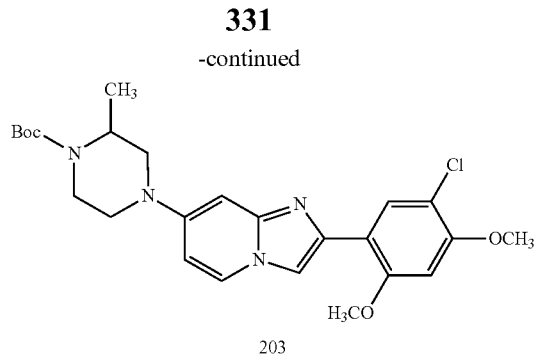

203

Preparation of tert-butyl 4-(2-(5-chloro-2,4-dimethoxyphenyl)imidazo[1,2-a]pyridin-7-yl)-2-methylpiperazine-1-carboxylate 203 (Example 275)

A suspension of 7-bromo-2-(5-chloro-2,4-dimethoxyphenyl) imidazo[1,2-a]pyridine 22 (200 mg, 0.544 mmol), tert-butyl 2-methylpiperazine-1-carboxylate 202 (218 mg, 1.09 mmol), Xanthphos (34 mg, 0.059 mmol) and t-BuOK (181 mg, 1.62 mmol) in toluene (10 mL) was degassed with argon for 15 min. Subsequently the mixture was charged with Pd$_2$(dba)$_3$ (24 mg, 0.026 mmol) and again degassed with argon for another 5 min. The resulting reaction mixture was heated at 100-110° C. for 16 h. The reaction mixture was cooled, filtered through a pad of celite and evaporated to dryness. The residue obtained was purified by combi-flash companion (silica gel, CH$_2$OH/CH$_2$Cl$_2$) to provide tert-butyl 4-(2-(5-chloro-2,4-dimethoxyphenyl)-imidazo[1,2-a]pyridin-7-yl)-2-methylpiperazine-1-carboxylate 203 (90 mg, 34%) as an off-white solid.

$^1$H NMR (400 MHz, DMSO-d$_6$): δ 8.32 (d, J=7.6 Hz, 1H), 8.16 (s, 1H), 8.02 (s, 1H), 6.86 (s, 1H), 6.78 (dd, J=2.4, 7.6 Hz, 1H), 6.66 (d, J=1.6 Hz, 1H), 4.22-4.20 (m, 1H), 4.00 (s, 3H), 3.93 (s, 3H), 3.83-3.79 (m, 1H), 3.70-3.60 (m, 2H), 3.22-3.16 (m, 1H), 2.97-2.91 (m, 1H), 2.76-2.70 (m, 1H), 1.42 (s, 9H), 1.18 (d, J=6.4 Hz, 3H); HPLC (Method 6) 97.0% (AUC), t$_R$=14.23 min.; ESI+APCI MS m/z 487 [M+H]$^+$.

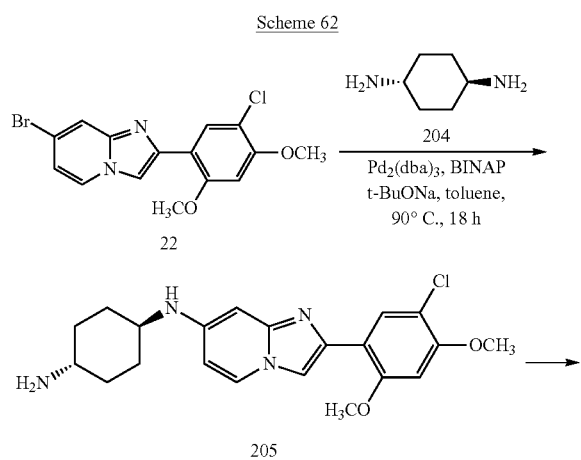

Scheme 62

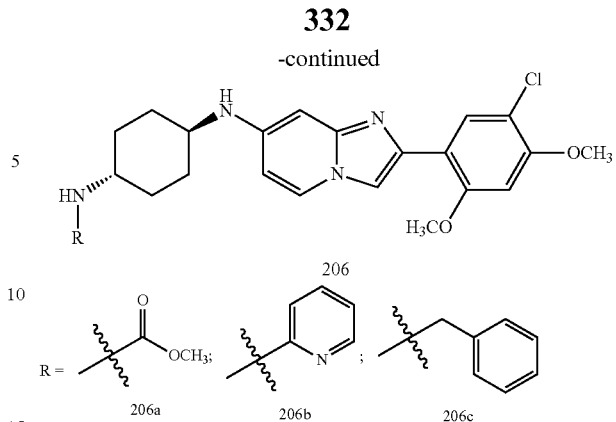

Preparation of trans-N$^1$-(2-(5-chloro-2,4-dimethoxyphenyl)imidazo[1,2-a]pyridin-7-yl)-cyclohexane-1,4-diamine 205

A mixture of 7-bromo-2-(5-chloro-2,4-dimethoxyphenyl) imidazo[1,2-a]pyridine 22 (1.00 g, 2.73 mmol), trans-cyclohexane-1,4-diamine 204 (311 mg, 2.73 mmol), Pd$_2$(dba)$_3$ (125 mg, 0.13 mmol), BINAP (170 mg, 0.27 mmol), and sodium tert-butoxide (786 mg, 8.19 mmol) were taken up in toluene (20 mL) and degassed with argon. The reaction mixture was heated at 100° C. for 18 h. The reaction mixture was cooled to room temperature, diluted with CH$_2$Cl$_2$ (30 mL) and filtered through a pad of celite. The filtrate was concentrated under reduced pressure and the residue obtained was purified by silica gel chromatography (CH$_3$OH/CH$_2$Cl$_2$) to obtain trans-N$^1$-(2-(5-chloro-2,4-dimethoxyphenyl)imidazo[1,2-a]pyridin-7-yl)cyclohexane-1,4-diamine 205 (500 mg, 46%) as a green solid.

$^1$H NMR (400 MHz, DMSO-d$_6$): δ 8.14 (s, 1H), 8.10 (d, J=7.6 Hz, 1H), 7.86 (s, 1H), 6.84 (s, 1H), 6.33 (dd, J=2.0, 7.2 Hz, 1H), 6.19 (s, 1H), 5.97 (d, J=7.6 Hz, 1H), 3.99 (s, 3H), 3.92 (s, 3H), 3.15-3.12 (m, 1H), 2.58-2.55 (m, 1H), 2.01-1.99 (m, 2H), 1.81-1.79 (m, 2H), 1.23-1.16 (m, 4H); ESI+APCI MS m/z 401 [M+H]$^+$.

Preparation of (methyl-4-((2-(5-chloro-2,4-dimethoxyphenyl)imidazo[1,2-a]pyridin-7-yl)amino)-trans-cyclohexyl)carbamate 206a (Example 277)

A mixture of N$^1$-(2-(5-chloro-2,4-dimethoxyphenyl)imidazo[1,2-a]pyridin-7-yl)-N$^4$-(pyridin-2-yl)-trans-cyclohexane-1,4-diamine 205 (250 mg, 0.62 mmol), triethylamine (260 µL, 1.86 mmol) and methyl chloroformate (71 µL, 0.93 mmol) in CH$_2$Cl$_2$ (20 mL) was stirred at room temperature for 16 h under nitrogen atmosphere. The reaction mixture was quenched with water and extracted with CH$_2$Cl$_2$ (2×20 mL). The combined organic layers were dried over sodium sulfate, filtered and concentrated under reduced pressure: the residue was purified by combi-flash companion (silica gel, 10:1 CH$_3$OH/CH$_2$Cl$_2$) to afford (methyl (4-((2-(5-chloro-2,4-dimethoxyphenyl)imidazo[1,2-a]pyridin-7-yl)-trans-amino)cyclohexyl)carbamate 206a (100 mg, 35%) as an off-white solid.

$^1$H NMR (400 MHz, DMSO-d$_6$): δ 8.13 (s, 1H), 8.11 (d, J=7.2 Hz, 1H), 7.87 (s, 1H), 7.10 (d, J=6.8 Hz, 1H), 6.84 (s, 1H), 6.35 (dd, J=2.4, 7.6 Hz, 1H), 6.21 (s, 1H), 6.02 (d, J=7.2 Hz, 1H), 3.99 (s, 3H), 3.92 (s, 3H), 3.51 (s, 3H), 3.18-3.16 (m, 1H), 2.04 (d, J=11.2 Hz, 2H), 1.85 (d, J=10.0

Hz, 2H), 1.39-1.30 (m, 2H), 1.25-1.16 (m, 2H); HPLC (Method 8) >99% (AUC), $t_R$=13.19 min.; ESI+APCI MS m/z 459 [M+H]$^+$.

Preparation of N$^1$-(2-(5-chloro-2,4-dimethoxyphenyl)imidazo[1,2-a]pyridin-7-yl)-N$^4$-(pyridin-2-yl)-trans-cyclohexane-1,4-diamine 206b (Example 287)

A mixture of N$^1$-(2-(5-chloro-2,4-dimethoxyphenyl)imidazo[1,2-a]pyridin-7-yl)-N$^4$-(pyridin-2-yl)-trans-cyclohexane-1,4-diamine 205 (100 mg, 0.25 mmol), 2-bromo pyridine (44 mg, 0.28 mmol), Pd$_2$(dba)$_3$ (11 mg, 0.013 mmol), BINAP (15 mg, 0.025 mmol), and sodium tert-butoxide (72 mg, 0.75 mmol) were taken up in toluene (5.0 mL) and degassed with argon. The reaction mixture was heated at 100° C. for 18 h. The reaction mixture was cooled to room temperature, diluted with CH$_2$Cl$_2$ (10 mL), and filtered through a pad of celite. The filtrate was concentrated under reduced pressure and the residue was purified by combi-flash companion (silica gel, CH$_3$OH/CH$_2$Cl$_2$) to afford N$^1$-(2-(5-chloro-2,4-dimethoxyphenyl)imidazo[1,2-a]-pyridin-7-yl)-N$^4$-(pyridin-2-yl)-trans-cyclohexane-1,4-diamine 206b (13 mg, 9%) as an off-white solid.

$^1$H NMR (400 MHz, DMSO-d$_6$): δ 8.20 (d, J=6.0 Hz, 1H), 8.04 (s, 1H), 7.98 (s, 1H), 7.94 (d, J=5.2 Hz, 1H), 7.34-7.30 (m, 1H), 6.89 (s, 1H), 6.53 (br s, 1H), 6.46-6.40 (m, 2H), 6.37 (d, J=7.6 Hz, 1H), 6.30 (s, 1H), 4.01 (s, 3H), 3.94 (s, 3H), 3.77-3.63 (m, 1H), 2.05 (t, J=10.8 Hz, 4H), 1.38-1.26 (m, 4H); HPLC (Method 6) 93.4% (AUC), $t_R$=11.91 min.; ESI+APCI MS m/z 478 [M+H]$^+$.

Preparation of N$^1$-benzyl-N$^4$-(2-(5-chloro-2,4-dimethoxyphenyl)imidazo[1,2-a]pyridin-7-yl)-trans-cyclohexane-1,4-diamine 206c (Example 291)

A mixture of N-(2-(5-chloro-2,4-dimethoxyphenyl)imidazo[1,2-a]pyridin-7-yl)-N$^4$-(pyridin-2-yl)-trans-cyclohexane-1,4-diamine 205 (200 mg, 0.50 mmol), triethylamine (228 μL, 1.63 mmol), DMAP (10 mg, 0.081 mmol) and benzyl bromide (8 μL, 0.7 mmol) in CH$_2$Cl$_2$ (10 mL) was stirred at room temperature for 16 h. The reaction mixture was diluted with water and extracted with CH$_2$Cl$_2$ (2×10 mL). The combined organic layers were dried over sodium sulfate, filtered and concentrated under reduced pressure and the residue was purified by combi-flash companion (silica gel, CH$_3$OH/CH$_2$Cl$_2$) to afford N$^1$-benzyl-N$^4$-(2-(5-chloro-2,4-dimethoxyphenyl)imidazo[1,2-a]pyridin-7-yl)-trans-cyclohexane-1,4-diamine 206c (25 mg, 10%) as an off-white solid.

$^1$H NMR (400 MHz, DMSO-d$_6$): δ 8.13 (s, 1H), 8.11 (d, J=7.6 Hz, 1H), 7.87 (s, 1H), 7.40-7.32 (m, 4H), 7.27 (d, J=7.2 Hz, 1H), 6.84 (s, 1H), 6.29 (dd, J=2.0, 7.2 Hz, 1H), 6.23 (s, 1H), 6.00 (d, J=7.6 Hz, 1H), 3.99 (s, 3H), 3.92 (s, 3H), 3.86 (br s, 1H), 3.22-3.20 (m, 1H), 2.04 (t, J=13.6 Hz, 4H), 1.37-1.29 (m, 2H), 1.20-1.11 (m, 2H); HPLC (Method 6) 93.1% (AUC), $t_R$=12.18 min.; ESI+APCI MS m/z 491 [M+H]$^+$.

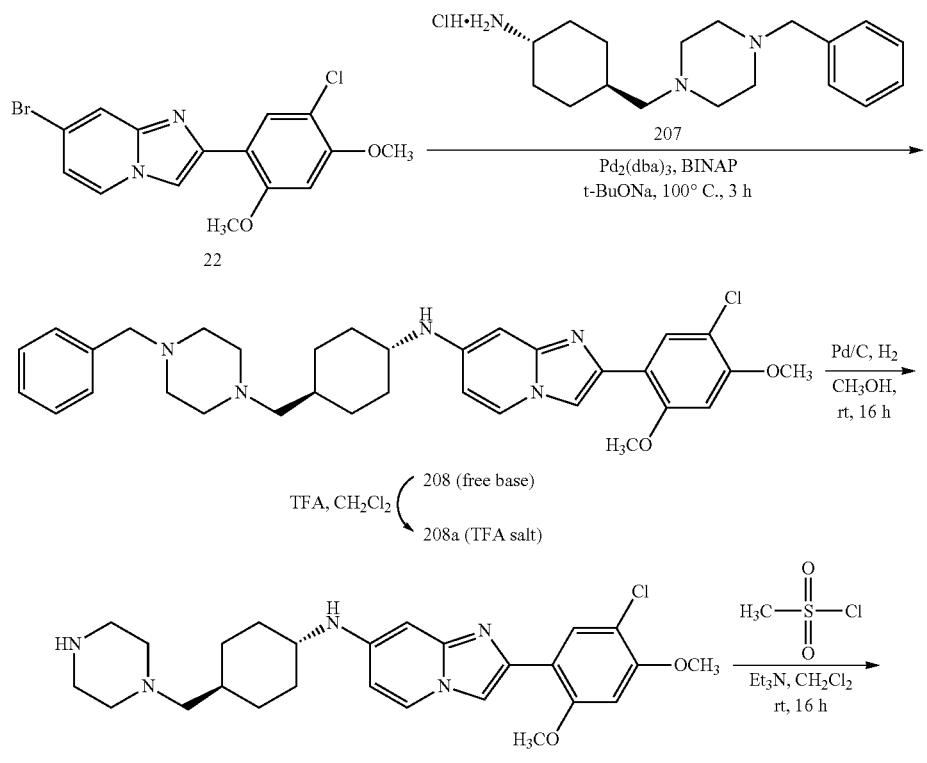

Scheme 63

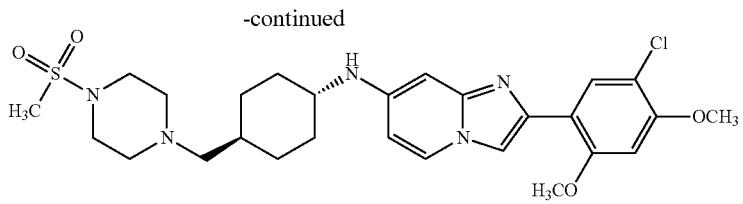

210

Preparation of (trans-N-(4-((4-benzylpiperazin-1-yl)methyl)cyclohexyl)-2-(5-chloro-2,4-dimethoxyphenyl)imidazo[1,2-a]pyridin-7-amine 208

A mixture of 7-bromo-2-(5-chloro-2,4-dimethoxyphenyl)imidazo[1,2-a]pyridine 22 (100 mg, 0.27 mmol), trans-4-((4-benzylpiperazin-1-yl)methyl)cyclohexanamine hydrochloride 207 (94 mg, 0.29 mmol), $Pd_2(dba)_3$ (12 mg, 0.013 mmol), BINAP (15 mg, 0.024 mmol), and sodium tert-butoxide (100 mg, 1.04 mmol) were taken up in toluene (5 mL) and degassed with argon. The reaction mixture was heated at 100° C. for 3 h. The reaction mixture was cooled to room temperature, diluted with $CH_2Cl_2$ (20 mL) and filtered through a pad of celite. The filtrate was concentrated under reduced pressure and the residue was purified by silica gel chromatography ($CH_3OH/CH_2Cl_2$) to obtain trans-N-(4-((4-benzylpiperazin-1-yl)methyl)-cyclohexyl)-2-(5-chloro-2,4-dimethoxyphenyl)imidazo[1,2-a]pyridin-7-amine 208 (50 mg, 32%) as an off-white solid.

$^1$H NMR (400 MHz, DMSO-$d_6$): δ 8.13 (s, 1H), 8.10 (d, J=7.6 Hz, 1H), 7.86 (s, 1H), 7.33-7.21 (m, 5H), 6.84 (s, 1H), 6.34 (dd, J=2.0, 7.2 Hz, 1H), 6.18 (s, 1H), 5.99 (d, J=7.6 Hz, 1H), 3.98 (s, 3H), 3.92 (s, 3H), 3.44 (s, 2H), 3.17-3.14 (m, 1H), 2.35 (br s, 7H), 2.09 (d, J=7.2 Hz, 2H), 2.04 (d, J=10.4 Hz, 2H), 1.80 (d, J=12.0 Hz, 21-), 1.52-1.45 (m, 1H), 1.18-1.09 (m 2H), 1.04-0.93 (m, 2H); ESI+APCI MS m/z 574 [M+H]$^+$.

Preparation of trans-N-(4-((4-benzylpiperazin-1-yl)methyl)cyclohexyl)-2-(5-chloro-2,4-dimethoxyphenyl)imidazo[1,2-a]pyridin-7-amine 2,2,2-trifluoroacetate 208a (Example 278)

A mixture of trans-N-(4-((4-benzylpiperazin-1-yl)methyl)cyclohexyl)-2-(5-chloro-2,4-dimethoxyphenyl)imidazo[1,2-a]pyridin-7-amine 208 (100 mg, 0.17 mmol) and trifluoroacetic acid (1.0 mL) in $CH_2Cl_2$ (20 mL) was stirred at room temperature for 3 h. The reaction mixture was concentrated under reduced pressure, the residue was triturated with pentane to afford trans-N-(4-((4-benzylpiperazin-1-yl)methyl)cyclohexyl)-2-(5-chloro-2,4-dimethoxyphenyl)imidazo[1,2-a]pyridin-7-amine as TFA salt 208a (40 mg, 33%) as an off-white solid.

$^1$H NMR (400 MHz, $D_2O$): δ 7.84 (d, J=7.2 Hz, 1H), 7.58 (s, 1H), 7.52-7.47 (m, 5H), 7.33 (s, 1H), 6.55 (d, J=7.6 Hz, 1H), 6.44 (s, 1H), 6.20 (s, 1H), 4.33 (s, 2H), 3.91 (s, 3H), 3.79 (s, 3H), 3.52 (br s, 8H), 3.29 (br s, 1H), 3.11 (d, J=6.4 Hz, 2H), 2.12 (d, J=12.4 Hz, 2H), 1.87 (d, J=8.8 Hz, 2H), 1.31-1.20 (m, 4H); HPLC (Method 8) 97.5% (AUC), $t_R$=10.08 min.; ESI+APCI MS m/z 574 [M+H]$^+$.

Preparation of 2-(5-chloro-2,4-dimethoxyphenyl)-trans-N-(4-(piperazin-1-ylmethyl)-cyclohexyl)imidazo[1,2-a]pyridin-7-amine 209

A mixture of trans-N-(4-((4-benzylpiperazin-1-yl)methyl)cyclohexyl)-2-(5-chloro-2,4-dimethoxyphenyl)imidazo[1,2-a]pyridin-7-amine 208 (200 mg, 0.34 mmol) and 10% Pd/C (50 mg) in $CH_3OH$ (25 mL) was stirred at room temperature for 16 h under hydrogen atmosphere (1 atm). The reaction mixture was filtered through a pad of celite and the catalyst was washed with $CH_3OH$ (2×20 mL) and the filtrate was concentrated under reduced pressure to afford 2-(5-chloro-2,4-dimethoxyphenyl)-trans-N-(4-(piperazin-1-ylmethyl)cyclohexyl)imidazo[1,2-a]pyridin-7-amine 209 (100 mg, 60%) as an off-white solid.

$^1$H NMR (400 MHz, DMSO-$d_6$): δ 8.13 (s, 1H), 8.10 (d, J=7.6 Hz, 1H), 7.86 (s, 1H), 6.84 (s, 1H), 6.34 (d, J=6.8 Hz, 1H), 6.18 (s, 1H), 6.01 (d, J=7.6 Hz, 1H), 3.98 (s, 3H), 3.92 (s, 3H), 3.22 (br s, 1H), 3.16 (s, 2H), 2.67 (br s, 3H), 2.23-2.16 (m, 4H), 2.07-2.03 (m, 4H), 1.81 (d, J=10.8 Hz, 2H), 1.49 (br s, 1H), 1.31-1.09 (m, 2H), 1.04-0.96 (m, 2H); ESI+APCI MS m/z 483 [M+H]$^+$.

Preparation of 2-(5-chloro-2,4-dimethoxyphenyl)-trans-N-(4-((4-(methylsulfonyl)-piperazin-1-yl)methyl)cyclohexyl)imidazo[1,1,2-a]pyridin-7-amine 210 (Example 289)

A mixture of 2-(5-chloro-2,4-dimethoxyphenyl)-trans-N-(4-(piperazin-1-ylmethyl)-cyclohexyl)imidazo[1,2-a]pyridin-7-amine 209 (200 mg, 0.41 mmol), triethylamine (125 μL, 1.24 mmol) and methane sulfonyl chloride (38 μL, 0.49 mmol) in dichloromethane (10 mL) was stirred at room temperature for 16 h under nitrogen atmosphere. The reaction mixture was quenched with water and extracted with $CH_2Cl_2$ (2×20 mL) and the combined organic layers were dried over sodium sulfate, filtered and concentrated under reduced pressure. The residue was purified by combi-flash companion (silica gel, $CH_3OH/CH_2Cl_2$) to afford 2-(5-chloro-2,4-dimethoxyphenyl)-trans-N-(4-((4-(methylsulfonyl)piperazin-1-yl)methyl)cyclohexyl)imidazo-[1,2-a]pyridin-7-amine 210 (45 mg, 20%) as an off-white solid.

$^1$H NMR (400 MHz, DMSO-$d_6$): δ 8.12-8.10 (m, 2H), 7.87 (s, 1H), 6.84 (s, 1H), 6.35 (d, J=6.4 Hz, 1H), 6.19 (s, 1H), 6.01 (d, J=7.6 Hz, 1H), 3.99 (s, 3H), 3.92 (s, 3H), 3.17 (br s, 1H), 3.10 (br s, 4H), 2.86 (s, 3H), 2.43 (br s, 4H), 2.16 (d, J=6.0 Hz, 2H), 2.05 (d, J=10.8 Hz, 2H), 1.82 (d, J=11.6 Hz, 2H), 1.51 (br s, 1H), 1.23-1.11 (m, 2H), 1.07-0.98 (m, 2H); HPLC (Method 6) >99% (AUC), $t_R$=11.73 min.; ESI+APCI MS m/z 562 [M+H]$^+$.

Scheme 64

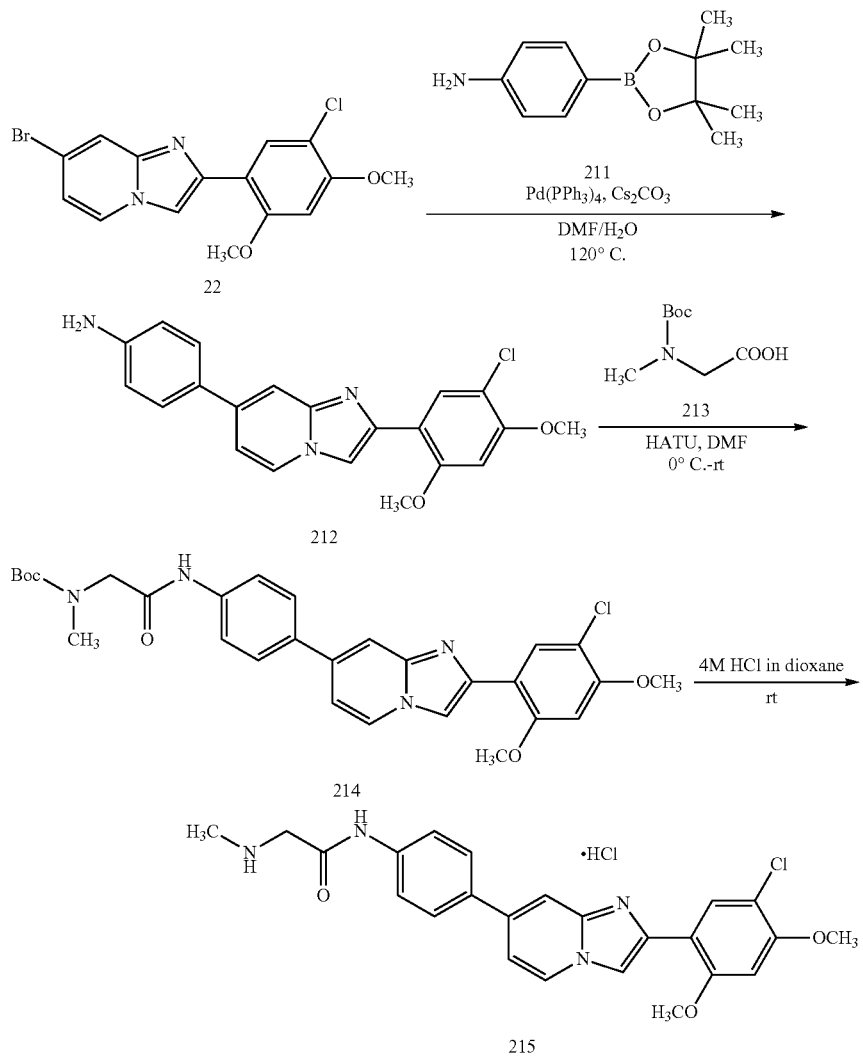

Preparation of 4-(2-(5-chloro-2,4-dimethoxyphenyl)imidazo[1,2-a]pyridin-7-yl)aniline 212

A mixture of 7-bromo-2-(5-chloro-2,4-dimethoxyphenyl)imidazo[1,2-a]pyridine 22 (3.00 g, 8.16 mmol), 4-(4,4,55-tetramethyl-1,3,2-dioxaborolan-2-yl)aniline 211 (2.12 g, 9.67 mmol) and Cs$_2$CO$_3$ (6.60 g, 20.5 mmol) in DMF/H$_2$O (30 mL/3 mL) was degassed with argon and charged with Pd(PPh$_3$) (470 mg, 0.41 mmol). The reaction mixture was heated at 120° C. for 3 h. The reaction mixture was cooled to room temperature and diluted with ethyl acetate and filtered through a pad of celite. The filtrated was poured in water (20 mL), the precipitate so obtained was filtered, washed with water, and dried under reduced pressure to provide 4-(2-(5-chloro-2,4-dimethoxyphenyl)imidazo[1,2-a]pyridin-7-yl)aniline 212 (2.1 g, 67%/o) as a yellow solid.

$^1$H NMR (400 MHz, CDCl$_3$): δ 8.42 (s, 1H), 8.08 (dd, J=0.4, 6.8 Hz, 1H), 8.03 (s, 1H), 7.77 (s, 1H), 7.48 (dd, J=1.2, 6.4 Hz, 2H), 7.01 (dd, J=1.6, 6.8 Hz, 1H), 6.77 (dd, J=2.0, 6.8 Hz, 2H), 6.58 (s, 1H), 4.01 (s, 3H), 3.95 (s, 3H).

Preparation of tert-butyl (2-((4-(2-(5-chloro-2,4-dimethoxyphenyl)imidazo[1,2-a]pyridin-7-yl)phenyl)amino)-2-oxoethyl)(methyl)carbamate 214

A mixture of 4-(2-(5-chloro-2,4-dimethoxyphenyl)imidazo[1,2-a]pyridin-7-yl)aniline 212 (500 mg, 1.31 mmol), 2-((tert-butoxycarbonyl)methyl)amino)acetic acid 213 (250 mg, 1.31 mmol), HATU (800 mg, 2.10 mmol) and DIPEA (0.75 mL, 4.31 mmol) in DMF (5 mL) was stirred at room temperature for 16 h under nitrogen atmosphere. The reaction mixture was quenched with water and the solid obtained was filtered, washed with water and MTBE, dried under vacuum to afford tert-butyl (2-((4-(2-(5-chloro-2,4-dimethoxyphenyl)imidazo[1,2-a]-pyridin-7-yl)phenyl)amino)-2-oxoethyl)(methyl) carbamate 214 (450 mg, 62%) as a pale yellow solid.

$^1$H NMR (300 MHz, CDCl$_3$): δ 9.29-9.24 (m, 1H), 7.80-7.78 (m, 2H), 7.65 (s, 1H), 7.21-7.17 (m, 3H), 7.09 (d, J=8.1 Hz, 2H), 6.57 (d, J=7.2 Hz, 1H), 6.15 (s, 1H), 3.51 (br s, 5H), 3.43 (s, 3H), 2.43 (s, 3H), 0.90 (br s, 9H).

Preparation of N-(4-(2-(5-chloro-2,4-dimethoxyphenyl)imidazo[1,2-a]pyridin-7-yl)phenyl)-2-(methylamino)acetamide hydrochloride 215 (Example 273)

To a solution of tert-butyl (2-((4-(2-(5-chloro-2,4-dimethoxyphenyl)imidazo[1,2-a]-pyridin-7-yl)phenyl)amino)-2-oxoethyl)(methyl)carbamate 214 (100 mg, 0.18 mmol) in dioxane (2 mL) was added 4.0 M HCl in dioxane (2 mL), the reaction mixture was stirred at room temperature overnight. The precipitate was filtered, washed with MTBE and dried under reduced pressure to afford the N-(4-(2-(5-chloro-2,4-dimethoxyphenyl)imidazo[1,2-a]pyridin-7-yl)phenyl)-2-(methylamino)acetamide hydrochloride 215 (60 mg, 68%) as an off-white solid.

$^1$H NMR (400 MHz, DMSO-$d_6$): δ 11.11 (s, 1H), 9.05 (d, J=4.8 Hz, 2H), 8.90 (d, J=7.2 Hz, 1H), 8.65 (s, 1H), 8.23 (s, 1H), 8.04 (s, 1H)), 7.85 (d, J=8.8 Hz, 2H), 7.82 (d, J=6.8 Hz, 2H), 7.01 (s, 1H), 4.10 (s, 3H), 4.01 (br s, 5H), 2.65 (t, J=5.2 Hz), HPLC (Method 9) 95.8% (AUC), $t_R$=11.44 min.; ESI+ APCI MS m/z 450 [M+H]$^+$.

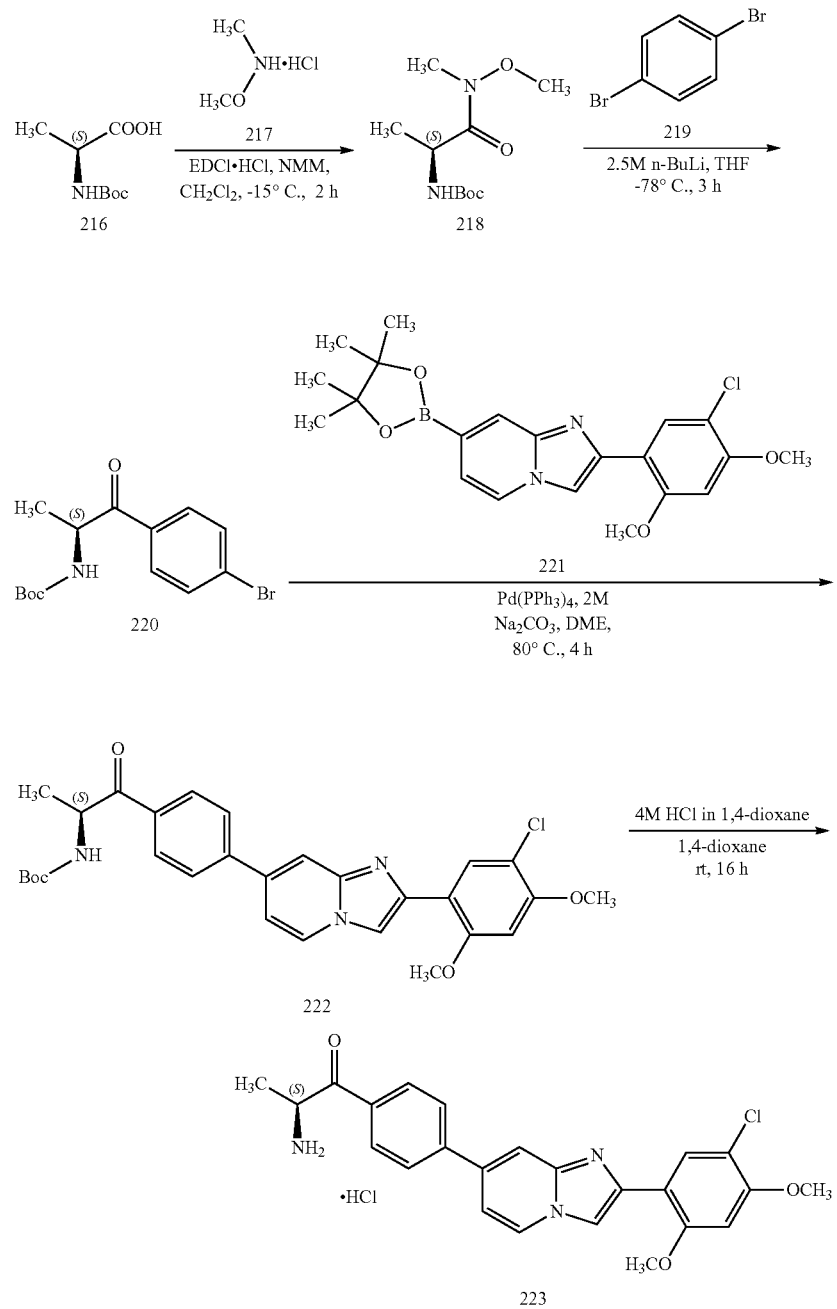

-continued

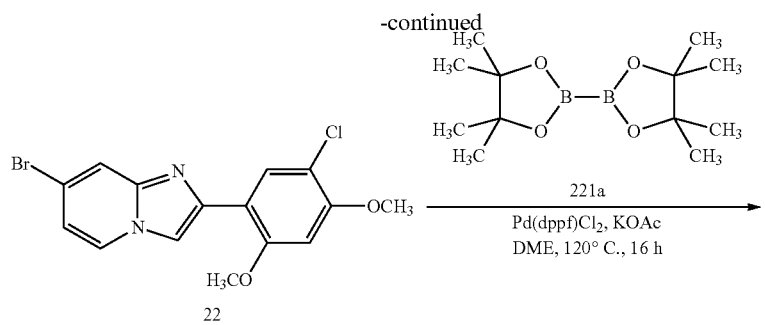

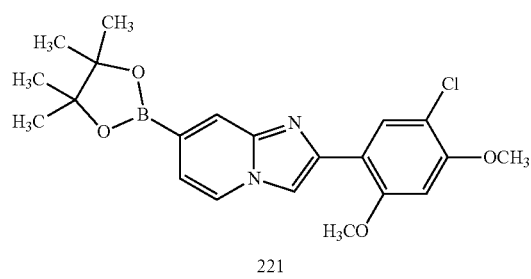 [SMILES: COc1cc(OC)c(-c2cn3ccc(B4OC(C)(C)C(C)(C)O4)cc3n2)cc1Cl]

Preparation of (S)-tert-butyl (1-(methoxy(methyl)amino)-1-oxopropan-2-yl)carbamate 218

A solution of (S)-2-((tert-butoxycarbonyl)amino)propanoic acid 216 (5.00 g, 26.4 mmol) in $CH_2Cl_2$ (50 mL) was cooled to −15° C., and was added N,O-dimethylhydroxylamine hydrochloride 217 (2.81 g, 28.8 mmol) followed by NMM (2.90 g, 28.6 mmol) under nitrogen atmosphere. Then EDCI.HCl (5.56 g, 29.0 mmol) was added to the reaction mixture in portions while maintaining the temperature at −15° C., and the reaction mixture was stirred at the same temperature for 1 h. The reaction mixture was diluted with $CH_2Cl_2$ (50 mL) and washed with water (60 mL) and the organic layer was separated and washed with brine (50 mL). The organic layer was dried over sodium sulfate, filtered and concentrated under reduced pressure to provide (S)-tert-butyl (1-(methoxy (methyl) amino)-1-oxopropan-2-yl)carbamate 218 (4.0 g, crude).

$^1$H NMR (400 MHz, DMSO-$d_6$): δ 7.01 (d, J=7.6 Hz, 1H), 4.41-4.36 (m, 1H), 3.71 (s, 3H), 3.09 (s, 3H), 1.36 (s, 9H), 1.14 (d, J=7.2 Hz, 3H).

Preparation of (S)-tert-butyl (1-(4-bromophenyl)-1-oxopropan-2-yl)carbamate 220

A solution of 1,4-dibromobenzene 219 (6.00 g, 25.4 mmol) in dry THF (40 mL) was cooled to −78° C. under nitrogen atmosphere. To the solution was added n-BuLi (2.5 M, 10.3 mL, 25.8 mmol) slowly and the reaction mixture was stirred at same temperature for 45 min.; white precipitation was formed during the period. A solution of (S)-tert-butyl (1-(methoxy(methyl)-amino)-1-oxopropan-2-yl)carbamate 218 (1.50 g, 6.46 mmol) in THF (20 mL) was added to the reaction mixture slowly, the reaction mixture was stirred at same temperature for another 2 h before it was quenched with saturated $NH_4Cl$ solution (50 mL). The aqueous layer was extracted with EtOAc (100 mL) and the organic layer was concentrated and the crude was purified by combi-flash companion (silica gel, 10% EtOAc/hexanes) to give (S)-tert-butyl (1-(4-bromophenyl)-1-oxopropan-2-yl)carbamate 220 (320 mg, 15%).

$^1$H NMR (400 MHz, DMSO-$d_6$): δ 7.88 (d, J=8.4 Hz, 2H), 7.73 (d, J=8.4 Hz, 2H), 7.37 (d, J=7.2 Hz, 1H), 4.99-4.96 (m, 1H), 1.33 (s, 9H), 1.21 (d, J=6.8 Hz, 3H).

Preparation of 2-(5-chloro-2,4-dimethoxyphenyl)-7-(4,4,5,5-tetramethyl-1,3,2-dioxaborolan-2-yl)imidazo[1,2-a]pyridine 221

To a solution of 7-bromo-2-(5-chloro-2,4-dimethoxyphenyl)imidazo[1,2-a]pyridine 5 (5.00 g, 13.6 mmol) in DME (100 mL) was added 4,4,4',4',5,5,5',5'-octamethyl-2,2'-bi(1,3,2-dioxaborolane) 221a (3.82 g, 15.0 mmol) followed by KOAc (4.01 g, 41.0 mmol). The reaction mixture was degassed with argon for 10 min and then $Pd(dppf)Cl_2$ (516 mg, 0.70 mmol) was added and the reaction mixture was degassed for further 10 minutes. The reaction flask was sealed and stirred at 120° C. for 16 h. The reaction mixture was cooled to room temperature, diluted with $CH_2Cl_2$ (100 mL) and filtered through a pad of celite. The filtrate was concentrated under reduced pressure to yield the crude product which was further triturated with hexane (100 mL) to give 2-(5-chloro-2,4-dimethoxyphenyl)-7-(4,4,5,5-tetramethyl-1,3,2-dioxaborolan-2-yl)imidazo[1,2-a]pyridine 221 (4.0 g, 71%).

$^1$H NMR (300 MHz, DMSO-$d_6$): δ 8.53 (d, J=6.6 Hz, 1H), 8.39 (s, 1H), 7.94 (s, 1H), 7.77 (s, 1H), 6.97 (d, J=6.9 Hz, 1H), 6.90 (s, 1H), 4.03 (s, 3H), 3.95 (s, 3H), 1.32 (s, 12H).

Preparation of (S)-tert-butyl (1-(4-(2-(5-chloro-2,4-dimethoxyphenyl)imidazo[1,2-a]-pyridin-7-yl)phenyl)-1-oxopropan-2-yl)carbamate 222

To a solution of (S)-tert-butyl (1-(4-bromophenyl)-1-oxopropan-2-yl)carbamate 220 (237 mg, 0.72 mmol) and 2-(5-chloro-2,4-dimethoxyphenyl)-7-(4,4,5,5-tetramethyl-1,3,2-dioxaborolan-2-yl)imidazo[1,2-a]pyridine 221 (300 mg, 0.72 mmol) in DME (10 mL) was added $Na_2CO_3$ solution (2 M, 1.08 mL, 2.16 mmol). The reaction mixture was degassed with argon for 10 minutes and then $Pd(PPh_3)_4$ (42 mg, 0.036 mmol) was added. The reaction mixture was stirred at 80° C. for 4 h under argon atmosphere. The reaction mixture was cooled to room temperature and was evaporated under reduced pressure. The crude material was purified by combi-flash companion (silica gel, 60% EtOAc/hexanes) to yield (S)-tert-butyl (1-(4-(2-(5-chloro-2,4-dimethoxyphenyl)imidazo[1,2-a]pyridin-7-yl)phenyl)-1-oxopropan-2-yl)carbamate 222 (100 mg, 26%) as an off-white solid.

$^1$H NMR (400 MHz, DMSO-d$_6$): δ 8.67 (d, J=7.2 Hz, 1H), 8.39 (s, 1H), 8.27 (s, 1H), 8.09-7.99 (m, 5H), 7.38-7.34 (m, 2H), 6.92 (s, 1H), 5.13-5.05 (m, 1H), 4.06 (s, 3H), 3.97 (s, 3H), 1.37 (s, 9H), 1.27 (d, J=6.8 Hz, 3H).

Preparation of (S)-2-amino-1-(4-(2-(5-chloro-2,4-dimethoxyphenyl) imidazo[1,2-a]-pyridin-7-yl)phenyl)propan-1-one hydrochloride 223 (Example 274)

A solution of (S)-tert-butyl (1-(4-(2-(5-chloro-2,4 dimethoxyphenyl)imidazo[1,2-a]-pyridin-7-yl)phenyl)-1-oxopropan-2-yl)carbamate 222 (70 mg, 0.13 mmol) in 1,4-dioxane (2 mL) was added 4 M HCl in 1,4-dioxane (2 mL) slowly at room temperature under nitrogen atmosphere. The reaction mixture was stirred for 16 h and evaporated. The resulted solid was triturated with MTBE (3 mL) to yielded (S)-2-amino-1-(4-(2-(5-chloro-2,4-dimethoxyphenyl) imidazo[1,2-a]pyridin-7-yl)phenyl)propan-1-one hydrochloride 223 (20 mg, 35%) as a yellow solid.

$^1$H NMR (400 MHz, CD$_3$OD): δ 8.76 (d, J=7.2 Hz, 1H), 8.50 (s, 1H), 8.16 (d, J=8.4 Hz, 2H), 8.07 (s, 1H), 8.01 (d, J=8.4 Hz, 2H), 7.84 (s, 1H), 7.75 (dd, J=1.6, 7.2 Hz, 1H), 6.86 (s, 1H), 5.12-5.07 (m, 1H), 4.04 (s, 3H), 3.93 (s, 3H), 1.52 (d, J=7.6 Hz, 3H); HPLC (Method 6) 96.1% (AUC), t$_R$=11.55 min.; ESI+APCI MS m/z 435 [M+H]$^+$.

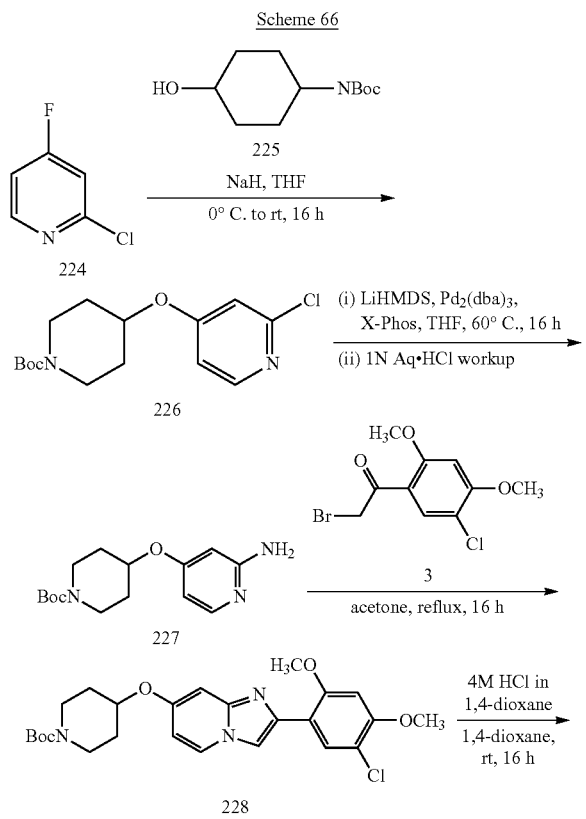

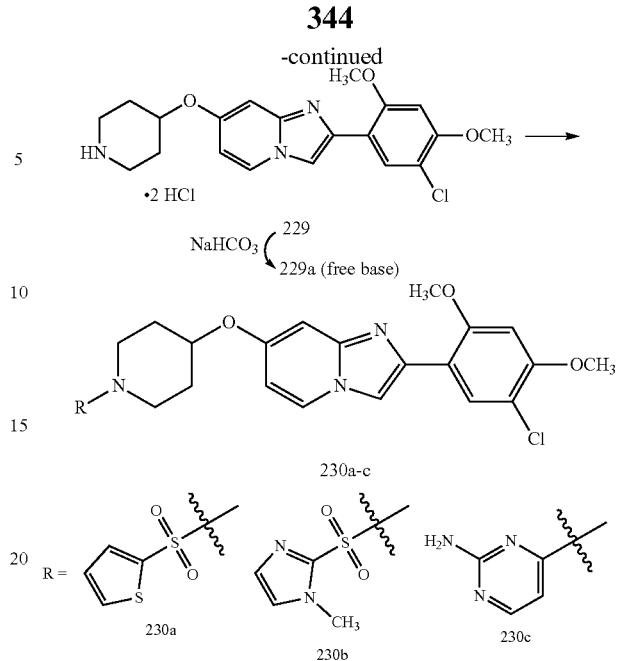

Preparation of tert-butyl 4-((2-chloropyridin-4-yl) oxy)piperidine-1-carboxylate 226

A solution of tert-butyl 4-hydroxypiperidine-1-carboxylate 225 (7.65 g, 38.0 mmol) in THF (60 mL) was charged with NaH (2.00 g, 50.0 mmol) under nitrogen atmosphere at 0° C., and was stirred for 1 h. A solution of 2-chloro-4-fluoropyridine 224 (5.50 g, 41.8 mmol) in THF (20 mL) wad added dropwise to the above reaction mixture at 0° C., and the reaction mixture was stirred at room temperature for 16 h. Water (70 mL) was added to the reaction mixture at 0° C., and the aqueous layer was extracted with EtOAc (2×70 mL). The combined organic layers were dried over sodium sulfate, filtered and concentrated under reduced pressure to provide tert-butyl 4-((2-chloropyridin-4-yl)oxy)piperidine-1-carboxylate 226 (8.5 g, 72%) as an off-white solid.

$^1$H NMR (400 MHz, CDCl$_3$): δ 8.18 (s, 1H), 6.82 (d, J=2.0 Hz, 1H), 6.74 (dd, J=2.0, 5.6 Hz, 1H), 4.58-4.53 (m, 1H), 3.71-3.65 (m, 2H), 3.40-3.34 (m, 2H), 1.98-1.91 (m, 2H), 1.80-1.75 (m, 2H), 1.47 (s, 9H), ESI+APCI m/z 313 [M+H]$^+$.

Preparation of tert-butyl 4-((2-aminopyridin-4-yl) oxy)piperidine-1-carboxylate 227

A steady stream of argon was passed through a mixture of tert-butyl 4-((2-chloropyridin-4-yl)oxy)piperidine-1-carboxylate 226 (8.00 g, 25.6 mmol), Pd$_2$(dba)$_3$ (470 mg, 0.51 mmol) and XPhos (490 mg, 1.03 mmol) in THF (100 mL). To the resulting degassed mixture was added LiHMDS (1.0 M, 54 mL, 54 mmol) slowly at room temperature. The reaction mixture was heated to 60° C. for 16 h. The reaction mixture was cooled to 0° C., diluted with 1N HCl (100 mL) and extracted with EtOAc (2×90 mL). The combined organic layers were dried over sodium sulfate, filtered and concentrated under reduced pressure. The residue was triturated with n-pentane to provide tert-butyl 4-((2-aminopyridin-4-yl)oxy)-piperidine-1-carboxylate 227 (6.0 g, 80%) as an off-white solid.

$^1$H NMR (400 MHz, CDCl$_3$): δ 7.89 (d, J=5.6 Hz, 1H), 6.24 (dd, J=2.0, 6.0 Hz, 1H), 5.97 (d, J=2.0 Hz, 1H), 4.50-4.46 (m, 1H), 4.39 (br s, 2H), 3.69-3.63 (m, 2H), 3.38-3.31 (m, 2H), 1.93-1.88 (m, 2H), 1.77-1.70 (m, 2H), 1.46 (s, 9H); ESI+APCI MS m/z 294 [M+H]$^+$.

Preparation of tert-butyl 4-((2-(5-chloro-2,4-dimethoxyphenyl)imidazo[1,2-a]pyridin-7-yl)oxy)piperidine-1-carboxylate 228

A solution of 2-bromo-1-(5-chloro-2,4-dimethoxyphenyl)ethanone 3 (6.00 g, 20.4 mmol) and tert-butyl 4-((2-aminopyridin-4-yl)oxy)piperidine-1-carboxylate 227 (6.20 g, 21.1 mmol) in acetone (80 mL) was refluxed for 16 h. The reaction mixture was cooled to room temperature. The solid formed was filtered and washed with acetone and hexane. The solid was suspended in saturated NaHCO$_3$ solution and CH$_2$Cl$_2$ mixture and stirred for 1 h. The organic layer was separated, dried over sodium sulfate, filtered and concentrated under reduced pressure to yield tert-butyl 4-((2-(5-chloro-2,4-dimethoxyphenyl)imidazo[1,2-a]pyridin-7-yl)oxy)piperidine-1-carboxylate 228 (8.5 g, 85%) as an off-white solid.

$^1$H NMR (400 MHz, DMSO-d$_6$): δ 8.39 (d, J=7.6 Hz, 1H), 8.18 (s, 1H), 8.11 (s, 1H), 7.03 (d, J=2.0 Hz, 1H), 6.87 (s, 1H), 6.57 (dd, J=2.0, 7.2 Hz, 1H), 4.69-4.65 (m, 1H), 4.06 (s, 3H), 3.94 (s, 3H), 3.73-3.67 (m, 2H), 3.22-3.17 (m, 2H), 2.00-1.97 (m, 2H), 1.59-1.51 (m, 2H), 1.41 (s, 9H); ESI+APCI MS m/z 488 [M+H]$^+$.

Preparation of 2-(5-chloro-2,4-dimethoxyphenyl)-7-(piperidin-4-yloxy)imidazo-[1,2-a]pyridine dihydrochloride 229

A solution of tert-butyl 4-((2-(5-chloro-2,4-dimethoxyphenyl)imidazo[1,2-a]pyridin-7-yl)oxy)piperidine-1-carboxylate 228 (8.50 g, 17.4 mmol) in dioxane (50 mL) was charged with 4.0 M HCl in dioxane (20 mL), the resulting mixture was stirred at room temperature for 16 h. The solvent was removed under reduced pressure, solid formed was filtered and washed with CH$_2$Cl$_2$ and n-hexane, and dried under reduced pressure to give the 2-(5-chloro-2,4-dimethoxyphenyl)-7-(piperidin-4-yloxy)imidazo[1,2-a]pyridine dihydrochloride 229 (7.6 g, 95%) as a white solid. The salt was neutralized for the synthesis of 230c (The compound 229 was suspended in saturated NaHCO$_3$ solution and CH$_2$Cl$_2$ stirred for 1 h at room temperature. The organic layer was separated and concentrated under reduced pressure to give the free base 2-(5-chloro-2,4-dimethoxyphenyl)-7-(piperidin-4-yloxy)imidazo[1,2-a]pyridine 229a as an off-white solid).

$^1$H NMR (400 MHz, CD$_3$OD): δ 8.53 (d, J=7.2 Hz, 1H), 8.23 (s, 1H), 7.72 (s, 1H), 7.31 (d, J=2.4 Hz, 1H), 7.09 (dd, J=2.4, 7.6 Hz, 1H), 6.81 (s, 1H), 5.00-4.97 (m, 1H), 4.0 (s, 3H), 3.91 (s, 3H), 3.39-3.33 (m, 2H), 3.28-3.20 (m, 2H), 2.27-2.22 (m, 2H), 2.08-2.02 (m, 2H); ESI+APCI MS m/z 388 [M+H]$^+$.

Preparation of 2-(5-chloro-2,4-dimethoxyphenyl)-7-((1-(thiophen-2-ylsulfonyl)piperidin-4-yl)oxy)imidazo[1,2-a]pyridine 230a (Example 280)

To a solution of 2-(5-chloro-2,4-dimethoxyphenyl)-7-(piperidin-4-yloxy)imidazo-[1,2-a]pyridine dihydrochloride 229 (200 mg, 0.434 mmol) and triethylamine (0.31 mL, 2.2 mmol) in CH$_2$Cl$_2$ (10 mL) was added thiophene-2-sulfonyl chloride (159 mg, 0.871 mmol) at 0° C. The reaction mixture was stirred at room temperature for 16 h. The reaction mixture was then suspended in saturated NaHCO$_3$ solution and excess of CH$_2$Cl$_2$ and stirred for 1 h. The organic layer was separated, dried over sodium sulfate, filtered and concentrated under reduced pressure. The residue was purified by combi-flash companion (silica gel, CH$_3$OH/CH$_2$Cl$_2$) to afford 2-(5-chloro-2,4-dimethoxyphenyl)-7-((1-(thiophen-2-ylsulfonyl)-piperidin-4-yl)oxy)imidazo[1,2-a]pyridine 230a (50 mg, 21% yield) as an off-white solid.

$^1$H NMR (400 MHz, DMSO-d$_6$): δ 8.36 (d, J=7.2 Hz, 1H), 8.28 (d, J=1.2 Hz, 1H), 8.16 (s, 1H), 8.10 (s, 1H), 7.86 (dd, J=2.8, 5.2 Hz, 1H), 7.37 (dd, J=1.2, 4.8 Hz, 1H), 6.99 (d, J=2.0 Hz, 1H), 6.87 (s, 1H), 6.50 (dd, J=2.0, 7.2 Hz, 1H), 4.60-4.56 (m, 1H), 4.0 (s, 3H), 3.93 (s, 3H), 3.35-3.30 (m, 2H), 2.93-2.87 (m, 2H), 2.09-2.06 (m, 2H), 1.76-1.67 (m, 2H); HPLC (Method 6) 98.8% (AUC), t$_R$=12.88 min.; ESI+APCI MS m/z 534 [M+H]$^+$.

Preparation of 2-(5-chloro-2,4-dimethoxyphenyl)-7-((1-((1-methyl-1H-imidazol-2-yl)sulfonyl)piperidin-4-yl)oxy)imidazo[1,2-a]pyridine 230b (Example 288)

Compound 2-(5-chloro-2,4-dimethoxyphenyl)-7-((1-((1-methyl-1H-imidazol-2-yl)-sulfonyl)piperidin-4-yl)oxy)imidazo[1,2-a]pyridine 230b was prepared in the same manner as 2-(5-chloro-2,4-dimethoxyphenyl)-7-((1-(thiophen-2-ylsulfonyl)piperidin-4-yl)oxy)imidazo[1,2-a]pyridine 230a and was obtained as a white solid (20% yield).

$^1$H NMR (400 MHz, DMSO-d$_6$): δ 8.39 (d, J=7.6 Hz, 1H), 8.17 (s, 1H), 8.11 (s, 1H), 7.48 (s, 1H), 7.13 (s, 1H), 7.04 (d, J=2.0 Hz, 1H), 6.87 (s, 1H), 6.57 (dd, J=2.4, 7.6 Hz, 1H), 4.70-4.66 (m, 1H), 4.01 (s, 3H), 3.93 (s, 3H), 3.87 (s, 3H), 3.61-3.57 (m, 2H), 3.34-3.33 (m, 2H), 2.12-2.08 (m, 2H), 1.79-1.71 (m, 2H); HPLC (Method 6) >99% (AUC), t$_R$=13.11 min.; ESI+APCI MS m/z 532 [M+H]$^+$.

Preparation of 4-(4-((2-(5-chloro-2,4-dimethoxyphenyl)imidazo[1,2-a]pyridin-7-yl)oxy)-piperidin-1-yl)pyrimidin-2-amine 230c (Example 284)

To a solution of 2-(5-chloro-2,4-dimethoxyphenyl)-7-(piperidin-4-yloxy)imidazo-[1,2-a]pyridine 229a (100 mg, 0.258 mmol) and N,N-diisopropylethylamine (0.22 mL, 1.3 mmol) in DMF (3 mL) was added 4-chloropyrimidin-2-amine (67 mg, 0.52 mmol). The reaction mixture was stirred at 110-120° C. for 16 h in a sealed tube before it was cooled to room temperature. Water was added to the reaction mixture and the aqueous layer was extracted with CH$_2$Cl$_2$. The organic layer was washed twice with ice cold water, dried over sodium sulfate, filtered and concentrated under reduced pressure. The residue was purified by combi-flash companion (silica gel, CH$_3$OH/CH$_2$Cl$_2$) to provide 4-(4-((2-(5-chloro-2,4-dimethoxyphenyl)-imidazo[1,2-a]pyridin-7-yl)oxy)piperidin-1-yl)pyrimidin-2-amine 230c (30 mg, 24%) as an off-white solid.

$^1$H NMR (400 MHz, DMSO-d$_6$): δ 8.40 (d, J=7.2 Hz, 1H), 8.19 (s, 1H), 8.12 (s, 1H), 7.76 (d, J=6.4 Hz, 1H), 7.06 (d, J=2.0 Hz, 1H), 6.88 (s, 1H), 6.58 (dd, J=2.4, 7.2 Hz, 1H), 6.08 (d, J=6.0 Hz, 1H), 6.01 (s, 2H), 4.78-4.74 (m, 1H), 4.06-3.97 (m, 2H), 4.01 (s, 3H), 3.94 (s, 3H), 3.38-3.31 (m, 2H), 2.05-2.03 (m, 2H), 1.63-1.56 (m, 2H); HPLC (Method 6) 97.0% (AUC), t$_R$=11.75 min.; ESI+APCI MS m/z 481 [M+H]$^+$.

Scheme 67

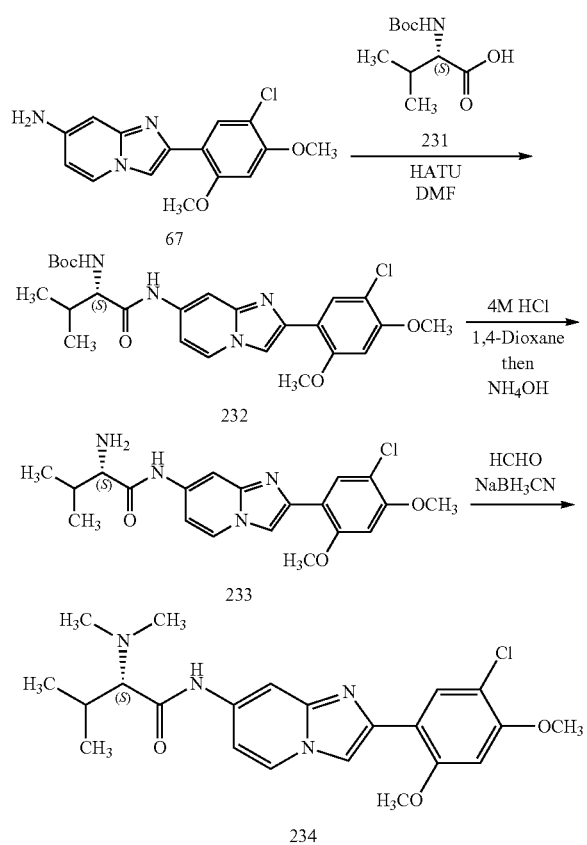

Preparation of (S)-tert-butyl (1-((2-(5-chloro-2,4-dimethoxyphenyl)imidazo[1,2-a]pyridin-7-yl)amino)-3-methyl-1-oxobutan-2-yl)carbamate 232

A mixture of 2-(5-chloro-2,4-dimethoxyphenyl)imidazo[1,2-a]pyridin-7-amine 67 (300 mg, 0.99 mmol) and (S)-2-((tert-butoxycarbonyl)amino)-3-methylbutanoic acid 231 (652 mg, 3.00 mmol) in N,N-dimethylformamide (5.0 mL) was charged with N,N-diisopropylethylamine (1.1 mL, 6.3 mmol) followed by the addition of HATU (1.70 g, 4.47 mmol). The reaction mixture was stirred at room temperature for 16 h. The reaction mixture was quenched with water (10 mL) and the precipitate was collected by filtration, the solid obtained was washed with water and dried under reduced pressure. The solid was purified by column chromatography (silica gel, 9.5:0.5 CHCl$_3$/methanol) to afford (S)-tert-butyl (1-((2-(5-chloro-2,4-dimethoxy-phenyl)imidazo[1,2-a]pyridin-7-yl)amino)-3-methyl-1-oxobutan-2-yl)carbamate 232 (350 mg, 70%) as a brown solid.

ESI MS m/z 503 [M+H]$^+$.

Preparation of (S)-2-amino-N-(2-(5-chloro-2,4-dimethoxyphenyl)imidazo[1,2-a]-pyridin-7-yl)-3-methylbutanamide 233

A mixture of (S)-tert-butyl (1-((2-(5-chloro-2,4-dimethoxyphenyl)imidazo[1,2-a]-pyridin-7-yl)amino)-3-methyl-1-oxobutan-2-yl)carbamate 232 (350 mg, 0.696 mmol) and 4 M HCl in 1,4-dioxane (5 mL) were stirred at room temperature for 3 h. The solvent was removed under reduced pressure and the residue was basified with aqueous ammonia solution (30%) to afford (S)-2-amino-N-(2-(5-chloro-2,4-dimethoxyphenyl)imidazo[1,2-a]pyridin-7-yl)-3-methylbutanamide 233 (175 mg, 62%) as a brown solid.

ESI MS m/z 403 [M+H]$^+$.

Preparation of (S)—N-(2-(5-chloro-2,4-dimethoxyphenyl)imidazo[1,2-a]pyridin-7-yl)-2-(dimethylamino)-3-methylbutanamide 234 (Example 272)

A solution of (S)-2-amino-N-(2-(5-chloro-2,4-dimethoxyphenyl)imidazo[1,2-a]-pyridin-7-yl)-3-methylbutanamide 233 (100 mg, 0.248 mmol) and formaldehyde (37% in MeOH) (200 μL, 2.48 mmol) in methanol (5 mL) was charged with catalytic AcOH and sodium cyanoborohydride (47 mg, 0.75 mmol). The reaction mixture was stirred at room temperature for 16 h. The solvent was removed under reduced pressure and the residue was diluted with aqueous ammonia solution (30%) (10 mL) and extracted with chloroform (2×10 mL). The organic layer was dried over sodium sulfate, filtered and concentrated under reduced pressure, and the residue was purified by column chromatography (silica gel, 9:1 CHCl$_3$/MeOH) to provide to afford (S)—N-(2-(5-chloro-2,4-dimethoxyphenyl)imidazo[1,2-a]pyridin-7-yl)-2-(dimethylamino)-3-methylbutanamide 234 (40 mg, 37% yield) as an off-white solid.

$^1$H NMR (400 MHz, CDCl$_3$): δ 8.60 (br s, 1H), 8.38 (s, 1H), 8.03 (d, J=0.64 Hz, 1H), 8.01 (s, 1H), 7.60 (d, J=2.0 Hz, 1H), 7.29 (dd, J=2.6, 7.2 Hz, 1H), 6.58 (s, 1H), 4.00 (s, 3H), 3.95 (s, 3H), 2.61 (d, J=4.6 Hz, 1H), 2.34 (s, 6H), 2.25-2.16 (m, 2H), 1.08 (d, J=6.8 Hz, 3H), 0.97 (d, J=6.8 Hz, 3H); HPLC (Method 1) 95.3% (AUC), t$_R$=9.44 min.; ESI MS m/z 431 [M+H]$^+$.

Scheme 68

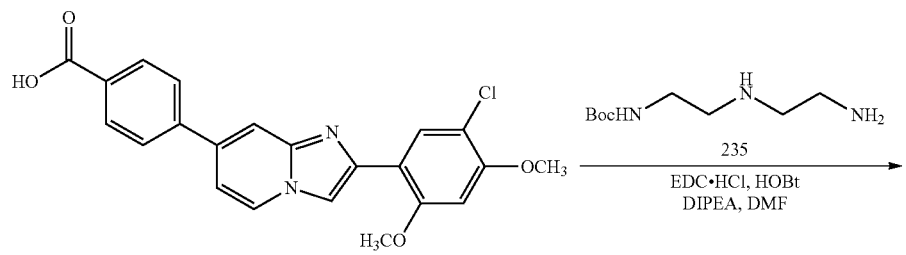

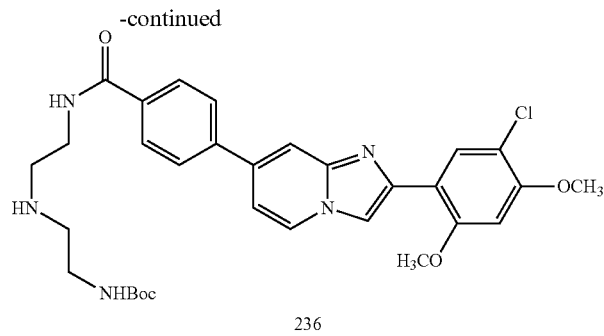

236

Preparation of tert-butyl (2-((2-(4-(2-(5-chloro-2,4-dimethoxyphenyl)imidazo[1,2-a]pyridin-7-yl)benzamido)ethyl)amino)ethyl)carbamate 236 (Example 269)

A mixture of 4-(2-(5-chloro-2,4-dimethoxyphenyl)imidazo[1,2-a]pyridin-7-yl)benzoic acid 111 (200 mg, 0.489 mmol) and tert-butyl (2-((2-aminoethyl)amino)ethyl)carbamate 235 (145 µL, 0.73 mmol) in N,N-dimethylformamide (5.0 mL) was charged with N,N-diisopropylethylamine (250 µL, 1.44 mmol) followed by the addition of EDC.HCl (140 mg, 0.73 mmol) and HOBt (131 mg, 0.98 mmol). The reaction mixture was stirred at room temperature for 16 h. The reaction mixture was quenched with water (10 mL) and the precipitate was collected by filtration: the solid obtained was washed with water and dried under reduced pressure. The solid was purified by column chromatography (silica gel, 9:1 CHCl₃/methanol with 0.5 ml aqueous ammonia solution (30%) per 100 mL) to afford tert-butyl (2-((2-(4-(2-(5-chloro-2,4-dimethoxyphenyl)imidazo[1,2-a]pyridin-7-yl)benzamido)ethyl)-amino)ethyl)carbamate 236 (130 mg, 45%) as a yellow solid.

¹H NMR (400 MHz, CDCl₃): δ 8.42 (s, 1H), 8.09 (d, J=7.0 Hz, 1H), 8.04 (br s, 1H), 7.98 (d, J=8.4 Hz, 2H), 7.77 (br s, 1H), 7.66 (d, J=8.3 Hz, 2H), 7.34 (br s, 1H), 6.97 (d, J=6.8 Hz, 1H), 6.65 (s, 1H), 5.25 (br s, 1H), 4.00 (s, 3H), 3.96 (s, 3H), 3.75-3.68 (m, 2H), 3.42-3.35 (m, 2H), 3.39 (td. J=5.5, 10.8 Hz, 2H), 2.98 (td. J=5.5, 10.8 Hz, 2H), 1.39 (s, 9H); HPLC (Method 1) 96.3% (AUC), t$_R$=10.00 min.; ESI MS m/z 594 [M+H]⁺.

Preparation of N-((1H-imidazol-2-yl)methyl)-4-(2-(5-chloro-2,4-dimethoxyphenyl)-imidazo[1,2-a]pyridin-7-yl)aniline 238 (Example 270)

A solution of 4-(2-(5-chloro-2,4-dimethoxyphenyl)imidazo[1,2-a]pyridin-7-yl)aniline 212 (75 mg, 0.20 mmol) and 1H-imidazole-2-carbaldehyde 237 (22 mg, 0.23 mmol) in methanol (5 mL) was charged with catalytic AcOH and sodium cyanoborohydride (47 mg, 0.75 mmol). The reaction mixture was stirred at room temperature for 16 h. The solvent was removed under reduced pressure and the residue was diluted with aqueous ammonia solution (30%, 10 mL) and extracted with chloroform (2×10 mL). The organic layer was dried over sodium sulfate, filtered and concentrated under reduced pressure. The residue was purified by column chromatography (silica gel, 9:1 CHCl₃/MeOH) to afford N-((1H-imidazol-2-yl)methyl)-4-(2-(5-chloro-2,4-dimethoxyphenyl)imidazo[1,2-a]pyridin-7-yl)aniline 238 (60 mg, 65% yield) as green-yellow solid.

¹H NMR (400 MHz, CD₃OD): δ 8.33 (d, J=7.1 Hz, 1H), 8.16 (s, 1H), 8.11 (s, 1H), 7.58 (br s, 1H), 7.53 (d, J=8.7 Hz, 2H), 7.14 (dd, J=1.8, 7.1 Hz, 1H), 6.99 (br s, 2H), 6.79 (s, 1H), 6.74 (d, J=8.7 Hz, 2H), 4.45 (br s, 2H), 4.00 (s, 3H), 3.95 (s, 3H); HPLC (Method 1) 97.5% (AUC), t$_R$=9.67 min.; ESI MS m/z 460 [M+H]⁺.

Scheme 69

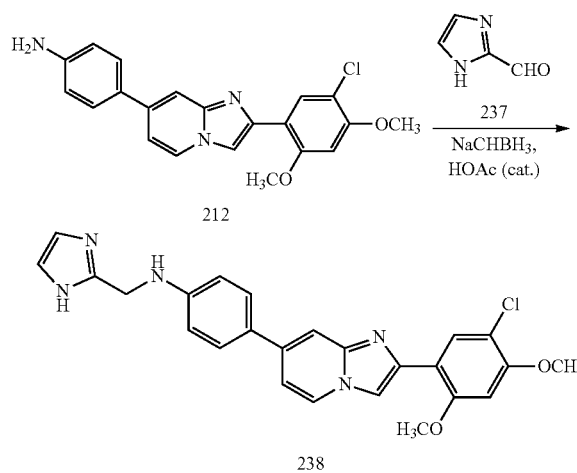

Scheme 70

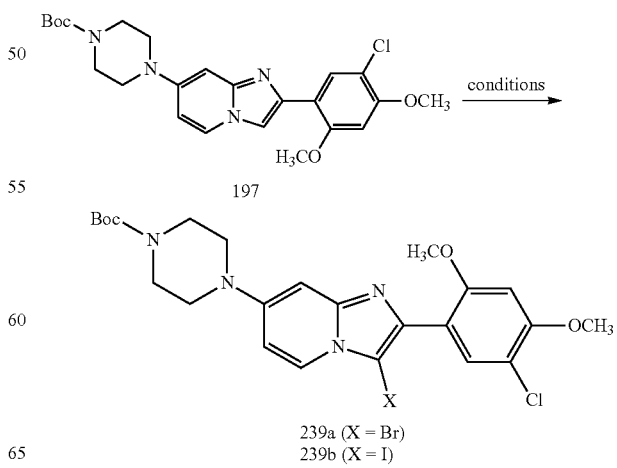

Preparation of tert-butyl 4-(3-bromo-2-(2-chloro-4, 5-dimethoxyphenyl)imidazo[1,2-a]-pyridin-7-yl)piperazine-1-carboxylate 239a (Example 271)

To a solution of tert-butyl 4-(2-(5-chloro-2,4-dimethoxyphenyl)imidazo[1,2-a]pyridin-7-yl)piperazine-1-carboxylate 197 (400 mg, 0.846 mmol) in CH$_2$Cl$_2$/MeOH (3 ml/1 ml), TBATB (488 mg, 1.01 mmol) was added slowly. The reaction mixture was stirred at room temperature for 2 h. The reaction mixture was diluted with CH$_2$Cl$_2$ (30 ml), washed with water (2 t 10 ml) and then brine (10 ml). The organic layer was dried over sodium sulfate, filtered and concentrated under reduced pressure. The residue was purified by combi-flash companion (silica gel, 20% EtOAc/Hexanes) to provide tert-butyl 4-(3-bromo-2-(5-chloro-2,4-dimethoxyphenyl)imidazo[1,2-a]pyridin-7-yl)piperazine-1-carboxylate 239a as a white solid (350 mg, 75%).

$^1$H NMR (400 MHz, CDCl$_3$): δ 7.95 (d, J=7.6 Hz, 1H), 7.56 (s, 1H), 6.83 (d, J=2 Hz, 1H), 6.71 (dd, J=2.4, 7.6 Hz, 1H), 6.59 (s, 1H), 3.97 (s, 3H), 3.87 (s, 3H), 3.61 (m, 4H), 3.21 (m, 4H), 1.49 (s, 9H); HPLC (Method 1) >99% (AUC), t$_R$=11.77 min.; ESI MS m/z 553 [(M+2)+H].

Preparation of tert-butyl 4-(2-(5-chloro-2,4-dimethoxyphenyl)-3-iodoimidazo[1,2-a]-pyridin-7-yl)piperazine-1-carboxylate 239b (Example 290)

A suspension of tert-butyl 4-(2-(5-chloro-2,4-dimethoxyphenyl)-imidazo[1,2-a]pyridin-7-yl)piperazine-1-carboxylate 7 (142 mg, 0.300 mmol) in acetonitrile (8 mL) was charged with N-iodosuccinimide (95 mg, 0.42 mmol). The reaction mixture was stirred at room temperature for 2 h under nitrogen atmosphere. The suspension was filtered and the solid obtained was washed with small amount of acetonitrile to afford a yellow solid which was recrystallized from methanol to provide tert-butyl 4-(2-(5-chloro-2,4-dimethoxyphenyl)-3-iodoimidazo[1,2-a]-pyridin-7-yl)piperazine-1-carboxylate 239b (120 mg, 67%) as a yellow solid.

$^1$H NMR (300 MHz, DMSO-d$_6$): δ 8.10 (d, J=7.5 Hz, 1H), 7.32 (s, 1H), 6.98 (dd, J=2.4, 7.8 Hz, 1H), 6.87 (s, 1H), 6.76 (d, J=2.1 Hz, 1H), 3.96 (s, 3H), 3.82 (s, 3H), 3.49-3.47 (m, 4H), 3.25-3.23 (m, 4H), 1.43 (s, 9H); HPLC (Method 1) 94.2% (AUC), t$_R$=11.86 min.; ESI MS m/z 599 [M+H]$^+$.

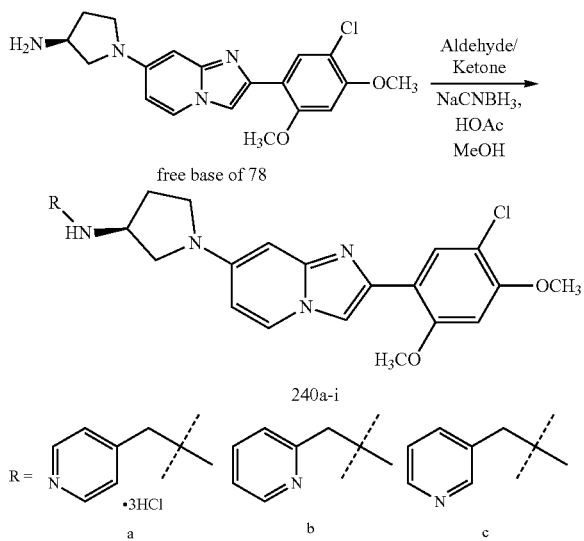

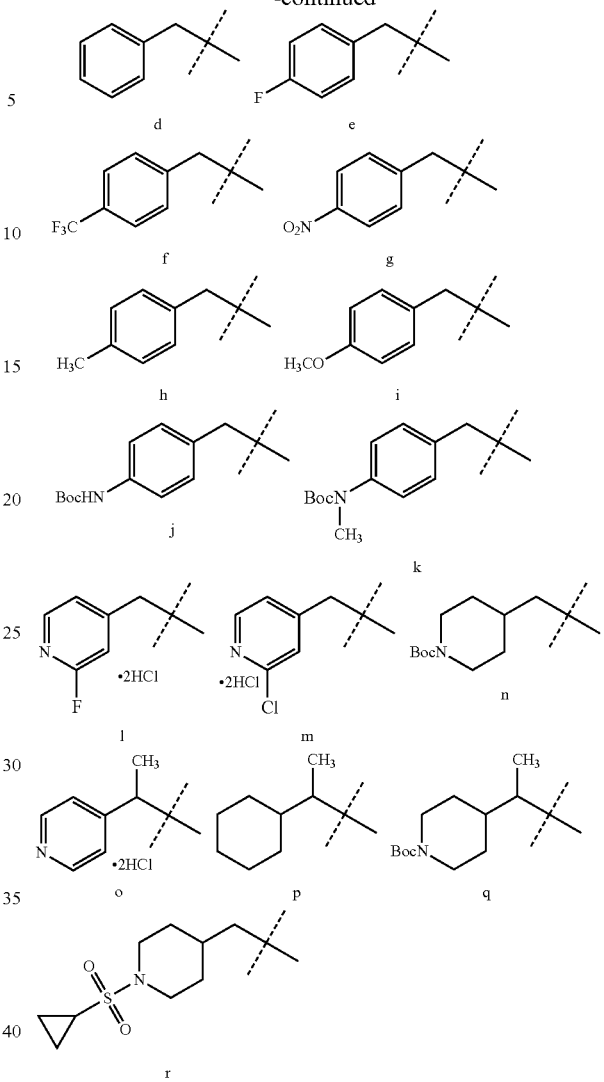

Preparation of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a (Example 298)

A 250 mL RBF was charged with (S)-1-(2-(5-chloro-2,4-dimethoxyphenyl)imidazo[1,2-a]pyridin-7-yl)pyrrolidin-3-amine (1.0 g, 2.69 mmol), isonicotinaldehyde (316 mg, 2.95 mmol), 60 mL of methanol and HOAc (154 µL, 2.69 mmol). The reaction mixture was stirred at room temperature for 30 minutes before NaCNBH$_3$ (186 mg, 2.96 mmol) was added. The reaction mixture was stirred at room temperature overnight. The reaction mixture was concentrated under reduced pressure and then diluted with dichloromethane (500 mL). The organic layer was washed with NaHCO$_3$ solution, followed by water and then brine; dried over Na$_2$SO$_4$, filtered and concentrated. The residue was purified by column chromatography (silica-gel, 90:9:1 Dichloromethane/MeOH/Ammonium hydroxide) to afford (S)-1-(2-(5-chloro-2,4-dimethoxyphenyl)imidazo[1,2-a]pyridin-7-yl)-N-(pyridin-4-ylmethyl)pyrrolidin-3-amine (1.0 g, 80%) as an off-white solid.

¹H NMR (400 MHz, CDCl₃): δ 8.56 (dd, J=1.6, 4.5 Hz, 2H), 8.35 (s, 1H), 7.86 (d, J=7.5 Hz, 1H), 7.79 (s, 1H), 7.29 (dd, J=1.6, 4.5 Hz, 2H), 6.57 (s, 1H), 6.51 (br s, 1H), 6.32 (dd, J=2.4, 7.5 Hz, 1H), 4.00 (s, 3H), 3.96 (s, 3H), 3.88 (s, 2H), 3.61-3.50 (m, 3H), 3.44-3.36 (m, 1H), 3.23-3.18 (m, 1H), 2.31-2.21 (m, 1H), 2.00-1.91 (m, 1H); ESI MS m/z 464 [M+H]⁺.

The freebase was then converted into its trihydrochloride salt using the following procedure: (S)-1-(2-(5-chloro-2,4-dimethoxyphenyl)imidazo[1,2-a]pyridin-7-yl)-N-(pyridin-4-ylmethyl)pyrrolidin-3-amine (1.0 g) was taken up in 10 ml of water with HCl (4 N aqueous solution, 2 ml). The solution was sonicated for 5 minutes and then freeze dried overnight. The desired (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a was obtained as a yellow solid (1.15 g, 93%).

¹H NMR (300 MHz, DMSO-d₆): δ 13.74 (br s, 1H), 10.57 (br s, 1H), 10.41 (br s, 1H), 8.87-8.79 (m, 2H), 8.57 (d, J=7.6 Hz, 1H), 8.27 (s, 1H), 8.06 (s, 1H), 8.02 (d, J=6.1 Hz, 2H), 7.00-6.95 (m, 2H), 6.45 (d, J=2.2 Hz, 1H), 4.48 (s, 2H), 4.05 (s, 3H), 3.98 (s, 3H), 3.92-3.75 (m, 5H), 3.58-3.49 (m, 2H); HPLC (Method 4) 98.8% (AUC), t_R=16.07 min.; ESI MS m/z 464 [M+H]⁺.

Preparation of (S)-1-(2-(5-chloro-2,4-dimethoxyphenyl)imidazo[1,2-a]pyridin-7-yl)-N-(pyridin-2-ylmethyl)pyrrolidin-3-amine 240b (Example 299)

Compound (S)-1-(2-(5-chloro-2,4-dimethoxyphenyl)imidazo[1,2-a]pyridin-7-yl)-N-(pyridin-2-ylmethyl)pyrrolidin-3-amine 240b was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous brown solid (25% yield*).

¹H NMR (400 MHz, CDCl₃): δ 8.56 (d, J=4.3 Hz, 1H), 8.38 (s, 1H), 7.89-7.76 (m, 2H), 7.70-7.59 (m, 1H), 7.31 (d, J=7.7 Hz, 1H), 7.21-7.14 (m, 1H), 6.57 (s, 1H), 6.44 (s, 1H), 6.36-6.27 (m, 1H), 4.06-3.87 (m, 8H), 3.62-3.48 (m, 3H), 3.44-3.34 (m, 1H), 3.28-3.18 (m, 1H), 2.32-2.20 (m, 1H), 2.04-1.93 (m, 1H); HPLC (same as Method 1, except detection (i 220 nm) 94.2% (AUC), t_R=9.49 min.; ESI MS m/z 464 [M+H]⁺.

Preparation of (S)-1-(2-(5-chloro-2,4-dimethoxyphenyl)imidazo[1,2-a]pyridin-7-yl)-N-(pyridin-3-ylmethyl)pyrrolidin-3-amine 240c (Example 300)

Compound (S)-1-(2-(5-chloro-2,4-dimethoxyphenyl)imidazo[1,2-a]pyridin-7-yl)-N-(pyridin-3-ylmethyl)pyrrolidin-3-amine 240c was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous off-white solid (16% yield*).

¹H NMR (400 MHz, CDCl₃): δ 8.59 (d, J=1.8 Hz, 1H), 8.52 (dd, J=1.6, 4.8 Hz, 1H), 8.36 (s, 1H), 7.86 (d, J=7.5 Hz, 1H), 7.78 (s, 1H), 7.72-7.68 (m, 1H), 7.30-7.26 (m, 1H), 6.57 (s, 1H), 6.54 (br s, 1H), 6.34 (dd, J=2.2, 7.4 Hz, 1H), 4.00 (s, 3H), 3.95 (s, 3H), 3.88 (s, 2H), 3.62-3.50 (m, 3H), 3.44-3.36 (m, 1H), 3.23-3.18 (m, 1H), 2.31-2.22 (m, 1H), 2.00-1.91 (m, 1H); HPLC (Method 1) 94.3% (AUC), t_R=9.12 min.; ESI MS m/z 464 [M+H]⁺.

Preparation of (S)—N-benzyl-1-(2-(5-chloro-2,4-dimethoxyphenyl)imidazo[1,2-a]pyridin-7-yl)pyrrolidin-3-amine 240d (Example 301)

Compound (S)—N-benzyl-1-(2-(5-chloro-2,4-dimethoxyphenyl)imidazo[1,2-a]pyridin-7-yl)pyrrolidin-3-amine 240d was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous off-white solid (40% yield).

¹H NMR (300 MHz, CDCl₃): δ 8.39 (s, 1H), 7.84 (d, J=7.4 Hz, 1H), 7.81 (s, 1H), 7.38-7.30 (m, 4H), 7.30-7.26 (m, 1H), 6.57 (s, 1H), 6.42 (s, 1H), 6.30 (dd, J=2.4, 7.4 Hz, 1H), 3.99 (s, 3H), 3.94 (s, 3H), 3.86 (s, 2H), 3.60-3.46 (m, 3H), 3.42-3.32 (m, 1H), 3.22-3.13 (m, 1H), 2.32-2.19 (m, 1H), 1.99-1.87 (m, 1H); HPLC (Method 1) 92.0% (AUC), t_R=9.85 min.; ESI MS m/z 463 [M+H]⁺.

Preparation of (S)-1-(2-(5-chloro-2,4-dimethoxyphenyl)imidazo[1,2-a]pyridin-7-yl)-N-(4-fluorobenzyl)pyrrolidin-3-amine 240e (Example 302)

Compound (S)-1-(2-(5-chloro-2,4-dimethoxyphenyl)imidazo[1,2-a]pyridin-7-yl)-N-(4-fluorobenzyl)pyrrolidin-3-amine 240e was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous off-white solid (15% yield*).

¹H NMR (400 MHz, CDCl₃): δ 8.39 (s, 1H), 7.84 (d, J=7.6 Hz, 1H), 7.82 (s, 1H), 7.34-7.28 (m, 2H), 7.05-6.98 (m, 2H), 6.57 (s, 1H), 6.42 (s, 1H), 6.30 (dd, J=2.4, 7.5 Hz, 1H), 3.99 (s, 3H), 3.95 (s, 3H), 3.82 (s, 2H), 3.59-3.47 (m, 3H), 3.41-3.33 (m, 1H), 3.20-3.15 (m, 1H), 2.30-2.21 (m, 1H), 1.98-1.89 (m, 1H); HPLC (Method 1) 95.0% (AUC), t_R=9.99 min.; ESI MS m/z 481 [M+H]⁺.

Preparation of (S)-1-(2-(5-chloro-2,4-dimethoxyphenyl)imidazo[1,2-a]pyridin-7-yl)-N-(4-(trifluoromethyl)benzyl)pyrrolidin-3-amine 240f (Example 303)

Compound (S)-1-(2-(5-chloro-2,4-dimethoxyphenyl)imidazo[1,2-a]pyridin-7-yl)-N-(4-(trifluoromethyl)benzyl)pyrrolidin-3-amine 240f was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous off-white solid (52% yield).

¹H NMR (400 MHz, CDCl₃): δ 8.38 (s, 1H), 7.85 (d, J=7.4 Hz, 1H), 7.81 (s, 1H), 7.59 (d, J=8.1 Hz, 2H), 7.47 (d, J=8.0 Hz, 2H), 6.57 (s, 1H), 6.46 (br s, 1H), 6.31 (dd, J=2.3, 7.5 Hz, 1H), 3.99 (s, 3H), 3.95 (s, 3H), 3.92 (s, 2H), 3.61-3.49 (m, 3H), 3.42-3.35 (m, 1H), 3.22-3.17 (m, 1H), 2.30-2.21 (m, 1H), 1.99-1.90 (m, 1H); HPLC (Method 1) >99% (AUC), t_R=10.43 min.; ESI MS m/z 531 [M+H]⁺.

Preparation of (S)-1-(2-(5-chloro-2,4-dimethoxyphenyl)imidazo[1,2-a]pyridin-7-yl)-N-(4-nitrobenzyl)pyrrolidin-3-amine 240e (Example 304)

Compound (S)-1-(2-(5-chloro-2,4-dimethoxyphenyl)imidazo[1,2-a]pyridin-7-yl)-N-(4-nitrobenzyl)pyrrolidin-3- amine 240g was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous yellow brown solid (44% yield).

$^1$H NMR (400 MHz, CDCl$_3$): δ 8.37 (s, 1H), 8.19 (d, J=8.7 Hz, 2H), 7.85 (d, J=7.5 Hz, 1H), 7.80 (s, 1H), 7.54 (d, J=8.6 Hz, 2H), 6.57 (s, 1H), 6.50 (br s, 1H), 6.32 (dd, J=2.3, 7.4 Hz, 1H), 4.00 (s, 3H), 3.97 (s, 2H), 3.95 (s, 3H), 3.62-3.50 (m, 3H), 3.44-3.36 (m, 1H), 3.24-3.17 (m, 1H), 2.30-2.22 (m, 1H), 2.00-1.92 (m, 1H); HPLC (same as Method 1, except detection @ 220 nm) 93.4% (AUC), t$_R$=10.06 min.; ESI MS m/z 508 [M+H]$^+$.

Preparation of (S)-1-(2-(5-chloro-2,4-dimethoxyphenyl)imidazo[1,2-a]pyridin-7-yl)-N-(4-methylbenzyl)pyrrolidin-3-amine 240h (Example 305)

Compound (S)-1-(2-(5-chloro-2,4-dimethoxyphenyl)imidazo[1,2-a]pyridin-7-yl)-N-(4-methylbenzyl)pyrrolidin-3-amine 240h was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous off-white solid (50% yield).

$^1$H NMR (400 MHz, CDCl$_3$): δ 8.38 (s, 1H), 7.84 (d, J=7.4 Hz, 1H), 7.80 (s, 1H), 7.22 (d, J=8.0 Hz, 2H), 7.47 (d, J=7.9 Hz, 2H), 6.57 (s, 1H), 6.43 (s, 1H), 6.30 (dd, J=2.3, 7.4 Hz, 1H), 3.99 (s, 3H), 3.94 (s, 3H), 3.81 (s, 2H), 3.59-3.47 (m, 3H), 3.40-3.33 (m, 1H), 3.20-3.15 (m, 1H), 2.34 (s, 3H), 2.29-2.20 (m, 1H), 1.97-1.88 (m, 1H); HPLC (Method 1) >99% (AUC), t$_R$=10.09 min.; ESI MS m/z 477 [M+H]$^+$.

Preparation of (S)-1-(2-(5-chloro-2,4-dimethoxyphenyl)imidazo[1,2-a]pyridin-7-yl)-N-(4-methoxybenzyl)pyrrolidin-3-amine 240i (Example 306)

Compound (S)-1-(2-(5-chloro-2,4-dimethoxyphenyl)imidazo[1,2-a]pyridin-7-yl)-N-(4-methoxybenzyl)pyrrolidin-3-amine 240i was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous off-white solid (53% yield).

$^1$H NMR (400 MHz, CDCl$_3$): δ 8.38 (s, 1H), 7.84 (d, J=7.5 Hz, 1H), 7.80 (s, 1H), 7.27-7.23 (m, 2H), 6.89-6.85 (m, 2H), 6.57 (s, 1H), 6.45 (s, 1H), 6.31 (dd, J=2.3, 7.4 Hz, 1H), 3.99 (s, 3H), 3.94 (s, 3H), 3.80 (s, 3H), 3.79 (s, 2H), 3.59-3.47 (m, 3H), 3.40-3.33 (m, 1H), 3.21-3.14 (m, 1H), 2.29-2.19 (m, 1H), 1.98-1.89 (m, 1H); HPLC (Method 1) >99% (AUC), t$_R$=9.95 min.; ESI MS m/z 493 [M+H]$^+$.

Preparation of (S)-tert-butyl (4-(((1-(2-(5-chloro-2,4-dimethoxyphenyl)imidazo[1,2-a]pyridin-7-yl)pyrrolidin-3-yl)amino)methyl)phenyl)carbamate 240j (Example 386)

Compound (S)-tert-butyl (4-(((1-(2-(5-chloro-2,4-dimethoxyphenyl)imidazo[1,2-a]pyridin-7-yl)pyrrolidin-3-yl)amino)methyl)phenyl)carbamate 240j was prepared in the same manner as (S)-1-(2-(5-chloro-2,4-dimethoxyphenyl)imidazo[1,2-a]pyridin-7-yl)-N-(pyridin-4-ylmethyl)pyrrolidin-3-amine (the free base of 240a), and was obtained as an amorphous off-white solid (60% yield).

$^1$H NMR (400 MHz, CDCl$_3$): δ 8.39 (s, 1H), 7.84 (d, J=7.5 Hz, 1H), 7.80 (s, 1H), 7.32 (d, J=8.5 Hz, 2H), 7.28-7.23 (m, 2H), 6.57 (s, 1H), 6.45 (bs, 2H), 6.31 (dd, J=2.3, 7.5 Hz, 1H), 3.99 (s, 3H), 3.94 (s, 3H), 3.80 (s, 2H), 3.58-3.46 (m, 3H), 3.40-3.32 (m, 1H), 3.20-3.11 (m, 1H), 2.28-2.18 (m, 1H), 1.96-1.86 (m, 1H), 1.51 (s, 9H). HPLC (Method 1) 97.8%/o (AUC), t$_R$=10.54 min; ESI MS m/z 578 [M+H]$^+$.

Preparation of (S)-tert-butyl (4-(((1-(2-(5-chloro-2,4-dimethoxyphenyl)imidazo[1,2-a]pyridin-7-yl)pyrrolidin-3-yl)amino)methyl)phenyl)(methyl)carbamate 240k (Example 394)

Compound (S)-tert-butyl (4-(((1-(2-(5-chloro-2,4-dimethoxyphenyl)imidazo[1,2-a]pyridin-7-yl)pyrrolidin-3-yl)amino)methyl)phenyl)(methyl)carbamate 240k was prepared in the same manner as (S)-1-(2-(5-chloro-2,4-dimethoxyphenyl)imidazo[1,2-a]pyridin-7-yl)-N-(pyridin-4-ylmethyl)pyrrolidin-3-amine (the free base of 240a), and was obtained as an amorphous off-white solid (40% yield).

$^1$H NMR (400 MHz, CDCl$_3$): δ 8.38 (s, 1H), 7.84 (d, J=7.4 Hz, 1H), 7.80 (s, 1H), 7.29 (d, J=8.5 Hz, 2H), 7.19 (d, J=8.4 Hz, 2H), 6.57 (s, 1H), 6.46 (bs, 1H), 6.31 (dd, J=2.3, 7.5 Hz, 1H), 3.99 (s, 3H), 3.94 (s, 3H), 3.83 (s, 2H), 3.60-3.48 (m, 3H), 3.41-3.34 (m, 1H), 3.24 (s, 3H), 3.21-3.16 (m, 1H), 2.29-2.20 (m, 1H), 1.98-1.89 (m, 1H), 1.44 (s, 9H). HPLC (Method 1) 94.9% (AUC), t$_R$=10.59 min; ESI MS m/z 592 [M+H]$^+$.

Preparation of (S)-1-(2-(5-chloro-2,4-dimethoxyphenyl)imidazo[1,2-a]pyridin-7-yl)-N-((2-fluoropyridin-4-yl)methyl)pyrrolidin-3-amine dihydrochloride 240l (Example 412)

Compound (S)-1-(2-(5-chloro-2,4-dimethoxyphenyl)imidazo[1,2-a]pyridin-7-yl)-N-((2-fluoropyridin-4-yl)methyl)pyrrolidin-3-amine dihydrochloride 240l was prepared in the same manner as the (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous off-white solid (60% yield).

$^1$H NMR (400 MHz, DMSO-d$_6$): δ 13.52 (s, 1H), 10.30 (bs, 1H), 10.09 (bs, 1H), 8.56 (d, J=7.2 Hz, 1H), 8.33 (d, J=4.4 Hz, 1H), 8.26 (s, 1H), 8.00 (s, 1H), 7.61 (bs, 1H), 7.50 (bs, 1H), 7.01-6.95 (m, 2H), 6.42 (s, 1H), 4.37 (bs, 2H), 4.05 (s, 3H), 3.98 (s, 3H), 3.82 (bs, 2H), 3.74 (bs, 1H), 3.58-3.48 (m, 1H), 2.44 (bs, 1H); HPLC (same as Method 1, except detection a) 220 nm) 94.5% (AUC), t$_R$=9.60 min; ESI MS m/z 482 [M+H]$^+$.

Preparation of (S)-1-(2-(5-chloro-2,4-dimethoxyphenyl)imidazo[1,2-a]pyridin-7-yl)-N-((2-chloropyridin-4-yl)methyl)pyrrolidin-3-amine dihydrochloride 240m (Example 413)

Compound (S)-1-(2-(5-chloro-2,4-dimethoxyphenyl)imidazo[1,2-a]pyridin-7-yl)-N-((2-chloropyridin-4-yl)methyl)pyrrolidin-3-amine dihydrochloride 240m was prepared in the same manner as the (S)-1-(2-(5-chloro-2,4-dimethoxyphenyl)imidazo[1,2-a]pyridin-7-yl)-N-(pyridin-4-ylmethyl)pyrrolidin-3-amine trihydrochloride 240a, and was obtained as an amorphous off-white solid (65% yield).

$^1$H NMR (400 MHz, DMSO-d$_6$): δ 13.58 (s, 1H), 10.26 (bs, 1H), 10.08 (bs, 1H), 8.56 (d, J=7.9 Hz, 1H), 8.50 (d, J=4.7 Hz, 1H), 8.27 (s, 1H), 8.02 (s, 1H), 7.85 (bs, 1H), 7.69 (d, J=4.2 Hz, 1H), 7.01-6.94 (m, 2H), 6.43 (s, 1H), 4.34 (bs, 2H), 4.09-3.95 (m, 7H), 3.84 (bs, 2H), 3.78-3.69 (m, 1H), 3.58-3.49 (m, 1H), 2.45 (bs, 1H). HPLC (Method 1) >99% (AUC), t$_R$=9.71 min; ESI MS m/z 498 [M+H]$^+$.

Preparation of (S)-tert-butyl 4-(((1-(2-(5-chloro-2,4-dimethoxyphenyl)imidazo[1,2-a]pyridin-7-yl)pyrrolidin-3-yl)amino)methyl)piperidine-1-carboxylate 240n (Example Compound (S)-tert-butyl 4-(((1-(2-(5-chloro-2,4-dimethoxyphenyl)imidazo[1,2-a]pyridin-7-yl)pyrrolidin-3-yl)amino)methyl)piperidine-1-carboxylate 240n was prepared in the same manner as (S)-1-(2-(5-chloro-2,4-dimethoxyphenyl)imidazo[1,2-a]pyridin-7-yl)-N-(pyridin-4-ylmethyl)pyrrolidin-3-amine (the free base of 240a), and was obtained as an amorphous off-white solid (40% yield).

$^1$H NMR (400 MHz, CDCl$_3$): δ 8.38 (s, 1H), 7.85 (d, J=7.5 Hz, 1H), 7.79 (s, 1H), 6.57 (s, 1H), 6.48 (bs, 1H), 6.33 (dd, J=2.2, 7.4 Hz, 1H), 4.11 (bs, 2H), 3.99 (s, 3H), 3.95 (s, 3H), 3.61-3.54 (m, 1H), 3.54-3.45 (m, 2H), 3.42-3.34 (m, 1H), 3.15-3.10 (m, 1H), 2.751-2.62 (m, 2H), 2.60-2.50 (m, 2H), 2.29-2.19 (m, 1H), 1.93-1.83 (m, 1H), 1.70 (bs, 3H), 1.45 (s, 9H), 1.19-1.06 (m, 2H), HPLC (Method 1) >99% (AUC), t$_R$=10.28 min; ESI MS m/z 570 [M+H]$^+$.

Preparation of (3S)-1-(2-(5-chloro-2,4-dimethoxyphenyl)imidazo[1,2-a]pyridin-7-yl)-N-(1-(pyridin-4-yl)ethyl)pyrrolidin-3-amine dihydrochloride 240o (Example 407)

A 50 mL RBF was charged with (S)-1-(2-(5-chloro-2,4-dimethoxyphenyl)imidazo[1,2-a]pyridin-7-yl)pyrrolidin-3-amine (50 mg, 0.134 mmol), 1-(pyridin-4-yl)ethanone (18 mg, 0.147 mmol), 4 mL of methanol/l-IF (1:1) and HOAc (15.4 µL, 0.147 mmol). The reaction mixture was stirred at 50° C. for 3 hours before NaCNBH$_3$ (10 mg, 0.147 mmol) was added. The reaction mixture was stirred at room temperature overnight. The reaction mixture was concentrated under reduced pressure and then diluted with dichloromethane (500 mL). The organic layer was washed with NaHCO$_3$ solution, followed by water and then brine; dried over Na$_2$SO$_4$, filtered and concentrated. The residue was purified by column chromatography (silica-gel, 90:9:1 Dichloromethane/MeOH/Ammonium hydroxide) to afford (3S)-1-(2-(5-chloro-2,4-dimethoxyphenyl)imidazo[1,2-a]pyridin-7-yl)-N-(1-(pyridin-4-yl)ethyl)pyrrolidin-3-amine which was converted to dihydrochloride salt 240o (18 mg, 28%) as a light brown solid.

$^1$H NMR (400 MHz, DMSO-d$_6$): δ 13.54 (s, 1H), 10.97-10.11 (m, 2H), 8.76 (s, 2H), 8.56 (t, J=6.6, 13.8 Hz, 1H), 8.27 (s, 1H), 8.00 (d, J=6.3 Hz, 1H), 7.89 (s, 2H), 6.98 (s, 1H), 6.97-6.90 (m, 1H), 6.39 (dd, J=2.2, 16.2 Hz, 1H), 4.67 (bs, 1H), 4.05 (s, 3H), 3.98 (s, 3H), 3.83-3.64 (m, 6H), 2.34 (bs, 2H), 1.68 (d, J=6.7 Hz, 3H). HPLC (Method 1) 95.2% (AUC), t$_R$=9.12 min; ESI MS m/z 478 [M+H]$^+$.

Preparation of (3S)-1-(2-(5-chloro-2,4-dimethoxyphenyl)imidazo[1,2-a]pyridin-7-yl)-N-(1-cyclohexylethyl)pyrrolidin-3-amine 240 (Example 416)

Compound (3S)-1-(2-(5-chloro-2,4-dimethoxyphenyl)imidazo[1,2-a]pyridin-7-yl)-N-(1-cyclohexylethyl)pyrrolidin-3-amine 240p was prepared in the same manner as (3S)-1-(2-(5-chloro-2,4-dimethoxyphenyl)imidazo[1,2-a]pyridin-7-yl)-N-(1-(pyridin-4-yl)ethyl)pyrrolidin-3-amine (the free base of dihydrochloride salt 240o), and was obtained as an amorphous off-white solid (20% yield).

$^1$H NMR (400 MHz, CDCl$_3$): δ 8.38 (d, J=1.2 Hz, 1H), 7.84 (d, J=7.4 Hz, 1H), 7.79 (s, 1H), 6.57 (s, 1H), 6.47 (bs, 1H), 6.33 (d, J=7.2 Hz, 1H), 3.99 (s, 3H), 3.94 (s, 3H), 3.64-3.53 (m, 2H), 3.53-3.45 (m, 1H), 3.41-3.32 (m, 1H), 3.12-3.04 (m, 1H), 2.58-2.48 (m, 1H), 2.30-2.16 (m, 1H), 1.89-1.80 (m, 1H), 1.79-1.71 (m, 3H), 1.71-1.63 (m, 3H), 1.35-1.09 (m, 5H), 1.08-0.94 (m, 5H). HPLC (Method 1) >99% (AUC), t$_R$=10.21 min; ESI MS m/z 483 [M+H]$^+$.

Preparation of tert-butyl 4-(1-(((S)-1-(2-(5-chloro-2,4-dimethoxyphenyl)imidazo[1,2-a]pyridin-7-yl)pyrrolidin-3-yl)amino)ethyl)piperidine-1-carboxylate 240a (Example Compound tert-butyl 4-(1-(((S)-1-(2-(5-chloro-2,4-dimethoxyphenyl)imidazo[1,2-a]pyridin-7-yl)pyrrolidin-3-yl)amino)ethyl)piperidine-1-carboxylate 240q was prepared in the same manner as (3S)-1-(2-(5-chloro-2,4-dimethoxyphenyl)imidazo[1,2-a]pyridin-7-yl)-N-(1-(pyridin-4-yl)ethyl)pyrrolidin-3-amine (the free base of dihydrochloride salt 240o), and was obtained as a light yellow solid (65% yield).

$^1$H NMR (300 MHz, CDCl$_3$): δ 8.38 (s, 1H), 7.85 (d, J=7.6 Hz, 1H), 7.81 (s, 1H), 6.57 (s, 1H), 6.43 (bs, 1H), 6.31 (dd, J=2.2, 7.5 Hz, 1H), 4.15 (bs, 2H), 3.99 (s, 3H), 3.94 (s, 3H), 3.63-3.52 (m, 2H), 3.52-3.44 (m, 1H), 3.41-3.31 (m, 1H), 3.10-3.02 (m, 1H), 2.71-2.49 (m, 3H), 2.29-2.13 (m, 1H), 1.90-1.68 (m, 2H), 1.45 (s, 9H), 1.26-1.13 (m, 2H), 1.09-1.02 (m, 3H). HPLC (same as Method 1, except detection @ 220 nm) 94.7% (AUC), t$_R$=10.34 min; ESI MS m/z 584 [M+H]$^+$.

Preparation of (S)-1-(2-(5-chloro-2,4-dimethoxyphenyl)imidazo[1,2-a]pyridin-7-yl)-N-((1-(cyclopropylsulfonyl)piperidin-4-yl)methyl)pyrrolidin-3-amine 240r (Example 421)

Compound (S)-tert-butyl 4-(((1-(2-(5-chloro-2,4-dimethoxyphenyl)imidazo[1,2-a]pyridin-7-yl)pyrrolidin-3-yl)amino)methyl)piperidine-1-carboxylate 240n was treated with TFA/CH$_2$Cl$_2$ for 2 h at room temperature concentrated and basified with ammonium hydroxide to give (S)-1-(2-(5-chloro-2,4-dimethoxyphenyl)imidazo[1,2-a]pyridin-7-yl)-N-(piperidin-4-ylmethyl)pyrrolidin-3-amine, which was converted to (S)-1-(2-(5-chloro-2,4-dimethoxyphenyl)imidazo[1,2-a]pyridin-7-yl)-N-((1-(cyclopropylsulfonyl)piperidin-4-yl)methyl)pyrrolidin-3-amine 240r in the same manner as N-(1-(2-(5-chloro-2,4-dimethoxyphenyl)imidazo[1,2-a]pyridine-7-yl)pyrrolidin-3-yl)cyclopropanesulfonamide (17a, Example 63).

$^1$H NMR (400 MHz, CDCl$_3$): δ 8.38 (s, 1H), 7.85 (d, J=7.3 Hz, 1H), 7.81 (s, 1H), 6.57 (s, 1H), 6.46 (bs, 1H), 6.32 (dd, J=2.3, 7.4 Hz, 1H), 3.99 (s, 3H), 3.95 (s, 3H), 3.86-3.78 (m, 2H), 3.61-3.54 (m, 1H), 3.54-3.45 (m, 2H), 3.42-3.34 (m, 1H), 3.16-3.10 (m, 1H), 2.84-2.72 (m, 2H), 2.63-2.53 (m, 2H), 2.29-2.19 (m, 2H), 1.93-1.79 (m, 3H), 1.39-1.24 (m, 3H), 1.19-1.12 (m, 2H), 1.00-0.93 (m, 2H). HPLC (same as Method 1, except detection @ 220 nm) 94.2% (AUC), t$_R$=9.79 min; ESI MS m/z 574 [M+H]$^+$.

Scheme 2-1

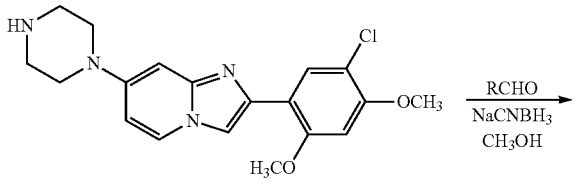

301

-continued

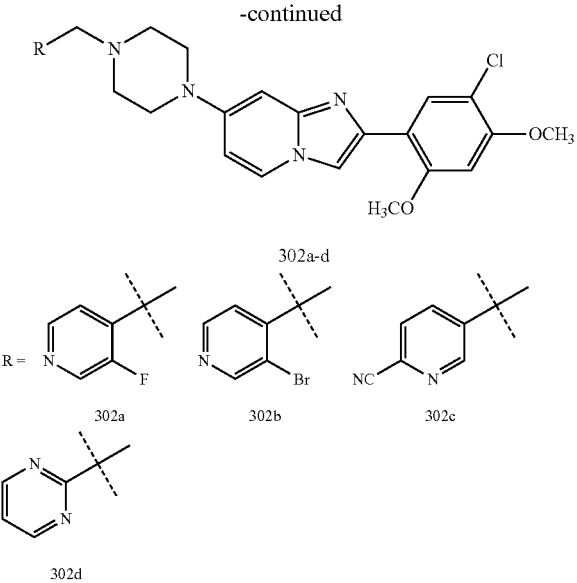

302a-d

R = 302a (3-fluoropyridin-4-yl), 302b (3-bromopyridin-4-yl), 302c (pyridine-nitrile), 302d (pyrimidin-2-yl)

Preparation of 2-(5-chloro-2,4-dimethoxyphenyl)-7-(4-((3-fluoropyridin-4-yl)methyl)piperazin-1-yl) imidazo[1,2-a]pyridine 302a (Example 336)

A suspension of 2-(5-chloro-2,4-dimethoxyphenyl)-7-(piperazin-1-yl)imidazo[1,2-a]pyridine 301 (150 mg, 0.40 mmol), 3-fluoroisonicotinaldehyde (75 mg, 0.60 mmol), in CH$_3$OH (10 mL) was added acetic acid (0.2 mL) and the resulting mixture was stirred for 1 h. Sodium cyanoborohydride (126 mg, 2.0 mmol) was added and the reaction mixture was stirred at room temperature overnight. The reaction mixture was diluted with aqueous sodium bicarbonate solution and extracted with CH$_2$Cl$_2$ (2×20 mL). The combined organic layers were dried over sodium sulfate, filtered and concentrated under reduced pressure and the residue was purified by combi-flash companion (silica gel, CH$_3$OH/CH$_2$Cl$_2$) to afford 2-(5-chloro-2,4-dimethoxyphenyl)-7-(4-((3-fluoropyridin-4-yl)methyl)piperazin-1-yl)imidazo[1,2-a]pyridine 302a (25 mg, 13%) as an off-white solid.

$^1$H NMR (400 MHz, DMSO-d$_6$): δ 8.56 (s, 1H), 8.43 (d, J=4.0 Hz, 1H), 8.30 (d, 7.6 Hz, 1H), 8.16 (s, 1H), 8.01 (s, 1H), 7.54 (t, J=5.6 Hz, 1H), 6.86 (s, 1H), 6.80 (dd, J=2.0, 7.6 Hz, 1H), 6.65 (s, 1H), 4.00 (s, 3H), 3.93 (s, 3H), 3.67 (s, 2H), 3.24 (br s, 4H), 2.57 (br s, 4H), HPLC (Method 1) 98.2% (AUC), t$_R$=11.34 min, ESI+APCI MS m/z 482 [M+H].

Preparation of 7-(4-((3-bromopyridin-4-yl)methyl) piperazin-1-yl)-2-(5-chloro-2,4-dimethoxyphenyl) imidazo[1,2-a]pyridine 302b (Example 345)

7-(4-((3-Bromopyridin-4-yl)methyl)piperazin-1-yl)-2-(5-chloro-2,4-dimethoxyphenyl)imidazo[1,2-a]pyridine 302b was prepared in the same manner as 2-(5-chloro-2,4-dimethoxyphenyl)-7-(4-((3-fluoropyridin-4-yl)methyl)piperazin-1-yl)imidazo[1,2-a]pyridine 302a and was obtained as an off-white solid (34% yield).

$^1$H NMR (400 MHz, DMSO-d$_6$): δ 8.71 (s, 1H), 8.54 (d, J=5.2 Hz, 1H), 8.31 (d, J=7.6 Hz, 1H), 8.16 (s, 1H), 8.02 (s, 1H), 7.58 (d, J=4.6 Hz, 1H), 6.87 (s, 1H), 6.82 (d, J=7.6 Hz, 1H), 6.67 (s, 1H), 4.00 (s, 3H), 3.93 (s, 3H), 3.65 (s, 2H), 3.27 (br s, 4H), 2.62 (br s, 4H); HPLC (Method 1) 91.7% (AUC), t$_R$=11.74 min; ESI+APCI MS m/z 542 [M+H]$^+$.

Preparation of 5-((4-(2-(5-chloro-2,4-dimethoxyphenyl)imidazo[1,2-a]pyridin-7-yl) piperazin-1-yl) methyl)nicotinonitrile 302c (Example 339)

Compound 5-((4-(2-(5-chloro-2,4-dimethoxyphenyl)imidazo[1,2-a]pyridin-7-yl)piperazin-1-yl)methyl)picolinonitrile 302c was prepared in the same manner as 2-(5-chloro-2,4-dimethoxyphenyl)-7-(4-((3-fluoropyridin-4-yl)methyl) piperazin-1-yl)imidazo[1,2-a]pyridine 302a, and was obtained as an off-white solid (16% yield).

$^1$H NMR (400 MHz, DMSO-d$_6$): δ 8.73 (s, 1H), 8.30 (d, J=7.5 Hz, 1H), 8.16 (s, 1H), 8.02 (d, J=2.7 Hz, 3H), 6.86 (s, 1H), 6.79 (dd, J=2.1, 7.5 Hz, 1H), 6.66 (s, 1H), 4.00 (s, 3H), 3.93 (s, 3H), 3.69 (s, 2H), 3.24 (br s, 4H), 2.54 (br s, 4H); HPLC (Method 1) 96.4% (AUC), t$_R$=11.47 min: ESI+APCI MS m/z 489 [M+H]$^+$.

Preparation of 2-(5-chloro-2,4-dimethoxyphenyl)-7-(4-(pyrimidin-2-ylmethyl)piperazin-1-yl)imidazo[1, 2-a]pyridine 2d (Example 352)

Compound 2-(5-chloro-2,4-dimethoxyphenyl)-7-(4-(pyrimidin-2-ylmethyl)piperazin-1-yl)imidazo[1,2-a]pyridine 302d was prepared in the same manner as 2-(5-chloro-2,4-dimethoxyphenyl)-7-(4-((3-fluoropyridin-4-yl)methyl)piperazin-1-yl)imidazo[1,2-a]pyridine 302a, and was obtained as an off-white solid (18% yield).

$^1$H NMR (400 MHz, DMSO-d$_6$): δ 8.80 (d, J=5.2 Hz, 2H), 8.30 (d, J=7.6 Hz, 1H), 8.16 (s, 1H), 8.01 (s, 1H), 7.42 (t, J=4.8 Hz, 1H), 6.86 (s, 1H), 6.79 (dd, J=2.0, 7.6 Hz, 1H), 6.64 (s, 1H), 4.00 (s, 3H), 3.93 (s, 3H), 3.78 (s, 2H), 3.22 (br s, 4H), 2.67 (br s, 4H); HPLC (Method 1) 97.6% (AUC), t$_R$=11.11 min: ESI+APCI MS m/z 465 [M+H]$^+$.

Scheme 2-2

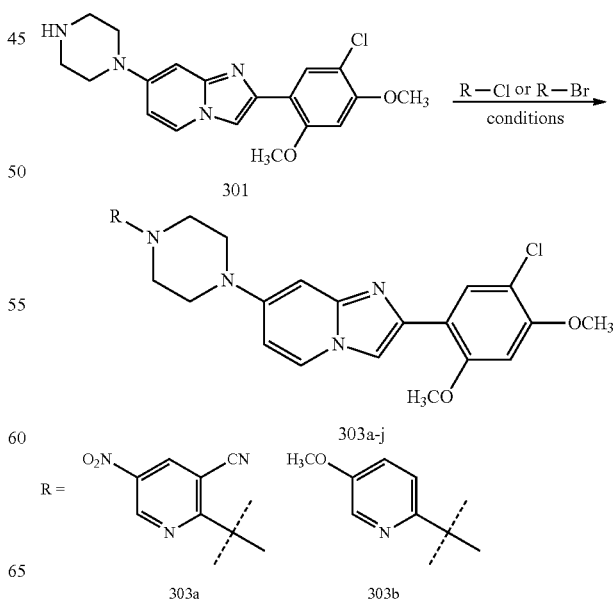

-continued

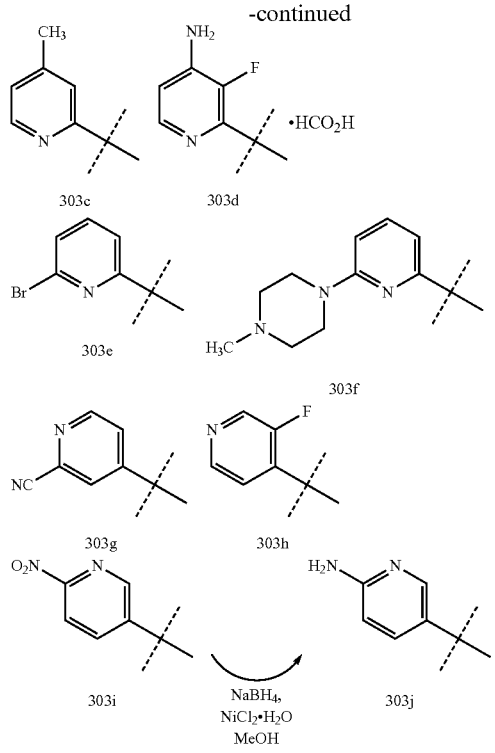

Preparation of 2-(4-(2-(5-chloro-2,4-dimethoxyphenyl)imidazo[1,2-a]pyridin-7-yl)piperazin-1-yl)-5-nitronicotinonitrile 303a (Example 349)

A solution of 2-(5-chloro-2,4-dimethoxyphenyl)-7-(piperazin-1-yl)imidazo [1,2-a]pyridine 301 (100 mg, 0.26 mmol) and N,N-diisopropylethylamine (0.13 mL, 0.80 mmol) in DMF (3 mL) was charged with 2-chloro-5-nitronicotinonitrile (58 mg, 0.31 mmol). The reaction mixture was stirred at 80-90° C. for 16 h. The reaction mixture was cooled to room temperature, suspended in water and stirred for 1 h. The precipitate was collected by filtration, the solid obtained was washed with water, dried under reduced pressure, and purified by combi-flash companion (silica gel, $CH_3OH/CH_2Cl_2$) to provide 2-(4-(2-(5-chloro-2,4-dimethoxyphenyl)imidazo[1,2-a]pyridin-7-yl)piperazin-1-yl)-5-nitronicotinonitrile 303a (25 mg, 18%) as an off-white solid.
$^1$H NMR (400 MHz, DMSO-$d_6$): δ 9.15 (d, J=2.8 Hz, 1H), 8.87 (d, J=2.8 Hz, 1H), 8.36 (d, J=7.6 Hz, 1H), 8.17 (s, 1H), 8.03 (s, 1H), 6.87 (s, 1H), 6.84 (dd, J=7.6, 2.4 Hz, 1H), 6.71 (s, 1H), 4.15 (br s, 4H), 4.01 (s, 3H), 3.93 (s, 3H), 3.47 (br s, 4H); HPLC (Method 1) 99.0% (AUC), $t_R$=14.11 min.; ESI+APCI MS m/z 520 [M+H]$^+$.

Preparation of 2-(5-chloro-2,4-dimethoxyphenyl)-7-(4-(5-methoxypyridin-2-yl)piperazin-1-yl)imidazo[1,2-a]pyridine 303b (Example 321)

A suspension of 2-(5-chloro-2,4-dimethoxyphenyl)-7-(piperazin-1-yl)imidazo[1,2-a]pyridine 1 (100 mg, 0.27 mmol), 2-chloro-5-methoxypyridine (42 mg, 0.29 mmol), (±)BINAP (17 mg, 0.027 mmol) and t-BuOK (90 mg, 0.80 mmol) in 1,4-dioxane (20 mL) was degassed with argon for 15 min. The mixture was then charged with Pd(OAc)$_2$ (9.0 mg, 0.013 mmol) and degassed with argon for another 5 min. The resulting reaction mixture was stirred at 100-110° C. for 16 h in a sealed tube. The reaction mixture was cooled, filtered through a pad of celite and evaporated to dryness. The residue obtained was purified by combi-flash companion (silica gel, $CH_3OH/CH_2Cl_2$) to provide 2-(5-chloro-2,4-dimethoxyphenyl)-7-(4-(pyridin-3-yl)piperazin-1-yl)imidazo[1,2-a]pyridine 303b (25 mg, 19%) as an off-white solid.
$^1$H NMR (400 MHz, DMSO-$d_6$): δ 8.33 (d, J=2.8 Hz, 1H), 8.35 (d, J=7.6 Hz, 1H), 8.18 (s, 1H), 8.03 (m, 1H), 7.91 (d, J=2.8 Hz, 1H), 7.30 (dd, J=9.2, 3.2 Hz, 1H), 6.91 (d, J=9.2 Hz, 1H), 6.87 (s, 1H), 6.85 (d, J=2.4 Hz, 1H), 6.27 (s, 1H), 4.01 (s, 3H), 3.93 (s, 3H), 3.74 (s, 3H), 3.54-3.52 (m, 4H), 3.51-3.32 (m, 4H); HPLC (Method 1) 92.8% (AUC), $t_R$=11.80 min.; ESI+APCI MS m/z 480 [M+H]$^+$.

Preparation of 2-(5-chloro-2,4-dimethoxyphenyl)-7-(4-(4-methylpyridin-2-yl)piperazin-1-yl)imidazo[1,2-a]pyridine 303c (Example 327)

Compound 2-(5-chloro-2,4-dimethoxyphenyl)-7-(4-(4-methylpyridin-2-yl)piperazin-1-yl)imidazo[1,2-a]pyridine 303c was prepared in the same manner as 2-(5-chloro-2,4-dimethoxyphenyl)-7-(4-(5-methoxypyridin-2-yl)piperazin-1-yl)imidazo[1,2-a]pyridine 303b and was obtained as an off-white solid (20% yield).
$^1$H NMR (400 MHz, DMSO-$d_6$): δ 8.33 (d, J=7.6 Hz, 1H), 8.17 (s, 1H), 8.03 (s, 1H), 8.00 (d, J=1.2 Hz, 1H), 6.87 (s, 2H), 6.73 (d, J=9.6 Hz, 2H), 6.52 (d, J=9.8 Hz, 1H), 4.01 (s, 3H), 3.93 (s, 3H), 3.66-3.63 (m, 4H), 3.39-3.35 (m, 4H), 2.24 (s, 3H); HPLC (Method 1) 90.2% (AUC), $t_R$=11.77 min.; ESI+APCI MS m/z 464 [M+H]$^+$.

Preparation of 2-(4-(2-(5-chloro-2,4-dimethoxyphenyl)imidazo[1,2-a]pyridin-7-yl)piperazin-1-yl)-3-fluoropyridin-4-amine formate 303d (Example 365)

A suspension of 2-(5-chloro-2,4-dimethoxyphenyl)-7-(piperazin-1-yl)imidazo[1,2-a]pyridine 301 (500 mg, 1.3 mmol), 2-chloro-3-fluoropyridin-4-amine (286 mg, 2.0 mmol), (±)BINAP (84 mg, 0.1 mmol) and t-BuOK (376 mg, 3.3 mmol) in 1,4-dioxane (20 mL) was degassed with argon for 15 min. The mixture was charged with Pd$_2$(dba)$_3$ (122 mg, 0.13 mmol) and degassed with argon for another 5 min. The resulting reaction mixture was stirred at 100-110° C. for 16 h. The reaction mixture was cooled, filtered through a pad of celite and evaporated to dryness. The residue obtained was purified by Prep HPLC to provide 2-(4-(2-(5-chloro-2,4-dimethoxyphenyl)imidazo[1,2-a]pyridin-7-yl)piperazin-1-yl)-3-fluoropyridin-4-amine formate 303d (18 mg) as an off-white solid.
$^1$H NMR (300 MHz, DMSO-$d_6$): δ 8.33 (d, J=7.5 Hz, 1H), 8.20 (d, J=16.8 Hz, 2H), 8.03 (s, 1H), 7.53 (d, J=5.1 Hz 1H), 6.85 (d, J=9.9, 2H), 6.71 (s, 1H), 5.90 (s, 2H), 4.01 (s, 3H), 3.93 (s, 3H), 3.42 (s, 4H), 3.34 (s, 4H). HPLC (Method 1) 94.9% (AUC), $t_R$=11.75 min. ESI+APCI MS m/z 483 [M+H]$^+$.

Preparation of 7-(4-(6-bromopyridin-2-yl)piperazin-1-yl)-2-(5-chloro-2,4-dimethoxyphenyl)imidazo[1,2-a]pyridine 303e Compound 7-(4-(6-bromopyridin-2-yl)piperazin-1-yl)-2-(5-chloro-2,4-dimethoxyphenyl) imidazo[1,2-a]pyridine 303e was prepared in the same manner as 2-(4-(2-(5-chloro-2,4-dimethoxyphenyl)imidazo[1,2-a]pyridin-7-yl)piperazin-1-yl)-5-nitronicotinonitrile 303a and was obtained as an off-white solid (46% yield). ESI+APCI MS m/z 528 [M+H]$^+$.

Preparation of 2-(5-chloro-2,4-dimethoxyphenyl)-7-(4-(6-(4-methylpiperazin-1-yl)pyridin-2-yl)piperazin-1-yl)imidazo[1,2-a]pyridine 303f (Example 381)

Compound 2-(5-chloro-2,4-dimethoxyphenyl)-7-(4-(4-methylpiperazin-1-yl)pyridin-2-yl)piperazin-1-yl)imidazo[1,2-a]pyridine 303f was prepared in the same manner as 2-(5-chloro-2,4-dimethoxyphenyl)-7-(4-(5-methoxypyridin-2-yl)piperazin-1-yl)imidazo[1,2-a]pyridine 303b and was obtained as an off-white solid (29% yield).

$^1$H NMR (400 MHz, DMSO-d$_6$): δ 8.34 (d, J=7.5 Hz, 1H), 8.17 (s, 1H), 8.03 (s, 1H), 7.35 (t, J=8.1 Hz, 1H), 6.87-6.84 (m, 2H), 6.71 (s, 1H), 6.18-6.10 (m, 2H), 4.01 (s, 3H), 3.93 (s, 3H), 3.58 (brs, 4H), 3.43 (brs, 4H), 3.35 (br s, 4H), 2.43 (br s, 4H), 2.24 (s, 3H); HPLC (Method 1) 90.2% (AUC), t$_R$=12.21 min.; ESI+APCI MS m/z 548 [M+H]$^+$.

Preparation of 4-(4-(2-(5-chloro-2,4-dimethoxyphenyl)imidazo[1,2-a]pyridin-7-yl)piperazin-1-yl)picolinonitrile 303g (Example 330)

A solution of 2-(5-chloro-2,4-dimethoxyphenyl)-7-(piperazin-1-yl) imidazo[1,2-a]pyridine 301 (150 mg, 0.40 mmol) and N,N-diisopropylethylamine (0.2 mL, 1.2 mmol) in DMF (3 mL) was charged with 4-chloropicolinonitrile (67 mg, 0.48 mmol). The reaction mixture was stirred at 100-110° C. for 16 h in a sealed tube. The reaction mixture was cooled to room temperature, suspended in water and stirred for 1 h. The precipitate was collected by filtration, the solid obtained was washed with water, dried under reduced pressure, and purified by combi-flash companion (silica gel, CH$_3$OH/CH$_2$Cl$_2$) to provide 4-(4-(2-(5-chloro-2,4-dimethoxyphenyl)imidazo[1,2-a]pyridin-7-yl)piperazin-1-yl)picolinonitrile 303g (40 mg, 21%) as an off-white solid.

$^1$H NMR (400 MHz, DMSO-d$_6$): δ 8.34 (d, J=7.6 Hz, 1H), 8.26 (d, J=6 Hz, 1H), 8.17 (s, 1H), 8.03 (s, 1H), 7.56 (d, J=2.4 Hz, 1H), 7.13 (dd, J=2.4, 6 Hz, 1H), 6.87 (m, 2H), 6.72 (s, 1H), 4.01 (s, 3H), 3.93 (s, 3H), 3.61 (br s, 4H), 3.37 (br s, 4H); HPLC (Method 1) 91.4% (AUC), t$_R$=12.34 min.; ESI+APCI MS m/z 475 [M+H]$^+$.

Preparation of 2-(5-chloro-2,4-dimethoxyphenyl)-7-(4-(3-fluoropyridin-4-yl)piperazin-1-yl)imidazo[1,2-a]pyridine 303h (Example 322)

Compound 2-(5-chloro-2,4-dimethoxyphenyl)-7-(4-(3-fluoropyridin-4-yl)piperazin-1-yl)imidazo[1,2-a]pyridine 303h was prepared in the same manner as 4-(4-(2-(5-chloro-2,4-dimethoxyphenyl)imidazo[1,2-a]pyridin-7-yl)piperazin-1-yl)picolinonitrile 303 g, and was obtained as an off-white solid (16% yield).

$^1$H NMR (400 MHz, DMSO-d$_6$): δ 8.34 (d, J=7.2 Hz, 1H), 8.29 (d, J=5.6 Hz, 1H), 8.18 (s, 1H), 8.03 (s, 1H), 7.04 (t, J=7.6 Hz, 1H), 6.87 (s, 1H), 6.84 (s, 1H), 6.73 (s, 1H), 4.01 (s, 3H), 3.93 (s, 3H), 3.42 (br s, 4H), 3.40 (br s, 4H), HPLC (Method 1) 93.2%0/(AUC), t$_R$=11.96 min.; ESI+APCI MS m/z 468 [M+H]$^+$.

Preparation of 2-(5-chloro-2,4-dimethoxyphenyl)-7-(4-(6-nitropyridin-3-yl)piperazin-1-yl)imidazo[1,2-a]pyridine 303i A solution of 2-(5-chloro-2,4-dimethoxyphenyl)-7-(piperazin-1-yl)imidazo[1,2-a]pyridine 301 (200 mg, 0.53 mmol) and N,N-diisopropylethylamine (0.26 mL, 1.59 mmol) in DMF (4 mL) was charged with 5-bromo-2-nitropyridine (130 mg, 0.64 mmol). The reaction mixture was stirred at 65° C. for 16 h. The reaction mixture was cooled to room temperature, suspended in water and stirred for 1 h. The precipitate was collected by filtration, the solid obtained was washed with water, dried under reduced pressure, and purified by combi-flash companion (silica gel, CH$_3$OH/CH$_2$Cl$_2$) to provide 2-(5-chloro-2,4-dimethoxyphenyl)-7-(4-(6-nitropyridin-3-yl)piperazin-1-yl)imidazo[1,2-a]pyridine 303i (110 mg, 41%) as pale yellow solid. ESI+APCI MS m/z 495 [M+H]$^+$.

Preparation of 5-(4-(2-(5-chloro-2,4-dimethoxyphenyl)imidazo[1,2-a]pyridin-7-yl)piperazin-1-yl)pyridin-2-amine 303j (Example 323)

To a solution of 2-(5-chloro-2,4-dimethoxyphenyl)-7-(4-(6-nitropyridin-3-yl)piperazin-1-yl)imidazo[1,2-a]pyridine 303i (110 mg, 0.22 mmol) in CH$_3$OH (10 mL) cooled at 0-5° C., was added NiCl$_2$.H$_2$O (212 mg, 0.89 mmol). The resulting mixture was stirred for 10 min and then charged with NaBH$_4$ (66 mg, 1.7 mmol). The reaction mixture was stirred for another 20 min at the same temperature. The reaction mixture was diluted with water, filtered through a pad of celite and the filtrate was extracted with CH$_2$Cl$_2$ (2×20 mL). The combined organic layers were dried over sodium sulfate, filtered and concentrated under reduced pressure and the residue was purified by combi-flash companion (silica gel, CH$_3$OH/CH$_2$Cl$_2$) to afford 5-(4-(2-(5-chloro-2,4-dimethoxyphenyl)imidazo[1,2-a]pyridin-7-yl)piperazin-1-yl)pyridin-2-amine 303j (10 mg, 10%) as an off-white solid.

$^1$H NMR (400 MHz, DMSO-d$_6$): δ 8.33 (d, J=7.6 Hz, 1H), 8.17 (s, 1H), 8.03 (s, 1H), 7.67 (d, J=2.8 Hz, 1H), 7.25 (dd, J=3.2, 9.2 Hz, 1H), 6.86 (m, 2H), 6.71 (s, 1H), 6.44 (d, J=8.8 Hz, 1H), 5.46 (br s, 2H), 4.01 (s, 3H), 3.93 (s, 3H), 3.36 (br s, 4H), 3.09 (br s, 4H); ESI+APCI MS m/z 465 [M+H]$^+$.

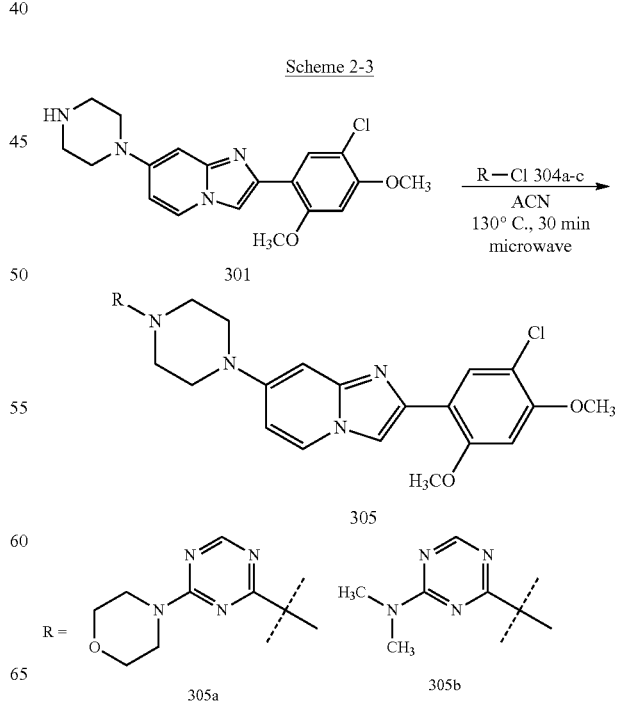

Scheme 2-3

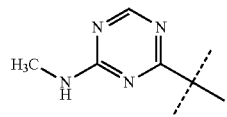
305c

Synthesis of R—Cl 304:

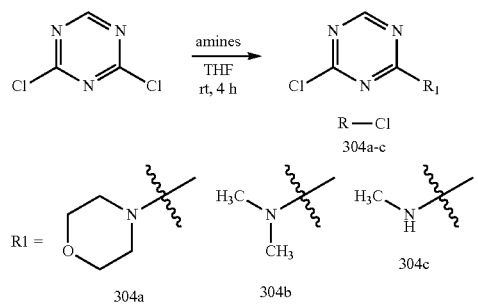

Preparation of 4-(4-(4-(2-(5-chloro-2,4-dimethoxy-phenyl)imidazo[1,2-a]pyridin-7-yl)piperazin-1-yl)-1,3,5-triazin-2-yl)morpholine 305a; (Example 449)

To a solution of 2,4-dichloro-1,3,5-triazine (200 mg, 1.34 mmol) in THF (5.0 mL) was added morpholine (151.0 mg, 1.74 mmol). The reaction mixture was stirred at ambient temperature for 3 h and then quenched with water. The precipitate was collected by filtration, washed with water and dried to give compound 4-(4-chloro-1,3,5-triazin-2-yl)morpholine 304a (150 mg, crude), which was used in the next step without further purification. ESI+APCI MS m/z 201 [M+H]$^+$.

To a solution of 2-(5-chloro-2,4-dimethoxyphenyl)-7-(piperazin-1-yl)imidazo[1,2-a]pyridine 301 (100 mg, 0.26 mmol) in CH$_3$CN (1.0 mL) was added 4-(4-chloro-1,3,5-triazin-2-yl)morpholine 304a (81 mg, 1.40 mmol). The reaction mixture was heated at 130° C. in a microwave reactor for 30 min before it was quenched with water. The precipitate formed was collected by filtration, washed with water and dried. The crude material was purified by combi-flash companion (silica gel, 90:9:1 CH$_2$Cl$_2$/MeOH/Ammonium hydroxide) to provide 4-(4-(4-(2-(5-chloro-2,4-dimethoxyphenyl)imidazo[1,2-a]pyridin-7-yl)piperazin-1-yl)-1,3,5-triazin-2-yl)morpholine 305a as an off-white solid (7.0 mg, 5%).

$^1$H NMR (300 MHz, DMSO-d$_6$): δ 8.38 (d, J=7.5 Hz, 1H), 8.19 (s, 1H), 8.14 (s, 1H), 8.06 (s, 1H), 6.90 (d, J=7.8 Hz, 1H), 6.88 (s, 1H), 6.71 (s, 1H), 4.01 (s, 3H), 3.94 (s, 3H), 3.89 (s, 4H), 3.72 (d, J=4.2 Hz, 4H), 3.62 (s, 4H), 3.33 (s, 4H). HPLC (Method 4) 97.5% (AUC), t$_R$=12.41 min. ESI+APCI MS m/z 537 [M+H]$^+$.

Preparation of 4-(4-(2-(5-chloro-2,4-dimethoxyphenyl)imidazo[1,2-a]pyridin-7-yl)piperazin-1-yl)-N,N-dimethyl-1,3,5-triazin-2-amine 305b (Example 450)

To a solution of 2,4-dichloro-1,3,5-triazine (200 mg, 1.34 mmol) in THF (5.0 mL) was added N,N-dimethylamine hydrochloride (119 mg, 1.47 mmol) and DIPEA (518 mg, 4.0 mmol). The reaction mixture was stirred at ambient temperature for 3 h and then quenched with water. The precipitate formed was collected by filtration, washed with water and dried to give compound 4-chloro-N,N-dimethyl-1,3,5-triazin-2-amine 304b (120 mg). The crude material was used in the next step without further purification. ESI+APCI MS m/z 159 [M+H]$^+$.

Compound 4-(4-(2-(5-chloro-2,4-dimethoxyphenyl)imidazo[1,2-a]pyridin-7-yl)piperazin-1-yl)-N,N-dimethyl-1,3,5-triazin-2-amine 305b was prepared in the same manner as 4-(4-(4-(2-(5-chloro-2,4-dimethoxyphenyl)imidazo[1,2-a]pyridin-7-yl)piperazin-1-yl)-1,3,5-triazin-2-yl)morpholine 305a, and was obtained as an off-white solid (22% yield).

$^1$H NMR (300 MHz, DMSO-d$_6$): δ 8.36 (d, J=7.5 Hz, 1H), 8.15 (s, 1H), 8.14 (s, 1H), 8.04 (s, 1H), 6.87 (bs, 2H), 6.71 (s, 1H), 4.01 (s, 3H), 3.93 (s, 3H), 3.89 (s, 4H), 3.33 (s, 4H), 3.09 (s, 6H). HPLC (Method 4) 98.5% (AUC), t$_R$=12.00 min. ESI+APCI MS m/z 495 [M+H]$^+$.

Preparation 4-(4-(2-(5-chloro-2,4-dimethoxyphenyl)imidazo[1,2-a]pyridin-7-yl)piperazin-1-yl)-N-methyl-1,3,5-triazin-2-amine 305c (Example 451)

Compound 4-chloro-N-methyl-1,3,5-triazin-2-amine 304c was prepared in the same manner as 4-chloro-N,N-dimethyl-1,3,5-triazin-2-amine 304b, and the crude material was used in the next step without further purification. ESI+APCI MS m/z 145 [M+H]$^+$.

Compound 4-(4-(2-(5-chloro-2,4-dimethoxyphenyl)imidazo[1,2-a]pyridin-7-yl)piperazin-1-yl)-N-methyl-1,3,5-triazin-2-amine 305c was prepared in the same manner as 4-(4-(4-(2-(5-chloro-2,4-dimethoxyphenyl)imidazo[1,2-a]pyridin-7-yl)piperazin-1-yl)-1,3,5-triazin-2-yl)morpholine 305a, and was obtained as an off-white solid (23% yield).

$^1$H NMR (300 MHz, DMSO-d$_6$): δ 8.35 (d, J=7.5 Hz, 1H), 8.17 (s, 1H), 8.03 (bs, 2H), 7.35-7.23 (m, 1H), 6.87 (s, 1H), 6.87 (d, J=10.5 Hz, 1H), 6.72 (s, 1H), 4.01 (s, 3H), 3.93 (s, 3H), 3.89 (bs, 4H), 3.33 (bs, 4H), 2.78 (d, J=4.5 Hz, 3H). HPLC (Method 4) 95.1% (AUC), t$_R$=11.91 min. ESI+APCI MS m/z 481 [M+H]$^+$.

Scheme 2-4

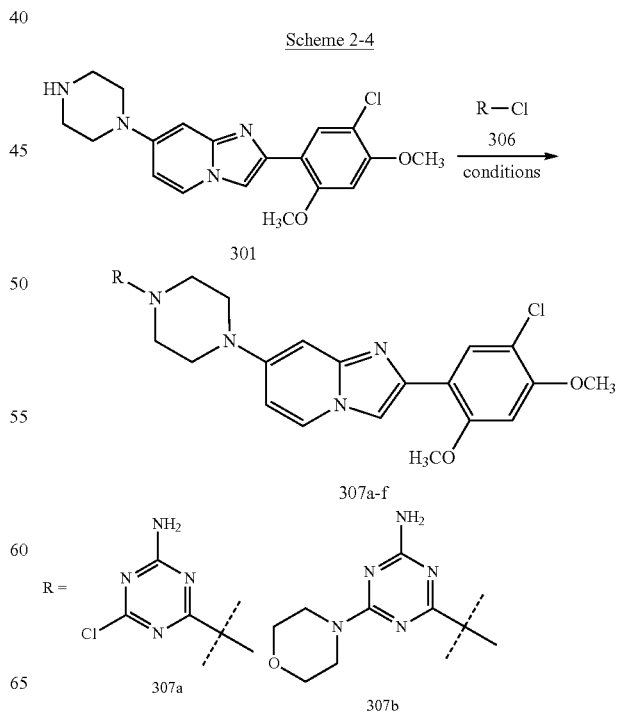

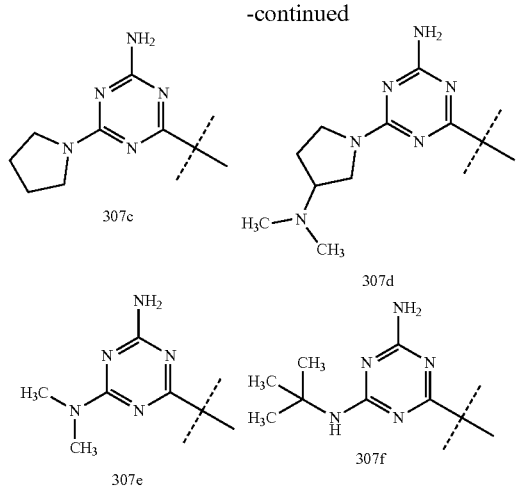

307c

307d

307e

307f

Synthesis of R—Cl 306:

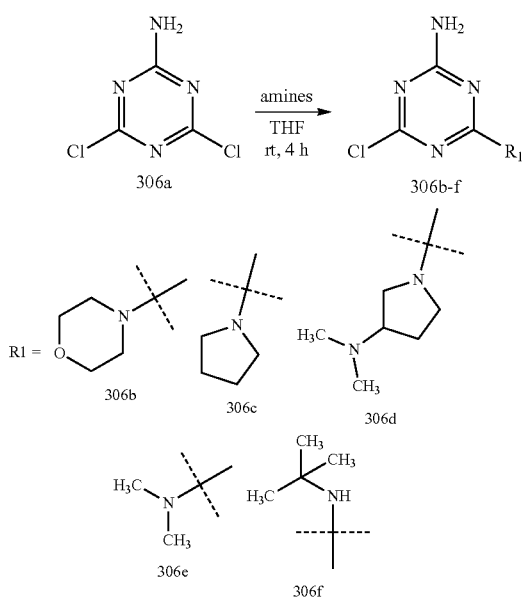

$R_1 =$ 306b 306c 306d 306e 306f

Preparation of 4-chloro-6-(4-(2-(5-chloro-2,4-dimethoxyphenyl)imidazo[1,2-a]pyridin-7-yl)piperazin-1-yl)-1,3,5-triazin-2-amine 307a (Example 361)

To a solution of 2-(5-chloro-2,4-dimethoxyphenyl)-7-(piperazin-1-yl)imidazo[1,2-a]pyridine 301 (300 mg, 0.80 mmol) in CH$_3$CN (1.0 mL) was added 4,6-dichloro-1,3,5-triazin-2-amine 306a (266 mg, 1.61 mmol). The reaction mixture was heated at 130° C. in a microwave reactor for 30 min. The reaction mixture was then quenched with water and the precipitate formed was collected by filtration, washed with water and dried. The crude material was purified by combi-flash companion (silica gel, 90:9:1 CH$_2$Cl$_2$/MeOH/Ammonium hydroxide) to give 4-chloro-6-(4-(2-(5-chloro-2,4-dimethoxyphenyl)imidazo[1,2-a]pyridin-7-yl)piperazin-1-yl)-1,3,5-triazin-2-amine 307a (120 mg, 29%) as an off-white solid.
$^1$H NMR (300 MHz, DMSO-d$_6$): δ 8.38 (d, J=7.5 Hz, 1H), 8.14 (s, 1H), 8.06 (s, 1H), 7.43 (d, J=15.3 Hz, 2H), 6.91-6.85 (m, 2H), 6.73 (s, 1H), 4.01 (s, 3H), 3.94 (s, 3H), 3.90-3.80 (m, 4H), 3.40-3.30 (m, 4H). HPLC (Method 1) 91.4% (AUC), t$_R$=13.0 min.

ESI+APCI MS m/z 501 [M+H]$^+$.

Preparation of 4-(4-(2-(5-chloro-2,4-dimethoxyphenyl)imidazo[1,2-a]pyridin-7-yl)piperazin-1-yl)-6-morpholino-1,3,5-triazin-2-amine 307b (Example 379)

To a solution of 4,6-dichloro-1,3,5-triazin-2-amine 306a (150 mg, 0.90 mmol) in THF (5.0 mL) was added morpholine (87 mg, 1.00 mmol). The reaction mixture was stirred at ambient temperature for 1 h. The reaction mixture was quenched with water and the precipitate formed was collected by filtration, washed with water and dried to give compound 4-chloro-6-morpholino-1,3,5-triazin-2-amine 306b (150 mg). The crude compound was used in the next step without further purification. ESI+APCI MS m/z 216 [M+H]$^+$.

Compound 4-(4-(2-(5-chloro-2,4-dimethoxyphenyl)imidazo[1,2-a]pyridin-7-yl)piperazin-1-yl)-6-morpholino-1,3,5-triazin-2-amine 307b was prepared in the same manner as compound 4-chloro-6-(4-(2-(5-chloro-2,4-dimethoxyphenyl)imidazo[1,2-a]pyridin-7-yl)piperazin-1-yl)-1,3,5-triazin-2-amine 307a, and was obtained as an off-white solid (7% yield).
$^1$H NMR (300 MHz, DMSO-d$_6$): δ 8.35 (d, J=7.5 Hz, 1H), 8.16 (s, 1H), 8.03 (s, 1H), 6.87 (s, 1H), 6.87 (d, J=12.9 Hz, 1H), 6.72 (s, 1H), 6.36 (bs, 2H), 4.01 (s, 3H), 3.93 (s, 3H), 3.87-3.75 (m, 4H), 3.69-3.54 (m, 8H), 3.28-3.20 (m, 4H). HPLC (Method 1) 98.1% (AUC), t$_R$=11.86 min. ESI+APCI MS m/z 552 [M+H]$^+$.

Preparation 4-(4-(2-(5-chloro-2,4-dimethoxyphenyl)imidazo[1,2-a]pyridin-7-yl)piperazin-1-yl)-6-(pyrrolidin-1-yl)-1,3,5-triazin-2-amine 307c (Example 431)

Compound 4-chloro-6-(pyrrolidin-1-yl)-1,3,5-triazin-2-amine 306c was prepared in the same manner as 4-chloro-6-morpholino-1,3,5-triazin-2-amine 306b and the crude material was used in the next step without further purification. ESI+APCI MS m/z 200 [M+H]$^+$.

Compound 4-(4-(2-(5-chloro-2,4-dimethoxyphenyl)imidazo[1,2-a]pyridin-7-yl)piperazin-1-yl)-6-(pyrrolidin-1-yl)-1,3,5-triazin-2-amine 307c was prepared in the same manner as 4-chloro-6-(4-(2-(5-chloro-2,4-dimethoxyphenyl)imidazo[1,2-a]pyridin-7-yl)piperazin-1-yl)-1,3,5-triazin-2-amine 307a, and was obtained as an off-white solid (10% yield).
$^1$H NMR (400 MHz, DMSO-d$_6$): δ 8.35 (d, J=7.2 Hz, 1H), 8.17 (s, 1H), 8.03 (s, 1H), 6.87-6.83 (m, 2H), 6.72 (s, 1H), 6.26 (bs, 2H), 4.01 (s, 3H), 3.93 (s, 3H), 3.87-3.79, 3.49-3.35 (m, 4H), 3.38-3.21 (m, 4H), 1.86 (t, J=6.4 Hz, 4H). HPLC (Method 5) 98.7% (AUC), t$_R$=12.74 min. ESI+APCI MS m/z 536 [M+H]$^+$.

Preparation of 4-(4-(2-(5-chloro-2,4-dimethoxyphenylimidazo[1,2-a]pyridin-7-yl)piperazin-1-yl)-6-(3-(dimethylamino)pyrrolidin-1-yl-1,3,5-triazin-2-amine 307d (Example 436)

Compound 4-chloro-6-(3-(dimethylamino)pyrrolidin-1-yl)-1,3,5-triazin-2-amine 306d was prepared in the same manner as 4-chloro-6-morpholino-1,3,5-triazin-2-amine 306b, the crude material was used in the next step without further purification. ESI+APCI MS m/z 243 [M+H]$^+$.

Compound 4-(4-(2-(5-chloro-2,4-dimethoxyphenyl)imidazo[1,2-a]pyridin-7-yl)piperazin-1-yl)-6-(3-(dimethylamino)pyrrolidin-1-yl)-1,3,5-triazin-2-amine 307d was prepared in the same manner as 4-chloro-6-(4-(2-(5-chloro-2,4-dimethoxyphenyl)imidazo[1,2-a]pyridin-7-yl)piperazin-1-yl)-1,3,5-triazin-2-amine 307a, and was obtained as an off-white solid (6.4% yield).

$^1$H NMR (400 MHz, DMSO-d$_6$): δ 8.35 (d, J=7.6 Hz, 1H), 8.18 (s, 1H), 8.03 (s, 1H), 6.87 (s, 1H), 8.85 (dd, J=2.4 Hz, 7.6 Hz, 1H), 6.72 (d, J=2.0 Hz, 1H), 6.30 (bs, 2H), 4.01 (s, 3H), 3.94 (s, 3H), 3.87-3.79 (m, 4H), 3.76-3.58 (m, 2H), 3.28-3.21 (m, 4H). 3.13-2.92 (m, 1H), 2.69-2.62 (m, 2H), 2.21-2.15 (m, 6H), 2.12-2.03 (m, 1H), 1.75-1.71 (m, 1H), HPLC (Method 1) 97.0% (AUC), t$_R$=11.1 min. ESI+APCI MS m/z 579 [M+H]$^+$.

Preparation of 6-(4-(2-(5-chloro-2,4-dimethoxyphenyl)imidazo[1,2-a]pyridin-7-yl)piperazin-1-yl)-N$^2$,N$^2$-dimethyl-1,3,5-triazine-2,4-diamine 307e (Example 440)

To a solution of 4,6-dichloro-1,3,5-triazin-2-amine 306a (300 mg, 2.72 mmol) in THF (5.0 mL) was added dimethylamine hydrochloride (220 mg, 1.00 mmol) and DIPEA (703 mg, 5.45 mmol). The reaction mixture was stirred at ambient temperature for 1 h and then quenched with water. The precipitate formed was collected by filtration, washed with water and dried to give 6-chloro-N$^2$,N$^2$-dimethyl-1,3,5-triazine-2,4-diamine 306e (150 mg).

The crude material was used in the next step without further purification.

ESI+APCI MS m/z 174 [M+H]$^+$.

Compound 6-(4-(2-(5-chloro-2,4-dimethoxyphenyl)imidazo[1,2-a]pyridin-7-yl)piperazin-1-yl)-N$^2$,N$^2$-dimethyl-1,3,5-triazine-2,4-diamine 307e was prepared in the same manner as 4-chloro-6-(4-(2-(5-chloro-2,4-dimethoxyphenyl)imidazo[1,2-a]pyridin-7-yl)piperazin-1-yl)-1,3,5-triazin-2-amine 307a, and was obtained as an off-white solid (22% yield).

$^1$H NMR (300 MHz, DMSO-d$_6$): δ 8.36 (d, J=7.5 Hz, 1H), 8.14 (s, 1H), 8.05 (s, 1H), 6.90-6.88 (m, 2H), 6.72 (s, 1H), 6.25 (bs, 2H), 4.01 (s, 3H), 3.94 (s, 3H), 3.88-3.80 (m, 4H), 3.28-3.21 (m, 4H), 3.02 (s, 6H). HPLC (Method 5) 99.69% (AUC), t$_R$=12.39 min. ESI+APCI MS m/z 510 [M+H]$^+$.

Preparation N$^2$-(tert-butyl)-6-(4-(2-(5-chloro-2,4-dimethoxyphenyl)imidazo[1,2-a]pyridin-7-yl)piperazin-1-yl)-1,3,5-triazine-2,4-diamine 307f (Example 446)

Compound N$^2$-(tert-butyl)-6-chloro-1,3,5-triazine-2,4-diamine 306f was prepared in the same manner as 4-chloro-6-morpholino-1,3,5-triazin-2-amine 306b, the crude material was used in the next step without further purification.
ESI+APCI MS m/z 202 [M+H]$^+$.

Compound N$^2$-(tert-butyl)-6-(4-(2-(5-chloro-2,4-dimethoxyphenyl)imidazo[1,2-a]pyridin-7-yl)piperazin-1-yl)-1,3,5-triazine-2,4-diamine 307f was prepared in the same manner as 4-chloro-6-(4-(2-(5-chloro-2,4-dimethoxyphenyl)imidazo[1,2-a]pyridin-7-yl)piperazin-1-yl)-1,3,5-triazin-2-amine 307a, and was obtained as an off-white solid (14% yield).

$^1$H NMR (400 MHz, DMSO-d$_6$): δ 8.34 (d, J=7.6 Hz, 1H), 8.17 (s, 1H), 8.02 (s, 1H), 6.86 (s, 1H), 6.85 (dd, J=2.4 Hz, 7.6 Hz, 1H), 6.72 (d, J=1.6 Hz 1H), 6.06 (bs, 3H), 4.00 (s, 3H), 3.93 (s, 3H), 3.85-3.78 (m, 4H), 3.30-3.23 (m, 4H), 1.36 (s, 9H). HPLC (Method 1) 99.2% (AUC), t$_R$=12.69 min. ESI+APCI MS m/z 538 [M+H]$^+$.

Scheme 2-5

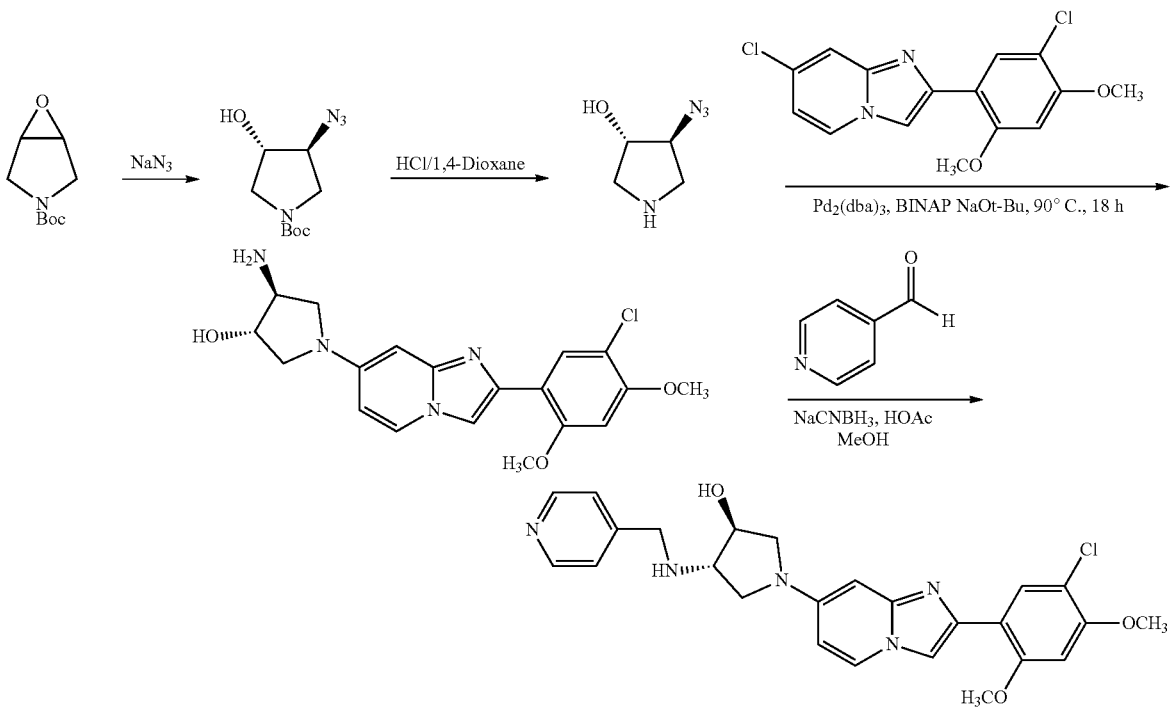

Preparation of trans-tert-butyl 3-azido-4-hydroxypyrrolidine-1-carboxylate

A 50 mL RBF was charged with tert-butyl 6-oxa-3-azabicyclo[3.1.0]hexane-3-carboxylate (500 mg, 2.69 mmol), 16 mL of methanol and 2 mL of water. To this solution NaN$_3$ (877 mg, 13.5 mmol) and NH$_4$Cl (647 mg, 12.1 mmol) were added and the reaction mixture was heated at 60° C. for 16 h. The reaction mixture was diluted with water and extracted with ethyl acetate (2×50 mL). The combined organic layers were washed with NaHCO$_3$ solution, followed by water and then brine; dried over Na$_2$SO$_4$, filtered and concentrated to afford trans-tert-butyl 3-azido-4-hydroxypyrrolidine-1-carboxylate (575 mg, 93%) as colorless syrup.

$^1$H NMR (400 MHz, CDCl$_3$): δ 4.27-4.21 (m, 1H), 3.92 (bs, 1H), 3.76-3.55 (m, 2H), 3.49-3.27 (m, 2H), 2.65-2.37 (m, 1H), 1.46 (s, 9H).

Preparation of trans-4-azidopyrrolidin-3-ol hydrochloride

A 50 mL RBF was charged with trans-tert-butyl 3-azido-4-hydroxypyrrolidine-1-carboxylate (570 mg, 2.49 mmol) and 5 mL of dichloromethane. To this solution was added HCl/1,4-dioxane (4 M, 2 mL) and the reaction mixture was stirred at room temperature for 2 h. Excess solvents were removed under reduced pressure to afford product trans-4-azidopyrrolidin-3-ol hydrochloride (400 mg, 95%) as brown solid, which was carried forward to the next step without further purification.

Preparation of trans-4-amino-1-(2-(5-chloro-2,4-dimethoxyphenyl)imidazo[1,2-a]pyridin-7-yl)pyrrolidin-3-ol A suspension of 7-chloro-2-(5-chloro-2,4-dimethoxyphenyl)imidazo[1,2-a]pyridine (50 mg, 0.15 mmol), trans-4-azidopyrrolidin-3-ol hydrochloride (28 mg, 0.17 mmol), (±) BINAP (12 mg, 0.01 mmol) and NaOt-Bu (45 mg, 0.46 mmol) in dioxane (5 mL) was degassed with argon for 15 min. Pd$_2$(dba)$_3$ (5.6 mg, 0.006 mmol) was added quickly. The resulting reaction mixture was stirred at 90° C. for 16 h. The reaction mixture was cooled, filtered through a pad of celite and evaporated to dryness. The residue obtained was purified by combi-flash companion (silica gel, CH$_1$OH/CH$_2$Cl$_2$) to provide trans-4-amino-1-(2-(5-chloro-2,4-dimethoxyphenyl)imidazo[1,2-a]pyridin-7-yl)pyrrolidin-3-ol (14 mg, 23%) as a light brown solid.

$^1$H NMR (400 MHz, CDCl$_3$): δ 8.25 (d, J=7.7 Hz, 1H), 8.16 (s, 1H), 7.93 (s, 1H), 6.85 (s, 1H), 6.45 (dd, J=2.3, 7.5 Hz, 1H), 6.17 (s, 1H), 5.15 (d, J=3.2 Hz, 1H), 3.99 (s, 3H), 3.97 (bs, 2H), 3.92 (s, 3H), 3.66-3.58 (m, 1H), 3.58-3.51 (m, 1H), 3.16-3.10 (m, 1H), 3.08-3.01 (m, 1H), HPLC (Same as Method 1, except the detection on 220 nM) 96.0% (AUC), $t_R$=9.21 min; ESI MS m/z 389 [M+H]$^+$.

Preparation of trans-1-(2-(5-chloro-2,4-dimethoxyphenyl)imidazo[1,2-a]pyridin-7-yl)-4-((pyridin-4-ylmethyl)amino)pyrrolidin-3-ol (Example 439)

Compound trans-1-(2-(5-chloro-2,4-dimethoxyphenyl)imidazo[1,2-a]pyridin-7-yl)-4-((pyridin-4-ylmethyl)amino)pyrrolidin-3-ol was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride (Example 298) and was obtained as a brown solid (50%).

$^1$H NMR (400 MHz, DMSO-d$_6$): 8.48 (dd, J=1.6, 4.5 Hz, 2H), 8.25 (d, J=7.4 Hz, 1H), 8.16 (s, 1H), 7.93 (s, 1H), 7.37 (d, J=6.0 Hz, 2H), 6.85 (s, 1H), 6.45 (dd, J=2.2, 7.4 Hz, 1H), 6.17 (d, J=1.8 Hz, 1H), 5.13 (d, J=4.0 Hz, 1H), 4.16 (s, H), 3.99 (s, 3H), 3.92 (s, 3H), 3.82 (s, 2H), 3.64-3.58 (m, 1H), 3.57-3.49 (m, 1H), 3.22-3.08 (m, 1H), ESI MS m/z 480 [M+H]I.

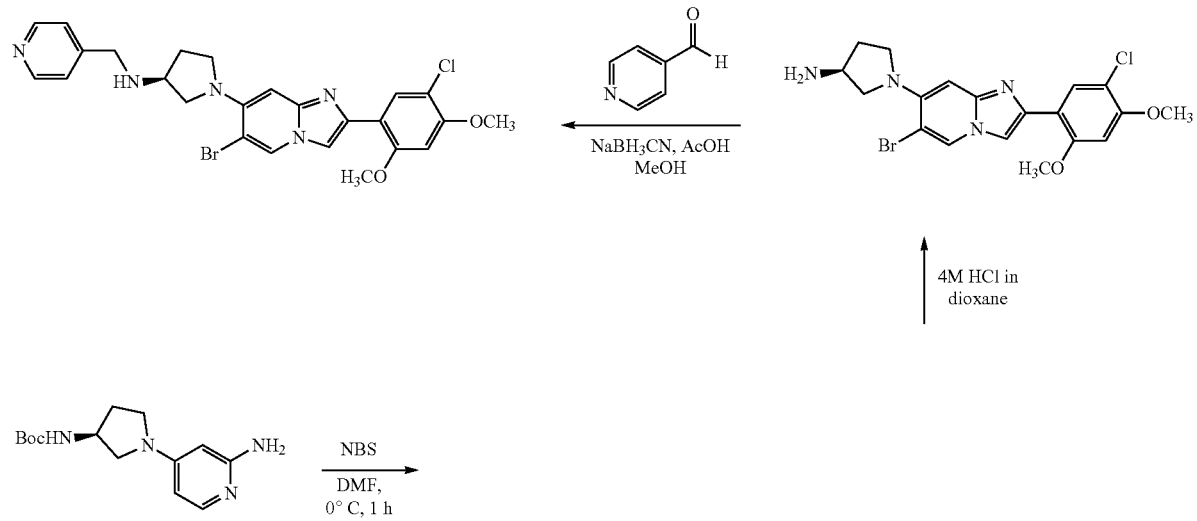

Scheme 2-6

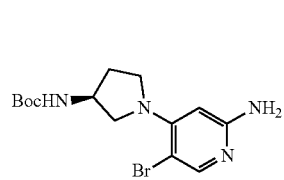
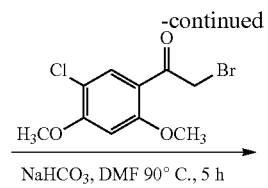
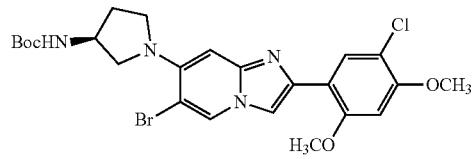

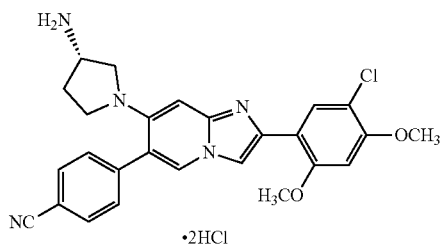
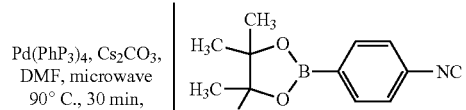
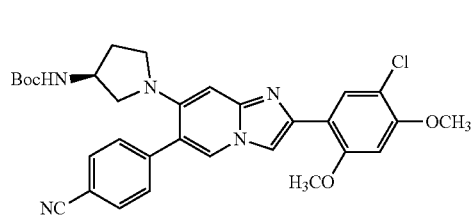

Preparation of tert-butyl (1-(2-amino-5-bromopyridin-4-yl)pyrrolidin-3-yl)carbamate To a solution of tert-butyl (1-(2-aminopyridin-4-yl) pyrrolidin-3-yl) carbamate (1.80 g, 6.47 mmol) in 20 mL of DMF was added NBS (1.15 g, 6.47 mmol) in portion at 0° C., and the reaction mixture was stirred at the same temperature for 1 h. The reaction mixture was diluted with water and extracted with CHCl$_3$ (4×100 mL). The organic layer was washed with NaHCO$_3$ solution, followed by water and then brine; dried over Na$_2$SO$_4$, filtered and concentrated under reduced pressure. The residue was purified by column chromatography (silica gel, 9:1 CHCl$_3$/MeOH) to afford tert-butyl (1-(2-amino-5-bromopyridin-4-yl) pyrrolidin-3-yl) carbamate (700 mg, 30%) as a light brown solid.

$^1$H NMR (400 MHz, CDCl$_3$): δ 7.93 (s, 1H), 5.73 (s, 1H), 4.27 (bs, 1H), 4.23 (s, 2H), 3.78-3.68 (m, 2H), 3.54-3.46 (m, 1H), 3.44-3.37 (m, 1H), 2.25-2.14 (m, 1H), 1.95-1.85 (m, 1H),

Preparation of (S)-tert-butyl (1-(6-bromo-2-(5-chloro-2,4-dimethoxyphenyl)imidazo[1,2-a]pyridin-7-yl)pyrrolidin-3-yl)carbamate Compound (S)-tert-butyl (1-(6-bromo-2-(5-chloro-2,4-dimethoxyphenyl)imidazo[1,2-a]pyridin-7-yl)pyrrolidin-3-yl)carbamate was prepared in the same manner as (S)-tert-Butyl (1-(2-(5-chloro-2,4-dimethoxyphenyl)imidazo[1,2-a]pyridin-7-yl)pyrrolidin-3-yl)carbamate 77 (Example 44) and was obtained as a light brown solid (765 mg, 47%).

$^1$H NMR (400 MHz, CDCl$_3$): δ 8.33 (s, 1H), 8.21 (s, 1H), 7.85 (s, 1H), 6.95 (s, 1H), 6.57 (s, 1H), 4.83 (bs, 1H), 4.35 (bs, 1H), 4.00 (s, 3H), 3.96 (s, 3H), 3.68-3.60 (m, 1H), 3.60-3.52 (m, 1H), 3.42-3.35 (m, 1H), 3.34-3.25 (m, 1H), 2.38-2.27 (m, 1H), 1.95-1.86 (m, 1H), 1.46 (s, 9H).

Preparation of (S)-1-(6-bromo-2-(5-chloro-2,4-dimethoxyphenyl)imidazo[1,2-a]pyridin-7-yl)pyrrolidin-3-amine Compound (S)-tert-butyl (1-(6-bromo-2-(5-chloro-2,4-dimethoxyphenyl)-imidazo[1,2-a]pyridin-7-yl)pyrrolidin-3-yl)carbamate was treated with 4M HCl in 1,4-dioxane for 2 h; concentrated under reduced pressure and then basified with aqueous ammonia to afford (S)-1-(6-bromo-2-(5-chloro-2,4-dimethoxyphenyl)imidazo[1,2-a]pyridin-7-yl) pyrrolidin-3-amine as a yellow solid (78% yield).

$^1$H NMR (400 MHz, CDCl$_3$): δ 8.35 (s, 1H), 8.19 (s, 1H), 7.85 (s, 1H), 6.87 (s, 1H), 6.58 (s, 1H), 3.99 (s, 3H), 3.95 (s, 3H), 3.72-3.65 (m, 1H), 3.65-3.60 (m, 1H), 3.60-3.54 (m, 1H), 3.44-3.36 (m, 1H), 3.27-3.22 (m, 1H), 2.31-2.21 (m, 1H), 1.82-1.72 (m, 1H),

Preparation of (S)-1-(6-bromo-2-(5-chloro-2,4-dimethoxyphenyl)imidazo[1,2-a]pyridin-7-yl)-N-(pyridin-4-ylmethyl)pyrrolidin-3-amine (Example 438)

Compound (5)-1-(6-bromo-2-(5-chloro-2,4-dimethoxyphenyl)imidazo[1,2-a]pyridin-7-yl)-N-(pyridin-4-ylmethyl) pyrrolidin-3-amine was prepared in the same manner as the free base of (S)-1-(2-(5-chloro-2,4-dimethoxyphenyl)imidazo[1,2-a]pyridin-7-yl)-N-(pyridin-4-ylmethyl)pyrrolidin-3-amine trihydrochloride (Example 298) and was obtained as a yellow solid (48%).

$^1$H NMR (400 MHz, CDCl$_3$): δ 8.58-8.51 (m, 2H), 8.35 (s, 1H), 8.20 (s, 1H), 7.86 (s, 1H), 7.31-7.28 (m, 2H), 6.91 (s, 1H), 6.58 (s, 1H), 3.99 (s, 3H), 3.96 (s, 3H), 3.87 (s, 2H), 3.61-3.45 (m, 3H), 3.45-3.33 (m, 2H), 2.31-2.21 (m, 1H), 1.93-1.82 (m, 1H), HPLC (Method 2) 97.1% (AUC), $t_R$=11.69 min: ESI MS m/z 544[(M+2)+H]$^+$.

Preparation of (S)-tert-butyl (1-(2-(5-chloro-2,4-dimethoxyphenyl)-6-(4-cyanophenyl)imidazo[1,2-a]pyridin-7-yl)pyrrolidin-3-yl)carbamate Compound (S)-tert-butyl (1-(2-(5-chloro-2,4-dimethoxyphenyl)-6-(4-cyanophenyl)imidazo[1,2-a]pyridin-7-yl)pyrrolidin-3-yl)carbamate was prepared in the same manner as 4-(2-(5-chloro-2,4-dimethoxyphenyl)imidazo[1,2-a]pyridin-7-yl)-benzoic acid and was obtained as a yellow solid (42%).

¹H NMR (400 MHz, CDCl₃): δ 8.38 (s, 1H), 7.91 (s, 1H), 7.82 (s, 1H), 7.73 (d, J=8.4 Hz, 2H), 7.62 (d, J=8.4 Hz, 2H), 6.93 (s, 1H), 6.59 (s, 1H), 4.52 (bs, 1H), 4.14 (bs, 1H), 3.99 (s, 3H), 3.96 (s, 3H), 3.12-3.02 (m, 2H), 2.99-2.90 (m, 1H), 2.77-2.69 (m, 1H), 2.23-2.12 (m, 1H), 1.77-1.70 (m, 1H), 1.43 (s, 9H).

Preparation of (S)-4-(7-(3-aminopyrrolidin-1-yl)-2-(5-chloro-2,4-dimethoxyphenyl)imidazo[1,2-a]pyridin-6-yl)benzonitrile dihydrochloride (Example 445)

Compound (S)-4-(7-(3-aminopyrrolidin-1-yl)-2-(5-chloro-2,4-dimethoxyphenyl)imidazo[1,2-a]pyridin-6-yl)benzonitrile dihydrochloride was prepared by treating (S)-tert-butyl (1-(2-(5-chloro-2,4-dimethoxyphenyl)-6-(4-cyanophenyl)imidazo[1,2-a]pyridin-7-yl)pyrrolidin-3-yl)carbamate with 4M HCl in 1,4-dioxane for 2 h, concentrated under reduced pressure and finally lyophilized and was obtained as a white solid (69%).

¹H NMR (400 MHz, DMSO): δ 13.95 (s, 1H), 8.57 (s, 1H), 8.25 (s, 1H), 8.17 (s, 3H), 8.07 (s, 1H), 8.01 (d, J=8.2 Hz, 2H), 7.72 (d, J=8.2 Hz, 2H), 6.99 (s, 1H), 6.78 (s, 1H), 4.05 (s, 3H), 3.99 (s, 3H), 3.77 (s, 1H), 3.28-3.22 (m, 1H), 3.21-3.12 (m, 1H), 3.06-2.97 (m, 1H), 2.23-2.12 (m, 1H), 2.04-1.93 (m, 1H); HPLC (Method 1) 97.3% (AUC), t_R=9.62 in APCI MS m/z 474 [M+H]⁺.

Scheme 2-7

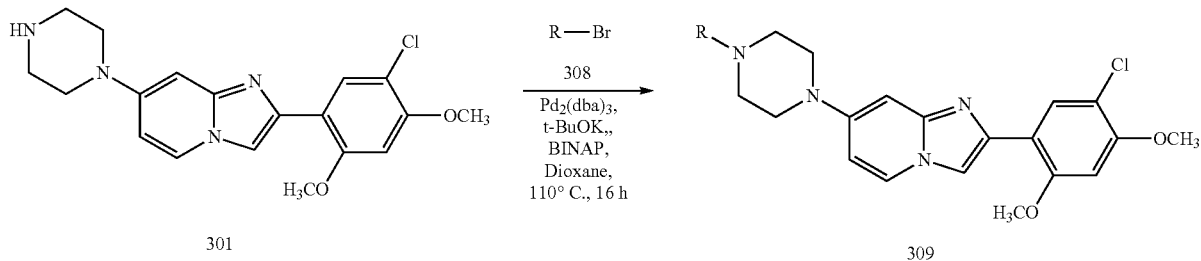

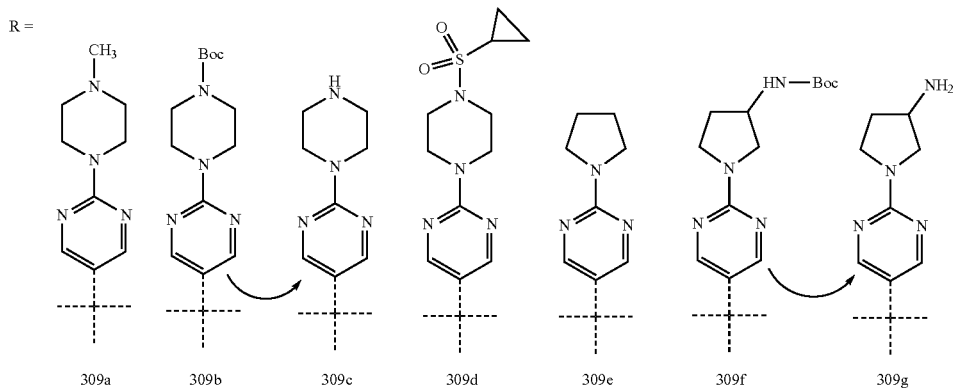

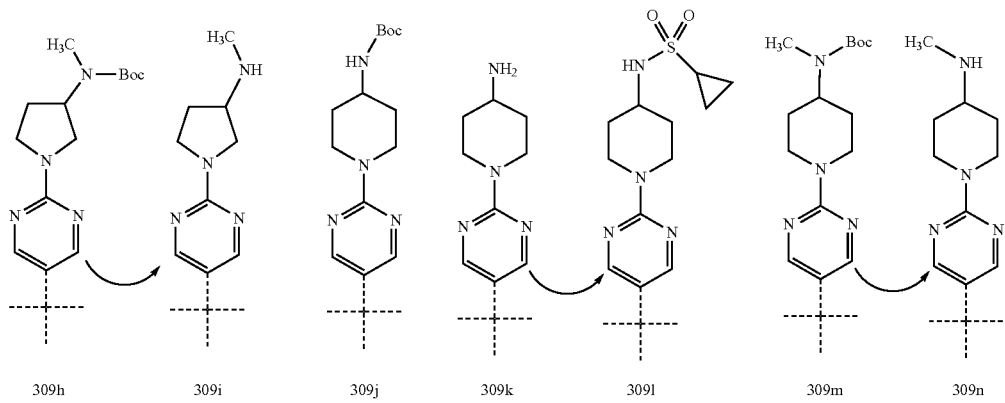

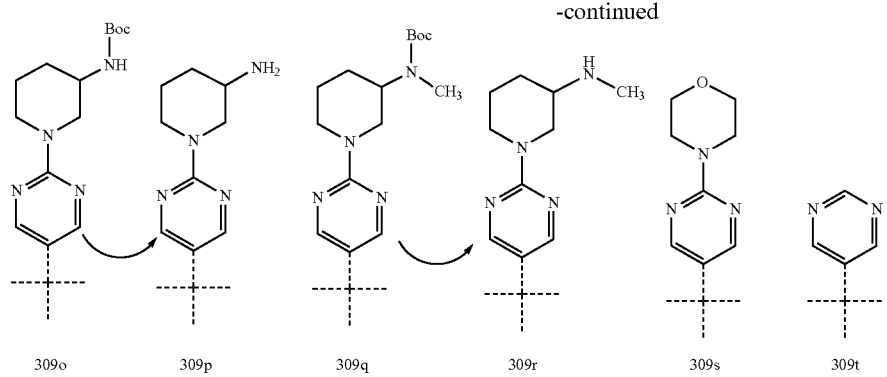

309o    309p    309q    309r    309s    309t

Synthesis of R-Cl 308:

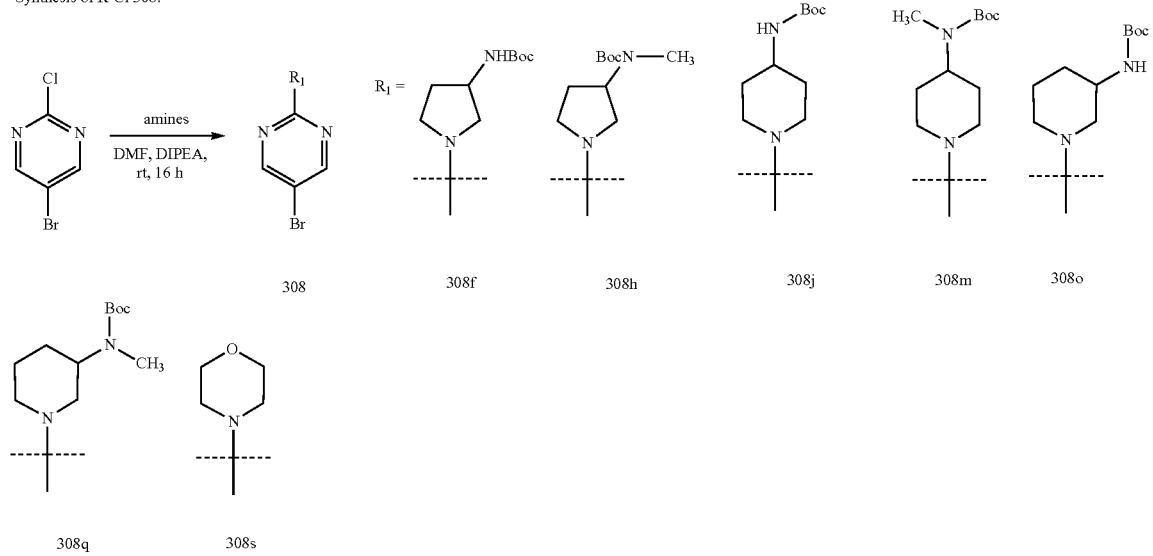

308    308f    308h    308j    308m    308o 308q    308s

Preparation of 2-(5-chloro-2,4-dimethoxyphenyl)-7-(4-(2-(4-methylpiperazin-1-yl)pyrimidin-5-yl)piperazin-1-yl)imidazo[1,2-a]pyridine 309a (Example 358)

A suspension of 2-(5-chloro-2,4-dimethoxyphenyl)-7-(piperazin-1-yl)imidazo[1,2-a]pyridine 301 (200 mg, 0.53 mmol), 5-bromo-2-(4-methylpiperazin-1-yl)pyrimidine (165 mg, 0.64 mmol), BINAP (33 mg, 0.05 mmol) and KOt-Bu (150 mg, 1.3 mmol) in 1,4-dioxane (8.0 mL) was degassed with argon for 15 min. To the suspension was added Pd$_2$(dba)$_3$ (49 mg, 0.05 mmol) and the reaction mixture was further degassed with argon for 5 min. The reaction mixture was stirred at 100-110° C. for 16 h before it was cooled to room temperature. The reaction mixture was filtered through a pad of celite and the filtrate was concentrated to dryness. The residue obtained was purified by combi-flash companion (silica gel, CH$_3$OH/CH$_2$Cl$_2$) to give 2-(5-chloro-2,4-dimethoxyphenyl)-7-(4-(2-(4-methylpiperazin-1-yl)pyrimidin-5-yl)piperazin-1-yl)imidazo[1,2-a]pyridine 309a (Example 358) (20 mg, 6.8%) as an off-white solid.

$^1$H NMR (400 MHz, DMSO-d$_6$): δ 8.34 (d, J=7.6 Hz, 1H), 8.27 (s, 2H), 8.18 (s, 1H), 8.04 (s, 1H), 6.87 (s, 1H), 6.85 (s, 1H), 6.74 (s, 1H), 4.01 (s, 3H), 3.94 (s, 3H), 3.63 (s, 4H), 3.37 (s, 4H), 3.16 (s, 4H), 2.38 (s, 4H), 2.22 (s, 3H). HPLC (Method 1) 92.31% (AUC), t$_R$=12.03 min. ESI+APCI MS m/z 549 [M+H]$^+$.

Preparation of tert-butyl 4-(5-(4-(2-(5-chloro-2,4-dimethoxyphenyl)imidazo[1,2-a]pyridin-7-yl)piperazin-1-yl)pyrimidin-2-yl)piperazine-1-carboxylate 309b A suspension of 2-(5-chloro-2,4-dimethoxyphenyl)-7-(piperazin-1-yl)imidazo[1,2-a]pyridine 301 (2.0 g, 5.3 mmol), tert-butyl 4-(5-bromopyrimidin-2-yl)piperazine-1-carboxylate (3.68 g, 10.8 mmol), BINAP (334 mg, 0.536 mmol) and NaOt-Bu (1.29 g, 13.4 mmol) in 1,4-dioxane (30 mL) was degassed with argon for 15 min. To the suspension was added Pd$_2$(dba)$_3$ (344 mg, 0.37 mmol) and the reaction mixture was further degassed with argon for 5 min. The reaction mixture was then stirred at 100-110° C. for 16 h before it was cooled to room temperature. The reaction mixture was filtered through a pad of celite and the filtrate was concentrated to dryness. The residue obtained was purified by combi-flash companion (silica gel, CH$_3$OH/CH$_2$Cl$_2$) to give tert-butyl 4-(5-(4-(2-(5-chloro-2,4-dimethoxyphenyl)imidazo[1,2-a]pyridin-7-yl)piperazin-1-yl)pyrimidin-2-yl)piperazine-1-carboxylate 309b (670 mg, 20%) as an light brown solid. ESI+APCI MS m/z 635 [M+H]$^+$.

Preparation of 2-(5-chloro-2,4-dimethoxyphenyl)-7-(4-(2-(piperazin-1-yl)pyrimidin-5-yl)piperazin-1-yl)imidazo[1,2-a]pyridine 309c (Example 344)

To a stirred solution of tert-butyl 4-(5-(4-(2-(5-chloro-2,4-dimethoxyphenyl)-imidazo[1,2-a]pyridin-7-yl)piperazin- 1-yl)pyrimidin-2-yl)piperazine-1-carboxylate 309b (30 mg, 0.047 mmol) in 2,2,2-trifluoroethanol (2.0 mL) was added trimethylsilyl chloride (0.04 mL) at 0° C., and the reaction mixture was stirred at same temperature until the consumption of the staring material as indicated by TLC analysis. The above reaction mixture was concentrated and lyophilized to give 2-(5-chloro-2,4-dimethoxyphenyl)-7-(4-(2-(piperazin-1-yl)pyrimidin-5-yl)piperazin-1-yl)imidazo[1,2-a]pyridine bis(2,2,2-trifluoroacetate) 309c (Example 344) (18 mg, 60%) as an yellow solid.

$^1$H NMR (400 MHz, DMSO-d$_6$): δ 13.73 (s, 1H), 9.10 (s, 2H), 8.57 (d, J=7.6 Hz, 1H), 8.34 (s, 2H), 8.29 (s, 1H), 8.03 (s, 1H), 7.39 (d, J=6.4 Hz, 1H), 6.99 (s, 1H), 6.83 (s, 1H), 4.06 (s, 3H), 3.99 (s, 3H), 3.85-3.84 (m, 4H), 3.67 (s, 4H), 3.22 (s, 4H), 3.14 (s, 4H). HPLC (Method 1) 94.80% (AUC), t$_R$=11.83 min. ESI+APCI MS m/z 534 [M+H]$^+$.

Preparation of 2-(5-chloro-2,4-dimethoxyphenyl)-7-(4-(2-(4-(cyclooroylsulfonyl)piperazin-1-yl)pyrimidin-5-yl)piperazin-1-yl)imidazo[1,2-a]pyridine 309d (Example 369)

A mixture of 2-(5-chloro-2,4-dimethoxyphenyl)-7-(4-(2-(piperazin-1-yl)pyrimidin-5-yl)piperazin-1-yl)imidazo[1,2-a]pyridine 309c (100 mg, 0.18 mmol), N,N-diisopropylethylamine (80 µL, 0.47 mmol) and cyclopropanesulfonyl chloride (20 µL, 0.49 mmol) in dichloromethane (4.0 mL) was stirred at room temperature for 2 h under N$_2$ atmosphere. The reaction mixture was diluted with water and extracted with CH$_2$Cl$_2$ (2×20 mL), the combined organic layers were dried over sodium sulfate, filtered and concentrated under reduced pressure. The residue was purified by prep HPLC to afford 2-(5-chloro-2,4-dimethoxyphenyl)-7-(4-(2-(4-(cyclopropylsulfonyl)piperazin-1-yl)pyrimidin-5-yl)piperazin-1-yl)imidazo[1,2-a]pyridine 2,2,2-trifluoroacetate 309d (Example 369) (10 mg, 7.3%) as an off-white solid.

$^1$H NMR (400 MHz, DMSO-d$_6$): δ 8.58 (d, J=8.0 Hz, 1H), 8.32 (s, 1H), 8.29 (s, 1H), 7.93 (s, 1H), 7.41 (dd, J=2.4, 7.6 Hz, 1), 6.96 (s, 1H), 6.79 (d, J=2 Hz, 1H), 4.06 (s, 3H), 3.99 (s, 3H), 3.75 (t, J=4.4 Hz, 4H), 3.67 (t, J=5.6 Hz, 4H), 3.25 (t, J=4.8 Hz, 4H), 3.22 (t, J=4.8 Hz, 4H), 2.63-2.59 (m, 1H), 1.01-0.91 (m, 4H), HPLC (Method 1) 95.71% (AUC), t$_R$=13.37 min. ESI+APCI MS m/z 638.8 [M+H]$^+$.

Preparation of 2-(5-chloro-2,4-dimethoxyphenyl)-7-(4-(2-(pyrrolidin-1-yl)pyrimidin-5-yl)piperazin-1-yl)imidazo[1,2-a]pyridine 309e (Example 333)

A suspension of 2-(5-chloro-2,4-dimethoxyphenyl)-7-(piperazin-1-yl)imidazo[1,2-a]pyridine 301 (200 mg, 0.53 mmol), 5-bromo-2-(pyrrolidin-1-yl)pyrimidine (236 mg, 1.00 mmol), BINAP (33 mg, 0.053 mmol) and KOt-Bu (180 mg, 1.6 mmol) in 1,4-dioxane (4.0 mL) was degassed with argon for 15 min. To the suspension was added Pd(OAc)$_2$ (18 mg, 0.026 mmol) and the reaction mixture was further degassed with argon for 5 min. The reaction mixture was stirred at 100-110° C. for 16 h before it was cooled to room temperature. The reaction mixture was filtered through a pad of celite, and the filtrate was concentrated to dryness. The residue was purified combi-flash companion (silica gel, CH$_3$OH/CH$_2$Cl$_2$) to provide 2-(5-chloro-2,4-dimethoxyphenyl)-7-(4-(2-(pyrrolidin-1-yl) pyrimidin-5-yl) piperazin-1-yl) imidazo[1,2-a]pyridine 309e (Example 333) (12 mg, 4%) as an off-white solid.

$^1$H NMR (300 MHz, DMSO-d$_6$): δ 8.34 (d, J=7.5 Hz, 1H), 8.24 (s, 2H), 8.17 (s, 1H), 8.04 (s, 1H), 6.88 (d, J=5.4 Hz, 2H), 6.73 (s, 1H), 4.01 (s, 3H), 3.93 (s, 3H), 3.46-3.37 (m, 8H), 3.12 (s, 4H), 1.93-1.89 (m, 4H). HPLC (Method 1) 98.4% (AUC), t$_R$=12.25 min. ESI+APCI MS m/z 520.0 [M+H]$^+$.

Preparation of tert-butyl (1-(5-bromopyrimidin-2-yl)pyrrolidin-3-yl)carbamate 308f To a solution of 5-bromo-2-chloropyrimidine (600 mg, 3.1 mmol) and N,N-diisopropylethylamine (1.35 mL, 7.7 mmol) in DMF (5 mL) was added tert-butyl pyrrolidin-3-ylcarbamate (634 mg, 3.4 mmol), the reaction mixture was stirred at room temperature for 16 h under N$_2$ atmosphere. The reaction mixture was diluted with water and extracted with EtOAc (2×20 mL). The combined organic layers were dried over Na$_2$SO$_4$, filtered and concentrated. The residue was triturated with n-Hexane and dried to give tert-butyl (1-(5-bromopyrimidin-2-yl)pyrrolidin-3-yl)carbamate 308f (700 mg, 66%) as an off-white solid. ESI+APCI MS m/z 344 [M+H]$^+$.

Preparation of tert-butyl (1-(5-(4-(2-(5-chloro-2,4-dimethoxyphenyl)imidazo[1,2-a]pyridin-7-yl)piperazin-1-yl)pyrimidin-2-yl)pyrrolidin-3-yl)carbamate 309f A suspension of 2-(5-chloro-2,4-dimethoxyphenyl)-7-(piperazin-1-yl)imidazo[1,2-a]pyridine 301 (300 mg, 0.81 mmol), tert-butyl (1-(5-bromopyrimidin-2-yl)pyrrolidin-3-yl)carbamate 308f (550 mg, 1.6 mmol), [(t-Bu)$_3$PH]BF$_4$ (11 mg, 0.04 mmol) and NaOt-Bu (232 mg, 2.4 mmol) in 1,4-dioxane (8 mL) was degassed with argon for 15 min. To the suspension was added Pd(OAc)$_2$ (9 mg, 0.04 mmol) and the reaction mixture was further degassed with argon for 5 min. The reaction mixture was stirred at 100-110° C. for 16 h before it was cooled to room temperature. The reaction mixture was filtered through a pad of celite and the filtrate was concentrated to dryness. The residue was purified by combi-flash companion (silica gel, CH$_3$OH/CH$_2$Cl$_2$) to give tert-butyl (1-(5-(4-(2-(5-chloro-2,4-dimethoxyphenyl)imidazo[1,2-a]pyridin-7-yl)piperazin-1-yl)pyrimidin-2-yl)pyrrolidin-3-yl)carbamate 309f (38 mg, 7%) as a light-yellow solid. ESI+APCI MS m/z 633 [M+H]$^+$.

Preparation of 1-(5-(4-(2-(5-chloro-2,4-dimethoxyphenyl)imidazo[1,2-a]pyridin-7-yl)piperazin-1-yl)pyrimidin-2-yl)pyrrolidin-3-amine dihydrochloride 309e (Example 378)

To a solution of tert-butyl (1-(5-(4-(2-(5-chloro-2,4-dimethoxyphenyl)imidazo[1,2-a]pyridin-7-yl)piperazin-1-yl)pyrimidin-2-yl)pyrrolidin-3-yl)carbamate 309f (75 mg, 0.11 mmol) in 2,2,2-trifluoroethanol (1 mL) was added TMS-Cl (0.1 mL) and the reaction mixture was stirred at room temperature for 1 h. The reaction mixture was evaporated to dryness and the residue was triturated with n-pentane to provide 1-(5-(4-(2-(5-chloro-2,4-dimethoxyphenyl)imidazo[1,2-a]pyridin-7-yl)piperazin-1-yl)pyrimidin-2-yl)pyrrolidin-3-amine dihydrochloride 309g (Example 378) (40 mg, 63%) as an off-white solid.

$^1$H NMR (300 MHz, DMSO-d$_6$): δ 13.84 (bs, 1H), 8.62 (d, J=6.0 Hz, 1H), 8.4-8.29 (m, 6H), 8.06 (t, J=7.2 Hz, 1H), 7.38 (d, J=7.8 Hz, 1H), 4.06 (s, 3H), 3.99 (s, 3H), 3.75-3.56 (m, 9H), 3.52-3.48 (m, 1H), 3.17 (m, 3H), 2.14-2.06 (m, 1H), HPLC (Method 1) 90.23% (AUC), t$_R$=11.49 min. ESI+APCI MS m/z 533 [M+H]$^+$.

Preparation of tert-butyl (1-(5-bromopyrimidin-2-yl) pyrrolidin-3-yl)(methyl)carbamate 308h Compound tert-butyl (1-(5-bromopyrimidin-2-yl)pyrrolidin-3-yl)(methyl)carbamate 308h was prepared in the same manner as compound tert-butyl (1-(5-bromopyrimidin-2-yl)pyrrolidin-3-yl)carbamate 308f, and was obtained in 76% yield. ESI+APCI MS m/z 357 [M+H]$^+$.

Preparation of tert-butyl (1-(5-(4-(2-(5-chloro-2,4-dimethoxyphenyl)imidazo[1,2-a]pyridin-7-yl)piperazin-1-yl)pyrimidin-2-yl)pyrrolidin-3-yl)(methyl)carbamate 309h Compound tert-butyl (1-(5-(4-(2-(5-chloro-2,4-dimethoxyphenyl)imidazo[1,2-a]pyridin-7-yl)piperazin-1-yl)pyrimidin-2-yl)pyrrolidin-3-yl)(methyl)carbamate 309h was prepared in the same manner as tert-butyl (1-(5-(4-(2-(5-chloro-2,4-dimethoxyphenyl)imidazo[1,2-a]pyridin-7-yl)piperazin-1-yl)pyrimidin-2-yl)pyrrolidin-3-yl)carbamate 309f and was obtained in 20% yield. ESI+APCI MS m/z 649 [M+H]$^+$.

Preparation of 1-(5-(4-(2-(5-chloro-2,4-dimethoxyphenyl)imidazo[1,2-a]pyridin-7-yl)piperazin-1-yl)pyrimidin-2-yl)-N-methylpyrrolidin-3-amine dihydrochloride 309i (Example 401)

Compound 1-(5-(4-(2-(5-chloro-2,4-dimethoxyphenyl)imidazo[1,2-a]pyridin-7-yl)piperazin-1-yl)pyrimidin-2-yl)-N-methylpyrrolidin-3-amine dihydrochloride 309i was prepared in the same manner as compound 1-(5-(4-(2-(5-chloro-2,4-dimethoxyphenyl)imidazo[1,2-a]pyridin-7-yl)piperazin-1-yl)pyrimidin-2-yl)pyrrolidin-3-amine dihydrochloride 309 g, and was obtained as amorphous yellow solid (78% yield).
$^1$H NMR (300 MHz, DMSO-d$_6$): δ 13.84 (bs, 1H), 9.44 (t, J=4.8 Hz, 1H), 9.3 (t, J=5.6 Hz, 1H), 8.58 (d, J=7.6 Hz, 1H), 8.31 (d, J=8.8 Hz, 3H), 8.09 (s, 1H), 7.4 (dd, J$_1$=2.4 Hz, J$_2$=7.6 Hz, 1H), 6.98 (s, 1H), 6.86 (s, 1H), 4.06 (s, 3H), 3.99 (s, 3H), 3.71-3.68 (m, 3H), 3.65-3.60 (m, 6H), 3.26-3.19 (m, 4H), 2.61 (s, 1H), 2.40-2.28 (m, 1H), 2.25-2.15 (m, 1H), HPLC (Method 6) 92.4% (AUC), t$_R$=12.97 min. ESI+APCI MS m/z 549 [M+H]$^+$.

Preparation tert-butyl (1-(5-bromopyrimidin-2-yl)piperidin-4-yl)carbamate 308i Compound tert-butyl (1-(5-bromopyrimidin-2-yl)piperidin-4-yl)carbamate 308j was prepared in the same manner as tert-butyl (1-(5-bromopyrimidin-2-yl)pyrrolidin-3-yl)carbamate 308f and was obtained as an off-white solid (81% yield). ESI+APCI MS m/z 357 [M+H]$^+$.

Preparation of tert-butyl (1-(5-(4-(2-(5-chloro-2,4-dimethoxyphenyl)imidazo[1,2-a]pyridin-7-yl)piperazin-1-yl)pyrimidin-2-yl)piperidin-4-yl)carbamate 309i A suspension of 2-(5-chloro-2,4-dimethoxyphenyl)-7-(piperazin-1-yl)imidazo[1,2-a]pyridine 301 (500 mg, 1.3 mmol), tert-butyl (1-(5-bromopyrimidin-2-yl)piperidin-4-yl)carbamate 308j (717 mg, 2.0 mmol), [(t-Bu)$_3$PH]BF$_4$ (19 mg, 0.06 mmol) and KOt-Bu (450 mg, 4.0 mmol) in xylene (25 mL) was degassed with argon for 15 min. Subsequently the mixture was charged with Pd(OAc)$_2$ (15 mg, 0.06 mmol) and further degassed with argon for 5 min. The resulting reaction mixture was stirred at 100-110° C. for 16 h. The reaction mixture was cooled to room temperature, filtered through a pad of celite. The filtrate was concentrated and the residue was purified by combi-flash companion (silica gel, CH$_3$OH/CH$_2$Cl$_2$) to give tert-butyl (1-(5-(4-(2-(5-chloro-2,4-dimethoxyphenyl)imidazo[1,2-a]pyridin-7-yl)piperazin-1-yl)pyrimidin-2-yl)piperidin-4-yl)carbamate 309j (300 mg, 34%) as a light yellow solid. ESI+APCI MS m/z 649 [M+H]$^+$.

Preparation of 1-(5-(4-(2-(5-chloro-2,4-dimethoxyphenyl)imidazo[1,2-a]pyridin-7-yl)piperazin-1-yl)pyrimidin-2-yl)piperidin-4-amine 309k (Example 350)

To a suspension of tert-butyl (1-(5-(4-(2-(5-chloro-2,4-dimethoxyphenyl)imidazo[1,2-a]pyridin-7-yl)piperazin-1-yl)pyrimidin-2-yl)piperidin-4-yl)carbamate 309j (250 mg, 0.38 mmol) in 2,2,2-trifluoroethanol (5 mL) was added TMS-Cl (0.1 mL). The reaction mixture was stirred at room temperature for 1 h. The reaction mixture was evaporated to dryness and diluted with aqueous NaHCO$_3$ solution. The aqueous layer was extracted with EtOAc (2×50 mL). The combined organic layers were dried over Na$_2$SO$_4$, filtered and concentrated. The residue was purified by combi-flash companion (silica gel, CH$_3$OH/CH$_2$Cl$_2$) to provide 1-(5-(4-(2-(5-chloro-2,4-dimethoxyphenyl)imidazo[1,2-a]pyridin-7-yl)piperazin-1-yl)pyrimidin-2-yl)piperidin-4-amine 309k (Example 350) (25 mg, 11%) as a light yellow solid.
$^1$H NMR (300 MHz, DMSO-d$_6$): δ 8.33 (d, J=7.8 Hz, 1H), 8.24 (s, 2H), 8.19 (s, 1H), 8.04 (s, 1H), 6.87 (bs, 2H), 6.73 (s, 1H), 4.47-4.38 (m, 2H), 4.0 (s, 3H), 3.93 (s, 3H), 3.37-3.35 (m, 4H), 3.20-3.18 (m, 4H), 3.03-2.82 (m, 2H), 2.80-2.77 (m, 1H); HPLC (Method 1) 98.7% (AUC), t$_R$=11.74 min. ESI+APCI MS m/z 549 [M+H]$^+$.

Preparation of N-(1-(5-(4-(2-(5-chloro-2,4-dimethoxyphenyl)imidazo[1,2-a]pyridin-7-yl)piperazin-1-yl)pyrimidin-2-yl)piperidin-4-yl)cyclopropanesulfonamide 309l (Example 393)

To a suspension of tert-butyl (1-(5-(4-(2-(5-chloro-2,4-dimethoxyphenyl)-imidazo[1,2-a]pyridin-7-yl)piperazin-1-yl)pyrimidin-2-yl)piperidin-4-yl)carbamate 309j (250 mg, 0.38 mmol) in 2,2,2-trifluoroethanol (5 mL) was added TMS-Cl (0.1 mL) and the reaction mixture was stirred at room temperature for 1 h. The reaction mixture was concentrated and the residue was taken up in dichloromethane (4 mL), N,N-diisopropylethylamine (80 µL, 0.45 mmol). To the suspension was added cyclopropanesulfonyl chloride (20 µL, 0.23 mmol). The reaction mixture was stirred at room temperature for 2 h under N$_2$ atmosphere and then diluted with water. The aqueous layer was extracted with CH$_2$Cl$_2$ (2×20 mL). The combined organic layers were dried over sodium sulfate, filtered and concentrated. The residue was purified by combi-flash companion (silica gel, CH$_3$OH/CH$_2$Cl$_2$ to afford 2-(5-chloro-2,4-dimethoxyphenyl)-7-(4-(2-(4-(cyclopropylsulfonyl)piperazin-1-yl)pyrimidin-5-yl)piperazin-1-yl)imidazo[1,2-a]pyridine 309l (Example 393) (30 mg, 25%) as a light yellow solid.
$^1$H NMR (300 MHz, DMSO-d$_6$): δ 8.32 (d, J=7.5 Hz, 1H), 8.26 (s, 2H), 8.18 (s, 1H), 8.04 (s, 1H), 7.15 (d, J=7.8 Hz, 1H), 6.74 (s, 1H), 4.42 (d, J=12.6 Hz, 2H), 4.02 (s, 3H), 3.94 (s, 3H), 3.62-3.57 (m, 4H), 3.18-3.16 (m, 4H), 3.0 (t, J=12.0 Hz, 2H), 2.62-2.56 (m, 1H), 1.90-1.86 (m, 2H), 1.44-1.40

(m, 2H), 0.96-0.93 (m, 4H); HPLC (Method 1) 90.58% (AUC), $t_R$=12.56 min.; ESI+APCI MS m/z 653 [M+H]$^+$.

Preparation of tert-butyl (1-(5-bromopyrimidin-2-yl) piperidin-4-yl(methyl)carbamate 308m Compound tert-butyl (1-(5-bromopyrimidin-2-yl)piperidin-4-yl)(methyl)carbamate 8m was prepared in the same manner as compound tert-butyl (1-(5-bromopyrimidin-2-yl) pyrrolidin-3-yl)carbamate 308lf, and was obtained as an off-white solid (80% yield).

ESI+APCI MS m/z 371 [M+H]$^+$.

Preparation of tert-butyl (1-(5-(4-(2-(5-chloro-2,4-dimethoxyphenyl)imidazo[1,2-a]pyridin-7-yl)piperazin-1-yl)pyrimidin-2-yl)piperidin-4-yl)(methylcarbamate 309m A suspension of 2-(5-chloro-2,4-dimethoxyphenyl)-7-(piperazin-1-yl)imidazo[1,2-a]pyridine 301 (500 mg, 1.3 mmol), tert-butyl (1-(5-bromopyrimidin-2-yl)piperidin-4-yl)(methyl)carbamate (745 mg, 2.0 mmol), BINAP (83 mg, 0.1 mmol) and NaOt-Bu (387 mg, 4.0 mmol) in toluene (20 mL) was degassed with argon for 15 min. Subsequently the mixture was charged with Pd$_2$(dba)$_3$ (123 mg, 0.13 mmol) and further degassed with argon for 5 min. The reaction mixture was stirred at 100-110° C. for 16 h. The reaction mixture was cooled to room temperature, filtered through a pad of celite bed. The filtrate was concentrated and the residue was purified by combi-flash companion (silica gel, CH$_3$OH/CH$_2$Cl$_2$) to give tert-butyl (1-(5-(4-(2-(5-chloro-2,4-dimethoxyphenyl)imidazo[1,2-a]pyridin-7-yl)piperazin-1-yl)pyrimidin-2-yl)piperidin-4-yl)(methyl)carbamate 309m (150 mg, 17%) as a light yellow solid. ESI+APCI MS m/z 663 [M+H]$^+$.

Preparation of 1-(5-(4-(2-(5-chloro-2,4-dimethoxyphenyl)imidazo[1,2-a]pyridin-7-yl)piperazin-1-yl) pyrimidin-2-yl)-N-methylpiperidin-4-amine dihydrochloride 309n (Example 396)

Compound 1-(5-(4-(2-(5-chloro-2,4-dimethoxyphenyl) imidazo[1,2-a]pyridin-7-yl)piperazin-1-yl)pyrimidin-2-yl)-N-methylpiperidin-4-amine dihydrochloride 309n was prepared in the same manner as 1-(5-(4-(2-(5-chloro-2,4-dimethoxyphenyl)imidazo[1,2-a]pyridin-7-yl)piperazin-1-yl)pyrimidin-2-yl)pyrrolidin-3-amine dihydrochloride 309 g, and was obtained as a yellow solid (70% yield).

$^1$H NMR (300 MHz, DMSO-d$_6$): δ 14.07 (s, 1H), 9.19 (bs, 2H), 8.32 (s, 2H), 8.29 (s, 2H), 8.11 (s, 1H), 7.38 (d, J=8.4 Hz, 1H), 6.97 (s, 1H), 6.88 (s, 1H), 4.62 (d, J=13.8 Hz, 2H), 4.06 (s, 3H), 3.98 (s, 3H), 3.78-3.65 (m, 8H), 2.90 (t, J=12.0 Hz, 2H), 2.07 (d, J=12.0 Hz, 2H), 1.5 (q, J=2.7 Hz, 2H); HPLC (Method 1) 92.14% (AUC), $t_R$=10.55 min.; ESI+APCI MS m/z 563 [M+H]$^+$.

Preparation of tert-butyl (1-(5-bromopyrimidin-2-yl) piperidin-3-yl)carbamate 308o Compound tert-butyl (1-(5-bromopyrimidin-2-yl)piperidin-3-yl)carbamate 308o was prepared in the same manner as tert-butyl (I-(5-bromopyrimidin-2-yl)pyrrolidin-3-yl)carbamate 308f, and was obtained as an off-white solid (67% yield). ESI+APCI MS m/z 357 [M+H]$^+$.

Preparation of tert-butyl (1-(5-(4-(2-(5-chloro-2,4-dimethoxyphenyl)imidazo[1,2-a]pyridin-7-yl)piperazin-1-yl)pyrimidin-2-yl)piperidin-3-yl)carbamate 309o Compound tert-butyl (1-(5-(4-(2-(5-chloro-2,4-dimethoxyphenyl)imidazo[1,2-a]pyridin-7-yl)piperazin-1-yl)pyrimidin-2-yl)piperidin-3-yl)carbamate 309o was prepared in the same manner as tert-butyl (1-(5-(4-(2-(5-chloro-2,4-dimethoxyphenyl)imidazo[1,2-a]pyridin-7-yl)piperazin-1-yl)pyrimidin-2-yl)pyrrolidin-3-yl)carbamate 309f, and was obtained as a brown solid (27% yield). ESI+APCI MS m/z 649 [M+H]$^+$ Preparation of 1-(5-(4-(2-(5-chloro-2,4-dimethoxyphenyl)imidazo[1,2-a]pyridin-7-yl)piperazin-1-yl) pyrimidin-2-yl)piperidin-3-amine 309D (Example 417)

To a suspension of tert-butyl (1-(5-(4-(2-(5-chloro-2,4-dimethoxyphenyl)imidazo[1,2-a]pyridin-7-yl)piperazin-1-yl)pyrimidin-2-yl)piperidin-3-yl)carbamate 309o (150 mg, 0.23 mmol) in 2,2,2-trifluoroethanol (5 mL) was added TMS-Cl (0.2 mL), the reaction mixture was stirred at room temperature for 1 h. The reaction mixture was concentrated to dryness. The residue was taken up in NaHCO$_3$ aqueous solution (10 mL) and extracted with DCM (2×20 mL). The combined organic layers were dried over Na$_2$SO$_4$, filtered and concentrated. The residue was purified by combi-flash companion (silica gel, CH$_3$OH/CH$_2$Cl$_2$) to provide 1-(5-(4-(2-(5-chloro-2,4-dimethoxyphenyl)imidazo[1,2-a]pyridin-7-yl)piperazin-1-yl)pyrimidin-2-yl)piperidin-3-amine 309p (Example 417) (25 mg, 20%) as an off-white solid.

$^1$H NMR (400 MHz, DMSO-d$_6$): δ 8.45 (d, J=7.6 Hz, 1H), 8.26 (s, 2H), 8.04 (s, 1H), 6.87 (bs, 2H), 6.74 (s, 1H), (bs, 2H), 4.4 (d, J=8.8 Hz, 1H), 4.24 (d, J=12.8 Hz, 1H), 4.01 (s, 3H), 3.94 (s, 3H), 3.42-3.36 (m, 4H), 3.2 (bs, 4H), 2.93 (t, J=10.4 Hz, 1H), 2.82-2.77 (m, 2H), 1.92-1.89 (m, 1H), 1.72-1.69 (m, 2H); HPLC (Method 5) 95.8% (AUC), $t_R$=18.45 min; ESI+APCI MS m/z 549 [M+H]$^+$.

Preparation of tert-butyl (1-(5-bromopyrimidin-2-yl) piperidin-3-yl)(methyl)carbamate 308q Compound tert-butyl (1-(5-bromopyrimidin-2-yl)piperidin-3-yl)(methyl)carbamate 308q was prepared in the same manner as compound tert-butyl (1-(5-bromopyrimidin-2-yl) pyrrolidin-3-yl)carbamate 308f, and was obtained as an off-white solid (71% yield).

ESI+APCI MS m/z 371 [M+H]$^+$.

Preparation of tert-butyl (1-(5-(4-(2-(5-chloro-2,4-dimethoxyphenyl)imidazo[1,2-a]pyridin-7-yl)piperazin-1-yl)pyrimidin-2-yl)piperidin-3-yl)(methyl) carbamate 309q A suspension of 2-(5-chloro-2,4-dimethoxyphenyl)-7-(piperazin-1-yl)imidazo[1,2-a]pyridine 301 (500 mg, 1.3 mmol), tert-butyl (1-(5-bromopyrimidin-2-yl)piperidin-3-yl)(methyl)carbamate 308q (743 mg, 2.0 mmol), [(t-Bu)$_3$PH]BF$_4$ (40 mg, 0.13 mmol) and NaOt-Bu (380 mg, 4.0 mmol) in xylene (15 mL) was degassed with argon for 15 min. Subsequently the mixture was charged with Pd(OAc)$_2$ (30 mg, 0.13 mmol) and further degassed with argon for 5 min. The resulting reaction mixture was stirred at 100-110° C. for 16 h. The reaction mixture was cooled to room temperature, filtered through a pad of celite, the filtrate was concentrated to dryness. The residue was purified by combi-flash companion (silica gel, CH$_3$OH/CH$_2$Cl$_2$) to provide tert-butyl (1-(5-(4-(2-(5-chloro-2,4-dimethoxyphenyl)imidazo[1,2-a]pyridin-7-yl)piperazin-1-yl)pyrimidin-2-yl)piperidin-3-yl)(methyl)carbamate 309q (200 mg, 22%) as brown solid. ESI+APCI MS m/z 663 [M+H]$^+$ Preparation of 1-(5-(4-(2-(5-chloro-2,4-dimethoxyphenyl)imidazo[1,2-a]pyridin-7-yl)piperazin-1-yl)pyrimidin-2-yl)-N-methylpiperidin-3-amine 309r (Example 428)

Compound 1-(5-(4-(2-(5-chloro-2,4-dimethoxyphenyl)imidazo[1,2-a]pyridin-7-yl)piperazin-1-yl)pyrimidin-2-yl)-N-methylpiperidin-3-amine 309r was prepared in the same manner as 1-(5-(4-(2-(5-chloro-2,4-dimethoxyphenyl)imidazo[1,2-a]pyridin-7-yl)piperazin-1-yl)pyrimidin-2-yl)piperidin-3-amine 309p, and was obtained as an off-white solid (32% yield).

$^1$H NMR (400 MHz, DMSO-d$_6$): δ 8.34 (d, J=7.6 Hz, 1H), 8.25 (s, 2H), 8.18 (s, 1H), 8.04 (s, 1H), 6.87 (bs, 2H), 6.74 (s, 1H), 4.4 (d, J=30.4 Hz, 1H), 4.01 (s, 3H), 3.94 (s, 3H), 3.34 (bs, 4H), 3.11 (bs, 4H), 2.93 (t, J=8.4 Hz, 1H), 2.83 (t, J=8.8 Hz, 1H), 2.3 (s, 3H), 1.99-1.92 (m, 1H), 1.48-1.28 (m, 2H). HPLC (Method 5) 97.02% (AUC), t$_R$=12.24 min; ESI+APCI MS m/z 563 [M+H]$^+$.

Preparation of 4-(5-bromopyrimidin-2-yl)morpholine 308s

Compound 4-(5-bromopyrimidin-2-yl)morpholine 308s was prepared in the same manner as tert-butyl (1-(5-bromopyrimidin-2-yl)pyrrolidin-3-yl)carbamate 308f, and was obtained as white solid (87% yield).

$^1$H NMR (400 MHz, CDCl$_3$): δ 8.3 (s, 2H), 3.74 (br s, 8H); ESI+APCI MS m/z 244 [M+H]$^+$.

Preparation of 4-(5-(4-(2-(5-chloro-2,4-dimethoxyphenyl)imidazo[1,2-a]pyridin-7-yl)piperazin-1-yl)pyrimidin-2-yl)morpholine 309s (Example 335)

Compound 4-(5-(4-(2-(5-chloro-2,4-dimethoxyphenyl)imidazo[1,2-a]pyridin-7-yl)piperazin-1-yl)pyrimidin-2-yl)morpholine 309s was prepared in the same manner as 2-(5-chloro-2,4-dimethoxyphenyl)-7-(4-(2-(pyrrolidin-1-yl)pyrimidin-5-yl)piperazin-1-yl)imidazo[1,2-a]pyridine 309e, and was obtained as an off-white solid (9 yield).

$^1$H NMR (400 MHz, DMSO-d$_6$): δ 8.33 (d, J=7.6 Hz, 1H), 8.29 (s, 2H), 8.18 (s, 1H), 8.03 (s, 1H), 6.87 (s, 1H), 6.85 (s, 1H), 6.73 (s, 1H), 4.01 (s, 3H), 3.67-3.64 (m, 3H), 3.59-3.57 (s, 3H), 3.37 (br s, 3H), 3.17 (br s, 3H); HPLC (Method 1) 93.9% (AUC), t$_R$=13.01 min.; ESI+APCI MS m/z 536 [M+H]$^+$.

Preparation of 2-(5-chloro-2,4-dimethoxyphenyl)-7-(4-(pyrimidin-5-yl)piperazin-1-yl)imidazo[1,2-a]pyridine 309t (Example 317)

A suspension of 2-(5-chloro-2,4-dimethoxyphenyl)-7-(piperazin-1-yl)imidazo[1,2-a]pyridine 301 (500 mg, 1.34 mmol), 5-bromopyrimidine (330 mg, 2.07 mmol), (±) BINAP (90 mg, 0.14 mmol) and NaOt-Bu (390 mg, 4.05 mmol) in toluene (15 mL) was degassed with argon for 15 min. Subsequently the mixture was charged with Pd$_2$(dba)$_3$ (70 mg, 0.076 mmol) and further degassed with argon for 5 min. The resulting reaction mixture was stirred at 100-110° C. for 16 h. The reaction mixture was cooled to room temperature, filtered through a pad of celite and the filtrate was evaporated to dryness. The residue was purified by combi-flash companion (silica gel, CH$_3$OH/CH$_2$Cl$_2$) to give 2-(5-chloro-2,4-dimethoxyphenyl)-7-(4-(pyrimidin-5-yl)piperazin-1-yl)imidazo[1,2-a]pyridine 309t (Example 317) (275 mg, 45%) as off-white solid.

$^1$H NMR (300 MHz, DMSO-d$_6$): δ 8.63 (s, 1H), 8.58 (s, 2H), 8.35 (d, J=7.5 Hz, 1H), 8.18 (s, 1H), 8.04 (s, 1H), 6.90 (s, 1H), 6.87 (s, 1H), 6.76 (s, 1H), 4.01 (s, 3H), 3.93 (s, 3H), 3.43 (br s, 4H), 3.41 (br s, 4H); HPLC (Method 1) 98.0% (AUC), t$_R$=12.61 min.; ESI+APCI MS m/z 451 [M+H]$^+$.

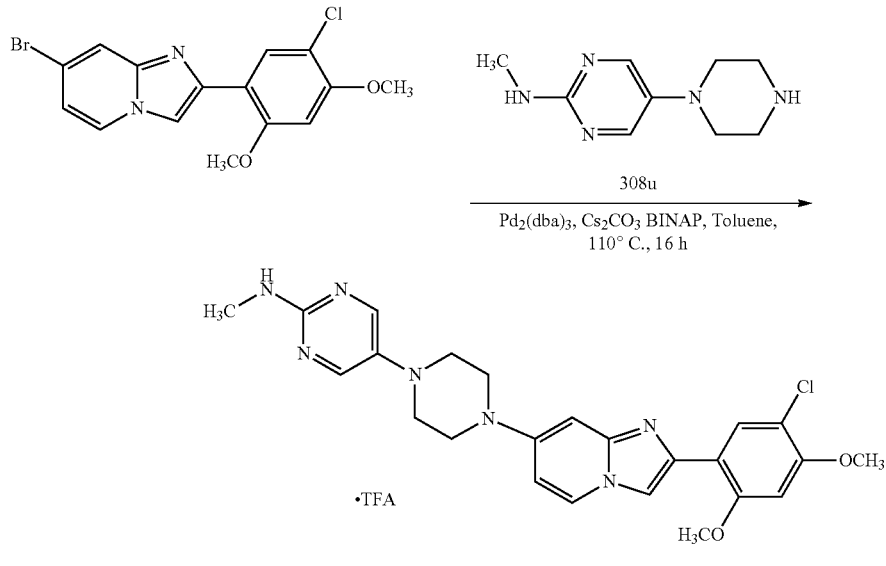

Scheme 2-8

309u
after pre-HPLC purification

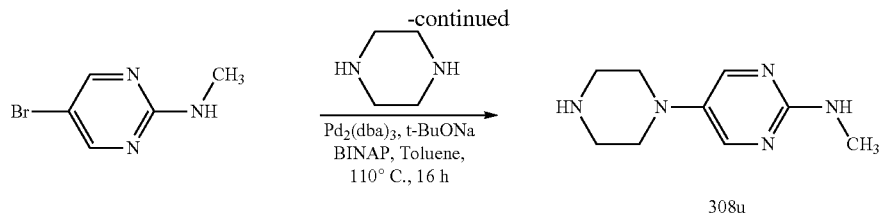

308u

Preparation of N-methyl-5-(piperazin-1-yl)pyrimidin-2-amine 308u

A suspension of 5-bromo-N-methylpyrimidin-2-amine (300 mg, 1.6 mmol), piperazine (692 mg, 8.0 mmol), BINAP (47 mg, 0.16 mmol) and NaOt-Bu (308 mg, (3.2 mmol) in toluene (8.0 mL) was degassed with argon for 5 min. Subsequently the mixture was charged with $Pd_2(dba)_3$ (76 mg, 0.080 mmol) and further degassed with argon for 5 min. The reaction mixture was stirred at 100-110° C. for 16 h. The reaction mixture was cooled to room temperature and filtered through a pad of celite. The filtrate was evaporated to dryness. The residue was purified by combi-flash companion (silica gel, $CH_3OH/CH_2Cl_2$) to give N-methyl-5-(piperazin-1-yl) pyrimidin-2-amine 308u (220 mg, crude) as a yellow solid. ESI+APCI MS m/z 193 $[M+H]^+$.

Preparation of 5-(4-(2-(5-chloro-2,4-dimethoxyphenyl)imidazo[1,2-a]pyridin-7-yl)piperazin-1-yl)-N-methylpyrimidin-2-amine trifluoroacetate 309u (Example 340)

A suspension of 7-bromo-2-(5-chloro-2,4-dimethoxyphenyl)imidazo[1,2-a]pyridine (200 mg, 0.54 mmol), N-methyl-5-(piperazin-1-yl)pyrimidin-2-amine 308u (211 mg, 1.0 mmol), BINAP (34 mg, 0.054 mmol) and $Cs_2CO_3$ (532 mg, 1.63 mmol) in toluene (8.0 mL) was degassed with argon for 5 min. Subsequently the mixture was charged with $Pd_2(dba)_3$ (51 mg, 0.054 mmol) and further degassed with argon for another 5 min. The reaction mixture was stirred at 100-110° C. for 16 h. The reaction mixture was cooled to room temperature, filtered through a pad of celite. The filtrate was evaporated to dryness. The residue was purified by combi-flash companion (silica gel, $CH_3OH/CH_2Cl_2$), followed by prep-HPLC to provide 5-(4-(2-(5-chloro-2,4dimethoxyphenyl)imidazo[1,2-a]pyridin-7-yl)piperazin-1-yl)-N-methylpyrimidin-2-amine trifluoroacetate 309u (Example 340) (10 mg, 3%) as a yellow solid.

$^1$H NMR (400 MHz, DMSO-$d_6$): δ 13.40 (s, 1H), 8.57 (d, J=8.0 Hz, 1H), 8.28 (s, 1H), 8.21 (s, 2H), 7.93 (s, 1H), 7.4 (dd, J=4.0, 8.0 Hz, 1H), 6.99 (s, 1H), 6.80 (s, 1H), 4.05 (s, 3H), 3.99 (s, 3H), 3.66 (s, 4H), 3.16-3.14 (m, 4H), 2.78 (s, 3H). HPLC (Method 1) 94.70% (AUC), $r_R$=11.94 min. ESI+APCI MS m/z 480 $[M+H]^+$.

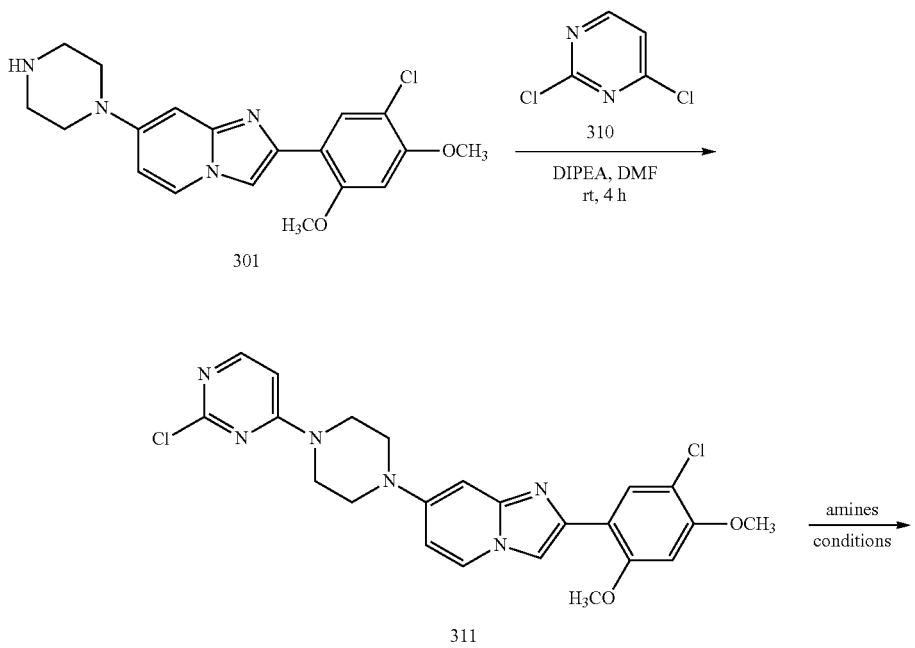

Scheme 2-9

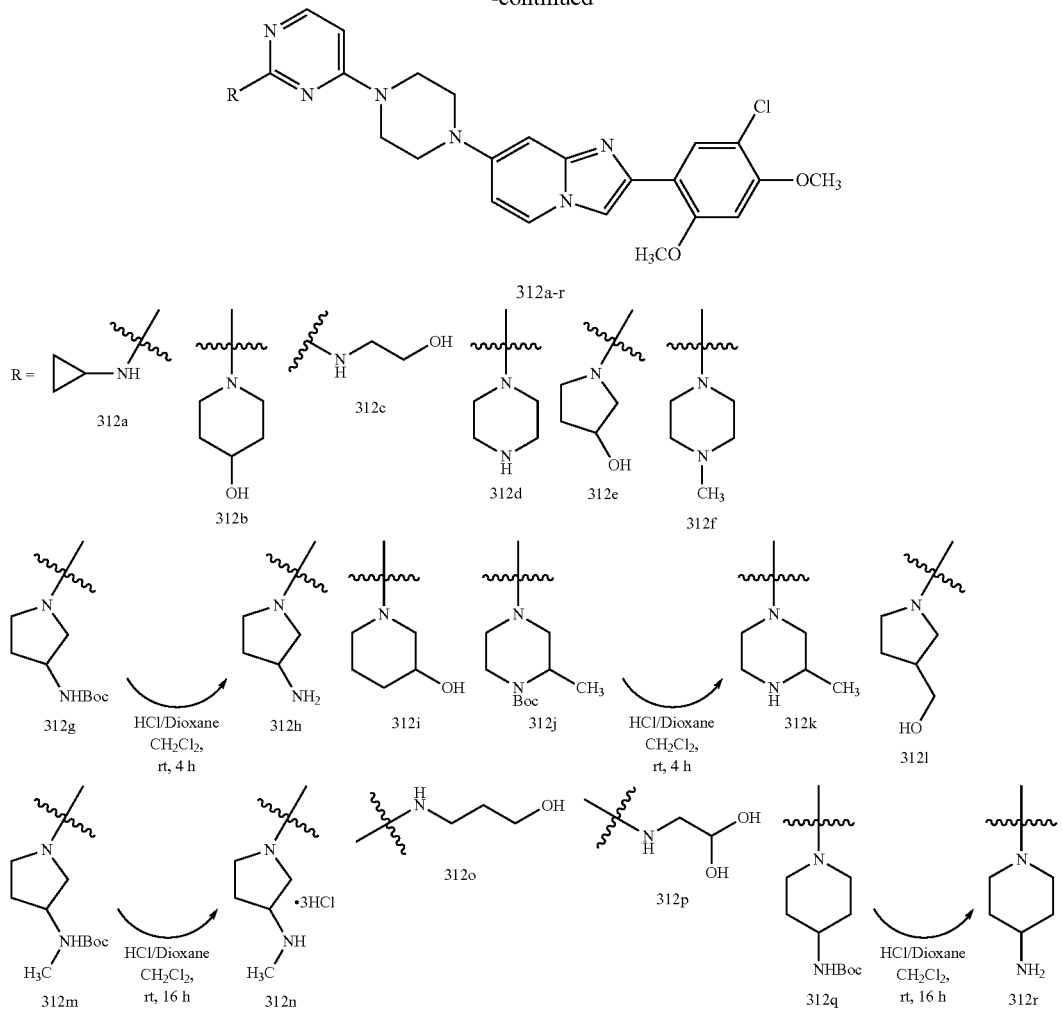

Preparation of 2-(5-chloro-2,4-dimethoxyphenyl-7-(4-(2-chloropyrimidin-4-yl)piperazin-1-yl)imidazo[1,2-a]pyridine 311

A solution of 2-(5-chloro-2,4-dimethoxyphenyl)-7-(piperazin-1-yl) imidazo[1,2-a]pyridine 301 (1.00 g, 2.68 mmol) and N,N-diisopropylethylamine (0.70 mL, 4.0 mmol) in DMF (10 mL) was charged with 2,4-dichloropyrimidine 310 (400 mg, 2.69 mmol). The reaction mixture was stirred at room temperature for 4 h under $N_2$ atmosphere. The reaction mixture was diluted with MTBE (100 mL) and stirred vigorously for 1 h. The precipitate was collected by filtration, dried under reduced pressure and purified by combi-flash companion (silica gel, $CH_3OH/CH_2Cl_2$) to provide 2-(5-chloro-2,4-dimethoxyphenyl)-7-(4-(2-chloropyrimidin-4-yl)piperazin-1-yl)imidazo[1,2-a]pyridine 311 (600 mg, 46%) as a brown solid.

$^1$H NMR (400 MHz, DMSO-$d_6$): δ 8.34 (d, J=7.5 Hz, 1H), 8.20 (s, 1H), 8.10 (d, J=6.1 Hz, 1H), 8.04 (s, 1H), 6.89 (d, J=6.2 Hz, 1H), 6.87 (s, 1H), 6.83 (dd, J=2.2, 7.6 Hz, 1H), 6.72 (d, J=1.6 Hz, 1H), 4.02 (s, 3H), 3.94 (s, 3H), 3.79 (bs, 4H), 3.33-3.36 (m, 4H).

ESI+APCI MS m/z 485 [M+H]$^+$.

Preparation of 4-(4-(2-(5-chloro-2,4-dimethoxyphenyl)imidazo[1,2-a]pyridin-7-yl)piperazin-1-yl)-N-cyclopropylpyrimidin-2-amine 312a (Example 331)

Compound 2-(5-chloro-2,4-dimethoxyphenyl)-7-(4-(2-chloropyrimidin-4-yl)piperazin-1-yl)imidazo[1,2-a]pyridine 311 (100 mg, 0.206 mmol) was added to cyclopropyl amine (1 mL), the reaction mixture was heated at 130° C. in a microwave reactor for 30 min. The reaction mixture was diluted with water and the precipitate formed was collected by filtration, washed and dried. The crude material was purified by combi-flash companion (silica gel, $NH_4OH/CH_3OH/CH_2Cl_2$) to provide 4-(4-(2-(5-chloro-2,4-dimethoxyphenyl)imidazo[1,2-a]pyridin-7-yl)piperazin-1-yl)-N-cyclopropylpyrimidin-2-amine 312a (15 mg, 14%) as an off-white solid.

$^1$H NMR (400 MHz, DMSO-$d_6$): δ 8.34 (d, J=7.2 Hz, 1H), 8.17 (s, 1H), 8.02 (s, 1H), 7.86 (d, J=6.0 Hz, 1H), 6.86-6.84 (m, 2H), 6.71 (s, 1H), 6.14 (d, J=6 Hz, 1H), 4.00 (s, 3H), 3.93 (s, 3H), 3.71 (s, 4H), 3.33 (s, 4H), 2.50 (m, 1H), 0.63 (dd, J=6.8, 11.6 Hz, 2H), 0.44 (dd, J=4.4, 8 Hz, 2H); HPLC (Method 1) 94.1% (AUC), $t_R$=12.0 min. ESI+APCI MS m/z 506 [M+H]$^+$.

Preparation of 1-(4-(4-(2-(5-chloro-2,4-dimethoxyphenyl)imidazo[1,2-a]pyridin-7-yl)piperazin-1-yl)pyrimidin-2-yl)piperidin-4-ol 312b (Example 332)

To a solution of 2-(5-chloro-2,4-dimethoxyphenyl)-7-(4-(2-chloropyrimidin-4-yl)piperazin-1-yl)imidazo[1,2-a]pyridine 311 (100 mg, 0.206 mmol) and DIPEA (79 mg, 0.61 mmol) in acetonitrile (1.0 mL), was added piperidin-4-ol (31 mg, 0.30 mmol). The reaction mixture was heated at 100° C. in a microwave reactor for 40 min. The reaction mixture was quenched with water, and the precipitate formed was collected by filtration, washed and dried. The crude compound was purified by combi-flash companion (silica gel, $NH_4OH/CH_2OH/CH_2Cl_2$) to provide 1-(4-(4-(2-(5-chloro-2,4-dimethoxyphenyl)imidazo[1,2-a]pyridin-7-yl)piperazin-1-yl)pyrimidin-2-yl)piperidin-4-ol 312b (10 mg, 8.8%) as an off-white solid.

$^1$H NMR (300 MHz, DMSO-$d_6$): δ 8.35 (d, J=7.5 Hz, 1H), 8.17 (s, 1H), 8.03 (s, 1H), 7.91 (d, J=6 Hz, 1H), 6.87-6.83 (m, 2H), 6.71 (s, 1H), 6.13 (d, J=6 Hz, 1H), 4.68 (d, J=4.5 Hz, 1H), 4.30-4.24 (m, 2H), 4.01 (s, 3H), 3.93 (s, 3H), 3.75-3.54 (m, 5H), 3.49-3.35 (m, 4H), 3.17-3.09 (m, 2H), 1.17-1.73 (m, 2H), 1.34-1.14 (m, 2H); HPLC (Method 1) 96.3% (AUC), $t_R$=11.75 min.; ESI+APCI MS m/z 550 [M+H]$^+$.

Preparation 2-((4-(4-(2-(5-chloro-2,4-dimethoxyphenyl)imidazo[1,2-a]pyridin-7-yl)piperazin-1-yl)pyrimidin-2-yl)amino)ethanol 312c (Example 334)

Compound 2-(5-chloro-2,4-dimethoxyphenyl)-7-(4-(2-chloropyrimidin-4-yl)piperazin-1-yl)imidazo[1,2-a]pyridine 311 (20 mg, 0.041 mmol) was added to 2-aminoethanol (0.5 mL) and the reaction mixture was heated at 130° C. in a microwave reactor for 30 min. The reaction mixture was diluted with water, and the precipitate formed was collected by filtration, washed and dried. The crude compound was purified by combi-flash companion (silica gel, $NH_4OH/CH_3OH/CH_2Cl_2$) to provide 2-((4-(4-(2-(5-chloro-2,4-dimethoxyphenyl)imidazo[1,2-a]pyridin-7-yl)piperazin-1-yl)pyrimidin-2-yl)amino)ethanol 312c (10 mg, 47%) as an off-white solid.

$^1$H NMR (400 MHz, DMSO-$d_6$): δ 8.34 (d, J=7.6 Hz, 1H), 8.17 (s, 1H), 8.03 (s, 1H), 7.83 (d, J=6 Hz, 1H), 6.86-6.83 (m, 2H), 6.71 (s, 1H), 6.38 (bs, 2H), 6.10 (d, J=5.6 Hz, 1H), 4.65 (bs, 1H), 4.01 (s, 3H), 3.93 (s, 3H), 3.75-3.67 (m, 4H), 3.49 (bs, 2H), 3.33 (bs, 4H), 2.5 (bs, 2H); HPLC (Method 1) 98.4% (AUC), $r_R$=11.65 min.; ESI+APCI MS m/z 536 [M+H]$^+$.

Preparation of 2-(5-chloro-2,4-dimethoxyphenyl)-7-(4-(2-(piperazin-1-yl)pyrimidin-4-yl)piperazin-1-yl)imidazo[1,2-a]pyridine 312d (Example 341)

To a solution of 2-(5-chloro-2,4-dimethoxyphenyl)-7-(4-(2-chloropyrimidin-4-yl)piperazin-1-yl)imidazo[1,2-a]pyridine 311 (200 mg, 0.412 mmol) and DIPEA (159 mg, 1.23 mmol) in acetonitrile (1.0 mL) was added piperizine hydrochloride (70 mg, 0.82 mmol) and the reaction mixture was heated at 130° C. in a microwave reactor for 30 min. The reaction mixture was diluted with water. The precipitate formed was collected by filtration, washed with water and dried. The crude compound was purified by combi-flash companion (silica gel, $NH_4OH/H_3OH/CH_2Cl_2$) to provide 2-(5-chloro-2,4-dimethoxyphenyl)-7-(4-(2-(piperazin-1-yl)pyrimidin-4-yl)piperazin-1-yl)imidazo[1,2-a]pyridine 312d (20 mg, 9%/o) as an off-white solid.

$^1$H NMR (400 MHz, DMSO-$d_6$): δ 8.35 (d, J=7.6 Hz, 1H), 8.17 (s, 1H), 8.03 (s, 1H), 7.91 (d, J=6 Hz, 1H), 6.87-6.84 (m, 2H), 6.71 (s, 1H), 6.15 (d, J=5.6 Hz, 1H), 4.01 (s, 3H), 3.93 (s, 3H), 3.70 (bs, 4H), 3.59 (bs, 4H), 3.33-3.25 (m, 4H), 2.69 (bs, 4H); HPLC (Method 1) 99.6% (AUC), $t_R$=11.03 min.; ESI+APCI MS m/z 535 [M+H]$^+$.

Preparation of 1-(4-(4-(2-(5-chloro-2,4-dimethoxyphenyl)imidazo[1,2-a]pyridin-7-yl)piperazin-1-yl)pyrimidin-2-yl)pyrrolidin-3-ol 312e (Example 346)

A mixture of 2-(5-chloro-2,4-dimethoxyphenyl)-7-(4-(2-chloropyrimidin-4-yl)piperazin-1-yl)imidazo[1,2-a]pyridine 311 (150 mg, 0.30 mmol) and pyrrolidin-3-ol (40 mg, 0.46 mmol) was heated at 130° C. in a microwave reactor for 30 min. The reaction mixture was diluted with water; the precipitate formed was collected by filtration, washed with water and dried. The crude compound was purified by combi-flash companion (silica gel. $NH_4OH/CH_3OH/CH_2Cl_2$) to provide 1-(4-(4-(2-(5-chloro-2,4-dimethoxyphenyl)imidazo[1,2-a]pyridin-7-yl)piperazin-1-yl)pyrimidin-2-yl)pyrrolidin-3-ol 312e (20 mg, 12%) as an off-white solid.

$^1$H NMR (400 MHz, DMSO-$d_6$): δ 8.35 (d, J=7.2 Hz, 1H), 8.17 (s, 1H), 8.03 (s, 1H), 7.89 (d, J=6 Hz, 1H), 6.87-6.84 (m, 2H), 6.71 (s, 1H), 6.12 (d, J=6 Hz, 1H), 4.88 (d, J=3.2 Hz, 1H), 4.32 (bs, 1H), 4.01 (s, 3H), 3.93 (s, 3H), 3.71 (bs, 4H), 3.57-3.43 (m, 3H), 3.40 (d, J=12 Hz, 1H), 3.33-3.12 (m, 4H), 2.09-1.93 (m, 1H), 1.89-1.80 (m, 1H); HPLC (Method 1) 91.3% (AUC), $t_R$=11.73 min.; ESI+APCI MS m/z 536 [M+H]$^+$.

Preparation 2-(5-chloro-2,4-dimethoxyphenyl)-7-(4-(2-(4-methylpiperazin-1-yl)pyrimidin-4-yl)piperazin-1-yl)imidazo[1,2-a]pyridine 312f (Example 351)

Compound 2-(5-chloro-2,4-dimethoxyphenyl)-7-(4-(2-(4-methylpiperazin-1-yl)pyrimidin-4-yl)piperazin-1-yl)imidazo[1,2-a]pyridine 312f was prepared in the same manner as compound 1-(4-(4-(2-(5-chloro-2,4-dimethoxyphenyl)imidazo[1,2-a]pyridin-7-yl)piperazin-1-yl)pyrimidin-2-yl)pyrrolidin-3-ol 312e, and was obtained as an off-white solid (13% yield).

$^1$H NMR (300 MHz, DMSO-$d_6$): δ 8.35 (d, J=7.5 Hz, 1H), 8.17 (s, 1H), 8.03 (s, 1H), 7.92 (d, J=6 Hz, 1H), 6.87-6.83 (m, 2H), 6.71 (s, 1H), 6.17 (d, J=6 Hz, 1H), 4.01 (s, 3H), 3.93 (s, 3H), 3.71-3.64 (m, 8H), 3.33-3.12 (m, 41H), 2.33-2.30 (m, 41H), 2.20 (s, 3H); HPLC (Method 1) 99.1% (AUC), $t_R$=11.43 min.; ESI+APCI MS m/z 549 [M+H]$^+$.

Preparation of tert-butyl (1-(4-(4-(2-(5-chloro-2,4-dimethoxyphenyl)imidazo[1,2-a]pyridin-7-yl)piperazin-1-yl)pyrimidin-2-yl)pyrrolidin-3-yl)carbamate 312n A mixture of 2-(5-chloro-2,4-dimethoxyphenyl)-7-(4-(2-chloropyrimidin-4-yl)piperazin-1-yl)imidazo[1,2-a]pyridine 311 (150 mg, 0.309 mmol), tert-butyl pyrrolidin-3-ylcarbamate (85 mg, 0.46 mmol) and DIPEA (119 mg, 0.92 mmol) was heated at 130° C. in a microwave reactor for 30 min. The reaction mixture was diluted with water: the precipitate formed was collected by filtration, washed with water and dried. The crude compound was purified by combi-flash companion (silica gel, $NH_4OH/CH_3OH/CH_2Cl_2$) to provide tert-butyl (1-(4-(4-(2-(5-chloro-2,4-dimethoxyphenyl)imidazo[1,2-a]pyridin-7-yl)piperazin-1-yl)pyrimidin-2-yl)pyrrolidin-3-yl)carbamate 312g (180 mg, 92%) as an off-white solid.

$^1$H NMR (300 MHz, DMSO-d$_6$): δ 8.35 (d, J=7.5 Hz, 1H), 8.17 (s, 1H), 8.03 (s, 1H), 7.89 (d, J=6 Hz, 1H), 7.17 (d, J=6 Hz, 1H), 6.87-6.83 (m, 2H), 6.71 (s, 1H), 6.14 (d, J=6.3 Hz, 1H), 4.01 (s, 3H), 3.93 (s, 3H), 3.75-3.64 (m, 5H), 3.62-3.40 (m, 2H), 3.33-3.12 (m, 4H), 3.00-2.91 (m, 1H), 2.45-2.38 (m, 1H), 2.10-2.04 (m, 1H), 1.84-1.78 (m, 1H), 1.39 (s, 9H).

Preparation of 1-(4-(4-(2-(5-chloro-2,4-dimethoxyphenyl)imidazo[1,2-a]pyridin-7-yl)piperazin-1-yl)pyrimidin-2-yl)pyrrolidin-3-amine 312h (Example 354)

To a solution of tert-butyl (1-(4-(4-(2-(5-chloro-2,4-dimethoxyphenyl)imidazo[1,2-a]pyridin-7-yl)piperazin-1-yl)pyrimidin-2-yl)pyrrolidin-3-yl)carbamate 312g (150 mg, 0.236 mmol) in CH$_2$Cl$_2$ (2 mL) was added a solution of HCl in 1,4-dioxane (4.0 M, 0.5 mL) and the resulting mixture was stirred at room temperature for 4 h. The white precipitation was collected by filtration, washed with dichloromethane. The solid was suspended in water (5.0 mL), and basified with saturated sodium bicarbonate solution (5.0 mL, stirred for 1 h at room temperature). The suspension was filtered to provide 1-(4-(4-(2-(5-chloro-2,4-dimethoxyphenyl)imidazo[1,2-a]pyridin-7-yl)piperazin-1-yl)pyrimidin-2-yl)pyrrolidin-3-amine 312h (15 mg, 12%) as an off-white solid.

$^1$H NMR (400 MHz, DMSO-d$_6$): δ 8.35 (d, J=7.6 Hz, 1H), 8.17 (s, 1H), 8.03 (s, 1H), 7.88 (d, J=6 Hz, 1H), 6.86-6.84 (m, 2H), 6.71 (s, 1H), 6.11 (d, J=6.0 Hz, 1H), 4.01 (s, 3H), 3.93 (s, 3H), 3.75-3.64 (m, 4H), 3.58-3.41 (m, 4H), 3.33-3.12 (m, 4H), 3.12 (dd, J=4.8, 10.8 Hz, 1H), 2.02-1.95 (m, 1H), 1.67-1.60 (m, 1H); HPLC (Method 1) 99.7% (AUC), t$_R$=11.1 min.; ESI+APCI MS m/z 535 [M+H]$^+$.

Preparation of 1-(4-(4-(2-(5-chloro-2,4-dimethoxyphenyl)imidazo[1,2-a]pyridin-7-yl)piperazin-1-yl)pyrimidin-3-ol 312i (Example 357)

To a solution of 2-(5-chloro-2,4-dimethoxyphenyl)-7-(4-(2-chloropyrimidin-4-yl)piperazin-1-yl)imidazo[1,2-a]pyridine 311 (300 mg, 0.206 mmol) in acetonitrile (1.0 mL) was added piperidin-3-ol (92 mg, 0.927 mmol) followed by DIPEA (239 mg, 1.85 mmol). The reaction mixture was heated at 130° C. in a microwave reactor for 30 min. The reaction mixture was diluted with water; the precipitate formed was collected by filtration, washed and dried. The crude compound was purified by combi-flash companion (silica gel, NH$_4$OH/CH$_3$OH/CH$_2$Cl$_2$) to provide 1-(4-(4-(2-(5-chloro-2,4-dimethoxyphenyl)imidazo[1,2-a]pyridin-7-yl)piperazin-1-yl)pyrimidin-2-yl)piperidin-3-ol 312i (15 mg) as an off-white solid.

$^1$H NMR (400 MHz, DMSO-d$_6$): δ 8.35 (d, J=7.6 Hz, 1H), 8.17 (s, 1H), 8.03 (s, 1H), 7.90 (d, J=6 Hz, 1H), 6.87-6.83 (m, 2H), 6.71 (s, 1H), 6.12 (d, J=5.6 Hz, 1H), 4.83 (d, J=4.4 Hz, 1H), 4.49 (d, J=8 Hz, 1H), 4.35 (d, J=13.2 Hz, 1H), 4.01 (s, 3H), 3.93 (s, 3H), 3.80-3.66 (m, 4H), 3.45-3.38 (m, 1H), 3.33-3.12 (m, 4H), 2.88-2.82 (m, 1H), 2.72-2.67 (m, 1), 1.89 (bs, 1H), 1.67 (bs, 1H), 1.34 (bs, 2H); HPLC (Method 1) 94.3% (AUC), t$_R$=11.8 min. ESI+APCI MS m/z 550 [M+H]$^+$.

Preparation tert-butyl 4-(4-(4-(2-(5-chloro-2,4-dimethoxyphenyl)imidazo[1,2-a]pyridin-7-yl)piperazin-1-yl)pyrimidin-2-yl)-2-methylpiperazine-1-carboxylate 312j A mixture of 2-(5-chloro-2,4-dimethoxyphenyl)-7-(4-(2-chloropyrimidin-4-yl)piperazin-1-yl)imidazo[1,2-a]pyridine 311 (200 mg, 0.41 mmol) and tert-butyl 2-methylpiperazine-1-carboxylate (164 mg, 0.824 mmol) was heated at 125° C. in a microwave reactor for 3 h. The reaction mixture was diluted with water; the precipitate was collected by filtration, washed with water and dried. The crude compound was purified by combi-flash companion (silica gel, NH$_4$OH/CH$_3$OH/CH$_2$Cl$_2$) to provide tert-butyl 4-(4-(4-(2-(5-chloro-2,4-dimethoxyphenyl)imidazo[1,2-a]pyridin-7-yl)piperazin-1-yl)pyrimidin-2-yl)-2-methylpiperazine-1-carboxylate 312j (125 mg, 47%) as an off-white solid.

$^1$H NMR (300 MHz, DMSO-d$_6$): δ 8.36 (d, J=7.5 Hz, 1H), 8.17 (s, H), 8.03 (s, 1H), 7.92 (d, J=6 Hz, 1H), 6.87-6.84 (m, 2H), 6.71 (s, 1H), 6.18 (d, J=6 Hz, 1H), 4.51 (dd, J=13.2, 20.7 Hz, 2H), 4.18 (bs, 1H), 4.01 (s, 3H), 3.93 (s, 3H), 3.78-3.68 (m, 4H), 3.33-3.12 (m, 4H), 3.07-2.99 (m, 2H), 2.90-2.81 (m, 1H), 1.42 (s, 9H), 1.05 (d, J=6.6 Hz, 3H); HPLC (Method 1) 96.1% (AUC), t$_R$=13.0 min.; ESI+APCI MS m/z 649 [M+H]$^+$.

Preparation of 2-(5-chloro-2,4-dimethoxyphenyl)-7-(4-(2-(3-methylpiperazin-1-yl)pyrimidin-4-yl)piperazin-1-yl)imidazo[1,2-a]pyridine 312k (Example 362)

To a solution of tert-butyl 4-(4-(4-(2-(5-chloro-2,4-dimethoxyphenyl)imidazo[1,2-a]pyridin-7-yl)piperazin-1-yl)pyrimidin-2-yl)-2-methylpiperazine-1-carboxylate 312j (250 mg, 0.386 mmol) in CH$_2$Cl$_2$ (2 mL) was added a solution of HCl in 1,4-dioxane (4.0 M, 1.0 mL). The reaction mixture was stirred at room temperature for 4 h. The reaction mixture was filtered and the solid obtained was washed with dichloromethane. The solid was suspended in water (5.0 mL), basified with saturated sodium bicarbonate (5.0 mL, stirred for 1 h at room temperature), and the suspension was filtered to provide 2-(5-chloro-2,4-dimethoxyphenyl)-7-(4-(2-(3-methylpiperazin-1-yl)pyrimidin-4-yl)piperazin-1-yl)imidazo[1,2-a]pyridine 312k (60 mg, 28%) as an off-white solid.

$^1$H NMR (300 MHz, DMSO-d$_6$): δ 8.35 (d, J=7.5 Hz, 1H), 8.18 (s, 1H), 8.03 (s, 1H), 7.90 (d, J=5.7 Hz, 1H), 6.87-6.83 (m, 2H), 6.71 (s, 1H), 6.14 (d, J=6 Hz, 1H), 4.45 (d, J=11.7 Hz, 2H), 4.01 (s, 3H), 3.93 (s, 3H), 3.81-3.70 (m, 4H), 3.33-3.12 (m, 4H), 2.91 (d, J=10.8 Hz, 1H), 2.73-2.58 (m, 2H), 2.37-2.27 (m, 2H), 1.00 (d, J=6.3 Hz, 3H); HPLC (Method 1) 98.3% (AUC), t$_R$=11.0 min.; ESI+APCI MS m/z 549 [M+H]$^+$.

Preparation of (1-(4-(4-(2-(5-chloro-2,4-dimethoxyphenyl)imidazo[1,2-a]pyridine-7-yl)piperazin-1-yl)pyrimidin-2-yl)pyrrolidin-3-yl)methanol 312l (Example 367)

A solution of 2-(5-chloro-2,4-dimethoxyphenyl)-7-(4-(2-chloropyrimidin-4-yl)piperazin-1-yl)imidazo[1,2-a]pyridine 311 (250 mg, 0.515 mmol), pyrrolidin-3-ylmethanol (104 mg, 1.03 mmol) and DIPEA (198 mg, 1.54 mmol) in acetonitrile (1.0 mL) was heated at 130° C. in a microwave reactor for 1 h. The reaction mixture was diluted with water; the precipitate was collected by filtration, washed with water and dried. The crude compound was purified by combi-flash companion (silica gel, NH$_4$OH/CH$_3$OH/CH$_2$Cl$_2$) to provide (1-(4-(4-(2-(5-chloro-2,4-dimethoxyphenyl)imidazo[1,2-a]pyridine-7-yl)piperazin-1-yl)pyrimidin-2-yl)pyrrolidin-3-yl)methanol 312l (25 mg, 8.8%) as an off-white solid.

$^1$H NMR (400 MHz, DMSO-d$_6$): δ 8.35 (d, J=7.6 Hz, 1H), 8.17 (s, 1H), 8.03 (s, 1H), 7.88 (d, J=6.0 Hz, 1H), 6.87-6.84 (m, 2H), 6.71 (d, J=2 Hz, 1H), 6.11 (d, J=6 Hz, 1H), 4.69 (bs,

1H), 4.01 (s, 3H), 3.93 (s, 3H), 3.82-3.71 (m, 4H), 3.59-3.50 (m, 2H), 3.45-3.38 (m, 3H), 3.31-3.28 (m, 4H), 3.22-3.16 (m, 1H), 2.40-2.29 (m, 1H), 1.99-1.91 (m, 1H), 1.71-1.62 (m, 1H); HPLC (Method 1) 98.5% (AUC), $t_R$=11.8 min.; ESI+APCI MS m/z 550 [M+H]$^+$.

Preparation of tert-butyl (1-(4-(4-(2-(5-chloro-2,4-dimethoxyphenyl)imidazo[1,2-a]pyridin-7-yl)piperazin-1-yl)pyrimidin-2-yl)pyrrolidin-3-yl)(methyl)carbamate 312m A mixture of 2-(5-chloro-2,4-dimethoxyphenyl)-7-(4-(2-chloropyrimidin-4-yl)piperazin-1-yl)imidazo[1,2-a]pyridine 311 (300 mg, 0.618 mmol) and tert-butyl methyl (pyrrolidin-3-yl)carbamate (247 mg, 1.23 mmol) was heated at 115° C. in a microwave reactor for 1 h. The reaction mixture was diluted with water; the precipitate was collected by filtration, washed with water and dried. The crude compound was purified by combi-flash companion (silica gel, NH$_4$OH/CH$_3$OH/CH$_2$Cl$_2$) to provide tert-butyl (1-(4-(4-(2-(5-chloro-2,4-dimethoxyphenyl)imidazo[1,2-a]pyridin-7-yl)piperazin-1-yl)pyrimidin-2-yl)pyrrolidin-3-yl)(methyl)carbamate 312m (300 mg, 75%) as an off-white solid. ESI+APCI MS m/z 649 [M+H]$^+$.

Preparation of 1-(4-(4-(2-(5-chloro-2,4-dimethoxyphenyl)imidazo[1,2-a]pyridine-7-yl)piperazin-1-yl)pyrimidin-2-yl)-N-methylpyrrolidin-3-amine trihydrochloride 312n (Example 372)

To a solution of tert-butyl (1-(4-(4-(2-(5-chloro-2,4-dimethoxyphenyl)imidazo[1,2-a]pyridin-7-yl)piperazin-1-yl)pyrimidin-2-yl)pyrrolidin-3-yl)(methyl)carbamate 312m (150 mg, 0.23 mmol) in CH$_2$Cl$_2$ (3 mL) was added a solution of HCl in 1,4-dioxane (4.0 M, 1.0 mL) and the reaction mixture was stirred at room temperature for 16 h. The reaction mixture was filtered and the solid obtained was washed with dichloromethane to provide 1-(4-(4-(2-(5-chloro-2,4-dimethoxyphenyl)imidazo[1,2-a]pyridine-7-yl)piperazin-1-yl)pyrimidin-2-yl)-N-methylpyrrolidin-3-amine trihydrochloride 312n (6 mg, 4.7%) as a pale yellow solid.

$^1$H NMR (300 MHz, DMSO-d$_6$): δ 9.74 (s, 1H), 9.54 (s, 1H), 8.62 (d, J=7.8 Hz, 1H), 8.30 (s, 1H), 8.11 (s, 1H), 7.96 (d, J=7.5 Hz, 2H), 7.35 (dd, J=2.1, 7.8 Hz, 1H), 6.98 (s, 1H), 6.80 (s, 1H), 6.64 (d, J=7.2 Hz, 1H), 4.06-3.73 (m, 18H), 2.59 (s, 3H), 2.37 (s, 1H); HPLC (Method 1) 96.7% (AUC), $t_R$=11.0 min.; ESI+APCI MS m/z 549 [M+H]$^+$.

Preparation 3-((4-(4-(2-(5-chloro-2,4-dimethoxyphenyl)imidazo[1,2-a]pyridine-7-yl)piperazin-1-yl)pyrimidin-2-yl)amino)propan-1-ol 312o (Example 395)

To a solution of 2-(5-chloro-2,4-dimethoxyphenyl)-7-(4-(2-chloropyrimidin-4-yl)piperazin-1-yl)imidazo[1,2-a]pyridine 311 (100 mg, 0.20 mmol) in acetonitrile (2.0 mL) was added 3-aminopropan-1-ol (23 mg, 0.309 mmol) followed by DIPEA (80 mg, 0.619 mmol). The reaction mixture was heated at 130° C. in a microwave reactor for 1 h. The reaction mixture was diluted with water: the precipitate was collected by filtration, washed with water and dried. The crude compound was purified by combi-flash companion (silica gel, NH$_4$OH/CH$_3$OH/CH$_2$Cl$_2$) to provide 3-((4-(4-(2-(5-chloro-2,4-dimethoxyphenyl)imidazo[1,2-a]pyridine-7-yl)piperazin-1-yl)pyrimidin-2-yl)amino)propan-1-ol 312o (15.0 mg, 14%) as an off-white solid.

$^1$H NMR (400 MHz, DMSO-d$_6$): δ 8.34 (d, J=7.6 Hz, 1H), 8.17 (s, 1H), 8.03 (s, 1H), 7.83 (d, J=6.0 Hz, 1H), 6.86-6.83 (m, 2H), 6.71 (d, J=2 Hz, 1H), 6.48 (bs, 1H), 6.09 (d, J=6 Hz, 1H), 4.46 (bs, 1H), 4.01 (s, 3H), 3.93 (s, 3H), 3.74-3.69 (m, 4H), 3.47 (t, J=6.4 Hz, 2H), 3.37-3.25 (m, 6H), 1.69 (m, 2H); HPLC (Method 1) 98.2% (AUC), $t_R$=10.3 min.; ESI+APCI MS m/z 524 [M+H]$^+$.

Preparation 1-((4-(4-(2-(5-chloro-2,4-dimethoxyphenyl)imidazo[1,2-a]pyridine-7-yl)piperazin-1-yl)pyrimidin-2-yl)amino)propan-2-ol 312n (Example 399)

A solution of 2-(5-chloro-2,4-dimethoxyphenyl)-7-(4-(2-chloropyrimidin-4-yl)piperazin-1-yl)imidazo[1,2-a]pyridine 311 (100 mg, 0.20 mmol), 1-aminopropan-2-ol (23 mg, 0.309 mmol) and DIPEA (80 mg, 0.619 mmol) in acetonitrile (2.0 mL) was heated at 130° C. in a microwave reactor for 2 h. The reaction mixture was diluted with water; the precipitate was collected by filtration, washed with water and dried. The crude compound was purified by combi-flash companion (silica gel, NH$_4$OH/CH$_3$OH/CH$_2$Cl$_2$) to provide 1-((4-(4-(2-(5-chloro-2,4-dimethoxyphenyl)imidazo[1,2-a]pyridine-7-yl)piperazin-1-yl)pyrimidin-2-yl)amino)propan-2-ol 312p (25 mg, 23%) as an off-white solid.

$^1$H NMR (400 MHz, DMSO-d$_6$): δ 8.35 (d, J=7.6 Hz, 1H), 8.17 (s, 1H), 8.03 (s, 1H), 7.83 (d, J=6.0 Hz, 1H), 6.87-6.84 (m, 2H), 6.71 (d, J=2 Hz, 1H), 6.39 (bs, 1H), 6.11 (d, J=6 Hz, 1H), 4.72 (bs, 1H), 4.01 (s, 3H), 3.93 (s, 3H), 3.80-3.69 (m, 5H), 3.30-3.12 (m, 6H), 1.06 (d, J=6.4 Hz, 3H); HPLC (Method 2) 99.5% (AUC), $t_R$=11.7 min.; ESI+APCI MS m/z 524 [M+H]$^+$.

Preparation of tert-butyl (1-(4-(4-(2-(5-chloro-2,4-dimethoxyphenyl)imidazo[1,2-a]pyridin-7-yl)piperazin-1-yl)pyrimidin-2-yl)piperidin-4-yl)arbamate 312a A mixture of 2-(5-chloro-2,4-dimethoxyphenyl)-7-(4-(2-chloropyrimidin-4-yl)piperazin-1-yl)imidazo[1,2-a]pyridine 311 (200 mg, 0.412 mmol), tert-butyl piperidin-4-ylcarbamate (113 mg, 0.618 mmol) and DIPEA (159 mg, 1.23 mmol) was heated at 100° C. in a microwave reactor for 40 min. The reaction mixture was diluted with water; the precipitate was collected by filtration, washed with water and dried. The crude compound was purified by combi-flash companion (silica gel, NH$_4$CH$_3$OCH$_2$Cl$_2$) to provide tert-butyl (1-(4-(4-(2-(5-chloro-2,4-dimethoxyphenyl)imidazo[1,2-a]pyridin-7-yl)piperazin-1-yl)pyrimidin-2-yl)piperidin-4-yl)carbamate 312q (150 mg, 56%) as an off-white solid.

$^1$H NMR (300 MHz, DMSO-d$_6$): δ 8.35 (d, J=7.5 Hz, 1H), 8.17 (s, H), 8.03 (s, 1H), 7.91 (d, J=6 Hz, 1H), 6.87-6.80 (m, 3H), 6.71 (s, 1H), 6.14 (d, J=8 Hz, 1H), 4.56 (d, J=13.2 Hz, 2H), 4.01 (s, 3H), 3.93 (s, 3H), 3.80-3.75 (m, 4H), 3.54-3.47 (m, 1H), 3.45-3.30 (m, 4H), 2.91 (t, J=12.3 Hz, 2H), 1.75 (d, J=9.3 Hz, 2H), 1.38 (s, 9H), 1.35-1.23 (m, 2H); HPLC (Method 1) 95.1% (AUC), $t_R$=12.7 min.; ESI+APCI MS m/z 649 [M+H]$^+$.

Preparation of 1-(4-(4-(2-(5-chloro-2,4-dimethoxyphenyl)imidazo[1,2-a]pyridin-7-yl)piperazin-1-yl)pyrimidin-2-yl)piperidin-4-amine 312r (Example 338)

To a solution of tert-butyl (1-(4-(4-(2-(5-chloro-2,4-dimethoxyphenyl)imidazo[1,2-a]pyridin-7-yl)piperazin-1-yl)pyrimidin-2-yl)piperidin-4-yl)carbamate 312q (130 mg, 0.20 mmol) in CH$_2$Cl$_2$ (1.0 mL) was added a solution of HCl in 1,4-dioxane (4.0 M, 1.0 mL). The suspension was stirred at room temperature for 4 h and then filtered. The solid obtained was washed with dichloromethane and then re-suspended in water (5.0 mL), basified with saturated sodium bicarbonate (5.0 mL, stirred for 1 h at room temperature).

The suspension was filtered to provide 1-(4-(4-(2-(5-chloro-2,4-dimethoxyphenyl)imidazo[1,2-a]pyridin-7-yl) piperazin-1-yl)pyrimidin-2-yl)piperidin-4-amine 312r (30 mg, 27%/8) as an off-white solid.

$^1$H NMR (400 MHz, DMSO-d$_6$): δ 8.34 (d, J=7.6 Hz, 1H), 8.17 (s, 1H), 8.03 (s, 1H), 7.90 (d, J=6 Hz, 1H), 6.86 (s, 1H), 6.85 (dd, J=2.4, 7.6 Hz, 1H), 6.70 (s, 1H), 6.11 (d, J=6 Hz, 1H), 4.49 (d, J=12.8 Hz, 2H), 4.01 (s, 3H), 3.93 (s, 3H), 3.75-3.67 (m, 4H), 3.45-3.30 (m, 4H), 2.91-2.75 (m, 3H), 1.73 (d, J=10.8 Hz, 2H), 1.15 (m, 2H); HPLC (Method 1) 93.2% (AUC), t$_R$=11.1 min.; ESI+APCI MS m/z 549 [M+H]$^+$.

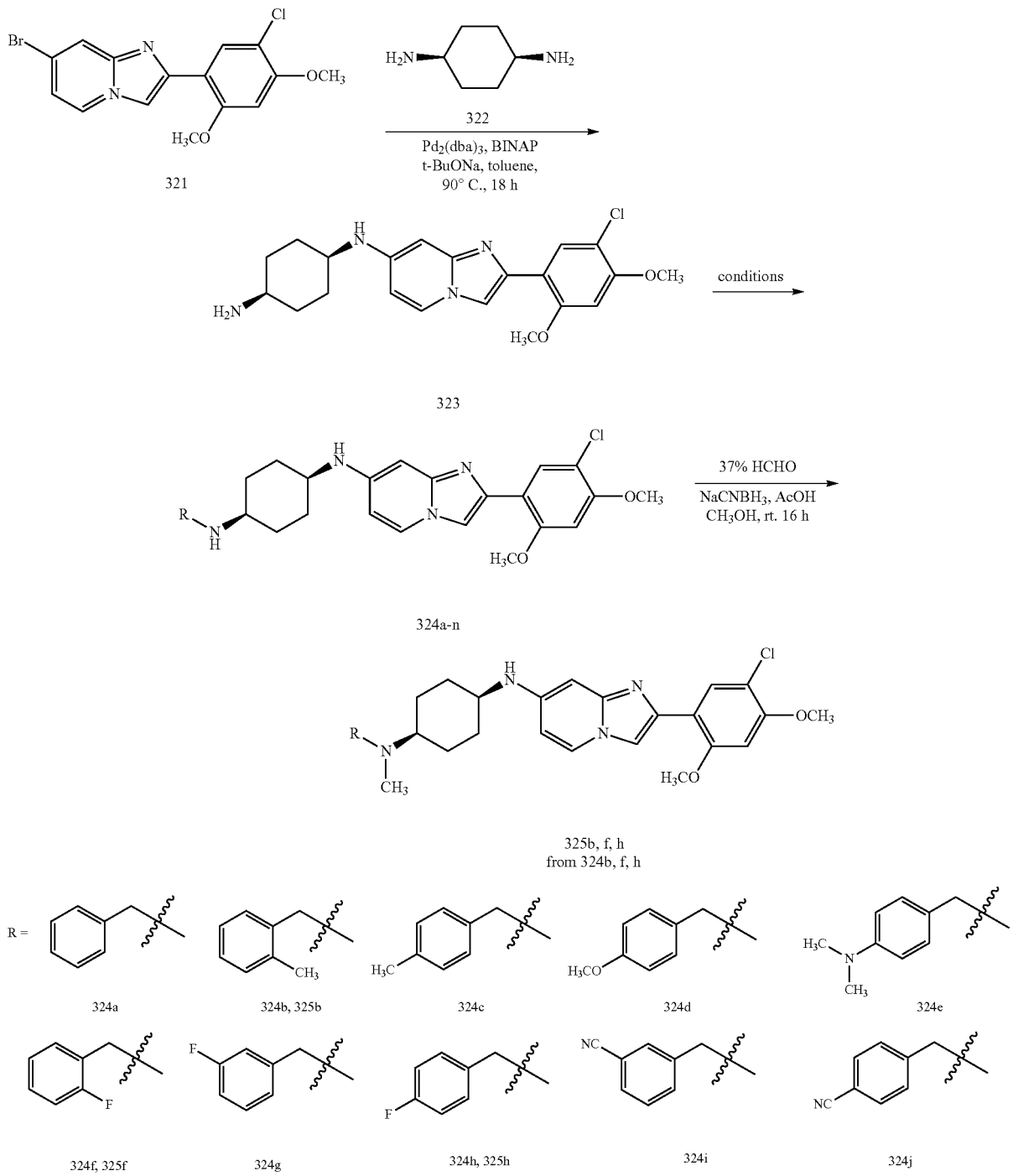

Scheme 2-10

-continued

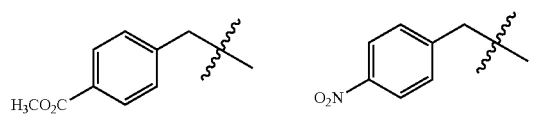

324k     324l

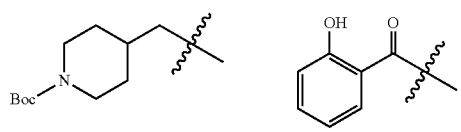

324m     324n

Preparation of cis-N$^1$-(2-(5-chloro-2,4-dimethoxyphenyl)imidazo[1,2-a]pyridin-7-yl)cyclohexane-1,4-diamine 323

A suspension of 7-bromo-2-(5-chloro-2,4-dimethoxyphenyl)imidazo[1,2-a]pyridine 321 (5.00 g, 13.7 mmol), cis-cyclohexane-1,4-diamine (1.55 g, 13.7 mmol), BINAP (849 mg, 1.36 mmol), and NaOt-Bu (3.93 g, 40.9 mmol) in toluene (150 mL) was degassed with argon for 15 min. To the suspension was added Pd$_2$(dba)$_3$ (625 mg, 0.68 mmol) and the resulting mixture was further degassed with argon for 5 min. The reaction mixture was heated at 100° C. for 18 h. The reaction mixture was cooled to room temperature, diluted with CH$_2$Cl$_2$ (500 mL) and filtered through a pad of celite. The filtrate was concentrated under reduced pressure and the residue obtained was purified by silica gel chromatography (CH$_3$OH/CH$_2$Cl$_2$) to give cis-N$^1$-(2-(5-chloro-2,4-dimethoxyphenyl)imidazo[1,2-a]pyridin-7-yl)cyclohexane-1,4-diamine 323 (1.50 g, 27%) as a green solid.

$^1$H NMR (400 MHz, DMSO-d$_6$): δ 8.13 (s, 1H), 8.10 (d, J=3.8 Hz, 1H), 7.86 (s, 1H), 6.84 (s, 1H), 6.44 (dd, J=2.0, 7.2 Hz, 1H), 6.18 (s, 1H), 5.98 (d, J=8.0 Hz, 1H), 3.99 (s, 3H), 3.92 (s, 3H), 3.38-3.35 (m, 1H), 2.83-2.80 (m, 1H), 1.72-1.70 (m, 2H), 1.63-1.54 (m, 2H), 1.49-1.44 (m, 4H); ESI+APCI MS m/z 401 [M+H]$^+$.

Preparation of cis-N$^1$-benzyl)-N$^4$-(5-chloro-2,4-dimethoxyphenyl)imidazo[1,2-a]pyridin-7-yl)cyclohexane-1,4-diamine 324a (Example 325)

A solution of cis-N$^1$-(2-(5-chloro-2,4-dimethoxyphenyl)imidazo[1,2-a]pyridin-7-yl)cyclohexane-1,4-diamine 323 (100 mg, 0.25 mmol), benzaldehyde (26 mg, 0.25 mmol) and AcOH (0.1 mL) in CH$_3$OH (5 mL) was stirred at room temperature for 1 h; the reaction mixture was charged with NaCNBH$_3$ (85 mg, 1.24 mmol) at 0° C., and was then stirred at room temperature for 16 h under nitrogen atmosphere. The reaction mixture was diluted with water and extracted with CH$_2$Cl$_2$ (2×10 mL). The combined organic layers were dried over sodium sulfate, filtered and concentrated under reduced pressure and the residue was purified by combiflash companion (silica gel, CH$_3$OH/CH$_2$Cl$_2$) to afford cis-N$^1$-benzyl)-N$^4$-(2-(5-chloro-2,4-dimethoxyphenyl)imidazo[1,2-a]pyridin-7-yl)cyclohexane-1,4-diamine 324a (Example 325) (20 mg, 16%) as an off-white solid.

$^1$H NMR (400 MHz, DMSO-d$_6$): δ 8.13 (s, 1H), 8.10 (d, J=7.2 Hz, 1H), 7.86 (s, 1H), 7.36-7.29 (m, 4H), 7.23-7.20 (m, 1H), 6.84 (s, 1H), 6.43 (d, J=8.0 Hz, 1H), 6.19 (s, 1H), 6.02 (d, J=7.2 Hz, 1H), 3.99 (s, 3H), 3.92 (s, 3H), 3.73 (s, 2H), 3.39-3.35 (m, 1H), 2.68-2.64 (m, 1H), 1.73-1.70 (m, 2H), 1.60-1.62 (m, 6H); HPLC (Method 3) 96.5% (AUC), $t_R$=12.21 min.; ESI+APCI MS m/z 491 [M+H]$^+$.

Preparation of cis-N$^1$-(2-(5-chloro-2,4-dimethoxyphenyl)imidazo[1,2-a]pyridin-7-yl)-N$^1$-(2-methylbenzyl)cyclohexane-1,4-diamine Compound cis-N$^1$-(2-(5-chloro-2,4-dimethoxyphenyl)imidazo[1,2-a]pyridin-7-yl)-N$^1$-(2-methylbenzyl)cyclohexane-1,4-diamine 324b was prepared in the same manner as cis-N$^1$-benzyl)-N$^4$-(2-(5-chloro-2,4-dimethoxyphenyl)imidazo[1,2-a]pyridin-7-yl)cyclohexane-1,4-diamine 324a, and was obtained as an off-white solid (20 mg, 16% yield).

$^1$H NMR (400 MHz, DMSO-d$_6$): δ 8.14 (s, 1H), 8.10 (d, J=7.2 Hz, 1H), 7.86 (s, 1H), 7.33-7.32 (m, 2H), 7.14-7.13 (m, 3H), 6.84 (s, 1H), 6.43 (dd, J=2.0, 7.2 Hz, 1H), 6.20 (s, 1H), 6.03 (d, J=7.2 Hz, 1H), 3.99 (s, 3H), 3.92 (s, 3H), 3.73 (s, 2H), 3.43-3.38 (m, 1H), 2.71-2.69 (m, 1H), 2.32 (s, 3H), 1.72-1.65 (m, 8H); HPLC (Method 3) 92.2% (AUC), $t_R$=12.45 min.; ESI+APCI MS m/z 505 [M+H]$^+$.

Preparation of cis-N$^1$-(2-(5-chloro-2,4-dimethoxyphenyl)imidazo[1,2-a]pyridin-7-yl)-N$^4$-(4-methylbenzyl)cyclohexane-1,4-diamine 324c (Example 329)

Compound cis-N$^1$-(2-(5-chloro-2,4-dimethoxyphenyl)imidazo[1,2-a]pyridin-7-yl)-N$^4$-(4-methylbenzyl)cyclohexane-1,4-diamine 324c was prepared in the same manner as cis-N$^1$-benzyl)-N$^4$-(2-(5-chloro-2,4-dimethoxyphenyl)imidazo[1,2-a]pyridin-7-yl)cyclohexane-1,4-diamine 324a, and was obtained as an off-white solid (20 mg, 19% yield).

$^1$H NMR (400 MHz, DMSO-d$_6$): δ 8.13 (s, 1H), 8.10 (d, J=7.6 Hz, 1H), 7.22 (d, J=7.6 Hz, 2H), 7.10 (d, J=7.6 Hz, 2H), 6.84 (s, 1H), 6.42 (d, J=5.6 Hz, 1H), 6.19 (s, 1H), 6.01 (d, J=7.2 Hz, 1H), 3.99 (s, 3H), 3.92 (s, 3H), 3.65 (s, 2H), 3.39-3.35 (m, 1H), 2.64-2.60 (m, 1H), 2.60 (s, 3H), 1.72-1.68 (m, 2H), 1.50-1.59 (m, 6H); HPLC (Method 1) 97.4% (AUC), $t_R$=12.58 min.; ESI+APCI MS m/z 505 [M+H]$^+$.

Preparation of cis-N$^1$-(2-(5-chloro-2,4-dimethoxyphenyl)imidazo[1,2-a]pyridin-7-yl)-N$^4$-(4-methoxybenzyl)cyclohexane-1,4-diamine bis(2,2,2-trifluoroacetate) 324d (Example 380)

Compound cis-N$^1$-(2-(5-chloro-2,4-dimethoxyphenyl)imidazo[1,2-a]pyridin-7-yl)-N$^4$-(4-methoxybenzyl)cyclohexane-1,4-diamine was prepared in the same manner as cis-N$^1$-benzyl)-N$^4$-(2-(5-chloro-2,4-dimethoxyphenyl)imidazo[1,2-a]pyridin-7-yl)cyclohexane-1,4-diamine 324a, and the free base was purified by prep-HPLC to give the TFA salt cis-N$^1$-(2-(5-chloro-2,4-dimethoxyphenyl)imidazo[1,2-a]pyridin-7-yl)-N$^4$-(4-methoxybenzyl)cyclohexane-1,4-diamine bis(2,2,2-trifluoroacetate) 324d (Example 380) as an off-white solid (7% yield).

$^1$H NMR (400 MHz, DMSO-d$_6$) δ: 13.20 (bs, 1H), 8.76 (bs, 1H), 8.40 (d, J=7.2 Hz, 1H), 8.23 (s, 1H), 7.88 (s, 1H), 7.6 (d, J=7.8 Hz, 1H), 7.40-7.38 (m, 2H), 7.02-6.93 (m, 4H), 6.44 (bs, 1H), 4.13 (d, J=5.2 Hz, 2H), 4.05 (s, 3H), 3.99 (s, 3H), 3.8 (s, 3H), 3.7 (bs, 1H), 3.1 (bs, 1H), 1.95-1.93 (m, 4H), 1.85-1.70 (m, 4H); HPLC (Method 1) 98.21% (AUC), $t_R$=12.1 min.; ESI+APCI MS m/z 521 [M+H]$^+$.

Preparation of cis-N$^1$-(2-(5-chloro-2,4-dimethoxyphenyl)imidazo[1,2-a]pyridin-7-yl)-N$^4$-(4-(dimethylamino)benzyl)cyclohexane-1,4-diamine bis(2,2,2-trifluoroacetate) 324e (Example 418)

Compound cis-N$^1$-(2-(5-chloro-2,4-dimethoxyphenyl)imidazo[1,2-a]pyridin-7-yl)-N$^4$-(4-(dimethylamino)benzyl)

cyclohexane-1,4-diamine was prepared in the same manner as cis-N$^1$-benzyl-N$^4$-(2-(5-chloro-2,4-dimethoxyphenyl)imidazo[1,2-a]pyridin-7-yl)cyclohexane-1,4-diamine 324a. The free base was purified by prep-HPLC to give cis-N$^1$-(2-(5-chloro-2,4-dimethoxyphenyl)imidazo[1,2-a]pyridin-7-yl)-M-(4-(dimethylamino)benzyl)cyclohexane-1,4-diamine bis(2,2,2-trifluoroacetate) 324e (Example 418) as an off-white solid (4% yield).

$^1$H NMR (300 MHz, DMSO-d$_6$) δ: 13.27 (s, 1H), 8.68 (bs, 2H), 8.41 (d, J=7.5 Hz, 1H), 8.20 (s, 1H), 7.89 (s, 1H), 7.56 (d, J=5.4 Hz, 1H), 7.31 (d, J=8.7 Hz, 2H), 6.98-6.75 (m, 2H), 6.78-6.75 (m, 2H), 6.45 (bs, 1H), 4.05 (s, 5H), 3.99 (s, 3H), 3.68 (bs, 1H), 3.14-3.11 (m, 1H), 3.09 (s, 6H), 2.08-1.92 (m, 4H), 1.81-1.76 (m, 4H); HPLC (Method 5) >99% (AUC), t$_R$=11.96 min.; ESI+APCI MS m/z 534 [M+H]$^+$.

Preparation of cis-N$^1$-(2-(5-chloro-2,4-dimethoxyphenyl)imidazo[1,2-a]pyridin-7-yl)-N-(2-fluorobenzyl)cyclohexane-1,4-diamine 324f Compound cis-N$^1$-(2-(5-chloro-2,4-dimethoxyphenyl)imidazo[1,2-a]pyridin-7-yl)-N$^4$-(2-fluorobenzyl)cyclohexane-1,4-diamine 324f was prepared in the same manner as cis-N$^1$-benzyl-N$^4$-(2-(5-chloro-2,4-dimethoxyphenyl)imidazo[1,2-a]pyridin-7-yl)cyclohexane-1,4-diamine 324a, and was obtained as an off-white solid (16% yield).

$^1$H NMR (400 MHz, DMSO-d$_6$): δ 8.13 (s, 1H), 8.10 (d, J=7.6 Hz, 1H), 7.86 (s, 1H), 7.50 (t, J=6.8 Hz, 2H), 7.28-7.26 (m, 1H), 7.18-7.11 (m, 2H), 6.84 (s, 1H), 6.43 (d, J=6.4 Hz, 1H), 6.19 (s, 1H), 6.02 (d, J=7.6 Hz, 1H), 3.99 (s, 3H), 3.92 (s, 3H), 3.76 (s, 2H), 3.37 (br s, 1H), 2.64 (bs, 1H), 1.71-1.69 (m, 2H), 1.68-1.62 (m, 6H); HPLC (Method 3) 90.5% (AUC), t$_R$=12.23 min.; ESI+APCI MS m/z 509 [M+H]$^+$.

Preparation of cis-N-(2-(5-chloro-2,4-dimethoxyphenyl)imidazo[1,2-a]pyridin-7-yl)-N$^4$-(3-fluorobenzyl)cyclohexane-1,4-diamine bis(2,2,2-trifluoroacetate) 324e (Example 402)

Compound cis-N$^1$-(2-(5-chloro-2,4-dimethoxyphenyl)imidazo[1,2-a]pyridin-7-yl)-N$^4$-(3-fluorobenzyl)cyclohexane-1,4-diamine was prepared in the same manner as cis-N$^1$-benzyl)-N$^4$-(2-(5-chloro-2,4-dimethoxyphenyl)imidazo[1,2-a]pyridin-7-yl)cyclohexane-1,4-diamine 324a. The free base was purified by prep-HPLC to give cis-N$^1$-(2-(5-chloro-2,4-dimethoxyphenyl)imidazo[1,2-a]pyridin-7-yl)-N$^4$-(3-fluorobenzyl)cyclohexane-1,4-diamine bis(2,2,2-trifluoroacetate) 324g as an off-white solid (4% yield).

$^1$H NMR (400 MHz, DMSO-d$_6$) δ: 13.17 (s, 1H), 8.97 (bs, 2H), 8.40 (d, J=7.6 Hz, 1H), 8.23 (s, 1H), 7.89 (s, 1H), 7.55-7.49 (m, 2H), 7.42-7.36 (m, 2H), 7.31-7.26 (m, 1H), 6.98 (s, 1H), 6.96 (d, J=12.4 Hz, 1H), 6.44 (bs, 1H), 4.24-4.16 (m, 2H), 4.05 (s, 3H), 3.99 (s, 3H), 3.69-3.64 (m, 1H), 3.25-3.15 (m, 1H), 1.94-1.85 (m, 4H), 1.75-1.85 (m, 4H); HPLC (Method 4) 98.65% (AUC), t$_R$=13.57 min.; ESI+APCI MS m/z 509 [M+H]$^+$.

Preparation of cis-N$^1$-(2-(5-chloro-2,4-dimethoxyphenyl)imidazo[1,2-a]pyridin-7-yl)-N$^4$-(4-fluorobenzyl)cyclohexane-1,4-diamine 324h (Example 326)

Compound cis-N$^1$-(2-(5-chloro-2,4-dimethoxyphenyl)imidazo[1,2-a]pyridin-7-yl)-N$^4$-(4-fluorobenzyl)cyclohexane-1,4-diamine 324h was prepared in the same manner as cis-N$^1$-benzyl)-N$^4$-(2-(5-chloro-2,4-dimethoxyphenyl)imidazo[1,2-a]pyridin-7-yl)cyclohexane-1,4-diamine 324a and was obtained as an off-white solid (19% yield).

$^1$H NMR (400 MHz, DMSO-d$_6$): δ 8.13 (s, 1H), 8.10 (d, J=7.2 Hz, 1H), 7.86 (s, 1H), 7.40-7.37 (m, 2H), 7.12 (t, J=8.8 Hz, 2H), 6.84 (s, 1H), 6.43 (d, J=7.2 Hz, 1H), 6.19 (s, 1H), 6.04 (d, J=7.2 Hz, 1H), 3.99 (s, 3H), 3.92 (s, 3H), 3.70 (s, 2H), 3.39-3.35 (m, 1H), 2.66-2.63 (m, 1H), 1.73-1.61 (m, 8H); HPLC (Method 3) 96.2% (AUC), t$_R$=12.31 min.; ESI+APCI MS m/z 509 [M+H]$^+$.

Preparation of 3-(((cis-4-((2-(5-chloro-2,4-dimethoxyphenyl)imidazo[1,2-a]pyridin-7-yl)amino)cyclohexyl)amino)methyl)benzonitrile 324i (Example 371)

Compound 3-(((cis-4-((2-(5-chloro-2,4-dimethoxyphenyl)imidazo[1,2-a]pyridin-7-yl)amino)cyclohexyl)amino)methyl)benzonitrile 324i was prepared in the same manner as as cis-N$^1$-benzyl)-N$^4$-(2-(5-chloro-2,4-dimethoxyphenyl)imidazo[1,2-a]pyridin-7-yl)cyclohexane-1,4-diamine 324a and was obtained as an off-white solid (26% yield).

$^1$H NMR (300 MHz, DMSO-d$_6$) δ: 8.17 (d, J=7.5 Hz, 1H), 8.09 (s, 1H), 7.93 (s, 1H), 7.90 (s, 1H), 7.78-7.76 (m, 2H), 7.59 (t, J=8.4 Hz, 1H), 6.87 (s, 1H), 6.52 (d, J=6.9 Hz, 1H), 6.3 (bs, 1H), 6.24 (bs, 1H), 4.0 (s, 4H), 3.93 (s, 4H), 3.46 (bs, 2H), 1.98-1.50 (m, 2H); HPLC (Method 1) 97.6% (AUC), t$_R$=12.02 min.; ESI+APCI MS m/z 516 [M+H]$^+$.

Preparation of 4-((cis-4-((2-(5-chloro-2,4-dimethoxyphenyl)imidazo[1,2-a]pyridin-7-yl)amino)cyclohexyl)amino)methyl)benzonitrile bis(2,2,2-trifluoroacetate) 324j Compound 4-(((cis-4-((2-(5-chloro-2,4-dimethoxyphenyl)imidazo[1,2-a]pyridin-7-yl)amino)cyclohexyl)amino)methyl)benzonitrile was prepared in the same manner as cis-N$^1$-benzyl)-N$^4$-(2-(5-chloro-2,4-dimethoxyphenyl)imidazo[1,2-a]pyridin-7-yl)cyclohexane-1,4-diamine 324a. The free base was purified by prep-HPLC to give 4-(((cis-4-((2-(5-chloro-2,4-dimethoxyphenyl)imidazo[1,2-a]pyridin-7-yl)amino)cyclohexyl)amino)-methyl)benzonitrile bis(2,2,2-trifluoroacetate) 324j as an off-white solid (4% yield).

$^1$H NMR (400 MHz, DMSO-d$_6$) δ: 13.38 (s, 1H), 9.0 (bs, 2H), 8.45 (d, J=7.6 Hz, 1H), 8.23 (s, 1H), 7.96 (d, J=8.4 Hz, 2H), 7.88 (s, 1H), 7.73-7.71 (m, 2H), 7.5 (d, J=4.4 Hz, 1H), 6.98 (s, 1H), 6.95 (d, J=4.4 Hz, J=7.2 Hz, 1H), 6.44 (bs, 1H), 4.32 (bs, 2H), 4.05 (s, 3H), 3.99 (s, 3H), 3.7 (bs, 1H), 3.20 (bs, 1H), 1.96-1.94 (m, 4H), 1.81-1.72 (m, 4H); HPLC (Method 1) 96.22% (AUC), t$_R$=12.74 min.; ESI+APCI MS m/z 516 [M+H]$^+$.

Preparation of methyl 4-(((cis-4-((2-(5-chloro-2,4-dimethoxyphenyl)imidazo[1,2-a]pyridin-7-yl)amino)cyclohexyl)amino)methyl)benzoate bis(2,2,2-trifluoroacetate) 324k (Example 409)

Compound methyl 4-(((cis-4-((2-(5-chloro-2,4-dimethoxyphenyl)imidazo[1,2-a]pyridin-7-yl)amino)cyclohexyl)amino)methyl)benzoate was prepared in the same manner as cis-N$^1$-benzyl)-N$^4$-(2-(5-chloro-2,4-dimethoxyphenyl)imidazo[1,2-a]pyridin-7-yl)cyclohexane-1,4-diamine 324a. The free base was purified by prep-HPLC to give methyl 4-(((cis-4-((2-(5-chloro-2,4-dimethoxyphenyl)imidazo[1,2-a]pyridin-7-yl)amino)cyclohexyl)amino)methyl)benzoate bis(2,2,2-trifluoroacetate) 324k as an off-white solid (12% yield).

¹H NMR (400 MHz, DMSO-d₆) δ: 13.23 (s, 1H), 9.0 (bs, 2H), 8.40 (d, J=7.5 Hz, 1H), 8.23 (s, 1H), 8.04 (d, J=8.1 Hz, 2H), 7.88 (s, 1H), 7.67 (d, J=8.4 Hz, 2H), 7.57 (d, J=5.7 Hz, 1H), 6.98-6.93 (m, 2H), 6.46 (bs, 1H), 4.31 (bs, 2H), 4.05 (s, 3H), 3.98 (s, 3H), 3.87 (s, 3H), 3.7 (bs, 1H), 3.30-3.22 (m, 1H), 1.96-1.88 (m, 4H), 1.84-1.73 (m, 4H); HPLC (Method 1) 96.22% (AUC), $t_R$=12.74 min.; ESI+APCI MS m/z 516 [M+H]⁺.

Preparation of cis-N¹-(2-(5-chloro-2,4-dimethoxyphenyl)imidazo[1,2-a]pyridin-7-yl)-N⁴-(4-nitrobenzyl)cyclohexane-1,4-diamine 324l (Example 411)

Compound) cis-N¹-(2-(5-chloro-2,4-dimethoxyphenyl)imidazo[1,2-a]pyridin-7-yl)-N⁴-(4-nitrobenzyl)cyclohexane-1,4-diamine 324l was prepared in the same manner cis-N¹-benzyl)-N⁴-(2-(5-chloro-2,4-dimethoxyphenyl)imidazo[1,2-a]pyridin-7-yl)cyclohexane-1,4-diamine 324a and was obtained as an off-white solid (13% yield).

¹H NMR (300 MHz, DMSO-d₆) δ: 8.19 (d, J=5.7 Hz, 2H), 8.12 (d, J=7.8 Hz, 2H), 7.87 (s, 1H), 7.65 (d, J=5.7 Hz, 2H), 6.84 (s, 1H), 6.45 (dd, J=1.8, 9.0 Hz, 1H), 6.19 (s, 1H), 6.06 (d, J=6.6 Hz, 1H), 3.99 (s, 3H), 3.92 (s, 3H), 3.86 (bs, 2H), 2.65-2.55 (m, 2H), 1.85-1.51 (m, 8H); HPLC (Method 5) 93.57% (AUC), $t_R$=12.19 min.; ESI+APCI MS m/z 536 [M+H]⁺.

Preparation of tert-butyl 4-(((cis-4-((2-(5-chloro-2,4-dimethoxyphenyl)imidazo[1,2-a]pyridin-7-yl)amino)cyclohexyl)amino)methyl)piperidine-1-carboxylate 324m (Example 423)

Compound of tert-butyl 4-(((cis-4-((2-(5-chloro-2,4-dimethoxyphenyl)-imidazo[1,2-a]pyridin-7-yl)amino)cyclohexyl)amino)methyl)piperidine-1-carboxylate 324m was prepared in the same manner as cis-N¹-benzyl-N⁴-(2-(5-chloro-2,4-dimethoxyphenyl)imidazo[1,2-a]pyridin-7-yl)cyclohexane-1,4-diamine 324a, and was obtained as an off-white solid (4% yield).

¹H NMR (400 MHz, DMSO-d₆) δ: 8.26 (d, J=7.6 Hz, 2H), 7.87 (s, 1H), 6.85 (s, 1H), 6.50 (d, J=7.6 Hz, 2H), 6.20 (s, 1H), 6.06 (d, J=5.6 Hz, 1H), 3.99 (s, 3H), 3.93 (s, 5H), 3.45 (bs, 1H), 2.65-2.55 (m, 4H), 1.72-1.54 (m, 11H), 1.54 (s, 9H), 1.01 (bs, 2H), 0.99-0.85 (m, 2H); HPLC (Method 5) 98.29% (AUC), $t_R$=12.93 min.; ESI+APCI MS m/z 598 [M+H]⁺.

Preparation of N-(cis-4-((2-(5-chloro-2,4-dimethoxyphenyl)imidazo[1,2-a]pyridin-7-yl)amino)cyclohexyl)-2-hydroxybenzamide trifluoroacetate 324n (Example 392)

A mixture of cis-N¹-(2-(5-chloro-2,4-dimethoxyphenyl)imidazo[1,2-a]pyridin-7-yl)cyclohexane-1,4-diamine 323 (200 mg, 0.5 mmol), 2-hydroxybenzoic acid (83 mg, 0.6 mmol), HATU (285 mg, 0.75 mmol) and N,N-diisopropylethylamine (0.17 mL, 1.0 mmol) in DMF (3 mL) was stirred at room temperature for 16 h. The reaction mixture was quenched with water and extracted with EtOAc (2×25 mL). Combined organic layers were dried over Na₂SO₄, filtered and concentrated. The residue was purified by prep-HPLC to afford N-(cis-4-((2-(5-chloro-2,4-dimethoxyphenyl)imidazo[1,2-a]pyridin-7-yl)amino)cyclohexyl)-2-hydroxybenzamide trifluoroacetate 324n (Example 392) (40 mg, 20%) as an off-white solid.

¹H NMR (300 MHz, DMSO-d₆) 5:12.98 (bs, 1H), 12.36 (s, 1H), 8.57 (bs, 1H), 8.44-8.38 (m, 1H), 8.20 (s, 1H), 7.94 (d, J=7.4 Hz, 1H), 7.88 (s, 1H), 7.51-7.40 (m, 2H), 6.97-6.91 (m, 4H), 6.4 (bs, 1H), 4.05 (s, 3H), 3.99 (s, 4H), 3.65 (bs, 1H), 1.8 (bs, 8H); HPLC (Method 1) 97.61% (AUC), $t_R$=13.89 min.; ESI+APCI MS m/z 521 [M+H]⁺.

Preparation of cis-N¹-(2-(5-chloro-2,4-dimethoxydiphenyl)imidazo[1,2-a]pyridin-7-yl)-N⁴-methyl-N⁴-(2-methylbenzyl)cyclohexane-1,4-diamine bis(2,2,2-trifluoroacetate) 325b (Example 348)

A solution of cis-N¹-(2-(5-chloro-2,4-dimethoxyphenyl)imidazo[1,2-a]pyridin-7-yl)-N⁴-(2-methylbenzyl)cyclohexane-1,4-diamine 324b (200 mg, 0.39 mmol), 37% formaldehyde (11 mg, 0.43 mmol), AcOH (50 μL) in CH₃OH (5.0 mL) was stirred at room temperature for 1 h; the reaction mixture was charged with NaCNBH₃ (27 mg, 0.43 mmol) at 0° C., and was then stirred at room temperature for 16 h under nitrogen atmosphere. The reaction mixture was diluted with water and extracted with CH₂Cl₂ (2×10 mL). The combined organic layers were dried over sodium sulfate, filtered and concentrated under reduced pressure and the residue was purified by combi-flash companion (silica gel, CH₃OH/CH₂Cl₂) followed by prep-HPLC to afford cis-N¹-(2-(5-chloro-2,4-dimethoxyphenyl)imidazo[1,2-a]pyridin-7-yl)-N⁴-methyl)-N⁴-(2-methylbenzyl)cyclohexane-1,4-diamine bis(2,2,2-trifluoroacetate) 325b (20 mg, 16%) as an off-white solid.

¹H NMR (400 MHz, DMSO-d₆): δ 13.20 (s, 1H), 9.13 (s, 1H), 8.42 (d, J=8.0 Hz, 1H), 8.23 (s, 1H), 7.89 (s, 1H), 7.58 (d, J=6.8 Hz, 1H), 7.49 (d, J=7.6 Hz, 1H), 7.41-7.30 (m, 3H), 6.98 (s, 2H), 6.47 (s, 1H), 4.54 (d, J=12.0 Hz, 1H), 4.16-4.10 (m, 1H), 4.05 (s, 3H), 3.98 (s, 3H), 3.83 (s, 1H), 3.47 (s, 1H), 2.69 (s, 3H), 2.42 (s, 3H), 2.1-1.90 (m, 6H), 1.75-1.73 (m, 2H); HPLC (Method 3) 98.4% (AUC), $t_R$=12.45 min.; ESI+APCI MS m/z 520 [M+H]⁺.

Preparation of cis-N¹-(2-(5-chloro-2,4-dimethoxyphenyl)imidazo[1,2-a]pyridin-7-yl)-N⁴-(2-fluorobenzyl)-N¹-methylcyclohexane-1,4-diamine bis(2,2,2-trifluoroacetate) 325f (Example 347)

Compound cis-N¹-(2-(5-chloro-2,4-dimethoxyphenyl)imidazo[1,2-a]pyridin-7-yl)-N⁴-(2-fluorobenzyl)-N¹-methylcyclohexane-1,4-diamine bis(2,2,2-trifluoroacetate) 325f was prepared in the same manner cis-N¹-(2-(5-chloro-2,4-dimethoxyphenyl)imidazo[1,2-a]pyridin-7-yl)-N⁴-methyl-N⁴-(2-methylbenzyl)cyclohexane-1,4-diamine bis(2,2,2-trifluoroacetate) 325b and was obtained as an off-white solid (5% yield).

¹H NMR (400 MHz, DMSO-d₆): δ 13.24 (s, 1H), 9.62 (s, 1H), 8.42 (d, J=8.0 Hz, 1H), 8.23 (s, 1H), 7.89 (s, 1H), 7.66-7.56 (m, 3H), 7.40-7.33 (m, 2H), 6.98-6.96 (m, 2H), 6.47 (s, 1H), 4.56 (d, J=12.8 Hz, 1H), 4.25-4.20 (m, 1H), 4.05 (s, 3H), 3.98 (s, 3H), 3.81 (s, 1H), 3.42 (s, 1H), 2.71 (s, 3H), 2.10-1.77 (m, 6H), 1.75-1.73 (m, 2H); HPLC (Method 3) >99% (AUC), $t_R$=12.32 min.; ESI+APCI MS m/z 523 [M+H]⁺.

Preparation of cis-N¹-(2-(5-chloro-2,4-dimethoxyphenyl)imidazo[1,2-a]pyridin-7-yl)-N⁴-(4-fluorobenzyl)-N¹-methylcyclohexane-1,4-diamine 325h (Example 342)

A mixture of cis-N¹-(2-(5-chloro-2,4-dimethoxyphenyl)imidazo[1,2-a]pyridin-7-yl)-N⁴-(4-fluorobenzyl)cyclohexane-1,4-diamine 324h (250 mg, 0.49 mmol), 37% formaldehyde (16 mg, 0.54 mmol) and AcOH (100 μL) in CH$_3$OH (5 mL) was stirred at room temperature for 1 h. The reaction mixture was charged with NaCNBH$_3$ (34 mg, 0.54 mmol) at 0° C., and was stirred at room temperature for 16 h under nitrogen atmosphere. The reaction mixture was diluted with water and extracted with CH$_2$Cl$_2$ (2×20 mL). The combined organic layers were dried over sodium sulfate, filtered and concentrated under reduced pressure and the residue was purified by combi-flash companion (silica gel, CH$_3$OH/CH$_2$Cl$_2$) to afford cis-N$^1$-(2-(5-chloro-2,4-dimethoxyphenyl)imidazo[1,2-a]pyridin-7-yl)-N$^4$-(4-fluorobenzyl)-N$^1$-methylcyclohexane-1,4-diamine 325h (Example 342) (50 mg, 19%) as a brown solid.

$^1$H NMR (400 MHz, DMSO-d$_6$): δ 8.14 (d, J=7.2 Hz, 1H), 8.12 (s, 1H), 7.89 (s, 1H), 7.35 (m, 2H), 7.13 (t, J=8.8 Hz, 2H), 6.85 (s, 1H), 6.53-6.51 (m, 1H), 6.22-6.19 (m, 2H), 3.99 (s, 3H), 3.92 (s, 3H), 3.55 (s, 3H), 2.11 (s, 3H), 1.84-1.73 (m, 4H), 1.62-1.59 (m, 4H); HPLC (Method 3) 98.10% (AUC), t$_R$=12.34 min.; ESI+APCI MS m/z 523 [M+H]$^+$.

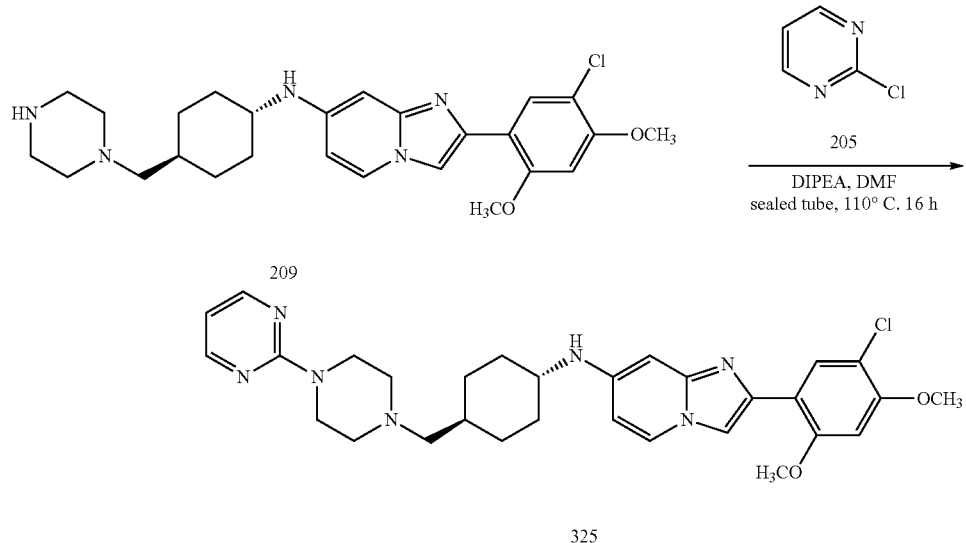

Preparation of 2-(5-chloro-2,4-dimethoxyphenyl)-N-((trans)-4-((4-(pyrimidin-2-yl)piperazin-1-yl)methyl)cyclohexyl)imidazo[1,2-a]pyridin-7-amine 325 (Example 316)

To a solution of 2-(5-chloro-2,4-dimethoxyphenyl)-trans-N-(4-(piperazin-1-ylmethyl)cyclohexyl)imidazo[1,2-a]pyridin-7-amine 324 (100 mg, 0.24 mmol) in DMF (2 mL) was added 2-chloropyrimidine (39 mg, 0.24 mmol) and the reaction mixture was stirred at 110-120° C. for 16 h in a sealed tube. The reaction mixture was quenched with water and extracted with EtOAc (2×10 mL) and the combined organic layers were dried over sodium sulfate, filtered and concentrated under reduced pressure. The residue was purified by combi-flash companion (silica gel, CH$_3$OH/CH$_2$Cl$_2$) to afford 2-(5-chloro-2,4-dimethoxyphenyl)-N-((trans)-4-((4-(pyrimidin-2-yl)piperazin-1-yl)methyl)cyclohexyl)imidazo[1,2-a]pyridin-7-amine 325 (Example 316) (20 mg, 17%) as an off-white solid.

$^1$H NMR (400 MHz, DMSO-d$_6$): δ 8.34 (d, J=4.8 Hz, 2H), 8.14 (d, J=7.2 Hz, 1H), 8.09 (s, 1H), 7.91 (s, 1H), 6.86 (s, 1H), 6.60 (t, d, J=4.8 Hz, 1H), 6.42 (d, J=6.4 Hz, 1H), 6.22 (s, 1H), 3.99 (s, 3H), 3.93 (s, 3H), 3.72 (br s, 4H), 3.22-3.16 (m, 1H), 2.39 (br s, 4H), 2.16 (d, J=7.2 Hz, 2H), 2.06 (d, J=10 Hz, 2H), 1.86 (d, J=11.6 Hz, 2H), 1.58-1.54 (m, 1H), 1.23-1.14 (m, 2H), 1.09-1.03 (m, 2H); HPLC (Method 3) 92.2% (AUC), t$_R$=11.97 min.; ESI+APCI MS m/z 562 [M+H]$^+$.

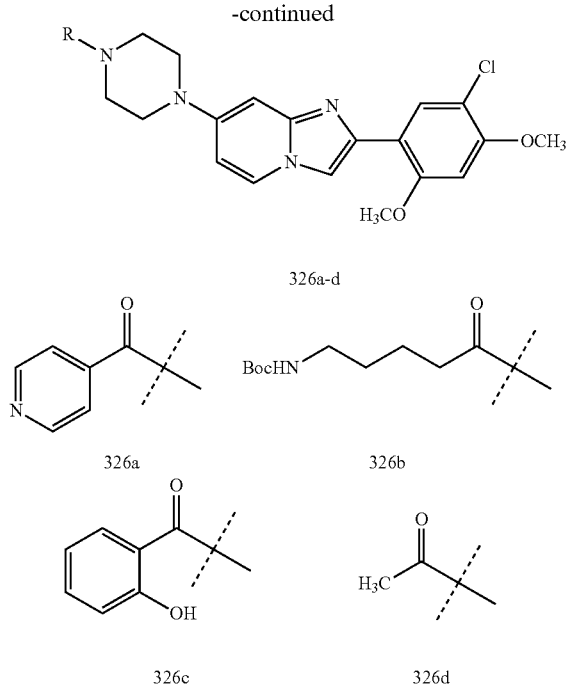

326a-d

Preparation of (4-(2-(5-chloro-2,4-dimethoxyphenyl)imidazo[1,2-a]pyridin-7-yl)piperazin-1-yl)(pyridin-4-yl)methanone 326a (Example 319)

A solution of isonicotinic acid (75 mg, 0.60 mmol) in dry DMF (5.0 mL) was charged with HATU (232 mg, 0.60 mmol) and DIPEA (0.22 mL, 1.2 mmol). The reaction mixture was stirred at room temperature for 1 h. To this reaction mixture was added 2-(5-chloro-2,4-dimethoxyphenyl)-7-(piperazin-1-yl)imidazo[1,2-a]pyridine 301 (150 mg, 0.40 mmol) and the resulting reaction mixture was stirred for additional 4 h. The reaction mixture was diluted with EtOAc (10 mL) and washed with water (2×10 mL), followed by brine. The organic extract was dried over sodium sulfate, filtered and concentrated under reduced pressure. The crude product was purified by combi-flash companion (silica gel, $CH_3OH/CH_2Cl_2$) to provide (4-(2-(5-chloro-2,4-dimethoxyphenyl)imidazo[1,2-a]pyridin-7-yl)piperazin-1-yl)(pyridin-4-yl)methanone 326a (Example 319) (30 mg, 15%) as an off-white solid.

$^1$H NMR (400 MHz, DMSO-$d_6$): δ 8.70 (dd, J=1.6 4.4 Hz, 2H), 8.37 (d, J=7.6 Hz, 1H), 8.13 (s, 1H), 8.06 (s, 1H), 7.45 (dd, J=1.6, 4.4 Hz, 2H), 6.88 (bs, 2H), 6.70 (d, J=2.0 Hz, 1H), 4.01 (s, 3H), 3.94 (s, 3H), 3.79 (s, 2H), 3.42 (s, 4H).

HPLC (Method 1) 98.43% (AUC), $t_R$=11.61 min.; ESI+APCI MS m/z 478.1 [M+H]$^+$.

Preparation of tert-butyl (5-(4-(2-(5-chloro-2,4-dimethoxyphenyl)imidazo[1,2-a]pyridin-7-yl)piperazin-1-yl)-5-oxopentyl)carbamate 326b (Example 315)

Compound tert-butyl (5-(4-(2-(5-chloro-2,4-dimethoxyphenyl)imidazo[1,2-a]pyridin-7-yl)piperazin-1-yl)-5-oxopentyl)carbamate 326b was prepared in the same manner as 4-(2-(5-chloro-2,4-dimethoxyphenyl)imidazo[1,2-a]pyridin-7-yl)piperazin-1-yl)(pyridin-4-yl)methanone 326a, and was obtained as an off-white solid (32% yield).

$^1$H NMR (400 MHz, DMSO-$d_6$): δ 8.55 (d, J=7.6 Hz, 1H), 8.26 (s, 1H), 7.91 (s, 1H), 7.28 (dd, J=2.0, 8.0 Hz, 1H), 6.98 (s, 1H), 6.77 (s, 1H), 6.66 (d, J=2.0 Hz, 1H), 4.05 (s, 3H), 3.99 (s, 3H), 3.65 (s, 4H), 3.58 (s, 2H), 3.53 (s, 2H), 2.92 (q. J=6.8 Hz, 2H), 2.36 (t, J=7.2 Hz, 2H), 1.50 (q, J=7.6 Hz, 2H), 1.41 (d, J=6.8 Hz, 2H), 1.36 (s, 9H); HPLC (Method 1) 98.28% (AUC), $t_R$=13.41 min.; ESI+APCI MS m/z 572.3 [M+H]$^+$.

Preparation of (4-(2-(5-chloro-2,4-dimethoxyphenyl)imidazo[1,2-a]pyridin-7-yl)piperazin-1-yl)(2-hydroxyphenyl)methanone 326c (Example 314)

To a stirred solution of 2-(5-chloro-2,4-dimethoxyphenyl)-7-(piperazin-1-yl)imidazo[1,2-a]pyridine 301 (100 mg, 0.26 mmol) and 2-(trifluoromethyl)phenol (53 mg, 0.32 mmol) in 1,4-dioxane (2.5 mL) was added NaOH aqueous solution (1N, 0.81 mL, 0.81 mmol). The resulting solution was heated at 80° C. for 6 h. The reaction mixture was cooled to room temperature, diluted with water. The Precipitate formed was collected by filtration, washed with hexanes to give (4-(2-(5-chloro-2,4-dimethoxyphenyl)imidazo[1,2-a]pyridin-7-yl)piperazin-1-yl)(2-hydroxyphenyl)methanone 326c (Example 314) as an off-white solid (120 mg, 90%).

$^1$H NMR (400 MHz, DMSO-$d_6$): δ 9.86 (s, 1H), 8.46 (d, J=7.6 Hz, 1H), 8.17 (s, 1H), 8.01 (s, 1H), 7.28-7.23 (m, 1H), 7.17 (dd, J=1.6, 7.6 Hz, 1H), 7.08 (d, J=7.6 Hz, 1H), 6.93-6.85 (m, 3H), 6.70 (d, J=2.0 Hz, 1H), 4.03 (s, 3H), 3.96 (s, 3H), 3.78-3.70 (m, 2H), 3.43 (s, 6H); HPLC (Method 1) 92.21% (AUC), $t_R$=12.76 min.; ESI+APCI MS m/z 493 [M+H]$^+$.

Preparation of 1-(4-(2-(5-chloro-2,4-dimethoxyphenyl)imidazo[1,2-a]pyridin-7-yl)piperazin-1-yl)ethanone 326d (Example 307)

To a stirred solution of 2-(5-chloro-2,4-dimethoxyphenyl)-7-(piperazin-1-yl)imidazo[1,2-a]pyridine 301 (100 mg, 0.26 mmol) and triethylamine (0.1 mL, 0.67 mmol) in $CH_2Cl_2$ (10 mL) was added acetyl chloride (0.1 mL, 0.24 mmol) at 0° C., and the resulting mixture was stirred at room temperature for 6 h. The reaction mixture was diluted with water and extracted with $CH_2Cl_2$ (2×20 mL). The combined organic layers were washed with water followed by brine, dried over $Na_2SO_4$, filtered and concentrated. The crude product was purified by combi-flash companion (silica gel, $CH_3OH/CH_2Cl_2$) to provide 326d (Example 307) as an off-white solid (10 mg, 9%).

$^1$H NMR (400 MHz, DMSO-$d_6$): δ 8.33 (d, J=7.6 Hz, 1H), 8.17 (s, 1H), 8.02 (s, 1H), 6.86 (s, 1H), 6.82 (dd, J=2.0, 7.6 Hz, 1H), 6.69 (s, 1H), 4.00 (s, 3H), 3.93 (s, 3H), 3.59 (s, 4H), 3.19 (s, 4H), 2.05 (s, 3H); HPLC (Method 1) 97.4% (AUC), $t_R$=12.46 min.; ESI+APIC MS m/z 415 [M+H]$^+$.

Scheme 2-13

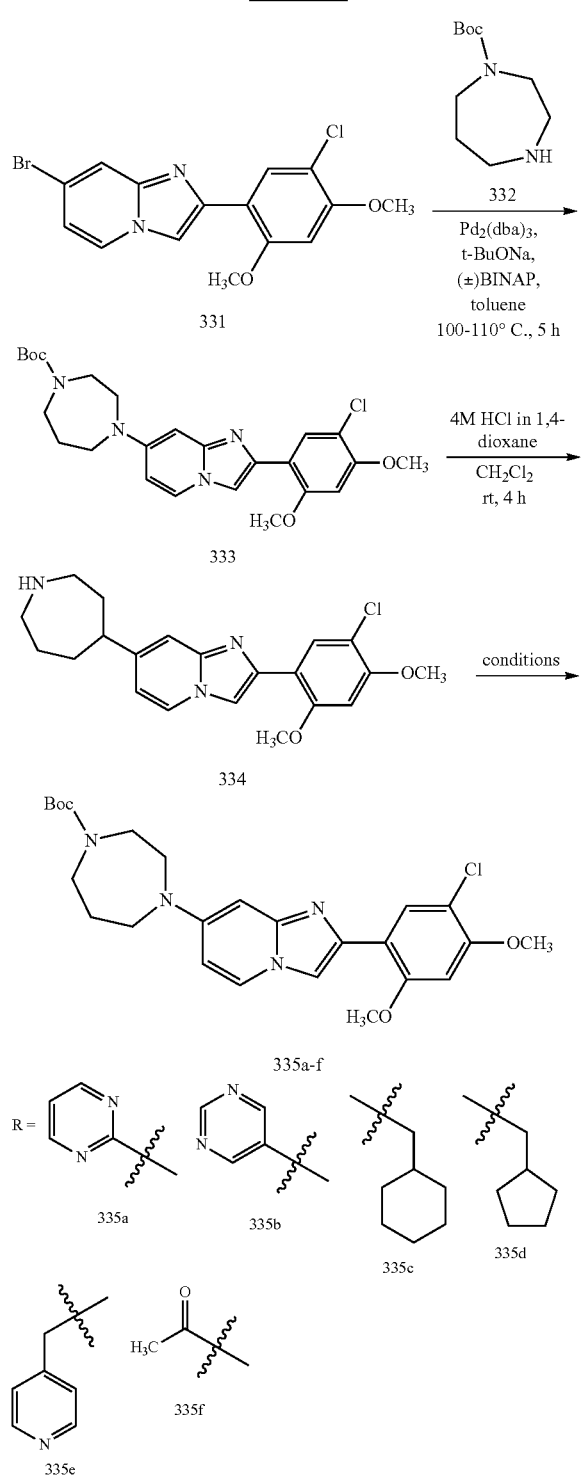

Preparation of tert-butyl 4-(2-(5-chloro-2,4-dimethoxyphenyl)imidazo[1,2-a]pyridin-7-yl)-1,4-diazepane-1-carboxylate 333

A suspension of 7-bromo-2-(5-chloro-2,4-dimethoxyphenyl)imidazo[1,2-a]pyridine 331 (8.00 g, 21.8 mmol), tert-butyl 1,4-diazepane-1-carboxylate 332 (5.24 g, 26.2 mmol), (±) BINAP (1.49 g, 2.39 mmol) and NaOt-Bu (6.28 g, 65.4 mmol) in toluene (100 mL) was degassed with argon for 15 min. The resulting mixture was charged with $Pd_2(dba)_3$ (998 mg, 1.09 mmol) and degassed with argon for another 5 min. The reaction mixture was stirred at 100-110° C. for 5 h. The reaction mixture was cooled, filtered through a pad of celite (the celite was washed with 10% MeOH/$CH_2Cl_2$) and the combined filtrate was evaporated to dryness. The residue was purified by combi-flash companion (silica gel, $CH_3$OH/ $CH_2Cl_2$) to provide tert-butyl 4-(2-(5-chloro-2,4-dimethoxyphenyl)imidazo[1,2-a]pyridin-7-yl)-1,4-diazepane-1-carboxylate 333 (4.50 g, 42%) as a brown solid. ESI+APCI MS m/z 487 [M+H]$^+$.

Preparation of 2-(5-chloro-2,4-dimethoxyphenyl)-7-(1,4-diazepan-1-yl)imidazo[1,2-a]pyridine 334

A solution of tert-butyl 4-(2-(5-chloro-2,4-dimethoxyphenyl)imidazo[1,2-a]pyridin-7-yl)-1,4-diazepane-1-carboxylate 333 (4.30 g, 8.84 mmol) in $CH_2Cl_2$ (100 mL) was charged with a solution of HCl in 1,4-dioxane (4.0 M, 20 mL) and stirred at room temperature for 4 h. The reaction mixture was filtered and the solid obtained was washed with $CH_2Cl_2$. The solid was then suspended in water (55 mL), basified with saturated sodium bicarbonate solution (55 mL), stirred for 1 h at room temperature and filtered to provide 2-(5-chloro-2,4-dimethoxyphenyl)-7-(1,4-diazepan-1-yl)imidazo[1,2-a]pyridine 334 (3.60 g, 94%) as a brown solid. ESI+APCI MS m/z 387 [M+H]$^+$.

Preparation of 2-(5-chloro-2,4-dimethoxyphenyl)-7-(4-(pyrimidin-2-yl-1,4-diazepan-1-yl)imidazo[1,2-a]pyridine 335a (Example 368)

A suspension of 2-(5-chloro-2,4-dimethoxyphenyl)-7-(1,4-diazepan-1-yl)imidazo[1,2-a]pyridine 334 (150 mg, 0.38 mmol) and N,N-diisopropylethylamine (0.19 mL, 1.14 mmol) in DMF (3 mL) was charged with 2-chloropyrimidine (87 mg, 0.76 mmol).

Resulting mixture was subjected to microwave irradiation at 100° C. for 30 min. The reaction mixture was cooled to room temperature, diluted with water and stirred for 1 h. The precipitate was collected by filtration, the solid obtained was washed with water, dried under reduced pressure, and purified by combi-flash companion (silica gel, $CH_3OH/CH_2Cl_2$) to provide 2-(5-chloro-2,4-dimethoxyphenyl)-7-(4-(pyrimidin-2-yl)-1,4-diazepan-1-yl)imidazo[1,2-a]pyridine 335a (Example 368) (25 mg, 14%) as an off-white solid.

$^1$H NMR (400 MHz, DMSO-$d_6$): δ 8.31 (d, J=4.8 Hz, 2H), 8.25 (d, J=7.6 Hz, 1H), 8.14 (s, 1H), 7.94 (s, 1H), 6.85 (s, 1H), 6.70 (dd, J=2.4, 7.6 Hz, 1H), 6.55 (t, J=4.8 Hz, 1H), 3.99 (s, 3H), 3.95 (m, 5H), 3.70 (t, J=5.2 Hz, 2H), 3.64 (t, J=5.6 Hz, 2H), 3.53 (t, J=5.6 Hz, 2H), 1.96 (t, J=5.6 Hz, 2H), HPLC (Method 1) 99.4% (AUC), $t_R$=12.74 min.; ESI+APCI MS m/z 465 [M+H]$^+$.

Preparation of 2-(5-chloro-2,4-dimethoxyphenyl)-7-(4-(pyrimidin-5-yl)-1,4-diazepan-1-yl)imidazo[1,2-a]pyridine 335b (Example 383)

A suspension of 2-(5-chloro-2,4-dimethoxyphenyl)-7-(1, 4-diazepan-1-yl)imidazo[1,2-a]pyridine 334 (100 mg, 0.25 mmol), 5-bromopyrimidine (62 mg, 0.38 mmol), (±) BINAP (17 mg, 0.02 mmol) and NaOt-Bu (72 mg, 0.75 mmol) in toluene (10 mL) was degassed with argon for 15 min. Then this mixture was charged with $Pd_2(dba)_3$ (11 mg, 0.01 mmol) and degassed with argon for another 5 min. The resulting reaction mixture was stirred at 100-110° C. for 16 h. The reaction mixture was cooled to room temperature, filtered through a pad of celite (the celite was washed with 10% MeOH/CH$_2$Cl$_2$) and the combined filtrate was evaporated to dryness. The residue was purified by combi-flash companion (silica gel, CH$_3$OH/CH$_2$Cl$_2$) to provide 2-(5-chloro-2,4-dimethoxyphenyl)-7-(4-(pyrimidin-5-yl)-1,4-diazepan-1-yl)imidazo[1,2-a]pyridine 335b (Example 383) (25 mg, 20%) as an off-white solid.

$^1$H NMR (300 MHz, DMSO-d$_6$): δ 8.39 (s, 1H), 8.34 (s, 2H), 8.24 (d, J=7.5 Hz, 1H), 8.15 (s, 1H), 7.93 (s, 1H), 6.85 (s, 1H), 6.68 (d, J=6 Hz, 1H), 6.50 (s, 1H), 3.99 (s, 3H), 3.92 (s, 3H), 3.72 (s, 4H), 3.50 (br s, 4H), 1.98 (br s, 2H); HPLC (Method 1) 93.0% (AUC), t$_R$=12.42 min.; ESI+APCI MS m/z 465 [M+H]$^+$.

Preparation of 2-(5-chloro-2,4-dimethoxyphenyl)-7-(4-(cyclohexylmethyl)-1,4-diazepan-1-yl)imidazo[1,2-a]pyridine 335c (Example 435)

A solution of 2-(5-chloro-2,4-dimethoxyphenyl)-7-(1,4-diazepan-1-yl)imidazo[1,2-a]pyridine 334 (150 mg, 0.38 mmol), cyclohexanecarbaldehyde (65 mg, 0.58 mmol) and acetic acid (0.2 mL) in CH$_3$OH (10 mL) was stirred for 1 h. Sodium cyanoborohydride (122 mg, 1.94 mmol) was added and the reaction mixture was stirred at room temperature for 16 h. The reaction mixture was diluted with aqueous sodium bicarbonate solution and extracted with CH$_2$Cl$_2$ (2×20 mL). The combined organic layers were dried over sodium sulfate, filtered and concentrated under reduced pressure. The residue was purified by combi-flash companion (silica gel, CH$_3$OH/CH$_2$Cl$_2$) to afford 2-(5-chloro-2,4-dimethoxyphenyl)-7-(4-(cyclohexylmethyl)-1,4-diazepan-1-yl)imidazo[1,2-a]pyridine 335c (Example 435) (18 mg, 10%) as an off-white solid.

$^1$H NMR (400 MHz, DMSO-d$_6$): δ 8.25 (d, J=7.6 Hz, 1H), 8.15 (s, 1H), 7.94 (s, 1H), 6.86 (s, 1H), 6.65 (dd, J=2.4, 7.6 Hz, 1H), 6.39 (d, J=2.0 Hz, 1H), 4.00 (s, 3H), 3.93 (s, 3H), 3.55-3.49 (m, 4H), 2.70 (br s, 2H), 2.45 (br s, 2H), 2.23 (d, J=6.0 Hz, 2H), 1.87 (br s, 2H), 1.71-1.61 (m, 5H), 1.40 (br s, 1H), 1.19-1.08 (m, 3H), 0.86-0.72 (m, 2H); HPLC (Method 1) 99.5% (AUC), t$_R$=11.89 min.; ESI+APCI MS m/z 483 [M+H]$^+$.

Preparation of 2-(5-chloro-2,4-dimethoxyphenyl)-7-(4-(cyclopentylmethyl)-1,4-diazepan-1-yl)imidazo[1,2-a]pyridine 335d (Example 442)

Compound 2-(5-chloro-2,4-dimethoxyphenyl)-7-(4-(cyclopentylmethyl)-1,4-diazepan-1-yl)imidazo[1,2-a]pyridine 335d was prepared in the same manner as 2-(5-chloro-2,4-dimethoxyphenyl)-7-(4-(cyclohexylmethyl)-1,4-diazepan-1-yl)imidazo[1,2-a]pyridine 335c and was obtained as an off-white solid (11% yield).

$^1$H NMR (300 MHz, DMSO-d$_6$): δ 8.36 (d, J=7.5 Hz, 1H), 8.08 (s, 1H), 8.05 (s, 1H), 6.90 (s, 1H), 6.84 (d, J=6.0 Hz 1H), 6.49 (s, 1H), 4.02 (s, 3H), 3.95 (s, 3H), 3.71 (br s, 2H), 3.55 (br s, 2H), 3.49-3.34 (m, 6H), 2.21-1.93 (m, 3H), 1.81-1.65 (m, 2H), 1.61-1.42 (m, 4H), 1.25-1.11 (m, 2H); HPLC (Method 1) 92.6% (AUC), t$_R$=11.75 min.; ESI+APCI MS m/z 469 [M+H]$^+$.

Preparation of 2-(5-chloro-2,4-dimethoxyphenyl)-7-(4-(pyridin-4-ylmethyl)-1,4-diazepan-1-yl)imidazo[1,2-a]pyridine dihydrochloride 335e (Example 388)

Compound 2-(5-chloro-2,4-dimethoxyphenyl)-7-(4-(pyridin-4-ylmethyl)-1,4-diazepan-1-yl)imidazo[1,2-a]pyridine was prepared in the same manner as 2-(5-chloro-2,4-dimethoxyphenyl)-7-(4-(cyclohexylmethyl)-1,4-diazepan-1-yl)imidazo[1,2-a]pyridine 335c and was obtained as an off-white solid (45% yield). ESI+APCI MS m/z 478 [M+H]$^+$.

The freebase was treated with HCl aqueous solution (1 N, 2.0 equiv) to afford 2-(5-chloro-2,4-dimethoxyphenyl)-7-(4-(pyridin-4-ylmethyl)-1,4-diazepan-1-yl)imidazo[1,2-a]pyridine dihydrochloride 335e (Example 388) as a light yellow solid (quantitative) after lyophilization.

Preparation of 1-(4-(2-(5-chloro-2,4-dimethoxyphenyl)imidazo[1,2-a]pyridin-7-yl)-1,4-diazepan-1-yl)ethanone 335f (Example 429)

A solution of 2-(5-chloro-2,4-dimethoxyphenyl)-7-(1,4-diazepan-1-yl)imidazo[1,2-a]pyridine 334 (150 mg, 0.38 mmol) and Et$_3$N (0.16 mL, 1.14 mmol) in CH$_2$Cl$_2$ (15 mL) was charged with acetyl chloride (44 mg, 0.57 mmol). The reaction mixture was stirred at room temperature for 16 h. The reaction mixture was diluted with water and extracted with CH$_2$Cl$_2$ (2×20 mL). The combined organic layers were dried over sodium sulfate, filtered and concentrated under reduced pressure and the residue was purified by combi-flash companion (silica gel, CH$_3$OH/CH$_2$Cl$_2$) to afford 1-(4-(2-(5-chloro-2,4-dimethoxyphenyl)imidazo[1,2-a]pyridin-7-yl)-1,4-diazepan-1-yl)ethanone 335f (Example 429) (25 mg, 15%) as an off-white solid.

$^1$H NMR (400 MHz, DMSO-d$_6$): δ 8.25 (d, J=7.2 Hz, 1H), 8.13 (s, 1H), 7.96 (s, 1H), 6.89 (s, 1H), 6.72 (d, J=5.6 Hz, 1H), 6.53 (s, 1H), 4.01 (s, 3H), 3.95 (s, 3H), 3.69-3.63 (m, 6H), 3.46 (br s, 2H), 1.97-1.91 (m, 5H); HPLC (Method 5) 97.6% (AUC), t$_R$=12.70 min.; ESI+APCI MS m/z 429 [M+H]$^+$.

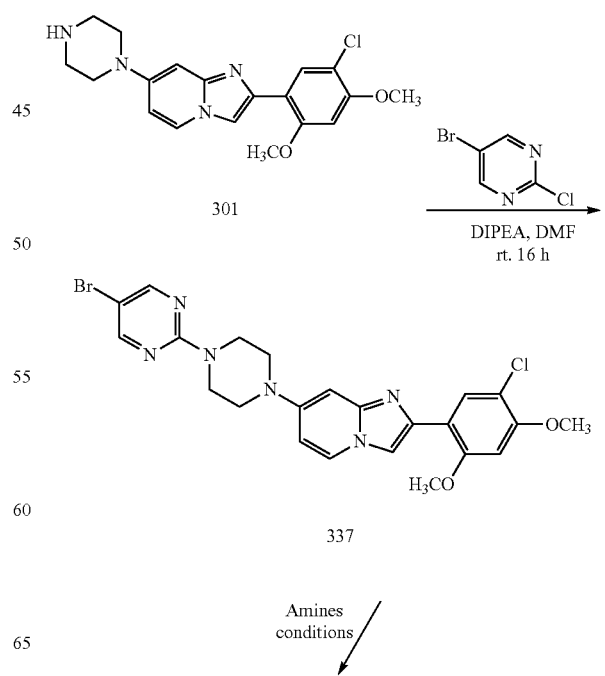

Scheme 2-14

-continued

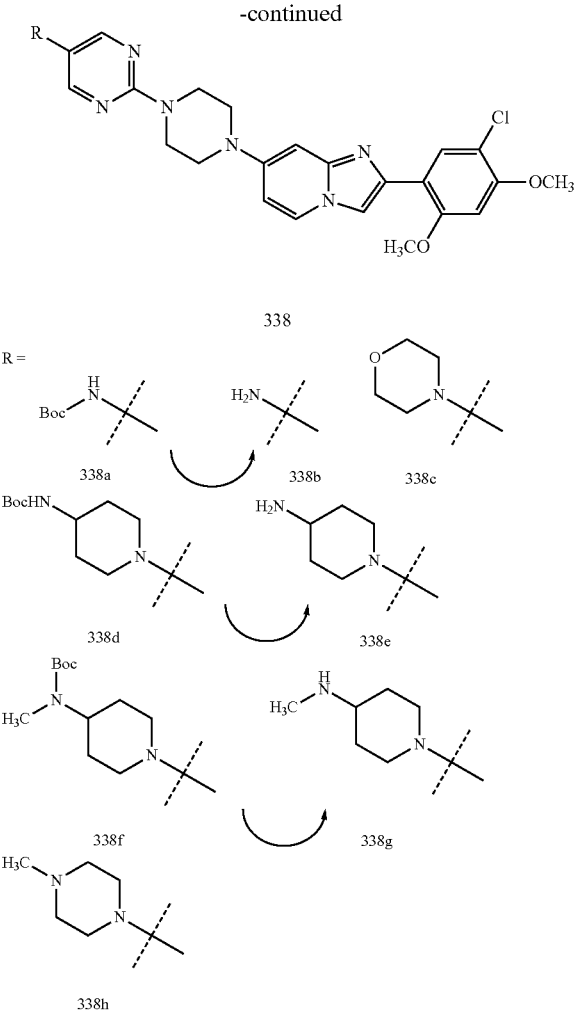

338

Preparation of 7-(4-(5-bromopyrimidin-2-yl)piperazin-1-yl-2-(5-chloro-2,4-dimethoxyphenyl)imidazo[1,2-a]pyridine 337

A solution of 2-(5-chloro-2,4-dimethoxyphenyl)-7-(piperazin-1-yl)imidazo[1,2-a]pyridine 301 (5.00 g, 13.4 mmol) and N,N-diisopropylethylamine (10.0 mL, 57.4 mmol) in DMF (10 mL) was charged with 5-bromo-2-chloropyrimidine (5.20 g, 26.9 mmol). The reaction mixture was stirred at ambient temperature for 16 h. The reaction mixture was suspended in water and stirred for 1 h. The precipitate was collected by filtration, the solid obtained was washed with water, dried under reduced pressure, and purified by combi-flash companion (silica gel, $CH_3OH/CH_2Cl_2$) to provide 7-(4-(5-bromopyrimidin-2-yl)piperazin-1-yl)-2-(5-chloro-2,4-dimethoxyphenyl)imidazo[1,2-a]pyridine 337 (5.5 g, 77%) as a brown solid.

$^1$H NMR (300 MHz, DMSO-$d_6$): δ 8.50 (s, 2H), 8.34 (d, J=7.5 Hz, 1H), 8.17 (s, 1H), 8.03 (s, 1H), 6.86 (s, 1H), 6.83 (s, 1H), 6.72 (s, 1H), 4.01 (s, 3H), 3.93 (s, 3H), 3.88 (br s, 4H), 3.33 (br s, 4H); ESI+APCI MS m/z 529 [M+H]$^+$.

Preparation of tert-butyl (2-(4-(2-(5-chloro-2,4-dimethoxyphenyl)imidazo[1,2-a]pyridin-7-yl)piperazin-1-yl)pyrimidin-5-yl)carbamate 338a A suspension of 7-(5-bromopyrimidin-2-yl)-2-(5-chloro-2,4-dimethoxyphenyl)imidazo[1,2-a]pyridine 337 (200 mg, 0.37 mmol), tert-butyl carbamate (100 mg, 0.84 mmol), X-phos (36 mg, 0.075 mmol) and NaOt-Bu (112 mg, 1.13 mmol) in toluene (8 mL) was degassed with argon for 15 min. The resulting mixture was charged with $Pd_2(dba)_3$ (36 mg, 0.037 mmol) and further degassed with argon for 5 min. The reaction mixture was stirred at 110° C. for 30 min under microwave. The reaction mixture was cooled, filtered through a pad of celite (the celite was washed with 10% MeOH/$CH_2Cl_2$) and the combined filtrate was evaporated to dryness. The residue obtained was purified by combi-flash companion (silica gel, $CH_3OH/CH_2Cl_2$) to provide tert-butyl (2-(4-(2-(5-chloro-2,4-dimethoxyphenyl)imidazo[1,2-a]pyridin-7-yl)piperazin-1-yl)pyrimidin-5-yl)carbamate 338a (140 mg, crude) as light yellow solid. ESI+APCI MS m/z 566 [M+H]$^+$.

Preparation of 2-(4-(2-(5-chloro-2,4-dimethoxyphenyl)imidazo[1,2-a]pyridin-7-yl)piperazin-1-yl)pyrimidin-5-amine hydrochloride 338b (Example 422)

A solution of tert-butyl (2-(4-(2-(5-chloro-2,4-dimethoxyphenyl)imidazo[1,2-a]pyridin-7-yl)piperazin-1-yl)pyrimidin-5-yl)carbamate 338a (15 mg, 0.032 mmol) in 2,2,2-trifluoroethanol (2 mL) was charged with trimethylsilyl chloride (0.05 mL) at 0° C. The reaction mixture was stirred at ambient temperature for 1 h. The reaction mixture was evaporated to dryness. The residue was triturated with $CH_2Cl_2$ and n-pentane to provide 2-(4-(2-(5-chloro-2,4-dimethoxyphenyl)imidazo[1,2-a]pyridin-7-yl)piperazin-1-yl)pyrimidin-5-amine hydrochloride 338b (Example 422) (15 mg, 92%) as a light yellow solid.

$^1$H NMR (400 MHz, DMSO-$d_6$): δ 13.58 (br s, 1H), 9.32 (br s, 2H), 8.58 (d, J=7.6 Hz, 1H), 8.34 (s, 2H), 8.29 (s, 1H), 8.04 (s, 1H), 7.33 (s, 1H), 6.98 (s, 1H), 6.76 (s, 1H), 4.06 (s, 3H), 3.99 (s, 3H), 3.89 (br s, 4H), 3.55 (br s, 4H); HPLC (Method 6) 96.7% (AUC), $t_R$=12.10 min.; ESI+APCI MS m/z 466 [M+H]$^+$.

Preparation of 4-(2-(4-(2-(5-chloro-2,4-dimethoxyphenyl)imidazo[1,2-a]pyridin-7-yl)piperazin-1-yl)pyrimidin-5-yl)morpholine 338c (Example 427)

A suspension of 7-(4-(5-bromopyrimidin-2-yl)piperazin-1-yl)-2-(5-chloro-2,4-dimethoxyphenyl)imidazo[1,2-a]pyridine 337 (250 mg, 0.47 mmol), morpholine (0.6 mL, 6.93 mmol), (±) BINAP (60 mg, 0.096 mmol) and NaOt-Bu (140 mg, 1.45 mmol) in toluene (12.5 mL) was degassed with argon for 15 min. The resulting mixture was charged with $Pd_2(dba)_3$ (45 mg, 0.049 mmol) and further degassed with argon for 5 min. The reaction mixture was stirred at 90-100° C. for 12 h in a sealed tube. The reaction mixture was cooled, filtered through a pad of celite (the celite was washed with 10% MeOH/$CH_2Cl_2$) and the combined filtrate was evaporated to dryness. The residue obtained was purified by combi-flash companion (silica gel, $CH_3OH/CH_2Cl_2$) to provide 4-(2-(4-(2-(5-chloro-2,4-dimethoxyphenyl)imidazo[1,2-a]pyridin-7-yl)piperazin-1-yl)pyrimidin-5-yl)morpholine 338c (Example 427) (120 mg, 23%) as a light yellow solid.

$^1$H NMR (400 MHz, DMSO-$d_6$): δ 8.33 (d, J=7.6 Hz, 1H), 8.24 (s, 2H), 8.18 (s, 1H), 8.03 (s, 1H), 6.87 (s, 1H), 6.85 (s, 1H), 6.72 (s, 1H), 4.01 (s, 3H), 3.93 (s, 3H), 3.79 (br s, 4H), 3.73 (br s, 4H), 3.31 (br s, 4H), 3.01 (br s, 4H); HPLC (Method 6) >99% (AUC), $t_R$=13.23 min.; ESI+APCI MS m/z 536 [M+H]$^+$.

Preparation of tert-butyl (1-(2-(4-(2-(5-chloro-2,4-dimethoxyphenyl)imidazo[1,2-a]pyridin-7-yl)piperazin-1-yl)pyrimidin-5-yl)piperidin-4-yl)carbamate 338d A suspension of 7-(4-(5-bromopyrimidin-2-yl)piperazin-1-yl)-2-(5-chloro-2,4-dimethoxyphenyl)imidazo[1,2-a]pyridine 337 (400 mg, 0.75 mmol), tert-butyl piperidin-4-ylcarbamate (304 mg, 1.51 mmol), (±) BINAP (96 mg, 0.15 mmol) and NaOt-Bu (220 mg, 2.28 mmol) in toluene (20 mL) was degassed with argon for 15 min. The resulting mixture was charged with $Pd_2(dba)_3$ (72 mg, 0.078 mmol) and further degassed with argon for 5 min. The resulting reaction mixture was stirred at 90-100° C. for 12 h in a sealed tube. The reaction mixture was cooled, filtered through a pad of celite (the celite was washed with 10% $MeOH/CH_2Cl_2$) and the combined filtrate was evaporated to dryness. The residue obtained was purified by combi-flash companion (silica gel, $CH_3OH/CH_2Cl_2$) to provide tert-butyl (1-(2-(4-(2-(5-chloro-2,4-dimethoxyphenyl)imidazo[1,2-a]pyridin-7-yl)piperazin-1-yl)pyrimidin-5-yl)piperidin-4-yl)carbamate 338d (210 mg, crude). ESI+APCI MS m/z 649 [M+H]$^+$.

Preparation of 1-(2-(4-(2-(5-chloro-2,4-dimethoxyphenyl)imidazo[1,2-a]pyridin-7-yl)piperazin-1-yl)pyrimidin-5-yl)piperidin-4-amine 338e (Example 441)

A solution of tert-butyl (1-(2-(4-(2-(5-chloro-2,4-dimethoxyphenyl)imidazo[1,2-a]pyridin-7-yl)piperazin-1-yl)pyrimidin-5-yl)piperidin-4-yl)carbamate 338d (60 mg) in $CH_2Cl_2$ (2.5 mL) was charged with 4.0 M HCl in 1,4-dioxane (0.5 mL) and stirred at room temperature for 16 h. The reaction mixture was filtered and the solid obtained was partitioned between saturated bicarbonate solution and $CH_2Cl_2$ and the layers were separated. The organic layer was washed with brine; dried over sodium sulphate, filtered and concentrated. The residue was triturated with $CH_2Cl_2$ and n-pentane and filtered to provide 1-(2-(4-(2-(5-chloro-2,4-dimethoxyphenyl)imidazo[1,2-a]pyridin-7-yl)piperazin-1-yl)pyrimidin-5-yl)piperidin-4-amine 338e (Example 441) (6 mg, 12%) as an off-white solid.

$^1$H NMR (300 MHz, DMSO-d$_6$): δ 8.33 (d, J=7.5 Hz, 1H), 8.22 (s, 2H), 8.11 (s, 1H), 8.03 (s, 1H), 6.86 (s, 1H), 6.83 (s, 1H), 6.72 (s, 1H), 4.01 (s, 3H), 3.93 (s, 3H), 3.78 (br s, 4H), 3.43-3.39 (m, 2H), 3.31 (br s, 4H), 2.72-2.59 (m, 3H), 1.80-1.76 (m, 2H), 1.39-1.35 (m, 2H); ESI+APCI MS m/z 549 [M+H]$^+$.

Preparation of tert-butyl (1-(2-(4-(2-(5-chloro-2,4-dimethoxyphenyl)imidazo[1,2-a]pyridin-7-yl)piperazin-1-yl)pyrimidin-5-yl)piperidin-4-ylmethyl)carbamate 338f Compound tert-butyl (1-(2-(4-(2-(5-chloro-2,4-dimethoxyphenyl)imidazo[1,2-a]pyridin-7-yl)piperazin-1-yl)pyrimidin-5-yl)piperidin-4-yl)(methyl)carbamate 338f was prepared in the same manner as tert-butyl (1-(2-(4-(2-(5-chloro-2,4-dimethoxyphenyl)imidazo[1,2-a]pyridin-7-yl)piperazin-1-yl)pyrimidin-5-yl)piperidin-4-yl)carbamate 338d and was obtained as an off-white solid (14% yield).

$^1$H NMR (400 MHz, DMSO-d$_6$): δ 8.34 (d, J=7.6 Hz, 1H), 8.24 (s, 2H), 8.17 (s, 1H), 8.03 (s, 1H), 6.86-6.84 (m, 2H), 6.72 (d, J=2.0 Hz, 1H), 4.01 (s, 3H), 3.93 (s, 3H), 3.80-3.77 (m, 4H), 3.55 (d, J=12.0 Hz, 2H), 3.31-3.28 (m, 4H), 2.69 (s, 3H), 2.67-2.55 (m, 3H), 1.83-1.75 (m, 2H), 1.61-1.56 (m, 2H), 1.40 (s, 9H); HPLC (Method 1) 96.6% (AUC), t$_R$=14.2 min.; ESI+APCI MS m/z 663 [M+H]$^+$.

Preparation of 1-(2-(4-(2-(5-chloro-2,4-dimethoxyphenyl)imidazo[1,2-a]pyridin-7-yl)piperazin-1-yl)pyrimidin-5-yl)-N-methylpiperidin-4-amine 338k (Example 458)

Compound 1-(2-(4-(2-(5-chloro-2,4-dimethoxyphenyl)imidazo[1,2-a]pyridin-7-yl)piperazin-1-yl)pyrimidin-5-yl)-N-methylpiperidin-4-amine 338g was prepared in the same manner as 1-(2-(4-(2-(5-chloro-2,4-dimethoxyphenyl)imidazo[1,2-a]pyridin-7-yl)piperazin-1-yl)pyrimidin-5-yl)piperidin-4-amine 338e and was obtained as an off-white solid (32% yield).

$^1$H NMR (300 MHz, DMSO-d$_6$): δ 8.34 (d, J=6.3 Hz, 1H), 8.22 (s, 2H), 8.17 (s, 1H), 8.03 (s, 1H), 6.86-6.84 (m, 2H), 6.72 (s, 1H), 4.01 (s, 3H), 3.93 (s, 3H), 3.78 (bs, 4H), 3.45-3.33 (m, 6H), 2.72-2.60 (m, 2H), 2.27 (s, 3H), 1.88-1.84 (m, 2H), 1.54-1.51 (m, 1H), 1.40-1.35 (m, 2H); HPLC (Method 1) >99% (AUC), t$_R$=11.8 min.; ESI+APCI MS m/z 563 [M+H]$^+$.

Preparation of 2-(5-chloro-2,4-dimethoxyphenyl)-7-(4-(5-(4-methylpiperazin-1-yl)pyrimidin-2-yl)piperazin-1-yl)imidazo[1,2-a]pyridine 338h (Example 430)

A suspension of 7-(4-(5-bromopyrimidin-2-yl)piperazin-1-yl)-2-(5-chloro-2,4-dimethoxyphenyl)imidazo[1,2-a]pyridine 337 (250 mg, 0.47 mmol), 1-methylpiperazine (0.5 mL, 4.50 mmol), X-phos (46 mg, 0.096 mmol) and NaOt-Bu (140 mg, 1.45 mmol) in toluene (12.5 mL) was degassed with argon for 15 min. The resulting mixture was charged with $Pd_2(dba)_3$ (45 mg, 0.049 mmol) and further degassed with argon for 5 min. The reaction mixture was stirred at 90-100° C. for 12 h in a sealed tube. The reaction mixture was cooled, filtered through a pad of celite (the celite was washed with 10% $MeOH/CH_2Cl_2$) and the combined filtrate was evaporated to dryness. The residue obtained was purified by combi-flash companion (silica gel, $CH_3OH/CH_2Cl_2$) to provide 2-(5-chloro-2,4-dimethoxyphenyl)-7-(4-(5-(4-methylpiperazin-1-yl)pyrimidin-2-yl)piperazin-1-yl)imidazo[1,2-a]pyridine 338h (Example 430) (20 mg, 4%) as an off-white solid.

$^1$H NMR (400 MHz, DMSO-d$_6$): δ 8.36 (d, J=7.6 Hz, 1H), 8.26 (s, 2H), 8.15 (s, 1H), 8.06 (s, 1H), 6.91 (d, J=7.2 Hz, 1H), 6.88 (s, 1H), 6.73 (s, 1H), 4.01 (s, 3H), 3.94 (s, 3H), 3.79 (br s, 4H), 3.73 (br s, 4H), 3.31 (br s, 4H), 3.12 (br s, 4H), 2.79 (br s, 4H), 2.47 (s, 3H); HPLC (Method 6) 91.8% (AUC), t$_R$=12.17 min.; ESI+APCI MS m/z 549 [M+H]$^+$.

Scheme 2-15

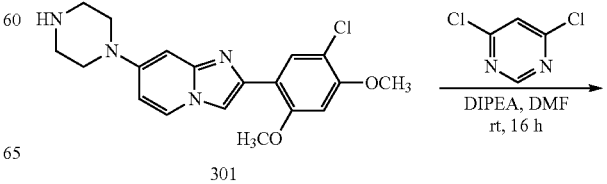

301

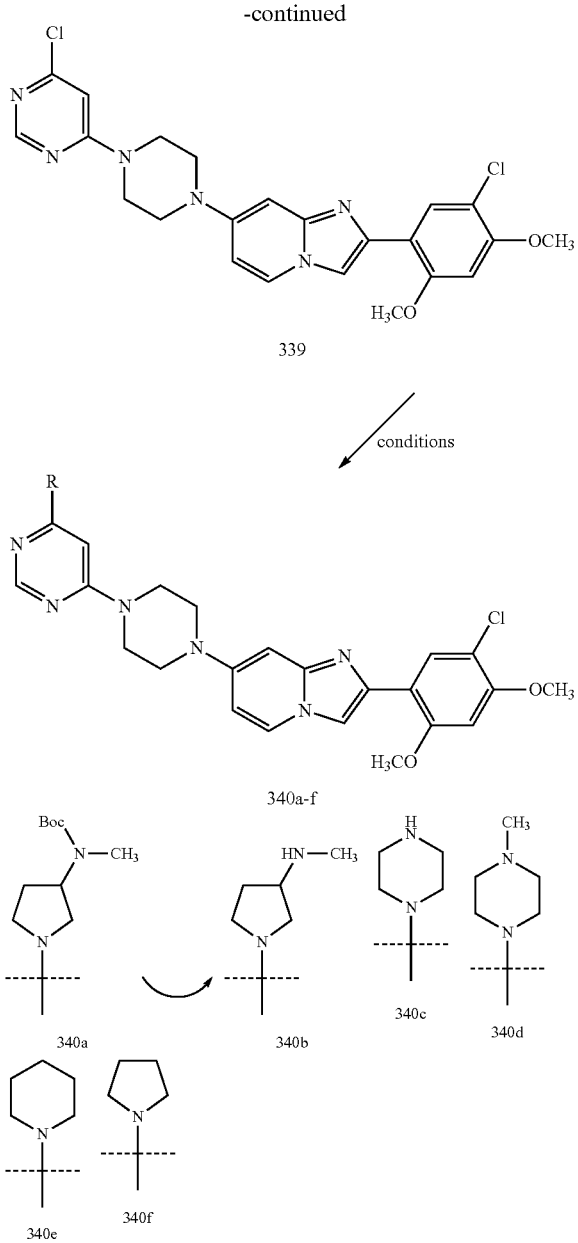

Preparation of 2-(5-chloro-2,4-dimethoxyphenyl)-7-(4-(6-chloropyrimidin-4-yl)piperazin-1-yl)imidazo[1,2-a]pyridine 339

A solution of 2-(5-chloro-2,4-dimethoxyphenyl)-7-(piperazin-1-yl)imidazo[1,2-a]pyridine 301 (1.00 g, 2.68 mmol) and N,N-diisopropylethylamine (2.0 mL, 11.5 mmol) in DMF (20 mL) was charged with 4,6-dichloropyrimidine (800 mg, 5.37 mmol). The reaction mixture was stirred at ambient temperature for 16 h. The reaction mixture was suspended in water and stirred for 1 h. The precipitate was collected by filtration, washed with water, dried and purified by combi-flash companion (silica gel, $CH_3OH/CH_2Cl_2$) to provide 2-(5-chloro-2,4-dimethoxyphenyl)-7-(4-(6-chloropyrimidin-4-yl)piperazin-1-yl)imidazo[1,2-a]pyridine 339 (1.1 g, 85%).

$^1$H NMR (400 MHz, DMSO-$d_6$): δ 8.38 (s, 1H), 8.35 (d, J=7.2 Hz, 1H), 8.17 (s, 1H), 8.04 (s, 1H), 7.07 (s, 1H), 6.88 (s, 1H), 6.87 (s, 1H), 6.72 (d, J=2.0 Hz, 1H), 4.01 (s, 3H), 3.93 (s, 3H), 3.82 (br s, 4H), 3.35 (br s, 4H); ESI+APCI MS m/z 485 [M+H]$^+$.

Preparation of tert-butyl (1-(6-(4-(2-(5-chloro-2,4-dimethoxyphenyl)imidazo[1,2-a]pyridin-7-yl)piperazin-1-yl)pyrimidin-4-yl)pyrrolidin-3-yl)(methyl)carbamate 340a A solution of 2-(5-chloro-2,4-dimethoxyphenyl)-7-(4-(6-chloropyrimidin-4-yl)piperazin-1-yl)imidazo[1,2-a]pyridine 339 (200 mg, 0.41 mmol) and triethylamine (0.6 mL, 4.30 mmol) in DMSO (4 mL) was charged with tert-butyl methyl(pyrrolidin-3-yl)carbamate (416 mg, 2.07 mmol). The reaction mixture was stirred at 90-100° C. for 1 h. The reaction mixture was cooled to ambient temperature and diluted with water. The solids formed were collected by filtration, washed with water, dried and purified by combi-flash companion (silica gel, $CH_3OH/CH_2Cl_2$) to provide tert-butyl (1-(6-(4-(2-(5-chloro-2,4-dimethoxyphenyl)imidazo[1,2-a]pyridin-7-yl)piperazin-1-yl)pyrimidin-4-yl)pyrrolidin-3-yl)(methyl)carbamate 340a (130 mg, 48%). ESI+APCI MS m/z 649 [M+H]$^+$.

Preparation of 1-(6-(4-(2-(5-chloro-2,4-dimethoxyphenyl)imidazo[1,2-a]pyridin-7-yl)piperazin-1-yl)pyrimidin-4-yl)-N-methylpyrrolidin-3-amine 340b
(Example 424)

A solution of tert-butyl (1-(6-(4-(2-(5-chloro-2,4-dimethoxyphenyl)imidazo[1,2-a]pyridin-7-yl)piperazin-1-yl)pyrimidin-4-yl)pyrrolidin-3-yl)(methyl)carbamate 340a (155.0 mg) in 2,2,2-trifluoroethanol (2.5 mL) was charged with trimethylsilyl chloride (0.2 mL) at 0° C. The reaction mixture was stirred at 0° C. for 30 min. The reaction mixture was evaporated to dryness and the residue was taken up in water. The resulting mixture was basified with saturated sodium bicarbonate solution and extracted with $CH_2Cl_2$. The combined organic layers were washed with brine; dried over sodium sulphate, filtered and concentrated. The crude product was purified by combi-flash companion (silica gel, $CH_3OH/CH_2Cl_2$) and the isolated compound was triturated with $CH_2Cl_2$ and hexanes to provide 1-(6-(4-(2-(5-chloro-2,4-dimethoxyphenyl)imidazo[1,2-a]pyridin-7-yl)piperazin-1-yl)pyrimidin-4-yl)-N-methylpyrrolidin-3-amine 340b (45 mg, 34%) as a light brown solid.

$^1$H NMR (400 MHz, CD$_3$OD): δ 8.08 (d, J=7.2 Hz, 1H), 7.97 (s, 1H), 7.96 (s, 1H), 7.88 (s, 1H), 6.71 (d, J=7.2 Hz, 1H), 6.68 (s, 1H), 6.59 (s, 1H), 5.5 (s, 1H), 3.92 (s, 3H), 3.85 (s, 3H), 3.64 (br s, 4H), 3.60-3.35 (m, 4H), 3.28 (br s, 4H), 2.38 (s, 3H), 2.18-2.13 (m, 1H), 1.84-1.80 (m, 1H); HPLC (Method 6) 95.4% (AUC), $t_R$=11.35 min.; ESI+APCI MS m/z 549 [M+H]$^+$.

Preparation of 2-(5-chloro-2,4-dimethoxyphenyl)-7-(4-(6-(piperazin-1-yl)pyrimidin-4-yl)piperazin-1-yl)imidazo[1,2-a]pyridine 340c (Example 375)

A solution of 2-(5-chloro-2,4-dimethoxyphenyl)-7-(4-(6-chloropyrimidin-4-yl)piperazin-1-yl)imidazo[1,2-a]pyridine 339 (200 mg, 0.41 mmol) in DMF (5 mL) was charged with piperazine (142 mg, 1.65 mmol). The reaction mixture was stirred at 90-100° C. for 16 h in a sealed tube. The reaction mixture was suspended in water and stirred for 1 h. The precipitate was collected by filtration, washed with water, dried and purified by mass triggered preparative HPLC to provide 2-(5-chloro-2,4-dimethoxyphenyl)-7-(4-

(6-(piperazin-1-yl)pyrimidin-4-yl)piperazin-1-yl)imidazo[1,2-a]pyridine 340c (55 mg, 25%) as a yellow solid.

$^1$H NMR (400 MHz, DMSO-d$_6$): δ 8.33 (d, J=7.2 Hz, 1H), 8.17 (s, 1H), 8.09 (s, 1H), 8.03 (s, 1H), 6.86 (s, 1H), 6.84 (d, J=3.2 Hz, 1H), 6.72 (s, 1H), 5.95 (s, 1H), 4.01 (s, 3H), 3.93 (s, 3H), 3.71 (br s, 4H), 3.47 (br s, 4H), 3.32 (br s, 4H), 2.71 (br s, 4H); HPLC (Method 1) 98.1% (AUC), t$_R$=11.02 min.; ESI+APCI MS m/z 535 [M+H]$^+$.

Preparation of 2-(5-chloro-2,4-dimethoxyphenyl)-7-(4-(6-(4-methylpiperazin-1-yl)pyrimidin-4-yl)piperazin-1-yl)imidazo[1,2-a]pyridine dihydrochloride 340d (Example 377)

A mixture of 2-(5-chloro-2,4-dimethoxyphenyl)-7-(4-(6-chloropyrimidin-4-yl)piperazin-1-yl)imidazo[1,2-a]pyridine 339 (170 mg, 0.35 mmol) and 1-methylpiperazine (1.7 mL) was stirred at 90-100° C. for 16 h in a sealed tube. The reaction mixture was suspended in water and stirred for 1 h. The precipitate was collected by filtration, washed with water, dried and purified by combi-flash companion (silica gel, CH$_3$OH/CH$_2$Cl$_2$). The free base was converted to its hydrochloride salt and the salt was triturated with n-pentane to provide 2-(5-chloro-2,4-dimethoxyphenyl)-7-(4-(6-(4-methylpiperazin-1-yl)pyrimidin-4-yl)piperazin-1-yl)imidazo[1,2-a]pyridine dihydrochloride 340d (115 mg, 53%) as a light yellow solid.

$^1$H NMR (400 MHz, DMSO-d$_6$): δ 13.90 (br s, 1H), 11.3 (br s, 1H), 8.60 (d, J=8.0 Hz, 1H), 8.30 (d, J=2.0 Hz, 2H), 8.12 (s, 1H), 7.07 (dd, J=2.4 Hz, J=7.6 Hz, 1H), 6.98 (s, 1H), 6.79 (d, J=2.0 Hz, 1H), 6.21 (s, 1H), 4.54 (d, J=13.5 Hz, 2H), 4.06 (s, 3H), 3.99 (s, 3H), 3.89 (br s, 4H), 3.68 (br s, 4H), 3.49 (d, J=11.6 Hz, 2H), 3.43-3.37 (m, 2H), 3.08-3.02 (m, 2H), 3.78 (d, J=4.4 Hz, 3H); HPLC (Method 1) 93.7% (AUC), t$_R$=11.05 min.; ESI+APCI MS m/z 549 [M+H]$^+$.

Preparation of 2-(5-chloro-2,4-dimethoxyphenyl)-7-(4-(6-(piperidin-1-yl)pyrimidin-4-yl)piperazin-1-yl)imidazo[1,2-a]pyridine 340e (Example 353)

A mixture of 2-(5-chloro-2,4-dimethoxyphenyl)-7-(4-(6-chloropyrimidin-4-yl)piperazin-1-yl)imidazo[1,2-a]pyridine 339 (100 mg, 0.1 mmol) and piperidine (1.0 mL) was stirred at 100° C. for 2 h in a sealed tube. The reaction mixture was suspended in water and stirred for 1 h. The precipitate was collected by filtration, washed with water, dried and purified by combi-flash companion (silica gel, CH$_3$OH/CH$_2$Cl$_2$). The isolated compound was triturated with CH$_2$Cl$_2$ and hexanes to provide 2-(5-chloro-2,4-dimethoxyphenyl)-7-(4-(6-(piperidin-1-yl)pyrimidin-4-yl)piperazin-1-yl)imidazo[1,2-a]pyridine 340e (30 mg, 54%) as an off-white solid.

$^1$H NMR (300 MHz, DMSO-d$_6$): δ 8.34 (d, J=7.8 Hz, 1H), 8.17 (s, 1H), 8.08 (s, 1H), 8.03 (s, 1H), 6.88 (s, 1H), 6.86 (d, J=2.7 Hz, 1H), 6.72 (s, 1H), 5.96 (s, 1H), 4.01 (s, 3H), 3.93 (s, 3H), 3.71 (br s, 4H), 3.55 (br s, 4H), 3.31 (br s, 4H), 1.61 (br s, 2H), 1.49 (br s, 4H); HPLC (Method 1) 92.2% (AUC), t$_R$=12.48 min.; ESI+APCI MS m/z 534 [M+H]$^+$.

Preparation of 2-(5-chloro-2,4-dimethoxyphenyl)-7-(4-(6-(pyrrolidin-1-yl)pyrimidin-4-yl)piperazin-1-yl)imidazo[1,2-a]pyridine 340f (Example 355)

A mixture of 2-(5-chloro-2,4-dimethoxyphenyl)-7-(4-(6-chloropyrimidin-4-yl)piperazin-1-yl)imidazo[1,2-a]pyridine 339 (100 mg, 0.1 mmol) and pyrrolidine (1.0 mL) was stirred at 100° C. for 2 h in a sealed tube. The reaction mixture was suspended in water and stirred for 1 h. The precipitate was collected by filtration, washed with water, dried and purified by combi-flash companion (silica gel, CH$_3$OH/CH$_2$Cl$_2$). The isolated compound was triturated with CH$_2$Cl$_2$ and hexanes to provide 2-(5-chloro-2,4-dimethoxyphenyl)-7-(4-(6-(pyrrolidin-1-yl)pyrimidin-4-yl)piperazin-1-yl)imidazo[1,2-a]pyridine 340f (55 mg, 51%) as an off-white solid.

$^1$H NMR (400 MHz, DMSO-d$_6$): δ 8.35 (d, J=7.6 Hz, 1H), 8.16 (s, 1H), 8.06 (s, 1H), 8.04 (s, 1H), 6.89 (s, 1H), 6.87 (s, 1H), 6.71 (s, 1H), 5.62 (s, 1H), 4.01 (s, 3H), 3.93 (s, 3H), 3.69 (br s, 4H), 3.37 (br s, 4H), 3.31 (br s, 4H), 1.90 (br s, 4H), HPLC (Method 1) 91.4% (AUC), t$_R$=12.25 min.; ESI+APCI MS m/z 520 [M+H]$^+$.

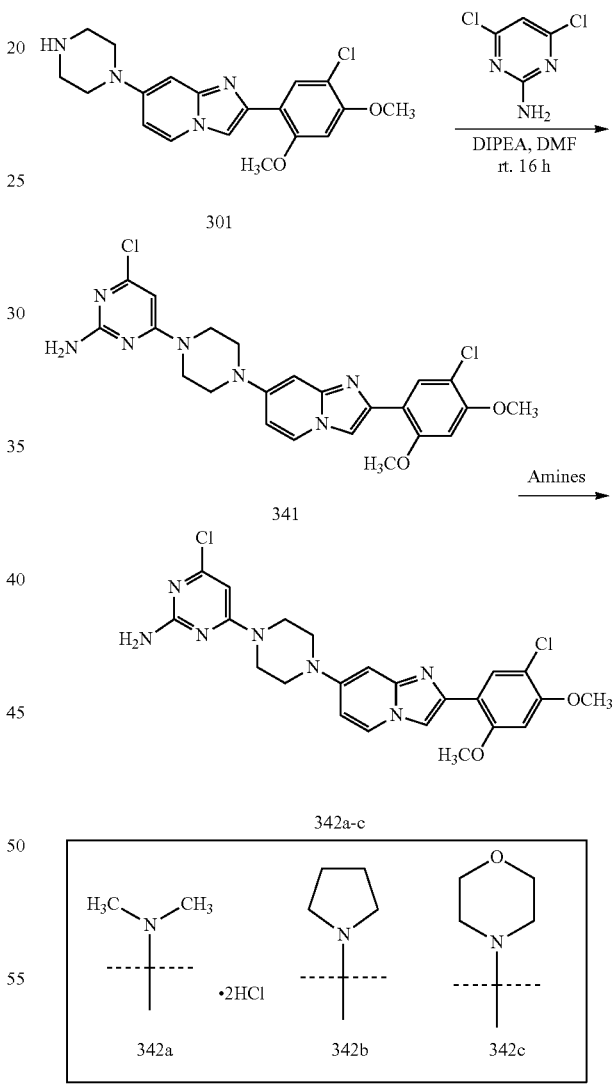

Preparation of 4-chloro-6-(4-(2-(5-chloro-2,4-dimethoxyphenyl)imidazo[1,2-a]pyridin-7-yl)piperazin-1-yl)pyrimidin-2-amine 341 (Example 360)

A solution of 2-(5-chloro-2,4-dimethoxyphenyl)-7-(piperazin-1-yl)imidazo[1,2-a]pyridine 301 (500 mg, 1.34 mmol) and N,N-diisopropylethylamine (1.0 mL, 5.74 mmol) in DMF (10 mL) was charged with 4,6-dichloropyrimidin-2-amine (440 mg, 2.68 mmol). The reaction mixture was stirred at ambient temperature for 16 h. The reaction mixture was suspended in water and stirred for 1 h. The precipitate was collected by filtration, washed with water, dried and purified by combi-flash companion (silica gel, $CH_3OH/CH_2Cl_2$). The isolated compound was triturated with methanol and hexanes to provide 4-chloro-6-(4-(2-(5-chloro-2,4-dimethoxyphenyl)imidazo[1,2-a]pyridin-7-yl)piperazin-1-yl)pyrimidin-2-amine 341 (Example 360) (450 mg, 62%) as an off-white solid.

$^1$H NMR (300 MHz, DMSO-$d_6$): δ 8.34 (d, J=7.8 Hz, 1H), 8.17 (s, 1H), 8.03 (s, 1H), 6.87 (s, 1H), 6.84 (d, J=2.4 Hz, 1H), 6.72 (s, 1H), 6.55 (br s, 2H), 6.18 (s, 1H), 4.01 (s, 3H), 3.93 (s, 3H), 3.72 (br s, 4H), 3.29 (br s, 4H); HPLC (Method 1) 96.5% (AUC), $t_R$=12.33 min.; ESI+APCI MS m/z 500 [M+H]$^+$.

Preparation of 6-(4-(2-(5-chloro-2,4-dimethoxyphenyl)imidazo[1,2-a]pyridin-7-yl)piperazin-1-yl)-N$^4$,N$^4$-dimethylpyrimidine-2,4-diamine dihydrochloride 342a (Example 389)

A solution of 4-chloro-6-(4-(2-(5-chloro-2,4-dimethoxyphenyl)imidazo[1,2-a]pyridin-7-yl)piperazin-1-yl)pyrimidin-2-amine 341 (200 mg, 0.40 mmol) and dimethylamine hydrochloride (330 mg, 4.04 mmol) in DMSO (5 mL) was charged with triethylamine (0.6 mL, 4.30 mmol). The reaction mixture was stirred at 90-100° C. for 16 h in a sealed tube. The reaction mixture was suspended in water and stirred for 1 h. The precipitate was collected by filtration, washed with water, dried and purified by combi-flash companion (silica gel, $CH_3OH/CH_2Cl_2$). The isolated compound was further purified by mass triggered prep-HPLC. The product was converted to its hydrochloride salt and triturated with n-pentane to provide 6-(4-(2-(5-chloro-2,4-dimethoxyphenyl)imidazo[1,2-a]pyridin-7-yl)piperazin-1-yl)-N$^4$,N$^4$-dimethylpyrimidine-2,4-diamine dihydrochloride 342a (21 mg, 11%) as a light yellow solid.

$^1$H NMR (400 MHz, DMSO-$d_6$): δ 13.6 (br s, 1H), 11.5 (br s, 1H), 8.58 (d, J=7.6 Hz, 1H), 8.29 (s, 1H), 8.01 (s, 1H), 7.56 (br s, 2H), 7.33 (d, J=6.0 Hz, 1H), 6.99 (s, 1H), 6.72 (s, 1H), 5.34 (s, 1H), 4.06 (s, 3H), 3.99 (s, 3H), 3.87 (br s, 4H), 3.68 (br s, 4H), 3.10 (s, 6H); HPLC (Method 1) >99% (AUC), $t_R$=11.51 min.; ESI+APCI MS m/z 509 [M+H]$^+$.

Preparation of 4-(4-(2-(5-chloro-2,4-dimethoxyphenyl)imidazo[1,2-a]pyridin-7-yl)piperazin-1-yl)-6-(pyrrolidin-1-yl)pyrimidin-2-amine 342b (Example 385)

A solution of 4-chloro-6-(4-(2-(5-chloro-2,4-dimethoxyphenyl)imidazo[1,2-a]pyridin-7-yl)piperazin-1-yl)pyrimidin-2-amine 341 (150 mg, 0.3 mmol) in DMSO (3 mL) was charged with pyrrolidine (0.3 mL, 3.59 mmol). The reaction mixture was stirred at 90-100° C. for 16 h in a sealed tube. The reaction mixture was suspended in water and stirred for 1 h. The precipitate was collected by filtration, washed with water, dried and purified by combi-flash companion (silica gel. $CH_3OH/CH_2Cl_2$). The isolated compound was triturated with $CH_2Cl_2$ and hexanes to provide 4-(4-(2-(5-chloro-2,4-dimethoxyphenyl)imidazo[1,2-a]pyridin-7-yl)piperazin-1-yl)-6-(pyrrolidin-1-yl)pyrimidin-2-amine 342b (45 mg, 21%) as an off-white solid.

$^1$H NMR (300 MHz, DMSO-$d_6$): δ 8.34 (d, J=7.5 Hz, 1H), 8.16 (s, 1H), 8.04 (s, 1H), 6.87 (s, 1H), 6.85 (s, 1H), 6.71 (s, 1H), 5.68 (br s, 2H), 5.07 (s, 1H), 4.01 (s, 3H), 3.93 (s, 3H), 3.62 (br s, 4H), 3.32 (br s, 4H), 3.28 (br s, 4H), 1.87 (br s, 4H); HPLC (Method 1) 96.3% (AUC), $t_R$=12.27 min.; ESI+APCI MS m/z 535 [M+H]$^+$.

Preparation of 4-(4-(2-(5-chloro-2,4-dimethoxyphenyl)imidazo[1,2-a]pyridin-7-yl)piperazin-1-yl)-6-morpholinopyrimidin-2-amine 342c (Example 384)

A solution of provide 4-chloro-6-(4-(2-(5-chloro-2,4-dimethoxyphenyl)imidazo[1,2-a]pyridin-7-yl)piperazin-1-yl)pyrimidin-2-amine 341 (150 mg, 0.3 mmol) in DMSO (3 mL) was charged with morpholine (0.3 mL, 3.46 mmol). The reaction mixture was stirred at 90-100° C. for 16 h in a sealed tube. The reaction mixture was suspended in water and stirred for 1 h. The precipitate was collected by filtration, washed with water, dried and purified by combi-flash companion (silica gel, $CH_3OH/CH_2Cl_2$). The obtained product was further purified by mass triggered preparative HPLC. The obtained product was triturated with saturated sodiumbicarbonate solution, solid formed were filtered, washed with water and dried to provide 4-(4-(2-(5-chloro-2,4-dimethoxyphenyl)imidazo[1,2-a]pyridin-7-yl)piperazin-1-yl)-6-morpholinopyrimidin-2-amine 342c (25 mg, 13%) as an off-white solid.

$^1$H NMR (400 MHz, DMSO-$d_6$): δ 8.34 (d, J=7.6 Hz, 1H), 8.17 (s, 1H), 8.03 (s, 1H), 6.88-6.86 (m, 2H), 6.72 (d, J=2.0 Hz, 1H), 5.71 (br s, 2H), 5.40 (s, 1H), 4.01 (s, 3H), 3.93 (s, 3H), 3.62 (br s, 8H), 3.43 (br s, 4H), 3.26 (br s, 4H); HPLC (Method 1) 99.0% (AUC), $t_R$=11.94 min.; ESI+APCI MS m/z 551 [M+H]$^+$.

Scheme 2-17

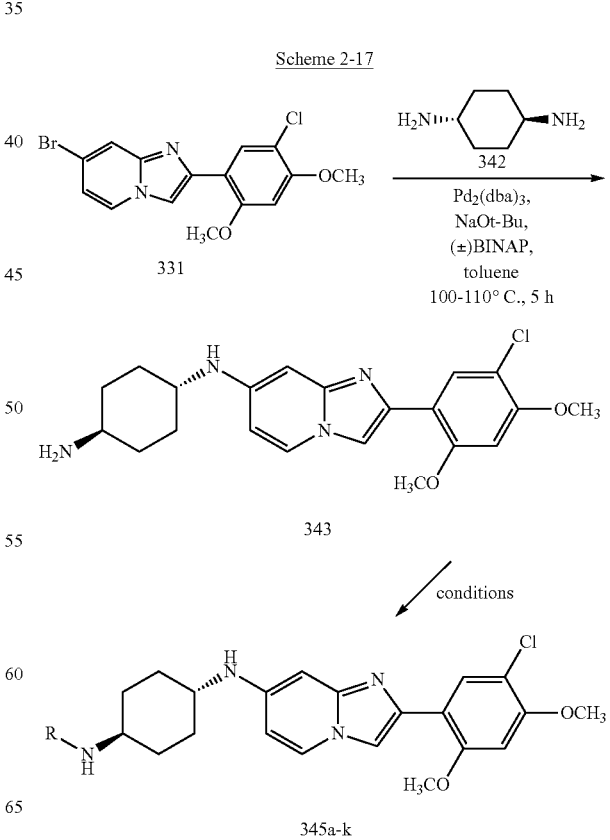

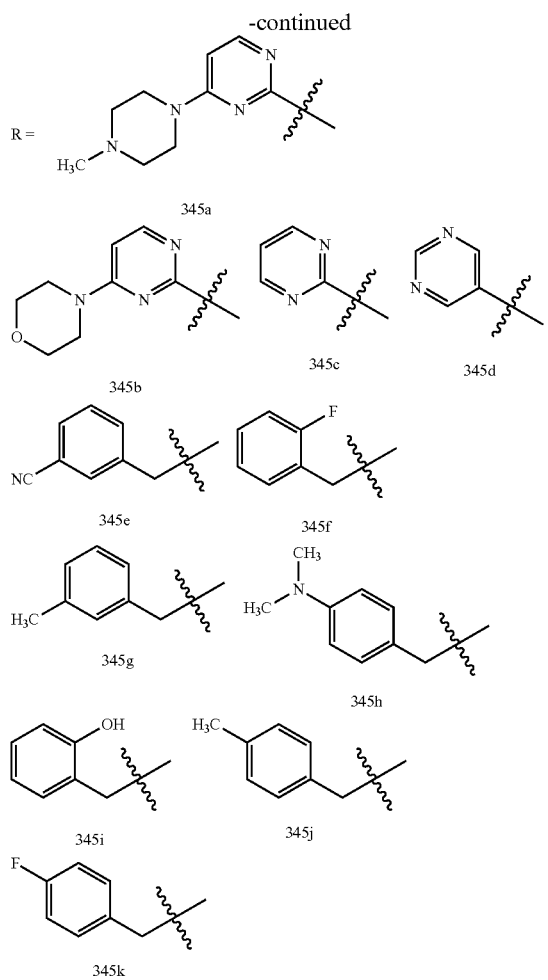

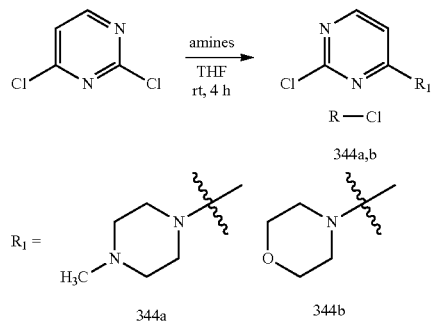

Preparation of (1r,4r)-N$^1$-(2-(5-chloro-2,4-dimethoxyphenyl)imidazo[1,2-a]pyridin-7-yl)cyclohexane-1,4-diamine 343

A mixture of 7-bromo-2-(5-chloro-2,4-dimethoxyphenyl)imidazo[1,2-a]pyridine 331 (1.00 g, 2.73 mmol), trans-cyclohexane-1,4-diamine 342 (311 mg, 2.73 mmol), Pd$_2$(dba)$_3$ (125 mg, 0.13 mmol), (+) BINAP (170 mg, 0.27 mmol), and NaOt-Bu (786 mg, 8.19 mmol) in toluene (20 mL) was degassed with argon for 15 min and was then heated at 100° C. for 5 h. The reaction mixture was cooled to room temperature, diluted with CH$_2$Cl$_2$ (30 mL) and filtered through a pad of celite. The filtrate was concentrated under reduced pressure and the residue obtained was purified by column chromatography (silica-gel, CH$_3$OH/CH$_2$Cl$_2$) to give (1r,4r)-N$^1$-(2-(5-chloro-2,4-dimethoxyphenyl)imidazo[1,2-a]pyridin-7-yl)cyclohexane-1,4-diamine 343 (500 mg, 46%) as a green solid.

$^1$H NMR (400 MHz, DMSO-d$_6$): δ 8.14 (s, 1H), 8.10 (d, J=7.6 Hz, 1H), 7.86 (s, 1H), 6.84 (s, 1H), 6.33 (dd, J=2.0, 7.2 Hz, 1H), 6.19 (s, 1H), 5.97 (d, J=7.6 Hz, 1H), 3.99 (s, 3H), 3.92 (s, 3H), 3.15-3.12 (m, 1H), 2.58-2.55 (m, 1H), 2.01-1.99 (m, 2H), 1.81-1.79 (m, 2H), 1.23-1.16 (m, 4H); ESI+APCI MS m/z 401 [M+H]$^+$.

Preparation of (1r,4r)-N$^1$-(2-(5-chloro-2,4-dimethoxyphenyl)imidazo[1,2-a]pyridin-7-yl)-N$^4$-(4-(4-methylpiperazin-1-yl)pyrimidin-2-yl)cyclohexane-1,4-diamine 345a (Example 398)

A solution of 2,4-dichloropyrimidine (1.00 g, 6.71 mmol) and 1-methylpiperazine (671 mg, 6.71 mmol) in THF (25 mL) was charged with triethyl amine (1.41 mL, 10.1 mmol). The reaction mixture was stirred at ambient temperature for 16 h. The reaction mixture was partitioned between NH$_4$Cl solution and ethylacetate and the layers were separated. The organic layer was washed with brine; dried over sodium sulphate, filtered and concentrated. The residue was purified by combi-flash companion (silica gel, CH$_3$OH/CH$_2$Cl$_2$) to provide 2-chloro-4-(4-methylpiperazin-1-yl)pyrimidine 344a (830 mg, 53%). ESI+APCI MS m 213 [M+H]$^+$.

A suspension of (1r,4r)-N$^1$-(2-(5-chloro-2,4-dimethoxyphenyl)imidazo[1,2-a]pyridin-7-yl)cyclohexane-1,4-diamine 343 (150 mg, 0.37 mmol), 2-chloro-4-(4-methylpiperazin-1-yl)pyrimidine 344a (119 mg, 0.56 mmol). (±) BINAP (25 mg, 0.04 mmol) and NaOt-Bu (106 mg, 1.11 mmol) in toluene (10 mL) was degassed with argon for 15 min. Then resulting mixture was charged with Pd$_2$(dba)$_3$ (16 mg, 0.01 mmol) and was further degassed with argon for 5 min. The reaction mixture was stirred at 100-110° C. for 16 h. The reaction mixture was cooled, filtered through a pad of celite (the celite was washed with 10% MeOH/CH$_2$Cl$_2$) and the combined filtrate was evaporated to dryness. The residue was purified by preparative-HPLC to provide (1r,4r)-N$^1$-(2-(5-chloro-2,4-dimethoxyphenyl) imidazo[1,2-a]pyridin-7-yl)-N$^4$-(4-(4-methylpiperazin-1-yl)pyrimidin-2-yl)cyclohexane-1,4-diamine 345a (10 mg, 5%) as an off-white solid.

$^1$H NMR (400 MHz, DMSO-d$_6$): δ 8.13 (s, 1H), 8.11 (d, J=7.6 Hz, 1H), 7.87 (s, 1H), 7.79 (d, J=6.0 Hz, 1H), 6.84 (s, 1H), 6.35 (dd, J=2.0, 7.6 Hz, 2H), 6.22 (s, 1H), 6.03 (d, J=7.2 Hz, 1H), 5.99 (d, J=6.0 Hz, 1H), 3.99 (s, 3H), 3.92 (s, 3H), 3.68-3.66 (m, 1H), 3.51 (br s, 4H), 3.24-3.16 (m, 1H), 2.32 (br s, 4H), 2.19 (s, 3H), 2.08-2.06 (m, 21H), 1.97-1.94 (m, 2H), 1.44-1.35 (m, 2H), 1.29-1.20 (m, 2H); HPLC (Method 3) 93.2% (AUC), t$_R$=13.06 min. ESI+APCI MS m/z 577 [M+H]$^+$.

Preparation of (1r,4r)-N$^1$-(2-(5-chloro-2,4-dimethoxyphenyl)imidazo[1,2-a]pyridin-7-yl)-N$^4$-(4-morpholinopyrimidin-2-yl)cyclohexane-1,4-diamine 345b (Example 406)

Compound 4-(2-chloropyrimidin-4-yl)morpholine 344b was prepared in the same manner as 2-chloro-4-(4-methylpiperazin-1-yl)pyrimidine 344a: ESI+APCI MS m/z 200 [M+H]$^+$.

Compound (1r,4r)-N$^1$-(2-(5-chloro-2,4-dimethoxyphenyl)imidazo[1,2-a]pyridin-7-yl)-N$^4$-(4-morpholinopyrimidin-2-yl)cyclohexane-1,4-diamine 345b was prepared in the same manner as (1r,4r)-N$^1$-(2-(5-chloro-2,4-dimethoxyphenyl) imidazo[1,2-a]pyridin-7-yl)-N$^4$-(4-(4-methylpiperazin- 1-yl)pyrimidin-2-yl)cyclohexane-1,4-diamine 345a, and was obtained as an off-white solid (10% yield).

$^1$H NMR (400 MHz, DMSO-d$_6$): δ 8.13 (s, 1H), 8.12 (d, J=4.8 Hz, 1H), 7.88 (s, 1H), 7.82 (d, J=6.0 Hz, 1H), 6.85 (s, 1H), 6.36 (d, J=5.6 Hz, 2H), 6.22 (s, 1H), 6.01 (d, J=7.2 Hz, 1H), 6.00 (d, J=5.6 Hz, 1H), 3.99 (s, 3H), 3.92 (s, 3H), 3.68-3.66 (m, 1H), 3.63 (br s, 4H), 3.48 (br s, 4H), 3.28-3.20 (m, 1H), 2.08-2.05 (m, 2H), 1.97-1.94 (m, 2H), 1.44-1.35 (m, 2H), 1.29-1.20 (m, 2H); HPLC (Method 5) 97.4% (AUC), t$_R$=12.93 min.; ESI+APCI MS m/z 564 [M+H]$^+$.

Preparation of (1r,4r)-N$^1$-(2-(5-chloro-2,4-dimethoxyphenyl)imidazo[1,2-a]pyridin-7-yl)-N$^4$-(pyrimidin-2-yl)cyclohexane-1,4-diamine hydrochloride 345c (Example 318)

Compound (1r,4r)-N$^1$-(2-(5-chloro-2,4-dimethoxyphenyl)imidazo[1,2-a]pyridin-7-yl)-N$^4$-(pyrimidin-2-yl)cyclohexane-1,4-diamine was prepared in the same manner as (1r,4r)-N$^1$-(2-(5-chloro-2,4-dimethoxyphenyl) imidazo[1,2-a]pyridin-7-yl)-N$^4$-(4-(4-methylpiperazin-1-yl)pyrimidin-2-yl)cyclohexane-1,4-diamine 345a, and was converted to the hydrochloride salt (1r,4r)-N$^1$-(2-(5-chloro-2,4-dimethoxyphenyl)imidazo[1,2-a]pyridin-7-yl)-N$^4$-(pyrimidin-2-yl)cyclohexane-1,4-diamine hydrochloride 345c as an amorphous yellow green solid (10% yield for 2 steps).

$^1$H NMR (400 MHz, DMSO-d$_6$): δ 13.32 (s, 1H), 8.84-8.32 (m, 3H), 8.20 (s, 1H), 7.97 (s, 1H), 7.89 (bs, 1H), 7.66 (d, J=5.8 Hz, 1H), 6.97 (s, 1H), 6.88 (bs, 1H), 6.70 (t, J=4.9, 9.9 Hz, 1H), 6.49 (bs, 1H), 4.04 (s, 3H), 3.98 (s, 3H), 3.40 (bs, 1H), 2.04 (t, J=11.7, 22.5 Hz, 4H), 1.56-1.32 (m, 4H); HPLC (Method 4) 98.2% (AUC), t$_R$=17.46 min. ESI MS m/z 479 [M+H]$^+$.

Preparation of (1r,4r)-N$^1$-(2-(5-chloro-2,4-dimethoxyphenyl)imidazo[1,2-a]pyridin-7-yl)-N$^4$-(pyrimidin-5-yl)cyclohexane-1,4-diamine 345d (Example 337)

Compound (1r,4r)-N$^1$-(2-(5-chloro-2,4-dimethoxyphenyl)imidazo[1,2-a]pyridin-7-yl)-N$^4$-(pyrimidin-5-yl)cyclohexane-1,4-diamine 345d was prepared in the same manner as (1r,4r)-N$^1$-(2-(5-chloro-2,4-dimethoxyphenyl) imidazo[1,2-a]pyridin-7-yl)-N$^4$-(4-(4-methylpiperazin-1-yl)pyrimidin-2-yl)cyclohexane-1,4-diamine 345a, and was obtained as an off-white solid (11% yield).

$^1$H NMR (400 MHz, DMSO-d$_6$): δ 8.34 (s, 1H), 8.14-8.11 (m, 4H), 7.87 (s, 1H), 6.84 (s, 1H), 6.38 (dd, J=2.0, 7.2 Hz, 1H), 6.06 (s, 1H), 6.08 (d, J=7.6 Hz, 1H), 6.01 (d, J=8.0 Hz, 1H), 3.99 (s, 3H), 3.92 (s, 1H), 2.07-2.02 (m, 4H), 1.40-1.39 (m, 4H); HPLC (Method 1) 97.9% (AUC), t$_R$=12.65 min.; ESI+APCI MS m/z 479 [M+H]$^+$.

Preparation of 3-((((1r,4r)-4-((2-(5-chloro-2,4-dimethoxyphenyl)imidazo[1,2-a]pyridin-7-yl)amino)cyclohexyl)amino)methyl)benzonitrile 345e (Example 397)

To a suspension of (1r,4r)-N$^1$-(2-(5-chloro-2,4-dimethoxyphenyl)imidazo[1,2-a]pyridin-7-yl)cyclohexane-1,4-diamine 343 (200 mg, 0.50 mmol), 3-formylbenzonitrile (98 mg, 0.75 mmol) in CH$_3$OH (10 mL) was added acetic acid (0.2 mL) and the resulting mixture was stirred for 1 h. The reaction mixture was then charged with NaCNBH$_3$ (157 mg, 2.5 mmol) and was then stirred at room temperature for 16 h. The reaction mixture was diluted with aqueous sodium bicarbonate solution and extracted with CH$_2$Cl$_2$ (2×20 mL). The combined organic layers were dried over sodium sulfate, filtered and concentrated under reduced pressure and the residue was purified by combi-flash companion (silica gel, NH$_4$OH/CH$_3$OH/CH$_2$Cl$_2$) to afford 3-((((1r,4r)-4-((2-(5-chloro-2,4-dimethoxyphenyl) imidazo[1,2-a]pyridin-7-yl)amino)cyclohexyl)amino)methyl)benzonitrile 345e (20 mg, 8%) as an off-white solid.

$^1$H NMR (400 MHz, DMSO-d$_6$): δ 8.13-8.10 (m, 2H), 7.87 (s, 1H), 7.81 (s, 1H), 7.70 (s, 2H), 7.55-7.53 (m, 1H), 6.84 (s, 1H), 6.34 (d, J=5.6 Hz, 1H), 6.21 (s, 1H), 6.01 (d, J=6.4 Hz, 1H), 3.99 (s, 3H), 3.92 (s, 3H), 3.81 (s, 2H), 3.32-3.21 (m, 2H), 2.05-1.95 (m, 4H), 1.23-1.13 (m, 4H); HPLC (Method 3) 94.2% (AUC), t$_R$=13.38 min.; ESI+APCI MS m/z 516 [M+H]$^+$.

Preparation of (1r,4r)-N$^1$-(2-(5-chloro-2,4-dimethoxyphenyl)imidazo[1,2-a]pyridin-7-yl)-N$^4$-(2-fluorobenzyl)cyclohexane-1,4-diamine 345f (Example 414)

Compound (1r,4r)-N$^1$-(2-(5-chloro-2,4-dimethoxyphenyl)imidazo[1,2-a]pyridin-7-yl)-N$^4$-(2-fluorobenzyl)cyclohexane-1,4-diamine 345f was prepared in the same manner as 3-((((1r,4r)-4-((2-(5-chloro-2,4-dimethoxyphenyl) imidazo[1,2-a]pyridin-7-yl)amino) cyclohexyl)amino)methyl) benzonitrile 345e and was obtained as an off-white solid (15% yield).

$^1$H NMR (300 MHz, DMSO-d$_6$): δ 8.13 (s, 1), 8.11 (d, J=7.2 Hz, 1H), 7.87 (s, 1H), 7.50 (t, J=7.5 Hz, 1H), 7.28 (t, J=7.5 Hz, 1H), 7.20-7.11 (m, 2H), 6.84 (s, 1H), 6.33 (dd, J=1.8, 7.5 Hz, 1H), 6.20 (s, 1H), 6.01 (d, J=7.8 Hz, 1H), 3.99 (s, 3H), 3.92 (s, 3H), 3.80 (s, 2H), 3.35-3.19 (m, 2H), 2.06-1.95 (m, 4H), 1.31-1.09 (m, 4H); HPLC (Method 5) 90.2% (AUC), t$_R$=12.71 min.; ESI+APCI MS m/z 509 [M+H]$^+$.

Preparation of (1r,4r)-N$^1$-(2-(5-chloro-2,4-dimethoxyphenyl)imidazo[1,2-a]pyridin-7-yl)-N$^4$-(3-methylbenzyl)cyclohexane-1,4-diamine 345e (Example 415)

Compound (1r,4r)-N$^1$-(2-(5-chloro-2,4-dimethoxyphenyl)imidazo[1,2-a]pyridin-7-yl)-N$^4$-(3-methylbenzyl)cyclohexane-1,4-diamine 345g was prepared in the same manner as 3-((((1r,4r)-4-((2-(5-chloro-2,4-dimethoxyphenyl) imidazo[1,2-a]pyridin-7-yl)amino) cyclohexyl)amino)methyl) benzonitrile 345e and was obtained as an off-white solid (13% yield).

$^1$H NMR (400 MHz, DMSO-d$_6$): δ 8.14 (s, 1H), 8.11 (d, J=7.2 Hz, 1H), 7.87 (s, 1H), 7.20-7.12 (m, 2H), 7.02 (d, J=6.8 Hz, 1H), 6.84 (s, 1H), 6.33 (d, J=7.6 Hz, 1H), 6.20 (s, 1H), 6.00 (d, J=7.6 Hz, 1H), 3.99 (s, 3H), 3.92 (s, 3H), 3.70 (s, 2H), 3.35-3.19 (m, 2H), 2.29 (s, 3H), 2.04-1.94 (m, 4H), 1.27-1.12 (m, 4H); HPLC (Method 5) 91.5% (AUC), t$_R$=12.88 min. ESI+APCI MS m/z 505 [M+H]$^+$.

Preparation of (1r,4r)-N$^1$-(2-(5-chloro-2,4-dimethoxyphenyl)imidazo[1,2-a]pyridin-7-yl)-N$^4$-(4-(dimethylamino)benzyl)cyclohexane-1,4-diamine 345h (Example 419)

Compound (1r,4r)-N$^1$-(2-(5-chloro-2,4-dimethoxyphenyl)imidazo[1,2-a]pyridin-7-yl)-N$^4$-(4-(dimethylamino) benzyl)cyclohexane-1,4-diamine 345h was prepared in the same manner as 3-((((1 r,4r)-4-((2-(5-chloro-2,4-dimethoxyphenyl) imidazo[1,2-a]pyridin-7-yl)amino) cyclohexyl)amino)methyl)benzonitrile 345e and was obtained as an off-white solid (12% yield).

$^1$H NMR (400 MHz, DMSO-d$_6$): δ 8.14 (s, 1H), 8.11 (d, J=7.2 Hz, 1H), 7.87 (s, 1H), 7.15 (d, J=8.4 Hz, 2H), 6.84 (s, 1H), 6.68 (d, J=8.4 Hz, 2H), 6.33 (d, J=7.2 Hz, 1H), 6.20 (s, 1H), 6.00 (d, J=7.6 Hz, 1H), 3.99 (s, 3H), 3.92 (s, 3H), 3.65 (s, 2H), 3.35-3.29 (m, 1H), 3.19-3.18 (m, 1H), 2.86 (s, 6H), 2.05-1.95 (m, 4H), 1.28-1.12 (m, 4H); HPLC (Method 5) 91.6% (AUC), t$_R$=12.45 min.; ESI+APCI MS m/z 534 [M+H]$^+$.

Preparation of 2-((((1 r,4r)-4-((2-(5-chloro-2,4-dimethoxyphenyl)imidazo[1,2-a]pyridin-7-yl)amino) cyclohexyl)amino)methyl)phenol 345i (Example 420)

Compound 2-((((1r,4r)-4-((2-(5-chloro-2,4-dimethoxyphenyl)imidazo[1,2-a]pyridin-7-yl)amino)cyclohexyl)amino)methyl)phenol 345i was prepared in the same manner as 3-((((1r,4r)-4-((2-(5-chloro-2,4-dimethoxyphenyl) imidazo[1,2-a]pyridin-7-yl)amino) cyclohexyl)amino)methyl)benzonitrile 345e and was obtained as an off-white solid (10% yield).

$^1$H NMR (400 MHz, DMSO-d$_6$): δ 8.14 (s, 1H), 8.11 (d, J=7.6 Hz, 1H), 7.87 (s, 1H), 7.08-7.05 (m, 2H), 6.84 (s, 1H), 6.72-6.67 (m, 2H), 6.33 (d, J=7.2 Hz, 1H), 6.21 (s, 1H), 6.02 (d, J=7.6 Hz, 1H), 3.99 (s, 3H), 3.92 (s, 3H), 3.90 (s, 2H), 3.35-3.22 (m, 2H), 2.06-1.98 (m, 4H), 1.32-1.10 (m, 4H); HPLC (Method 5) 93.9% (AUC), t$_R$=12.58 min. ESI+APCI MS m/z 507 [M+H]$^+$.

Preparation of (1r,4r-N$^1$-(2-(5-chloro-2,4-dimethoxyphenyl)imidazo[1,2-a]pyridin-7-yl)-N$^4$-(4-methylbenzyl)cyclohexane-1,4-diamine (2,2,2-trifluoroacetate) 345j (Example 328)

Compound (1r,4r)-N$^1$-(2-(5-chloro-2,4-dimethoxyphenyl)imidazo[1,2-a]pyridin-7-yl)-N$^4$-(4-methylbenzyl)cyclohexane-1,4-diamine was prepared in the same manner as 3-((((1r,4r)-4-((2-(5-chloro-2,4-dimethoxyphenyl)imidazo[1,2-a]pyridin-7-yl)amino) cyclohexyl)amino)methyl)benzonitrile 345e. The crude material was purified by prep-HPLC to give (1r,4r)-N$^1$-(2-(5-chloro-2,4-dimethoxyphenyl)imidazo[1,2-a]pyridin-7-yl)-N$^4$-(4-methylbenzyl)cyclohexane-1,4-diamine (2,2,2-trifluoroacetate) was obtained as an off-white solid (10% yield).

$^1$H NMR (400 MHz, DMSO-d$_6$): δ 13.28 (br s, 1H), 8.91 (br s, 2H), 8.37 (d, J=6.0 Hz, 1H), 8.19 (s, 1H), 7.90 (s, 1H), 7.49 (br s, 1H), 7.40 (d, J=7.2 Hz, 2H), 7.27 (d, J=7.6 Hz, 2H), 6.96 (s, 1H), 6.83 (s, 1H), 6.52 (s, 1H), 4.15 (s, 2H), 4.04 (s, 3H), 3.98 (s, 3H), 3.17-3.10 (m, 2H), 2.33 (s, 3H), 2.22-2.09 (m, 4H), 1.57-1.55 (m, 2H), 1.31-1.28 (m, 2H); HPLC (Method 5) 99.1% (AUC), t$_R$=12.43 min.; ESI+APCI MS m/z 505 [M+H]$^+$.

Preparation of (1r,4r)-N$^1$-(2-(5-chloro-2,4-dimethoxyphenyl)imidazo[1,2-a]pyridin-7-yl)-N$^4$-(4-fluorobenzyl)cyclohexane-1,4-diamine 345k (Example 320)

Compound (1r,4r)-N$^1$-(2-(5-chloro-2,4-dimethoxyphenyl)imidazo[1,2-a]pyridin-7-yl)-N$^4$-(4-fluorobenzyl)cyclohexane-1,4-diamine 345k was prepared in the same manner as 3-((((1r,4r)-4-((2-(5-chloro-2,4-dimethoxyphenyl) imidazo[1,2-a]pyridin-7-yl)amino) cyclohexyl)amino)methyl)benzonitrile 345e and was obtained as an off-white solid (19% yield).

$^1$H NMR (400 MHz, DMSO-d$_6$): δ 8.13 (s, 1H), 8.10 (d, J=7.6 Hz, 1H), 7.86 (s, 1H), 7.40-7.37 (m, 2H), 7.12 (d, =8.8 Hz, 2H), 6.84 (s, 1H), 6.33 (dd, J=2.4, 7.6 Hz, 1H), 6.20 (s, 1H), 5.97 (d, J=7.6 Hz, 1H), 3.98 (s, 3H), 3.92 (s, 3H), 3.74 (s, 2H), 3.20-3.19 (m, 2H), 2.05-1.95 (m, 4H), 1.25-1.12 (m, 4H); HPLC (Method 2) 91.8% (AUC), t$_R$=12.15 min.; ESI+APCI MS m 509 [M+H]$^+$.

Scheme 2-18

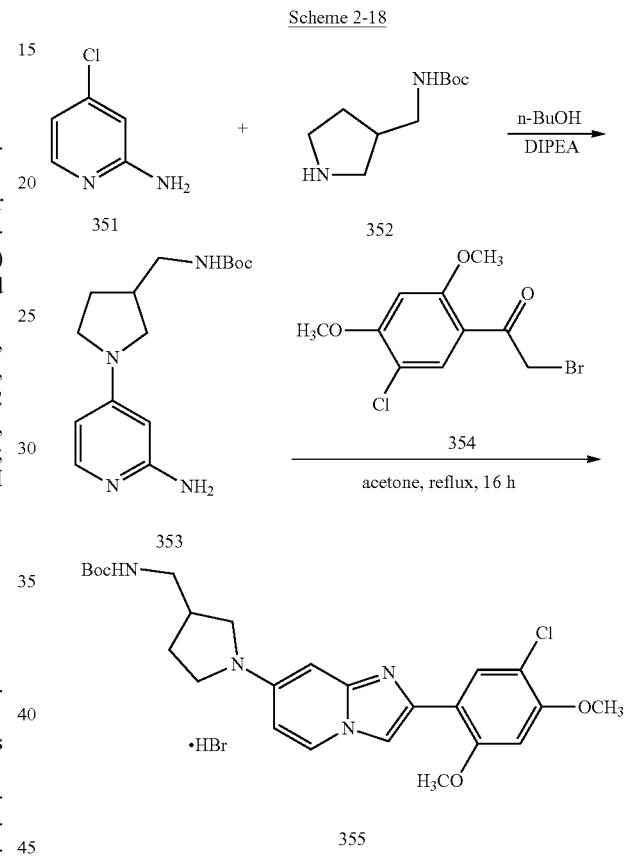

Preparation of tert-butyl ((1-(2-aminopyridin-4-yl)pyrrolidin-3-yl)methyl)carbamate 353

A solution of 4-chloropyridin-2-amine 351 (500 mg, 3.90 mmol) in n-BuOH/N,N-diisopropylethylamine (10 mL/5 mL) was charged with tert-butyl (pyrrolidin-3-ylmethyl)carbamate 352 (937 mg, 4.68 mmol). The reaction mixture was stirred at 110-120° C. for 16 h in a sealed tube. The reaction mixture was concentrated under reduced pressure and the residue was partitioned between CH$_2$Cl$_2$ (50 mL) and saturated sodium bicarbonate solution (30 mL). The layers were separated and the organic layer was dried over Na$_2$SO$_4$, filtered and concentrated. The solid obtained was triturated with hexanes to give tert-butyl ((1-(2-aminopyridin-4-yl)pyrrolidin-3-yl)methyl)carbamate 353 (900 mg, 79%) as an off-white solid. The compound was used for next step without further purification. ESI+APCI MS nm/z 293 [M+H]$^+$.

Preparation of tert-butyl ((1-(2-(5-chloro-2,4-dimethoxyphenyl)imidazo[1,2-a]pyridin-7-yl)pyrrolidin-3-yl)methyl)carbamate 355 (Example 459)

A solution of tert-butyl ((1-(2-aminopyridin-4-yl)pyrrolidin-3-yl)methyl)carbamate 353 (800 mg, 2.73 mmol) and 2-bromo-1-(5-chloro-2,4-dimethoxyphenyl)ethanone 354 (880 mg, 3.01 mmol) in acetone (15 mL) was heated at 75° C. for 16 h. The reaction mixture was cooled to room temperature and the white precipitate formed was collected by filtration and washed with hexanes to afford tert-butyl ((1-(2-(5-chloro-2,4-dimethoxyphenyl)imidazo[1,2-a]pyridin-7-yl)pyrrolidin-3-yl)methyl)carbamate hydrobromide 355 (600 mg, 45%) as an off-white solid.

$^1$H NMR (400 MHz, DMSO-$d_6$): δ 12.99 (s, 1H), 8.49 (d, J=7.6 Hz, 1H), 8.22 (s, 1H), 7.88 (s, 1H), 7.06 (t, J=5.2 Hz, 1H), 6.98 (s, 1H), 6.92 (d, J=8.0 Hz, 1H), 6.28 (s, 1H), 4.05 (s, 3H), 3.98 (s, 3H), 3.52-3.44 (m, 3H), 3.18-3.16 (m, 1H), 3.03 (t, J=6.8 Hz, 2H), 2.51-2.49 (m, 1), 2.12-2.08 (m, 1H), 1.87-1.72 (m, 1H), 1.39 (s, 9H); HPLC (Method 1) 95.82% (AUC), $t_R$=14.25 min.; ESI+APCI MS m/z 487 [M+H]$^+$.

Preparation of tert-butyl 4-(2-(5-chloro-2,4-dimethoxyphenyl)imidazo[1,2-a]pyridin-7-yl-3-methyl-piperazine-1-carboxylate 363

A suspension of 7-bromo-2-(5-chloro-2,4-dimethoxyphenyl) imidazo[1,2-a]pyridine 331 (1.00 g, 2.73 mmol), tert-butyl 3-methylpiperazine-1-carboxylate 362 (819 mg, 4.09 mmol), Xanthphos (173 mg, 0.30 mmol) and t-BuOK (917 mg, 8.19 mmol) in toluene (30 mL) was degassed with argon for 15 min. Subsequently the mixture was charged with Pd$_2$(dba)$_3$ (125 mg, 0.13 mmol) and further degassed with argon for 5 min. The reaction mixture was heated at 100-110° C. for 16 h. The reaction mixture was cooled, filtered through a pad of celite (the celite was wash with 10% MeOH/CH$_2$Cl$_2$) and the combined filtrate was evaporated to dryness. The residue obtained was purified by combi-flash companion (silica gel, CH$_3$OH/CH$_2$Cl$_2$) to provide tert-butyl 4-(2-(5-chloro-2,4-dimethoxyphenyl)imidazo[1,2-a]pyridin-7-yl)-3-methylpiperazine-1-carboxylate 363 (800 mg, 60%) as an off-white solid. ESI+APCI MS m/z 487 [M+H]$^+$.

Preparation of 2-(5-chloro-2,4-dimethoxyphenyl)-7-(2-methylpiperazin-1-yl)imidazo[1,2-a]pyridine 364

A solution of tert-butyl 4-(2-(5-chloro-2,4-dimethoxyphenyl)imidazo[1,2-a]pyridin-7-yl)-3-methylpiperazine-1-carboxylate 363 (800 mg, 1.64 mmol) in CH$_2$Cl$_2$ (10 mL) was charged with a solution of HCl in 1,4-dioxane (4.0 M, 5 mL) and the reaction mixture was stirred at room temperature for 4 h. The reaction mixture was filtered and the solid obtained was washed with CH$_2$Cl$_2$. The solid was then suspended in water (15 mL), basified with saturated sodium bicarbonate solution (15 mL) by stirring for 1 h at room temperature and filtered to provide 2-(5-chloro-2,4-dimethoxyphenyl)-7-(2-methylpiperazin-1-yl)imidazo[1,2-a]pyridine 364 (600 mg, 94%) as an off-white solid.

ESI+APCI MS m/z 387 [M+H]$^+$.

Preparation of 1-(4-(2-(5-chloro-2,4-dimethoxyphenyl)imidazo[1,2-a]pyridin-7-yl)-3-methylpiperazin-1-yl)ethanone 365a (Example 308)

A solution of 2-(5-chloro-2,4-dimethoxyphenyl)-7-(2-methylpiperazin-1-yl)imidazo[1,2-a]pyridine 364 (150 mg, 0.38 mmol) and Et$_3$N (0.16 mL, 1.16 mmol) in CH$_2$Cl$_2$ (15 mL) was charged with acetyl chloride (44 mg, 0.57 mmol). The reaction mixture was stirred at room temperature for 16 h. The reaction mixture was diluted with water and extracted with CH$_2$Cl$_2$ (2×20 mL). The combined organic layers were dried over sodium sulfate, filtered and concentrated under reduced pressure and the residue was purified by combi-flash companion (silica gel, CH$_3$OH/CH$_2$Cl$_2$) to afford 1-(4-(2-(5-chloro-2,4-dimethoxyphenyl)imidazo[1,2-a]pyridin-7-yl)-3-methylpiperazin-1-yl)ethanone 365a (20 mg, 12%) as an off-white solid.

$^1$H NMR (400 MHz, 353K DMSO-$d_6$): δ 8.27 (d, J=7.2 Hz, 1H), 8.19 (s, 1H), 7.98 (s, 1H), 6.88 (s, 1H), 6.73 (d, J=6.0 Hz, 1H), 6.63 (s, 1H), 4.11 (br s, 1H), 4.01 (s, 3H), 3.95 (s, 3H), 3.94-3.92 (m, 1H), 3.49-3.41 (m, 1H), 3.21-3.13 (m, 2H), 2.98-2.91 (m, 2H), 2.07 (s, 3H), 1.05 (d, J=6.0 Hz, 3H); HPLC (Method 1) 97.6% (AUC), $t_R$=12.55 min.; ESI+APCI MS m/z 429 [M+H]$^+$.

Preparation of 1-(4-(2-(5-chloro-2,4-dimethoxyphenyl)imidazo[1,2-a]pyridin-7-yl)-3-methylpiperazin-1-yl)-2-methoxyethanone 365b (Example 313)

Compound 1-(4-(2-(5-chloro-2,4-dimethoxyphenyl)imidazo[1,2-a]pyridin-7-yl)-3-methylpiperazin-1-yl)-2-

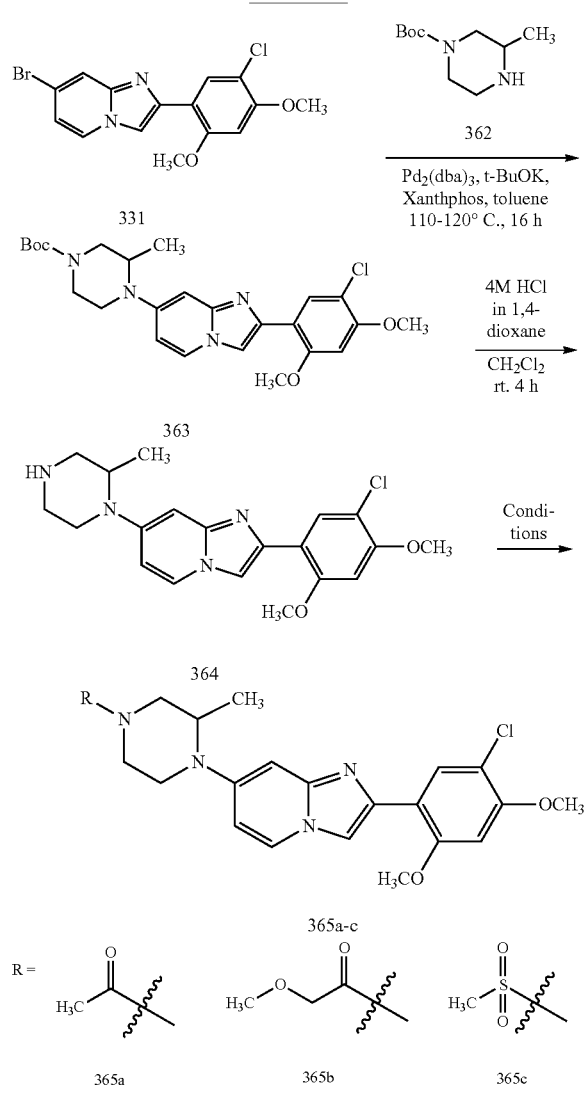

Scheme 2-19 methoxyethanone 365b was prepared in the same manner as 1-(4-(2-(5-chloro-2,4-dimethoxyphenyl)imidazo[1,2-a]pyridin-7-yl)-3-methylpiperazin-1-yl)ethanone 365a and was obtained as an off-white solid (12% yield).

$^1$H NMR (400 MHz, 353K DMSO-d$_6$): δ 8.28 (d, J=7.6 Hz, 1H), 8.19 (s, 1H), 7.99 (s, 1H), 6.88 (s, 1H), 6.75 (dd, J=2.0, 7.6 Hz, 1H), 6.64 (s, 1H), 4.19-4.10 (m, 4H), 4.01 (br s, 4H), 3.95 (s, 3H), 3.48-3.45 (m, 1H), 3.36 (br s, 4H), 3.16-3.14 (m, 2H), 1.05 (d, J=6.4 Hz, 3H); HPLC (Method 1) 97.9% (AUC), t$_R$=12.36 min.; ESI+APCI MS m/z 459 [M+H]$^+$.

Preparation of 2-(5-chloro-2,4-dimethoxyphenyl)-7-(2-methyl-4-(methylsulfonyl)piperazin-1-yl)imidazo[1,2-a]pyridine 365c (Example 311)

Compound 2-(5-chloro-2,4-dimethoxyphenyl)-7-(2-methyl-4-(methylsulfonyl)piperazin-1-yl)imidazo[1,2-a]pyridine 365c was prepared in the same manner as 1-(4-(2-(5-chloro-2,4-dimethoxyphenyl)imidazo[1,2-a]pyridin-7-yl)-3-methylpiperazin-1-yl)ethanone 365a (by using methanesulfonyl chloride in place of acetyl chloride) and was obtained as an off-white solid (20% yield).

$^1$H NMR (400 MHz, DMSO-d$_6$): δ 8.35 (d, J=7.6 Hz, 1H), 8.15 (s, 1H), 8.04 (s, 1H), 6.87 (s, 1H), 6.85 (d, J=6.4 Hz, 1H), 6.67 (s, 1H), 4.35-4.25 (m, 1H), 4.01 (s, 3H), 3.93 (s, 3H), 3.61-3.54 (m, 2H), 3.42-3.35 (m, 1H), 3.11-3.08 (m, 2H), 2.93 (br s, 4H), 1.07 (d, J=6.4 Hz, 3H); HPLC (Method 1) 95.3% (AUC), t$_R$=12.85 min.; ESI+APCI MS m/z 465 [M+H]$^+$.

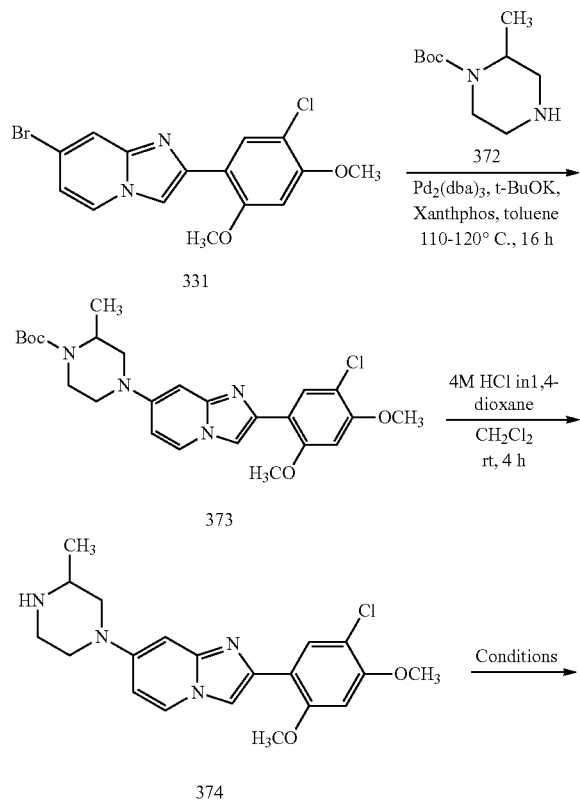

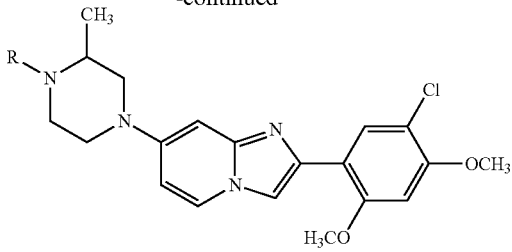

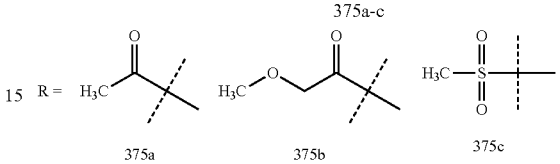

Preparation of tert-butyl 4-(2-(5-chloro-2,4-dimethoxyphenyl)imidazo[1,2-a]pyridin-7-yl)-2-methylpiperazine-1-carboxylate 373

A suspension of 7-bromo-2-(5-chloro-2,4-dimethoxyphenyl)imidazo[1,2-a]pyridine 1 (200 mg, 0.544 mmol), tert-butyl 2-methylpiperazine-1-carboxylate 372 (218 mg, 1.09 mmol), Xanthphos (34 mg, 0.059 mmol) and t-BuOK (181 mg, 1.62 mmol) in toluene (10 mL) was degassed with argon for 15 min. Subsequently the mixture was charged with Pd$_2$(dba)$_3$ (24 mg, 0.026 mmol) and further degassed with argon for another 5 min. The reaction mixture was heated at 100-110° C. for 16 h. The reaction mixture was cooled, filtered through a pad of celite (the celite was washed with 10% MeOH/CH$_2$Cl$_2$) and the combined filtrate was evaporated to dryness. The residue obtained was purified by combi-flash companion (silica gel, CH$_3$OH/CH$_2$Cl$_2$) to provide tert-butyl 4-(2-(5-chloro-2,4-dimethoxyphenyl) imidazo[1,2-a]pyridin-7-yl)-2-methylpiperazine-1-carboxylate 373 (90 mg, 34%) as an off-white solid.

$^1$H NMR (400 MHz, DMSO-d$_6$): δ 8.32 (d, J=7.6 Hz, 1H), 8.16 (s, 1H), 8.02 (s, 1H), 6.86 (s, 1H), 6.78 (dd, J=2.4, 7.6 Hz, 1H), 6.66 (d, J=1.6 Hz, 1H), 4.22-4.20 (m, 1H), 4.00 (s, 3H), 3.93 (s, 3H), 3.83-3.79 (m, 1H), 3.70-3.60 (m, 2H), 3.22-3.16 (m, 1H), 2.97-2.91 (m, 1H), 2.76-2.70 (m, 1H), 1.42 (s, 9H), 1.18 (d, J=6.4 Hz, 3H); HPLC (Method 1) 97.0% (AUC), t$_R$=14.23 min.; ESI+APCI MS m/z 487 [M+H]$^+$.

Preparation of 2-(5-chloro-2,4-dimethoxyphenyl)-7-(3-methylpiperazin-1-yl)imidazo[1,2-a]pyridine 374

A solution of tert-butyl 4-(2-(5-chloro-2,4-dimethoxyphenyl) imidazo[1,2-a]pyridin-7-yl)-2-methylpiperazine-1-carboxylate 373 (1.50 g, 3.08 mmol) in CH$_2$Cl$_2$ (20 mL) was charged with a solution of HCl in 1,4-dioxane (4.0 M, 15 mL) and stirred at room temperature for 4 h. The reaction mixture was filtered and the solid obtained was washed with CH$_2$Cl$_2$. The solid was then suspended in water (35 mL), basified with saturated sodium bicarbonate solution (35 mL) by stirring for 1 h at room temperature. The solid was filtered, washed with water and dried to provide 2-(5-chloro-2,4-dimethoxyphenyl)-7-(3-methylpiperazin-1-yl)imidazo[1,2-a]pyridine 374 (1.10 g, 91%) as an off-white solid.

ESI+APCI MS m/z 387 [M+H]$^+$.

Preparation of 1-(4-(2-(5-chloro-2,4-dimethoxyphenyl)imidazo[1,2-a]pyridin-7-yl)-2-methylpiperazin-1-yl)ethanone 375a (Example 309)

A solution of 2-(5-chloro-2,4-dimethoxyphenyl)-7-(3-methylpiperazin-1-yl)imidazo[1,2-a]pyridine 374 (150 mg, 0.38 mmol) and Et$_3$N (0.16 mL, 1.16 mmol) in CH$_2$Cl$_2$ (15 mL) was charged with acetyl chloride (44 mg, 0.57 mmol). The reaction mixture was stirred at room temperature for 16 h. The reaction mixture was diluted with water and extracted with CH$_2$Cl$_2$ (2×20 mL). The combined organic layers were dried over sodium sulfate, filtered and concentrated under reduced pressure and the residue was purified by combi-flash companion (silica gel, CH$_3$OH/CH$_2$Cl$_2$) to afford 1-(4-(2-(5-chloro-2,4-dimethoxyphenyl)imidazo[1,2-a]pyridin-7-yl)-2-methylpiperazin-1-yl)ethanone 375a (15 mg, 9%) as an off-white solid.

$^1$H NMR (400 MHz, 353K DMSO-d$_6$): δ 8.28 (d, J=7.6 Hz, 1H), 8.19 (s, 1H), 7.99 (s, 1H), 6.88 (s, 1H), 6.73 (dd, J=2.8, 7.6 Hz, 1H), 6.66 (d, J=2.0 Hz, 1H), 4.46 (br s, 1H), 4.01 (s, 3H), 3.95 (s, 3H), 3.73-3.69 (m, 1H), 3.63-3.60 (m, 1H), 3.31 (br s, 1H), 3.04 (dd, J=4.0, 12.8 Hz, 1H), 2.88-2.83 (m, 2H), 2.06 (s, 3H), 1.25 (d, J=6.8 Hz, 3H); HPLC (Method 1) 99.2% (AUC), t$_R$=12.54 min.; ESI+APCI MS m/z 429 [M+H]$^+$.

Preparation of 1-(4-(2-(5-chloro-2,4-dimethoxyphenyl)imidazo[1,2-a]pyridin-7-yl)-2-methylpiperazin-1-yl)-2-methoxyethanone 375b (Example 310)

Compound 1-(4-(2-(5-chloro-2,4-dimethoxyphenyl)imidazo[1,2-a]pyridin-7-yl)-2-methylpiperazin-1-yl)-2-methoxyethanone 375b was prepared in the same manner as 1-(4-(2-(5-chloro-2,4-dimethoxyphenyl)imidazo[1,2-a]pyridin-7-yl)-2-methylpiperazin-1-yl)ethanone 375a and was obtained as an off-white solid (8% yield).

$^1$H NMR (400 MHz, 353K DMSO-d$_6$): δ 8.28 (d, J=7.6 Hz, 1H), 8.19 (s, 1H), 7.99 (s, 1H), 6.88 (s, 1H), 6.74-6.72 (m, 1H), 6.67 (s, 1H), 4.45-4.42 (m, 1H), 4.12 (s, 2H), 4.01 (br s, 4H), 3.95 (s, 3H), 3.74-3.71 (m, 1H), 3.64-3.61 (m, 1H), 3.34 (br s, 4H), 3.05 (dd, J=4.0, 12.8 Hz, 1H), 2.93-2.85 (m, 1H), 1.28 (d, J=6.4 Hz, 3H); HPLC (Method 1) 98.2% (AUC), t$_R$=12.33 min.; ESI+APCI MS m/z 459 [M+H]$^+$.

Preparation of 2-(5-chloro-2,4-dimethoxyphenyl)-7-(3-methyl-4-(methylsulfonyl)piperazin-1-yl)imidazo[1,2-a]pyridine 375c (Example 312)

Compound 2-(5-chloro-2,4-dimethoxyphenyl)-7-(3-methyl-4-(methylsulfonyl)piperazin-1-yl)imidazo[1,2-a]pyridine 375c was prepared in the same manner as 1-(4-(2-(5-chloro-2,4-dimethoxyphenyl)imidazo[1,2-a]pyridin-7-yl)-2-methylpiperazin-1-yl)ethanone 375a (by using methanesulfonic chloride in place of acetyl chloride) and was obtained as an off-white solid (25% yield).

$^1$H NMR (400 MHz, DMSO-d$_6$): δ 8.33 (d, J=7.6 Hz, 1H), 8.16 (s, 1H), 8.03 (s, 1H), 6.87 (s, 1H), 6.79 (dd, J=2.4, 7.6 Hz, 1H), 6.68 (d, J=2.0 Hz, 1H), 4.05-4.02 (m, 1H), 4.00 (s, 3H), 3.93 (s, 3H), 3.70-3.53 (m, 3H), 3.38-3.37 (m, 1H), 3.03 (dd, J=3.6, 12.8 Hz, 1H), 2.99 (s, 3H), 2.91-2.84 (m, 1H), 1.29 (d, J=6.8 Hz, 3H); HPLC (Method 1) 99.2% (AUC), t$_R$=12.81 min.; ESI+APCI MS m/z 465 [M+H]$^+$.

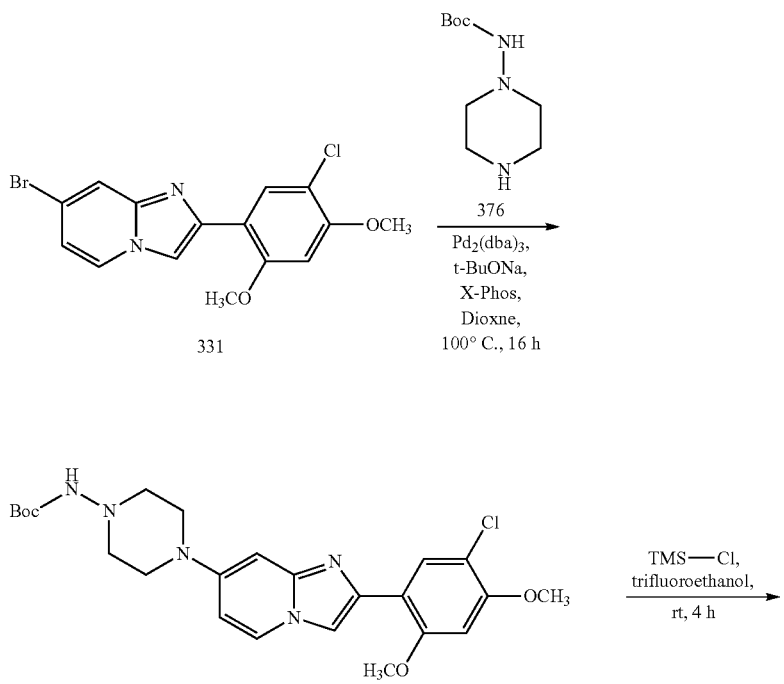

Scheme 2-21

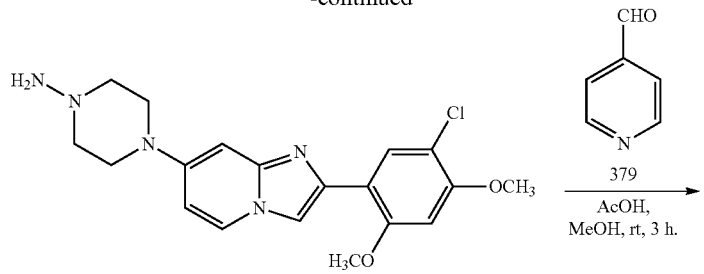
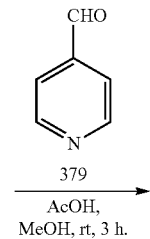
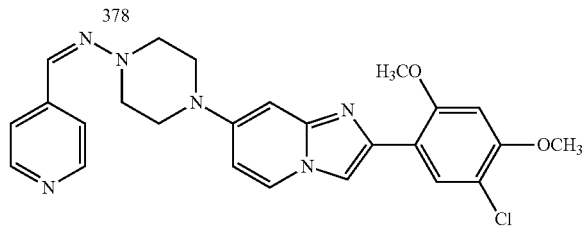

Preparation of tert-butyl (4-(2-(5-chloro-2,4-dimethoxyphenyl)imidazo[1,2-a]pyridin-7-yl)piperazin-1-yl)carbamate 377

A suspension of 7-bromo-2-(5-chloro-2,4-dimethoxyphenyl)imidazo[1,2-a]pyridine 331 (1.00 g, 2.73 mmol), tert-butyl piperazin-1-ylcarbamate 376 (823 mg, 4.08 mmol), X-Phos (130 mg, 0.27 mmol) and NaOt-Bu (787 mg, 8.2 mmol) in 1,4-dioxane (20 mL) was degassed with argon for 15 min. Subsequently the mixture was charged with $Pd_2(dba)_3$ (250 mg, 0.27 mmol) and further degassed with argon for 5 min. The reaction mixture was stirred at 100° C. for 16 h. The reaction mixture was cooled, filtered through a pad of celite and the filtrate was evaporated to dryness. The residue obtained was purified by combi-flash (silica-gel, MeOH/$CH_2Cl_2$) to give tert-butyl (4-(2-(5-chloro-2,4-dimethoxyphenyl)imidazo[1,2-a]pyridin-7-yl)piperazin-1-yl)carbamate 377 (500 mg, 37%) as a light-yellow solid. ESI+APCI MS nm/z 488 [M+H]$^+$.

Preparation of 4-(2-(5-chloro-2,4-dimethoxyphenyl)imidazo[1,2-a]pyridin-7-yl)piperazin-1-amine hydrochloride 378

A suspension of tert-butyl (4-(2-(5-chloro-2,4-dimethoxyphenyl)imidazo[1,2-a]pyridin-7-yl)piperazin-1-yl)carbamate 377 (120 mg, 0.24 mmol) in 2,2,2-trifluoroethanol (3 mL) was charged with TMS-Cl (0.1 mL). The reaction mixture was stirred at room temperature for 1 h. The reaction mixture was evaporated to dryness to provide 4-(2-(5-chloro-2,4-dimethoxyphenyl)imidazo[1,2-a]pyridin-7-yl)piperazin-1-amine hydrochloride 378 (60 mg, 57%) as a light-yellow solid.

$^1$H NMR (300 MHz, DMSO-$d_6$): δ 9.62 (bs, 3H), 8.58 (d, J=7.8 Hz, 1H), 8.30 (s, 1H), 7.95 (s, 1H), 7.24 (d, J=8.1 Hz, 1H), 6.99 (s, 1H), 6.80 (s, 1H), 4.05 (s, 3H), 3.99 (s, 3H), 3.63 (bs, 4H), 3.03 (bs, 4H); HPLC (Method) 99.2% (AUC), $t_R$=11.22 min.; ESI+APCI MS m/z 388 [M+H]$^+$.

Preparation of (Z)-4-(2-(5-chloro-2,4-dimethoxyphenyl)imidazo[1,2-a]pyridin-7-yl)-N-(pyridin-4-ylmethylene)piperazin-1-amine 380 (Example 410)

A mixture of 4-(2-(5-chloro-2,4-dimethoxyphenyl)imidazo[1,2-a]pyridin-7-yl)piperazin-1-amine hydrochloride 378 (50 mg, 0.11 mmol), trimethylamine (0.045 mL, 0.33 mmol) isonicotinaldehyde 379 (0.011 mL, 0.13 mmol) and AcOH (0.05 mL) in $CH_3OH$ (2 mL) was stirred at room temperature for 16 h. The reaction mixture was diluted with water, and extracted with $CH_2Cl_2$ (2 t 10 mL). The combined organic layers were dried over sodium sulfate, filtered and concentrated under reduced pressure and the residue was purified by combi-flash companion (silica gel, $CH_3OH$/$CH_2Cl_2$) to afford to afford (Z)-4-(2-(5-chloro-2,4-dimethoxyphenyl)imidazo[1,2-a]pyridin-7-yl)-N-(pyridin-4-ylmethylene)piperazin-1-amine 380 (10 mg, 16%) as a light yellow solid.

$^1$H NMR (300 MHz, DMSO-$d_6$) δ: 8.54 (bs, 2H), 8.36 (d, J=6.9 Hz, 1H), 8.18 (s, 1H), 8.05 (s, 1H), 7.69 (bs, 1H), 7.52 (bs, 2H), 6.88 (bs, 1H), 6.78 (s, 1H), 4.0 (s, 3H), 3.94 (s, 3H), 3.45 (bs, 4H), 3.35 (bs, 4H), HPLC (Method 5) 96.6% (AUC), $t_R$=12.65 min.; ESI+APCI MS m z 477 [M+H]$^+$.

Scheme 2-22

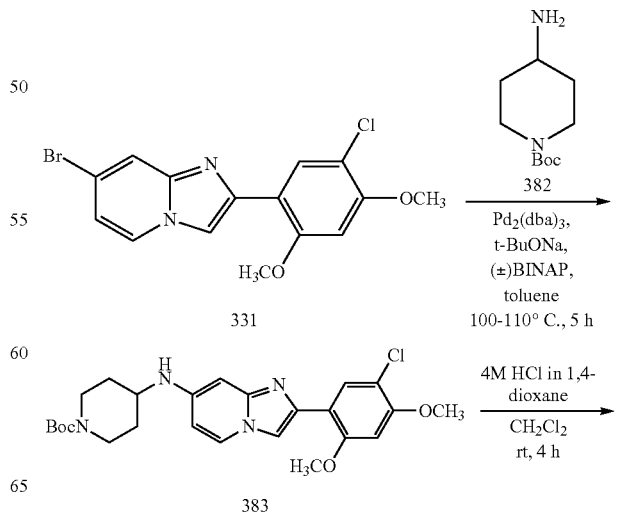

-continued

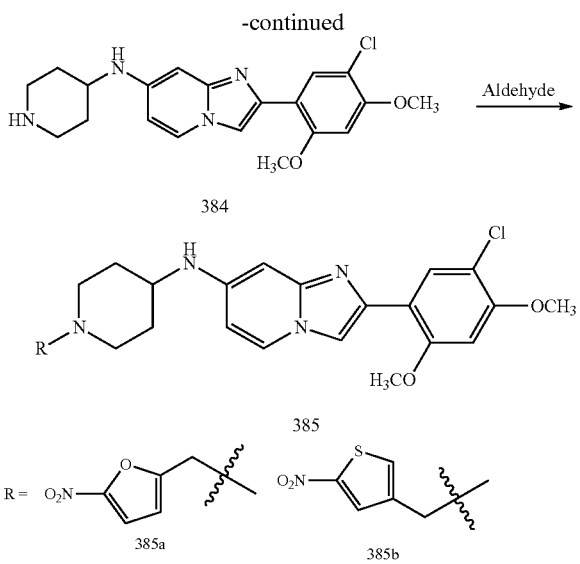

Preparation of tert-butyl (1-(2-(5-chloro-2,4-dimethoxyphenyl)imidazo[1,2-a]pyridin-7-yl tert-butyl 4-((2-(5-chloro-2,4-dimethoxyphenyl)imidazo[1,2-a]pyridin-7-yl)amino)piperidine-1-carboxylate 383

A suspension of 7-bromo-2-(5-chloro-2,4-dimethoxyphenyl)imidazo[1,2-a]pyridine 331 (5.00 g, 13.7 mmol), tert-butyl 4-aminopiperidine-1-carboxylate 382 (2.7 g, 13.7 mmol), (+) BINAP (849 mg, 1.36 mmol) and NaOt-Bu (3.9 g, 40.98 mmol) in toluene (50 mL) was degassed with argon for 15 min. Then this mixture was charged with $Pd_2(dba)_3$ (625 mg, 0.683 mmol) and was further degassed with argon for another 5 min. The reaction mixture was stirred at 100-110° C. for 16 h. The reaction mixture was cooled, filtered through a pad of celite (the celite pad was washed with 10% $MeOH/CH_2Cl_2$) and the combined filtrate was evaporated to dryness. The residue obtained was triturated with 10% MTBE in hexanes to provide tert-butyl 4-((2-(5-chloro-2,4-dimethoxyphenyl)imidazo[1,2-a]pyridin-7-yl)amino)piperidine-1-carboxylate 383 (2.50 g, 31%) as a brown solid.

$^1$H NMR (400 MHz, DMSO-$d_6$): δ 8.13-8.12 (m, 2H), 7.88 (s, 1H), 6.84 (s, 1H), 6.36 (dd, J=2.0, 7.2 Hz, 1H), 6.31 (s, 1H), 6.09 (s, 1H), 3.99 (s, 3H), 3.92-3.86 (m, 5H), 3.48-3.40 (m, 1H), 3.02-2.92 (m, 2H), 1.95 (d, J=9.2 Hz, 2H), 1.41 (s, 9H), 1.33-1.23 (m, 2H).

Preparation of 2-(5-chloro-2,4-dimethoxyphenyl)-N-(piperidin-4-yl)imidazo[1,2-a]pyridin-7-amine 384

A solution of tert-butyl 4-((2-(5-chloro-2,4-dimethoxyphenyl)imidazo[1,2-a]pyridin-7-yl)amino)piperidine-1-carboxylate 383 (1.50 g, 3.08 mmol) in $CH_2Cl_2$ (25 mL) was charged with a solution of HCl in 1,4-dioxane (4.0 M, 15 mL) and the reaction mixture was stirred at room temperature for 4 h. The reaction mixture was filtered and the solid obtained was washed with $CH_2Cl_2$. The solid was then suspended in water (55 mL), basified with saturated sodium bicarbonate solution (55 mL) by stirred for 1 h at room temperature. The solid was collected by filtration, washed with water and dried to provide 2-(5-chloro-2,4-dimethoxyphenyl)-N-(piperidin-4-yl)imidazo[1,2-a]pyridin-7-amine 384 (500 mg, 42%) as a brown solid.

$^1$H NMR (400 MHz, DMSO-$d_6$): δ 8.14-8.11 (m, 2H), 7.87 (s, 1H), 6.84 (s, 1H), 6.36 (dd, J=1.6, 7.2 Hz, 1H), 6.25 (s, 1H), 6.08 (d, J=7.2 Hz, 1H), 3.99 (s, 3H), 3.92 (s, 3H), 3.36-2.67 (m, 5H), 1.92 (d, J=10.8 Hz, 2H), 1.29-1.22 (m, 2H).

Preparation of 2-(5-chloro-2,4-dimethoxyphenyl)-N-(1-((5-nitrofuran-2-yl)methyl)piperidin-4-yl)imidazo[1,2-a]pyridin-7-amine 385a (Example 343)

To a solution of 2-(5-chloro-2,4-dimethoxyphenyl)-N-(piperidin-4-yl)imidazo[1,2-a]pyridin-7-amine 384 (200 mg, 0.518 mmol) in $CH_3OH$ (2 mL) was charged with 5-nitrofuran-2-carbaldehyde (109 mg, 0.777 mmol) and acetic acid (0.2 mL). The resulting mixture was stirred at ambient temperature for 1 h. To the reaction mixture was added NaCNBH$_3$ (96 mg, 1.55 mmol) and the reaction mixture was stirred for 16 h. The reaction mixture was concentrated, the residue was taken up in aqueous NaHCO$_3$ solution (5.0 mL) and the aqueous layer was extracted with ethyl acetate (2×10 mL). The combined organic layers were dried over Na$_2$SO$_4$, filtered and concentrated. The residue was purified by combi-flash companion (silica gel, CH$_3$OH/CH$_2$Cl$_2$) to provide 2-(5-chloro-2,4-dimethoxyphenyl)-N-(1-((5-nitrofuran-2-yl)methyl)piperidin-4-yl)imidazo[1,2-a]pyridin-7-amine 385a (15 mg, 5.6%) as an off-white solid.

$^1$H NMR (300 MHz, DMSO-$d_6$): δ 8.14-8.11 (m, 2H), 7.89 (s, 1H), 7.67 (d, J=3.6 Hz, 1H), 6.85 (s, 1H), 6.78 (d, J=3.6 Hz, 1H), 6.39 (d, J=5.7 Hz, 1H), 6.24 (s, 1H), 6.15 (d, J=6 Hz, 1H), 3.99 (s, 4H), 3.92 (s, 3H), 3.67 (s, 2H), 3.33-3.22 (m, 1H), 2.86 (d, J=11.7 Hz, 2H), 2.29-2.22 (m, 2H), 1.98 (d, J=10.5 Hz, 2H), 1.48-1.38 (m, 2H); HPLC (Method 1) 97.6% (AUC), $t_R$=11.9 min.; ESI+APCI MS m/z 512 [M+H]$^+$.

Preparation of 2-(5-chloro-2,4-dimethoxyphenyl)-N-(1-((5-nitrothiophen-3-yl)methyl)piperidin-4-yl)imidazo[1,2-a]pyridin-7-amine 385b (Example 324)

To a solution of 2-(5-chloro-2,4-dimethoxyphenyl)-N-(piperidin-4-yl)imidazo[1,2-a]pyridin-7-amine 384 (200 mg, 0.518 mmol) in methanol (2 mL) was charged with 5-nitrothiophene-3-carbaldehyde (163 mg, 1.03 mmol) and acetic acid (0.1 mL). The resulting mixture was stirred at room temperature for 1 h. The reaction mixture was charged with NaCNBH$_3$ (163 mg, 2.58 mmol) and was stirred at room temperature for 16 h. The reaction mixture was concentrated. The residue was taken up in aqueous NaHCO$_3$ (5.0 mL) solution and extracted with 10% CH$_3$OH/CH$_2$Cl$_2$ (20 mL). The combined organic layers were dried over Na$_2$SO$_4$, filtered and concentrated. The crude compound was purified by combi-flash companion (silica gel, CH$_3$OH/CH$_2$Cl$_2$) to provide 2-(5-chloro-2,4-dimethoxyphenyl)-N-(1-((5-nitrothiophen-2-yl)methyl)piperidin-4-yl)imidazo[1,2-a]pyridin-7-amine 385b (40 mg, 12%); as a brown solid.

$^1$H NMR (400 MHz, DMSO-$d_6$): δ 8.15 (d, J=7.2 Hz, 1H), 8.09 (s, 1H), 8.01 (d. J=2.0 Hz, 1H), 7.92 (s, 1H), 7.85 (s, 1H), 6.86 (s, 1H), 6.43 (d, J=6.0 Hz, 1H), 6.28 (s, 1H), 6.26 (s, 1H), 3.99 (s, 3H), 3.93 (s, 3H), 3.53 (s, 2H), 3.17 (s, 1H), 2.82 (d, J=11.6 Hz, 2H), 2.19 (t, J=10.8 Hz, 2H), 1.96 (d, J=10.8 Hz, 2H), 1.48-1.40 (m, 2H); HPLC (Method 1) 92.1% (AUC), $t_R$=12.05 min.; ESI+APCI MS m/z 528 [M+H]$^+$.

Scheme 2-23

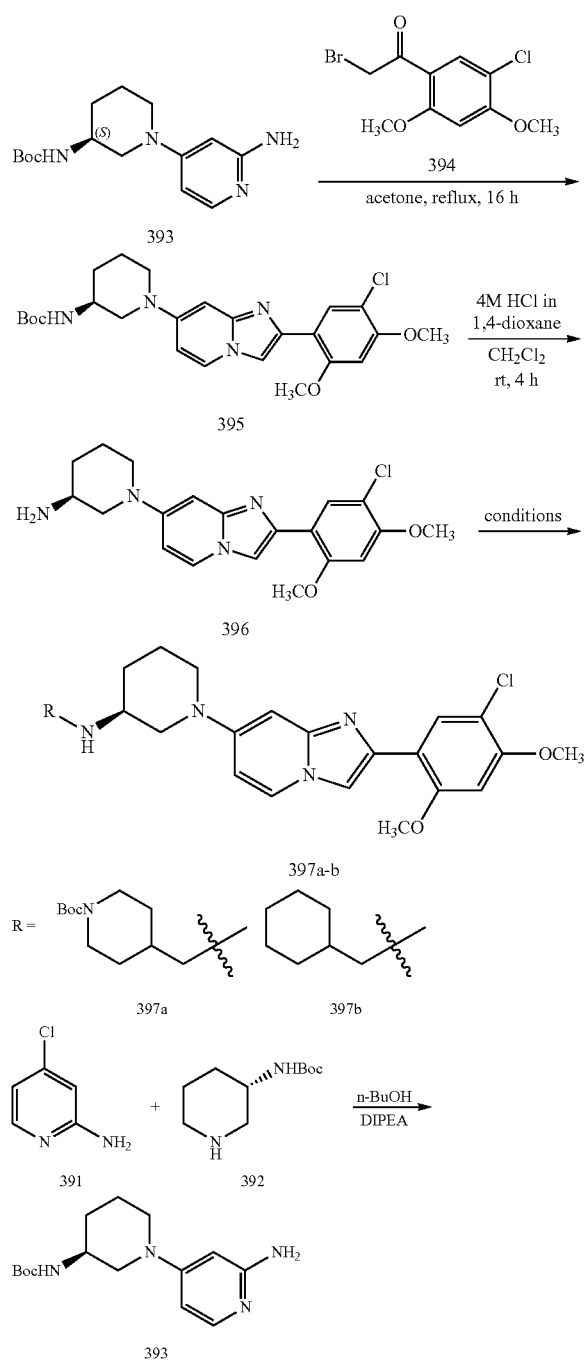

Preparation of (S)-tert-butyl (1-(2-aminopyridin-4-yl)piperidin-3-yl)carbamate 393

A solution of 4-chloropyridin-2-amine 391 (5.00 g, 39.1 mmol) in n-BuOH/N,N-diisopropylethylamine (100 mL/20 mL) was charged with (S)-tert-butyl piperidin-3-ylcarbamate 392 (15.6 g, 78.1 mmol). The reaction mixture was stirred at 110-120° C. for 16 h in a sealed tube. The reaction mixture was cooled to room temperature and concentrated under reduced pressure; the crude material was taken up in saturated sodium bicarbonate solution (100 mL) and was extracted with $CH_2Cl_2$ (150 mL). The organic layer was dried over $Na_2SO_4$, filtered and concentrated. The residue was triturated with hexanes to provide (S)-tert-butyl (1-(2-aminopyridin-4-yl)piperidin-3-yl)carbamate 393 (5.80 g, 50%) as an off-white solid. The compound was used for next step without further purification. ESI+APCI MS m/z 293 $[M+H]^+$.

Preparation of (S)-tert-butyl (1-(2-(5-chloro-2,4-dimethoxyphenyl)imidazo[1,2-a]pyridin-7-yl)piperidin-3-yl)carbamate 395

A solution of (S)-tert-butyl (1-(2-aminopyridin-4-yl)piperidin-3-yl)carbamate 3 (5.00 g, 17.1 mmol) and 2-bromo-1-(5-chloro-2,4-dimethoxyphenyl)ethanone 394 (5.49 g, 18.8 mmol) in acetone (100 mL) was heated at 75° C. for 16 h. The reaction mixture was cooled to room temperature, the white precipitate formed was collected by filtration and washed with hexanes. The solid was suspended in aqueous ammonia hydroxide and stirred at room temperature for 4 h. The suspension was filtered and the solid obtained was washed with hexane and dried under reduced pressure to give (S)-tert-butyl (1-(2-(5-chloro-2,4-dimethoxyphenyl)imidazo[1,2-a]pyridin-7-yl)piperidin-3-yl)carbamate 395 (6.50 g, 78%) as a white solid. ESI+APCI MS m/z 487 $[M+H]^+$.

Preparation of (S)-1-(2-(5-chloro-2,4-dimethoxyphenyl)imidazo[1,2-a]pyridin-7-yl)piperidin-3-amine 396

A solution of (S)-tert-butyl (1-(2-(5-chloro-2,4-dimethoxyphenyl)imidazo[1,2-a]pyridin-7-yl)piperidin-3-yl)carbamate 395 (5.50 g, 11.3 mmol) in $CH_2Cl_2$ (50 mL) was charged with 4.0 M HCl in 1,4-dioxane (25 mL) and was stirred at room temperature for 4 h. The reaction mixture was filtered and the solid obtained was washed with $CH_2Cl_2$. The solid was then suspended in water (55 mL), basified with saturated sodium bicarbonate solution (55 mL) by stirring at room temperature for 1 h. The suspension was filtered and the solid obtained was washed with water and dried to provide (S)-1-(2-(5-chloro-2,4-dimethoxyphenyl)imidazo[1,2-a]pyridin-7-yl)piperidin-3-amine 396 (4.30 g, 95%) as an off-white solid. ESI+APCI MS m/z 387 $[M+H]^+$.

Preparation of (S)-tert-butyl 4-(((1-(2-(5-chloro-2,4-dimethoxyphenyl)imidazo[1,2-a]pyridin-7-yl)piperidin-3-yl)amino)methyl)piperidine-1-carboxylate 397a (Example 454)

A solution of (S)-1-(2-(5-chloro-2,4-dimethoxyphenyl)imidazo[1,2-a]pyridin-7-yl)piperidin-3-amine 396 (250 mg, 0.64 mmol), tert-butyl 4-formylpiperidine-1-carboxylate (194 mg, 0.97 mmol) and acetic acid (0.2 mL) in $CH_3OH$ (10 mL) was stirred at room temperature for 1 h. Sodium cyanoborohydride (201 mg, 3.2 mmol) was added and the reaction mixture was stirred at room temperature for 16 h. The reaction mixture was diluted with aqueous sodium bicarbonate solution and extracted with $CH_2Cl_2$ (2×20 mL). The combined organic layers were dried over sodium sulfate, filtered and concentrated under reduced pressure and the residue was purified by combi-flash companion (silica gel, $NH_4OH/CH_3OH/CHCl_3$) to afford (S)-tert-butyl 4-(((1-(2-(5-chloro-2,4-dimethoxyphenyl)imidazo[1,2-a]pyridin-7-yl)piperidin-3-yl)amino)methyl)piperidine-1-carboxylate 397a (130 mg, 34%) as an off-white solid.

441

$^1$H NMR (300 MHz, Methanol-$d_4$): δ 8.04 (d, J=7.5 Hz, 1H), 7.97 (s, 1H), 7.86 (s, 1H), 6.69-6.65 (m, 2H), 6.58 (s, 1H), 4.00-3.96 (m, 2H), 3.92 (s, 3H), 3.85 (s, 3H), 3.73-3.70 (m, 1H), 3.57-3.53 (m, 1H), 2.84-2.76 (m, 1H), 2.66-2.63 (m, 4H), 2.50 (d, J=6.6 Hz, 2H), 1.97-1.93 (m, 1H), 1.78-1.56 (m, 5H), 1.35 (s, 9H), 1.10-0.95 (m, 2H), 0.81-0.75 (m, 1H); HPLC (Method 1) >99% (AUC), $t_R$=12.65 min.; ESI+APCI MS m/z 584 [M+H]$^+$.

Preparation of (S)-1-(2-(5-chloro-2,4-dimethoxyphenyl)imidazo[1,2-a]pyridin-7-yl)-N-(cyclohexylmethyl)piperidin-3-amine 397b (Example 455)

Compound (S)-1-(2-(5-chloro-2,4-dimethoxyphenyl)imidazo[1,2-a]pyridin-7-yl)-N-(cyclohexylmethyl)piperidin-3-amine 397b was prepared in the same manner as (S)-tert-butyl 4-(((1-(2-(5-chloro-2,4-dimethoxyphenyl)imidazo[1,2-a]pyridin-7-yl)piperidin-3-yl)amino)methyl)piperidine-1-carboxylate 397a and was obtained as an off-white solid (16% yield).

$^1$H NMR (300 MHz, Methanol-$d_4$): δ 8.27 (d, J=7.5 Hz, 1H), 8.16 (s, 1H), 7.98 (s, 1H), 6.86 (s, 1H), 6.75 (d, J=7.5 Hz, 1H), 6.61 (s, 1H), 4.00 (s, 3H), 3.93 (s, 3H), 3.77-3.74 (m, 1H), 3.64-3.60 (m, 1H), 2.81-2.72 (m, 1H), 2.50 (d, J=6.6 Hz, 2H), 1.93-1.90 (m, 1H), 1.77-1.52 (m, 8H), 1.35-1.23 (m, 6H), 0.63-0.83 (m, 2H); HPLC (Method 1) 96.9% (AUC), $t_R$=12.67 min.; ESI+APCI MS m/z 483 [M+H]$^+$.

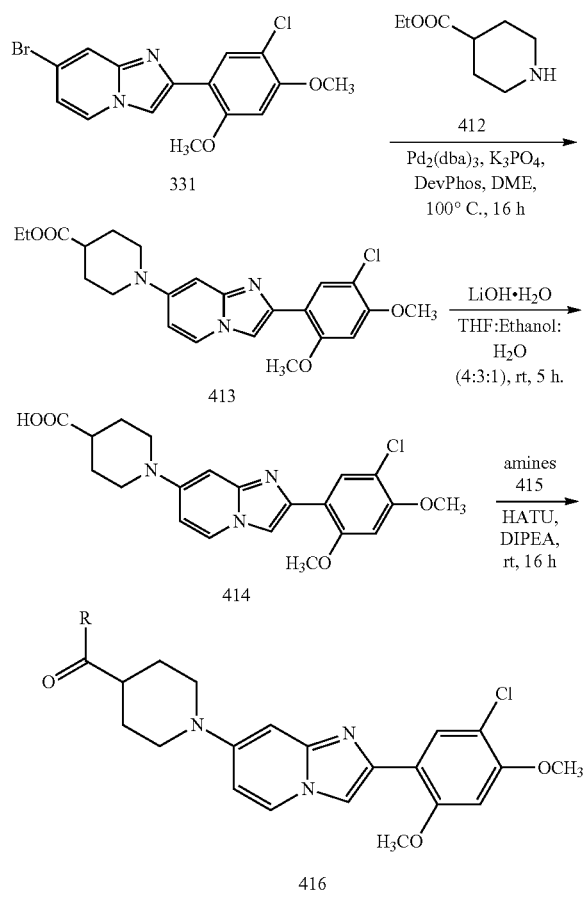

442

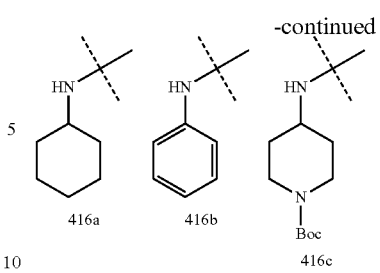

Preparation of ethyl 1-(2-(5-chloro-2,4-dimethoxyphenyl)imidazo[1,2-a]pyridin-7-yl)piperidine-4-carboxylate 413

A suspension of 7-bromo-2-(5-chloro-2,4-dimethoxyphenyl)imidazo[1,2-a]pyridine 331 (4.00 g, 10.9 mmol), ethyl piperidine-4-carboxylate 412 (1.50 g, 16.5 mmol), DavePhos (643 mg, 1.63 mmol) and $K_3PO_4$ (4.70 g, 22.4 mmol) in dimethoxy ethane (80 mL) was degassed with argon for 15 min. Subsequently the mixture was charged with $Pd_2(dba)_3$ (503 mg, 0.55 mmol) and was degassed further with argon for another 5 min. The reaction mixture was stirred at 90-100° C. for 16 h. The reaction mixture was cooled, filtered through a pad of celite and the filtrate was evaporated to dryness. The residue obtained was purified by combi-flash companion (silica gel, $CH_3OH/CH_2Cl_2$) to provide ethyl 1-(2-(5-chloro-2,4-dimethoxyphenyl)imidazo[1,2-a]pyridin-7-yl)piperidine-4-carboxylate 413 (3.0 g, 63%) as an off-white solid. ESI+APCI m/z 444 [M+H]$^+$.

Preparation of 1-(2-(5-chloro-2,4-dimethoxyphenyl)imidazo[1,2-a]pyridin-7-yl)piperidine-4-carboxylic acid 414

A solution of ethyl 1-(2-(5-chloro-2,4-dimethoxyphenyl)imidazo[1,2-a]pyridin-7-yl)piperidine-4-carboxylate 413 (3.00 g, 6.77 mmol) in a mixture of solvents THF (12 mL), ethanol (6 mL), and water (3 mL) was charged with LiOH·$H_2O$ (2.05 g, 27.1 mmol) and the reaction mixture was stirred at room temperature for 5 h. Most of the organic solvents were evaporated and the residue was diluted water and extracted with EtOAc (2×25 mL). The aqueous layer was acidified to pH 3.0 with 10% $KHSO_4$ solution and the solid formed was collected by filtration and dried to provide 1-(2-(5-chloro-2,4-dimethoxyphenyl)imidazo[1,2-a]pyridin-7-yl)piperidine-4-carboxylic acid 414 (1.8 g, 64%) as a light-yellow solid.

$^1$H NMR (400 MHz, DMSO-$d_6$): δ 11.59 (bs, 1H), 8.37 (d, J=8.0 Hz, 1H), 8.05 (s, 1H), 7.84 (s, 1H), 7.0 (dd, J=2.4, 8.0 Hz, 1H), 6.98 (s, 1H), 6.67 (d, J=2.0 Hz, 1H), 4.02 (s, 3H), 3.95 (s, 3H), 3.88-3.84 (m, 2H), 2.99 (t, J=6.8 Hz, 2H), 2.58-2.55 (m, 1H), 1.98-1.92 (m, 2H), 1.69-1.59 (m, 2H); ESI+APCI m: 416 [M+H]$^+$.

Preparation of 1-(2-(5-chloro-2,4-dimethoxyphenyl)imidazo[1,2-a]pyridin-7-yl)-N-cyclohexylpiperidine-4-carboxamideacid 416a (Example 453)

A mixture of 1-(2-(5-chloro-2,4-dimethoxyphenyl)imidazo[1,2-a]pyridin-7-yl)piperidine-4-carboxylic acid 414 (150 mg, 0.36 mmol), cyclohexanamine 415a (0.05 mL, 0.47 mmol), HATU (205 mg, 0.54 mmol) and N,N-diisopropylethylamine (0.09 mL, 0.54 mmol) in DMF (3 mL) was stirred at room temperature for 16 h under nitrogen atmosphere. The reaction mixture was quenched with crushed ice and extracted with EtOAc (2×25 mL). The combined organic layers were dried over Na₂SO₄, filtered and concentrated. The residue was purified by combi-flash companion (silica gel, CH₃OH/CH₂Cl₂) to afford 1-(2-(5-chloro-2,4-dimethoxyphenyl)imidazo[1,2-a]pyridin-7-yl)-N-cyclohexylpiperidine-4-carboxamide 416a (20 mg, 11%) as an off-white solid.

¹H NMR (400 MHz, DMSO-d₆) δ: 8.28 (d, J=5.7 Hz, 1H), 8.16 (s, 1H), 8.0 (s, 1H), 7.64 (d, J=6.0 Hz, 1H), 6.86 (s, 1H), 6.78 (dd, J=1.8, 5.7 Hz, 1H), 6.65 (s, 1H), 4.0 (s, 3H), 3.93 (s, 3H), 3.83-3.79 (m, 2H), 3.51-3.47 (m, 1H), 2.77-2.74 (m, 2H), 2.30-2.26 (m, 1H), 1.82-1.56 (m, 10H), 1.26-1.23 (m, 2H), 1.15-1.1 (m, 2H); HPLC (Method 5) 97.2% (AUC), t_R=13.72 min.; ESI+APCI MS m/z 497 [M+H]⁺.

Preparation of 1-(2-(5-chloro-2,4-dimethoxyphenyl) imidazo[1,2-a]pyridin-7-yl)-N-phenylpiperidine-4-carboxamide 416b (Example 456)

A mixture of 1-(2-(5-chloro-2,4-dimethoxyphenyl)imidazo[1,2-a]pyridin-7-yl)piperidine-4-carboxylic acid 414 (150 mg, 0.36 mmol), aniline 415b (43 mg, 0.47 mmol), HATU (205 mg, 0.54 mmol) and N,N-diisopropylethylamine (0.09 mL, 0.54 mmol) in DMF (3 mL) was stirred at room temperature for 16 h under nitrogen atmosphere. The reaction mixture was quenched with water and extracted with EtOAc (2×25 mL). The combined organic layers were dried over Na₂SO₄, filtered and concentrated. The residue was purified by combi-flash companion (silica gel, CH₃OH/CH₂Cl₂) to afford 1-(2-(5-chloro-2,4-dimethoxyphenyl)imidazo[1,2-a]pyridin-7-yl)-N-phenylpiperidine-4-carboxamidecarboxamide 416b (25 mg, 14%) as a light-yellow solid.

¹H NMR (400 MHz, DMSO-d₆) δ: 9.94 (s, 1H), 8.36 (d, J=7.6 Hz, 1H), 8.11 (s, 1H), 8.07 (s, 1H), 7.61 (d, J=7.6 Hz, 2H), 7.28 (t, J=7.2 Hz, 2H), 7.03 (t, J=7.2 Hz, 1H), 6.95 (d, J=5.6 Hz, 1H), 6.90 (s, 1H), 6.70 (d, J=2.0 Hz, 1H), 4.02 (s, 3H), 3.95 (s, 3H), 3.93 (bs, 2H), 2.90 (t, J=12.0 Hz, 2H), 2.68-2.55 (m, 1H), 1.99-1.90 (m, 2H), 1.80-1.70 (m, 2H), 1.15-1.1 (m, 2H); HPLC (Method 5) 98.3% (AUC), t_R=13.81 min.; ESI+APCI MS mm/z 491 [M+H]⁺.

Preparation of tert-butyl 4-(1-(2-(5-chloro-2,4-dimethoxyphenyl)imidazo[1,2-a]pyridin-7-yl)piperidine-4-carboxamido)piperidine-1-carboxylate 416c (Example 460)

A mixture of 1-(2-(5-chloro-2,4-dimethoxyphenyl)imidazo[1,2-a]pyridin-7-yl)piperidine-4-carboxylic acid 414 (150 mg, 0.36 mmol), tert-butyl 4-aminopiperidine-1-carboxylate 415c (94 mg, 0.47 mmol), HATU (205 mg, 0.54 mmol) and N,N-diisopropylethylamine (0.09 mL, 0.54 mmol) in DMF (3 mL) was stirred at room temperature for 16 h under nitrogen atmosphere. The reaction mixture was quenched with water and extracted with EtOAc (2×25 mL). The combined organic layers were dried over Na₂SO₄, filtered and concentrated. The residue was purified by combi-flash companion (silica gel, CH₃OH/CHCl₃) to afford tert-butyl 4-(1-(2-(5-chloro-2,4-dimethoxyphenyl)imidazo [1,2-a]pyridin-7-yl)piperidine-4-carboxamido)piperidine-1-carboxylate 416c (60 mg, 28%) as a light-yellow solid.

¹H NMR (400 MHz, DMSO-d₆) δ: 8.28 (d, J=7.6 Hz, 1H), 8.16 (s, 1H), 8.0 (s, 1H), 7.76 (d, J=7.6 Hz, 1H), 6.86 (s, 1H), 6.79 (dd, J=2.4, 7.6 Hz, 1H), 6.65 (d, J=1.6 Hz, 1H), 4.0 (s, 3H), 3.93 (s, 3H), 3.70-3.73 (m, 4H), 3.72-3.68 (m, 1H), 2.84-2.72 (m, 4H), 2.30-2.24 (m, 1H), 1.76-7.60 (m, 6H), 1.39 (s, 9H), 1.28-1.18 (m, 2H); HPLC (Method 5) 98.1% (AUC), t_R=13.79 min.; ESI+APCI MS m/z 598 [M+H]⁺.

Scheme 2-25

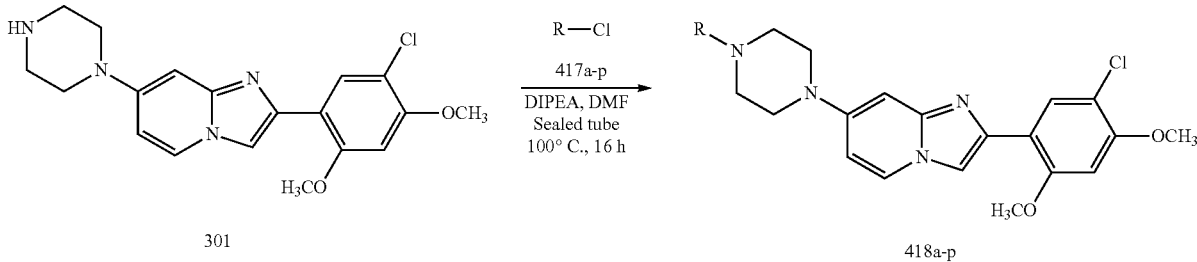

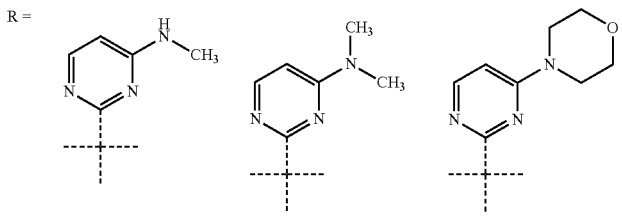

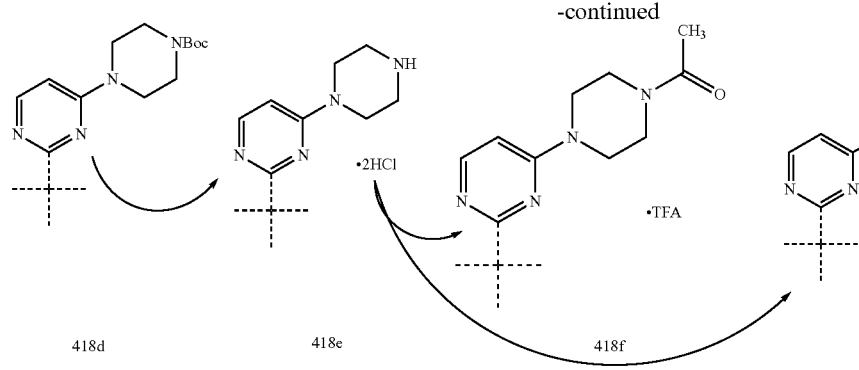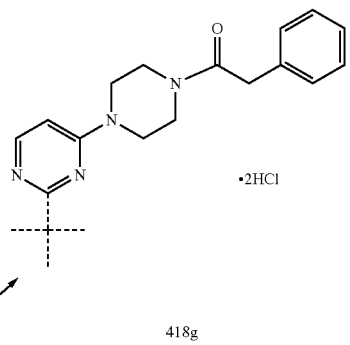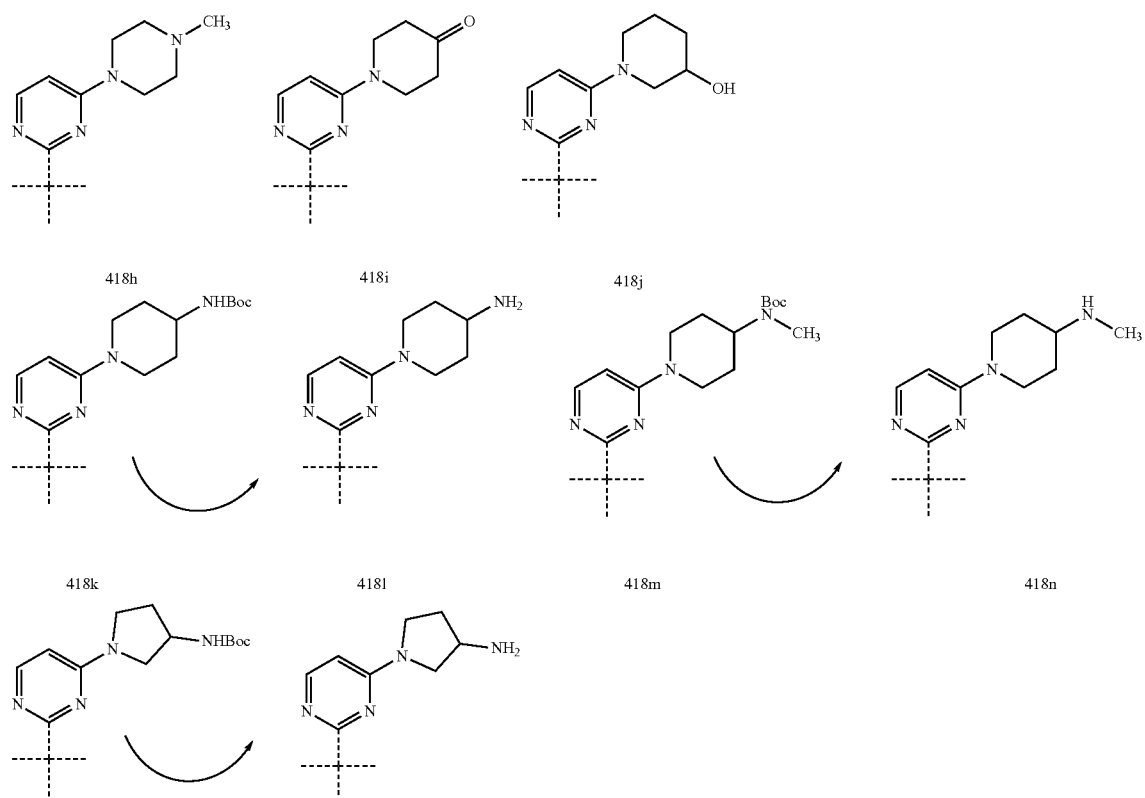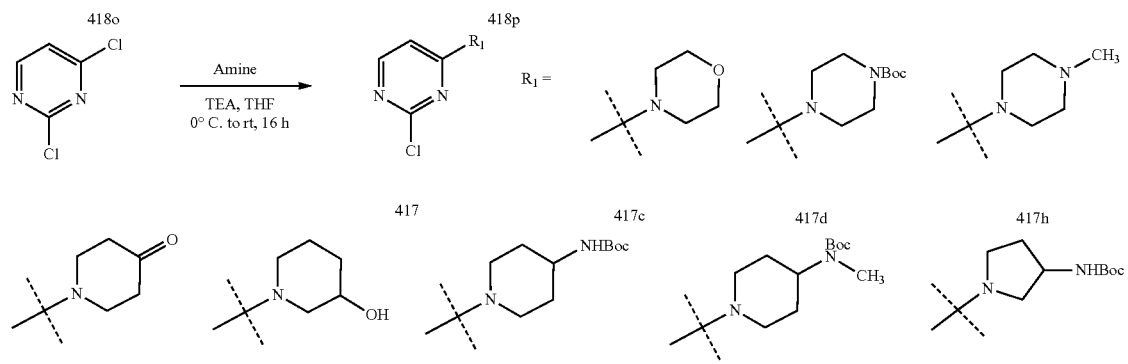

Preparation of 2-(4-(2-(5-chloro-2,4-dimethoxyphenyl)imidazo[1,2-a]pyridin-7-yl)piperazin-1-yl)-N-methylpyrimidin-4-amine 413a (Example 364)

A solution of 2-(5-chloro-2,4-dimethoxyphenyl)-7-(piperazin-1-yl)imidazo[1,2-a]pyridine 301 (200 mg, 0.53 mmol) and N,N-diisopropylethylamine (0.4 mL, 2.29 mmol) in DMF (5 mL) was charged with 2-chloro-N-methylpyrimidin-4-amine (155 mg, 1.07 mmol). The reaction mixture was stirred at 100° C. for 16 h. The reaction mixture was cooled to room temperature, suspended in water and stirred for 1 h. The precipitate was collected by filtration; the solid obtained was washed with water, dried under reduced pressure and purified by combi-flash companion (silica gel, CH$_3$OH/CH$_2$Cl$_2$). The product was further triturated with methanol and filtered. The solids were washed with hexanes and dried to provide 2-(4-(2-(5-chloro-2,4-dimethoxyphenyl)imidazo[1,2-a]pyridin-7-yl)piperazin-1-yl)-N-methylpyrimidin-4-amine 418a (20 mg, 8%) as light brown solid.

$^1$H NMR (300 MHz, DMSO-d$_6$): δ 8.34 (d, J=7.5 Hz, 1H), 8.15 (s, 1H), 8.04 (s, 1H), 7.75 (br s, 1H), 6.97 (br s, 1H), 6.89 (s, 1H), 6.87 (s, 1H), 6.71 (s, 1H), 5.78 (d, J=5.7 Hz, 1H), 4.01 (s, 3H), 3.93 (s, 3H), 3.83 (br s, 4H), 3.33 (br s, 4H), 2.78 (d, J=4.2 Hz, 3H); HPLC (Method 1) 92.8% (AUC), t$_R$=11.85 min.; ESI+APCI MS m/z 480 [M+H]$^+$.

Preparation of 2-(4-(2-(5-chloro-2,4-dimethoxyphenyl)imidazo[1,2-a]pyridin-7-yl)piperazin-1-yl)-N,N-dimethylpyrimidin-4-amine 418b (Example 356)

Compound 2-(4-(2-(5-chloro-2,4-dimethoxyphenyl)imidazo[1,2-a]pyridin-7-yl)piperazin-1-yl)-N,N-dimethylpyrimidin-4-amine 418b was prepared in the same manner as 2-(4-(2-(5-chloro-2,4-dimethoxyphenyl)imidazo[1,2-a]pyridin-7-yl)piperazin-1-yl)-N-methylpyrimidin-4-amine 418a, and was obtained as a brown solid (18% yield).

$^1$H NMR (300 MHz, DMSO-d$_6$): δ 8.33 (d, J=7.5 Hz, 1H), 8.17 (s, 1H), 8.04 (s, 1H), 7.87 (d, J=6.0 Hz, 1H), 6.86 (s, 1H), 6.83 (s, 1H), 6.71 (s, 1H), 5.98 (d, J=6.0 Hz, 1H), 4.01 (s, 3H), 3.93 (s, 3H), 3.83 (br s, 4H), 3.26 (br s, 4H), 3.01 (s, 6H); HPLC (Method 1) 97.8% (AUC), t$_R$=12.10 min.; ESI+APCI MS m/z 494 [M+H]$^+$.

Preparation of 4-(2-(4-(2-(5-chloro-2,4-dimethoxyphenyl)imidazo[1,2-a]pyridin-7-yl)piperazin-1-yl)pyrimidin-4-yl)morpholine 418c (Example 363)

A solution of 2,4-dichloropyrimidine (1.00 g, 6.71 mmol) and morpholine (0.59 mL, 6.81 mmol) in THF (25 mL) was charged with triethylamine (1.4 mL, 10.0 mmol) at 0° C. The reaction mixture was stirred at ambient temperature for 3 h. The reaction mixture was evaporated to dryness, the residue was taken up in CH$_2$Cl$_2$, and the organic layer was washed with water followed by brine; dried over sodium sulphate, filtered and concentrated. The residue was purified by combi-flash companion (silica gel, CH$_3$OH/CH$_2$Cl$_2$) to provide 4-(2-chloropyrimidin-4-yl)morpholine 417c (1.0 g, 70%) as a white solid.

$^1$H NMR (300 MHz, CDCl$_3$): δ 8.17 (d, J=5.1 Hz, 1H), 6.53 (d, J=5.1 Hz, 1H), 3.81 (t, J=4.5 Hz, 4H), 3.75 (t, J=4.5 Hz, 4H); ESI+APCI MS m/z 200 [M+H]$^+$.

A solution of 2-(5-chloro-2,4-dimethoxyphenyl)-7-(piperazin-1-yl)imidazo[1,2-a]pyridine 301 (250 mg, 0.67 mmol) and N,N-diisopropylethylamine (0.5 mL, 2.87 mmol) in DMF (7.5 mL) was charged with 4-(2-chloropyrimidin-4-yl)morpholine 417c (238 mg, 1.34 mmol). The reaction mixture was stirred at 100° C. for 16 h. The reaction mixture was cooled to room temperature, suspended in water and stirred for 1 h. The precipitate was collected by filtration: the solid obtained was washed with water, dried under reduced pressure and purified by combi-flash companion (silica gel, CH$_3$OH/CH$_2$Cl$_2$). The product obtained was further triturated with methanol and filtered. The solids were washed with hexanes and dried to provide 4-(2-(4-(2-(5-chloro-2,4-dimethoxyphenyl)imidazo[1,2-a]pyridin-7-yl)piperazin-1-yl)pyrimidin-4-yl)morpholine 418c (20 mg, 5%) as an off-white solid.

$^1$H NMR (300 MHz, DMSO-d$_6$): δ 8.34 (d, J=10.0 Hz, 1H), 8.16 (s, 1H), 8.03 (s, 1H), 7.94 (d, J=8.0 Hz, 1H), 6.87 (s, 1H), 6.85 (s, 1H), 6.71 (s, 1H), 6.12 (d, J=7.6 Hz, 1H), 4.01 (s, 3H), 3.93 (s, 3H), 3.82 (br s, 4H), 3.65 (br s, 4H), 3.53 (br s, 4H), 3.28 (br s, 4H); HPLC (Method 6) 97.4% (AUC), t$_R$=11.89 min.; ESI+APCI MS m/z 536 [M+H]$^+$.

Preparation of 2-(5-chloro-2,4-dimethoxyphenyl)-7-(4-(4-(piperazin-1-yl)pyrimidin-2-yl)piperazin-1-yl)imidazo[1,2-a]pyridine dihydrochloride 418e (Example 359)

A solution of 2,4-dichloropyrimidine (500 mg, 3.35 mmol) and tert-butyl piperazine-1-carboxylate (685 mg, 3.67 mmol) in DMF (5 mL) was charged with triethylamine (0.7 mL, 5.02 mmol). The reaction mixture was stirred at ambient temperature for 16 h. The reaction suspended in water, the solids formed were collected by filtration, washed with water, dried under reduced pressure. The crude material was purified by combi-flash companion (silica gel, CH$_3$OH/CH$_2$Cl$_2$) to provide tert-butyl 4-(2-chloropyrimidin-4-yl)piperazine-1-carboxylate 417d (510 mg, 51%) as a white solid.

$^1$H NMR (400 MHz, CDCl$_3$): δ 8.06 (d, J=6.0 Hz, 1H), 6.40 (d, J=6.0 Hz, 1H), 3.65 (br s, 4H), 3.52 (br s, 4H), 1.49 (s, 9H); ESI+APCI MS m/z 299 [M+H]$^+$.

A solution of 2-(5-chloro-2,4-dimethoxyphenyl)-7-(piperazin-1-yl)imidazo[1,2-a]pyridine 301 (150 mg, 0.40 mmol) and N,N-diisopropylethylamine (0.3 mL, 1.72 mmol) in DMF (3 mL) was charged with tert-butyl 4-(2-chloropyrimidin-4-yl)piperazine-1-carboxylate 417d (243 mg, 0.81 mmol). The reaction mixture was stirred at 100° C. for 16 h. The reaction mixture was cooled to room temperature, suspended in water and stirred for 1 h. The precipitate was collected by filtration, washed with water, dried under reduced pressure. The solid obtained was purified by combi-flash companion (silica gel, CH$_3$OH/CH$_2$Cl$_2$) to provide tert-butyl 4-(2-(4-(2-(5-chloro-2,4-dimethoxyphenyl)imidazo[1,2-a]pyridin-7-yl)piperazin-1-yl)pyrimidin-4-yl)piperazine-1-carboxylate 418d (70 mg, 39%) as an off-white solid.

$^1$H NMR (400 MHz, DMSO-d$_6$): δ 8.34 (d, J=7.6 Hz, 1H), 8.17 (s, 1H), 8.03 (s, 1H), 7.93 (d, J=6.0 Hz, 1H), 6.87 (s, 1H), 6.85 (s, 1H), 6.71 (s, 1H), 6.12 (d, J=6.0 Hz, 1H), 4.01 (s, 3H), 3.93 (s, 3H), 3.82 (br s, 4H), 3.56 (br s, 4H), 3.40 (br s, 4H), 3.27 (br s, 4H), 1.42 (s, 9H); ESI+APCI MS m/z 635 [M+H]$^+$.

A solution of tert-butyl 4-(2-(4-(2-(5-chloro-2,4-dimethoxyphenyl)imidazo[1,2-a]pyridin-7-yl)piperazin-1-yl)pyrimidin-4-yl)piperazine-1-carboxylate 418d (90 mg, 0.14 mmol) in 2,2,2-trifluoroethanol (3 mL) was charged with trimethylsilyl chloride (0.2 mL) at 0° C. The reaction mixture was stirred at ambient temperature for 3 h. The reaction mixture was evaporated to dryness to provide 2-(5-chloro-2,4-dimethoxyphenyl)-7-(4-(4-(piperazin-1-yl)pyrimidin-2-yl)piperazin-1-yl)imidazo[1,2-a]pyridine dihydrochloride 418e (80 mg, 93%) as an off-white solid.

$^1$H NMR (400 MHz, DMSO-d$_6$): δ 13.97 (br s, 1H), 9.55 (br s, 2H), 8.60 (d, J=10.0 Hz, 1H), 8.30 (s, 1H), 8.10 (s, 1H), 8.01 (d, J=9.2 Hz, 1H), 7.35 (dd, J=2.8 Hz, J=10.4 Hz, 1H), 6.98 (s, 1H), 6.80 (d, J=2.0 Hz, 1H), 6.59 (s, 1H), 4.06 (s, 3H), 3.99 (br s, 11H), 3.71 (br s, 4H), 3.21 (br s, 4H); HPLC (Method 1) 91.7% (AUC), t$_R$=10.95 min.; ESI+APCI MS m/z 535 [M+H]$^+$.

Preparation of 1-(4-(2-(4-(2-(5-chloro-2,4-dimethoxyphenyl)imidazo[1,2-a]pyridin-7-yl)piperazin-1-yl)pyrimidin-4-yl)piperazin-1-yl)ethanone 2,2,2-trifluoroacetate 418f (Example 373)

A solution of 2-(5-chloro-2,4-dimethoxyphenyl)-7-(4-(4-(piperazin-1-yl)pyrimidin-2-yl)piperazin-1-yl)imidazo[1,2-a]pyridine dihydrochloride 418e (65 mg, 0.10 mmol) and triethyl amine (0.1 mL, 0.71 mmol) in CH$_2$Cl$_2$ (2 mL) was charged with acetic anhydride (0.02 mL, 0.21 mmol). The reaction mixture was stirred at ambient temperature for 16 h. The reaction mixture was diluted with water and the aqueous layer was extracted with CH$_2$Cl$_2$. The organic layers were combined, washed with brine, dried over sodium sulphate, filtered and concentrated. The crude product was purified by combi-flash companion (silica gel, CH$_3$OH/CH$_2$Cl$_2$). The product was further purified by mass triggered preparative HPLC to provide 1-(4-(2-(4-(2-(5-chloro-2,4-dimethoxyphenyl)imidazo[1,2-a]pyridin-7-yl)piperazin-1-yl)pyrimidin-4-yl)piperazin-1-yl)ethanone 2,2,2-trifluoroacetate 418f (15 mg, 20%) as an off-white solid.

$^1$H NMR (400 MHz, DMSO-d$_6$): δ 8.58 (d, J=7.6 Hz, 1H), 8.28 (s, 1H), 7.97 (d, J=6.8 Hz, 1H), 7.93 (s, 1H), 7.33 (dd, J=2.4, 7.6 Hz, 1H), 6.99 (s, 1H), 6.73 (d, J=2.4 Hz, 1H), 6.47 (br s, 1H), 4.05 (s, 3H), 3.99 (s, 3H), 3.90 (br s, 4H), 3.70 (br s, 4H), 3.54 (br s, 8H), 2.06 (s, 3H); HPLC (Method 1) >99% (AUC), t$_R$=11.71 min.; ESI+APCI MS m/z 577 [M+H]$^+$.

Preparation of 1-(4-(2-(4-(2-(5-chloro-2,4-dimethoxyphenyl)imidazo[1,2-a]pyridin-7-yl)piperazin-1-yl)pyrimidin-4-yl)piperazin-1-yl-2-phenylethanone dihydrochloride 418k (Example 382)

A solution of 2-(5-chloro-2,4-dimethoxyphenyl)-7-(4-(4-(piperazin-1-yl)pyrimidin-2-yl)piperazin-1-yl)imidazo[1,2-a]pyridine dihydrochloride 418e (100 mg, 0.16 mmol) and triethylamine (0.16 mL, 1.14 mmol) in CH$_2$Cl$_2$ (2 mL) was charged with 2-phenylacetyl chloride (0.05 mL, 0.37 mmol). The reaction mixture was stirred at ambient temperature for 16 h. The reaction mixture was diluted with CH$_2$Cl$_2$ and washed with saturated sodium bicarbonate solution. The organic layers were combined, washed with brine, dried over sodium sulphate, filtered and concentrated. The crude product was purified by combi-flash companion (silica gel, CH$_3$OH/CH$_2$Cl$_2$). The product obtained was further triturated with methanol and washed with hexanes to provide 1-(4-(2-(4-(2-(5-chloro-2,4-dimethoxyphenyl)imidazo[1,2-a]pyridin-7-yl)piperazin-1-yl)pyrimidin-4-yl)piperazin-1-yl)-2-phenylethanone, which was dissolved in 2,2,2-trifluoroethanol (3 mL), charged with trimethylsilyl chloride (0.2 mL) at 0° C., and stirred for 10 min. The reaction mixture was evaporated to dryness to provide 1-(4-(2-(4-(2-(5-chloro-2,4-dimethoxyphenyl)imidazo[1,2-a]pyridin-7-yl)piperazin-1-yl)pyrimidin-4-yl)piperazin-1-yl)-2-phenylethanone dihydrochloride 418g (28 mg, 80%) as an off-white solid.

$^1$H NMR (400 MHz, DMSO-d$_6$): δ 13.8 (br s, 1H), 12.9 (br s, 1H), 8.59 (d, J=7.6 Hz, 1H), 8.29 (s, 1H), 8.06 (s, 1H), 7.93 (d, J=7.2 Hz, 1H), 7.34-7.30 (m, 3H), 7.25-7.22 (m, 3H), 7.33 (dd, J=2.4 Hz, J=7.6 Hz, 1H), 6.99 (s, 1H), 6.76 (d, J=1.6 Hz, 1H), 6.56 (br s, 1H), 4.06 (s, 3H), 3.99 (s, 3H), 3.95 (br s, 4H), 3.79 (s, 2H), 3.72 (br s, 8H), 3.63 (br s, 4H); HPLC (Method 6) 95.0% (AUC), t$_R$=11.43 min.; ESI+APCI MS m/z 653 [M+H]$^+$.

Preparation of 2-(5-chloro-2,4-dimethoxyphenyl)-7-(4-(4-(4-methylpiperazin-1-yl)pyrimidin-2-yl)piperazin-1-yl)imidazo[1,2-a]pyridine 418h (Example 370)

A solution of 2,4-dichloropyrimidine (1.0 g, 6.71 mmol) and 1-methylpiperazine (0.75 mL, 6.76 mmol) in THF (25 mL) was charged with triethylamine (1.4 mL, 10.2 mmol) at 0° C. The reaction mixture was stirred at ambient temperature for 16 h. The reaction mixture was evaporated to dryness, the residue was taken up in CH$_2$Cl$_2$; the organic layer was washed with water followed by brine; dried over sodium sulphate, filtered and concentrated. The crude material obtained was purified by combi-flash companion (silica gel, CH$_3$OH/CH$_2$Cl$_2$) to provide 2-chloro-4-(4-methylpiperazin-1-yl)pyrimidine 417h (830 mg, 53%) as a white solid.

$^1$H NMR (300 MHz, CDCl$_3$): δ 8.02 (d, J=6.3 Hz, 1H), 6.40 (d, J=6.0 Hz, 1H), 3.67 (br s, 4H), 2.47 (br s, 4H), 2.34 (s, 3H); ESI+APCI MS m/z 213 [M+H]$^+$.

A solution of 2-(5-chloro-2,4-dimethoxyphenyl)-7-(piperazin-1-yl)imidazo[1,2-a]pyridine 301 (150 mg, 0.40 mmol) and N,N-diisopropylethylamine (0.3 mL, 1.72 mmol) in DMF (5 mL) was charged with 2-chloro-4-(4-methylpiperazin-1-yl)pyrimidine 417h (171 mg, 0.80 mmol). The reaction mixture was stirred at 100° C. for 16 h. The reaction mixture was cooled to room temperature, suspended in water and stirred for 1 h. The precipitate was collected by filtration: the solid obtained was washed with water, dried under reduced pressure and purified by combi-flash companion (silica gel. CH$_3$OH/CH$_2$Cl$_2$).

The product was further triturated with CH$_2$Cl$_2$/hexanes and dried to provide 2-(5-chloro-2,4-dimethoxyphenyl)-7-(4-(4-(4-methylpiperazin-1-yl)pyrimidin-2-yl)piperazin-1-yl)imidazo[1,2-a]pyridine 418h (30 mg, 12%) as an off-white solid.

$^1$H NMR (400 MHz, DMSO-d$_6$): δ 8.33 (d, J=7.6 Hz, 1H), 8.17 (s, 1H), 8.03 (s, 1H), 7.91 (d, J=6.0 Hz, 1H), 6.87 (s, 1H), 6.85 (dd, J=2.4, 7.6 Hz, 1H), 6.70 (d, J=2.0 Hz, 1H), 6.12 (d, J=6.0 Hz, 1H), 4.01 (s, 3H), 3.93 (s, 3H), 3.81 (br s, 4H), 3.55 (br s, 4H), 3.27 (br s, 4H), 2.38 (br s, 4H), 2.23 (s, 3H); HPLC (Method 1) 97.0% (AUC), t$_R$=10.91 min.; ESI+APCI MS m/z 549 [M+H]$^+$.

Preparation of 1-(2-(4-(2-(5-chloro-2,4-dimethoxyphenyl)imidazo[1,2-a]pyridin-7-yl)piperazin-1-yl)pyrimidin-4-yl)piperidin-4-one 418i (Example 366)

A solution of 2,4-dichloropyrimidine (1.0 g, 6.71 mmol) and piperidin-4-one hydrochloride (910 mg, 6.71 mmol) in THF (25 mL) was charged with triethylamine (2.8 mL, 10.2 mmol) at 0° C. The reaction mixture was stirred at ambient temperature for 16 h. The reaction mixture was evaporated to dryness. The residue was taken up in CH$_2$Cl$_2$; the organic layer was washed with water followed by brine; dried over sodium sulphate, filtered and concentrated. The crude obtained was purified by combi-flash companion (silica gel, CH$_3$OH/CH$_2$Cl$_2$) to provide 1-(2-chloropyrimidin-4-yl)piperidin-4-one 2i (890 mg, 62%) as a white solid.

¹H NMR (400 MHz, CDCl₃): δ 8.13 (d, J=6.0 Hz, 1H), 6.49 (d, J=6.4 Hz, 1H), 3.98 (t, J=6.0 Hz, 4H), 2.59 (t, J=6.4 Hz, 4H); ESI+APCI MS m/z 212 [M+H]⁺.

A solution of 2-(5-chloro-2,4-dimethoxyphenyl)-7-(piperazin-1-yl)imidazo[1,2-a]pyridine 301 (100 mg, 0.26 mmol) and N,N-diisopropylethylamine (0.2 mL, 1.14 mmol) in DMF (5 mL) was charged with 1-(2-chloropyrimidin-4-yl)piperidin-4-one 417i (115 mg, 0.54 mmol). The reaction mixture was stirred at 100° C. for 16 h. The reaction mixture was cooled to room temperature, suspended in water and stirred for 1 h. The precipitate was collected by filtration: the solid obtained was washed with water, dried under reduced pressure and purified by combi-flash companion (silica gel, CH₃OH/CH₂Cl₂). The product obtained was further triturated with methanol, washed with hexanes and dried to provide 1-(2-(4-(2-(5-chloro-2,4-dimethoxyphenyl)imidazo[1,2-a]pyridin-7-yl)piperazin-1-yl)pyrimidin-4-yl)piperidin-4-one 418i (20 mg, 9%) as an off-white solid.

¹H NMR (400 MHz, DMSO-d₆): δ 8.33 (d, J=7.6 Hz, 1H), 8.17 (s, 1H), 8.03 (s, 1H), 7.97 (d, J=6.0 Hz, 1H), 6.87-6.84 (m, 2H), 6.71 (s, 1H), 6.24 (d, J=6.0 Hz, 1H), 4.01 (s, 3H), 3.93 (s, 3H), 3.89 (d, J=6.0 Hz, 4H), 3.84 (d, J=4.8 Hz, 4H), 3.28 (d, J=5.2 Hz, 4H), 2.43 (d, J=6.0 Hz, 4H); HPLC (Method 6) 90.2% (AUC), t$_R$=11.71 min.; ESI+APCI MS m/z 548 [M+H]⁺.

Preparation of 1-(2-(4-(2-(5-chloro-2,4-dimethoxyphenyl)imidazo[1,2-a]pyridin-7-yl)piperazin-1-yl)pyrimidin-4-yl)piperidin-3-ol 418i (Example 376)

A solution of 2,4-dichloropyrimidine (1.00 g, 6.71 mmol) and piperidin-3-ol (680 mg, 6.72 mmol) in THF (25 mL) was charged with triethylamine (1.4 mL, 10.0 mmol) at 0° C. The reaction mixture was stirred at ambient temperature for 16 h. The reaction mixture was evaporated to dryness, taken up in CH₂Cl₂ and the organic layer was washed with water followed by brine; dried over sodium sulphate, filtered and concentrated. The crude obtained was purified by combi-flash companion (silica gel, CH₃OH/CHCl₃) to provide 1-(2-chloropyrimidin-4-yl)piperidin-3-ol 417j (1.1 g, 69%) as a white solid.

¹H NMR (300 MHz, CDCl₃): δ 7.99 (d, J=6.3 Hz, 1H), 6.43 (d, J=6.3 Hz, 1H), 3.96-3.73 (m, 3H), 3.45-3.38 (m, 2H), 2.92 (d, J=4.8 Hz, 2H), 2.04-1.84 (m, 2H), 1.73-1.59 (m, 2H); ESI+APCI MS m/z 213 [M+H]⁺.

A solution of 2-(5-chloro-2,4-dimethoxyphenyl)-7-(piperazin-1-yl)imidazo[1,2-a]pyridine 301 (200 mg, 0.53 mmol) and N,N-diisopropylethylamine (0.4 mL, 2.29 mmol) in DMF (5 mL) was charged with 1-(2-chloropyrimidin-4-yl)piperidin-3-ol 417j (232 mg, 1.08 mmol). The reaction mixture was stirred at 90-100° C. for 16 h. The reaction mixture was cooled to room temperature, suspended in water and stirred for 1 h. The precipitate was collected by filtration; the solid obtained was washed with water, dried under reduced pressure and purified by combi-flash companion (silica gel, CH₃OH/CH₂Cl₂).

The product obtained was further triturated with CH₂Cl₂/hexanes and dried to provide 1-(2-(4-(2-(5-chloro-2,4-dimethoxyphenyl)imidazo[1,2-a]pyridin-7-yl)piperazin-1-yl)pyrimidin-4-yl)piperidin-3-ol 418j (40 mg, 11%) as a light brown solid.

¹H NMR (400 MHz, DMSO-d₆): δ 8.33 (d, J=7.6 Hz, 1H), 8.17 (s, 1H), 8.03 (s, 1H), 7.87 (d, J=6.0 Hz, 1H), 6.87-6.84 (m, 2H), 6.71 (d, J=2.0 Hz, 1H), 6.09 (d, J=6.0 Hz, 1H), 4.88 (d, J=4.4 Hz, 1H), 4.01 (s, 3H), 3.95-3.93 (m, 4H), 3.81 (t, J=4.8 Hz, 4H), 3.47-3.44 (m, 1H), 3.27 (t, J=4.8 Hz, 4H), 3.04-2.99 (m, 1H), 2.84-2.79 (m, 1H), 1.90-1.88 (m, 1H), 1.72-1.69 (m, 1H), 1.41-1.33 (m, 2H); HPLC (Method 1) 94.1% (AUC), t$_R$=11.71 min.; ESI+APCI MS m/z 550 [M+H]⁺.

Preparation of 1-(2-(4-(2-(5-chloro-2,4-dimethoxyphenyl)imidazo[1,2-a]pyridin-7-yl)piperazin-1-yl)pyrimidin-4-yl)piperidin-4-amine 418l (Example 437)

A solution of 2,4-dichloropyrimidine (2.0 g, 13.4 mmol) and tert-butyl piperidin-4-ylcarbamate (2.7 g, 13.9 mmol) in THF (50 mL) was charged with triethyl amine (2.8 mL, 20.1 mmol) at 0° C. The reaction mixture was stirred at ambient temperature for 16 h.

The reaction mixture was concentrated, and the residue was taken up in ethyl acetate; the organic layer was washed with NH₄Cl solution followed by brine; dried over sodium sulphate, filtered and concentrated. The crude obtained was purified by combi-flash companion (silica gel, CH₃OH/CH₂Cl₂) to provide tert-butyl (1-(2-chloropyrimidin-4-yl)piperidin-4-yl)carbamate 417k (2.4 g, 73%).

¹H NMR (400 MHz, CDCl₃): δ 8.01 (d, J=6.0 Hz, 1H), 6.41 (d, J=6.0 Hz, 1H), 4.63 (d, J=6.4 Hz, 1H), 4.29 (br s, 2H), 3.74 (br s, 1H), 3.06 (t, J=12.0 Hz, 2H), 2.05 (br s, 2H), 1.51 (s, 9H), 1.40-1.33 (m, 2H); ESI+APCI MS m/z 313 [M+H]⁺.

A solution of 2-(5-chloro-2,4-dimethoxyphenyl)-7-(piperazin-1-yl)imidazo[1,2-a]pyridine 301 (250 mg, 0.67 mmol) and N,N-diisopropylethylamine (0.5 mL, 2.87 mmol) in DMF (7.5 mL) was charged with tert-butyl (1-(2-chloropyrimidin-4-yl)piperidin-4-yl)carbamate 417k (315 mg, 1.01 mmol). The reaction mixture was stirred at 100° C. for 16 h. The reaction mixture was cooled to room temperature, suspended in water and stirred for 1 h. The precipitate was collected by filtration, the solid obtained was washed with water, dried under reduced pressure and purified by combi-flash companion (silica gel, CH₃OH/CH₂Cl₂) to provide tert-butyl (1-(2-(4-(2-(5-chloro-2,4-dimethoxyphenyl)imidazo[1,2-a]pyridin-7-yl)piperazin-1-yl)pyrimidin-4-yl)piperidin-4-yl)carbamate 418k (260 mg, crude). ESI+APCI MS m/z 649 [M+H]⁺.

A solution of tert-butyl (1-(2-(4-(2-(5-chloro-2,4-dimethoxyphenyl)imidazo[1,2-a]pyridin-7-yl)piperazin-1-yl)pyrimidin-4-yl)piperidin-4-yl)carbamate 418k (110 mg) in CH₂Cl₂ (2.5 mL) was charged with 4M HCl in 1,4-dioxane (0.5 mL) at 0° C. The reaction mixture was stirred at ambient temperature for 16 h. The reaction mixture was evaporated to dryness and taken up in water. The solution was basified with saturated sodium bicarbonate solution, the solid formed was filtered, washed with water and dried to provide 1-(2-(4-(2-(5-chloro-2,4-dimethoxyphenyl)imidazo[1,2-a]pyridin-7-yl)piperazin-1-yl)pyrimidin-4-yl)piperidin-4-amine 418l (60 mg, 64%) as a brown solid.

¹H NMR (400 MHz, DMSO-d₆): δ 8.39 (dd, J=3.6, 7.6 Hz, 1H), 8.24 (s, 1H), 8.09 (d, J=2.4 Hz, 1H), 7.93 (dd, J=4.0, 8.0 Hz, 1H), 6.93-6.90 (m, 2H), 6.77 (s, 1H), 6.19-6.17 (m, 1H), 4.25 (br s, 2H), 4.07 (s, 3H), 3.99 (s, 3H), 3.87 (br s, 4H), 3.33 (br s, 4H), 3.03-2.98 (m, 2H), 2.87 (br s, 1H), 1.81 (br s, 2H), 1.29-1.18 (m, 2H); HPLC (Method 1) 93.7% (AUC), t$_R$=10.57 min.; ESI+APCI MS m/z 549 [M+H]⁺.

Preparation of 1-(2-(4-(2-(5-chloro-2,4-dimethoxyphenyl)imidazo[1,2-a]pyridin-7-yl)piperazin-1-yl)pyrimidin-4-yl)-N-methylpiperidin-4-amine 418n (Example 426)

A solution of 2,4-dichloropyrimidine (2.0 g, 13.4 mmol) and tert-butyl methyl(piperidin-4-yl)carbamate (2.7 g, 13.5 mmol) in THF (50 mL) was charged with triethyl amine (2.8 mL, 20.1 mmol) at 0° C. The reaction mixture was stirred at ambient temperature for 16 h. The reaction mixture was concentrated and the residue was taken up in ethylacetate and the organic layer was washed with $NH_4Cl$ solution followed by brine; dried over sodium sulphate, filtered and concentrated. The crude material obtained was purified by combi-flash companion (silica gel, $CH_3OH/CH_2Cl_2$) to provide tert-butyl (1-(2-chloropyrimidin-4-yl)piperidin-4-yl)(methyl)carbamate 417m (2.4 g, 73%).

$^1$H NMR (400 MHz, $CDCl_3$): δ 7.93 (d, J=5.6 Hz, 1H), 6.34 (d, J=6.0 Hz, 1H), 4.41 (br s, 1H), 4.24 (br s, 1H), 2.87 (t, J=11.2 Hz, 2H), 2.64 (s, 3H), 1.71 (br s, 2H), 1.58 (br s, 3H), 1.41 (s, 9H); ESI+APCI MS m/z 327 [M+H]$^+$.

A solution of 2-(5-chloro-2,4-dimethoxyphenyl)-7-(piperazin-1-yl)imidazo[1,2-a]pyridine 301 (250 mg, 0.67 mmol) and N,N-diisopropylethylamine (0.5 mL, 2.87 mmol) in DMF (10 mL) was charged with tert-butyl (1-(2-chloropyrimidin-4-yl)piperidin-4-yl)(methyl)carbamate 417m (330 mg, 1.01 mmol). The reaction mixture was stirred at 100° C. for 16 h. The reaction mixture was cooled to room temperature, suspended in water and stirred for 1 h. The precipitate was collected by filtration, the solid obtained was washed with water, dried under reduced pressure and purified by combi-flash companion (silica gel, $CH_3OH/CH_2Cl_2$) to provide tert-butyl (1-(2-(4-(2-(5-chloro-2,4-dimethoxyphenyl)imidazo[1,2-a]pyridin-7-yl)piperazin-1-yl)pyrimidin-4-yl)piperidin-4-yl)(methyl)carbamate 418m (155 mg, 17%).

ESI+APCI MS m/z 663 [M+H]$^+$.

A solution of tert-butyl (1-(2-(4-(2-(5-chloro-2,4-dimethoxyphenyl)imidazo[1,2-a]pyridin-7-yl)piperazin-1-yl)pyrimidin-4-yl)piperidin-4-yl)(methyl)carbamate 418m (155 mg) in 2,2,2-trifluoroethanol (2.5 mL) was charged with trimethylsilyl chloride (0.2 mL) at 0° C. The reaction mixture was stirred at ambient temperature for 2 h. The reaction mixture was evaporated to dryness and taken up in water. The solution obtained was basified with saturated sodium bicarbonate solution and extracted with $CH_2Cl_2$. The combined organic layers were washed with brine, dried over sodium sulphate, filtered and concentrated. The crude product was purified by combi-flash companion (silica gel, $CH_3OH/CH_2Cl_2$). The product obtained was triturated with $CH_2Cl_2$ and n-pentane to provide 1-(2-(4-(2-(5-chloro-2,4-dimethoxyphenyl)imidazo[1,2-a]pyridin-7-yl)piperazin-1-yl)pyrimidin-4-yl)-N-methylpiperidin-4-amine 418n (80 mg, 60%) as a light brown solid.

$^1$H NMR (400 MHz, DMSO-$d_6$): δ 8.33 (d, J=7.2 Hz, 1H), 8.18 (s, 1H), 8.03 (s, 1H), 7.88 (d, J=6.0 Hz, 1H), 6.87 (s, 1H), 6.84 (d, J=8.4 Hz, 1H), 6.71 (s, 1H), 6.12 (d, J=6.0 Hz, 1H), 4.17 (br s, 2H), 4.01 (s, 3H), 3.93 (s, 3H), 3.81 (br s, 4H), 3.27 (br s, 4H), 2.98 (t, J=11.6 Hz, 2H), 2.54-2.58 (m, 2H), 2.29 (s, 3H), 1.83 (br s, 2H), 1.19-1.14 (m, 2H); HPLC (Method 6) 95.0% (AUC), $t_R$=11.43 min.; ESI+APCI MS m/z 563 [M+H]$^+$.

Preparation of 1-(2-(4-(2-(5-chloro-2,4-dimethoxyphenyl)imidazo[1,2-a]pyridin-7-yl)piperazin-1-yl)pyrimidin-4-yl)pyrrolidin-3-amine 418o (Example 405)

A solution of 2,4-dichloropyrimidine (1.0 g, 6.71 mmol) and tert-butyl pyrrolidin-3-ylcarbamate (1.35 g, 6.74 mmol) in THF (25 mL) was charged with triethylamine (1.4 mL, 10.0 mmol) at 0° C. The reaction mixture was stirred at ambient temperature for 16 h. The reaction mixture was evaporated to dryness, and the residue was taken up in $CH_2Cl_2$; the organic layer was washed with water followed by brine; dried over sodium sulphate, filtered and concentrated. The crude material obtained was purified by combi-flash companion (silica gel, $CH_3OH/CH_2Cl_2$) to provide tert-butyl (1-(2-chloropyrimidin-4-yl)pyrrolidin-3-yl)carbamate 417o (550 mg, 69%).

$^1$H NMR (300 MHz, $CDCl_3$): δ 8.01 (d, J=6.0 Hz, 1H), 6.20 (d, J=6.0 Hz, 1H), 4.86 (br s, 1H), 3.85 (br s, 1H), 3.66-3.12 (m, 3H), 2.18 (br s, 2H), 1.58-1.35 (m, 10H); ESI+APCI MS m/z 313 [M+H]$^+$.

A solution of 2-(5-chloro-2,4-dimethoxyphenyl)-7-(piperazin-1-yl)imidazo[1,2-a]pyridine 301 (200 mg, 0.53 mmol) and N,N-diisopropylethylamine (0.4 mL, 2.29 mmol) in DMF (10 mL) was charged with tert-butyl (1-(2-chloropyrimidin-4-yl)pyrrolidin-3-yl)carbamate 417o (240 mg, 0.8 mmol). The reaction mixture was stirred at 100° C. for 16 h. The reaction mixture was cooled to room temperature, suspended in water and stirred for 1 h. The precipitate was collected by filtration, the solid obtained was washed with water, dried under reduced pressure and purified by combi-flash companion (silica gel, $CH_3OH/CH_2Cl_2$). The product was further triturated with $CH_2Cl_2$/hexanes and dried to tert-butyl (1-(2-(4-(2-(5-chloro-2,4-dimethoxyphenyl)imidazo[1,2-a]pyridin-7-yl)piperazin-1-yl)pyrimidin-4-yl)pyrrolidin-3-yl)carbamate 418o (140 mg, crude). ESI+APCI MS m/z: 635 [M+H]$^+$.

A solution of tert-butyl (1-(2-(4-(2-(5-chloro-2,4-dimethoxyphenyl)imidazo[1,2-a]pyridin-7-yl)piperazin-1-yl)pyrimidin-4-yl)pyrrolidin-3-yl)carbamate 418o (140.0 mg) in 2,2,2-trifluoroethanol (5 mL) was charged with trimethylsilyl chloride (0.2 mL) at 0° C. The reaction mixture was stirred at 0° C. for 30 min. The reaction mixture was evaporated to dryness and purified by mass triggered preparative HPLC. The isolated product was taken up in water, basified with saturated sodium bicarbonate solution and extracted with $CH_2Cl_2$. The combined organic layers were washed with brine; dried over sodium sulphate, filtered and concentrated. The residue was triturated with $CH_2Cl_2$/hexanes and dried to provide 1-(2-(4-(2-(5-chloro-2,4-dimethoxyphenyl)imidazo[1,2-a]pyridin-7-yl)piperazin-1-yl)pyrimidin-4-yl)pyrrolidin-3-amine 418p (15 mg, 13%) as an off-white solid.

$^1$H NMR (400 MHz, DMSO-$d_6$): δ 8.33 (d, J=7.6 Hz, 1H), 8.17 (s, 1H), 8.03 (s, 1H), 7.87 (d, J=6.0 Hz, 1H), 6.86 (s, 1H), 6.84 (s, 1H), 6.71 (s, 1H), 5.79 (d, J=5.2 Hz, 1H), 4.01 (s, 3H), 3.93 (s, 3H), 3.83 (br s, 4H), 3.65-3.44 (m, 5H), 3.26 (br s, 4H), 2.07 (s, 1H), 1.74 (s, 1H); HPLC (Method 6) 96.1% (AUC), $t_R$=11.45 min.; ESI+APCI MS m/z 535 [M+H]$^+$.

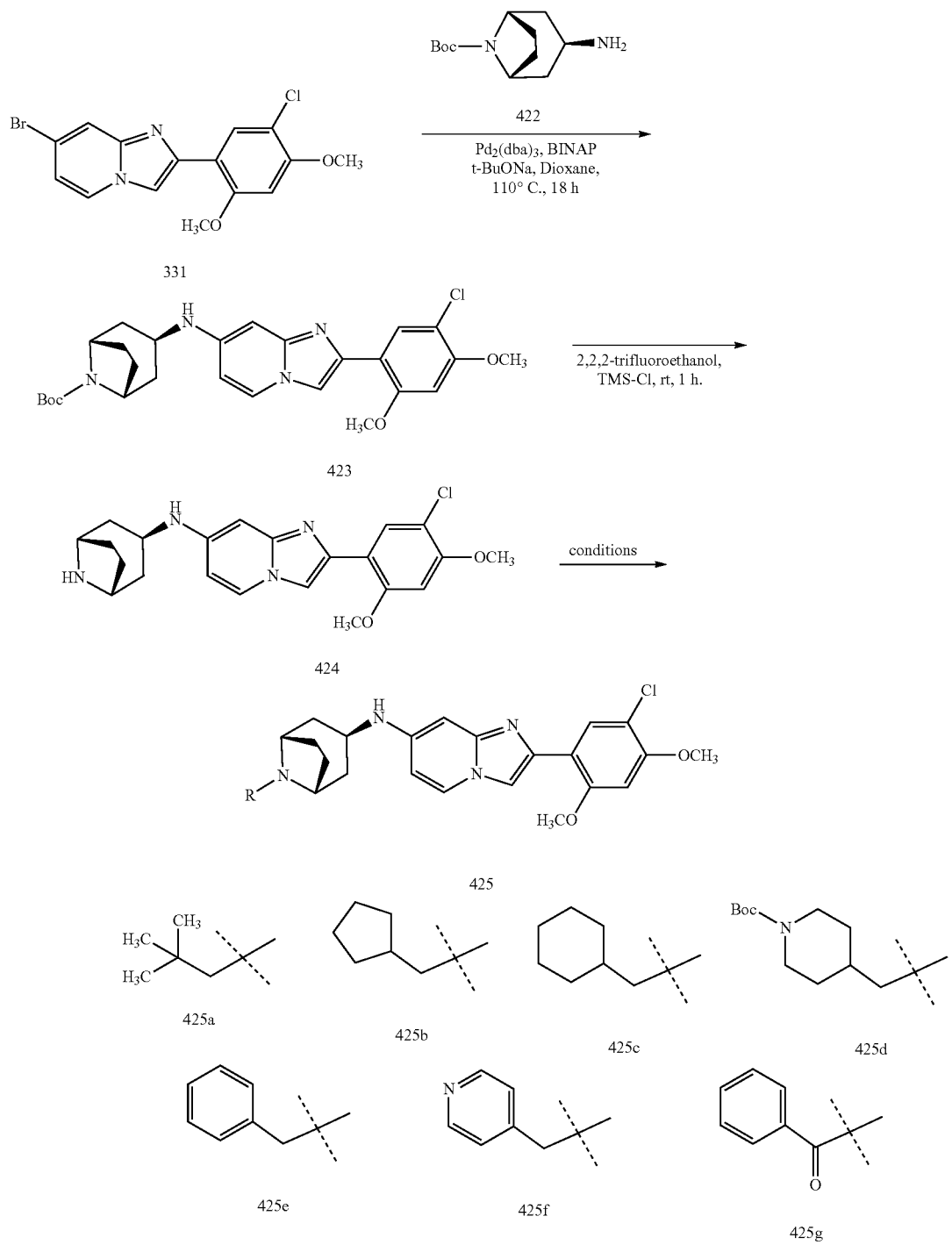

Preparation of (1R,3r,5S)-tert-butyl 3-((2-(5-chloro-2,4-dimethoxyphenyl)imidazo[1,2-a]pyridin-7-yl)amino)-8-azabicyclo[3.2.1]octane-8-carboxylatediamine 423 (Example 444)

A mixture of 7-bromo-2-(5-chloro-2,4-dimethoxyphenyl)imidazo[1,2-a]pyridine 331 (1.50 g, 4.08 mmol), (1R,3r,5S)-tert-butyl 3-amino-8-azabicyclo[3.2.1]octane-8-carboxylate 422 (1.39 g, 6.14 mmol), BINAP (255 mg, 0.41 mmol), and sodium tert-butoxide (1.18 g, 12.3 mmol) in dioxane (20 mL) was degassed with argon for 15 min. Tris(dibenzylideneacetone)dipalladium(0) (375 mg, 0.41 mmol) was added and the resulting mixture was further degassed with argon for another 5 min. The reaction mixture was heated at 100° C. for 18 h with stirring. The reaction mixture was cooled to room temperature, diluted with CH$_2$Cl$_2$ (500 mL) and filtered through a pad of celite. The filtrate was concentrated and the residue obtained was purified by silica gel chromatography (CH$_3$OH/CH$_2$Cl$_2$) to afford (1R,3r,5S)-tert-butyl 3-((2-(5-chloro-2,4-dimethoxyphenyl)imidazo[1,2-a]pyridin-7-yl)amino)-8-azabicyclo[3.2.1]octane-8-carboxylate 423 (1.40 g, 67%) as a green solid.

$^1$H NMR (300 MHz, DMSO-d$_6$): δ 8.14 (d, J=7.6 Hz, 2H), 7.89 (s, 1H), 6.85 (s, 1H), 6.18 (d, J=7.2 Hz, 1H), 6.07 (s, 1H), 4.06 (bs, 2H), 3.99 (s, 3H), 3.92 (s, 3H), 3.58 (bs, 1H), 2.18-2.07 (m, 4H), 1.86-1.75 (m, 4H), 1.43 (s, 9H); HPLC (Method 1) >99% (AUC), t$_R$=14.75 min.; ESI+APCI MS m/z 513 [M+H]$^+$.

Preparation of N-((1R,3r,5S)-8-azabicyclo[3.2.1]octan-3-yl)-2-(5-chloro-2,4-dimethoxyphenyl)imidazo[1,2-a]pyridin-7-amine 424

A suspension of (1R,3r,5S)-tert-butyl 3-((2-(5-chloro-2,4-dimethoxyphenyl)imidazo[1,2-a]pyridin-7-yl)amino)-8-azabicyclo[3.2.1]octane-8-carboxylate 423 (2.8 g, 5.4 mmol) in 2,2,2-trifluoroethanol (10 mL) was charged with TMS-Cl (3 mL) and the reaction mixture was stirred at room temperature for 1 h. The reaction mixture was evaporated to dryness and the residue was taken up in NaHCO$_3$ solution. The resulting suspension was stirred for 30 min at room temperature and then filtered. The solid isolated was washed with water and then dried to provide N-((1R,3r,5S)-8-azabicyclo[3.2.1]octan-3-yl)-2-(5-chloro-2,4-dimethoxyphenyl)imidazo[1,2-a]pyridin-7-amine 424 (2.0 g, 59%) as a light yellow solid.

$^1$H NMR (300 MHz, DMSO-d$_6$): δ 8.14 (t, J=3.6 Hz, 2H), 7.89 (s, 1H), 6.85 (s, 1H), 6.48 (dd, J=5.4 Hz, J=16.5 Hz, 1H), 6.18 (d, J=3.0 Hz, 1H), 6.08 (s, 1H), 4.06 (s, 3H), 3.99 (s, 3H), 3.61-3.55 (m, 3H), 2.27-2.1 (m, 4H), 1.84-1.79 (m, 4H); ESI+APCI MS m/z 413 [M+H]$^+$.

Preparation of 2-(5-chloro-2,4-dimethoxyphenyl)-N-((1R,3r,5S)-8-neopentyl-8-azabicyclo[3.2.1]octan-3-yl)imidazo[1,2-a]pyridin-7-amine 425a (Example 452)

A mixture of N-((1R,3r,5S)-8-azabicyclo[3.2.1]octan-3-yl)-2-(5-chloro-2,4-dimethoxyphenyl)imidazo[1,2-a]pyridin-7-amine 424 (100 mg, 0.24 mmol), pivalaldehyde (31 mg, 0.36 mmol) and AcOH (0.1 mL) in CH$_3$OH (4 mL) was stirred at room temperature for 1 h. Sodium cyano borohydride (23 mg, 0.36 mmol) was then added and the reaction mixture was stirred at room temperature for 16 h under nitrogen atmosphere. The reaction mixture was diluted with water and extracted with CH$_2$Cl$_2$ (2×10 mL). The combined organic layers were dried over sodium sulfate, filtered and concentrated under reduced pressure and the residue was purified by combi-flash companion (silica gel, CH$_3$OH/CH$_2$Cl$_2$) to afford 2-(5-chloro-2,4-dimethoxyphenyl)-N-((1R,3r,5S)-8-neopentyl-8-azabicyclo[3.2.1]octan-3-yl)imidazo[1,2-a]pyridin-7-amine 425a (6 mg, 5%) as a light-yellow solid.

$^1$H NMR (300 MHz, MeOD-d$_6$): δ 7.97 (d, J=7.2 Hz, 1H), 7.85 (s, 1H), 7.81 (s, 1H), 6.71 (s, 1H), 6.47 (d, J=7.2 Hz, 1H), 6.14 (s, 1H), 3.93 (s, 3H), 3.86 (s, 3H), 3.51 (t, J=6.9 Hz, 1H), 3.25 (bs, 2H), 2.21-1.73 (m, 10H), 0.88 (s, 9H); HPLC (Method 1) 92.99% (AUC), t$_R$=12.22 min.; ESI+APCI MS m/z 483 [M+H]$^+$.

Preparation of 2-(5-chloro-2,4-dimethoxyphenyl)-N-((1R,3r,5S)-8-(cyclopentylmethyl)-8-azabicyclo[3.2.1]octan-3-yl)imidazo[1,2-a]pyridin-7-amine 425b (Example 443)

A mixture of N-((1R,3r,5S)-8-azabicyclo[3.2.1]octan-3-yl)-2-(5-chloro-2,4-dimethoxyphenyl)imidazo[1,2-a]pyridin-7-amine 424 (150 mg, 0.36 mmol), cyclopentanecarbaldehyde (43 mg, 0.4 mmol) and AcOH (0.1 mL) in CH$_3$OH (4 mL) was stirred at room temperature for 1 h. Sodium cyano borohydride (34 mg, 0.54 mmol) was then added and the reaction mixture was stirred for 16 h at room temperature under nitrogen atmosphere. The reaction mixture was diluted with water and extracted with CH$_2$Cl$_2$ (2×10 mL). The combined organic layers were dried over sodium sulfate, filtered and concentrated under reduced pressure and the residue was purified by combi-flash companion (silica gel, CH$_3$OH/CH$_2$Cl$_2$) to afford 2-(5-chloro-2,4-dimethoxyphenyl)-N-((1R,3r,5S)-8-(cyclopentylmethyl)-8-azabicyclo[3.2.1]octan-3-yl)imidazo[1,2-a]pyridin-7-amine 425b (60 mg, 33%) as an off-white solid.

$^1$H NMR (300 MHz, DMSO-d$_6$): δ 8.12 (d, J=9.2 Hz, 2H), 7.87 (s, 1H), 6.85 (s, 1H), 6.45 (dd, J=2.0 Hz, J=7.2 Hz, 1H), 6.01 (bs, 2H), 3.99 (s, 3H), 3.92 (s, 3H), 3.48 (bs, 1H), 3.17 (bs, 2H), 2.22-1.87 (m, 9H), 1.83-1.69 (m, 4H), 1.58-1.49 (m, 4H), 1.26-1.14 (2H); HPLC (Method 1) 98.33% (AUC), t$_R$=12.41 min.; ESI+APCI MS m/z 495 [M+H]$^+$.

Preparation of 2-(5-chloro-2,4-dimethoxyphenyl)-N-((1R,3r,5S)-8-(cyclohexylmethyl)-8-azabicyclo[3.2.1]octan-3-yl)imidazo[1,2-a]pyridin-7-amine 425c (Example 434)

A mixture of N-((1R,3r,5S)-8-azabicyclo[3.2.1]octan-3-yl)-2-(5-chloro-2,4-dimethoxyphenyl)imidazo[1,2-a]pyridin-7-amine 424 (150 mg, 0.36 mmol), cyclohexanecarbaldehyde (60 mg, 0.54 mmol) and AcOH (0.1 mL) in CH$_3$OH (4 mL) was stirred at room temperature for 1 h. Sodium cyano borohydride (34 mg, 0.54 mmol) was then added and the reaction mixture was stirred for 16 h at room temperature under nitrogen atmosphere. The reaction mixture was diluted with water and extracted with CH$_2$Cl$_2$ (2×10 mL). The combined organic layers were dried over sodium sulfate, filtered and concentrated under reduced pressure and the residue was purified by combi-flash companion (silica gel, CH$_3$OH/CH$_2$Cl$_2$) to afford to afford 2-(5-chloro-2,4-dimethoxyphenyl)-N-((1R,3r,5S)-8-(cyclohexylmethyl)-8-azabicyclo[3.2.1]octan-3-yl)imidazo[1,2-a]pyridin-7-amine 425c (20 mg, 11%) as an off-white solid.

$^1$H NMR (300 MHz, DMSO-d$_6$): δ 8.12 (d, J=7.8 Hz, 2H), 7.87 (s, 1H), 6.85 (s, 1H), 6.45 (dd, J=12, 17.4 Hz, 1H), 6.07-6.01 (m, 2H), 3.99 (s, 3H), 3.92 (s, 3H), 3.48 (bs, 1H), 3.10 (bs, 2H), 2.10-1.99 (m, 4H), 1.91-1.57 (m, 11H), 1.44-1.37 (m, 1H), 1.27-1.11 (3H), 0.92-0.83 (m, 2H); HPLC (Method 1) 96.77% (AUC), r$_R$=12.49 min.; ESI+APCI MS m/z 509 [M+H]$^+$.

Preparation of tert-butyl 4-(((1R,3r,5)-3-((2-(5-chloro-2,4-dimethoxyphenyl)imidazo[1,2-a]pyridin-7-yl)amino)-8-azabicyclo[3.2.1]octan-8-yl)methyl)piperidine-1-carboxylate 425d (Example 447)

A mixture of N-((1R,3r,5S)-8-azabicyclo[3.2.1]octan-3-yl)-2-(5-chloro-2,4-dimethoxyphenyl)imidazo[1,2-a]pyridin-7-amine 424 (200 mg, 0.48 mmol), tert-butyl 4-formylpiperidine-1-carboxylate (155 mg, 0.73 mmol) and AcOH (0.1 mL) in CH$_3$OH (5 mL) was stirred at room temperature for 1 h. Sodium cyano borohydride (45 mg, 0.73 mmol) was then added and the reaction mixture was stirred at room temperature for 16 h under nitrogen atmosphere. The reaction mixture was diluted with water and extracted with CH$_2$Cl$_2$ (2×10 mL). The combined organic layers were dried over sodium sulfate, filtered and concentrated under reduced pressure and the residue was purified by combi-flash companion (silica gel, CH₃OH/CH₂Cl₂) to afford tert-butyl 4-(((1R,3r,5S)-3-((2-(5-chloro-2,4-dimethoxyphenyl)imidazo[1,2-a]pyridin-7-yl)amino)-8-azabicyclo[3.2.1]octan-8-yl)methyl)piperidine-1-carboxylate 425d (110 mg, 37.3%) as an off-white solid.

$^1$H NMR (400 MHz, MeOD-d₆): δ 7.95 (d, J=7.2 Hz, 1H), 7.90 (s, 1H), 7.80 (s, 1H), 6.69 (s, 1H), 6.41 (dd, J=2.0 Hz, J=7.2 Hz, 1H), 6.11 (d, J=1.6 Hz, 1H), 4.01-3.96 (m, 2H), 3.98 (s, 3H), 3.85 (s, 3H), 3.54 (t, J=6.4 Hz, 1H), 3.38 (t, J=1.6 Hz, 2H), 2.69-2.58 (m, 2H), 2.43-2.42 (m, 2H), 2.25-2.20 (m, 2H), 2.06-1.98 (m, m, 4H), 1.85-1.81 (m, 2H), 1.73-1.70 (m, 3H), 1.36 (s, 9H), 1.09-1.0 (m, 2H); HPLC (Method 1) 97.50% (AUC), $t_R$=12.73 min.; ESI+APCI MS m/z 610 [M+H]⁺.

Preparation of N-((1R,3r,5S)-8-benzyl-8-azabicyclo[3.2.1]octan-3-yl)-2-(5-chloro-2,4-dimethoxyphenyl)imidazo[1,2-a]pyridin-7-amine 425e (Example 433)

A mixture of N-((1R,3r,5S)-8-azabicyclo[3.2.1]octan-3-yl)-2-(5-chloro-2,4-dimethoxyphenyl)imidazo[1,2-a]pyridin-7-amine 424 (150 mg, 0.36 mmol), benzaldehyde (42 mg, 0.4 mmol) and AcOH (0.1 mL) in CH₃OH (4 mL) was stirred at room temperature for 1 h. To the reaction mixture was added NaCNBH₃ (23 mg, 0.43 mmol) and the reaction mixture was stirred at room temperature for 16 h under nitrogen atmosphere. The reaction mixture was diluted with water and extracted with CH₂Cl₂ (2×10 mL). The combined organic layers were dried over sodium sulfate, filtered and concentrated under reduced pressure and the residue was purified by combi-flash companion (silica gel, CH₃OH/CH₂Cl₂) to afford N-((1R,3r,5S)-8-benzyl-8-azabicyclo[3.2.1]octan-3-yl)-2-(5-chloro-2,4-dimethoxyphenyl)imidazo[1,2-a]pyridin-7-amine 425e (18 mg, 10%) as an off-white solid.

$^1$H NMR (300 MHz, DMSO-d₆): δ 8.13 (t, J=4.4 Hz, 2H), 7.88 (s, 1H), 7.46-7.25 (m, 5H), 6.85 (s, 1H), 6.48 (dd, J=1.6 Hz, J=7.2 Hz, 1H), 6.09-6.04 (m, 2H), 3.99 (s, 3H), 3.92 (s, 3H), 3.52 (bs, 3H), 3.11 (bs, 2H), 2.23-2.12 (m, 2H), 2.10-1.90 (m, 4H), 1.74-1.70 (m, 2H); HPLC (Method 1) 94.87% (AUC), $t_R$=11.75 min.; ESI+APCI MS m/z 503 [M+H]⁺.

Preparation of 2-(5-chloro-2,4-dimethoxyphenyl)-N-((1R,3r,5S)-8-(pyridin-4-ylmethyl)-8-azabicyclo[3.2.1]octan-3-yl)imidazo[1,2-a]pyridin-7-amine 425f (Example 448)

A mixture of N-((1R,3r,5S)-8-azabicyclo[3.2.1]octan-3-yl)-2-(5-chloro-2,4-dimethoxyphenyl)imidazo[1,2-]pyridin-7-amine 424 (200 mg, 0.36 mmol), 4-(chloromethyl)pyridine hydrochloride (118 mg, 0.73 mmol) and N,N-diisopropylethylamine (0.42 mL, 0.9 mmol) in DMF (3 mL) was stirred at 100° C. for 16 h under nitrogen atmosphere. The reaction mixture was quenched with water and extracted with EtOAc (2:25 mL). The combined organic layers were dried over Na₂SO₄, filtered and evaporated under reduced pressure. The residue was purified by combi-flash companion (silica gel, CH₃OH/CH₂Cl₂) to afford 2-(5-chloro-2,4-dimethoxyphenyl)-N-((1R,3r,5S)-8-(pyridin-4-ylmethyl)-8-azabicyclo[3.2.1]octan-3-yl)imidazo[1,2-a]pyridin-7-amine 425f (15 mg, 6%) as a light-yellow solid.

$^1$H NMR (300 MHz, DMSO-d₆) δ: 8.50 (d, J=5.7 Hz, 2H), 8.12 (d, J=6.9 Hz, 2H), 7.87 (s, 1H), 7.40 (d, J=5.1 Hz, 2H), 6.84 (s, 1H), 6.46 (d, J=6.0 Hz, 1H), 6.04 (s, 2H), 3.99 (s, 3H), 3.92 (s, 3H), 3.55 (bs, 3H), 3.17 (bs, 2H), 2.27-2.13 (m, 2H), 2.02-1.99 (m, 4H), 1.73 (d, l=14.1 Hz, 2H); HPLC (Method 1) 93.99% (AUC), $t_R$=11.09 min.; ESI+APCI MS m/z 504 [M+H]⁺.

Preparation of ((1R,3r,5S)-3-((2-(5-chloro-2,4-dimethoxyphenyl)imidazo[1,2-a]pyridin-7-yl)amino)-8-azabicyclo[3.2.1]octan-8-yl)(phenyl) methanone 425k (Example 457)

A mixture of N-((1R,3r,5S)-8-azabicyclo[3.2.1]octan-3-yl)-2-(5-chloro-2,4-dimethoxyphenyl)imidazo[1,2-a]pyridin-7-amine 424 (150 mg, 0.36 mmol), benzoic acid (67 mg, 0.54 mmol), HATU (207 mg, 0.54 mmol) and N,N-diisopropylethylamine (0.16 mL, 0.9 mmol) in DMF (3 mL) was stirred at room temperature for 16 h at room temperature under nitrogen atmosphere. The reaction mixture was quenched with water and extracted with EtOAc (2×25 mL). The combined organic layers were washed with water, followed by brine; dried over Na₂SO₄, filtered and concentrated. The residue was purified by combi-flash companion (silica gel, CH₃OH/CH₂Cl₂) to afford ((1R,3r,5S)-3-((2-(5-chloro-2,4-dimethoxyphenyl)imidazo[1,2-a]pyridin-7-yl)amino)-8-azabicyclo[3.2.1]octan-8-yl)(phenyl)methanone 425g (25 mg, 13%) as a light-yellow solid.

$^1$H NMR (400 MHz, DMSO-d₆) δ: 8.14 (t, J=3.6 Hz, 2H), 7.88 (s, 1H), 7.5-7.43 (m, 5H), 6.84 (s, 1H), 6.46 (dd, J=2.0 Hz, J=7.2 Hz, 1H), 6.18 (d, J=3.6 Hz, 1H), 6.09 (s, 1H), 4.06 (bs, 1H), 3.99 (s, 4H), 3.92 (s, 3H), 3.67-3.56 (m, 1H), 2.28-2.05 (m, 4H), 1.93-1.82 (m, 4H); HPLC (Method 5) >99% (AUC), $t_R$=13.76 min.; ESI+APCI MS m/z 517 [M+H]⁺.

Scheme 2-27

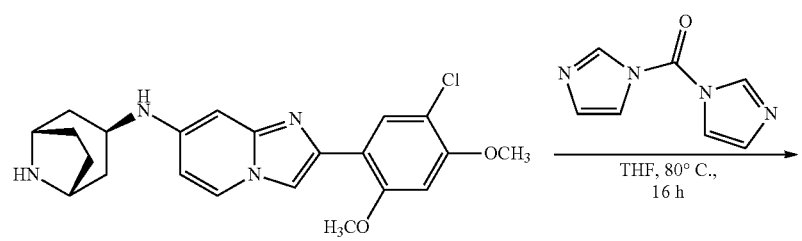

424

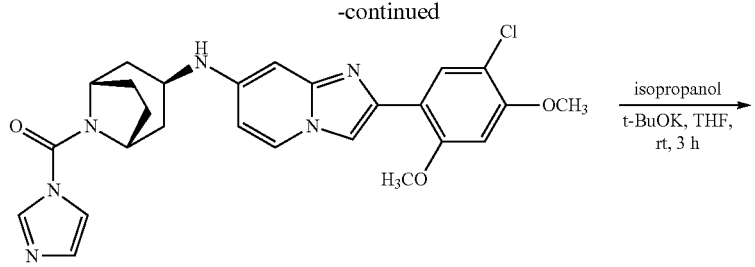

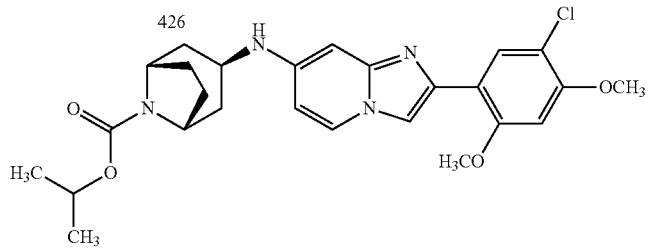

Preparation of ((1R,3r,5S)-3-((2-(5-chloro-2,4-dimethoxyphenyl)imidazo[1,2-a]pyridin-7-yl)amino)-8-azabicyclo[3.2.1]octan-8-yl)(1H-imidazol-1-yl)methanone 426

A mixture of N-((1R,3r,5S)-8-azabicyclo[3.2.1]octan-3-yl)-2-(5-chloro-2,4-dimethoxyphenyl)imidazo[1,2-a]pyridin-7-amine 424 (1.0 g, 2.4 mmol), di(1H-imidazol-1-yl)methanone (507 mg, 3.1 mmol) in THF (30 mL) was stirred at 80° C. for 16 h. The reaction mixture was diluted with water and extracted with EtOAc (2×25 mL). The combined organic layers were dried over sodium sulfate, filtered and concentrated under reduced pressure and the residue was triturated with n-Hexane to afford ((1R,3r,5S)-3-((2-(5-chloro-2,4-dimethoxyphenyl)imidazo[1,2-a]pyridin-7-yl)amino)-8-azabicyclo[3.2.1]octan-8-yl)(1H-imidazol-1-yl)methanone 426 (1.0 g, 83%) as a light-yellow solid. ESI+ APCI MS m/z 507 [M+H]$^+$.

Preparation of (1R,3r,5S)-isopropyl 3-((2-(5-chloro-2,4-dimethoxyphenyl)imidazo[1,2-a]pyridin-7-yl)amino)-8-azabicyclo[3.2.1]octane-8-carboxylate 427 (Example 391)

To a mixture of ((1R,3r,5S)-3-((2-(5-chloro-2,4-dimethoxyphenyl)imidazo[1,2-a]pyridin-7-yl)amino)-8-azabicyclo[3.2.1]octan-8-yl)(1H-imidazol-1-yl)methanone 426 (125 mg, 0.24 mmol), propan-2-ol 7(17 mg, 0.3 mmol) in THF (4 mL) was added a solution of KOt-Bu (80 mg, 0.72 mmol) in THF (4 mL) at 10° C., and the reaction mixture was stirred at room temperature for 3 h under nitrogen atmosphere. The reaction mixture was diluted with brine and extracted with EtOAc (2×10 mL). The combined organic layers were dried over Na$_2$SO$_4$, filtered and concentrated. The residue was purified by combi-flash companion (silica gel, CH$_3$OH/CH$_2$Cl$_2$) to afford (1R,3r,5S)-isopropyl 3-((2-(5-chloro-2,4-dimethoxyphenyl)imidazo[1,2-a]pyridin-7-yl)amino)-8-azabicyclo[3.2.1]octane-8-carboxylate 427 (Example 391) (20 mg, 16%) as an light-yellow solid.

$^1$H NMR (400 MHz, DMSO-d$_6$) δ: 8.15 (s, 1H), 8.13 (d, J=2.4 Hz, 1H), 7.89 (s, 1H), 6.47 (dd, J=2.0 Hz, J=7.2 Hz, 1H), 6.21 (bs, 1H), 4.86-4.77 (m, 1H), 4.12 (bs, 2H), 3.99 (s, 3H), 3.92 (s, 3H), 3.62-3.59 (m, 1H), 2.20-2.09 (m, 4H), 1.90-1.87 (m, 4H), 1.2 (bs, 6H); HPLC (Method 5) 97.76% (AUC), t$_R$=14.01 min.; ESI+APCI MS m/z 499 [M+H]$^+$.

Scheme 2-28

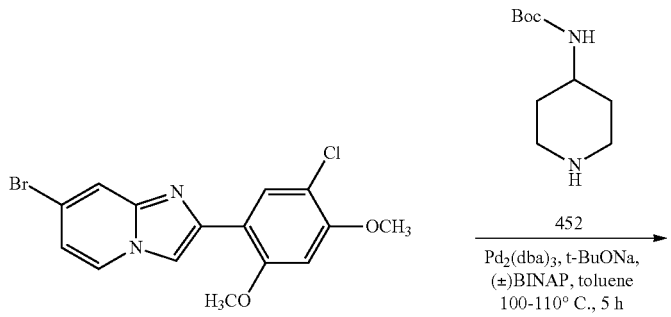

-continued

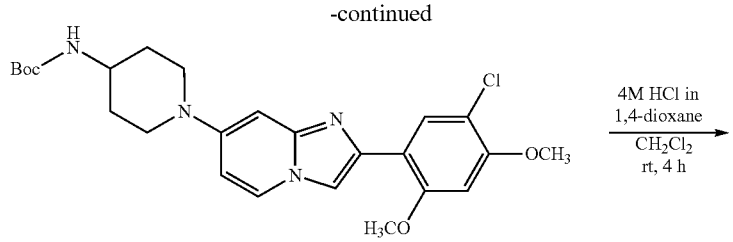

453

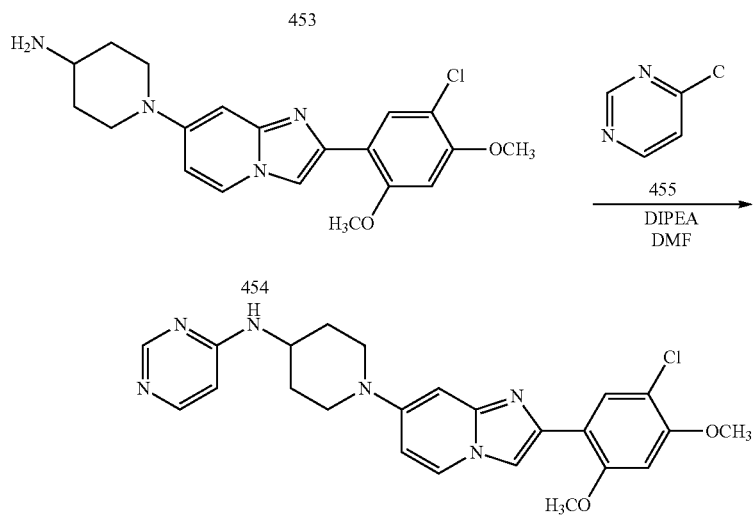

Preparation of tert-butyl (1-(2-(5-chloro-2,4-dimethoxyphenyl)imidazo[1,2-a]pyridin-7-yl)piperidin-4-yl)carbamate 453

A suspension of 7-bromo-2-(5-chloro-2,4-dimethoxyphenyl)imidazo[1,2-a]pyridine 331 (6.00 g, 16.4 mmol), tert-butyl piperidin-4-ylcarbamate 452 (4.91 g, 24.6 mmol), (±) BINAP (1.12 g, 1.80 mmol) and NaOt-Bu (4.72 g, 49.2 mmol) in toluene (100 mL) was degassed with argon for 15 min. The mixture was charged with $Pd_2(dba)_3$ (750 mg, 0.81 mmol) and was further degassed with argon for another 5 min. The resulting reaction mixture was stirred at 100-110° C. for 5 h. The reaction mixture was cooled, filtered through a pad of celite (the celite pad was washed with 10% MeOH/$CH_2Cl_2$) and the combined filtrated was evaporated to dryness. The residue obtained was purified by combi-flash companion (silica gel, $CH_3OH/CH_2Cl_2$) to provide tert-butyl (1-(2-(5-chloro-2,4-dimethoxyphenyl)imidazo[1,2-a]pyridin-7-yl)piperidin-4-yl)carbamate 3 (2.50 g, 31%) as a brown solid. ESI+APCI MS m/z 487 [M+H]$^+$.

Preparation of 1-(2-(5-chloro-2,4-dimethoxyphenyl)imidazo[1,2-a]pyridin-7-yl)piperidin-4-amine 454

A solution of tert-butyl (1-(2-(5-chloro-2,4-dimethoxyphenyl)imidazo[1,2-a]pyridin-7-yl)piperidin-4-yl)carbamate 453 (2.50 g, 5.14 mmol) in $CH_2Cl_2$ (50 mL) was charged with 4.0 M HCl in 1,4-dioxane (10 mL) and stirred at room temperature for 4 h. The reaction mixture was filtered and the solid obtained was washed with $CH_2Cl_2$. The solid was then suspended in water (55 mL), basified with saturated sodium bicarbonate solution (55 mL) by stirring at room temperature for 1 h. The solid was collected by filtration, washed with water and dried to provide 1-(2-(5-chloro-2,4-dimethoxyphenyl)imidazo[1,2-a]pyridin-7-yl)piperidin-4-amine 454 (1.80 g, 91%) as a brown solid. ESI+APCI MS m/z 387 [M+H]$^+$.

Preparation of N-(1-(2-(5-chloro-2,4-dimethoxyphenyl)imidazo[1,2-a]pyridin-7-yl)piperidin-4-yl)pyrimidin-4-amine 456 (Example 374)

A suspension of 1-(2-(5-chloro-2,4-dimethoxyphenyl)imidazo[1,2-a]pyridin-7-yl)piperidin-4-amine 454 (100 mg, 0.25 mmol) and N,N-diisopropylethylamine (0.13 mL, 0.77 mmol) in DMF (2 mL) was charged with 4-chloropyrimidine 455 (57 mg, 0.50 mmol). The resulting mixture was subjected to microwave irradiation at 100° C. for 30 min. The reaction mixture was cooled to room temperature, suspended in water and stirred for 1 h.

The precipitate was collected by filtration, the solid obtained was washed with water, dried under reduced pressure, and purified by combi-flash companion (silica gel, $CH_3OH/CH_2Cl_2$) to provide N-(1-(2-(5-chloro-2,4-dimethoxyphenyl)imidazo[1,2-a]pyridin-7-yl)piperidin-4-yl)pyrimidin-4-amine 456 (30 mg, 25%) as an off-white solid.

$^1$H NMR (400 MHz, DMSO-d$_6$): δ 8.40 (s, 1H), 8.29 (d, J=7.5 Hz, 1H), 8.17 (s, 1H), 8.02 (s, 1H), 8.00 (s, 1H), 7.37 (d, J=7.5 Hz, 1H), 6.86 (s, 1H), 6.81 (dd, J=2.1, 9.6 Hz, 1H), 6.69 (s, 1H), 6.45 (d, J=5.7 Hz, 1H), 4.00 (s, 4H), 3.93 (s, 3H), 3.79-3.75 (m, 2H), 2.98-2.90 (m, 2H), 1.99-1.96 (m, 2H), 1.60-1.49 (m, 2H); HPLC (Method 1) 96.1% (AUC), $t_R$=11.55 min.; ESI+APCI MS m/z 465 [M+H]$^+$.

Scheme 2-29

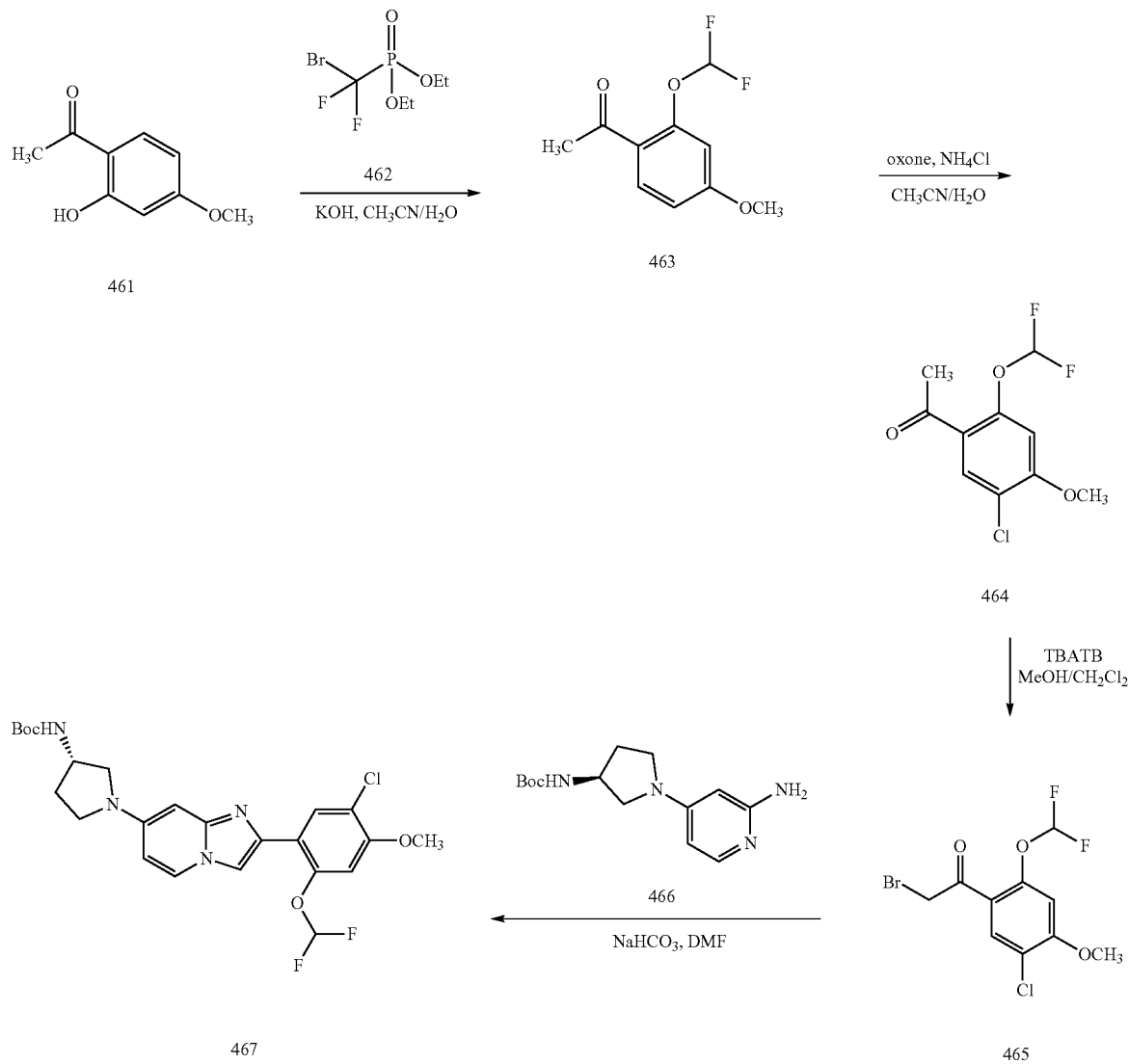

Preparation of
1-(2-(difluoromethoxy)-4-methoxyphenyl)ethanone
463

To a mixture of 1-(2-hydroxy-4-methoxyphenyl)ethanone 461 (3.3 g, 20 mmol), KOH (22.4 g, 40 mmol) in CH₃CN/water (20 mL/20 mL) cooled in a dry ice acetone bath, was added diethyl (bromodifluoromethyl)phosphonate 462 (7.1 mL, 40 mmol) quickly. The cold bath was removed after the addition and the reaction mixture was stirred at room temperature for 16 h. The reaction mixture was partitioned between ethyl acetate and water, the layers were separated and the aqueous layer was extracted with ethyl acetate (3×50 mL). The combined organic layers were washed with water, followed by brine; dried over Na₂SO₄, filtered and concentrated to give 1-(2-(difluoromethoxy)-4-methoxyphenyl)ethanone 463 as a yellowish oil, which solidified upon standing (4.4 g, crude). The crude material was used in next step directly without further purification.

$^1$H NMR (300 MHz, CDCl₃): δ 7.84 (d, J=8.8 Hz, 1H), 6.79 (dd, J=2.3, 8.8 Hz, 1H), 6.66 (d, J=2.3 Hz, 1H), 6.59 (t, J=74 Hz, 1H), 3.86 (s, 3H), 2.59 (s, 3H). $^{19}$F NMR (282 MHz, CDCl₃): δ −81.19.

Preparation of 1-(5-chloro-2-(difluoromethoxy)-4-methoxyphenyl)ethanone 464

To a suspension of 1-(2-(difluoromethoxy)-4-methoxyphenyl)ethanone 463 (4.3 g, 20 mmol), NH₄Cl (1.39 g, 26 mmol) in a mixture of CH₃CN/water (100 mL/10 mL) was added Oxone® (7.38 g, 24 mmol) portionwise at room temperature. The resulting suspension was vigorously stirred at room temperature for 16 h. The reaction mixture was filtered, and the filtrate was concentrated. The residue was diluted with water (100 mL) and extracted with ethyl acetate (3×50 mL). The combined organic layers were washed with water followed by brine, dried over Na₂SO₄ and concentrated. The residue was purified by silica-gel chromatography (1:9, ethyl acetate/Hexanes) to give 1-(5- chloro-2-(difluoromethoxy)-4-methoxyphenyl)ethanone 464 (3.2 g, 64%) as a wax like white solid.

$^1$H NMR (300 MHz, CDCl$_3$): δ 7.89 (s, 1H), 6.71 (s, 1H), 6.59 (t, J=73 Hz, 1H), 3.96 (s, 3H), 2.58 (s, 3H). $^{19}$F NMR (282 MHz, CDCl$_3$): δ -81.24.

Preparation of 2-bromo-1-(5-chloro-2-(difluoromethoxy)-4-methoxyphenyl)ethanone 465

To a solution of 1-(5-chloro-2-(difluoromethoxy)-4-methoxyphenyl)ethanone 464 (3.2 g, 12.8 mmol) in a mixture of MeOH/CH$_2$Cl$_2$ (10 mL/20 mL) cooled in an ice-water bath, was added tetrabutylammonium tribromide (6.8 g, 14.0 mmol) portionwise. The reaction mixture was stirred at room temperature for 16 h. The solvents were removed under reduced pressure and the residue was taken up in ethyl acetate (150 mL). The organic layer was washed with water (3×20 mL), followed by brine, dried over Na$_2$SO$_4$, filtered and concentrated. The crude product was purified by silica-gel chromatography (1:3, CH$_2$Cl$_2$/Hexanes) to give 2-bromo-1-(5-chloro-2-(difluoromethoxy)-4-methoxyphenyl)ethanone 465 (2.7 g, 63%) as a white solid.

$^1$H NMR (300 MHz, CDCl$_3$): δ 7.94 (s, 1H), 6.72 (s, 1H), 6.64 (t, J=72 Hz, 1H), 4.45 (s, 2H), 3.98 (S, 3H).

Preparation of (S)-tert-butyl (1-(2-(5-chloro-2-(difluoromethoxy)-4-methoxyphenyl)imidazo[1,2-a]pyridin-7-yl)pyrrolidin-3-yl)carbamate 467 (Example A mixture of (S)-tert-butyl (1-(2-aminopyridin-4-yl)pyrrolidin-3-yl)carbamate 6 (170 mg, 0.607 mmol), 2-bromo-1-(5-chloro-2-(difluoromethoxy)-4-methoxyphenyl)ethanone 465 (200 mg, 0.607 mmol) and NaHCO$_3$ (102 mg, 1.21 mmol) in anhydrous DMF (3 mL) was subjected to microwave irradiation at 90° C. for 1 h. The reaction mixture was diluted with water (30 mL) and extracted with ethyl acetate (2×30 mL). The combined organic layers were washed with water (3×30 mL) followed by brine, dried over Na$_2$SO$_4$, filtered and concentrated. The crude product was purified by silica-gel chromatography (5:95; MeOH/CH$_2$Cl$_2$) to give (S)-tert-butyl (1-(2-(5-chloro-2-(difluoromethoxy)-4-methoxyphenyl)imidazo[1,2-a]pyridin-7-yl)pyrrolidin-3-yl)carbamate 467 (200 mg, 65%) as a greenish solid.

$^1$H NMR (400 MHz, CDCl$_3$): δ 8.42 (s, 1H), 7.89 (d, J=7.3 Hz, 1H), 7.77 (s, 1H), 6.75 (s, 1H), 6.50 (t, J=74 Hz, 1H), 6.44 (br s, 1H), 6.36 (dd, J=2.4, 7.5 Hz, 1H), 4.72 (br s, 1H), 4.40 (br s, 1H), 3.93 (s, 3H), 3.66 (dd, J=6.1, 10.2 Hz, 1H), 3.51-3.38 (m, 2H), 3.24 (dd, J=4.3, 9.9 Hz, 1H), 2.36-2.31 (m, 1H), 2.07-1.96 (m, 1H), 1.47 (s, 9H); HPLC (Method 1) 97.0% (AUC), t$_R$=11.81 min.; ESI MS m/z 509 [M+H]$^+$.

Compounds of the invention of this application not particularly described in the Examples above were also be synthesized by similar or analogous methods by referring to the above-mentioned Examples and such.

Next, the pharmacological activities of compound (I) will be described in the following Test Examples.

Test Examples

Preparation of Compound Dilution Plates (96 Well Plate)
To the test compound 100% DMSO was added to obtain a stock solution with a final concentration of 10 mM and the solution was incubated overnight on a shaker at 150 rpm. In a 96 well plate, 75 µL of 50% DMSO (in water) was dispensed to all wells from Col 3 to Col 1, 76 µl of 50% DMSO was added to Col 2 (Row A-RowH) 24 µl of 10 mM compound stock was added to Col 2 (Row A-Row H) to obtain a final concentration of 2.4 mM. The mixture (25 µl) in each well of Col 2 was mixed and transferred to a corresponding well of Col 3. Similar procedure was repeated till Col 11 to obtain 10 serial dilutions (1:4) of each compound.

Preparation of Standard Compound Plate (96 Well Plate)
Assay buffer (18 µl) was added in Row A, Col 3-11, and Sinefungin (24 µl, 12.5 mM) was added to Col 2. The mixture (6 µl) in Row A-Col 2 was transferred to the corresponding wells of Col 3. The mixture (24 µl) in wells of Col 3 were mixed and transferred to Col 4, and the similar procedure was continued till Col 11 to obtain a 10 point serial dilution of Sinefungin.

Preparation of 384 Well Test Plate
Water (0.25 µl) was added to Col 1 and Col 23 (minimum and maximum signal wells respectively), and 50% DMSO (0.25 µl) was added to Col 2 and Col 24 (minimum and maximum signal wells respectively). The test compounds (0.25 µl) were added to the respective wells in 'Row A-Row N'. 'Row O' contained the internal standard compound. Sinefungin (4 µl) was added to 'Row P'. Each compound concentration was tested in duplicates.

Suv 39H2 Assay
Assay buffer (4 µL) was added into all the wells, including test compound and control wells (except for Sinefungin control wells), using the Multidrop Combi. The plate was centrifuged at 1000 rpm for 1 min. Substrate mix (8 µL) containing radiolabelled $^3$H-SAM (final conc: 100 nM) and H3 Histone Peptide (final conc: 350 nM) was added to all wells using Multidrop Combi and centrifuged at 1000 rpm for 1 min. SUV39H2 (8 µL, final conc: optimized for each lot of the enzyme based on specific activity) was added by using the Multidrop Combi. The assay plate was centrifuged at 1000 rpm for 1 min. Assay buffer was used as background control, and incubated at room temperature for 3 hours. The reaction was stopped with 20 µL of 2.5 mg/mL Streptavidin SPA beads (final conc. 50 µg/well) in buffer using the Multidrop Combi and centrifuged for 1 min. The plate was loaded into the Trilux-Microbeta counter and a delayed read of 10 hours was made. The radioactive signal was measured at 1 min/well. Sinefungin and the internal standard compound were used as tool compounds to determine assay performance.

Data Analysis
The following calculations were made using the obtained CPM raw data: Software used: XLFit from IDBS. Model used was—Dose Response One Site—Model 205

1% DMSO/water Negative Control(minimum signal–Column 1 and 2)=Average of all background control wells 1% DMSO/water Positive Control(maximum signal–Column 23 and 24)=Average of all control wells Signal Ratio=(Positive Control)/(Negative Control)

Z'=1-(((3*StdDev Negative Control)+(3*StdDev Positive Control))/(Avg. Positive Control–Avg. Negative Control))

% Inhibition of test compound=(100−((AVG. CPM$_{test\ compound}$−Avg. CPM$_{Negative\ Ctrl}$)/(Avg. CPM$_{Positive\ Ctrl}$−Avg. CPM$_{Negative\ Ctrl}$))×100)

For each test plate the following results were calculated:
Average, Standard Deviation, and % CV of Background Controls
Average, Standard Deviation, and % CV of Positive Controls
Z' value of the plate
$IC_{50}$ values of standard and test compounds (in nM)
$R^2$ value of fitted concentration response curve
Hill slope coefficient of fitted concentration response curve
Signal to Noise Ratio For each sample compound the following results were reported:
Concentration dependent response curve for each compound
Concentration of compound causing 50% inhibition of enzyme activity ($IC_{50}$ values (in nM))
% Inhibition at Maximum Concentration tested.
Maximum Concentration tested
$R^2$ value of fitted concentration response curve
Hill slope coefficient of fitted concentration response curve $IC_{50}$ values of the typical compounds of the present invention are shown in the following tables 3 and 4:

Western Blot Analysis

To evaluate the expression status of SUV39H2 in several cell lines, western blot analysis was performed using crude cell lysate collected from those cells. Anti-SUV39H2 antibody was used to visualize the expression. Cancer cell lines, A549, HCT-116, HFL1, CCD-18Co and PC14, expressed SUV39H2 significantly.

Cell-Based Assay

Active candidate inhibitors against SUV39H2 were evaluated for their target-specific cytotoxicity using A549, HCT-116, HFL1, CCD-18Co and PC14. 100 micro-L of cell suspension was seeded onto 96-well microtiter plate (ViewPlate-96FTC, PerkinElmer). The initial cell concentration of A549, HCT-116, HFL1, CCD-18Co and PC14 were 3,000 cells/well, 2,000 cells/well and 2,500 cells/well, respectively. Cellular growth was determined using Cell Counting Kit-8 (DOJINDO) at 72 hours after the exposure of the candidate inhibitors. IC50 was used as an indicator of the anti-proliferative activity of the inhibitors, and calculated by serial dilution method (0, 1.5625, 3.125, 6.25, 12.5, 25, 50, and 100 micro-M). Accurate IC50 values were calculated as described previously.

$IC_{50}$ values of the typical compounds (Examples 1 to 460) of the present invention are shown in the following tables 3 and 4:

TABLE 3

| No. | Compound Name | A549 | HCT-116 | HFL1 | CCD-18Co | PC14 | IC50 (µM) Suv 39H2 assay |
|---|---|---|---|---|---|---|---|
| 1 | 2-(5-bromo-2,4-dimethoxyphenyl)-7-(pyrrolidin-1-yl)imidazo[1,2-a]pyridine | 2.5 | 1.7 | 1.6 | 2.6 | | 0.0182 |
| 2 | 2-(5-bromo-2,4-dimethoxyphenyl)imidazo[1,2-a]pyrimidin-7-amine hydrochloride | 18 | 17 | 16 | 16 | | 0.0169 |
| 3 | 2-(5-bromo-2,4-dimethoxyphenyl)-7-(pyrrolidin-1-yl)imidazo[1,2-a]pyrimidine | 11 | 8.1 | 7.4 | 6.8 | 7.1 | 0.00858 |
| 4 | 2-(5-chloro-2,4-dimethoxyphenyl)-7-(pyrrolidin-1-yl)imidazo[1,2-a]pyridine hydrobromide | 2 | 1.5 | 1.4 | 1.1 | 1.4 | 0.0031 |
| 5 | 2-(5-bromo-2,4-dimethoxyphenyl)imidazo[1,2-a]pyridin-7-amine | 3.6 | 3.1 | 2.1 | 3.8 | | 0.0103 |
| 6 | 2-(5-chloro-2,4-dimethoxyphenyl)-N-methylimidazo[1,2-a]pyridin-7-amine hydrobromide | 2.2 | 1.7 | 1 | 2.7 | 1.4 | 0.00943 |
| 7 | 1-(2-(5-bromo-2,4-dimethoxyphenyl)imidazo[1,2-a]pyridin-7-yl)pyrrolidin-3-ol | 6.9 | 7 | 6.8 | 7.6 | 6.1 | 0.00544 |
| 8 | 2-(5-chloro-2,4-dimethoxyphenyl)imidazo[1,2-a]pyrimidin-7-amine | 17 | 16 | 21 | 19 | | 0.0182 |
| 9 | 2-(5-chloro-2,4-dimethoxyphenyl)-7-(pyrrolidin-1-yl)imidazo[1,2-a]pyrimidine hydrobromide | 8 | 6.8 | 7.1 | 8 | 6.3 | 0.00608 |
| 10 | $N^1$-(2-(5-chloro-2,4-dimethoxyphenyl)imidazo[1,2-a]pyridin-7-yl)ethane-1,2-diamine dihydrochloride | 6.8 | 4.2 | 3.7 | 7.1 | | 0.015 |
| 11 | 2-(5-bromo-2,4-dimethoxyphenyl)-N-methylimidazo[1,2-a]pyridin-7-amine hydrobromide | 1.4 | 1.1 | 1.7 | 2 | 0.88 | 0.0094 |
| 12 | 4-(2-(5-chloro-2,4-dimethoxyphenyl)imidazo[1,2-a]pyridin-7-yl)morpholine hydrobromide | 6.9 | 5.1 | 6.8 | 9 | 2.9 | 0.012 |
| 13 | tert-butyl (1-(2-(5-bromo-2,4-dimethoxyphenyl)imidazo[1,2-a]pyrimidin-7-yl)pyrrolidin-3-yl)carbamate | 5.7 | 6.6 | 3.7 | 4.4 | | 0.0219 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 14 | tert-butyl (1-(2-(5-chloro-2,4-dimethoxyphenyl)imidazo[1,2-a]pyridin-7-yl)piperidin-4-yl)carbamate | 2.7 | 2 | 1.8 | 1.9 | | 0.0341 |
| 15 | 1-(2-(5-chloro-2,4-dimethoxyphenyl)imidazo[1,2-a]pyridin-7-yl)piperidin-4-amine dihydrochloride | 3.5 | 3.4 | 2.7 | 6.7 | | 0.0133 |
| 16 | (1-(2-(5-chloro-2,4-dimethoxyphenyl)imidazo[1,2-a]pyridin-7-yl)piperidin-4-yl)methanamine dihydrochloride | 8.8 | 8.7 | 11 | 14 | | 0.0122 |
| 17 | 2-(5-chloro-2,4-dimethoxyphenyl)-7-(piperazin-1-yl)imidazo[1,2-a]pyridine dihydrochloride | 6.1 | 4.5 | 3.3 | 8.6 | | 0.0195 |
| 18 | tert-butyl (2-((2-(5-bromo-2,4-dimethoxyphenyl)imidazo[1,2-a]pyrimidin-7-yl)amino)ethyl)carbamate | 14 | 13 | 11 | 12 | | 0.0884 |
| 19 | 1-(2-(5-bromo-2,4-dimethoxyphenyl)imidazo[1,2-a]pyrimidin-7-yl)pyrrolidin-3-amine dihydrochloride | 11 | 7.9 | 4.2 | 16 | | 0.0292 |
| 20 | 2-(5-chloro-2,4-dimethoxyphenyl)imidazo[1,2-a]pyridin-7-ol | | | | | | 0.09 |
| 21 | 2-methoxy-5-(7-(pyrrolidin-1-yl)imidazo[1,2-a]pyridin-2-yl)benzonitrile hydrobromide | 4.2 | 3.1 | 2.5 | 5.5 | | 0.0733 |
| 22 | 2-(5-chloro-2,4-dimethoxyphenyl)-N,N-dimethylimidazo[1,2-a]pyridin-7-amine hydrobromide | 1.6 | 3.3 | 1.7 | 3.6 | 1.6 | 0.00515 |
| 23 | tert-butyl (1-(2-(5-chloro-2,4-dimethoxyphenyl)imidazo[1,2-a]pyridin-7-yl)pyrrolidin-3-yl)carbamate | 2.4 | 1.8 | 1.2 | 2.8 | 1.7 | 0.00635 |
| 24 | 1-(2-(5-chloro-2,4-dimethoxyphenyl)imidazo[1,2-a]pyridin-7-yl)-N-methylpiperidin-4-amine dihydrochloride | 5.5 | 4.4 | 2.7 | 11 | 5.7 | 0.00939 |
| 25 | 2-(5-chloro-2,4-dimethoxyphenyl)-7-(piperidin-1-yl)imidazo[1,2-a]pyridine hydrobromide | 3 | 2 | 1.4 | 2.3 | | 0.0122 |
| 26 | tert-butyl (1-(2-(5-chloro-2,4-dimethoxyphenyl)imidazo[1,2-a]pyrimidin-7-pyrrolidin-3-yl)carbamate | 7.9 | 13 | 6.7 | 7.9 | | 0.017 |
| 27 | 5-(2-(5-chloro-2,4-dimethoxyphenyl)imidazo[1,2-a]pyridin-7-yl)pyridin-3-amine | 1.9 | 3.3 | 1.8 | 3.3 | | 0.0396 |
| 28 | tert-butyl (2-(4-(2-(5-chloro-2,4-dimethoxyphenyl)imidazo[1,2-a]pyridin-7-yl)piperazin-1-yl)ethyl)carbamate dihydrochloride | 3.6 | 2.8 | 3.4 | 4 | | 0.021 |
| 29 | 2-(4-(2-(5-chloro-2,4-dimethoxyphenyl)imidazo[1,2-a]pyridin-7-yl)piperazin-1-yl)ethanamine trihydrochloride | 7 | 9.7 | 4.5 | 12 | | 0.012 |
| 30 | (R)-1-(5-chloro-2,4-dimethoxyphenyl)imidazo[1,2-a]pyridine-7-yl)piperidin-3-amine dihydrochloride | 3.4 | 5.1 | 2 | 3.9 | 2.3 | 0.009 |
| 31 | (1-(2-(5-chloro-2,4-dimethoxyphenyl)imidazo[1,2-a]pyrimidin-7-yl)piperidin-4-yl)methanamine dihydrochloride | 18 | 22 | 9.3 | 23 | | 0.0489 |
| 32 | tert-butyl ((1-(2-(5-chloro-2,4-dimethoxyphenyl)imidazo[1,2-a]pyrimidin-7-yl)piperidin-4-yl)methyl)carbamate | 6.7 | 8.4 | 4.6 | 6.3 | | 0.037 |
| 33 | 1-(2-(5-chloro-2,4-dimethoxyphenyl)imidazo[1,2-a]pyridine-7-yl)pyrrolidin-3-amine | 3.1 | 3.3 | 2.2 | 3.2 | 1.7 | 0.00704 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 34 | 1-(2-(5-chloro-2,4-dimethoxyphenyl)imidazo[1,2-a]pyrimidin-7-yl)pyrrolidin-3-amine dihydrochloride | 12 | 9.6 | 4.4 | 11 | | 0.0273 |
| 35 | N¹-(2-(5-chloro-2,4-dimethoxyphenyl)imidazo[1,2-a]pyridine-7-yl)propane-1,3-diamine | 14 | 9.8 | 7 | 14 | | 0.0124 |
| 36 | tert-butyl (1-(2-(5-chloro-2,4-dimethoxyphenyl)imidazo[1,2-a]pyrimidin-7-yl)piperidin-4-yl)carbamate | 5.6 | 4.1 | 3.2 | 3.8 | | 0.0552 |
| 37 | N-(1-(2-(5-chloro-2,4-dimethoxphenyl)imidazo[1,2-a]pyridin-7-yl)pyrrolidin-3-yl)acetamide | 14 | 12 | 5.4 | 11 | 8.2 | 0.00435 |
| 38 | 1-(1-(2-(5-chloro-2,4-dimethoxyphenyl)imidazo[1,2-a]pyridine-7-yl)pyrroidin-3-yl)urea | | | | | | 0.00411 |
| 39 | tert-butyl ((2S)-5-amino-1-(1-(2-(5-chloro-2,4-dimethoxyphenyl)imidazo[1,2-a]pyridin-7-yl)pyrrolidin-3-yl)amino)-1,5-dioxopentan-2-yl)carbamate | | | | | | 0.00489 |
| 40 | N-(1-(2-(5-chloro-2,4-dimethoxyphenyl)imidazo[1,2-a]pyridine-7-yl)pyrrolidin-3-yl)methanesulfonamide | 17 | 14 | 14 | 15 | 6.7 | 0.00381 |
| 41 | (1-(2-(5-chloro-2,4-dimethoxyphenyl)imidazo[1,2-a]pyridine-7-yl)piperidin-4-yl)methanol | 3.2 | 3.5 | 2.9 | 3.1 | 2.8 | 0.0054 |
| 42 | 1-(2-(5-chloro-2,4-dimethoxyphenyl)imidazo[1,2-a]pyrimidin-7-yl)piperidin-4-amine dihydrochloride | 10 | 6.6 | 4.2 | 13 | | 0.079 |
| 43 | 2-(4-(2-(5-chloro-2,4-dimethoxyphenyl)imidazo[1,2-a]pyridine-7-yl)piperazin-1-yl)ethanol dihydrochloride | 14 | 14 | 6.9 | 11 | 9.8 | 0.00854 |
| 44 | (S)-tert-butyl (1-(2-(5-chloro-2,4-dimethoxyphenyl)imidazo[1,2-a]pyridine-7-yl)pyrrolidin-3-yl)carbamate | 3 | 3.4 | 1.1 | 2.2 | 1.6 | 0.00982 |
| 45 | 2-(4-(2-(5-chloro-2,4-dimethoxyphenyl)imidazo[1,2-a]pyrimidin-7-yl)piperazin-1-yl)ethanol dihydrochloride | 18 | 12 | 17 | 21 | | 0.0365 |
| 46 | 5-(7-aminoimidazo[1,2-a]pyrimidin-2-yl)-2,4-dimethoxybenzonitrile hydrochloride | | | | | | 0.0453 |
| 47 | (S)-1-(2-(5-chloro-2,4-dimethoxyphenyl)imidazo[1,2-a]pyridine-7-yl)pyrrolidin-3-amine dihydrochloride | 3 | 3.4 | 2 | 3.5 | 4.5 | 0.00829 |
| 48 | tert-butyl (2-((2-(5-chloro-2,4-dimethoxyphenyl)imidazo[1,2-a]pyridine-7-yl)(methyl)aimno)ethyl)carbamate | 8.2 | 7.3 | 3.8 | 6.4 | | 0.0124 |
| 49 | 2,4-dimethoxy-5-(7-(pyrrolidin-1-yl)imidazo[1,2-a]pyridine-2-yl)benzonitrile hydrobromide | 1.5 | 1.3 | 0.8 | 1.1 | 1.3 | 0.00371 |
| 50 | 3-amino-N-(1-(2-(5-chloro-2,4-dimethoxyphenyl)imidazo[1,2-a]pyridine-7-yl)pyrrolidin-3-yl)propanamide | | | | | | 0.00575 |
| 51 | 2-(5-chloro-2,4-dimethoxyphenyl)imidazo[1,2-c]pyrimidin-7-amine | 9.8 | 8.9 | 8.4 | 6.8 | | 0.0531 |
| 52 | 2-(5-chloro-2,4-dimethoxyphenyl)-7-(1,2,3,6-tetrahydropyridin-4-yl)imidazo[1,2-a]pyridine dihydrochloride | 1.5 | 1.4 | 1.6 | 1.3 | | 0.0616 |
| 53 | 2-(5-bromo-2-isopropoxy-4-methoxyphenyl)-7-(pyrrolidin-1-yl)imidazo[1,2-a]pyridine hydrobromide | 2.5 | 2.4 | 1.9 | 2.1 | | 0.0181 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 54 | N¹-(2-(5-chloro-2,4-dimethoxyphenyl)imidazo[1,2-a]yridine-7-yl)-N1-metylethane-1,2-diamine | 4.2 | 3.1 | 2.5 | 3.3 | 4.9 | 0.00585 |
| 55 | (R)-1-(2-(5-chloro-2,4-dimethoxyphenyl)imidazo[1,2-a]pyrimidin-7-yl)pyrrolidin-3-amine dihydrochloride | 12 | 10 | 4.8 | 14 | | 0.0262 |
| 56 | (S)-tert-butyl (1-(2-(5-chloro-2,4-dimethoxyphenyl)imidazo[1,2-a]pyrimidin-7-yl)pyrrolidin-3-yl)carbamate | 7.5 | 7 | 5.7 | 7 | | 0.0168 |
| 57 | (R)--tert-butyl (1-(2-(5-chloro-2,4-dimethoxyphenyl)imidazo[1,2-a]pyrimidin-7-yl)pyrrolidin-3-yl)carbamate | 7.1 | 7.2 | 4 | 4.8 | | 0.0108 |
| 58 | (S)-1-(2-(5-chloro-2,4-dimethoxyphenyl)imidazo[1,2-a]pyrimidin-7-yl)pyrrolidin-3-amine dihydrochloride | 14 | 9.4 | 6.2 | 13 | | 0.0296 |
| 59 | (S)-1-(2-(5-bromo-2-isopropoxy-4-methoxyphenyl)imidazo[1,2-a]pyridine-7-yl)pyrrolidin-3-amine dihydrochloride | 3.4 | 2.6 | 1.8 | 3.7 | | 0.0112 |
| 60 | N¹-(2-(5-chloro-2,4-dimethoxyphenyl)-7-(pyrrolidin-1-yl)imidazo[1,2-a]pyridine-6-yl)ethane-1,2-diamine | 6.8 | 6.8 | 2 | 6 | 2.6 | 0.0094 |
| 61 | tert-butyl (2-(1-(2-(5-chloro-2,4-dimethoxyphenyl)imidazo[1,2-a]pyrimidin-7-yl)piperidin-4-yl)ethyl)carbamate | 4.5 | 4.1 | 3.4 | 4.3 | 1.7 | 0.00831 |
| 62 | 1-(2-aminoethyl)-3-(1-(2-(5-chloro-2,4-dimethoxyphenyl)imidazo[1,2-a]pyridine-7-yl)pyrrolidin-3-yl)urea | | | | | | 0.00514 |
| 63 | N-(1-(5-chloro-2,4-dimethoxyphenyl)imidazo[1,2-a]pyridine-7-yl)pyrrolidin-3-yl)cyclopropanesulfonamide | 3 | 1.6 | 1.7 | 3.8 | 2.1 | 0.00395 |
| 64 | 2-(5-chloro-2,4-dimethoxyphenyl)-N-(2-(piperidin-1-yl)ethyl)imidazo[1,2-a]pyridine-7-amine | 4.2 | 3.4 | 2.6 | 4.5 | | 0.0265 |
| 65 | tert-butyl (3-((1-(2-(5-bromo-2,4-dimethoxyphenyl)imidazo[1,2-a]pyrimidin-7-yl)pyrrolidin-3-yl)amino)-3-oxopropyl)carbamate | 28 | 17 | 27 | 26 | | 0.014 |
| 66 | N-(1-(2-(5-bromo-2,4-dimethoxyphenyl)imidazo[1,2-a]pyrimidin-7-yl)pyrrolidin-3-yl)acetamide | 25 | 18 | 26 | 27 | 16 | 0.00747 |
| 67 | 2-(1-(2-(5-chloro-2,4-dimethoxyphenyl)imidazo[1,2-a]pyrimidin-7-yl)piperidin-4-yl)ethanamine dihydrochloride | 12 | 13 | 9.6 | 13 | | 0.0216 |
| 68 | 3-amino-N-(1-(2-(5-bromo-2,4-dimethoxyphenyl)imidazo[1,2-a]pyrimidin-7-yl)pyrrolidin-3-yl)propanamide hydrochloride | | | | | | 0.0162 |
| 69 | 2,4-dimethoxy-5-(7-(pyrrolidin-1-yl)imidazo[1,2-a]pyrimidin-2-yl)benzonitrile dihydrobromide | | | | | | 0.0141 |
| 70 | 2-(5-chloro-2,4-dimethoxyphenyl)-N-(2-morpholinoethyl)imidazo[1,2-a]pyridine-7-amine | 14 | 10 | 8.4 | 14 | | 0.0165 |
| 71 | tert-butyl (1-(2-(5-cyano-2,4-dimethoxyphenyl)imidazo)[1,2-a]pyridine-7-yl)pyrrolidin-3-yl)carbamate | 2.6 | 1.9 | 1.6 | 3.2 | 2 | 0.0075 |
| 72 | 2-(1-(2-(5-chloro-2,4-dimethoxyphenyl)imidazo[1,2-a]pyridine-7-yl)piperidin-4-yl)ethanamine dihydrochloride | 5.3 | 4.9 | 3.7 | 7 | 2.5 | 0.00875 |
| 73 | 5-(7-(3-aminopyrrolidin-1-yl)imidazo[1,2-a]pyridine-2-yl)-2,4-dimethoxybenzonitrile dihydrochloride | 2.3 | 1.5 | 1.5 | 5.6 | | 0.0112 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 74 | tert-butyl (1-(2-(5-cyano-2,4-dimethoxyphenyl)imidazo[1,2-a]pyrimidin-7-yl)pyrrolidin-3-yl)carbamate | 8.5 | 8.1 | 3.9 | 6.4 | | 0.0303 |
| 75 | $N^1$-(2-(5-chloro-2,4-dimethoxyphenyl)-7-methoxyimidazo[1,2-a]pyridine-6-yl)ethane-1,2-diamine | 6.9 | 6.7 | 3.5 | 7.2 | 5.7 | 0.00271 |
| 76 | 2-(5-chloro-2,4-dimethoxyphenyl)-7-methylimidazo[1,2-a]pyridine hydrobromide | | | | | | 0.0665 |
| 77 | $N^1$-(2-((2-(5-chloro-2,4-dimethoxyphenyl)imidazo[1,2-a]pyridine-7-yl)amino)ethyl)acetamide | 30 | 21 | 15 | 31 | | 0.0101 |
| 78 | $N^1$-(2-(5-chloro-2,4-dimethoxyphenyl)-7-methylimidazo[1,2-a]pyridine-6-yl)ethane-1,2-diamine | 6.3 | 5.6 | 2.7 | 5.7 | 6.1 | 0.00431 |
| 79 | 4-(2-(5-chloro-2,4-dimethoxyphenyl)imidazo[1,2-a]pyrimidin-7-yl)morpholine hydrobromide | 21 | 21 | 15 | 22 | | 0.0344 |
| 80 | 3-(4-chloro-5-methoxy-2-(7-(pyrrolidin-1-yl)imidazo[1,2-a]pyridine-2-yl)phenoxy)-N,N-dimethylpropan-1-amine | 1.6 | 1.1 | 0.85 | 1.8 | 1.7 | 0.00531 |
| 81 | $N^1$-(2-(5-chloro-2,4-dimethoxyphenyl)imidazo[1,2-a]pyridine-6-yl)ethane-1,2-diamine | 13 | 11 | 5.6 | 11 | | 0.0179 |
| 82 | 2-(5-chloro-2-(cyclopropylmethoxy)-4-methoxyphenyl)-7-(pyrrolidin-1-yl)imidazo[1,2-a]pyridine | 3.5 | 3.2 | 2 | 3.8 | 4.7 | 0.00538 |
| 83 | $N^1$-(2-(5-chloro-2,4-dimethoxyphenyl)imidazo[1,2-a]pyridine-7-yl)$N^2$-N2-dimethylethane-1,2-diamine | 5.5 | 6.7 | 2.2 | 7.1 | | 0.0373 |
| 84 | 4-(2-(5-chloro-2-(cyclopropylmethoxy)-4-methoxyphenyl)imidazo[1,2-a]pyridine-7-morpholine | 4.6 | 3.8 | 3.2 | 4.3 | | 0.0138 |
| 85 | 3-(4-chloro-5-methoxy-2-(7-morpholinoimidazo[1,2-a]pyridine-2-yl)phenoxy)N,N-dimethylpropan-1-amine | 8.7 | 9 | 3.5 | 7.9 | | 0.0338 |
| 86 | 4-(2-(2,4-dimethoxy-5-methylphenyl)imidazo[1,2-a]pyridine-7-yl)morpholine | 14 | 14 | 8 | 13 | | 0.0207 |
| 87 | 4-(2-(5-fluoro-2,4-dimethoxyphenyl)imidazo[1,2-a]pyridine-7-yl)morpholine hydrobromide | 3.3 | 2.3 | 4 | 5.6 | | 0.032 |
| 88 | 2-(4-(2-(5-chloro-2,dimethoxyphenyl)imidazo[1,2-a]pyridine-7-yl)piperazin-1-yl)-N,N-dimethylethanamine | 3.3 | 3.9 | 3 | 5.6 | 2.9 | 0.00884 |
| 89 | $N^1$-(2-(5-chloro-2,4-dimethoxyphenyl)-7-morpholinoimidazo[1,2-a]pyridine-6-yl)ethane-1,2-diamine | 3 | 4.4 | 1.6 | 3 | 2.7 | 0.00335 |
| 90 | 4-(2-(5-chloro-2-(cyclopentyloxy)-4-methoxyphenyl)imidazo[1,2-a]pyridine-7-yl)morpholine | 7.1 | 4.7 | 3.9 | 6 | | 0.0584 |
| 91 | methyl (2-((2-(5-chloro-2,4-dimethoxyphenyl)-7-methoxyimidazo[1,2-a]pyridine-6-yl)amino)ethyl)carbamate | 3.1 | 2.2 | 2.9 | 4.7 | | 0.0263 |
| 92 | 1-(2-(5-chloro-2,4-dimethoxyphenyl)imidazo[1,2-a]pyridine-7-yl)N,N-dimethylpiperidin-4-amine | 6 | 7 | 5.5 | 8.8 | | 0.0135 |
| 93 | 2,4-dimethoxy-5-(7-morpholinoimidazo[1,2-a]pyridine-2-yl)benzonitrile | 6.4 | 6.4 | 9.6 | 6.3 | | 0.0119 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 94 | 2-(1-(2-(5-chloro-2,4-dimethoxyphenyl)imidazo[1,2-a]pyridine-7-yl)piperidin-4-yl)-N,N-dimethylethanamine | 2.5 | 2.7 | 4.5 | 3.6 | 2.3 | 0.00887 |
| 95 | 2-(4-(2-(5-chloro-2,4-dimethoxyphenyl)imidazo[1,2-a]pyridine-7-yl)piperazin-1-yl)acetonitrile | 2.9 | 3.4 | 4.1 | 5.3 | 3 | 0.00807 |
| 96 | 2-(5-chloro-2,4-dimethoxyphenyl)-7-(4-(3-methoxypropyl)piperazin-1-yl)imidazo[1,2-a]pyridine | 6.9 | 9 | 8.4 | 6.8 | 6.4 | 0.00833 |
| 97 | 1-(1-(2-(5-chloro-2,4-dimethoxyphenyl)imidazo[1,2-a]pyridine-7-yl)piperidin-4-yl)-N,N-dimethylmethanamine | 3.2 | 2.8 | 2.4 | 6.5 | 2.3 | 0.00768 |
| 98 | 2-(4-chloro-5-methoxy-2-(7-morpholinoimidazo[1,2-a]pyridine-2-yl)phenoxy)-N,N-dimethylethanamine | 22 | 13 | 15 | 9.9 | | 0.0372 |
| 99 | methyl 4-(2-(5-chloro-2,4-dimethoxyphenyl)imidazo[1,2-a]pyridine-7-yl)piperazine-1-carboxylate | 1.5 | 1.5 | 1.8 | 1.6 | 1.9 | 0.00606 |
| 100 | 2-(5-chloro-2,4-dimethoxyphenyl)-7-(4-isopropylpiperazin-1-yl)imidazo[1,2-a]pyridine | 5.6 | 3.2 | 3.2 | 5.8 | | 0.0136 |
| 101 | 4-(2-(5-chloro-2,4-dimethoxyphenyl)-6-(1,2,3,6-tetrahydropyridin-4-yl)imidazo[1,2-a]pyridine-7-yl)morpholine dihydrochloride | 8.3 | 8.6 | 7.5 | 6.6 | | 0.0105 |
| 102 | methyl 4-(2-(5-chloro-2,4-dimethoxyphenyl)imidazo[1,2-1]pyridine-7-yl)-5,6-dihydropyridine-a(2H)-carboxylate | 1.6 | 1.9 | 2.3 | 2.8 | | 0.0756 |
| 103 | 2-(5-chloro-2,4-dimethoxyphenyl)-7-(4-(cyclopropylsulfonyl)piperazin-1-yl)imidazo[1,2-a]pyridine | 1.3 | 0.55 | 0.61 | 1.6 | 0.7 | 0.0103 |
| 104 | 2-(5-chloro-2,4-dimethoxyphenyl)-7-(4-(2-fluoroethyl)piperazin-1-yl)imidazo[1,2-a]pyridine | 6.7 | 8.3 | 4.2 | 8.9 | 4.7 | 0.00666 |
| 105 | 2-(5-chloro-2,4-dimethoxyphenyl)-7-(4-(2-methoxyethyl)piperazin-1-yl)imidazo[1,2-a]pyridine | 7.2 | 7 | 8.3 | 8.1 | | 0.0111 |
| 106 | 2-(5-chloro-2,4-dimethoxyphenyl)-7-(4-methylpiperazin-1-yl)imidazo[1,2-a]pyridine | 6.3 | 6.8 | 3.9 | 6.8 | | 0.0167 |
| 107 | ethyl 4-(2-(5-chloro-2,4-dimethoxyphenyl)imidazo[1,2-a]pyridine-7-yl)piperazine-1-carboxylate | 2.3 | 1.7 | 1.7 | 3.2 | | 0.0116 |
| 108 | 3-(4-(2-(5-chloro-2,4-dimethoxyphenyl)imidazo[1,2-a]pyridine-7-yl)piperazin-1-yl)propanenitrile | 6.3 | 10 | 3 | 5.9 | | 0.0142 |
| 109 | 3-(4-(2-(5-chloro-2,4-dimethoxyphenyl)imidazo[1,2-a]pyridine-7-yl)-5,6-dihydropyridin-1(2H)-yl)propanenitrile | 5.9 | 5.1 | 1.8 | 2.6 | | 0.0417 |
| 100 | 2-(5-chloro-2,4-dimethoxyphenyl)-7-(4-isopropylpiperazin-1-yl)imidazo[1,2-a]pyridine | | | | | | 0.0154 |
| 111 | 2-(4-(2-(5-chloro-2,4-dimethoxyphenyl)imidazo[1,2-a]pyridine-7-yl)-5,6-dihydropyridin-1(2H)-yl)acetonitrile | 3.3 | 3.5 | 1.9 | 4.8 | | 0.0614 |
| 112 | 2-(5-chloro-2,4-dimethoxyphenyl)-7-(piperidin-4-yl)imidazo[1,2-a]pyridine | 6.3 | 7.5 | 6.7 | 8.8 | | 0.0623 |
| 113 | 2-(5-chloro-2,4-dimethoxyphenyl)-7-(1-(2-fluoroethyl)-1,2,3,6-tetrahydropyridin-4-yl)imidazo[1,2 a]pyridine | 6.7 | 6.7 | 5.2 | 7.6 | | 0.0571 |
| 114 | 4-(2-(5-chloro-2,4-dimethoxyphenyl)-7-morpholinoimidazo[1,2-a]pyridine-6-yl)butan-1-amine | 8.7 | 7.9 | 6.2 | 8.9 | | 0.0502 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 115 | 2-(5-chloro-2,4-dimethoxyphenyl)-6-(piperazin-1-yl)imidazo[1,2-a]pyridine hydrochloride | 9.4 | 7.7 | 8.4 | 13 | | 0.0179 |
| 116 | 2-(5-chloro-2,4-dimethoxyphenyl-7-(1-(3-methoxypropyl)-1,2,3,6-tetrahydropyridin-4-yl)imidazo[1,2-a]pyridine | 6.1 | 7 | 6.6 | 11 | | 0.0738 |
| 117 | 2-(5-chloro-2,4-dimethoxyphenyl)-7-(1,4-dioxaspiro[4.5]dec-7-en-8-yl)imidazo[1,2a]pyridine | 3.5 | 3 | 5.2 | 7.7 | | 0.0633 |
| 118 | 2-(5-chloro-2,4-dimethoxylphenyl)-7-(3,6-dihydro-2H-pyran-4-yl)imidazo[1,2-a]pyridine | 6.9 | 9.1 | 6.9 | 11 | | 0.0661 |
| 119 | 4-(2-(5-chloro-2,4-dimethoxyphenyl)imidazo[1,2-a]pyridine-7-yl)cyclohexanone | 5.8 | 9.7 | 3.5 | 3.6 | | 0.0429 |
| 120 | 1-(4-(2-(5-chloro-2,4-dimethoxyphenyl)imidazo[1,2-a[pyridine-yl)5,6-dihydropyridin-1(2H)-yl)ethanone | 6.5 | 6.6 | 7.6 | 6.8 | | 0.0364 |
| 121 | 1-(2-(5-chloro-2,4-dimethoxyphenyl)imidazo[1,2-a]pyridine-6-yl)piperidin-4-amine | 8.1 | 18 | 6.8 | 6.8 | | 0.0514 |
| 122 | methyl (1-(2-(5-chloro-2,4-dimethoxyphenyl)imidazo[1,2-a]pyridine-7-yl)piperidin-4-yl)carbamate | 2.7 | 5.8 | 4.9 | 6.4 | 3.3 | 0.00814 |
| 123 | N-(1-(2-(5-chloro-2,4-dimethoxyphenyl)imidazo[1,2-a]pyridine-7-yl)piperidine-4-yl)pivalamide | 3.3 | 2.6 | 2 | 3.4 | 2.2 | 0.00771 |
| 124 | N-(1-(2-(5-chloro-2,4-dimethoxyphenyl)imidazo[1,2-a]pyridine-7-yl)piperidin-4-yl)acetamide | 2.2 | 1.9 | 3.1 | 3.1 | 1.9 | 0.00327 |
| 125 | 4-(2-(5-chloro-2,4-dimethoxypheny)imidazo[1,2-a]pyridine-7-yl)cyclohexanamine | 2.3 | 2.7 | 2.7 | 2.9 | 5 | 0.0651 |
| 126 | N-(1-(2-(5-chloro-2,4-dimethoxyphenyl)imidazo[1,2-a]pyridine-7-yl)piperidin-4-yl)cyclopropanesulfonamide | 2.1 | 1.9 | 1.4 | 1.8 | 3.1 | 0.014 |
| 127 | tert-butyl 4-(2-(5-chloro-2-(3-(dimethlamino)propoxy)-4-methoxyphenyl)imidazo[1,2-a]pyridine-7-yl)piperazine-1-carboxylate | 1.6 | 1.2 | 0.5 | 0.83 | 1.6 | 0.0995 |
| 128 | N-(1-(2-(5-chloro-2,4-dimethoxyphenyl)imidazo[1,2-a]pyridine-7-yl)piperidin-4-yl)methanesulfonamide | 1.5 | 4.5 | 0.58 | 1.1 | 1.8 | 0.00883 |
| 129 | 1-(2-(5-chloro-2,4-dimethoxyphenyl)imidazo[1,2-a]pyridine-7-yl)-N-pentylpiperidin-4-amine | 1.5 | 0.74 | 0.7 | 1.3 | 1.7 | 0.00841 |
| 130 | 3-(4-(2-(5-bromo-2,4-dimethoxyphenyl)imidazo[1,2-a]pyridine-7-yl)piperazin-l-yl)-N,N-dimethylpropan-1-amine | 2.7 | 2.8 | 4.6 | 6.6 | 2.6 | 0.003 |
| 131 | 4-(2-(4-(2-(5-bromo-2,4 dimethoxyphenyl)imidazo[1,2-a]pyridine-7-yl)piperazin-1-yl)ethyl)morpholine | 8.3 | 8.4 | 7.3 | 8.3 | 6.8 | 0.00349 |
| 132 | ethyl 3-(4-(2-(5-chloro-2,4-dimethoxyphenyl)imidazo[1,2-a]pyridine-7-yl)piperazin-1-yl)propanate | 11 | 9.8 | 7.6 | 22 | 9 | 0.0124 |
| 133 | 3-(4-(2-(5-chloro-2,4-dimethoxyphenyl)imidazo[1,2-a]pyridine-7-yl)piperazin-1-yl)propanoic acid | | | | | | 0.0137 |
| 134 | 2-(4-(2-(5-chloro-2,4-dimethoxyphenyl)imidazo[1,2-a]pyridine-7-yl)-5,6-dihydropyridin-1(2H)-yl)ethanol | 5 | 6.8 | 3.8 | 5.4 | 5.3 | 0.0576 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 135 | 2-(5-chloro-2,4-dimethoxyphenyl)-7-(4-(2-(piperidin-1-yl)ethy)piperazin-1-yl)imidazo[1,2-a]pyridine | 3 | 2.4 | 4.8 | 2.8 | 2.6 | 0.0128 |
| 136 | tert-butyl 4-(2-(4-(2-(5-chloro-2,4-dimethoxyphenyl)imidazo[1,2-a]pyridine-7-yl)piperazin-1-yl)ethyl)piperazine-1-carboxylate | 1.5 | 1.5 | 1.8 | 1.8 | 2.2 | 0.0166 |
| 137 | 3-(4-(2-(5-chloro-2,4-dimethoxyphenyl)imidazo[1,2-a]pyridine-7-yl)piperazin-1-yl)propanamide | 24 | 14 | 13 | 14 | 12 | 0.00454 |
| 138 | 1-(2-(5-chloro-2,4-dimethoxyphenyl)imidazo[1,2-a]pyridine-7-yl)imidazolidin-2-one | 5.2 | 16 | 5.5 | 2.2 | 3.6 | 0.0201 |
| 139 | 3-(4-chloro-5-methoxy-2-(7-(piperazin-1-yl)imidazo[1,2-a]pyridine-2-yl)phenoxy)-N,N-dimethylpropan-1-amine | 1.7 | 2.4 | 1.6 | 2.5 | 2.1 | 0.025 |
| 140 | ethyl 3-(4-(2-(5-chloro-2,4-dimethoxyphenyl)imidazo[1,2-a]pyridine-7-yl)-5,6-dihydropyridin-1(2H)-yl)propanoate | 25 | 16 | 27 | 56 | 12 | 0.0578 |
| 141 | 3-(4-(2-(5-chloro-2,4-dimethoxyphenyl)imidazo[1,2-a]pyridine-7-yl)-5,6-dihydropyridin-1(2H)-yl)propanoic acid | | | | | | 0.0777 |
| 142 | 2-(5-chloro-2,4-dimethoxyphenyl)-7-(4-(2-(piperazin-1-yl)ethyl)piperazin-1-yl)imidazo[1,2-a]pyridine | 6.6 | 8.2 | 7.1 | 7.8 | 8.7 | 0.00785 |
| 143 | 2-(5-chloro-2,4-dimethoxyphenyl)-7-(4-(2-(pyrrolidin-1-yl)ethyl)piperazin-1-yl)imidazo[1,2-a]pyridine | 4 | 8.1 | 8.5 | 2.7 | 4.4 | 0.0044 |
| 144 | 4-(2-(4-(2-(5-chloro-2,4-dimethoxyphenyl)imidazo[1,2-a]pyridine-7-yl)-5,6-dihydropyridin-1(2H)-yl)ethyl)morpholine | 3.9 | 5.9 | 7 | 6.3 | 1.5 | 0.0191 |
| 145 | tert-butyl 4-(2-(5-chloro-2,4-dimethoxyphenyl)imidazo[1,2-a]pyrimidin-7-yl)piperazine-1-carboxylate | 1.9 | 3.1 | 2.8 | 2.8 | 1.5 | 0.0738 |
| 146 | 2-(5-chloro-2,4-dimethoxyphenyl)-7-(4-(cyclopropylsulfonyl)piperazin-1-yl)imidazo[1,2-a]pyrimidine hydrochloride | 0.49 | 0.69 | 1.4 | 4.2 | 0.24 | 0.0247 |
| 147 | 2-(5-chloro-2,4-dimethoxyphenyl)-7-(1-(2-(piperidin-1-yl)ethyl)-1,2,3,6-tetrahydropyridin-4-yl)imidazo[1,2-a]pyridine | 7 | 7.3 | 8.7 | 6 | 5.9 | 0.0295 |
| 148 | tert-butyl (1-(2-(5-chloro-2-(3-(dimethylamino)propoxy)-4-methoxyphenyl)imidazo[1,2-a]pyridine-7-yl)piperidin-4-yl)carbamate | 1.8 | 1.3 | 0.53 | 0.78 | 1.4 | 0.0373 |
| 149 | N-((1-(2-(5-chloro-2,4-dimethoxyphenyl)imidazo[1,2-a]pyridine-7-yl)piperidin-4-yl)methyl)cyclopropanesulfonamide | 2.5 | 2.3 | 1.9 | 4.8 | 2.4 | 0.00672 |
| 150 | 1-(2-(5-chloro-2-(3-(dimethylamino)propoxy)-4-methoxyphenyl)imidazo[1,2-a]pyridine-7-yl)piperidin-4-amine | 2.3 | 2.1 | 0.86 | 2.4 | 2.2 | 0.035 |
| 151 | 2-(5-chloro-2,4-dimethoxyphenyl)imidazo[1,2-a]pyridine-7-amine hydrochloride | 5.1 | 2.3 | 1.9 | 2.4 | 2.9 | 0.00827 |
| 152 | methyl 4-(2-(5-chloro-2-(3-(dimethylamino)propoxy)-4-methoxyphenyl)imidazo[1,2-a]pyridine-7-yl)piperazine-1-caboxylate | 6.4 | 7.1 | 1.9 | 5.3 | 2.7 | 0.0199 |
| 153 | 2-(5-chloro-2,4-dimethoxyphenyl)-7-(piperazin-1-yl)imidazo[1,2-a]pyrimidine | 10 | 8.6 | 5.3 | 11 | 4.1 | 0.0526 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 154 | 1-(4-(2-(5-chloro-2-(3-(dimethylamino)propoxy)-4-methoxyphenyl)imidazo[1,2-a]pyridine-7-yl)piperazin-1-yl)ethanone | 6.9 | 7.9 | 4.3 | 8.7 | 8 | 0.0135 |
| 155 | 3-(4-chloro-5-methoxy-2-(7-(4-(methylsulfonyl)piperazin-1-yl)imidazo[1,2-a]pyridine-2-yl)phenoxy-N,N-dimethylpropan-1-amine | 7.5 | 5.8 | 5.5 | 7.5 | 3.8 | 0.0127 |
| 156 | 1-(4-(2-(5-chloro-2-(3-(dimethylamino)propoxy)-4-methoxyphenyl)imidazo[1,2-a]pyridine-7-yl)piperazin-1-yl)-2,2-dimethylpropan-1-one | 6.3 | 6.2 | 4.4 | 7.2 | 5.8 | 0.0344 |
| 157 | tert-butyl (3-((2-(5-chloro-2,4-dimethoxyphenyl)imidazo[1,2-a]pyridine-7-yl)amino)-3-oxopropyl)carbamate | 7.5 | 6.8 | 4.7 | 7.1 | 6.2 | 0.0628 |
| 158 | 3-(4-(2-(5-chloro-2,4-dimethoxyphenyl)imidazo[1,2-a]pyridine-7-yl)piperazin-1-yl)-N-(2-(dimethylamino))ethyl)propanamide | 9.3 | 9.4 | 7.7 | 14 | 9.8 | 0.00353 |
| 159 | methyl 4-(2-(5-chloro-2,4-dimethoxyphenyl)imidazo[1,2-a]pyrimidin-7-yl)piperazine-1-carboxylate | 2.7 | 3.2 | 3.4 | 3.7 | 4.7 | 0.0157 |
| 160 | 3-(4-chloro-2-(7-(4-(cyclopropylsulfonyl)piperazin-1-yl)imidazo[1,2-a]pyridine-2-yl)-5-methoxyphenoxy)-N,N-dimethylpropan-1-amine | 1.4 | 1.2 | 1.5 | 2.9 | 1.9 | 0.0277 |
| 161 | tert-butyl (2-((2-(5-chloro-2,4-dimethoxyphenyl)imidazo[1,2-a]pyridine-7-yl)amino)-2-oxoethyl)carbamate | 8.8 | 7 | 8.4 | 7.8 | 8.7 | 0.0379 |
| 162 | N-(1-(2-(5-chloro-2-(3-(dimethylamino)propoxy)-4-methoxyphenyl)imidazo[1,2-a]pyridine-7-yl)piperidin-4-yl)pivalamide | 2.8 | 3.3 | 2.1 | 5 | 2.1 | 0.0211 |
| 163 | N-(1-(2-(5-chloro-2-(3-(dimethylamino)propoxy)-4-methoxyphenyl)imidazo[1,2-a]pyridine-7-yl)piperidin-4-yl)cyclopropanesulfonamide | 6.4 | 5.9 | 2.7 | 5.6 | 3.4 | 0.0206 |
| 164 | N-(1-(2-(5-chloro-2-(3-(dimethylamino)propoxy)-4-methoxyphenyl)imidazo[1,2-a]pyridine-7-yl)piperidin-4-yl)methanesulfonamide | 10 | 9 | 8.6 | 7.2 | 8.8 | 0.0211 |
| 165 | 1-(2-(5-chloro-2-(3-(dimethylamino)propoxy)-4-methoxyphenyl)imidazo[1,2-a]pyridine-7-yl)-N-pentylpiperidin-4-amine | 2.2 | 1.7 | 1.7 | 2.1 | 2.2 | 0.0593 |
| 166 | 2-amino-N-(2-(5-chloro-2,4-dimethoxyphenyl)imidazo[1,2-a]pyridine-7-yl)acetamide | 7.1 | 6.1 | 22 | 7.9 | 6.5 | 0.031 |
| 167 | 1-(2-(5-chloro-2,4-dimethoxphenyl)imidazo[1,2-a]pyridine-7-yl)-3-(3-(dimethylamino)propyl)imidazolidin-2-one | 6.4 | 6.8 | 6.5 | 6.9 | 3.9 | 0.0124 |
| 168 | 3-amino-N-(2-(5-chloro-2,4-dimethoxyphenyl)imidazo[1,2-a]pyridine-7-yl)propanamide | 39 | 1.4 | 2.7 | 9.5 | 6.2 | 0.0283 |
| 169 | 2-(5-chloro-2,4-dimethoxyphenyl)-7-(4-(methylsulfonyl)piperazin-1-yl)imidazo[1,2-a]pyridine | 1.8 | 2.1 | 4.7 | 2.8 | 2.2 | 0.0101 |
| 170 | 2-(5-chloro-2,4-dimethoxyphenyl)-7-(4-(propylsulfonyl)piperazin-1-yl)imidazo[1,2-a]pyridine | 1.7 | 2.1 | 1.9 | 2.6 | 1.6 | 0.0219 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 171 | 4-(2-(5-chloro-2,4-dimethoxyphenyl)imidazo[1,2-a]pyridine-7-yl)-N,N-dimethylpiperazine-1-sulfonamide | 0.83 | 0.94 | 1.2 | 0.84 | 2 | 0.0135 |
| 172 | 2-(5-chloro-2,4-dimethoxyphenyl)-7-(4-(ethysulfonyl)piperazin-1-yl)imidazo[1,2-a]pyridine | 1.9 | 1.2 | 1.8 | 1.8 | 1.6 | 0.0125 |
| 173 | N-(1-(2-(5-chloro-2,4-dimethoxyphenyl)imidazo[1,2-a]pyridine-7-yl)piperidin-4-yl)ethanesulfonamide | 1.5 | 1.9 | 0.53 | 0.99 | 1.6 | 0.00961 |
| 174 | N-(1-(2-(5-chloro-2,4-dimethoxyphenyl)imidazo[1,2-a]pyridine-7-yl)piperidin-4-yl)propane-1-sulfonamide | 3 | 1.8 | 1.7 | 2 | 2.3 | 0.0104 |
| 175 | N-(1-(2-(5-chloro-2,4-dimethoxyphenyl)imidazo[1,2-a]pyridine-7-yl)piperidin-4-yl)-1-phenylmethanesulfonamide | 2 | 1.5 | 1.9 | 2 | 1.8 | 0.0263 |
| 176 | N-(1-(2-(5-chloro-2,4-dimethoxyphenyl)imidazo[1,2-a]pyridine-7-yl)piperidin-4-yl)-1,1,1-trifluoromethanesulfonamide | 0.51 | 0.55 | 0.36 | 0.53 | 0.75 | 0.0641 |
| 177 | 2-(5-chloro-2,4-dimethoxyphenyl)-7-(4-(methylsulfonyl)piperazin-1-yl)imidazo[1,2-a]pyrimidine | 3.8 | 6 | 8 | 11 | 2.5 | 0.0408 |
| 178 | 2-(5-chloro-2,4-dimethoxyphenyl)-7-(4-(isopropylsulfonyl)piperazin-1-yl)imidazo[1,2-a]pyridine | 1 | 1.5 | 1.7 | 2.1 | 0.74 | 0.0143 |
| 179 | 7-(4-(benzylsulfonyl)piperazin-1-yl)-2-(5-chloro-2,4-dimethoxyphenyl)imidazo[1,2-a]pyridine | 2.1 | 1.6 | 1.8 | 1.8 | 1.6 | 0.0322 |
| 180 | 4-(2-(5-chloro-2,4-dimethoxyphenyl)imidazo[1,2-a]pyrimidin-7-yl)-N,N-dimethylpiperazine-1-sulfonamide | 1.1 | 1.5 | 1.7 | 2.6 | 1.6 | 0.0241 |
| 181 | 7-(4-(N,N-dimethylamino-sulfonylamino)piperidin-1-yl)-2-(5-chloro-2,4-dimethoxy-phenyl)imidazo[1,2-a]pyridine | 0.76 | 1.6 | 0.35 | 0.38 | 1.5 | 0.0139 |
| 182 | 2-(1-(2-(5-chloro-2,4-dimethoxyphenyl)imidazo[1,2-a]pyridine-7-yl)piperidin-4-yl)isothiazolidine 1,1-dioxide | 1.7 | 1.9 | 1.8 | 2.6 | 1.5 | 0.00697 |
| 183 | methyl(2-(5-chloro-2,4-dimethoxyphenyl)imidazo[1,2-a]pyridine-yl)carbamate | 1.8 | 2.1 | 2 | 1.8 | 1.9 | 0.0241 |
| 184 | tert-butyl 4-(2-(5-chloro-2,4-dimethoxyphenyl)imidazo[1,2-a]pyridine-7-yl)-]1,4-diazepane-1-carboxylate hydrobromide | 3.8 | 5.7 | 2.2 | 4.9 | 2.5 | 0.0285 |
| 185 | N-(1-(2-(5-chloro-2,4-dimethoxyphenyl)imidazo[1,2-a]pyridine-7-yl)piperdin-4-yl)-2-methylpropane-1-sulfonamide | 1.6 | 1.1 | 2 | 1.9 | 1.4 | 0.0127 |
| 186 | 3-(4-chloro-5-methoxy-2-(7-(piperazin-1-yl)imidazo[1,2-a]pyrimidin-2-yl)phenoxy)-N,N-dimethylpropan-1-amine | 22 | 17 | 7.3 | 35 | 12 | 0.0619 |
| 187 | 2-(5-chloro-2,4-dimethoxyphenyl)-7-(4-(cyclopropylsulfonyl)-1,4-diazepan-1-yl)imidazo[1,2-a]pyridine | 2.1 | 1.9 | 2.1 | 5 | 1.4 | 0.00574 |
| 188 | 2-(5-chloro-2,4-dimethoxyphenyl)-7-(4-((trifluoromethyl)sulfony1)-1,4-diazepan-1-yl)imidazo[1,2-a]pyridine | 1.6 | 1.6 | 1.5 | 1.4 | 1.6 | 0.0369 |
| 189 | 2-(5-chloro-2,4-dimethoxyphenyl)-7-(1,4-diazepan-1-yl)imidazo[1,2-a]pyridine | 3.5 | 3 | 2 | 6.3 | 2.9 | 0.00433 |
| 190 | 2-(5-chloro-2,4-dimethoxyphenyl)-7-(4-(ethylsulfonyl)piperazin-1-yl)imidazo[1,2-a]pyrimidine | 1.8 | 2.3 | 2.7 | 4.5 | 1 | 0.0306 |
| 191 | 2-(5-chloro-2,4-dimethoxyphenyl)-7-(4-(propylsulfonyl)piperazin-1-yl)imidazo[1,2-a]pyrimidine | 1.5 | 1.9 | 2 | 3.2 | 1.5 | 0.0293 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 192 | N-(1-(2-(5-chloro-2,4-dimethoxyphenyl)imidazo[1,2-a]pyrimidin-7-yl)piperidin-4-yl)methanesulfonamide | 10 | 10 | 5.1 | 5.3 | 10 | 0.0148 |
| 193 | N-(1-(2-(5-chloro-2,4-dimethoxyphenyl)imidazo[1,2-a]pyrimidin-7-yl)piperidin-4-yl)propane-1-sulfonamide | 10 | 10 | 10 | 10 | 6.7 | 0.0327 |
| 194 | diethyl (2-(4-(2-(5-chloro-2,4-dimethoxyphenyl)imidazo[1,2-a]pyridine-7-yl)-5,6-dihydropyridin-1(2H)-yl)ethyl)phosphonate | 9 | 8.6 | 10 | 10 | 5.7 | 0.0696 |
| 195 | dimethyl (4-(2-(5-chloro-2,4-dimethoxyphenyl)imidazo[1,2-a]pyridine-7-yl)-5,6-dihydropyridin-1(2H)-yl)phosphonate | 0.7 | 0.93 | 2.8 | 5.5 | 0.51 | 0.0375 |
| 196 | 4-(2-(5-chloro-2-(3-(dimethylamino)propoxy)-4-methoxyphenyl)imidazo[1,2-a]pyridine-7-yl)-N,N-dimethylpiperazine-1-sulfonamide | 2.1 | 2.2 | 2.4 | 2.8 | 1.9 | 0.0147 |
| 197 | 3-(4-chloro-2-(7-(4-(isopropylsulfonyl)piperazin-1-yl)imidazo[1,2-a]pyridine-2-yl)-5-methoxyphenoxy)-N,N-dimethylpropan-1-amine | 3.4 | 3.8 | 2.9 | 2.9 | 2.3 | 0.0144 |
| 198 | dimethyl (1-(2-(5-chloro-2,4-dimethoxyphenyl)imidazo[1,2-a]pyridine-7-yl)piperidin-4-yl)phosphoramidate | 3.2 | 5.7 | 1.6 | 3.5 | 3.7 | 0.00435 |
| 199 | 3-(4-chloro-2-(7-(4-(ethylsulfonyl)piperazin-1-yl)imidazo[1,2-a]pyridine-2-yl)-5-methoxyphenoxy)-N,N-dimethylpropan-1-amine | 5.2 | 6.4 | 4.8 | 3.9 | 3 | 0.0168 |
| 200 | 4-(2-(5-chloro-2,4-dimethoxyphenyl)imidazo[1,2-a]pyridine-7-yl)-N,N-dimethyl-1,4-diazepane-1-sulfonamide | 1.6 | 2 | 1.7 | 3 | 1.3 | 0.00674 |
| 201 | 2-(5-chloro-2,4-dimethoxyphenyl)-7-(4-(methylsulfonyl)-1,4-diazepan-1-yl)imidazo[1,2-a]pyridine | 2.2 | 2.7 | 3 | 3.2 | 1.9 | 0.0064 |
| 202 | diethyl (2-(4-(2-(5-chloro-2,4-dimethoxyphenyl)imidazo[1,2-a]pyridine-7-yl)piperazin-1-yl)ethyl)phosphonate | 10 | 10 | 7.2 | 5.6 | 8 | 0.0064 |
| 203 | dimethyl (4-(2-(5-chloro-2,4-dimethoxyphenyl)imidazo[1,2-a]pyridine-7-yl)piperazin-1-yl)phosphonate | 3.9 | 5.1 | 4 | 6 | 1.8 | 0.00177 |
| 204 | 2-(5-chloro-2,4-dimethoxyphenyl)-7-(4-(cyclopentylsulfonyl)piperazin-1-yl)imidazo[1,2-a]pyrimidine hydrochloride | 0.75 | 1 | 1.7 | 4.5 | 0.6 | 0.0448 |
| 205 | 2-(5-chloro-2,4-dimethoxyphenyl)-7-(4-(isopropylsulfonyl)piperazin-1-yl)imidazo[1,2-a]pyrimidine | 1.2 | 1.9 | 2 | 3.1 | 0.62 | 0.0291 |
| 206 | 2-(5-chloro-2,4-dimethoxyphenyl)-7-(4-(ethylsulfonyl)-1,4-diazepan-1-yl)imidazo[1,2-a]pyridine | 2.6 | 3.3 | 2.3 | 2.9 | 1.6 | 0.00561 |
| 207 | dimethyl (4-(2-(5-chloro-2,4-dimethoxyphenyl)imidazo[1,2-a]pyridine-7-yl)-1,4-diazepan-1-yl)phosphonate | 10 | 10 | 10 | 10 | 10 | 0.0113 |
| 208 | N$^1$-(2-(5-chloro-2,4-dimethoxyphenyl)-8-fluoro-7-morpholinoimidazo[1,2-a]pyridine-6-yl)ethane-1,2-diamine | 10 | 10 | 8.4 | 5.9 | 8.4 | 0.0291 |
| 209 | 3-(2-(7-(1,4-diazepan-1-yl)imidazo[1,2-a]pyridine-2-yl)-4-chloro-5-methoxyphenoxy)-N,N-dimethylpropan-1-amine | 3 | 3.7 | 1.2 | 3.2 | 2.7 | 0.00207 |
| 210 | diethyl (2-(4-(2-(5-chloro-2,4-dimethoxyphenyl)imidazo[1,2-a]pyridine-7-yl)-1,4-diazepan-1-yl)ethyl)phosphonate | 10 | 10 | 7.2 | 5.5 | 4.5 | 0.0029 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 211 | tert-butyl 4-(2-(5-chloro-2-(3-(dimethylamino)propxy)-4-methoxyphenyl)imidazo[1,2-a]pyridine-7-yl)-1,4-diazepane-1-carboxylate | 2.9 | 2.4 | 1.4 | 1.4 | 0.8 | 0.0563 |
| 212 | 3-(4-chloro-2-(7-(4-(cyclopropylsulfonyl)-1,4-diazepan-1-yl)imidazo[1,2-a]pyridine-2-yl)-5-methoxyphenoxy)-N,N-dimethylpropan-1-amine | 8.1 | 8.6 | 5.8 | 6 | 4.2 | 0.0161 |
| 213 | 3-(4-chloro-5-methoxy-2-(7-(4-(methylsulfonyl)-1,4-diazepan-1-yl)imidazo[1,2-a]pyridine-2-yl)phenoxy)-N,N-dimethylpropan-1-amine | 10 | 5.5 | 7.4 | 10 | 9.1 | 0.0145 |
| 214 | diethyl (2-(4-(2-(5-chloro-2-(3-(dimethylamino)propoxy)-4-methoxyphenyl)imidazo[1,2-a]pyridine-7-yl)-1,4-diazepan-1-yl)ethyl)phosphonate | 10 | 10 | 10 | 10 | 10 | 0.0106 |
| 215 | 3-(4-chloro-2-(7-(4-(ethylsulfonyl-1,4-diazepan-1-yl)imidazo[1,2-a]pyridine-2-yl)-5-methoxyphenoxy)-N,N-dimethylpropan-1-amine | 10 | 10 | 6.4 | 7.4 | 6.5 | 0.0135 |
| 216 | 4-(2-(5-chloro-2-(3-(dimethylamino)propoxy)-4-methoxyphenyl)imidazo[1,2-a]pyrridine-7-yl)-N,N-dimethyl-1,4-diazepane-1-sulfonamide | 1.9 | 3.3 | 1.5 | 2.7 | 1.6 | 0.0194 |
| 217 | 6-bromo-2-(5-chloro-2,4-dimethoxyphenyl)-7-(piperazin-1-yl)imidazo[1,2-a]pyridine | 7.2 | 5.5 | 4.9 | 4.3 | 3.4 | 0.0416 |
| 218 | dimethyl (4-(2-(5-chloro-2,4-dimethoxyphenyl)imidazo[1,2-a]pyrimidin-7-yl)pipeiazin-1-yl)phosphonate | 6.5 | 5.6 | 10 | 10 | 3.4 | 0.0111 |
| 219 | diethyl (2-(4-(2-(5-chloro-2-(3-(dimethylamino)propoxy)-4-methoxyphenyl)imidazo[1,2-a]pyridine-7-yl)piperazin-1-yl)ethyl)phosphonate | 10 | 10 | 7.4 | 10 | 7.6 | 0.0201 |
| 220 | 6-bromo-2-(5-chloro-2,4-dimethoxyphenyl)-7-(piperazin-1-yl)imidazo[1,2-a]pyrimidine | 2.6 | 2.4 | 3.1 | 3.1 | 2.4 | 0.0262 |
| 221 | tert-butyl 4-(6-((2-aminoethyl)amino)-2-(5-chloro-2,4-dimethoxyphenyl)imidazo[1,2-a]pyrimidin-7-yl)piperazine-1-carboxylate | 10 | 5.4 | 4.9 | 5.6 | 9.5 | 0.0118 |
| 222 | $N^1$-(2-(5-chloro-2,4-dimethoxyphenyl)-7-(4-(cyclopropylsulfonyl)piperazin-1-yl)imidazo[1,2-a]pyrimidin-6-yl)ethane-1,2-diamine | 10 | 10 | 10 | 10 | 10 | 0.00597 |
| 223 | $N^1$-(2-(5-chloro-2,4-dimethoxyphenyl)-7-(piperazin-1-yl)imidazo[1,2-a]pyrimidin-6-y)ethane-1,2-diamine | 10 | 10 | 10 | 10 | 10 | 0.00866 |
| 224 | N-(2-((2-(5-chloro-2,4-dimethoxyphenyl)-7-morpholinoimidazo[1,2-a]pyridine-6-yl)amino)ethyl)acetamide | 10 | 10 | 10 | 10 | 10 | 0.0337 |
| 225 | $N^1$-(2-5-chloro-2,4-dimethoxyphenyl)-7-(4-(cyclopropylsulfonyl)piperazin-1-yl)imidazo[1,2-a]pyridine-6-yl)ethane-1,2-diamine | 10 | 9.6 | 7.3 | 7.3 | 6.9 | 0.0022 |
| 226 | 3-(4-chloro-2-(7-(4-(isopropylsulfonyl)piperazin-1-yl)imidazo[1,2-a]pyrimidin-2-yl)-5-methoxyphenoxy)-N,N-dimethylpropan-1-amine | 10 | 7.8 | 8.9 | 10 | 5.5 | 0.0655 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 227 | 3-(4-chloro-2-(7-(4-(cyclopentylsulfonyl)piperazin-1-yl)imidazo[1,2-a]pyrimidin-2-yl)-5-methoxyphenoxy)-N,N-dimethylpropan-1-amine | 7 | 5.2 | 5.7 | 6.2 | 5.4 | 0.0382 |
| 228 | 2-(5-chloro-2-methoxy-4-methylphenyl)-7-(piperazin-1-yl)imidazo[1,2-a]pyridine dihydrochloride | 2.8 | 2 | 1.6 | 2.6 | 2.3 | 0.033 |
| 229 | 2-(5-chloro-2-methoxy-4-methylphenyl)-7-(4-(cyclopropylsulfonyl)piperazin-1-yl)imidazo[1,2-a]pyridine | 1.9 | 2.1 | 2.3 | 3.8 | 0.8 | 0.0775 |
| 230 | 4-(2-(5-chloro-2-methoxy-4-methylphenyl)imidazo[1,2-a]pyridine-7-yl)morpholine | 4.4 | 4 | 2.8 | 3.5 | 1.6 | 0.0183 |
| 231 | 1-(2-(5-chloro-2,4-dimethoxyphenyl)imidazo[1,2-a]pyridine-7-yl)piperidin-4-ol | 10 | 10 | 6.7 | 9.1 | 3.9 | 0.00488 |
| 232 | tert-butyl 4-(2-(5-chloro-2,4-dimethoxyphenyl)imidazo[1,2-a]pyridine-7-yl)piperazine-1-carboxylate | 1.5 | 1.7 | 1.1 | 1.5 | 0.73 | 0.0291 |
| 233 | 2-(4,5-dichloro-2-methoxyphenyl)-7-(pyrrolidin-1-yl)imidazo[1,2-a]pyridine | 2.6 | 2.7 | 2.7 | 2.8 | 1.8 | 0.085 |
| 234 | 2-(4-chloro-2-(7-(4-(cyclopropylsulfonyl)piperazin-1-yl)imidazo[1,2-a]pyridine-2-yl)-5-methoxyphenoxy)ethanamine | 10 | 5.3 | 6.2 | 6.1 | 6.4 | 0.0418 |
| 235 | (4-(2-(5-chloro-2,4-dimethoxyphenyl)imidazo[1,2-a]pyridine-7-yl)piperazin-2-yl)methanol | 5.3 | 6.6 | 4.3 | 6.7 | 5.6 | 0.0115 |
| 236 | (4-(2-(5-chloro-2,4-dimethoxyphenyl)imidazo[1,2-a]pyridine-7-yl)-1-(cyclopropylsulfonyl)piperazin-2-yl)methanol | 4.8 | 4.4 | 4.1 | 4 | 3.3 | 0.00655 |
| 237 | methyl 4-(4-(2-(5-chloro-2,4-dimethoxyphenyl)imidazo[1,2-a]pyridine-7-yl)piperazin-1-yl)butanoate | 10 | 10 | 10 | 10 | 10 | 0.0113 |
| 238 | (4-(2-(5-chloro-2,4-dimethoxyphenyl)imidazo[1,2-a]pyridine-7-yl)piperazin-1-yl)(cyclopropyl)methanone | 2.5 | 2.9 | 2.4 | 3 | 1.6 | 0.00416 |
| 239 | 2-(5-chloro-2,4-dimethoxyphenyl)-7-(4-cyclopentylpiperazin-1-yl)imidazo[1,2-a]pyridine | 1.5 | 1.5 | 1.7 | 2.1 | 1.8 | 0.021 |
| 240 | 4-(4-(2-(5-chloro-2,4-dimethoxyphenyl)imidazo[1,2-a]pyridine-7-yl)piperazin-1-yl)butanoic acid | 10 | 10 | 10 | 10 | 10 | 0.0063 |
| 241 | (4-(2-(5-chloro-2,4-dimethoxyphenyl)imidazo[1,2-a]pyridine-7-yl)piperazin-1-yl)(cyclopentyl)methanone | 2.3 | 2.4 | 1.5 | 2.5 | 1.6 | 0.00768 |
| 242 | (4-(2-(5-chloro-2,4-dimethoxyphenyl)imidazo[1,2-a]pyrimidin-7-yl)piperazin-1-yl)(cyclopropyl)methanone hydrochloride | 10 | 10 | 10 | 10 | 6.3 | 0.0154 |
| 243 | (4-(2-(5-chloro-2,4-dimethoxyphenyl)imidazo[1,2-a]pyrimidin-7-yl)piperazin-1-yl)(cyclopentyl)methanone hyrochloride | 4.7 | 5.8 | 4.8 | 6.1 | 3.3 | 0.0183 |
| 244 | (S)-N-(2-(5-chloro-2,4-dimethoxyphenyl)imidazo[1,2-a]pyridine-7-yl)pyrrolidine-2-carboxamide | 10 | 10 | 9.8 | 8.8 | 5.2 | 0.0533 |

TABLE 3-continued

| No. | Compound Name | A549 | HCT-116 | HFL1 | CCD-18Co | PC14 | IC50 (μM) Suv 39H2 assay |
|-----|---------------|------|---------|------|----------|------|--------------------------|
| 245 | 2-((4-(2-(5-chloro-2,4-dimethoxyphenyl)imidazo[1,2-a]pyridine-7-yl)-1-(cyclopropylsulfonyl)piperazin-2-yl)methoxy)-N,N-dimethylethanamine | 5.5 | 9.4 | 5.4 | 5 | 5.1 | 0.00863 |
| 246 | 4-(2-(5-chloro-2,4-dimethoxyphenyl)imidazo[1,2-a]pyridine-7-yl)benzoic acid | 10 | 10 | 10 | 10 | 10 | 0.0143 |
| 247 | (S)-2,6-diamino-N-(2-(5-chloro-2,4-dimethoxyphenyl)imidazo[1,2-a]pyridine-7-yl)hexanamide | 10 | 10 | 10 | 10 | 5.7 | 0.0543 |
| 248 | 4-(2-(5-chloro-2,4-dimethoxyphenyl)imidazo[1,2-a]pyridine-7-yl)-N-(pyrrolidin-2-ylmethyl)benzamide | 4.6 | 2.3 | 5.7 | 3.1 | 2.6 | 0.0157 |
| 249 | 4-(2-(5-chloro-2,4-dimethoxyphenyl)imidazo[1,2-a]pyridine-7-yl)-N-(pyrrolidin-3-yl)benzamide | 5.4 | 3.7 | 5.4 | 5.2 | 4.8 | 0.035 |
| 250 | (S)-2-amino-N-(2-(5-chloro-2,4-dimethoxyphenyl)imidazo[1,2-a]pyridine-7-yl)-3-(1H-indol-3-yl)propanamide | 6.6 | 6.9 | 3.6 | 4 | 4.2 | 0.0427 |
| 251 | 4-(2-(5-chloro-2,4-dimethoxyphenyl)imidazo[1,2-a]pyridine-7-yl)-N-(piperidin-3-ylmethyl)benzamide | 9.7 | 5.8 | 8.3 | 10 | 5.4 | 0.0308 |
| 252 | (S)-2-amino-N-(2-(5-chloro-2,4-dimethoxyphenyl)imidazo[1,2-a]pyridine-7-yl)-3-methylbutanamide | 7.8 | 5.4 | 5.9 | 4.7 | 6.3 | 0.0423 |
| 253 | (S)-tert-butyl (1-((2-(5-chloro-2,4-dimethoxyphenyl)imidazo[1,2-a[pyridine-7-y])amino)-1-oxopropan-2-yl)carbamate | 10 | 10 | 6.5 | 6.7 | 6.9 | 0.0582 |
| 254 | (4-(2-(5-chloro-2,4-dimethoxyphenyl)imidazo[1,2-a]pyridine-7-yl)phenyl)(piperazin-1-yl)methanone | 2.7 | 2.6 | 2.8 | 3.1 | 0.99 | 0.0383 |
| 255 | 2-(5-chloro-4-methoxy-2-((methylthio)methoxy)phenyl)-7-(4-(cyclopropylsulfonyl)piperazin-1-yl)imidazo[1,2-a]pyridine | 2.5 | 2.3 | 1.7 | 1.9 | 1.5 | 0.00672 |
| 256 | N-(3-amino-2-hydroxypropyl)-4-(2-(5-chloro-2,4-dimethoxyphenyl)imidazo[1,2-a]pyridine-7-yl)benzamide | 10 | 10 | 10 | 10 | 10 | 0.0217 |
| 257 | tert-butyl ((2S,3R)-1-((2-(5-chloro-2,4-dimethoxyphenyl)imidazo[1,2-a]pyridine-7-yl)amino)-3-methyl-1-oxopentan-2-yl)carbamate | 5 | 5.5 | 5.2 | 5.1 | 3 | 0.0435 |
| 258 | (2S,3R)-2-amino-N-(5-chloro-2,4-dimethoxyphenyl)imidazo[1,2-a]pyridine-7-yl)-3-methylpentanamide | 5.8 | 7.6 | 6.8 | 4.6 | 5.7 | 0.0639 |
| 259 | (4-aminopiperidin-1-yl)(4-(2-(5-chloro-2,4-dimethoxyphenyl)imidazo[1,2-a]pyridine-7-yl)phenyl)methanone | 10 | 7.3 | 8.6 | 10 | 7.9 | 0.0586 |
| 260 | 2-(5-chloro-2-ethyl-4-methoxyphenyl)-7-(piperazin-1-yl)imidazo[1,2-a]pyridine | 6.1 | 3.4 | 3.6 | 3.5 | 3.4 | 0.0344 |
| 261 | 2-(5-chloro-2-ethyl-4-methoxyphenyl)-7-(4-(cyclopropylsulfonyl)piperazin-1-yl)imidazo[1,2-a]pyridine | 0.12 | 0.18 | 0.18 | 0.36 | 0.059 | 0.0966 |
| 262 | (4-(2-(5-chloro-4-methoxy-2-methylphenyl)imidazo[1,2-a]pyridine-7-yl)-1-(cyclopropylsulfonyl)piperazin-2-yl)methanol | 2.4 | 3.2 | 3.2 | 5.5 | 1.1 | 0.0453 |
| 263 | (S)-N-(2-(5-chloro-2,4-dimethoxphenyl)imidazo[1,2-a]pyridine-7-yl)-1-methylpyrrolidine-2-carboxamide | 1.8 | 0.99 | 1.8 | 1.4 | 1.7 | 0.065 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 264 | 2-((4-(2-(5-chloro-4-methoxy-2-metthylphenyl)imidazo[1,2-a]pyridine-7-yl)-1-(cyclopropylsulfonyl)piperazin-2-yl)methoxy)-N,N-dimethylethanamine | 5.6 | 8.5 | 4.7 | 5 | 4.5 | 0.07 |
| 265 | N-(3-aminopropyl)-4-(2-(5-chloro-2,4-dimethoxyphenyl)imidazo[1,2-a]pyridine-7-yl)benzamide | 5.5 | 5.2 | 4.7 | 7.3 | 4.2 | 0.036 |
| 266 | (2S,3S)-N-(2-(5-chloro-2,4-dimethoxyphenyl)imidazo[1,2-a]pyridine-7-yl)-3-methyl-2-(methylamino)pentanamide | 1.5 | 2.8 | 1.2 | 1.3 | 1.5 | 0.0454 |
| 267 | 4-(2-(5-chloro-2,4-dimethoxyphenyl)imidazo[1,2-a]pyridin-7-yl)-N-(piperidin-4-ylmethyl)benzamide | 10 | 10 | 10 | 10 | 10 | 0.0458 |
| 268 | 4-(2-(5-chloro-2,4-dimethoxyphenyl)imidazo[1,2-a]pyridin-7-yl)-N-(piperidin-4-yl)benzamide | 4.3 | 2.8 | 3.8 | 4.3 | 3 | 0.0383 |
| 269 | tert-butyl (2-((2-(4-(2-(5-chloro-2,4-dimethoxyphenyl)imidazo[1,2-a]pyridin-7-yl)benzamido)ethyl)amino)ethyl)carbamate | 1.2 | 0.75 | 1.3 | 0.87 | 0.94 | 0.0408 |
| 270 | N-(1H-imidazol-2-yl)methyl)-(2-(5-chloro-2,4-dimethoxyphenyl)imidazo[1,2-a]pyridin-7-yl)aniline | 0.99 | 1 | 0.89 | 1.7 | 0.45 | 0.0199 |
| 271 | tert-butyl 4-(3-bromo)-2-(5-chloro-2,4-dimethoxyphenyl)imidazo[1,2-a]pyridin-7-yl)piperazine-1-carboxylate | 1.3 | 1.5 | 1.2 | 1.4 | 0.57 | 0.0267 |
| 272 | (S)-N-(2-(5-chloro-2,4-dimethoxyphenyl)imidazo[1,2-a]pyridin-7-yl)-2-(dimethylamino)-3-methylbutanamide | 0.86 | 2.9 | 0.45 | 0.47 | 0.98 | 0.0961 |
| 273 | N-(4-(2-(5-chloro-2,4-dimethethoxyphenyl)imidazo[1,2-a]pyridin-7-yl)phenyl)-2-(methylamino)acetamide hydrochloride | 1.5 | 0.86 | 1.2 | 1.1 | 1.1 | 0.0801 |
| 274 | (S)-2-amino-1-(2-(5-chloro-2,4-dimethoxyphenyl) imidazo[1,2-a]pyridin-7-yl)phenyl)propane-1-one hydrochloride | 1.2 | 1.6 | 1.4 | 1.5 | 0.74 | 0.0995 |
| 275 | tert-butyl 4-(2-(5-chloro-2,4-dimethoxyphenyl) imidazo[1,2-a]pyridin-7-yl)-2-methylpiperazine-1 carboxylate | 1.3 | 1.4 | 1.1 | 1.4 | 0.87 | 0.00333 |
| 276 | 2-(5-chloro-2,4-dimethoxyphenyl)-7-(4-(pyridin-2-yl)piperazin-1-yl)imidazo[1,2-a]pyridine | 1.2 | 0.71 | 0.69 | 1.1 | 1.2 | 0.00774 |
| 277 | (methyl (4-((2-(5-chloro-2,4-dimethoxyphenyl)imidazo[1,2-a]pyridin-7-yl)-trans-amino)cyclohexyl)carbamate | 0.98 | 0.8 | 0.7 | 0.78 | 0.93 | 0.00524 |
| 278 | trans-N-(4-((4-benzylpiperazin-1-yl)methyl)cyclohexyl)-2-(5-chloro-2,4-dimethoxyphenyl)imidazo[1,2-a]pyridin-7-amine trifluoroacetate | 1.4 | 0.84 | 0.73 | 1.2 | 1.3 | 0.0707 |
| 279 | 4-(4-(2-(5-chloro-2,4-dimethoxyphenyl)imidazo[1,2-a]pyridin-7-yl)piperazin-1-yl)pyrimidin-2-amine | 0.32 | 0.32 | 0.33 | 0.33 | 0.38 | 0.00938 |
| 280 | 2-(5-chloro-2,4-dimethoxyphenyl)-7-((1-(thiophen-2-ylsulfonyl)piperidin-4-yl)oxy)imidazo[1,2-a]pyridine | 2 | 1.9 | 1.6 | 1.7 | 0.8 | 0.0711 |
| 281 | 2-(5-chloro-2,4-dimethoxyphenyl)-7-(4-(6-fluoropyridin-2-yl)piperazin-1-yl)imidazo[1,2-a]pyridine | 1.2 | 0.82 | 0.76 | 0.83 | 0.9 | 0.0988 |
| 282 | 2-(5-chloro-2,4-dimethhoxyphenyl)-7-(4-phenylpiperazin-1-yl)imidazo[1,2-a]pyridine | 1.5 | 1.4 | 1.4 | 1.5 | 0.96 | 0.0349 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 283 | 2-(4-(2-(5-chloro-2,4-dimethoxyphenyl)imidazo[1,2-a]pyridin-7-yl)piperazin-1-yl)nicotinonitrile | 0.66 | 0.42 | 0.69 | 0.45 | 0.68 | 0.0141 |
| 284 | 4-(4-((2-(5-chloro-2,4-dimethoxyphenyl)imidazo[1,2-a]pyridin-7-yl)oxy)piperidin-1-yl)pyrimidin-2-amine | 1.5 | 0.71 | 1.1 | 1.3 | 0.98 | 0.0918 |
| 285 | 2-(5-chloro-2,4-dimethoxyphenyl)-7-(4-(pyrazin-2-yl)piperazin-1-yl)imidazo[1,2-a]pyridine | 0.72 | 0.67 | 0.69 | 0.7 | 0.7 | 0.00747 |
| 286 | 2-(4-(2-(5-chloro-2,4-dimethoxyphenyl)imidazo[1,2-a]pyridin-7-yl)piperazin-1-yl)pyrimidin-4-amine | 0.65 | 0.56 | 0.7 | 0.71 | 0.63 | 0.00881 |
| 287 | $N^1$-(2-(5-chloro-2,4-dimethoxyphenyl)imidazo[1,2-a]pyridin-7-yl)-$N^4$-(pyridin-2-yl)-trans-cyclohexane-1,4-diamine | 0.8 | 0.91 | 0.78 | 0.81 | 0.94 | 0.0327 |
| 288 | 2-(5-chloro-2,4-dimethoxyphenyl)-7-((1-((1-methyl-1H-imidazol-2-yl)sulfonyl)piperidin-4-yl)oxy)imidazo[1,2-a]pyridine | 0.8 | 0.98 | 1.7 | 1.5 | 1.2 | 0.0928 |
| 289 | 2-(5-chloro-2,4-dimethoxyphenyl)-trans-N-(4-((4-(methylsulfonyl)piperazin-1-yl)methyl)cyclohexyl)imidazo[1,2-a]pyridin-7-amine | 0.63 | 0.83 | 0.74 | 0.72 | 0.77 | 0.028 |
| 290 | tert-butyl 4-(2-(5-chloro-2,4-dimethoxyphenyl)-3-iodoimidazo[1,2-a]pyridin-7-yl)piperazine-1-carboxylate | 1.3 | 1.3 | 1.3 | 1.4 | 0.61 | 0.00975 |
| 291 | $N^1$-benzyl-$N^4$-(2-(5-chloro-2,4-dimethoxyphenyl)imidazo[1,2-a]pyridin-7-yl)-trans-cyclohexane-1,4-diamine | 0.72 | 0.67 | 0.93 | 0.76 | 0.71 | 0.041 |
| 292 | 2-(5-chloro-2,4-dimethoxyphenyl)-7-(4-(pyridin-4-ylmethyl)piperazin-1-yl)imidazo[1,2-a]pyridine | 1.2 | 1.3 | 1.2 | 1.3 | 0.68 | 0.00637 |
| 293 | 6-(4-(2-(5-chloro-2,4-dimethoxyphenyl)imidazo[1,2-a]pyridin-7-yl)piperazin-1-yl)nicotinonitrile | 0.67 | 0.33 | 1.3 | 0.62 | 1 | 0.0226 |
| 294 | 4-(4-(4-(2-(5-chloro-2,4-dimethoxyphenyl)imidazo[1,2-a]pyridin-7-yl)piperazin-1-yl)pyrimidin-2-yl)morpholine | 1.1 | 0.78 | 2.3 | 1.3 | 1 | 0.0283 |
| 295 | 2-(5-chloro-2,4-dimethoxyphenyl)-7-(4-(2-(piperidin-1-yl)pyrimidin-4-yl)piperazin-1-yl)imidazo[1,2-a]pyridine | 0.89 | 0.93 | 1.4 | 1.3 | 0.93 | 0.0598 |
| 296 | 2-(5-chloro-2,4-dimethoxypheny])-7-(4-(pyridin-3-yl)piperazin-1-yl)imidazo[1,2-a]pyridine | 0.66 | 0.56 | 0.73 | 0.79 | 0.64 | 0.013 |
| 297 | 4-(4-(2-(5-chloro-2,4-dimethoxyphenyl)imidazo[1,2-a]pyridin-7-yl)piperazin-1-yl)-N,N-dimethylpyrimidin-2-amine | 0.43 | 0.33 | 0.65 | 0.72 | 0.47 | 0.0342 |
| 298 | (S)-1-(2-(5-chloro-2,4-dimethoxyphenyl)imidazo[1,2-a]pyridin-7-yl)-N-(pyridin-4-ylmethyl)pyrrolidin-3-amine | 0.67 | 0.5 | 0.84 | 1.4 | 0.79 | 0.00649 |
| 299 | (S)-1-(2-(5-chloro-2,4-dimethoxyphenyl)imidazo[1,2-a]pyridin-7-yl)-N-(pyridin-2-ylmethyl)pyrrolidin-3-amine | 5.3 | 4.5 | 6.2 | 5.5 | 3.5 | 0.00721 |
| 300 | (S)-1-(2-(5-chloro-2,4-dimethoxyphenyl)imidazo[1,2-a]pyridin-7-yl)-N-(pyridin-3-ylmethyl)pyrrolidin-3-amine | 6 | 4.7 | 7.1 | 6.1 | 3.5 | 0.0127 |
| 301 | (S)-N-benzyl-1-(2-(5-chloro)-2,4-dimethoxyphenyl)imidazo[1,2-a]pyridin-7-yl)pyrrolidin-3-amine | 1.4 | 0.79 | 0.69 | 1.1 | 1.5 | 0.0107 |

TABLE 3-continued

| No. | Compound Name | A549 | HCT-116 | HFL1 | CCD-18Co | PC14 | IC50 (μM) Suv 39H2 assay |
|---|---|---|---|---|---|---|---|
| 302 | (S)-1-(2-(5-chloro-2,4-dimethoxyphenyl)imidazo[1,2-a]pyridin-7-yl)-N-(4-fluorobenzyl)pyrrolidin-3-amine | 1.5 | 0.92 | 0.72 | 1.1 | 1.4 | 0.0153 |
| 303 | (S)-1-(2-(5-chloro-2,4-dimethoxyphenyl)imidazo[1,2-a]pyridin-7-yl)-N-(4-(trifluoromethyl)benzyl)pyrrolidin-3-amine | 1 | 0.7 | 0.68 | 0.86 | 0.95 | 0.0278 |
| 304 | (S)-1-(2-(5-chloro-2,4-dimethoxyphenyl)imidazo[1,2-a]pyridin-7-yl)-N-(4-nitrobenzyl)pyrrolidin-3-amine | 0.87 | 0.52 | 0.7 | 0.49 | 0.88 | 0.00888 |
| 305 | (S)-1-(2-(5-chloro)-2,4-dimethoxyphenyl)imidazo[1,2-a]pyridin-7-yl)-N-(4-methylbenzyl)pyrrolidin-3-amine | 1.1 | 0.59 | 0.67 | 0.82 | 0.99 | 0.0117 |
| 306 | (S)-1-(2-(5-chloro-2,4-dimethoxyphenyl)imidazo[1,2-a]pyridin-7-yl)-N(4-methoxybenzyl)pyrrolidin-3-amine | 1.3 | 0.69 | 0.72 | 1.4 | 1.4 | 0.00881 |

TABLE 4

| Example No. | SUV39H2 | A549 |
|---|---|---|
| 307 | 0.002 | 2.2 |
| 308 | 0.0035 | 8.6 |
| 309 | 0.00197 | 2.1 |
| 310 | 0.00178 | 10 |
| 311 | 0.00494 | 3.8 |
| 312 | 0.00381 | 2.5 |
| 313 | 0.00188 | 10 |
| 314 | 0.00729 | 1.7 |
| 315 | 0.0105 | 4.4 |
| 316 | 0.077 | 0.7 |
| 317 | 0.0116 | 0.65 |
| 318 | 0.00973 | 0.18 |
| 319 | 0.0164 | 4.6 |
| 320 | 0.095 | 0.43 |
| 321 | 0.0874 | 0.87 |
| 322 | 0.0575 | 0.56 |
| 323 | 0.0304 | 0.93 |
| 324 | 0.0339 | 0.59 |
| 325 | 0.0234 | 0.8 |
| 326 | 0.0203 | 0.66 |
| 327 | 0.0467 | 0.87 |
| 328 | 0.0605 | 0.36 |
| 329 | 0.0388 | 0.78 |
| 330 | 0.098 | 0.56 |
| 331 | 0.0569 | 0.82 |
| 332 | 0.0216 | 0.91 |
| 333 | 0.062 | 0.72 |
| 334 | 0.0213 | 0.72 |
| 335 | 0.0685 | 0.69 |
| 336 | 0.0161 | 0.97 |
| 337 | 0.0799 | 0.83 |
| 338 | 0.017 | 1.2 |
| 339 | 0.0357 | 0.96 |
| 340 | 0.0171 | 0.69 |
| 341 | 0.0234 | 0.74 |
| 342 | 0.0388 | 1.3 |
| 343 | 0.0479 | 0.91 |
| 344 | 0.0148 | 0.35 |
| 345 | 0.0354 | 0.85 |
| 346 | 0.0153 | 0.59 |
| 347 | 0.0248 | 0.74 |
| 348 | 0.0312 | 0.75 |
| 349 | 0.0149 | 0.61 |
| 350 | 0.00735 | 0.68 |
| 351 | 0.0286 | 0.86 |
| 352 | 0.00925 | 10 |
| 353 | 0.0419 | 0.78 |
| 354 | 0.0129 | 0.49 |
| 355 | 0.0388 | 0.67 |
| 356 | 0.0606 | 0.38 |
| 357 | 0.0258 | 0.6 |
| 358 | 0.0171 | 0.39 |
| 359 | 0.0122 | 0.4 |
| 360 | 0.056 | 0.62 |
| 361 | 0.0433 | 0.87 |
| 362 | 0.0155 | 0.68 |
| 363 | 0.0265 | 0.49 |
| 364 | 0.0407 | 0.55 |
| 365 | 0.0297 | 0.63 |
| 366 | 0.0629 | 0.86 |
| 367 | 0.0262 | 0.98 |
| 368 | 0.0157 | 0.99 |
| 369 | 0.0572 | 0.63 |
| 370 | 0.012 | 0.73 |
| 371 | 0.0161 | 0.69 |
| 372 | 0.0183 | 0.7 |
| 373 | 0.0136 | 0.64 |
| 374 | 0.0314 | 0.66 |
| 375 | 0.0231 | 0.69 |
| 376 | 0.0665 | 0.98 |
| 377 | 0.0144 | 0.66 |
| 378 | 0.0228 | 0.68 |
| 379 | 0.0269 | 0.42 |
| 380 | 0.0333 | 0.6 |
| 381 | 0.0431 | 0.77 |
| 382 | 0.0317 | 0.68 |
| 383 | 0.0138 | 0.88 |
| 384 | 0.0109 | 0.94 |
| 385 | 0.038 | 0.66 |
| 386 | 0.0248 | 0.73 |
| 387 | 0.0332 | 1.6 |
| 388 | 0.00505 | 0.56 |
| 389 | 0.0393 | 0.75 |
| 390 | 0.0996 | 0.39 |
| 391 | 0.0793 | 0.99 |
| 392 | 0.0527 | 0.68 |
| 393 | 0.0283 | 0.67 |
| 394 | 0.0103 | 0.8 |
| 395 | 0.014 | 0.77 |
| 396 | 0.0146 | 0.78 |
| 397 | 0.0646 | 0.7 |
| 398 | 0.0233 | 0.44 |

TABLE 4-continued

| Example No. | SUV39H2 | A549 |
|---|---|---|
| 399 | 0.0117 | 0.66 |
| 400 | 0.00715 | 0.93 |
| 401 | 0.00681 | 0.5 |
| 402 | 0.0187 | 0.74 |
| 403 | 0.0151 | 0.75 |
| 404 | 0.00403 | 1.5 |
| 405 | 0.0153 | 0.69 |
| 406 | 0.037 | 0.74 |
| 407 | 0.0077 | 0.95 |
| 408 | 0.0127 | 0.56 |
| 409 | 0.0241 | 0.86 |
| 410 | 0.00829 | 0.78 |
| 411 | 0.0263 | 0.37 |
| 412 | 0.00683 | 0.85 |
| 413 | 0.00635 | 0.77 |
| 414 | 0.0848 | 0.82 |
| 415 | 0.098 | 0.62 |
| 416 | 0.0476 | 0.67 |
| 417 | 0.00991 | 0.62 |
| 418 | 0.0413 | 0.61 |
| 419 | 0.082 | 0.49 |
| 420 | 0.0646 | 0.72 |
| 421 | 0.00605 | 0.94 |
| 422 | 0.0112 | 0.72 |
| 423 | 0.0269 | 0.59 |
| 424 | 0.0114 | 0.7 |
| 425 | 0.0579 | 0.89 |
| 426 | 0.0177 | 0.67 |
| 427 | 0.0251 | 0.82 |
| 428 | 0.0143 | 0.77 |
| 429 | 0.0161 | 10 |
| 430 | 0.0137 | 0.95 |
| 431 | 0.0884 | 0.76 |
| 432 | 0.0318 | 0.71 |
| 433 | 0.0576 | 0.82 |
| 434 | 0.0887 | 0.55 |
| 435 | 0.00646 | 0.65 |
| 436 | 0.0117 | 0.65 |
| 437 | 0.0159 | 0.74 |
| 438 | 0.0231 | 2.4 |
| 439 | 0.00676 | 10 |
| 440 | 0.0358 | 0.62 |
| 441 | 0.00499 | 0.54 |
| 442 | 0.0139 | 0.73 |
| 443 | 0.0173 | 0.82 |
| 444 | 0.078 | 0.78 |
| 445 | 0.0859 | 0.94 |
| 446 | 0.0974 | 0.43 |
| 447 | 0.0852 | 0.44 |
| 448 | 0.0226 | 0.34 |
| 449 | 0.0175 | 0.87 |
| 450 | 0.0336 | 0.73 |
| 451 | 0.017 | 0.46 |
| 452 | 0.0426 | 0.83 |
| 453 | 0.0105 | 0.54 |
| 454 | 0.027 | 0.76 |
| 455 | 0.0123 | 0.92 |
| 456 | 0.0255 | 0.63 |
| 457 | 0.0348 | 0.82 |
| 458 | 0.0175 | 0.42 |
| 459 | 0.00769 | 0.99 |
| 460 | 0.0207 | 0.69 |

What is claimed is:

1. A compound represented by formula (I) or a pharmaceutically acceptable salt thereof:

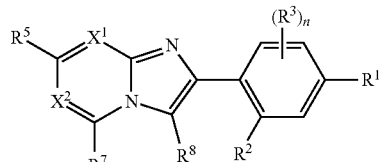

wherein $R^1$ is selected from the group consisting of a halogen atom, hydroxy, $C_1$-$C_6$ alkyl, and $C_1$-$C_6$ alkoxy, wherein the alkyl and the alkoxy may be substituted with one or more substituents selected from $A^1$;

$R^2$ is selected from the group consisting of a hydrogen atom, a halogen atom, hydroxy, $C_1$-$C_6$ alkyl, $C_1$-$C_6$ alkoxy, and $C_3$-$C_{10}$ cycloalkoxy, wherein the alkyl and the alkoxy may be substituted with one or more substituents selected from $A^2$;

$R^3$ is independently selected from the group consisting of a halogen atom, cyano, nitro, hydroxy, carboxy, $C_1$-$C_6$ alkyl, $C_1$-$C_6$ alkoxy, ($C_1$-$C_6$ alkoxy)carbonyl, $C_1$-$C_6$ alkylthio, $C_1$-$C_6$ alkylsulfinyl, and $C_1$-$C_6$ alkylsulfonyl;

n is an integer selected from 0 to 3;

$X^1$ is N and $X^2$ is N; or $X^1$ is $CR^4$ and $X^2$ is N or $CR^6$;

$R^4$ is selected from the group consisting of a hydrogen atom, a halogen atom, $C_1$-$C_6$ alkyl, and $C_1$-$C_6$ alkoxy;

$R^5$ and $R^6$ are independently selected from the group consisting of a hydrogen atom, a halogen atom, and Y, wherein at least one of $R^5$ and $R^6$ is Y;

Y is independently selected from the group consisting of —$NR^{11}R^{12}$, $C_{10}$ cycloalkyl optionally substituted with one or more substituents selected from Rc, $C_6$-$C_{10}$ aryl optionally substituted with one or more substituents selected from Rd, 3- to 12-membered non-aromatic heterocyclyl optionally substituted with one or more substituents selected from Re, and 5- to 10-membered heteroaryl optionally substituted with one or more substituents selected from Rf;

$R^{11}$ is selected from the group consisting of a hydrogen atom, $C_1$-$C_6$ alkyl optionally substituted with one or more substituents selected from Ra, $C_3$-$C_{10}$ cycloalkyl optionally substituted with one or more substituents selected from Rb, $C_6$-$C_{10}$ aryl optionally substituted with one or more substituents selected from Rb, 5- to 10-membered heteroaryl optionally substituted with one or more substituents selected from Rb, 3- to 12-membered non-aromatic heterocyclyl optionally substituted with one or more substituents selected from Rb, ($C_1$-$C_6$ alkoxy)carbonyl optionally substituted with one or more substituents selected from Ra, ($C_1$-$C_6$ alkyl)carbonyl optionally substituted with one or more substituents selected from Ra, ($C_3$-$C_{10}$ cycloalkyl)carbonyl optionally substituted with one or more substituents selected from Rg, ($C_6$-$C_{10}$ aryl)carbonyl optionally substituted with one or more substituents selected from Rh, (3- to 12-membered non-aromatic heterocyclyl)carbonyl optionally substituted with one or more substituents selected from Rg, (5- to 10-membered heteroaryl)carbonyl optionally substituted with one or more substituents selected from Rg, aminocarbonyl, ($C_1$-$C_6$ alkyl)aminocarbonyl, and di($C_1$-$C_6$ alkyl)aminocarbonyl;

$R^{12}$ is selected from the group consisting of a hydrogen atom, and $C_1$-$C_6$ alkyl optionally substituted with one or more substituents selected from Ra;

$R^{13}$ is selected from the group consisting of a hydrogen atom, $C_1$-$C_6$ alkyl optionally substituted with one or more substituents selected from Ra, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

$R^{14}$ is selected from the group consisting of a hydrogen atom, and $C_1$-$C_6$ alkyl optionally substituted with one or more substituents selected from Ra;

$R^{15}$ is selected from the group consisting of $C_3$-$C_{10}$ cycloalkyl optionally substituted with one or more substituents selected from Rc, $C_6$-$C_{10}$ aryl optionally substituted with one or more substituents selected from Rd, 4- to 12-membered heterocyclyl optionally substituted with one or more substituents selected from Re, and 5- to 10-membered heteroaryl optionally substituted with one or more substituents selected from Rf;

$A^1$ is independently selected from the group consisting of a halogen atom and cyano;

$A^2$ is independently selected from the group consisting of a halogen atom, cyano, amino, $C_1$-$C_6$ alkylamino, di($C_1$-$C_6$ alkyl)amino, $C_1$-$C_6$ alkylthio, $C_1$-$C_6$ alkylsulfinyl, $C_1$-$C_6$ alkylsulfonyl, $C_3$-$C_{10}$ cycloalkyl, and $C_1$-$C_6$ alkoxy;

$A^3$ independently is selected from the group consisting of a halogen atom, cyano, amino, $C_1$-$C_6$ alkylamino, di($C_1$-$C_6$ alkyl)amino, $C_1$-$C_6$ alkylthio, $C_1$-$C_6$ alkylsulfinyl, $C_1$-$C_6$ alkylsulfonyl, $C_3$-$C_{10}$ cycloalkylsulfonyl, $C_3$-$C_{10}$ cycloalkyl, and $C_1$-$C_6$ alkoxy;

Ra is independently selected from the group consisting of a halogen atom, hydroxy, $C_1$-$C_6$ alkoxy, cyano, ($C_1$-$C_6$ alkoxy)carbonyl, carboxy, ($C_1$-$C_6$ alkoxy)carbonylamino, ($C_1$-$C_6$ alkyl)carbonylamino, amino, $C_1$-$C_6$ alkylamino, di($C_1$-$C_6$ alkyl)amino, aminocarbonyl, ($C_1$-$C_6$ alkyl)aminocarbonyl, di($C_1$-$C_6$ alkyl)aminocarbonyl, $C_1$-$C_6$ alkylsulfonylamino, $C_3$-$C_{10}$ cycloalkylsulfonylamino, di($C_1$-$C_6$ alkyl)phosphono, $C_7$-$C_{14}$ aralkyl, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 4- to 12-membered non-aromatic heterocyclyl optionally substituted with one or more substituents selected from Rg;

Rb is independently selected from the group consisting of a halogen atom, hydroxy, $C_1$-$C_6$ alkyl optionally substituted with one or more substituents selected from Ra, $C_1$-$C_6$ alkoxy optionally substituted with one or more substituents selected from Ra, cyano, ($C_1$-$C_6$ alkoxy)carbonyl, carboxy, —$NR^{21}R^{22}$, —$CONR^{23}R^{24}$, di($C_1$-$C_6$ alkyl)phosphono, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

Rc, Re and Rf are independently selected from the group consisting of a halogen atom, hydroxy, cyano, carboxy, —$NR^{21}R^{22}$, —$CONR^{23}R^{24}$, —N=CH—$R^{25}$, $C_1$-$C_6$ alkyl optionally substituted with one or more substituents selected from Ra, ($C_1$-$C_6$ alkoxy)$C_1$-$C_6$ alkyl optionally substituted with one or more substituents selected from Ra, ($C_1$-$C_6$ alkyl)carbonyl optionally substituted with one or more substituents selected from Ra, ($C_1$-$C_6$ alkoxy)carbonyl, ($C_6$-$C_{10}$ aryl)carbonyl optionally substituted with one or more substituents selected from Rh, ($C_3$-$C_{10}$ cycloalkyl)carbonyl optionally substituted with one or more substituents selected from Rg, (3- to 12-membered non-aromatic heterocyclyl)carbonyl optionally substituted with one or more substituents selected from Rg, $C_3$-$C_{10}$ cycloalkyl optionally substituted with one or more substituents selected from Rg, 3- to 12-membered non-aromatic heterocyclyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl)aminocarbonyl optionally substituted with one or more substituents selected from Ra, [($C_1$-$C_6$ alkyl)aminocarbonyl]$C_1$-$C_6$ alkyl optionally substituted with one or more substituents selected from Ra, [di($C_1$-$C_6$ alkyl)aminocarbonyl]$C_1$-$C_6$ alkyl optionally substituted with one or more substituents selected from Ra, 5- to 10-membered heteroaryl optionally substituted with one or more substituents selected from Rg, $C_1$-$C_6$ alkylsulfonyl optionally substituted with one or more halogen atoms, $C_3$-$C_{10}$ cycloalkylsulfonyl optionally substituted with one or more substituents selected from Rg, ($C_6$-$C_{10}$ aryl)sulfonyl optionally substituted with one or more substituents selected from Rh, $C_7$-$C_{14}$ aralkylsulfonyl, (3- to 12-membered non-aromatic heterocyclyl)sulfonyl optionally substituted with one or more substituents selected from Rg, 5- to 10-membered heteroarylcarbonyl optionally substituted with one or more substituents selected from Rg, 5- to 10-membered heteroarylsulfonyl optionally substituted with one or more substituents selected from Rg, aminosulfonyl, $C_1$-$C_6$ alkylaminosulfonyl, di($C_1$-$C_6$ alkyl)aminosulfonyl, di($C_1$-$C_6$ alkyl)phosphono, and oxo;

Rd is independently selected from the group consisting of a halogen atom, hydroxy, cyano, carboxy, —$NR^{21}R^{22}$, —$CONR^{23}R^{24}$, $C_1$-$C_6$ alkyl optionally substituted with one or more substituents selected from Ra, ($C_1$-$C_6$ alkoxy)$C_1$-$C_6$ alkyl optionally substituted with one or more substituents selected from Ra, ($C_1$-$C_6$ alkyl)carbonyl optionally substituted with one or more substituents selected from Ra, ($C_1$-$C_6$ alkoxy)carbonyl, ($C_6$-$C_{10}$ aryl)carbonyl optionally substituted with one or more substituents selected from Rh, ($C_3$-$C_{10}$ cycloalkyl)carbonyl optionally substituted with one or more substituents selected from Rg, (3- to 12-membered non-aromatic heterocyclyl)carbonyl optionally substituted with one or more substituents selected from Rg, $C_3$-$C_{10}$ cycloalkyl optionally substituted with one or more substituents selected from Rg, 3- to 12-membered non-aromatic heterocyclyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl)aminocarbonyl optionally substituted with one or more substituents selected from Ra, [($C_1$-$C_6$ alkyl)aminocarbonyl]$C_1$-$C_6$ alkyl optionally substituted with one or more substituents selected from Ra,

[di($C_1$-$C_6$ alkyl)aminocarbonyl]$C_1$-$C_6$ alkyl optionally substituted with one or more substituents selected from Ra, 5- to 10-membered heteroaryl optionally substituted with one or more substituents selected from Rg, $C_1$-$C_6$ alkylsulfonyl optionally substituted with one or more halogen atoms, $C_3$-$C_{10}$ cycloalkylsulfonyl optionally substituted with one or more substituents selected from Rg, ($C_6$-$C_{10}$ aryl)sulfonyl optionally substituted with one or more substituents selected from Rh, $C_7$-$C_{14}$ aralkylsulfonyl, (3- to 12-membered non-aromatic heterocyclyl)sulfonyl optionally substituted with one or more substituents selected from Rg, 5- to 10-membered heteroarylsulfonyl optionally substituted with one or more substituents selected from Rg, aminosulfonyl, $C_1$-$C_6$ alkylaminosulfonyl, di($C_1$-$C_6$ alkyl)aminosulfonyl, and di($C_1$-$C_6$ alkyl)phosphono;

Rg is independently selected from the group consisting of nitro, hydroxy, $C_1$-$C_6$ alkyl optionally substituted with one or more halogen atoms, $C_1$-$C_6$ alkoxy optionally substituted with one or more halogen atoms, a halogen atom, amino, cyano, $C_1$-$C_6$ alkylamino optionally substituted with one or more hydroxy groups, di($C_1$-$C_6$ alkyl)amino optionally substituted with one or more hydroxy groups, $C_3$-$C_{10}$ cycloalkylamino, ($C_1$-$C_6$ alkyl)carbonyl, ($C_1$-$C_6$ alkoxy)carbonyl, $C_1$-$C_6$ alkylsulfonyl, $C_3$-$C_{10}$ cycloalkylsulfonyl, $C_7$-$C_{14}$ aralkyl optionally substituted with one or more substituents selected from Ri, $C_6$-$C_{10}$ aryl optionally substituted with one or more substituents selected from Ri, $C_3$-$C_{10}$ cycloalkyl optionally substituted with one or more substituents selected from Ri, 3- to 12-membered non-aromatic heterocyclyl optionally substituted with one or more substituents selected from Ri, 5- to 10-membered heteroaryl optionally substituted with one or more substituents selected from Ri, and oxo;

Rh is independently selected from the group consisting of nitro, hydroxy, $C_1$-$C_6$ alkyl optionally substituted with one or more halogen atoms, $C_1$-$C_6$ alkoxy optionally substituted with one or more halogen atoms, a halogen atom, amino, cyano, $C_1$-$C_6$ alkylamino, di($C_1$-$C_6$ alkyl)amino, $C_1$-$C_6$ alkylcarbonyl, ($C_1$-$C_6$ alkoxy)carbonyl, ($C_1$-$C_6$ alkoxy)carbonylamino, N—($C_1$-$C_6$ alkoxy)carbonyl-N—($C_1$-$C_6$ alkyl)amino, $C_1$-$C_6$ alkylsulfonyl, $C_3$-$C_8$ cycloalkylsulfonyl, $C_7$-$C_{14}$ aralkyl optionally substituted with one or more substituents selected from Ri, $C_6$-$C_{10}$ aryl optionally substituted with one or more substituents selected from Ri, $C_3$-$C_8$ cycloalkyl optionally substituted with one or more substituents selected from Ri, 3- to 12-membered non-aromatic heterocyclyl optionally substituted with one or more substituents selected from Ri, and 5- to 10-membered heteroaryl optionally substituted with one or more substituents selected from Ri;

Ri is independently selected from the group consisting of nitro, hydroxy, $C_1$-$C_6$ alkyl optionally substituted with one or more substituents selected from a halogen atom and hydroxy, a halogen atom, amino, cyano, $C_1$-$C_6$ alkylamino, di($C_1$-$C_6$ alkyl)amino, $C_1$-$C_6$ alkylcarbonyl optionally substituted with one or more substituents selected from phenyl and hydroxy, ($C_1$-$C_6$ alkoxy)carbonyl optionally substituted with one or more substituents selected from phenyl and hydroxy, $C_1$-$C_6$ alkylsulfonyl, $C_3$-$C_8$ cycloalkylsulfonyl, $C_1$-$C_6$ alkylsulfonylamino, $C_3$-$C_8$ cycloalkylsulfonylamino, and oxo;

$R^{21}$ is selected from the group consisting of a hydrogen atom, $C_1$-$C_6$ alkyl optionally substituted with one or more substituents selected from Ra, $C_6$-$C_{10}$ aryl optionally substituted with one or more substituents selected from Rh, 4- to 12-membered heterocyclyl optionally substituted with one or more substituents selected from Rg, 5- to 10-membered heteroaryl optionally substituted with one or more substituents selected from Rg, ($C_1$-$C_6$ alkoxy)carbonyl optionally substituted with one or more substituents selected from Ra, ($C_1$-$C_6$ alkyl)carbonyl optionally substituted with one or more substituents selected from Ra, ($C_3$-$C_{10}$ cycloalkyl)carbonyl, ($C_6$-$C_{10}$ aryl)carbonyl optionally substituted with one or more substituents selected from Rh, (3- to 12-membered non-aromatic heterocyclyl)carbonyl optionally substituted with one or more substituents selected from Rg, (5- to 10-membered heteroaryl)carbonyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl)aminocarbonyl optionally substituted with one or more substituents selected from Ra, $C_1$-$C_6$ alkylsulfonyl optionally substituted with one or more halogen atoms, $C_7$-$C_{14}$ aralkyl sulfonyl, $C_3$-$C_{10}$ cycloalkylsulfonyl, aminosulfonyl, $C_1$-$C_6$ alkylaminosulfonyl, di($C_1$-$C_6$ alkyl)aminosulfonyl, and di($C_1$-$C_6$ alkyl)phosphono;

$R^{22}$ is selected from the group consisting of a hydrogen atom, and $C_1$-$C_6$ alkyl optionally substituted with one or more substituents selected from Ra;

$R^{23}$ is selected from the group consisting of a hydrogen atom, $C_1$-$C_6$ alkyl optionally substituted with one or more substituents selected from Ra, [($C_1$-$C_6$ alkyl)amino]$C_1$-$C_6$ alkyl optionally substituted with one or more substituents selected from Ra, [di($C_1$-$C_6$ alkyl)amino]$C_1$-$C_6$ alkyl optionally substituted with one or more substituents selected from Ra, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

$R^{24}$ is selected from the group consisting of a hydrogen atom, and $C_1$-$C_6$ alkyl optionally substituted with one or more substituents selected from Ra;

$R^{25}$ is selected from the group consisting of $C_1$-$C_6$ alkyl optionally substituted with one or more substituents selected from Ra, $C_3$-$C_{10}$ cycloalkyl optionally substituted with one or more substituents selected from Rc, $C_6$-$C_{10}$ aryl optionally substituted with one or more substituents selected from Rd, 4- to 12-membered heterocyclyl optionally substituted with one or more substituents selected from Re, and 5- to 10-membered heteroaryl optionally substituted with one or more substituents selected from Rf;

$R^7$ is selected from the group consisting of a hydrogen atom, a halogen atom, $C_1$-$C_6$ alkyl, and $C_1$-$C_6$ alkoxy;

$R^8$ is selected from the group consisting of a hydrogen atom, a halogen atom, $C_1$-$C_6$ alkyl, and $C_1$-$C_6$ alkoxy; and wherein a sulfur atom included in heterocyclyl or heteroaryl may be oxidized to be SO or $SO_2$.

2. The compound or a pharmaceutically acceptable salt thereof according to claim 1, wherein the compound is represented by Formula (Ia):

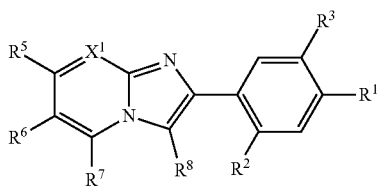

(Ia)

wherein R¹, R², R³, R⁵, R⁶, R⁷, R⁸ and X¹ are as defined in claim 1.

3. The compound or a pharmaceutically acceptable salt thereof according to claim 1, wherein R¹ is methoxy.

4. The compound or a pharmaceutically acceptable salt thereof according to claim 1, wherein R⁷ and R⁸ are hydrogen atoms.

5. The compound or a pharmaceutically acceptable salt thereof according to claim 1, wherein R³ is a halogen atom.

6. The compound or a pharmaceutically acceptable salt thereof according to claim 1, wherein R² is methoxy.

7. The compound or a pharmaceutically acceptable salt thereof according to claim 1, wherein R⁵ is Y and R⁶ is a hydrogen atom.

8. The compound or a pharmaceutically acceptable salt thereof according to claim 1, wherein Y is selected from the group consisting of:
  piperazin-1-yl substituted with one or more substituents selected from Re;
  pyrrolidin-1-yl substituted with one or more substituents selected from Re;
  1,4-diazepan-1-yl substituted with one or more substituents selected from Re;
  8-azabicyclo[3.2.1]octan-3-ylamino wherein the 8-azabicyclo[3.2.1]octan-3-yl moiety is substituted with one or more substituents selected from Rb;
  piperidine-4-ylamino wherein the piperidine-4-yl moiety is substituted with one or more substituents selected from Rb; and
  cyclohexylamino wherein the cyclohexyl moiety is substituted with one or more substituents selected from Rb.

9. The compound or a pharmaceutically acceptable salt thereof according to claim 1, wherein Y is selected from the group consisting of:
  piperazin-1-yl substituted at 4-position with 5- to 10-membered heteroaryl optionally substituted with one or more substituents selected from Rg;
  1,4-diazepan-1-yl substituted at 4-position with methyl substituted with a substituent selected from Ra;
  pyrrolidin-1-yl substituted at 3-position with a group —NHR²¹, wherein R²¹ is methyl substituted with a substituent selected from Ra;
  8-azabicyclo[3.2.1]octan-3-ylamino wherein the 8-azabicyclo[3.2.1]octan-3-yl moiety is substituted at 8-position with methyl substituted with a substituent selected from Ra,
  piperidine-4-ylamino wherein the piperidine-4-yl moiety is substituted at 1-position with methyl substituted with a substituent selected from Ra, and
  cyclohexylamino wherein the cyclohexyl moiety is substituted at 4-position with a group —NHR²¹, wherein R²¹ is methyl substituted with a substituent selected from Ra.

10. The compound or a pharmaceutically acceptable salt thereof according to claim 1, wherein Y is selected from the group consisting of:
  piperazin-1-yl substituted with one or more substituents selected from Re,
  pyrrolidin-1-yl substituted with one or more substituents selected from Re, and
  cyclohexylamino wherein the cyclohexyl moiety is substituted with one or more substituents selected from Rb.

11. The compound or a pharmaceutically acceptable salt thereof according to claim 1, wherein Y is selected from the group consisting of:
  piperazin-1-yl substituted at 4-position with 5- to 10-membered heteroaryl optionally substituted with one or more substituents selected from Rg;
  pyrrolidin-1-yl substituted at 3-position with a group —NHR²¹, wherein $R^{ei}$ is methyl substituted with a substituent selected from Ra; and
  cyclohexylamino wherein the cyclohexyl moiety is substituted at 4-position with 5- to 10-membered heteroarylamino wherein the heteroaryl moiety may be substituted with one or more substituents selected from Rg.

12. The compound or a pharmaceutically acceptable salt thereof according to claim 1, which is selected from the group consisting of:
  2-(5-bromo-2,4-dimethoxyphenyl)-N-methylimidazo[1,2-a]pyridin-7-amine;
  2-(5-chloro-2,4-dimethoxyphenyl)-7-(4-(cyclopropylsulfonyl)piperazin-1-yl)imidazo-[1,2-a]pyridine;
  N-(1-(2-(5-chloro-2,4-dimethoxyphenyl)imidazo [1,2-a]pyridine-7-yl)piperidin-4-yl)-methanesulfonamide;
  tert-butyl (1-(2-(5-chloro-2-(3-(dimethylamino)propoxy)-4-methoxyphenyl)imidazo-[1,2-a]pyridine-7-yl)piperidin-4-yl)carbamate;
  1-(2-(5-chloro-2-(3-(dimethylamino)propoxy)-4-methoxyphenyl)imidazo [1,2-a]-pyridine-7-yl)piperidin-4-amine;
  4-(2-(5-chloro-2,4-dimethoxyphenyl)imidazo[1,2-a]pyridine-7-yl)-N,N-dimethyl-piperazine-1-sulfonamide;
  N-(1-(2-(5-chloro-2,4-dimethoxyphenyl)imidazo[1,2-c]pyridine-7-yl)piperidin-4-yl)ethanesulfonamide;
  N-(1-(2-(5-chloro-2,4-dimethoxyphenyl)imidazo[1,2-c]pyridine-7-yl)piperidin-4-yl)-1,1,1-trifluoromethanesulfonamide;
  2-(5-chloro-2,4-dimethoxyphenyl)-7-(4-(isopropylsulfonyl)piperazin-1-yl)imidazo-[1,2-a]pyridine;
  7-(4-(N,N-dimethylaminosulfonylamino)piperidin-1-yl)-2-(5-chloro-2,4-dimethoxyphenyl)imidazo[1,2-a]pyridine;
  dimethyl (4-(2-(5-chloro-2,4-dimethoxyphenyl)imidazo[1,2-c]pyridine-7-yl)-5,6-dihydropyridin-1(2H)-yl)phosphonate;
  tert-butyl 4-(2-(5-chloro-2-(3-(dimethylamino)propoxy)-4-methoxyphenyl)-imidazo[1,2-c]pyridine-7-yl)-1,4-diazepane-1-carboxylate;
  2-(5-chloro-2-methoxy-4-methylphenyl)-7-(4-(cyclopropylsulfonyl)piperazin-1-yl)-imidazo[1,2-a]pyridine;
  tert-butyl 4-(2-(5-chloro-2,4-dimethoxyphenyl)imidazo[1,2-c]pyridine-7-yl)piperazine-1-carboxylate;
  2-(5-chloro-2-ethyl-4-methoxyphenyl)-7-(4-(cyclopropylsulfonyl)piperazin-1-yl)-imidazo[1,2-a]pyridine
  (S)—N-(2-(5-chloro-2,4-dimethoxyphenyl)imidazo[1,2-c]pyridine-7-yl)-1-methylpyrrolidine-2-carboxamide
  tert-butyl (2-((2-(4-(2-(5-chloro-2,4-dimethoxyphenyl)imidazo[1,2-a]pyridin-7-yl)benzamido)ethyl)amino)ethyl)carbamate;
  N-((1H-imidazol-2-yl)methyl)-4-(2-(5-chloro-2,4-dimethoxyphenyl)imidazo-[1,2-a]pyridin-7-yl)aniline;

(S)—N-(2-(5-chloro-2,4-dimethoxyphenyl)imidazo[1,2-a]pyridin-7-yl)-2-(dimethylamino)-3-methylbutanamide;
N-(4-(2-(5-chloro-2,4-dimethoxyphenyl)imidazo[1,2-a]pyridin-7-yl)phenyl)-2-(methylamino)acetamide;
(S)-2-amino-1-(4-(2-(5-chloro-2,4-dimethoxyphenyl)imidazo[1,2-a]pyridin-7-yl)phenyl)propan-1-one;
tert-butyl 4-2-(5-chloro-2,4-dimethoxyphenyl) imidazo[1,2-a]pyridin-7-yl)-2-methylpiperazine-1-carboxylate;
2-(5-chloro-2,4-dimethoxyphenyl)-7-(4-(pyridin-2-yl)piperazin-1-yl)imidazo-[1,2-a]pyridine;
methyl (4-((2-(5-chloro-2,4-dimethoxyphenyl)imidazo[1,2-a]pyridin-7-yl)-trans-amino)cyclohexyl)carbamate;
trans-N-(4-((4-benzylpiperazin-1-yl)methyl)cyclohexyl)-2-(5-chloro-2,4-dimethoxy-phenyl)imidazo[1,2-a]pyridin-7-amine trifluoroacetate;
4-(4-(2-(5-chloro-2,4-dimethoxyphenyl)imidazo[1,2-a]pyridin-7-yl)piperazin-1-yl)pyrimidin-2-amine;
2-(5-chloro-2,4-dimethoxyphenyl)-7-((1-(thiophen-2-ylsulfonyl)piperidin-4-yl)oxy)imidazo[1,2-a]pyridine;
2-(5-chloro-2,4-dimethoxyphenyl)-7-(4-(6-fluoropyridin-2-yl)piperazin-1-yl)imidazo[1,2-a]pyridine;
2-(5-chloro-2,4-dimethoxyphenyl)-7-(4-phenylpiperazin-1-yl)imidazo-[1,2-a]pyridine;
2-(4-(2-(5-chloro-2,4-dimethoxyphenyl)imidazo[1,2-a]pyridin-7-yl)piperazin-1-yl)nicotinonitrile;
4-(4-((2-(5-chloro-2,4-dimethoxyphenyl)imidazo[1,2-a]pyridin-7-yl)oxy)piperidin-1-yl)pyrimidin-2-amine;
2-(5-chloro-2,4-dimethoxyphenyl)-7-(4-(pyrazin-2-yl)piperazin-1-yl)imidazo-[1,2-a]pyridine;
2-(4-(2-(5-chloro-2,4-dimethoxyphenyl)imidazo[1,2-a]pyridin-7-yl)piperazin-1-yl)pyrimidin-4-amine;
$N^1$-(2-(5-chloro-2,4-dimethoxyphenyl)imidazo[1,2-a]pyridin-7-yl)-$N^4$-(pyridin-2-yl)-trans-cyclohexane-1,4-diamine;
2-(5-chloro-2,4-dimethoxyphenyl)-7-((1-((1-methyl-1H-imidazol-2-yl)sulfonyl)-piperidin-4-yl)oxy)imidazo[1,2-a]pyridine;
2-(5-chloro-2,4-dimethoxyphenyl)-trans-N-(4-((4-(methylsulfonyl)piperazin-1-yl)methyl)cyclohexyl)imidazo[1,2-a]pyridin-7-amine;
tert-butyl 4-(2-(5-chloro-2,4-dimethoxyphenyl)-3-iodoimidazo[1,2-a]pyridin-7-yl)piperazine-1-carboxylate;
$N^1$-benzyl-$N^4$-(2-(5-chloro-2,4-dimethoxyphenyl)imidazo[1,2-a]pyridin-7-yl)-trans-cyclohexane-1,4-diamine;
2-(5-chloro-2,4-dimethoxyphenyl)-7-(4-(pyridin-4-ylmethyl)piperazin-1-yl)imidazo[1,2-a]pyridine;
6-(4-(2-(5-chloro-2,4-dimethoxyphenyl)imidazo[1,2-a]pyridin-7-yl)piperazin-1-yl)nicotinonitrile;
4-(4-(4-(2-(5-chloro-2,4-dimethoxyphenyl)imidazo[1,2-a]pyridin-7-yl)piperazin-1-yl)pyrimidin-2-yl)morpholine;
2-(5-chloro-2,4-dimethoxyphenyl)-7-(4-(2-(piperidin-1-yl)pyrimidin-4-yl)piperazin-1-yl)imidazo[1,2-a]pyridine;
2-(5-chloro-2,4-dimethoxyphenyl)-7-(4-(pyridin-3-yl)piperazin-1-yl)imidazo-[1,2-a]pyridine;
4-(4-(2-(5-chloro-2,4-dimethoxyphenyl)imidazo[1,2-a]pyridin-7-yl)piperazin-1-yl)-N,N-dimethylpyrimidin-2-amine;
(S)-1-(2-(5-chloro-2,4-dimethoxyphenyl)imidazo[1,2-a]pyridin-7-yl)-N-(pyridin-4-ylmethyl)pyrrolidin-3-amine;
(S)-1-(2-(5-chloro-2,4-dimethoxyphenyl)imidazo[1,2-a]pyridin-7-yl)-N-(pyridin-2-ylmethyl)pyrrolidin-3-amine;
(S)-1-(2-(5-chloro-2,4-dimethoxyphenyl)imidazo[1,2-a]pyridin-7-yl)-N-(pyridin-3-ylmethyl)pyrrolidin-3-amine;
(S)—N-benzyl-1-(2-(5-chloro-2,4-dimethoxyphenyl)imidazo[1,2-a]pyridin-7-yl)pyrrolidin-3-amine;
(S)-1-(2-(5-chloro-2,4-dimethoxyphenyl)imidazo[1,2-a]pyridin-7-yl)-N-(4-fluorobenzyl)pyrrolidin-3-amine;
(S)-1-(2-(5-chloro-2,4-dimethoxyphenyl)imidazo[1,2-a]pyridin-7-yl)-N-(4-(trifluoromethyl)benzyl)pyrrolidin-3-amine;
(S)-1-(2-(5-chloro-2,4-dimethoxyphenyl)imidazo[1,2-a]pyridin-7-yl)-N-(4-nitrobenzyl)pyrrolidin-3-amine;
(S)-1-(2-(5-chloro-2,4-dimethoxyphenyl)imidazo[1,2-a]pyridin-7-yl)-N-(4-methylbenzyl)pyrrolidin-3-amine; and
a pharmaceutically acceptable salt thereof.

13. The compound or a pharmaceutically acceptable salt thereof according to claim 1, which is selected from the group consisting of:
2-(4-(2-(5-chloro-2,4-dimethoxyphenyl)imidazo[1,2-c]pyridin-7-yl)piperazin-1-yl)nicotinonitrile;
(S)-1-(2-(5-chloro-2,4-dimethoxyphenyl)imidazo[1,2-c]pyridin-7-yl)-N-(pyridin-4-ylmethyl)pyrrolidin-3-amine;
2-(5-chloro-2,4-dimethoxyphenyl)-7-(4-(pyridine-4-ylmethyl)-1,4-diazepan-1-yl)imidazo[1,2-a]pyridine;
2-(5-chloro-2,4-dimethoxyphenyl)-7-(4-(4-(piperazin-1-yl)pyrimidin-2-yl)piperazin-1-yl)imidazo[1,2-a]pyridine;
1-(2-(4-(2-(5-chloro-2,4-dimethoxyphenyl)imidazo[1,2-c]pyridine-7-yl)piperazin-1-yl)pyrimidin-5-yl)piperidin-4-amine;
1-(5-(4-(2-(5-chloro-2,4-dimethoxyphenyl)imidazo[1,2-c]pyridine-7-yl)piperazin-1-yl)pyrimidin-2-yl)-N-methylpyrrolidin-3-amine;
4-(4-(2-(5-chloro-2,4-dimethoxyphenyl)imidazo[1,2-c]pyridine-7-yl)piperazin-1-yl)-6-morpholino-1,3,5-triazin-2-amine;
2-(5-chloro-2,4-dimethoxyphenyl)-N-(1-((5-nitrothiophen-3-yl)methyl)piperidin-4-yl)imidazo[1,2-a]ppyridin-7-amine;
2-(5-chloro-2,4-dimethoxyphenyl)-N-((1R,3r,5S)-8-(pyridine-4-ylmethyl)-8-azabicyclo[3.2.1]octan-3-yl)imidazo[1,2-a]pyridine-7-amine;
tert-butyl 4-(((((1s,4s)-4-((2-(5-chloro-2,4-dimethoxyphenyl)imidazo[1,2-a]pyridine-7-yl)amino)cyclohexyl)amino)methyl)piperidine-1-carboxylate; and
a pharmaceutically acceptable salt thereof.

14. A pharmaceutical composition comprising as an active ingredient a compound or a pharmaceutically acceptable salt thereof according to claim 1.

15. A method for treating a disease that involves overexpression of SUV39H2, which comprises administering an effective amount of a compound or a pharmaceutically acceptable salt thereof according to claim 1 to a subject in need thereof.

16. The method according to claim 15, wherein the disease is cancer.

17. The method according to claim 16, wherein the cancer is selected from the group consisting of lung cancer, cervical cancer, bladder cancer, esophageal cancer, osteosarcoma, prostate cancer and soft tissue tumor.

* * * * *